(12) United States Patent
Kume et al.

(10) Patent No.: US 8,349,857 B2
(45) Date of Patent: *Jan. 8, 2013

(54) QUINAZOLINE DERIVATIVES HAVING TYROSINE KINASE INHIBITORY ACTIVITY

(75) Inventors: Masaharu Kume, Osaka (JP); Kenji Matsuo, Osaka (JP); Naoki Omori, Osaka (JP); Masami Takayama, Osaka (JP); Aiko Omori, Osaka (JP); Takeshi Endo, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/359,326

(22) Filed: Jan. 26, 2012

(65) Prior Publication Data

US 2012/0123114 A1 May 17, 2012

Related U.S. Application Data

(63) Continuation of application No. 11/884,819, filed as application No. PCT/JP2006/303125 on Feb. 22, 2006, now Pat. No. 8,202,879.

(30) Foreign Application Priority Data

Feb. 23, 2005 (JP) .................. 2005-047383
May 30, 2005 (JP) .................. 2005-156828

(51) Int. Cl.
*A01N 43/54* (2006.01)
*A61K 31/517* (2006.01)
*C07D 239/72* (2006.01)

(52) U.S. Cl. ............. 514/266.4; 514/266.23; 514/266.3; 544/284; 544/287; 544/293

(58) Field of Classification Search ............... 514/266.4, 514/266.23, 266.3; 544/284, 287, 293
See application file for complete search history.

(56) References Cited

U.S. PATENT DOCUMENTS

| 8,202,879 B2 * | 6/2012 | Kume et al. ............... 514/266.4 |
| 2002/0147214 A1 | 10/2002 | Cockerill et al. |
| 2003/0018029 A1 | 1/2003 | Barker et al. |
| 2004/0116422 A1 | 6/2004 | Kitano et al. |

FOREIGN PATENT DOCUMENTS

| EP | 0 520 722 | 12/1992 |
| EP | 0 566 226 | 10/1993 |
| EP | 0 602 851 | 6/1994 |
| JP | 5-208911 | 8/1993 |
| WO | 92/20642 | 11/1992 |
| WO | 98/02434 | 1/1998 |
| WO | 01/21594 | 3/2001 |
| WO | 03/031406 | 4/2003 |
| WO | 2004/026307 | 4/2004 |
| WO | 2004/069145 | 8/2004 |
| WO | 2004/105765 | 12/2004 |
| WO | 2005/067667 | 7/2005 |
| WO | 2005/070020 | 8/2005 |

OTHER PUBLICATIONS

Vippagunta et al.*
"The Anitproliferative Effects of Tyrosine Kinase Inhibitors Tyrphostins on a Human Squamous Cell Carcinoma in Vitro and in Nude Mice", Yoneda et al., Cancer Research 51, 4430-4435, Aug. 15, 1991.
"Inhibition of Breast Cancer Cell Growth in Vitro by a Tyrosine Kinase Inhibitor", Reddy et al., Cancer Research 52, 3636-3641, Jul. 1, 1992.

(Continued)

*Primary Examiner* — Paul V. Ward
(74) *Attorney, Agent, or Firm* — Hamre, Schumann, Mueller & Larson, P.C.

(57) ABSTRACT

A compound which inhibits both of EGF receptor tyrosine kinase and HER2 tyrosine kinase is provided.
A compound represented by the general formula (I):

[Chemical formula 1]

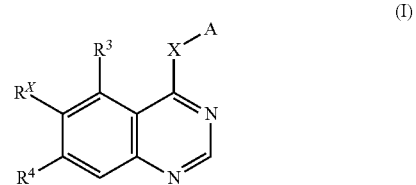

(I)

wherein $R^X$ is a group represented by the formula:

[Chemical formula 2]

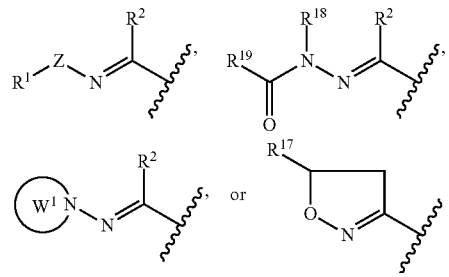

wherein $R^1$ is a hydrogen atom, optionally substituted alkyl, etc.; Z is —O—, —N($R^{10}$)—, etc.; $R^{10}$ is a hydrogen atom, alkyl, etc.; $R^2$ is a hydrogen atom, optionally substituted alkyl, etc.; $R^{18}$ is a hydrogen atom, optionally substituted alkyl, etc.; $R^{19}$ is optionally substituted alkyl, etc.; $W^1$ is an optionally substituted non-aromatic nitrogen-containing group; $R^{17}$ is a hydrogen atom, optionally substituted alkyl, etc.; $R^3$ and $R^4$ are independently a hydrogen atom, optionally substituted alkyl, etc.; X is —O—, —S—, or —N($R^{12}$)—, etc.; $R^{12}$ is a hydrogen atom, alkyl, etc.; and A is phenyl optionally having a substituent, etc.,
its pharmaceutically acceptable salt, or a solvate thereof.

14 Claims, No Drawings

OTHER PUBLICATIONS

"Review—Cell-Signaling targets for antitumour drug development", Brunton et al., Cancer Chemother Pharmacol (1993) 32: 1-19.

"Protein tyrosine kinases as therapeutic targets in cancer chemotherapy and recent advances in the development of new inhibitors", David W. Fry, Exp. Opion. Invest. Drugs 1994 3(6):577-595.

"Synergistic Interaction of p185c-neu and the EGF Receptor Leads to Transformation of Rodent Fibroblasts", Cell, vol. 58, 287-292, Jul. 28, 1989.

"Combination of EGFR, HER-2/neu, and HER-3 Is a Stronger Predictor for the Outcome of Oral Squamous Cell Carcinoma Than Any Individual Family Members", Xia et al., Clin. Cancer Res. 1999, 5, 4164-4174.

Russian Office Action mailed Apr. 24, 2009 (with English translation).

Khimicheskiy Entsiklopedicheskiy Slovar, Sovetskaya Entsiklopedia Publishers, 1983, pp. 130-131.

Supplementary European Search Report dated May 15, 2009.

ATCC: Catalog Search: NCI-N87, http://www.atcc.org/ATCCAdvancedCatalogSearch/ProductDetails/tabid452/Default.aspx . . . , Sep. 12, 2011.

\* cited by examiner

QUINAZOLINE DERIVATIVES HAVING TYROSINE KINASE INHIBITORY ACTIVITY

This application is a Continuation of U.S. Ser. No. 11/884,819 filed Nov. 1, 2007, which is a National Stage Application of PCT/JP2006/303125, filed Feb. 22, 2006, which applications are incorporated herein by reference.

TECHNICAL FIELD

The present invention relates to a compound which inhibits both of EGF receptor tyrosine kinase and HER2 tyrosine kinase, and a pharmaceutical composition containing it as an active ingredient.

BACKGROUND ART

Tyrosine kinase is an enzyme which phosphorylates tyrosine residues in substrate proteins, and is known to play an important role in an intracellular signal transduction system concerning cellular differentiation and proliferation. Two receptor tyrosine kinases, EGF receptor (hereinafter EGFR) and HER2 (also called ErbB2 or Neu) are considerably involved in cancer development, and their activities are increased in a variety of human cancers (Non-Patent Literature 1, Non-Patent Literature 2 and Non-Patent Literature 3). It is also shown that these kinases are aberrantly expressed in cancers of brain, lung, stomach, intestine, pancreas, head and neck part, esophagus, bladder, kidney, prostate, ovary, breast, uterine, and thyroid gland (Non-Patent Literature 4 and Patent Literature 1). Therefore, it is thought that an inhibitor of these kinases is useful as an anti-cancer drug which can be efficacious in many types of cancers and has little side effect. As the tyrosine kinase inhibitor, compounds described in Patent Literature 2, Patent Literature 3, Patent Literature 4, Patent Literature 5, Patent Literature 6, Patent Literature 7 are known.

In addition, it is known that cellular transformation due to EGFR is accelerated by additional coexpression of HER2 (Non-Patent Literature 5). Further, concomitant expression of EGFR and HER2 is reported as a marker of poor prognosis in breast, oral cavity and lung cancers (Non-Patent Literature 6). As a drug which inhibits both EGFR and HER2, compounds described in Patent Literature 8 are known.

An anti-cancer agent having an oxime-type substituent at a 4-position of a quinazoline derivative is described in Patent Literature 9 and Patent Literature 10.

[Patent Literature 1] Japanese Patent Application Laid-Open (JP-A) No. 5-208911
[Patent Literature 2] WO 92/20642
[Patent Literature 3] EPA No. 92305703.8
[Patent Literature 4] EPA No. 0566266
[Patent Literature 5] EPA No. 0602851
[Patent Literature 6] EPA No. 0520722
[Patent Literature 7] WO 98/02434
[Patent Literature 8] WO 02/066445
[Patent Literature 9] WO 2004/0691545
[Patent Literature 10] WO 2004/105765
[Non-Patent Literature 1] Cancer Res., 1991, vol. 51, p. 4430-4435
[Non-Patent Literature 2] Cancer Res., 1992, vol. 52, p. 3636-3641
[Non-Patent Literature 3] Cancer Chemother. Pharmacol., 1993, vol. 32, p. 1-19
[Non-Patent Literature 4] Expart. Opin. Invest. Drugs, 1994, vol. 3, No. 6, p. 577-595
[Non-Patent Literature 5] Cell, 1989, vol. 58, p. 287-292
[Non-Patent Literature 6] Clin. Cancer Res., 1999, vol. 5, p. 4164-4174

DISCLOSURE OF INVENTION

Problems to be Solved by the Invention

In comparison with a EGFR or HER2 selective inhibitor, a dual inhibitor for both EGFR and HER2 is expected to be more efficacious, because latter inhibitor would show stronger effect in wider range of disease by synergistic effect of dual inhibition. Therefore, a compound which inhibits both of EGFR and HER2 has been desired.

Means to Solve the Problems

In the above situation, the present inventors intensively studied and, as a result, found out that a quinazoline derivative having a certain substituent at a 6-position has the excellent dual inhibitory activity on an EGF receptor and HER2.

That is, the present invention relates to:
(1) A compound represented by the general formula (I):

[Chemical formula 1]

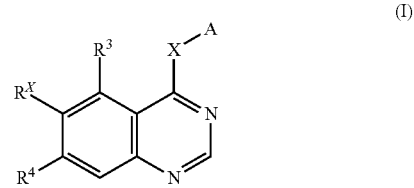

wherein $R^X$ is a group represented by the formula:

[Chemical formula 2]

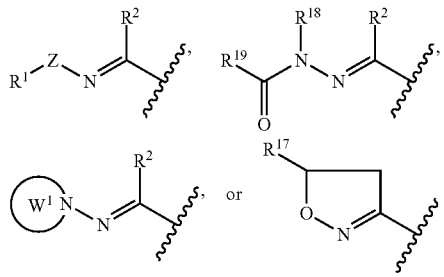

wherein $R^1$ is a hydrogen atom, optionally substituted alkyl, optionally substituted alkenyl, optionally substituted aryl, or an optionally substituted non-aromatic nitrogen-containing heterocyclic group;
Z is —O—, —N($R^{10}$)—, or alkylene which may be intervened with —O— or —N($R^{11}$)—; wherein
$R^{10}$ and $R^{11}$ are independently a hydrogen atom, alkyl, acyl, alkyloxycarbonyl, alkenyloxycarbonyl, or aralkyloxycarbonyl;
$R^2$ is a hydrogen atom, optionally substituted alkyl, optionally substituted alkenyl, optionally substituted alkynyl, optionally substituted cycloalkyl, optionally substituted aryl, or optionally substituted heteroaryl;
$R^{19}$ is optionally substituted alkyl, optionally substituted aryl, optionally substituted heteroaryl, or an optionally substituted non-aromatic heterocyclic group;

$R^{18}$ is a hydrogen atom, optionally substituted alkyl, optionally substituted alkenyl, or optionally substituted alkynyl;
$W^1$ is an optionally substituted non-aromatic nitrogen-containing heterocyclic group or optionally substituted heteroaryl;
$R^{17}$ is a hydrogen atom, optionally substituted alkyl, optionally substituted alkenyl, or an optionally substituted non-aromatic nitrogen-containing heterocyclic group;
$R^3$ and $R^4$ are independently a hydrogen atom, optionally substituted alkyl, optionally substituted alkenyl, optionally substituted alkynyl, optionally substituted alkyloxy, optionally substituted alkenyloxy, halogen, hydroxy, mercapto, or optionally substituted amino;
X is —O—, —S—, —N($R^{12}$)—, or alkylene which may be intervened with —O—, —S—, or —N($R^{13}$)—;
wherein $R^{12}$ and $R^{13}$ are independently a hydrogen atom, alkyl, acyl, alkyloxycarbonyl, alkenyloxycarbonyl, or aralkyloxycarbonyl; and
A is a group represented by the formula:

[Chemical formula 3]

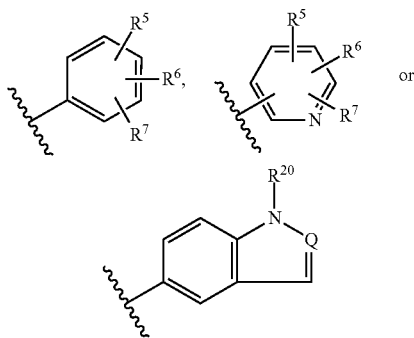

wherein $R^5$ is a hydrogen atom, halogen, optionally substituted alkyloxy, optionally substituted alkenyloxy, optionally substituted alkynyloxy, or a group represented by the formula: —Y—$R^8$ wherein Y is —O—, —S—, —SO$_2$—, or alkylene which may be intervened with —O—, —S—, or —N($R^9$)—, $R^8$ is optionally substituted aryl or optionally substituted heteroaryl;
$R^9$ is a hydrogen atom, alkyl, acyl, alkyloxycarbonyl, alkenyloxycarbonyl, or aralkyloxycarbonyl;
$R^6$ and $R^7$ are independently a hydrogen atom, optionally substituted alkyl, optionally substituted alkenyl, optionally substituted alkynyl, optionally substituted alkyloxy, optionally substituted alkenyloxy, optionally substituted alkynyloxy, halogen, hydroxy, mercapto, cyano, or optionally substituted amino;
$R^{20}$ is optionally substituted alkyl, optionally substituted alkenyl, optionally substituted alkynyl, or a group represented by the formula:

[Chemical formula 4]

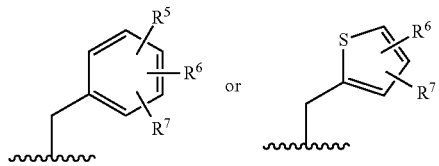

wherein $R^5$, $R^6$ and $R^7$ are as defined above;

Q is N or CH,
its pharmaceutically acceptable salt, or a solvate thereof.
More particularly, the present invention relates to the following (2) to (20).
(2) The compound according to (1), wherein $R^X$ is a group represented by the formula:

[Chemical formula 5]

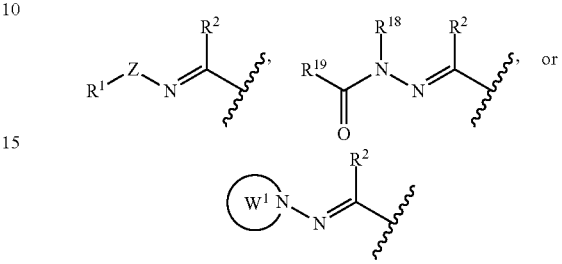

wherein $R^1$, $R^2$, $R^{18}$, $R^{19}$, Z, and $W^1$ are as defined in (1), its pharmaceutically acceptable salt, or a solvate thereof
(3) The compound according to (1) or (2), wherein $R^1$ is alkyl optionally substituted with a substituent selected from substituent group A consisting of hydroxy, heteroaryl, carboxy, optionally substituted amino, optionally substituted non-aromatic nitrogen-containing heterocyclic group, optionally substituted aminocarbonyl, and optionally substituted non-aromatic nitrogen-containing heterocyclic carbonyl, or a non-aromatic nitrogen-containing heterocyclic group optionally substituted with a substituent selected from substituent group B consisting of alkyloxycarbonyl, optionally substituted aminocarbonyl, oxo, amino, carboxy, cyano, cyanoalkyl, hydroxyalkyl, alkylcarbonylamino, alkylsulfonylamino, and aminocarbonylalkyl,
its pharmaceutically acceptable salt, or a solvate thereof.
(4) The compound according to any one of (1) to (3), wherein $R^1$ is alkyl substituted with amino optionally substituted with a substituent selected from substituent group C consisting of alkyl, alkenyl, alkynyl, optionally substituted aryl, araklyl, alkyloxy, hydroxyalkyl, hydroxyalkyoxyalkyl, haloalkyl, aminoalkyl optionally substituted with 1 or 2 alkyls, alkylsulfonyl, alklysulfonylalkyl, alkylcarbonyl optionally substituted with halogen or alkyloxy, alkyloxycarbonyl, optionally substituted cycloalkyl, carboxyalkyl, optionally substituted aminocarbonylalkyl, optionally substituted aminocarbonyloxyalkyl, alkyloxyalkyl, alkylthioalkyl, alkylcarbonylaminoalkyl, alkylsulfonylaminoalkyl, alkylsulfonyl(alkyl)aminoalkyl, alkyloxycarbonylalkyl, alkylthio(hydroxy)alkyl, cycloalkylalkyl, cyanoalkyl, optionally substituted aminoalkylcarbonyl, option ally substituted heteroaryl, heteroarylalkyl, hydroxyalkyloxyalkyl, optionally substituted non-aromatic heterocyclic group, and optionally substituted non-aromatic heterocyclic alkyl,
alkyl substituted with a non-aromatic nitrogen-containing heterocyclic group optionally substituted with a substituent selected from substituent group D consisting of halogen; aryl; hydroxy; oxo; optionally substituted aminocarbonyl; alkyloxycarbonyl; alkyl optionally substituted with a substituent selected from substituent group H consisting of optionally substituted aminocarbonyl, cyano, alkyloxy, alkylsulfonylamino, amino, carboxy, alkyloxycarbonyl, and hydroxy; alkylaminocarbonyl; carboxy; cyano; alkylsulfonyl; alkylcarbonyl; alkenylcarbonyl; alkylsulfonylalkylcarbonyl; alkyloxy, alkylcarbonyl; alkylcarbonylamino; aminocarbonyloxy; a non-aromatic nitrogen-containing heterocyclic group;

and non-aromatic heterocyclic carbonyl, or a non-aromatic nitrogen-containing heterocyclic group optionally substituted with a substituent selected from substituent group B, its pharmaceutically acceptable salt, or a solvate thereof.

(5) The compound according to any one of (1) to (4), wherein Z is —O—, its pharmaceutically acceptable salt, or a solvate thereof.

(6) The compound according to (1) or (2), wherein $R^{19}$ is alkyl optionally substituted with a substituent selected from substituent group A;

aryl optionally substituted with a substituent selected from substituent group I consisting of alkyloxycarbonyl, optionally substituted aminocarbonyl, cyano, cyanoalkyl, hydroxyalkyl, and aminocarbonylalkyl, or heteroaryl optionally substituted with substituent selected from substituent group I;

its pharmaceutically acceptable salt, or a solvate thereof.

(7) The compound according to any one of (1), (2), and (6), wherein $R^{19}$ is alkyl substituted with amino optionally substituted with a substituent selected from a substituent group C; or alkyl substituted with a non-aromatic nitrogen-containing heterocyclic group optionally substituted with a substituent selected from substituent group D; its pharmaceutically acceptable salt, or a solvate thereof.

(8) The compound according to (1) or (2), wherein $W^1$ is a group represented by a non-aromatic nitrogen-containing heterocyclic group optionally substituted with a substituent selected from substituent group J consisting of alkyl, cyanoalkyl, hydroxyalkyl, aminocarbonylalkyl, alkyloxy, alkyloxycarbonyl, optionally substituted aminocarbonyl, and cyano; or a group represented by heteroaryl optionally substituted with a substituent selected from substituent group J;

its pharmaceutically acceptable salt, or a solvate thereof.

(9) The compound according to any one of (1) to (8), wherein $R^2$ is a hydrogen atom, C1-C6 alkyl optionally substituted with halogen, C2-C6 alkenyl, C2-C6 alkynyl, halogen, or phenyl, its pharmaceutically acceptable salt, or a solvate thereof.

(10) The compound according to any one of (1) to (9), wherein $R^2$ is C2-C4 alkynyl, its pharmaceutically acceptable salt, or a solvate thereof

(11) The compound according to any one of (1) to (10), wherein one of $R^3$ and $R^4$ is a hydrogen atom, and the other is a hydrogen atom, optionally substituted alkyloxy or optionally substituted alkenyloxy, its pharmaceutically acceptable salt, or a solvate thereof.

(12) The compound according to any one of (1) to (11), wherein X is —NH—, its pharmaceutically acceptable salt, or a solvate thereof.

(13) The compound according to any one of (1) to (12), wherein A is a group represented by the formula:

[Chemical formula 6]

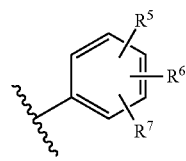

wherein $R^5$ is a hydrogen atom or halogen; $R^6$ is halogen or alkynyl; and $R^7$ is a hydrogen atom, its pharmaceutically acceptable salt, or a solvate thereof.

(14) The compound according to any one of (1) to (12), wherein A is a group represented by the formula:

[Chemical formula 7]

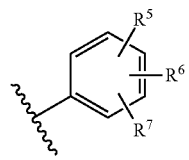

wherein $R^5$ is alkyloxy optionally substituted with a substituent selected from substituent group E consisting of carboxy, alkoxyooxycarbonyl, cycloalkyl, and optionally substituted aminocarbonyl;

alkenyloxy optionally substituted with a substituent selected from substituent group E; or alkynyloxy optionally substituted with a substituent selected from substituent group E;

$R^6$ is optionally substituted alkynyl, optionally substituted alkyloxy, or halogen; and $R^7$ is a hydrogen atom, its pharmaceutically acceptable salt, or a solvate thereof.

(15) The compound according to any one of (1) to (12), wherein A is a group represented by the formula:

[Chemical formula 8]

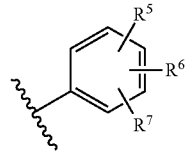

wherein $R^5$ is a group represented by the formula: —Y—$R^8$ wherein Y is alkylene which may be intervened with —O—;

$R^8$ is phenyl optionally substituted with substituent selected from a substituent group F consisting of halogen, carboxy, alkyl, haloalkyl, hydroxyalkyl, alkyloxy, alkyloxycarbonyl, and optionally substituted amino; pyridyl optionally substituted with a substituent selected from substituent group F;

furyl optionally substituted with a substituent selected from substituent group F;

thienyl optionally substituted with a substituent selected from substituent group F;

thiazolyl optionally substituted with a substituent selected from substituent group F; or oxazolyl optionally substituted with a substituent selected from substituent group F;

$R^6$ is optionally substituted alkynyl, optionally substituted alkyloxy, or halogen; and $R^7$ is a hydrogen atom.

its pharmaceutically acceptable salt, or a solvate thereof.

(16) The compound according to (1), wherein $R^X$ is a group represented by the formula:

[Chemical formula 9]

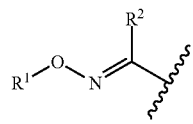

wherein $R^1$ is alkyl substituted with amino optionally substituted with alkyl, hydroxyalkyl, alkylcarbonylaminoalkyl or a non-aromatic heterocycle; alkyl substituted with a non-aromatic nitrogen-containing heterocycle optionally substituted with alkyl, hydroxyalkyl or alkylcarbonylamino; or a non-aromatic nitrogen-containing heterocyclic group substituted with hydroxyalkyl; and $R^2$ is C2-C4 alkynyl;

$R^3$ and $R^4$ are both a hydrogen atom;

X is —NH— and

A is a group represented by the formula:

[Chemical formula 10]

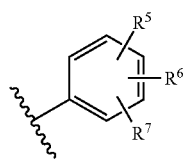

wherein $R^5$ is a group represented by the formula: —Y—R, wherein Y is C1-C3 alkylene which may be intervened with —O—;

$R^8$ is phenyl optionally substituted with halogen, or pyridyl optionally substituted with halogen;

$R^6$ is halogen; and $R^7$ is a hydrogen atom, its pharmaceutically acceptable salt, or a solvate thereof.

(17) A pharmaceutical composition containing the compound as defined in any one of (1) to (16) as an active ingredient.

(18) A pharmaceutical composition useful for treating cancer containing the compound as defined in any one of (1) to (16) as an active ingredient.

(19) A method for preventing and/or treating a cancer, comprising administering the compound according to any one of (1) to (16), its pharmaceutically acceptable salt or a solvate thereof.

(20) Use of the compound according to any one of (1) to (16), its pharmaceutically acceptable solvate or a salt for producing a composition for preventing and/or treating a cancer.

In addition, the present invention includes the following Inventions as other aspect.

(I) A compound represented by the general formula (I):

[Chemical formula 11]

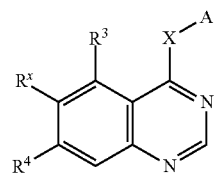

wherein $R^X$ is a group represented by the formula:

[Chemical formula 12]

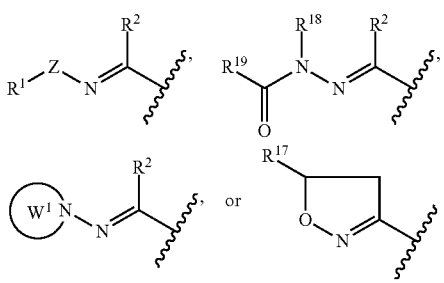

wherein $R^1$ is a hydrogen atom, optionally substituted alkyl, optionally substituted alkenyl, or an optionally substituted non-aromatic nitrogen-containing heterocyclic group;

Z is —O— or —N($R^{10}$)—, or alkylene which may be intervened with —O— or —N($R^{11}$)—;

$R^{10}$ and $R^{11}$ are independently a hydrogen atom, alkyl, acyl, alkyloxycarbonyl, alkenyloxycarbonyl, or aralkyloxycarbonyl;

$R^2$ is a hydrogen atom, optionally substituted alkyl, optionally substituted alkenyl, optionally substituted alkynyl, optionally substituted aryl, or optionally substituted heteroaryl;

$R^{19}$ is optionally substituted alkyl, optionally substituted aryl, optionally substituted heteroaryl, or an optionally substituted non-aromatic heterocyclic group;

$R^{18}$ is a hydrogen atom, optionally substituted alkyl, optionally substituted alkenyl, or optionally substituted alkylnyl;

$W^1$ is an optionally substituted non-aromatic nitrogen-containing heterocyclic group or optionally substituted heteroaryl;

$R^{17}$ is a hydrogen group, optionally substituted alkyl, optionally substituted alkenyl, or optionally substituted non-aromatic nitrogen-containing heterocyclic group;

$R^3$ and $R^4$ are independently a hydrogen atom, optionally substituted alkyl, optionally substituted alkenyl, optionally substituted alkynyl, optionally substituted alkyloxy, optionally substituted alkenyloxy halogen, hydroxy mercapto, or optionally substituted amino;

X is —O—, —S—, —N($R^{12}$)—, or alkylene which may be intervened with —O—, —S—, or —N($R^{13}$)—; wherein $R^{12}$ and $R^{13}$ are independently a hydrogen atom, alkyl, acyl, alkyloxycarbonyl, alkenyloxycarbonyl, or aralkyloxycarbonyl; and A is a group represented by the formula:

[Chemical formula 13]

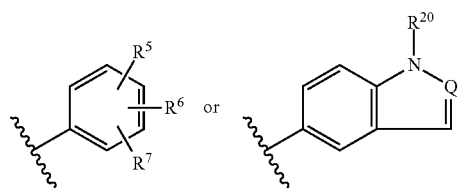

wherein $R^5$ is a hydrogen atom, halogen, optionally substituted alkyloxy, optionally substituted alkenyloxy, optionally substituted alkynyloxy, or a group represented by the formula: —Y—$R^8$ wherein Y is —O—, —S—, or alkylene which may be intervened with —N($R^9$)—; $R^8$ is optionally substituted aryl, or optionally substituted heteroaryl; $R^9$ is a hydrogen atom, alkyl, acyl, alkyloxycarbonyl, alkenyloxycarbonyl, or aralkyloxycarbonyl;

$R^6$ and $R^7$ are independently a hydrogen atom, optionally substituted alkyl, optionally substituted alkenyl, optionally substituted alkynyl, optionally substituted alkyloxy, optionally substituted alkenyloxy, optionally substituted alkynyloxy, halogen, hydroxy, mercapto, or optionally substituted amino;

$R^{20}$ is optionally substituted alkyl, optionally substituted alkenyl, optionally substituted alkynyl, or a group represented by the formula:

[Chemical formula 14]

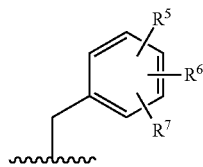

wherein $R^5$, $R^6$ and $R^7$ are as defined above:
Q is N or $CH_2$,
its pharmaceutically acceptable salt, or a solvate thereof.

More particularly, the present invention relates to the following (II) to (XV).

(II) A compound according to (I), wherein $R^X$ is a group represented by the formula:

[Chemical formula 15]

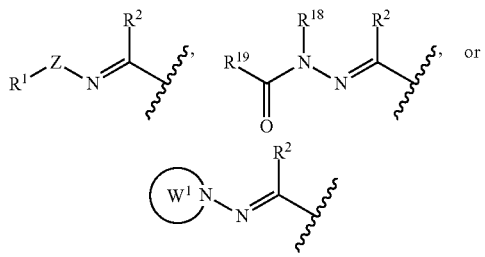

wherein $R^1$, $R^2$, $R^{18}$, $R^{19}$, Z, and $W^1$ are as defined in (I), its pharmaceutically acceptable salt, or a solvate thereof.
(III) The compound according to (I) or (II), wherein $R^1$ is alkyl optionally substituted with a substituent selected from substituent group A' consisting of hydroxy, optionally substituted amino, optionally substituted non-aromatic nitrogen-containing heterocyclic group, optionally substituted aminocarbonyl, and optionally substituted non-aromatic nitrogen-containing heterocyclic carbonyl, or
a non-aromatic nitrogen-containing heterocyclic group optionally substituted with a substituent selected from substituent group B' consisting of alkyloxycarbonyl, optionally substituted aminocarbonyl, cyano, cyanoalkyl, hydroxyalkyl, and aminocarbonylalkyl,
its pharmaceutically acceptable salt, or a solvate thereof.
(IV) The compound according to any one of (I) to (III), wherein $R^1$ is alkyl optionally substituted with amino substituted with a substituent selected from substituent group C' consisting of alkyl, alkynyl, alkylsulfonylalkyl, hydroxyalkyl, alkylcarbonyl optionally substituted with halogen, alkyloxycarbonyl, cycloalkyl, optionally substituted with aminocarbonylalkyl, optionally substituted aminocarbonyloxyalkyl, alkyloxyalkyl, cycloalkylalkyl, cyanoalkyl, and optionally substituted aminoalkylcarbonyl, or alkyl substituted with a non-aromatic nitrogen-containing heterocyclic group optionally substituted with a substituent selected from a substituent group D' consisting of hydroxy; oxo; optionally substituted aminocarbonyl; alkyloxycarbonyl; alkyl optionally substituted with a substituent selected from substituent group H' consisting of optionally substituted aminocarbonyl, cyano, alkyloxy, and hydroxy; alkylaminocarbonyl; cyano; alkylsulfonyl; alkylcarbonyl; alkenylcarbonyl; alkylsulfonylalkylcarbonyl; alkyloxyalkylcarbonyl; alkylcabonylamino; and non-aromatic heterocyclic carbonyl,
its pharmaceutically acceptable salt, or a solvate thereof.
(V) The compound according to (I) or (II), wherein $R^{19}$ is alkyl optionally substituted with a substituent selected from substituent group A', aryl optionally substituted with a substituent selected from substituent group I' consisting of alkyloxycarbonyl, optionally substituted aminocarbonyl, cyano, cyanoalkyl, hydroxyalkyl, and aminocarbonylalkyl, or
heteroaryl substituted with a substituent selected from substituent group I',
its pharmaceutically acceptable salt, or a solvate thereof.
(VI) The compound according to any one of (I), (II) and (V), wherein $R^{19}$ is alkyl substituted with amino optionally substituted with a substituent selected from substituent group C', or
alkyl substituted with a non-aromatic nitrogen-containing heterocyclic group optionally substituted with a substituent selected from substituent group D',
its pharmaceutically acceptable salt, or a solvate thereof.
(VII) The compound according to (I) or (II), wherein $W^1$ is a group represented by a non-aromatic nitrogen-containing heterocyclic group optionally substituted with a substituent selected from substituent group J' consisting of alkyl, cyanoalkyl, hydroxyalkyl, aminocarbonylalkyl, alkyloxy, alkyloxycarbonyl, optionally substituted aminocarbonyl, and cyano, or a group represented by heteroaryl optionally substituted with a substituent selected from substituent group J',
its pharmaceutically acceptable salt, or a solvate thereof.
(VIII) The compound according to any one of (1) to (VII), wherein $R^2$ is a hydrogen atom, C1-C6 alkyl optionally substituted halogen, C2-C6 alkenyl, C2-C6 alkynyl, halogen, or phenyl,
its pharmaceutically acceptable salt, or a solvate thereof.
(IX) The compound according to any one of (I) to (VIII), wherein one of $R^3$ and $R^4$ is a hydrogen atom, and the other is a hydrogen atom, optionally substituted alkyloxy or optionally substituted alkenyloxy,
its pharmaceutically acceptable salt, or a solvate thereof.

(X) The compound according to any one of (I) to (IX), wherein X is —NH—,
its pharmaceutically acceptable salt, or a solvate thereof.
(XI) The compound according to any one of (I) to (IX), wherein A is a group represented by the formula:

[Chemical formula 16]

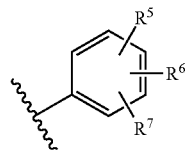

wherein $R^5$ is a hydrogen atom or halogen; $R^6$ is halogen or alkynyl; and $R^7$ is a hydrogen,
its pharmaceutically acceptable salt, or a solvate thereof.
(XII) The compound according to any one of (I) to (IX), wherein A is a group represented by the formula:

[Chemical formula 17]

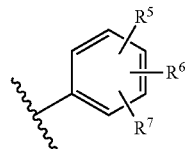

wherein R is alkyloxy optionally substituted with a substituent selected from substituent group E' consisting of carboxy, alkyloxycarbonyl, cycloalkyl, and optionally substituted aminocarbonyl,
alkenyloxy optionally substituted with a substituent selected from substituent group E', or
alkynyloxy optionally substituted with a substituent selected from substituent group E';
$R^6$ is optionally substituted alkynyl, optionally substituted alkyloxy, or halogen; and
$R^7$ is a hydrogen atom,
its pharmaceutically acceptable salt, or a solvate thereof.
(XIII) The compound according to any one of (I) to (IX), wherein A is a group represented by the formula:

[Chemical formula 18]

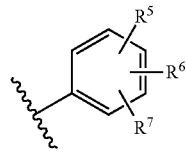

wherein $R^5$ is a group represented by the formula: —Y—$R^8$
wherein Y is alkylene which may be intervened with —O—;
$R^8$ is phenyl optionally substituted with a substituent selected from substituent group F' consisting of halogen, carboxy, alkyl, haloalkyl, hydroxyalkyl, alkyloxy, alkyloxycarbonyl, and optionally substituted amino; pyridyl optionally substituted with a substituent selected from substituent group F';
furyl optionally substituted with a substituent selected from a substituent group F';
thienyl optionally substituted with a substituent selected from a substituent group F';
thiazolyl optionally substituted with a substituent selected from a substituent group F'; or
oxazolyl optionally substituted with a substituent selected from a substituent group F';
$R^6$ is optionally substituted alkynyl, optionally substituted alkyloxy, or halogen; and
$R^7$ is a hydrogen atom,
its pharmaceutically acceptable salt, or a solvate thereof.
(XIV) A pharmaceutical composition containing the compound as defined in any one of (I) to (XIII) as an active ingredient.
(XV) A pharmaceutical composition useful for treating cancer containing the compound as defined in any one of (I) to (XIII) as an active ingredient.
(XVI) A method for preventing and/or treating a cancer, comprising administering the compound as defined in any one of (I) to (XIII), its pharmaceutically acceptable salt, or a solvate thereof.
(XVII) Use of the compound as defined in any one of (I) to (XIII), its pharmaceutically acceptable salt, or a solvate thereof for producing a composition for preventing and/or a cancer.

A still other aspect of the present invention includes the following inventions.
(i) A compound represented by the general formula (I'):

[Chemical formula 19]

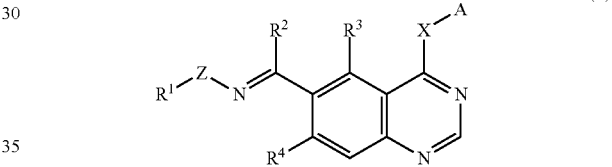

(I')

wherein $R^1$ is a hydrogen atom, optionally substituted alkyl, optionally substituted alkenyl, or optionally substituted non-aromatic nitrogen-containing heterocyclic group;
Z is —O— or —N($R^{10}$)—, or alkylene which may be intervened with —O— or —N($R^{11}$)—;
$R^{10}$ and $R^{11}$ are independently a hydrogen atom, alkyl, acyl, alkyloxycarbonyl, alkenyloxycarbonyl, or aralkyloxycarbonyl;
$R^2$ is a hydrogen atom, optionally substituted alkyl, alkenyl, alkynyl, optionally substituted aryl, or optionally substituted heteroaryl, or a group represented by —C($R^2$)=N—Z—$R^1$ is a group represented by the formula:

[Chemical formula 20]

wherein $R^{17}$ is a hydrogen atom, optionally substituted alkyl, optionally substituted alkenyl, or an optionally substituted non-aromatic nitrogen-containing heterocyclic group;
$R^3$ and $R^4$ are independently a hydrogen atom, optionally substituted alkyl, optionally substituted alkenyl, optionally substituted alkynyl, optionally substituted alkyloxy, optionally substituted alkenyloxy, halogen, hydroxy, mercapto or optionally substituted amino;

X is —O—, —S—, or —N(R$^{12}$)—, or alkylene which may be intervened with —O—, —S—, or —N(R$^{13}$)—; wherein R$^{12}$ and R$^{13}$ are independently a hydrogen atom, alkyl, acyl, alkyloxycarbonyl, alkenyloxycarbonyl, or aralkyloxycarbonyl; and A is a group represented by the formula:

[Chemical formula 21]

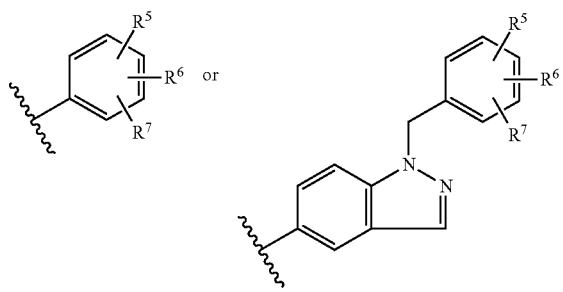

wherein R$^5$ is a hydrogen atom, halogen, optionally substituted alkyloxy, optionally substituted alkenyloxy, optionally substituted alkynyloxy, or a group represented by the formula: —Y—R$^8$ wherein Y is —O—, —S—, or alkylene which may be intervened with —N(R$^9$)—; R$^8$ is optionally substituted aryl, or optionally substituted heteroaryl; R$^9$ is a hydrogen atom, alkyl, acyl, alkyloxycarbonyl, alkenyloxycarbonyl, or aralkyloxycarbonyl;

R$^6$ and R$^7$ are independently a hydrogen atom, optionally substituted alkyl, optionally substituted alkenyl, optionally substituted alkynyl, optionally substituted alkyloxy, optionally substituted alkenyloxy, optionally substituted alkynyloxy, halogen, hydroxy, mercapto, or optionally substituted amino, its pharmaceutically acceptable salt, or a solvate thereof.

(ii) The compound according to (i), wherein R$^1$ is alkyl optionally substituted with a substituent selected from substituent group A" consisting of optionally substituted amino and optionally substituted non-aromatic nitrogen-containing heterocyclic group, or a non-aromatic nitrogen-containing heterocyclic group optionally substituted with a substituent selected from substituent group B" consisting of alkyloxycarbonyl, optionally substituted aminocarbonyl, and cyano, its pharmaceutically acceptable salt, or a solvate thereof.

(iii) The compound according to (i) or (ii), wherein R$^1$ is alkyl substituted with amino optionally substituted with a substituent selected from substituent group C" consisting of alkyl, alkylsulfonylalkyl, alkylcarbonyl optionally substituted with halogen, alkyloxycarbonyl, cycloalkyl, optionally substituted aminocarbonylalkyl, optionally substituted aminocarbonyloxyalkyl, alkyloxyalkyl, and optionally substituted aminoalkylcarbonyl, or alkyl substituted with a non-aromatic nitrogen-containing heterocyclic group optionally substituted with a substituent selected from substituent group D" consisting of oxo, optionally substituted aminocarbonyl, alkyloxycarbonyl, alkyl optionally substituted with cyano or alkyloxy, cyano, alkylsulfonyl, alkylcarbonyl, alkenylcarbonyl, and alkylsulfonylalkylcarbonyl, its pharmaceutically acceptable salt, or a solvate thereof.

(iv) The compound according to any one of (i) to (iii), wherein one of R$^3$ and R$^4$ is a hydrogen atom, and the other is a hydrogen atom, optionally substituted alkyloxy or optionally substituted alkenyloxy, its pharmaceutically acceptable salt, or a solvate thereof.

(v) The compound according to any one of (i) to (iv), wherein X is —NH—, its pharmaceutically acceptable salt, or a solvate thereof.

(vi) The compound according to any one of (i) to (v), wherein A is a group represented by the formula:

[Chemical formula 22]

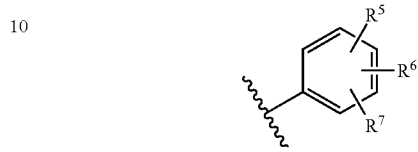

wherein R$^5$ is a hydrogen atom or halogen; R$^6$ is halogen or alkynyl; and R$^7$ is a hydrogen atom, its pharmaceutically acceptable salt, or a solvate thereof.

(vii) The compound according to any one of (i) to (vi), wherein A is a group represented by the formula:

[Chemical formula 23]

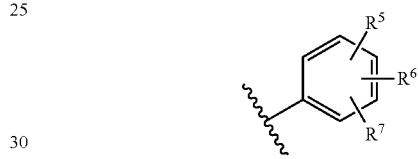

wherein R$^5$ is alkyloxy optionally substituted with a substituent selected from substituent group E" consisting of carboxy, alkyloxycarbonyl, and optionally substituted aminocarbonyl, alkenyloxy optionally substituted with a substituent selected from a substituent group E", or alkynyloxy optionally substituted with a substituent selected from a substituent group E";

R$^6$ is optionally substituted alkynyl, optionally substituted alkyloxy, or halogen; and R$^7$ is a hydrogen atom, its pharmaceutically acceptable salt, or a solvate thereof.

(viii) The compound according to any one of (i) to (vii), wherein A is a group represented by the formula:

[Chemical formula 24]

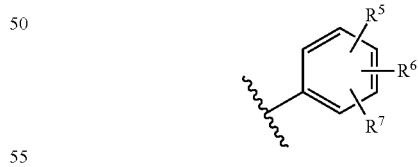

wherein R$^5$ is a group represented by the formula: —Y—R$^8$ wherein Y is alkylene which may be intervened with —O—;

R$^8$ is phenyl optionally substituted with a substituent selected from substituent group F" consisting of halogen, carboxy, alkyl, haloalkyl, hydroxyalkyl, alkyloxy, alkyloxycarbonyl, and optionally substituted amino; pyridyl optionally substituted with a substituent selected from a substituent group F"; furyl optionally substituted with a substituent selected from a substituent group F";

thienyl optionally substituted with a substituent selected from a substituent group F";

thiazolyl optionally substituted with a substituent selected from a substituent group F"; or oxazolyl optionally substituted with a substituent selected from a substituent group F";

$R^6$ is optionally substituted alkynyl, optionally substituted alkyloxy, or halogen; and R' is a hydrogen atom, its pharmaceutically acceptable salt, or a solvate thereof.

(ix) A pharmaceutical composition containing the compound as defined in any one of (i) to (viii) as an active ingredient.

(x) A pharmaceutical composition useful for treating cancer containing the compound as defined in any one of (i) to (viii) as an active ingredient.

(xi) A method for preventing and/or treating a cancer, comprising administering the compound as defined in any one of (i) to (viii), its pharmaceutically acceptable salt, or a solvate thereof.

(xii) Use of the compound as defined in any one of (i) to (viii), its pharmaceutically acceptable salt, or a solvate thereof for producing a composition for preventing and/or treating a cancer.

As used herein, the "halogen" means fluorine, chlorine, bromine, or iodine. Fluorine, chorine, and bromine are preferable.

As used herein, the "alkyl" which is used alone or in combination with other term includes a straight or branched monovalent hydrocarbon group having 1 to 10 carbon atom(s). Examples include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, n-nonanyl, and n-decanyl. Preferable examples include C1-C10 alkyl. Further preferable examples include C1-C6 alkyl. Most preferable examples include C1-C4 alkyl.

As used herein, the term "haloalkyl" which is used alone or in combination with other term includes the "alkyl" which is substituted with the "halogen" at 1 to 8 places, preferably 1 to 5 places. Examples include trifluoromethyl, trichloromethyl, difluoroethyl, trifluoroethyl, dichloroethyl, and trichloroethyl. Preferable examples include C1-C6 alkyl which is substituted with the "halogen" at 1 to 5 places. Particularly, C1-C3 alkyl substituted with the "halogen" at 1 to 3 places is preferable. Most preferable examples include trifluoromethyl.

As used herein, the "alkylsulfonyl" includes methylsulfonyl, ethylsulfony, and propylsulfonyl. Preferable examples include C1-C6 alkylsulfonyl. Particularly, C1-C3 alkylsulfonyl is preferable.

As used herein, examples of the "alkylsulfonylalkyl" include methylsulfonylmethyl, methylsulformylethyl, methylsulfonylpropyl, methylsulfonylbutyl, and methylsulfonylpropyl. Preferable examples include C1-C6 alkylsulfonyl C1-C6 alkyl. Particularly, C1-C8 alkylsulfonyl C1-C4 alkyl is preferable.

As used herein, examples of the "alkyloxy" include methyloxy, ethyloxy, n-propyloxy, isopropyloxy, n-butyloxy, isobutyloxy, sec-butyloxy, tert-butyloxy, n-pentyloxy, n-hexyloxy, n-heptyloxy, n octyloxy, n-nonanyloxy, and n-decanyloxy. Preferable examples include C1-C6 alkyloxy. Particularly, C1-C8 alkyloxy is preferable.

As used herein, examples of the "alkyloxyalkyl" include methyloxymethyl, methyloxyethyl, methyloxypropyl, ethyoxymethyl, ethyloxyethyl, and ethyloxypropyl. Preferable examples include C1-C6 alkyloxy C1-C6 alkyl. Particularly, C1-C3 alkyloxy C1-C4 alkyl is preferable.

As used herein, examples of the "alkyloxycarbonyl" include methyloxycarbonyl, ethyloxycarbonyl, n-propyloxycarbonyl, isopropyloxycarbonyl, n-butyloxycarbonyl, t-butyloxycarbonyl, and n-pentyloxycarbonyl. Preferable examples include C1-C6 alkyloxycarbonyl. Particularly, C1-C3 alkyloxycarbonyl is preferable.

As used herein, examples of the "alkylcarbonyl" include methylcarbonyl, ethylcarbonyl, n-propylcarbonyl, isopropylcarbonyl, n-butylcarbonyl t-butylcarbonyl, and n-pentylcarbonyl. Preferable examples include C1-C6 alkylcarbonyl. Particularly, C1-C3 alkylcarbonyl is preferable.

As used herein, examples of the "haloalkyloxy" include trifluoromethyloxy, trichloromethyloxy, difluoroethyloxy, trifluoroethyloxy, dichloroethyloxy, and trichloroethyloxy. Preferable examples include halo C1-C6 alkyloxy. Particularly, halo C1-C3 alkyloxy is preferable. Most preferable examples include trifluoromethyloxy.

As used herein, examples of the "aminocarbonylalkyl" include aminocarbonylmethyl, aminocarbonylethyl, aminocarbonylpropyl, and aminocarbonylbutyl. Preferable examples include aminocarbonyl C1-C6 alkyl. Particularly, aminocarbonyl C1-C3 alkyl is preferable.

As used herein, examples of the "aminocarbonylakyloxy" include aminocarbonylmethyloxy, aminocarbonylethyloxy, aminocarbonylpropyloxy, and aminocarbonylbutyloxy. Preferable examples include aminocarbonyl C1-C6 alkyloxy. Particularly, aminocarbonyl C1-C3 alkyloxy is preferable.

As used herein, examples of the "hydroxyalkyl" include hydroxymethyl, hydroxyethyl, hydroxypropyl, and hydroxybutyl. Preferable examples include hydroxy C1-C6 alkyl. Particularly, hydroxy C1-C3 alkyl is preferable.

As used herein, examples of the "alkylthio" include methylthio, ethylthio, propylthio, and butylthio. Preferable examples include C1-C6 alkylthio. Particularly, C1-C3 alkylthio is preferable.

As used herein, the "alkylene" which is used alone or in combination with other term includes a straight or branched divalent hydrocarbon group having 1 to 4 carbon atom(s). Examples include methylene, ethylene, propylene, and butylene. Preferable examples include C1-C3 alkylene. Particularly, C1-C2 alkylene is preferable.

The "alkylene which may be intervened with —O— or —N($R^{11}$)—" in Z includes —$CH_2$—O—, —O—$CH_2$—, $CH_2$—N($R^{11}$)—, —N($R^{13}$)$CH_2$—, —($CH_2$)$_2$—O—, —O—($CH_2$)$_2$—, —($CH_2$)$_2$—N($R^{11}$)—, and —N($R^{11}$)—($CH$)$_2$—. Particularly, —O—$CH_2$—, —N($R^{11}$)—$CH_2$—, —O—($CH_2$)$_2$—, and —N($R^{11}$)—($CH_2$)$_2$— are preferable.

The "alkylene which may be intervened with —O—, —S—, or —N($R^{12}$)—" in X includes —$CH_2$—O—, —O—$CH_2$—, —$CH_2$—S—, —S—$CH_2$—, $CH_2$—N($R^{12}$)—, —N($R^{12}$)—$CH_2$—, —($CH_2$)$_2$—O—, —O—($CH_2$)$_2$—, —($CH_2$)$_2$—S—, —S—($CH_2$)$_2$—, —($CH_2$)$_2$—N($R^{12}$)—, and —N($R^{12}$)—($CH_2$)$_2$—.

The "alkylene which may be intervened with —O—, —S—, or —N($R^9$)—" in Y includes —$CH_2$—O—, —O—$CH_2$—$CH_2$S—, —S—$CH_2$—, —$CH_2$—N($R^9$)—, —N($R^9$)—$CH_2$—, —($CH$)$_2$—O—, —O($CH_2$)$_2$—, —($CH_2$)$_2$—S—, —S—($CH_2$)$_2$—, —($CH_2$)N($R^9$)—, N($R^9$)($CH_2$)$_2$—, and —O—$CH(CH_3)$—.

As used herein, the "cycloalkyl" which is used alone or in combination with other term includes cycloalkyl having 3 to 8 carbon atom(s). Examples include cyclopropyl, cyclobutyl, cyclopentyl, cyclohexyl, cycloheptyl, and cyclooctyl. Preferable examples include C5-C6 cycloalkyl.

As used herein, the "alkenyl" includes a straight or branched monovalent hydrocarbon having 2 to 8 carbon atom(s) and having 1 or 2 or more double bond(s). The alkenyl may have a triple bond in a chain. Examples include vinyl, allyl, 1-propenyl, 2-propenyl, and various butenyl isomers. Preferable examples include C2-C6 alkenyl. Further preferable examples include C2-C4 alkenyl.

As used herein, examples of the "alkenyloxy" include vinyloxy, allyloxy, 1-propenyloxy, 2-propenyloxy, and various butenyloxys. Preferable examples include C2-C6 alkenyloxy. Particularly, C2-C4 alkenyloxy is preferable.

As used herein, examples of the "alkenyloxycarbonyl" include vinyloxycarbonyl, allyloxycarbonyl, 1-propenyloxycarbonyl, 2-propenyloxycarbonyl, and various butenyloxycarbonyls. Preferable examples include C2-C6 alkenyloxycarbonyl. Particularly, C2-C4 alkenyloxycarbonyl is preferable.

As used herein, the "alkynyl" includes a straight or branched monovalent hydrocarbon group having 2 to 8 carbon atom(s) and having 1 or 2 or more triple bond(s). Examples include ethylnyl, 1-propynyl, 2-propynyl, 1-butynyl, 2-butynyl, 3-butynyl, 1-pentynyl, 2-pentynyl, and various pentynyl isomers. Preferable examples include C2-C6 alkynyl. Further preferable examples include C2-C4 alkynyl.

As used herein, examples of the "alkynyloxy" include ethynyloxy, propynyloxy, butynyloxy, and pentynyloxy. Preferable examples include C2-C6 alkynyloxy. Particularly, C2-C4 alkynyloxy is preferable.

As used herein, the "aryl" which is used alone or in combination with other term includes a monocyclic or fused cyclic aromatic hydrocarbon. Examples include phenyl, 1-naphthyl, 2-naphthyl, and anthryl. Phenyl, 1-naphthyl, and 2-naphthyl are preferable. Particularly, phenyl is preferable.

As used herein, the "aralkyl" includes the "alkyl" substituted with one or two or more of the "aryl", and these can be substituted at all possible positions. Examples include benzyl, phenylethyl (e.g. 2-phenylethyl, etc.), phenylpropyl (e.g. 3-phenylpropyl, etc.), naphthylmethyl (e.g. 1-naphthylmethyl, 2-naphthylmethyl, etc.), and anthrylmethyl (e.g. 9-anthrylmethyl, etc.). Preferable examples include benzyl, and phenylethyl.

As used herein, examples of the "aralkyloxy" include benzyloxy, phenylethyloxy (e.g. 2-phenylethyloxy, etc.), phenylpropyloxy (e.g. 3-phenylpropyloxy, etc.), naphthylmethyloxy (e.g. 1-naphthylmethyloxy, 2-naphthylmethyloxy, etc.), anthrylmethyloxy (e.g. 9-anthrylmethyloxy, etc.). Preferable examples include benzyloxy, and phenylethyloxy.

As used herein, examples of the "aralkyloxycarbonyl" include benzyloxycarbonyl, phenylethyloxycarbonyl (e.g. 2-phenylethyloxycarbonyl, etc.), phenylpropyloxycarbonyl (e.g. 3-phenylpropyloxycarbonyl, etc.), naphthylmethyloxycarbonyl (e.g. 1-naphthylmethyl, 2-naphthylmethyloxycarbonyl, etc.), anthrylmethyloxycarbonyl (e.g. 9-anthrylmethyloxycarbonyl, etc.). Preferable examples include benzyloxycarbonyl, and phenylethyloxycarbonyl.

As used herein, the term "non-aromatic heterocyclic group" which is used alone or in combination with other term includes a non-aromatic 5- to 7-membered ring containing one or more arbitrary selected an oxygen atom, a sulfur atom or a nitrogen atom in a ring, and a group derived from a ring in which other one or more "non-aromatic heterocyclic groups" or "heteroaryls" is fused thereto. Examples include pyrrolidinyl (e.g. 1-pyrrolidinyl, 2-pyrrolidinyl), pyrrolinyl (e.g. 3-pyrrolinyl), imidazolidinyl (e.g. 2-imidazolidinyl), imidazolinyl (e.g. imidazolinyl), pyrazolidinyl (e.g. 1-pyrazolidinyl, 2-pyrazolidinyl), pyrazolinyl (e.g. pyrazolinyl), piperidyl (e.g. piperidino, 2-piperidyl), piperazinyl (e.g. 1-piperazinyl, 2-piperazinyl), indolinyl (e.g. 1-indolinyl), isoindolinyl (e.g. isoindolinyl), morpholinyl (e.g. morpholino, 2-morphohnyl, 3-morpholinyl), tetrahydrofuranyl, dihydropyranyl, tetrahydropyranyl, dioxolanyl, tetrahydrothienyl, dihydrothiopyranyl, tetrahydrothiofuranyl, decahydroisoquinolinyl, azepinyl, oxepinyl, dihydrooxepinyl, tetrahydrooxepinyl, oxepanyl, 4,5,6,7-tetrahydrothieno[3,2]pyridyl, 2-oxa-5-aza-bicyclo[2.2.1]hepta-5-yl, and hexahydropyrazyl[2.1-b][1,3]ozadin-8-yl.

As the "non-aromatic heterocyclic group" in $R^{19}$, pyrrodilinyl (e.g. 1-pyrrodilinyl, 2-pyrrolidinyl), piperidyl (e.g. piperidino, 2-piperidyl), piperazinyl (e.g. 1-piperazinyl), morpholinyl (e.g. morpholino, 3-morpholinyl), and tetrahydrofuranyl are preferable.

As used herein, a term "non-aromatic nitrogen-containing heterocyclic group" which is used alone, or in combination with other term includes a non-aromatic 4- to 7-membered ring containing at least one nitrogen atom in a ring and, further optionally, containing one or more atoms arbitrarily selected from an oxygen atom and a sulfur atom in a ring, or a group derived from a ring in which two or more of them are fused. Examples include azetidinyl (e.g. 1-azetidinyl, 2-azetidinyl, 3-azetidinyl), pyrrolidinyl (e.g. 1-pyrrolidinyl, 2-pyrrolidinyl, 3-pyrrolidinyl), pyrrolinyl (e.g. 3-pyrrolinyl), imidazolidinyl (e.g. 2-imidazolidinyl), imidazolinyl (e.g. imidazolinyl), pyrazolidinyl (e.g. 1-pyrazolidinyl, 2-pyrazolidinyl), pyrazolinyl (e.g. pyrazolinyl), piperidyl (e.g. piperidino, 2-piperidyl, 3-piperidyl, 4-piperidyl), piperazinyl (e.g. 1-piperazinyl, 2-piperazinyl), indolinyl (e.g. 1-indolinyl), isoindolinyl (e.g. isoindolinyl), morpholinyl (e.g. morpholino, 2-morpholinyl, 3-morpholinyl), 1,4-thiazinyl (e.g. 1,4-thiazin-1-yl, 1,4-thiazin-2-yl), thiomorpholinyl (e.g. 1-thiomorpholinyl, 2-thiomorpholinyl), decahydroisoquinolyl (e.g. 2-decahydroisoquinolyl), azepinyl (e.g. 1-azepinyl), diazepinyl, 4,5,6,7-tetrahydrothieno[3,2]pyridyl, 2-oxa-5-aza-bicyclo[2.2.1]hept-5-yl, and hexahydropyrazyl[2.1-b][1,3]oxazin-3-yl.

As the "non-aromatic nitrogen-containing heterocyclic group" in $R^1$ and $R^{17}$, azetidinyl (e.g. 1-azetidinyl, 2-azetidinyl, 3-azetidinyl), pyrrolidinyl (e.g. 1-pyrrolidinyl, 2-pyrrolidinyl, 3-pyrrolidinyl), and piperidyl (e.g. piperidino, 2-piperidyl, 3-piperidyl, 4-piperidyl) are preferable.

As the "non-aromatic nitrogen-containing heterocyclic group" in $W^1$, azetidinyl (e.g. 1-azetidinyl, 2-azetidinyl, 3-azetidinyl), pyrrolidinyl (e.g. 1-pyrrolidinyl, 2-pyrrolidinyl, 3-pyrrolidinyl), piperidyl (e.g. piperidino, 2-piperidyl, 3-piperidyl, 4-piperidyl), piperazinyl (e.g. 1-piperazinyl), and morpholinyl (e.g. morpholino, 3-morpholinyl) are preferable.

As the "non-aromatic nitrogen-containing heterocyclic group" in the substituent group A, pyrrolidinyl (e.g. 1-pyrrolidinyl, 2-pyrrolidinyl, 3-pyrrolidinyl), piperidyl (e.g. piperidino, 2-piperidyl, 3-piperidyl, 4-piperidyl), piperazinyl (e.g. 1-piperazinyl, 2-piperazinyl), morpholinyl (e.g. morpholino, 2-morpholinyl, 3-morpholinyl), thiomorpholinyl (e.g. 1-thiomorpholinyl, 2-thiomorpholinyl), decahydroisoquinolyl (e.g. 2-decahydroisoquinolyl), azepinyl (e.g. 1-azepinyl), diazepinyl, 4,5,6,7-tetrahydrothieno[3,2]pyridyl, 2-oxa-5-aza-bicyclo [2.2.1]hept-5-yl, and hexahydropyrazyl[2.1-b][1,3]oxazin-8-yl are preferable.

As used herein, the "heteroaryl" which is used alone, or in combination with other term includes a 5- to 6-membered aromatic group containing one or more of arbitrarily selected an oxygen atom, a sulfur atom and a nitrogen atom in a ring. This may be fused with the "cycloalkyl", the "aryl", the "non-aromatic heterocyclic group", or other heteroaryl at all possible positions. When heteroaryl is any of a monocycle and a fused cycle, it can bind at all possible positions. Examples include pyrrolyl (e.g. 1-pyrrolyl, 2-pyrrolyl, 3-pyrrolyl), furyl (e.g. 2-furyl, 3-furyl), thienyl (e.g. 2-thienyl, 3-thienyl), imidazolyl (e.g. 2-imidazolyl, 4-imidazolyl), pyrazolyl (e.g. 1-pyrazolyl, 3-pyrazolyl), isothiazolyl (e.g.

3-isothiazolyl), isooxazolyl (e.g. 3-isooxazolyl), oxazolyl (e.g. 2-oxazolyl), thiazolyl (e.g. 2-thiazolyl, 5-thiazolyl), pyridyl (e.g. 2-pyridyl, 3-pyridyl, 4-pyridyl), pyrazinyl (e.g. 2-pyrazinyl), pyrimidinyl (e.g. 2-pyrimidinyl, 4-pyrimidinyl), pyridazinyl (e.g. 3-pyridazinyl), triazolyl, tetrazolyl (e.g. 1H-tetrazolyl), oxadiazolyl (e.g. 1,3,4-oxadiazolyl), thiadiazolyl (e.g. 1,3,4-thiadiazolyl), indolydinyl (e.g. 2-indolydinyl, 6-indolydinyl), isoindolyl (e.g. 2-isoindolyl), indolyl (e.g. 1-indolyl, 2-indolyl, 3-indolyl), indazolyl (e.g. 3-indazolyl), purinyl (e.g. 8-purinyl), quinolizinyl (e.g. 2-quinolizinyl), isoquinolyl (e.g. 3-isoquinolyl), quinolyl (e.g. 2-quinolyl, 5-quinolyl), phthalazinyl (e.g. 1-phthalazinyl), naphthyridinyl (e.g. 2-naphthyridinyl), quinolanyl (e.g. 2-quinolanyl), quinazolinyl (e.g. 2-quinazolinyl), cinnolinyl (e.g. 3-cinnolinyl), pteridinyl (e.g. 2-pteridinyl), carbazolyl (e.g. 2-carbazolyl, 4-carbazolyl), phenanthridinyl (e.g. 2-phenanthridinyl, 3-phenanthridinyl), acridinyl (e.g. 1-acridinyl, 2-acridinyl), dibenzofuranyl (e.g. 1-dibenzofuranyl, 2-dibenzofuranyl), benzoimidazolyl (e.g. 2-benzoimidazolyl), benzoisooxazolyl (e.g. 3-benzoisooxazolyl), benzooxazolyl (e.g. 2-benzooxazolyl), bezooxadiazolyl (e.g. 4-benzooxadiazolyl), benzoisothiazolyl (e.g. 3-benzoisothiazolyl), benzothiazolyl (e.g. 2-benzothiazolyl), benzofuryl (e.g. 3-benzofuryl), benzothienyl (e.g. 2-benzothienyl), 4,5-dihydronaphtho[1,2-d]thiazolyl, 4H-chromeno[4,3-d]thiazolyl, 4H-thiochromeno[4,3-d]thiazolyl, 4,5-dihydrothiazolo[5,4-c]quinolyl, 8H-indeno[1,2-d]thiazolyl, and 5,6-dihydro-4H-3-thia-1-aza-benzo[e]azuenyl.

As the "heteroaryl" in $R^2$, pyridyl, furyl, thienyl, thiazolyl, oxazolyl, thiadiazolyl, oxadiazolyl, and triazolyl are preferable. Further preferable examples include pyridyl, furyl, thienyl, thiazolyl.

As the "heteroaryl" in $R^8$, pyridyl, furyl, thienyl, thiazolyl, oxazolyl, thiadiazolyl, oxadiazolyl, and triazolyl are preferable. Further preferable examples include pyridyl, furyl, thienyl, and thiazolyl.

As the "heteroaryl" in $R^{19}$, pyridyl, furyl, and thienyl are preferable.

As the "heteroaryl" in $W^1$, pyrrolyl, imidazolyl, pyrazolyl, triazolyl, and tetrazolyl are preferable.

As used herein, the "heteroarylalkyl" includes the "alkyl" in which one or two or more of the "heteroaryl" are replaced at an arbitrary position thereof, and these can be substituted at all possible positions. Examples include thienylmethyl (e.g. 2-thienylmethyl), thienylethyl (e.g. 2-(thiophen-2-yl)ethyl), furylmethyl (e.g. 2-furylmethyl), furylethyl (e.g. 2-(furan-2-yl)ethyl), pyrrolylmethyl (e.g. 2-pyrrolylmethyl), pyrrolylethyl (e.g. 2-(pyrrol-2-yl)ethyl), imidazolylmethyl (e.g. 2-imidazolylmethyl, 4-imidazolylmethyl), imidazolylethyl (e.g. 2-(imidazol-2-yl)ethyl), pyrazolylmethyl (e.g. 3-pyrazolylmethyl), pyrazolylethyl (e.g. 2-(pyrazol-3-yl)ethyl), thiazolylmethyl (e.g. 2-thiazolylmethyl), thiazolylethyl (e.g. 2-(thiazol-2-yl)ethyl), isothiazolylmethyl (e.g. 3-iso thiazolylmethyl), isooxazolylmethyl (e.g. 3-isooxazolylmethyl), oxazolylmethyl (e.g. 2-oxazolylmethyl), oxazolylethyl (e.g. 2-(oxazol-2-yl)ethyl), pyridylmethyl (e.g. 2-pyridylmethyl, 3-pyridylmethyl, 4-pyridiylmethyl), and pyridylethyl (e.g. 2-pyridylethyl).

As used herein, a term of the "acyl" which is used alone, or in combination with other term includes alkylcarbonyl in which an alkyl part is the "alkyl", haloalkylcarbonyl in which a haloalkyl part is the "haloalkyl", alkenylcarbonyl in which an alkenyl part is the "alkenyl", aralkylcarbonyl in which an aralkyl part is the "aralkyl", and arylcarbonyl in which an aryl part is the "aryl". Examples include acetyl, propionyl, butyroyl, trifluoromethylcarbonyl, vinylcarbonyl, phenylacetyl, and benzoyl. The "alkyl", the "alkenyl" and the "aryl" may be substituted with each substituent described below.

As the "acyl" in $R^{10}$ and $R^{11}$, acetyl, benzoyl, and phenylacetyl are preferable.

As the "acyl" in $R^{12}$ and $R^{13}$, acetyl, benzoyl, and phenylacetyl are preferable.

As the "acyl" in $R^9$, acetyl, benzoyl, and phenylacetyl are preferable.

As used herein, examples of the "acyloxy" include acetyloxy, propionyloxy, and benzoyloxy.

As used herein, a term of the "optionally substituted amino" which is used alone, or in combination with other term includes amino optionally substituted with the "alkyl" optionally substituted with a substituent selected from substituent group A, the "haloalkyl", the "alkenyl", the "alkynyl", the "alkylsulfonyl", the "alkylsulfonylalkyl", the "alkyloxycarbonyl", the "aminocarbonyloxyalkyl", the "alkyloxy", the "alkyloxyalkyl" optionally substituted with a substituent selected from substituent group A, the "cycloalkyl" optionally substituted with a substituent selected from substituent group A, the "aryl" optionally substituted with a substituent selected from substituent group G consisting of alkyl, alkenyl, and aralkyl, the "aralkyl", the "heteroaryl", the "heteroarylalkyl", the "acyl", the "aminocarbonylalkyl" optionally substituted with a substituent selected from substituent group G, the "aminoalkylcarbonyl" optionally substituted with a substituent selected from substituent group G, "alkenyloxycarbonyl" in which an alkenyloxy part is the "alkenyloxy", and "aralkyloxycarbonyl" in which an aralkyloxy part is the "aralkyloxy" at one or two place(s). Examples include amino, methylamino, dimethylamino, ethylmethylamino, diethylamino, ethylmethylamino, diisopropylamino, benzylamino, acetylamino, trifluoromethylcarbonyl, benzoylamino, methyloxycarbonylamino, ethyloxycarbonylamino, n-propyloxycarbonylamino, isopropyloxycarbonylamino, n-butyloxy, isobutyloxycarbonylamino, sec-butyloxycarbonylamino, tert-butyloxycarbonylamino, alyloxycarbonylamino, benzyloxycarbonylamino, cyclopentylamino, and cyclohexylamino.

As a substituent of the "optionally substituted amino" in $R^3$ and $R^4$, alkyl, acyl, and the like are preferable.

As a substituent of the "optionally substituted amino" in $R^6$ and $R^7$, alkyl and the like are preferable.

As a substituent of the "optionally substituted amino" and the "optionally substituted aminocarbonyl" in substituent group A, alkyl, alkenyl, alkynyl, aryl optionally substituted with a substituent selected from substituent group I, aralkyl, alkyloxy, hydroxyalkyl, hydroxyalkyloxyalkyl, haloalkyl, aminoalkyl optionally substituted with 1 or 2 alkyl(s), alkylsulfonyl, alkylsulfonylalkyl, alkylcarbonyl optionally substituted with halogen or alkyloxy, alkyloxycarbonyl, cycloalkyl optionally substituted with a substituent selected from substituent group I, carboxyalkyl, aminocarbonylalkyl optionally substituted with a substituent selected from substituent group G, aminocarbonyloxyalkyl optionally substituted with a substituent selected from substituent group G, alkyloxyalkyl, alkylthioalkyl, alkylcarbonylaminoalkyl, alkylsulfonylaminoalkyl, alkylsulfonyl(alkyl)aminoalkyl, alkyloxycarbonylalkyl, alkylthio(hydroxy) alkyl, cycloalkylalkyl, cyanoalkyl, aminoalkylcarbonyl optionally substituted with a substituent selected from substituent group G, heteroaryl optionally substituted with a substituent selected from substituent group C, heteroarylalkyl, hydroxyalkyloxyalkyl, a non-aromatic heterocyclic group optionally substituted with a substituent selected from substituent group 1, and a non-aromatic heterocyclic alkyl optionally substituted with a substituent selected from substituent group I.

Herein, as a substituent in the "optionally substituted aminocarbonyl", alkyl, alkenyl, aralkyl, and the like are preferable. Particularly, alkyl is preferable.

As a substituent in the "optionally substituted aminocarbonyl" in a substituent group B, alkyl, alkenyl, aralkyl, and the like are preferable.

As a substituent in the "optionally substituted aminocarbonyl" in a substituent group D, alkyl, alkenyl, aralkyl, and the like are preferable.

As a substituent in the "optionally substituted aminocarbonyl" in a substituent group E, alkyl, alkenyl, aralkyl, and the like are preferable.

As a substituent in the "optionally substituted aminocarbonyl" in a substituent group H, alkyl, alkenyl, aralkyl, and the like are preferable.

Herein, as a substituent in the "optionally substituted aminocarbonylalkyl", alkyl, alkenyl aralkyl, and the like are preferable. Particularly, alkyl is preferable.

As a substituent in the "optionally substituted aminocarbonylalkyl" in a substituent group C, alkylalkenyl, aralkyl, and the like are preferable.

Herein, as a substituent in the "optionally substituted aminocarbonyloxyalkyl", alkyl, alkenyl, aralkyl, and the like are preferable. Particularly, alkyl is preferable.

As a substituent in the "optionally substituted aminocarbonyloxyalkyl" in a substituent group C, alkyl, alkenyl, aralkyl, and the like are preferable.

Herein, as a substituent in the "optionally substituted aminoalkylcarbonyl", alkyl, alkenyl, aralkyl, and the like are preferable. Particularly, alkyl is preferable.

As a substituent in the "optionally substituted aminoalkylcarbonyl" in a substituent group C, alkyl, alkenyl, aralkyl, and the like are preferable.

Herein, a term of the "optionally substituted ureido" includes ureido optionally substituted with the "alkyl", the "cycloalkyl", the "aryl", the "aralkyl", the "heteroaryl", the "heteroarylalkyl", the "acyl", cyanoalkyl, or alkyloxyalkyl at one or two or more places.

Herein, a term of the "optionally substituted guanidino" includes guanidino optionally substituted with the "alkyl", the "cycloalkyl", the "aryl", the "aralkyl", the "heteroaryl", the "heteroarylalkyl", the "acyl", cyano, cyanoalkyl or alkyloxyalkyl at one or two or more places.

Herein, examples of a substituent in the "optionally substituted alkyl" include optionally substituted amino, an optionally substituted non-aromatic nitrogen-containing heterocyclic group, optionally substituted non-aromatic nitrogen-containing heterocyclic carbonyl, alkyl, alkyloxy, cyano, alkylsulfonyl, cylcoalkyl, alkenyl, heteroaryl, heteroaryloxy, hydroxy, mercapto, alkylthio, halogen, nitro, carboxy, alkyloxycarbonyl, hydroxyalkyl, haloalkyl, haloalkyloxy, alkylcarbonyloxy, carbamoyloxy, optionally substituted aminocarbonyl, aminocarbonylalkyloxy, acyl, acyloxy, aryloxy, aralkyl, aralkyloxy, optionally substituted guanidino, an azo group, and optionally substituted ureido. These can be substituted with one or more substituent(s) at all possible positions.

As a substituent in the "optionally substituted alkyl" in $R^1$, $R^{17}$ and $R^{19}$, a substituent selected from substituent group A, alkyloxy, cyano, halogen, heteroaryl, and the like are preferable. Particularly, amino optionally substituted with a substituent selected from substituent group C, and a non-aromatic nitrogen-containing heterocyclic group optionally substituted with a substituent selected from substituent group D are preferable.

As a substituent of the "optionally substituted alkyl" in $R^2$, a substituent selected from substituent group A, alkyloxy, alkylcarbonyl, and halogen are preferable. Particularly, hydroxy, alkyloxy, and halogen are preferable.

As a substituent of the "optionally substituted alkyl" in $R^3$ and $R^4$, alkyloxy, alkyloxycarbonyl, aminocarbonyl, cyano, and the like are preferable.

As a substituent of the "optionally substituted alkyl" in $R^6$ and $R^7$, alkyloxy, alkyloxycarbonyl, aminocarbonyl, cyano, hydroxy, and the like are preferable.

As a substituent of the "optionally substituted alkyl" in $R^{18}$, hydroxy, alkyloxy, halogen, cyano, and the like are preferable.

As a substituent of the "optionally substituted alkyl" in $R^{20}$, hydroxy, alkyloxy, halogen, cyano, and the like are preferable.

Herein, examples of a substituent in the "optionally substituted alkenyl" and the "optionally substituted alkynyl" include optionally substituted amino, an optionally substituted non-aromatic nitrogen-containing heterocyclic group, cycloalkyl, hydroxy, alkyloxy, mercapto, alkylthio, halogen, nitro, cyano, carboxy, alkyloxycarbonyl, haloalkyl, haloalkyloxy, optionally substituted aminocarbonyl, acyl, acyloxy, aryl, aryloxy, aralkyl, aralkyloxy, alkylsulfonyl, guanidino, an azo group, optionally substituted ureido, and the like. These can be substituted with one or more substituent(s) at all possible positions.

As a substituent of the "optionally substituted alkenyl" in $R^1$ and $R^{17}$, a substituent selected from substituent group A is preferable. In particular, amino optionally substituted with a substituent selected from substituent group C, and a non-aromatic nitrogen-containing heterocyclic group optionally substituted with a substituent selected from substituent group D are preferable.

As a substituent of the "optionally substituted alkenyl" and the "optionally substituted alkynyl" in $R^2$, a substituent selected from substituent group A, cycloalkyl, alkyloxy, and halogen are preferable. Particularly, hydroxy, cycloalkyl, alkyloxy, and halogen are preferable.

As a substituent of the "optionally substituted alkenyl" and the "optionally substituted alkynyl" in $R^3$ and $R^4$, alkyloxy, alkyloxycarbonyl, aminocarbonyl, alkyl optionally substituted with cyano and the like, alkyloxy, alkyloxycarbonyl, aminocarbonyl, alkyloxycarbonyl optionally substituted with cyano and the like, and optionally substituted aminocarbonyl, and the like are preferable.

As a substituent of the "optionally substituted alkenyl" and the "optionally substituted alkynyl" in $R^6$ and $R^7$, alkyloxy, alkyloxycarbonyl, aminocarbonyl, alkyl optionally substituted with cyano and the like, alkyloxy, alkyloxycarbonyl, aminocarbonyl, alkylcarbonyl, aminocarbonyl, alkyloxycarbonyl optionally substituted with cyano and the like, and optionally substituted aminocarbonyl, and the like are preferable.

As a substituent of the "optionally substituted alkenyl" and the "optionally substituted alkynyl" in $R^{18}$, hydroxy, alkyloxy, halogen, cyano, and the like are preferable.

As a substituent of the "optionally substituted alkenyl" and the "optionally substituted alkynyl" in $R^{20}$, hydroxy, alkyloxy, halogen, cyano, and the like are preferable.

Herein, examples of a substituent in the "optionally substituted cycloalkyl" include alkyloxycarbonyl, aminocarbonyl optionally substituted with a substituent selected from substituent group G, cyano, alkyl optionally substituted with a substituent selected from substituent group M consisting of cyano, hydroxy, carboxy, aminocarbonyl, alkyloxycarbonyl, and alkyloxy, alkylsulfonyl, alkylsulfonylalkylcarbonyl, cycloalkyl, hydroxy, alkyloxy, mercapto, alkylthio, halogen, nitro, carboxy, haloalkyl, haloalkyloxy, acyl, acyloxy, aryl, aryloxy (e.g. phenyloxy), aralkyl, aralkyloxy (e.g. benzyloxy), a non-aromatic nitrogen-containing heterocyclic group, alkylcarbonylamino, aminocarbonyloxy, amino, oxo, guanidino, an azo group, and optionally substituted ureido.

As a substituent of the "optionally substituted cycloalkyl" in substituent group C, substituents exemplified in substituent group I are preferable.

Herein, examples of a substituent of the "optionally substituted alkyloxy", the "optionally substituted alkenyloxy", and the "optionally substituted alkynyloxy" include cycloalkyl, alkenyl, hydroxy, alkyloxy, mercapto, alkylthio, halogen, nitro, cyano, carboxy, alkyloxycarbonyl, haloalkyl, haloalkyloxy, optionally substituted amino, optionally substituted aminocarbony, acyl, acyloxy, an optionally substituted non-aromatic heterocyclic group, aryloxy, aralkyloxy, alkylsulfonyl, guanidino, an azo group, and optionally substituted ureido. These can replace at one or more places of all possible positions. Preferable examples include halogen.

As a substituent of the "optionally substituted alkyloxy" and the "optionally substituted alkenyloxy" in $R^3$ and $R^4$, alkyloxy, optionally substituted amino, a non-aromatic heterocyclic group optionally substituted with a substituent selected from substituent group D, cyano, and the like are preferable.

As a substituent of the "optionally substituted alkyloxy", the "optionally substituted alkenyloxy", and the "optionally substituted alkynyloxy" in $R^5$, a substituent selected from substituent group E is preferable.

As a substituent of the "optionally substituted alkyloxy", the "optionally substituted alkenyloxy", and the "optionally substituted alkynyloxy" in $R^6$ and $R^7$, alkyloxy, cyano, alkyloxycarbonyl, optionally substituted aminocarbonyl, and the like are preferable.

Herein, examples of a substituent in the "optionally substituted non-aromatic heterocyclic group" include alkyloxycarbonyl, aminocarbonyl optionally substituted with a substituent selected from substituent group G, cyano, alkyl optionally substituted with a substituent selected from substituent group M consisting of cyano, hydroxy, carboxy, aminocarbonyl, alkyloxycarbony, and alkyloxy, alkylsulfonyl, alkylsulfonylalkylcarbonyl, cycloalkyl, hydroxy, alkyloxy, mercapto, alkylthio, halogen, nitro, carboxy, haloalkyl, haloalkyloxy, acyl, acyloxy, aryl, aryloxy (e.g. phenyloxy), aralkyl, aralkyloxy (e.g. benzyloxy), a non-aromatic nitrogen-containing heterocyclic group, alkylcarbonylamino, aminocarbonyloxy, amino, Oxo, guanidino, an azo group, and optionally substituted ureido.

Herein, examples of a substituent in the "optionally substituted non-aromatic nitrogen containing heterocyclic group" include alkyloxycarbonyl, aminocarbonyl optionally substituted with a substituent selected from substituent group G, cyano, alkyl optionally substituted with a substituent selected from substituent group M consisting of cyano, hydroxy, carboxy, aminocarbonyl, alkyloxycarbonyl, and alkyloxy, alkylsulfonyl, alkylsulfonylalkylcarbonyl, cycloalkyl, hydroxy, alkyloxy, mercapto, alkylthio, halogen, nitro, carboxy, haloalkyl, haloalkyloxy, acyl, acyloxy, aryl, aryloxy (e.g. phenyloxy), aralkyl, aralkyloxy (e.g. benzyloxy), a non-aromatic nitrogen-containing heterocyclic group, alkylcarbonylamino, aminocarbonyloxy, optionally substituted amino, oxo, guanidino, an azo group, and optionally substituted ureido.

As a substituent of the "optionally substituted non-aromatic nitrogen-containing heterocyclic group" in $R^1$ and $R^{17}$, alkyl, alkyloxycarbonyl, aminocarbonyl optionally substituted with a substituent selected from substituent group G, cyano, oxo, amino, carboxyl, hydroxyalkyl, cyanoalkyl, alkyloxyalkyl, alkylsulfonyl, alkylcarbonyl, alkenylcarbonyl, alkylsulfonylalkylcarbonyl, alkylcarbonylamino, alkylsulfonylamino, carboxyalkyl, alkyloxycarbonylalkyl, and the like are preferable. Particularly, substituents exemplified in substituent group B are preferable.

As a substituent of the "optionally substituted non-aromatic nitrogen-containing heterocyclic group" in $W^1$, alkyl, alkyloxycarbonyl, optionally substituted aminocarbonyl, cyano, hydroxyalkyl, cyanoalkyl, alkyloxyalkyl, alkylsulfonyl, alkylcarbonyl, alkenylcarbonyl, alkylsulfonylalkylcarbonyl, and the like are preferable. Particularly, substituents exemplified in substituent group J are preferable.

As a substituent of the "optionally substituted non-aromatic nitrogen-containing heterocyclic group" and the "optionally substituted non-aromatic nitrogen-containing heterocyclic carbonyl" in substituent group A, a substituent selected from substituent group D is preferable.

Herein, examples of a substituent in the "optionally substituted aryl", the "optionally substituted phenyl", the "optionally substituted heteroaryl", the "optionally substituted pyridyl", the "optionally substituted furyl", the "optionally substituted thienyl", the "optionally substituted thiazolyl", the "optionally substituted oxazolyl", the "optionally substituted non-aromatic heterocyclic group", the "optionally substituted non-aromatic heterocyclic alkyl", the "optionally substituted cycloalkyl", the "optionally substituted aralkyl", and the "optionally substituted heteroarylalkyl" include optionally substituted alkyl (as a substituent, halogen, hydroxy, nitro, cyano, carboxy, alkyloxy, alkyloxycarbonyl, acyl, etc), cycloalkyl, alkenyl, alkynyl, hydroxy, alkyloxy, aralkyloxy, mercapto, alkylthio, halogen, nitro, cyano, carboxy, alkyloxycarbonyl, aryloxycarbonyl, haloalkyl, haloalkyloxy, optionally substituted amino, optionally substituted aminocarbonyl, acyl, acyloxy, optionally substituted aryl (as a substituent, halogen, hydroxy, nitro, cyano, carboxy, alkyloxy, alkyloxycarbonyl, acyl, etc.), optionally substituted heteroaryl (as a substituent, halogen, hydroxy, nitro, cyano, carboxy, alkyloxy, alkyloxycarbonyl, acyl, etc.), an optionally substituted non-aromatic heterocyclic group (as a substituent, halogen, hydroxy, nitro, cyano, carboxy, alkyloxy, alkyloxycarbonyl, acyl, etc.), optionally substituted aralkyl (as a substituent, halogen, hydroxy, nitro, cyano, carboxy, alkyloxy, alkyloxycarbonyl, acyl, etc.), alkylsulfonyl, guanidino, an azo group, —N=N— (optionally substituted phenyl), and optionally substituted ureido. These can replace at one or more of all possible position(s).

As a substituent of the "optionally substituted aryl" in $R^1$, substituents exemplified in substituent group I are preferable.

As a substituent of the "optionally substituted aryl" and the "optionally substituted heteroaryl" in $R^2$, alkyl optionally substituted with hydroxy or optionally substituted amino, optionally substituted amino, halogen, and the like are preferable. Particularly, alkyl optionally substituted with hydroxy or optionally substituted amino is preferable.

As a substituent of the "optionally substituted aryl", the "optionally substituted heteroaryl", and the "optionally substituted non-aromatic heterocyclic group" in $R^8$, alkyloxycarbonyl, optionally substituted aminocarbonyl, cyano, halogen, alkyl, alkyloxy, alkylthio, haloalkyl, and the like are preferable. Particularly, substituents exemplified in substituent group F are preferable.

As a substituent of the "optionally substituted aryl" and the "optionally substituted heteroaryl" in $R^{19}$, alkyloxycarbonyl, optionally substituted aminocarbonyl, cyano, cyanoalkyl, hydroxyalkyl, aminocarbonylalkyl, and the like are preferable. Particularly substituents exemplified in substituent group I are preferable.

As a substituent of the "optionally substituted heteroaryl" in $W^1$, alkyl, hydroxy, alkyloxy, and the like are preferable. Particularly, substituents exemplified in substituent group J are preferable.

As a substituent of the "optionally substituted aryl", the "optionally substituted heteroaryl", the "optionally substituted non-aromatic heterocyclic group" and the "optionally substituted non-aromatic heterocyclic alkyl" in a substituent group C, substituents exemplified in substituent group I are preferable.

Herein, the "pharmaceutical composition useful for treating cancer" and the "therapeutic for a cancer" include therapeutics for brain tumor (e.g. glioblastoma), urinary organ cancer (e.g. bladder cancer, kidney cancer), genital cancer (prostate cancer, ovary cancer, uterine cancer), lymphoid tumor, digestive tract cancer (e.g. stomach cancer, large intestine cancer), pharynx cancer, lung cancer (e.g. lung gland cancer, small cell lung cancer, non-small cell lung cancer), pancreas cancer, breast cancer, head and neck cancer, esophagus cancer, and thyroid gland. Particularly, the composition is preferably used as therapeutics for breast cancer, brain tumor, bladder cancer, kidney cancer, prostate cancer, ovary cancer, uterine cancer, lung cancer, pancreas cancer, large intestine cancer, and head and neck cancer.

The present invention includes a method for treating or preventing a cancer in a mammal in which it is necessary to treat or prevent a cancer, and the method comprises administering a therapeutically effective amount of the compound of the formula (I) to the mammal. A cancer which is preferably treated is selected from brain tumor (e.g. glioblastoma), urinary organ cancer (e.g. bladder cancer, kidney cancer), genital cancer (prostate cancer, ovary cancer, uterine cancer), lymphoid tumor, digestive tract cancer (e.g. stomach cancer), pharynx cancer, lung cancer, (e.g. lung gland cancer, small cell lung cancer, non-small cell lung cancer), pancreas cancer, breast cancer, head and neck cancer, esophagus cancer, and thyroid gland. More preferable are breast cancer, brain tumor, bladder cancer, kidney cancer, prostate cancer, ovary cancer, uterine cancer, lung cancer, pancreas cancer, large intestine cancer, and head and neck cancer.

EFFECT OF THE INVENTION

The present compound has the excellent action of inhibiting an EGF receptor and HER2, and has high safety (has reduced CYP inhibitory activity) and, therefore, it is useful as a medicament, inter alia, a therapeutic for a cancer.

Best Mode for Carrying out the Invention

The present compound (I) can be synthesized by any of methods A to E described below. Alternatively, since a method of synthesizing a quinazoline derivative is described in WO 96/09294, WO 98/02434 and the like, the present compound (I) can be also synthesized according to this. When the compound has a group influencing on each reaction, the group can be protected with a suitable protecting group, and can be deprotected at a suitable stage. In addition, when a raw material, a reagent, an intermediate, and a reaction product at each step can form a salt, the salt is included.

(Method A)

[Chemical formula 25]

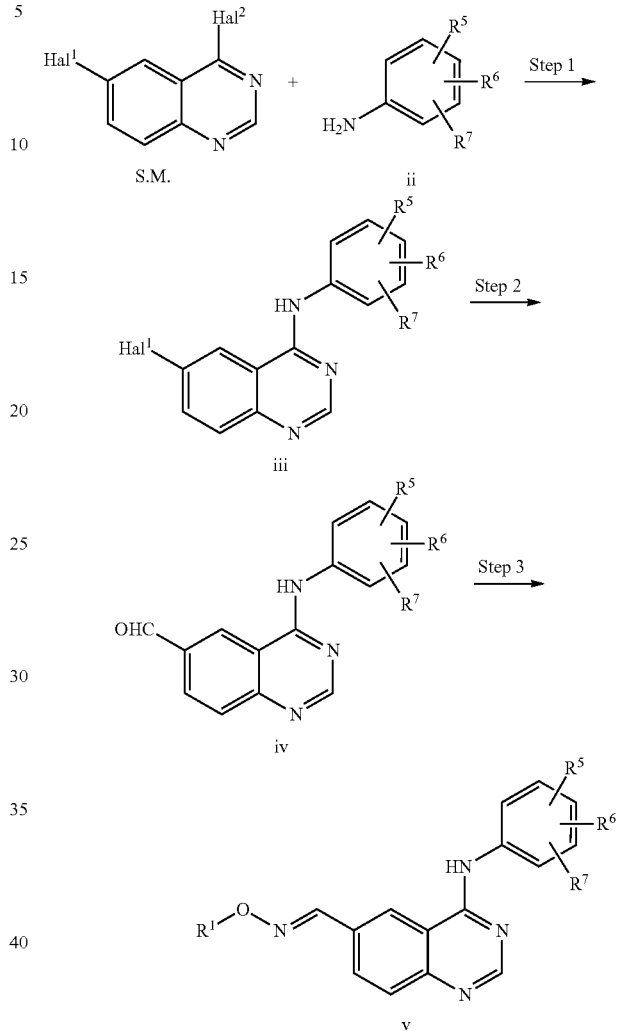

wherein $Hal^1$ and $Hal^2$ are each independently halogen; $R^1$, $R^5$, $R^6$, and $R^7$ are as defined in (1).

(Step 1)

The first step is a step of synthesizing a compound (iii) by reacting a starting raw material (S.M.) which can be synthesized according to the method described in WO 96/09294 or the like, or is commercially available, and a compound (II) which can be synthesized according to the method described in WO 98/02434 or the like, or is commercially available.

The starting raw material (S.M.) and the compound (ii) can be reacted in a solvent such as tetrahydrofuran, acetonitrile and the like at 20° C. to under heat refluxing, preferably at 60° C. to under heat refluxing, to obtain the compound (iii).

(Step 2)

The second step is a step of inserting carbon monoxide into the compound (iii) in the presence of a palladium catalyst to obtain a compound (iv).

The compound (iii) can be reacted at 50° C. to 150° C., preferably 70° C. to 90° C. under the carbon monoxide atmosphere in a solvent such as N,N-dimethylformamide, N,N-dimethylacetamide, N,N'-dimethylimidazolidinone, dimethyl sulfoxide and the like, in the presence of a hydrogen source such as sodium formate, tributyltin hydride and the like, a palladium catalyst such as dichlorobis(triphenylphosphine)palladium, tetrakis(triphenylphosphine)palladium, tris(dibenzylideneacetone)dipalladium, [1,1'-bis(diphenylphosphino)ferrocene]dichloropalladium, palladium acetate+ triphenylphosphine and the like, and a base such as triethylamine, di(isopropyl)ethylamine and the like to obtain the compound (iv).

(Step 3)

The third step is a step of synthesizing an objective compound (v) by reacting the compound (iv) and a compound represented by the formula: $R^1$—O—$NH_2$ wherein $R^1$ is as defined in (1).

The starting raw material (iv) and the compound represented by the formula: $R^1$—O—$NH_2$ wherein $R^1$ is as defined in (1) or a salt can be reacted at 0° C. to under heat refluxing, preferably at 20° C. to 70° C. in a solvent such as tetrahydrofuran, dioxane, methanol and the like, or in a mixed solvent of them and water, if necessary, in the presence of an acid such as hydrochloric acid, sulfuric acid, p-toluenesulfonic acid, methanesulfonic acid, formic acid, acetic acid, trifluoroacetic acid and the like to obtain the compound (v).

(Method B)

[Chemical formula 26]

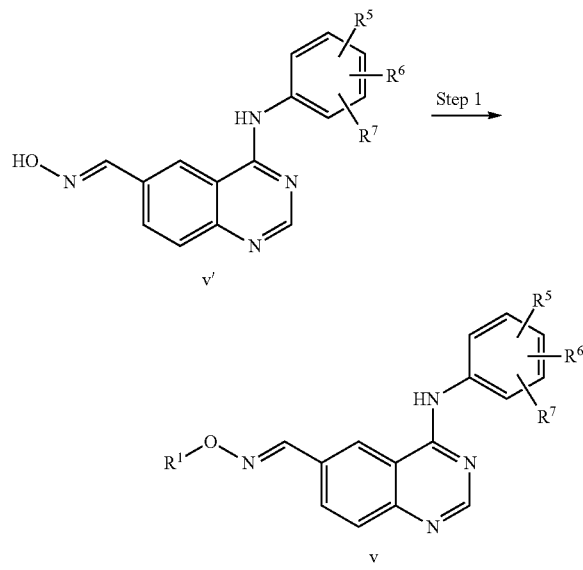

wherein $R^1$, $R^5$, $R^6$, and $R^7$ are as defined in (1).

(Step 1)

The first step is a step of synthesizing an objective compound (v) by reacting a compound (v') obtained by reacting the compound (iv) obtained in the Method A with hydroxylamine, and a compound represented by the formula: $R^1$-$Hal^3$ wherein $Hal^3$ is halogen; $R^1$ is as defined in (1).

The compound (v') and the compound represented by the formula: $R^1$-$Hal^3$ wherein $Hal^3$ is halogen; $R^1$ is as defined in (1) can be dissolved in a solvent such as N,N-dimethylacetamide, N,N-dimethylacetamide, N,N'-dimethylimidazolidinone, dimethyl sulfoxide and the like, and reacted at 50° C. to 150° C., preferably 60° C. to 80° C. in the presence of a base such as potassium carbonate, sodium carbonate, and the like to obtain the compound (v).

(Method C)

[Chemical formula 27]

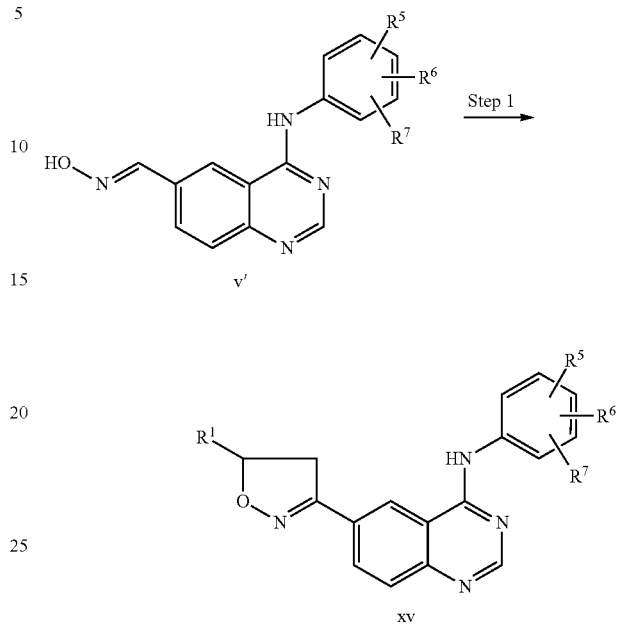

Wherein $R^1$, $R^5$, $R^6$, and $R^7$ as defined in (1).

(Step 1)

The first step is a step of synthesizing an objective compound (xv) by reacting a compound (v') obtained by reacting the compound (iv) obtained in the Method A with hydroxylamine, and a compound represented by the formula: $R^1$—CH=$CH_2$ wherein $R^1$ is as defined in (1).

The compound (xv) can be obtained by dissolving the compound (v') in a solvent such as chloroform, dichloromethane, 1,2-dichloroethane and the like, and reacting with a chlorine-based oxidizing agent such as N-chlorosuccinimide, N-chlorophthalimide and the like at 20° C. to 100° C., preferably 50° C. to 60° C. in the presence of a catalytic amount of a based such as pyridine, 4-dimethylaminopyridine and the like, subsequently, adding a compound represented by the formula: $R^1$—CH=$CH_2$ wherein $R^1$ is as defined in (1), and a base such as triethylamine, di(isopropyl)ethylamine and the like, and reacting them at 0° C. to 100° C., preferably 10° C. to 30° C.

(Method D)

[Chemical formula 28]

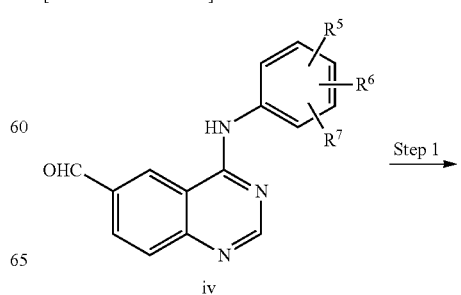

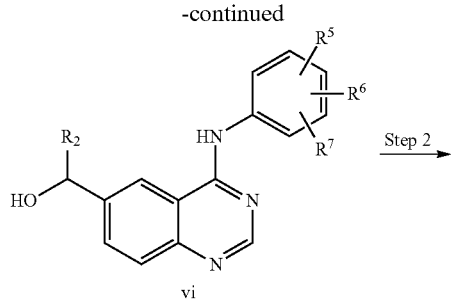

vi

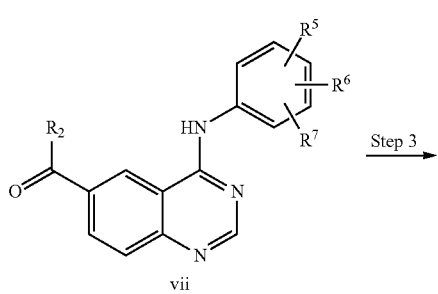

vii

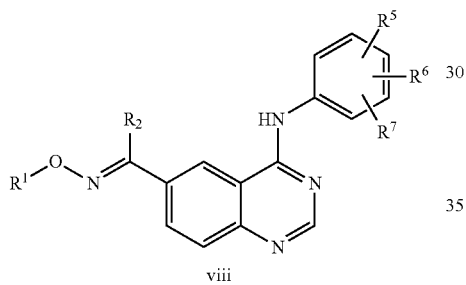

viii

Wherein $R^1$, $R^2$, $R^5$, $R^6$, and $R^7$ are as defined in (1)

(Step 1)

the first step is a step of reacting the compound (iv) obtained in Method A with a reagent represented by the formula: $R^2MgHal^4$ or $R^2Li$ wherein $Hal^4$ is halogen; $R^2$ is as defined in (1) to obtain a compound (vi).

The compound (vi) can be obtained by reacting the compound (iv) and the reagent represented by the formula: $R^2MgHal^4$ or $R^2Li$ wherein $Hal^4$ is halogen; $R^2$ is as defined in (1) at −100° C. to 50° C., preferably −78° C. to 10° C. in a solvent such as tetrahydrofuran, diethyl ether, toluene, n-hexane and the like.

(Step 2)

The second step is a step of oxidizing the compound (vi) to synthesize a compound (vii).

The compound (vii) can be obtained by oxidizing the compound (vi) by a general method of oxidizing a secondary alcohol described in Experimental Chemistry Course, vol. 23, Fourth edition (edited by The Chemical Society of Japan) or the like.

(Step 3)

According to the same method as the third step of the Method A, a compound (viii) can be obtained from the compound (vii).

(Method E)

[Chemical formula 29]

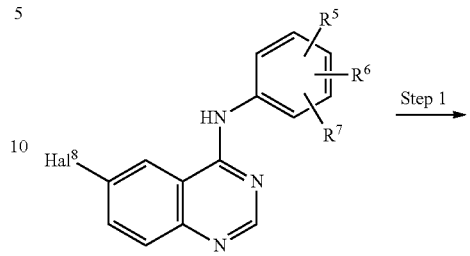

iii

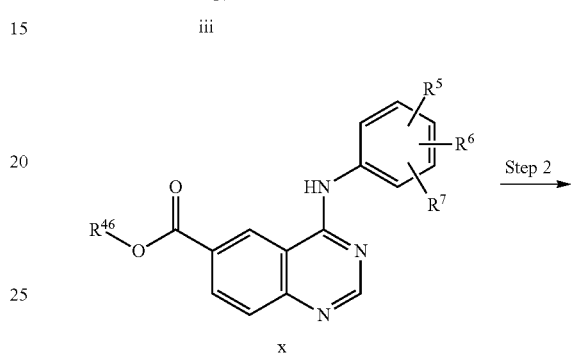

x

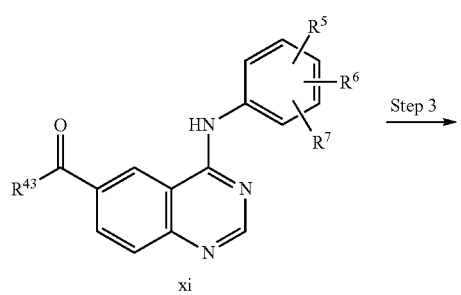

xi

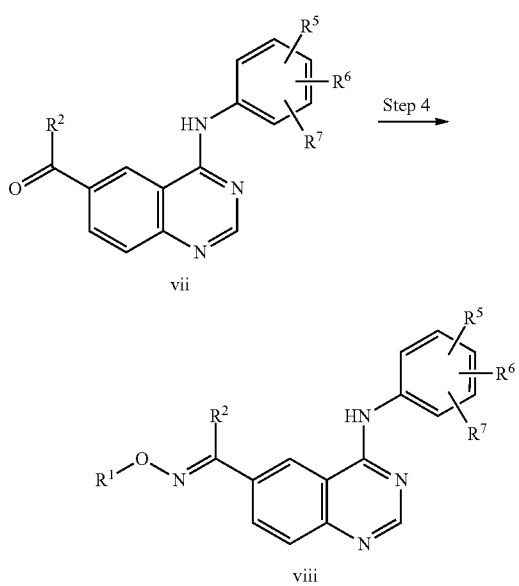

wherein $Hal^8$ is halogen; $R^{43}$ is a group represented by the formula: $R^{44}(R^{45}O)N$ wherein $R^{44}$ and $R^{45}$ are independently C1-C3 ally or a group represented by the formula:

[Chemical formula 30]

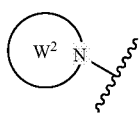

wherein $W^2$ is a non-aromatic nitrogen-containing heterocyclic group; $R^{46}$ is C1-C3 alkyl or a group represented by the formula:

[Chemical formula 31]

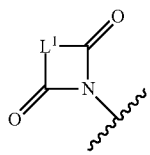

wherein $L^1$ is C2-C3 alkylene;
$R^1$, $R^2$, $R^5$, $R^6$, and $R^7$ are as defined in (1)
(Step 1)

The first step is a step of obtaining a compound (x) by reacting the compound (iii) obtained in the A method with an alcohol or a reagent represented by the formula:

[Chemical formula 32]

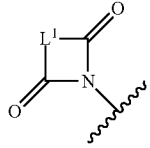

wherein $L^1$ is C2-C3 alkylene while carbon monoxide is inserted in the presence of a palladium catalyst.

The compound (x) can be obtained by reacting the compound (iii) with an alcohol such as methanol, ethanol, n-propanol, isopropanol and the like, or a reagent such as N-hydroxysuccinic acid imide and the like at 50° C. to 150° C., preferably 70° C. to 90° C. under the carbon monoxide atmosphere in a solvent such as N,N-dimethylformamide, N,N-dimethylacetamide, N,N'-dimethylimidazolidinone, dimethyl sulfoxide and the like in the presence of a palladium catalyst such as dichlorobis(triphenylphosphine)palladium, tetrakis(triphenylphosphine)palladium, tris(dibenzylideneacetone)dipalladium, [1,1'-bis(diphenylphosphino)ferrocene]dichloropalladium, palladium acetate+triphenylphosphine, palladium acetate+1,3-bisdiphenylphosphinopropane and the like, and a base such as triethylamine, di(isopropyl)ethylamine and the like.

(Step 2)

The second step is a step of obtaining a compound (xi) by reacting the compound (x) with a reagent represented by the formula: $R^{44}$ ($R^{45}$O)NH wherein $R^{44}$ and $R^{45}$ are independently C1-C3 alkyl or a reagent represented by the formula:

[Chemical formula 33]

wherein $W^2$ is a non-aromatic nitrogen-containing heterocyclic group.

The compound (xi) can be obtained by mixing the compound (x) with a reagent represented by the formula: $R^{44}$ ($R^{45}$O)NH wherein $R^{44}$ and $R^{45}$ are independently C1-C3 alkyl or a reagent represented by the formula:

[Chemical formula 34]

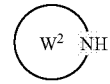

wherein $W^2$ is a non-aromatic nitrogen-containing heterocyclic group in a solvent such as tetrahydrofuran, N,N-dimethylformamide, chloroform, dichloromethane and the like, and adding a reagent such as methylmagnesium chloride, methylmagnesium bromide, isopropylmagnesium chloride, methyllithium and the like at −100° C. to 50° C., preferably −78° C. to 20° C. to react them (Step 3)

The third step is a step of reacting the compound (xi) with a reagent represented by the formula: $R^2M$ wherein M is Li, Na, K, or a group represented by the formula: $MgHal^5$ wherein $Hal^5$ is halogen; $R^2$ is as defined in (1) to obtain a compound (vii).

The compound (vii) can be obtained by reacting the compound (xi) with a reagent represented by the formula: $R^2M$ wherein M is Li, Na, K, or a group represented by the formula: $MgHal^5$ wherein $Hal^5$ is halogen; $R^2$ is as defined in (1) at −100° C. to 50° C., preferably −78° C. to 20° C. in a solvent such as tetrahydrofuran, diethyl ether, toluene, n-hexane and the like.

(Step 4)

According to the same manner as the third step of the Method A, a compound (viii) can be obtained from the compound (vii).

As an alternative method for the first step and the second step of Method E, there is following Method E'.

(Method E')

[Chemical formula 35]

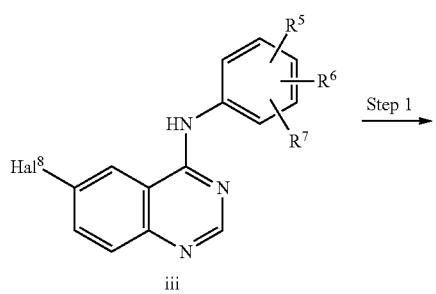

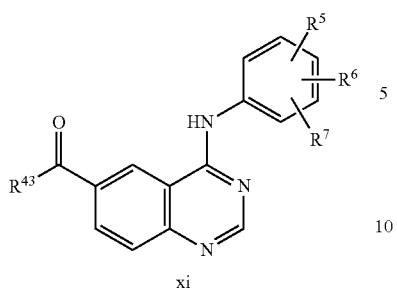

Wherein $Hal^8$ and $R^{43}$ are as defined above; $R^5$, $R^6$, and $R^7$ re as defined in (1).

(Step 1)

The first step is a step of obtaining a compound (xi) by reacting the compound (iii) with a reagent represented by the formula: $R^{43}H$ wherein $R^{43}$ is as defined above while carbon monoxide is inserted in the presence of a palladium catalyst.

By reacting a reagent represented by $R^{43}H$ wherein $R^{43}$ is as defined above in place of an alcohol or the like according to the same manner as that of the first step of the Method E, the compound (xi) can be obtained from the compound (iii).

As another method of obtaining an amide derivative (xi) of method E, there is following Method E".

(Method E")

[Chemical formula 36]

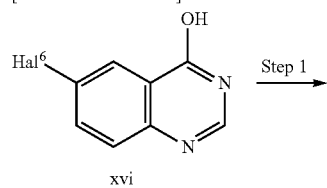

xvi

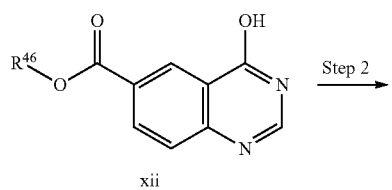

xii

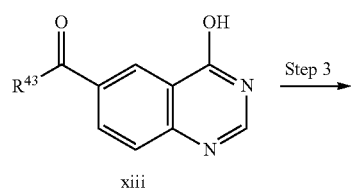

xiii

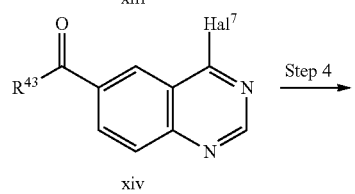

xiv

Wherein $Hal^6$ s halogen; $Hal^7$ is halogen; $R^{43}$ and $R^{46}$ are as defined above; $R^5$, $R^6$, and $R^7$ are as defined in (1).

(Step 1)

According to the same manner as that of the first step of the Method E, a compound (xii) can be obtained from a compound (xvi).

(Step 2)

According to the same manner as that of the second step of Method E, a compound (xiii) can be obtained from the compound (xii).

(Step 3)

The third step is a step of converting a hydroxyl group of the compound (xiii) into halogen to obtain a compound (xiv).

The compound (xiv) can be obtained by reacting the compound (xiii) with a halogenating agent such as phosphorus oxychloride, phosphorus oxybromide and the like at 00° C. to 200° C., preferably 200° C. to 150° C. in a solvent such as toluene, tetrahydrofuran and the like in the presence of a base such as triethylamine, diisopropylethylamine, pyridine and the like.

(Step 4)

According to the same manner as that of the first step of Method A, a compound (xi) can be obtained from the compound (xiv).

The present compound (I) in which A is a group represented by the formula:

[Chemical formula 37]

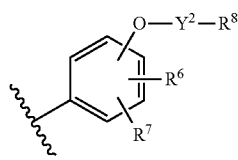

wherein $Y^2$ is a single bond or C1-C3 alkylene; $R^6$, $R^7$, and $R^8$ are as defined in (1) can be also synthesized by the following Method F.

(Method F)

[Chemical formula 38]

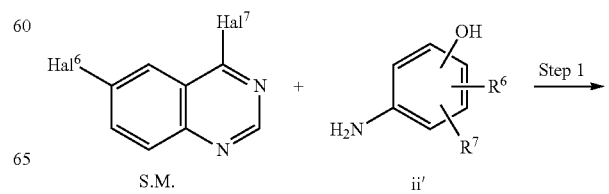

S.M.                    ii'

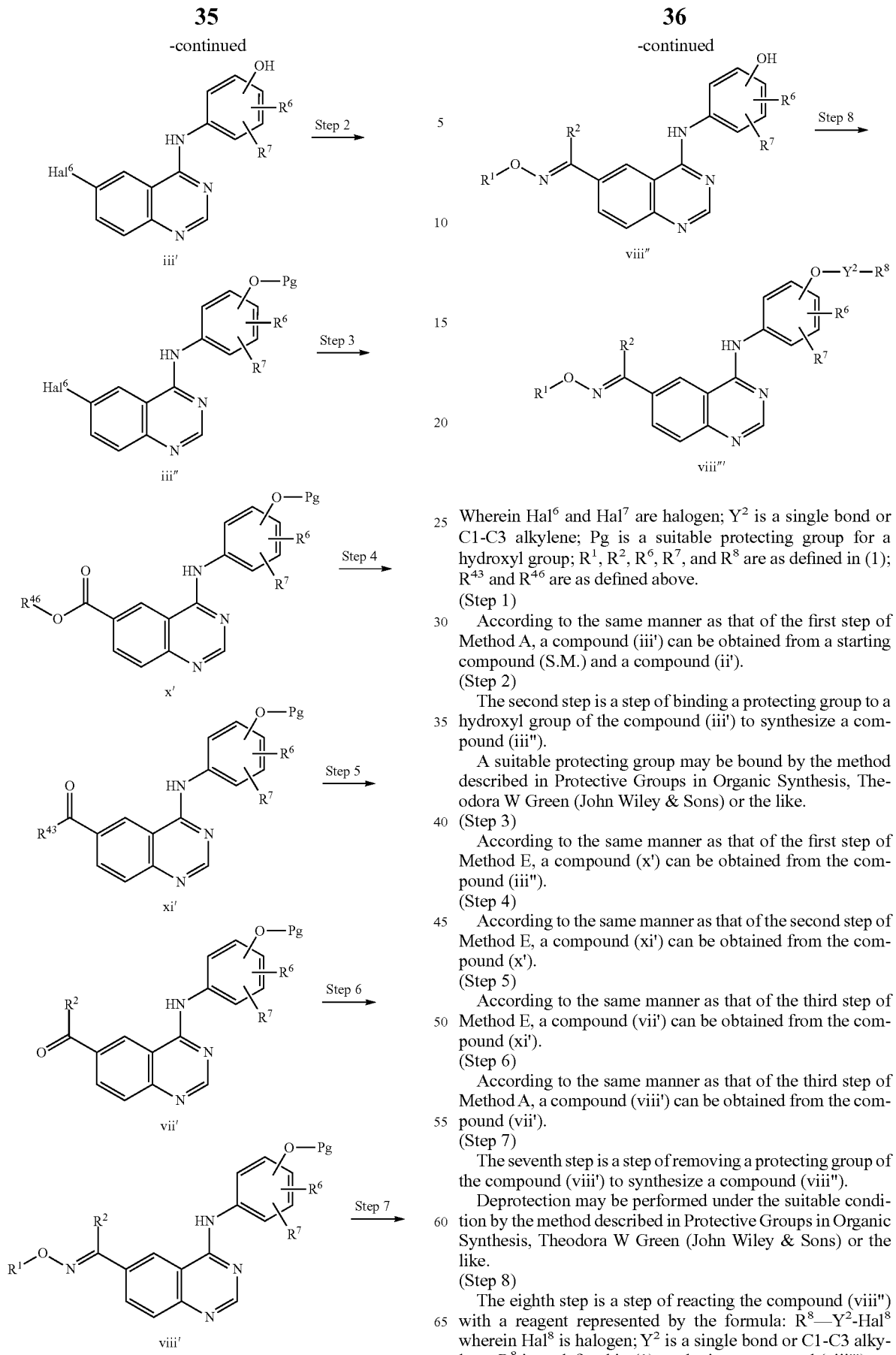

Wherein Hal⁶ and Hal⁷ are halogen; $Y^2$ is a single bond or C1-C3 alkylene; Pg is a suitable protecting group for a hydroxyl group; $R^1$, $R^2$, $R^6$, $R^7$, and $R^8$ are as defined in (1); $R^{43}$ and $R^{46}$ are as defined above.

(Step 1)

According to the same manner as that of the first step of Method A, a compound (iii') can be obtained from a starting compound (S.M.) and a compound (ii').

(Step 2)

The second step is a step of binding a protecting group to a hydroxyl group of the compound (iii') to synthesize a compound (iii").

A suitable protecting group may be bound by the method described in Protective Groups in Organic Synthesis, Theodora W Green (John Wiley & Sons) or the like.

(Step 3)

According to the same manner as that of the first step of Method E, a compound (x') can be obtained from the compound (iii").

(Step 4)

According to the same manner as that of the second step of Method E, a compound (xi') can be obtained from the compound (x').

(Step 5)

According to the same manner as that of the third step of Method E, a compound (vii') can be obtained from the compound (xi').

(Step 6)

According to the same manner as that of the third step of Method A, a compound (viii') can be obtained from the compound (vii').

(Step 7)

The seventh step is a step of removing a protecting group of the compound (viii') to synthesize a compound (viii").

Deprotection may be performed under the suitable condition by the method described in Protective Groups in Organic Synthesis, Theodora W Green (John Wiley & Sons) or the like.

(Step 8)

The eighth step is a step of reacting the compound (viii") with a reagent represented by the formula: $R^8$—$Y^2$-Hal⁸ wherein Hal⁸ is halogen; $Y^2$ is a single bond or C1-C3 alkylene; $R^8$ is as defined in (1) to obtain a compound (viii''').

The compound (viii''') can be obtained by reacting the compound (viii'') with a reagent represented by the formula: $R^8$—$Y^2$-$Hal^8$ wherein $Hal^8$ is halogen; $Y^2$ is a single bond or C1-C3 alkylene; $R^8$ is as defined in (1) at −20° C. to 200° C., preferably 0° C. to 100° C. in a solvent such as N,N-dimethylformamide, dimethyl sulfoxide, tetrahydrofuran, diethyl ether, toluene, n-hexane and the like in the presence of a base such as cesium carbonate, potassium carbonate, sodium carbonate, lithium carbonate, potassium bicarbonate, sodium bicarbonate, potassium hydroxide, sodium hydroxide, triethylamine, pyridine and the like.

As $Y^2$ in Method F, C1-C3 alkylene is preferable. Particularly, methylene is preferable.

As $R^8$ in Method F, phenyl optionally substituted with halogen, or pyridyl optionally substituted with halogen is preferable.

An alkoxyamine reagent represented by the formula: R—O—$NH_2$ wherein $R^1$ is as defined in (1) used in the third step of Method A is commercially available, or can be synthesized using, as a starting raw material, an alcohol compound which can be synthesized according to the method described in J. Med. Chem., 1999, 42:2007-2020, Liebigs Ann. Chem., 1988:1149-1153, Organic Letters, 2004, 6:4069-4072, Organic Letters, 2005, 7:937-939, WO 04/054514 or the like, according to the method described in WO 02/062313 or the like.

In the compound represented by the formula (I), compounds represented by the following formula (I-A) to formula (I-P) are preferable.

A compound represented in the formula (I-A):

[Chemical formula 39]

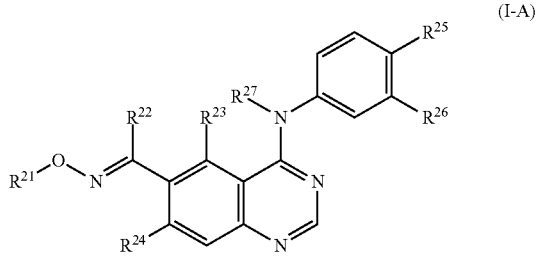

(I-A)

wherein $R^{21}$ is alkyl substituted with amino optionally substituted with a substituent selected from substituent group C consisting of alkyl, alkenyl, alkynyl, optionally substituted aryl, araklyl, alkyloxy, hydroxyalkyl, hydroxyalkyloxyalkyl, haloalkyl, aminoalkyl optionally substituted with 1 or 2 alkyl(s), alkylsulfonyl, alklysulfonylalkyl, alkylcarbonyl optionally substituted with halogen or alkyloxy, alkyloxycarbonyl, optionally substituted cycloalkyl, carboxyalkyl, optionally substituted aminocarbonylalkyl, optionally substituted aminocarbonyloxyalkyl, alkyloxyalkyl, alkylthioalkyl, alkylcarbonylaminoalkyl, alkylsulfonylaminoalkyl, alkylsulfonyl(alkyl)aminoalkyl, alkyloxycarbonylalkyl, alkylthio(hydroxy)alkyl, cycloalkylalkyl, cyanoalkyl, optionally substituted aminoalkylcarbonyl, optionally substituted heteroaryl, heteroarylalkyl, hydroxyalkyloxyalkyl, optionally substituted non-aromatic heterocyclic group, and optionally substituted non-aromatic heterocyclic alkyl; alkyl substituted with a non-aromatic nitrogen-containing heterocyclic group, wherein the non-aromatic nitrogen-containing heterocyclic group is selected from pyrrolidinyl, piperidyl, piperazinyl, morpholinyl, and thiomorpholinyl, optionally substituted with a substituent selected from substituent group D consisting of halogen; aryl; hydroxy; oxo; optionally substituted aminocarbonyl; alkyloxycarbonyl; alkyl optionally substituted with a substituent selected from substituent group H consisting of optionally substituted aminocarbonyl, cyano, alkyloxy, alkylsulfonylamino, amino, carboxy, alkyloxycarbonyl, and hydroxy; alkylaminocarbonyl; carboxy; cyano; alkylsulfonyl; alkylcarbonyl; alkenylcarbonyl; alkylsulfonylalkylcarbonyl; alkyloxyalkylcarbonyl; alkylcarbonylamino; aminocarbonyloxy; a non-aromatic nitrogen-containing heterocyclic group; and non-aromatic heterocyclic carbonyl; or a non-aromatic nitrogen-containing heterocyclic group, wherein the non-aromatic nitrogen-containing heterocyclic group is selected from azetidinyl, pyrrolidinyl, and piperidyl, optionally substituted with a substituent selected from substituent group B consisting of alkyloxycarbonyl, optionally substituted aminocarbonyl, oxo, amino, carboxy, cyano, cyanoalkyl, hydroxyalkyl, alkylcarbonylamino, alkylsulfonylamino, and aminocarbonylalkyl; $R^{22}$ is alkyl optionally substituted with a substituent selected from substituent group K consisting of amino optionally substituted with alkyl, hydroxy, alkyloxy, and halogen; alkenyl optionally substituted with a substituent selected from substituent group K, alkynyl optionally substituted with a substituent selected from substituent group K; hydroxy; halogen; phenyl; pyridyl; furyl; thienyl; or thiazolyl;

one of $R^{23}$ and $R^{24}$ is a hydrogen atom, and the other is a hydrogen atom, alkyloxy, alkyloxyalkyloxy, halogen, or aminoalkyl optionally substituted with alkyl, $R^{27}$ is a hydrogen atom, alkyl, or acyl; and $R^{25}$ and $R^{26}$ are each independently a hydrogen atom, halogen, alkynyl, hydroxy, alkyloxy, alkenyloxy, alkynyloxy, or heteroarylalkyloxy, its pharmaceutically acceptable salt, or a solvate thereof.

A compound represented by the formula (I-B):

[Chemical formula 40]

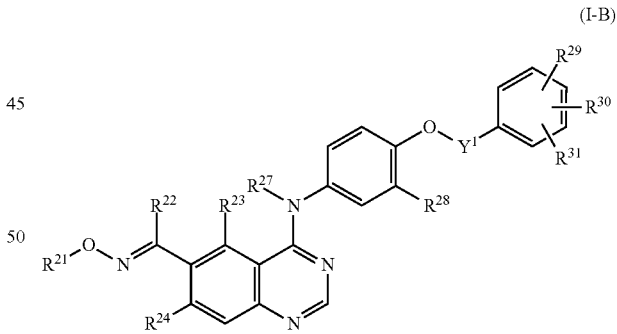

(I-B)

wherein $R^{21}$, $R^{22}$, $R^{23}$, $R^{24}$ and $R^{27}$ are as defined above;

$Y^1$ is C1-C3 alkylene;

$R^{28}$ is alkyl, alkyloxy, alkynyl, or halogen; and $R^{29}$, $R^{30}$, and $R^{31}$ are each independently a hydrogen atom or a substituent selected from substituent group F consisting of halogen, carboxy, alkyl, haloalkyl, hydroxyalkyl, alkyloxy, alkyloxycarbonyl, and optionally substituted amino, its pharmaceutically acceptable salt, or a solvate thereof A compound represented by the formula (I-C):

[Chemical formula 41]

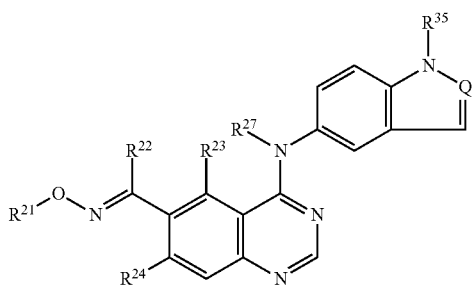
(I-C)

wherein $R^{21}$, $R^{22}$, $R^{23}$, $R^{24}$, and $R^{27}$ are as defined above;
$R^{35}$ is alkyl optionally substituted with a substituent selected from substituent group L consisting of hydroxy, alkyloxy, halogen, and cyano; alkenyl optionally substituted with a substituent selected from substituent group L; alkynyl optionally substituted with a substituent selected from substituent group L; or a group represented by the formula:

[Chemical formula 42]

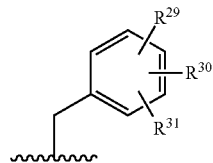

wherein $R^{21}$, $R^{30}$, and $R^{31}$ are as defined above;
Q is N or CH$_2$,
its pharmaceutically acceptable salt, or a solvate thereof.

A compound represented by the formula (I-D):

[Chemical formula 43]

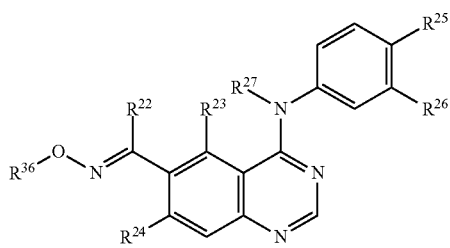
(I-D)

wherein $R^{21}$, $R^{22}$$R^{23}$, $R^{24}$, $R^{25}$, $R^{26}$, and $R^{27}$ are as defined above; and $R^{36}$ is alkyl substituted with aminocarbonyl optionally substituted with a substituent selected from substituent group C or
alkyl substituted with non-aromatic heterocyclic carbonyl, wherein the non-aromatic nitrogen-containing heterocycle is selected from pyrrolidinyl, piperidinyl, piperazinyl, morpholinyl, and thiomorpholinyl, optionally substituted with a substituent selected from substituent group D,
its pharmaceutically acceptable salt, or a solvate thereof.

A compound represented by the formula (I-E):

[Chemical formula 44]

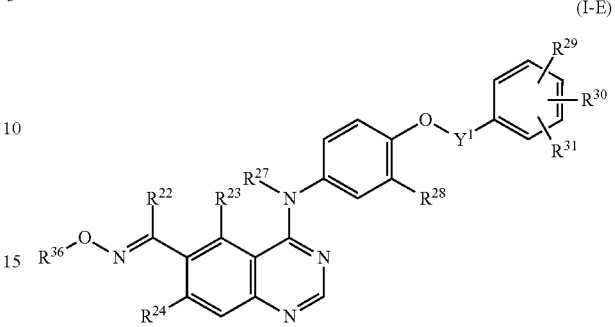
(I-E)

wherein $R^{21}$, $R^{22}$, $R^{23}$, $R^{24}$, $R^{27}$, $R^{28}$, $R^{29}$, $R^{30}$, $R^{31}$, $R^{36}$, and $Y^1$ are as defined above,
its pharmaceutically acceptable salt, or a solvate thereof.

A compound represented by the formula (I-F):

[Chemical formula 45]

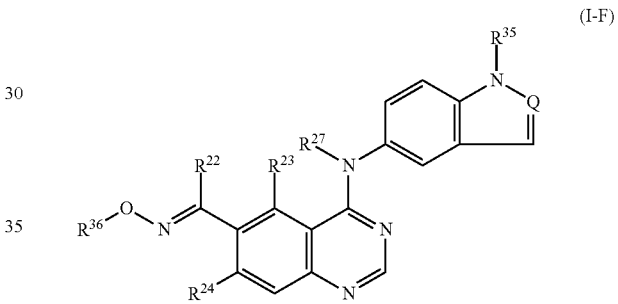
(I-F)

wherein $R^{22}$, $R^{23}$, $R^{24}$, $R^{27}$, $R^{36}$, and Q are as defined above,
its pharmaceutically acceptable salt, or a solvate thereof.

A compound represented by the formula (I-G):

[Chemical formula 46]

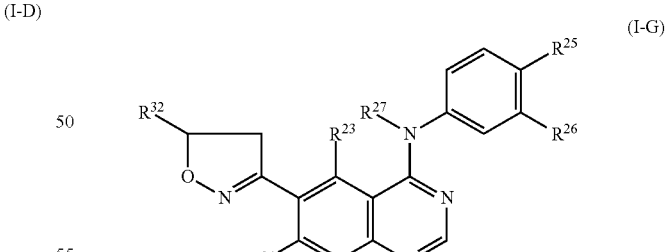
(I-G)

wherein $R^{23}$, $R^{24}$, $R^{25}$, $R^{26}$, and $R^{27}$ are as defined above;
$R^{32}$ is alkyl substituted with amino optionally substituted with a substituent selected from substituent group C,
alkyl substituted with a non-aromatic nitrogen-containing heterocyclic group, wherein the non-aromatic nitrogen-containing heterocyclic group is selected from pyrrolidinyl, piperidyl, piperazinyl, morpholinyl, and thiomorpholinyl, optionally substituted with a substituent selected from substituent group D, or a non-aromatic nitrogen-containing heterocyclic group, wherein the non-aromatic nitrogen-containing heterocyclic group is selected from azetidinyl, pyrrodilinyl, and piperidyl, optionally substituted with a substituent selected from substituent group B,
its pharmaceutically acceptable salt, or a solvate thereof.

A compound represented by the formula (I-H):

[Chemical formula 47]

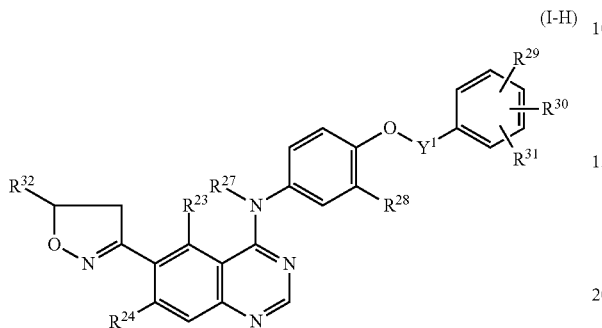
(I-H)

wherein $R^{23}$, $R^{24}$, $R^{27}$, $R^{28}$, $R^{29}$, $R^{30}$, $R^{31}$, $R^{32}$, and $Y^1$ are as defined above, its pharmaceutically acceptable salt, or a solvate thereof.

A compound represented by the formula (I-I):

[Chemical formula 48]

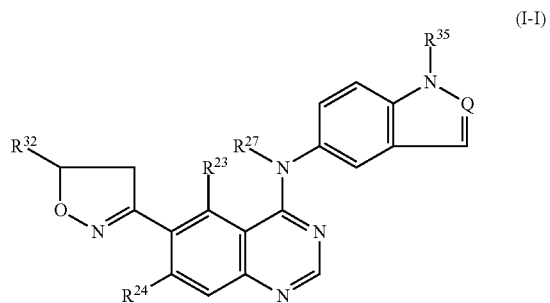
(I-I)

wherein $R^{23}$, $R^{24}R^{27}$, $R^{32}$, $R^{35}$, and Q are as defined above, its pharmaceutically acceptable salt, or a solvate thereof.

A compound represented by the formula (I-J):

[Chemical formula 49]

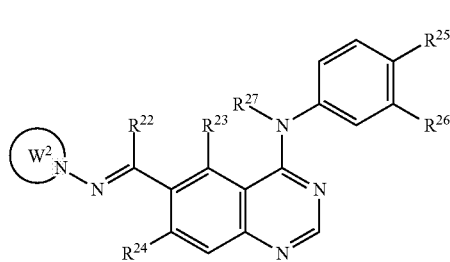
(I-J)

wherein $R^{22}$, $R^{23}$, $R^{24}$, $R^{25}$, $R^{25}$, and $R^{27}$ are as defined above;
$W^2$ is pyrrolidinyl optionally substituted with a substituent selected from substituent group J, piperidyl optionally substituted with a substituent selected from substituent group J, piperazinyl optionally substituted with a substituent selected from substituent group J, morpholinyl optionally substituted with a substituent selected from substituent group J, or triazolyl optionally substituted with a substituent selected from substituent group J, its pharmaceutically acceptable salt, or a solvate thereof.

A compound represented by the formula (I-K):

[Chemical formula 50]

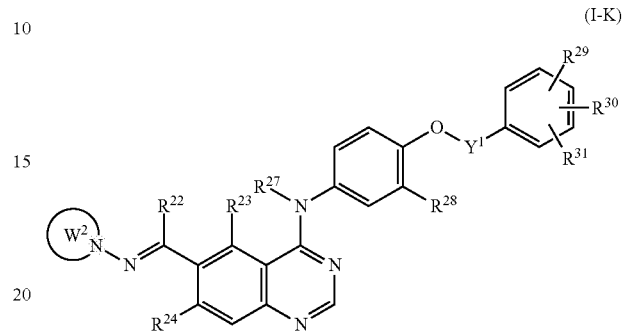
(I-K)

wherein $R^{22}$, $R^{23}$, $R^{24}$, $R^{27}$, $R^{28}$, $R^{29}$, $R^{30}$, $R^{31}$, $Y^1$, and $W^2$ are as defined above,
its pharmaceutically acceptable salt, or a solvate thereof.

A compound represented by the formula (I-L):

[Chemical formula 51]

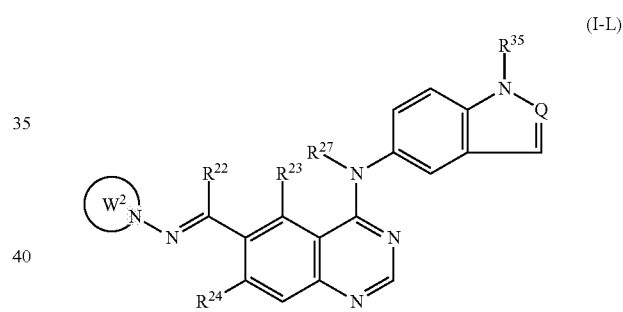
(I-L)

wherein $R^{22}$, $R^{23}$, $R^{24}$, $R^{27}$, $R^{35}$, $W^2$, and Q are as defined above,
its pharmaceutically acceptable salt, or a solvate thereof.

A compound represented by the formula (IM):

[Chemical formula 52]

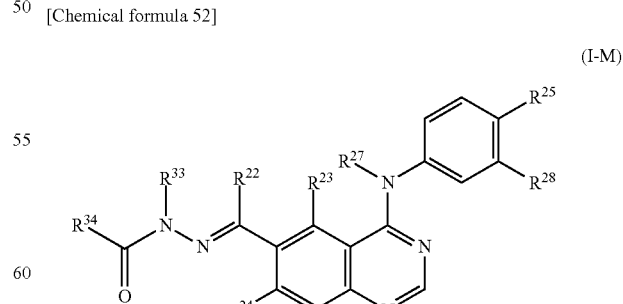
(I-M)

wherein $R^{22}$, $R^{23}$, $R^{24}$, $R^{25}$, $R^{26}$, and $R^{27}$ are as defined above;
$R^{33}$ is a hydrogen atom, C1-C6 alkyl optionally substituted with a substituent selected from substituent group L, C2-C6 alkenyl optionally substituted with a substituent selected from substituent group L, or C2-C6 alkynyl optionally substituted with a substituent selected from substituent group L; and $R^{34}$ is alkyl substituted with amino optionally substituted with a substituent selected from substituent group C, alkyl substituted with a non-aromatic nitrogen-containing heterocyclic group optionally substituted with a substituent selected from substituent group D, aryl optionally substituted with a substituent selected from substituent group F, heteroaryl optionally substituted with a substituent selected from substituent group F, or a non-aromatic heterocyclic group optionally substituted with a substituent selected from substituent group F, its pharmaceutically acceptable salt, or a solvate thereof.

A compound represented by the formula (I-N):

[Chemical formula 53]

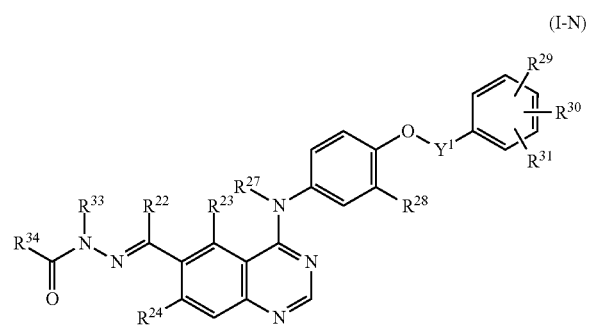

(I-N)

wherein $R^{22}$, $R^{23}$, $R^{24}$, $R^{27}$, $R^{28}$, $R^{29}$, $R^{30}$, $R^{31}$, $R^{33}$, $R^{34}$, and $Y^1$ are as defined above, its pharmaceutically acceptable salt, or a solvate thereof.

A compound represented by the formula (I-O):

[Chemical formula 54]

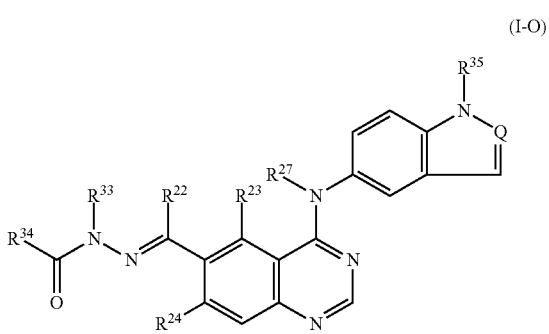

(I-O)

wherein $R^{22}$, $R^{23}$, $R^{24}$, $R^{27}$, $R^{34}$, $R^{35}$, and Q are as defined above, its pharmaceutically acceptable salt, or a solvate thereof.

A compound represented by the formula (I-P):

[Chemical formula 55]

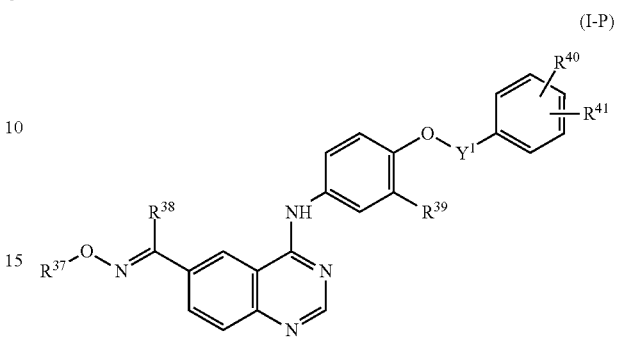

(I-P)

wherein $R^{37}$ is alkyl substituted with amino optionally substituted with alkyl, hydroxyalkyl, alkylcarbonylaminoalkyl or a non-aromatic heterocyclic group; alkyl substituted with a non-aromatic nitrogen-containing heterocyclic group optionally substituted with alkyl, hydroxyalkyl or alkylcarbonylamino; or a non-aromatic nitrogen-containing heterocyclic group substituted with hydroxyalkyl;

$R^{38}$ is C2-C4 alkynyl;

$R^{39}$ is halogen;

$R^{40}$ is a group represented by the formula: $-Y^3-R^{42}$ wherein $Y^3$ is alkylene which may be intervened with $-O-$; $R^{42}$ is phenyl optionally substituted with halogen, or pyridyl optionally substituted with halogen;

$R^{41}$ is halogen;

$Y^1$ is as defined above, its pharmaceutically acceptable salt, or a solvate thereof.

A compound represented by the formula (I-Q):

[Chemical formula 56]

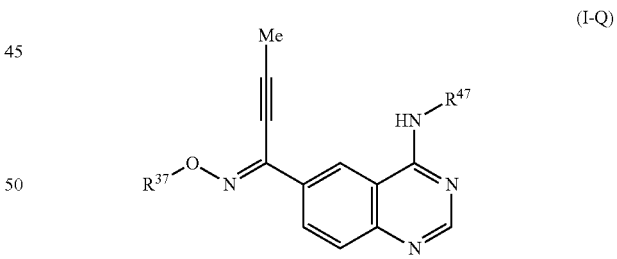

(I-Q)

wherein $R^{47}$ is a group represented by the formula:

[Chemical formula 57]

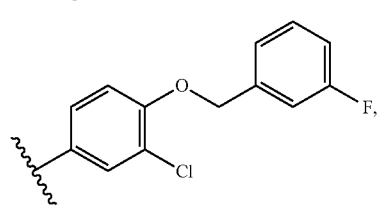

-continued

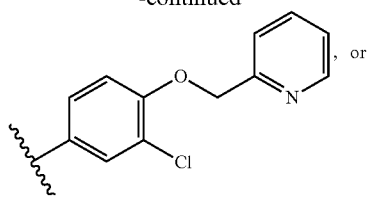, or

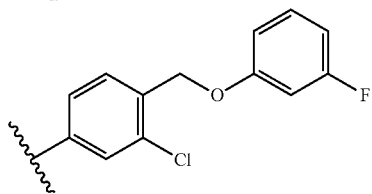

$R^{37}$ is as defined above,
its pharmaceutically acceptable salt, or a solvate thereof.

As $R^{22}$ in compounds represented by the formula (I-A) to the formula (I-F) and the formula (I-J) to the formula (I-O), methyl, ethyl, n-propyl, isopropyl, propynyl, butynyl, or phenyl is preferable.

Herein, the "solvate" includes, for example, a solvate with an organic solvent, a hydrate and the like. When a solvate is formed, the compound may be coordinated with an arbitrary number of water molecules.

When referred to the "present compound", a pharmaceutically acceptable salt, and a hydrate thereof are also included. Examples include salts of alkali metals (lithium, sodium, potassium etc.), or alkaline-earth metals (magnesium, calcium etc.), and ammonium, organic bases and amino acid, and salts with inorganic acids (hydrochloric acid, hydrobromic acid, phosphoric acid, sulfuric acid etc.), or organic acids (acetic acid, citric acid, maleic acid, fumaric acid, benzenesulfonic acid, p-toluenesulfonic acid etc.). These salts can be formed by methods which are usually performed.

In addition, the present compound is not limited to specified isomers, but includes all possible isomers and racemates.

The present compound, as described in Experiment Examples described later, exhibits the excellent cell proliferation inhibiting activity, and can be used as an "pharmaceutical composition useful for treating cancer" and a "therapeutic for a cancer".

When the present compound is administered to a human for the purpose of treating the aforementioned diseases, it can be orally administered as powders, granules, tablets, capsules, pills, solutions or the like, or parenterally administered as injectables, suppositories, transdermal absorbing agents, inhalants or the like. And, an effective amount of the present compound is mixed, if necessary, with pharmaceutical additives such as excipients, binders, wetting agents, disintegrating agents, lubricants and the like which are suitable for a dosage form, thereby, the present compound can be formulated into pharmaceutical preparations. In the case of injectables, the present compound together with a suitable carrier is subjected to sterilization treatment to obtain preparations.

A dose is different depending on the condition of a disease, an administration route, and an age or a weight of a patient, and is usually 0.1 to 100 mg/kg/day, preferably 1 to 20 mg/kg/day when orally administered to an adult.

The following Examples and Test Examples illustrate the present invention in more detail below, but the present invention is not limited by them.

In Examples, following abbreviations are used.
Me: methyl
Et: ethyl
nPr: n-propyl
iPr: isopropyl
Ph: phenyl

EXAMPLES

Example 1

[Chemical formula 58]

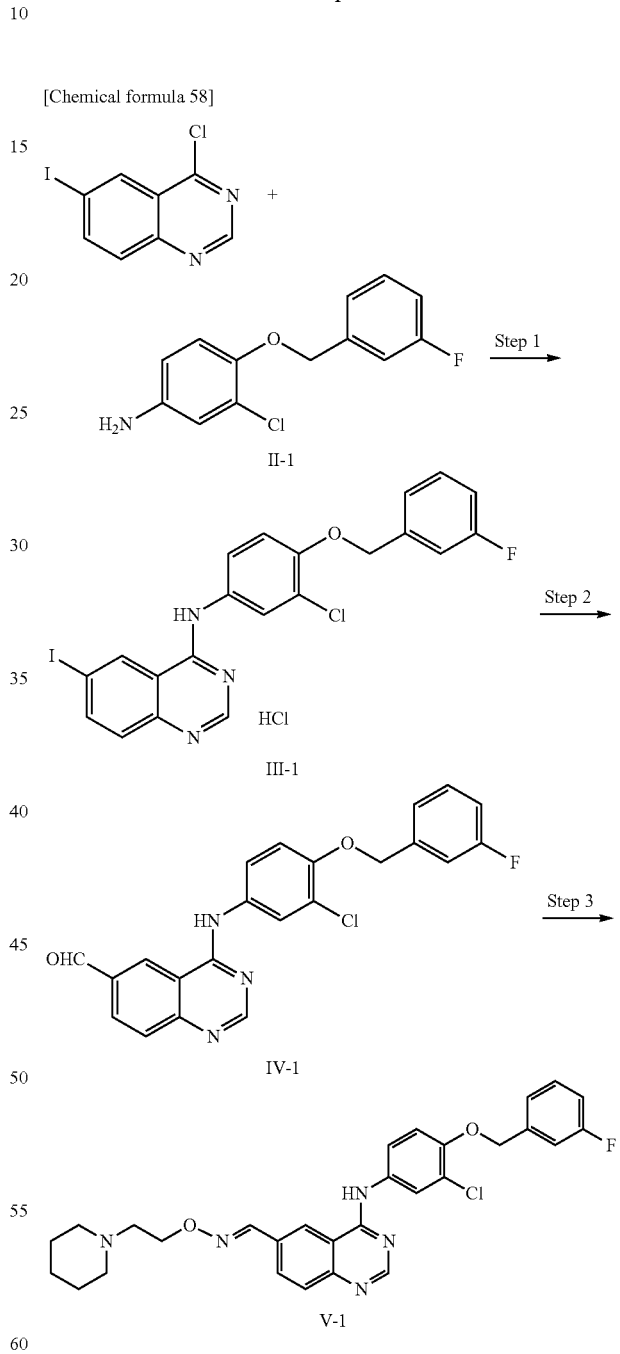

(Step 1) Synthesis of 4-(3-chloro-4-(3-fluorobenzyloxy)phenylamino)-6-iodoquinazoline (III-1) hydrochloride In 180 ml of tetrahydrofuran were dissolved 4-chloro-6-iodoquinazoline (6.0 g) and 3-chloro-4-(3-fluorobenzyloxy)

aniline (II-1, 5.2 g), followed by heat refluxing for 3 hours. A precipitate was filtered, and washed with tetrahydrofuran to obtain 4-(4-(3-fluorobenzyloxy)phenylamino)-6-iodoquinazoline hydrochloride (III-1, 10.5 g) as a yellow solid.

$^1$H NMR (d$_6$-DMSO δ): 11.47 (1H, brs), 9.25 (1H, s), 8.94 (1H, s), 8.36 (1H, dd, J=1.8 Hz, J=8.7 Hz), 7.92 (1H, d, J=2.7 Hz), 7.71 (1H, d, J=8.7 Hz), 7.66 (1H, dd, J=2.7 Hz, J=8.7 Hz), 7.48 (1H, dt, J=6.0 Hz, J=7.8 Hz), 7.37-7.30 (3H, m), 7.19 (1H, dt, J=2.7 Hz, J=8.7 Hz), 5.30 (2H, s).

The following compound was synthesized according to the same method as that of the above first step.

TABLE 1

[Chemical formula 59]

(III)

| Compound No. | R$^A$ | $^1$H-NMR(d$_6$-DMSO) |
|---|---|---|
| III-2 | —F | 9.86 (1H, s), 8.95 (1H, d, J = 1.5 Hz), 8.61 (1H, s), 8.11 (1H, dd, J = 1.8 Hz, J = 8.7 Hz), 7.89 (1H, J = 2.4 Hz, J = 13.5 Hz), 7.60-7.49 (2H, m), 7.45 (1H, dd, J = 6.3 Hz, J = 8.1 Hz), 7.36-7.23 (3H, m), 7.19 (1H, dt, J = 8.4 Hz, J = 2.1 Hz), 5.22 (2H, s). |
| III-3 | —OMe | 11.26 (1H, brs), 9.18 (1H, s), 8.89 (1H, s), 8.34 (1H, dd, J = 1.5 Hz, J = 8.7 Hz), 7.66 (1H, d, J = 8.7 Hz), 7.46 (1H, dt, J = 6.3 Hz, J = 8.1 Hz), 7.39 (1H, d, J = 2.1 Hz), 7.34-7.25 (3H, m), 7.22-7.13 (1H, m), 7.13 (1H, d, J = 8.7 Hz), 5.17 (2H, s), 3.82 (3H, s). |

(Step 2) Synthesis of 4-(3-chloro-4-(3-fluorobenzyloxy)phenylamino)-6-formylquinazoline (IV-1)

In 100 ml of dimethylformamide was dissolved 4-(4-(3-fluorobenzyloxy)phenylamino)-6-iodoquinazoline hydrochloride (III-1, 5.0 g), and 1.25 g of sodium formate, dichlorobis(triphenylphosphine)palladium (324 mg), and triethylamine (3.2 ml) were added. The reaction mixture was degassed, and stirred under heating at 80° C. for 3 hours under the carbon monoxide atmosphere. Thereafter, the reaction mixture was poured into ice water, and extracted with ethyl acetate. The extract was washed with water and sodium chloride solution, and dried with magnesium sulfate. The dried solution was filtered with Celite, concentrated, and powdered with an ethyl acetate-hexane (1:2) to obtain 4-(4-(3-fluorobenzyloxy)phenylamino)-6-formylquinazoline (IV-1, 2.86 g) as a yellow solid.

$^1$H NMR (d$_6$-DMSO δ): 10.24 (1H, s), 10.13 (1H, s), 9.16 (1H, s), 8.69 (1H, s), 8.27 (1H, br d, J=8.7 Hz), 8.03 (1H, d, J=2.1 Hz), 7.90 (1H, d, J=9.0 Hz), 7.74 (1H, dd, J=2.7 Hz, J=8.7 Hz), 7.48 (1H, dt, J=6.0 Hz, J=8.4 Hz), 7.36-7.30 (2H, m), 7.30 (1H, d, J=8.7 Hz), 7.19 (1H, br t, J=8.7 Hz), 5.27 (2H, s).

The following compound was synthesized according to the same method as that of the above second step.

TABLE 2

[Chemical formula 60]

(IV)

| Compound No. | R$^A$ | $^1$H-NMR(d$_6$-DMSO) |
|---|---|---|
| IV-2 | —F | 10.24 (1H, s), 10.14 (1H, s), 9.16 (1H, s), 8.69 (1H, s), 8.26 (1H, dd, J = 1.5 Hz, J = 8.7 Hz), 7.94-7.85 (2H, m), 7.55 (1H, br d, J = 9.0 Hz), 7.47 (1H, dt, J = 6.3 Hz, J = 8.1 Hz), 7.36-7.26 (3H, m), 7.23-7.15 (1H, m), 5.23 (2H, s). |
| IV-3 | —OMe | 10.13 (2H, s), 9.18 (1H, s), 8.64 (1H, s), 8.25 (1H, dd, J = 1.5 Hz, J = 8.7 Hz), 7.88 (1H, d, J = 8.4 Hz), 7.52-7.38 (3H, m), 7.34-7.26 (2H, m), 7.22-7.12 (1H, m), 7.07 (1H, d, J = 8.7 Hz), 5.14 (2H, s), 3.83 (3H, s). |

(Step 3) Synthesis of 4-(3 chloro-4-(3-fluorobenzyloxy)phenylamino)-6-(2-(1-piperidyl)ethoxyimino) quinazoline (V-1)

In a mixture of tetrahydrofuran (2 ml) and water (0.1 ml) were dissolved 4-(3-chloro-4-(3-fluorobenzyloxy)phenylamino)-6-formylquinazoline (IV-1, 50 mg) and 2-(1-piperidyl)ethoxyamine dihydrochloride (36.5 mg), and the mixture was stirred at room temperature overnight. The reaction mixture was diluted with ethyl acetate, washed sequentially with aqueous saturated sodium bicarbonate solution, and aqueous sodium chloride solution, and dried over magnesium sulfate. After concentration, the residue was purified by chromatography (eluting with hexane:ethyl acetate=2:3) using an amino column, and further re-purified by thin layer chromatography to obtain 4-(3-chloro-4-(3-fluorobenzyloxy)phenylamino)-6-(2-(1-piperidyl)ethoxyimino)$_q$ quinazoline (V-1, 13 mg).

$^1$H NMR (d$_6$-DMSO, δ): 9.95 (1H, s), 8.63 (1H, s), 8.59 (1H, s), 8.34 (1H, s), 8.10 (1H, d, J=9.3 Hz), 8.00 (1H, d, J=2.4 Hz), 7.79 (1H, d, J=8.7 Hz), 7.72 (1H, dd, J=9.0 Hz, J=2.1 Hz), 7.51-47.4 (1H, m), 7.36-7.31 (2H, m), 7.28 (1H, d, J=9.0 Hz), 7.19 (1H, br t, J=9.0 Hz), 5.26 (2H, s), 4.28 (2H, t, J=6.0 Hz), 2.63 (2H, t, J=6.0 Hz), 2.41 (4H, t, J=4.8 Hz), 1.50 (4H, quin, J=5.3 Hz), 1.45-1.35 (2H, m).

Example 2

[Chemical formula 61]

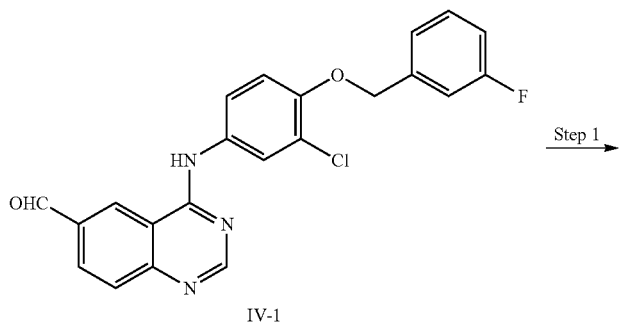

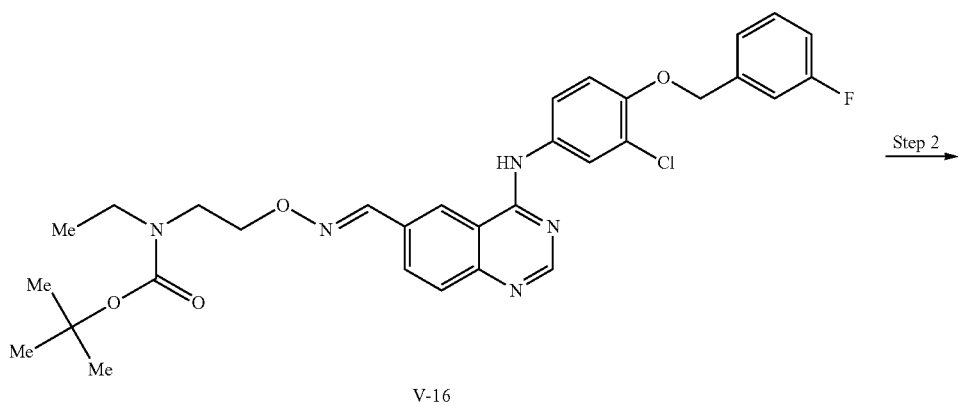

(Step 1) Synthesis of 4-(3-chloro-4-(3-fluorobenzyloxy)phenylamino)-6-(2-(N-(t-butoxycarbonyl)-N-ethylamino)ethyloxyimino)quinazoline (V-16)

In tetrahydrofuran (1.5 ml) were dissolved 4-(3-chloro-4-(3-fluorobenzyloxy)phenylamino)-6-formylquinazoline (IV-1, 120 mg) and N-(t-butoxycarbonyl)ethylaminoethoxyamine (110 mg), and 134 μl of 2 mol/L hydrochloric acid was added, then the mixture was stirred at room temperature for 4 hours. After completion of the reaction, the reaction mixture was poured into aqueous ice-cooled saturated sodium bicarbonate solution, and extracted with ethyl acetate. The organic layer was washed with water and aqueous sodium chloride solution, dried over magnesium sulfate, and concentrated. The resulting residue was purified by amino column chromatography (eluting with hexane:ethyl acetate=1:1), and further re-purified by silica gel chromatography (eluting with hexane:ethyl acetate=1:1) to obtain 4-(3-chloro-4-(3-fluorobenzyloxy)phenylamino)-6-(2-(N-(t-butoxycarbonyl)-N-ethylamino)ethyloxyimino)quinazoline (V-16, 96 mg) as a yellow viscous oil.

$^1$H NMR (d$_6$-DMSO, δ): 9.93 (1H, s), 8.63 (1H, brs), 8.60 (1H, s), 8.34 (1H, s), 8.12 (1H: dd, J=1.2 Hz, J=9.0 Hz), 8.01 (1H, d, J=2.4 Hz), 7.79 (1H, d, J=8.4 Hz), 7.72 (1H, dd, J=2.4 Hz, J=8.4 Hz), 7.48 (1H, dt, J=6.0 Hz, J=8.1 Hz), 7.36-7.30 (2H, m), 7.28 (1H, d, J=9.0 Hz), 7.23-7.14 (1H, m), 5.26 (2H, s), 4.26 (2H, t, J=5.7 Hz), 3.50 (2H, t, J=63 Hz), 3.23 (2H, q, J=6.9 Hz), 1.38 (9H, s), 1.12-1.00 (3H, m).

The following compound was synthesized according to the same manner as that of the above first step.

TABLE 3

[Chemical formula 62]

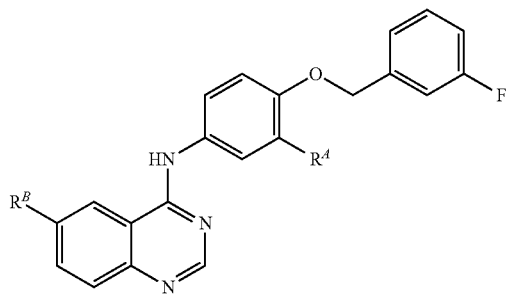

(V)

| Compound No. | $R^A$ | $R^B$ | $^1$H-NMR($d_6$-DMSO) |
|---|---|---|---|
| V-18 | Cl | Me-N(Me)-C(Me)₃-O-C(=O)-N(Me)-CH₂CH₂-O-N= | 9.92 (1H, s), 8.62 (1H, s), 8.60 (1H, s), 8.34 (1H, s), 8.12 (1H, d, J = 8.4 Hz), 8.00 (1H, d, J = 2.4 Hz), 7.79 (1H, d, J = 8.7 Hz), 7.72 (1H, dd, J = 2.4 Hz, J = 8.7 Hz), 7.47 (1H, dt, J = 6.0 Hz, J = 7.8 Hz), 7.36-7.30 (2H, m), 7.28 (1H, d, J = 9.0 Hz), 7.23-7.14 (1H, m), 5.26 (2H, s), 4.28 (2H, t, J = 5.7 Hz), 3.57-3.48 (2H, m), 2.84 (3H, brs), 1.36 (9H, s). |
| V-19 | Cl | Boc-N(cyclohexyl)-CH₂CH₂-O-N= | 9.92 (1H, s), 8.63 (1H, s), 8.60 (1H, s), 8.33 (1H, s), 8.12 (1H, dd, J = 1.5 Hz, J = 9.0 Hz), 8.01 (1H, d, J = 2.4 Hz), 7.80 (1H, d, J = 8.7 Hz), 7.72 (1H, dd, J = 2.7 Hz, J = 9.0 Hz), 7.47 (1H, dt, J = 6.0 Hz, J = 7.8 Hz), 7.36-7.30 (2H, m), 7.28 (1H, d, J = 9.0 Hz), 7.22-7.14 (1H, m), 5.26 (2H, s), 4.21 (2H, t, J = 6.0 Hz), 3.8-3.5 (1H, brs), 3.48-3.37 (2H, m), 1.8-1.4 (6H, m), 1.35-1.0 (4H, m). |
| V-20 | OMe | Boc-N(Et)-CH₂CH₂-O-N= | 9.83 (1H, s), 8.64 (1H, s), 8.57 (1H, s), 8.34 (1H, s), 8.12 (1H, dd, J = 1.5 Hz, J = 8.7 Hz), 7.78 (1H, d, J = 8.7 Hz), 7.50-7.36 (3H, m), 7.34-7.26 (2H, m), 7.21-7.13 (1H, m), 7.06 (1H, d, J = 8.7 Hz), 5.13 (2H, s), 4.26 (2H, t, J = 5.7 Hz), 3.82 (3H, s), 3.50 (2H, t, J = 5.7 Hz), 3.23 (2H, q, J = 7.2 Hz), 1.38 (9H, s), 1.12-1.02 (3H, m). |
| V-21 | OMe | Boc-N(Me)-CH₂CH₂-O-N= | 9.84 (1H, s), 8.63 (1H, s), 8.56 (1H, s), 8.36 (1H, s), 8.12 (1H, dd, J = 1.5 Hz, J = 8.7 Hz), 7.77 (1H, d, J = 8.7 Hz), 7.50-7.35 (3H, m), 7.33-7.25 (2H, m), 7.20-7.12 (1H, m), 7.05 (1H, d, J = 8.7 Hz), 5.13 (2H, s), 4.27 (2H, t, J = 5.7 Hz), 3.82 (3H, s), 3.55-3.47 (2H, m), 2.84 (3H, brs), 1.36 (9H, s). |
| V-22 | OMe | Boc-N(cyclohexyl)-CH₂CH₂-O-N= | 9.82 (1H, s), 8.64 (1H, s), 8.56 (1H, s), 8.33 (1H, s), 8.11 (1H, dd, J = 1.5 Hz, J = 8.7 Hz), 7.78 (1H, d, J = 8.7 Hz), 7.50-7.36 (3H, m), 7.33-7.26 (2H, m), 7.21-7.12 (1H, m), 7.05 (1H, d, J = 8.7 Hz), 5.13 (2H, s), 4.21 (2H, t, J = 6.6 Hz), 3.82 (3H, s), 3.8-3.5 (1H, m), 3.47-3.35 (2H, m), 1.8-1.35 (6H, m), 1.41 (9H, s), 1.35-0.95 (4H, m). |
| V-28 | Cl | N-Boc-pyrrolidin-2-yl-CH₂-O-N= | 9.91 (1H, s), 8.62 (1H, brs), 8.60 (1H, s), 8.36 (1H, s), 8.10 (1H, dd, J = 8.7 Hz), 8.01 (1H, brs), 7.79 (1H, d, J = 8.4 Hz), 7.73 (1H, d, J = 8.1 Hz), 7.52-7.44 (1H, m), 7.35-7.27 (3H, m), 7.19 (1H, dt, J = 8.1 Hz, J = 2.4 Hz), 5.26 (2H, s), 4.28 (1H, brs), 4.17 (1H, dd, J = 10.5 Hz, J = 6.9 Hz), 4.00 (1H, brs), 3.25 (3H, br), 1.92 (3H, br), 1.80 (1H, br), 1.43 (9H, s) |

(Step 2) Synthesis of 4-(3-chloro-4-(3-fluorobenzyloxy)phenylamino)-6-(2-(N-ethylamino)ethyloxyimino)quinazoline (V-17)

In chloroform (1.8 ml) was dissolved 4-(3-chloro-4-(3-fluorobenzyloxy)phenylamino)-6-(2-(N-(t-butoxycarbonyl)-N-ethylamino)ethyloxyimino)quinazoline (V-16, 54 mg), and trifluoroacetic acid (1.8 ml) was added, followed by stirring at room temperature for 1 hour. After completion of the reaction, the reaction mixture was concentrated, and diluted with ethyl acetate. The mixture was sequentially washed with aqueous saturated sodium bicarbonate solution, water, and aqueous sodium chlorite solution, and dried over magnesium sulfate. After concentration, the crystalline residue was washed with a mixture of dichloromethane-hexane (1:4) to obtain 4-(3-chloro-4-(3-fluorobenzyloxy)phenylamino)-6-(2-(N-ethylamino)ethyloxyimino)quinazoline (V-17, 28 mg) as a white solid.

$^1$H NMR (d$_6$-DMSO, δ): 9.96 (1H, s), 8.65 (1H, brs), 8.60 (1H, s), 8.35 (1H, s), 8.11 (1H, d, J=9.0 Hz), 8.01 (1H, J=3.0 Hz), 7.80 (1H, d, J=9.0 Hz), 7.75-7.70 (1H, m), 7.52-7.43 (1H, m), 7.36-7.31 (2H, m), 7.28 (1H, d, J=9.3 Hz), 7.23-7.14 (1H, m), 5.26 (2H, s), 4.26 (2H, t, J=6.0 Hz), 2.03 (2H, t, J=6.0 Hz), 2.66 (2H, q, J=7.2 Hz), 1.05 (3H, t, J=7.2 Hz).

Example 3

(Step 1) Synthesis of 4-(3-chloro-4-(3-fluorobenzyloxy)phenylamino)-6-(1-(N-cyanomethylpyrrolidin-2-yl)methoxyimino)methylquinazoline (V-30)

In 0.4 mL of N,N-dimethylacetamide were dissolved 40 mg of Compound V-29 and 8 μL of iodoacetonitrile, and 15 mg of potassium carbonate was added, followed by stirring at room temperature for 1 hour. After the reaction, aqueous saturated sodium chloride solution was added, followed by extraction with ethyl acetate. The organic layer was dehydrated by passing through Presep (registered trademark), and the filtrate was concentrated. The concentrated residue was purified by silica gel chromatography (eluting with hexane:ethyl acetate=2:1) to obtain 35 mg of 4-(3-chloro-4 (3-fluorobenzyloxy)phenylamino)-6-(1-(N-cyanomethylpyrrolidin-2-yl)methoxyimino)methylquinazoline (V-30).

$^1$H NMR (d$_6$-DMSO, δ): 9.92 (1H, s), 8.62 (1H, d, J=1.5 Hz), 8.58 (1H, s), 8.36 (1H, s), 8.00 (1H, dd, J=8.7 Hz, J=1.5 Hz), 7.99 (1H, d, J=2.6 Hz), 7.78 (1H, d. J=8.7 Hz), 7.71 (1H, dd, J=9.0 Hz, J=2.6 Hz), 7.49-7.42 (1H, m), 7.33-7.25 (3H, m), 7.16 (1H, dt. J=8.1 Hz, J=1.8 Hz), 5.24 (2H, s), 4.17 (2H, d, J=5.7 Hz), 3.97 (1H, d, J=1.7 Hz), 3.90 (1H, J=17 Hz), 3.00-2.89 (2H, m), 2.01-1.89 (1H, m), 1.78-1.54 (3H, m).

[Chemical formula 63]

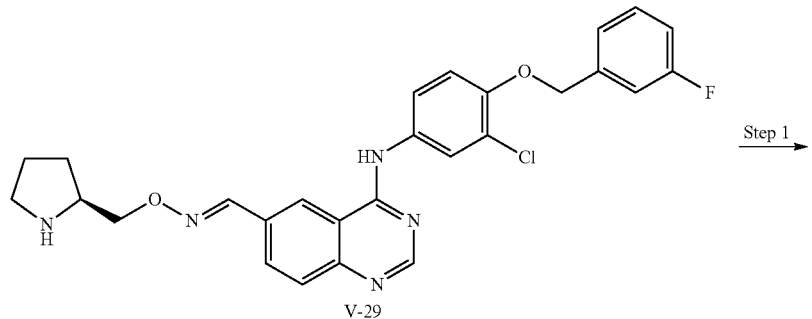

V-29

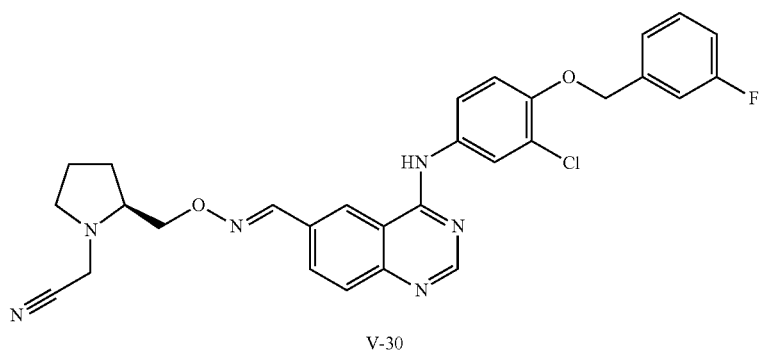

V-30

Example 4

[Chemical formula 64]

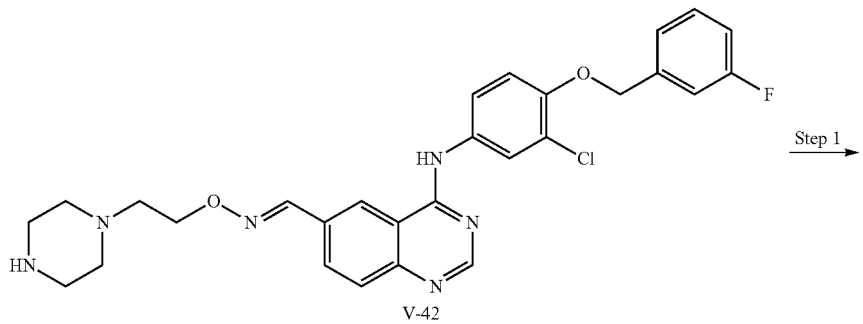

(Step 1) Synthesis of 4-(3-chloro-4-(3-fluorobenzyloxy)phenylamino)-6-(2-(4-acryloyl-1-piperazin-1-yl)ethoxyimino)methylquinazoline (V-43)

In 1.5 mL of tetrahydrofuran were dissolved 40 mg of Compound V-42 and 6 μL of acryloyl chloride, followed by stirring at room temperature for 2 hours. After the reaction, aqueous saturated sodium, chloride solution was added, followed by extraction with ethyl acetate. The organic layer was dehydrated by passing through CHEM ELUT (trade name), and the filtrate was concentrated. The concentrated residue was purified by chromatography (eluting with 1% methanol-containing ethyl acetate), and the resulting residue was solidified with hexane-ethyl acetate (6:1) to obtain 20 mg of 4-(3-chloro-4-(3-fluorobenzyloxy)phenylamino)-6-(2-(4-acryloyl-1-piperazin-1-yl)ethoxyimino)methylquinazoline (V-43).

$^1$H NMR (d$_6$-DMSO, δ): 9.95 (1H, s), 8.64 (1H, s), 8.59 (1H, s), 8.35 (1H, s), 8.10 (1H, d, J=8.7 Hz), 8.00 (1H, d, J=2.4 Hz), 7.78 (1H, d, J=8.7 Hz), 7.72 (1, dd, J=9.0 Hz, 2.7 Hz), 7.44-7.51 (1H, m), 7.26-7.35 (3H, m), 7.15-7.22 (1H, m), 6.79 (1H, dd, J=16.5 Hz, 10.2 Hz), 6.10 (1H, dd, J=16.5 Hz, 2.4 Hz), 6.17 (1H, dd, J=10.5 Hz, 2.4 Hz), 5.26 (2H, s), 4.32 (2H, t, J=5.7 Hz), 3.55 (4H, m), 2.72 (2H, t, J=5.7 Hz), 2.50 (4H, m)

Example 5

[Chemical formula 65]

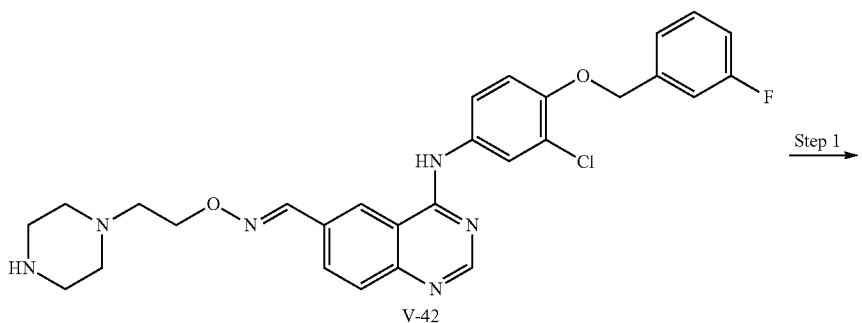

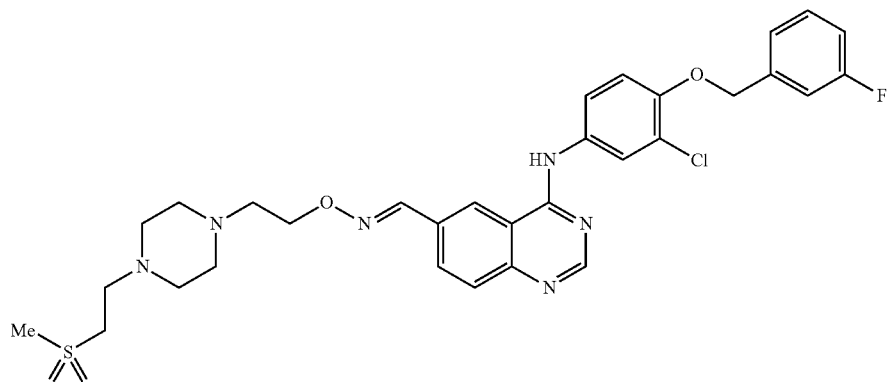

V-44

(Step 1) Synthesis of 4-(3-chloro-4-(3-fluorobenzy-loxy)phenylamino)-6-(2-(4-(2-methanesulfonyl-ethyl)-1-piperazin-1-yl)ethoxyimino)methylquinazo-line (V-44)

In 1 mL of tetrahydrofuran were dissolved 25 mg of Compound V-42 and 4 μL of methylvinylsulfone, followed by stirring at room temperature for 21 hours. Further, 4 μL of methylvinylsulfone was added, followed by stirring at room temperature for 29 hours. After the reaction, aqueous saturated sodium chloride solution was added, followed by extraction with ethyl acetate. The organic layer was washed sequentially with water, and aqueous saturated sodium chloride solution, and dried over magnesium sulfate. The concentrated residue was purified by chromatography (eluting with ethyl acetate) using an amino column, and the resulting residue was solidified with hexane-ethyl acetate (6:1) to obtain 15 mg of 4-(3-chloro-4-(3-fluorobenzyloxy)phenylamino)-6-(2-(4-(2-methanesulfonylethyl)-1-piperazin-1-yl)ethoxy-imino)methylquinazoline (V-44).

$^1$H NMR (d$_6$-DMSO, δ): 9.95 (1H, s), 8.63 (1H, s), 8.59 (1H, s), 8.34 (1H, s), 8.10 (1H, d, J-9.6 Hz), 8.00 (1H, d, J=2.4 Hz), 7.79 (1H, d, J=8.4 Hz), 7.71 (1H, dd, J=8.7 Hz, 2.7 Hz), 7.44-7.51 (1H, m), 7.26-7.34 (3H, m), 7.15-7.22 (1H, m), 5.26 (2H, s), 4.29 (2H, t, J=6.0 Hz), 3.27 (2H, t, J=6.6 Hz), 3.02 (3H, s), 2.67-2.70 (4H, m), 2.46 (8H, m)

The following compound was synthesized according to the same methods as that of Examples 1 to 5.

TABLE 4

[Chemical formula 66]

(V)

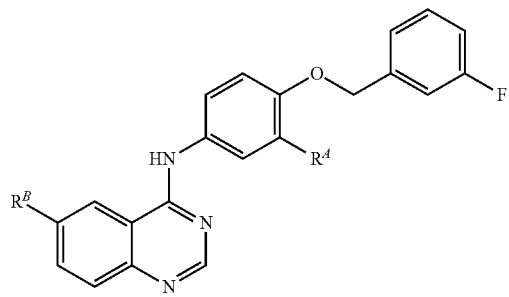

| Compound No. | R$^A$ | R$^B$ | $^1$H-NMR(d$_6$-DMSO) |
|---|---|---|---|
| V-2 | Cl | HO-N= | 11.69 (1H, s), 11.11 (1H, brs), 8.84 (1H, s), 8.83 (1H, s), 8.29 (1H, s), 8.26 (1H, d, J = 8.7 Hz), 7.95 (1H, d, J = 2.7 Hz), 7.88 (1H, d, J = 8.7 Hz), 7.67 (1H, dd, J = 2.3 Hz, J = 9.2 Hz), 7.48 (1H, dt, J = 6.0 Hz, J = 7.8 Hz), 7.37-7.29 (3H, m), 7.20 (1H, br t, J = 9.2 Hz), 5.30 (2H, s). |
| V-3 | Cl | MeO-N= | 9.96 (1H, s), 8.65 (1H, s), 8.60 (1H, s), 8.34 (1H, s), 8.10 (1H, br d, J = 8.7 Hz), 8.01 (1H, d, J = 2.4 Hz), 7.79 (1H, d, J = 8.4 Hz), 7.73 (1H, dd, J = 2.7 Hz, J = 9.0 Hz), 7.48 (1H, dt, J = 6.0 Hz, J = 8.1 Hz), 7.36-7.31 (2H, m), 7.28 (1H, d, J = 9.0 Hz), 7.19 (1H, br t, J = 8.7 Hz), 5.26 (2H, s), 3.98 (3H, s). |

TABLE 4-continued

[Chemical formula 66]

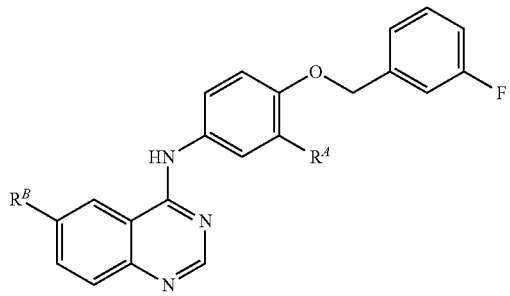
(V)

| Compound No. | $R^A$ | $R^B$ | $^1$H-NMR(d$_6$-DMSO) |
|---|---|---|---|
| V-4 | Cl | Me-CH(Me)-CH2-O-N=CH- | 9.95 (1H, s), 8.63 (1H, s), 8.60 (1H, s), 8.36 (1H, s), 8.10 (1H, dd, J = 8.7 Hz, J = 1.2 Hz), 8.01 (1H, d, J = 2.4 Hz), 7.79 (1H, d, J = 8.4 Hz), 7.72 (1H, dd, J = 2.6 Hz, J = 8.9 Hz), 7.48 (1H, dt, J = 6.0 Hz, J = 8.1 Hz), 7.36-7.29 (2H, m), 7.28 (1H, d, J = 9.0 Hz), 7.19 (1H, dt, J = 2.4 Hz, J = 8.6 Hz), 5.27 (2H, s), 3.97 (2H, d, J = 6.9 Hz), 2.05 (1H, m), 0.95 (6H, d, J = 6.9 Hz). |
| V-5 | Cl | CH2=CH-CH2-O-N=CH- | 9.96 (1H, s), 8.64 (1H, s), 8.60 (1H, s), 8.39 (1H, s), 8.11 (1H, dd, J = 1.5 Hz, J = 8.7 Hz), 8.01 (1H, d, J = 2.7 Hz), 7.79 (1H, d, J = 8.7 Hz), 7.72 (1H, dd, J = 2.7 Hz, J = 9.0 Hz), 7.48 (1H, dt, J = 6.3 Hz, J = 7.8 Hz), 7.36-7.29 (2H, m), 7.28 (1H, d, J = 9.0 Hz), 7.19 (1H, dt, J = 2.2 Hz, J = 8.6 Hz), 6.08 (1H, ddt, J = 17.4 Hz, J = 10.5 Hz, J = 5.7 Hz), 5.38 (1H, ddd, J = 17.4 Hz, J = 3.6 Hz, J = 1.8 Hz), 5.30-5.24 (1H, m), 5.26 (2H, s), 4.72 (2H, dt, J = 5.7 Hz, J = 1.5 Hz). |
| V-6 | Cl | pyrrolidin-1-yl-CH2CH2-O-N=CH- | 9.95 (1H, s), 8.64 (1H, s), 8.60 (1H, s), 8.35 (1H, s), 8.11 (1H, br d, J = 8.7 Hz), 8.00 (1H, d, J = 2.7 Hz), 7.79 (1H, d, J = 8.7 Hz), 7.72 (1H, dd, J = 2.7 Hz, J = 9.0 Hz), 7.51-7.44 (1H, m), 7.36-7.31 (2H, m), 7.28 (1H, d, J = 9.3 Hz), 7.19 (1H, br t, J = 8.4 Hz), 5.26 (2H, s), 4.29 (2H, t, J = 6.3 Hz), 2.810 (2H, t, J = 4.8 Hz), 2.6-2.5 (4H, m), 1.75-1.65 (4H, m). |
| V-7 | Cl | morpholin-4-yl-CH2CH2-O-N=CH- | 9.95 (1H, s), 8.64 (1H, s), 8.60 (1H, s), 8.35 (1H, s), 8.11 (1H, dd, J = 8.7 Hz, J = 1.5 Hz), 8.01 (1H, d, J = 2.7 Hz), 7.80 (1H, d, J = 9.0 Hz), 7.72 (1H, dd, J = 9.0 Hz, J = 2.7 Hz), 7.48 (1H, dt, J = 6.0 Hz, J = 8.1 Hz), 7.36-7.31 (2H, m), 7.28 (1H, d, J = 9.3 Hz), 7.19 (1H, br t J = 9.0 Hz), 5.27 (2H, s), 4.31 (2H, t, J = 5.7 Hz), 2.46 (4H, t, J = 4.5 Hz). |

TABLE 5

| Compound No. | $R^A$ | $R^B$ | $^1$H-NMR(d$_6$-DMSO) |
|---|---|---|---|
| V-8 | —Cl | (2-ethoxyethyl)(ethyl)amino-propyl-O-N=CH- | 9.94 (1H, s), 8.63 (1H, s), 8.59 (1H, s), 8.33 (1H, s), 8.10 (1H, br d, J = 7.2 Hz), 8.00 (1H, d, J = 2.4 Hz), 7.78 (1H, d, J = 8.7 Hz), 7.71 (1H, dd, J = 8.7 Hz, J = 2.1 Hz), 7.47 (1H, dt, J = 6.3 Hz, J = 8.1 Hz), 7.36-7.31 (2H, m), 7.28 (1H, d, J = 9.0 Hz), 7.18 (1H, br t, J = 9.0 Hz), 5.26 (2H, s), 4.23 (2H, t, J = 6.3 Hz), 3.57 (4H, t, J = 4.5 Hz), 2.45-2.35 (6H, m), 1.87 (2H, quin, J = 6.8 Hz). |
| V-9 | —Cl | Me2N-CH2CH2-O-N=CH- | 9.95 (1H, s), 8.63 (1H, s), 8.60 (1H, s), 8.34 (1H, s), 8.11 (1H, dd, J = 8.7 Hz, J = 1.5 Hz), 8.00 (1H, d, J = 2.7 Hz), 7.79 (1H, d, J = 8.7 Hz), 7.72 (1H, dd, J = 8.7 Hz, J = 2.7 Hz), 7.48 (1H, dt, J = 6.0 Hz, J = 8.1 Hz), 7.36-7.31 (2H, m), 7.28 (1H, d, J = 9.0 Hz), 7.18 (1H, dt, J = 2.4 Hz, J = 8.4 Hz), 5.26 (2H, s), 4.28 (2H, t, J = 5.7 Hz), 2.63 (2H, t, J = 5.7 Hz), 2.23 (6H, s). |
| V-10 | —Cl | Et2N-CH2CH2-O-N=CH- | 9.93 (1H, s) 8.63 (1H, s), 8.60 (1H, s), 8.33 (1H, s), 8.11 (1H, dd, J = 8.7 Hz, J = 1.5 Hz), 8.01 (1H, d, J = 2.4 Hz), 7.79 (1H, d, J = 8.7 Hz), 7.72 (1H, dd, J = 2.7 Hz, J = 8.7 Hz), 7.47 (1H, dt, J = 5.7 Hz, J = 8.1 Hz), 7.36-7.31 (2H, m), 7.28 (1H, d, J = 9.3 Hz), 7.18 (1H, dt, J = 8.7 Hz, J = 2.7 Hz), 5.26 (2H, s), 4.25 (2H, t, J = 6.2 Hz), 2.79 (2H, brs), 2.57 (4H, q, J = 6.6 Hz), 0.99 (6H, t, J = 7.1 Hz). |

TABLE 5-continued

| Compound No. | $R^A$ | $R^B$ | $^1$H-NMR($d_6$-DMSO) |
|---|---|---|---|
| V-11 | —Cl | Me₂CH-N(CHMe₂)-CH₂CH₂-O-N= (diisopropylamino-ethoxyimino) | 9.91 (1H, s), 8.61 (1H, d, J = 1.5 Hz), 8.60 (1H, s), 8.31 (1H, s), 8.12 (1H, dd, J = 1.5 Hz, J = 8.7 Hz), 8.01 (1H, d, J = 2.4 Hz), 7.79 (1H, d, J = 8.7 Hz), 7.72 (1H, dd, J = 2.4 Hz, J = 8.7 Hz), 7.47 (1H, dt, J = 5.7 Hz, J = 8.1 Hz), 7.36-7.31 (2H, m), 7.28 (1H, d, J = 9.3 Hz), 7.18 (1H, dt, J = 8.7 Hz, J = 2.7 Hz), 5.26 (2H, s), 4.10 (2H, t, J = 6.9 Hz), 3.01 (2H, quin, J = 6.3 Hz), 2.74 (2H, t, J = 6.9 Hz), 1.99 (12H, d, 6.3 Hz). |
| V-12 | —F | pyrrolidin-1-yl-CH₂CH₂-O-N= | 9.94 (1H, s), 8.64 (1H, s), 8.60 (1H, s), 8.34 (1H, s), 8.11 (1H, d, J = 8.8 Hz), 7.88 (1H, d, J = 13.2 Hz), 7.79 (1H, d, J = 8.8 Hz), 7.56-7.44 (2H, m), 7.36-7.24 (3H, m), 7.19 (1H, br t, J = 8.8 Hz), 5.18 (2H, s), 4.32-4.27 (2H, m), 2.82-2.74 (2H, m), 2.55-2.48 (4H, m), 1.73-1.65 (4H, m). |
| V-13 | —OMe | pyrrolidin-1-yl-CH₂CH₂-O-N= | 9.84 (1H, s), 8.64 (1H, d, J = 1.5 Hz), 8.55 (1H, s), 8.34 (1H, s), 8.09 (1H, dd, J = 1.5 Hz, J = 8.7 Hz), 7.77 (1H, d, J = 8.7 Hz), 7.49-7.36 (3H, m), 7.33-7.26 (2H, m), 7.20-7.12 (1H, m), 7.05 (1H, d, J = 9.0 Hz), 5.13 (2H, s), 4.28 (2H, t, J = 6.0 Hz), 3.82 (3H, s), 2.76 (2H, t, J = 6.0 Hz), 2.54-2.46 (4H, m), 1.76-1.62 (4H, m). |

TABLE 6

| Compound No. | $R^A$ | $R^B$ | $^1$H-NMR($d_6$-DMSO) |
|---|---|---|---|
| V-23 | Cl | Me-NH-CH₂CH₂-O-N= | 9.96 (1H, s), 8.64 (1H, s), 8.60 (1H, s), 8.34 (1H, s), 8.11 (1H, dd, J = 1.2 Hz, J = 8.4 Hz), 8.01 (1H, d, J = 2.4 Hz), 7.79 (1H, d, J = 8.7 Hz), 7.72 (1H, dd, J = 2.4 Hz, J = 8.7 Hz), 7.48 (1H, dt, J = 6.0 Hz, J = 8.4 Hz), 7.36-7.30 (2H, m), 7.28 (1H, d, J = 9.0 Hz), 7.23-7.15 (1H, m), 5.27 (2H, s), 4.24 (2H, t, J = 5.7 Hz), 2.81 (2H, t, J = 5.7 Hz), 2.33 (3H, s). |
| V-24 | Cl | cyclohexyl-NH-CH₂CH₂-O-N= | 9.95 (1H, s), 8.65 (1H, d, J = 1.2 Hz), 8.60 (1H, s), 8.35 (1H, s), 8.11 (1H, dd, J = 1.5 Hz, J = 8.7 Hz), 8.01 (1H, d, J = 2.7 Hz), 7.79 (1H, d, J = 8.7 Hz), 7.73 (1H, dd, J = 2.7 Hz, J = 9.0 Hz), 7.47 (1H, dt, J = 6.0 Hz, J = 8.1 Hz), 7.36-7.30 (2H, m), 7.28 (1H, d, J = 9.0 Hz), 7.23-7.14 (1H, m), 5.26 (2H, s), 4.25 (2H, t, J = 5.7 Hz), 2.95 (2H, t, J = 5.7 Hz), 2.55-2.4 (1H, m), 1.9-1.8 (2H, m), 1.75-1.62 (2H, m), 1.6-1.5 (1H, m), 1.3-0.97 (5H, m). |
| V-25 | OMe | Me-CH₂-NH-CH₂CH₂-O-N= | 9.86 (1H, s), 8.64 (1H, s), 8.56 (1H, s), 8.34 (1H, s), 8.10 (1H, d, J = 8.4 Hz), 7.77 (1H, d, J = 8.7 Hz), 7.5-7.35 (3H, m), 7.34-7.26 (2H, m), 7.21-7.13 (1H, m), 7.06 (1H, d, J = 8.7 Hz), 5.13 (2H, s), 4.23 (2H, t, J = 6.0 Hz), 3.82 (3H, s), 2.86 (2H, t, J = 6.0 Hz), 2.59 (2H, q, J = 7.2 Hz), 1.02 (3H, t, J = 7.2 Hz). |
| V-26 | OMe | Me-NH-CH₂CH₂-O-N= | 9.86 (1H, s), 8.64 (1H, s), 8.56 (1H, s), 8.33 (1H, s), 8.10 (1H, d, J = 8.7 Hz), 7.77 (1H, d, J = 9.0 Hz), 7.50-7.35 (3H, m), 7.33-7.26 (2H, m), 7.21-7.13 (1H, m), 7.05 (1H, d, J = 8.4 Hz), 5.13 (2H, s), 4.23 (2H, t, J = 5.7 Hz), 3.82 (3H, s), 2.81 (2H, d, J = 6.0 Hz), 2.33 (3H, s). |
| V-27 | Ome | cyclohexyl-NH-CH₂CH₂-O-N= | 9.86 (1H, s), 8.64 (1H, s), 8.56 (1H, s), 8.34 (1H, s), 8.09 (1H, dd, J = 1.5 Hz, J = 8.7 Hz), 7.77 (1H, d, J = 8.7 Hz), 7.50-7.35 (3H, m), 7.33-7.26 (2H, m), 7.21-7.13 (1H, m), 7.05 (1H, d, J = 8.7 Hz), 5.13 (2H, s), 4.22 (2H, t, J = 5.7 Hz), 3.82 (3H, s), 2.88 (2H, t, J = 5.7 Hz), 2.45-2.35 (1H, m), 1.88-1.76 (2H, m), 1.72-1.62 (2H, m), 1.6-1.5 (2H, m), 1.3-0.93 (4H, m). |
| V-29 | Cl | pyrrolidin-2-yl-CH₂-O-N= | 9.94 (1H, s), 8.65 (1H, trs), 8.60 (1H, s), 8.35 (1H, s), 8.11 (1H, dd, J = 8.7 Hz, J = 1.2 Hz), 8.00 (1H, d, J = 2.4 Hz), 7.79 (1H, d, J = 8.7 Hz), 7.72 (1H, dd, J = 9.0 Hz, J = 2.1 Hz), 7.51-7.44 (1H, m), 7.35-7.27 (3H, m), 7.18 (1H, dt, J = 8.1 Hz, J = 1.5 Hz), 5.26 (2H, s), 4.12 (2H, d, J = 6.3 Hz), 3.53-3.44 (1H, m), 2.96-2.82 (2H, m), 1.94-1.64 (3H, m), 1.53-1.41 (1H, m) |

TABLE 7

| Compound No. | $R^A$ | $R^B$ | $^1$H-NMR(d$_6$-DMSO) |
|---|---|---|---|
| V-30 | —Cl | (1,1-dioxo-thiomorpholin-4-yl)ethyl-O-N= | 9.95 (1H, s), 8.64 (1H, s), 8.59 (1H, s), 8.35 (1H, s), 8.11 (1H, d, J = 8.7 Hz), 8.00 (1H, d, J = 2.4 Hz), 7.79 (1H, d, J = 8.7 Hz), 7.71 (1H, dd, J = 8.4 Hz, J = 1.8 Hz), 7.44-7.51 (1H, m), 7.26-7.35 (3H, m), 7.15-7.22 (1H, m), 5.26 (2H, s), 4.31 (2H, t, J = 5.7 Hz), 3.08-3.10 (4H, m), 3.02-3.04 (4H, m), 2.91 (2H, t, J = 5.7 Hz) |
| V-31 | —Cl | (1,1-dioxo-thiomorpholin-4-yl)propyl-O-N= | 9.95 (1H, s), 8.63 (1H, s), 8.60 (1H, s), 8.34 (1H, s), 8.11 (1H, d, J = 9.3 Hz), 8.00 (1H, d, J = 2.7 Hz), 7.79 (1H, d, J = 8.7 Hz), 7.72 (1H, dd, J = 9.0 Hz, J = 2.4 Hz), 7.51-7.44 (1H, m), 7.35-7.27 (3H, m), 7.22-7.15 (1H, m), 5.26 (2H, s), 4.23 (2H, t, J = 6.3 Hz), 3.09-3.07 (4H, m), 2.92-2.90 (4H, m), 2.59 (2H, t, J = 6.9 Hz), 1.90-1.85 (2H, m) |
| V-32 | —Cl | Et$_2$N-propyl-O-N= | 9.94 (1H, s), 8.64 (1H, s), 8.59 (1H, s), 8.33 (1H, s), 8.10 (1H, d, J = 8.7 Hz), 8.00 (1H, d, J = 2.7 Hz), 7.79 (1H, d, J = 8.7 Hz), 7.72 (1H, dd, J = 8.7 Hz, 2.4 Hz), 7.44-7.51 (1H, m), 7.26-7.35 (3H, m), 7.15-7.22 (1H, m), 5.26 (2H, s), 4.22 (2H, t, J = 6.3 Hz), 2.49-2.51 (6H, m), 1.78-1.83 (2H, m), 0.95 (6H, t, J = 7.2 Hz) |
| V-33 | —Cl | morpholino-CH$_2$-CH(Me)-O-N= | 9.94 (1H, s), 8.61 (1H, s), 8.59 (1H, s), 8.31 (1H, s), 8.11 (1H, dd, J = 8.4 Hz, 1.5 Hz), 8.00 (1H, d, J = 2.7 Hz), 7.79 (1H, d, J = 8.7 Hz), 7.71 (1H, dd, J = 9.3 Hz, 2.7 Hz), 7.44-7.51 (1H, m), 7.26-7.35 (3H, m), 7.15-7.22 (1H, m), 5.26 (2H, s), 4.50-4.56 (1H, m), 3.57 (4H, t, J = 4.8 Hz), 2.59-2.65 (2H, m), 2.46 (4H, m), 1.31 (3H, d, J = 6.0 Hz) |
| V-34 | —Cl | MeSO$_2$-CH$_2$CH$_2$-NH-CH$_2$CH$_2$-O-N= | 9.95 (1H, s), 8.65 (1H, s), 8.60 (1H, s), 8.34 (1H, s), 8.12 (1H, dd, J = 9.0 Hz, 1.8 Hz), 8.01 (1H, d, J = 2.7 Hz), 7.79 (1H, d, J = 8.7 Hz), 7.72 (1H, dd, J = 8.7 Hz, J = 2.4 Hz), 7.44-7.52 (1H, m), 7.27-7.35 (3H, m), 7.16-7.22 (1H, m), 5.27 (2H, s), 4.25 (2H, t, J = 5.4 Hz), 3.25 (2H, t, J = 6.9 Hz), 3.02 (3H, s), 2.99 (2H, t, J = 6.9 Hz), 2.89 (2H, t, J = 5.7 Hz) |
| V-35 | —Cl | MeSO$_2$-CH$_2$CH$_2$-NH-CH(Me)-CH$_2$-O-N= | 9.95 (1H, s), 8.65 (1H, s), 8.60 (1H, s), 8.36 (1H, s), 8.12 (1H, dd, J = 8.7 Hz, 1.8 Hz), 8.01 (1H, d, J = 2.7 Hz), 7.80 (1H, d, J = 8.7 Hz), 7.72 (1H, dd, J = 9.0 Hz, 2.4 Hz), 7.44-7.52 (1H, m), 7.27-7.35 (3H, m), 7.16-7.22 (1H, m), 5.27 (2H, s), 4.04-4.09 (2H, m), 3.20-3.26 (2H, m), 2.98-3.08 (6H, m), 1.06 (3H, d, J = 6.3 Hz) |

TABLE 8

| Compound No. | $R^A$ | $R^B$ | $^1$H-NMR(d$_6$-DMSO) |
|---|---|---|---|
| V-36 | —Cl | MeSO$_2$-CH$_2$CH$_2$-NH-CH(CH$_2$O-N=)-Me | 9.95 (1H, s), 8.63 (1H, s), 8.60 (1H, s), 8.32 (1H, s), 8.13 (1H, d, J = 9.0 Hz), 8.00 (1H, d, J = 2.7 Hz), 7.80 (1H, d, J = 8.4 Hz), 7.72 (1H, dd, J = 9.3 Hz, 2.7 Hz), 7.44-7.52 (1H, m), 7.27-7.35 (3H, m), 7.16-7.22 (1H, m), 5.27 (2H, s), 4.40-4.46 (1H, m), 3.27 (2H, t, J = 6.9 Hz), 2.99-3.02 (5H, m), 2.74-2.90 (2H, m), 1.30 (3H, d, J = 6.6 Hz) |
| V-37 | —Cl | MeSO$_2$-CH$_2$CH$_2$-NH-CH$_2$CH$_2$CH$_2$-O-N= | 9.95 (1H, s), 8.64 (1H, s), 8.60 (1H, s), 8.34 (1H, s), 8.11 (1H, dd, J = 9.0 Hz, 1.2 Hz), 8.01 (1H, d, J = 2.7 Hz), 7.79 (1H, d, J = 8.7 Hz), 7.72 (1H, dd, J = 8.7 Hz, 2.7 Hz), 7.44-7.51 (1H, m), 7.26-7.34 (3H, m), 7.16-7.22 (1H, m), 5.26 (2H, s), 4.25 (2H, t, J = 6.3 Hz), 3.25 (2H, t, J = 7.2 Hz), 3.03 (3H, s), 2.98 (2H, t, J = 6.9 Hz), 2.70 (2H, t, J = 6.9 Hz), 1.84-1.91 (2H, m) |
| V-38 | —Cl | MeCH$_2$-O-CH$_2$CH$_2$-NH-CH$_2$CH$_2$-O-N= | 9.96 (1H, s), 8.64 (1H, s), 8.60 (1H, s), 8.35 (1H, s), 8.11 (1H, dd, J = 8.7 Hz, 1.5 Hz), 8.01 (1H, d, J = 2.4 Hz), 7.79 (1H, d, J = 8.7 Hz), 7.73 (1H, dd, J = 9.0 Hz, 2.7 Hz), 7.44-7.52 (1H, m), 7.27-7.35 (3H, m), 7.16-7.22 (1H, m), 5.27 (2H, s), 4.25 (2H, t, J = 5.4 Hz), 3.38-3.46 (4H, m), 2.91 (2H, t, J = 5.7 Hz), 2.73 (2H, t, J = 5.4 Hz), 1.09 (3H, t, J = 6.9 Hz) |

TABLE 8-continued

| Compound No. | R^A | R^B | ^1H-NMR(d_6-DMSO) |
|---|---|---|---|
| V-39 | —Cl | H_2N-CH_2-CH_2-O-N=CH- (wavy) | 9.96 (1H, s), 8.63 (1H, brs), 8.60 (1H, s), 8.34 (1H, s), 8.11 (1H, dd, J = 8.7 H, J = 1.5 Hz), 8.00 (1H, d, J = 2.4 Hz), 7.79 (1H, d, J = 8.7 Hz), 7.72 (1H, dd, J = 9.0 Hz, J = 2.4 Hz), 7.52-7.44 (1H, m), 7.35-7.27 (3H, m), 7.20 (1H, dt, J = 9.3 Hz, J = 2.7 Hz), 5.27 (2H, s), 4.37 (2H, t, J = 6.0 Hz), 3.51 (2H, t, J = 6.0 Hz) |
| V-40 | —Cl | azetidinyl-O-N=CH- | 9.95 (1H, s), 8.64 (1H, brs), 8.59 (1H, s), 8.40 (1H, s), 8.09 (1H, d, J = 6.6 Hz), 8.01 (1H, brs), 7.78 (1H, d, J = 6.3 Hz), 7.72 (1H, d, J = 6.3 Hz), 7.50-7.45 (1H, m), 7.35-7.26 (3H, m), 7.19 (1H, t, J = 6.3 Hz), 5.26 (2H, s), 5.09 (1H, m), 3.69 (2H, t-like, J = 5.1 Hz), 3.60 (2H, t-like, J = 5.1 Hz) |
| V-41 | —Cl | pyrrolidinyl-O-N=CH- | 9.93 (1H, s), 8.62(1H, brs), 8.59 (1H, s), 8.30 (1H, s), 8.11 (1H, d, J = 6.3 Hz), 8.00 (1H, d, J = 1.5 Hz), 7.79 (1H, d, J = 6.6 Hz), 7.72 (1H, dd, J = 6.6 Hz, J = 1.8 Hz), 7.50-7.45 (1H, m), 7.35-7.27 (3H, m), 7.19 (1H, t, J = 5.7 Hz), 5.26 (2H, s), 4.88 (1H, brs), 3.01-2.88 (3H, m), 2.79-2.73 (1H, m), 1.99-1.85 (2H, m) |
| V-42 | —Cl | piperazinyl-CH_2CH_2-O-N=CH- | 9.95 (1H, s), 8.63 (1H, brs), 8.60 (1H, s), 8.35 (1H, s), 8.11 (1H, dd, J = 8.7 Hz, J = 1.5 Hz), 8.01 (1H, d, J = 2.4 Hz), 7.79 (1H, d, J = 8.7 Hz), 7.72 (1H, dd, J = 9.3 Hz, J = 2.7 Hz), 7.52-7.44 (1H, m), 7.35-7.27 (3H, m), 7.19 (1H, dt, J = 9.3 Hz, J = 2.7 Hz), 5.27 (2H, s), 4.29 (2H, t, J = 6.0 Hz), 2.69 (4H, t, J = 4.8 Hz), 2.63 (2H, t, J = 6.0 Hz), 2.39 (4H, brs) |

TABLE 9

| Compound No. | R^A | R^B | ^1H-NMR(d_6-DMSO) |
|---|---|---|---|
| V-45 | —Cl | H_2N-C(O)-CH_2-N(pyrrolidinyl)-CH_2-O-N=CH- | 9.93 (1H, s), 8.63 (1H, brs), 8.60 (1H, s), 8.33 (1H, s), 8.10 (1H, d, J = 6.6 Hz), 8.02 (1H, d, J = 1.5 Hz), 7.79 (1H, d, J = 6.6 Hz), 7.73 (1H, d, J = 6.9 Hz), 7.50-7.45 (1H, m), 7.35-7.27 (3H, m), 7.19 (2H, m), 7.08 (1H, brs), 5.26 (2H, s), 4.20 (1H, dd, J = 8.1 Hz, J = 4.2 Hz), 4.13 (1H, dd, J = 8.1 Hz, J = 4.2 Hz), 3.38 (1H, d, J = 12 Hz), 3.08-2.93 (3H, m), 2.38 (1H, m), 1.99-1.89 (1H, m), 1.76-1.57 (3H, m) |
| V-46 | —Cl | HO-CH_2CH_2-N(pyrrolidinyl)-CH_2-O-N=CH- | 9.93 (1H, s), 8.63 (1H, brs), 8.60 (1H, s), 8.34 (1H, s), 8.11 (1H, d, J = 6.6 Hz), 8.01 (1H, d, J = 2.1 Hz), 7.80 (1H, d, J = 6.6 Hz), 7.73 (1H, d, J = 8.1 Hz), 7.51-7.44 (1H, m), 7.35-7.27 (3H, m), 7.19 (1H, m), 5.27 (2H, s), 4.38 (1H, brs), 4.19 (1H, dd, J = 8.1 Hz, J = 4.2 Hz), 4.03 (1H, dd, J = 8.1 Hz, J = 4.2 Hz), 3.49 (2H, dd, J = 9.3Hz, J = 4.5 Hz), 3.09-3.05 (1H, m), 2.95-2.90 (1H, m), 2.84-2.82 (1H, m), 2.47-2.40 (1H, m), 2.29-2.22 (1H, m), 1.91-1.85 (1H, m), 1.73-1.57 (3H, m) |
| V-47 | —Cl | N≡C-CH_2-N(azetidinyl)-O-N=CH- | 9.94 (1H, s), 8.66 (1H, brs), 8.60 (1H, s), 8.43 (1H, s), 8.12 (1H, d, J = 6.6 Hz), 8.01 (1H, d, J = 1.2 Hz), 7.79 (1H, d, J = 6.9 Hz), 7.72 (1H, d, J = 6.6 Hz), 7.50-7.45 (1H, m), 7.35-7.27 (3H, m), 7.19 (1H, t, J = 6.0 Hz), 5.27 (2H, s), 4.97 (1H, m), 3.74 (2H, s), 3.68 (2H, t-like, J = 5.1 Hz), 3.37 (2H, t-like, J = 5.1 Hz) |
| V-48 | —Cl | HO-CH_2CH_2-N(azetidinyl)-O-N=CH- | 9.95 (1H, s), 8.64 (1H, brs), 8.60 (1H, s), 8.39 (1H, s), 8.09 (1H, d, J = 6.6 Hz), 8.01 (1H, brs), 7.79 (1H, d, J = 6.3 Hz), 7.73 (1H, d, J = 6.6 Hz), 7.50-7.45 (1H, m), 7.35-7.27 (3H, m), 7.19 (1H, t, J = 6.6 Hz), 5.26 (2H, s), 4.92 (1H, m), 4.42 (1H, brs), 3.62 (2H, t, J = 5.4 Hz), 3.14 (2H, t, J = 5.4 Hz), 2.54 (2H, t, J = 4.5 Hz) |
| V-49 | —Cl | N≡C-CH_2-N(pyrrolidinyl)-O-N=CH- | 9.94 (1H, s), 8.63 (1H, brs), 8.60 (1H, s), 8.32 (1H, s), 8.11 (1H, d, J = 6.6 Hz), 8.01 (1H, d, J = 1.8 Hz), 7.79 (1H, d, J = 6.6 Hz), 7.72 (1H, dd, J = 6.9 Hz, J = 1.8 Hz), 7.50-7.45 (1H, m), 7.35-7.27 (3H, m), 7.19 (1H, t, J = 6.3 Hz), 5.26 (2H, s), 4.95 (1H, brs), 3.87 (2H, s), 2.91-2.81 (3H, m), 2.57-2.51 (1H, m), 2.30-2.21 (1H, m), 2.00-1.91 (1H, m) |

TABLE 9-continued

| Compound No. | $R^A$ | $R^B$ | $^1$H-NMR($d_6$-DMSO) |
|---|---|---|---|
| V-50 | —Cl | 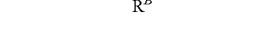 | 9.95 (1H, s), 8.62 (1H, brs), 8.59 (1H, s), 8.32 (1H, s), 8.10 (1H, d, J = 6.3 Hz), 8.00 (1H, brs), 7.79 (1H, d, J = 6.3 Hz), 7.72 (1H, d, J = 6.3 Hz), 7.50-7.45 (1H, m), 7.35-7.27 (3H, m), 7.19 (1H, t, J = 6.0 Hz), 5.26 (2H, s), 4.89 (1H, brs), 4.45 (1H, brs), 3.49 (3H, m), 2.82-2.75 (3H, m), 2.41-2.39 (1H, m), 2.17 (1H, m), 1.86 (1H, brs) |

TABLE 10

| Compound No. | $R^A$ | $R^B$ | $^1$H-NMR($d_6$-DMSO) |
|---|---|---|---|
| V-51 | —Cl | | 9.94 (1H, s), 8.64 (1H, s), 8.60 (1H, s), 8.33 (1H, s), 8.12 (1H, d, J = 10.2 Hz), 8.01 (1H, d, J = 2.4 Hz), 7.79 (1H, d, J = 8.7 Hz), 7.72 (1H, dd, J = 8.7 Hz, 2.4 Hz), 7.44-7.51 (1H, m), 7.26-7.34 (3H, m), 7.16-7.22 (1H, m), 5.26 (2H, s), 4.29 (2H, t, J = 5.7 Hz), 3.27 (2H, t, J = 7.2 Hz), 3.02 (3H, s), 2.84 (2H, t, J = 6.9 Hz), 2.75 (2H, t, J = 5.7 Hz), 2.29 (3H, s) |
| V-52 | —Cl | | 9.94 (1H, s), 8.64 (1H, s), 8.59 (1H, s), 8.35 (1H, s), 8.10 (1H, dd, J = 8.7 Hz, 1.5 Hz), 8.00 (1H, d, J = 2.7 Hz), 7.78 (1H, d, J = 8.7 Hz), 7.71 (1H, dd, J = 8.7 Hz, 2.4 Hz), 7.44-7.51 (1H, m), 7.26-7.35 (3H, m), 7.15-7.21 (1H, m), 5.26 (2H, s), 4.32 (2H, t, J = 5.7 Hz), 3.42-3.43 (4H, m), 2.71 (2H, t, J = 5.7 Hz), 2.41 (4H, t, J = 5.1 Hz), 1.98 (3H, s) |
| V-53 | —Cl | | 9.95 (1H, s), 8.63 (1H, s), 8.59 (1H, s), 8.35 (1H, s), 8.10 (1H, dd, J = 8.4 Hz, 1.2 Hz), 8.00 (d, 1H, J = 2.4 Hz), 7.79 (1H, d, J = 8.4 Hz), 7.71 (1H, dd, J = 9.3 Hz, 2.4 Hz), 7.44-7.51 (1H, m), 7.26-7.34 (3H, m), 7.15-7.22 (1H, m), 5.26 (2H, s), 4.32 (2H, t, J = 5.4 Hz), 3.43-3.45 (4H, m), 2.70 (2H, t, J = 5.7 Hz), 2.41-2.46 (4H, m), 2.26 (2H, t, J = 7.2 Hz), 1.43-1.56 (2H, m), 0.87 (3H, t, J = 7.5 Hz) |
| V-54 | —Cl | | 9.94 (1H, s), 8.63 (1H, s), 8.59 (1H, s), 8.35 (1H, s), 8.10 (1H, dd, J = 8.7 Hz, 1.5 Hz), 8.00 (1H, d, J = 2.4 Hz), 7.78 (1H, d, J = 8.7 Hz), 7.71 (1H, dd, J = 9.0 Hz, 2.4 Hz), 7.44-7.51 (1H, m), 7.26-7.35 (3H, m), 7.15-7.21 (1H, m), 5.26 (2H, s), 4.32 (2H, t, J = 5.7 Hz), 4.06 (3H, s), 3.37-3.42 (4H, m), 3.27 (2H, s), 2.71 (2H, t, J = 5.7 Hz), 2.46 (4H, m) |
| V-55 | —Cl | | 9.94 (1H, s), 8.63 (1H, s), 8.59 (1H, s), 8.35 (1H, s), 8.10 (1H, dd, J = 8.7 Hz, 1.5 Hz), 8.00 (1H, d, J = 2.4 Hz), 7.79 (1H, d, J = 8.7 Hz), 7.71 (1H, dd, J = 9.0 Hz, 2.4 Hz), 7.44-7.51 (1H, m), 7.26-7.35 (3H, m), 7.15-7.21 (1H, m), 5.26 (2H, s), 4.32 (2H, t, J = 5.7 Hz), 3.53 (2H, t, J = 6.6 Hz), 3.43-3.47 (4H, m), 3.21 (3H, s), 2.71 (2H, t, J = 6.0 Hz), 2.55 (2H, t, J = 6.6 Hz), 2.42-2.50 (4H, m) |
| V-56 | —Cl | | 9.94 (1H, s), 8.64 (1H, s), 8.59 (1H, s), 8.35 (1H, s), 8.10 (1H, dd, J = 8.7 Hz, 1.5 Hz), 8.00 (1H, d, J = 2.7 Hz), 7.79 (1H, d, J = 9.0 Hz), 7.71 (1H, dd, J = 8.7 Hz, 2.4 Hz), 7.44-7.51 (1H, m), 7.26-7.35 (3H, m), 7.15-7.22 (1H, m), 5.26 (2H, s), 4.61-4.66 (1H, m), 4.32 (2H, t, J = 5.7 Hz), 3.68-3.80 (2H, m), 3.44-3.54 (4H, m), 2.71 (2H, 5.7 Hz), 2.44-2.50 (4H, m), 1.95-2.04 (2H, m), 1.75-1.86 (2H, m) |

TABLE 11
| Compound No. | $R^A$ | $R^B$ | $^1$H-NMR($d_6$-DMSO) |
|---|---|---|---|
| V-57 | —Cl | 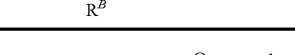 | 9.94 (1H, s), 8.64 (1H, s), 8.59 (1H, s), 8.35 (1H, s), 8.10 (1H, dd, J = 8.7 Hz, 1.2 Hz), 8.00 (1H, d, J = 2.7 Hz), 7.79 (1H, d, J = 8.7 Hz), 7.71 (1H, dd, J = 9.0 Hz, 2.4 Hz), 7.44-7.51 (1H, m), 7.26-7.35 (3H, m), 7.16-7.21 (1H, m), 5.26 (2H, s), 4.45 (2H, s), 4.32 (2H, t, J = 5.4 Hz), 3.49-3.53 (4H, m), 3.09 (3H, s), 2.72 (2H, t, J = 5.7 Hz), 2.44-2.50 (4H, m) |
| V-58 | —Cl | 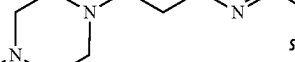 | 9.95 (1H, s), 8.64 (1H, s), 8.59 (1H, s), 8.35 (1H, s), 8.10 (1H, d, J = 8.7 Hz), 8.00 (1H, d, J = 2.7 Hz), 7.78 (1H, d, J = 8.7 Hz), 7.69-7.73 (1H, m), 7.44-7.51 (1H, m), 7.26-7.34 (3H, m), 7.16-7.22 (1H, m), 5.26 (2H, s), 4.31 (2H, t, J = 5.7 Hz), 3.12 (4H, t, J = 5.1 Hz), 2.87 (3H, s), 2.75 (2H, t, J = 5.4 Hz), 2.58 (4H, t, J = 5.3 Hz) |
Example 6
[Chemical formula 67]
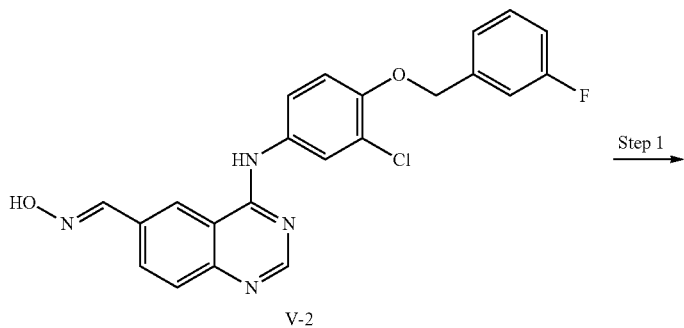
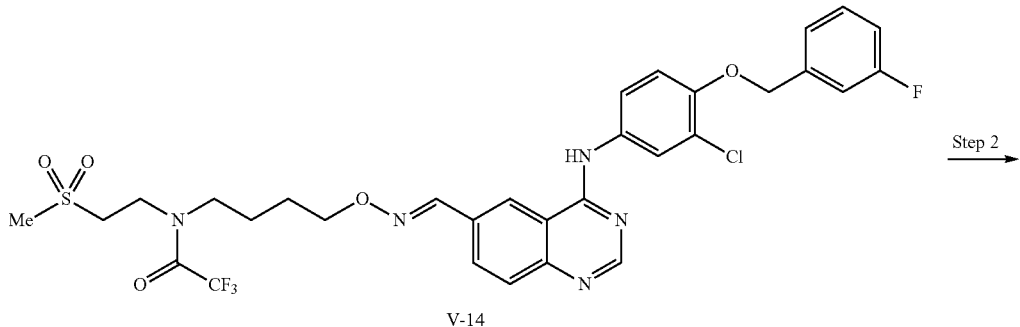
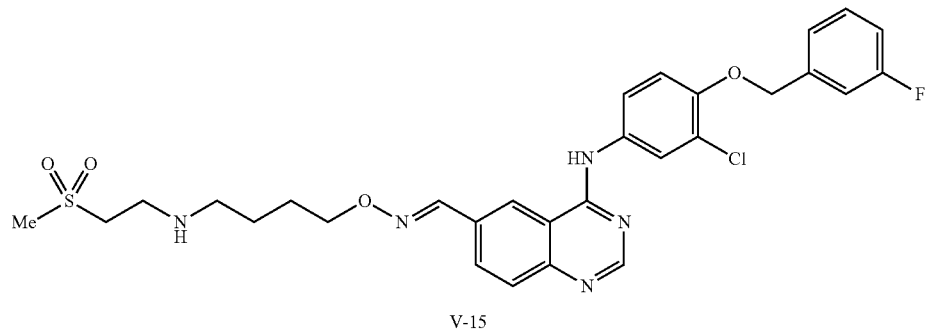

(Step 1) Synthesis of 4-(3-chloro-4-(3-fluorobenzyloxy)phenylamino)-6-(4-(N-(2-(methanesulfonyl)ethyl)-N-(2,2,2-trifluoroacetyl)amino)butyloxyimino)quinazoline (V-14)

In N,N-dimethylacetamide (1.5 ml) were dissolved 4-(3-chloro-4-(3-fluorobenzyloxy)phenylamino)-6-(hydroxyimino)quinazoline (V-2, 84 mg) and N-(4-bromobutyl)-N-(2-methanesulfonylethyl)-2,2,2-trifluoroacetamide (71 mg), and potassium carbonate (41 mg) was added, followed by stirring at 60° C. for 13 hours with heating. Thereafter, the reaction mixture was poured into 0.5M citric acid, followed by extraction with ethyl acetate. The organic layer was washed with water and aqueous sodium chloride solution, and dried over magnesium sulfate. The crude product was purified by silica gel chromatography (eluting with hexane:ethyl acetate=1:4) to obtain 4-(3-chloro-4-(3-fluorobenzyloxy)phenylamino)-6-(4-(N-(2-(methanesulfonyl)ethyl)-2,2,2-trifluoroacetamido)butyloxyimino)quinazoline (V-14, 41 mg) as a pale yellow solid.

$^1$H NMR (d$_6$-DMSO, δ): 9.94 (1H, s), 8.63 (1H, s), 8.59 (1H, s), 8.33 (1H, s), 8.10 (1H, dd, J=8.4 Hz, J=1.5 Hz), 8.00 (1H, d, J=2.4 Hz), 7.78 (1H, d, J=8.7 Hz), 7.71 (1H, dd, J=2.3 Hz, J=8.7 Hz), 7.47 (1H, dt, J-6.0 Hz, J=8.1 Hz), 7.36-7.31 (2H, m), 7.28 (1H, d, J=9.0 Hz), 7.18 (1H, dt, J=2.0 Hz, J=8.6 Hz), 5.26 (2H, s), 4.26-4.18 (2H, m), 3.79 (2H, t, J=7.1 Hz), 3.60-3.44 (4H, m), 3.05 (3H, s), 1.78-1.66 (4H, m).

(Step 2) Synthesis of 4-(3-chloro-4-(3-fluorobenzyloxy)phenylamino)-6-(4-(2-(methanesulfonyl)ethylamino)butyloxyimino)quinazoline (V-15)

In 2.6 ml of a mixture (1:1) of tetrahydrofuran and methanol was dissolved 4-(3-chloro-4-(3-fluorobenzyloxy)phenylamino)-6-(4-(N-(2-(methanesulfonyl)ethyl)-2,2,2-trifluoroacetamido)butyloxyimino)quinazoline (V-14, 40 mg), and 86 µl of 1 mol/L aqueous sodium hydroxide solution was added, followed by stirring at room temperature for 14 hours, and at 40° C. for 2 hour. After the reaction, the reaction mixture was extracted with ethyl acetate, the organic layer was dried, and filtrate was concentrated. The concentrated residue was purified by chromatography (eluting with 0 to 3% methanol-contenting ethyl acetated) using an amino column, and the resulting pale yellow oil was powdered with a mixture of hexane and ethyl acetate to obtain 4 (3-chloro 4-(3-fluorobenzyloxy)phenylamino) 6 (4 (2-(methanesulfonyl)ethylamino)butyloxyimino)quinazoline (V-15, 12 mg) as a pale yellow solid.

$^1$H NMR (d$_6$-DMSO, δ): 9.95 (1H, s), δ 63 (1H, s), 8.59 (1H, s), 8.33 (1H, s), 8.11 (1H, d, J=8.7 Hz), 8.01 (1H, d, J=2.4 Hz), 7.79 (1H, d, J=8.7 Hz), 7.72 (1H, br d, J=9.0 Hz), 7.51-7.44 (1H, m), 7.36-7.31 (2H, m), 7.28 (1H, d, J=9.0 Hz), 7.19 (1H, br t, J=9 Hz), 5.26 (2H, s), 4.20 (2H, t, J=6.6 Hz), 3.21 (2H, t, J=6.9 Hz), 2.91 (2H, t, J=6.6 Hz), 2.56 (2H, t, J=6.9 Hz), 1.73 (2H, quin, J=7 Hz), 1.51 (2H, quin, J=7 Hz).

Example 7

[Chemical formula 68]

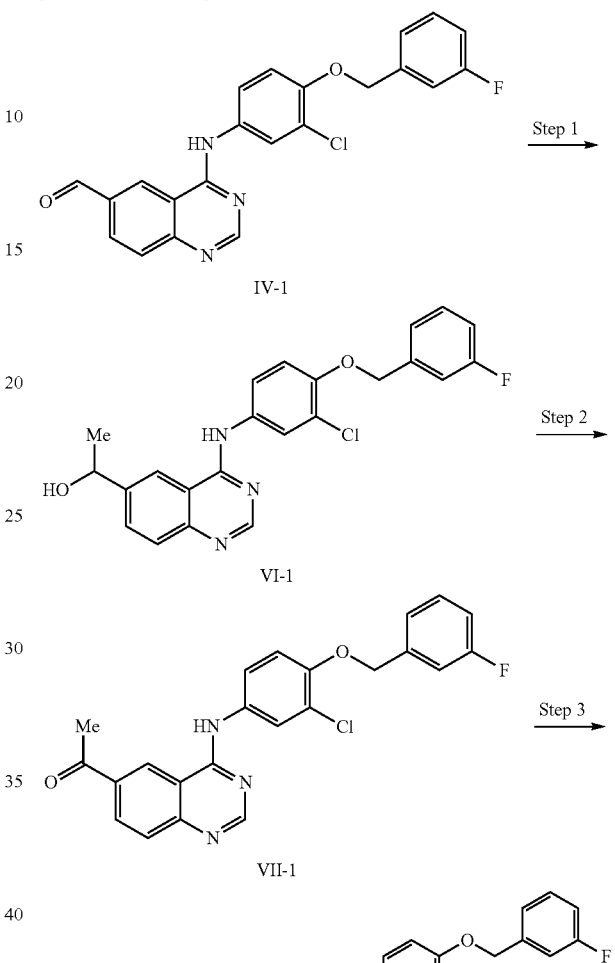

(Step 1) Synthesis of 4-(3-chloro-4-(3-fluorobenzyloxy)phenylamino)-6-(1-hydroxyethan-1-yl)quinazoline (VI-1)

In 30 mL of tetrahydrofuran was dissolved 620 mg of 4-(3-chloro-4-(3-fluorobenzyloxy)phenylamino)-6-formylquinazoline (IV-1), the solution was cooled to 0° C. under the nitrogen atmosphere, and 4.9 mL of methylmagnesium bromide (0.93M tetrahydrofuran solution) was added dropwise. After the reaction at 0° C. for 1 hour under the nitrogen atmosphere, water and ethyl acetate were added to separate the layers. The organic layer was washed sequentially with water and aqueous saturated sodium chloride solution, and dried over magnesium sulfate. After concentration, the resulting crystal was washed with chloroform to obtain 330 mg of 4-(3-chloro-4-(3-fluorobenzyloxy)phenylamino)-6-(1-hydroxyethan-1-yl)quinazoline (VI-1).

$^1$H NMR (d$_6$-DMSO δ): 9.81 (1H, s), 8.55 (1H, s), 8.44 (1H, s), 8.03 (1H, J=2.4 Hz), 7.86 (1H, dd, J=8.7 Hz, J=1.2 Hz), 7.78-7.73 (2H, m), 7.51-7.44 (1H, m), 7.35-7.25 (3H, m), 7.18 (1H, dt, J=8.4 Hz, J=2.4 Hz), 5.44 (1H, d, J=3.9 Hz), 5.26 (2H, s), 4.93 (1H, m), 1.45 (3H, d, J=6.6 Hz)

(Step 2) Synthesis of 4-(3-chloro-4-(3-fluorobenzyloxy)phenylamino)-6-(ethane-4-one)quinazoline (VII-1)

In 150 mL of tetrahydrofuran was dissolved 360 mg of 4-(3-chloro-4-(3-fluorobenzyloxy)phenylamino-6-(1-hydroxyethan-1-yl)quinazoline (VI-1), and 3.7 g of manganese dioxide was added, followed by stirring at room temperature overnight. After the reaction, inorganic substances were filtered, and the filtrate was concentrated. The resulting crystal was washed with chloroform to obtain 320 mg of 4-(3-chloro-4-(3-fluorobenzyloxy)phenylamino)-6-(ethane-4-one)quinazoline (VII-1).

$^1$H NMR (d$_6$-DMSO δ): 10.18 (1H, s), 9.16 (1H, d, J=1.5 Hz), 8.64 (1H, s), 8.31 (1H, dd, J=8.4 Hz, J=2.4 Hz), 7.97 (1H, d, J=24 Hz), 7.83 (1H, d, J=8.7 Hz), 7.71 (1H, dd, J=8.7 Hz, J=2.4 Hz), 7.51-7.44 (1H, m), 7.35-7.29 (3H, m), 7.19 (1H, dt, J=8.1 Hz, J=2.7 Hz), 5.27 (2H, s), 2.74 (3H, s)

The following compounds were synthesized according to the same manner as that of the above first step and second step.

TABLE 12

[Chemical formula 69]

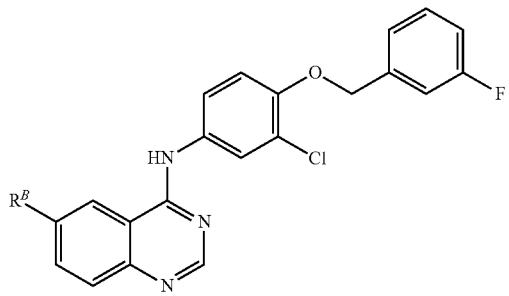

(VII)

| Compound No. | R$^B$ | $^1$H-NMR(d$_6$-DMSO) |
|---|---|---|
| VII-2 | Et, C(=O)- | 10.17 (1H, s), 9.17 (1H, d, J = 1.5 Hz), 8.64 (1H, s), 8.32 (1H, dd, J = 8.7 Hz, J = 1.5 Hz), 7.97 (1H, d, J = 2.7 Hz), 7.84 (1H, d, J = 8.7 Hz), 7.72 (1H, dd, J = 8.7 Hz, J = 2.7 Hz), 7.52-7.44 (1H, m), 7.35-7.29 (3H, m), 7.20 (1H, dt, J = 8.7 Hz, J = 2.7 Hz), 5.28 (2H, s), 3.22 (2H, q, J = 7.2 Hz), 1.17 (3H, t, J = 7.2 Hz) |
| VII-3 | iPr, C(=O)- | (CDCl$_3$) 8.76 (1H, s), 8.65 (1H, brs), 8.29 (1H, d, J = 9.0 Hz), 7.97 (1H, d, J = 8.4 Hz), 7.88 (1H, brs), 7.52 (1H, d, J = 9.0 Hz), 7.40-7.33 (1H, m), 7.25-7.19 (3H, m), 7.05-6.97 (2H, m), 5.16 (2H, s), 3.72-3.63 (1H, m), 1.28 (3H, d, J = 1.8 Hz), 1.26 (3H, d, J = 1.8 Hz) |
| VII-4 | Me–C≡C–C(=O)– | 10.34 (1H, s), 9.23 (1H, s), 8.66 (1H, s), 8.44 (1H, dd, J = 9 Hz, J = 1.5 Hz), 7.99 (1H, d, J = 2.7 Hz), 7.88 (1H, d, J = 8.7 Hz), 7.72 (1H, dd, J = 9 Hz, J = 2.4 Hz), 7.43-7.52 (1H, m), 7.14-7.36 (4H, m), 5.28 (2H, s), 2.28 (3H, s) |
| VII-5 | Ph, C(=O)- | 10.14 (1H, s), 8.98 (1H, s), 8.67 (1H, s), 8.11 (1H, dd, J = 8.7 Hz, J = 0.9 Hz), 7.98-7.82 (4H, m), 7.78-7.58 (4H, m), 7.52-7.43 (1H, m), 7.36-7.14 (4H, m), 5.26 (2H, s) |
| VII-6 | CF$_3$, C(=O)- | 10.50 (1H, s), 9.27 (1H, s), 8.67 (1H, s), 8.35 (1H, d, J = 9.3 Hz), 7.99 (1H, d, J = 2.7 Hz), 7.88 (1H, brs), 7.70 (1H, d, J = 7.5 Hz), 7.52-7.43 (1H, m), 7.36-7.14 (4H, m), 5.28 (2H, s) |

TABLE 12-continued
[Chemical formula 69]
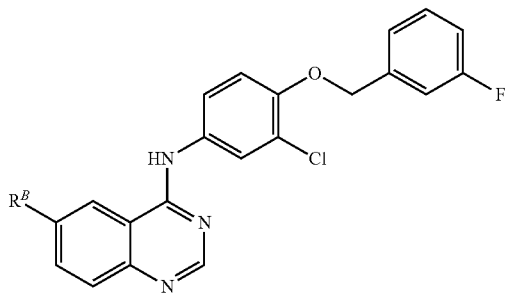
(VII)
| Compound No. | $R^B$ | $^1$H-NMR($d_6$-DMSO) |
|---|---|---|
| VII-8 | 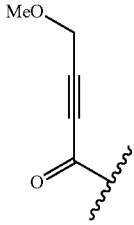 | 10.36 (1H, s), 9.26 (1H, s), 8.67 (1H, s), 8.44 (1H, dd, J = 8.7 Hz, J = 1.8 Hz), 8.00 (1H, d, J = 2.4 Hz), 7.91 (1H, d, J = 8.7 Hz), 7.72 (1H, dd, J = 9.0 Hz, J = 2.4 Hz), 7.51-7.44 (1H, m), 7.35-7.28 (3H, m), 7.22-7.15 (1H, m), 5.27 (2H, s), 4.55 (2H, s). |
| VII-9 | 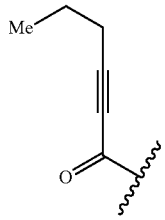 [SMILES: *C(=O)C#CCCC] | 10.4 (1H, s), 9.24 (1H, s), 8.67 (1H, s), 8.46 (1H, d, J = 8.7 Hz), 8.01 (1H, d, J = 2.7 Hz), 7.90 (1H, d, J = 8.7 Hz), 7.70-7.80 (1H, m), 7.44-7.54 (1H, m), 7.15-7.40 (4H, m), 5.27 (2H, s), 2.64 (2H, t, J = 6.9 Hz), 1.63-1.75 (2H, m), 1.05 (3H, t, J = 7.5 Hz) |
| VII-10 | 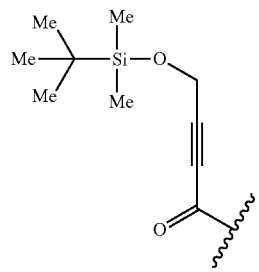 [SMILES: *C(=O)C#CCO[Si](C)(C)C(C)(C)C] | 10.34 (1H, s), 9.24 (1H, s), 8.67 (1H, s), 8.42 (1H, d, J = 8.4 Hz), 7.99 (1H, s), 7.88 (1H, d, J = 8.7 Hz), 7.73 (1H, d, J = 9.0 Hz), 7.48-7.44 (1H, m), 7.34-7.27 (3H, m), 7.21-7.16 (1H, m), 5.27 (2H, s), 4.76 (2H, s), 0.94 (9H, s), 0.16 (6H, s). |

TABLE 13

[Chemical formula 70]

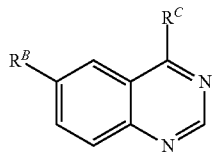

(VII)

| Compound No. | R$^B$ | R$^C$ | $^1$H-NMR(d$_6$-DMSO) |
|---|---|---|---|
| VII-11 | Me | (alkyne-ketone linked to 1-(3-fluorobenzyl)-1H-indazol-5-ylamino) | 10.44 (1H, s), 9.24 (1H, s), 8.60 (1H, s), 8.43 (1H, dd, J = 2.4, 11.6 Hz), 8.17 (2H, s), 7.87 (1H, d, J = 12.0 Hz), 7.78-7.67 (2H, m), 7.41-7.34 (1H, m), 7.14-7.04 (3H, m), 5.72 (2H, s), 2.28 (3H, s) |
| VII-12 | MeO | (MeO-CH$_2$-alkyne-ketone linked to 1-(3-fluorobenzyl)-1H-indazol-5-ylamino) | 10.47 (1H, s), 9.29 (1H, d, J = 1.8 Hz), 8.62 (1H, s), 8 43 (1H, dd, J = 1.5 Hz, J = 9 0 Hz), 8.21-8.17 (2H, m), 7.89 (1H, d, J = 8.7 Hz), 7.78-7.68 (2H, m), 7.41-7.33 (1H, m), 7.15-7.04 (3H, m), 5.71 (2H, s), 4.55 (2H, s), 3.42 (3H, s). |
| VII-13 | Me | (alkyne-ketone linked to 4-((3-fluorophenoxy)methyl)phenylamino) | 10.44 (1H, s), 9.25 (1H, s), 8.73 (1H, s), 8.44 (1H, d, J = 8.8 Hz), 8.16 (1H, s), 7.89 (1H, d, J = 8.4 Hz), 7.62 (1H, d, J = 8.4 Hz), 7.34 (1H, dd, J = 8.4, 16.0 Hz), 6.95-6.86 (2H, m), 6.82-6.77 (1H, m), 5.15 (2H, s), 2.27 (3H, s). |
| VII-14 | Me | (alkyne-ketone linked to 4-(pyridin-2-ylmethoxy)phenylamino) | 10.34 (1H, s), 9.22 (1H, s), 8.64-8.59 (2H, m), 8.43-8.41 (1H, m), 7.98 (1H, s), 7.87-7 85 (2H, m), 7.71-7.68 (1H, m), 7.59-7.58 (1H, m), 7.40-7.34 (1H, m), 7.29-7.27 (1H, m), 5.30 (2H, s). |
| VII-15 | Me | (alkyne-ketone linked to 4-(pyridin-4-ylmethoxy)phenylamino) | 9.21 (1H, s), 8.64-8.58 (2H, m), 8.45-8.39 (1H, m), 7.97 (1H, s), 7.88-7.84 (1H, m), 7.71-7.66 (1H, m), 7.45-7.51 (1H, m), 7.27-7.23 (1H, m), 7.29-7 27 (1H, m), 5.30 (2H, s). |

TABLE 13-continued

[Chemical formula 70]

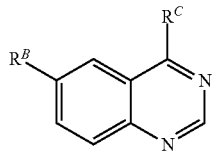

(VII)

| Compound No. | $R^B$ | $R^C$ | $^1$H-NMR($d_6$-DMSO) |
|---|---|---|---|
| VII-16 | MeO-C≡C-C(=O)- (with MeO-CH2-C≡C-C(=O)- structure) | 4-(pyridin-2-ylmethoxy)phenylamino | 10.35 (1H, s), 9.24 (1H, s), 8.67 (1H, s), 8.60 (1H, d, J = 4.4 Hz), 8.42 (1H, d, J = 8.8 Hz), 8.01 (1H, s), 7.91-7.87 (2H, m), 7.73-7.71 (1H, m), 7.59 (1H, d, J = 8.0 Hz), 7.39-7.36 (1H, m), 7.29 (1H, d, J = 8.8 Hz), 5.31 (2H, s), 4.55 (2H, s), 3.42 (3H, s). |

TABLE 14

| Compound No. | $R^B$ | $R^C$ | $^1$H-NMR($d_6$-DMSO) |
|---|---|---|---|
| VII-17 | Me-C≡C-C(=O)- | 4-(phenylsulfonyl)phenylamino | 10.32 (1H, s), 8.85 (1H, s), 8.74 (1H, s), 8.20 (2H, d, J = 6.0 Hz), 8.01-7.96 (4H, m), 7.87 (1H, d, J = 6.0 Hz), 7.68-7.64 (3H, m), 3.56 (3H, s). |
| VII-18 | MeO-CH2-C≡C-C(=O)- | 4-(phenylsulfonyl)phenylamino | 10.52 (1H, s), 9.14 (1H, s), 8.60 (1H, s), 8.31 (1H, d, J = 8.4 Hz), 8.40 (2H, d, J = 8.4 Hz), 7.84-7.78 (5H, m), 7.52-7.43 (3H, m), 4.37 (2H, s), 3.24 (3H, s). |
| VII-19 | Me-C≡C-C(=O)- | 4-(phenylthio)phenylamino | 10.44 (1H, s), 9.28 (1H, s), 8.70 (1H, s), 8.45 (1H, d, J = 8.8 Hz), 7.92 (3H, t, J = 8.8 Hz), 7.46 (2H, d, J = 8.8 Hz), 7.37 (2H, t, J = 7.6 Hz), 7.30-7.26 (3H, m), 4.24-4.20 (2H, m), 2.28 (3H, s). |

(Step 3) Synthesis of 4-(3-chloro-4-(3-fluorobenzyloxy)phenylamino)-6-(1-(2-(1-morpholino)ethoxyimino)ethyl)quinazoline (VIII-1)

In 6 mL (20:1) of a mixture of tetrahydrofuran and water were dissolved 100 mg of Compound VII-1 and 78 mg of 2-(1-morpholino)ethoxyamine dihydrochloride, followed by stirring at room temperature overnight. The reaction mixture was diluted with ethyl acetate, washed with aqueous saturated sodium bicarbonate solution, and dried over magnesium sulfate. After concentration, the solid was washed with a mixture (2:1) of hexane and ethyl acetate to obtain 72 mg of 4-(3-chloro-4-(3-fluorobenzyloxy)phenylamino)-6-(1-(2-(1-morpholino)ethoxyimino)ethyl)quinazoline (VIII-1).

$^1$H NMR (d-DMSO, δ): 9.93 (1H, s), 8.62 (1H, brs), 8.58 (1H, s), 8.22 (1H, d, J=6.6 Hz), 7.96 (1H, d, J=1.8 Hz), 7.76 (1H, d, J=6.6 Hz), 7.70 (1H, dd, J=6.6 Hz, J=1.8 Hz), 7.51-7.45 (1H, m), 7.35-7.28 (3H, m), 7.19 (1H, t, J=6.0 Hz), 5.27 (2H, s), 4.33 (2H, t, J=6.0 Hz), 3.59 (41H, t, J=4.5 Hz), 2.69 (2H, t, J=6.0 Hz), 2.47 (4H, t, J=45 Hz), 2.36 (3H, s)

Reference Example 1

As a method of obtaining a ketone derivative (VII), the following method is exemplified in addition to the first step and the second step of Example 7.

[Chemical formula 71]

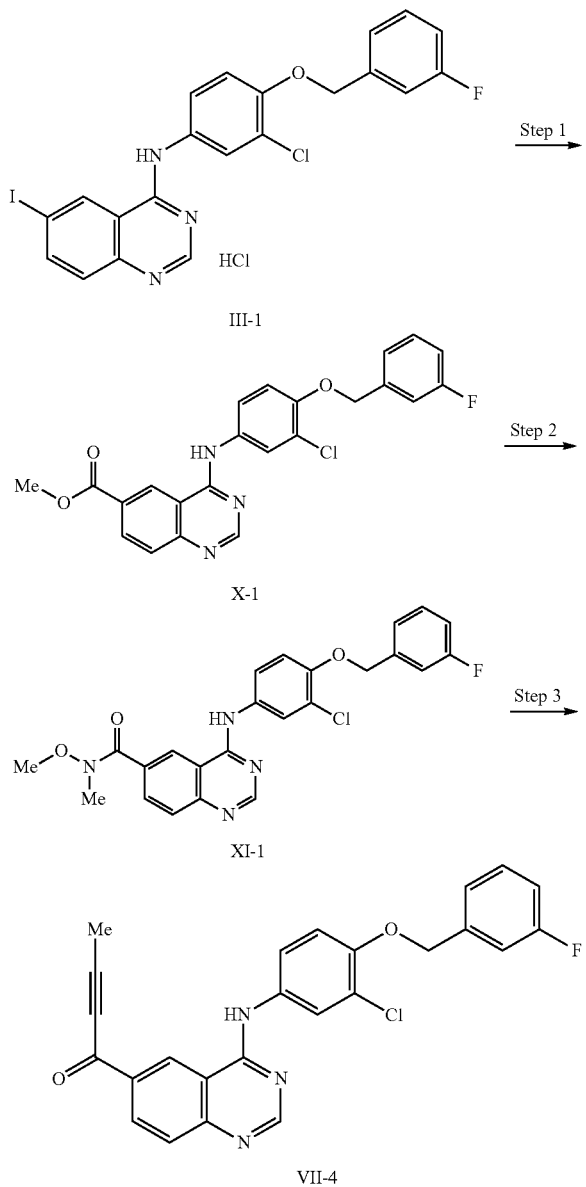

(Step 1) Synthesis of 4-(3-chloro-4-(3-fluorobenzyloxy)phenylamino)-quinazoline-6-carboxylic acid methyl ester (X-1)

In a mixture of 200 ml of dimethylformamide and 200 ml of methanol were dissolved 4-(3-chloro-4-(3-fluorobenzyloxy)phenylamino)-6-iodoquinazoline hydrochloride (III-1, 20 g) and 1.29 g of dichlorobis(triphenylphosphine)palladium, and 25.7 ml of triethylamine was added. The interior of a reaction vessel was sufficiently replaced with a carbon monoxide gas, followed by a reaction at 80° C. for 15 hours under the carbon monoxide atmosphere. The reaction mixture was filtered with Celite, and the filtrate was cooled to 0° C. with stirring. A precipitate was filtered, washed with cold methanol, and dried to obtain 4-(3-chloro-4-(3-fluorobenzyloxy)phenylamino)quinazoline-6 carboxylic acid methyl ester (X-1, 13.5 g) as a colorless solid.

$^1$H NMR ($d_6$-DMSO, δ): 10.26 (1H, s), 9.25 (1H, d, J=1.5 Hz), 8.65 (1H, s), 8.31 (1H, dd, J=1.5 Hz, J=8.7 Hz), 8.02 (1H, d, J=2.7 Hz), 7.85 (1H, d, J=2.7 Hz), 7.77 (1H, dd, J=2.7 Hz, J=8.7 Hz), 7.49-7.44 (1H, m), 7.35-7.27 (3H, m), 7.20-7.16 (1H, m), 5.27 (2H, s), 3.96 (3H, s).

(Step 2) Synthesis of 4-(3-chloro-4-(3-fluorobenzyloxy)phenylamino)quinazoline-6-carboxylic acid methoxy methyl amide (XI-1)

In tetrahydrofuran (230 ml) was dissolved 4-(3-chloro-4-(3-fluorobenzyloxy)phenylamino)-quinazoline-6-carboxylic acid methyl ester (X-1, 11.6 g), N,O-dimethylhydroxylamine hydrochloride (7.8 g) was added, and 2 mol/L iPrMgCl tetrahydrofuran solution (79.8 ml) was added dropwise over 30 minutes under ice cooling. After completion of addition, the mixture was stirred for 20 minutes under ice cooling and, after completion of the reaction, 200 ml of aqueous saturated ammonium chloride solution was added. After 100 ml of water was added to the mixture, the mixture was extracted with ethyl acetate, and the organic layer was dried over sodium sulfate. The filtrate was concentrated to obtain 4-(3-chloro-4-(3-fluorobenzyloxy)phenylamino)-quinazoline-6-carboxylic acid methoxy methyl amide (XI-1, 12.7 g) as a pale yellow solid.

$^1$H NMR ($d_6$-DMSO, δ): 10.01 (1H, s), 8.79 (1H, d, J=1.5 Hz), 8.64 (1H, s), 8.05 (1-H, d, J=2.7 Hz), 8.00 (1H, dd, J=1.5 Hz, J=8.7 Hz), 7.81 (1H, d, J=–8.7 Hz), 7.76 (1H, dd, J=2.7 Hz, J=8.7 Hz), 7.52-7.44 (1H, m), 7.35-7.26 (3H, m), 7.22-7.16 (1H, m), 5.27 (2H, s), 3.57 (3H, s), 3.34 (3H, s).

(Step 3) Synthesis of 4-(3-chloro-4-(3-fluorobenzyloxy)phenylamino)-6-(1-oxo-2-butyn-1-yl)quinazoline (VI-4)

To a solution of 4.22 ml of N,N-diisopropylamine in tetrahydrofuran (25 ml) cooled to –78° C. was added dropwise 18.8 ml of 1.6 mol/L n-BuLi hexane solution. After completion of addition, a temperature was elevated to 0° C., and the mixture was stirred at 0° C. for 20 minutes, and cooled again to –78° C. 1.33 ml of 2-bromo-1-propene in tetrahydrofuran (25 ml) was added, and the mixture was stirred at –78° C. for 2 hours. To the mixture was added dropwise a solution of 4-(3-chloro-4-(3-fluorobenzyloxy)phenylamino)-quinazoline-6-carboxylic acid methoxy methyl amide (XI-1, 2.33 g) in tetrahydrofuran (50 ml) and, after completion of addition, a temperature was elevated to 0° C., followed by stirring for 3 hours. After completion of the reaction, the reaction mixture was poured into ice water, neutralized with 2 mol/L hydrochloric acid, and extracted with ethyl acetate. The organic layer was dried over sodium sulfate, the filtrate was concentrated, and the resulting crystalline residue was washed with methylene chloride to obtain 4-(3-chloro-4-(3-fluorobenzyloxy)phenylamino)-6-(1-oxo-2-butyn-1-yl)quinazoline (VII-4, 1.71 g) as a yellow solid.

Reference Example 2

As other method of the third step of Reference Example 1, there is following method.

[Chemical formula 72]

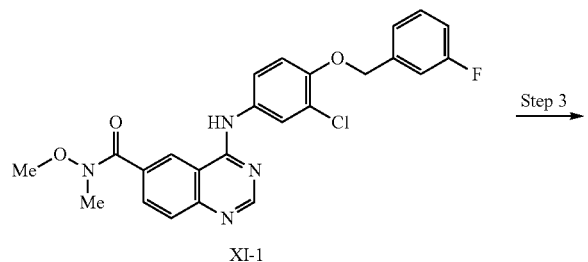

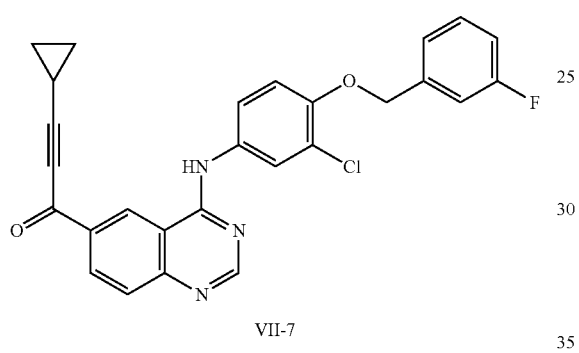

(Step 3) Synthesis of 4-(3-chlor-4-(3-fluorobenzyloxy)phenylamino)-6-(1-oxo-2-propyne-3-cyclopropyl-1-1-yl)quinazoline (VII-7)

To a solution of 0.16 ml of ethynylcyclopropane in tetrahydrofuran (3 ml) cooled to −78° C. was added dropwise 1.25 ml of 1.54 mol/L n-BuLi hexane solution. After completion of addition, the mixture was stirred at −78° C. for 1 hour. To the mixture was added dropwise a solution of 4-(3-chloro-4-(3-fluorobenzyloxy)phenylamino)-quinazoline-6-carboxylic acid methoxy methyl amide (XI-1, 300 mg) in tetrahydrofuran (3 ml) and, after completion of addition, a temperature was elevated to 0° C., and the mixture was stirred for 3 hours. After completion of the reaction, 10 ml of water and ml of ethyl acetate were added to the reaction mixture to separate the layers. After the aqueous layer was re-extracted with 10 ml of ethyl acetate two times, all organic layers were combined, and dried over sodium sulfate, and the filtrate was concentrated. The residue was purified by silica gel column chromatography to obtain 4-(3-chloro-4-(3-fluorobenzyloxy)phenylamino)-6-(1-oxo-2-propyne-3-cyclopropyl-1-yl)quinazoline) (VII-7, 265 mg) as a yellow solid.

$^1$H NMR (d$_6$-DMSO, δ): 10.4 (1H, s), 9.21 (1H, s), 8.67 (1H, s), 8.41 (1H, d, J=8.7 Hz), 8.01 (1H, d, J=2.7 Hz), 7.88 (1H, d, J=8.7 Hz), 7.73 (1H, dd, J=8.7 Hz, J 3 Hz), 7.40-7.52 (1H, m), 7.15-7.4 (4H, m), 5.28 (2H, s), 1.77-1.87 (1H, m), 1.05-1.20 (3H, m).

Reference Example 3

As a method of obtaining an amide derivative (XI), there is following method in addition to the first step and the second step of Reference Example 1.

[Chemical formula 73]

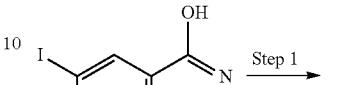

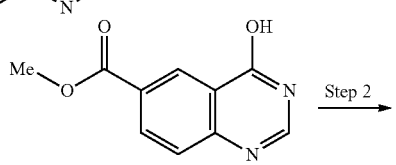

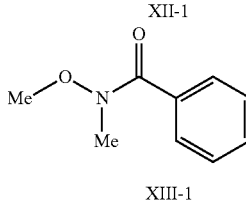

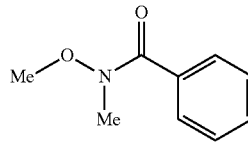

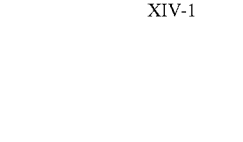

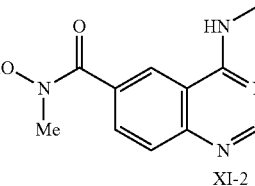

(Step 1) Synthesis of 4-hydroxyquinazoline-6-carboxylic acid methyl ester (XII-1)

4-Hydroxy-6-iodoquinazoline (250 mg), a catalytic amount of palladium (II) acetate and 1,3-bis(diphenylphosphino)propane were dissolved in N,N-dimethylformamide (3.8 ml) and methanol (1.5 ml) and 1.5 ml of triethylamine was added. After the interior of a reaction vessel was sufficiently replaced with a carbon monoxide gas, a reaction was performed at 80° C. for 20 hours under the carbon monoxide atmosphere. After completion of the reaction, the reaction mixture was poured into 10% aqueous citric acid, followed by extraction with ethyl acetate. The organic layer was washed with water, and dried over sodium sulfate, and the filtrate was concentrated. The resulting residue was purified by silica gel column chromatography (eluting with ethyl acetate) to obtain 4-hydroxyquinazoline-6-carboxylic acid methyl ester (XII-1, 157 mg) as a brown solid.

$^1$H NMR (d$_6$-DMSO, δ): 12.48 (1H, s), 8.63 (1H, s), δ 26 (1H, d, J=8.4 Hz), 8.19 (1H, s), 7.73 (1H, d, J=8.4 Hz).

(Step 2) Synthesis of 4-hydroxyquinazoline-6-carboxylic acid methoxymethylamide (XIII-1)

4-Hydroxyquinazoline-6-carboxylic acid methyl ester (XII-1, 4.0 g) was dissolved in tetrahydrofuran (120 ml), N,O-dimethylhydroxylamine hydrochloride (5.7 g) was added, and 2 mol/L iPrMgCl tetrahydrofuran solution (59 ml) was added dropwise over 30 minutes. After completion of addition, the mixture was stirred for 30 minutes under ice cooling and, after completion of the reaction, 40 ml of 2 mol/L hydrochloric acid was added dropwise. The mixture was neutralized with aqueous saturated sodium bicarbonate solution, and extracted with chloroform, and the organic layer was washed with aqueous sodium chloride solution, and dried over sodium sulfate. After concentration, the crystalline residue was purified by silica gel column chromatography (eluting ethyl acetate: methanol=9:1) to obtain 4-hydroxyquinazoline-6-carboxylic acid methoxymethylamide (XIII-1, 2.9 g) as a white solid.

$^1$H NMR (d$_6$-DMSO, δ): 12.42 (1H, s), 8.36 (1H, s), 8.18 (1H, s), 8.02 (1, d, J=8.4 Hz), 7.73 (1H, d, J=8.4 Hz), 3.57 (3H, s), 3.32 (3H, s).

(Step 3) Synthesis of 4-chloroquinazoline-6-carboxylic acid methoxymethylamide (XIV-1)

4-Hydroxyquinazoline-6-carboxylic acid methoxymethylamide (XIII-1, 2.9 g) was suspended in toluene (57 ml), and 6.8 ml of triethylamine and 3.4 ml of phosphorus oxychloride were added, followed by stirring at 130° C. for 30 minutes. After completion of the reaction, the reaction mixture was cooled to room temperature, and 50 ml of aqueous saturated sodium bicarbonate solution and ethyl acetate were added. Sodium bicarbonate was added until the aqueous layer exhibited a pH 8, followed by extraction with ethyl acetate. The organic layer was washed with aqueous saturated sodium bicarbonate solution, dried over sodium sulfate. After concentration, the crystalline residue was washed with diethyl ether, and dried to obtain 4-chloroquinazoline-6-carboxylic acid methoxymethylamide (XIV-1, 2.3 g) as a white solid.

$^1$H NMR (d$_6$-DMSO, δ): 8.75 (1H, s), 8.36 (1H, s), 8.11 (1H, dd, J=2.0 Hz, J=8.4 Hz), 7.87 (1H, d, J=8.4 Hz), 3.56 (3H, s), 3.32 (3H, s).

(Step 4) Synthesis of 4-(3-chloro-4-(pyridin-2-ylmethoxy)phenylamino)-quinazoline-6-carboxylic acid methoxymethylamide (XI-2)

4-Chloroquinazoline-6-carboxylic acid methoxymethylamide (XIV-1, 5.78 g) was dissolved in tetrahydrofuran (100 ml), and 5.39 g of 3-chloro-4-(pyridin-2-ylmethoxy)aniline was added, followed by stirring at 60° C. for 1 hour. A precipitate was filtered, and washed with tetrahydrofuran to obtain 4-(3-chloro-4-(pyridin-2-ylmethoxy)phenylamino)-quinazoline-6-carboxylic acid methoxymethylamide (XI-2, 7.87 g) as a white solid. The filtrate was allowed to stand at room temperature, and the resulting precipitate was collected by filtration, to newly obtain 2.21 g of XI-2.

$^1$H NMR (ds-DMSO, δ): 10.02 (1H, s), 8.79 (1H, s), 8.62-8.59 (2H, m), 8.04 (1H, s), 8.00-7.98 (1H, m), 7.90-7.86 (1H, s), 7.80-7.78 (1H, m), 7.75-7.73 (1H, m), 7.59-7.57 (1H, m), 7.37-7.35 (1H, m), 7.28-7.26 (1H, m), 5.29 (2H, s), 3.57 (3H, s).

[Chemical formula 74]

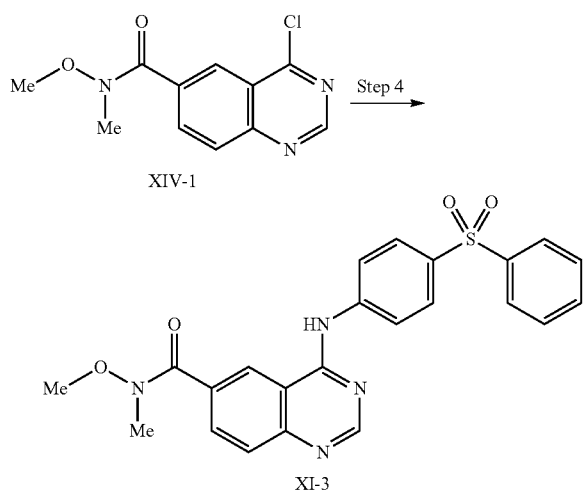

Reference Example 4

As other method of the fourth step of Reference Example 3, there is following method.

(Step 4) Synthesis of 4-(4-benzenesulfonylphenylamino)-quinazoline-6-carboxylic acid methoxymethylamide (XI-3)

4-Chloroquinazoline-6-carboxylic acid methoxymethylamide (XIV-1, 550 rag), 611 mg of 4-benzenesulfonylphenylamine, 49 mg of palladium (II) acetate, 190 mg of Xant phos and 997 mg of cesium carbonate were added to 1,4-dioxane (30 ml), and the interior of a reaction vessel was replaced with a nitrogen gas, followed by stirring at 100° C. for 2.5 hours. The reaction mixture was filtrated with Celite, and water was added to the filtrate, followed by extraction with ethyl acetate. The organic layer was washed with aqueous saturated sodium chloride solution, and dried over sodium sulfate. The filtrated was concentrated, and the residue was purified by silica gel column chromatography (eluting with ethyl acetate:methanol=95:5) to obtain 4-(4-benzenesulfonylphenylamino)-quinazoline-6-carboxylic acid methoxymethylamide (XI-3, 651 tag) as a pale yellow solid.

$^1$H NMR (d$_6$-DMSO, δ): 10.66 (1H, s), 9.29 (1H, s), 8.80 (1H, s), 8.48 (1H, d, J=7.7 Hz), 8.16 (2H, d, J=7.7 Hz), 7.99-7.94 (5H, m), 7.80-7.61 (3H, m), 2.27 (3H, s).

Reference Example 5

As a method of obtaining an amide derivative (XI), there is further the following method in addition to the first step and the second step of Reference Example 1, and Reference Example 3.

[Chemical formula 75]

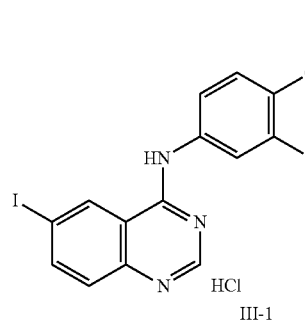

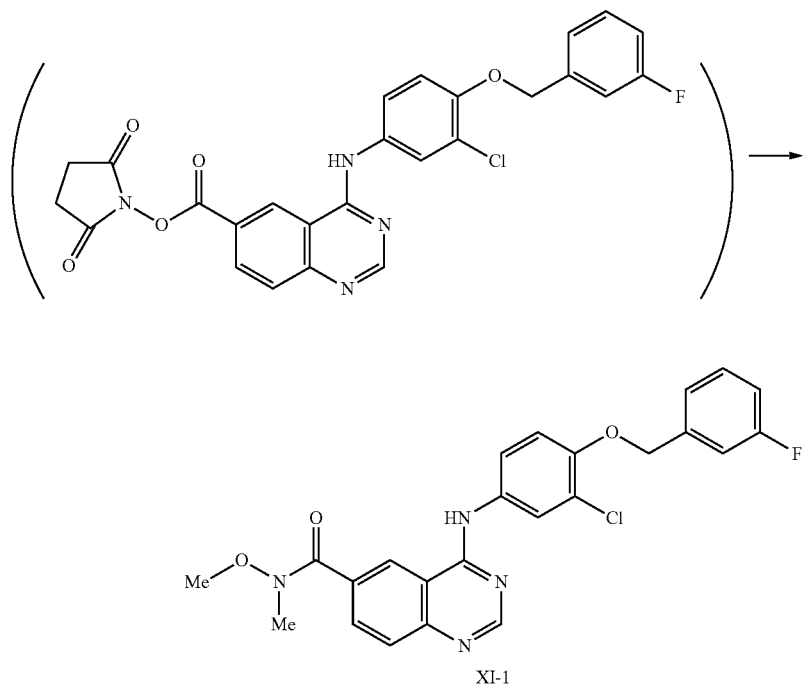

(Step 1) Synthesis of 4-(3-chloro-4-(3-fluorobenzy-loxy)phenylamino)-quinazoline-6-carboxylic acid methoxymethylamide (XI-1)

4 (3 Chloro-4-((3-fluorobenzyloxy)phenylamino)-6-iodoquinazoline hydrochloride (III-1, 500 mg), 32 mg of dichlorobis(triphenylphosphine)palladium, and 191 mg of N-hydroxysuccinimide were dissolved in 10 ml of dimethylformamide, and 360 td of triethylamide was added. The interior of a reaction vessel was sufficiently replaced with a carbon monoxide gas, followed by a reaction at 80° C. for 3 hours under the carbon monoxide atmosphere. To ⅕ of the reaction mixture was added 0.3 ml of a 40% N,O-dimethylhydroxylamine aqueous solution, followed by stirring at room temperature overnight. After completion of the reaction, water was added to the reaction mixture, followed by extraction with ethyl acetate. The organic layer was washed with water and aqueous saturated sodium chloride solution in this order, and dried over sodium sulfate. The concentrated residue of the filtrate was purified by silica gel column chromatography (eluting with ethyl acetate) to obtain 4-(3-chloro-4-(3-fluorobenzyloxy)phenylamino)-quinazoline-6-carboxylic acid methoxymethylamide (XI-1, 74 mg) as a pale yellow solid.

Example 8

[Chemical formula 76]

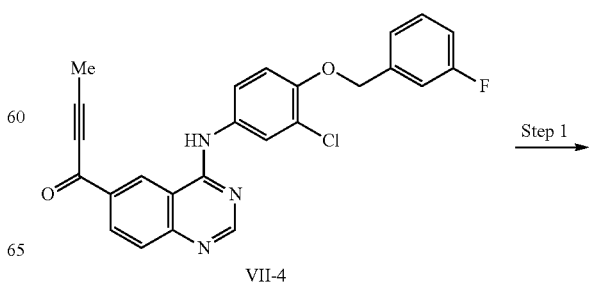

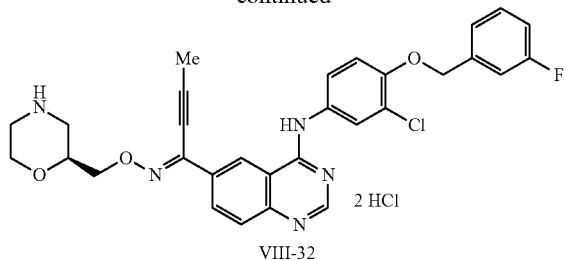

(Step 1) Synthesis of 4-(3-chloro-4-(3-fluorobenzyloxy)phenylamino)-6-(1-((S)-morpholin-2-yl-methoxyimino)-2-butyn-1-yl)quinazoline dihydrochloride (VIII-32)

To a suspension of 4-(3-chloro-4-(3-fluorobenzyloxy)phenylamino)-6-(1-oxo-2-butyn-1-yl)quinazoline (VII-4, 786 mg) and 614 mg of (S)-2-aminooxymethyl-morpholine-4-carboxylic acid tert-butyl ester in 31 ml of 1,4-dioxane was added 2.21 ml of 2 mol/L methanesulfonic acid aqueous solution, followed by stirring at 80° C. for 22 hours. And, 1.32 ml of 2 mol/L methanesulfonic acid aqueous solution was additionally added, followed by further stirring for 5.5 hours. After completion of the reaction, the reaction mixture was poured into aqueous sodium bicarbonate solution, followed by extraction with ethyl acetate. After an aqueous layer was re-extracted with ethyl acetate, all organic layers were combined, washed with water, and dried over anhydrous magnesium sulfate. After the filtrate was concentrated, the residue was purified by silica gel column chromatography (eluting with chloroform: methanol=9:1) to obtain a yellow oil. This oil was dissolved in 50 ml of ethyl acetate, and filtered, and 0.95 ml of 4 mol/L hydrochloric acid-ethyl acetate solution was added with stirring, followed by stirring at room temperature for 1 hour. A precipitate was filtered, and washed with ethyl acetate and hexane in this order. A substance collected by filtration was recrystallized with methanol-ethyl acetate to obtain 4-(3-chloro-4-(3-fluorobenzyloxy)phenylamino)-6-(1-((S)-morpholin-2-ylmethoxyimino)-2-butyn-1-yl)quinazoline dihydrochloride (VIII-32, 839 mg) as a yellow crystal.

$^1$H NMR (d$_6$-DMSO, δ): 11.69 (1H, bs), 9.49-9.37 (2H, m), 9.05 (1H, s), 8.88 (1H, s), 8.38 (1H, dd, J=1.5 Hz, J=8.7 Hz), 7.96 (1H, d, J=8.7 Hz), 7.89 (1H, d, J=2.7 Hz), 7.64 (1H, dd, J=2.4 Hz, J=9.0 Hz), 7.52-7.45 (1H, m), 7.36-7.30 (3H, m), 7.23-7.16 (1H, m), 5.31 (2H, s), 4.36-4.34 (1H, m), 4.25-4.22 (1H, m), 4.04-3.98 (1H, m), 3.84-3.77 (1H, m), 3.04-2.85 (3H, m), 2.28 (3H, s).

Example 9

[Chemical formula 77]

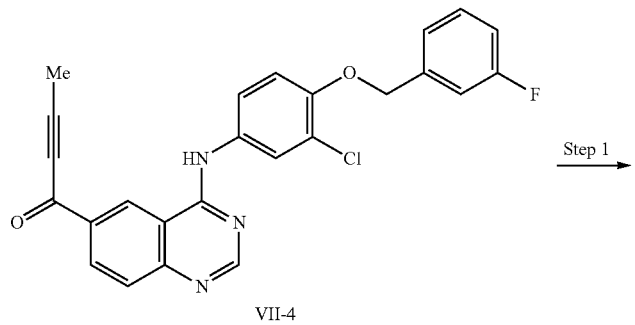

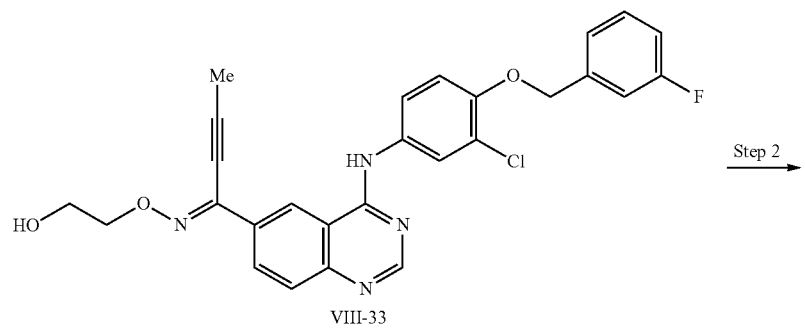

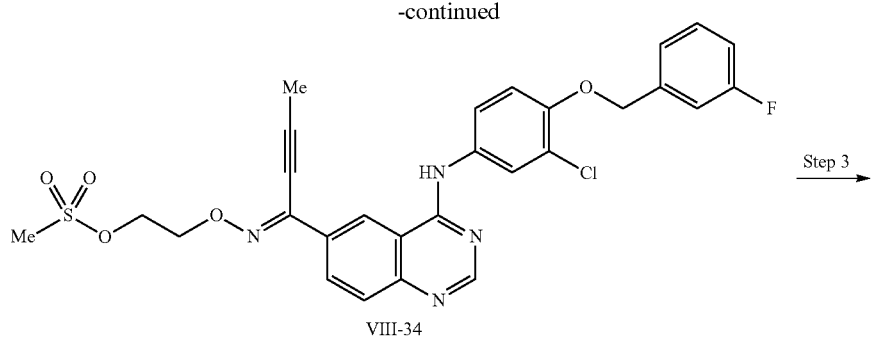

VIII-34

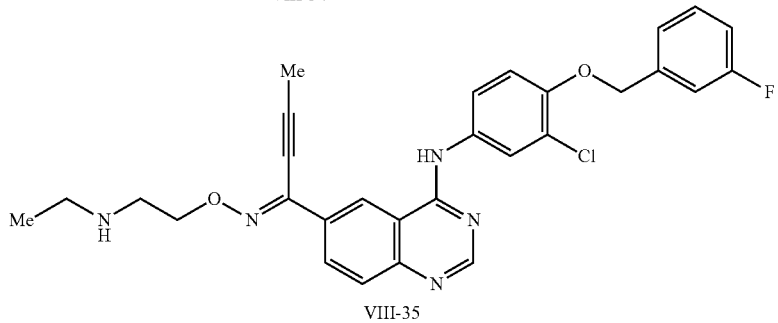

VIII-35

(Step 1) Synthesis of 4-(3-chloro-4-(3-fluorobenzyloxy)phenylamino)-6-(1-(2-hydroxyethoxyimino)-2-butyn-1-yl)quinazoline (VII-33)

4-(3-Cloro-4-(3-fluorobenzyloxy)phenylamino)-6-(1-oxo-2-butyn-1-yl)quinazoline (VII-4, 10 g) was dissolved in 300 ml of 1,4-dioxane, 1.5 equivalent of 2-(acetoxy) ethoxyamine was added, and 28 ml of 2 mol/L aqueous methanesulfonic acid solution was added, followed by stirring at 60° C. for 17 hours. The reaction mixture was poured into aqueous saturated sodium bicarbonate solution, and the mixture was extracted with ethyl acetate. The organic layer was washed with water, and dried over sodium sulfate. The residue obtained by concentrating the filtrate was recrystallized from hydrous ethanol-water, filtered, and dried to obtain 4-(3-chloro-4-(3-fluorobenzyloxy)phenylamino)-6-(1-(2-hydroxyethoxyimino)-2-butyn-1-yl)quinazoline (VIII-33, 7.6 g) as a colorless solid.
$^1$H NMR (d$_6$-DMSO, δ): 10.07 (1H, s), 8.74 (1H, s), 8.58 (1H, s), 8.22 (1H, d, J=8.8 Hz), 7.96 (1H, d, J=2.4 Hz), 7.80 (1H, d, J=8.8 Hz), 7.69 (1H, dd, J=2.4 Hz, J=8.8 Hz), 7.50-7.45 (1H, m), 7.35-7.24 (3H, m), 7.20-7.16 (1H, m), 5.27 (2H, s), 4.79 (1H, t, J=5.6 Hz), 4.29 (2H, t, J=5.6 Hz), 3.75 (2H, dd, J=5.2 Hz, J=10.4 Hz), 2.26 (3H, s).

(Step 2) Synthesis of 4-(3-chloro-4-(3-fluorobenzyloxy)phenylamino)-6-(1-(2-sulfonyloxyethoxyimino)-2-butyn-1-yl)quinazoline (VIII-34)

4-(3-Chloro-4-(3-fluorobenzyloxy)phenylamino)-6-(1-(2-hydroxyethoxyimino)-2-butyn-1-yl)quinazoline (VIII-33, 7.6 g) was dissolved in 150 ml of tetrahydrofuran, and 4.19 ml of triethylamine and 2.33 ml of methanesulfonyl chloride were added, followed by stirring for 3.5 hours. After completion of the reaction, the reaction mixture was poured into water, and aqueous saturated sodium bicarbonate solution was added, followed by extraction with ethyl acetate. The organic layer was dried over sodium sulfate, and the filtrate was concentrated. Ethyl acetate was added to the concentrated residue, this was allowed to stand at room temperature, a crystal was precipitated, and diluted with hexane, and the crystal was collected by filtration to obtain 4-(3-chloro-4-(3-fluorobenzyloxy)phenylamino)-6-(1-(2-sulfonyloxyethoxyimino)-butyn-1-yl)quinazoline (VIII-34, 7.66 g) as a pale yellow crystal. $^1$H NMR (d$_6$-DMSO, δ): 10.07 (1H, s), 8.77 (1H, s), 8.60 (1H, s), 8.24 (1H, d, J=8.8 Hz), 7.97 (1H, d, J=2.4 Hz), 7.81 (1H, d, J=8.8 Hz), 7.69 (1H, dd, J=2.4 Hz, J=8.8 Hz), 7.51-7.45 (1H, m), 7.35-7.27 (3H, m), 7.21-7.17 (1H, m), 5.27 (2H, s), 4.58 (2H, t, J=4.8 Hz), 4.54 (2H, t, J=4.8 Hz), 3.24 (3H, s), 2.27 (3H, s).

[Chemical formula 78]

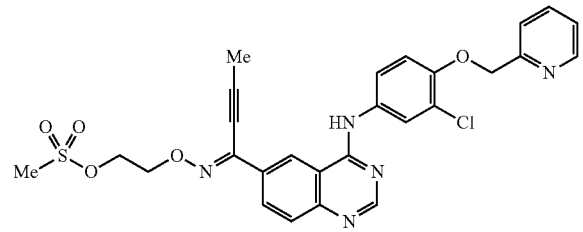

VIII-36

4-(3 Chloro-4-(pyridin-2-ylmethoxy)phenylamino)-6-(1-(2-sulfonyloxyethoxyimino)-2-butyn-1-yl)quinazoline (VIII-36)

The compound was synthesized according to the same manner as that of the first step and the second step.
$^1$H NMR (d$_6$-DMSO, δ): 10.09 (1H, s), 8.77 (1H, s), 8.61 (1H, s), 8.59 (1H, s), 8.24 (1H, d, J=8.1 Hz), 7.97 (1H, d, J=2.4 Hz), 7.89 (1H, t, J=7.5 Hz), 7.81 (1H, d, J=9.0 Hz), 7.68 (1H, dd, J=2.4 Hz, J=9.0 Hz), 7.59 (1H, d, J=8.1 Hz), 7.40-7.35 (1H, m), 7.29 (1H, d, J=9.0 Hz), 5.31 (2H, s), 4.57 (2H, bs), 4.55 (2H, bs), 3.24 (3H, s). 2.27 (3H, s).

[Chemical formula 79]

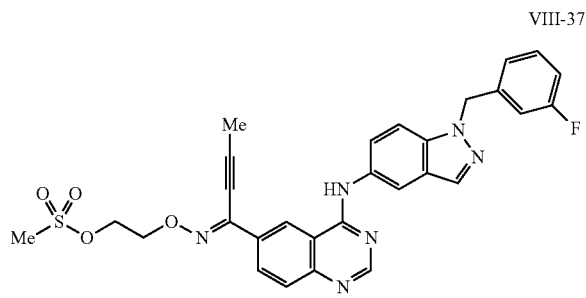

VIII-37

4-(1-(3-Fluorobenzyl)-1H-indazol-5-ylamino) 6-(1-(2-sulfonyloxyethoxyimino)-2-butyn-1-yl)quinazoline (VIII-37)

The compound was synthesized according to the same manner as that of the first step and the second step.

$^1$H NMR (d$_6$-DMSO, δ): 10.20 (1H, s), 8.81 (1H, s), 8.53 (1H, s), 8.24 (1H, d, J=8.7 Hz), 8.17 (1H, s), 8.13 (1H, s), 7.80 (1H, d, J=8.7 Hz), 7.75 (1H, d, J=8.7 Hz), 7.67 (1H, d, J=9.3 Hz), 7.41-7.36 (1H, m), 7.14-7.04 (3H, m), 5.72 (2H, s), 4.58 (2H, t, J=5.4 Hz), 4.54 (2H, t. J=5.4 Hz), 3.24 (3H, s), 2.26 (3H, s).

(Step 3) Synthesis of 4-(3-chloro-4-3-fluorobenzyloxy)phenylamino)-6-(1-2-ethylaminoethoxyimino)-2-butyn-1-yl)quinazoline (VIII-35)

4-(3-Chloro-4-(3-fluorobenzyloxy)phenylamino)-6-(1-(2-sulfonyloxyethoxyimino)-2-butyn-1-yl)quinazoline (VIII-34, 10 mg) was dissolved in 3 ml of N,N-dimethylformamide, and 160.1 g of 70% aqueous ethylamine solution was added, followed by stirring at 60° C. for 14 hours. Water was added to the reaction mixture, followed by extraction with ethyl acetate. The organic layer was dried over magnesium sulfate, and the concentrated residue of the filtrate was purified by chromatography (eluting with ethyl acetate) using an amino column to obtain 4-(3-chloro-4-3-fluorobenzyloxy)phenylamino)-6-(1-(2-ethylaminoethoxyimino)-2-butyn-1-yl)quinazoline (VIII-35, 53 mg) as a colorless solid.

$^1$H NMR (d$_6$-DMSO, δ): 10.08 (1H, s), 8.74 (1H, s), 8.50 (1H, s), 8.21 (1H, d, J=8.4 Hz), 7.96 (1H, s), 7.80 (1H, d, J=8.8 Hz), 7.69 (1H, d, J=8.0 Hz), 7.51-7.45 (1H, m), 7.35-7.27 (3H, m), 7.21-7.16 (1H, m), 5.27 (2H, s), 4.31 (2H, t, J=5.6 Hz), 2.80 (2H, t, J=6.0 Hz), 2.61 (2H, q, J=7.2 Hz), 2.26 (3H, s), 1.02 (3H, t, J=7.6 Hz).

In amination of the third step, amine which is commercially available or amine which can be synthesized according to the method described in J. Syn. Org. Chem., Jpn., 2001, 59:779-789, Tetrahedron Lett., 1995, 36:6373-6374, Synlett, 1999:1301-1303, Tetrahedron, 2002, 58:6267-6276 or a salt thereof can be used.

Example 10

[Chemical formula 80]

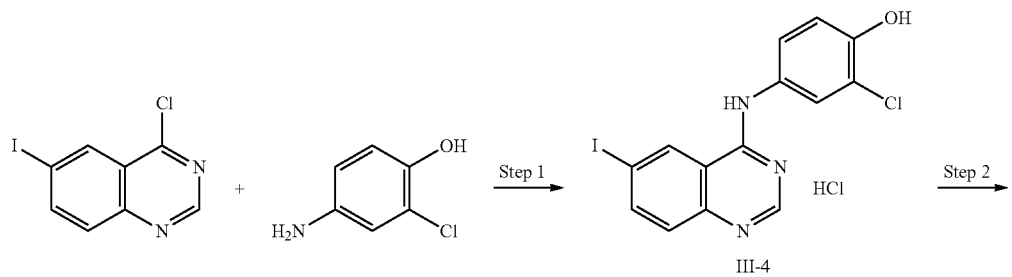

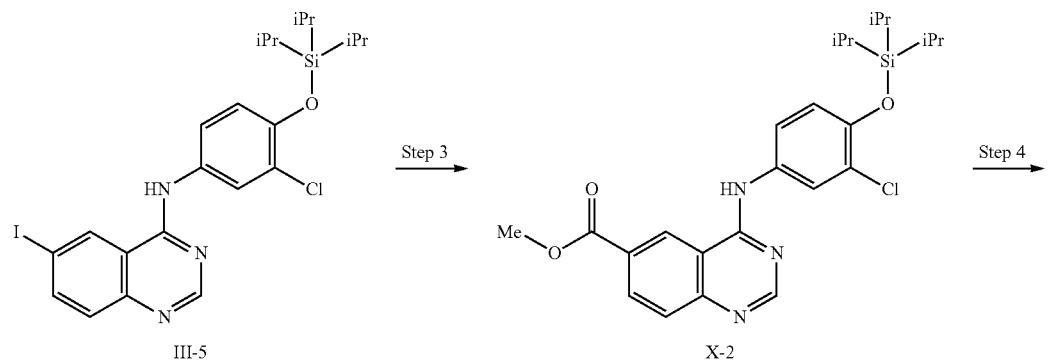

-continued
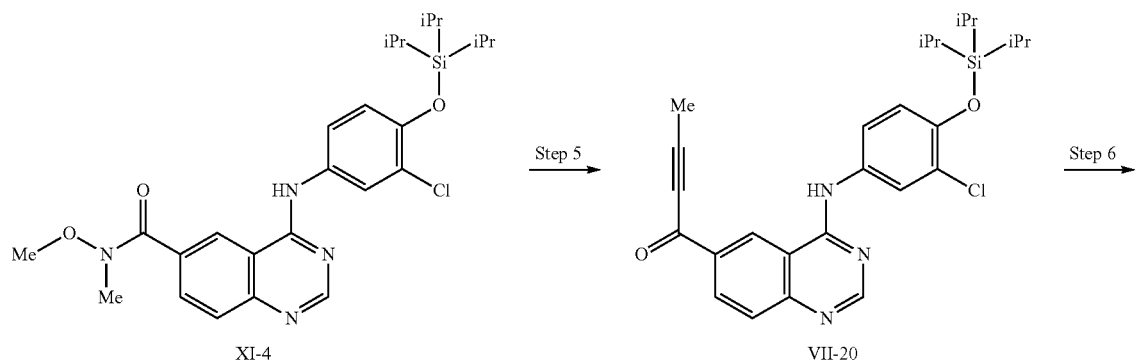
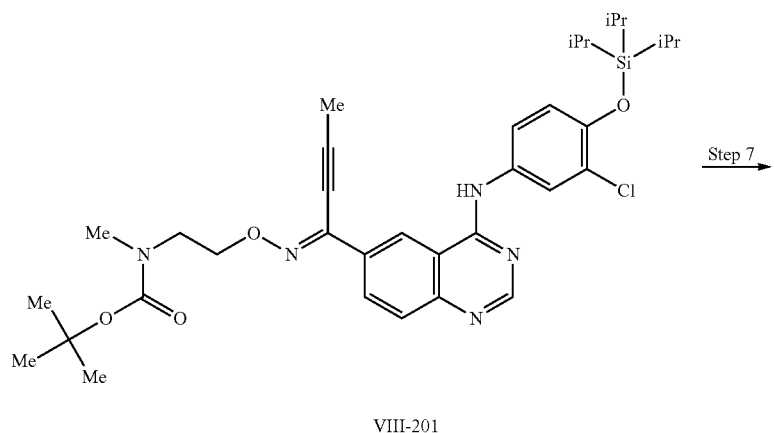
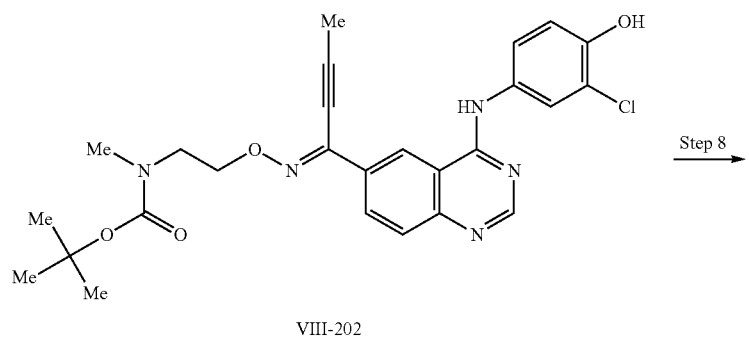
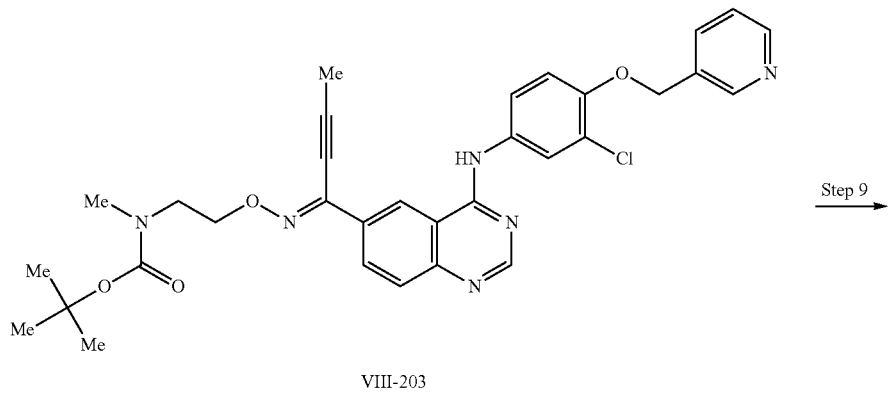

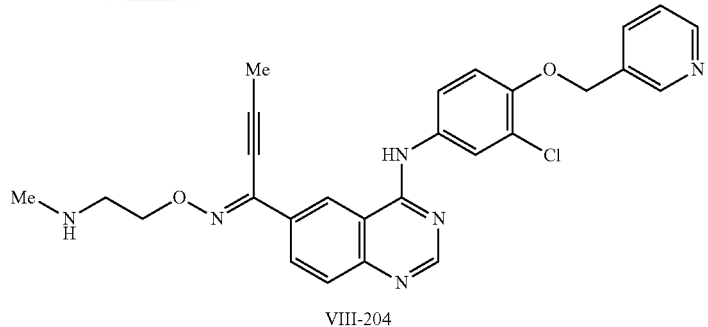

VIII-204

(Step 1) Synthesis of 4-(3-Chloro-4-hydroxyphenylamino)-6-iodoquinazoline (III-4)

According to the same manner as that of the first step of Example 1 and using 20.3 g of 4-chloro-6-iodoquinazoline and 10 g of 3-chloro-4-hydroxyaniline, 4-(3-chloro-4-hydroxyphenylamino)-6-iodoquinazoline hydrochloride (III-4, 26.6 g) was obtained as a yellow solid.

$^1$H NMR (d$_6$-DMSO, δ): 11.4 (1H, s), 10.5 (1H, s), 9.21 (1H, s), 8.93 (1H, s). 8.35 (1H, d, J=8.4 Hz), 7.79 (1H, s), 7.69 (1H, d, J=9.0 Hz), 7.48 (1H, d, J=9.0 Hz), 7.10 (1H, d, J=8.4 Hz).

(Step 2) Synthesis of 4-(3-chloro-4-triisopropylsilyloxyphenylamino)-6-iodoquinazoline (III-5)

4-(3-Chloro-4-3-fluorobenzyloxy)phenylamino)-6-iodoquinazoline hydrochloride (II-4, 20 g), 13.3 g of triisopropylsilane chloride, and 12.6 g of imidazole were dissolved in 200 ml of N,N-dimethylformamide, followed by stirring at room temperature for 4 hour. After completion of the reaction. 200 ml of aqueous saturated sodium bicarbonate solution and 200 ml of ethyl acetate were added to separate the layers. The aqueous layer was re-extracted with 200 ml of ethyl acetate two times, and all organic layer were combined, washed with water and aqueous saturated sodium chloride solution in this order, and dried over anhydrous magnesium sulfate. The filtrate was concentrated, and the residue was washed with a hexane-ethyl acetate (2:1) to obtain 4-(3-chloro-4-triisopropylsilyloxyphenylamino)-6-iodoquinazoline (III-5, 25.3 g) as a colorless solid.

$^1$H NMR (d$_6$-DMSO, δ): 9.8 (1H, s), 8.96 (1H, s), 8.62 (1H, s), 8.12 (1H, d, J=8.7 Hz). 8.02 (1H, d, J=2.7 Hz), 7.70 (1H, dd, J=8.7 Hz, J=2.7 Hz), 7.56 (1H, d, J=8.7 Hz), 7.04 (1H, d, J=8.7 Hz), 1.25-1.40 (3H, m), 1.1 (18H, d, J=7.2 Hz).

(Step 3) Synthesis of 4-(3-chloro-4-triisopropylsilyloxyphenylamino)-quinazoline-6-carboxylic acid methyl ester (X-2)

From 4-(3-chloro-4-triisopropylsilyloxyphenylamino)-6-iodoquinazoline (III-5, 21.8 g), 4-(3-chloro 4-triisopropylsilyloxyphenylamino)-quinazoline-6-carboxylic acid methyl ester (X-2, 20.4 g) was obtained as a yellow solid according to the same manner as that of the first step of Reference Example 1.

$^1$H NMR (d$_6$-DMSO, δ): 10.2 (1H, s), 9.26 (1H, s), 8.66 (1H, s), 8.30 (1H, d, J=8.7 Hz), 8.01 (1H, d, J=2.4 Hz). 7.84 (1H, d, J=8.7 Hz), 7.71 (1H, dd, J=9 Hz, J=2.1 Hz), 7.04 (1H, d, J=8.7 Hz), 3.96 (3H, s), 1.29-1.41 (3H, m), 1.11 (18H, d, J=7.2 Hz).

(Step 4) Synthesis of 4-(3-chloro-4-triisopropylsilyloxyphenylamino)-quinazoline-6-carboxy ic acid methoxymethylamide (XI-4)

From 4-(3-chloro-4-triisopropylsilyloxyphenylamino)-quinazoline-6-carboxylic acid methyl ester (X-2, 10 g), 4-(3-chloro-4-triisopropylsilyloxyphenylamino)-quinazoline-6-carboxylic acid methoxymethylamide (XI-4, 4.1 g) was obtained as a colorless solid according to the same manner as that of the second step of Reference Example 1.

$^1$H NMR (d$_6$-DMSO, δ): 10.0 (1H, s), 8.80 (1H, s), 8.65 (1H, s), 7.97-8.08 (2H, m), 7.81 (1H, d, J=8.7 Hz), 7.70-7.75 (1H, m), 7.04 (1H, d, J=9.0 Hz), 3.58 (3H, s), 3.35 (3H, s), 1.29-1.41 (3H, m), 1.11 (18H, d, J=7.5 Hz).

(Step 5) Synthesis of 4-(3-chloro-4-triisopropylsilyloxyphenylamino)-6-(1-oxo-2-butyn-1-yl)quinazoline (VII-20)

From 4-(3-chloro-4-triisopropylsilyloxyphenylamino)-quinazoline-6-carboxylic acid methoxymethylamide (XI-4, 4.1 g), 4-(3-chloro-4-triisopropylsilyloxyphenylamino)-6-(1-oxo-2-butyn-1-yl)quinazoline (VII-20, 1.3 g) was obtained as a yellow oil according to the same manner as that of the third step of Reference Example 1.

$^1$H NMR (d$_6$-DMSO, δ): 10.3 (1H, s), 9.24 (1H, s), 8.67 (1H, s), 8.45 (H, d, J=8.7 Hz), 7.99 (1H, s), 7.88 (1H, s, J=8.7 Hz). 7.68 (1H, d, J=9.0 Hz), 7.06 (1H, d, J=9.0 Hz), 2.28 (3H, s), 1.29-1.41 (3H, m), 1.11 (0.8H, d, J=6.9 Hz).

(Step 6) Synthesis of 4-(3-chloro-4-triisopropylsilyloxyphenylamino)-6-1-(1-(N-(tert-butoxycarbonyl)-N-methylaminoethoxyimino)-2-butyn-1-yl)quinazoline (VIII-201)

From 4-(3-chloro-4-triisopropylsilyloxyphenylamino)-6-(1-oxo-2-butyn-1-yl)quinazoline (VII-20, 1.3 g), 4-(3-chloro-4-triisopropylsilyloxyphenylamino)-6-(2-((N-(tert-butoxycarbonyl)-N-methylaminoethoxyimino)-2-butyn-1-yl)quinazoline (VII-201, 1.1 g) was obtained as a yellow solid according to the same manner as that of the second step of Example 2.

ESI-MS (M/Z): (M+)=666.71, (M+H)=667.73

(Step 7) Synthesis of 4-(3-chloro-4-hydroxyphenylamino)-6-(1-(2-(N-(tert-butoxycarbonyl)-N-methyl aminoethoxyimino)-2 butyn-1-yl)quinazoline (VIII-202)

4-(3-Chloro-4-triisopropylsilyloxyphenylamino)-6-(1-(2-(N-(tert-butoxycarbonyl)-N-methylaminoethoxyimino)-2- butyn-1-yl)quinazoline (VIII-201, 1.1 g) was dissolved in 20 ml of tetrahydrofuran, and 6.7 ml of 1 mol/L solution of tetrabutylammonium fluoride in tetrahydrofuran was added, followed by stirring at room temperature for 30 minutes. After completion of the reaction, ml of water and 10 ml of ethyl acetate were added to separate the layers. The aqueous layer was re-extracted with 10 ml of ethyl acetate two times, and all organic layers were combined, washed with water and aqueous saturated sodium chloride solution, and dried over anhydrous magnesium sulfate. The filtrate was concentrated, and the residue was washed with a hexane-ethyl acetate (1:1) to obtain 4-(3-chloro-4-hydroxyphenylamino)-6-(1-(2-(N-(tert-butoxycarbonyl)-N-methylaminoethoxyimino)-2-butyn-1-yl)quinazoline (VIII-202, 0.7 g) as a yellow solid.

$^1$H NMR (d$_6$-DMSO, δ): 9.96 (1H, s), 8.73 (1H, s), 8.55 (1H, s), 8.21 (1H, d, J=8.7 Hz), 7.75-7.86 (2H, m), 7.50 (1H, d, J=7.8 Hz), 7.00 (1H, d, J=8.7 Hz), 4.36 (2H, bs), 3-56 (2H, bs), 2.86 (3H, bs), 2.25 (3H, bs), 1.36 (9-H, s).

(Step 8) Synthesis of 4-(3-chloro-4-(pyridin-3-yl-methoxy)phenylamino)-6-(1-(2-(N-(tert-butoxycarbonyl)-N-methylaminoethoxyimino)-2-butyn-1-yl)quinazoline (VIII-203)

4-(3-Chloro-4-hydroxyphenylamino)-6-(1 (2-(N-(tert-butoxycarbonyl)-N-methylaminoethoxyimino)-2-butyn-1-yl)quinazoline (VIII-202, 70 mg), 87 mg of 3-bromomethylpyridine hydrobromide, and 223 mg of cesium carbonate were dissolved in 1.1 ml of a N,N-dimethylformamide-water (10.1), followed by stirring at room temperature for 3 hours. After completion of the reaction, 5 ml of water and 5 ml of ethyl acetate were added to separate the layers. The aqueous layer was re-extracted with 5 ml of ethyl acetate two times, and all organic layers were combined, washed with water and aqueous saturated sodium chloride solution in this order, and dried over anhydrous magnesium sulfate. The filtrate was concentrated, and the residue was purified by silica gel column chromatography (eluting with hexane:ethyl acetate=1:1) to obtain 4-(3-chloro 4-(pyridin-3 ylmethoxy)phenylamino)-6-(1-(2-(N-(tert-butoxycarbonyl)-N-methylaminoethoxyimino)-2-butyn-1-yl)quinazoline (VIII-203, 70 mg) as a yellow oil.

$^1$H NMR (d$_6$-DMSO, δ): 10.0 (1H, bs), 8.74 (1H, bs), 8.72 (1H, bs), 8.60 (1H, s), 8.57 (1H, d, J=4.4 Hz), 8.23 (1H, d, J=8.8 Hz), 7.97 (1H, bs), 7.91 (1H, d, J=8.0 Hz), 7.80 (1H, d, J=8.8 Hz), 7.72 (1H, d, J=8.8 Hz), 7.46 (1H, dd, J=7.6 Hz, J=4.4 Hz), 7.33 (1H, d, J=8.8 Hz), 5.29 (2H, s), 4.37 (2H, bs), 3.56 (2H, bs), 2.86 (3H, bs), 2.25 (3H, bs), 1.36 (9H, s).

(Step 9) Synthesis of 4-(3-chloro-4-(pyridin-3-yl-methoxy)phenylamino) 6-(1-(2-N-methylaminoethoxyimino)-2-butyn-1-yl)quinazoline (VIII-204)

Starting from 4-(3-chloro-4-(pyridin-3-ylmethoxy)phenylamino)-6-(1-(2-(N-(tert-butoxycarbonyl)-N-methylaminoethoxyimino)-2-butyn-1-yl)quinazoline (VIII-203, 70 mg), and according to the same manner as that of the second step of Example 2, the reaction was performed, and purification was performed by recrystallization from hexane-ethyl acetate to obtain 4-(3-chloro-4-(pyridin-3-ylmethoxy)phenylamino)-6-(1-(2-N-methylaminoethoxyimino)-2-butyn-1-yl)quinazoline (VIII-204, 7 mg) as a yellow solid. 10.3 (1H, s), 8.84 (1H, s), 8.72 (1H, s), 8.42-8.65 (2H, m), 8.26 (1H, d. J=7.6 Hz), 7.98 (1H, s), 7.91 (1H, brs), 7.81 (1H, bs), 7.71 (1H, brs), 7.47 (1H, brs), 7.34 (1H, d, J=8.0 Hz), 5.30 (2H, s), 4.53 (2H, brs), 3.38 (2H, brs), 2.68 (3H, s), 2.26 (3H, s).

According to the same manner as that of Examples 7 to 10, the following compound was synthesized.

TABLE 15

[Chemical formula 81]

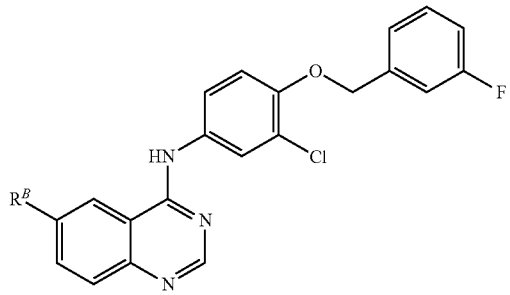

(VIII)

| Compound | R$^B$ | $^1$H-NMR(d$_6$-DMSO) |
|---|---|---|
| VIII-2 | Me, piperidinyl-CH$_2$CH$_2$-O-N= | 9.92 (1H, s), 8.65 (1H, brs), 8.62 (1H, s), 8.22 (1H, d, J = 6 6 Hz), 7.96 (1H, d, J = 2.1 Hz), 7.76 (1H, d, J = 6.6 Hz), 7.70 (1H, dd, J = 6.6 Hz, J = 1.8 Hz), 7.53-7.45 (1H, m), 7.35-7.28 (3H, m), 7.18 (1H, t, J = 5.7 Hz), 5.27 (2H, s), 4.30 (2H, t, J = 4.5 Hz), 2.64 (2H, t, J = 4.5 Hz), 2.43 (4H, brs), 2.35 (3H, s), 1.53-1.47 (4H, m), 1.40-1.36 (2H, m). |
| VIII-3 | Me, Me$_2$N-CH$_2$CH$_2$-O-N= | 9.92 (1H, 8), 8.62 (1H, brs), 8.58 (1H, s), 8.23 (1H, d, J = 6.6 Hz), 7.96 (1H, d, J = 1.8 Hz), 7.76 (1H, d, J = 6.6 Hz), 7.70 (1H, d, J = 6.9 Hz), 7.50-7.45 (1H, m), 7.35-7.28 (3H, m), 7.18 (1H, t, J = 6.9 Hz), 5.27 (2H, s), 4.26 (2H, t, J = 4.5 Hz), 2.77 (2H, t, J = 4.5 Hz), 2.55 (4H, q, J = 5.4 Hz), 2.36 (3H, s), 0.96 (2H, t, J = 5.4 Hz) |

TABLE 15-continued

[Chemical formula 81]

(VIII)

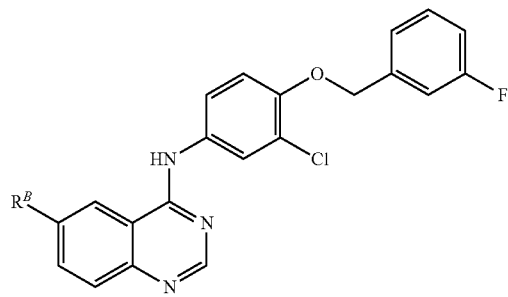

| Compound | $R^B$ | $^1$H-NMR($d_6$-DMSO) |
|---|---|---|
| VIII-4 | 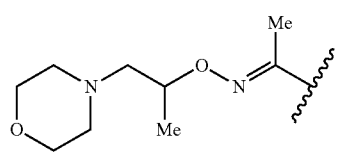 [SMILES: */C(C)=N/OC(C)CN1CCOCC1] | (mono · HCl salt) 11.4 (1H, brs), 10.82 (1H, brs), 9.07 (1H, s), 8.82 (1H, s), 8.40 (1H, d, J = 10.2 Hz), 7.94 (1H, d, J = 2.7 Hz), 7.88 (1H, d, J = 9.0 Hz), 7.70 (1H, dd, J = 8.7 Hz, 2.7 Hz), 7.45-7.52 (1H, m), 7.31-7.36 (3H, m), 7.17-7.23 (1H, m), 5.30 (2H, s), 4.94 (1H, m), 3.85 (4H, m), 3.36-3.60 (6H, m), 2.44 (3H, s), 1.38 (3H, d, J = 6.3 Hz) |
| VIII-5 | 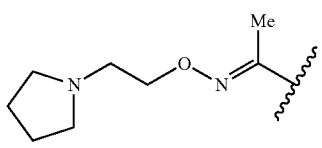 [SMILES: */C(C)=N/OCCN1CCCC1] | 9.93 (1H, s), 8.62 (1H, brs), 8.58 (1H, s), 8.22 (1H, d, J = 6.6 Hz), 7.96 (1H, d, J = 1.8 Hz), 7.76 (1H, d, J = 6.6 Hz), 7.70 (1H, dd, J = 6.6 Hz, J = 1.8 Hz), 7.50-7.45 (1H, m), 7.35-7.28 (3H, m), 7.19 (1H, t, J = 6.6 Hz), 5.27 (2H, s), 4.31 (2H, t, J = 4.5 Hz), 2.78 (2H, t, J = 4.5 Hz), 2.50 (4H, br), 2.36 (3H, s), 1.69 (4H, br) |
| VIII-6 | 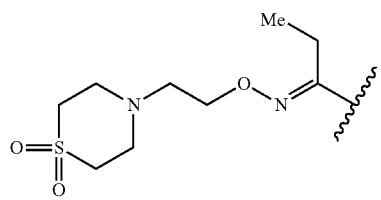 [SMILES: */C(CC)=N/OCCN1CCS(=O)(=O)CC1] | 9.95 (1H, s), 8.62 (1H, brs), 8.58 (1H, s), 8.21 (1H, d, J = 6.9 Hz), 7.94 (1H, d, J = 1.5 Hz), 7.77 (1H, d, J = 6.6 Hz), 7.69 (1H, d, J = 6.9Hz), 7.51-7.45 (1H, m), 7.35-7.28 (3H, m), 7.19 (1H, t, J = 6.3 Hz), 5.28 (2H, s), 4.32 (2H, t, J = 4.2 Hz), 3.09 (4H, brd, J = 4.5 Hz), 3.05 (4H, brd, J = 4.5 Hz), 2.97-2.89 (4H, m), 1.13 (3H, t, J = 5.4 Hz) |
| VIII-7 | 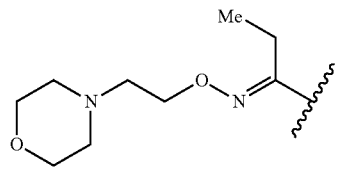 [SMILES: */C(CC)=N/OCCN1CCOCC1] | 9.95 (1H, s), 8.61 (1H, brs), 8.58 (1H, s), 8.20 (1H, d, J = 6 6 Hz), 7.94 (1H, brs), 7 77 (1H, d, J = 6.6 Hz), 7.69 (1H, d, J = 6.9 Hz), 7.51-7.45 (1H, m), 7.35-7.28 (3H, m), 7.19 (1H, t, J = 6.0 Hz), 5.27 (2H, s), 4.32 (2H, t, J = 4.2 Hz), 3.59 (4H, t, J = 3.3 Hz), 2.91 (2H, q, J = 5.4 Hz), 2.68 (2H, t, J = 4.2 Hz), 1.13 (3H, t, J = 5.4 Hz) |

TABLE 16

| Compound No. | $R^B$ | $^1$H-NMR($d_6$-DMSO) |
|---|---|---|
| VIII-8 | 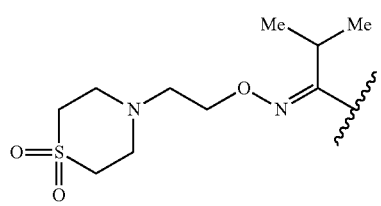 [SMILES: */C(=N/OCCN1CCS(=O)(=O)CC1)C(C)C] | (E/Z mixture) 8.61 (0.5H, s), 8.58 (0.5H, s), 8.48 (0 5H, s), 8.25 (0.5H, s), 7.99 (0.5H, d, J = 2.4 Hz), 7.97 (0.5H, d, J = 2.4 Hz), 7.90 (0.5H, d, J = 7.9 Hz), 7.65-7.73 (2.5H, m), 7.50-7.55 (0 5H, m), 7.26-7.34 (3.5H, m), 7.16 (1H, d, t J = 7.9, 2.4 Hz), 5.26 (2H, s), 4.29 (1H, t, J = 7.0 Hz), 4.15 (1H, t, J = 7.0 Hz), 3.50-3.55 (1H, m), 3.28-3.35 (2H, m), 3.20-3.28 (2H, m), 3.10-3.20 (2H, m), 2.99-3.07 (2H, m), 2.90-2.96 (1H, m), 2.87-2.95 (1H, m), 1.21 (3H, d, J = 7.0 Hz), 1.16 (3H, d, J = 7.0 Hz) |

TABLE 16-continued

| Compound No. | R^B | ¹H-NMR(d₆-DMSO) |
|---|---|---|
| VIII-9 | (pyrrolidine-CH₂CH₂-O-N=C(Me)(CHMe₂) structure) | (E/Z mixture) 8.58 (0.5H, s), 8.56 (0.5H, s), 8.44 (0.5H, s), 8 36 (0 5H, s), 7.99 (0.5H, d, J = 2.4 Hz), 7.97 (0.5H, d, J = 2.4 Hz), 7.90 (0.5H, d, J = 7.9 Hz), 7.65-7.73 (2.5H, m), 7.50-7.55 (0.5H, m), 7.26-7.34 (3.5H, m), 7.16 (1H, d, t J = 7.9, 2.4 Hz), 5.24 (2H, s), 4.21 (1H, t, J = 7.0 Hz), 4.05 (1H, t, J = 7.0 Hz), 2.73 (1H, t, J = 7.2 Hz), 2.57 (1H, t, J = 7.2 Hz), 2.45-2 55 (2H, m), 2.30-2.35 (2H, m), 1.64-1.70 (2H, m), 1.50-1.58 (2H, m), 1.21 (3H, d, J = 7.0 Hz), 1.16 (3H, d, J = 7.0 Hz) |
| VIII-10 | (morpholine-CH₂CH₂-O-N=C(C≡C-Me) structure) | (E/Z mixture) 10.09 (1H, s, major), 10.00 (1H, s, minor), 8.74 (1H, s, major), 8.59 (1H, s), 8.22 (1H, d, J = 9 Hz, major), 7.94-8.02 (1H, m), 7.64-7.82 (2H, m), 7.44-7.52 (1H, m), 7.16-7.36 (4H, m), 5.27 (2H, s), 4.32-4.43 (2H, m), 3.56-3.62 (4H, m), 2.66-2.74 (2H, m), 2.34 (3H, s, minor), 2.25 (3H, s, major) |
| VIII-11 | (pyrrolidine-CH₂CH₂-O-N=C(C≡C-Me) structure) | 10.08 (1H, s), 8.74 (1H, s), 8.58 (1H, s), 8.22 (1H, d, J = 8.4 Hz), 7.96 (1H, brs), 7.80 (1H, d, J = 8.4 Hz), 7.68 (1H, d, J = 9.6 Hz), 7.43-7.52 (1H, m), 7.14-7 36 (4H, m), 5.27 (2H, s), 4.37 (2H, t, J = 6 0 Hz), 2.80 (2H, t, J = 6.0 Hz), 2.25 (3H, s), 1.69 (4H, brs), 1.24 (4H, brs) |
| VIII-12 | (thiomorpholine-1,1-dioxide-CH₂CH₂-O-N=C(Ph) structure) | (E/Z mixture) 9.95 (1H, s, major), 9.80 (1H, s, minor), 8.65 (1H, s, minor), 8.58 (1H, s, major), 8.54 (1H, s, major), 8.44 (1H, s, minor), 7 99 (1H, d, J = 1.5 Hz, minor), 7.91 (1H, d, J = 1.8 Hz, major), 7 15-7 92 (14H, m), 5.26 (2H, s), 5.25 (2H, s), 4.32 (2H, d, J = 3.9 Hz, major), 4.27 (2H, t, J = 4.2 Hz, minor), 2.82-3.06 (10H, m) |
| VIII-13 | (morpholine-CH₂CH₂-O-N=C(Ph) structure) | (E/Z mixture) 9.96 (1H, s, major), 9.82 (1H, s, minor), 8.64 (1H, s, minor), 8.57 (1H, s, major), 8.53 (1H, brs, major), 8.44 (1H, brs, minor), 7.99 (1H, d, J = 2.7 Hz, minor), 7.90 (1H, d, J = 2.4 Hz, major), 7.14-7.88 (13H, m), 5.26 (2H, s, major), 5.24 (2H, s, minor), 4 32 (2H, t, J = 5.7 Hz, major), 4.27 (2H, t, J = 5 4 Hz, minor), 3.53-3.58 (4H, m, major), 3.44-3.50 (4H, m, minor), 2.56-2.70 (2H, m), 2.32-2.46 (4H, m) |

TABLE 17

| Compound No. | R^B | ¹H-NMR(d₆-DMSO) |
|---|---|---|
| VIII-14 | (morpholine-CH₂CH₂-O-N=C(CF₃) structure) | 9.99 (1H, s), 8.65 (s, 1H), 8.61 (1H, s), 7.98 (1H, brs), 7.90 (1H, d, J = 6 9 Hz), 7.87 (1H, d, J = 6.9 Hz), 7.70 (1H, d, J = 6.3 Hz), 7.40-7.51 (1H, m), 7.27-7.35 (3H, m), 7.15-7.21 (1H, m), 5.27 (2H, s), 4.38 (2H, t, J = 3.9 Hz), 3.47-3.51 (4H, m), 2.57-2.65 (2H, m), 2.33-2.40 (4H, m) |

TABLE 17-continued

| Compound No. | R$^B$ | $^1$H-NMR(d$_6$-DMSO) |
|---|---|---|
| VIII-15 | [structure: MeSO$_2$CH$_2$CH$_2$NH-CH(Me)-CH$_2$-O-N=C(Me)-] | 9.94 (1H, s), 8.63 (1H, s), 8.58 (1H, s), 8.23 (1H, dd, J = 8.7 Hz, 1.2 Hz), 7.96 (1H, d, J = 2.4 Hz), 7.76 (1H, d, J = 9.0 Hz), 7.70 (1H, dd, J = 8.4 Hz, 2.4 Hz), 7.44-7.52 (1H, m), 7.28-7.35 (3H, m), 7.16-7.22 (1H, m), 5.27 (2H, s), 4.07-4.10 (2H, m), 3.23 (2H, t, J = 6.9 Hz), 3.01-3.04 (6H, m), 2.38 (3H, s), 1.05 (3H, d, J = 6.3 Hz) |
| VIII-16 | [structure: MeSO$_2$CH$_2$CH$_2$NH-CH$_2$-CH(Me)-O-N=C(Me)-] | 9.94 (1H, s), 8.62 (1H, s), 8.58 (1H, s), 8.25 (1H, dd, J = 9.0 Hz, 1.5 Hz), 7.95 (1H, d, J = 2.7 Hz), 7.76 (1H, d, J = 8.7 Hz), 7.69 (1H, dd, J = 8.7 Hz, 2.4 Hz), 7.44-7.52 (1H, m), 7.28-7.35 (3H, m), 7.16-7.22 (1H, m), 5.27 (2H, s), 4.39-4.45 (1H, m), 3.25 (2H, t, J = 6.9 Hz), 2.95-3 01 (5H, m), 2.73-2.92 (2H, m), 2 36 (3H, s), 1.30 (3H, d, J = 6.3 Hz) |
| VIII-17 | [structure: MeOCH$_2$CH$_2$-O-CH$_2$CH$_2$NH-CH$_2$CH$_2$-O-N=C(Me)-] | (di-HCl salt) 11.09 (1H, brs), 9.00 (1H, s), 8.90 (2H, brs), 8.75 (1H, s), 8.34 (1H, d, J = 9.3 Hz), 7.96 (1H, d, J = 2.7 Hz), 7.85 (1H, d, J = 8.7 Hz), 7.72 (1H, dd, J = 9.0 Hz, 2.7 Hz), 7.45-7.52 (1H, m), 7.31-7.35 (3H, m), 7.17-7.22 (1H, m), 5.29 (2H, s), 4.49 (2H, t, J = 5.4 Hz), 3.67 (2H, t, J = 5.4 Hz), 3.49 (2H, q, J = 6.9 Hz), 3.21-3 23 (4H, m), 2.45 (3H, s), 1.13 (3H, t, J = 6.9 Hz) |
| VIII-18 | [structure: pyrrolidine-CH$_2$-O-N=C(Me)-] | 9.93 (1H, s), 8.62 (1H, brs), 8.58 (1H, s), 8.22 (1H, d, J = 6 9 Hz), 7.95 (1H, brs), 7.76 (1H, d, J = 6.0 Hz), 7.70 (1H, d, J = 6.3 Hz), 7.50-7.45 (1H, m), 7.35-7 28 (3H, m), 7.18 (1H, t, J = 5.4 Hz), 5.27 (2H, s), 4.11-4 03 (2H, m), 2.87-2.67 (2H, m), 2.37 (3H, s), 1.85-1.76 (1H, m), 1.73-1.59 (2H, m), 1.48-1.39 (1H, m) |
| VIII-19 | [structure: MeSO$_2$CH$_2$CH$_2$NH-CH$_2$CH$_2$-O-N=C(Et)-] | (bis-trifluoroacetate salt) 11.40 (1H, s), 9.10 (2H, s), 8.89 (1H, s), 8.81 (1H, s), 8.42 (1H, d, J = 6.0 Hz), 7.90-7.87 (2H, m), 7.62 (1H, d, J = 6.6 Hz), 7.51-7.46 (1H, m), 7.38-7.31 (3H, m), 7.20 (1H, t, J = 6.3 Hz), 5 32 (2H, s), 4.48 (2H, brs), 3.61-3.46 (6H, m), 3.13 (3H, s), 2.97 (2H, q, J = 5.7 Hz), 1.14 (3H, t, J = 5.7 Hz). |
| VIII-20 | [structure: MeNH-CH$_2$CH$_2$-O-N=C(Et)-] | (bis-trifluoroacetate salt) 11.07 (1H, s), 8.82 (1H, s), 8.78 (3H, brs), 8.37 (1H, d, J = 6.6 Hz), 7.89-7.86 (2H, m), 7.64 (1H, d, J = 6.6 Hz), 7.51-7.46 (1H, m), 7.36-7.32 (3H, m), 7.20 (1H, t, J = 6.3 Hz), 5 31 (2H, s), 4.45 (2H, brs), 2.97 (2H, q, J = 5.4 Hz), 2.67 (3H, brs), 1.13 (3H, t, J = 5.4 Hz). |

TABLE 18

| Compound No. | R$^B$ | $^1$H-NMR(d$_6$-DMSO) |
|---|---|---|
| VIII-21 | [structure: cyclohexyl-NH-CH$_2$CH$_2$-O-N=C(Et)-] | (bis-trifluoroacetate salt) 11.03 (1H, s), 8.81 (1H, s), 8.78 (1H, s), 8.71 (2H, s), 8.37 (1H, d, J = 6.6 Hz), 7.88-7.86 (2H, m), 7.64 (1H, d, J = 6.6 Hz), 7.51-7.46 (1H, m), 7.36-7.31 (3H, m), 7.20 (1H, t, J = 6.3 Hz), 5.31 (2H, s), 4.46 (2H, brs), 3.39 (2H, brs), 3.10 (1H, brs), 2.97 (2H, q, J = 6.3 Hz), 2.06 (2H, brd, J = 8.4 Hz), 1.78 (2H, brd, J = 8.4 Hz), 1.37-1.04 (9H, m). |
| VIII-22 | [structure: pyrrolidine-CH$_2$-O-N=C(Et)-] | 9.95 (1H, s), 8.61 (1H, brs), 8.58 (1H, s), 8.19 (1H, d, J = 6.3 Hz), 7.94 (1H, brs), 7.77 (1H, d, J = 6.6 Hz), 7.69 (1H, d, J = 6.6 Hz), 7.50-7.45 (1H, m), 7.35-7.28 (3H, m), 7.19 (1H, t, J = 6.0 Hz), 5.27 (2H, s), 4.14-4.07 (2H, m), 3.43 (1H, br), 2.95-2.82 (4H, m), 1.86-1.80 (1H, m), 1.69 (2H, m), 1.46 (1H, m), 1.14 (3H, t, J = 5.4 Hz) |

TABLE 18-continued

| Compound No. | R^B | ^1H-NMR(d_6-DMSO) |
|---|---|---|
| VIII-23 | (structure: MeSO_2-CH_2CH_2-NH-CH_2CH_2-O-N=C(CH(Me)_2)-) | (E/Z mixture) 8.60 (0.5H, s), 8.58 (0.5H, s), 8.47 (0.5H, s), 8.39 (0.5H, s), 7.96 (0.5H, d, J = 2.4 Hz), 7.93 (0.5H, d, J = 2.4 Hz), 7.88 (0.5H, d, J = 7.9 Hz), 7.65-7.73 (2.5H, m), 7.50-7.55 (0.5H, m), 7.26-7.34 (3.5H, m), 7.16 (1H, d, t J = 7.9, 2.4 Hz), 5.26 (2H, s), 4.19 (1H, t, J = 7.0 Hz), 4.03 (1H, t, J = 7.0 Hz), 3.50-3.55 (1H, m), 3.22-3.30 (1H, m), 3.16-3.23 (1H, m), 2.96-3.03 (1H, m), 3.04 (1.5H, s), 2.90-2.95 (2H, m), 2.93 (1.5H, s), 2.70-2.80 (1H, m), 1.21 (3H, d, J = 7.0 Hz), 1.16 (3H, d, J = 7.0 Hz) |
| VIII-24 | (structure: MeNH-CH_2CH_2-O-N=C(CH(Me)_2)-) | (E/Z mixture) 8.61 (0.5H, s), 8.59 (0.5H, s), 8.47 (0.5H, s), 8.41 (0.5H, s), 7.99 (0.5H, d, J = 2.4 Hz), 7.97 (0.5H, d, J = 2.4 Hz), 7.90 (0.5H, d, J = 7 9 Hz), 7.65-7.73 (2.5H, m), 7.50-7.55 (0.5H, m), 7.26-7.34 (3.5H, m), 7.16 (1H, d, t J = 7.9, 2.4 Hz), 5.26 (2H, s), 4.29 (1H, t, J = 7.0 Hz), 4.13 (1H, t, J = 7.0 Hz), 3.50-3.55 (1H, m), 3.14-3 30 (1H, m), 2.96-3.04 (1H, m), 2.54 (1.5H, s), 2.49 (1.5H, s), 1.21 (3H, d, J = 7.0 Hz), 1 16 (3H, d, J = 7 0 Hz), 1.00 (3H, t, J = 7.2 Hz) |
| VIII-25 | (structure: MeCH_2-NH-CH_2CH_2-O-N=C(CH(Me)_2)-) | (E/Z mixture) 8.61 (0.5H, s), 8.58 (0.5H, s), 8.48 (0 5H, s), 8.31 (0.5H, s), 7.99 (0.5H, d, J = 2.4 Hz), 7.97 (0.5H, d, J = 2.4 Hz), 7.90 (0.5H, d, J = 7 9 Hz), 7 65-7.73 (2.5H, m), 7.50-7.55 (0.5H, m), 7.26-7.34 (3.5H, m), 7.16 (1H, d, t J = 7.9, 2.4 Hz), 5 26 (2H, s), 4.29 (1H, t, J = 7.0 Hz), 4.15 (1H, t, J = 7.0 Hz), 3.50-3.55 (1H, m), 3.24-3.30 (1H, m), 3.10-3.14 (1H, m), 2.99 (1H, q, J = 7.2 Hz), 2.89 (1H, q, J = 7.2 Hz), 1.21 (3H, d, J = 7.0 Hz), 1.16 (3H, d, J = 7.0 Hz), 1.00 (3H, t, J = 7.2 Hz) |

TABLE 19

| Compound No. | R^B | ^1H-NMR(d_6-DMSO) |
|---|---|---|
| VIII-26 | (structure: cyclohexyl-NH-CH_2CH_2-O-N=C(CH(Me)_2)-) | (E/Z mixture) 8.61 (0.5H, s), 8.58 (0.5H, s), 8.48 (0.5H, s), 8.31 (0.5H, s), 7.99 (0.5H, d, J = 2.4 Hz), 7.94 (0.5H, d, J = 2.4 Hz), 7 90 (0 5H, d, J = 7.9 Hz), 7.65-7 73 (2.5H, m), 7.50-7 55 (0.5H, m), 7.26-7.34 (3.5H, m), 7.16 (1H, d, t J = 7.9, 2.4 Hz), 5.26 (2H, s), 4.29 (1H, t, J = 7.0 Hz), 4.11 (1H, t, J = 7.0 Hz), 3.50-3.55 (1H, m), 3.14-3.17 (1H, m), 3.00-3.04 (1H, m), 2.00-2.10 (2H, m), 1.70-1.85 (2H, m), 1.00-1.30 (6H, m), 1.23 (3H, d, J = 7.0 Hz), 1.16 (3H, d, J = 7.0 Hz) |
| VIII-27 | (structure: MeNH-CH_2CH_2-O-N=C(C≡C-Me)-) | 10.10 (1H, s), 8.76 (1H, s), 8.60 (1H, s), 8.25 (1H, d, J = 8.7 Hz), 7.96 (1H, brs), 7.82 (1H, d, J = 9.0 Hz), 7.69 (1H, d, J = 9.0 Hz), 7.43-7.52(1H, m), 7.14-7.36 (4H, m), 5.28 (2H, s), 4.43 (2H, brs), 2.98 (2H, brs), 2.54 (3H, s), 2.27 (3H, brs), 1.60 (1H, s) |
| VIII-28 | (structure: cyclohexyl-NH-CH_2CH_2-O-N=C(C≡C-Me)-) | 10.10 (1H, s), 8.77 (1H, s), 8.60 (1H, s), 8.25 (1H, d, J = 8.7 Hz), 7.95 (1H, brs), 7.82 (1H, d, J = 9.6 Hz), 7.69 (1H, d, J = 9.3 Hz), 7.43-7.52 (1H, m), 7.14-7.36 (4H, m), 5.28 (2H, s), 4.45 (2H, brs), 2.91 (2H, brs), 2.27 (3H, s), 2.00 (2H, brs), 1.73 (2H, brs), 1.60 (1H, brs), 1.23 (7H, brs) |

TABLE 19-continued

| Compound No. | $R^B$ | $^1$H-NMR($d_6$-DMSO) |
|---|---|---|
| VIII-29 | (structure: MeS(O)₂CH₂CH₂NHCH₂CH₂O-N=C(Ph)-) | (E/Z mixture) 9.94 (1H, s, major), 9.78 (1H, s, minor), 8.62 (1H, s, minor), 8.56 (1H, s, major), 8.51 (1H, brs, major), 8.42 (1H, brs, minor), 7.12-7.53 (14H, m), 5.24 (2H, s,), 4.15-4.28 (2H, m), 3.13-3.25 (2H, m), 2.80-3.00 (7H, m) |
| VIII-30 | (structure: 1-Me-pyrrolidin-2-yl-CH₂-O-N=C(Me)-) | 9.93 (1H, s), 8.62 (1H, brs), 8.58 (1H, s), 8.22 (1H, d, J = 6.3 Hz), 7.96 (1H, d, J = 1.2 Hz), 7.76 (1H, d, J = 6.6 Hz), 7.70 (1H, d, J = 6.6 Hz), 7.50-7.45 (1H, m), 7.35-7.28 (3H, m), 7.19 (1H, t, J = 6.6 Hz), 5.27 (2H, s), 4.23 (1H, dd, J = 8.1 Hz, J = 4.2 Hz), 4.11 (1H, dd, J = 8.1 Hz, J = 4.2 Hz), 2.98-2.93 (1H, m), 2.59-2.54 (1H, m), 2.36 (6H, s), 2.17 (1H, dd, J = 13 Hz, J = 6.6 Hz), 1.97-1.88 (1H, m), 1.71-1.54 (3H, m) |
| VIII-31 | (structure: 1-(MeOCH₂CH₂)-pyrrolidin-2-yl-CH₂-O-N=C(Me)-) | 9.92 (1H, s), 8.62 (1H, brs), 8.58 (1H, s), 8.22 (1H, d, J = 6.9 Hz), 7.96 (1H, brs), 7.76 (1H, d, J = 6.6Hz), 7.70 (1H, d, J = 6.6 Hz), 7.50-7.45 (1H, m), 7.35-7.28 (3H, m), 7.19 (1H, t, J = 6.6 Hz), 5.27 (2H, s), 4.18 (1H, dd, J = 7.8 Hz, J = 4.5 Hz), 4.06 (1H, dd, J = 7.8 Hz, J = 4.5 Hz), 3.43 (1H, t, J = 4.8 Hz), 3.24 (3H, s), 3.08-2.99 (2H, m), 2.88-2.81 (1H, m), 2.36 (3H, s), 2.27 (1H, dd, J = 13 Hz, J = 6.6 Hz), 1.93-1.84 (1H, m), 1.72-1.54 (3H, m) |

TABLE 20

| Compound No. | $R^B$ | $^1$H-NMR($d_6$-DMSO) |
|---|---|---|
| VIII-40 | (structure: H₂N-CH(Me)-CH₂-O-N=C(C≡CH)-) | 10.08 (1H, bs), 8.74 (1H, s), 8.58 (1H, s), 8.21 (1H, d, J = 8.8 Hz), 7.96 (1H, s), 7.80 (1H, d, J = 8.8 Hz), 7.51-7.45 (1H, m), 7.35-7.27 (3H, m), 7.19 (1H, t, J = 8.0 Hz), 5.27 (2H, s), 4.04 (2H, t, J = 5.6 Hz), 3.08-3.05 (1H, m), 2.22 (3H, s), 1.04 (3H, d, J = 6.4 Hz). |
| VIII-41 | (structure: HOCH₂-CH(NH₂)-CH₂-O-N=C(C≡CH)-) | 10.13-10.09 (1H, m), 8.82 (1H, s), 8.74 (1H, s), 8.21 (1H, d, J = 14.0 Hz), 7 69-7.62 (1H, m), 7.50-7.45 (1H, m), 7 35-7 26 (3H, m), 7.18 (1H, t, J = 8.2 Hz), 5.27 (2H, s), 4 69 (1H, bs), 4.25-4.21 (1H, m), 4.13-4.09 (1H, m), 3.46-3.44 (2H, m), 3.09 (1H, t, J = 5.6 Hz), 2.26 (3H, s) |
| VIII-42 | (structure: H₂N-CH₂CH₂-O-N=C(C≡CH)-) | 10.2 (1H, s), 8.78 (1H, s), 8.59 (1H, s), 8.24 (1H, d, J = 8.8 Hz), 7.96 (1H, s), 7.81 (1H, d, J = 8.8 Hz), 7.66-7.73 (1H, m), 7.43-7.50 (1H, m), 7 23-7.36 (3H, m), 7 15-7.22 (1H, m), 5.27 (2H, s), 4.31-4.48 (2H, m), 3.07-3 15 (2H, m), 2.27 (3H, s) |
| VIII-43 | (structure: MeO₂C-CH₂-O-N=C(C≡CH)-) | 10.10 (1H, brs), 8.75 (1H, d, J = 2.0 Hz), 8.59 (1H, s), 8.17 (1H, dd, J = 2.4, 11.6 Hz), 7.96 (1H, d, J = 3.2 Hz), 7.80 (1H, d, J = 12.0 Hz), 7.68 (1H, dd, J = 3.6, 12.0 Hz), 7.51-7.44 (1H, m), 7.34-7.26 (3H, m), 7.22-7.15 (1H, m), 5.27 (2H, s), 4.94 (2H, s), 3.71 (3H, s), 2.27 (3H, s) |

TABLE 20-continued

| Compound No. | $R^B$ | $^1$H-NMR(d$_6$-DMSO) |
|---|---|---|
| VIII-44 | 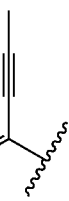 | (CDCl3) 8.71 (1H, s), 8.53 (1H, s), 8.39 (1H, s), 8.23 (1H, d, J = 9.0 Hz), 7.88 (1H, d, J = 9.0 Hz), 7.81 (1H, d, J = 2.4 Hz), 7.57 (1H, dd, J = 2.4, 9.0 Hz), 7.40-7.33 (1H, m), 7.26-7.21 (2H, m), 7.06-6.97 (2H, m), 5.17 (2H, s), 4.49 (2H, t, J = 5.4 Hz), 3.40 (2H, d, J = 6.0 Hz), 3.25 (3H, s), 3.14-2.98 (3H, m), 2.25 (3H, s), 1.06 (3H, d, J = 6.6 Hz). |
| VIII-45 | 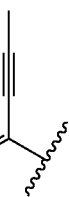 | (di-HCl salt) 12.2 (1H, s), 9.61 (2H, brs), 9.38 (1H, s), 8.93 (1H, s), 8.46 (1H, d, J = 8.8 Hz), 8.03 (1H, d, J = 8.4 Hz), 7.93 (1H, d, J = 2.4 Hz), 7.69 (1H, dd, J = 8.8 Hz, J = 2.4 Hz), 7.44-7.52 (1H, m), 7.30-7.36 (3H, m), 7.15-7.23 (1H, m), 5.32 (2H, s), 4.61 (2H, brs), 3.65-3.70 (2H, m), 3 45-3.56 (5H, m), 3.12 (3H, s). 2.28 (3H, s) |
| VIII-46 |  | 10.07 (1H, brs), 8.73 (1H, s), 8.58 (1H, s), 8.21 (1H, d, 6.6 Hz), 7.96 (1H, s), 7.79 (1H, d, J = 6.6 Hz), 7.68 (1H, d, J = 6.6 Hz), 7.49-7 44 (1H, m), 7.34-7.25 (3H, m), 7.19-7.15 (1H, m), 5.26 (2H, s), 4.31 (2H, t, 4.5 Hz), 2.95 (2H, t, 4 5 Hz), 2.25 (3H, s), 2.16 (1H, m), 0.36 (2H, m), 0.25 (2H, m) |
| VIII-47 | 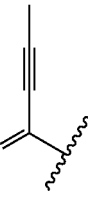 | (di-HCl salt) 12.26 (1H, brs), 9.36 (1H, s), 8.91 (1H, s), 8.45 (1H, d, 6.6 Hz), 8.29 (1H, m), 8.00 (1H, d, J = 6.6 Hz), 7.91 (1H, s), 7.68 (1H, d, J = 6.6 Hz), 7.51-7.45 (1H, m), 7.36-7.31 (3H, m), 7.23-7.17 (1H, m), 5.32 (2H, s), 4.59 (2H, m), 3.48 (2H, m), 3 41 (2H, m), 3.10 (2H, m), 2.28 (3H, s), 1.82 (3H, s) |

TABLE 21

| Compound No. | $R^B$ | $^1$H-NMR(d$_6$-DMSO) |
|---|---|---|
| VIII-48 | (tetrahydrofuran-2-ylmethylamine structure) | (di-HCl salt) 12.49 (1H, brs), 9.43 (1H, s), 8 93 (1H, s), 8.43 (1H, d, 6.6 Hz), 8.09 (1H, d, J = 6.6 Hz), 7.93 (1H, s), 7.70 (1H, d, J = 6.6 Hz), 7.51-7.45 (1H, m), 7.36-7.31 (3H, m), 7.23-7.17 (1H, m), 5.32 (2H, s), 4.61 (2H, m), 4.24 (1H, m), 3.80 (1H, m), 3.68 (1H, m), 3.49 (2H, m), 3.20 (1H, m), 3.05 (1H, m), 2.28 (3H, s), 1.99 (1H, m), 1.83 (2H, m), 1.58 (1H, m) |
| VIII-49 | (tetrahydrofuran-2-ylmethylamine structure) | (di-HCl salt) 12.44 (1H, brs), 9.41 (1H, s), 8.92 (1H, s), 8.43 (1H, d, 6.6 Hz), 8.08 (1H, d, J = 6.6 Hz), 7.92 (1H, s), 7.70 (1H, d, J = 6.6 Hz), 7.51-7.45 (1H, m), 7.36-7.31 (3H, m), 7.23-7.16 (1H, m), 5.31 (2H, s), 4.61 (2H, m), 4.24 (1H, m), 3.80 (1H, m), 3.68 (1H, m), 3.48 (2H, m), 3.19 (1H, m), 3.05 (1H, m), 2.28 (3H, s), 1.99 (1H, m), 1.84 (2H, m), 1.58 (1H, m). |

TABLE 21-continued

| Compound No. | R$^B$ | $^1$H-NMR(d$_6$-DMSO) |
|---|---|---|
| VIII-50 | (pyrrolidinone-propyl-NH-ethyl-O-N=) | (di-HCl salt) 12.37 (1H, brs), 9 41 (1H, s), 8.91 (1H, s), 8.41 (1H, d, 6.0 Hz), 8.04 (1H, d, J = 6 0 Hz), 7.91 (1H, s), 7.68 (1H, d, J = 6 0 Hz), 7.45 (1H, m), 7.36-7.31 (3H, m), 7.20-7.14 (1H, m), 5 29 (2H, s), 4.58 (2H, m), 3.44 (2H, m), 3 31 (2H, m), 3.22 (2H, m), 2.95 (2H, m), 2.27-1.55 (9H, m) |
| VIII-51 | (methanesulfonamido-ethyl-NH-ethyl-O-N=) | (di-HCl salt) 10.07 (1H, brs), 8.74 (1H, s), 8.58 (1H s), 8.20 (1H, d, 6.6 Hz), 7.96 (1H, s), 7.79 (1H, d, J = 6.6 Hz) 7.69 (1H, d, J = 6.6 Hz), 7.66 (1H, s), 7.49-7.43 (1H, m), 7.34-7.24 (3H, m), 7.19-7.15 (1H, m), 5.26 (2H, s), 4.32 (2H, m), 3.61 (1H, m), 2.93 (2H, m), 2.61 (2H, d, 4.5 Hz), 2.25 (3H, s), 2.09 (3H, m), 1.70 (H, m) |
| VIII-52 | (5-oxopyrrolidin-2-ylmethyl-NH-ethyl-O-N=) | 10.07 (1H, brs), 8.74 (1H, s), 8 58 (1H, s), 8 20 (1H, d, 6.6 Hz), 7.96 (1H, s), 7.79 (1H, d, J = 6.6 Hz) 7.69 (1H, d, J = 6.6 Hz), 7.66 (1H, s), 7.49-7.43 (1H, m), 7.34-7.24 (3H, m), 7.19-7.15 (1H, m), 5 26 (2H, s), 4.32 (2H, m), 3.61 (1H, m), 2.93 (2H, m), 2.61 (2H, d, 4.5 Hz), 2.25 (3H, s), 2.09 (3H, m), 1.70 (1H, m) |
| VIII-53 | (H$_2$N-C(O)-O-ethyl-NH-ethyl-O-N=) | (di-HCl salt) 12 04 (1H, brs), 9.26 (1H, s), 8.91 (1H, s), 8.45 (1H, d, 10.5 Hz), 7.99 (1H, d, 9.0 Hz), 7.91 (1H, s), 7.67 (1H, d, J = 9.0 Hz), 7.53-7.45 (1H, m), 7 37-7.31 (3H, m), 7.23-7.17 (1H, m), 6.65 (2H, s), 5 32 (2H, s), 4.58 (2H, m), 4.23 (2H, m), 3.50 (2H, m), 3.30 (2H, m), 2.28 (3H, s) |
| VIII-54 | (1-methylpiperidin-4-yl-NH-ethyl-O-N=) | (tri-HCl salt) 10.88 (1H, bs), 9.68 (1H, bs), 9.33 (1H, s), 8.83 (1H, s), 8.61 (1H, bs), 8.54 (2H, d, J = 5.2 Hz), 8.00 (1H, d, J = 7.96 Hz), 7.95 (1H, s), 7.71 (1H, d, J = 8.4 Hz), 7.49-7.45 (1H, m), 7.33 (2H, d, J = 5.6 Hz), 7.24-7.17 (1H, m), 5.31 (2H, s), 4.61 (2H, bs), 2 91 (2H, bs), 2.68 (3H, s), 2.37-2.33 (2H, m), 2.29 (3H, s), 2 05-1.79 (5H, m), 1.24 (2H, s). |

TABLE 22

| Compound No. | R$^B$ | $^1$H-NMR(d$_6$-DMSO) |
|---|---|---|
| VIII-55 | (tetrahydropyran-4-yl-NH-ethyl-O-N=) | 10.07(1H, bs), 8.74(1H, s), 8.59(1H, s), 8.31(1H, s), 8.21(1H, d, J = 8.8 Hz), 7.96(1H, s), 7.80(1H, d, J = 8.4 Hz), 7.69(1H, d, J = 9.2 Hz), 7.50-7.45 (3H, m), 7.18(1H, t, J = 6.4 Hz), 5.27(2H, s), 4.33-4.30(2H, m), 3.81(2H, d, J = 7.2 Hz), 2.93 (2H, t, J = 5.9 Hz), 2.67-2.65(1H, m), 2.33(3H, s), 1.76(2H, d, J = 11.6 Hz), 1.24-1.16(4H, m). |

TABLE 22-continued

| Compound No. | R[B] | ¹H-NMR(d₆-DMSO) |
|---|---|---|
| VIII-56 | | 10.08(1H, s), 8.75(1H, s), 8.59(1H, s), 8.21(1H, d, J = 10.0 Hz), 7.80(1H, d, J = 10.0 Hz), 7.69(1H, d, J = 8.4 Hz), 7.47(1H, t, J = 6.8 Hz), 7.35-7.17(4H, m), 5.27(2H, s), 3.29(3H, s), 3 08-2.93(1H, m), 2.41(3H, s), 2.26(3H, s). |
| VIII-57 | | 10 1(1H, s), 8.75(1H, s), 8.59(1H, s), 8.22(1H, d, J = 8.4 Hz), 7.96(1H, s), 7.80(1H, d, J = 8.8 Hz), 7.69(1H, d, J = 8.8 Hz), 7.43-7.51(1H, m), 7.23-7.36(3H, m), 7.18(1H, t, J = 6.4 Hz), 5 27(2H, s), 4.33(2H, t, J = 5.6 Hz), 3.30-3.33(2H, m), 2.98-3.05(2H, m), 2.25(3H, s) |
| VIII-58 | | 10.1(1H, s), 8.75(1H, s), 8.59(1H, s), 8.23(1H, d, J = 8.8 Hz), 7.96(1H, s), 7.80(1H, d, J = 8.8 Hz), 7.74(1H, d, J = 8.8 Hz), 7.43-7.50(1H, m), 7.25-7.35(3H, m), 7.18(1H, t, J = 7.6 Hz), 6.99-7.08(2H, m), 5.27(2H, s), 4 35(2H, t, J = 5.6 Hz), 3.48-3.53(2H, m), 2.68(3H, d, J = 4.4 Hz), 2.26(3H, s) |
| VIII-59 | | (di-HCl salt) 11.83(1H, brs), 9.02(1H, s), 8.93(1H, s), 8 45(1H, d, J = 8.7 Hz), 7 89(1H, d, 8.7 Hz), 7.87(1H, d, J = 2.4 Hz), 7.62(1H, dd, J = 2.4 Hz, J = 9.0 Hz), 7.53-7.45(1H, m), 7.38-7.31(3H, m), 7.82-7.20(1H, m), 5 32(2H, s), 4.37(2H, m), 3.56-3.25(10 H, m), 2.26(3H, s) |
| VIII-60 | | 10.08(1H, s), 8.74(1H, s), 8.59(1H, s), 8.22(1H, d, J = 8.8 Hz), 7.76(1H, s), 7.81(1H, d, J = 8.8 Hz), 7.69(1H, d, J = 7.2 Hz), 7.47(1H, t, J = 7.2 Hz), 7.35-7 27(2H, m), 7.22-7.17(1H, m), 5.27(2H, s), 4.31-4.26(2H, m), 3.51-3.44(2H, m), 2.93-2.88 (2H, m), 2.83(3H, s), 2 63-2.59(1H, m), 2.26 (3H, s), 1.91-1.88(2H, m), 1.33-1.24(2H, m). |
| VIII-61 | | 10.07(1H, s), 8.75(1H, s), 8.59(1H, s), 8.21(1H, d, J = 7.2 Hz), 7.96(1H, s), 7.80(1H, d, J = 7.2 Hz), 7.69(1H, d, J = 8.8 Hz), 7.48(1H, dd, J = 8.4 Hz), J = 7.2 Hz), 7 34-7.27(3H, m), 7.18(1H, t, J = 7.2 Hz), 5 27(2H, s), 4.32(2H, t, J = 6.8 Hz), 4.15(1H, bs), 3.72(1H, d, J = 12.8 Hz), 3.05(1H, t, J = 10.8 Hz), 2 94(1H, t, J = 5.6 Hz), 2.26(3H, s), 1.97(3H, s), 1.24(2H, bs). |

TABLE 23

| Compound No. | R^B | $^1$H-NMR(d$_6$-DMSO) |
|---|---|---|
| VIII-62 | (structure: HO-CH2-CH(CH3)-NH-CH2-CH2-O-N=) | (di-HCl salt) 12 14(1H, bs), 9.16-9.08(1H, m), 8 91(2H, s), 8.44(1H, d, J = 8.0 Hz), 8.91(2H, s), 8 44(1H, d, J = 8.0 Hz), 8.02(1H, d, J = 8.8 Hz), 7 91(1H, s), 7.68(1H, d, J = 8.4 Hz), 7.51-7.46(1H, m), 7.37-7.31(2H, m), 7.21-7.18(1H, m), 5.32(2H, s), 4.62(2H, bs), 3.44-3.38(2H, m), 3.32-3 21(2H, m), 3.08-3.07(1H, m), 2.99-2.91(1H, m), 2.28(3H, s), 2.08-2.02(1H, m), 1.24-1.19(1H, m), 0.91(3H, d, J = 6.4 Hz). |
| VIII-63 | (structure) | 10.08(1H, s), 8.75(1H, s), 8.68(1H, s), 8.22(1H, d, J = 8.8 Hz), 7 79(1H, s), 7.80(1H, d, J = 7.2 Hz), 7.70(1H, d, J = 8.8 Hz), 7.50-7.45(1H, m), 7.35-7.27(3H, m), 7.18(1H, t, J = 8.8 Hz), 5.27(2H, s), 4.34(2H, t, J = 5.6 Hz), 3.35-3.32(2H, m), 2.92(2H, t, J = 5.6 Hz), 2.65-2.61(1H, m), 2.26(3H, s), 1 75-1.70(1H, bs), 0.84(3H, d, J = 5.6 Hz). |
| VIII-64 | (structure) | 10.09(1H, s), 8.58(1H, s), 8.22(1H, dd, J = 8.7 Hz, 1.8 Hz), 7.95(1H, d, J = 2.7 Hz), 7.80(1H, d, J = 9.0 Hz), 7.68(1H, dd, J = 8.7 Hz, 2.7 Hz), 7.51-7.44(1H, m), 7.35-7.16(4H, m), 3.22(3H, s), 2.77(2H, t, J = 5.7 Hz), 2.60(2H, t, J = 5.7 Hz), 2.29(3H, s), 2.24(3H, s). |
| VIII-65 | (structure) | 10.09(1H, bs), 8.74(1H, s), 8.58(1H, s), 7.96(1H, d, J = 2.1 Hz), 7.80(1H, d, J = 8.7 Hz), 7.68(1H, d, J = 9.0 Hz), 7.48(1H, dd, J = 8.1 Hz), 7.35-7.26(3H, m), 7.19(1H, t, J = 8.1 Hz), 5.27(2H, s), 4.32(2H, t, J = 6.0 Hz), 3.23(3H, s), 2.86(2H, t, J = 6.0 Hz), 2.87-2.59(4H, m), 2.24(3H, s), 0.98(3H, t, J = 7.2 Hz). |
| VIII-66 | (structure) | (di-HCl salt) 10.70(1H, brs), 9.92(1H, brs), 8.94(1H, s), 8.69(1H, s), 8.30(1H, d, J = 12), 7.95-7.94(1H, m), 786(1H, d, J = 12), 7.71-7.68(1H, m), 7.52-7.44(1H, m), 7.35-7.28(3H, m), 7.22-7.15(1H, m), 5.40(1H, br), 5.30(2H, s), 4.74-4.60(2H, m), 3.83-3.75(2H, m), 3.70-3.55(2H, m), 2.92(3H, s), 2.28(3H, s) |
| VIII-67 | (structure) | 10.09(1H, s), 8.75(1H, s), 8.59(1H, s), 8.22(1H, d, J = 8.7 Hz), 7.95(1H, d, J = 2.1 Hz), 7.81(1H, d, J = 9.0 Hz), 7.69(1H, d, J = 8.7 Hz), 7.51-7.34(1H, m), 7.34-7.26(2H, m), 7.21-7.16(1H, m), 5.27(2H, s), 4 34(2H, t, J = 6.3 Hz), 2.96(2H, t, J = 6.9 Hz), 2.56(3H, s), 2.26(3H, s). |
| VIII-68 | (structure) | 10.4(1H, s), 9.06(1H, s), 8.59(1H, s), 8.30(1H, d J = 8 Hz), 8.01(1H, s), 7.81(1H, d, J = 8.8 Hz), 7.74(1H, d, J = 8.8 Hz), 7.44-7.50(1H, m), 7.24-7.36(3H, m), 7.18(1H, t, J = 7.2 Hz), 5.27(2H, s), 4.21-4.36(4H, m), 3.98-4.04(1H, m), 2.25(3H, s) |

TABLE 24

| Compound No. | R$^B$ | $^1$H-NMR(d$_6$-DMSO) |
|---|---|---|
| VIII-69 | (structure: 2-(hydroxymethyl)pyrrolidin-1-yl-ethyl-O-N= with alkyne) | (di-HCl salt) 9.37(1H, s), 8.91(1H, s), 8.42(1H, d, 7.8 Hz), 8.00(1H, d, J = 6.6 Hz), 7.92(1H, s), 7.69(1H, d, J = 7.8 Hz), 7.51-7.45(1H, m), 7.36-7.31(3H, m), 7.22-7.17(1H, m), 5.32(2H, s), 4.75-4.60(2H, m), 3.85-3.10(7 H, m), 2.27(3H, s), 2.15-1.74(4H, m) |
| VIII-70 | (structure: 3-acetamidopyrrolidin-1-yl-ethyl-O-N= with alkyne) | 10.07(1H, bs), 8.74(1H, bs), 8.59(1H, s), 8.22 (1H, d, J = 8.8 Hz), 7.98-7.96(2H, m), 7.80(1H, d, J = 8.8 Hz), 7.68(1H, d, J = 8.8 Hz), 7.50-7.45(1H, m), 7.35-7.27(3H, m), 7.20-7.16(1H, m), 5.27 (2H, s), 4.37(2H, t, J = 5.6 Hz), 4.16(1H, bs), 2.79-2.66(4H, m), 2.46-2.42(3H, m), 2.25(3H, s), 2.06(1H, bs), 1.78(3H, s), 1.56-1.51(1H, m). |
| VIII-71 | (structure: 3-(carbamoylmethyl)pyrrolidin-1-yl-ethyl-O-N= with alkyne) | (di-HCl salt) 9.29(1H, m), 8.91(1H, s), 8.42(1H, m), 7.99(1H, d, 8.7 Hz), 7.92(1H, s), 7.67(1H, d, J = 9.0 Hz), 7.53-7.45(1H, m), 7.37-7.31(3H, m), 7.23-7.17(1H, m), 6.68(2H, brs), 5.32(2H, s), 5.11(1H, m), 4.66(3H, m), 3.72-3.70(5 H, m), 3.51(1H, m), 3.26(2H, m), 2.28(3H, s) |
| VIII-72 | (structure: pyrrolidin-2-ylmethyl-O-N= with alkyne) | 10.08(1H, bs), 8.74(1H, s), 8.56(1H, s), 8.21(1H, d, J = 8.0 Hz), 7.93(1H, s), 7.79(1H, d, J = 8.8 Hz), 7.67-7.65(1H, m), 7.50-7 40(1H, m), 7.33-7.24 (2H, m), 7.20-7.12(1H, m), 5.25(2H, s), 4.36-4.30 (1H, m), 4.22-4.17(1H, m), 4.08-3.92(2H, m), 2.98(2H, bs), 2.24(3H, s), 2.00-1.90(1H, m), 1.80-1.70(2H, m), 1.62-1 52(1H, m) |
| VIII-73 | (structure: 1-(cyanomethyl)pyrrolidin-2-ylmethyl-O-N= with alkyne) | 10.08(1H, bs), 8.80(1H, s), 8.57(1H, s), 8.21(1H, d, J = 8.8 Hz), 7.97(1H, s), 7.79(1H, d, J = 8.8 Hz), 7 71-7.68(1H, m), 7.46(1H, dd, J = 8.0, J = 14.4), 7 34-7 25(2H, m), 7.19-7 15(1H, m), 5 26(2H, s), 4.22-4.20(2H, m), 2.98-2.84(2H, m), 2.25(2H, s), 1.92-1.82(1H, m), 1.79-1.62(2H, m), 1.54-1.45(1H, m). |
| VIII-74 | (structure: 1-(2-methoxyethyl)pyrrolidin-2-ylmethyl-O-N= with alkyne) | 10.07(1H, bs), 8.74(1H, s), 8.58(1H, s), 8.21(1H, d, J = 8.4 Hz), 7.95(1H, s), 7.79(1H, d, J = 8.8 Hz), 7.69-7.67(1H, m), 7.47(1H, dd, J = 8.4, J = 15.2), 7.34-7.26(2H, m), 7.19-7.15(1H, m), 5.26(2H, s), 4.23-4.13(2H, m), 3.43(2H, t, J = 6.0), 3.23(3H, s), 3.11-3.03(2H, m), 2.91-2.86(1H, m), 2.53-2.47(1H, m), 2.30-2.24(1H, m), 2.24(3H, s), 1.90-1.83(1H, m), 1.72-1.67(2H, m), 1.59-1.53(1H, m). |
| VIII-75 | (structure: 1-methylpyrrolidin-2-ylmethyl-O-N= with alkyne) | 10.07(1H, s), 8.73(1H, s), 8.57(1H, s), 8.20(1H, d, J = 8.8 Hz), 7.95-7.94(1H, m), 7.79(1H, d, J = 8.8 Hz), 7.68-7.63(1H, m), 7.46(1H, dd, J = 8.0, J = 14.0), 7 33-7.25(2H, m), 7.19-7.14(1H, m), 5.26(2H, s), 4.27-4.18(2H, m), 2.95-2.92(1H, m), 2.62-2.57(1H, m), 2.41(3H, s), 2.23(3H, s), 2.19-2.15(1H, m), 1.96-1.87(1H, m), 1.74-1.61(2H, m), 1 59-1.53(1H, m). |

TABLE 25

| Compound No. | $R^B$ | $^1$H-NMR($d_6$-DMSO) |
|---|---|---|
| VIII-76 | (5-methyl-2-oxo-oxazolidin-4-yl)methyl-O-N=C(propynyl)- | 10.09(1H, bs), 8.76(1H, d, J = 1.8 Hz), 8.58(1H, s), 8.22(1H, dd, J = 1.8 Hz, J = 8.7 Hz), 7.96(1H, d, J = 2.4 Hz), 7.87-7.78(2H, m), 7.68(1H, dd, J = 2.1 Hz, J = 9.0 Hz), 7.52-7.44(1H, m), 7.35-7.26(3H, m), 7.22-7 16(1H, m), 5.27(2H, s), 4.57-4.49(1H, m), 4.35-4.27(2H, m), 3.77-3.71(1H, m), 2.26(3H, s), 1.36(3H, d, J = 6.3 Hz). |
| VIII-77 | (5-methyl-2-oxo-oxazolidin-4-yl)methyl-O-N=C(propynyl)- | 10.08(1H, bs), 8.75(1H, d, J = 1.8 Hz), 8.58(1H, s), 8.22(1H, dd, J = 1.8 Hz, J = 9.0 Hz), 7.96(1H, d, J = 2.4 Hz), 7.80(1H, d, J = 9.0 Hz), 7.76(1H, dd, J = 2.4 Hz, J = 9.0 Hz), 7.51-7.44(1H, m), 7.35-7.26(3H, m), 7.21-7.15(1H, m), 5.26(2H, s), 4 85-4.76(1H, m), 4.39(1H, dd, J = 5.7 Hz, J = 11.4 Hz), 4.30(1H, dd, J = 4.5 Hz, J = 11.4 Hz), 4 11-4 07(1H, m), 2.25(3H, s), 1.40(3H, d, J = 6.6 Hz). |
| VIII-78 | (5-oxopyrrolidin-2-yl)methyl-O-N=C(propynyl)- | 10.07(1H, brs), 8.74(1H, s), 8.58(1H, s), 8.21(1H, d, 9.0 Hz), 7.97(1H, s), 7.82-7.78(2H, m), 7.69(1H, d, 9.0 Hz), 7.51-7.44(1H, m), 7.35-7.26(3H, m), 7.22-7.15(1H, m), 5.27(2H, s), 4.24(2H, d, 4.8 Hz), 3.91(1H, m), 2.31-2.06(6 H, m), 1.95-1.87(1H, m) |
| VIII-79 | (4-acetamidopyrrolidin-2-yl)methyl-O-N=C(propynyl)- | 10.09(1H, s), 8.74(1H, s), 8.59(1H, s), 8.21(1H, d, J = 8.8 Hz), 7.97(1H, s), 7.91-7.89(1H, m), 7.80(1H, d, J = 8.4 Hz), 7.69(1H, d, J = 8.8 Hz), 7 51-7.45(1H, m), 7.35-7.27(3H, m), 7.20-7.17(1H, m), 5 27(2H, s), 4.26-4.06(3H, m), 3.46(1H, t, J = 6.8 Hz), 3.02-2.98(1H, m), 2.58(1H, dd, J = 12.0 Hz, J = 5.6 Hz), 2.26(3H, s), 2.20-2.10(1H, m), 1.77(3H, m), 1.38-1.31(1H, m). |
| VIII-80 | (5-(hydroxymethyl)pyrrolidin-3-yl)oxy-N=C(propynyl)- | 10.3(1H, s), 8.95(1H, s), 8.57(1H, s), 8.22(1H, d, J = 9.6), 8.01(1H, s), 7.80-7.73(2H, m), 7.47-7.41(1H, m), 7.34-7.25(2H, m), 7.20-7.12(1H, m), 5 37(1H, br), 5.26(2H, s), 5.10(1H, brs), 3.78-3.48(5 H, m), 2.45-2.35(1H, m), 2 26(3H, s), 2.05-1.96(1H, m). |
| VIII-81 | (4-hydroxypyrrolidin-2-yl)methyl-O-N=C(propynyl)- | 10 45(1H, s), 8.92(1H, s), 8.65(1H, s), 8.31(1H, d, J = 8.4 Hz), 7.97(1H, s), 7.77(1H, d, J = 8.8 Hz), 7.71(1H, d, J = 9.2 Hz), 7.51-7.45(1H, m), 7 35-7.28(2H, m), 7.19(1H, t, J = 8.4 Hz), 5 28(2H, s), 4.56-4.47(3H, m), 4.15(1H, bs), 3.60(1H, bs), 3.12(1H, bs), 2.28(3H, s), 2.09(1H, dd, J = 13.2 Hz, J = 6.0 Hz), 1.862-1.81(1H, m). |
| VIII-82 | (4-hydroxypyrrolidin-2-yl)methyl-O-N=C(propynyl)- | 10.08(1H, s), 8.75(1H, s), 8.59(1H, s), 8.22(1H, d, J = 8.8 Hz), 7.97(1H, s), 7.80(1H, d, J = 8.8 Hz), 7.69(1H, d, J = 8.0 Hz), 7 51-7 45(1H, m), 7.35-7.27(m, 3 H), 7.20-7.17(1H, m), 5.27(2 H s), 4.67(1H, m), 4 29-4.19(3H, m), 3.45-4.40(1H, m), 2.88(1H, dd, J = 11.2 Hz, J = 5 6 Hz), 2.70(1H, dd, J = 11.0, J = 3.6 Hz), 2.27(3H, s), 2.10-2.02(1H, m), 1.46-1.39(1H, m). |

TABLE 26

| Compound No. | R^B | $^1$H-NMR(d$_6$-DMSO) |
|---|---|---|
| VIII-83 | (5-oxopyrrolidin-2-yl)methyloxyimino structure | 10.07(1H, brs), 8.74(1H, s), 8.58(1H, s), 8.21(1H, d, 8.7 Hz), 7.97(1H, s), 7.82-7.78(2H, m), 7.69(1H, d, 9.0 Hz), 7.51-7.44(1H, m), 7.35-7.26(3H, m), 7.22-7.15(1H, m), 5.27(2H, s), 4.24(2H, d, 4.8 Hz), 3.91(1H, m), 2.31-2.06(6 H, m), 1.95-1.87(1H, m) |
| VIII-84 | (4-acetamidopyrrolidin-2-yl)methyloxyimino structure | 10.35(1H, s), 9 08(1H, s), 8.60(1H, s), 8.40(1H, s), 8.22(1H, d, J = 8.4 Hz), 8.09(1H, s), 7.83-7.82(2H, m), 7.49-7.47(1H, m), 7.33-7.19(4H, m), 5.27(2H, s), 4.43-4.16(4H, m), 3.01-2.98(2H, M), 2 28(3H, s), 1.92(2H, bs), 1.83(3H, s). |
| VIII-85 | (pyrrolidin-2-yl)methyloxyimino structure | 10.1(1H, brs), 8.82(1H, s), 8.58(1H, s), 8.21(1H, d, J = 8.8), 7.98(1H, s), 7.80(1H, d, J = 8.4), 7.72-7.70(1H, m), 7.50-7.44(1H, m), 7.34-7.26(3H, m), 7.20-7.15(1H, m), 5.26(2H, s), 4.22(2H, s), 3.57(1H, br), 2.96-2.89(2H, m), 2.26(3H, s), 1.98-1.62(3H, m), 1.58-1.45(1H, m). |
| VIII-86 | (1-cyanomethylpyrrolidin-2-yl)methyloxyimino structure | 10.07(1H, bs), 8.75(1H, s), 8.57(1H, s), 8.21(1H, d, J = 8.8 Hz), 7.95(1H, s), 7.79(1H, d, J = 8.8 Hz), 7.71-7.68(1H, m), 7.50-7.44(1H, m), 7.34-7.26(2H, m), 7.19-7.15(1H, m), 5.26(2H, s), 4.22-4.20(2H, m), 3.03-2.95(2H, m), 2.26(3H, s), 2.02-1.93(1H, m), 1.80-1.73(2H, m), 1.62-1.56(1H, m) |
| VIII-87 | (1-(methoxycarbonylmethyl)pyrrolidin-2-yl)methyloxyimino structure | 10.0(1H, brs), 8.73(1H, s), 8.57(1H, s), 8.19(1H, d, J = 9.2), 7.95(1H, s), 7.79(1H, d, J = 8.8), 7 69-7 67(1H, m), 7.50-7.44(1H, m), 7.34-7.26(3H, m), 7 20-7.16(1H, m), 5.26(2H, s), 4.24-4.17(2H, m), 3 77(1H, d, J = 17.2), 3.58(1H, s), 3.50(1H, d, J = 17.6), 3.22-3.12(1H, m), 3.10-3.00(1H, m), 2.58-2.52(1H, m), 2.23(3H, s), 1 98-1.89(1H, m), 1.77-1.70(2H, m), 1.59-1.52(1H, m). |
| VIII-88 | (1-(carboxymethyl)pyrrolidin-2-yl)methyloxyimino structure | 10.8(1H, s), 8.98(1H, s), 8.58(1H, s), 8.20-8.16(2H, m), 7.91-7.88(1H, m), 7.80(1H, d, J = 7 6), 7.50-7.44(1H, m), 7 34-7.30(2H, m), 7 23(1H, d, J = 8.8), 7.20-7.15(1H, m), 5.26(2H, s), 4 23-4.41(2H, m), 3.76(1H, d, J = 16.4), 3.52(1H, d, J = 16.4), 3.61-3.52(1H, m), 3.45-3 36(1H, m), 2 91-2 85(1H, m), 2.25(3H, s), 2 09-2.02(1H, m), 1 91-1 79(2H, m), 1.73-1.66(1H, m). |

TABLE 26-continued

| Compound No. | $R^B$ | $^1$H-NMR($d_6$-DMSO) |
|---|---|---|
| VIII-89 | (structure: pyrrolidine with N-CH2-CO2H, 2-position CH2-O-N=C with alkyne) | 10.87(1H, s), 8.97(1H, s), 8.58(1H, s), 8.20-8 15(2H, m), 7.91-7 88(1H, m), 7.80(1H, d, J = 8.8), 7.50-7.44(1H, m), 7 34-7.30(2H, m), 7.23(1H, d, J = 8.8), 7.20-7.15(1H, m), 5.26(2H, s), 4.22-4.41(2H, m), 3.76(1H, d, J = 16.4), 3.52(1H, d, J = 16.4), 3.61-3.52(1H, m), 3.45-3.36(1H, m), 2.91-2.85(1H, m), 2.25(3H, s), 2.09-2 02(1H, m), 1.91-1 79(2H, m), 1.73-1.66(1H, m). |

TABLE 27

| Compound No. | $R^B$ | $^1$H-NMR($d_6$-DMSO) |
|---|---|---|
| VIII-90 | (structure: pyrrolidine with N-CH2CH2OH, 2-position CH2-O-N=C with alkyne) | 10.0(1H, s), 8.72(1H, s), 8.56(1H, s), 8.21-8.19(1H, m), 7.93(1H, s), 7.80-7.78(1H, m), 7.67-7.65(1H, m), 7.49-7.42(1H, m), 7.33-7.25(3H, m), 7.19-7.14(1H, m), 5.26(2H, s), 4.40(1H, brs), 4.27-4.19(1H, m), 4.16-4.09(1H, m), 3.10-2.94(2H, m), 2.90-2.80(1H, m), 2.23(3H, s), 1.93-1.82(1H, m), 1.75-1.62(2H, m), 1.61-1.52(1H, m). |
| VIII-91 | (structure: N-methylpyrrolidine, 2-position CH2-O-N=C with alkyne) | 10.08(1H, s), 8.74(1H, s), 8.56(1H, s), 8.21(1H, d, J = 8.8 Hz), 7.93(1H, s), 7.89(1H, d, J = 8.8 Hz), 7.68-7.63(1H, m), 7.46(1H, dd, J = 8.0, J = 14.0), 7.33-7.24(2H, m), 7.19-7.14(1H, m), 5.25(2H, s), 4.27-4.18(2H, m), 2.95-2.92(1H, m), 2.62-2.57(1H, m), 2.41(3H, s), 2.23(3H, s), 2.46-2.39(1H, m), 2.04-1 95(1H, m), 1.78-1.73(2H, m), 1.65-1.56(1H, m) |
| VIII-92 | (structure: 4-hydroxymethyl pyrrolidine with O-N=C alkyne at 3-position) | 10.0(1H, s), 8.72(1H, s), 8.57(1H, s), 8.21(1H, d, J = 8.4), 7.94(1H, s), 7.79(1H, d, J = 8.8), 7.68-7.66(1H, m), 7.49-7.44(1H, m), 7.34-7.25(3H, m), 7.19-7.15(1H, m), 5.26(2H, s), 4.93(1H, brs), 3.02(1H, d, J = 10.7), 2.25(3H, s), 2.09-2.01(1H, m), 1.77-1.70(1H, m) |
| VIII-93 | (structure: 2,6-dimethylmorpholine-N-CH2CH2-O-N=C alkyne) | 10.07(1H, bs), 8.74(1H, bs), 8.59(1H, s), 8.22(1H, d, J = 7.6 Hz), 7.96(1H, d, J = 2.4 Hz), 7.80(1H, d, J = 8.8 Hz), 7.69(1H, dd, J = 2.4 Hz, J = 8.8 Hz), 7.50-7.45(1H, m), 7.35-7 27(3H, m), 7.20-7.17(1H, m), 5.27(2H, s), 4.40(2H, t, J = 5.6 Hz), 3.56(2H, t, J = 8.0 Hz), 2.85(2H, t, J = 8.4 Hz), 2.69(2H, t, J = 5.6 Hz), 2.25(3H, s), 1.04(6 H, d, J = 5.6 Hz). |
| VIII-94 | (structure: 3-oxopiperazine-N-CH2CH2-O-N=C alkyne) | 10.07(1H, bs), 8.74(1H, bs), 8.59(1H, s), 8.22(1H, d, J = 8.8 Hz), 7.97(1H, d, J = 2.4 Hz), 7.80(1H, d, J = 8.8 Hz), 7.72(1H, bs), 7.69(1H, dd, J = 2.4 Hz, J = 8.8 Hz), 7.50-7.45(1H, m), 7 35-7.27(3H, m), 7.21-7.16(1H, m), 5.27(2H, s), 4.41(2H, t, J = 5.6 Hz), 3.17(2H, bs), 3.10(2H, s), 2.80(2H, t, J = 5.6 Hz), 2.70(2H, t, J = 5.6 Hz), 2.26(3H, s). |

TABLE 27-continued

| Compound No. | $R^B$ | $^1$H-NMR($d_6$-DMSO) |
|---|---|---|
| VIII-95 | (thiomorpholine-1,1-dioxide-ethoxyimino structure) | 10.27(1H, brs), 8.74(1H, s), 8.58(1H, s), 8.23-8.21(1H, m), 7.95(1H, s), 7.80(1H, d, J = 8.8), 7.69-7.67(1H, m), 7.50-7.44(1H, m), 7.34-7.26(2H, m), 7.20-7.16(1H, m), 5.27(2H, s), 4.39(2H, t, J = 5.6 Hz), 3.18(8 H, brs), 2.96(2H, t, J = 5.6 Hz), 2.55(3H, s) |
| VIII-96 | (4-methylpiperazine-ethoxyimino structure) | 10.1(1H, s), 8.79(1H, s), 8.59(1H, s), 8.21(1H, d, J = 8 Hz), 7.96(1H, s), 7.79(1H, d, J = 8.8 Hz), 7.68(1H, d, J = 8.8 Hz), 7.44-7.50(1H, m), 7.24-7.36(3H, m), 7.18(1H, t, J = 7.2 Hz), 5.27(2H, s), 4.87(2H, t, J = 10 Hz), 3.29-3.34(2H, m), 2.70(2H, t, J = 6.4 Hz), 2.26-2.35(4H, m), 2.25(3H, s), 2.14(3H, s) |
| VIII-97 | (4-hydroxypiperidine-ethoxyimino structure) | 10.1(1H, s), 8.74(1H, s), 8.59(1H, s), 8.21(1H, d, J = 8.8 Hz), 7.96(1H, s), 7.80(1H, s), 7.69(1H, s), 7.42-7.50(1H, m), 7.13-7.36(4H, m), 5.27(2H, s), 4.52(1H, s), 4.36(2H, brs), 3.40-3.50(1H, brs), 2.80(2H, brs), 2.69(2H, brs), 2.10-2.27(5 H, m), 1.69(2H, brs), 1.40(2H, brs) |

TABLE 28

| Compound No. | $R^B$ | $^1$H-NMR($d_6$-DMSO) |
|---|---|---|
| VIII-98 | (4-aminopiperidine-ethoxyimino structure) | 8.74(1H, s), 8.58(1H, s), 8.21(1H, d, J = 9.2 Hz), 7.96(1H, s), 7.79(1H, d, J = 9.2 Hz), 7.68(1H, d, J = 9.2 Hz), 7.48(1H, dd, J = 5.8 Hz, J = 7.2 Hz), 7.35-7.26(3H, m), 7.18(1H, t, J = 9.2 Hz), 5.27(2H, s), 4.36(2H, t, J = 9.2 Hz), 3.38(1H, dd, J = 5.8 Hz, J = 7.2 Hz), 2.86(2H, d, J = 11.6 Hz), 2.68(2H, t, J = 6.0 Hz), 2.25(3H, s), 2.06(2H, t, J = 11.2 Hz), 1.66(2H, d, J = 11.7 Hz), 1.09(2H, t, J = 7.2 Hz). |
| VIII-99 | (4-acetamidopiperidine-ethoxyimino structure) | 10.1(1H, bs), 8.78(1H, bs), 8.59(1H, s), 8.22(1H, d, J = 8.0 Hz), 7.97(1H, s), 7.81(1H, d, J = 8.8 Hz), 7.70(1H, d, J = 6.4 Hz), 7.49-7.45(1H, m), 5.27(2H, s), 4.49-4.12(2H, m), 3.41-3.38(1H, m), 2.82-2.65(2H, m), 2.25(3H, s), 1.79(3H, s), 1.09(2H, t, J = 7.2 Hz). |

TABLE 28-continued

| Compound No. | $R^B$ | $^1$H-NMR(d$_6$-DMSO) |
|---|---|---|
| VIII-100 | (structure) | 10.07(1H, s), 8.74(1H, s), 8.59(1H, s), 8.21(1H, d, J = 9.2 Hz), 8.59(1H, s), 8.21(1H, d, J = 9.2 Hz), 7.96(1H, s), 7.80(1H, d, J = 8.4 Hz), 7.68(1H, d, J = 8.4 Hz), 7.50-7.45(1H, m), 7.35-7.27(3H, m), 7.19(1H, t, J = 8.0 Hz), 7.04(1H, t, J = 6.0 Hz), 5.20(2H, s), 4.30(2H, bs), 3.10(1H, bs), 2.91(3H, s), 2.63(2H, d, J = 2.4 Hz), 2.55(3H, s), 2.03-1.99(2H, m), 1.77(2H, d, J = 22.0 Hz), 1.48-1.38(2H, m), 1.24(2H, bs). |
| VIII-101 | (structure) | 10.09(1H, bs), 8.75(1H, s), 8.58(1H, s), 8.20(1H, d, J = 8.7 Hz), 7.95(3H, d, J = 2.1 Hz), 7.80(1H, d, J = 8.7 Hz), 7.68(1H, d, J = 9.0 Hz), 7.51-7.44(1H, m), 7.35-7.26(3H, m), 7.21-7.16(1H, m), 5.27(2H, s), 4.20-4.09(2H, m), 3.79(1H, dd, J = 2.7 Hz, J = 10.8 Hz), 3.68-3.64(1H, m), 3.13-3.08(1H, m), 2.82-2.71(3H, m), 2.26(3H, s) |
| VIII-102 | (structure) | 10.11(1H, bs), 8.74(1H, s), 8.57(1H, s), 8.22-8.19(1H, m), 7.96(1H, m), 7.80(1H, d, J = 9.0 Hz), 7.69-7.66(1H, m), 7.51-7.44(1H, m), 7.35-7.26(3H, m), 7.21-7.16(1H, m), 5.27(2H, s), 4 20-4 09(2H, m), 3.79(1H, dd, J = 3.0 Hz, J = 10.8.Hz), 3 68-3.64(1H, m), 3.25-3.18(1H, m), 3.13-3.05(1H, m), 2.82-2.71(2H, m), 2.26(3H, s). |
| VIII-103 | (structure) | 10.09(1H, brs), 8.74(1H, s), 8 59(1H, s), 8.21(1H, d, 9.0 Hz), 7.96(1H, s), 7.79(1H, d, J = 9.0 Hz) 7.68(1H, d, J = 9.0 Hz), 7.49-7.44(1H, m), 7.34-7.22(3H, m), 7.19-7.15(1H, m), 5.27(2H, s), 4.11(2H, d, J = 4.8 Hz), 2.95-2.50(6 H, m), 2.34-2.26(4H, m) |
| VIII-104 | (structure) | 10.07(1H, s), 8.75(1H, d, J = 1.8 Hz), 8.58(1H, s), 8.22(1H, dd, J = 1.8 Hz, J = 9.0 Hz), 7.96(1H, d, J = 2.4 Hz), 7.79(1H, d, J = 8.7 Hz), 7.68(1H, dd, J = 1.8 Hz, J = 9.3 Hz), 7.51-7.44(1H, m), 7.35-7.26(3H, m), 7.21-7.15(1H, m), 5.27(2H, s), 4.35(1H, dd, J = 2.7 Hz, J = 11 7 Hz), 4.24(1H, dd, J = 3.9 Hz, J = 11.7 Hz), 4.12(1H, d, J = 17.4 Hz), 3.90-3.76(3H, m), 3.50(1H, dt, J = 2.4 Hz, J = 11.1 Hz), 2.83-2 71(2H, m), 2.26(3H, s). |

TABLE 29

| Compound No | $R^B$ | $^1$H-NMR(d$_6$-DMSO) |
|---|---|---|
| VIII-105 | (structure) | 10 09(1H, brs), 8.73(1H, s), 8.58(1H, s), 8.20(1H, d, 7.8 Hz), 7.96(1H, s), 7.79(1H, d, J = 9.0 Hz), 7.69(1H, d, J = 8.4 Hz), 7.51-7.42(1H, m), 7.35-7.25(3H, m), 7.22-7.16(1H, m), 5.27(2H, s), 4.31(2H, d, 4.5 Hz), 2.95-2.53(5 H, m), 2.34-2.10(5 H, m) |

TABLE 29-continued

| Compound No | R^B | $^1$H-NMR($d_6$-DMSO) |
|---|---|---|
| VIII-106 | (2-methylmorpholin-3-yl)methyl-O-N= structure | 10 1(1H, s), 8.75(1H, s), 8.59(1H, s), 8.21(1H, d, J = 8.8 Hz), 7.97(1H, s), 7.80(1H, d, J = 8.4 Hz), 7.69(1H, d, J = 8.8 Hz), 7.43-7.52(1H, m), 7.15-7.37(4H, m), 5.27(2H, s), 4.23-4.29(1H, m), 4.11-4.17(1H, m), 3.69(1H, d, J =12 Hz), 3.37-3.45(1H, m), 3.23-3.32(1H, m), 2.66-2.80(3H, m), 2.28-2.40(1H, m), 2.26(3H, s), 1.16(3H, d, J = 6 Hz) |
| VIII-107 | (2-methylmorpholin-3-yl)methyl-O-N= structure | 10.1(1H, s), 8.75(1H, s), 8 59(1H, s), 8.21(1H, d, J = 8.8 Hz), 7.97(1H, s), 7.80(1H, d, J = 8 4 Hz), 7.69(1H, d, J = 8.8 Hz), 7.43-7.52(1H, m), 7.15-7 37(4H, m), 5.27(2H, s), 4.23-4.29(1H, m), 4.11-4.17(1H, m), 3.69(1H, d, J = 12 Hz), 3 37-3.45(1H, m), 3.23-3.32(1H, m), 2.66-2.80(3H, m), 2.28-2.40(1H, m), 2.26(3H, s), 1.16(3H, d, J = 6 Hz) |
| VIII-108 | (1,4-dimethylpiperazin-2-yl)methyl-O-N= structure | 10.09(1H, brs), 8.75(1H, s), 8.59(1H, s), 8.21(1H, d, 10.5 Hz), 7.96(1H, s), 7.80(1H, d, J = 9.0 Hz), 7.68(1H, d, J = 9.0 Hz), 7.52-7.44(1H, m), 7.35-7.25(3H, m), 7.22-7.16(1H, m), 5.27(2H, s), 4.44(1H, m), 4.18(1H, m), 2.80-2.60(4H, m), 2.32-2.00(12H, m) |
| VIII-109 | (6-methylmorpholin-2-yl)methyl-O-N= structure | 10.1(1H, s), 8.74(1H, s). 8.59(1H, s), 8.21(1H, d, J = 8.0 Hz), 7.96(1H, s), 7.80(1H, d, J = 8.8 Hz), 7.66-7.70(1H, m), 7.43-7.50(1H, m), 7 15-7.36(4H, m), 5.72(2H, s), 4.10-4.27(2H, m), 3.75-3.82(1H, m), 3.45-3.55(1H, m), 2.85(1H, d, J = 10 Hz), 2 74(1H, d, J = 11 Hz), 2.37(1H, t, J = 11 Hz), 2.26(4H, brs), 1.03(3H, d, J = 6.4 Hz). |
| VIII-110 | (6-methylmorpholin-2-yl)methyl-O-N= structure | 10.1(1H, s), 8.74(1H, s), 8.58(1H, s), 8.21(1H, d, J = 8.8 Hz), 7.96(1H, s), 7.80(1H, d, J = 8.4 Hz), 7.68(1H, s, J = 9.6 Hz), 7.42-7.52(1H, m), 7.14-7.37(4H, m), 5.27(2H, s), 4.38-4.55(2H, m), 3.80-4.05(2H, m), 2.75-2.85(2H, m), 2.65-2.72(1H, m), 2.30-2.40(1H, m), 2.26(3H, s), 1.06(3H, d, J = 5 Hz) |
| VIII-111 | (5-oxopiperazin-2-yl)methyl-O-N= structure | 10.08(1H, s), 8.74(1H, s), 8.59(1H, s), 8.20(1H, d, J = 8.7 Hz), 7.98(1H, d, J = 0.9 Hhz), 7.83-7.72(2H, m), 7.10(1H, dd, J = 2.7 Hz, J = 9.0 Hz), 7.51-7.44(1H, m), 7.34-7.26(3H, m), 7.22-7.16(1H, m), 5.27(2H, s), 4.32(2H, m), 3.65(1H, m), 3.17(2H, s), 3.10-2.84(3H, m), 2.26(3H, s). |
| VIII-112 | (4-(2-hydroxyethyl)piperazin-2-yl)methyl-O-N= structure | (di-HCl salt) 12.03(1H, brs), 8.93(1H, s), 8.46(1H, d, J = 9.0 Hz), 8.02(1H, d, J = 8.7 Hz), 7.92(1H, d, J = 2.4 Hz), 7.68-7.67(1H, m9, 7.52-7.36(1H, m), 7.35-7.31(3H, m), 7.23-7.19(1H, m), 5.31(2H, s), 4.58(2H, m), 4.33(1H, brs), 3.99-3.23(12H, m), 2.29(3H, s). |

TABLE 30

| Compound No. | R^B | $^1$H-NMR(d$_6$-DMSO) |
|---|---|---|
| VIII-113 | (1-methylpiperazinyl-methyleneoxyimino group) | 10.09(1H, brs), 8.74(1H, s), 8.58(1H, s), 8.20(1H, d, J = 8.7 Hz), 7.96(1H, d, J = 2.4 Hz), 7.79(1H, d, J = 8.7 Hz), 7.68(1H, dd, J = 2.7 Hz, J = 9.0 Hz), 7.51-7.44(1H, m), 7.36-7.16(4H, m), 5.27(2H, s), 4.15(2H, m), 3.07(1H, m), 2.87-2.55(4H, m), 2.26(3H, s), 2.15(3H, s), 1.90(1H, m), 1.71(1H, m). |
| VIII-114 | (morpholinyl-methyleneoxyimino group) | (di-HCl salt) 11.65(1H, bs), 9.46-9.35(2 H m), 9.04(1H, s), 8.88(1H, s), 7.95(1H, d, J = 9.0 Hz), 7.89(1H, d, J = 2.4 Hz), 7.66-7.62(1H, m), 7.52-7.45(1H, m), 7.36-7.31(3H, m), 7.23-7.17(1H, m), 5.31(2H, s), 4.35-4.34(2H, m), 4.24-4.21(1H, m), 4.04-3.98(1H, m), 3.85-3.77(1H, m), 3.05-2.85(3H, m), 2.28(3H, s). |
| VIII-115 | (N-acetyl-methylpiperazinyl-methyleneoxyimino group) | |
| VIII-116 | (methylmorpholinyl-methyleneoxyimino group) | 10.1(1H, s), 8.74(1H, s), 8.59(1H, s), 8.21(1H, d, J = 8.0 Hz), 7.96(1H, s), 7.80(1H, d, J = 8.8 Hz), 7.66-7.70 (1H, m), 7 43-7 50(1H, m), 7.15-7.36(4H, m), 5.72(2H, s), 4.10-4.27(2H, m), 3.75-3.82(1H, m), 3 45-3 55(1H, m), 2.85(1H, d, J = 10 Hz), 2.74(1H, d, J = 11 Hz), 2.37(1H, t, J = 11 Hz), 2.26(4H, brs), 1.03(3H, d, J = 6.4 Hz). |
| VIII-117 | (methylmorpholinyl-methyleneoxyimino group) | 10.1(1H, s), 8.74(1H, s), 8.58(1H, s), 8.21(1H, d, J = 8.8 Hz), 7.96(1H, s), 7.80(1H, d, J = 8.4 Hz), 7.68(1H, s, J = 9.6 Hz), 7.42-7.52(1H, m), 7.14-7.37(4H, m), 5.27(2H, s), 4.38-4.55(2H, m), 3.80-4.05(2H, m), 2.75-2.85(2H, m), 2.65-2.72(1H, m), 2.30-2.40(1H, m), 2.26(3H, s), 1.06(3H, d, J = 5 Hz) |
| VIII-118 | (thiomorpholinyl dioxide-methyleneoxyimino group) | 10.10(1H, s), 8.76(1H, s), 8.59(1H, s), 8.22(1H, d, J = 8.7 Hz), 7.96(1H, d, J = 2.1 Hz), 7.81(2H, d, J = 8.7 Hz), 7.69(1H, dd, J = 2 1 Hz, J = 8.7 Hz), 7.44-7.52(1H, m), 7.27-7.35(2H, m), 7 16-7.22(1H, m), 5.27(2H, s), 4.20-4.35(2H, m), 3 84-3.98(1H, m), 2.85-3.15(6 H, m), 2.28(3H, m). |
| VIII-119 | (oxopiperazinyl-methyleneoxyimino group) | (di-HCl salt) 9.14(1H, s), 8.91(1H, s), 8 61-8.55(1H, m), 8.41(1H, d, J = 9.0 Hz), 8.22(1H, d, J = 9.0 Hz), 8.00-7.97(1H, m), 7 91(1H, s), 7.66(1H, d, J = 9.0 Hz), 7.52-7.45(1H, m), 7.37-7.30(3H, m), 7.23-7.17(1H, m), 5.32(2H, s), 4.40(2H, m), 4.18(1H, m), 3 65-3.20(4H, m), 2.287(3H, s) |

TABLE 30-continued

| Compound No. | R^B | ^1H-NMR(d_6-DMSO) |
|---|---|---|
| VIII-120 | (structure: CH3NH-CH2CH2-O-N=C(cyclopropyl-C≡C-)—) | 10 1(1H, s), 8.71(1H, s), 8.59(1H, s), 8.16(1H, d, J = 8.8 Hz), 7.98(1H, s), 7.80(1H, d, J = 9 2 Hz), 7 69(1H, d, J = 9.2 Hz), 7.44-7.51(1H, m), 7.14-7.36(4H, m), 5.27(2H, s), 4.31(2H, t, J = 5.6 Hz), 2.85(2H, t, J = 5.6 Hz), 2.35(3H, s), 1.70-1.78(1H, m), 1.02-1.07(2H, m), 0.90-0 95(2H, m) |

TABLE 31

| Compound No. | R^B | ^1H-NMR(d_6-DMSO) |
|---|---|---|
| VIII-121 | (structure with HOCH2-C≡C- and CH3NH-CH2CH2-O-N=) | 10.1(1H, s), 8.82(1H, s), 8.61(1H, s), 8.27(1H, d, J = 7.6 Hz), 7.97(1H, s), 7.84(1H, d, J = 9.6 Hz), 7.70(1H, d, J = 7.6 Hz), 7.43-7.51(1H, m), 7.25-7.36(3H, m), 7.15-7.22(1H, m), 5.62(1H, s), 5 72(2H, s), 4.49-4.55(4H, m), 3.29-3.40(2H, m), 2.66(3 H s) |
| VIII-122 | (structure with HOCH2-C≡C- and pyrrolidine-CH2CH2-O-N=) | 10.05(1H, s), 8.76(1H, s), 8.60(1H, s), 8.20(1H, d, J = 9.2 Hz), 7.97(1H, s), 7.82(1H, d, J = 8.8 Hz), 7.68(1H, d, J = 9.2 Hz), 7.53-7.45(1H, m), 7.37-7.27(3H, m), 7.19(1H, t, J = 8.4 Hz), 5.63(1H, t, J = 5.2 Hz), 5.27(2H, s), 4.70(2H, d, J = 5.2 Hz), 4.40(2H, t, J = 6.0 Hz), 2.81(2H, t, J = 6.0 Hz), 2.53(4H, bs), 1.68(4H, bs). |
| VIII-123 | (structure with CH3O-CH2-C≡C- and CH3NH-CH2CH2-O-N=) | 10 02(1H, s), 8.89(1H, s), 8.60(1H, s), 8.22(1H, d, J = 9.3 Hz), 8.00(1H, s), 7.83(1H, d, J = 8 7 Hz), 7.73(1H, d, J = 9 6 Hz), 7 51-7 44(1H, m), 7.35-7.29(2H, m), 7.22-7.16(1H, m), 5.27 82H, s), 4 53(2H, s), 3.40(5 H, bs), 2.51(5 H, bs). |
| VIII-124 | (structure with CH3O-CH2-C≡C- and pyrrolidine-CH2CH2-O-N=) | 10.13(1H, s), 8.80(1H, s), 8.61(1H, s), 8.21(1H, d, J = 8.4 Hz), 7 99(1H, s), 7.83(1H, d, J = 8.8 Hz), 7.71(1H, d, J = 8.8 Hz), 7.51-7.45(1H, m), 7.35-7 27(3H, m), 7.19(1H, t, J = 8.4 Hz), 5.27(2H, s), 4.53(2H, s), 4 46(2H, t, J = 5.6 Hz), 2.93(2H, bs), 2.65(4H, bs), 1.72(4H, bs). |

TABLE 31-continued

| Compound No. | R$^B$ | $^1$H-NMR(d$_6$-DMSO) |
|---|---|---|
| VIII-125 | (morpholine-CH$_2$-O-N=, with CH$_2$-C≡C-CH$_2$-OMe) | 10.09(1H, s), 8.76(1H, bs), 8.59(1H, s), 8.19(1H, d, J = 9.0 Hz), 7.96(1H, bs), 7.82(1H, d, J = 8.7 Hz), 7.67(1H, bd, J = 7.5 Hz), 7.51-7.44(1H, m), 7.35-7.26(3H, m), 7.21-7.16(1H, m), 5.27(2H, s), 4.52(2H, s), 4.23(1H, dd, J = 5.7 Hz, J = 10.8 Hz), 4.17(1H, dd, J = 6.3 Hz, J = 10.8 Hz), 3.79(1H, dd, J = 8.0 Hz, J = 10.8 Hz), 3.65(1H, bd, J = 7.8 Hz), 3.40(3H, s), 3.27-3.20(1H, m), 3.13-3.04(1H, m). |
| VIII-126 | (morpholine-CH$_2$-O-N=, with C≡C-CH$_2$-) | 10.10(1H, bs), 8.76(1H, d, J = 1.5 Hz), 8.59(1H, s), 8.19(1H, dd, J = 1.8 Hz, J = 8.7 Hz), 7.96(1H, d, J = 2.1 Hz), 7.83(1H, d, J = 9.0 Hz), 7.71-7.64(1H, m), 7.52-7.44(1H, m), 7.35-7.27(3H, m), 7.22-7.16(1H, m), 5.27(2H, s), 4.53(2H, s), 4.23(1H, dd, J = 6.3 Hz, J = 11.4 Hz), 4.17(1H, dd, J = 6.3 Hz, J = 10.8 Hz), 3.80(1H, dd, J = 3.0 Hz, J = 10.8 Hz), 3.68-3.64(1H, m), 3.12-3.07(1H, m), 2.82-2.70(2H, m). |
| VIII-127 | (MeNH-CH$_2$CH$_2$-O-N=, with C≡C-propyl) | 10.1(1H, s), 8.76(1H, s), 8.59(1H, t, J = 5.6 Hz), 8.20(1H, d, J = 8.8 Hz), 7.98(1H, s), 7.81(1H, d, J = 8.8 Hz), 7.70(1H, d, J = 8.8 Hz), 7.44-7.51(1H, m), 7.15-7.37(4H, m), 5.27(2H, s), 4.34(2H, t, J = 6 Hz), 2.86(2H, t, J = 5.6 Hz), 2.61(2H, t, J = 7.2 Hz), 2.36(3H, s), 1.67(2H, q, J = 7.2 Hz), 1.05(3H, t, J = 7.2 Hz) |

TABLE 32

[Chemical formula 82]

(VIII)

| Compound No. | R$^B$ | $^1$H-NMR(d$_6$-DMSO) |
|---|---|---|
| VIII-128 | (3-hydroxypiperidine-N-CH$_2$CH$_2$-O-N=, with C≡C-Me) | 10.0(1H, s), 8.74(1H, s), 8.60-8.58(2H, m), 8.21(1H, d, J = 8.8), 7.96(1H, s), 7.90-7.86(1H, m), 7.79(1H, d, J = 8.8), 7.68-7.66(1H, m), 7.58(1H, d, J = 7.6), 7.38-7.35(1H, m), 7.27(1H, d, J = 8.8), 5.30(2H, s), 4.61-4.60(1H, m), 4.37-4.35(2H, m), 3.52-3.38(1H, m), 2.93-2.92(1H, m), 2.76-2.66(2H, m), 2.24(3H, s), 2.00-1.95(1H, m), 1.89-1.84(1H, m), 1.79-1.77(1H, m), 1.62-1.59(1H, m), 1.45-1.36(1H, m), 1.10-1.02(1H, m). |

TABLE 32-continued

[Chemical formula 82]

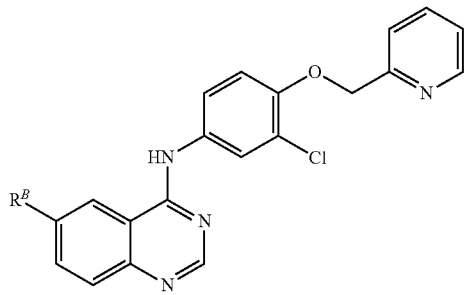

(VIII)

| Compound No. | $R^B$ | $^1$H-NMR($d_6$-DMSO) |
|---|---|---|
| VIII-129 | 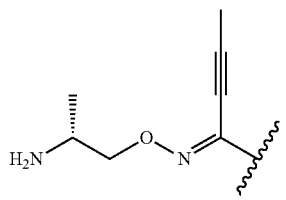 [SMILES: */C(C#CC)=N/OC[C@@H](C)N] | 10.09(1H, s), 8.61-8.59(2H, m), 8.21(1H, d, J = 9.2 Hz), 8 07(1H, s), 7.89(1H, d, J = 7.6 Hz), 7.80(1H, d, J = 8.4 Hz), 7 68(1H, d, J = 9.2 Hz), 7.37(1H, t, J = 7.6 Hz), 7.28(1H, d, J = 8.8 Hz), 5.31(2H, s), 4.60(2H, d J = 6.0 Hz), 2.27(3H, s), 0.89(3H, d, J = 7.6 Hz). |
| VIII-130 | 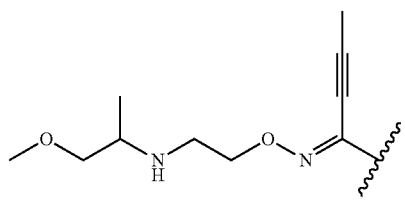 [SMILES: */C(C#CC)=N/OCCNC(C)COC] | (tri-HCl salt) 12.58(1H, s), 9.44(1H, s), 9.33(1H, bs), 9.09(1H, bs), 8.95(1H, s), 8.78(1H, d, J = 4.4 Hz), 8.46(1H, d, J = 8.8 Hz), 8.23(1H, t, J = 6.8 Hz), 8.09(1H, d, J = 8.4 Hz), 7.94(1H, d, J = 2.4 Hz), 7.86(1H, d, J = 8.0 Hz), 7.72-7.67(2H, m), 7.39(1H, d, J = 9.2 Hz), 5.51(2H, s), 4.61(2H, bs), 3.61-3.47(5 H, m), 2.28(3H, s), 1.28(3H, d, J = 6.4 Hz). |
| VIII-131 | 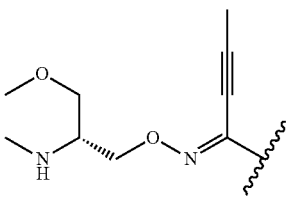 [SMILES: */C(C#CC)=N/OC[C@@H](COC)NC] | 10.0(1H, s), 8 74(1H, s), 8.60-8.58(2H, m), 8.20(1 H d, J = 8.8), 7.97(1H, s), 7.90-7.86(1H, m), 7.79(1H, d, J = 8.4), 7 69-7 67(1H, m), 7.58(1H, d, J = 7.6), 7 38-7.35(1H, m), 7.27(1H, d, J = 9.2), 5.30(2H, s), 4.24 4.23(2H, m), 3.44-3.34(2H, m), 2.97-2.92(1H, m), 2.38(3H, s), 2.26(3H, s). |
| VIII-132 | 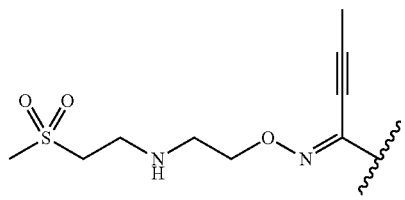 [SMILES: */C(C#CC)=N/OCCNCCS(C)(=O)=O] | 10.08(1H, s), 8.98(1H, s), 8.61-8.59(2H, m), 8.23(1H, d, J = 8.8 Hz), 7.98(1H, s), 7.89(1H, t, J = 7.2 Hz), 7.80(1H, d, J = 8.8 Hz), 7 69(1H, d, J = 9.2 Hz), 7.59(1H, t, J = 8.0 Hz), 7.37(1H, d, J = 7.6 Hz), 7.28(1H, d, J = 8.8 Hz), 5.31(2H, s), 4.33(2H, t J = 4.8 Hz), 3.26(2H, t, J = 6.4 Hz), 3.03(5 H, bs), 2.94(2H, bs), 2.26(3H, s). |
| VIII-133 | 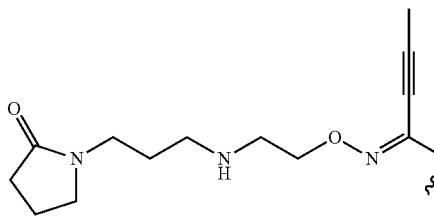 | 10.0(1H, s), 8.74(1H, s), 8.60-8.58(2H, m), 8.21(1H, d, J = 8.0), 7.97(1H, m), 7.90-7.86(1H, m), 7.80(1H, d, J = 8.8), 7.69-7.67(1H, m), 7.59(1H, d, J = 8.0), 7.38-7.35(1H, m), 7.28(1H, d, J = 9 2), 5.30(2H, s), 4.32-4.29(2H, m), 3.22-3.18(2H, m), 2.90-2.87(2H, m), 2.57-2.53(2H, m), 2.25(3H, s), 2.20-2.16(2H, m), 1.91-1.84(2H, m), 1.62-1.55(1H, m) |

TABLE 32-continued

[Chemical formula 82]

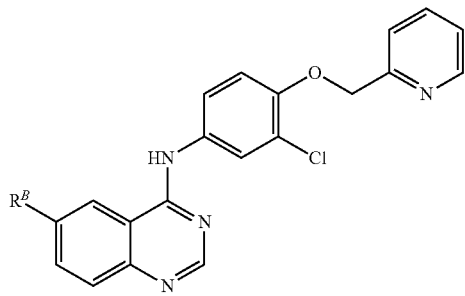

(VIII)

| Compound No. | $R^B$ | $^1$H-NMR($d_6$-DMSO) |
|---|---|---|
| VIII-134 | (structure: acetamido-ethyl-NH-ethyl-O-N= with methyl and propynyl substituents) | 10.11(1H, brs), 8.75(1H, s), 8.61-8.59(2H, m), 8.22(1H, d, J = 9.0 Hz), 7.91-7 78(3H, m), 7.67(1H, d, J = 9.0 Hz), 7 59(1H, d, J = 7.8 Hz), 7.40-7.36(1H, m), 7.29(1H, d, J = 9 0 Hz), 5.31(2H, s), 4.32(2H, m), 3.13(2H, m), 2.93(2H, m), 2.66(2H, m), 2.26(3H, s), 1.78(3H, s) |

TABLE 33

| Compound No. | $R^B$ | $^1$H-NMR($d_6$-DMSO) |
|---|---|---|
| VIII-135 | (structure: H2N-C(O)-O-ethyl-NH-ethyl-O-N=) | 10.09(1H, brs), 8.75(1H, s), 8.61-8.59(2H, m), 8.22(1H, d, J = 9.0 Hz), 7.97(1H, s), 7.92-7 86(1H, m), 7.81(1H, d, J = 9.0 Hz), 7.69(1H, d, J = 9.0 Hz), 7.59(1H, d, J = 7.8 Hz), 7.40-7.36(1H, m), 7.29(1H, d, J = 9.0 Hz), 6.47(2H, brs), 5.31(2H, s), 4.34(2H, m), 3.99(2H, m), 2.99(2H, m), 2.84(2H, m), 2.26(3H, s) |
| VIII-136 | (structure: cyclopropyl-NH-ethyl-O-N=) | 10.10(1H, brs), 8.75(1H, s), 8.61-8.59(2H, m), 8 22(1H, d, J = 9.0 Hz), 7.97(1H, s), 7.92-7.86(1H, m), 7.81(1H, d, J = 9.0 Hz), 7.69(1H, d, J = 9.0 Hz), 7 59(1H, d, J = 7.8 Hz), 7.40-7.36(1H, m), 7 29(1H, d, J = 9.0 Hz), 5.31(2H, s), 4.33(2H, t, 6 0 Hz), 3.00(2H, t, 6.0 Hz), 2.25(3H, s), 2.23(1H, m), 0.408(2H, m), 0.29(2H, m) |
| VIII-137 | (structure: tetrahydrofuran-CH2-NH-ethyl-O-N=) | (tri-HCl salt) 12.14(1H, brs), 9.28(1H, s), 8.93(1H, s), 8.64(1H, d, J = 4.2 Hz), 8.44(1H, d, J = 10.5 Hz), 8.02-7.91(3H, m), 7.69-7.62(1H, m), 7.46-7.42(1H, m), 7.37(1H, d, 9.0 Hz), 5.38(2H, s), 4.59(2H, m), 4.19(1H, m), 3.81(1H, m), 3.71(1H, m), 3 47(2H, m), 3.21(1H, m), 3.02(1H, m), 2.28(3H, s), 2.02(1H, m), 1.84(2H, m), 1.56(1H, m) |
| VIII-138 | (structure: tetrahydrofuran-CH2-NH-ethyl-O-N=, other stereochem) | (tri-HCl salt) 9.28(1H, s), 8.93(1H, s), 8.64(1H, d, J = 4.2 Hz), 8.44(1H, d, J = 10.5 Hz), 8.02-7.91 (3H, m), 7.69-7.62(1H, m), 7.46-7.42(1H, m), 7.37(1H, d, 9.0 Hz), 5.38(2H, s), 4.59(2H, m), 4 19(1H, m), 3.81(1H, m), 3.71(1H, m), 3.47(2H, m), 3.21(1H, m), 3.02(1H, m), 2.28(3H, s), 2.02(1H, m), 1.84(2H, m), 1.56(1H, m) |

TABLE 33-continued

| Compound No. | $R^B$ | $^1$H-NMR($d_6$-DMSO) |
|---|---|---|
| VIII-139 | (structure: HO-CH2-CH(CH3)-NH-CH2-CH2-O-N=C(C≡C-CH3)-) | 10.08(1H, s), 8.75(1H, s), 8.61-8.58(2H, m), 8.22(1H, d J = 8.8 Hz), 7.98(1H, s), 7.89(1H, t, J = 8.0 Hz), 7.68(1H, d, J = 8.4 Hz), 7.37(1H, t, J = 6.4 Hz), 7.37(1H, t, J = 6.4 Hz), 7.28(1H, d, J = 8.4 Hz), 5.31(2H, s), 4.34(2H, t, J = 6.4 Hz), 3.33(1H, t, J = 6.4 Hz), 2.92(2H, t, J = 5.2 Hz), 2.65-2.61(1H, m), 2.26(3H, s), 1.75-1.70(1H, m), 0.83(3H, d, J = 6.8 Hz). |
| VIII-140 | (structure: HO-CH2-CH(CH3)-NH-CH2-CH2-O-N=C(C≡C-CH3)-, stereo) | 10 09(1H, s), 8.75(1H, s), 8.59(2H, bs), 8.22(1H, d, J = 8.8 Hz), 7.98(1H, s), 7.89(1H, t, J = 6.4 Hz), 7.80(1H, d, J = 8.8 Hz), 7.69(1H, t, J = 8.4 Hz), 7.59 (1H, t, J = 8.4 Hz), 7.37(1H, d, J = 5.2 Hz), 7.28(1H, d, J = 8.8 Hz), 5.31(2H, s), 4.34(2H, t, J = 6.4 Hz), 3.32(2H, t, J = 6.4 Hz), 2.92(2H, t, J = 5.6 Hz), 2.65-2.61(1H, m), 2.26(3H, s), 1.75-1.68(1H, m), 1.24(1H, bs), 0.83(3H, d, J = 6.8 Hz). |
| VIII-141 | (tetrahydropyran-4-yl-NH-CH2-CH2-O-N=C(C≡C-CH3)-) | (tri-HCl salt) 12.48(1H, s), 9.48(1H, s), 9.42(1H, bs), 9.29(2H, bs), 8.94(1H, s), 8 72(1H, s), 8.47 (1H, s), 8.13-8.06(1H, m), 7.92(1H, s), 7 76(1H, bs), 7.68(1H, bs), 7.59(1H, bs), 7.39(1H, bs), 5.46(2H, s), 4.62(2H, bs), 3.88(4H, bs), 2.28(3H, s), 2.01-1.94(4H, m), 1.69-1.60(4H, m). |

TABLE 34

| Compound No. | $R^B$ | $^1$H-NMR($d_6$-DMSO) |
|---|---|---|
| VIII-142 | (methylsulfonyl-piperidin-4-yl-NH-CH2-CH2-O-N=C(C≡C-CH3)-) | 10.07(1H, s), 8.74(1H, s), 8.59(2H, s), 8.20(1H, bs), 7.97(1H, s), 7.89(1H, bs), 7.80(1H, d, J = 8.0 Hz), 7.68(1H, bs), 7.58(1H, d, J = 8.8 Hz), 7.38(1H, bs), 7.28(1H, d, J = 9.2 Hz), 5.31(2H, s), 4.31(2H, bs), 3.45(2H, bs), 2.94(2H, bs), 2.85-2.81(5 H, m), 2.26(3H, s), 1.89-1 85(2H, m), 1.36-1.28(2H, m) |
| VIII-143 | (HO-CH2-CH2-NH-CH2-CH2-O-N=C(C≡C-CH3)-) | 10.09(1H, brs), 8.74(1H, s), 8.61-8.59(2H, m), 8.22(1H, d, J = 9.0 Hz), 7.97(1H, s), 7.92-7.86(1H, m), 7.81(1H, d, J = 9.0 Hz), 7.69(1H, d, J = 9.0 Hz), 7.59(1H, d, J = 7.8 Hz), 7.40-7.36(1H, m), 7.29(1H, d, J = 9.0 Hz), 5.31(2H, s), 4.23(2H, t, 5.4 Hz), 3 47(2H, t, 5.4 Hz)), 2.91(2H, t, 5.4 Hz), 2 65(2H, m), 2.25(3H, s) |
| VIII-144 | (CH3O-CH2-CH2-N(Et)-CH2-CH2-O-N=C(C≡C-CH3)-) | (tri-HCl salt) 12.4(1H, s), 10.5(1H, s), 9.34(1H, s), 8.93(1H, s), 8.68-8.67(1H, m), 8.45(1H, d, J = 9.2), 8.05-8.02(2H, m), 7.92-7.91(1H, m), 7.71-7.66(2H, m), 7.52-7.49(1H, m), 7.37(1H, d, J = 8.8), 5.41(2H, s), 4.73-4.67(1H, m), 3.30(6 H, s), 2.27(3H, s), 1.29-1.25(1H, m). |

TABLE 34-continued

| Compound No. | R$^B$ | $^1$H-NMR(d$_6$-DMSO) |
|---|---|---|
| VIII-145 | (structure) | 10.08(1H, s), 8.75(1H, s), 8 59(2H, bs), 8.22(1H, d, J = 8.4 Hz), 7.98(1H, bs), 7.89(1H, t, J = 8.0 Hz), 7.80(1H, d, J = 9.2 Hz), 7.68(1H, d, J = 8.8 Hz), 7.38(1H, d, J = 6.4 Hz), 7.28(1H, d, J = 8.8 Hz), 5.31(2H, s), 4.36(4H, t, J = 6.4 Hz), 3.49(2H, bs), 2.79(2H, t, J = 6.0 Hz), 2 30(3H, s), 2.25(3H, s). |
| VIII-146 | (structure) | (tri-HCl salt) 12.70(1H, s), 10.83(1H, bs), 9.49(1H, s), 8.95(1H, s), 8.77(1H, bs), 8.44(1H, d, J = 8.84 Hz), 8.23(1H, bs), 8.10(1H, d, J = 8.8 Hz), 7.95(1H, s), 7.85(1H, d, J = 6.8 Hz), 7.74-7.68(2H, m), 7.39(1H, d, J = 8.4 Hz), 5.51(2H, s), 4.70(2H, bs), 7 75-7 42(4H, m), 3.48-3.44(1H, m), 3.40(1H, bs), 3.30(3H, s), 2.90(3H, s), 2.28(3H, s). |
| VIII-147 | (structure) | 10.28-10.03(1H, m), 8.75(1H, s), 8.61-8.58(2H, m), 8.21(1H, d, J = 8.8 Hz), 7.98(1H, s), 7 89(1H, t, J = 8.0 Hz), 7.79(1H, d, J = 7 2 Hz), 7.68(1H, d, J = 8.0 Hz), 7.37(3H, t, J = 6.0 Hz), 7.28(1H, t, J = 8.8 Hz), 5.31(2H, s), 4.33(2H, t J = 6.4 Hz), 2.31(3H, s), 2.06(3H, s), 1.88(2H, t, J = 6.4 Hz). |
| VIII-148 | (structure) | 10.09(1H, brs), 8.75(1H, s), 8.61-8.57(2H, m), 8.22(1H, d, J = 9.0 Hz), 7.98(1H, s), 7.92-7.86(1H, m), 7.80(1H, d, J = 9.0 Hz), 7.68(1H, d, J = 9.0 Hz), 7 59(1H, d, J = 7.8 Hz), 7.40-7.36(1H, m), 7.28(1H, d, J = 9.0 Hz), 5.31(2H, s), 4.37(2H, m), 2.82(2H, m), 2.54(4H, m), 2.25(3H, s), 1.69(4H, m) |

TABLE 35

| Compound No | R$^B$ | $^1$H-NMR(d$_6$-DMSO) |
|---|---|---|
| VIII-149 | (structure) | 10.09(1H, s), 8.75(1H, s), 8.70(2H, s), 8.20(1H, d, J = 8.0 Hz), 8.07(2H, s), 7.98(1H, t, J = 4.8 Hz), 7.88(1H, t, J = 8.0 Hz), 7.68(1H, d, J = 8.0 Hz), 7.38(1H, s), 7.28(1H, d, J = 9.6 Hz), 5.31(2H, s), 4.42(2H, s), 4.29-4.24(1H, m), 2.91-2.76(2H, m), 2.25(3H, s), 2.17-2.12(1H, m), 1.75(3H, s), 1.53-1.34(1H, m), 1.11(2H, d, J = 4.4 Hz). |
| VIII-150 | (structure) | 10.09(1H, s), 8.75(1H, s), 8.59(2H, s), 8.21(1H, bs), 7.98(1H, s), 7.89(1H, s), 7.79(1H, s), 7.68(1H, s), 7.58(1H, s), 7.37(1H, s), 7.28(1H, s), 5.31(2H, s), 4.36(2H, bs), 2.71(2H, bs), 2.25(3H, s), 1.81(1H, bs), 1.66(2H, bs), 1.52(1H, bs), 1.24(2H, bs). |

TABLE 35-continued

| Compound No | R$^B$ | $^1$H-NMR(d$_6$-DMSO) |
|---|---|---|
| VIII-151 | [structure] | 10.09(1H, brs), 8.75(1H, s), 8.61-8.59(2H, m), 8.22(1H, d, J = 9.0 Hz), 7.97(1H, s), 7.92-7.86(1H, m), 7.80(1H, d, J = 9.0 Hz), 7.69(1H, d, J = 9.0 Hz), 7.59(1H, d, J = 7.8 Hz), 7.40-7.36(1H, m), 7.28 (1H, d, J = 9.0 Hz), 6.48(2H, brs), 5.31(2H, s), 4.94 (1H, m), 4.37(2H, m), 2.81-2.63(5H, m), 2.44 (1H, m), 2.25(3H, s), 2.14(1H, m), 1.69(1H, m) |
| VIII-152 | [structure] | 10.13(1H, brs), 8.79(1H, s), 8.61-8.58(2H, m), 8.23(1H, dd, J = 1.8 Hz, J = 8.7 Hz), 7.98(1H, d, J = 2.7 Hz), 7.92-7.86(1H, m), 8.80(1H, d, J = 8.7 Hz), 7.79(1H, dd, J = 2.7 Hz, J = 9.0 Hz), 7.59(1H, d, J = 7.8 Hz), 7.39-7.35(1H, m), 7.28(1H, d, J = 9.0 Hz), 5.31(2H, s), 4.91(1H, brs), 4.36-4.24(3H, m), 3.59(1H, m), 2.99-2.812(2H, m), 2.26(3H, s), 2.13(1H, m), 1.50(1H, m). |
| VIII-153 | [structure] | 10.0(1H, br), 8.64(1H, s), 8.62-8.55(2H, m), 8.20(1H, d, J = 8.8), 7.96(1H, s), 7.90-7.87(1H, m), 7.79(1H, d, J = 8.4), 7.68-7.66(1H, m), 7.58(1H, d, J = 8.4), 7.38-7.35(1H, m), 7.27(1H, d, J = 8.8), 5.30(2H, s), 4.18-4.08(2H, m), 3.43-3.40(1H, m), 3.69(3H, s), 2.84-2.77(2H, m), 2.25(3H, s), 1.88-1.55(3H, m), 1.50-1.38(1H, m). |
| VIII-154 | [structure] | 10.08(1H, br), 8.75(1H, s), 8.60-8.58(2H, m), 8.21-8.19(1H, m), 7.98-7.97(1H, m), 7.93-7.86(1H, m), 7.79(1H, d, J = 8.8), 7.70-7.67(1H, m), 7.58(1H, d, J = 8.0), 7.38-7.35(1H, m), 7.27(1H, d, J = 9.2), 5.30(2H, s), 4.30-4.20(2H, m), 3.01-2.96(1H, m), 2.68(1H, br), 2.41(3H, s), 2.24(3H, s), 1.99-1.89(1H, m), 1.73-1.66(2H, m), 1.62-1.53(1H, m). |
| VIII-155 | [structure] | 10.0(1H, brs), 8.73(1H, s), 8.50-8.58(2H, m), 8.31(1H, s), 8.22-8.20(1H, m), 7.96(1H, s), 7.90-7.86(1H, m), 7.79(1H, d, J = 8.8), 7.68-7.66(1H, m), 7.59(1H, d, J = 7.6), 7.38-7.35(1H, m), 7.28(1H, d, J = 9.2), 5.30(2H, s), 4.93(1H, brs), 3.02(1H, d, J = 11.6), 2.24(3H, s), 2.06-2.01(1H, m), 1.77-1.70(1H, m). |

TABLE 36

| Compound No. | R$^B$ | $^1$H-NMR(d$_6$-DMSO) |
|---|---|---|
| VIII-156 | [structure] | 10.13(1H, brs), 8.81(1H, s), 8.61-8.59(2H, m), 8.24(1H, d, J = 10.5 Hz), 7.99(1H, s), 7.92-7.88(1H, m), 7.81(1H, d, J = 9.0 Hz), 7.70(1H, d, J = 9.0 Hz), 7.59(1H, d, J = 7.8 Hz), 7.38-7.36(1H, m), 7.28(1H, d, J = 9.0 Hz), 5.31(2H, s), 4.92(1H, s), 4.28(3H, m), 3.82(1H, m), 3.09(1H, d, 11.4 Hz), 3.83(1H, d, 11.4 Hz), 2.27(3H, s), 1.87(1H, m), 1.65(1H, m) |

TABLE 36-continued

| Compound No. | R^B | ^1H-NMR(d_6-DMSO) |
|---|---|---|
| VIII-157 | (pyrrolidin-2-ylmethyl-O-N= structure with NH) | 10.03(1H, br), 8.73(1H, s), 8.59-8.58(1H, m), 8.55(1H, s), 8.20(1H, d, J = 8.8), 7.94(1H, s), 7.89-7.85(1H, m), 7.78(1H, d, J = 8.4), 7.66-7.64(1H, m), 7.57(1H, d, J = 7.6), 7.38-7.35(1H, m), 7.25(1H, d, J = 8.8), 5.28(2H, s), 4.20-4.08(2H, m), 2.85-2.74(2H, m), 2.24(3H, s), 1.82-1.76(1H, m), 1.73-1.58(2H, m), 1.48-1.39(1H, m) |
| VIII-158 | (N-methyl-pyrrolidin-2-ylmethyl-O-N= structure) | 10.07(1H, br), 8.74(1H, s), 8.60-8.58(2H, m), 8.22-8.19(1H, m), 7.98-7.97(1H, m), 7.93-7.86(1H, m), 7.80(1H, d, J = 9.2), 7.70-7.67(1H, m), 7.59(1H, d, J = 7.6), 7.38-7.35(1H, m), 7.28(1H, d, J = 9.2), 5.30(2H, s), 4.30-4.20(2H, m), 3.01-2.96(1H, m), 2.65(1H, br), 2.40(3H, s), 2.24(3H, s), 1.99-1.89 (1H, m), 1.78-1.66(2H, m), 1.62-1.53(1H, m). |
| VIII-159 | (N-(2-hydroxyethyl)-pyrrolidin-2-ylmethyl-O-N= structure) | 10.08(1H, s), 8.73(1H, s), 8.59-8.56(2H, m), 8.21-8.19(1H, m), 7.94(1H, s), 7.90-7.86(1H, m), 7.79(1H, d, J = 8.8), 7.66-7.64(1H, m), 7.58(1H, d, J = 7.6), 7.38-7.35(1H, m), 7.26(1H, d, J = 9.2), 5.29(2H, s), 4.44(1H, brs), 4.25-4.21(1H, m), 4.15-4.11(1H, m), 3.05-2.96(2H, m), 2.46-2.39(1H, m), 2.23(2H, s), 1.92-1.82(1H, m), 1.73-1.63(2H, m), 1.59-1.54(1H, m). |
| VIII-160 | (N-(2-hydroxyethyl)-pyrrolidin-2-ylmethyl-O-N= structure) | 10.0(1H, s), 8.72(1H, s), 8.61-8.53(2H, m), 8.21-8.19(1H, m), 7.94(1H, s), 7.89-7.86(1H, m), 7.79(1H, d, J = 8.8), 7.66-7.64(1H, m), 7.58(1H, d, J = 8.0), 7.38-7.35(1H, m), 7.26(1H, d, J = 9.2), 5.29(2H, s), 4.44(1H, brs), 4.25-4.21(1H, m), 4.15-4.11(1H, m), 3.05-2.96(2H, m), 2.45-2.39(1H, m), 2.23(3H, s), 1.92-1.82(1H, m), 1.73-1.63(2H, m), 1.60-1.53(2H, m). |
| VIII-161 | (4-(hydroxymethyl)pyrrolidin-3-yloxy-N= structure) | 10.0(1H, brs), 8.73(1H, s), 8.60-8.57(2H, m), 8.21(1H, d, J = 8.4), 7.95(1H, s), 7.90-7.86(1H, m), 7.79(1H, d, J = 8.8), 7.67-7.65(1H, m), 7.58(1H, d, J = 7.6), 7.38-7.35(1H, m), 7.27(1H, d, J = 8.8), 5.30(2H, s), 4.93(1H, brs), 3.02(1H, d, J = 11.6), 2.24(3H, s), 2.06-2.01(1H, m), 1.77-1.70(1H, m) |
| VIII-162 | (thiomorpholine-1,1-dioxide-N-ethyl-O-N= structure) | 10.07(1H, s), 8.75(1H, s), 8.61-8.59(2H, m), 8.23(1H, d, J = 8.8 Hz), 7.98(1H, d, J = 2.4 Hz), 7.89(1H, t, J = 8.4 Hz), 7.80(1H, d, J = 8.8 Hz), 7.68(1H, d, J = 6.4 Hz), 7.57(1H, t, J = 11.8 Hz), 7.28(1H, d, J = 8.8 Hz), 5.31(2H, s), 4.40(2H, t, J = 5.2 Hz), 3.32(4H, s), 3.09(4H, bs), 2.96(2H, t, J = 5.6 Hz), 2.26(3H, s) |

TABLE 37

| Compound No. | R^B | ¹H-NMR(d₆-DMSO) |
|---|---|---|
| VIII-163 | (morpholine-CH₂CH₂-O-N=) | 10.07(1H, s), 8.75(1H, s), 8.59(2H, bs), 8.21(1H, d, J = 4.8 Hz), 7.98(1H, s), 7.89(1H, t, J = 7.6 Hz), 7.80(1H, d, J = 8.4 Hz), 7.68(1H, d, J = 8.4 Hz), 7.60(1H, t, J = 8.4 Hz), 7.37(1H, t, J = 7.6 Hz), 7.28(1H, d, J = 8.8 Hz), 5.31(2H, s), 4.40(2H, t J = 4.8 Hz), 3.60(4H, bs), 2.72(4H, t, J = 4.8 Hz), 2.25(3H, s). |
| VIII-164 | (4-methylpiperazine-CH₂CH₂-O-N=) | 10.0(1H, s), 8.73(1H, s), 8.60-8.57(2H, m), 8.20(1H, d, J = 8.8), 7.96(1H, s), 7.90-7.86(1H, m), 7.79(1H, d, J = 8.4), 7.67-7.65(1H, m), 7.58(1H, d, J = 7.6), 7.38-7.35(1H, m), 7.27(1H, d, J = 8.8), 5.30(2H, s), 4.38-4.35(2H, m), 2.71-2.68(2H, m), 2.31(1H, br), 2.24(3H, s), 2.13(3H, s). |
| VIII-165 | (4-hydroxypiperidine-CH₂CH₂-O-N=) | 10.0(1H, s), 8.73(1H, s), 8.62-8.54(2H, m), 8.21-8.19(1H, m), 7.96(1H, s), 7.90-7.86(1H, m), 7.80-7.78(1H, m), 7.68-7.66(1H, m), 7.59(1H, d, J = 8.0), 7.38-7.36(1H, m), 7.27(1H, d, J = 8.8), 5.30(2H, s), 4.54(1H, brs), 4.37-4.34(2H, m), 2.83-2.75(2H, m), 2.69-2.66(2H, m), 2.24(3H, s), 2.17-2.11(2H, m), 1.71-1.69(2H, m), 1.71-1.69(2H, m), 1.44-1.32(2H, m). |
| VIII-166 | (4-acetylpiperazine-CH₂CH₂-O-N=) | 10.08(1H, s), 8.75(1H, s), 8.59(2H, bs), 8.22(1H, d, J = 8.8 Hz), 7.80(1H, s), 7.89(1H, t, J = 6.4 Hz), 7.80(1H, d, J = 8.4 Hz), 7.70-7.67(1H, m), 7.59(1H, d, J = 8.4 Hz), 7.37(1H, bs), 7.28(1H, d, J = 8.0 Hz), 5.31(2H, s), 4.41(2H, t, J = 4.4 Hz), 3.43(2H, bs), 2.76(2H, bs), 2.26(3H, s), 1.99(3H, s). |
| VIII-167 | (morpholin-3-yl-CH₂-O-N=) | 10.10(1H, s), 8.73(1H, s), 8.60-8.56(2H, m), 8.20(1H, d, J = 8.8), 7.94(1H, s), 7.90-7.86(1H, m), 7.79(1H, d, J = 8.8), 7.68-7.64(1H, m), 7.58(1H, d, J = 7.6), 7.38-7.35(1H, m), 7.27(1H, d, J = 9.2), 5.29(2H, s), 4.20-4.08(2H, m), 3.79(1H, d, J = 10.4), 3.65(1H, d, J = 11.2), 3.25-3.20(1H, m), 3.09(1H, br), 2.83-2.70(2H, m), 2.25(3H, s) |
| VIII-168 | (morpholin-2-yl-CH₂-O-N=) | 10.0(1H, s), 8.73(1H, s), 8.59-8.57(2H, m), 8.19(1H, d, J = 8.8), 7.95(1H, s), 7.89-7.85(1H, m), 7.78(1H, d, J = 8.8), 7.68-7.65(1H, m), 7.58(1H, d, J = 7.6), 7.37-7.34(1H, m), 7.26(1H, d, J = 8.8), 5.29(2H, s), 4.26-4.14(2H, m), 3.75-3.72(2H, m), 2.85(1H, d, J = 12.4), 2.69-2.61(2H, m), 2.45(1H, d, J = 10.8), 2.25(3H, s). |

TABLE 37-continued

| Compound No. | R<sup>B</sup> | ¹H-NMR(d₆-DMSO) |
| --- | --- | --- |
| VIII-169 | (morpholine-CH₂-O-N= structure) | 10.0(1H, s), 8.74(1H, s), 8.60-8.58(2H, m), 8.20(1H, d, J = 8.8), 7.96(1H, s), 7.90-7.86(1H, m), 7.80(1H, d, J = 8.8), 7.68-7.66(1H, m), 7.59(1H, d, J = 7.6), 7.38-7.35(1H, m), 7.27(1H, d, J = 9.2), 5.30(2H, s), 4.20-4.08(2H, m), 3.79(1H, d, J = 10.4), 3.65(1H, d, J = 11.2), 3.25-3.20(1H, m), 3.09(1H, br), 2.83-2.70(2H, m), 2.26(2H, s). |

TABLE 38

| Compound No. | R<sup>B</sup> | ¹H-NMR(d₆-DMSO) |
| --- | --- | --- |
| VIII-170 | (piperazine-CH₂-O-N= structure) | 10.09(1H, brs), 8.74(1H, s), 8.61-8.58(2H, m), 8.22(1H, d, J = 10.5 Hz), 7.97(1H, s), 7.92-7.86(1H, m), 7.80(1H, d, J = 9.0 Hz), 7.68(1H, d, J = 10.5 Hz), 7.59(1H, d, J = 8.1 Hz), 7.39-7.35(1H, m), 7.28(1H, d, J = 9.0 Hz), 5.31(2H, s), 4.12(2H, d, 4.5 Hz), 2.95-2.53(5H, m), 2.34-2.09(5H, m) |
| VIII-171 | (piperazinone-CH₂-O-N= structure) | 10.08(1H, brs), 8.74(1H, s), 8.61-8.59(2H, m), 8.21(1H, d, J = 9.0 Hz), 7.98(1H, s), 7.92-7.86(1H, m), 7.81(1H, d, J = 9.0 Hz), 7.75(1H, s), 7.67(1H, d, J = 9.0 Hz), 7.59(1H, d, J = 7.8 Hz), 7.40-7.36(1H, m), 7.29(1H, d, J = 9.0 Hz), 5.31(2H, s), 4.31(2H, m), 3.66(1H, m), 3.27-3.10(2H, m), 2.99-2.80(2H, m) |
| VIII-172 | (N,N'-dimethylpiperazine-CH₂-O-N= structure) | 10.09(1H, brs), 8.74(1H, s), 8.61-8.59(2H, m), 8.22(1H, d, J = 9.0 Hz), 7.97(1H, s), 7.92-7.86(1H, m), 7.81(1H, d, J = 9.0 Hz), 7.68(1H, d, J = 9.0 Hz), 7.59(1H, d, J = 7.8 Hz), 7.40-7.36(1H, m), 7.29(1H, d, J = 9.0 Hz), 5.31(2H, s), 4.44(1H, m), 4.16(1H, m), 2.70-2.51(4H, m), 2.30-2.16(10H, m), 2.09-1.88(2H, m) |
| VIII-173 | (morpholine-CH₂-O-N= structure) | 10.0(1H, br), 8.74(1H, s), 8.60-8.58(2H, m), 8.20(1H, d, J = 8.8), 7.97(1H, s), 7.90-7.86(1H, m), 7.80(1H, d, J = 8.4), 7.68-7.66(1H, m), 7.59(1H, d, J = 8.0), 7.38-7.35(1H, m), 7.28(1H, d, J = 9.2), 5.30(2H, s), 4.26-4.14(2H, m), 3.75-3.72(2H, m), 3.48-3.42(2H, m), 2.85(1H, d, J = 12.4), 2.69-2.60(2H, m), 2.45(1H, d, J = 10.4), 2.26(3H, s) |
| VIII-174 | (HO-ethyl-piperazine-CH₂-O-N= structure) | (tri-HCl salt) 12.31(1H, brs), 9.41(1H, s), 8.97(1H, s), 8.73(1H, d, J = 1.8 Hz), 8.49(1H, d, 8.7 Hz), 8.17-8.05(2H, m), 7.94(1H, s), 7.77(1H, d, J = 7.5 Hz), 7.69(1H, d, 8.7 Hz), 7.59(1H, t, J = 5.7 Hz), 7.38(1H, d, J = 8.7 Hz), 5.46(2H, s), 4.60(2H, m), 4.35-3.31(12H, m), 2.30(3H, s). |

TABLE 38-continued

| Compound No. | $R^B$ | $^1$H-NMR($d_6$-DMSO) |
|---|---|---|
| VIII-175 | (structure) | |
| VIII-176 | (structure) | (tri-HCl salt) 12.31(1H, brs), 9.41(1H, s), 8.97(1H, s), 8.73(1H, d, J = 5.4 Hz), 8.49(1H, d, J = 8.7 Hz), 8.13(1H, s), 8.07(1H, d, J = 9.0 Hz), 7.94(1H, s), 7.72(1H, d, J = 8.7 Hz), 7.02(1H, d, J = 9.0 Hz), 7.59(1H, s), 7.38(1H, d, J = 9.0 Hz), 5.46(2H, s), 4.65-3.62(10H, m), 2.89(3H, s), 2.30(3H, s). |

TABLE 39

| Compound No. | $R^B$ | $^1$H-NMR($d_6$-DMSO) |
|---|---|---|
| VIII-177 | (structure) | 10.1(1H, s), 8.74(1H, s), 8.59(2H, brs), 8.21(1H, d, J = 8.8 Hz), 7.97(1H, s), 7.85-7.92(1H, m), 7.80(1H, d, J = 8.4 Hz), 7.67(1H, d, J = 9.6 Hz), 7.59(1H, d, J = 6.4 Hz), 7.34-7.40(1H, m), 7.29(1H, d, J = 8.8 Hz), 5.31(2H, m), 4.10-4.35(2H, m), 3.75-3.82(1H, m), 3.48(1H, m), 2.85(1H, d, J = 12 Hz), 2.74(1H, d, J = 13 Hz), 2.34-2.41(1H, m), 2.26(4H, brs), 1.03(3H, d, J = 6.0 Hz) |
| VIII-178 | (structure) | 10.1(1H, s), 8.74(1H, s), 8.59(2H, brs), 8.21(1H, d, J = 8.8 Hz), 7.97(1H, s), 7.79-7.93(2H, m), 7.66-7.70(1H, m), 7.59(1H, d, J = 6.4 Hz), 7.38(1H, brs), 7.29(1H, d, J =8.8 Hz), 5.31(2H, m), 4.37-4.56(2H, m), 3.95-4.02(1H, m), 3.80-3.88(1H, m), 2.62-2.85(3H, m), 2.31-2.4(1H, m), 2.26(3H, s), 1.06(3H, d, J = 5.2 Hz) |
| VIII-179 | (structure) | 10.06(1H, brs), 8.75(1H, s), 8.61-8.59(2H, m), 8.22(1H, d, J = 9.0 Hz), 7.97(1H, s), 7.92-7.86(1H, m), 7.81(1H, d, J = 9.0 Hz), 7.76(1H, s), 7.69(1H, d, J = 9.0 Hz), 7.59(1H, d, J = 7.8 Hz), 7.40-7.36(1H, m), 7.29(1H, d, J = 9.0 Hz), 5.31(2H, s), 4.30(2H, m), 3.65(1H, m), 3.16(2H, m), 2.99-2.80(2H, m), 2.26(3H, s) |
| VIII-180 | (structure) | 10.0(1H, brs), 8.76(1H, s), 8.60-8.58(2H, m), 8.19(1H, d, J = 8.8), 7.97(1H, s), 7.89-7.86(1H, m), 7.81(1H, d, J = 8.8), 7.68-7.66(1H, m), 7.58(1H, d, J = 7.6), 7.38-7.35(1H, m), 7.27(1H, d, J = 8.8), 5.30(2H, s), 4.51(2H, s), 4.38-4.35(2H, m), 3.40(3H, s), 2.87-2.84(2H, m), 2.34(3H, s) |

TABLE 39-continued

| Compound No. | R$^B$ | $^1$H-NMR(d$_6$-DMSO) |
|---|---|---|
| VIII-181 | (morpholine-CH$_2$-O-N=) | 10.0(1H, s), 8.76(1H, s), 8.59(2H, s), 8.19(1H, d, J = 8.8), 7.97(1H, s), 7.90-7.86(1H, m), 7.82(1H, d, J = 8.8), 7.69-7.66(1H, m), 7.59(1H, d, J = 8.0), 7.38-7.35(1H, m), 7.28(1H, d, J = 8.8), 5.30(2H, s), 4.52(2H, s), 4.25-4.15(2H, m), 3.82-3.79(1H, m), 3.67-3.64(1H, m), 3.40(3H, s), 3.26-3.21(2H, m), 3.14-3.05(1H, m), 2.81-2.72(2H, m) |
| VIII-182 | (MeNH-CH$_2$CH$_2$-O-N=) | 10.1(1H, s), 8.79(1H, s), 8.60(2H, s), 8.25(1H, d, J = 7.6 Hz), 7.98(1H, s), 7.89(1H, bs), 7.81(1H, d, J = 7.6 Hz), 7.69(1H, d, J = 7.6 Hz), 7.60(1H, d, J = 7.2 Hz), 7.38(1H, bs), 7.29(1H, d, J = 8.4 Hz), 5.31(2H, s), 4.43(2H, bs), 3.14(2H, bs), 2.52(3H, s), 2.27(3H, s) |

TABLE 40

[Chemical formula 83]

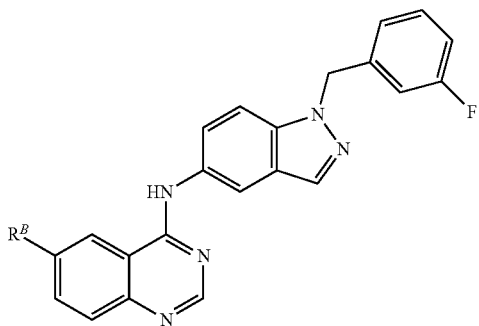

(VIII)

| Compound No. | R$^B$ | $^1$H-NMR(d$_6$-DMSO) |
|---|---|---|
| VIII-183 | (MeNH-CH$_2$CH$_2$-O-N=) | 10.19(1H, s), 8.78(1H, s), 8.53(1H, s), 8.23(1H, dd, J = 8.4 Hz, J = 4.0 Hz), 8.17(1H, s), 8.14(1H, s), 7.80-7.65(3H, m), 7.40-7.35(1H, m), 7.13-7.04(3H, m), 5.72(2H, s), 4.32(2H, t, J = 6.0 Hz), 2.86(2H, t, J = 6.0 Hz), 2.35(3H, s), 2.25(3H, s). |
| VIII-184 | (AcNH-CH$_2$CH$_2$-NH-CH$_2$CH$_2$-O-N=) | (di-HCl salt) 12.46(1H, s), 9.37(1H, s), 8.87(1H, s), 8.48(1H, d, J = 8.7 Hz), 8.27(1H, t, J = 5.4 Hz), 8.24(1H, s), 8.03(2H, m), 7.85(1H, d, J = 9.0 Hz), 7.68(1H, d, 9.0 Hz), 7.35(1H, s), 7.13-7.05(3H, m), 5.75(2H, s), 4.58(2H, m), 7.13-7.05(3H, m), 5.75(2H, s), 4.58(2H, m), 3.51-3.37(4H, m), 3.11(2H, m), 2.27(3H, s), 1.01(1H, s). |
| VIII-185 | (MeSO$_2$NH-CH$_2$CH$_2$-NH-CH$_2$CH$_2$-O-N=) | (di-HCl salt) 10.12(1Hs), 8.82(1H, d, J = 1.5 Hz), 8.52(1H, s), 8.22(1H, dd, J = 1.8 Hz, J = 8.7 Hz), 8.14(1H, s), 7.80(1H, s), 7.80(1H, s), 7.77-7.68(3H, m), 7.40-7.33(1H, m), 7.12-7.04(3H, m), 5.71(2H, s), 4.86(1H, brs), 4.28(3H, m), 3.58(1H, m), 2.95-2.78(2H, m), 2.25(3H, s), 2.11(1H, m), 1.47(1H, m). |

[Chemical formula 83]
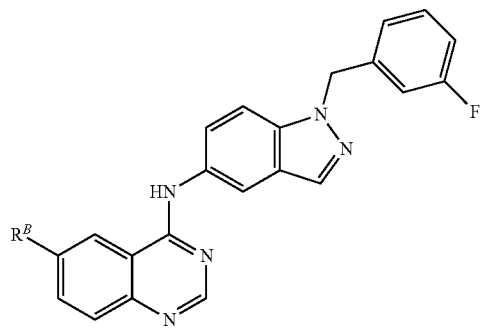
(VIII)
| Compound No. | $R^B$ | $^1$H-NMR($d_6$-DMSO) |
|---|---|---|
| VIII-186 | 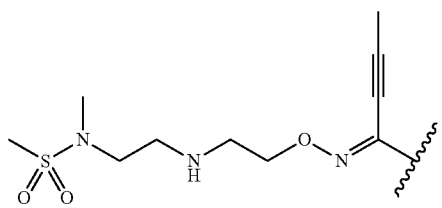 [SMILES: */C(C#CC)=N/OCCNCCN(C)S(C)(=O)=O] | 10.18(1H, s), 8.78(1H, s), 8.52(1H, s), 8.23-8.12(3H, m), 7.79-7.65(3H, m), 7.41-7.32(1H, m), 7.18(7.02)(3H, m), 5.71 (2H, s), 4.31(2H, m), 3.14(2H, m), 2.29(2H, m), 2.87(3H, s) 2.77(6H, m), 2.24(3H, s). |
| VIII-187 | 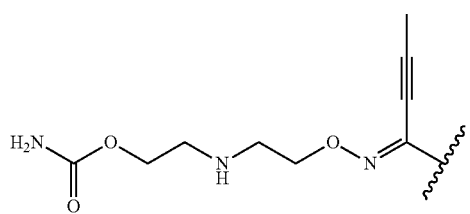 [SMILES: */C(C#CC)=N/OCCNCCOC(N)=O] | 10.19(1Hs), 8.78(1H, s), 8.52(1H, s), 8.23-8.12(3H, m), 7.80-7.65(3H, m), 7.38-7.33(1H, m), 7.13-7.03(3H, m), 6.49(2H, brs), 5.71(2H, s), 4.31(2H, m), 4.04-3.95(2H, m), 2.92(2H, m), 2.78(2H, m), 2.25(3H, s). |
| VIII-188 | 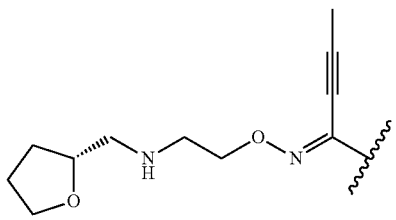 [SMILES: */C(C#CC)=N/OCCNC[C@H]1CCCO1] | (di-HCl salt) 12.09(1H, s), 8.96(1H, s), 8.83 (1H, s), 8.43(1H, d, J = 8.7 Hz), 8.06(1H, s), 7.97(1H, d, J = 8.4 Hz), 7.83(1H, d, J = 9.0 Hz), 7.67(1H, d, J = 1.8 Hz), 7.65(1H, dd, J = 2.1 Hz, J = 9.0 Hz), 7.41-7.34(1H, m), 7.14-7.05(3H, m), 5.71(2H, s), 4.54(2H, m), 4.19(1H, m), 3.83-3.70(2H, m), 3.68-2.95(5H, m), 2.27(3H, s), 2.04(1H, m), 1.93(1H, m), 1.56(1H, m). |
| VIII-189 | 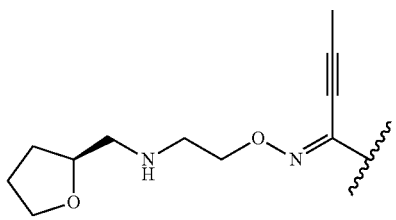 [SMILES: */C(C#CC)=N/OCCNC[C@@H]1CCCO1] | (di-HCl salt) 12.21(1H, brs), 8.97(1H, brs), 8.84(1H, s), 8.43(1H, dd, J = 1.5 Hz, J = 9.0 Hz), 8.07(1H, s), 8.01(1H, s), 7.99(1H, d, J = 9.0 Hz), 7.84(1H, d, J = 9.0 Hz), 7.67(1H, dd, J = 1.8 Hz, J = 9.0 Hz), 7.41-7.32(1H, m), 7.14-7.05(3H, m), 5.74(2H, s), 4.59(2H, m), 4.21(1H, m), 3.82-3.65(2H, m), 3.62-3.05(8H, m), 2.28(3H, s), 2.02(1H, m), 1.83(1H, M), 1.55(1H, m). |

TABLE 41

| Compound No. | R^B | $^1$H-NMR(d$_6$-DMSO) |
|---|---|---|
| VIII-190 | (pyrrolidinone-CH2-NH-CH2CH2-O-N=) | (di-HCl salt) 12.18(1H, s), 9.29(1H, s), 8.45(1H, dd, J = 1.2, J = 9.0 Hz), 8.23(1H, s), 8.06(1H, s), 8.06(1H, d, J = 1.2 Hz), 7.99(1H, d, J = 8.7 Hz), 7.87-7.82(1H, m), 7.67(1H, dd, J = 1.2 Hz, J = 9.0 Hz), 7.39-7.14(1H, m), 7.14-7.05(3H, m), 5.74(2H, s), 4.61(2H(, m), 3.95(1H, m), 8.23(2H, m), 3.13(3H, m), 2.28(3H,s), 2.17(1H, m), 1.78(1H, m). |
| VIII-191 | (oxazolidinone-CH2-NH-CH2CH2-O-N=) | (di-HCl salt) 12.18(1H, s), 9.12(1H, s), 8.87(1H, s), 8.46(1H, d, J = 8.7 Hz), 8.43(1H, s), 8.23(1H, s), 8.04-7.97(2H, m), 7.87-7.82(1H, m), 7.64(1H, dd, J = 1.2 Hz, J = 9.0 Hz), 7.37-7.14(1H, m), 7.11-7.05(3H, m), 5.74(2H, s), 4.61(2H, m), 4.09-3.26(7H, m), 2.26(3H, s), 2.17(1H, m), 1.79(1H, s). |
| VIII-192 | (MeO-CH2CH2-N(Et)-CH2CH2-O-N=) | 10.17(1H, s), 8.78(1H, s), 8.51(1H, s), 8.20(1H, dd, J = 1.8 Hz, J = 8.7 Hz), 8.14(1H, s), 7.80-7.65(3H, m), 7.40-7.33(1H, m), 7.13-7.03(3H, m), 5.71(2H, s), 4.31(2H, t, J = 5.7 Hz), 3.41(2H, t, J = 6.3 Hz), 3.22(3H, s), 2.85(2H, m), 2.70-2.57(4H, m), 2.23(3H, s), 0.99(2H, t, J = 7.2 Hz). |
| VIII-193 | (H2N-C(O)-O-pyrrolidinyl-CH2CH2-O-N=) | 10.19(1H, s), 8.78(1H, s), 8.52(1H, s), 8.21(1H, d, J = 8.4 Hz), 8.16(1H, s), 8.13(1H, s), 7.78-7.65(3H, m), 7.49-7.33(1H, m), 7.13-7.04(3H, m), 6.48(2H, brs), 5.71(2H, s), 4.93(1H, m), 4.36(2H, t, J = 5.7 Hz), 2.80(3H, m), 2.71(2H, m), 2.42(1H, m), 2.24(3H, s), 2.10(1b, m), 1.66(1H, m). |
| VIII-194 | (HO-pyrrolidinyl-CH2-O-N=) | 10.21(1H, s), 8.82(1H, d, J = 1.5 Hz), 8.52(1H, s), 8.22(1H, dd, J = 1.8 Hz, J = 8.7 Hz), 8.14(1H, s), 7.80(1H, s), 7.77-7.66(3H, m), 7.40-7.33(1H, m), 7.12-7.04(3H, m), 5.71(2H, s), 4.86(1H, brs), 4.28(3H, m), 3.58(1H, m), 2.95-2.78(2H, m), 2.25(3H, s), 2.11(1H, m), 1.47(1H, m). |
| VIII-195 | (morpholino-CH2CH2-O-N=) | 10.17(1H, s), 8.78(1H, d, J = 1.8 Hz), 8.52(1H, s), 8.19(1H, dd, J = 1.8 Hz, J = 10.5 Hz), 8.13(1H, s), 7.80(1H, s), 7.77-7.33(1H, m), 7.12-7.03(3H, m), 5.71(2H, s), 439(2H, t, J = 5.7 Hz), 3.58(4H, t, J = 4.8 Hz), 2.71(2H, t, J = 6.0 Hz),, 2.50(2H, m), 2.24(3H, s). |

TABLE 41-continued

| Compound No. | $R^B$ | $^1$H-NMR($d_6$-DMSO) |
|---|---|---|
| VIII-196 | 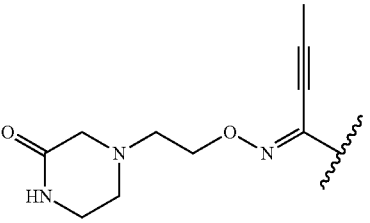 [SMILES: */C(C#CC)=N/OCCN1CCNC(=O)C1] | 10.19(1H, s), 8.78(1H, d, J = 1.5 Hz), 8.19(1H, dd, J = 1.8 Hz, J = 10.5 Hz), 8.16(1H, s), 8.13(1H, d, J = 1.5 Hz), 7.80(1H, s), 7.80-7.66(4H, m), 7.40-7.33(1H, m), 7.13-7.06(3H, m), 5.71(2H, s), 4.41(2H, t, J = 5.2 Hz), 3.16(2H, m), 3.10(2H, s), 2.80(1H, t, J = 5.7 Hz), 2.67(3H, s), 2.25(3H, s) |

TABLE 42

| Compound No. | $R^B$ | $^1$H-NMR($d_6$-DMSO) |
|---|---|---|
| VIII-197 | 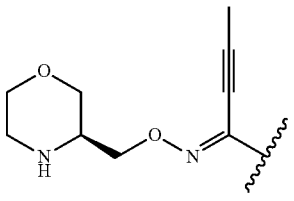 [SMILES: */C(C#CC)=N/OC[C@@H]1COCCN1] | 10.21(1H, s), 8.79(1H, d, J = 1.8 Hz), 8.53(1H, s), 8.21(1H, dd, J = 1.8 Hz, J = 8.7 Hz), 8.17(1H, s), 8.13(1H, d, J = 1.5 Hz), 7.79(1H, d, J = 13.2 Hz), 7.76(1H, d, J = 13.2 Hz), 7.67(1H, dd, J = 1.8 Hz, J = 9.0 Hz), 7.41-7.34(1H, m), 7.16-7.04(3H, m), 5.72(2H, s), 4.20-4.09(2H, m), 3.79(1H, dd, J = 2.7 Hz, J = 10.8 Hz), 3.68-3.64(1H, m), 3.30-3.19(1H, m), 3.13-3.10(1H, m), 2.78-2.74(3H, m), 2.26(3H, s). |
| VIII-198 | 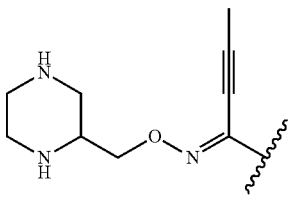 | 10.20(1H, brs), 8.79(1H, s), 8.53(1H, s), 8.22-8.13(3H, m), 7.81-7.66(3H, m), 7.41-7.33(1H, m) 7.13-7.04(3H, m), 5.72(2H, s), 4.13(2H, d, J = 5.2 Hz), 3.00-2.51(6H, m), 2.39-2.26(4H, m) |
| VIII-199 | 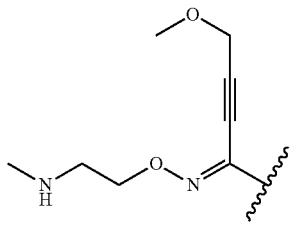 [SMILES: */C(C#CCOC)=N/OCCNC] | (di-HCl salt) 12.69(1Hbrs), 9.44(1H, s), 8.69(1H, s), 8.47(1H, d, J = 8.1 Hz), 8.23 (1H, d, J = 2.1 Hz), 7.38(1H, s), 7.19-7.01(1H, m), 5.74(2H, s), 4.64(5H, m), 4.01(1H, m), 3.39-3.21(4H, m), 2.59(3H, s). |
| VIII-200 | 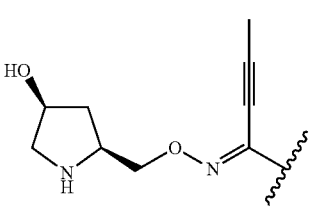 | 10.19(1H, s), 8.81(1H, s), 8.53(1H, s), 8.21-8.14(3H, m), 7.82(7.82-7.65(3H, m), 7.41(1H, m), 7.15-7.04(13H, m), 5.71(2H, s), 4.68(1H, brs), 4.51(2H, s), 4.27(2H, m), 4.18(1H, m), 3.42(2H, m), 3.45(3H, s), 2.87(1H, m), 2.69(1H, m), 2.04(1H, m), 1.41(1H, m). |

TABLE 43

[Chemical formula 84]

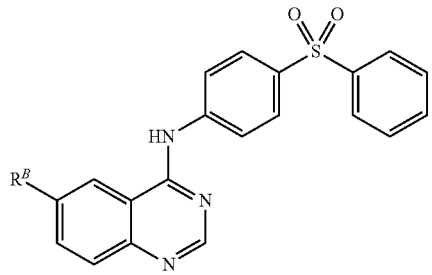

(VIII)

| Compound No. | $R^B$ | $^1$H-NMR($d_6$-DMSO) |
|---|---|---|
| VIII-205 | ![structure with Me, MeO, MeNH, O-N=, Me on alkyne] | 10.43-10.40(1H, m), 8.79(1H, s), 8.70(1H, s), 8.25(1H, d, J = 8.4 Hz), 8.11(2H, bs), 7.98-7.96(4H, m), 7.85(1H, d, J = 7.2 Hz), 7.69-7.62(3H, m), 4.24-4.20(2H, m), 3.28(3H, s), 2.94(1H, t, J = 6.4 Hz), 2.38(3H, s), 2.25(3H, s). |
| VIII-206 | ![morpholine-2-yl-CH2-O-N=, Me on alkyne] | 10.44(1H, bs), 8.78(1H, d, J = 1.5 Hz), 8.67(1H, bs), 8.24(1H, d, J = 9.0 Hz), 8.16-8.05(2H, m), 7.99-7.94(4H, m), 7.84(1H, d, J = 8.7 Hz), 7.71-7.60(3H, m), 4.24(1H, dd, J = 6.3 Hz, J = 11.7 Hz), 4.16(1H, dd, J = 4.8 Hz, J = 11.7 Hz), 3.75-3.71(2H, m), 3.51-3.37(1H, m), 2.84(1H, dd, J = 2.4 Hz, J = 12.3 Hz), 2.73-2.58(2H, m), 2.50-2.42(1H, m), 2.25(3H, s). |
| VIII-207 | ![morpholine-3-yl-CH2-O-N=, Me on alkyne] | 10.45(1H, bs), 8.78(1H, d, J = 1.5 Hz), 8.67(1H, bs), 8.24(1H, dd, J = 1.5 Hz, J = 8.7 Hz), 8.12-8.09(2H, m), 7.99-7.95(4H, m), 7.85(1H, d, J = 8.7 Hz), 7.71-7.61(3H, m), 4.18(1H, dd, J = 6.0 Hz, J = 11.1 Hz), 4.12(1H, dd, J = 6.3 Hz, J = 11.1 Hz), 3.78(1H, dd, J = 2.7 Hz, J = 1.5 Hz), 3.65(1H, dt, J = 11.1 Hz, J = 2.7 Hz), 3.11-3.07(1H, m), 2.81-2.69(3H, m), 2.25(3H, s). |
| VIII-208 | ![MeNH-CH2CH2-O-N=, CH2OMe on alkyne] | 10.42(1H, s), 8.84(1H, s), 8.69(1H, s), 8.25(1H, d, J = 8.8 Hz), 8.13(1H, d, J = 8.4 Hz), 8.00-7.97(3H, m), 7.87(1H, d, J = 8.8 Hz), 7.97-7.62(5H, m), 4.51(2H, s), 4.42(2H, t, J = 5.2 Hz), 3.37(3H, s), 2.97(2H, t, J = 4.8 Hz), 2.41(3H, s) |
| VIII-209 | ![morpholine-3-yl-CH2-O-N=, CH2OMe on alkyne] | 10.45(1H, bs), 8.80(1H, bs), 8.68(1H, bs), 8.23(1H, d, J = 7.5 Hz), 8.14-8.06(2H, m), 7.99-7.95(4H, m), 7.87(1H, d, J = 9.0 Hz), 7.69-7.60(3H, m), 4.52(2H, s), 4.23(1H, dd, J = 6.3 Hz, J = 10.8 Hz), 4.17(1H, dd, J = 6.3 Hz, J = 10.8 Hz), 3.80(1H, dd, J = 2.7 Hz, J = 11.1 Hz), 3.67-3.64(1H, m), 3.40(3H, s), 3.12-3.07(1H, m). |

TABLE 44

[Chemical formula 85]

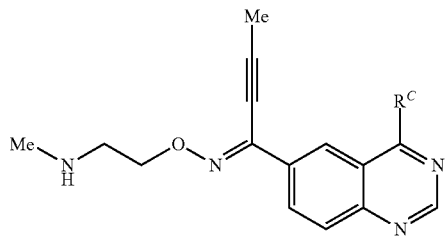

(VIII)

| Compound No. | $R^C$ | $^1$H-NMR($d_6$-DMSO) |
|---|---|---|
| VIII-210 | 3-Me-4-(6-Me-pyridin-3-yloxy)phenyl-NH- | 10.13(1H, s), 8.82(1H, s), 8.60(1H, s), 8.26(1H, d, J = 9.2 Hz), 8.18(1H, s), 7.82(1H, d, J = 8.8 Hz), 7.74(1H, s), 7.64(1H, d, J = 9.2 Hz), 7.27-7.22(2H, m), 6.99(1H, d, J = 8.4 Hz), 4.50(2H, t, J = 5.2 Hz), 2.64(3H, s), 2.50(2H, bs), 2.45(3H, s), 2.28(3H, s), 2.23(3H, s). |
| VIII-211 | 3-Cl-4-[(3-F-phenoxy)methyl]phenyl-NH- | 10.26(1H, brs), 8.80(1H, s), 8.66(1H, s), 8.26-8.23(1H, m), 8.14(1H, s), 7.88-7.79(2H, m), 7.62(1H, d, J = 8.4), 7.34(1H, dd, J = 8.4, 15.2), 6.95-6.88(1H, m), 6.82-6.78(1H, m), 5.16(2H, s), 4.35(2H, t, J = 6.0 Hz), 2.92(2H, t, J = 6.0 Hz), 2.38(3H, s), 2.26(3H, s), 2.26(3H, s). |
| VIII-212 | 3-Cl-4-(pyridin-4-ylmethoxy)phenyl-NH- | 10.0(1H, brs), 8.74(1H, s), 8.62-8.58(3H, m), 8.21(1H, d, J = 8.8), 7.97(1H, s), 7.80(1H, d, J = 8.8), 7.69-7.67(1H, m), 7.48-7.47(2H, m), 7.25(1H, d, J = 9.2), 5.32(2H, s), 4.34-4.31(2H, m), 2.89-2.86(2H, m), 2.36(3H, s), 2.25(3H, s). |
| VIII-213 | 4-(phenylthio)phenyl-NH- | 10.43(1H, s), 9.23(1H, s), 9.21(1H, s), 8.64(1H, s), 8.26(1H, d, J = 6.6 Hz), 7.93(2H, d, J = 3.9 Hz), 7.84(1H, d, J = 6.9 Hz), 7.45(2H, d, J = 5.7 Hz), 7.35(1H, d, J = 5.4 Hz), 7.27(2H, t, J = 5.7 Hz), 4.56(2H, d, J = 3.9 Hz), 2.64(3H, s), 2.28(3H, s), 1.99(3H, s). |
| VIII-214 | 4-(phenylsulfonyl)phenyl-NH- | 8.85(1H, s), 8.80(1H, s), 8.26(1H, d, J = 6.6 Hz), 8.12(1H, d, J = 6.3 Hz), 7.99-7.96(4H, m), 7.85(1H, d, J = 6.6 Hz), 7.71-7.62(3H, m), 4.33(2H, t, J = 4.2 Hz), 2.86(2H, t, J = 4.5 Hz), 2.35(3H, s), 2.25(3H, s). |
| VIII-215 | 6-[(3-F-benzyl)oxy]pyridin-3-yl-NH- | 10.15(1H, s), 8.77(1H, s), 8.55(1H, s), 8.47(1H, s), 8.24(1H, d, J = 9.2 Hz), 8.07(1H, d, J = 9.2 Hz), 7.81(1H, d, J = 9.2 Hz), 7.47-7.39(1H, m), 7.32-7.28(2H, m), 7.16(1H, t, J = 7.6 Hz), 7.00(1H, d, J = 8.8 Hz), 5.41(1H, s), 4.41(2H, t, J = 5.6 Hz), 3.10(2H, t, J = 5.2 Hz), 2.49(3H, s), 2.26(3H, s). |

TABLE 44-continued

[Chemical formula 85]

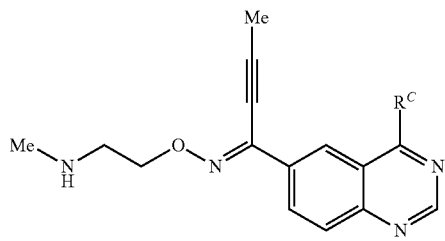

(VIII)

| Compound No. | R$^C$ | $^1$H-NMR(d$_6$-DMSO) |
|---|---|---|
| VIII-216 | 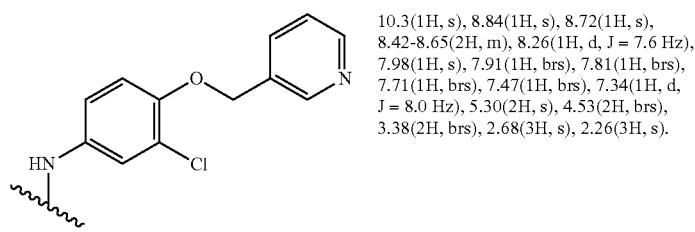 | 10.3(1H, s), 8.84(1H, s), 8.72(1H, s), 8.42-8.65(2H, m), 8.26(1H, d, J = 7.6 Hz), 7.98(1H, s), 7.91(1H, brs), 7.81(1H, brs), 7.71(1H, brs), 7.47(1H, brs), 7.34(1H, d, J = 8.0 Hz), 5.30(2H, s), 4.53(2H, brs), 3.38(2H, brs), 2.68(3H, s), 2.26(3H, s). |

TABLE 45

| Compound No. | R$^C$ | $^1$H-NMR(d$_6$-DMSO) |
|---|---|---|
| VIII-217 | 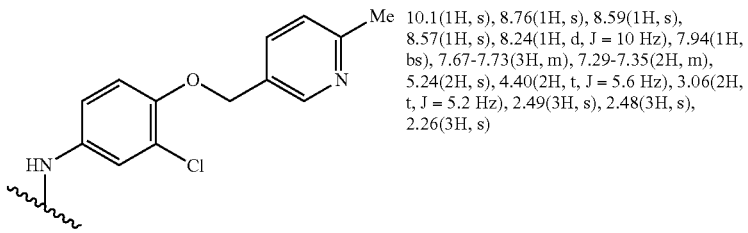 | 10.1(1H, s), 8.76(1H, s), 8.59(1H, s), 8.57(1H, s), 8.24(1H, d, J = 10 Hz), 7.94(1H, bs), 7.67-7.73(3H, m), 7.29-7.35(2H, m), 5.24(2H, s), 4.40(2H, t, J = 5.6 Hz), 3.06(2H, t, J = 5.2 Hz), 2.49(3H, s), 2.48(3H, s), 2.26(3H, s) |

TABLE 46

[Chemical formula 86]

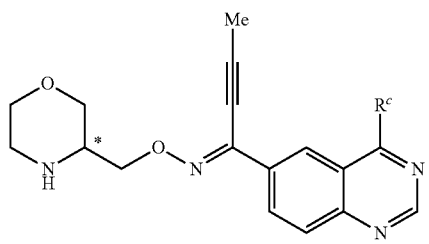

(VIII)

| Compound No. | * | R$^c$ | $^1$H-NMR(d$_6$-DMSO) |
|---|---|---|---|
| VIII-218 | S | 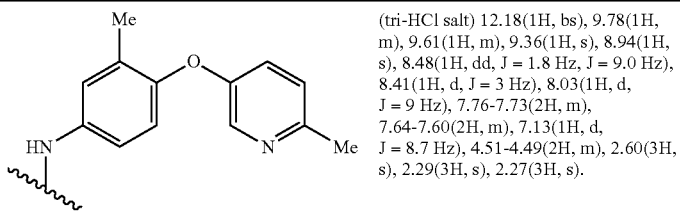 | (tri-HCl salt) 12.18(1H, bs), 9.78(1H, m), 9.61(1H, m), 9.36(1H, s), 8.94(1H, s), 8.48(1H, dd, J = 1.8 Hz, J = 9.0 Hz), 8.41(1H, d, J = 3 Hz), 8.03(1H, d, J = 9 Hz), 7.76-7.73(2H, m), 7.64-7.60(2H, m), 7.13(1H, d, J = 8.7 Hz), 4.51-4.49(2H, m), 2.60(3H, s), 2.29(3H, s), 2.27(3H, s). |

TABLE 46-continued

[Chemical formula 86]

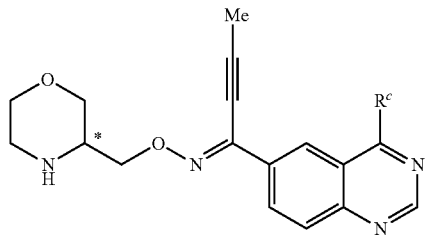
(VIII)

| Comopund No. | * | $R^C$ | $^1$H-NMR(d$_6$-DMSO) |
|---|---|---|---|
| VIII-219 | R | 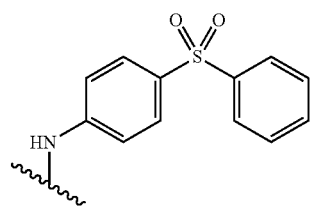 [SMILES: *Nc1ccc(S(=O)(=O)c2ccccc2)cc1] | 10.46(1H, bs), 8.78(1H, d, J = 1.5 Hz), 8.67(1H, s), 8.24(1H, dd, J = 1.5 Hz, J = 8.7 Hz), 8.12-8.09(2H, m), 7.99-7.95(4H, m), 7.85(1H, d, J = 8.7 Hz), 7.71-7.60(3H, m), 4.17(1H, dd, J = 5.7 Hz, J = 11.1 Hz), 4.12(1H, dd, J = 6.3 Hz, J = 11.1 Hz), 3.78(1H, dd, J = 2.7 Hz, J = 10.5 Hz), 3.65(1H, dt, J = 10.8 Hz, J = 2.7 Hz), 3.26-3.18(1H, m), 3.13-3.05(1H, m), 2.82-2.70(2H, m), 2.25(3H, s). |
| VIII-220 | S | 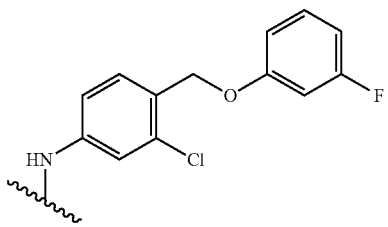 [SMILES: *Nc1ccc(COc2cccc(F)c2)c(Cl)c1] | 10.26(1H, bs), 8.79(1H, s), 8.67(1H, s), 8.23(1H, d, J = 8.8 Hz), 8.14(1H, s), 7.64(1H, d, J = 8.8 Hz), 7.62(1H, d, J = 8.8 Hz), 7.35(1H, dd, J = 8.0, J = 15.6), 6.96-6.86(2H, m), 6.82-6.78(1H, m), 5.16(2H, s), 4.20-4.11(2H, m), 3.79(1H, d, J = 10.8 Hz), 3.66(1H, d, J = 11.2 Hz), 3.22(2H, t, d = 10.4), 3.10-3.02(1H, m), 2.81-2.68(2H, m), 2.26(3H, s). |
| VIII-221 | R | 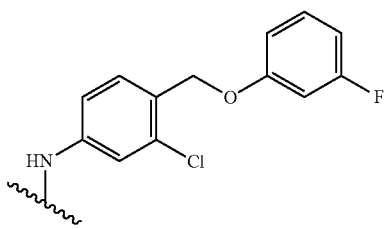 [SMILES: *Nc1ccc(COc2cccc(F)c2)c(Cl)c1] | 10.26(1H, bs), 8.79(1H, s), 8.67(1H, s), 8.23(1H, d, J = 9.6 Hz), 8.14(1H, s), 7.85-7.83(1H, m), 7.62(1H, d, J = 8.8 Hz), 7.35(1H, dd, J = 8.0, J = 15.6), 6.95-6.88(2H, m), 6.82-6.78(1H, m), 5.16(2H, s), 4.20-4.11(2H, m), 3.79(1H, d, J = 10.8 Hz), 3.66(1H, d, J = 11.2 Hz), 3.22(2H, t, d = 10.4), 3.10-3.02(1H, m), 2.81-2.68(2H, m), 2.26(3H, s) |

(wherein an atom marked with * is an asymmetric carbon atom)

Example 11

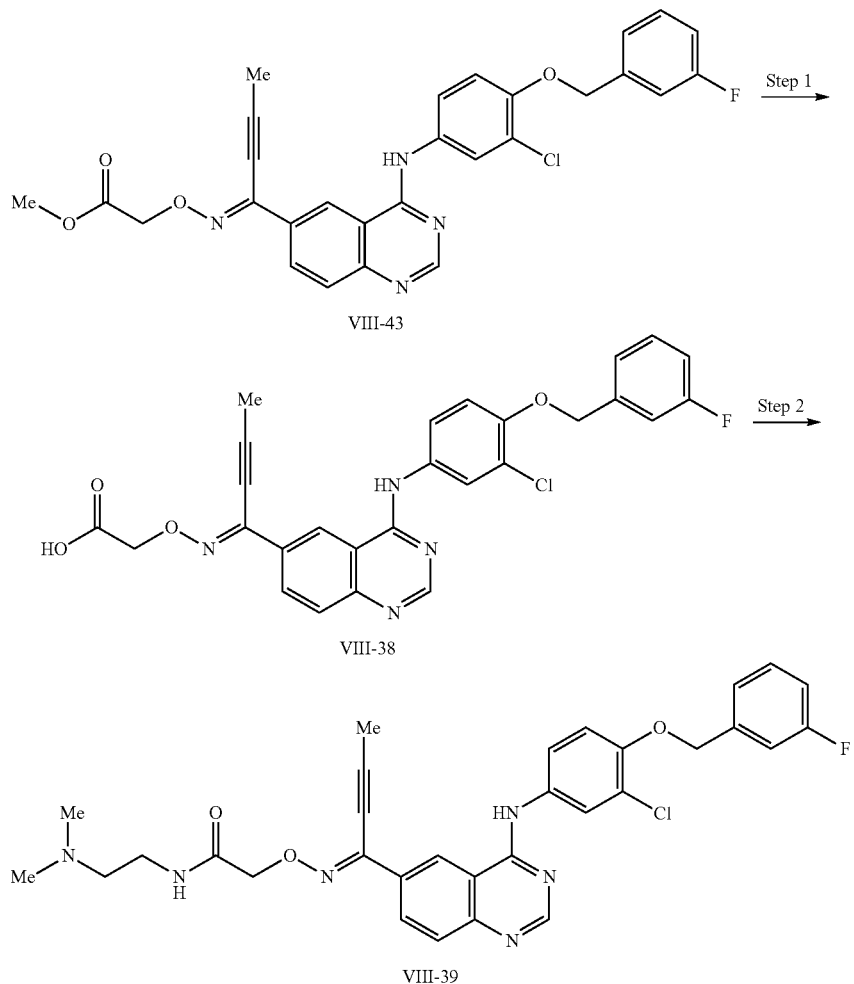

(Step 1) Synthesis of 4-(3-chloro-4-(3-fluorobenzyloxy)phenylamino)-6-(carboxymethoxyimino)-2-butyn-1-yl)quinazoline (VIII-38)

4-(3-Chloro-4-(3-fluorobenzyloxy)phenylamino)-6-(methoxycarbonylmethoxyimino)-2-butyn-1-yl)quinazoline (VIII-43, 1.2 g) was dissolved in a mixture of 12 ml of tetrahydrofuran and 12 ml of methanol, and 1.5 ml of 2 mol/L aqueous sodium hydroxide solution was added, followed by stirring at room temperature for 1.5 hours. The reaction mixture was diluted with 20 ml of ethyl acetate, 1.6 ml of 2 mol/L hydrochloric acid was added, and water was added, thereby, an objective substance was precipitated. A precipitate was collected by filtration, washed with water and ethyl acetate, and dried to obtain 4-(3-chloro-4-(3-fluorobenzyloxy)phenylamino)-6-(carboxymethoxyimino)-2-butyn-1-yl)quinazoline (VIII-38, 0.9 g) as a yellow solid.

$^1$H NMR (d$_6$-DMSO, δ): 10.18 (1H, brs), 8.77 (1H, s), 8.60 (1H, s), 8.19 (1H, dd, J=2.0, 11.6 Hz), 7.95 (1H, d, J=3.2 Hz), 7.80 (1H, d, J=11.6 Hz), 7.67 (1H, dd, J=3.2, 11.6 Hz), 7.51-7.44 (1H, m), 7.35-7.26 (3H, m), 7.22-7.15 (1H, m), 5.27 (2H, s), 4.83 (2H, s), 2.27 (3H, s).

(Step 2) Synthesis of 4-(3-chloro-4-(3-fluorobenzyloxy)phenylamino)-6-((2-dimethylaminoethylcarbamoyl)methoxyimino)-2-butyn-1-yl)quinazoline (VIII-39)

4-(3-Chloro-4-(3-fluorobenzyloxy)phenylamino)-6-(carboxymethoxyimino)-2-butyn-1-yl)quinazoline (VIII-38, 70 mg), 24 mg of 1-hydroxybenzotriazole, and 27 mg of 1-ethyl 3-(3-dimethylaminopropyl)carbodiimide hydrochloride were dissolved in 1.4 ml of N,N-dimethylformamide, this was stirred at room temperature for 5 minutes, and 22 μl of N,N-dimethylethylenediamine was added, followed by stirring at room temperature for 2 hours. After completion of the reaction, the reaction mixture was diluted with ethyl acetate, and water and aqueous saturated sodium bicarbonate solution were added to separate layers. The organic layer was washed with water, and dried over sodium sulfate, and the filtrate was concentrated. Ethyl acetate was added to the concentrated residue to solidify the material, and the solid was collected by filtration, and dried to obtain 4-(3-chloro-4-(3-fluorobenzyloxy)phenylamino)-6-((2-dimethylaminoethylcarbamoyl)methoxyimino)-2-butyn-1-yl)quinazoline (VIII-39, 30 mg) as a colorless crystal.

¹H NMR (d₆-DMSO, δ): 10.12 (1H, s), 8.77 (1H, s), 8.59 (1H, s), 8.19 (1H, dd, J=2.0, 12.0 Hz), 8.08 (1H, brs), 7.95 (1H, d, J=3.2 Hz), 7.80 (1H, d, J=11.6 Hz), 7.70-7.62 (2H, m), 7.51-7.44 (1H, m), 7.34-7.26 (3H, m), 7.21-7.15 (1H, s), 5.27 (2H, s), 4.69 (2H, s), 3.22 (2H, dd, J=8.4, 16.0 Hz) 2.31 (1H, t, J=8.4 Hz), 2.28 (3H, s), 2.11 (6H, s).

According to the same manner as that of the Example 11, the following compound was synthesized.

TABLE 47

(VIII)

| Comound No. | $R^B$ | ¹H-NMR(d₆-DMSO) |
| --- | --- | --- |
| VIII-222 | (structure with HOOC-CH₂-O-N=C(Me)-C≡C-) | 10.18(1H, brs), 8.77(1H, s), 8.60(1H, s), 8.19(1H, dd, J = 2.0, 11.6 Hz), 7.95(1H, d, J = 3.2 Hz), 7.80(1H, d, J = 11.6 Hz), 7.67(1H, dd, J = 3.2, 11.6 Hz), 7.51-7.44(1H, m), 7.35-7.26(3H, m), 7.22-7.15(1H, m), 5.27(2H, s), 4.83(2H, s), 2.27(3H, s). |
| VIII-223 | (structure with H₂N-C(O)-CH₂-O-N=C(Me)-C≡C-) | 10.12(1H, bs), 8.76(1H, d, J = 1.5 Hz), 8.59(1H, s), 8.20(1H, dd, J = 1.8 Hz, J = 8.7 Hz), 7.96(1H, d, J = 2.4 Hz), 7.81(1H, d, J = 8.7 Hz), 7.68(1H, dd, J = 2.7 Hz, J = 9.0 Hz), 7.52-7.44(1H, m), 7.35-7.16(6H, m), 5.27(2H, s), 4.65(2H, s), 2.28(3H, s). |
| VIII-224 | (structure with HO-CH₂CH₂-NH-C(O)-CH₂-O-N=C(Me)-C≡C-) | 10.10(1H, s), 8.59(1H, s), 8.19(1H, dd, J = 2.4, 11.6 Hz), 7.95(1H, d, J = 3.2 Hz), 7.80(1H, d, J = 11.6), 7.76-7.73(1H, m), 7.68(1H, dd, J = 3.6, 12 Hz), 7.48-7.44(1H, m), 7.35-7.26(3H, m), 7.21-7.15(1H, m), 5.27(2H, s), 4.73(1H, t, J = 7.2 Hz), 4.70(2H, s), 3.44(2H, dd, J = 8.0, 15.6 Hz), 3.21(2H, dd, J = 8.0, 15.6 Hz), 2.28(3H, s) |
| VIII-225 | (structure with MeS(O)₂O-CH₂CH₂-NH-C(O)-CH₂-O-N=C(Me)-C≡C-) | 10.10(1H, s), 8.76(1H, s), 8.59(1H, s), 8.19(1H, d, J = 12.0 Hz), 8.08(1H, brs), 7.95(1H, s), 7.80(1H, d, J = 11.6 Hz), 7.69-7.66(1H, m), 7.51-7.44(1H, m), 7.34-7.26(3H, m), 7.21-7.16(1H, m), 5.27(2H, s), 4.71(2H, s), 3.60-3.53(1H, m), 2.99(3H, s), 2.28(3H, s). |
| VIII-226 | (structure with Me₂N-CH₂CH₂-NH-C(O)-CH₂-O-N=C(Me)-C≡C-) | 10.12(1H, s), 8.77(1H, s), 8.59(1H, s), 8.19(1H, dd, J = 2.0, 12.0 Hz), 8.08(1H, brs), 7.95(1H, d, J = 3.2 Hz), 7.80(1H, d, J = 11.6 Hz), 7.70-7.62(2H, m), 7.51-7.44(1H, m), 7.84-7.26(3H, m), 7.21-7.15(1H, s), 5.27(2H, s), 4.69(2H, s), 3.22(2H, dd, J = 8.4, 16.0 Hz) 2.31(1H, t, J = 8.4 Hz), 2.28(3H, s), 2.11(6H, s). |

Example 12

[Chemical formula 88]

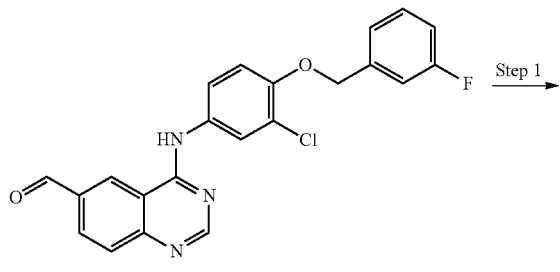

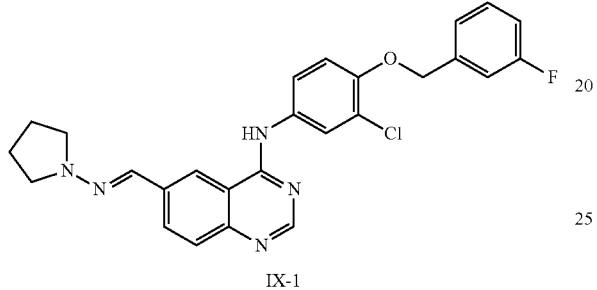

(Step 1) Synthesis of 4-(3-chloro-4-(3-fluorobenzyloxy)phenylamino)-6-(pyrrolidin-1-yliminomethyl)quinazoline (IX-1)

In a mixture of 1 mL of tetrahydrofuran and 0.1 mL of water were dissolved 40 mg of 4-(3-chloro-4-(3-fluorobenzyloxy)phenylamino) 6-formylquinazoline (IV-1) and 13 mg of 1-amino-pyrrolidine hydrochloride, followed by a reaction at room temperature overnight. After the reaction, aqueous saturated sodium bicarbonate solution was added, followed by extraction with ethyl acetate. The organic layer was dehydrated by passing through Presep (registered trademark), and the filtrate was concentrated. The concentrated residue was purified by chromatography (eluting with hexane:ethyl acetate-2:1→1:1) using an amino column to obtain 38 mg of 4-(3-chloro-4-(3-fluorobenzyloxy)phenylamino)-6-(pyrrolidin-1-yliminomethyl)quinazoline (IX-1) as a yellow solid.

$^1$H NMR ($d_6$-DMSO, δ): 9.76 (1H, s), 8.52 (1H, s), 8.40 (1H, brs), 8.08 (1H, d, J=6.6 Hz), 8.06 (1H, d, J=1.8 Hz), 7.76 (1H, dd, J=6.6 Hz, J=1.8 Hz), 7.69 (1H, dd, J=6.6 Hz), 7.50-7.45 (1H, m), 7.35-7.26 (3H, m), 7.19 (1H, t, J=66 Hz), 5.26 (2H, s), 3.39 (4H, br). 1.94 (4H, br)

According to the same manner as that of Example 12, the following compound was synthesized.

[Chemical formula 89]

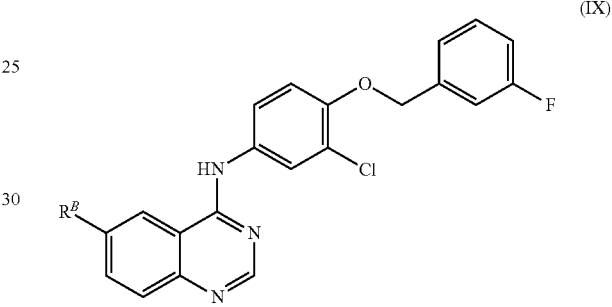

(IX)

TABLE 48

| Compound No. | $R^B$ | $^1$H-NMR($d_6$-DMSO) |
|---|---|---|
| IX-2 | morpholine-N-N=CH— | 9.86(1H, s), 8.56(1H, s), 8.55(1H, brs), 8.14(1H, d, J = 6.6 Hz), 8.05(1H, d, J = 1.8 Hz), 7.78-7.74(3H, m), 7.50-7.45(1H, m), 7.35-7.26(3H, m), 7.19(1H, t, J = 6.3 Hz), 5.26(2H, s), 3.18(4H, t-like, J = 3.6 Hz), 3.20(4H, t-like, J = 3.6 Hz) |
| IX-3 | Me-N-piperazine-N-N=CH— | 9.83(1H, s), 8.56(1H, s), 8.52(1H, brs), 8.13(1H, d, J = 6.6 Hz), 8.05(1H, brs), 7.77-7.73(3H, m ), 7.50-7.45(1H, m), 7.35-7.26(3H, m), 7.19(1H, t, J = 6.3 Hz), 5.26(2H, s), 3.21(4H, brs), 2.53(4H, brs), 2.25(3H, s) |
| IX-4 | piperidine-N-N=CH— | 9.83(1H, s), 8.54(1H, s), 8.50(1H, brs), 8.13(1H, d, J = 8.7 Hz), 8.04(1H, d, J = 2.7 Hz), 7.76-7.70(3H, m), 7.52-7.43(1H, m), 7.36-7.25(3H, m), 7.22-7.15(1H, m), 5.26(2H, s), 3.25-3.17(4H, m), 1.76-1.65(4H, m), 1.58-1.49(2H, m) |
| IX-5 | triazole-N-N=CH— | 9.19(3H, brs), 9.16(1H, s), 8.95(1H, brs), 8.52(1H, brs), 8.20(1H, d, J = 8.4 Hz), 7.95(1H, s), 7.79(1H, d, J = 6.9 Hz), 7.66-7.60(1H, m), 7.52-7.43(1H, m), 7.36-7.14(4H, m), 5.23(2H, s) |

TABLE 48-continued

| Compound No. | R^B | ¹H-NMR(d₆-DMSO) |
|---|---|---|
| IX-6 | (pyrrolidine with MeOCH₂ substituent, N–N=CH–) | 9.73(1H, s), 8.52(1H, s), 8.38(1H, brs), 8.13(1H, d, J = 6.6 Hz), 8.05(1H, d, J = 1.8 Hz), 7.75(1H, dd, J = 6.9 Hz, J = 1.8 Hz), 7.70(1H, dd, J = 6.6 Hz, J = 1.8 Hz), 7.50-7.45(1H, m), 7.33-7.26(3H, m), 7.18(1H, t, J = 6.6 Hz), 5.26(2H, s), 3.72(1H, brs), 3.64(1H, dd, J = 6.9 Hz, J = 2.7 Hz), 3.46(2H, dd, J = 7.2 Hz, J = 5.1 Hz), 3.13(1H, br), 1.99(3H, br.), 1.80(1H, br) |
| IX-7 | (PhNH–NH–N=CH–) | 10.59(1H, s), 9.84(1H, s), 8.56(1H, s), 8.53(1H, brs), 8.29(1H, d, J = 6.9 Hz), 8.03(2H, brs), 7.78-7.73(2H, m), 7.51-7.45(1H, m), 7.35-7.16(8H, m), 6.79(1H, t, J = 5.4 Hz), 5.27(2H, s) |
| IX-8 | (PhN(Me)–N=CH–) | 9.86(1H, s), 8.61(1H, s), 8.57(1H, brs), 8.32(1H, d, J = 7.2 Hz), 8.05(2H, d, J = 2.1 Hz), 7.80-7.73(3H, m), 7.52-7.45(3H, m), 7.37-7.28(5H, m), 7.19(1H, t, J = 6.3 Hz), 6.94(1H, t, J = 5.4 Hz), 5.27(2H, s), 3.51(3H, s) |
| IX-9 | HOCH₂CH₂–NH–N=CH– | 9.77(1H, s), 8.53(1H, s), 8.39(1H, brs), 8.09(1H, d, J = 6.3 Hz), 8.04(1H, s), 7.75-7.69(3H, m), 7.55-7.45(2H, m), 7.34-7.26(3H, m), 7.18(1H, t, J = 6.3 Hz), 5.21(2H, s), 4.69(1H, t, J = 3.6 Hz), 3.612H, dd, J = 8.4 Hz, J = 4.5 Hz), 3.29(2H, m) |

TABLE 49

| Compound No. | R^B | ¹H-NMR(d₆-DMSO) |
|---|---|---|
| IX-10 | Me₂N–CH₂–C(O)–NH–N=CH– | (E/Z mixture) 11.51(1H, s, minor), 11.45(1H, s, major), 10.00(1H, s, major), 9.89(1H, s, minor), 8.65(1H, brs, minor), 8.60(1H, brs), 8.53(1H, s, major), 8.26(1H, d, J = 6.6 Hz, minor), 8.22(1H, d, J = 6.6 Hz, major), 8.04(1H, brs, minor), 8.00(1H, d, J = 1.8 Hz, major), 7.80(1H, d, J = 6.6 Hz), 7.73(1H, d, J = 6.6 Hz), 7.51-7.45(1H, m), 7.35-7.27(3H, m), 7.19(1H, t, J = 6.6 Hz), 5.27(2H, s), 3.58(2H, s, minor), 3.08(2H, s, major), 2.34(3H, s, minor), 2.28(3H, s, major) |
| IX-11 | NC–CH₂–C(O)–NH–N=CH– | 12.04(1H, s), 9.88(1H, s), 8.64(1H, brs), 8.61(1H, s), 8.31(1H, d, J = 6.3 Hz), 8.17(1H, s), 8.01(1H, d, J = 2.1 Hz), 7.80(1H, d, J = 6.6 Hz), 7.72(1H, d, J = 6.6 Hz), 7.50-7.45(1H, m), 7.35-7.28(3H, m), 7.19(1H, t, J = 5.4 Hz), 5.27(2H, s), 4.31(2H, s) |
| IX-12 | Ph–C(O)–NH–N=CH– | 12.02(1H, s), 10.00(1H, s), 8.70(1H, brs), 8.65(1H, brs), 8.61(1H, s), 8.31(1H, d, J = 6.0 Hz), 8.02(1H, d, J = 1.8 Hz), 7.96-7.94(2H, m), 7.84(1H, d, J = 6.0 Hz), 7.72(1H, d, J = 13.8 Hz), 7.65-7.55(3H, m), 7.51-7.45(1H, m), 7.35-7.28(3H, m), 7.19(1H, t, J = 6.3 Hz), 5.27(2H, s) |
| IX-13 | (furan-2-yl)–C(O)–NH–N=CH– | 12.04(1H, s), 10.01(1H, s), 8.68(1H, brs), 8.65(1H, brs), 8.61(1H, s), 8.28(1H, d, J = 6.9 Hz), 8.02(1H, d, J = 1.8 Hz), 7.99(1H, s), 7.83(1H, d, J = 6.6 Hz), 7.74(1H, dd, J = 6.6 Hz, J = 1.8 Hz), 7.51-7.45(1H, m), 7.35-7.28(4H, m), 7.19(1H, t, J = 6.3 Hz), 6.74(1H, brs), 5.27(2H, s) |
| IX-14 | (pyridin-4-yl)–C(O)–NH–N=CH– | 12.22(1H, s), 10.02(1H, s), 8.82(2H, m), 8.73(1H, brs), 8.65(1H, s), 8.62(1H, s), 8.31(1H, d, J = 7.2 Hz), 8.01(1H, d, J = 1.8 Hz), 7.86-7.84(2H, m), 7.73-7.72(2H, m), 7.51-7.45(1H, m), 7.35-7.28(3H, m), 7.19(1H, t, J = 6.9 Hz), 5.27(2H, s) |

TABLE 49-continued

| Compound No. | $R^B$ | $^1$H-NMR($d_6$-DMSO) |
|---|---|---|
| IX-15 | 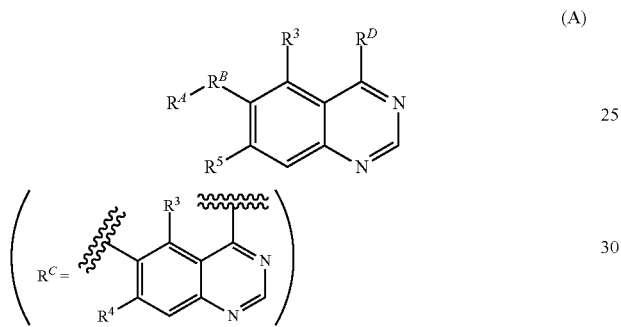 | 12.18(1H, s), 10.01(1H, s), 9.11(1H, s), 8.80(1H, d, J = 3.3 Hz), 8.72(1H, brs), 8.64-8.62(2H, m), 8.32-8.28(2H, m), 8.02(1H, d, J = 1.8 Hz), 7.85(1H, d, J = 6.3 Hz), 7.73(1H, dd, J = 6.6 Hz, J = 1.8 Hz), 7.62-7.59(1H, m), 7.51-7.45(1H, m), 7.35-7.28(3H, m), 7.19(1H, t, J = 6.9 Hz), 5.27(2H, s) |

According to the same manner as that of the above Example, the following compound can be synthesized. That is, in the compound represented by the following general formula (A):

[Chemical formula 90]

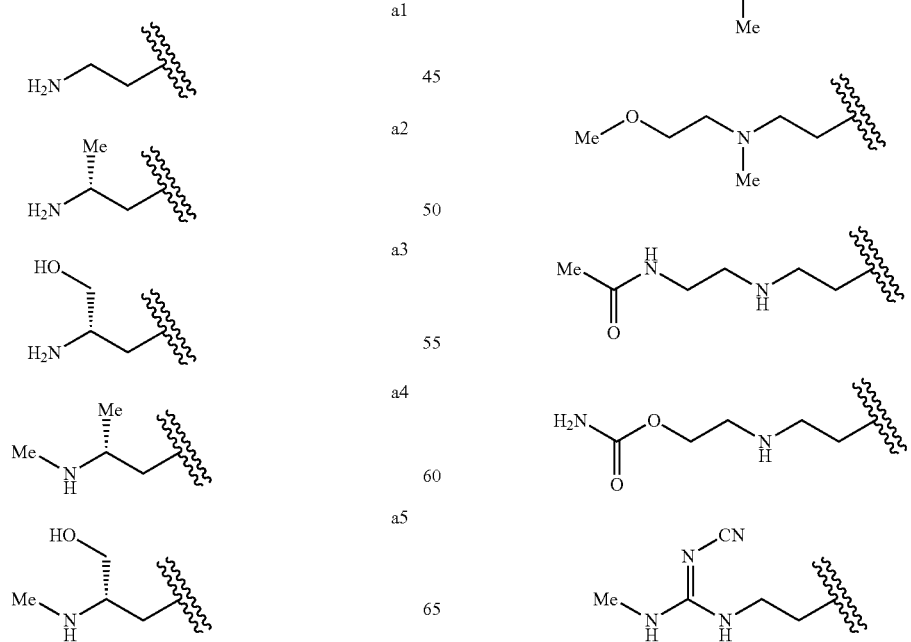

the following compounds represented by a combination of a group in which $R^A$ is a group selected from the following a1 to a90:

[Chemical formula 91]

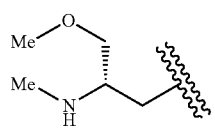 a6

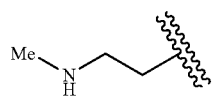 a7

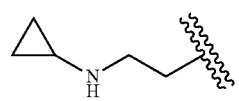 a8

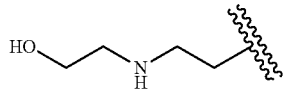 a9

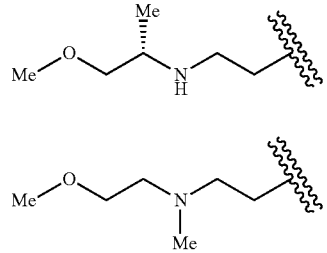 a10, a11, a12

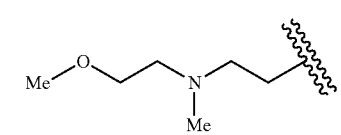 a13

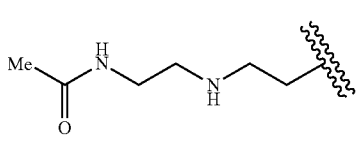 a14

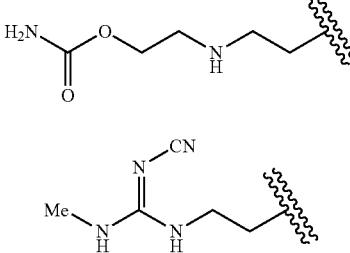 a15

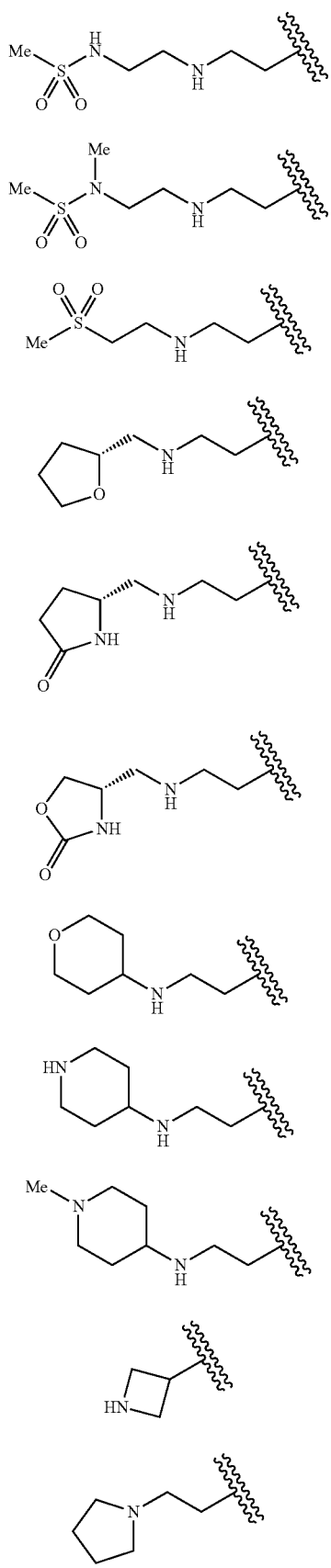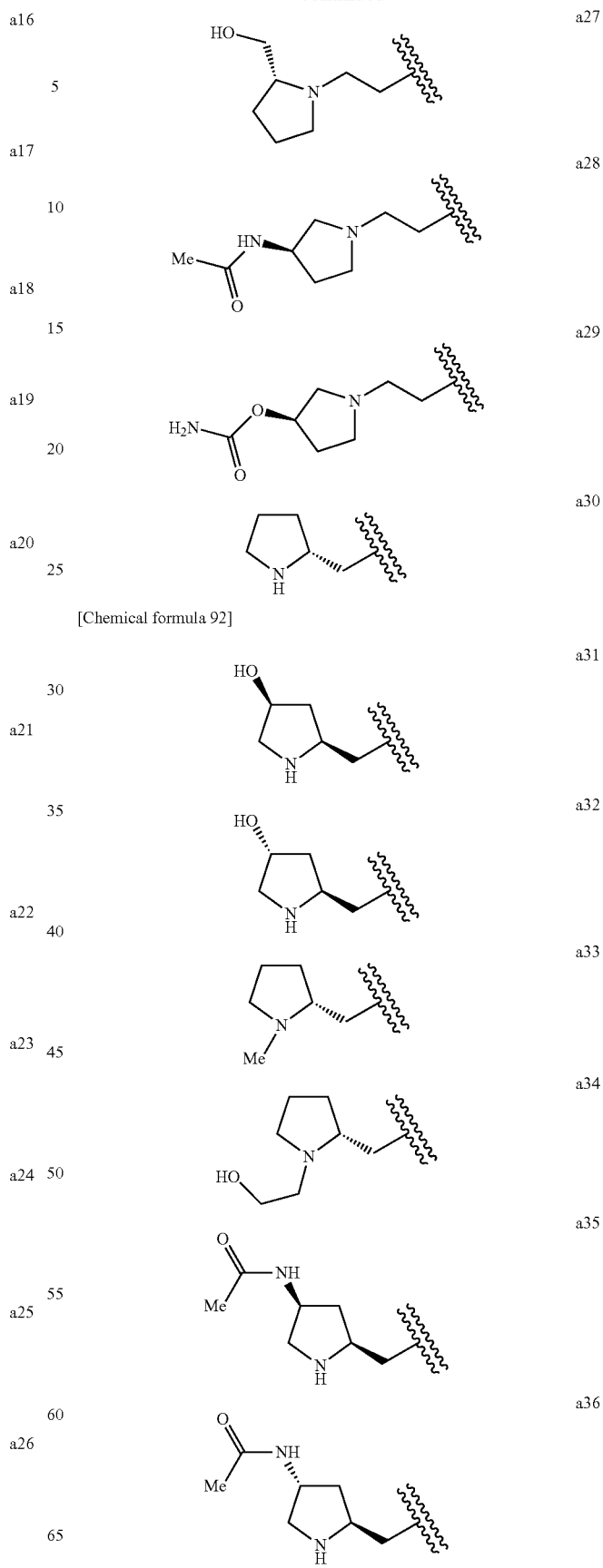

-continued
| | | |
|---|---|---|
| 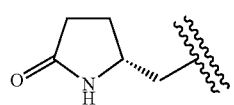 | a37 | |
| 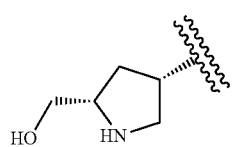 | a38 | |
| 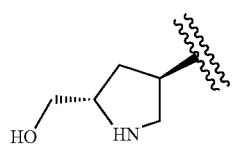 | a39 | |
| 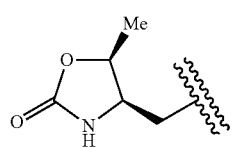 | a40 | |
| 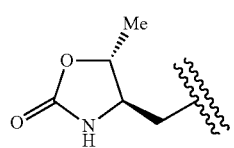 | a41 | |
| 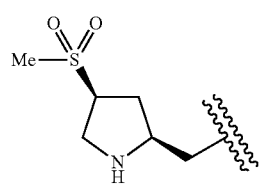 | a42 | |
| 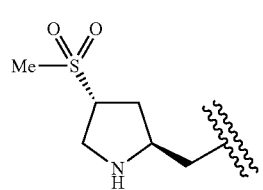 | a43 | |
| 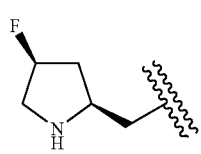 | a44 | |
| 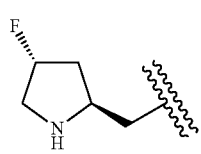 | a45 | |
| 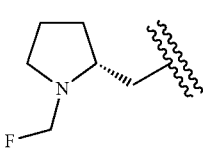 | a46 | |
-continued
| | | |
|---|---|---|
| 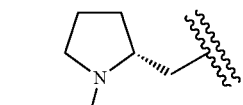 | a47 | |
| 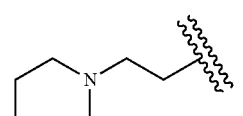 | a48 | |
| 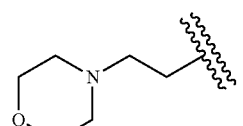 | a49 | |
| 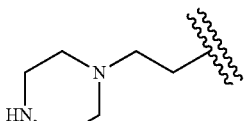 | a50 | |
| 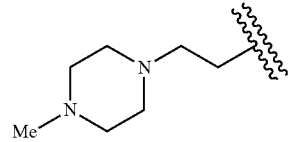 | a51 | |
| 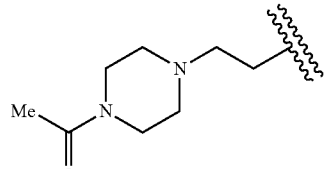 | a52 | |
| 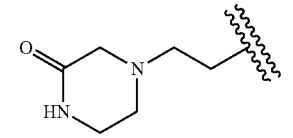 | a53 | |
| 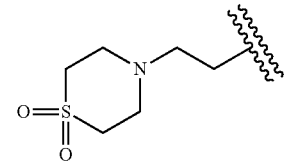 | a54 | |
| 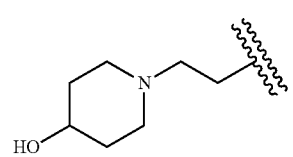 | a55 | |
| 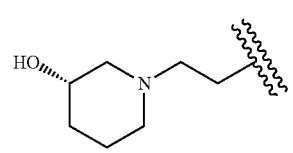 | a56 | |

| | | |
|---|---|---|
| a57 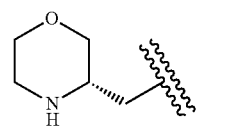 | a68 | 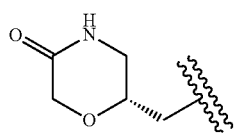 |
| a58 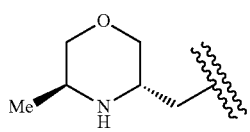 | a69 | 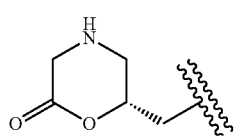 |
| a59 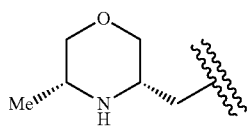 | a70 | 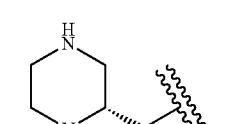 |
| a60 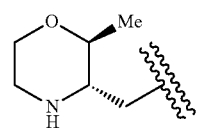 | a71 | 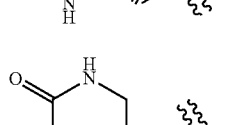 |
[Chemical formula 93]
| | | |
|---|---|---|
| a61 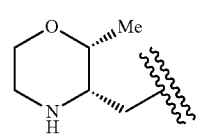 | a72 | 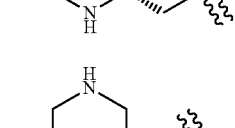 |
| a62 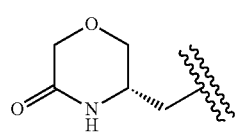 | a73 | 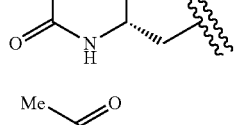 |
| a63 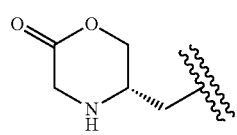 | a74 | 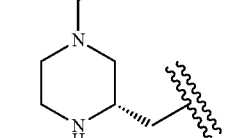 |
| a64 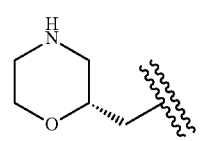 | a75 | 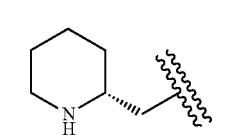 |
| a65 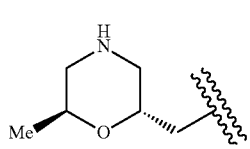 | a76 | 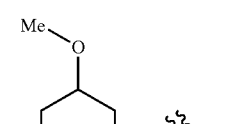 |
| a66 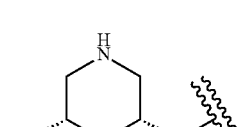 | a77 | 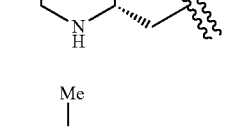 |
| a67 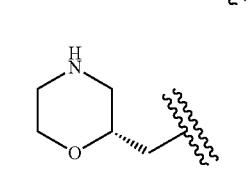 | | |

-continued
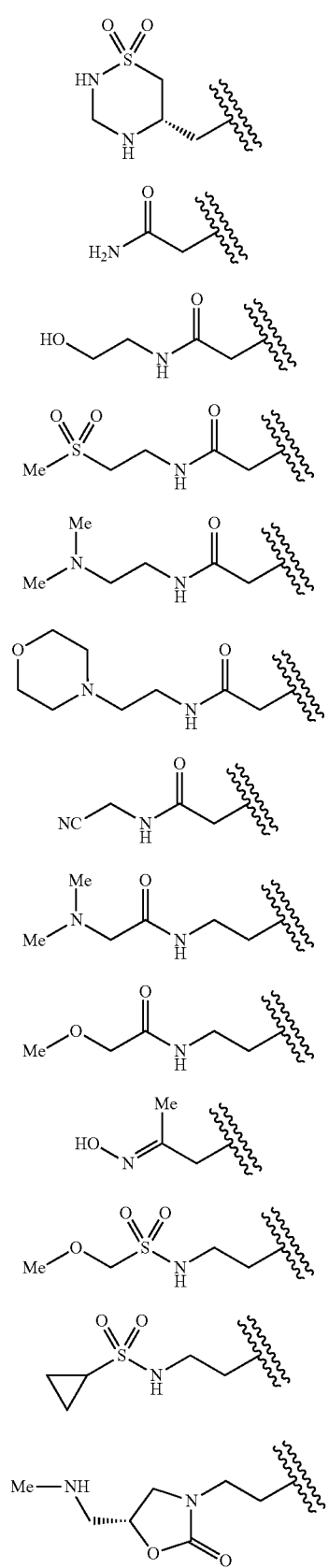
(wherein Me is methyl),
a group it which R$^B$ is selected from the following b1 to b6:
[Chemical formula 94]
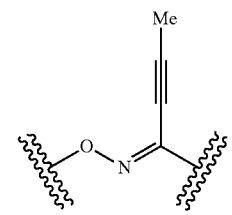 b1
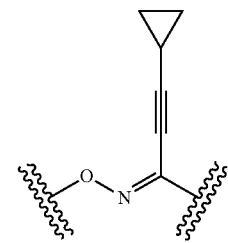 b2
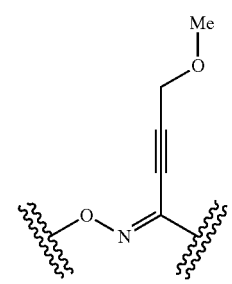 b3
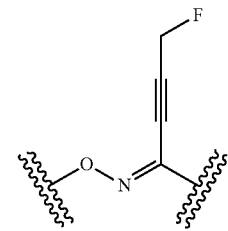 b4
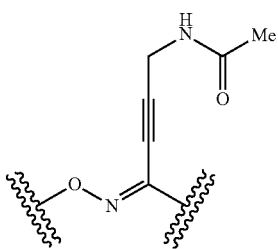 b5
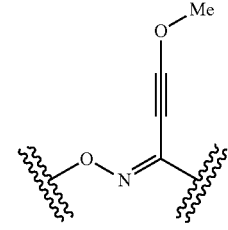 b6
(wherein Me is methyl),
a group in which R$^C$ is selected from the following c1 to c3

[Chemical formula 95]
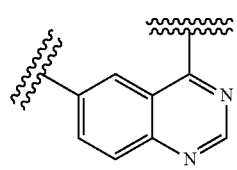 c1
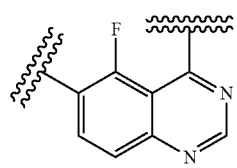 c2
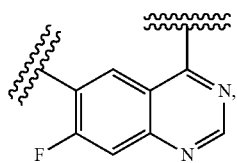 c3
a group in which R$^D$ is selected from the following d1 to d22:
[Chemical formula 96]
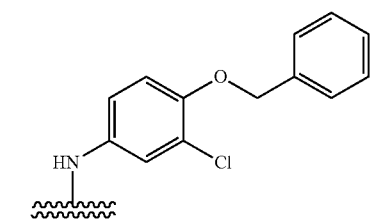 d1
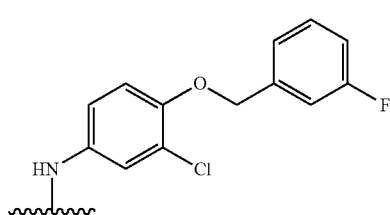 d2
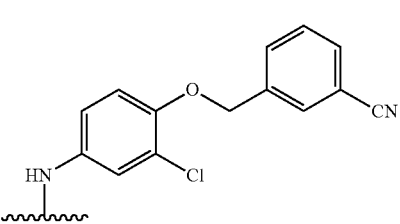 d3
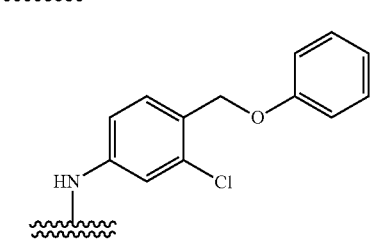 d4
-continued
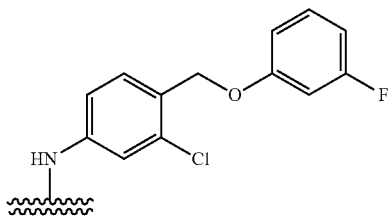 d5
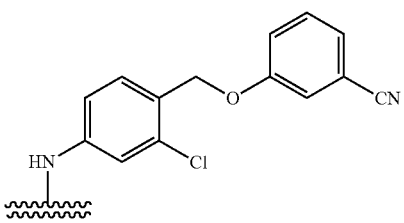 d6
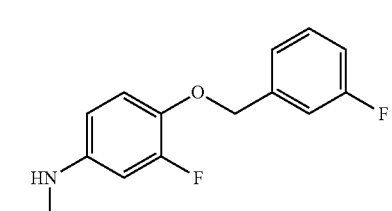 d7
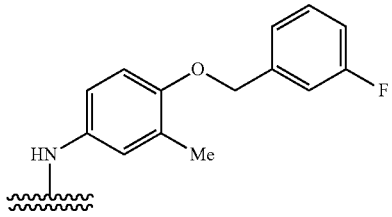 d8
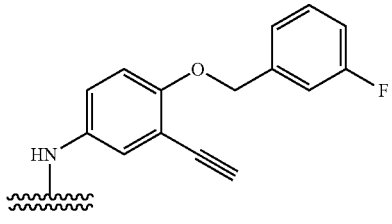 d9
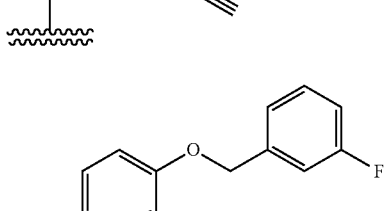 d10
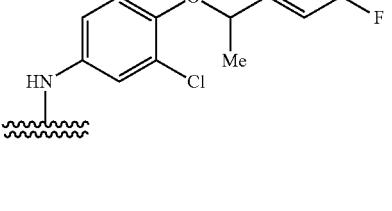 d11

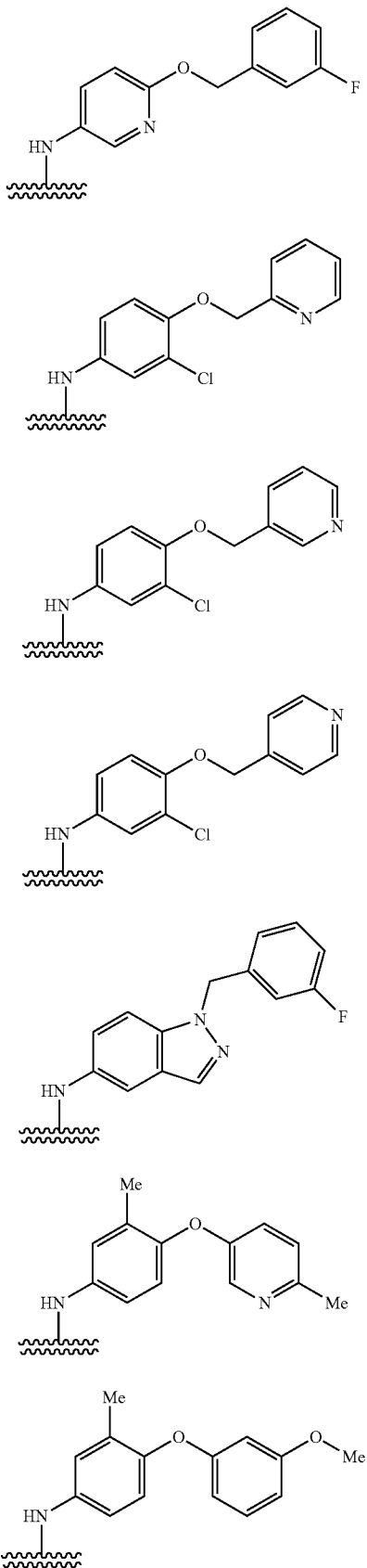
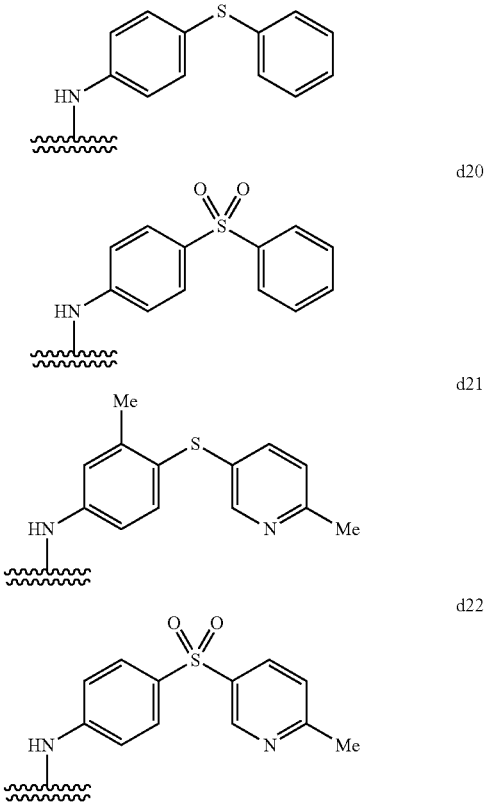

(wherein Me is methyl)
can be synthesized.
(a1, b1, c1, d1), (a1, b1, c1, d2), (a1, b1, c1, d3), (a1, b1, c1, d4), (a1, b1, c1, d5), (a1, b1, c1, d6), (a1, b1, c1, d7), (a1, b1, c1, d8), (a1, b1, c1, d9), (a1, b1, c1, d10), (a1, b1, c1, d11), (a1, b1, c1, d12), (a1, b1, c1, d13), (a1, b1, c1, d14), (a1, b1, c1, d15), (a1, b1, c1, d16), (a1, b1, c1, d17), (a1, b1, c1, d18), b1, c1, d19), (a1, b1, c1, d20), (a1, b1, c1, d21), (a1, b1, c1, d22), (a1, b1, c2, d1), (a1, b1, c2, d2), (a1, b1, c2, d3), (a1, b1, c2, d4), (a1, b1, c2, d5), (a1, b1, c2, d6), (a1, b1, c2, d7), (a1, b1, c2, d8), (a1, b1, c2, d9), (a1, b1, c2, d10), (a1, b1, c2, d11), (a1, b1, c2, d12), (a1, b1, c2, d13), (a1, b1, c2, d14), (a1, b1, c2, d15), (a1, b1, c2, d16), (a1, b1, c2, d17), (a1, b1, c2, d18), (a1, b1, c2, d19), (a1, b1, c2, d20), (a1, b1, c2, d21), (a1, b1, c2, d22), (a1, b1, c3, d1), (a1, b1, c3, d2), (a1, b1, c3, d3), (a1, b1, c3, d4), (a1, b1, c3, d5), (a1, b1, c3, d6), (a1, b1, c3, d7), (a1, b1, c3, d8), (a1, b1, c3, d9), (a1, b1, c3, d10), (a1, b1, c3, d11), (a1, b1, c3, d12), (a1, b1, c3, d13), (a1, b1, c3, d14), (a1, b1, c3, d15), (a1, b1, c3, d16), (a1, b1, c3, d17), (a1, b1, c3, d18), (a1, b1, c3, d19), (a1, b1, c3, d20), (a1, b1, c3, d21), (a1, b1, c3, d22), (a1, b2, c1, d1), (a1, b2, c1, d2), (a1, b2, c1, d3), (a1, b2, c1, d4), (a1, b2, c1, d5), (a1, b2, c1, d6), (a1, b2, c1, d7), (a1, b2, c1, d8), (a1, b2, c1, d9), (a1, b2, c1, d10), (a1, b2, c1, d11), (a1, b2, c1, d12), (a1, b2, c1, d13), (a1, b2, c1, d14), (a1, b2, c1, d15), (a1, b2, c1, d16), (a1, b2, c1, d17), (a1, b2, c1, d18), (a1, b2, c1, d19), (a1, b2, c1, d20), (a1, b2, c1, d21) (a1, b2, c1, d22), (a1, b2, c2, d1), (a1, b2, c2, d2), (a1, b2, c2, d3), (a1, b2, c2, d4), (a1, b2, c2, d5), (a1, b2, c2, d6), (a1, b2, c2, d7), (a1, b2, c2, d8), (a1, b2, c2, d9), (a1, b2, c2, d10), (a1, b2, c2, d11), (a1, b2, c2, d12), (a1, b2, c2, d13), (a1, b2, c2, d14), (a1, b2, c2, d15), (a1, b2, c2, d16), (a1, b2, c2, d17), (a1, b2, c2, d18), (a1, b2, c2, d19), (a1, b2, c2, d20), (a1, b2, c2, d21), (a1, b2, c2, d22), (a1, b2, c3, d1), (a1, b2, c3, d2), (a1, b2, c3, d3), (a1, b2, c3, d4), (a1, b2, c3, d5), (a1, b2, c3, d6), (a1, b2, c3, d7), (a1, b, b2, c3, d8), (a1, b2, c3, d9), (a1, b2, c3, d10), (a1, b2, c3, d11), (a1, b2, c3, d12), (a1, b2, c3, d13), (a1, b2, c3, d14), (a1, b2, c3, d15), (a1, b2, c3, d16), (a1, b2, c3, d17), (a1, b2, c3, d18), (a1, b2, c3, d19), (a1, b2, c3, d20), (a1, b2, c3, d21), (a1, b2, c3, d22), (a1, b3, c1, d1), (a1, b3, c1, d2), (a1, b3, c1, d3), (a1, b3, c1, d4), (a1, b3, c1, d5), (a1, b3, c1, d6), (a1, b3, c1, d7), (a1, b3, c1, d8), (a1, b3, c1, d9), (a., b3, c1, d10), (a1, b3, c1, d11), (a1, b3, c1, d12), (a1, b3, c1, d13), (a1, b3, c1, d14), (a1, b3, c1, d15), (a1, b3, c1, d16), (a1, b3, c1, d17), (a1, b3, c1, d18), (a1, b3, c1, d19), (a1, b3, c1, d20), (a1, b3, c1, d21), (a1, b3, c1, d22), (a1, b3, c2, d1), (a1, b3, c2, d2), (a1, b3, c2, d3), (a1, b3, c2, d4), (a1, b3, c2, d5), (a1, b3, c2, d6), (a1, b3, c2, d7), (a1, b3, c2, d3), (a1, b3, c2, d9), (a1, b3, c2, d10), (a1, b3, c2, d11), (a1, b3, c2, d12), (a1, b3, c2, d13), (a1, b3, c2, d14), (a1, b3, c2, d15), (a1, b3, c2, d16), (a1, b3, c2, d17), (a1, b3, c2, d18), (a1, b3, c2, d19), (a1, b3, c2, d20), (a1, b3, c2, d21), (a1, b3, c2, d22), (a1, b3, c3, d1), (a1, b3, c3, d2), (a1, b3, c3, d3), (a1, b3, c3, d4), (a1, b3, c3, d5), (a1, b3, c3, d6), (a1, b3, c3, d7), (a1, b3, c3, d3), (a1, b3, c3, d9), (a1, b3, c3, d10), (a1, b3, c3, d11), (a1, b3, c3, d12), (a1, b3, c3, d13), (a1, b3, c3, d14), (a1, b3, c3, d15), (a1, b3, c3, d16), (a1, b3, c3, d17), (a1, b3, c3, d18), (a1, b3, c3, d19), (a1, b3, c3, d20), (a1, b3, c3, d21), (a1, b3, c3, d22), (a1, b4, c1, d1), (a1, b4, c1, d2), (a1, b4, c1, d3), (a1, b4, c1, d4), (a1, b4, c1, d5), (a1, b4, c1, d6), (a1, b4, c1, d7), (a1, b4, c1, d8), (a1, b4, c1, d9), (a1, b4, c1, d10), (a1, b4, c1, d11), (a1, b4, c1, d12), (a1, b4, c1, d13), (a1, b4, c1, d14), (a1, b4, c1, d15), (a1, b4, c1, d16), (a1, b4, c1, d17), (a1, b4, c1, d13), (a1, b4, c1, d19), (a1, b4, c1, d20), (a1, b4, c1, d21), (a1, b4, c1, d22), (a1, b4, c2, d1), (c1, b4, c2, d2), (a1, b4, c2, c3), (a1, b4, c2, d4), (a1, b4, c2, d5), (a1, b4, c2, d6), (c1, b4, c2, d7), (a1, b4, c2, d8), (a1, b4, c2, d9), (a1, b4, c2, d10), (a1, b4, c2, d11), (a1, b4, c2, d12), (a1, b4, c2, d13), (a1, b4, c2, d14), (a1, b4, c2, d15), (a1, b4, c2, d16), (a1, b4, c2, d17), (a1, b4, c2, d18), (a1, b4, c2, d19), (a1, b4, c2, d20), (a1, b4, c2, d21), (a1, b4, c2, d22), (a1, b4, c3, d1), (a1, b4, c3, d2), (a1, b4, c3, d3), (a1, b4, c3, d4), (a1, b4, c3, d5), (a1, b4, c3, d6), (a1, b4, c3, d7), (a1, b4, c3, d8), (a1, b4, c3, d9), (a1, b4, c3, d10), (a1, b4, c3, d11), (a1, b4, c3, d12), (a1, b4, c3, d13), (a1, b4, c3, d14), (a1, b4, c3, d15), (a1, b4, c3, d16), (a1, b4, c3, d17), (a1, b4, c3, d18), (a1, b4, c3, d19), (a1, b4, c3, d20), (c1, b4, c3, d21), (a1, b4, c3, d22), (a1, b5, c1, d1), (a1, b5, c1, d2), (a1, b5, c1, d3), (a1, b5, c1, d4), (a1, b5, c1, d5), (a1, b5, c1, d6), (a1, b5, c1, d7), (a1, b5, c1, d8), (a1, b5, c1, d9), (a1, b5, c1, d10), (a1, b5, c1, d11), (a1, b5, c1, d12), (a1, b5, c1, d13), (a1, b5, c1, d14), (a1, b5, c1, d15), (a1, b5, c1, d16), (a1, b5, c1, d17), (a1, b5, c1, d18), (a1, b5, c1, d19), (a1, b5, c1, d20), (a1, b5, c1, d21), (a1, b5, c1, d22), (a1, b5, c2, d1), (a1, b5, c2, d2), (a1, b5, c2, d3), (a1, b5, c2, d4), (a1, b5, c2, d5), (a1, b5, c2, d6), (a1, b5, c2, d7), (a1, b5, c2, d8), (a1, b5, c2, d9), (a1, b5, c2, d10), (a1, b5, c2, d11), (a1, b5, c2, d12), (a1, b5, c2, d13), (a1, b5, c2, d14), (a1, b5, c2, d15), (a1, b5, c2, d16), (a1, b5, c2, d17), (a1, b5, c2, d18), (a1, b5, c2, d19), (a1, b5, c2, d20), (a1, b5, c2, d21), (a1, b5, c2, d22), (a1, b5, c3, d1), (a1, b5, c3, d2), (a1, b5, c3, d3), (a1, b5, c3, d4), (a1, b5, c3, d5), (a1, b5, c3, d6), (a1, b5, c3, d7), (a1, b5, c3, d8), (a1, b5, c3, d9), (a1, b5, c3 d10), (a1, b5, c3, d11), (a1, b5, c3, d12), (a1, b5, c3, d13), (a1, b5, c3, d14), a1, b5, c3, d15), a1, b5, c3, d16), a1, b5, c3, d17), a1, b5, c3, d18), a1, b5, c3, d19), a1, b5, b3, d20), a1, b5, c3, d21), a1, b5, c3, d22), (a1, b6, c1, d1), (a1, b6, c1, d2), (a1, b6, c1, d3), (a1, b6, c1, d4), (a1, b6, c1, d5), (a1, b6, c1, d6), (a1, b6, c1, d7), (a1, b6, c1, d8), (a1, b6, c1, d9), (a1, b6, c1, d10), (a1, b6, c1, d11), (a1, b6, c1, d12), (a1, b6, c1, d13), (a1, b6, c1, d14), (a1, b6, c1, d15), (a1, b6, c1, d16), (a1, b6, c1, d17), (a1, b6, c1, d18), (a1, b6, c1, d19), (a1, b6, c1, d20), (a1, b6, c1, d21), (a1, b6, c1, d22), (a1, b6, c2, d1), (a1, b6, c2, d2), (a1, b6, c2, d3), (a1, b6, c2, d4), (a1, b6, c2, d5), (a1, b6, c2, d6), (, b6, c2, d7), (a1, b6, c2, d8), (a1, b6, c2, d9), (a1, b6, c2, d10), (a1, b6, c2, d11), (a1, b6, c2, d12), (a1, b6, c2, d13), (a1, b6, c2, d14), (a1, b6, c2, d15), (a1, b6, c2, d16), (a1, b6, c2, d17), (a1, b6, c2, d18), (a1, b6, c2, d19), (a1, b6, c2, d20), (a1, b6, c2, d22), (a1, b6, c3, d1), (a1, b6, c3, d1), (a1, b6, c3, d1), (a1, b6, c3, d1), (a1, b6, c3, d1), (a1, b6, c3, d11), (a1, b6, c3, d1), (a1, b6, c3, d1), (a1, b6, c3, d1), (a1, b6, c3, d1), (a1, b6, c3, d12), (a1, b6, c3, d13), (a1, b6, c3, d14), (a1, b6, c3, d15), (a1, b6, c3, d16), (a1, b6, c3, d17), (a1, b6, c3, d18), (a1, b6, c3, d19), (a1, b6, c3, d20), (c1, b6, c3, d21), (a1, b6, c3, d22), (c2, b1, c1, d1), (a2, b1, c1, d2), (a2, b1, c1, d3), (a2, b1, c1, d4), (a2, b1, c1, d5), (a2, b1, c1, d6), (a2, b1, c1, d7), (a2, b1, c1, d8), (a2, b1, c1, d9), (a2, b1, c1, d10), (a2, b1, c1, d11), (a2, b1, c1, d12), (a2, b1, c1, d13), (a2, b1, c1, d14), (a2, b1, c1, d15), (a2, b1, c1, d16), (a2, b1, c1, d17), (a2, b1, c1, d18), (a2, b1, c1, d19), (a2, b1, c1, d20), (a2, b1, c1, d21), (a2, b1, c1, d22), (a2, b1, c2, d1), (a2, b1, c2, d2), (a2, b1, c2, d3), (a2, b1, c2, d4), (a2, b1, c2, d5), (a2, b1, c2, d6), (a2, b1, c2, d7), (a2, b1, c2, d8), (a2, b1, c2, d9), (a2, b1, c2, d10), (a2, b1, c2, d11), (a2, b1, c2, d12), (a2, b1, c2, d13), (a2, b1, c2, d14), (a2, b1, c2, d15), (a2, b1, c2, d16), (a2, b1, c2, d17), (a2, b1, c2, d18), (a2, b1, c2, d19), (a2, b1, c2, d20), (a2, b1, c2, d21), (a2, b1, c2, d22), (a2, b1, c3, d1), (a2, b1, c3, d2), (a2, b1, c3, d3), (a2, b1, c3, d4), (a2, b1, c3, d5), (a2, b1, c3, d6), (a2, b1, c3, d7), (a2, b1, c3, d8), (a2, b1, c3, d9), (a2, b1, c3, d10), (a2, b1, c3, d11), (a2, b1, c3, d12), (a2, b1, c3, d13), (a2, b1, c3, d14), (a2, b1, c3, d15), (a2, b1, c3, d16), (a2, b1, c3, d17), (a2, b1, c3, d18), (a2, b1, c3, d19), (a2, b1, c3, d20), (a2, b1, c3, d21), (a2, b1, c3, d22), (a2, b2, c1, d1), (a2, b2, c1, d2), (a2, b2, c1, d3), (a2, b2, c1, d4), (a2, b2, c1, d5), (a2, b2, c1, d6), (a2, b2, c1, d7), (a2, b2, c1, d8), (a2, b2, c1, d9), (a2, b2, c1, d10), (a2, b2, c1, d11), (a2, b2, c1, d12), (a2, b2, c1, d13), (a2, b2, c1, d14), (a2, b2, c1, d15), (a2, b2, c1, d16), (a2, b2, c1, d17), (a2, b2, c1, d18), (a2, b2, c1, d19), (a2, b2, c1, d20), (a2, b2, c1, d21), (a2, b2, c1, d22), (a2, b2, c2, d1), (a2, b2, c2, d2), (a2, b2, c2, d3), (a2, b2, c2, d4), (a2, b2, c2, d5), (a2, b2, c2, d6), (a2, b2, c2, d7), (a2, b2, c2, d8), (a2, b2, c2, d9), (a2, b2, c2, d10), (a2, b2, c2, d11), (a2, b2, c2, d12), (a2, b2, c2, d13), (a2, b2, c2, d24), (a2, b2, c2, d15), (a2, b2, c2, d16), (a2, b2, c2, d17), (a2, b2, c2, d18), (a2, b2, c2, d19), (a2, b2, c2, d20), (a2, b2, c2, d21) (a2, b2, c2, d22), (a2, b2, c3, d1), (a2, b2, c3, d2), (a2, b2, c3, d3), (a2, b2, c3, d4), (a2, b2, c3, d5), (a2, b2, c3, d6), (a2, b2, c3, d7), (a2, b2, c3, d8), (a2, b2, c3, d9), (a2, b2, c3, d10), (a2, b2, c3, d11), (a2, b2, c3, d12), (a2, b2, c3, d13), (a2, b2, c3, d14), (a2, b2, c3, d15), (a2, b2, c3, d16), (a2, b2, c3, d17), (a2, b2, c3, d18), (a2, b2, c3, d19), (a2, b2, c3, d20), (a2, b2, c3, d21), (a2, b2, c3, d22), (a2, b3, c1, d1), (a2, b3, c1, d2), (a2, b3, c1, d3), (a2, b3, c1, d4), (a2, b3, c1, d5), (a2, b3, c1, d6), (a2, b3, c1, d7), (a2, b3, c1, d8), (a2, b3, c1, d9), (a2, b3, c1, d10), (a2, b3, c1, d11), (a2, b3, c1, d12), (a2, b3, c1, d13), (a2, b3, c1, d14), (a2, b3, c1, d15), (a2, b3, c1, d16), (a2, b3, c1, d17), (a2, b3, c1, d18), (a2, b3, c1, d19), (a2, b3, c1, d20), (a2, b3, c1, d21), (a2, b3, c1, d22), (a2, b3, c2, d1), (a2, b3, c2, d2), (a2, b3, c2, d3), (a2, b3, c2, d4), (a2, b3, c2, d5), (a2, b3, c2, d6), (a2, b3, c2, d7), (a2, b3, c2, d8), (a2, b3, c2, d9), (a2, b3, c2, d10), (a2, b3, c2, d11), (a2, b3, c2, d12), (a2, b3, c2, d13), (a2, b3, c2, d14), (a2, b3, c2, d15), (a2, b3, c2, d16), (a2, b3, c2, d17), (a2, b3, c2, d18), (a2, b3, c2, d19), (a2, b3, c2, d20), (a2, b3, c2, d21), (a2, b3, c2, d22), (a2, b3, c3, d1), (a2, b3, c3, d2), (a2, b3, c3, d3), (a2, b3, c3, d4), (a2, b3, c3, d5), (a2, b3, c3, d6), (a2, b3, c3, d7), (a2, b3, c3, d8), (a2, b3, c3, d9), (a2, b3, c3, d10), (a2, b3, c3, d11), (a2, b3, c3, d12), (a2, b3, c3, d13), (a2, b3, c3, d14), (a2, b3, c3, d15), (a2, b3, c3, d16), (a2, b3, c3, d17), (a2, b3, c3, d18), (a2, b3, c3, d19), (a2, b3, c3, d20), (a2, b3, c3, d21), (a2, b3, c3, d22), (a2, b4, c1, d1), (a2, b4, c1, d2), (a2, b4, c1, d3), (a2, b4, c1, d4), (a2, b4, c1, d5), (a2, b4, c1, d6), (a2, b4, c1, d7), (a2, b4, c1, d8), (a2, b4, c1, d9), (a2, b4, c1, d10), (a2, b4, c1, d11), (a2, b4, c1, d12), (a2, b4, c1, d13), (a2, b4, c1, d14), (a2, b4, c1, d15), (a2, b4, c1, d16), (a2, b4, c1, d17), (a2, b4, c1, d18), (a2, b4, c1, d19), (a2, b4, c1, d20), (a2, b4, c1, d21), (a2, b4, c1, d22), (a2, b4, c2, d1), (a2, b4, c2, d2), (a2, b4, c2, d3), (a2, b4, c2, d4), (a2, b4, c2, d15), (a2, b4, c2, d6), (a2, b4, c2, d7), (a2, b4, c2, d8), (a2, b4, c2, d9), (a2, b4, c2, d10), (a2, b4, c2, d11), (a2, b4, c2, d12), (a2, b4, c2, d13), (a2, b4, c2, d14), (a2, b4, c2, d15), (a2, b4, c2, d16), (a2, b4, c2, d17), (a2, b4, c2, d18), (a2, b4, c2, d19), (a2, b4, c2, d20), (a2, b4, c2, d21), (a2, b4, c2, d22), (a2, b4, c3, d1), (a2, b4, c3, d2), (a2, b4, c3, d3), (a2, b4, c3, d4), (a2, b4, c3, d5), (a2, b4, c3, d6), (a2, b4, c3, d7), (a2, b4, c3, d8), (a2, b4, c3, d9), (a2, b4, c3, d10), (a2, b4, c3, d11), (a2, b4, c3, d12), (a2, b4, c3, d13), (a2, b4, c3, d14), (a2, b4, c3, d15), (a2, b4, c3, d16), (a2, b4, c3, d17), (a2, b4, c3, d18), (a2, b4, c3, d19), (a2, b4, c3, d20), (a2, b4, c3, d21), (a2, b4, c3, d22), (a2, b5, c1, d1), (a2, b5, c1, d2), (a2, b5, c1, d3), (a2, b5, c1, d4), (a2, b5, c1, d5), (a2, b5, c1, d6), (a2, b5, c1, d7), (a2, b5, c1, d8), (a2, b5, c1, d9), (a2, b5, c1, d10), (a2, b5, c1, d11), (a2, b5, c1, d12), (a2, b5, c1, d13), (a2, b5, c1, d14), (a2, b5, c1, d15), (a2, b5, c1, d16), (a2, b5, c5, d17), (a2, b5, c5, d18), (a2, b5, c1, d19), (a2, b5, c1, d20), (a2, b5, c1, d21), (a2, b5, c1, d22), (a2, b5, c2, d1), (a2, b5, c2, d2), (a2, b5, c2, d3), (a2, b5, c2, d4), (a2, b5, c2, d5), (a2, b5, c2, d6), (a2, b5, c2, d7), (a2, b5, c2, d8), (a2, b5, c2, d9), (a2, b5, c2, d10), (a2, b5, c2, d11), (a2, b5, c2, d12), (a2, b5, c2, d13), (a2, b5, c2, d14), (a2, b5, c2, d15), (a2, b5, c2, d16), (a2, b5, c2, d17), (a2, b5, c2, d18), (a2, b5, c2, d19), (a2, b5, c2, d20), (a2, b5, c2, d21), (a2, b5, c2, d22), (a2, b5, c3, d1), (a2, b5, c3, d2), (a2, b5, c3, d3), (a2, b5, c3, d4), (a2, b5, c3, d5), (a2, b5, c3, d6), (a2, b5, c3, d7), (a2, b, c3, d8), (a2, b5, c3, d9), (a2, b5, c3, d10), (a2, b5, c3, d11), (a2, b5, c3, d12), (a2, b5, c3, d13), (a2, b5, c3, d14), (a2, b5, c3, d15), (a2, b5, c3, d16), (a2, b5, c3, d17), (a2, b5, c3, d18), (a2, b3, c3, d19), (a2, b3, c3, d20), (a2, b3, c3, d21), (a2, b3, c3, d22), (a2, b6, c1, d1), (a2, b6, c1, d2), (a2, b6, c1, d3), (a2, b6, c1, d4), (a2, b6, c1, d5), (a2, b6, c1, d6), (a2, c1, d7), (a2, b6, c1, d8), (a2, b6, c1, d9), (a2, b6, c1, d10), (a2, b6, c1, d11), (a2, b6, c1, d12), (a2, b6, c1, d13), (a2, b6, c1, d14), (a2, b6, c1, d15), (a2, b6, c1, d16), (a2, b6, c1, d17), (a2, b6, c1, d18), (a2, b6, c1, d19), (a2, b6, c1, d20), (a2, b6, c1, d21), (a2, b6, c1, d22), (a2, b6, c2, d1), (a2, b6, c2, d2), (a2, b6, c2, d3), (a2, b6, c2, d4), (a2, b6, c2, d5), (a2, b6, c2, d6), (a2, b6, c2, d7), (a2, b6, c2, d8), (a2, b6, c2, d9), (a2, b6, c2, d10), (a2, b6, c2, d11), (a2, b6, c2, d12), (a2, b6, c2, d13), (a2, b6, c2, d14), (a2, b6, c2, d15), (a2, b6, c2, d16), (a2, b6, c2, d17), (a2, b6, c2, d18), (a2, b6, c2, d19), (a2, b6, c2, d20), (a2, b6, c2, d21), (a2, b6, c2, d22), (a2, b6, c3, d1), (a2, b6, c3, d2), (a2, b6, c3, d3), (a2, b6, c3, d4), (a2, b6, c3, d5), (a2, b6, c3, d6), (a2, b6, c3, d7), (a2, b6, c3, d8), (a2, b6, c3, d9), (a2, b6, c3, d10), (a2, b6, c3, d11), (a2, b6, c3, d12), (a2, b6, c3, d13), (a2, b6, c3, d14), (a2, b6, c3, d15), (a2, b6, c3, d16), (a2, b6, c3, d17), (a2, b6, c3, d18), (a2, b6, c3, d19), (a2, b6, c3, d20), (a2, b6, c3, d21), (a2, b6, c3, d22), (a3, b1, c1, d1), (a3, b1, c1, d2), (a3, b1, c1, d3), (a3, b1, c1, d4), (a3, b1, c1, d5), (a3, b1, c1, d6), (a3, b1, c1, d7), (a3, b1, c1, d8), (a3, b1, c1, d9), (a3, b1, c1, d10), (a3, b1, c1, d11), (a3, b1, c1, d12), (a3, b1, c1, d13), (a3, b1, c1, d14), (a3, b1, c1, d15), (a3, b1, c1, d16), (a3, b1, c1, d17), (a3, b1, c1, d18), (a3, b1, c1, d19), (a3, b1, c1, d20), (a3, b1, c1, d21), (a3, b1, c1, d22), (a3, b1, c2, d1), (a3, b1, c2, d2), (a3, b1, c2, d3), (a3, b1, c2, d4), (a3, b1, c2, d5), (a3, b1, c2, d6), (a3, b1, c2, d7), (a3, b1, c2, d8), (a3, b1, c2, d9), (a3, b1, c2, d10), (a3, b1, c2, d11), (a3, b1, c2, d12), (a3, b1, c2, d13), (a3, b1, c2, d14), (a3, b1, c2, d15), (a3, b1, c2, d16), (a3, b1, c2, d17), (a3, b1, c2, d18), (a3, b1, c2, d19), (a3, b1, c2, d20), (a3, b1, c2, d21), (a3, b1, c2, d22), (a3, b1, c3, d1), (a3, b1, c3, d2), (a3, b1, c3, d3), (a3, b1, c3, d4), (a3, b1, c3, d5), (a3, b1, c3, d6), (a3, b1, c3, d7), (a3, b1, c3, d8), (a3, b1, c3, d9), (a3, b1, c3, d10), (a3, b1, c3, d11), (a3, b1, c3, d12), (a3, b1, c3, d13), (a3, b1, c3, d14), (a3, b1, c3, d15), (a3, b1, c3, d16), (a3, b1, c3, d17), (a3, b1, c3, d18), (a3, b1, c3, d19), (a3, b1, c3, d20), (a3, b1, c3, d21), (a3, b1, c3, d22), (a3, b2, c1, d1), (a3, b2, c1, d2), (a3, b2, c1, d3), (a3, b2, c1, d4), (a3, b2, c1, d5), (a3, b2, c1, d6), (a3, b2, c1, d7), (a3, b2, c1, d8), (a3, b2, c1, c9), (a3, b2, c1, d10), (a3, b2, c1, d11), (a3, b2, c1, d12), (a3, b2, c1, d13), (a3, b2, c1, d14), (a3, b2, c1, d15), (a3, b2, c1, d16), (a3, b2, c1, d17), (a3, b2, c1, d18), (a3, b2, c1, d19), (a3, b2, c1, d20), (a3, b2, c1, d21), (a3, b2, c1, d22), (a3, b2, c2, d1), (a3, b2, c2, d2), (a3, b2, c2, d3), (a3, b2, c2, d4), (a3, b2, c2, d5), (a3, b2, c2, d6), (a3, b2, c2, d7), (a3, b2, c2, d8), (a3, b2, c2, d9), (a3, b2, c2, d10), (a3, b2, c2, d11), (a3, b2, c2, d12), (a3, b2, c2, d13), (a3, b2, c2, d14), (a3, b2, c2, d15), (a3, b2, c2, d16), (a3, b2, c2, d17), (a3, b2, c2, d18), (a3, b2, c2, d19), (a3, b2, c2, d20), (a3, b2, c2, d21), (a3, b2, c2, d22), (a3, b2, c3, d1), (a3, b2, c3, d2), (a3, b2, c3, d3), (a3, b2, c3, d4), (a3, b2, c3, d5), (a3, b2, c3, d6), (a3, b2, c3, d7), (a3, b2, c3, d8), (a3, b2, c3, d9), (a3, b2, c3, d10), (a3, b2, c3, d11), (a3, b2, c3, d12), (a3, b2, c3, d13), (a3, b2, c3, d14), (a3, b2, c3, d15), (a3, b2, c3, d16), (a3, b2, c3, d17), (a3, b2, c3, d18), (a3, b2, c3, d19), (a3, b2, c3, d20), (a3, b2, c3, d21), (a3, b2, c3, d22), (a3, b3, c1, d1), (a3, b3, c1, d2), (a3, b3, c1, d3), (a3, b3, c1, d4), (a3, b3, c1, d5), (a3, b3, c1, d6), (a3, b3, c1, d7), (a3, b3, c1, d8), (a3, b3, c1, d9), (a3, b3, c1, d10), (a3, b3, c1, d11), (a3, b3, c1, d12), (a3, b3, c1, d13), (a3, b3, c1, d14), (a3, b3, c1, d15), (a3, b3, c1, d16), (a3, b3, c1, d17), (a3, b3, c1, d18), (a3, b3, c1, d19), (a3, b3, c1, d20), (a3, b3, c1, d21), (a3, b3, c1, d22), (a3, b3, c2, d1), (a3, b3, c2, d2), (a3, b3, c2, d3), (a3, b3, c2, d4), (a3, b3, c2, d5), (a3, b3, c2, d6), (a3, b3, c2, d7), (a3, b3, c2, d8), (a3, b3, c2, d9), (a3, b3, c2, d10), (a3, b3, c2, d11), (a3, b3, c2, d12), (a3, b3, c2, d13), (a3, b3, c2, d14), (a3, b3, c2, d15), (a3, b3, c2, d16), (a3, b3, c2, d17), (a3, b3, c2, d18), (a3, b3, c2, d19), (as, b, c2, d20), (a3, b3, c2, d21), (a3, b3, c2, d22), (a3, b3, c3, d1), (a3, b3, c3, d2), (a3, b3, c3, d3), (a3, b3, c3, d4), (a3, b3, c3, d5), (a3, b3, c3, d6), (a3, b3, c3, d7), (a3, b3, c3, d8), (a3, b3, c3, d9), (a3, b3, c3, d10), (a3, b3, c3, d11), (a3, b3, c3, d12), (a3, b3, c3, d13), (a3, b3, c3, d14), (a3, b3, c3, d15), (a3, b3, c3, d16), (a3, b3, c3, d17), (a3, b3, c3, d18), (a3, b3, c3, d19), (a3, b3, c3, d20), (a3, b3, c3, d21), (a3, b3, c3, d22), (a3, b4, c1, d1), (a3, b4, c1, d2), (a3, b4, c1, d3), (a3, b4, c1, d4), (a3, b4, c1, d5), (a3, b4, c1, d6), (a3, b4, c1, d7), (a3, b4, c1, d8), (a3, b4, c1, d9), (a3, b4, c1, d10), (a3, b4, c1, d11), (a3, b4, c1, d12), (a3, b4, c1, d13), (a3, b4, c1, d14), (a3, b4, c1, d15), (a4, c1, d16), (a3, b4, c1, d17), (a3, b4, c1, d18), (a3, b4, c1, d19), (a3, b4, c1, d20), (a3, b4, c1, d21), (a3, b4, c1, d22), (a3, b4, c2, d1), (a3, b4, c2, d2), (a3, b4, c2, d3), (a3, b4, c2, d4), (a3, b4, c2, d5), (a3, b4, c2, d6), (a3, b4, c2, d7), (a3, b4, c2, d8), (a3, b4, c2, d9), (a3, b4, c2, d10), (a3, b4, c2, d11), (a3, b4, c2, d12), (a3, b4, c2, d13), (a3, b4, c2, d14), (a3, b4, c2, d15), (a3, b4, c2, d16), (a3, b4, c2, d17), (a3, b4, c2, d18), (a3, b4, c2, d19), (a3, b4, c2, d20), (a3, b4, c2, d21), (a3, b4, c2, d22), (a3, b4, c3, d1), (a3, b4, c3, d2), (a3, b4, c3, d3), (a3, b4, c3, d4), (a3, b4, c3, d5), (a3, b4, c3, d6), (a3, b4, c3, d7), (a3, b4, c3, d8), (a3, b4, c3, d9), (a3, b4, c3, d10), (a3, b4, c3, d11), (a3, b4, c3, d12), (a3, b4, c3, d13), (a3, b4, c3, d14), (a3, b4, c3, d15), (a3, b4, c3, d16), (a3, b4, c3, d17), (a3, b4, c3, d18), (a3, b4, c3, d19), (a3, b4, c3, d20), (a3, b4, c3, d21), (a3, b4, c3, d22), (a3, b5, c1, d1), (a3, b5, c1, d2), (a3, b5, c1, d3), (a3, b5, c1, d4), (a3, b5, c1, d5), (a3, b5, c1, d6), (a3, b5, c1, d7), (a3, b5, c1, d8), (a3, b5, c1, d9), (a3, b5, c1, d10), (a3, b5, c1, d11), (a3, b5, c1, d12), (a3, b5, c1, d13), (a3, b5, c1, d14), (a3, b5, c1, d15), (a3, b5, c1, d16), (a3, b5, c1, d17), (a3, b5, c1, d18), (a3, b5, c1, d19), (a3, b5, c1, d20), (a3, b5, c1, d21), (a3, b5, c1, d22), (a3, b5, c2, d1), (a3, b5, c2, d2), (a3, b5, c2, d3), (a3, b5, c2, d4), (a3, b5, c2, d5), (a3, b5, c2, d6), (a3, b5, c2, d7), (a3, b, c2, d8), (a3, b5, c2, d9), (a3, b5, c2, d10), (a3, b5, c2, d11), (a3, b5, c2, d12), (a3, b5, c2, d13), (a3, b5, c2, d14), (a3, b5, c2, d15), (a3, b5, c2, d16), (a3, b5, c2, d17), (a3, b5, c2, d18), (a3, b5, c2, d19), (a3, b5, c2, d20), (a3, b5, c2, d21), (a3, b5, c2, d22), (a3, b5, c3, d1), (a3, b5, c3, d2), (a3, b5, c3, d3), (a3, b5, c3, d4), (a3, b5, c3, d5), (a3, b5, c3, d6), (a3, b5, c3, d7), (a3, b5, c3, d8), (a3, b5, c3, d9), (a3, b5, c3, d10), (a3, b5, c3, d11), (a3, b5, c3, d12), (a3, b5, c3, d13), (a3, b5, c3, d14), (a3, b5, c3, d15), (a3, b5, c3, d16), (a3, b5, c3, d17), (a3, b5, c3, d18), (a3, b5, c3, d19), (a3, b5, c3, d20), (a3, b5, c3, d21), (a3, b5, c3, d22), (a3, b6, c1, d1), (a3, b6, c1, d2), (a3, b6, c1, d3), (a3, b6, c1, d4), (a3, b6, c1, d5), (a3, b6, c1, d6), (a3, b6, c1, d7), (a3, b6, c1, d8), (a3, b6, c1, d9), (a3, b6, c1, d10), (a3, b6, c1, d11), (a3, b6, c1, d12), (a3, b6, c1, d13), (a3, b6, c1, d14), (a3, b6, c1, d15), (a3, b6, c1, d16), (a3, b6, c1, d17), (a3, b6, c1, d18), (a3, b6, c1, d19), (a3, b6, c1, d20), (a3, b6, c1, d21), (a3, b6, c1, d22), (a3, b6, c2, d1), (a3, b6, c2, d2), (a3, b6, c2, d3), (a3, b6, c2, d4), (a3, b6, c2, d5), (a3, b6, c2, d6), (a3, b6, c2, d7), (a3, b6, c2, d8), (a3, b6, c2, d9), (a3, b6, c2, d10), (a3, b6, c2, d11), (a3, b6, c2, d12), (a3, b6, c2, d3), (a3, b6, c2, d14), (a3, b6, c2, d15), (a3, b6, c2, d16), (a3, b6, c2, d17), (a3, b6, c2, d18), (a3, b6, c2, d19), (a3, b6, c2, d20), (a3, b6, c2, d21), (a3, b6, c2, d22), (a3, b6, c3, d1), (a3, b6, c3, d2), (a3, b6, c3, d3), (a3, b6, c3, d4), (a3, b6, c3, d5), (a3, b6, c3, d6), (a3, b6, c3, d7), (a3, b6, c3, d8), (a3, b6, c3, d9), (a3, b6, c3, d10), (a3, b6, c3, d1), (a3, b6, c3, d12), (as, b6, c3, d13), (a3, b6, c3, d14), (a3, b6, c3, d15), (a3, b6, c3, d16), (a3, b6, c3, d17), (a3, b6, c3, d18), (a3, b6, c3, d19), (a3, b6, c3, d20), (a3, b6, c3, d21), (a3, b6, c3, d22), (a4, b1, c1, d1), (a4, b1, c1, d2), (a4, b1, c1, d3), (a4, b1, c1, d4), (a4, b1, c1, d5), (a4, b1, c1, d6), (a4, b1, c1, d7), (a4, b1, c1, d8), (a4, b1, c1, d9), (a4, b1, c1, d10), (a4, b1, c1, d11), (a4, b1, c1, d12), (a4, b1, c1, d13), (a4, b1, c1, d14), (a4, b1, c1, d15), (a4, b1, c1, d16), (a4, b1, c1, d17), (a4, b1, c1, d18), (a4, b1, c1, d19), (a4, b1, c1, d20), (a4, b1, c1, d21), (a4, b1, c1, d22), (a4, b1, c2, d1), (a4, b1, c2, d2), (a4, b1, c2, d3), (a4, b1, c2, d4), (a4, b1, c2, d5), (a4, b1, c2, d6), (a4, b1, c2, d7), (a4, b1, c2, d8), (a4, b1, c2, d9), (a4, b1, c2, d10), (a4, b1, c2, d11), (a4, b1, c2, d12), (a4, b1, c2, d13), (a4, b1, c2, d14), (a4, b1, c2, d15), (a4, b1, c2, d16), (a4, b1, c2, d17), (a4, b1, c2, d18), (a4, b1, c2, d19), (a4, b1, c2, d20), (a4, b1, c2, d21), (a4, b1, c2, d22), (a4, b1, c3, d1), (a4, b1, c3, d2), (a4, b1, c3, d3), (a4, b1, c3, d4), (a4, b1, c3, d5), (a4, b1, c3, d6), (a4, b1, c3, d7), (a4, b1, c3, d8), (a4, b1, c3, d9), (a4, b1, c3, d10), (a4, b1, c3, d11), (a4, b1, c3, d12), (a4, b1, c3, d13), (a4, b1, c3, d14), (a4, b1, c3, d15), (a4, b1, c3, d16), (a4, b1, c3, d17), (a4, b1, c3, d18), (a4, b1, c3, d19), (a4, b1, c3, d20), (a4, b1, c3, d21), (a4, b1, c3, d22), (a4, b2, c1, d1), (a4, b2, c1, d2), (a4, b2, c1, d3), (a4, b2, c1, d4), (a4, b2, c1, d5), (a4, b2, c1, d6), (a4, b2, c1, d7), (a4, b2, c1, d8), (a4, b2, c1, d9), (a4, b2, c1, d10), (a4, b2, c1, d11), (a4, b2, c1, d12), (a4, b2, c1, d13), (a4, b2, c1, d14), (a4, b2, c1, d15), (a4, b2, c1, d16), (a4, b2, c1, d17), (a4, b2, c1, d18), (a4, b2, c1, d19), (a4, b2, c1, d20), (a4, b2, c1, d21), (a4, b2, c1, d22), (a4, b2, c2, d1), (a4, b2, c2, d2), (a4, b2, c2, d3), (a4, b2, c2, d4), (a4, b2, c2, d5), (a4, b2, c2, d6), (a4, b2, c2, d7), (a4, b2, c2, d8), (a4, b2, c2, d9), (a4, b2, c2, d10), (a4, b2, c2, d11), (a4, b2, c2, d12), (a4, b2, c2, d13), (a4, b2, c2, d14), (a4, b2, c2, d15), (a4, b2, c2, d16), (a4, b2, c2, d17), (a4, b2, c2, d18), (a4, b2, c2, d19), (a4, b2, c2, d20), (a4, b2, c2, d21), (a4, b2, c2, d22), (a4, b2, c3, d1), (a4, b2, c3, d2), (a4, b2, c3, d3), (a4, b2, c3, d4), (a4, b2, c3, d5), (a4, b2, c3, d6), (a4, b2, c3, d7), (a4, b2, c3, d8), (a4, b2, c3, d9), (a4, b2, c3, d10), (a4, b2, c3, d11), (a4, b2, c3, d12), (a4, b2, c3, d13), (a4, b2, c3, d14), (a4, b2, c3, d15), (a4, b2, c3, d16), (a4, b2, c3, d17), (a4, b2, c3, d18), (a4, b2, c3, d19), (a4, b2, c3, d20), (a4, b2, c3, d21), (a4, b2, c3, d22), (a4, b2, c1, d1), (a4, b3, d2), (a4, b3, c1, d3), (a4, b3, c1, d4), (a4, b3, c1, d5), (a4, b3, c1, d6), (a4, b3, c1, d7), (a4, b3, c1, d8), (a4, b3, c1, d9), (a4, b3, c1, d10), (a4, b3, c1, d11), (a4, b3, c1, d12), (a4, b3, c1, d13), (a4, b3, c1, d14), (a4, b3, c1, d15), (a4, b3, c1, d16), (a4, b3, c1, d17), (a4, b3, c1, d18), (a4, b3, c1, d19), (a4, b3, c1, d20), (a4, b3, c1, d21), (a4, b3, c1, d22), (a4, b3, c2, d1), (a4, b3, c2, d2), (a4, b3, c2, d3), (a4, b3, c2, d4), (a4, b3, c2, d5), (a4, b3, c2, d6), (a4, b3, c2, d7), (a4, b3, c2, d8), (a4, b3, c2, d9), (a4, b3, c2, d10), (a4, b3, c2, d11), (a4, b3, c2, d12), (a4, b3, c2, d13), (a4, b3, c2, d14), (a4, b3, c2, d15), (a4, b3, c2, d16), (a4, b3, c2, d17), (a4, b3, c2, d18), (a4, b3, c2, d19), (a4, b3, c2, d20), (a4, b3, c2, d21), (a4, b3, c2, d22), (a4, b3, c3, d1), (a4, b3, c3, d2), (a4, b3, c3, d3), (a4, b3, c3, d4), (a4, b3, c3, d5), (a4, b3, c3, d6), (a4, b3, c3, d7), (a4, b3, c3, d8), (a4, b3, c3, d9), (a4, b3, c3, d10), (a4, b3, c3, d11), (a4, b3, c3, d12), (a4, b3, c3, d13), (a4, b3, c3, d14), (a4, b3, c3, d15), (a4, b3, c3, d16), (a4, b3, c3, d17), (a4, b3, c3, d18), (a4, b3, c3, d19), (a4, b3, c3, d20), (a4, b3, c3, d21), (a4, b3, c3, d22), (a4, b4, c1, d1), (a4, b4, c1, d2), (a4, b4, c1, d3), (a4, b4, c1, d4), (a4, b4, c1, d5), (a4, b4, c1, d6), (a4, b4, c1, d7), (a4, b4, c1, d8), (a4, b4, c1, d9), (a4, b4, c1, d10), (a4, b4, c1, d11), (a4, b4, c1, d12), (a4, b4, c1, d13), (a4, b4, c1, d14), (a4, b4, c1, d15), (a4, b4, c1, d16), (a4, b4, c1, d17), (a4, b4, c1, d18), (a4, b4, c1, d19), (a4, b4, c1, d20), (a4, b4, c1, d21), (a4, b4, c1, d22), (a4, b4, c2, d1), (a4, b4, c2, d2), (a4, b4, c2, d3), (a4, b4, c2, d4), (a4, b4, c2, d5), (a4, b4, c2, d6), (a4, b4, c2, d7), (a4, b4, c2, d8), (a4, b4, c2, d9), (a4, b4, c2, d10), (a4, b4, c2, d11), (a4, b4, c2, d12), (a4, b4, c2, d13), (a4, b4, c2, d14), (a4, b4, c2, d15), (a4, b4, c2, d16), (a4, b4, c2, d17), (a4, b4, c2, d18), (a4, b4, c2, d19), (a4, b4, c2, d20), (a4, b4, c2, d21), (a4, b4, c2, d22), (a4, b4, c3, d1), (a4, b4, c3, d2), (a4, b4, c3, d3), (a4, b4, c3, d4), (a4, b4, c3, d5), (a4, b4, c3, d6), (a4, b4, c3, d7), (a4, b4, c3, (a4, b4, c3, d9), (a4, b4, c3, d10), (a4, b4, c3, d11), (a4, b4, c3, d12), (a4, b4, c3, d13), (a4, b4, c3, d14), (a4, b4, c3, d15), (a4, b4, c3, d16), (a4, b4, c3, d17), (a4, b4, c3, d18), (a4, b4, c3, d19), (a4, b4, c3, d20), (a4, b4, c3, d21), (a4, b4, c3, d22), (a4, b5, c1, d1), (a4, b5, c1, d2), (a4, b5, c1, d3), (a4, b5, c1, d4), (a4, b5, c1, d5), (a4, b5, c1, d6), (a4, b5, c1, d7), (a4, b5, c1, d8), (a4, b5, c1, d9), (a4, b5, c1, d10), (a4, b5, c1, d11), (a4, b5, c1, d12), (a4, b5, c1, d13), (a4, b5, c1, d14), (a4, b5, c1, d15), (a4, b5, c1, d16), (a4, b5, c1, d17), (a4, b5, c1, d18), (a4, b5, c1, d19), (a4, b5, c1, d20), (a4, b5, c1, d21), (a4, b5, c1, d22), (a4, b5, c2, d1), (a4, b5, c2, d2), (a4, b5, c2, d3), (a4, b5, c2, d4), (a4, b5, c2, d5), (a4, b5, c2, d6), (a4, b5, c2, d7), (a4, b5, c2, d8), (a4, b5, c2, d9), (a4, b5, c2, d10), (a4, b5, c2, d11), (a4, b5, c2, d12), (a4, b5, c2, d13), (a4, b5, c2, d14), (a4, b5, c2, d15), (a4, b5, c2, d16), (a4, b5, c2, d17), (a4, b5, c2, d18), (a4, b5, c2, d19), (a4, b5, c2, d20), (a4, b5, c2, d21), (a4, b5, c2, d22), (a4, b5, c3, d1), (a4, b5, c3, d2), (a4, b5, c3, d3), (a4, b5, c3, d4), (a4, b5, c3, d5), (a4, b5, c3, d6), (a4, b5, c3, d7), (a4, b5, c3, d8), (a4, b5, c3, d9), (a4, b5, c3, d10), (a4, b5, c3, d11), (a4, b5, c3, d12), (a4, b5, c3, d13), (a4, b5, c3, d14), (a4, b5, c3, d15), (a4, b5, c3, d16), (a4, b5, c3, d17), (a4, b5, c3, d18), (a4, b5, c3, d9), (a4, b5, c3, d20) (a4, b5, c3, d21), (a4, b5, c3, d22), (a4, b6, c1, d1), (a4, b6, c1, d2), (a4, b6, c1, d3), (a4, b6, c1, d4), (a4, b6, c1, d5), (a4, b6, c1, d6), (a4, b6, c1, d7), (a4, b6, c2, d8), (a4, b6, c2, d9), (a4, b5, c2, d10), (a4, b6, c1, d11), (a4, b6, c1, d12), (a4, b6, c1, d13), (a4, b6, c1, d14), (a4, b6, c1, d15), (a4, b6, c1, d16), (a4, b6, c1, d17), (a4, b6, c1, d18), (a4, b6, c1, d19), (a4, b6, c1, d20), (a4, b6, c1, d21), (a4, b6, c1, d22), (a4, b6, c2, d1), (a4, b6, c2, d2), (a4, b6, c2, d3), (a4, b6, c2, d4), (a4, b6, c2, d5), (a4, b6, c2, d6), (a4, b6, c2, d7), (a4, b6, c2, d8), (a4, b6, c2, d9), (a4, b6, c2, d10), (a4, b6, c2, d11), (a4, b6, c2, d12), (a4, b6, c2, d13), (a4, b6, c2, d14), (a4, b6, c2, d15), (a4, b6, c2, d16), (a4, b6, c2, d17), (a4, b6, c2, d18), (a4, b6, c2, d19), (a4, b6, c2, d20), (a4, b6, c2, d21), (a4, b6, c2, d22), (a4, b6, c3, d1), (a4, b6, c3, d2), (a4, b6, c3, d3), (a4, b6, c3, d4), (a4, b6, c3, d5), (a4, b6, c3, d6), (a4, b6, c3, d7), (a4, b6, c3, d8), (a4, b6, c3, d9), (a4, b6, c3, d10), (a4, b6, c3, d11), (a4, b6, c3, d12), (a4, b6, c3, d13), (a4, b6, c3, d14), (a4, b6, c3, d15), (a4, b6, c3, d16), (a4, b6, c3, d17), (a4, b6, c3, d18), (a4, b6, c3, d19), (a4, b6, c3, d20), (a4, b6, c3, d21), (a4, b6, c3, d22), (a5, b1, c1, d1), (a5, b1, c1, d2), (a5, b1, c1, d3), (a5, b1, c1, d4), (a5, b1, c1, d5), (a5, b1, c1, d6), (a5, b1, c1, d7), (a5, b1, c1, d8), (a5, b1, c1, d9), (a5, b1, c1, d10), (a5, b1, c1, d11), (a5, b1, c1, d12), (a5, b1, c1, d13), (a3, b1, c1, d14), (a5, b1, c1, d15), (a5, b1, c1, d16), (a5, b1, c1, d17), (a5, b1, c1, d18), (a5, b1, c1, d19), (a5, b1, c1, d20), (a5, b1, c1, d21), (a5, b1, c1, d22), (a5, b1, c2, d1), (a5, b1, c2, d2), (a5, b1, c2, d3), (a5, b1, c2, d4), (a5, b1, c2, d5), (a5, b1, c2, d6), (a5, b1, c2, d7), (a5, b1, c2, d8), (a5, b1, c2, d9), (a5, b1, c2, d10), (a5, b1, c2, d11), (a5, b1, c2, d12), (a5, b1, c2, d13), (a5, b1, c2, d14), (a3, b1, c2, d15), (a5, b1, c2, d16), (a5, b1, c2, d17), (a5, b1, c2, d18), (a5, b1, c2, d19), (a5, b1, c2, d20), (a5, b1, c2, d21), (a5, b1, c2, d22), (a5, b1, c3, d1), (a5, b1, c3, d2), (a5, b1, c3, d3), (a5, b1, c3, d4), (a5, b1, c3, d5), (a5, b1, c3, d6), (a5, b1, c3, d7), (a5, b1, c3, d8), (a5, b1, c3, d9), (a5, b1, c3, d10), (a3, b1, c3, d11), (a5, b1, c3, d12), (a5, b1, c3, d13), (a5, b1, c3, d14), (a5, b1, c3, d15), (a5, b1, c3, d16), (a5, b1, c3, d17), (a5, b1, c3, d18), (a5, b1, c3, d19), (a5, b1, c3, d20), (a3, b1, c3, d21), (a5, b1, c3, d22), (a5, b2, c1, d1), (a5, b2, c1, d2), (a5, b2, c1, d3), (a5, b2, c1, d4), (a5, b2, c1, d5), (a5, b2, c1, d6), (a3, b2, c1, d7), (a5, b2, c1, d8), (a3, b2, c1, d9), (a5, b2, c1, d10), (a5, b2, c1, d11), (a5, b2, c1, d12), (a5, b2, c1, d13), (a3, b2, c1, d14), (a5, b2, c1, d15), (a5, b2, c1, d16), (a5, b2, c1, d17), (a5, b2, c1, d18), (a5, b2, c1, d19), (a5, b2, c1, d20), (a5, b2, c1, d21), (a5, b2, c1, d22), (a3, b2, c2, d1), (a5, b2, c2, d2), (a5, b2, c2, d3), (a5, b2, c2, d4), (a5, b2, c2, d5), (a5, b2, c2, d6), (a5, b2, c2, d7), (a5, b2, c2, d8), (a5, b2, c2, d9), (a5, b2, c2, d10), (a5, b2, c2, d11), (a5, b2, c2, d12), (a5, b2, c2, d13), (a3, b2, c2, d14), (a3, b2, c2, d15), (a5, b2, c2, d16), (a5, c2, c2, d17), (a5, b2, c2, d18), (a5, b2, c2, d19), (a5, b2, c2, d20), (a3, b2, c2, d21), (a3, b2, c2, d22), (a3, b2, c3, d1), (a5, b2, c3, d2), (a3, b2, c3, d3), (a5, b2, c3, d4), (a5, b2, c3, d5), (a3, b2, c3, d6), (a5, b2, c3, d7), (a5, b2, c3, d8), (a5, b2, c3, d9), (a3, b2, c3, d10), (a5, b2, c3, d11), (a5, b2, c3, d12), (a3, b2, c3, d13), (a5, b2, c3, d14), (a5, b2, c3, d15), (a5, b2, c3, d16), (a5, b2, c3, d17), (a5, b2, c3, d18), (a5, b2, c3, d19), (a5, b2, c3, d20), (a5, b2, c3, d21), (a5, b2, c3, d22), (a5, b3, c1, d1), (a5, b3, c1, d2), (a5, b3, c1, d3), (a5, b3, c1, d4), (a5, b3, c1, d5), (a3, b3, c1, d6), (a5, b3, c1, d7), (a5, b3, c1, d8), (a5, b3, c1, d9), (a5, b3, c1, d10), (a5, b3, c1, d11), (a5, b3, c1, d12), (a5, b3, c1, d13), (a5, b3, c1, d14), (a5, b3, c1, d15), (a5, b3, c1, d16), (a5, b3, c1, d17), (a5, b3, c1, d18), (a5, b3, c1, d19), (a5, b3, c1, d20), (a5, b3, c1, d21), (a5, b3, c1, d22), (a5, b3, c2, d1), (a5, b3, c2, d2), (a5, b3, c2, d3), (a5, b3, c2, d4), (a5, b3, c2, d5), (a5, b3, c2, d6), (a5, b3, c2, d7), (a5, b3, c2, d8), (a5, b3, c2, d9), (a5, b3, c2, d10), (a5, b3, c2, d11), (a5, b3, c2, d12), (a5, b3, c2, d13), (a5, b3, c2, d14), (a5, b3, c2, d15), (a5, b3, c2, d16), (a5, b3, c2, d17), (a5, b3, c2, d18), (a5, b3, c2, d19), (a5, b3, c2, d20), (a5, b3, c2, d21), (a5, b3, c2, d22), (a5, b3, c3, d1), (a5, b3, c3, d2), (a5, b3, c3, d3), (a5, b3, c3, d4), (a5, b3, c3, d5), (a5, b3, c3, d6), (a5, b3, c3, d7), (a5, b3, c3, d8), (a5, b3, c3, d9), (a5, b3, c3, d10), (a5, b3, c3, d11), (a5, b3, c3, d12), (a5, b3, c3, d13), (a5, b3, c3, d14), (a5, b3, c3, d15), (a5, b3, c3, d16), (a5, b3, c3, d17), (a5, b3, c3, d18), (a5, b3, c3, d19), (a5, b3, c3, d20), (a5, b3, c3, d21), (a3, b3, c3, d22), (a3, b4, c1, d1), (a5, b4, c1, d2), (a5, b4, c1, d3), (a5, b4, c1, d4), (a5, b4, c1, d5), (a5, b4, c1, d6), (a5, b4, c1, d7), (a5, b4, c1, d8), (a5, b4, c1, d9), (a5, b4, c1, d10), (a5, b4, c1, d11), (a5, b4, c1, d12), (a5, b4, c1, d13), (a5, b4, c1, d14), (a5, b4, c1, d15), (a5, b4, c1, d16), (a5, b4, c1, d17), (a5, b4, c1, d18), (a5, b4, c1, d19), (a5, b4, c1, d20), (a5, b4, c1, d21), (a5, b4, c1, d22), (a5, b4, c2, d1), (a5, b4, c2, d2), (a5, b4, c2, d3), (a5, b4, c2, d4), (a5, b4, c2, d5), (a5, b4, c2, d6), (a5, b4, c2, d7), (a5, b4, c2, d8), (a5, b4, c2, d9), (a5, b4, c2, d10), (a5, b4, c2, d11), (a5, b4, c2, d12), (a5, b4, c2, d13), (a5, b4, c2, d14), (a5, b4, c2, d15), (a5, b4, c2, d21), (a5, b4, c2, d22), (a5, b4, c3, d1), (a5, b4, c3, d2), (a5, b4, c3, d3), (a5, b4, c3, d4), (a5, b4, c3, d5), (a5, b4, c3, d6), (a5, b4, c3, d7), (a5, b4, c3, d8), (a5, b4, c3, d9), (a5, b4, c3, d10), (a5, b4, c3, d11), (a5, b4, c3, d12), (a5, b4, c3, d13), (a5, b4, c3, d14), (a5, b4, c3, d15), (a5, b4, c3, d16), (a5, b4, c3, d17), (a5, b4, c3, d18), (a5, b4, c3, d19), (a5, b4, c3, d20), (a5, b4, c3, d21), (a5, b4, c3, d22), (a3, b5, c1, d1), (a5, b5, c1, d2), (a5, b5, c1, d3), (a5, b5, c1, d4), (a5, b5, c1, d5), (a5, b5, c1, d6), (a5, b5, c1, d7), (a5, b5, c1, d8), (a5, b5, c1, d9), (a5, b5, c1, d10), (a5, b5, c1, d11), (a5, b5, c1, d12), (a3, b5, c1, d13), (a3, b5, c1, d14), (a5, b5, c1, d15), (a5, b5, c1, d16), (a5, b5, c1, d17), (a5, b5, c1, d18), (a5, b5, c1, d19), (a5, b5, c1, d20), (a5, b5, c1, d21), (a5, b5, c1, d22), (a5, b5, c2, d1), (a5, b5, c2, d2), (a5, b5, c2, d3), (a5, b5, c2, d4), (a5, b5, c2, d5), (a5, b5, c2, d6), (a3, b5, c2, d7), (a5, b5, c2, d8), (a5, b5, c2, d9), (a5, b5, c2, d10), (a5, b5, c2, d11), (a5, b5, c2, d12), (a5, b5, c2, d13), (a5, b5, c2, d14), (a3, b5, c2, d15), (a5, b5, c2, d16), (a5, b5, c2, d17), (a5, b5, c2, d18), (a5, b5, c2, d19), (a3, b5, c2, d20), (a3, b5, c2, d21), (a5, b5, c2, d22), (a5, b5, c3, d1), (a5, b5, c3, d2), (a3, b5, c3, d3), (a5, b5, c3, d4), (a5, b5, c3, d5), (a5, b5, c3, d6), (a5, b5, c3, d7), (a5, b5, c3, d8), (a5, b5, c3, d9), (a5, b5, c3, d10), (a5, b5, c3, d11), (a5, b5, c3, d12), (a3, b5, c3, d13), (a5, b5, c3, d14), (a5, b5, c3, d15), (a5, b5, c3, d16), (a5, b5, c3, d17), (a5, b5, c3, d18), (a5, b5, c3, d19), (a5, b5, c3, b20), (a5, b5, c3, d21), (a5, b5, c3, d22), (a5, b6, c1, d1), (a5, b6, c1, d2), (a5, b6, c1, d3), (a5, b6, c1, d4), (a5, b6, c1, d5), (a5, b6, c1, d6), (a5, b6, c1, d7), (a5, b6, c1, d8), (a5, b6, c1, d9), (a5, b6, c1, d10), (a5, b6, c1, d11), (a5, b6, c1, d12), (a5, b6, c1, d13), (a5, b6, c1, d14), (a5, b6, c1, d15), (a5, b6, c1, d16), (a5, b6, c1, d17), (a3, b6, c1, d18), (a5, b6, c1, d19), (a5, b6, c1, d20), (a5, b6, c1, d21), (a5, b6, c1, d22), (a5, b6, c2, d1), (a5, b6, c2, d2), (a5, b6, c2, d3), (a5, b6, c2, d4), (a5, b6, c2, d5), (a3, b6, c2, d6), (a3, b6, c2, d7), (a5, b6, c2, d8), (a5, b6, c2, d9), (a5, b6, c2, d10), (a5, b6, c2, d11), (a5, b6, c2, d12), (a5, b6, c2, d13), (a5, b6, c2, d14), (a5, b6, c2, d15), (a5, b6, c2, d16), (a5, b6, c2, d17), (a5, b6, c2, d18), (a5, b6, c2, d19), (a5, b6, c2, d20), (a5, b6, c2, d21), (a5, b6, c2, d22), (a5, b6, c3, d1), (a5, b6, c3, d2), (a5, b6, c3, d3), (a5, b6, c3, d4), (a5, b6, c3, d5), (a5, b6, c3, d6), (a5, b6, c3, d7), (a5, b6, c3, d8), (a5, b6, c3, d9), (a5, b6, c3, d10), (a5, b6, c3, d11), (a5, b6, c3, d12), (a5, b6, c3, d13), (a5, b6, c3, d14), (a5, b6, c3, d15), (a5, b6, c3, d16), (a5, b6, c3, d17), (a5, b6, c3, d18), (a5, b6, c3, d19), (a5, b6, c3, d20), (a5, b6, c3, d21), (a5, b6, c3, d22), (a6, b1, c1, d1), (a6, b1, c1, d2), (a6, b1, c1, d3), (a6, b1, c1, d4), (a6, b1, c1, d5), (a6, b1, c1, d6), (a6, b1, c1, d7), (a6, b1, c1, d8), (a6, b1, c1, d9), (a6, b1, c1, d10), (a6, b1, c1, d11), (a6, b1, c1, d12), (a6, b1, c1, d13), (a6, b1, c1, d14), (a6, b1, c1, d15), (a6, b1, c1, d16), (a6, b1, c1, d17), (a6, b1, c1, d18), (a6, b1, c1, d19), (a6, b1, c1, d20), (a6, b1, c1, d21), (a6, b1, c1, d22), (a6, b1, c2, d1), (a6, b1, c2, d2), (a6, b1, c2, d3), (a6, b1, c2, d4), (a6, b1, c2, d5), (a6, b1, c2, d6), (a6, b1, c2, d7), (a6, b1, c2, d8), (a6, b1, c2, d9), (a6, b1, c2, d10), (a6, b1, c2, d11), (a6, b1, c2, d12), (a6, b1, c2, d13), (a6, b1, c2, d14), (a6, b1, c2, d15), (a6, b1, c2, d16), (a6, b1, c2, d17), (a6, b1, c2, d18), (a6, b1, c2, d19), (a6, b1, c2, d20), (a6, b1, c2, d21), (a6, b1, c2, d22), (a6, b1, c3, d1), (a6, b1, c3, d2), (a6, b1, c3, d3), (a6, b1, c3, d4), (a6, b1, c3, d5), (a6, b1, c3, d6), (a6, b1, c3, d7), (a6, b1, c3, d8), (a6, b1, c3, d9), (a6, b1, c3, d10), (a6, b1, c3, d11), (a6, b1, c3, d12), (a6, b1, c3, d13), (a6, b1, c3, d14), (a6, b1, c3, d15), (a6, b1, c3, d16), (a6, b1, c3, d17), (a6, b1, c3, d18), (a6, b1, c3, d10), (a6, b1, c3, d20), (a6, b1, c3, d21), (a6, b1, c3, d22), (a6, b2, c1, d1), (a6, b2, c1, d2), (a6, b2, c1, d3), (a6, b2, c1, d4), (a6, b2, c1, d5), (a6, b2, c1, d6), (a6, b2, c1, d7), (a6, b2, c1, d8), (a6, b2, c1, d10), (a6, b2, c1, d10), (a6, b2, c1, d11), (a6, b2, c1, d12), (a6, b2, c1, d13), (a6, c1, d14), (a6, b2, c1, d15), (a6, b2, c1, d16), (a6, b2, c1, d17), (a6, b2, c1, d18), (a6, b2, c1, d19), (a6, b2, c1, d20), (a6, b2, c1, d21), (a6, b2, c1, d22), (a6, b2, c2, d1), (a6, b2, c2, d2), (a6, b2, c2, d3), (a6, b2, c2, d4), (a6, b2, c2, d5), (a6, b2, c2, d6), (a6, b2, c2, d7), (a6, b2, c2, d8), (a6, b2, c2, d9), (a6, b2, c2, d10), (a6, b2, c2, d11), (a6, b2, c2, d12), (a6, b2, c2, d13), (a6, b2, c2, d14), (a6, b2, c2, d15), (a6, b2, c2, d16), (a6, b2, c2, d17), (a6, b2, c2, d18), (a6, b2, c2, d19), (a6, b2, c2, d20), (a6, b2, c2, d21), (a6, b2, c2, d22), (a6, b2, c3, d1), (a6, b2, c3, d2), (a6, b2, c3, d3), (a6, b2, c3, d4), (a6, b2, c3, d5), (a6, b2, c3, d6), (a6, b2, c3, d7), (a6, b2, c3, d8), (a6, b2, c3, d9), (a6, b2, c3, d10), (a6, b2, c3, d11), (a6, b2, c3, d12), (a6, b2, c3, d13), (a6, b2, c3, d14), (a6, b2, c3, d15), (a6, b2, c3, d16), (a6, b2, c3, d17), (a6, b2, c3, d18), (a6, b2, c3, d19), (a6, b2, c3, d20), (a6, b2, c3, d21), (a6, b2, c3, d22), (a6, b3, c1, d1), (a6, b3, c1, d2), (a6, b3, c1, d3), (a6, b3, c1, d4), (a6, b3, c1, d5), (a6, b3, c1, d6), (a6, b3, c1, d7), (a6, b3, c1, d8), (a6, b3, c1, d9), (a6, b3, c1, d10), (a6, b3, c1, d11), (a6, b3, c1, d12), (a6, b3, c1, d13), (a6, b3, c1, d14), (a6, b3, c1, d15), (a6, b3, c1, d16), (a6, b3, c1, d17), (a6, b3, c1, d18), (a6, b3, c1, d19), (a6, b3, c1, d20), (a6, b3, c1, d21), (a6, b3, c1, d22), (a6, b3, c2, d1), (a6, b3, c2, d2), (a6, b3, c2, d3), (a6, b3, c2, d4), (a6, b3, c2, d5), (a6, b3, c2, d6), (a6, b3, c2, d7), (a6, b3, c2, d8), (a6, b3, c2, d9), (a6, b3, c2, d10), (a6, b3, c2, d11), (a6, b3, c2, d12), (a6, b3, c2, d13), (a6, b3, c2, d14), (a6, b3, c2, d15), (a6, b3, c2, d16), (a6, b3, c2, d17), (a6, b3, c2, d18), (a6, b3, c2, d19), (a6, b3, c2, d20), (a6, b3, c2, d21), (a6, b3, c2, d22), (a6, b3, c3, d1), (a6, b3, c3, d2), (a6, b3, c3, d3), (a6, b3, c3, d4), (a6, b3, c3, d5), (a6, b3, c3, d6), (a6, b3, c3, d7), (a6, b3, c3, d8), (a6, b3, c3, d9), (a6, b3, c3, d10), (a6, b3, c3, d11), (a6, b3, c3, d12), (a6, b3, c3, d13), (a6, b3, c3, d14), (a6, b3, c3, d15), (a6, b3, c3, d16), (a6, b3, c3, d17), (a6, b3, c3, d18), (a6, b3, c3, d19), (a6, b3, c3, d20), (a6, b3, c3, d21), (a6, b3, c3, d22), (a6, b4, c1, d1), (a6, b4, c1, d2), (a6, b4, c1, d3), (a6, b4, c1, d4), (a6, b4, c1, d5), (a6, b4, c1, d6), (a6, b4, c1, d7), (a6, b4, c1, d8), (a6, b4, c1, d9), (a6, b4, c1, d10), (a6, b4, c1, d11), (a6, b4, c1, d12), (a6, b4, c1, d13), (a6, b4, c1, d14), (a6, b4, c1, d15), (a6, b4, c1, d16), (a6, b4, c1, d17), (a6, b4, c1, d18), (a6, b4, c1, d19), (a6, b4, c1, d20), (a6, b4, c1, d21), (a6, b4, c1, d22), (a6, b4, c2, d1), (a6, b4, c2, d2), (a6, b4, c2, d3), (a6, b4, c2, d4), (a6, b4, c2, d5), (a6, b4, c2, d6), (a6, b4, c2, d7), (a6, b4, c2, d8), (a6, b4, c2, d9), (a6, b4, c2, d10), (a6, b4, c2, d11), (a6, b4, c2, d12), (a6, b4, c2, d13), (a6, b4, c2, d14), (a6, b4, c2, d15), (a6, b4, c2, d16), (a6, b4, c2, d17), (a6, b4, c2, d18), (a6, b4, c2, d19), (a6, b4, c2, d20), (a6, b4, c2, d21), (a6, b4, c2, d22), (a6, b4, c3, d1), (a6, b1, c3, d12), (a6, b4, c3, d3), (a6, b4, c3, d4), (a6, b4, c3, d5), (a6, b4, c3, d6), (a6, b4, c3, d7), (a6, b4, c3, d8), (a6, b4, c3, d9), (a6, b4, c3, d10), (a6, b4, c3, d11), (a6, b4, c3, d12), (a6, b4, c3, d13), (a6, b4, c3, d14), (a6, b4, c3, d15), (a6, b4, c3, d16), (a6, b4, c3, d17), (a6, b4, c3, d18), (a6, b4, c3, d19), (a6, b4, c3, d20), (a6, b4, c3, d21), (a6, b4, c3, d22), (a6, b5, c1, d1), (a6, b5, c1, d2), (a6, b5, c1, d3), (a6, b5, c1, d4), (a6, b5, c1, d5), (a6, b5, c1, d6), (a6, b5, c1, d7), (a6, b5, c1, d8), (a6, b5, c1, d9), (a6, b5, c1, d10), (a6, b5, c1, d11), (a6, b5, c1, d12), (a6, b5, c1, d13), (a6, b5, c1, d14), (a6, b5, c1, d15), (a6, b5, c1, d16), (a6, b5, c1, d17), (a6, b5, c1, d18), (a6, b5, c1, d19), (a6, b5, c1, d20), (a6, b5, c1, d21), (a6, b5, c1, d22), (a6, b5, c2, d1), (a6, b5, c2, d2), (a6, b5, c2, d3), (a6, b5, c2, d4), (a6, b5, c2, d5), (a6, b5, c2, d6), (a6, be, c2, d7), (a6, b5, c2, d8), (a6, b5, c2, d9), (a6, b5, c2, d10), (a6, b5, c2, d11), (a6, b5, c2, d12), (a6, b5, c2, d13), (a6, b5, c2, d14), (a6, b5, c2, d15), (a6, b5, c2, d16), (a6, b5, c2, d17), (a6, b5, c2, d18), (a6, b5, c2, d19), (a6, b5, c2, d20), (a6, b5, c2, d21), (a6, b5, c2, d22), (a6, b5, c3, d1), (a6, b5, c3, d2), (a6, b5, c3, d3), (a6, b5, c3, d4), (a6, b5, c3, d5), (a6, b5, c3, d6), (a6, b5, c3, d7), (a6, b5, c3, d8), (a6, b5, c3, d9), (a6, b5, c3, d10), (a6, b5, c3, d11), (a6, b5, c3, d12), (a6, b5, c3, d13), (a6, b5, c3, d14), (a6, b5, c3, d15), (a6, b5, c3, d16), (a6, b5, c3, d17), (a6, b5, c3, d18), (a3, b5, c3, d19), (a6, b5, c3, d20), (a6, b5, c3, d21), (a6, b5, c3, d22), (a6, b6, c1, d1), (a6, b6, c1, d2), (a6, b6, c1, d3), (a6, b6, c1, d4), (a6, b6, c1, d5), (a6, b6, c1, d6), (a6, b6, c1, d7), (a6, b6, c1, d8), (a6, b6, c1, d9), (a6, b6, c1, d10), (a6, b6, c1, d11), (a6, b6, c1, d12), (a6, b6, c1, d13), (a6, b6, c1, d14), (a6, b6, c1, d15), (a6, b6, c1, d16), (a6, b6, c1, d17), (a6, b6, c1, d18), (a6, b6, c1, d19), (a6, b6, c1, d20), (a6, b6, c1, d21), (a6, b6, c1, d22), (a6, b6, c2, d1), (a6, b6, c2, d2), (a6, b6, c2, d3), (a6, b6, c2, d4), (a6, b6, c2, d5), (a6, b6, c2, d6), (a6, b6, c2, d7), (a6, b6, c2, d8), (a6, b6, c2, d9), (a6, b6, c2, d10), (a6, b6, c2, d11), (a6, b6, c2, d12), (a6, b6, c2, d13), (a6, b6, c2, d14), (a6, b6, c2, d15), (a6, b6, c2, d16), (a6, b6, c2, d17), (a6, b6, c2, d18), (a6, b6, c2, d19), (a6, b6, c2, d20), (a6, b6, c2, d21), (a6, b6, c2, d22), (a6, b6, c3, d1), (a6, b6, c3, d2), (a6, b6, c3, d3), (a6, b6, c3, d4), (a6, b6, c3, d5), (a6, b6, c3, d6), (a6, b6, c3, d7), (a6, b6, c3, d8), (a6, b6, c3, d9), (a6, b6, c3, d10), (a6, b6, c3, d11), (a6, b6, c3, d12), (a6, b6, c3, d13), (a6, b6, c3, d14), (a6, b6, c3, d15), (a6, b6, c3, d16), (a6, b6, c3, d17), (a6, b6, c3, d18), (a6, b6, c3, d19), (a6, b6, c3, d20), (a6, b6, c3, d21), (a6, b6, c3, d22), (a7, b1, c1, d1), (a7, b1, c1, d2), (a7, b1, c1, d3), (a7, b1, c1, d4), (a7, b1, c1, d5), (a7, b1, c1, d6), (a7, b1, c1, d7), (a7, b1, c1, d8), (a7, b1, c1, d9), (a7, b1, c1, d10), (a7, b1, c1, d11), (a7, b1, c1, d12), (a7, b1, c1, d13), (a7, b1, c1, d14), (a7, b1, c1, d15), (a7, b1, c1, d16), (a7, b1, c1, d17), (a7, b1, c1, d18), (a7, b1, c1, d19), (a7, b1, c1, d20), (a7, b1, c1, d21), (a7, b1, c1, d22), (a7, b1, c2, d1), (a7, b1, c2, d2), (a7, b1, c2, d3), (a7, b1, c2, d4), (a7, b1, c2, d5), (a7, b1, c2, d6), (a7, b1, c2, d7), (a7, b1, c2, d8), (a7, b1, c2, d9), (a7, b1, c2, d10), (a7, b1, c2, d11), (a7, b1, c2, d12), (a7, b1, c2, d13), (a7, b1, c2, d14), (a7, b1, c2, d15), (a7, b1, c2, d16), (a7, b1, c2, d17), (a7, b1, c2, d18), (a7, b1, c2, d19), (a7, b1, c2, d20), (a7, b1, c2, d21), (a7, b1, c2, d22), (a7, b1, c3, d1), (a7, b1, c3, d2), (a7, b1, c3, d3), (a7, b1, c3, d4), (a7, b1, c3, d5), (a7, b1, c3, d6), (a7, b1, c3, d7), (a7, b1, c3, d8), (a7, b1, c3, d9), (a7, b, c3, d10), (a7, b1, c3, d8), (a7, b1, c3, d12), (a7, b1, c3, d13), (a7, b1, c3, d14), (a7, b1, c3, d15), (a7, b1, c3, d16), (a7, b1, c3, d17), (a7, b1, c3, d18), (a7, b1, c3, d19), (a7, b1, c3, d20), (a7, b1, c3, d21), (a7, b1, c3, d22), (a7, b2, c1, d1), (a7, b2, c1, d2), (a7, b2, c1, d3), (a7, b2, c1, d4), (a7, b2, c1, d5), (a7, b2, c1, d6), (a1, b2, c1, d7), (a7, b2, c1, d8), (a7, b2, c1, d9), (a7, b2, c1, d10), (a7, b2, c1, d11), (a7, b2, c1, d12), (a7, b2, c1, d13), (a7, b2, c1, d14), (a7, b2, c1, d15), (a7, b2, c1, d16), (a7, b2, c1, d17), (a7, b2, c1, d18), (a7, b2, c1, d19), (a7, b2, c1, d20), (a7, b2, c1, d21), (a7, b2, c1, d22), (a7, b2, c2, d1), (a7, b2, c2, d2), (a7, b2, c2, d3), (a7, b2, c2, d4), (a7, b2, c2, d5), (a7, b2, c2, d6), (a7, b2, c2, d7), (a7, b2, c2, d8), (a7, b2, c2, d9), (a7, b2, c2, d10), (a7, b2, c2, d11), (a7, b2, c2, d12), (a7, b2, c2, d13), (a7, b2, c2, d14), (a7, b2, c2, d15), (a7, b2, c2, d16), (a7, b2, c2, d17), (a7, b2, c2, d18), (a7, b2, c2, d19), (a7, b2, c2, d20), (a7, b2, c2, d21), (a7, b2, c2, d22), (a7, b2, c3, d1), (a7, b2, c3, d2), (a7, b2, c3, d3), (a7, b2, c3, d4), (a7, b2, c3, d5), (a7, b2, c3, d6), (a7, b2, c3, d7), (a7, b2, c3, d8), (a7, b2, c3, d9), (a7, b2, c3, d10), (a7, b2, c3, d11), (a7, b2, c3, d12), (a7, b2, c3, d13), (a7, b2, c3, d14), (a7, b2, c3, d15), (a7, b2, c3, d16), (a7, b2, c3, d17), (a7, b2, c3, d18), (a7, b2, c3, d19), (a7, b2, c3, d20), (a7, b2, c3, d21), (a7, b2, c3, d22), (a7, b3, c1, d1), (a7, b3, c1, d2), (a7, b3, c1, d3), (a7, b3, c1, d4), (a7, b3, c1, d5), (a7, b3, c1, d6), (a7, b3, c1, d7), (a7, b3, c1, d8), (a7, b3, c1, d9), (a7, b3, c1, d10), (a7, b3, c1, d11), (a7, b3, c1, d12), (a7, b3, c1, d13), (a7, b3, c1, d14), (a7, b3, c1, d15), (a7, b3, c1, d16), (a7, b3, c1, d17), (a7, b3, c1, d18), (a7, b3, c1, d19), (a7, b3, c1, d20), (a7, b3, c1, d21), (a7, b3, c1, d22), (a7, b3, c2, d1), (a7, b3, c2, d2), (a7, b3, c2, d3), (a7, b3, c2, d4), (a7, b3, c2, d5), (a7, b3, c2, d6), (a7, b3, c2, d7), (a7, b3, c2, d8), (a7, b3, c2, d9), (a7, b3, c2, d10), (a7, b3, c2, d11), (a7, b3, c2, d12), (a7, b3, c2, d13), (a7, b3, c2, d14), (a7, b3, c2, d15), (a7, b3, c2, d16), (a7, b3, c2, d17), (a7, b3, c2, d18), (a7, b3, c2, d19), (a7, b3, c2, d20), (a7, b3, c2, d21), (a7, b3, c2, d22), (a7, b3, c3, d1), (a7, b3, c3, d2), (a7, b3, c3, d3), (a7, b3, c3, d4), (a7, b3, c3, d5), (a7, b3, c3, d6), (a7, b3, c3, d7), (a7, b3, c3, d8), (a7, b3, c3, d9), (a7, b3, c3, d10), (a7, b3, c3, d11), (a7, b3, c3, d12), (a7, b3, c3, d13), (a7, b3, c3, d14), (a7, b3, c3, d15), (a7, b3, c3, d16), (a7, b3, c3, d17), (a7, b3, c3, d18), (a7, b3, c3, d19), (a7, b3, c3, d20), (a7, b3, c3, d21), (a7, b3, c3, d22), (a7, b4, c1, d1), (a7, b4, c1, d2), (a7, b4, c1, d3), (a7, b4, c1, d4), (a7, b4, c1, d5), (a7, b4, c1, d6), (a7, b4, c1, d7), (a7, b4, c1, d8), (a7, b4, c1, d9), (a7, b4, c1, d10), (a7, b4, c1, d11), (a7, b4, c1, d12), (a7, b4, c1, d13), (a7, b4, c1, d14), (a7, b4, c1, d15), (a7, b4, c1, d16), (a7, b4, c1, d17), (a7, b4, c1, d18), (a7, b4, c1, d19), (a7, b4, c1, d20), (a7, b4, c1, d21), (a7, b4, c1, d22), (a7, b4, c2, d1), (a7, b4, c2, d2), (a7, b4, c2, d3), (a7, b4, c2, d4), (a7, b4, c2, d5), (a7, b4, c2, d6), (a7, b4, c2, d7), (a7, b4, c2, d8), (a7, b4, c2, d9), (a7, b4, c2, d10), (a7, b4, c2, d11), (a7, b4, c2, d12), (a7, b4, c2, d13), (a7, b4, c2, d14), (a7, b4, c2, d15), (a7, b4, c2, d16), (a7, b4, c2, d17), (a7, b4, c2, d18), (a7, b4, c2, d19), (a7, b4, c2, d20), (a7, b4, c2, d21), (a7, b4, c2, d22), (a7, b4, c3, d1), (a7, b4, c3, d2), (a7, b4, c3, d3), (a7, b4, c3, d4), (a7, b4, c3, d5), (a7, b4, c3, d6), (a7, b4, c3, d7), (a7, b4, c3, d8), (a7, b4, c3, d9), (a7, b4, c3, d10), (a7, b4, c3, d11), (a7, b4, c3, d12), (a7, b4, c3, d13), (a7, b4, c3, d14), (a7, b4, c3, d15), (a7, b4, c3, d16), (a7, b4, c3, d17), (a7, b4, c3, d18), (a7, b4, c3, d19), (a7, b4, c3, d20), (a7, b4, c3, d21), (a7, b4, c3, d22), (a7, b5, c1, d1), (a7, b5, c1, d2), (a7, b5, c1, d3), (a7, b5, c1, d4), (a7, b5, c1, d5), (a7, b5, c1, d6), (a7, b5, c1, d7), (a7, b5, c1, d8), (a7, b5, c1, d9), (a7, b5, c1, d10), (a7, b5, c1, d11), (a7, b5, c1, d12), (a7, b5, c1, d13), (a7, b5, c1, d14), (a7, b5, c1, d15), (a7, b5, c1, d16), (a7, b5, c1, d17), (a7, b5, c1, d18), (a7, b5, c1, d19), (a7, b5, c1, d20), (a7, b5, c1, d21), (a7, b5, c1, d22), (a7, b5, c2, d1), (a7, b5, c2, d2), (a7, b5, c2, d3), (a7, b5, c2, d4), (a7, b5, c2, d5), (a7, b5, c2, d6), (a7, b5, c2, d7), (a7, b5, c2, d8), (a7, b5, c2, d9), (a7, b5, c2, d10), (a7, b5, c2, d11), (a7, b5, c2, d12), (a7, b5, c2, d13), (a7, b5, c2, d14), (a7, b5, c2, d15), (a7, b5, c2, d16), (a7, b5, c2, d17), (a7, b5, c2, d18), (a7, b5, c2, d19), (a7, b5, c2, d20), (a7, b5, c2, d21), (a7, b5, c2, d22), (a7, b5, c3, d1), (a7, b5, c3, d2), (a7, b5, c3, d3), (a7, b5, c3, d4), (a7, b5, c3, d5), (a7, b5, c3, d6), (a7, b5, c3, d7), (a7, b5, c3, d8), (a7, b6, c3, d9), (a7, b5, c3, d10), (a7, b5, c3, d11), (a7, b5, c3, d12), (a7, b5, c3, d13), (a7, b5, c3, d14), (a7, b5, c3, d15), (a7, b5, c3, d16), (a7, b5, c3, d17), (a7, b5, c3, d18), (a7, b5, c3, d19), (a7, b5, c3, d20), (a7, b5, c3, d21), (a7, b5, c3, d22), (a7, b6, c1, d1), (a7, b6, c1, d2), (a7, b6, c1, d3), (a7, b6, c1, d4), (a7, b6, c1, d5), (a7, b6, c1, d6), (a7, b6, c1, d7), (a7, b6, c1, d8), (a7, b6, c1, d9), (a7, b6, c1, d10), (a7, b6, c1, d11), (a7, b6, c1, d12), (a7, b6, c1, d13), (a7, b6, c1, d14), (a7, b6, c1, d15), (a7, b6, c1, d16), (a7, b6, c1, d17), (a7, b6, c1, d18), (a7, b6, c1, d19), (a7, b6, c1, d20), (a7, b6, c1, d21), (a7, b6, c1, d22), (a7, b6, c2, d1), (a7, b6, c2, d2), (a7, b6, c2, d3), (a7, b6, c2, d4), (a7, b6, c2, d5), (a7, b6, c2, d6), (a7, b6, c2, d7), (a7, b6, c2, d8), (a7, b6, c2, d9), (a7, b6, c2, d10), (a7, b6, c2, d11), (a7, b6, c2, d12), (a7, b6, c2, d13), (a7, b6, c2, d14), (a7, b6, c2, d15), (a7, b6, c2, d16), (a7, b6, c2, d17), (a7, b6, c2, d18), (a7, b6, c2, d19), (a7, b6, c2, d20), (a, b6, c2, d21), (a7, b6, c2, d22), (a7, b6, c3, d1), (a7, b6, c3, d2), (a7, b6, c3, d3), (a7, b6, c3, d4), (a7, b6, c3, d5), (a7, b6, c3, d6), (a7, b6, c3, d7), (a7, b6, c3, d8), (a7, b6, c3, d9), (a7, b6, c3, d10), (a7, b6, c3, d11), (a7, b6, c3, d12), (a7, b6, c3, d13), (a7, b6, c3, d14), (a7, b6, c3, d15), (a7, b6, c3, d16), (a7, b6, c3, d17), (a7, b6, c3, d18), (a7, b6, c3, d19), (a7, b6, c3, d20), (a7, b6, c3, d21), (a7, b6, c3, d22), (a8, b1, c1, d1), (a8, b1, c1, d2), (a8, b1, c1, d3), (a8, b1, c1, d4), (a3, b1, c1, d5), (a8, b1, c1, d6), (a8, b1, c1, d7), (a8, b1, c1, d8), (a8, b1, c1, d9), (a8, b1, c1, d10), (a8, b1, c1, d11), (a8, b1, c1, d12), (a8, b1, c1, d13), (a8, b1, c1, d14), (a8, b1, c1, d16), (a8, b1, c1, d16), (a8, b1, c1, d17), (a8, b1, c1, d18), (a8, b1, c1, d19), (a8, b1, c1, d20), (a8, b1, c1, d21), (a8, b1, c1, d22), (a8, b1, c2, d1), (a8, b1, c2, d2), (a8, b1, c2, d3), (a8, b1, c2, d4), (a8, b1, c2, d5), (a8, b1, c2, d6), (a8, b1, c2, d7), (a8, b1, c2, d8), (a8, b1, c2, d9), (a8, b1, c2, d10), (a8, b1, c2, d11), (a8, b1, c2, d12), (a8, b1, c2, d13), (a8, b1, c2, d14), (a8, b1, c2, d15), (a8, b1, c2, d16), (a8, b1, c2, d17), (a8, b1, c2, d18), (a8, b1, c2, d19), (a8, b1, c2, d20), (a8, b1, c2, d21), (a8, b1, c2, d22), (a8, b1, c3, d1), (a8, b1, c3, d2), (a8, b1, c3, d3), (a8, b1, c3, d4), (a8, b1, c3, d5), (a8, b1, c3, d6), (a8, b1, c3, d7), (a8, b1, c3, d8), (a8, b1, c3, d9), (a8, b1, b3, d10), (a8, b1, c3, d11), (a8, b1, c3, d12), (a8, b1, c3, d13), (a8, b1, c3, d14), (a8, b1, c3, d15), (a8, b1, c3, d16), (a8, b1, c3, d17), (a8, b1, c3, d18), (a8, b1, c3, d19), (a8, b1, c3, d20), (a8, b1, c3, d21), (a8, b1, c3, d22), (a8, b2, c1, d1), (a8, b2, c1, d2), (a8, b2, c1, d3), (a8, b2, c1, d4), (a8, b2, c1, d5), (a8, b2, c1, d6), (a8, b2, c1, d7), (a8, b2, c1, d8), (a8, b2, c1, d9), (a8, b2, c1, d10), (a8, b2, c1, d11), (a8, b2, c1, d12), (a8, b2, c1, d13), (a8, b2, c1, d14), (a8, b2, c1, d15), (a8, b2, c1, d16), (a8, b2, c1, d17), (a8, b2, c1, d18), (a8, b2, c1, d19), (a8, b2, c1, d20), (a8, b2, c1, d21), (a8, b2, c1, d22), (a8, b2, c2, d1), (a8, b2, c2, d2), (a8, b2, c2, d3), (a8, b2, c2, d4), (a8, b2, c2, d5), (a8, b2, c2, d6), (a8, b2, c2, d7), (a8, b2, c2, d8), (a8, b2, c2, d9), (a8, b2, c2, d10), (a8, b2, c2, d11), (a8, b2, c2, d12), (a8, b2, c2, d13), (a8, b2, c2, d14), (a8, b2, c2, d15), (a8, b2, c2, d16), (a8, b2, c2, d17), (a8, b2, c2, d18), (a8, b2, c2, d19), (a8, b2, c2, d20), (a8, b2, c2, d21), (a8, b2, c2, d22), (a8, b2, c3, d1), (a8, b2, c3, d2), (a8, b2, c3, d3), (a8, b2, c3, d4), (a8, b2, c3, d5), (a8, b2, c3, d6), (a8, b2, c3, d7), (a8, b2, c3, d8), (a8, b2, c3, d9), (a8, b2, c3, d10), (a8, b2, c3, d11), (a8, b2, c3, d12), (a8, b2, c3, d13), (a8, b2, c3, d14), (a8, b2, c3, d15), (a8, b2, c3, d16), (a8, b2, c3, d17), (a8, b2, c3, d18), (a8, b2, c3, d19), (a8, b2, c3, d20), (a8, b2, c3, d21), (a8, b2, c3, d22), (a8, b3, c1, d1), (a8, b3, c1, d2), (a8, b3, c1, d3), (a8, b3, c1, d4), (a8, b3, c1, d5), (a8, b3, c1, d6), (a8, b3, c1, d7), (a8, b3, c1, d8), (a8, b3, c1, d9), (a8, b3, c1, d10), (a8, b3, c1, d11), (a8, b3, c1, d12), (a8, b3, c1, d13), (a8, b3, c1, d14), (a8, b3, c1, d15), (a8, b3, c1, d16), (a8, b3, c1, d17), (a8, b3, c1, d18), (a8, b3, c1, d19), (a8, b3, c1, d20), (a8, b3, c1, d21), (a8, b3, c1, d22), (a8, b3, c2, d1), (a8, b3, c2, d2), (a8, b3, c2, d3), (a8, b3, c2, d4), (a8, b3, c2, d5), (a8, b3, c2, d6), (a8, b3, c2, d7), (a8, b3, c2, d8), (a8, b3, c2, d9), (a8, b3, c2, d10), (a8, b3, c2, d11), (a8, b3, c2, d12), (a8, b3, c2, d13), (a8, b3, c2, d14), (a8, b3, c2, d15), (a8, b3, c2, d16), (a8, b3, c2, d17), (a8, b3, c2, d18), (a8, b3, c2, d19), (a8, b3, c2, d20), (a8, b3, c2, d21), (a8, b3, c2, d22), (a8, b3, c3, d1), (a8, b3, c3, d2), (a8, b3, c3, d3), (a8, b3, c3, d4), (a8, b3, c3, d5), (a8, b3, c3, d6), (a8, b3, c3, d7), (a8, b3, c3, d8), (a8, b3, c3, d9), (a3, b3, c3, d10), (a8, b3, c3, d11), (a8, b3, c3, d12), (a8, b3, c3, d13), (a3, b3, c3, d14), (a8, b3, c3, d15), (a8, b3, c3, d16), (a8, b3, c3, d17), (a8, b3, c3, d18), (a8, b3, c3, d19), (a8, b3, c3, d20), (a8, b3, c3, d21), (a8, b3, c3, d22), (a3, b4, c1, d1), (a8, b4, c1, d2), (a8, b4, c1, d3), (a8, b4, c1, d4), (a8, b4, c1, d5), (a8, b4, c1, d6), (a8, b4, c1, d7), (a8, b4, c1, d8), (a8, b4, c1, d9), (a8, b4, c1, d10), (a3, b4, c1, d11), (a8, b4, c1, d12), (a8, b4, c1, d13), (a8, b4, c1, d14), (a3, b4, c1, d15), (a8, b4, c1, d16), (a8, b4, c1, d17), (a8, b4, c1, d18), (a8, b4, c1, d19), (a8, b4, c1, d20), (a8, b4, c1, d21), (a8, b4, c1, d22), (a8, b4, c2, d1), (a8, b4, c2, d2), (a8, b4, c2, d3), (a8, b4, c2, d4), (a8, b4, c2, d5), (a8, b4, c2, d6), (a8, b4, c2, d7), (a8, b4, c2, d8), (a3, b4, c2, d9), (a8, b4, c2, d10), (a8, b4, c2, d11), (a8, b4, c2, d12), (a8, b4, c2, d13), (a8, b4, c2, d14), (a8, b4, c2, d15), (a8, b4, c2, d16), (a8, b4, c2, d17), (a8, b4, c2, d18), (a8, b4, c2, d19), (a8, b4, c2, d20), (a8, b4, c2, d21), (a8, b4, c2, d22), (a8, b4, c3, d1), (a8, b4, c3, d2), (a8, b4, c3, d3), (a8, b4, c3, d4), (a8, b4, c3, d5), (a8, b4, c3, d6), (a8, b4, c3, d7), (a8, b4, c3, d8), (a8, b4, c3, d9), (a8, b4, c3, d10), (a8, b4, c3, d11), (a8, b4, c3, d12), (a8, b4, c3, d13), (a8, b4, c3, d14), (a8, b4, c3, d15), (a8, b4, c3, d16), (a3, b4, c3, d17), (a8, b4, c3, d18), (a8, b4, c3, d19), (a8, b4, c3, d20), (a3, b4, d21), (a3, b4, c3, d22), (a8, b5, c1, d1), (a8, b5, c1, d2), (a8, b5, c1, d3), (a8, b5, c1, d4), (a8, b5, c1, d5), (a5, b5, c1, d6), (a8, b5, c1, d7), (a8, b5, c1, d8), (a8, b5, c1, d9), (a8, b5, c1, d10), (a8, b5, c1, d11), (a8, b5, c1, d12), (a3, b5, c1, d13), (a8, b5, c1, d14), (a8, b5, c1, d15), (a8, b5, c1, d16), (a8, b5, c1, d17), (a8, b5, c1, d18), (a3, b5, c1, d19), (a8, b5, c1, d20), (a8, b5, c1, d21), (a8, b5, c1, d22), (a8, b5, c2, d1), (a8, b5, c2, d2), (a8, b5, c2, d3), (a8, b5, c2, d4), (a8, b5, c2, d5), (a8, b5, c2, d6), (a8, b5, c2, d7), (a8, b5, c2, d8), (a3, b5, c2, d9), (a8, b5, c2, d10), (a8, b5, c2, d11), (a8, b5, c2, d12), (a8, b5, c2, d13), (a8, b5, c2, d14), (a8, b5, c2, d15), (a8, b5, c2, d16), (a8, b5, c2, d17), (a8, b5, c2, d18), (a8, b5, c2, d19), (a3, b5, c2, d20), (a8, b5, c2, d21), (a8, b5, c2, d22), (a8, b5, c3, d1), (a8, b5, c3, d2), (a8, b5, c3, d3), (a8, b5, c3, d4), (a8, b5, c3, d5), (a8, b5, c3, d6), (a8, b5, c3, d7), (a8, b5, c3, d8), (a8, b5, c3, d9), (a3, b5, c3, d10), (a5, b5, c3, d11), (a8, b5, c3, d12), (a3, b5, c3, d13), (a8, b5, c3, d14), (a8, b5, c3, d15), (a8, b5, c3, d16), (a8, b5, c3, d17), (a8, b5, c3, d18), (a8, b5, c3, d19), (a8, b5, c3, d20), (a8, b5, c3, d21), (a8, b5, c3, d22), (a8, b6, c1, d1), (a8, b6, c1, d2), (a8, b6, c1, d3), (a8, b6, c1, d4), (a8, b6, c1, d5), (a8, b6, c1, d6), (a8, b6, c1, d7), (a8, b6, c1, d8), (a8, b6, c1, d9), (a8, b6, c1, d10), (a8, b6, c1, d11), (a8, b6, c1, d12), (a8, b6, c1, d13), (a3, b6, c1, d14), (a8, b6, c1, d15), (a8, b6, c1, d16), (a8, b6, c1, d17), (a8, b6, c1, d18), (a8, b6, c1, d19), (a3, b6, c1, d20), (a8, b6, c1, d21), (a8, b6, c1, d22), (a8, b6, c2, d1), (a8, b6, c2, d2), (a8, b6, c2, d3), (a8, b6, c2, d4), (a8, b6, c2, d5), (a8, b6, c2, d6), (a3, b6, c2, d7), (a8, b6, c2, d8), (a8, b6, c2, d9), (a8, b6, c2, d19), (a8, b6, c2, d11), (a8, b6, c2, d12), (a8, b6, c2, d13), (a8, b6, c2, d14), (a8, b6, c2, d15), (a8, b6, c2, d16), (a8, b6, c2, d17), (a8, b6, c2, d18), (a8, b6, c2, d19), (a3, b6, c2, d20), (a8, b6, c2, d21), (a8, b6, c2, d22), (a8, b6, c3, d1), (a8, b6, c3, d2), (a3, b6, c3, d3), (a8, b6, c3, d4), (a8, b6, c3, d5), (a8, b6, c3, d6), (a8, b6, c3, d7), (a3, b6, c3, d8), (a8, b6, c3, d9), (a8, b6, c3, d10), (a8, b7, c3, d11), (a8, b6, c3, d12), (a8, b6, c3, d13), (a8, b6, c3, d14), (a8, b6, c3, d15), (a8, b6, c3, d16), (a8, b6, c3, d17), (a8, b6, c3, d18), (a8, b6, c3, d19), (a3, b6, c3, d20), (a8, b6, c3, d21), (a3, b6, c3, d22), (a9, b1, c1, d1), (a9, b1, c1, d2), (a9, b1, c1, d3), (a9, b1, c1, d4), (a9, b1, c1, d5), (a9, b1, c1, d6), (a9, b1, c1, d7), (a9, b1, c1, d8), (a9, b1, c1, d9), (a9, b1, c1, d10), (a9, b1, c1, d11), (a9, b1, c1, d12), (a9, b1, c1, d13), (a9, b1, c1, d14), (a9, b1, c1, d15), (a9, b1, c1, d16), (a9, b1, c1, d17), (a9, b1, c1, d18), (a9, b1, c1, d19), (a9, b1, c1, d20), (a9, b1, c1, d21), (a9, b1, c1, d22), (a9, b1, c2, d1), (a9, b1, c2, d2), (a9, b1, c2, d3), (a9, b1, c2, d4), (a9, b1, c2, d5), (a9, b1, c2, d6), (a9, b1, c2, d7), (a9, b1, c2, d8), (a9, b1, c2, d9), (a9, b1, c2, d10), (a9, b1, c2, d11), (a9, (a9, c2, d12), (a9, b1, c2, d13), (a9, b1, c2, d14), (a9, b1, c2, d15), (a9, b1, c2, d16), (a9, b1, c2, d17), (a9, b1, c2, d18), (a9, b1, c2, d19), (a9, b1, c2, d20), (a9, b1, c2, d21), (a9, b1, c2, d22), (a9, b1, c3, d1), (a9, b1, c3, d2), (a9, b1, c3, d3), (a9, b1, c3, d4), (a9, b1, c3, d5), (a9, b1, c3, d6), (a9, b1, c3, d7), (a9, b1, c3, d8), (a9, b1, c3, d9), (a9, b1, c3, d10), (a9, b1, c3, d11), (a9, b1, c3, d12), (a9, b1, c3, d13), (a9, b1, c3, d14), (a9, b1, c3, d15), (a9, b1, c3, d16), (a9, b1, c3, d17), (a9, b1, c3, d18), (a9, b1, c3, d19), (a9, b1, c3, d20), (a9, b1, c3, d21), (a9, b1, c3, d22), (a9, b2, c1, d1), (a9, b2, c1, d2), (a9, b2, c1, d3), (a9, b2, c1, d4), (a9, b2, c1, d5), (a9, b2, c1, d6), (a9, b2, c1, d7), (a9, b2, c1, d8), (a9, b2, c1, d9), (a9, b2, c1, d10), (a9, b2, c1, d11), (a9, b2, c1, d12), (a9, b2, c1, d13), (a9, b2, c1, d14), (a9, b2, c1, d15), (a9, b2, c1, d16), (a9, b2, c1, d17), (a9, b2, c1, d18), (a9, b2, c1, d19), (a9, b2, c1, d20), (a9, b2, c1, d21), (a9, b2, c1, d22), (a9, b2, c2, d1), (a9, b2, c2, d2), (a9, b2, c2, d3), (a9, b2, c2, d4), (a9, b2, c2, d5), (a9, b2, c2, d6), (a9, b2, c2, d7), (a9, b2, c2, d8), (a9, b2, c2, d9), (a9, b2, c2, d10), (a9, b2, c2, d11), (a9, b2, c2, d12), (a9, b2, c2, d13), (a9, b2, c2, d14), (a9, b2, c2, d15), (a9, b2, c2, d16), (a9, b2, c2, d17), (a9, b2, c2, d18), (a9, b2, c2, d19), (a9, b2, c2, d20), (a9, b2, c2, d21), (a9, b2, c2, d22), (a9, b2, c3, d1), (a9, b2, c3, d2), (a9, b2, c3, d3), (a9, b2, c3, d4), (a9, b2, c3, d5), (a9, b2, c3, d6), (a9, b2, c3, d7), (a9, b2, c3, d8), (a9, b2, c3, d9), (a9, b2, c3, d10), (a9, b2, c3, d11), (a9, b2, c3, d12), (a9, b2, c3, d13), (a9, b2, c3, d14), (a9, b2, c3, d15), (a9, b2, c3, d16), (a9, b2, c3, d17), (a9, b2, c3, d18), (a9, b2, c3, d19), (a9, b2, c3, d20), (a9, b2, c3, d21), (a9, b2, c3, d22), (a9, b3, c1, d1), (a9, b3, c1, d2), (a9, b3, c1, d3), (a9, b3, c1, d4), (a9, b3, c1, d5), (a9, b3, c1, d6), (a9, b3, c1, d7), (a9, b3, c1, d8), (a9, b3, c1, d9), (a9, b3, c1, d10), (a9, b3, c1, d11), (a9, b3, c1, d12), (a9, b3, c1, d13), (a9, b3, c1, d14), (a9, b3, c1, d15), (a9, b3, c1, d16), (a9, b3, c1, d17), (a9, b3, c1, d18), (a9, b3, c1, d19), (a9, b3, c1, d20), (a9, b3, c1, d21), (a9, b3, c1, d22), (a9, b3, c2, d1), (a9, b3, c2, d2), (a9, b3, c2, d3), (a9, b3, c2, d4), (a9, b3, c2, d5), (a9, b3, c2, d6), (a9, b3, c2, d7), (a9, b3, c2, d8), (a9, b3, c2, d9), (a9, b3, c2, d10), (a9, b3, c2, d11), (a9, b3, c2, d12), (a9, b3, c2, d13), (a9, b3, c2, d14), (a9, b3, c2, d15), (a9, b3, c2, d16), (a9, b3, c2, d17), (a9, b3, c2, d18), (a9, b3, c2, d19), (a9, b3, c2, d20), (a9, b3, c2, d21), (a9, b3, c2, d22), (a9, b3, c3, d1), (a9, b3, c3, d2), (a9, b3, c3, d3), (a9, b3, c3, d4), (a9, b3, c3, d5), (a9, b3, c3, d6), (a9, b3, c3, d7), (a9, b3, c3, d8), (a9, b3, c3, d9), (a9, b3, c3, d10), (a9, b3, c3, d11), (a9, b3, c3, d12), (a9, b3, c3, d13), (a9, b3, c3, d14), (a9, b3, c3, d15), (a9, b3, c3, d16), (a9, b3, c3, d17), (a9, b3, c3, d18), (a9, b3, c3, d19), (a9, b3, c3, d20), (a9, b3, c3, d21), (a9, b3, c3, d22), (a9, b4, c1, d1), (a9, b4, c1, d2), (a9, b4, c1, d3), (a9, b4, c1, d4), (a9, b4, c1, d5), (a9, b4, c1, d6), (a9, b4, c1, d7), (a9, b4, c1, d8), (a9, b4, c1, d9), (a9, b4, c1, d10), (a9, b4, c1, d11), (a9, b4, c1, d12), (a9, b4, c1, d13), (a9, b4, c1, d14), (a9, b4, c1, d15), (a9, b4, c1, d16), (a9, b4, c1, d17), (a9, b4, c1, d18), (a9, b4, c1, d19), (a9, b4, c1, d20), (a9, b4, c1, d21), (a9, b4, c1, d22), (a9, b4, c2, d1), (a9, b4, c2, d2), (a9, b4, c2, d3), (a9, b4, c2, d4), (a9, b4, c2, d5), (a9, b4, c2, d6), (a9, b4, c2, d7), (a9, b4, c2, d8), (a9, b4, c2, d9), (a9, b4, c2, d10), (a9, b4, c2, d11), (a9, b4, c2, d12), (a9, b4, c2, d13), (a9, b4, c2, d14), (a9, b4, c2, d15), (a9, b4, c2, d16), (a9, b4, c2, d17), (a9, b4, c2, d18), (a9, b4, c2, d19), (a9, b4, c2, d20), (a9, b4, c2, d21), (a9, b4, c2, d22), (a9, b4, c3, d1), (a9, b4, c3, d2), (a9, b4, c3, d3), (a9, b4, c3, d4), (a9, b4, c3, d5), (a9, b4, c3, d6), (a9, b4, c3, d7), (a9, b4, c3, d8), (a9, b4, c3, d9), (a9, b4, c3, d10), (a9, b4, c3, d11), (a9, b4, c3, d12), (a9, b4, c3, d13), (a9, b4, c3, d14), (a9, b4, c3, d15), (a9, b4, c3, d16), (a9, b4, c3, d17), (a9, b4, c3, d18), (a9, b4, c3, d19), (a9, b4, c3, d20), (a9, b4, c3, d21), (a9, b4, c3, d22), (a9, b5, c1, d1), (a9, b6, c1, d2), (a9, b5, c1, d3), (a9, b5, c1, d4), (a9, b5, c1, d5), (a9, b5, c1, d6), (a9, b5, c1, d7), (a9, b5, c1, d8), (a9, b5, c1, d9), (a9, b5, c1, d10), (a9, b5, c1, d11), (a9, b5, c1, d12), (a9, b5, c1, d13), (a9, b5, c1, d14), (a9, b5, c1, d15), (a9, b5, c1, d16), (a9, b5, c1, d17), (a9, b5, c1, d18), (a9, b5, c1, d19), (a9, b5, c1, d20), (a9, b5, c1, d21), (a9, b5, c1, d22), (a9, b5, c2, d1), (a9, b5, c2, d2), (a9, b5, c2, d3), (a9, b5, c2, d4), (a9, b5, c2, d5), (a9, b5, c2, d6), (a9, b5, c2, d7), (a9, b5, c2, d8), (a9, b5, c2, d9), (a9, b5, c2, d10), (a9, b5, c2, d11), (a9, b5, c2, d12), (a9, b5, c2, d13), (a9, b5, c2, d14), (a9, b5, c2, d15), (a9, b5, c2, d16), (a9, b5, c2, d17), (a9, b5, c2, d18), (a9, b5, c2, d19), (a9, b5, c2, d20), (a9, b5, c2, d21), (a9, b5, c2, d22), (a9, b5, c3, d1), (a9, b5, c3, d2), (a9, b5, c3, d3), (a9, b5, c3, d4), (a9, b5, c3, d5), (a9, b9, c3, d6), (a9, b5, c3, d7), (a9, b5, c3, d8), (a9, b5, c3, d9), (a9, b5, c3, d10), (a9, b5, c3, d11), (a9, b9, c3, d12), (a9, b5, c3, d13), (a9, b5, c3, d14), (a9, b5, c3, d15), (a9, b5, c3, d16), (a9, b5, c3, d17), (a9, b5, c3, d18), (a9, b5, c3, d19), (a9, b5, c3, d20), (a9, b5, c3, d21), (a9, b5, c3, d22), (a9, b6, c1, d1), (a9, b6, c1, d2), (a9, b6, c1, d3), (a9, b6, c1, d4), (a9, b6, c1, d5), (a9, b6, c1, d6), (a9, b6, c1, d7), (a9, b6, c1, d8), (a9, b6, c1, d9), (a9, b6, c1, d10), (a9, b6, c1, d11), (a9, b6, c1, d12), (a9, b6, c1, d13), (a9, b6, c1, d14), (a9, b6, c1, d15), (a9, b6, c1, d16), (a9, b6, c1, d17), (a9, b6, c1, d18), (a9, b6, c1, d19), (a9, b6, c1, d20), (a9, b6, c1, d21), (a9, b6, c1, d22), (a9, b6, c2, d1), (a9, b6, c2, d2), (a9, b6, c2, d3), (a9, b6, c2, d4), (a9, b6, c2, d5), (a9, b6, c2, d6), (a9, b6, c2, d7), (a9, b6, c2, d8), (a9, b6, c2, d9), (a9, b6, c2, d10), (a9, b6, c2, d11), (a9, b6, c2, d12), (a9, b6, c2, d13), (a9, b6, c2, d14), (a9, b6, c2, d15), (a9, b6, c2, d16), (a9, b6, c2, d17), (a9, b6, c2, d18), (a9, b6, c2, d19), (a9, b6, c2, d20), (a9, b6, c2, d21), (a9, b6, c2, d22), (a9, b6, c3, d1), (a9, b6, c3, d2), (a9, b6, c3, d3), (a9, b6, c3, d4), (a9, b6, c3, d5), (a9, b6, c3, d6), (a9, b6, c3, d7), (a9, b5, c3, d8), (a9, b6, c3, d9), (a9, b6, c3, d10), (a9, b6, c3, d11), (a9, b6, c3, d12), (a9, b6, c3, d13), (a9, b, c3, d14), (a9, b6, c3, d15), (a9, b6, c3, d16), (a9, b6, c3, d17), (a9, b6, c3, d18), (a9, b6, c3, d19), (a9, b6, c3, d20), (a9, b6, c3, d21), (a9, b6, c3, d22), (a10, b1, c1, d1), (a10, b1, c1, d2), (a10, b1, c1, d3), (a10, b1, c1, d4), (a10, b1, c1, d5), (a10, b1, c1, d6), (a10, b1, c1, d7), (a10, b1, c1, d8), (a10, b1, c1, d9), (a10, b1, c1, d10), (a10, b1, c1, d11), (a10, b1, c1, d12), (a10, b1, c1, d13), (a10, b1, c1, d14), (a10, b1, c1, d15), (a10, b1, c1, d16), (a10, b1, c1, d17), (a10, b1, c1, d18), (a10, b1, c1, d19), (a10, b1, c1, d20), (a10, b1, c1, d21), (a10, b1, c1, d22), (a10, b1, c2, d1), (a10, b1, c2, d2), (a10, b1, c2, d3), (a10, b1, c2, d4), (a10, b1, c2, d5), (a10, b1, c2, d6), (a10, b1, c2, d7), (a10, b1, c2, d5), (a10, b1, c2, d9), (a10, b1, c2, d10), (a10, b1, c2, d11), (a10, b1, c2, d12), (a10, b1, c2, d13), (a10, b1, c2, d14), (a10, b1, c2, d15), (a10, b1, c2, d16), (a10, b1, c2, d17), (a10, b1, c2, d18), (a10, b1, c2, d19), (a10, b1, c2, d20), (a10, b1, c2, d21), (a10, b1, c2, d22), (a10, b1, c3, d1), (a10, b1, c3, d2), (a10, b1, c3, d3), (a10, b1, c3, d4), (a10, b1, c3, d5), (a10, b1, c3, d6), (a10, b1, c3, d7), (a10, b1, c3, d8), (a10, b1, c3, d9), (a10, b1, c3, d10), (a10, b1, c3, d11), (a10, b1, c3, d12), (a10, b1, c3, d13), (a10, b1, c3, d14), (a10, b1, c3, d15), (a10, b1, c3, d16), (a10, b1, c3, d17), (a10, b1, c3, d18), (a10, b1, c3, d19), (a10, b1, c3, d20), (a10, b1, c3, d21), (a10, b1, c3, d22), (a10, b2, c1, d1), (a10, b2, c1, d2), (a10, b2, c1, d3), (a10, b2, c1, d4), (a10, b2, c1, d5), (a10, b2, c1, d6), (a10, b2, c1, d7), (a10, b2, c1, d8), (a10, b2, c1, d9), (a10, b2, c1, d10), (a10, b2, c1, d11), (a10, b2, c1, d12), (a10, b2, c1, d13), (a10, b2, c1, d14), (a10, b2, c1, d15), (a10, b2, c1, d16), (a10, b2, c1, d17), (a10, b2, c1, d18), (a10, b2, c1, d19), (a10, b2, c1, d20), (a10, b2, c1, d21), (a10, b2, c1, d22), (a10, b2, c2, d1), (a10, b2, c2, d2), (a10, b2, c2, d3), (a10, b2, c2, d4), (a10, b2, c2, d5), (a10, b2, c2, d6), (a10, b2, c2, d7), (a10, b2, c2, d8), (a10, b2, c2, d9), (a10, b2, c2, d10), (a10, b2, c2, d1), (a10, b2, c2, d12), (a10, b2, c2, d13), (a10, b2, c2, d14), (a10, b2, c2, d15), (a10, b2, c2, d16), (a10, b2, c2, d17), (a10, b2, c2, d18), (a10, b2, c2, d19), (a10, b2, c2, d20), (a10, b2, c2, d21), (a10, b2, c2, d22), (a10, b2, c3, d1), (a10, b2, c3, d2), (a10, b2, c3, d3), (a10, b2, c3, d4), (a10, b2, c3, d5), (a10, b2, c3, d6), (a10, b2, c3, d7), (a10, b2, c3, d8), (a10, b2, c3, d9), (a10, b2, c3, d10), (a10, b2, c3, d11), (a10, b2, c3, d12), (a10, b2, c3, d13), (a10, b2, c3, d14), (a10, b2, c3, d15), (a10, b2, c3, d16), (a10, b2, c3, d17), (a10, b2, c3, d18), (a10, b2, c3, d19), (a10, b2, c3, d20), (a10, b2, c3, d21), (a10, b2, c3, d22), (a10, b3, c1, d1), (a10, b3, c1, d2), (a10, b3, c1, d3), (a10, b3, c1, d4), (a10, b3, c1, d5), (a10, b3, c1, d6), (a10, b3, c1, d7), (a10, b3, c1, d8), (a10, b3, c1, d9), (a10, b3, c1, d10), (a10, b3, c1, d11), (a10, b3, c1, d12), (a10, b3, c1, d13), (a10, b3, c1, d14), (a10, b3, c1, d15), (a10, b3, c1, d16), (a10, b3, c1, d17), (a10, b3, c1, d18), (a10, b3, c1, d19), (a10, b3, c1, d20), (a10, b3, c1, d21), (a10, b3, c1, d22), (a10, b3, c2, d1), (a10, b3, c2, d2), (a10, b3, c2, d3), (a10, b3, c2, d4), (a10, b3, c2, d5), (a10, b3, c2, d6), (a10, b3, c2, d7), (a10, b3, c2, d8), (a10, b3, c2, d9), (a10, b5, c2, d10), (a10, b3, c2, d11), (a10, b3, c2, d12), (a10, b3, c2, d13), (a10, b3, c2, d14), (a10, b3, c2, d15), (a10, b3, c2, d16), (a10, b3, c2, d17), (a10, b3, c2, d18), (a10, b3, c2, d19), (a10, b3, c2, d20), (a10, b3, c2, d21), (a10, b3, c2, d22), (a10, b3, c3, d1), (a10, b3, c3, d2), (a10, b3, c3, d3), (a10, b3, c3, d4), (a10, b3, c3, d5), (a10, b3, c3, d6), (a10, b3, c3, d7), (a10, b3, c3, d8), (a10, b3, c3, d9), (a10, b3, c3, d10), (a10, b3, c3, d11), (a10, b3, c3, d12), (a10, b3, c3, d13), (a10, b3, c3, d14), (a10, b3, c3, d15), (a10, b3, c3, d16), (a10, b3, c3, d17), (a10, b3, c3, d18), (a10, b3, c3, d19), (a10, b3, c3, d20), (a10, b3, c3, d21), (a10, b3, c3, d22), (a10, b4, c1, d1), (a10, b4, c1, d2), (a10, b4, c1, d3), (a10, b4, c1, d4), (a10, b4, c1, d5), (a10, b4, c1, d6), (a10, b4, c1, d7), (a10, b4, c1, d8), (a10, b4, c1, d9), (a10, b4, c1, d10), (a10, b4, c1, d11), (a10, b4, c1, d12), (a10, b4, c1, d13), (a10, b4, c1, d14), (a10, b4, c1, d15), (a10, b4, c1, d16), (a10, b4, c1, d17), (a10, b4, c1, d18), (a10, b4, c1, d19), (a10, b4, c1, d20), (a10, b4, c1, d21), (a10, b4, c1, d22), (a10, b4, c2, d1), (a10, b4, c2, d2), (a10, b4, c2, d3), (a10, b4, c2, d4), (a10, b4, c2, d5), (a10, b4, c2, d6), (a10, b4, c2, d7), (a10, b4, c2, d8), (a10, b4, c2, d9), (a10, b4, c2, d10), (a10, b4, c2, d11), (a10, b4, c2, d12), (a10, b4, c2, d13), (a10, b4, c2, d14), (a1, b4, c2, d15), (a10, b4, c2, d16), (a10, b4, c2, d17), (a10, b4, c2, d18), (a10, b4, c2, d19), (a10, b4, c2, d20), (a10, b4, c2, d21), (a10, b4, c2, d22), (a10, b4, c3, d1), (a10, b4, c3, d2), (a10, b4, c3, d3), (a10, b4, c3, d4), (a10, b4, c3, d5), (a10, b4, c3, d6), (a10, b4, c3, d7), (a10, b4, c3, d8), (a10, b4, c3, d9), (a10, b4, c3, d10), (a10, b4, c3, d11), (a10, b4, c3, d12), (a10, b4, c3, d13), (a10, b4, c3, d14), (a10, b4, c3, d15), (a10, b4, c3, d16), (a10, b4, c3, d17), (a10, b4, c3, d18), (a10, b4, c3, d19), (a10, b4, c3, d20), (a10, b4, c3, d21), (a10, b4, c3, d22), (a10, b5, c1, d1), (a1, b5, c1, d2), (a1, b5, c1, d3), (a10, b5, c1, d4), (a10, b5, c1, d5), (a10, b5, c1, d6), (a10, b5, c1, d7), (a10, b5, c1, d8), (a10, b5, c1, d9), (a10, b5, c1, d10), (a10, b5, c1, d11), (a10, b5, c1, d12), (a10, b5, c1, d13), (a10, b5, c1, d14), (a10, b5, c3, d15), (a10, b5, c1, d16), (a10, b5, c1, d17), (a10, b5, c1, d18), (a10, b5, c1, d19), (a10, b5, c1, d20), (a10, b5, c1, d21), (a10, b5, c1, d22), (a10, b5, c2, d1), (a10, b5, c2, d2), (a10, b5, c2, d3), (a10, b5, c2, d4), (a10, b5, c2, d5), (a10, b5, c2, d6), (a10, b5, c2, d7), (a10, b5, c2, d8), (a10, b5, c2, d9), (a10, b5, c2, d10), (a10, b5, c2, d11), (a10, b5, c2, d12), (a10, b5, c2, d13), (a10, b5, c2, d14), (a10, b5, c2, d15), (a10, b5, c2, d16), (a10, b5, c2, d17), (a10, b5, c2, d18), (a10, b5, c2, d19), (a10, b5, c2, d20), (a10, b5, c2, d21), (a10, b5, c2, d22), (a10, b5, c3, d1), (a10, b5, c3, d2), (a10, b5, c3, d3), (a10, b5, c3, d4), (a10, b5, c3, d5), (a10, b5, c3, d6), (a10, b5, c3, d7), (a10, b5, c3, d8), (a10, b5, c3, d9), (a10, b5, c3, d10), (a10, b5, c3, d11), (a10, b5, c3, d12), (a10, b5, c3, d13), (a10, b5, c3, d14), (a10, b5, c3, d15), (a10, b5, c3, d16), (a10, b5, c3, d17), (a10, b5, c3, d18), (a10, b5, c3, d19), (a10, b5, c3, d20), (a10, b5, c3, d21), (a10, b5, c3, d22), (a10, b6, c1, d1), (a10, b6, c1, d2), (a10, b6, c1, d3), (a10, b6, c1, d4), (a10, b6, c1, d5), (a10, b6, c1, d6), (a10, b6, c1, d7), (a10, b6, c1, d8), (a10, b6, c1, d9), (a10, b6, c1, d10), (a10, b6, c1, d11), (a10, b6, c1, d12), (a10, b6, c1, d3), (a10, b6, c1, d14), (a10, b6, c1, d15), (a10, b6, c1, d16), (a10, b6, c1, d17), (a10, b6, c1, d18), (a10, b6, c1, d19), (a10, b6, c1, d20), (a10, b6, c1, d21), (a10, b6, c1, d22), (a10, b6, c2, d1), (a10, b6, c2, d2), (a10, b6, c2, d3), (a10, b6, c2, d4), (a10, b6, c2, d5), (a10, b6, c2, d6), (a10, b6, c2, d7), (a10, b6, c2, d8), (a10, b6, c2, d9), (a10, b6, c2, d10), (a10, b6, c2, d11), (a10, b6, c2, d12), (a10, b6, c2, d13), (a10, b6, c2, d14), (a10, b6, c2, d15), (a10, b6, c2, d16), (a10, b6, c2, d17), (a10, b6, c2, d18), (a10, b6, c2, d19), (a10, b6, c2, d20), (a10, b6, c2, d21), (a10, b6, c2, d22), (a10, b6, c3, d1), (a10, b6, c3, d2), (a10, b6, c3, d3), (a10, b6, c3, d4), (a10, b6, c3, d5), (a10, b6, c3, d6), (a10, b6, c3, d7), (a10, b6, c3, d8), (a10, b6, c3, d9), (a10, b6, c3, d10), (a10, b6, c3, d11), (a10, b6, c3, d12), (a10, b6, c3, d13), (a10, b6, c3, d14), (a10, b6, c3, d15), (a10, b6, c3, d16), (a10, b6, c3, d17), (a10, b6, c3, d18), (a10, b6, c3, d19), (a10, b6, c3, d20), (a10, b6, c3, d21), (a10, b6, c3, d22), (a11, b1, d1), (a11, b1, c1, d2), (a11, b1, c1, d3), (a11, b1, c1, d4), (a11, b1, c1, d5), (a11, b1, c1, d6), (a11, b1, c1, d7), (a11, b1, c1, d8), (a11, b1, c1, d9), (a11, b1, c1, d10), (a11, b1, c1, d11), (a11, b1, c1, d12), (a11, b1, c1, d13), (a11, b1, c1, d14), (a11, b1, c1, d15), (a11, b1, c1, d16), (a11, b1, c1, d17), (a11, b1, c1, d18), (a11, b1, c1, d19), (a11, b1, c1, d20), (a11, b1, c1, d21), (a11, b1, c1, d22), (a11, b1, c2, d1), (a11, b1, c2, d2), (a11, b1, c2, d3), (a11, b1, c2, d4), (a11, b1, c2, d5), (a11, b1, c2, d6), (a11, b1, c2, d7), (a11, b1, c2, d8), (a11, b1, c2, d9), (a11, b1, c2, d10), (a11, b1, c2, d11), (a11, b1, c2, d12), (a11, b1, c2, d13), (a11, b1, c2, d14), (a11, b1, c2, d15), (a11, b1, c2, d16), (a11, b1, c2, d17), (a11, b1, c2, d18), (a11, b1, c2, d19), (a11, b1, c2, d20), (a11, b1, c2, d21), (a11, b1, c2, d22), (a11, b1, c3, d1), (a11, b1, c3, d2), (a11, b1, c3, d3), (a11, b1, c3, d4), (a11, b1, c3, d5), (a11, b1, c3, d6), (a11, b1, c3, d7), (a11, b1, c3, a8), (a11, b1, c3, d9), (a11, b1, c3, d10), (a11, b1, c3, d11), (a11, b1, c3, d12), (a11, b1, c3, d13), (a11, b1, c3, d14), (a11, b1, c3, d15), (a11, b1, c3, d16), (a11, b1, c3, d17), (a11, b1, c3, d18), (a11, b1, c3, d19), (a11, b1, c3, d20), (a11, b1, c3, d21), (a11, b1, c3, d22), (a11, b2, c1, d1), (a11, b2, c1, d2), (a11, b2, c1, d3), (a11, b2, c1, d4), (a11, b2, c1, d5), (a11, b2, c1, d6), (a11, b2, c1, d7), (a11, b2, c1, d8), (a11, b2, c1, d9), (a11, b2, c1, d10), (a11, b2, c1, d11), (a11, b2, c1, d12), (a11, b2, c1, d13), (a11, b2, c1, d14), (a11, b2, c1, d15), (a11, b2, c1, d16), (a11, b2, c1, d17), (a11, b2, c1, d18), (a11, b2, c1, d19), (a11, b2, c1, d20), (a11, b2, c1, d21), (a11, b2, c1, d22), (a11, b2, c2, d1), (a11, b2, c2, d2), (a11, b2, c2, d3), (a11, b2, c2, d4), (a11, b2, c2, d5), (a11, b2, c2, d6), (a11, b2, c2, d7), (a11, b2, c2, d8), (a11, b2, c2, d9), (a11, b2, c2, d10), (a11, b2, c2, d11), (a11, b2, c2, d12), (a11, b2, c2, d13), (a11, b2, c2, d14), (a11, b2, c2, d15), (a11, b2, c2, d16), (a11, b2, c2, d17), (a11, b2, c2, d18), (a11, b2, c2, d19), (a11, b2, c2, d20), (a11, b2, c2, d21), (a11, b2, c2, d22), (a11, b2, c3, d1), (a11, b2, c3, d2), (a11, b2, c3, d3), (a11, b2, c3, d4), (a11, b2, c3, d5), (a11, b2, c3, d6), (a11, b2, c3, d7), (a11, b2, c3, d8), (a11, b2, c3, d9), (a11, b2, c3, d10), (a11, b2, c3, d11), (a11, b2, c3, d12), (a11, b2, c3, d13), (a11, b2, c3, d14), (a11, b2, c3, d15), (a11, b2, c3, d16), (a11, b2, c3, d17), (a11, b2, c3, d18), (a11, b2, c3, d19), (a11, b2, c3, d20), (a11, b2, c3, d21), (a11, b2, c3, d22), (a11, b3, c1, d1), (a11, b3, c1, d2), (a11, b3, c1, d3), (a11, b3, c1, d4), (a11, b3, c1, d5), (a11, b3, c1, d6), (a11, b3, c1, d7), (a11, b3, c1, d8), (a11, b3, c1, d9), (a11, b3, c1, d10), (a11, b3, c1, d11), (a11, b3, c1, d12), (a11, b3, c1, d13), (a11, b3, c1, d14), (a11, b3, c1, d15), (a11, b3, c1, d16), (a11, b3, c1, d17), (a11, b3, c1, d18), (a11, b3, c1, d19), (a11, b3, c1, d20), (a11, b3, c1, d21), (a11, b3, c1, d22), (a11, b3, c2, d1), (a11, b3, c2, d2), (a11, b3, c2, d3), (a11, b3, c2, d4), (a11, b3, c2, d5), (a11, b3, c2, d6), (a11, b3, c2, d7), (a11, b3, c2, d8), (a11, b3, c2, d9), (a11, b3, c2, d10), (a11, b3, c2, d16), (a11, b3, c2, d12), (a11, b3, c2, d13), (a11, b3, c2, d14), (a11, b3, c2, d15), (a11, b3, c2, d16), (a11, b3, c2, d17), (a11, b3, c2, d18), (a11, b3, c2, d19), (a11, b3, c2, d20), (a11, b3, c2, d21), (a11, b3, c2, d22), (a11, b3, c3, d1), (a11, b3, c3, d2), (a11, b3, c3, d3), (a11, b3, c3, d4), (a11, b3, c3, d5), (a11, b3, c3, d6), (a11, b3, c3, d7), (a11, b3, c3, d8), (a11, b3, c3, d9), (a11, b3, c3, d10), (a11, b3, c3, d11), (a11, b3, c3, d12), (a11, b3, c3, d13), (a11, b3, c3, d14), (a11, b3, c3, d15), (a11, b3, c3, d16), (a11, b3, c3, d17), (a11, b3, c3, d18), (a11, b3, c3, d19), (a11, b3, c3, d20), (a11, b3, c3, d21), (a11, b3, c3, d22), (a11, b4, c1, d1), (a11, b4, c1, d2), (a11, b4, c1, d3), (a11, b4, c1, d4), (a11, b4, c1, d5), (a11, b4, c1, d6), (a11, b4, c1, d7), (a11, b4, c1, d8), (a11, b4, c1, d9), (a11, b4, c1, d10), (a11, b4, c1, d11), (a11, b4, c1, d12), (a11, b4, c1, d13), (a11, b4, c1, d14), (a11, b4, c1, d15), (a11, b4, c1, d16), (a11, b4, c1, d17), (a11, b4, c1, d18), (a11, b4, c1, d19), (a11, b4, c1, d20), (a11, b4, c1, d21), (a11, b4, c1, d22), (a11, b4, c2, d1), (a11, b4, c2, d2), (a11, b4, c2, d3), (a11, b4, c2, d4), (a11, b4, c2, d5), (a11, b4, c2, d6), (a11, b4, c2, d7), (a11, b4, c2, d8), (a11, b4, c2, d9), (a11, b4, c2, d10), (a11, b4, c2, d11), (a11, b4, c2, d12), (a11, b4, c2, d13), (a11, b4, c2, d14), (a11, b4, c2, d15), (a11, b4, c2, d16), (a11, b4, c2, d17), (a11, b4, c2, d18), (a11, b4, c2, d19), (a11, b4, c2, d20), (a11, b4, c2, d21), (a11, b4, c2, d22), (a11, b4, c3, d1), (a11, b4, c3, d2), (a11, b4, c3, d3), (a11, b4, c3, d4), (a11, b4, c3, d5), (a11, b4, c3, d6), (a11, b4, c3, d7), (a11, b4, c3, d8), (a11, b4, c3, d9), (a11, b4, c3, d10), (a11, b4, c3, d11), (a11, b4, c3, d12), (a11, b4, c3, d13), (a11, b4, c3, d14), (a11, b4, c3, d15), (a11, b4, c3, d16), (a11, b4, c3, d17), (a11, b4, c3, d18), (a11, b4, c3, d19), (a11, b4, c3, d20), (a11, b4, c3, d21), (a11, b4, c3, d22), (a11, b5, c1, d1), (a11, b5, c1, d2), (a11, b5, c1, d3), (a11, b5, c1, d4), (a11, b5, c1, d5), (a11, b5, c1, d6), (a11, b5, c1, d7), (a11, b5, c1, d8), (a11, b5, c1, d9), (a11, b5, c1, d10), (a11, b5, c1, d11), (a11, b5, c1, d12), (a11, b5, c1, d13), (a11, b5, c1, d14), (a11, b5, c1, d15), (a11, b5, c1, d16), (a11, b5, c1, d17), (a11, b5, c1, d18), (a11, b5, c1, d19), (a11, b5, c1, d20), (a11, b5, c1, d21), (a11, b5, c1, d22), (a11, b5, c2, d1), (a11, b5, c2, d2), (a11, b5, c2, d3), (a11, b5, c2, d4), (a11, b5, c2, d5), (a11, b5, c2, d6), (a11, b5, c2, d7), (a11, b5, c2, d8), (a11, b5, c2, d9), (a11, b5, c2, d10), (a11, b5, c2, d11), (a11, b5, c2, d12), (a11, b5, c2, d13), (a11, b5, c2, d14), (a11, b5, c2, d15), (a11, b5, c2, d6), (a11, b5, c2, d17), (a11, b5, c2, d18), (a11, b5, c2, d19), (a11, b5, c2, d20), (a11, b5, c2, d21), (a11, b5, c2, d22), (a11, b5, c3, d1), (a11, b5, c3, d2), (a11, b5, c3, d3), (a11, b5, c3, d4), (a11, b5, c3, d5), (a11, b5, c3, d6), (a11, b5, c3, d7), (a11, b5, c3, d8), (a11, b5, c3, d9), (a, b5, c3, d10), (a11, b5, c3, d11), (a11, b5, c3, d2), (a11, b5, c3, d13), (a11, b5, c3, d14), (a11, b5, c3, d15), (a11, b5, c3, d16), (a11, b5, c3, d17), (a11, b5, c3, d18), (a11, b5, c3, d19), (a11, b5, c3, d20), (a11, b5, c3, d21), (a11, b5, c3, d22), (a11, b6, c1, d1), (a11, b6, c1, d2), (a11, b6, c1, d3), (a11, b6, c1, d4), (a11, b6, c1, d5), (a11, b6, c1, d6), (a11, b6, c1, d7), (a11, b6, c1, d8), (a11, b6, c1, d9), (a11, b6, c1, d10), (a11, b6, c1, d11), (a11, b6, c1, d12), (a11, b6, c1, d13), (a11, b6, c1, d14), (a11, b6, c1, d15), (a11, b6, c1, d16), (a11, b6, c1, d17), (a11, b6, c1, d18), (a11, b6, c1, d19), (a11, b6, c1, d20), (a11, b6, c1, d21), (a11, b6, c1, d22), (a11, b6, c2, d1), (a11, b6, c2, d2), (a11, b6, c2, d3), (a11, b6, c2, d4), (a11, b6, c2, d5), (a11, b6, c2, d6), (a11, b6, c2, d7), (a11, b6, c2, d8), (a11, b6, c2, d9), (a11, b6, c2, d10), (a11, b6, c2, d11), (a11, b6, c2, d12), (a11, b6, c2, d13), (a11, b6, c2, d14), (a11, b6, c2, d15), (a11, b6, c2, d16), (a11, b6, c2, d17), (a11, b6, c2, d18), (a11, b6, c2, d19), (a11, b6, c2, d20), (a11, b6, c2, d21), (a11, b6, c2, d22), (a11, b6, c3, d1), (a11, b6, c3, d2), (a11, b6, c3, d3), (a11, b6, c3, d4), (a11, b6, c3, d5), (a11, b6, c3, d6), (all b6, c3, b6, d13), (a11, b6, c3, d8), (all b6, c3, d9), (a11, b6, c3, d10), (a11, b6, c3, d11), (a11, b6, c3, d12), (a11, b6, c3, d13), (a11, b6, c3, d14), (a11, b6, c3, d15), (a11, b6, c3, d16), (a11, b6, c3, d17), (a11, b6, c3, d18), (a11, b6, c3, d19), (a11, b6, c3, d20), (a11, b6, c3, d21), (a11, b6, c3, d22), (a12, b1, c1, d1), (a12, b1, c1, d2), (a12, b1, c1, d3), (a12, b1, c1, d4), (a12, b1, c1, d5), (a12, b1, c1, d6), (a12, b1, c1, d7), (a12, b1, c1, d8), (a12, b1, c1, d9), (a12, b1, c1, d10), (a12, b1, c1, d1), (a2, b1, c1, d12), (a12, b1, c1, d13), (a12, b1, c1, d14), (a12, b1, c1, d15), (a12, b1, c1, d16), (a12, b1, c1, d17), (a12, b1, c1, d18), (a12, b1, c1, d19), (a12, b1, c1, d20), (a12, b1, c1, d21), (a12, b1, c1, d22), (a12, b1, c2, d1), (a12, b1, c2, d2), (a12, b1, c2, d3), (a12, b1, c2, d4), (a12, b1, c2, d5), (a12, b1, c2, d6), (a12, b, c2, d7), (a12, b1, c2, d8), (a12, b1, c2, d9), (a12, b1, c2, d10), (a12, b1, c2, d11), (a12, b1, c2, d12), (a12, b1, c2, d13), (a12, b1, c2, d14), (a12, b1, c2, d15), (a12, b1, c2, d16), (a2, b1, c2, d17), (a12, b1, c2, d18), (a12, b1, c2, d19), (a12, b1, c2, d20), (a12, b1, c2, d21), (a12, b1, c2, d22), (a12, b1, c3, d1), (a12, b1, c3, d2), (a12, b1, c3, d3), (a12, b1, c3, d4), (a12, b1, c3, d5), (a12, b1, c3, d6), (a12, b1, c3, d7), (a12, b c3, d8), (a12, b1, c3, d9), (a2, b1, c3, d10), (a12, b1, c3, d11), (a12, b1, c3, d12), (a12, b1, c3, d13), (a12, b1, c3, d14), (a12, b1, c3, d15), (a12, b1, c3, d16), (a12, b1, c3, d17), (a12, b1, c3, d18), (a12, b1, c3, d19), (a12, b1, c3, d20), (a12, b1, c3, d21), (a12, b1, c3, d22), (a12, b2, c1, d1), (a12, b2, c1, d2), (a2, b2, c1, d3), (a12, b2, c1, d4), (a12, b2, c1, d5), (a12, b2, c1, d6), (a12, b2, c1, d7), (a12, b2, c1, d8), (a12, b2, c1, d9), (a12, b2, c1, d10), (a12, b2, c1, d11), (a12, b2, c1, d12), (a12, b2, c1, d13), (a12, b2, c1, d14), (a12, b2, c1, d15), (a12, b2, c1, d16), (a12, b2, c1, d17), (a12, b2, c1, d18), (a12, b2, c1, d19), (a12, b2, c1, d20), (a12, b2, c1, d21), (a12, b2, c1, d22), (a12, b2, c2, d1), (a12, b2, c2, d2), (a12, b2, c2, d3), (a12, b2, c2, d4), (a12, b2, c2, d5), (a12, b2, c2, d6) (a12, b2, c2, d10), (a12, b2, c2, d8), (a12, b2, c2, d9), (a12, b2, c2, d10), (a12, b2, c2, d11), (a12, b2, c2, d12), (a12, b2, c2, d13), (a12, b2, c2, d14), (a12, b2, c2, d15), (a12, b2, c2, d16), (a12, b2, c2, d17), (a12, b2, c2, d18), (a12, b2, c2, d19), (a12, b2, c2, d20), (a12, b2, c2, d21), (a12, b2, c2, d22), (a12, b2, co, d1), (a12, b2, c3, d2), (a12, b2, c3, d3), (a12, b2, c3, d4), (a12, b2, c3, d5), (a12, b2, c3, d6), (a12, b2, c3, d7), (a12, b2, c3, d8), (a12, b2, c3, d9), (a12, b2, c3, d10), (a12, b2, c3, d1), (a12, b2, c3, d12), (a12, b2, c3, d13), (a12, b2, c3, d14), (a12, b2, c3, d15), (a12, b2, c3, d16), (a2, b2, c3, d17), (a12, b2, c3, d18), (a12, b2, c3, d19), (a12, b2, c3, d20), (a12, b2, c3, d21), (a12, b2, c3, d22), (a12, b3, c1, d1), (a12, b3, c1, d2), (a12, b3, c1, d3), (a12, b3, c1, d4), (a12, b3, c1, d5), (a12, b3, c1, d6), (a12, b5, c1, d7), (a12, b3, c1, d8), (a12, b5, c1, d9), (a12, b3, c1, d10), (a12, b3, c1, d11), (a12, b3, c1, d12), (a12, b3, c1, d13), (a12, b3, c1, d14), (a12, b3, c1, d15), (a12, b3, c1, d16), (a12, b3, c1, d17), (a12, b5, c1, d18), (a12, b3, c1, d19), (a12, b3, c1, d20), (a12, b, c1, d21), (a12, b3, c1, d22), (a12, b3, c2, d1), (a12, b3, c2, d2), (a2, b3, c2, d3), (a12, b3, c2, d4), (a12, b3, c2, d5), (a12, b3, c2, d6), (a12, b3, c2, d7), (a2, b3, c2, d8), (a12, b3, c2, d9), (a12, b3, c2, d10), (a12, b3, c2, d11), (a12, b3, c2, d12), (a12, b3, c2, d13), (a12, b3, c2, d14), (a12, b3, c2, d15), (a12, b3, c2, d16), (a12, b3, c2, d17), (a12, b3, c2, d18), (a12, b3, c2, d19), (a12, b3, c2, d20), (a12, b3, c2, d21), (a12, b5, c2, d22), (a12, b5, c3, d1), (a12, b3, c3, d2), (a12, b3, c3, d3), (a12, b3, c3, d4), (a12, b3, c3, d5), (a12, b3, c3, d6), (a12, b3, c3, d7), (a12, b3, c3, d8), (a12, b3, c3, d9), (a12, b3, c3, d10), (a12, b3, c3, d11), (a12, b3, c3, d12), (a12, b3, c3, d13), (a12, b3, c3, d14), (a12, b3, c3, d15), (a12, b3, c3, d16), (a12, b3, c3, d17), (a12, b3, c3, d18), (a12, b3, c3, d19), (a12, b3, c3, d20), (a12, b3, c3, d21), (a12, b3, c3, d22), (a12, b4, c1, d1), (a12, b4, c1, d2), (a12, b4, c1, d3), (a12, b4, c1, d4), (a12, b4, c1, d5), (a12, b4, c1, d6), (a12, b4, c1, d7), (a12, b4, c1, d8), (a12, b4, c1, d9), (a12, b4, c1, d10), (a12, b4, c1, d11), (a12, b4, c1, d12), (a12, b4, c1, d13), (a12, b4, c1, d14), (a12, b4, c1, d15), (a12, b4, c1, d16), (a12, b4, c1, d17), (a12, b4, c1, d18), (a12, b4, c1, d19), (a12, b4, c1, d20), (a12, b4, c1, d21), (a12, b4, c1, d22), (a12, b4, c2, d1), (a12, b4, c2, d2), (a12, b4, c2, d3), (a12, b4, c2, d4), (a12, b4, c2, d5), (a12, b4, c2, d6), (a12, b4, c2, d7), (a12, b4, c2, d8), (a12, b4, c2, d9), (a12, b4, c2, d10), (a12, b4, c2, d11), (a12, b4, c2, d12), (a12, b4, c2, d13), (a12, b4, c2, d14), (a12, b4, c2, d15), (a12, b4, c2, d16), (a12, b4, c2, d17), (a12, b4, c2, d18), (a12, b4, c2, d19), (a12, b4, c2, d20), (a12, b4, c2, d21), (a12, b4, c2, d22), (a12, b4, c3, d1), (a12, b4, c3, d2), (a12, b4, c3, d3), (a12, b4, c3, d4), (a12, b4, c3, d5), (a12, b4, c3, d6), (a12, b4, c3, d7), (a12, b4, c3, d8), (a12, b4, c3, d9), (a12, b4, c3, d10), (a12, b4, c3, d11), (a12, b4, c3, d2), (a12, b4, c3, d13), (a12, b4, c3, d14), (a12, b4, c3, d15), (a12, b4, c3, d16), (a12, b4, c3, d17), (a12, b4, c3, d18), (a12, b4, c3, d19), (a12, b4, c3, d20), (a12, b4, c3, d21), (a12, b4, c3, d22), (a12, b5, c1, d1), (a12, b5, c1, d2), (a12, b5, c1, d3), (a12, b5, c1, d4), (a12, b5, c1, d5), (a12, b5, c1, d6), (a12, b5, c1, d7), (a12, b5, c1, d8), (a12, b5, c1, d9), (a12, b5, c1, d10), (a12, b5, c1, d11), (a12, b5, c1, d12), (a12, b5, c1, d13), (a12, b5, c1, d14), (a12, b5, c1, d15), (a12, b5, c1, d16), (a12, b5, c1, d17), (a12, b5, c1, d18), (a12, b5, c1, d19), (a12, b5, c1, d20), (a12, b5, c1, d21), (a12, b5, c1, d22), (a12, b5, c2, d1), (a12, b5, c2, d2), (a12, b5, c2, d3), (a12, b5, c2, d4), (a12, b5, c2, d5), (a12, b5, c2, d6), (a12, b5, c2, d7), (a12, b5, c2, d8), (a12, b5, c2, d9), (a12, b5, c2, d10), (a12, b5, c2, d11), (a12, b5, c2, d12), (a12, b5, c2, d13), (a12, b5, c2, d14), (a12, b5, c2, d15), (a12, b5, c2, d16), (a12, b5, c2, d17), (a12, b5, c2, d18), (a12, b5, c2, d19), (a12, b5, c2, d20), (a12, b5, c2, d21), (a12, b5, c2, d22), (a12, b5, c3, d1), (a12, b5, c3, d2), (a12, b5, c3, d3), (a12, b5, c3, d4), (a12, b5, c3, d5), (a12, b5, c3, d6), (a12, b5, c3, d7), (a12, b5, c3, d8), (a12, b5, c3, d9), (a12, b5, c3, d10), (a12, b5, c3, d11), (a12, b5, c3, d12), (a12, b5, c3, d13), (a12, b5, c3, d14), (a12, b5, c3, d15), (a12, b5, c3, d16), (a12, b5, c3, d17), (a12, b5, c3, d18), (a12, b5, c3, d19), (a12, b5, c3, d20), (a12, b5, c3, d21), (a12, b5, c3, d22), (a12, b6, c1, d1), (a12, b6, c1, d2), (a12, b6, c1, d3), (a12, b6, c1, d4), (a12, b6, c1, d5), (a12, b6, c1, d5, (a12, b6, c1, d7), (a12, b6, c1, d8), (a12, b6, c1, d9), (a12, b6, c1, d10), (a12, b6, c1, d11), (a12, b6, c1, d12), (a12, b3, c1, d13), (a12, b6, c1, d14), (a12, b6, c1, d15), (a12, b6, c11, d16), (a12, b6, c1, d17), (a12, b6, c1, d18), (a12, b6, c1, d19), (a12, b6, c1, d20), (a12, b6, c1, d21), (a12, b6, c1, d22), (a12, b6, c2, d1), (a12, b6, c2, d2), (a12, b5, c2, d3), (a12, b4, c2, d4), (a12, b4, c2, d5), (a12, b6, c2, d6), (a12, b6, c2, d7), (a12, b6, c2, d8), (a12, b6, c2, d9), (a12, b6, c2, d10), (a12, b6, c2, d11), (a12, b6, c2, d12), (a12, b5, c2, d13), (a12, b6, c2, d14), (a12, b5, c2, d5), (a12, b6, c2, d6), (a12, b6, c2, d17), (a12, b6, c2, d18), (a12, b6, c2, d19), (a12, b6, c2, d20), (a12, b6, c2, d21), (a12, b5, c2, d22), (a12, b6, c3, d1), (a12, b5, c3, d2), (a12, b6, c3, d3), (a12, b6, c3, d4), (a12, b6, c3, d5), (a12, b6, c3, d6), (a12, b6, c3, d7), (a12, b6, c3, d8), (a12, b6, c3, d9), (a12, b6, c3, d10), (a12, b6, c3, d11), (a12, b6, c3, d12), (a12, b6, c3, d13), (a12, b5, c3, d14), (a12, b6, c3, d15), (a12, b6, c3, d16), (a12, b6, c3, d17), (a12, b6, c3, d18), (a12, b6, c3, d19), (a12, b6, c3, d20), (a12, b6, c3, d21), (a12, b6, c3, d22), (a13, b1, c1, d1), (a13, b1, c1, d2), (a13, b1, c1, d3), (a13, b1, c1, d4), (a13, b1, c1, d5), (a13, b1, c1, d6), (a13, b1, c1, d7), (a13, b1, c1, d8), (a13, b1, c1, d9), (a13, b1, c1, d10), (a13, b1, c1, d11), (a13, b1, c1, d12), (a13, b1, c1, d13), (a13, b1, c1, d14), (a13, b1, c1, d15), (a13, b1, c1, d6), (a13, b1, c1, d17), (a13, b1, c1, d18), (a13, b1, c1, d19), (a13, b1, c1, d20), (a13, b1, c1, d21), (a13, b1, c1, d22), (a13, b1, c2, d1), (a13, b1, c2, d2), (a13, b1, c2, d3), (a13, b1, c2, d4), (a13, b1, c2, d5), (a13, b1, c2, d6), (a13, b1, c2, d7), (a13, b1, c2, d8), (a13, b1, c2, d9), (a13, b1, c2, d10), (a13, b1, c2, d11), (a13, b1, c2, d12), (a13, b1, c2, d13), (a13, b1, c2, d14), (a13, b1, c2, d15), (a13, b1, c2, d16), (a13, b1, c2, d17), (a13, b1, c2, d18), (a13, b1, c2, d19), (a13, b1, c2, d20), (a13, b1, c2, d21), (a13, b1, c2, d22), (a13, b1, c3, d1), (a13, b1, c3, d2), (a13, b1, c3, d3), (a13, b1, c3, d4), (a13, b1, c3, d5), (a13, b1, c3, d6), (a13, b1, c3, d7), (a13, b1, c3, d8), (a13, b1, c3, d9), (a13, b1, c3, d10), (a13, b1, c3, d11), (a13, b1, c3, d12), (a13, b1, c3, d13), (a13, b1, c3, d14), (a13, b1, c3, d15), (a13, b1, c3, d16), (a13, b1, c3, d17), (a13, b1, c3, d18), (a13, b1, c3, d19), (a13, b1, c3, d20), (a13, b1, c3, d21), (a13, b1, c3, d22), (a13, br, c1, d1), (a13, b2, c1, d2), (a13, b2, c1, d3), (a13, b2, c1, d4), (a13, b2, c1, d5), (a13, b2, c1, d6), (a13, b2, c1, d7), (a13, b2, c1, d8), (a13, b2, c1, d9), (a13, b2, c1, d10), (a13, b2, c1, d1), (a13, b2, c1, d12), (a3, b2, c1, d13), (a13, b2, c1, d14), (a13, b2, c1, d15), (a13, b2, c1, d16), (a13, b2, c1, d17), (a13, b2, c1, d8), (a13, b2, c1, d19), (a3, b2, c1, d20), (a13, b2, c1, d21), (a13, b2, c1, d22), (a13, b2, c2, d), (a13, b2, c2, d2), (a13, b2, c2, d3), (a13, b2, c2, d4), (a13, b2, c2, d5), (a13, b2, c2, d6), (a13, b2, c2, d7), (a13, b2, c2, d8), (a13, b2, c2, d9), (a13, b2, c2, d10), (a13, b2, c2, d11), (a13, b2, c2, d12), (a13, b2, c2, d13), (a13, b2, c2, d14), (a13, b2, c2, d15), (a13, b2, c2, d16), (a3, b2, c2, d7), (a13, b2, c2, d18), (a13, b2, c2, c2, d19), (a13, b2, c2, d20), (a13, b2, c2, d21), (a13, b2, c2, d22), (a13, b2, c3, d1), (a13, b2, c3, d2), (a13, b2, c3, d3), (a13, b2, c3, d4), (a13, b2, c3, d5), (a13, b2, c3, d6), (a13, b2, c3, d7), (a13, b2, c3, d8), (a13, b2, c3, d9), (a13, b2, c3, d10), (a13, b2, c3, d11), (a13, b2, c3, d12), (a13, b2, c3, d13), (a13, b2, c3, d14), (a13, b2, c3, d15), (a13, b2, c3, d16), (a13, b2, c3, d17), (a13, b2, c3, d18), (a13, b2, c3, d19), (a13, b2, c3, d20), (a13, b2, c3, d21), (a13, b2, c3, d22), (a13, b3, c1, d1), (a13, b3, c1, d2), (a13, b3, c1, d3), (a13, b3, c1, d4), (a 3, b3, c1, d5), (a13, b3, c1, d6), (a13, b3, c1, d7), (a13, b3, c1, d8), (a13, b3, c1, d9), (a13, b3, c1, d10), (a13, b3, c1, d11), (a13, b3, c1, d12), (a13, b3, c1, d13) (a13, b3, c1, d14), (a13, b3, c1, d15), (a13, b3, c1, d16), (a13, b3, c1, d17), (a13, b3, c1, d18), (a13, b3, c1, d19), (a13, b3, c1, d20), (a13, b3, c1, d21), (a13, b3, c1, d22), (a13, b3, c2, d1), (a13, b3, c2, d2), (a13, b3, c2, d3), (a13, b3, c2, d4), (a13, b3, c2, d5), (a13, b3, c2, d6), (a13, b3, c2, d7), (a13, b3, c2, d8), (a13, b3, c2, d9), (a13, b3, c2, d10), (a13, b3, c2, d11), (a13, b3, c2, d12), (a13, b3, c2, d13), (a13, b3, c2, d14), (a13, b3, c2, d15), (a13, b3, c2, d16), (a13, b3, c2, d17), (a13, b3, c2, d18), (a13, b3, c2, d19), (a13, b3, c2, d20), (a13, b3, c2, d21), (a13, b3, c2, d22), (a13, b3, c3, d1), (a13, b3, c3, d2), (a13, b3, c d3), (a13, b3, c3, d4), (a13, b3, c3, d5), (a13, b3, c3, d6), (a13, b3, c3, d7), (a13, b3, c3, d8), (a13, b3, c3, d9), (a13, b3, c3, d10), (a13, b3, c3, d11), (a13, b3, c3, d12), (a13, b3, c3, d13), (a3, b3, c3, d14), (a13, b3, c3, d15), (a13, b3, c3, d16), (a13, b3, c3, d17), (a13, b3, c3, d18), (a13, b3, b3, c3, d19), (a13, b3, c3, d20), (a13, b3, c1, d21), (a13, b3, c3, d22), (a13, b4, c1, d1), (a13, b4, c1, d2), (a13, b4, c1, d3), (a13, b4, c1, d4), (a13, b4, c1, d5), (a13, b4, c1, d6), (a13, b4, c1, d7), (a13, b4, c1, d8), (a13, b4, c1, d9), (a13, b4, c1, d10), (a13, b4, c1, d11), (a13, b4, c1, d12), (a13, b4, c1, d13), (a13, b4, c1, d14), (a13, b4, c1, d15), (a13, b4, c1, d16), (a13, b4, c1, d17), (a13, b4, c1, d18), (a13, b4, c1, d19) (a13, b4, c1, d20), (a13, b4, c1, d21), (a13, b4, c1, d22), (a13, b4, c2, d1), (a13, b4, c2, d2), (a13, b4, c2, d3), (a13, b4, c2, d4), (a13, b4, c2, d5), (a13, b4, c2, d6), (a13, b4, c2, d7), (a13, b4, c2, d3), (a13, b4, c2, d9), (a13, b4, c2, d10), (a13, b4, c2, d11), (a13, b4, c2, d12), (a13, b4, c2, d13), (a13, b4, c2, d14), (a13, b4, c2, d15), (a13, b4, c2, d16), (a13, b4, c2, d17), (a13, b4, c2, d18), (a13, b4, c2, d19), (a13, b4, c2, d20), (a13, b4, c2, d21), (a13, b4, c2, d22), (a13, b4, c3, d1), (a13, b4, c3, d2), (a13, b4, c3, d3), (a13, b4, c3, d4), (a13, b4, c3, d5), (a13, b4, c3, d6), (a13, b4, c3, d7), (a13, b4, c3, d8), (a13, b4, c3, d9), (a13, b4, c3, d10), (a13, b4, c3, d11), (a13, b4, c3, d12), (a13, b4, c3, d13), (a13, b4, c3, d14), (a13, b4, c3, d15), (a13, b4, c3, d16), (a13, b4, c3, d17), (a13, b4, c3, d18), (a13, b4, c3, d19), (a13, b4, c3, d20), (a13, b4, c3, d21), (a13, b4, c3, d22), (a13, b5, c1, d1), (a13, b5, c1, d2), (a13, b5, c1, d3), (a13, b5, c1, d4), (a13, b5, c1, d5), (a13, b5, c1, d6), (a13, b5, c1, d7), (a13, b5, c1, d8), (a13, b5, c1, d9), (a13, b5, c1, d10), (a13, b5, c1, d11), (a13, b5, c1, d12), (a13, b5, c1, d13), (a13, b5, c1, d14), (a13, b5, c1, d15), (a13, b5, c1, d16), (a13, b5, c1, d17), (a13, b5, c1, d18), (a13, b5, c1, d19), (a13, b5, c1, d20), (a13, b5, c1, d21), (a13, b5, c1, d22), (a13, b5, c2, d1), (a13, b5, c2, d2), (a13, b5, c2, d3), (a13, b5, c2, d4), (a13, b5, c2, d5), (a13, b5, c2, d6), (a13, b5, c2, d7), (a13, b5, c2, d8), (a13, b5, c2, d9), (a13, b5, c2, d10), (a13, b5, c2, d11), (a13, b5, c2, d12), (a13, b5, c2, d13), (a13, b5, c2, d14), (a13, b5, c2, d15), (a13, b5, c2, d16), (a13, b5, c2, d17), (a13, b5, c2, d18), (a13, b5, c2, d19), (a13, b5, c2, d20), (a13, b5, c2, d21), (a13, b5, c2, d22), (a13, b5, c3, d1), (a13, b5, c3, d2), (a13, b5, c3, d3), (a13, b5, c3, d4), (a13, b5, c3, d5), (a13, b5, c3, d6), (a13, b5, c3, d7), (a13, b5, c3, d8), (a13, b5, c3, d9), (a13, b5, c3, d10), (a13, b5, c3, d11), (a13, b5, c3, d12), (a13, b5, c3, d13), (a13, b5, c3, d14), (a13, b5, c3, d15), (a13, b5, c3, d6), (a13, b5, c3, d17), (a13, b5, c3, d18), (a13, b5, c3, d19), (a13, b5, c3, d20), (a13, b5, c3, d21), (a13, b5, c3, d22), (a13, b6, c1, d1), (a13, b6, c1, d2), (a13, b6, c1, d3), (a13, b6, c1, d4), (a13, b6, c1, d5), (a13, b6, c1, d6), (a13, b6, c1, d7), (a13, b6, c1, d8), (a13, b6, c1, d9), (a13, b6, c1, d10), (a13, b6, c1, d11), (a13, b6, c1, d12), (a13, b6, c1, d13), (a13, b6, c1, d14), (a13, b6, c1, d15), (a13, b6, c1, d16), (a13, b6, c1, d17), (a13, b6, c1, d18), (a13, b6, c1, d19), (a13, b6, c1, d20), (a13, b6, c1, d21), (a13, b6, c1, d22), (a13, b6, c2, d1), (a13, b6, c2, d2), (a13, b6, c2, d3), (a13, b6, c2, d4), (a13, b6, c2, d5), (a13, b6, c2, d6), (a13, b6, c2, d7), (a13, b6, c2, d8), (a13, b6, c2, d9), (a13, b6, c2, d10), (a13, b6, c2, d11), (a13, b6, c2, d12), (a13, b6, c2, d13), (a13, b6, c2, d14), (a13, b6, c2, d15), (a13, b6, c2, d16), (a13, b6, c2, d17), (a13, b6, c2, d18), (a13, b6, c2, d19), (a13, b6, c2, d20), (a13, b6, c2, d21), (a13, b6, c2, d22), (a13, b6, c3, d1), (a13, b6, c3, d2), (a13, b6, c3, d3), (a13, b6, c3, d4), (a13, b6, c3, d5), (a13, b6, c3, d6), (a13, b6, c3, d7), (a13, b6, c3, d8), (a13, b6, c3, d9), (a13, b6, c3, d10), (a13, b6, c3, d11), (a13, b6, c3, d12), (a13, b6, c3, d13), (a13, b6, c3, d14), (a13, b6, c3, d15), (a13, b6, c3, d16), (a13, b6, c3, d17), (a13, b6, c3, d18), (a13, b6, c3, d19), (a13, b6, c3, d20), (a13, b6, c3, d21), (a13, b6, c3, d22), (a14, b1, c1, d1), (a14, b1, c1, d2), (a14, b1, c1, d3), (a14, b1, c1, d4), (a14, b1, c1, d5), (a14, b1, c1, d6), (a14, b1, c1, d7), (a14, b1, c1, d8), (a14, b1, c1, d9), (a14, b1, c1, d10), (a14, b1, c1, d11), (a14, b1, c1, d12), (a14, b1, c1, d13), (a14, b1, c1, d14), (a14, b1, c1, d15), (a14, b1, c1, d16), (a14, b1, c1, d17), (a14, b1, c1, d18), (a14, b1, c1, d19), (a14, b1, c1, d20), (a14, b1, c1, d21), (a14, b1, c1, d22), (a14, b1, c2, d1), (a14, b1, c2, d2), (a14, b1, c2, d3), (a14, b1, c2, d4), (a14, b1, c2, d5), (a14, b1, c2, d6), (a14, b1, c2, d7), (a14, b1, c2, d8), (a14, b1, c2, d9), (a14, b1, c2, d10), (a14, b1, c2, d11), (a14, b1, c2, d12), (a14, b1, c2, d13), (a14, b1, c2, d14), (a14, b1, c2, d15), (a14, b1, c2, d16), (a14, b1, c2, d17), (a14, b1, c2, d18), (a14, b1, c2, d19), (a14, b1, c2, d20), (a14, b1, c2, d21), (a14, b1, c2, d22), (a14, b1, c3, d1), (a14, b1, c3, d2), (a14, b1, c3, d3), (a14, b1, c3, d4), (a14, b1, c3, d5), (a4, b1, c3, d6), (a14, b1, c3, d7), (a14, b1, c3, d8), (a14, b1, c3, d9), (a14, b1, c3, d10), (a14, b1, c3, d11), (a14, b1, c3, d12), (a14, b1, c3, d13), (a14, b1, c3, d14), (a14, b1, c3, d15), (a14, b1, c3, d16), (a14, b1, c3, d17), (a14, b1, c3, d18), (a14, b1, c3, d19), (a14, b1, c3, d20), (a14, b1, c3, d21), (a14, b1, c3, d22), (a14, b2, c1, d1), (a14, b2, c1, d2), (a14, b2, c1, d3), (a14, b2, c1, d4), (a14, b2, c1, d5), (a14, b2, c1, d6), (a14, b2, c1, d7), (a14, b2, c1, d8), (a14, b2, c1, d9), (a14, b2, c1, d10), (a14, b2, c1, d11), (a14, b2, c1, d12), (a14, b2, c1, d13), (a14, b2, c1, d14), (a14, b2, c1, d15), (a14, b2, c1, d16), (a14, b2, c1, d17), (a14, b2, c1, d18), (a14, b2, c1, d19), (a14, b2, c1, d20), (a14, b2, c1, d21), (a14, b2, c1, d22), (a14, b2, c2, d1), (a14, b2, c2, d2), (a14, b2, c2, d3), (a14, b2, c2, d4), (a14, b2, c2, d5), (a14, b2, c2, d6), (a14, b2, c2, d7), (a14, b2, c2, d8), (a14, b2, c2, d9), (a14, b2, c2, d10), (a14, b2, c2, d11), (a14, b2, c2, d12), (a14, b2, c2, d13), (a14, b2, c2, d14), (a4, b2, c2, d15), (a14, b2, c2, d16), (a14, b2, c2, d17), (a14, b2, c2, d18), (a14, b2, c2, d19), (a14, b2, c2, d20), (a14, b2, c2, d21), (a14, b2, c2, d22), (a14, b2, c3, d1), (a14, b2, c3, d2), (a14, b2, c3, d3), (a14, b2, c3, d4), (a14, b2, c3, d5), (a14, b2, c3, d6), (a14, b2, c3, d7), (a14, b2, c3, d8), (a14, b2, c3, d9), (a14, b2, c3, d10), (a14, b2, c3, d11), (a14, b2, c3, d12), (a14, b2, c3, d13), (a14, b2, c3, d14), (a14, b2, c3, d15), (a14, b2, c3, d16), (a14, b2, c3, d17), (a14, b2, c3, d18), (a14, b2, c3, d19), (a14, b2, c3, d20), (a14, b2, c3, d21), (a14, b2, c3, d22), (a14, b3, c3, d1), (a14, b3, c1, d2), (a14, b3, c1, d5), (a14, b3, c1, d4), (a14, b3, c1, d5), (a14, b3, c1, d6), (a14, b3, c1, d7), (a14, b3, c1, d8), (a14, b3, c1, d9), (a14, b3, c1, d10), (a14, b3, c1, d11), (a14, b3, c1, d12), (a14, b3, c1, d13), (a14, b3, c1, d14), (a14, b3, c1, d15), (a14, b3, c1, d16), (a14, b3, c1, d17), (a14, b3, c1, d18), (a14, b3, c1, d19), (a14, b3, c1, d20), (a14, b3, c1, d21), (a14, b3, c1, d22), (a14, b3, c2, d1), (a14, b3, c2, d2), (a14, b3, c2, d3), (a14, b3, c2, d4), (a14, b3, c2, d5), (a14, b3, c2, d6), (a14, b3, c2, d7), (a14, b3, c2, d8), (a14, b3, c2, d9), (a14, b3, c2, d10), (a14, b3, c2, d11), (a14, b3, c2, d12), (a14, b3, c2, d13), (a14, b3, c2, d14), (a14, b3, c2, d15), (a14, b3, c2, d16), (a14, b3, c2, d17), (a14, b3, c2, d18), (a14, b3, c2, d19), (a14, b3, c2, d20), (a14, b3, c2, d21), (a14, b3, c2, d22), (a14, b3, c3, d1), (a14, b3, c3, d2), (a14, b3, c3, d3), (a14, b3, c3, d4), (a14, b3, c3, d5), (a14, b3, c3, d6), (a14, b3, c3, d7), (a14, b3, d8), (a14, b3, c3, d9), (a14, b3, c3, d10), (a14, b3, c3, d11), (a14, b3, c3, d12), (a14, b3, c3, d13), (a14, b3, c3, d14), (a14, b3, c3, d15), (a14, b3, c3, d16), (a14, b3, c3, d17), (a14, b3, c3, d18), (a14, b3, c3, d19), (a14, b3, c3, d20), (a14, b3, c3, d21), (a14, b3, c3, d22), (a14, b4, c1, d1), (a14, b4, c1, d2), (a14, b4, c1, d3), (a14, b4, c1, d4), (a14, b4, c1, d5), (a14, b4, c1, d6), (a14, b4, c1, d7), (a14, b4, c1, d8), (a14, b4, c1, d9), (a14, b4, c1, d10), (a14, b4, c1, d11), (a14, b4, c1, d12), (a14, b4, c1, d13), (a14, b4, c1, d14), (a14, b4, c1, d15), (a14, b4, c1, d16), (a14, b4, c1, d17), (a14, b4, c1, d18), (a14, b4, c1, d19) (a14, b4, c1, d20), (a14, b4, c1, d21), (a14, b4, c1, d22), (a14, b4, c2, d1), (a14, b4, c2, d2), (a14, b4, c2, d3), (a14, b4, c2, d4), (a14, b4, c2, d5), (a14, b4, c2, d6), (a14, b4, c2, d7), (a14, b4, c2, d8), (a14, b4, c2, d9), (a14, b4, c2, d10), (a14, b4, c2, d11), (a14, b4, c2, d12), (a14, b4, c2, d13), (a14, b4, c2, d14), (a14, b4, c2, d15), (a14, b4, c2, d16), (a14, b4, c2, d17), (a14, b4, c2, d18), (a14, b4, c2, d19), (a14, b4, c2, d20), (a14, b4, c2, d21), (a4, b4, c2, d22), (a14, b4, c3, d1), (a14, b4, c3, d2), (a14, b4, c3, d3), (a14, b4, c3, d4), (a14, b4, c3, d5), (a14, b4, c3, d6), (a14, b4, c3, d7), (a14, b4, c3, d8), (a14, b4, c3, d9), (a14, b4, c3, d10), (a14, b4, c3, d11), (a14, b4, c3, d12), (a14, b4, c3, d13), (a14, b4, c3, d14), (a14, b4, c3, d15), (a14, b4, c3, d16), (a14, b4, c3, d17), (a14, b4, c3, d18), (a14, b4, c3, d19), (a14, b4, c3, d20), (a14, b4, c3, d21), (a14, b4, c3, d22), (a14, b5, c1, d1), (a14, b5, c1, d2), (a14, b5, c1, d3), (a14, b5, c1, d4), (a14, b5, c1, d5), (a14, b5, c1, d6), (a14, b5, c1, d7), (a14, b5, c1, d8), (a14, b5, c1, c9), (a14, b5, c1, d10), (a14, b5, c1, d11), (a14, b5, c1, d12), (a14, b5, c1, d13), (a14, b5, c1, d14), (a14, b5, c1, d15), (a14, b5, c1, d16), (a14, b5, c1, d16), (a1, b5, c1, d17), (a14, b5, c1, d18), (a14, b5, c1, d19), (a14, b5, c1, d20) (a14, b5, c1, d21), (a14, b5, c1, d22), (a14, b5, c2, d1), (a14, b5, c2, d2), (a14, b5, c2, d3), (a14, b5, c2, d4), (a14, b5, c2, d5), (a 4, b5, c2, d6), (a14, b5, c2, d7), (a14, b5, c2, d8), (a14, b5, c2, d9), (a14, b5, c2, d10), (a14, b5, c2, d11), (a14, b5, c2, d12), (a14, b5, c2, d13) (a14, b5, c2, d14), (a14, b5, c2, d15), (a14, b5, c2, d16), (a14, b5, c2, d17), (a14, b5, c2, d18), (a4, b5, c2, d19), (a14, b5, c2, d20), (a14, b5, c2, d21), (a14, b5, c2, d22), (a14, b5, c3, d1), (a14, b5, c3, d2), (a14, b5, c3, d3), (a14, b5, c3, d4), (a14, b5, c3, d5), (a14, b5, c3, d6), (a14, b5, c3, d7), (a14, b5, c3, d8), (a14, b5, c3, d9), (a14, b5, c3, d10), (a14, b5, c3, d11), (a14, b5, c3, d12), (a14, b5, c3, d13), (a14, b5, c3, d14), (a14, b5, c3, d15), (a14, b5, c3, d16), (a14, b5, c3, d17), (a14, b5, c3, d18), (a14, b5, c3, d19), (a14, b5, c3, d20), (a14, b5, c3, d21), (a14, b5, c3, d22), (a14, b6, c1, d1), (a14, b6, c1, d2), (a14, b6, c1, d3), (a14, b6, c1, d4), (a14, b6, c1, d5), (a14, b6, c1, d6), (a14, b6, c1, d7), (a14, b6, c1, d8), (a14, b6, c1, d9), (a14, b6, c1, d10), (a14, b6, c1, d11), (a14, b6, c1, d12), (a14, b6, c1, d13), (a14, b6, c1, d14), (a14, b6, c1, d15), (a14, b6, c1, d16), (a14, b6, c1, d17), (a14, b6, c1, d18), (a14, b6, c1, d19), (a14, b6, c1, d20), (a14, b6, c1, d21) (a14, b6, c1, d22), (a14, b6, c2, d1), (a14, b6, c2, d2), (a14, b6, c2, d3) (a14, b6, c2, d4), (a14, b6, c2, d5), (a14, b6, c2, d6), (a14, b6, c2, d7), (a14, b6, c2, d8), (a14, b6, c2, d9), (a14, b6, c2, d10), (a14, b6, c2, d11), (a14, b6, c2, d12), (a14, b6, c2, d13), (a14, b6, c2, d14), (a14, b6, c2, d15), (a14, b6, c2, d16), (a14, b6, c2, d17), (a14, b6, c2, d18), (a14, b6, c2, d19), (a14, b6, c2, d20), (a14, b6, c2, d21), (a14, b6, c2, d22), (a14, b6, c3, d1), (a14, b6, c3, d2), (a14, b6, c3, d3), (a14, b6, c3, d4), (a14, b6, c3, d5), (a14, b6, c3, d6), (a14, b6, c3, d7), (a14, b6, c3, d8), (a14, b6, c3, d9), (a14, b6, c3, d10), (a14, b6, c3, d11), (a14, b6, c3, d12), (a14, b6, c3, d13), (a14, b6, c3, d14), (a14, b6, c3, d15), (a14, b6, c3, d16), (a14, b6, c3, d17), (a14, b6, c3, d18), (a14, b6, c3, d19), (a14, b6, c3, d20), (a14, b6, c3, d21), (a14, b6, c3, d22), (a15, b1, c1, d1), (a15, b1, c1, d2), (a15, b1, c1, d3), (a15, b1, c1, d4), (a15, b1, c1, d5), (a15, b1, c1, d6), (a15, b1, c1, d7), (a15, b, c1, d8), (a15, b1, c1, d9), (a15, b1, c1, d10), (a15, b1, c1, d11), (a15, b1, c1, d12), (a15, b1, c1, d13), (a15, b1, c1, d14), (a15, b1, c1, d15), (a15, b1, c1, d16), (a15, b1, c1, d17), (a15, b1, c1, d18), (a15, b1, c1, d19), (a15, b1, c1, d20), (a15, b1, c1, d21), (a15, b1, c1, d22), (a15, b1, c2, d1), (a15, b1, c2, d2), (a15, b, c2, d3), (a15, b1, c2, d4), (a15, b1, c2, d5), (a15, b1, c2, d6), (a15, b1, c2, d7), (a15, b1, c2, d8), (a15, b1, c2, d9), (a15, b1, c2, d10), (a15, b1, c2, d11), (a15, b1, c2, d12), (a15, b1, c2, d13), (a15, b1, c2, d14), (a15, b1, c2, d15), (a15, b1, c2, d16), (a15, b1, c2, d17), (a15, b1, c2, d18), (a15, b1, c2, d19), (a15, b1, c2, d20), (a15, b1, c2, d21), (a15, b1, c2, d22), (a15, b1, c3, d1), (a15, b1, c3, d2), (a15, b1, c3, d3), (a15, b1, c3, d4), (a15, b1, c3, d5), (a15, b1, c3, d6), (a15, b1, c3, d7), (a15, b1, c3, d8), (a15, b1, c3, d9), (a15, b1, c3, d10), (a15, b1, c3, d11), (a15, b, c3, d12), (a15, b1, c3, d13), (a15, b1, c3, d14), (a15, b1, c3, d15), (a15, b1, c3, d16), (a15, b1, c3, d17), (a15, b1, c3, d18), (a15, b1, c3, d19), (a15, b1, c3, d20), (a15, b1, c3, d21), (a15, b1, c3, d22), (a15, b2, c1, d1), (a15, b2, c1, d2), (a15, b2, c1, d3), (a15, b2, c1, d4), (a15, b2, c1, d5), (a15, b2, c1, d6), (a15, b2, c1, d7), (a15, b2, c1, d8), (a15, b2, c1, d9), (a15, b2, c1, d10), (a15, b2, c1, d11), (a5, b2, c1, d12), (a15, b2, c1, d13), (a15, b2, c1, d14), (a15, b2, c1, d15), (a15, b2, c1, d16), (a15, b2, c1, d17), (a15, b2, c1, d18), (a15, b2, c1, d19), (a15, b2, c1, d20), (a15, b2, c1, d21), (a15, b2, c1, d22), (a15, b2, c2, d1), (a15, b2, c2, d2), (a15, b2, c2, d3), (a15, b2, c2, d4), (a15, b2, c2, d5), (a15, b2, c2, d6), (a15, b2, c2, d7), (a15, b2, c2, d3), (a15, b2, c2, d9), (a15, b2, c2, d10), (a15, b2, c2, d11), (a15, b2, c2, d12), (a15, b2, c2, d13), (a15, b2, c2, d14), (a15, b2, c2, d15), (a15, b2, c2, d16), (a15, b2, c2, d17), (a15, b2, c2, d18), (a15, b2, c2, d19), (a15, b2, c2, d20), (a15, b2, c2, d21), (a15, b2, c2, d22), (a15, b2)c3, d1), (a15, b2, c3, d2), (a15, b2, c3, d3), (a15, b2, c3, d4), (a15, b2, c3, d5), (a15, b2, c3, d16), (a15, b2, c3, d7), (a15, b2, c3, d8), (a1, b2, c3, d9), (a15, b2, c3, d10), (a15, b2, c3, d11), (a15, b2, c3, d12), (a15, b2, c3, d13), (a15, b2, c3, d14), (a15, b2, c3, d15), (a15, b2, c3, d16), (a15, b2, c3, d17), (a15, b2, c3, d18), (a15, b2, c3, d19), (a15, b2, c3, d20), (a15, b2, c3, d21), (a15, b2, c3, d22), (a15, b3, c1, d1), (a15, b3, c1, d2), (a15, b3, c1, d3), (a15, b3, c1, d4), (a15, b3, c1, d5), (a15, b3, c1, d6), (a15, b3, c1, d7), (a15, b3, c1, d8), (a15, b3, c1, d9), (a15, b3, c1, d10), (a15, b3, c1, d11), (a15, b3, c1, d12), (a15, b3, c1, d13), (a15, b3, c1, d14), (a15, b3, c1, d15), (a15, b3, c1, d16), (a15, b3, c1, d17), (a15, b3, c1, d18), (a15, b3, c1, d19), (a15, b3, c1, d20), (a15, b3, c1, d21), (a15, b3, c1, d22), (a15, b3, c2, d1), (a15, b3, c2, d2), (a15, b3, c2, d3), (a15, b3, c2, d4), (a15, b3, c2, d5), (a15, b5, c2, d6), (a15, b3, c2, d7), (a15, b3, c2, d8), (a15, b3, c2, d9), (a15, b3, c2, d10), (a15, b3, c2, d11), (a15, b3, c2, d12), (a15, b3, c2, d13), (a15, b3, c2, d14), (a15, b3, c2, d15), (a15, b3, c2, d16), (a15, b3, c2, d17), (a15, b3, c2, d18), (a15, b3, c2, d19), (a15, b3, c2, d20), (a15, b3, c2, d21), (a15, b3, c2, d22), (a15, b3, c3, d1), (a15, b3, c3, d2), (a15, b3, c3, d3), (a15, b5, c3, d4), (a15, b3, c3, d5), (a15, b3, c3, d6), (a15, b3, c3, d7), (a15, b3, c3, d8), (a15, b3, c3, d9), (a15, b3, c3, d10), (a15, b3, c3, d11), (a15, b3, c3, d12), (a15, b3, c3, d13), (a15, b3, c3, d14), (a15, b3, c3, d15), (a15, b3, c3, d16), (a15, b3, c3, d17), (a15, b3, c3, d18), (a15, b3, c3, d19), (a15, b3, c3, d20), (a15, b3, c3, d21), (a15, b3, c3, d22), (a15, b4, c1, d1), (a15, b4, c1, d2), (a15, b4, c1, d3), (a15, b4, c1, d4), (a15, b4, c1, d5), (a15, b4, c1, d6), (a15, b4, c1, d7), (a15, b4, c1, d3), (a15, b4, c1, d9), (a15, b4, c1, d10), (a15, b4, c1, d11), (a15, b4, c1, d12), (a15, b4, c1, d13), (a15, b4, c1, d14), (a15, b4, c1, d15), (a15, b4, c1, d16), (a15, b4, c1, d17), (a15, b4, c1, d18), (a15, b4, c1, d19), (a15, b4, c1, d20), (a15, b4, c1, d21), (a15, b4, c1, d22), (a15, b4, c2, d1), (a15, b4, c2, d2), (a15, b4, c2, d13), (a15, b4, c2, d4), (a15, b4, c2, d5), (a15, b4, c2, d6), (a15, b4, c2, d7), (a15, b4, c2, d8), (a15, b4, c2, d9), (a15, b4, c2, d10), (a15, b4, c2, d11), (a15, b4, c2, d12), (a15, b4, c2, d13), (a15, b4, c2, d14), (a15, b4, c2, d15), (a15, b4, c2, a16), (a15, b4, c2, d17), (a15, b4, c2, d18), (a15, b4, c2, d19), (a15, b4, c2, d20), (a15, b4, c2, d21), (a15, b4, c2, d22), (a15, b4, c3, d1), (a15, b4, c3, d2), (a15, b4, c3, d3), (a15, b4, c3, d4), (a15, b4, c3, d5), (a15, b4, c3, d6), (a15, b4, c3, d7), (a15, b4, c3, d8), (a15, b4, c3, d9), (a15, b4, c3, d10), (a15, b4, c3, d11), (a15, b4, c3, d12), (a15, b4, c3, d13), (a15, b4, c3, d14), (a15, b4, c3, d15), (a15, b4, c3, d16), (a15, b4, c3, d17), (a15, b4, c3, d18), (a15, b4, c3, d19), (a15, b4, c3, d20), (a15, b4, c3, d21), (a15, b4, c3, d22), (a15, b5, c1, d1), (a15, b5, c1, d2), (a15, b5, c1, d3), (a15, b5, c1, d4), (a15, b5, c1, d5), (a15, b5, c1, d6), (a15, b5, c1, d7), (a15, b5, c1, d8), (a15, b5, c1, d9), (a15, b5, c1, d10), (a15, b5, c1, d11), (a15, b5, c1, d12), (a15, b5, c1, d13), (a15, b5, c1, d14), (a15, b5, c1, d15), (a15, b5, c1, d16), (a15, b5, c1, d17), (a15, b5, c1, d18), (a15, b5, c1, d19), (a15, b5, c1, d20), (a15, b5, c1, d21), (a15, b5, c1, d22), (a15, b5, c2, d1), (a15, b5, c2, d2), (a15, b5, c2, d3), (a15, b5, c2, d4), (a15, b5, c2, d5), (a15, b5, c2, d6), (a15, b5, c2, d7), (a15, b5, c2, d8), (a15, b5, c2, d9), (a15, b5, c2, d10), (a15, b5, c2, d11), (a15, b5, c2, d12), (a15, b5, c2, d13), (a15, b5, c2, d14), (a15, b5, c2, d15), (a15, b5, c2, d16), (a15, b5, c2, d17), (a15, b5, c2, d18), (a15, b5, c2, d19), (a15, b5, c2, d20), (a15, b5, c2, d21), (a15, b5, c2, d22), (a15, b5, c3, d1), (a15, b5, c3, d2), (a15, b5, c3, d3), (a15, b5, c3, d4), (a15, b5, c3, d5), (a15, b5, c3, d6), (a15, b5, c3, d7), (a15, b5, c3, d8), (a15, b5, c3, d9), (a15, b5, c3, d10), (a15, b5, c3, d11), (a15, b5, c3, d12), (a15, b5, c3, d13), (a15, b5, c3, d14), (a15, b5, c3, d15), (a15, b5, c3, d16), (a15, b5, c3, d17), (a15, b5, c3, d18), (a15, b5, c3, d19), (a15, b5, c3, d20), (a15, b5, c3, d21), (a15, b5, c3, d22), (a15, b6, c1, d1), (a15, b6, c1, d2), (a15, b6, c1, d3), (a15, b6, c1, d4), (a15, b6, c1, d5), (a15, b6, c1, d6), (a15, b6, c1, d7), (a15, b6, c1, d8), (a15, b6, c1, d9), (a15, b6, c1, d10), (a15, b6, c1, d11), (a15, b6, c1, d12), (a15, b6, c1, d13), (a15, b6, c1, d14), (a15, b6, c1, d15), (a15, b6, c1, d16), (a15, b6, c1, d17), (a15, b6, c1, d18), (a15, b6, c1, d19), (a15, b6, c1, d20), (a15, b6, c1, d21), (a15, b6, c1, d22), (a15, b6, c2, d1), (a15, b6, c2, d2), (a15, b6, c2, d3), (a15, b6, c2, d4), (a15, b6, c2, d5), (a15, b6, c2, d6), (a15, b6, c2, d7), (a15, b6, c2, d8), (a15, b6, c2, d9), (a15, b6, c2, d10), (a15, b6, c2, d11), (a15, b6, c2, d12), (a15, b6, c2, d13), (a15, b6, c2, d14), (a15, b6, c2, d15), (a15, b6, c2, d16), (a15, b6, c2, d17), (a15, b6, c2, d18), (a15, b6, c2, d19), (a15, b6, c2, d20), (a15, b6, c2, d21), (a15, b6, c2, d22), (a15, b6, c3, d1), (a15, b6, c3, d2), (a15, b6, c3, d3), (a15, b6, c3, d4), (a15, b6, c3, d5), (a15, b6, c3, d6), (a15, b6, c3, d7), (a15, b6, c3, d8), (a15, b6, c3, d9), (a15, b6, c3, d10), (a15, b6, c3, d11), (a15, b6, c3, d12), (a15, b6, c3, d13), (a15, b6, c3, d14), (a15, b6, c3, d15), (a15, b6, c3, d16), (a15, b6, c3, d17), (a15, b6, c3, d18), (a15, b6, c3, d19), (a15, b6, c3, d20), (a15, b6, c3, d21), (a15, b6, c3, d22), (a16, b1, c1, d1), (a16, b1, c1, d2), (a16, b1, c1, d3), (a16, b1, c1, d4), (a16, b1, c1, d5), (a16, b1, c1, d6), (a16 b1, c1, d7), (a6, b1, c1, d8), (a16, b1, c1, d9), (a16, b1, c1, d10), (a16, b1, c1, d11), (a16, b1, c1, d12), (a16, b1, c1, d13), (a16, b1, c1, d14), (a16, b1, c1, d15), (a16, b1, c1, d16), (a16, b1, c1, d17), (a16, b1, c1, d18), (a16, b1, c1, d19), (a16, b1, c1, d20), (a16, b1, c1, d21), (a16, b1, c1, d22), (a16, b1, c2, d1), (a16, b1, c2, d2), (a16, b1, c2, d3), (a16, b1, c2, d4), (a16, b1, c2, d5), (a16, b1, c2, d6), (a16, b1, c2, d7), (a16, b1, c2, d8), (a16, b1, c2, d9), (a16, b1, c2, d10), (a16, b1, c2, d11), (a16, b1, c2, d12), (a16, b1, c2, d13), (a16, b1, c2, d14), (a16, b1, c2, d15), (a16, b1, c2, d16), (a16, b1, c2, d17), (a16, b1, c2, d18), (a16, b1, c2, d19), (a16, b1, c2, d20), (a16, b1, c2, d21), (a16, b1, c2, d22), (a16, b1, c3, d1), (a16, b1, c3, d2), (a16, b1, c3, d3), (a16, b1, c3, d4), (a16, b1, c3, d5), (a16, b1, c3, d6), (a16, b1, c3, d7), (a16, b1, c3, d8), (a16, b1, c3, d9), (a16, b1, c3, d10), (a16, b1, c3, d11), (a16, b1, c3, d12), (a16, b1, c3, d13), (a16, b1, c3, d14), (a16, b1, c3, d15), (a16, b1, c3, d16), (a16, b1, c3, d17), (a16, b1, c3, d18), (a16, b1, c3, d19), (a16, b1, c3, d20), (a16, b1, c3, d21), (a16, b1, c3, d22), (a16, b2, c1, d1), (a16, b2, c1, d2), (a16, b2, c1, d3), (a16, b2, c1, d4), (a16, b2, c1, d5), (a16, b2, c1, d6), (a16, b2, c1, d7), (a16, b2, c1, d8), (a16, b2, c1, d9), (a16, b2, c1, d10), (a16, b2, c1, d11), (a16, b2, c1, d12), (a16, b2, c1, d13), (a16, b2, c1, d14), (a16, b2, c1, d15), (a16, b2, c1, d16), (a16, b2, c1, d17), (a16, b2, c1, d18), (a16, b2, c1, d19), (a16, b2, c1, d20), (a16, b2, c1, d21), (a16, b2, c1, d22), (a16, b2, c2, d1), (a16, b2, c2, d2), (a16, b2, c2, d3), (a16, b2, c2, d4), (a16, b2, c2, d5), (a16, b2, c2, d6), (a16, b2, c2, d7), (a16, b2, c2, d8), (a16, b2, c2, d9), (a16, b2, c2, d10), (a16, b2, c2, d11), (a16, b2, c2, d12), (a16, b2, c2, d13), (a16, b2, c2, d14), (a16, b2, c2, d15), (a16, b2, c2, d16), (a16, b2, c2, d17), (a16, b2, c2, d18), (a16, b2, c2, d9), (a16, b2, c2, d20), (a6, b2, c2, d21), (a16, b2, c2, d22), (a16, b2, c3, d1), (a16, b2, c3, d2), (a16, b2, c3, d3), (a16, b2, c3, d4), (a16, b2, c3, d5), (a16, b2, c3, d6), (a16, b2, c3, d7), (a16, b2, c3, d8), (a16, b2, c3, d9), (a16, b2, c3, d10), (a16, b2, c3, d11), (a16, b2, c3, d12), (a16, b2, c3, d13), (a16, b2, c3, d14), (a16, b2, c3, d15), (a16, b2, c3, d16), (a16, b2, c3, d17), (a16, b2, c3, d18), (a16, b2, c3, d19), (a16, b2, c3, d20), (a16, b2, c3, d21), (a16, b2, c3, d22), (a16, b3, c1, d1), (a16, b3, c1, d2), (a16, b3, c1, d3), (a16, b3, c1, d4), (a16, b3, c1, d5), (a16, b3, c1, d6), (a16, b3, c1, d7), (a16, b3, c1, d8), (a16, b3, c1, d9), (a16, b3, c1, d10), (a16, b3, c1, d11), (a16, b3, c1, d12), (a16, b3, c1, d13), (a16, b3, c1, d14), (a16, b3, c1, d15), (a16, b3, c1, d16), (a16, b3, c1, d17), (a6, b3, c1, d18), (a16, b3, c1, d19), (a16, b3, c1, d20), (a16, b3, c1, d21), (a16, b3, c1, d22), (a16, b3, c2, d1), (a16, b3, c2, d2), (a16, b3, c2, d3), (a16, b3, c2, d4), (a16, b3, c2, d5), (a16, b3, c2, d6), (a16, b3, c2, d7), (a16, b3, c2, d8), (a16, b3, c2, d9), (a16, b3, c2, d10), (a16, b3, c2, d11), (a16, b3, c2, d12), (a16, b5, c2, d13), (a16, b3, c2, d14), (a16, b3, c2, d15), (a16, b3, c2, d16), (a16, b3, c2, d17), (a16, b3, c2, d18), (a16, b3, c2, d19), (a16, b3, c2, d20), (a16, b3, c2, d21), (a16, b3, c2, d22), (a16, b3, c3, d1), (a16, b3, c3, d2), (a16, b3, c3, d3), (a16, b3, c3, d4), (a16, b3, c3, d5), (a16, b3, c3, d6), (a16, b3, c3, d7), (a16, b3, c3, d8), (a16, b3, c3, d9), (a16, b3, c3, d10), (a16, b3, c3, d11), (a16, b3, c3, d12), (a16, b3, c3, d13), (a16, b3, c3, d14), (a16, b3, c3, d15), (a16, b3, c3, d16), (a6, b3, c3, d17), (a16, b3, c3, d18), (a16, b3, c3, d19), (a16, b3, c3, d20), (a16, b3, c3, d21), (a16, b3, c3, d22), (a16, b4, c1, d1), (a16, b4, c1, d2), (a16, b4, c1, d3), (a16, b4, c1, d4), (a16, b4, c1, d5), (a16, b4, c1, d6), (a16, b4, c1, d7), (a16, b4, c1, d8), (a16, b4, c1, d9), (a16, b4, c1, d10), (a16, b4, c1, d11), (a16, b4, c1, d12), (a16, b4, c1, d13), (a16, b4, c1, d14), (a16, b4, c1, d15), (a16, b4, c1, d16), (a16, b4, c1, d17), (a16, b4, c1, d18), (a16, b4, c1, d19), (a16, b4, c1, d20), (a16, b4, c1, d21), (a16, b4, c1, d22), (a16, b4, c2, d1), (a16, b4, c2, d2), (a16, b4, c2, d3), (a16, b4, c2, d4), (a16, b4, c2, d5), (a16, b4, c2, d6), (a16, b4, c2, d7), (a16, b4, c2, d8), (a16, b4, c2, d9), (a16, b4, c2, d10), (a16, b4, c2, d11), (a16, b4, c2, d12), (a16, b4, c2, d13), (a16, b4, c2, d14), (a16, b4, c2, d15), (a16, b4, c2, d16), (a16, b4, c2, d17), (a16, b4, c2, d18), (a16, b4, c2, d19), (a16, b4, c2, d20), (a16, b4, c2, d21), (a16, b4, c2, d22), (a16, b4, c3, d1), (a16, b4, c3, d2), (a16, b4, c3, d3), (a16, b4, c3, d4), (a16, b4, c3, d5), (a16, b4, c3, d6), (a16, b4, c3, d7), (a16, b4, c3, d8), (a16, b4, c3, d9), (a16, b4, c3, d10), (a16, b4, c3, d11), (a16, b4, c3, d12), (a16, b4, c3, d13), (a16, b4, c3, d14), (a16, b4, c3, d15), (a16, b4, c3, d16), (a16, b4, c3, d17), (a16, b4, c3, d18), (a16, b4, c3, d19), (a16, b4, c3, d20), (a16, b4, c3, d21), (a16, b4, c3, d22), (a16, b5, c1, d1), (a16, b5, c1, d2), (a16, b5, c1, d3), (a16, b5, c1, d4), (a16, b5, c1, d5), (a16, b5, c1, d6), (a16, b5, c1, d7), (a16, b5, c1 d8), (a16, b5, c1, d9), (a16, b5, c1, d10), (a16, b5, c1, d11), (a16, b5, c1, d12), (a16, b5, c1, d13), (a16, b5, c1, d14), (a16, b5, c1, d15), (a16, b5, c1, d16), (a16, b5, c1, d17), (a16, b5, c1, d18), (a16, b5, c1, d19), (a16, b5, c1, d20), (a16, b5, c1, d21), (a16, b5, c1, d22), (a16, b5, c2, d1), (a16, b5, c2, d2), (a16, b5, c2, d3), (a16, b5, c2, d4), (a16, b5, c2, d5), (a16, b5, c2, d6), (a16, b5, c2, d7), (a16, b5, c2, d8), (a16, b5, c2, d9), (a16, b5, c2, d10), (a16, b5, c2, d11), (a16, b5, c2, d12), (a16, b5, c2, d13), (a16, b5, c2, d14), (a16, b5, c2, d15), (a16, b5, c2, d16), (a16, b5, c2, d17), (a16, b5, c2, d18), (a16, b5, c2, d19), (a16, b5, c2, d20), (a16, b5, c2, d21), (a16, b5, c2, d22), (a16, b5, c3, d1), (a16, b5, c3, d2), (a16, b5, c3, d3), (a16, b5, c3, d4), (a16, b5, c3, d5), (a16, b5, c3, d6), (a16, b5, c3, d7), (a16, b5, c3, d8), (a16, b5, c3, d9), (a16, b5, c3, d10), (a16, b5, c3, d11), (a16, b5, c3, d12), (a16, b5, c3, d13), (a16, b5, c3, d14), (a16, b5, c3, d15), (a16, b5, c3, d16), (a16, b5, c3, d17), (a16, b5, c3, d18), (a16, b5, c3, d19), (a16, b5, c3, d20), (a16, b5, c3, d21), (a16, b5, c3, d22), (a16, b6, c1, d1), (a16, b6, c1, d2), (a16, b6, c1, d3), (a16, b6, c1, d4), (a16, b6, c1, d5), (a16, b6, c1, d6), (a16, b6, c1, d7), (a16, b6, c1, d8), (a16, b6, c1, d9), (a16, b6, c1, d10), (a16, b6, c1, d11), (a16, b6, c1, d12), (a16, b6, c1, d13), (a16, b6, c1, d14), (a16, b6, c1, d15), (a16, b6, c1, d16), (a16, b6, c1, d17), (a16, b6, c1, d18), (a16, b6, c1, d19), (a16, b6, c1, d20), (a16, b6, c1, d21), (a16, b6, c1, d22), (a16, b6, c2, d1), (a16, b6, c2, d2), (a16, b6, c2, d3), (a16, b6, c2, d4), (a16, b6, c2, d5), (a16, b6, c2, d6), (a16, b6, c2, d7), (a16, b6, c2, d8), (a16, b6, c2, d9), (a16, b6, c2, d10), (a16, b6, c2, d11), (a16, b6, c2, d12), (a16, b6, c2, d13), (a16, b6, c2, d14), (a16, b6, c2, d15), (a16, b6, c2, d16), (a16, b6, c2, d17), (a16, b6, c2, d18), (a16, b6, c2, d19), (a16, b6, c2, d20), (a16, b6, c2, d21), (a16, b6, c2, d22), (a16, b6, c3, d1), (a16, b6, c3, d2), (a16, b6, c3, d3), (a16, b6, c3, d4), (a16, b6, c3, d5), (a16, b6, c3, d6), (a16, b6, c3, d7), (a16, b6, c3, d8), (a16, b6, c3, d9), (a16, b6, c3, d10), (a16, b6, c3, d11), (a16, c3, d12), (a16, b6, c3, d13), (a16, b6, c3, d14), (a16, b6, c3, d15), (a16, b6, c3, d16), (a16, b6, c3, d17), (a16, b6, c3, d18), (a16, b6, c3, d19), (a16, b6, c3, d20), (a16, b6, c3, d21), (a16, b6, c3, d22), (a17, b1, c1, d1), (a17, b1, c1, d2), (a17, b1, c1, d3), (a17, b1, c1, d4), (a1, b1, c1, d5), (a17, b1, c1, d6), (a17, b1, c1, d7), (a17, b1, c1, d8), (a17, b1, c1, d9), (a17, b1, c1, d10), (a17, b1, c1, d11), (a17, b1, c1, d12), (a17, b1, c1, d13), (a17, b1, c1, d14), (a17, b1, c1, d15), (a11, b1, c16), (a7, b1, c1, d17), (a17, b1, c1, d18), (a7, b1, c1, d19), (a17, b1, c1, d20), (a17, b1, c1, d21), (a17, b1, c1, d22), (a17, b1, c2, d1), (a17, b1, c2, d2), (a17, b1, c2, d3), (a17, b1, c2, d4), (a7, b1, c2, d5), (a17, b1, c2, d6), (a17, b1, c2, d7), (a17, b1, c2, d8), (a17, b1, c2, d9), (a17, b1, c2, d10), (a17, b, c2, d11), (a17, b1, c2, d12), (a17, b1, c2, d13), (a7, b1, c2, d14), (a17, b1, c2, d15), (a17, b1, c2, d16), (a17, b1, c2, d17), (a17, b1, c2, d18), (a17, b1, c2, d19), (a17, b1, c2, d20), (a17, b1, c2, d21), (a17, b, c2, d22), (a17, b1, c3, d1), (a17, b1, c3, d2), (a17, b1, c3, d3), (a17, b1, c3, d4), (a17, b1, c3, d5), (a17, b1, c3, d6), (a17, b1, c3, d7), (a17, b1, c3, d8), (a17, b1, c3, d9), (a17, b1, c3, d10), (a17, b1, c3, d11), (a17, b1, c3, d12), (a17, b1, c3, d13), (a17, b1, c3, d14), (a17, b1, c3, d15), (a17, b1, c3, d16), (a17, b1, c3, d17), (a17, b1, c3, d18), (a17, b1, c3, d19), (a17, b1, c3, d20), (a17, b1, c3, d21), (a17, b1, c3, d22), (a17, b2, c1, d1), (a17, b2, c1, d2), (a17, b2, c1, d3), (a17, b2, c1, d4), (a17, b2, c1, d5), (a17, b2, c1, d6), (a17, b2, c1, d7), (a17, b2, c1, d8), (a17, b2, c1, d9), (a17, b2, c1, d10), (a17, b2, c1, d11), (a17, b2, c1, d12), (a17, b2, c1, d13), (a17, b2, c1, d14), (a17, b2, c1, d15), (a17, b2, c1, d16), (a17, b2, c1, d17), (a17, b2, c1, d18), (a17, b2, c1, d19), (a17, b2, c1, d20), (a17, b2, c1, d21), (a17, b2, c1, d22), (a11, b2, c2, d1), (a17, b2, c2, d2), (a17, b2, c2, d3), (a17, b2, c2, d4), (a17, b2, c2, d5), (a17, b2, c2, d6), (a17, b2, c2, d7), (a17, b2, c2, d8), (a11, b2, c2, d9), (a17, b2, c2, d10), (a17, b2, c2, d11), (a17, b2, c2, d12), (a17, b2, c2, d13), (a17, b2, c2, d14), (a17, b2, c2, d15), (a17, b2, c2, d16), (a17, b2, c2, d17), (a17, b2, c2, d18), (a17, b2, c2, d19), (a11, b2, c2, d20), (a17, b2, c2, d21), (a17, b2, c2, d22), (a17, b2, c3, d1), (a17, b2, c3, d2), (a17, b2, c3, c13), (a17, b2, c3, c14), (a17, b2, c3, d5), (a17, b2, c3, d6), (a11, b2, c3, d7), (a17, b2, c3, d8), (a11, b2, c3, d9), (a17, b2, c3, d10), (a17, b2, c3, d11), (a17, b2, c3, d12), (a17, b2, c3, d13), (a17, b2, c3, d14), (a17, b2, c3, d15), (a17, b2, c3, d16), (a17, b2, c3, d17), (a17, b2, c3, d18), (a17, b2, c3, d19), (a17, b2, c3, d20), (a17, b2, c3, d21), (a17, b2, c3, d22), (a11, b3, c1, d1), (a17, b3, c1, d2), (a17, b3, c1, d3), (a17, b3, c1, d4), (a17, b3, c1, d5), (a17, b3, c1, d6), (a17, b3, c1, d7), (a17, b3, c1, d8), (a17, b3, c1, d9), (a17, b3, c1, d10), (a17, b3, c1, d11), (a17, b3, c1, d12), (a17, b3, c1, d13), (a17, b3, c1, d14), (a17, b3, c1, d15), (a17, b3, c1, d16), (a17, b3, c1, d17), (a17, b3, c1, d18), (a17, b3, c1, d19), (a11, b3, c1, d20), (a11, b3, c1, d21), (a17, b3, c1, d22), (a11, b3, c2, d1), (a17, b3, c2, d2), (a17, b3, c2, d3), (a11, b3, c2, d4), (a17, b3, c2, d5), (a11, b3, c2, d6), (a17, b3, c2, d7), (a17, b3, c2, d8), (a17, b3, c2, d9), (a17, b3, c2, d10), (a17, b3, c2, d11), (a17, b3, c2, d12), (a11, b3, c2, d13), (a17, b3, c2, d14), (a17, b3, c2, d15), (a17, b3, c2, d16), (a17, b3, c2, d17), (a17, b3, c2, d18), (a17, b3, c2, d19), (a17, b3, c2, d20), (a17, b3, c2, d21), (a17, b3, c2, d22), (a17, b3, c3, d1), (a17, b3, c3, d2), (a11, b3, c3, d3), (a17, b3, c3, d4), (a17, b3, c3, d5), (a17, b3, c3, d6), (a17, b3, c3, d7), (a17, b3, c3, d8), (a17, b3, c3, d9), (a17, b3, c3, d10), (a17, b3, c3, d11), (a17, b3, c3, d12), (a17, b3, c3, d13), (a17, b3, c3, d14), (a17, b3, c3, d15), (a17, b3, c3, d16), (a17, b3, c3, d17), (a17, b3, c3, d18), (a17, b3, c3, d19), (a17, b3, c3, d20), (a17, b3, c3, d21), (a17, b3, c3, d22), (a17, b4, c1, d1), (a17, b4, c1, d2), (a17, b4, c1, d3), (a17, b4, c1, d4), (a17, b4, c1, d5), (a17, b4, c1, d6), (a17, b4, c1, d7), (a17, b4, c1, d8), (a17, b4, c1, d9), (a17, b4, c1, d10), (a17, b4, c1, d11), (a17, b4, c1, d12), (a17, b4, c1, d13), (a17, b4, c1, d14), (a17, b4, c1, d15), (a17, b4, c1, d16), (a17, b4, c1, d17), (a17, b4, c1, d18), (a17, b4, c1, d19), (a17, b4, c1, d20), (a17, b4, c1, d21), (a17, b4, c1, d22), (a17, b4, c2, d1), (a9, b4, c2, d2), (a17, b4, c2, d3), (a17, b4, c2, d4), (a17, b4, c2, d5), a7, b4, c2, d6), (a17, b4, c2, d7), (a17, b4, c2, d8), (a17, b4, c2, d9), (a17, b4, c2, d10), (a17, b4, c2, d11), (a17, b4, c2, d12), (a17, b4, c2, d13), (a17, b4, c2, d14), (a17, b4, c2, d15), (a17, b4, c2, d16), (a17, b4, c2, d17), (a17, b4, c2, d18), (a17, b4, c2, d19), (a17, b4, c2, d20), (a17, b4, c2, d21), (a17, b4, c2, d22), (a17, b4, c3, d1), (a17, b4, c3, d2), (a17, b4, c3, d3), (a17, b4, c3, d4), (a17, b4, c3, d5), (a17, b4, c3, d6), (a17, b4, c3, d7), (a17, b4, c3, d8), (a17, b4, c3, d9), (a17, b4, c3, d10), (a17, b4, c3, d11), (a17, b4, c3, d12), (a17, b4, c3, d13), (a17, b4, c3, d4), (a17, b4, c3, d15), (a17, b4, c3, d16), (a17, b4, c3, d17), (a17, b4, c3, d18), (a17, b4, c3, d19), (a17, b4, c3, d20), (a17, b4, c3, d21), (a17, b4, c3, d22), (a17, b5, c1, d1), (a17, b5, c1, d2), (a17, b5, c1, d3), (a17, b5, c1, d4), (a1, b5, c1, d5), (a17, b5, c1, d6), (a17, b5, c1, d7), (a17, b5, c1, d8), (a17, b5, c1, d9), (a17, b5, c1, d10), (a17, b5, c1, d11), (a17, b5, c1, d12), (a17, b5, c1, d13), (a17, b5, c1, d14), (a17, b5, c1, d15), (a17, b5, c1, d16), (a17, b5, c1, d17), (a17, b5, c1, d18), (a17, b5, c1, d19), (a17, b5, c1, d20), (a17, b5, c1, d21), (a17, b5, c1, d22), (a17, b5, c2, d1), (a17, b5, c2, d2), (a17, b5, c2, d3), (a17, b5, c2, d4), (a17, c1, d5), (a17, b5, c2, d6), (a17, b5, c2, d7), (a17, b5, c2, d10), (a17, b5, c2, d9), (a17, b5, c2, d10), (a17, b5, c2, d11), (a17, b5, c2, c2, d14), (a17, b5, c2, d13), (a17, b5, c2, d14), (a17, b5, c2, d15), (a17, b5, c2, d16), (a17, b5, c2, d17), (a17, b5, c2, d18), (a17, b5, c2, d19), (a17, b5, c2, d20), (a17, b5, c2, d21), (a17, b5, c2, d22), (a17, b5, c3, d1), (a17, b5, c3, d2), (a17, b5, c3, d3), (a17, b5, c3, d4), (a17, b5, c3, d5), (a17, b5, c3, d6), (a17, b5, c3, d7), (a17, b5, c3, d8), (a17, b5, c3, d9), (a17, b5, c3, d10), (a17, b5, c3, d11), (a17, b5, c3, d12), (a17, b5, c3, d13), (a17, b5, c3, d14), (a17, b5, c3, d15), (a17, b5, c3, d16), (a17, b5, c3, d17), (a17, b5, c3, d18), (a17, b5, c3, d19), (a17, b5, c3, d20), (a11, b5, c3, d21), (a17, b5, c3, d22), (a17, b6, c1, d1), (a17, b6, c1, d2), (a17, b6, c1, d3), (a17, b6, c1, d4), (a11, b6, c1, d5), (a17, b6, c1, d6), (a11, b6, c1, d7), (a17, b6, c1, d8), (a11, b6, c1, d9), (a17, b6, c1, d10), (a17, b6, c1, d11), (a17, b6, c1, d12), (a17, b6, c1, d13), (a17, b6, c1, d14), (a17, b6, c1, d15), (a17, b6, c1, d16); (a17, b6, c1, d17), (a17, b6, c1, d18), (a17, b6, c1, d10), (a17, b6, c1, d20), (a17, b6, c1, d21), (a17, b6, c1, d22), (a17, b6, c2, d1), (a17, b6, c2, d2), (a17, b6, c2, d3), (a17, b6, c2, d4), (a17, b6, c2, d15), (a17, b6, c2, d6), (a17, b6, c2, d17), (a17, b6, c2, d8), (a17, b6, c2, d9), (a17, b6, c2, d10), (a17, b6, c2, d11), (a17, b6, c2, d12), (a17, b6, c2, d13), (a17, b6, c2, d14), (a17, b6, c2, d15), (a17, b6, c2, d16), (a17, b6, c2, d17), (a17, b6, c2, d18), (a17, b6, c2, d19), (a17, b6, c2, d20), (a17, b6, c2, d21), (a17, b6, c2, d22), (a17, b6, c3, d1), (a17, b6, c3, d2), (a17, b6, c3, d3), (a17, b6, c3, d4), (a17, b6, c3, d5), (a17, b6, c3, d6), (a17, b6, c3, d17), (a17, b6, c3, d8), (a17, b6, c3, d9), (a17, b6, c3, d10), (a17, b6, c3, d11), (a17, b6, c3, d12), (a17, b6, c3, d13), (a17, b6, c3, d14), (a17, b6, c3, d15), (a17, b6, c3, d16), (a17, b6, c3, d17), (a17, b6, c3, d18), (a17, b6, c3, d19), (a17, b6, c3, d20), (a17, b6, c3, d21), (a17, b6, c3, d22), (a18, b1, c1, d1), (a18, b1, c1, d2), (a15, b1, c1, d3), (a18, b1, c1, d4), (a18, b1, c1, d5), (a18, b1, c1, d6), (a18, b1, c1, d7), (a18, b1, c1, d3), (a18, b1, c1, d9), (a15, b1, c1, d10), (a18, b1, c1, d11), (a18, b1, c1, d12), (a18, b1, c1, d13), (a18, b1, c1, d14), (a18, b1, c1, d15), (a18, b1, c1, d16), (a18, b1, c1, d17), (a18, b1, c1, d18), (a15, b1, c1, d19), (a18, b1, c1, d20), (a18, b1, c1, d21), (a18, b1, c1, d22), (a18, b1, c2, d1), (a18, b1, c2, d2), (a18, b1, c2, d3), (a18, b1, c2, d4), (a15, b1, c2, d5), (a18, b1, c2, d6), (a18, b1, c2, d7), (a18, b1, c2, d8), (a18, b1, c2, d9), (a18, b1, c2, d10), (a15, b1, c2, d11), (a18, b1, c2, d12), (a18, b1, c2, d13), (a18, b1, c2, d14), (a18, b1, c2, d15), (a18, b1, c2, d16), (a18, b1, c2, d17), (a18, b1, c2, d18), (a18, b1, c2, d19), (a18, b1, c2, d20), (a18, b1, c2, d21), (a18, b1, c2, d22), (a18, b1, c3, d1), (a18, b1, c3, d2), (a18, b1, c3, d3), (a18, b1, c3, d4), (a18, b1, c3, d5), (a18, b1, c3, d6), (a18, b1, c3, d7), (a15, b1, c3, d8), (a18, b1, c3, d9), (a18, b1, c3, d10), (a18, b1, c3, d11), (a18, b1, c3, d12), (a18, b1, c3, d13), (a18, b1, c3, d14), (a15, b1, c3, d15), (a18, b1, c3, d16), (a18, b1, c3, d17), (a15, b1, c3, d18), (a18, b1, c3, d19), (a15, b1, c3, d20), (a18, b1, c3, d21), (a18, b1, c3, d22), (a18, b2, c1, d1), (a18, b2, c1, d2), (a18, b2, c1, d3), (a18, b2, c1, d4), (a18, b2, c1, d5), (a18, b2, c1, d6), (a18, b2, c1, d1), (a18, b2, c1, d8), (a18, b2, c1, d9), (a18, b2, c1, d10), (a18, b2, c1, d11), (a18, b2, c1, d12), (a18, b2, c1, d13), (a18, b2, c1, d14), (a18, b2, c1, d15), (a18, b2, c1, d16), (a18, b2, c1, d17), (a18, b2, c1, d18), (a18, b2, c1, d19), (a15, b2, c1, d20), (a18, b2, c1, d21), (a18, b2, c1, d22), (a18, b2, c2, d11), (a18, b2, c2, d2), (a18, b2, c2, d3), (a18, b2, c2, d4), (a18, b2, c2, d5), (a18, b2, c2, d6), (a18, b2, c2, d7), (a18, b2, c2, d8), (a18, b2, c2, d9), (a18, b2, c2, d10), (a18, b2, c2, d11), (a18, b2, c2, d12), (a18, b2, c2, d13), (a18, b2, c2, d14), (a18, b2, c2, d15), b2, c2, d20), (a18, b2, c2, d21), (a18, b2, c2, d22), (a18, b2, c3, d1), (a15, b2, c3, b2, c3, d7), (a18, b2, c3, d8), (a18, b2, c3, d9), (a18, b2, c3, d10), (a18, b2, c3, d11), (a18, b2, c3, d12), (a18, b2, c3, d13), (a18, b2, c3, d14), (a18, b2, c3, d15), (a18, b2, c3, d16), (a18, b2, c3, d17), (a18, b2, c3, d18), (a18, b2, c3, d19), (a18, b2, c3, d20), (a18, b2, c3, d21), (a18, b2, c3, d22), (a18, b3, c1, d1), (a18, b3, c1, d2), (a18, b3, c1, d3), (a18, b3, c1, d4), (a18, b3, c1, d5), (a18, b3, c1, d6), (a18, b3, c1, d7), (a18, b3, c1, d8), (a18, b3, c1, d9), (a18, b3, c1, d10), (a18, b3, c1, d11), (a18, b3, c1, d12), (a18, b3, c1, d13), (a18, b3, c1, d14), (a18, b3, c1, d15), (a18, b3, c1, d16), (a18, b3, c1, d17), (a18, b3, c1, d18), (a18, b3, c1, d19), (a18, b3, c1, d20), (a18, b3, c1, d21), (a18, b3, c1, d22), (a18, b3, c2, d1), (a18, b3, c2, d2), (a18, b3, c2, d3), (a18, b3, c2, d4), (a18, b3, c2, d5), (a18, b3, c2, d6), (a18, b3, c2, d7), (a18, b3, c2, d8), (a18, b3, c2, d9), (a18, b3, c2, d10), (a18, b3, c2, d11), (a18, b3, c2, d12), (a18, b3, c2, d13), (a18, b3, c2, d14), (a18, b3, c2, d15), (a18, b3, c2, d16), (a18, b3, c2, d17), (a18, b3, c2, d18), (a18, b3, c2, d19), (a18, b3, c2, d20), (a18, b3, c2, d21), (a18, b3, c2, d22), (a18, b3, c3, d1), (a18, b3, c3, d2), (a18, b3, c3, d3), (a18, b3, c3, d4), (a18, b3, c3, d5), (a18, b3, c3, d6), (a15, b3, c3, d7), (a18, b3, c3, d8), (a18, b3, c3, d9), (a18, b3, c3, d10), (a8, b3, c3, d11), (a18, b3, c3, d12), (a18, b3, c3, d13), (a18, b3, c3, d14), (a18, b3, c3, d15), (a18, b3, c3, d16), (a18, b3, c3, d17), (a18, b3, c3, d18), (a18, b3, c3, d19), (a18, b3, c3, d20), (a18, b3, c3, d21), (a18, b3, c3, d22), (a18, b4, c1, d1), (a18, b4, c1, d2), (a18, b4, c1, d3), (a18, b4, c1, d4), (a18, b4, c1, d5), (a18, b4, c1, d6), (a18, b4, c1, d7), (a18, b4, c1, d8), (a18, b4, c1, d9), (a18, b4, c1, d10), (a18, b4, c1, d11), (a18, b4, c1, d12), (a18, b4, c1, d13), (a18, b4, c1, d14), (a18, b4, c1, d15), (a18, b4, c1, d16), (a18, b4, c1, d17), (a18, b4, c1, d18), (a18, b4, c1, d19), (a18, b4, c1, d20), (a18, b4, c1, d21), (a18, b4, c1, d22), (a18, b4, c2, d1), (a18, b4, c2, d2), (a18, b4, c2, d3), (a18, b4, c2, d4), (a18, b4, c2, d5), (a18, b4, c2, d6), (a18, b4, c2, d7), (a18, b4, c2, d8), (a18, b4, c2, d9), (a18, b4, c2, d10), (a18, b4, c2, d11), (a18, b4, c2, d12), (a18, b4, c2, d13), (a18, b4, c2, d14), (a18, b4, c2, d15), (a18, b4, c2, d16), (a18, b4, c2, d17), (a18, b4, c2, d18), (a18, b4, c2, d19), (a18, b4, c2, d20), (a18, b4, c2, d21), (a18, b4, c2, d22), (a8, b4, c3, d1), (a18, b4, c3, d2), (a18, b4, c3, d3), (a18, b4, c3, d4), (a18, b4, c3, d5), (a18, b4, c3, d6), (a18, b4, c3, d7), (a18, b4, c3, d8), (a18, b4, c3, d9), (a18, b4, c3, d10), (a18, b4, c3, d11), (a18, b4, c3, d12), (a18, b4, c3, d13), (a18, b4, c3, d14), (a18, b4, c3, d15), (a18, b4, c3, d16), (a18, b4, c3, d17), (a18, b4, c3, d18), (a18, b4, c3, d19), (a18, b4, c3, d20), (a18, b4, c3, d21), (a18, b4, c3, d22), (a18, b5, c1, dl), (a18, b5, c1, d2), (a18, b5, c1, d3), (a18, b5, c1, d4), (a18, b5, c1, d5), (a18, b5, c1, d6), (a18, b5, c1, d7), (a18, b5, c1, d8), (a18, b5, c1, d9), (a18, b5, c1, d10), (a18, b5, c1, d11), (a18, b5, c1, d12), (a18, b5, c1, d13), (a18, b5, c1, d14), (a18, b5, c1, d15), (a18, b5, c1, d16), (a18, b5, c1, d17), (a8, b5, c1, d18), (a18, b5, c1, d19), (a18, b5, c1, d20), (a18, b5, c1, d21), (a18, b5, c1, d22), (a18, b5, c2, d1), (a18, b5, c2, d2), (a18, b5, c2, d3), (a18, b5, c2, d4), (a18, b5, c2, d5), (a18, b5, c2, d6), (a18, b5, c2, d7), (a18, b5, c2, d8), (a18, b5, c2, d9), (a18, b5, c2, d10), (a18, b5, c2, d11), (a18, b5, c2, d12), (a18, b5, c2, d13), (a18, b5, c2, d14), (a18, b5, c2, d15), (a18, b5, c2, d16), (a18, b5, c2, d17), (a18, b5, c2, d18), (a18, b5, c2, d19), (a18, b5, c2, d20), (a18, b5, c2, d21), (a18, b5, c2, d22), (a18, b5, c3, d1), (a18, b5, c3, d2), (a18, b5, c3, d3), (a18, b5, c3, d4), (a18, b5, c3, d5), (a18, b5, c3, d6), (a18, b5, c3, d7), (a18, b5, c3, d8), (a18, b5, c3, d9), (a18, b5, c3, d10), (a18, b5, c3, d11), (a18, b5, c3, d12), (a18, b5, c3, d13), (a18, b5, c3, d14), (a18, b5, c3, d15), (a18, b5, c3, d16), (a18, b5, c3, d17), (a18, b5, c3, d18), (a18, b5, c3, d19), (a18, b5, c3, d20), (a18, b5, c3, d21), (a18, b5, c3, d22), (a18, b6, c1, d1), (a18, b6, c1, d2), (a18, b6, c1, d3), (a18, b6, c1, d4), (a18, b6, c1, d5), (a18, b6, c1, d6), (a18, b6, c1, d7), (a18, b6, c1, d8), (a18, b6, c1, d9), (a18, b6, c1, d10), (a18, b6, c1, d11), (a18, b6, c1, d12), (a18, b6, c1, d13), (a18, b6, c1, d14), (a18, b6, c1, d15), (a18, b6, c1, d16), (a18, b6, c1, d17), (a18, b6, c1, d18), (a18, b6, c1, d19), (a18, b6, c1, d20), (a18, b6, c1, d2), (a18, b1, c1, d22), (a18, b6, c2, d1), (a18, b6, c2, d2), (a15, b6, c2, d3), (a18, b6, c2, d4), (a8, b6, c2, d5), (a18, b6, c2, d6), (a18, b6, c2, d7), (a18, b6, c2, d8), (a18, b6, c2, d9), (a18, b6, c2, d10), (a18, b6, c2, d11), (a18, b6, c2, d12), (a18, b6, c2, d13), (a18, b6, c2, d14), (a18, b6, c2, d15), (a18, b6, c2, d16), (a18, b6, c2, d17), (a18, b6, c2, d18), (a18, b6, c2, d19), (a48, b6, c2, d20), (a1, b6, c2, d21), (a18, b6, c2, d22), (a18, b6, c3, d1), (a18, b6, c3, d2), (a18, b6, c3, d3), (a18, b6, c3, d4), (a18, b6, c3, d5), (a18, b6, c3, d6), (a18, b6, c3, d7), (a18, b6, c3, d8), (a18, b6, c3, d9), (a18, b6, c3, d10), (a8, b6, c3, d11), (a18, b6, c3, d12), (a18, b6, c3, d13), (a18, b6, c3, d14), (a18, b6, c3, d15), (a18, b6, c3, d16), (a18, b6, c3, d17), (a18, b6, c3, d18), (a18, b6, c3, d19), (a18, b6, c3, d20), (a18, b6, c3, d21), (a18, b6, c3, d22), (a19, b1, c1, d1), (a19, b1, c1, d2), (a19, b1, c1, d3), (a19, b1, c1, d4), (a19, b1, c1, d5), (a19, b1, c1, d6), (a19, b1, c1, d7), (a19, b1, c1, d8), (a19, b1, c1, d9), (a19, b1, c1, d10), (a19, b1, c1, d11), (a79, b1, c1, d12), (a79, b1, c1, d13), (a19, b1, c1, d14), (a19, b1, c1, d15), (a19, b1, c1, d6), (a19, b1, c1, d17), (a19, b1, c1, d18), (a19, b1, c1, d19), (a19, b1, c1, d20), (a19, b1, c1, d21), (a79, b1, c1, d22), (a79, b1, c2, d1), (a79, b1, c2, d2), (a19, b1, c2, d3), (a19, b1, c2, d4), (a19, b1, c2, d5), (a19, b1, c2, d6), (a79, b1, c2, d7), (a79, b1, c2, d8), (a19, b1, c2, d9), (a19, b1, c2, d11), (a19, b1, c2, d11), (a19, b1, c2, d12), (a19, b1, c2, d13), (a19, b1, c2, d14), (a9, b1, c2, d15), (a19, b1, c2, d16), (a19, b1, c2, d17), (a19, b1, c2, d18), (a19, b1, c2, d19), (a79, b1, c2, d20), (a19, b1, c2, d21), (a19, b1, c2, d22), (a19, b1, c3, d1), (a19, b1, c3, d2), (a19, b1, c3, d3), (a19, b1, c3, d4), (a19, b1, c3, d5), (a19, b1, c3, d6), (a19, b1, c3, d7), (a19, b1, c3, d8), (a19, b1, c3, d9), (a19, b1, c3, d10), (a19, b1, c3, d11), (a19, b1, c3, d12), (a19, b1, c3, d13), (a19, b1, c3, d14), (a19, b1, c3, d15), (a19, b1, c3, d16), (a19, b1, c3, d17), (a19, b1, c3, d18), (a19, b1, c3, d19), (a19, b1, c3, d20), (a19, b1, c3, d21), (a19, b1, c3, d22), (a19, b2, c1, d1), (a19, b2, c1, d2), (a19, b2, c1, d3), (a19, b2, c1, d4), (a19, b2, c1, d5), (a19, b2, c1, d6), (a19, b2, c1, d7), (a19, b2, c1, d8), (a19, b2, c1, d9), (a19, b2, c1, d10), (a19, b2, c1, d11), (a19, b2, c1, d12), (a19, b2, c1, d13), (a79, b2, c1, d14), (a79, b2, c1, d15), (a19, b2, c1, d16), (a19, b2, c1, d17), (a19, b2, c1, d18), (a19, b2, c1, d19), (a19, b2, c1, d20), (a19, b2, c1, d21), (a19, b2, c1, d22), (a19, b2, c2, d1), (a19, b2, c2, d2), (a19, b2, c2, d3), (a19, b2, c2, d4), (a19, b2, c2, d5), (a19, b2, c2, d6), (a9, b2, c2, d7), (a79, b2, c2, d8), (a19, b2, c2, d9), (a19, b2, c2, d10), (a19, b2, c2, d11), (a19, b2, c2, d12), (a19, b2, c2, d13), (a19, b2, c2, d14), (a19, b2, c2, d15), (a19, b2, c2, d16), (a19, b2, c2, d17), (a19, b2, c2, d18), (a9, b2, c2, d19), (a19, b2, c2, d20), (a19, b2, c2, d21), (a19, b2, c2, d22), (a19, b2, c3, d1), (a19, b2, c3, d2), (a19, b2, c3, d3), (a19, b2, c3, d4), (a79, b2, c3, d5), (a19, b2, c3, d6), (a19, b2, c3, d7), (a19, b2, c3, d8), (a19, b2, c3, d9), (a19, b2, c3, d10), (a19, b2, c3, d11), (a19, b2, c3, d12), (a19, b2, c3, d13), (a19, b2, c3, d14), (a79, b2, c3, d15), (a19, b2, c3, d16), (a19, b2, c3, d17), (a19, b2, c3, d18), (a19, b2, c3, d19), (a19, b2, c3, d20), (a19, b2, c3, d21), (a79, b2, c3, d22), (a19, b3, c1, d1), (a19, b3, c1, d2), (a9, b3, c1, d3), (a19, b3, c1, d4), (a19, b3, c1, d5), (a19, b5, c1, d6), (a19, b3, c1, d7), (a19, b3, c1, d8), (a19, b3, c1, d9), (a19, b3, c1, d10), (a19, b3, c1, d11), (a79, b3, c1, d12), (a19, b3, c3, d13), (a19, b3, c3, d14), (a19, b3, c1, d15), (a19, b3, c1, d16), (a79, b3, c1, d17), (a19, b3, c1, d18), (a19, b3, c1, d19), (a19, b3, c1, d20), (a19, b3, c1, d21), (a19, b3, c1, d22), (a19, b3, c2, d1), (a79, b3, c2, d2), (a19, b3, c2, d3), (a19, b3, c2, d4), (a19, b5, c2, d5), (a19, b3, c2, d6), (a19, b3, c2, d7), (a19, b3, c2, d8), (a19, b3, c2, d9), (a19, b3, c2, d10), (a19, b3, c2, d11), (a19, b3, c2, d12), (a19, b3, c2, d13), (a19, b3, c2, d14), (a19, b3, c2, d15), (a19, b3, c2, d16), (a9, b3, c2, d17), (a19, b3, c2, d8), (a19, b3, c2, d19), (a19, b3, c2, d20), (a19, b3, c2, d21), (a19, b3, c2, d22), (a19, b3, c3, d1), (a79, b3, c3, d2), (a19, b3, c3, d3), (a19, b3, c3, d4), (a19, b3, c3, d5), (a19, b3, c3, d6), (a79, b3, c3, d7), (a79, b3, c3, d8), (a19, b3, c3, d9), (a19, b3, c3, d10), (a19, b3, c3, d11), (a79, b3, c3, d12), (a19, b3, c3, d13), (a19, b3, c3, d14), (a19, b3, c3, d15), (a19, b3, c3, d16), (a19, b3, c3, d17), (a19, b3, c3, d18), (a79, b3, c3, d19), (a19, b3, c3, d20), (a19, b3, c3, d21), (a19, b3, c3, d22), (a19, b4, c1, d1), (a19, b4, c1, d2), (a19, b4, c1, d3), (a19, b4, c1, d5), (a19, b4, c1, d4), (a19, b4, c1, d5), (a79, b4, c1, d6), (a19, b4, c1, d7), (a19, b4, c., d8), (a79, b4, c1, d9), (a19, b4, c1, d10), (a19, b4, c1, d11), (a19, b4, c1, d12), (a19, b4, c1, d13), (a19, b4, c1, d14), (a19, b4, c1, d15), (a19, b4, c1, d6), (a19, b4, c1, d17), (a19, b4, c1, d18), (a19, b4, c1, d19), (a19, b4, c1, d20), (a19, b4, c1, d21), (a19, b4, c1, d22), (a19, b4, c2, d1), (a19, b4, c2, d2), (a19, b4, c2, d3), (a19, b4, c2, d4), (a19, b4, c2, d5), (a19, b4, c2, d6), (a19, b4, c2, d7), (a19, b4, c2, d8), (a19, b4, c2, d9), (a19, b4, c2, d10), (a19, b4, c2, d11), (a19, b4, c2, d12), (a19, b4, c2, d13), (a19, b4, c2, d14), (a19, b4, c2, d15), (a19, b4, c2, d16), (a19, b4, c2, d17), (a79, b4, c2, d18), (a79, b4, c2, d19), (a19, b4, c2, d20), (a19, b4, c2, d21), (a19, b4, c2, d22), (a19, b4, c3, d1), (a19, b4, c3, d2), (a19, b4, c3, d3), (a19, b4, c3, d4), (a19, b4, c3, d5), (a19, b4, c3, d6), (a19, b4, c3, d7), (a19, b4, c3, d8), (a19, b4, c3, d9), (a19, b4, c3, d10), (a19, b4, c3, d11), (a19, b4, c3, d12), (a19, b4, c3, d13), (a19, b4, c3, d14), (a19, b4, c3, d15), (a19, b4, c3, d16), (a79, b4, c3, d17), (a19, b4, c3, d18), (a19, b4, c3, d19), (a19, b4, c3, d20), (a79, b4, c3, d21), (a19, b4, c3, d22), (a19, b5, c1, d1), (a19, b5, c1, d2), (a19, b5, c1, d3), (a79, b5, c1, d4), (a9, b5, c1, d5), (a19, b5, c1, d6), (a19, b5, c1, d7), (a19, b5, c1, d8), (a19, b5, c1, d9), (a19, b5, c1, d10), (a19, b5, c1, d11), (a19, b5, c1, d12), (a19, b5, c1, d13), (a19, b5, c1, d14), (a19, b5, c1, d15), (a19, b5, c1, d16), (a19, b, c1, d17), (a19, b5, c1, d18), (a19, b5, c1, d19), (a19, b5, c1, d20), (a19, b5, cl d21), (a19, b5, c1, d22), (a79, b5, c2, d1), (a19, b5, c2, d2), (a19, b5, c2, d3), (a19, b5, c2, d4), (a19, b5, c2, d5), (a19, b5, c2, d6), (a19, b5, c2, d7), (a19, b5, c2, d8), (a19, b5, c2, d9), (a19, b5, c2, d10), (a19, b5, c2, d11), (a79, b5, c2, d12), (a19, b5, c2, d13), (a19, b5, c2, d14), (a19, b5, c2, d15), (a19, b5, c2, d16), (a19, b5, c2, d17), (a19, b5, c2, d18), (a19, b5, c2, d19), (a19, b5, c2, d20), (a19, b5, c2, d21), (a19, b5, c2, d22), (a19, b5, c3, d1), (a19, b5, c3, d2), (a19, b5, c3, d3), (a19, b5, c3, d4), (a19, b5, c3, d5), (a19, b5, c3, d6), (a19, b5, c3, d7), (a19, b5, c3, d8), (a19, b5, c3, d9), (a19, b5, c3, d10), (a19, b5, c3, d11), (a19, b5, c3, d12), (a19, b5, c3, d13), (a19, b5, c3, d14), (a19, b5, c3, d15), (a19, b5, c3, d16), (a19, b5, c3, d17), (a19, b5, c3, d18), (a19, b5, c3, d19), (a19, b5, c3, d20), (a19, b5, c3, d21), (a19, b5, c3, d22), (a19, b6, c1, d1), (a19, b6, c1, d2), (a19, b6, c1, d3), (a19, b6, c1, d4), (a19, b6, c1, d5), (a19, b6, c1, d6), (a19, b6, c1, d7), (a19, b6, c1, d5), (a19, b6, c1, d9), (a19, b6, c1, d10), (a19, b6, c1, d11), (a19, b6, c1, d12), (a39, b6, c1, d13), (a19, b6, c1, d14), (a19, b6, c1, d15), (a19, b6, c1, d16), (a19, b6, c1, d17), (a19, b6, c1, d18), (a19, b6, c1, d19), (a19, b6, c1, d20), (a19, b6, c1, d21), (a9, b6, c1, d22), (a19, b6, c2, d1), (a19, b6, c2, d2), (a19, b6, c2, d3), (a19, b6, c2, d4), (a19, b6, c2, d5), (a19, b6, c2, d6), (a19, b6, c2, d7), (a19, b6, c2, d8), (a19, b6, c2, d9), (a19, b6, c2, d10), (a19, b6, c2, d11), (a19, b6, c2, d12), (a19, b6, c2, d13), (a19, b6, c2, d14), (a19, b6, c2, d15), (a19, b6, c2, d16), (a19, b6, c2, d17), (a19, b6, c2, d18), (a19, b6, c2, d19), (a19, b6, c2, d20), (a19, b6, c2, d21), (a19, b6, c2, d22), (a19, b6, c3, d1), (a19, b6, c3, d2), (a19, b6, c3, d3), (a19, b6, c3, d4), (a19, b6, c3, d5), (a19, b6, c3, d6), (a19, b6, c3, d7), (a19, b6, c3, d8), (a19, b6, c3, d9), (a19, b6, c3, d10), (a19, b6, c3, d11), (a19, b6, c3, d12), (a19, b6, c3, d13), (a19, b6, c3, d14), (a19, b6, c3, d15), (a19, b6, c3, d16), (a19, b6, c3, d17), (a19, b6, c3, d18), (a19, b6, c3, d19), (a19, b6, c3, d20), (a19, b6, c3, d21), (a19, b6, c3, d22), (a20, b1, c1, d1), (a20, b1, c1, d2), (a20, b1, c1, d3), (a20, b1, c1, d4), (a20, b1, c1, d5), (a20, b1, c1, d6), (a20, b1, c1, d7), (a20, b1, c1, d8), (a20, b1, c1, d9), (a20, b1, c1, d10), (a20, b1, c1, d14), (a20, b1, c1, d12), (a20, b1, c1, d13), (a20, b1, c1, d14), (a20, b1, c1, d15), (a20, b1, c1, d16), (a20, b1, c1, d17), (a20, b1, c1, d18), (a20, b1, c1, d19), (a20, b1, c1, d20), (a20, b1, c1, d21), (a20, b1, c1, d22), (a20, b1, c2, d1), (a20, b1, c2, d2), (a20, b1, c2, d3), (a20, b1, c2, d4), (a20, b1, c2, d5), (a20, b1, c2, d6), (a20, b1, c2, d7), (a20, b1, c2, d8), (a20, b1, c2, d9), (a20, b1, c2, d10), (a20, b1, c2, d11), (a20, b1, c2, d12), (a20, b1, c2, d13) (a20, b1, c2, d14), (a20, b1, c2, d15), (a20, b1, c2, d16), (a20, b1, c2, d17), (a20, b1, c2, d18), (a20, b1, c2, d19), (a20, b1, c2, d20), (a20, b1, c2, d21), (a20, b1, c2, d22), (a20, b1, c3, d1), (a20, b1, c3, d2), (a20, b1, c3, d3), (a20, b1, c3, d4), (a20, b1, c3, d5), (a20, b1, c3, d6), (a20, b1, c3, d7), (a20, b1, c3, d8), (a20, b1, c3, d9), (a20, b1, c3, d10), (a20, b1, c3, d11), (a20, b1, c3, d12), (a20, b1, c3, d13), (a20, b1, c3, d14), (a20, b1, c3, d15), (a20, b1, c3, d16), (a20, b1, c3, d17), (a20, b1, c3, d18), (a20, b1, c3, d19), (a20, b1, c3, d20), (a20, b1, c3, d21), (a20, b1, c3, d22), (a20, b2, c1, d1), (a20, b2, c1, d2), (a20, b2, c1, d3), (a20, b2, c1, d4), (a20, b2, c1, d5), (a20, b2, c1, d6), (a20, b2, c1, d7), (a20, b2, c1, d8), (a20, b2, c1, d9), (a20, b2, c1, d10), (a20, b2, c1, d11), (a20, b2, c1, d12), (a20, b2, c1, d13), (a20, b2, c1, d14), (a20, b2, c1, d15), (a20, b2, c1, d16), (a20, b2, c1, d17), (a20, b2, c1, d18), (a20, b2, c1, d19), (a20, b2, c1, d20), (a20, b2, c1, d21), (a20, b2, c1, d22), (a20, b2, c2, d1), (a20, b2, c2, d2), (a20, b2, c2, d3), (a20, b2, c2, d4), (a20, b2, c2, d5), (a20, b2, c2, d6), (a20, b2, c2, d7), (a20, b2, c2, d8), (a20, b2, c2, d9), (a20, b2, c2, d10), (a20, b2, c2, d11), (a20, b2, c2, d12), (a20, b2, c2, d13), (a20, b2, c2, d14), (a20, b2, c2, d15), (a20, b2, c2, d16), (a20, b2, c2, d17), (a20, b2, c2, d18), (a20, b2, c2, d19), (a20, b2, c2, d20), (a20, b2, c2, d21), (a20, b2, c2, d22), (a20, b2, c3, d1), (a20, b2, c3, d2), (a20, b2, c3, d3), (a20, b2, c3, d4), (a20, b2, c3, d5), (a20, b2, c3, d6), (a20, b2, c3, d7), (a20, b2, c3, d8), (a20, b2, c3, d9), (a20, b2, c3, d10), (a20, b2, c3, d11), (a20, b2, c3, d12), (a20, b2, c3, d13), (a20, b2, c3, d14), (a20, b2, c3, d15), (a20, b2, c3, d16), (a20, b2, c3, d17), (a20, b2, c3, d18), (a20, b2, c3, d19), (a20, b2, c3, d20), (a20, b2, c3, d21), (a20, b2, c3, d22), (a20, b3, c1, d1), (a20, b3, c1, d2), (a20, b3, c1, d3), (a20, b3, c1, d4), (a20, b3, c1, d5), (a20, b3, c1, d6), (a20, b3, c1, d7), (a20, b3, c1, d8), (a20, b3, c1, d9), (a20, b3, c1, d10), (a20, b3, c1, d11), (a20, b3, c1, d12), (a20, b3, c1, d13), (a20, b3, c1, d14), (a20, b3, c1, d15), (a20, b3, c1, d16), (a20, b3, c1, d17), (a20, b3, c1, d18), (a20, b3, c1, d19), (a20, b3, c1, d20), (a20, b3, c1, d21), (a20, b3, c1, d22), (a20, b3, c2, d1), (a20, b3, c2, d2), (a20, b3, c2, d3), (a20, b3, c2, d4), (a20, b3, c2, d5), (a20, b3, c2, d6), (a20, b3, c2, d7), (a20, b3, c2, d8), (a20, b3, c2, d9), (a20, b3, c2, d10), (a20, b3, c2, d11), (a20, b3, c2, d12), (a20, b3, c2, d13), (a20, b3, c2, d14), (a20, b3, c2, d15), (a20, b3, c2, d16), (a20, b3, c2, d17), (a20, b3, c2, d18), (a20, b3, c2, d19), (a20, b3, c2, d20), (a20, b3, c2, d21), (a20, b3, c2, d22), (a20, b3, c3, d1), (a20, b3, c3, d2), (a20, b3, c3, d3), (a20, b3, c3, d4), (a20, b3, c3, d5), (a20, b3, c3, d6), (a20, b3, c3, d7), (a20, b3, c3, d8), (a20, b3, c3, d9), (a20, b3, c3, d10), (a20, b3, c3, d11), (a20, b3, c3, d12), (a20, b3, c3, d13), (a20, b3, c3, d14), (a20, b3, c3, d15), (a20, b3, c3, d16), (a20, b3, c3, d11), (a20, b3, c3, d18), (a20, b3, c3, d19), (a20, b3, c3, d20), (a20, b3, c3, d21), (a20, b3, c3, d22), (a20, b4, c1, d1), (a20, b4, c1, d2), (a20, b4, c1, d3), (a20, b4, c1, d4), (a20, b4, c1, d5), (a20, b4, c1, d6), (a20, b4, c1, d7), (a20, b4, c1, d8), (a20, b4, c1, d9), (a20, b4, c1, d10), (a20, b4, c1, d11), (a20, b4, c1, d12), (a20, b4, c1, d13), (a20, b4, c1, d14), (a20, b4, c1, d15), (a20, b4, c1, d16), (a20, b4, c1, d17), (a20, b4, c1, d18), (a20, b4, c1, d10), (a20, b4, c1, d20), (a20, b4, c1, d21), (a20, b4, c1, d22), (a20, b4, c2, d1), (a20, b4, c2, d2), (a20, b4, c2, d13), (a20, b4, c2, d4), (a20, b4, c2, d5), (a20, b4, c2, d6), (a20, b4, c2, d7), (a20, b4, c2, d8), (a20, b4, c2, d9), (a20, b4, c2, d10), (a20, b4, c2, d11), (a20, b4, c2, d12), (a20, b4, c2, d13), (a20, b4, c2, d14), (a20, b4, c2, d15), (a20, b4, c2, d16), (a20, b4, c2, d17), (a20, b4, c2, d18), (a20, b4, c2, d19), (a20, b4, c2, d20), (a20, b4, c2, d21), (a20, b4, c2, d22), (a20, b4, c3, d1), (a20, b4, c3, d2), (a20, b4, c3, d3), (a20, b4, c3, d4), (a20, b4, c3, d5), (a20, b4, c3, d6), (a20, b4, c3, d7), (a20, b4, c3, d8), (a20, b4, c3, d9), (a20, b4, c3, d10), (a20, b4, c3, d11), (a20, b4, c3, d12), (a20, b4, c3, d13), (a20, b4, c3, d14), (a20, b4, c3, d15), (a20, b4, c3, d16), (a20, b4, c3, d17), (a20, b4, c3, d18), (a20, b4, c3, d19), (a20, b4, c3, d20), (a20, b4, c3, d21), (a20, b4, c3, d22), (a20, b5, c1, d1), (a20, b5, c1, d2), (a20, b5, c1, d3), (a20, b5, c1, d4), (a20, b5, c1, d5), (a20, b5, c1, d6), (a20, b5, c1, d7), (a20, b5, c1, d8), (a20, b5, c1, d9), (a20, b5, c1, d10), (a20, b5, c1, d11), (a20, b5, c1, d12), (a20, b5, c1, d13), (a20, b5, c1, d14), (a20, b5, c1, d15), (a20, b5, c1, d16), (a20, b5, c1, d17), (a20, b5, c1, d18), (a20, b5, c1, d19), (a20, b5, c1, d20), (a20, b5, c1, d21), (a20, b5, c1, d22), (a20, b5, c2, d1), (a20, b5, c2, d2), (a20, b5, c2, d3), (a20, b5, c2, d4), (a20, b5, c2, d5), (a20, b5, c2, d6), (a20, b5, c2, d7), (a20, b5, c2, d8), (a20, b5, c2, d9), (a20, b5, c2, d10), (a20, b5, c2, d11), (a20, b5, c2, d12), (a20, b5, c2, d13), (a20, b5, c2, d14), (a20, b5, c2, d15), (a20, b5, c2, d16), (a20, b5, c2, d17), (a20, b5, c2, d18), (a20, b5, c2, d19), (a20, b5, c2, d20), (a20, b5, c2, d21), (a20, b5, c2, d22), (a20, b5, c3, d1), (a20, b5, c3, d2), (a20, b5, c3, d3), (a20, b5, c3, d4), (a20, b5, c3, d5), (a20, b5, c3, d6), (a20, b5, c3, d7), (a20, b5, c3, d3), (a20, b5, c3, d9), (a20, b5, c3, d10), (a20, b5, c3, d11), (a20, b5, c3, d12), (a20, b5, c3, d13), (a20, b5, c3, d14), (a20, b5, c3, d15), (a20, b5, c3, d16), (a20, b5, c3, d17), (a20, b5, c3, d18), (a20, b5, c3, d19), (a20, b5, c3, d20), (a20, b5, c3, d21), (a20, b5, c3, d22), (a20, b6, c1, d1), (a20, b6, c1, d2), (a20, b6, c1, d3), (a20, b6, c1, d4), (a20, b6, c1, d5), (a20, b6, c1, d6), (a20, b6, c1, d7), (a20, b6, c1, d8), (a20, b6, c1, d9), (a20, b6, c1, d10), (a20, b6, c1, d11), (a20, b6, c1, d12), (a20, b6, c1, d13), (a20, b6, c1, d14), (a20, b6, c1, d15), (a20, b6, c1, d16), (a20, b6, c1, d17), (a20, b6, c1, d18), (a20, b6, c1, d19), (a20, b6, c1, d20), (a20, b6, c1, d21), (a20, b6, c1, d22), (a20, b6, c2, d1), (a20, b6, c2, d2), (a20, b6, c2, d3), (a20, b6, c2, d4), (a20, b6, c2, d5), (a20, b6, c2, d6), (a20, b6, c2, d7), (a20, b6, c2, d8), (a20, b6, c2, d9) (a20, b6, c2, d10), (a20, b6, c2, d11), (a20, b6, c2, d12), (a20, b6, c2, d13), (a20, b6, c2, d14), (a20, b6, c2, d15), (a20, b6, c2, d16), (a20, b6, c2, d17), (a20, b6, c2, d18), (a20, b6, c2, d19), (a20, b6, c2, d20), (a20, b6, c2, d21), (a20, b6, c2, d22), (a20, b6, c3, d1), (a20, b6, c3, d2), (a20, b6, c3, d3), (a20, b6, c3, d4), (a20, b6, c3, d5), (a20, b6, c3, d6), (a20, b6, c3, d7), (a20, b6, c3, d8), (a20, b6, c3, d9), (a20, b6, c3, d10), (a20, b6, c3, d11), (a20, b6, c3, d12), (a20, b6, c3, d13), (a20, b6, c3, d14), (a20, b6, c3, d15), (a20, b6, c3, d16), (a20, b6, c3, d17), (a20, b6, c3, d18), (a20, b6, c3, d19), (a20, b6, c3, d20), (a20, b6, c3, d21), (a20, b6, c3, d22), (a21, b1, c1, d1), (a21, b1, c1, d2), (a21, b1, c1, d3), (a21, b1, c1, d4), (a21, b1, c1, d5), (a21, b1, c1, d6), (a21, b1, c1, d7), (a21, b1, c1, d8), (a21, b1, c1, d9), (a21, b1, c1, d10), (a21, b1, c1, d11), (a21, b1, c1, d12), (a21, b1, c1, d13), (a21, b1, c1, d14), (a21, b1, c1, d15), (a21, b1, c1, d16), (a21, b1, c1, d17), (a21, b1, c1, d13), (a21, b1, c1, d19), (a21, b1, c1, d20), (a21, b1, c1, d21), (a21, b1, c1, d22), (a21, b1, c2, d1), (a21, b1, c2, d2), (a21, b1, c2, d3), (a21, b1, c2, d4), (a21, b1, c2, d5), (a21, b1, c2, d6), (a21, b1, c2, d7), (a21, b1, c2, d8), (a21, b1, c2, d9), (a21, b1, c2, d10), (a21, b1, c2, d11), (a21, b1, c2, d12), (a21, b1, c2, d13), (a21, b1, c2, d14), (a21, b1, c2, d15), (a21, b1, c2, d16), (a21, b1, c2, d17), (a21, b1, c2, d13), (a21, b1, c2, d19), (a21, b1, c2, d20), (a21, b1, c2, d21), (a21, b1, c2, d22), (a21, b1, c3, d1), (a21, b1, c3, d2), (a21, b1, c3, d3), (a21, b1, c3, d4), (a21, b1, c3, d5), (a21, b1, c3, d6), (a21, b1, c3, d7), (a21, b1, c3, d8), (a21, b1, c3, d9), (a21, b1, c3, d10), (a21, b1, c3, d11), (a21, b1, c3, d12), (a21, b1, c3, d13), (a21, b1, c3, d14), (a21, b1, c3, d15), (a21, b1, c3, d16), (a21, b1, c3, d17), (a21, b1, c3, d18), (a21, b1, c3, d19), (a21, b1, c3, d20), (a21, b1, c3, d21), (a21, b1, c3, d22), (a21, b2, c1, d1), (a21, b2, c1, d2), (a21, b2, c1, d3), (a21, b2, c1, d4), (a21, b2, c1, d5), (a21, b2, c1, d6), (a21, b2, c1, d7), (a21, b2, c1, d8), (a21, b2, c1, d9), (a21, b2, c1, d10), (a21, b2, c1, d11), (a21, b2, c1, d12), (a21, b2, c1, d13), (a21, b2, c1, d14), (a21, b2, c1, d15), (a21, b2, c1, d16), (a21, b2, c1, d17), (a21, b2, c1, d18), (a21, b2, c1, d19), (a21, b2, c1, d20), (a21, b2, c1, d21), (a21, b2, c1, d22), (a21, b2, c2, d1), (a21, b2, c2, d2), (a21, b2, c2, d3), (a21, b2, c2, d4), (a21, b2, c2, d5), (a21, b2, c2, d6), (a21, b2, c2, d7), (a21, b2, c2, d8), (a21, b2, c2, d9), (a21, b2, c2, d10), (a21, b2, c2, d11), (a21, b2, c2, d12), (a21, b2, c2, d13), (a21, b2, c2, d14), (a21, b2, c2, d15), b2, c2, d20), (a21, b2, c2, d21), (a21, b2, c2, d22), (a21, b2, c3, d1), (a21, b2, c3, d2), (a21, b2, c3, d3), (a21, b2, c3, d4), (a21, b2, c3, d5), (a21, b2, c3, d6), (a21, b2, c3, d7), (a21, b2, c3, d8), (a21, b2, c3, d9), (a21, b2, c3, d10), (a21, b2, c3, d11), (a21, b2, c3, d12), (a21, b2, c3, d13), (a21, b2, c3, d14), (a21, b2, c3, d15), b2, c3, d20), (a21, b2, c3, d21), (a21, b2, c3, d22), (a21, b3, c1, d1), (a21, b3, c1, d2), (a21, b3, c1, d3), (a21, b3, c1, d4), (a21, b3, c1, d5), (a21, b3, c1, d6), (a21, b3, c1, d7), (a21, b3, c1, d8), (a21, b3, c1, d9), (a21, b3, c1, d10), (a21, b3, c1, d11), (a21, b3, c1, d12), (a21, b3, c1, d13), (a21, b3, c1, d14), (a21, b3, c1, d15), (a21, b3, c1, d16), (a21, b3, c1, d17), (a21, b3, c1, d18), (a21, b3, c1, d19), (a21, b3, c1, d20), (a21, b3, c1, d21), (a21, b3, c1, d22), (a21, b3, c2, d1), (a21, b3, c2, d2), (a21, b3, c2, d3), (a21, b3, c2, d4), (a21, b3, c2, d5), (a21, b3, c2, d6), (a21, b3, c2, d7), (a21, b3, c2, d8), (a21, b3, c2, d9), (a21, b3, c2, d10), (a21, b3, c2, d11), (a21, b3, c2, d12), (a21, b3, c2, d13), (a21, b3, c2, d14), (a21, b3, c2, d15), (a21, b3, c2, d16), (a21, b3, c2, d17), (a21, b3, c2, d18), (a21, b3, c2, d19), (a21, b3, c2, d20), (a21, b3, c2, d21), (a21, b3, c2, d22), (a21, b3, c3, d1), (a21, b3, c3, d2), (a21, b3, c3, d3), (a21, b3, c3, d4), (a21, b3, c3, d5), (a21, b3, c3, d6), (a21, b3, c3, d7), (a21, b3, c3, d8), (a21, b3, c3, d9), (a21, b3, c3, d10), (a21, b3, c3, d11), (a21, b3, c3, d12), (a21, b3, c3, d13), (a21, b3, c3, d14), (a21, b3, c3, d15), (a21, b3, c3, d16), (a21, b3, c3, d17), (a21, b3, c3, d18), (a21, b3, c3, d19), (a21, b3, c3, d20), (a21, b3, c3, d21), (a21, b3, c3, d22), (a21, b4, c1, d1), (a21, b4, c1, d2), (a21, b4, c1, d3), (a21, b4, c1, d4), (a21, b4, c1, d5), (a21, b4, c1, d6), (a21, b4, c1, d7), (a21, b4, c1, d8), (a21, b4, c1, d9), (a21, b4, c1, d10), (a21, b4, c1, dl), (a21, b4, c1, d12), (a21, b4, c1, d13), (a21, b4, c1, d14), (a21, b4, c1, d15), (a21, b4, c1, d16), (a21, b4, c1, d17), (a21, b4, c1, d18), (a21, b4, c1, d19), (a21, b4, c1, d20), (a21, b4, c1, d21), (a21, b4, c1, d22), (a21, b4, c2, d1), (a21, b4, c2, d2), (a21, b4, c2, d3), (a21, b4, c2, d4), (a21, b4, c2, d5), (a21, b4, c2, d6), (a21, b4, c2, d7), (a21, b4, c2, d8), (a21, b4, c2, d9), (a21, b4, c2, d10), (a21, b4, c2, d11), (a21, b4, c2, d12), (a21, b4, c2, d13), (a21, b4, c2, d14), (a21, b4, c2, d15), (a21, b4, c2, d16), (a21, b4, c2, d7), (a21, b4, c2, d18), (a21, b4, c2, d19), (a21, b4, c2, d20), (a21, b4, c2, d21), (a21, b4, c2, d22), (a21, b4, c3, d1), (a21, b4, c3, d2), (a21, b4, c3, d3), (a21, b4, c3, d4), (a21, b4, c3, d5), (a21, b4, c3, d6), (a21, b4, c3, d7), (a21, b4, c3, d8), (a21, b4, c3, d9), (a21, b4, c3, d10), (a21, b4, c3, d11), (a21, b4, c3, d12), (a21, b4, c3, d13), (a21, b4, c3, d14), (a21, b4, c3, d15), (a21, b4, c3, d16), (a21, b4, c3, d17), (a21, b4, c3, d18), (a21, b4, c3, d19), (a21, b4, c3, d20), (a21, b4, c3, d21), (a21, b4, c3, d22), (a21, b5, c1, d1), (a21, b5, c1, d2), (a21, b5, c1, d3), (a21, b5, c1, d4), (a21, b5, c1, d5), (a21, b5, c1, d6), (a21, b5, c1, d7), (a21, b5, c1, d8), (d21, b5, c1, d9), (a21, b5, c1, d10), (a21, b5, c1, d11), (a21, b5, c1, d12), (a21, b5, c1, d13), (a21, b5, c1, d14), (a21, b5, c1, d15), (a21, b5, c1, d16), (a21, b5, c1, d17), (a21, b5, c1, d18), (a21, b5, c1, d19), (a21, b5, c1, d20), (a21, b5, c1, d21), (a21, b5, c1, d22), (a21, b5, c2, d1), (a21, b5, c2, d2), (a21, b5, c2, d3), (a21, b5, c2, d4), (a21, b5, c2, d5), (a21, b5, c2, d6), (a21, b5, c2, d7), (a21, b5, c2, d8), (a21, b5, c2, d9), (a21, b5, c2, d10), (a21, b5, c2, d11), (a21, b5, c2, d12), (a21, b5, c2, d13), (a21, b5, c2, d14), (a21, b5, c2, d15), (a21, b5, c2, d16), (a21, b5, c2, d17), (a21, b5, c2, d18), (a21, b5, c2, d19), (a21, b5, c2, d20), (a21, b5, c2, d21), (a21, b5, c2, d22), (a21, b5, c3, d1), (a21, b5, c3, d2), (a21, b5, c3, d3), (a21, b5, c3, d4), (a21, b5, c3, d5), (a21, b5, c3, d6), (a21, b5, c3, d7), (a21, b5, c3, d8), (a21, b5, c3, d9), (a21, b5, c3, d10), (a21, b5, c3, d11); (a21, b5, c3, d12), (a21, b5, c3, d13), (a21, b5, c3, d14), (a21, b5, c3, d15), (a21, b5, c3, d16), (a21, b5, c3, d17), (a21, b5, c3, d18), (a21, b5, c3, d19), (a21, b5, c3, d20), (a21, b5, c3, d21), (a21, b5, c3, d22), (a21, b6, c1, d1), (a21, b6, c1, d2), (a21, b6, c1, d3), (a21, b6, c1, d4), (a21, b6, c1, d5), (a21, b6, c1, d6), (a21, b6, c1, d7), (a21, b6, c1, d8), (a21, b6, c1, d9), (a21, b6, c1, d10), (a21, b6, c1, d11), (a21, b6, c1, d12), (a21, b6, c1, d13), (a21, b6, c1, d14), (a21, b6, c1, d15), (a21, b6, c1, d16), (a21, b6, c1, d17), (a21, b6, c1, d18), (a21, b6, c1, d19), (a21, b6, c1, d20), (a21, b6, c1, d21), (a21, b6, c1, d22), (a21, b6, c2, d1), (a21, b6, c2, d2), (a21, b6, c2, d3), (a21, b6, c2, d4), (a21, b6, c2, d5), (a21, b6, c2, d6), (a21, b6, c2, d7), (a21, b6, c2, d8), (a21, b6, c2, d9), (a21, b6, c2, d10), (a21, b6, c2, d11), (a21, b6, c2, d12), (a21, b6, c2, d13), (a21, b6, c2, d14), (a21, b6, c2, d15), (a21, b6, c2, d16), (a21, b6, c2, d17), (a21, b6, c2, d18), (a21, b6, c2, d19), (a21, b6, c2, d20), (a21, b6, c2, d21), (a21, b6, c2, d22), (a21, b6, c3, d1), (a21, b6, c3, d2), (a21, b6, c3, d3), (a21, b6, c3, d4), (a21, b6, c3, d5), (a21, b6, c3, d6), (a21, b6, c3, d7), (a21, b6, c3, d8), (a21, b6, c3, d9), (a21, b6, c3, d10), (a21, b6, c3, d11), (a21, b6, c3, d12), (a21, b6, c3, d13), (a21, b6, c3, d14), (a21, b6, c3, d15), (a21, b6, c3, d16), (a21, b6, c3, d17), (a21, b6, c3, d18), (a21, b6, c3, d19), (a21, b6, c3, d20), (a21, b6, c3, d21), (a21, b6, c3, d22), (a22, b1, (c1, d1), (a22, b1, c1, d2), (a22, b1, c1, d3), (a22, b1, c1, d4), (a22, b1, c1, d5), (a22, b1, c1, d6), (a22, b1, c1, d7), (a22, b1, c1, d8), (a22, b1, c1, d9), (a22, b1, c1, d10), (a22, b1, c1, d11), (a22, b1, c1, d12), (a22, b1, c1, d13), (a22, b1, c1, d14), (a22, b1, c1, d15), (a22, b1, c1, d16), (a22, b1, c1, d17), (a22, b1, c1, d18), (a22, b1, c1, d19), (a22, b1, c1, d20), (a22, b1, c1, d21), (a22, b1, c1, d22), (a22, b1, c2, d1), (a22, b1, c2, d2), (a22, b1, c2, d3), (a22, b1, c2, d4), (a22, b1, c2, d5), (a22, b1, c2, d6), (a22, b1, c2, d7), (a22, b1, c2, d8), (a22, b1, c2, d9), (a22, b1, c2, d10), (a22, b1, c2, d11), (a22, b1, c2, d12), (a22, b1, c2, d13), (a22, b1, c2, d14), (a22, b1, c2, d15), (a22, b1, c2, d16), (a22, b1, c2, d17), (a22, b1, c2, d18), (a22, b1, c2, d19), (a22, b1, c2, b20), (a22, b1, c2, d21), (a22, b1, c2, d22), (a22, b1, c3, d1), (a22, b1, c3, d2), (a22, b1, c3, d3), (a22, b1, c3, d4), (a22, b1, c3, d5), (a22, b1, c3, d6), (a22, b1, c3, d7), (a22, b1, c3, d8), (a22, b1, c3, d9), (a22, b1, c3, d10), (a22, b1, c3, d11), (a22, b1, c3, d12), (a22, b1, c3, d13), (a22, b1, c3, d14), (a22, b1, c3, d15), (a22, b1, c3, d16), (a22, b1, c3, d17), (a22, b1, c3, d18), (a22, b1, c3, d19), (a22, b1, c3, d20), (a22, b1, c3, d21), (a22, b1, c3, d22), (a22, b2, c1, d1), (a22, b2, c1, d2), (a22, b2, c1, d3), (a22, b2, c1, d4), (a22, b2, c1, d5), (a22, b2, c1, d6), (a22, b2, c1, d7), (a22, b2, c1, d8), (a22, b2, c1, d9), (a22, b2, c1, d10), (a22, b2, c1, d11), (a22, b2, c1, d12), (a22, b2, c1, d13), (a22, b2, c1, d14), (a22, b2, c1, d15), (a22, b2, c1, d16), (a22, b2, c1, d17), (a22, b2, c1, d18), (a22, b2, c1, d19), (a22, b2, c1, d20), (a22, b2, c1, d21), (a22, b2, c1, d22), (a22, b2, c2, d1), (a22, b2, c2, d2), (a22, b2, c2, d3), (a22, b2, c2, d4), (a22, b2, c2, d5), (a22, b2, c2, d6), (a22, b2, c2, d7), (a22, b2, c2, d8), (a22, b2, c2, d9), (a22, b2, c2, d10), (a22, b2, c2, d11), (a22, b2, c2, d12), (a22, b2, c2, d13), (a22, b2, c2, d14), (a22, b2, c2, d15), (a22, b2, c2, d16), (a22, b2, c2, d17), (a22, b2, c2, d18), (a22, b2, c2, d19), (a22, b2, c2, d20), (a22, b2, c2, d21), (a22, b2, c2, d22), (a22, b2, c3, d1), (a22, b2, c3, d2), (a22, b2, c3, d3), (a22, b2, c3, d4), (a22, b2, c3, d5), (a22, b2, c3, d6), (a22, b2, c3, d7), (a22, b2, c3, d8), (a22, b2, c3, d9), (a22, b2, c3, die), (a22, b2, c3, d11), (a22, b2, c3, d12), (a22, b2, c3, d13), (a22, b2, c3, d14), (a22, b2, c3, d15), (a22, b2, c3, d16), (a22, b2, c3, d17), (a22, b2, c3, d18), (a22, b2, c3, d19), (a22, b2, c3, d20), (a22, b2, c3, d21), (a22, b2, c3, d22), (a22, b3, c1, d1), (a22, b3, c1, d2), (a22, b5, c1, d3), (a22, b3, c1, d4), (a22, b3, c1, d5), (a22, b3, c1, d6), (a22, b3, c1, d7), (a22, b3, c1, d8), (a22, b3, c1, d9), (a22, b3, c1, d10), (a22, b3, c1, d11), (a22, b3, c1, d12), (a22, b3, c1, d13), (a22, b3, c1, d14), (a22, b3, c1, d15), (a22, b3, c1, d16), (a22, b3, c1, d17), (a22, b3, c1, d18), (a22, b3, c1, d19), (a22, b3, c1, d20), (a22, b3, c1, d21), (a22, b3, c1, d22), (a22, b3, c2, d1), (a22, b3, c2, d2), (a22, b3, c2, d3), (a22, b3, c2, d4), (a22, b3, c2, d5), (a22, b3, c2, d6), (a22, b3, c2, d7), (a22, b5, c2, d8), (a22, b3, c2, d9), (a22, b3, c2, d10), (a22, b3, c2, d11), (a22, b3, c2, d12), (a22, b5, c2, d13), (a22, b3, c2, d14), (a22, b3, c2, d15), (a22, b3, c2, d16), (a22, b3, c2, d17), (a22, b3, c2, d18), (a22, b3, c2, d19), (a22, b3, c2, d20), (a22, b3, c2, d21), (a22, b3, c2, d22), (a22, b3, c3, d1), (a22, b3, c3, d2), (a22, b3, c3, d5), (a22, b3, c3, d4), (a22, b3, c3, d5), (a22, b3, c3, d6), (a22, b3, c3, d7), (a22, b3, c3, d8), (a22, b3, c3, d9), (a22, b3, c3, d10), (a22, b3, c3, d11), (a22, b3, c3, d12), (a22, b3, c3, d13), (a22, b3, c3, d14), (a22, b3, c3, d15), (a22, b3, c3, d16), (a22, b3, c3, d17), (a22, b3, c3, d18), (a22, b3, c3, d19), (a22, b3, c3, d20), (a22, b3, c3, d21), (a22, b3, c3, d22), (a22, b4, c1, d1), (a22, b4, c1, d2), (a22, b4, c1, d3), (a22, b4, c1, d4), (a22, b4, c1, d5), (a22, b4, c1, d6), (a22, b4, c1, d7), (a22, b4, c1, d8), (a22, b4, c1, d9), (a22, b4, c1, d10), (a22, b4, c1, d11), (a22, b4, c1, d12), (a22, b4, c1, d13), (a22, b4, c1, d14), (a22, b4, c1, d15), (a22, b4, c1, d16), (a22, b4, c1, d17), (a22, b4, c1, d18), (a22, b4, c1, d19), (a22, b4, c1, d20), (a22, b4, c1, d21), (a22, b4, c1, d22), (a22, b4, c2, d1), (a22, b4, c2, d2), (a22, b4, c2, d3), (a22, b4, c2, d4), (a22, b4, c2, d5), (a22, b4, c2, d6), (a22, b4, c2, d7), (a22, b4, c2, d8), (a22, b4, c2, d9), (a22, b4, c2, d10), (a22, b4, c2, d11), (a22, b4, c2, d12), (a22, b4, c2, d13), (a22, b4, c2, d14), (a22, b4, c2, d15), (a22, b4, c2, d16), (a22, b4, c2, d17), (a22, b4, c2, d18), (a22, b4, c2, d19), (a22, b4, c2, d20), (a22, b4, c2, d21), (a22, b4, c2, d22), (a22, b4, c3, d1), (a22, b4, c3, d2), (a22, b4, c3, d3), (a22, b4, c3, d4), (a22, b4, c3, d5), (a22, b4, c3, d6), (a22, b4, c3, d7), (a22, b4, c3, d8), (a22, b4, c3, d9), (a22, b4, c3, d10), (a22, b4, c3, d11), (a22, b4, c3, d12), (a22, b4, c3, d13), (a22, b4, c3, d14), (a22, b4, c3, d15), (a22, b4, c3, d16), (a22, b4, c3, d17), (a22, b4, c3, d18), (a22, b4, c3, d19), (a22, b4, c3, d20), (a22, b4, c3, d21), (a22, b4, c3, d22), (a22, b5, c1, d1), (a22, b5, c1, d2), (a22, b5, c1, d3), (a22, b5, c1, d4), (a22, b5, c1, d5), (a22, b5, c1, d6), (a22, b5, c1, d7), (a22, b5, c1, d8), (a22, b5, c1, d9), (a22, b5, c1, d10), (a22, b5, c1, d11), (a22, b5, c1, d12), (a22, b5, c1, d13), (a22, b5, c1, d14), (a22, b5, c1, d15), (a22, b5, c1), (a22, b5, c1, d17), (a22, b5, c1, d18), (a22, b5, c1, d19), (a22, b5, c1, d20), (a22, b5, c1, d21), (a22, b5, c1, d22), (a22, b5, c2, d1), (a22, b5, c2, d2), (a22, b5, c2, d3), (a22, b5, c2, d4), (a22, b5, c2, d5), (a22, b5, c2, d6), (a22, b5, c2, d7), (a22, b5, c2, d8), (a22, b5, c2, d9), (a22, b5, c2, d10), (a22, b5, c2, d11), (a22, b5, c2, d12), (a22, b5, c2, d13), (a22, b5, c2, d14), (a22, b5, c2, d15), (a22, b5, c2, d16), (a22, b5, c2, d17), (a22, b5, c2, d18), (a22, b5, c2, d19), (a22, b5, c2, d20), (a22, b5, c2, d21), (a22, b5, c2, d22), (a22, b5, c3, d11), (a22, b5, c3, d2), (a22, b5, c3, d3), (a22, b5, c3, d4), (a22, b5, c3, d5), (a22, b5, c3, d6), (a22, b5, c3, d7), (a22, b5, c3, d8), (a22, b5, c3, d9), (a22, b5, c3, d10), (a22, b5, c3, d11), (a22, b5, c3, d12), (a22, b5, c3, d13), (a22, b5, c3, d14), (a22, b5, c3, d15), (a22, b5, c3, d16), (a22, b5, c3, d17), (a22, b5, c3, d18), (a22, b5, c3, d19), (a22, b5, c3, d20), (a22, b5, c3, d21), (a22, b5, c3, d22), (a22, b6, c1, d1), (a22, b6, c1, d2), (a22, b6, c1, d3), (a22, b6, c1, d4), (a22, b6, c1, d5), (a22, b6, c1, d6), (a22, b6, c1, d7), (a22, b6, c1, d8), (a22, b6, c1, d9), (a22, b6, c1, d10), (a22, b6, c1, d11), (a22, b6, c1, d12), (a22, b6, c1, d13), (a22, b6, c1, d14) (a22, b6, c1, d15), (a22, b6, c1, d16), (a22, b6, c1, d17), (a22, b6, c1, d18), (a22, b6, c1, d19), (a22, b6, c1, d20), (a22, b6, c1, d21), (a22, b6, c1, d22), (a22, b6, c2, d1), (a22, b6, c2, d2), (a22, b6, c2, d3), (a22, b6, c2, d4), (a22, b6, c2, d5), (a22, b6, c2, d6), (a22, b6, c2, d7), (a22, b6, c2, d8), (a22, b6, c2, d9), (a22, b6, c2, d6), (a22, b6, c2, d11), (a22, b6, c2, d12), (a22, b6, c2, d13), (a22, b6, c2, d14), (a22, b6, c2, d15), (a22, b6, c2, d16), (a22, b6, c2, d17), (a22, b6, c2, d18), (a22, b6, c2, d19), (a22, b6, c2, d20), (a22, b6, c2, d21), (a22, b6, c2, d22), (a22, b6, c3, d1), (a22, b6, c3, d2), (a22, b6, c3, d3), (a22, b6, c3, d4), (a22, b6, c3, d5), (a22, b6, c3, d6), (a22, b6, c3, d7), (a22, b6, c3, d8), (a22, b6, c3, d9), (a22, b6, c3, d10), (a22, b6, c3, d11), (a22, b6, c3, d12), (a22, b6, c3, d13), (a22, b6, c3, d14), (a22, b6, c3, d15), (a22, b6, c3, d16), (a22, b6, c3, d17), (a22, b6, c3, d18), (a22, b6, c3, d19), (a22, b6, c3, d20), (a22, b6, c3, d21), (a22, b6, c3, d22), (a23, b1, c1, d1), (a23, b1, c1, d2), (a23, b1, c1, d3), (a23, b1, c1, d4), (a23, b1, c1, d5), (a23, b1, c1, d6), (a23, b1, c1, d7), (a23, b1, c1, d8), (a23, b1, c1, d9), (a23, b1, c1, d10), (a23, b1, c1, d11), (a23, b1, c1, d12), (a23, b1, b1, c1, d13), (a23, b1, c1, d14), (a23, b1, c1, d15), (a23, b1, c1, d16), (a23, b1, c1, d17), (a23, b1, c1, d18), (a23, b1, c1, d19), (a23, b1, c1, d20), (a23, b1, c1, d21), (a23, b1, c1, d22), (a23, b1, c2, d1), (a23, b1, c2, d2), (a23, b1, c2, d3), (a23, b1, c2, d4), (a23, b1, c2, d5), (a23, b1, c2, d6), (a23, b1, c2, d7), (a23, b1, c2, d8), (a23, b1, c2, d9), (a23, b1, c2, d10), (a23, b1, c2, d11), (a23, b1, c2, d12), (a23, b1, c2, d13), (a23, b1, c2, d14), (a23, b1, c2, d15), (a23, b1, c2, d16), (a23, b1, c2, d17), (a23, b1, c2, d8), (a23, b1, c2, d19), (a23, b1, c2, d20), (a23, b1, c2, d21), (a23, b1, c2, d22), (a23, b1, c3, d1), (a23, b1, c3, d2), (a23, b1, c3, d3), (a23, b1, c3, d4), (a23, b1, c3, d5), (a23, b1, c3, d6), (a23, b1, c3, d7), (a23, b1, c3, d8), (a23, b1, c3, d9), (a23, b1, c3, d10), (a23, b1, c3, d11), (a23, b1, c3, d12), (a23, b1, c3, d13), (a23, b1, c3, d14), (a23, b1, c3, d15), (a23, b1, c3, d16), (a23, b1, c3, d17), (a23, b1, c3, d18), (a23, b1, c3, d19), (a23, b1, c3, d20), (a23, b1, c3, d21), (a23, b1, c3, d22), (a23, b2, c1, d1), (a23, b2, c1, d2), (a23, b2, c1, d3), (a23, b2, c1, d4), (a23, b2, c3, d5), (a23, b2, c1, d6), (a23, b2, c1, d7), (a23, b2, c1, d8), (a23, b2, c1, d9), (a23, b2, c1, d10), (a23, b2, c1, d11), (a23, b2, c1, d12), (a23, b2, c1, d13), (a23, b2, c1, d14), (a23, b2, c1, d15), (a23, b2, c1, d16), (a23, b2, c1, d17), (a23, b2, c1, d18), (a23, b2, c1, d19), (a23, b2, c1, d20), (a23, b2, c1, d21), (a23, b2, c1, d22), (a23, b2, c2, d1), (a23, b2, c2, d2), (a23, b2, c2, d3), (a23, b2, c2, d4), (a23, b2, c2, d5), (a23, b2, c2, d6), (a23, b2, c2, d7), (a23, b2, c2, d8), (a23, b2, c2, d9), (a23, b2, c2, d10), (a23, b2, c2, d11), (a23, b2, c2, d12), (a23, b2, c2, d13), (a23, b2, c2, d14), (a23, b2, c2, d15), (a23, b2, c2, d16), (a23, b2, c2, d17), (a23, b2, c2, d18), (a23, b2, c2, d19), (a23, b2, c2, d20), (a23, b2, c2, d21), (a23, b2, c2, d22), (a23, b2, c3, d1), (a23, b2, c3, d2), (a23, b2, c3, d3), (a23, b2, c3, d4), (a23, b2, c3, d5), (a23, b2, c3, d6), (a23, b2, c3, d7), (a23, b2, c3, d8), (a23, b2, c3, d9), (a23, b2, c3, d10), (a23, b2, c3, d11), (a23, b2, c3, d12), (a23, b2, c3, d13), (a23, b2, c3, d14), (a23, b2, c3, d15), (a23, b2, c3, d16), (a23, b2, c3, d17), (a23, b2, c3, d18), (a23, b2, c3, d19), (a23, b2, c3, d20), (a23, b2, c3, d21), (a23, b2, c3, d22), (a23, b3, c1, d1), (a23, b3, c1, d2), (a23, b3, c1, d3), (a23, b3, c1, d4), (a23, b3, c1, d5), (a23, b3, c1, d6), (a23, b3, c1, d7), (a23, b3, c1, d8), (a23, b3, c1, d9), (a23, b3, c1, die), (a23, b3, c1, d11), (a23, b3, c1, d12), (a23, b3, c1, d13), (a23, b3, c1, d14), (a23, b3, c1, d15), (a23, b3, c1, d16), (a23, b3, c1, d17), (a23, b3, c1, d18), (a23, b3, c1, d19), (a23, b3, c1, d20), (a23, b3, c1, d21), (a23, b3, c1, d22), (a23, b5, c2, d1), (a23, b3, c2, d2), (a23, b3, c2, d3), (a23, b3, c2, d4), (a23, b3, c2, d5), (a23, b3, c2, d6), (a23, b3, c2, d7), (a23, b3, c2, d8), (a23, b3, c2, d9), (a23, b3, c2, d10), (a23, b3, c2, d11), (a23, b3, c2, d12), (a23, b3, c2, d13), (a23, b3, c2, d14), (a23, b3, c2, d15), (a23, b3, c2, d16), (a23, b3, c2, d17), (a23, b3, c2, d18), (a23, b3, c2, d19), (a23, b3, c2, d20), (a23, b3, c2, d21), (a23, b3, c2, d22), (a23, b3, c3, d1), (a23, b3, c3, d2), (a23, b3, c3, d3), (a23, b3, c3, d4), (a23, b3, c3, d5), (a23, b3, c3, d6), (a23, b3, c3, d17), (a23, b3, c3, d18), (a23, b3, c3, d9), (a23, b3, c3, d10), (a23, b3, c3, d11), (a23, b5, c3, d12) (a23, b3, c3, d13), (a23, b3, c3, d14), (a23, b3, c3, d15), (a23, b3, c3, d16), (a23, b3, c3, d17), (a23, b3, c3, d18), (a23, b3, c3, d19), (a23, b3, c3, d20), (a23, b3, c3, d21), (a23, b3, c3, d22), (a23, b4, c1, d1), (a23, b4, c1, d2), (a23, b4, c1, d3), (a23, b4, c1, d4), (a23, b4, c1, d5), (a23, b4, c1, d6), (a23, b4, c1, d7), (a23, b4, c1, d8), (a23, b4, c1, d9), (a23, b4, c1, d10), (a23, b4, c1, d11), (a23, b4, c1, d12), (a23, b4, c1, d13), (a23, b4, c1, d14), (a23, b4, c1, d15), (a23, b4, c1, d16), (a23, b4, c1, d17), (a23, b4, c1, d18), (a23, b4, c1, d19), (a23, b4, c1, d20), (a23, b4, c1, d21), (a23, b4, c1, d22), (a23, b4, c2, d1), (a23, b4, c2, d2), (a23, b4, c2, d3), (a23, b4, c2, d4), (a23, b4, c2, d5), (a23, b4, c2, d6), (a23, b4, c2, d7), (a23, b4, c2, d8), (a23, b4, c2, d9), (a23, b4, c2, d10), (a23, b4, c2, d11), (a23, b4, c2, d12), (a23, b4, c2, d13), (a23, b4, c2, d14), (a23, b4, c2, d15), (a23, b4, c2, d10), (a23, b4, c2, d17), (a23, b4, c2, d18), (a23, b4, c2, d19), (a23, b4, c2, d20), (a23, b4, c2, d21), (a23, b4, c2, d22), (a23, b4, c3, dl), (a23, b4, c3, d2), (a23, b4, c3, d3), (a23, b4, c3, d4), (a23, b4, c3, d5), (a23, b4, c3, d6), (a23, b4, c3, d7), (a23, b4, c3, d8), (a23, b4, c3, d9), (a23, b4, c3, d10), (a23, b4, c3, d11), (a23, b4, c3, d12), (a23, b4, c3, d13), (a23, b4, c3, d14), (a23, b4, c3, d15), (a23, b4, c3, d16), (a23, b4, c3, d17), (a23, b4, c3, d18), (a23, b4, c3, d19), (a23, b4, c3, d20), (a23, b4, c3, d21), (a23, b4, c3, d22), (a23, b5, c1, d1), (a23, b5, c1, d2), (a23, b5, c1, d3), (a23, b5, c1, d4), (a23, b5, c1, d5), (a23, b5, c1, d6), (a23, b5, c1, d7), (a23, b5, c1, d8), (a23, b5, c1, d9), (a23, b5, c1, d10), (a23, b5, c1, d11), (a23, b5, c1, d12), (a23, b5, c1, d13), (a23, b5, c1, d14), (a23, b5, c1, d15), (a23, b5, c1, d16), (a23, b5, c1, d17), (a23, b5, c1, d18), (a23, b5, c1, d19), (a23, b5, c1, d20), (a23, b5, c1, d21), (a23, b5, c1, d22), (a23, b5, c2, d1), (a23, b5, c2, d12), (a23, b5, c2, d3), (a23, b5, c2, d4), (a23, b5, c2, c5), (a23, b5, c2, d6), (a23, b5, c2, d7), (a23, b5, c2, d8), (a23, b5, c2, d9), (a23, b5, c2, d10), (a23, b5, c2, d11), (a23, b5, c2, d12), (a23, b5, c2, d13), (a23, b5, c2, d14), (a23, b5, c2, d15), (a23, b5, c2, d16), (a23, b5, c2, d17), (a23, b5, c2, d18), (a23, b5, c2, d19), (a23, b5, c2, d20), (a23, b5, c2, d21), (a23, b5, c2, d22), (a23, b5, c3, d1), (a23, b5, c3, d2), (a23, b5, c3, d3), (a23, b5, c3, d4), (a23, b5, c3, d5), (a23, b5, c3, d6), (a23, b5, c3, d7), (a23, b5, c3, d8), (a23, b5, c3, d9), (a23, b5, c3, d10), (a23, b5, c3, d11), (a23, b5, c3, d12), (a23, b5, c3, d13), (a23, b5, c3, d14), (a23, b5, c3, d15), (a23, b5, c3, d16), (a23, b5, c3, d17), (a23, b5, c3, d18), (a23, b5, c3, d19), (a23, b5, c3, d20), (a23, b5, c3, d21), (a23, b5, c3, d22), (a23, b5, c1, d1), (a23, b6, c1, d2), (a23, b6, c1, d3), (a23, b6, c1, d4), (a23, b6, c1, d5), (a23, b6, c1, d6), (a23, b6, c1, d7), (a23, b6, c1, d8), (a23, b6, c1, d9), (a23, b6, c1, d10), (a23, b6, c1, d11), (a23, b6, c1, d12), (a23, b6, c1, d13), (a23, b6, c1, d14), (a23, b6, c1, d15), (a23, b6, c1, d16), (a23, b6, c1, d17), (a23, b6, c1, d18), (a23, b6, c1, d19), (a23, b6, c1, d20), (a23, b6, c1, d21), (a23, b6, c1, d22), (a23, b6, c2, d1), (a23, b6, c2, d2), (a23, b6, c2, d3), (a23, b6, c2, d4), (a23, b6, c2, d5), (a23, b6, c2, d6), (a23, b6, c2, d7), (a23, b6, c2, d8), (a23, b6, c2, d9), (a23, b6, c2, d10), (a23, b6, c2, d11), (a23, b6, c2, d12), (a23, b6, c2, d13), (a23, b6, c2, d14), (a23, b6, c2, d15), (a23, b6, c2, d16), (a23, b6, c2, d17), (a23, b6, c2, d18), (a23, b6, c2, d19), (a23, b6, c2, d20), (a23, b6, c2, d21), (a23, b6, c2, d22), (a23, b6, c3, d1), (a23, b6, c3, d2), (a23, b6, c3, d3), (a23, b6, c3, d4), (a23, b6, c3, d5), (a23, b6, c3, d6), (a23, b6, c3, d7), (a23, b6, c3, d8), (a23, b6, c3, d9), (a23, b6, c3, d10), (a23, b6, c3, d11), (a23, b6, c3, d12), (a23, b6, c3, d13), (a23, b6, c3, d14), (a23, b6, c3, d15), (a23, b6, c3, d16), (a23, b6, c3, d17), (a23, b6, c3, d18), (a23, b6, c3, d19), (a23, b6, c3, d20), (a23, b6, c3, d21), (a23, b6, c3, d22), (a24, b1, c1, d1), (a24, b1, c1, d2), (a24, b1, c1, d3), (a24, b1, c1, d4), (a24, b1, c1, d5), (a24, b1, c1, d6), (a24, b1, c1, d7), (a24, b1, c1, d8), (a24, b1, c1, d9), (a24, b1, c1, d10), (a24, b1, c1, d11), (a24, b1, c1, d12), (a24, b1, c1, d13), (a24, b1, c1, d14), (a24, b1, c1, d15), (a24, b1, c1, d16), (a24, b1, c1, d17), (a24, b1, c1, d18), (a24, b1, c1, d19), (a24, b1, c1, d20), (a24, b1, c1, d21), (a24, b1, c1, d22), (a24, b1, c2, d1), (a24, b1, c2, d2), (a24, b1, c2, d3), (a24, b1, c2, d4), (a24, b1, c2, d5), (a24, b1, c2, d6), (a24, b1, c2, d7), (a24, b1, c2, d8), (a24, b1, c2, d9), (a24, b1, c2, d10) (a24, b1, c2, d11), (a24, b1, c2, d12), (a24, b1, c2, d13), (a24, b1, c2, d14), (a24, b1, c2, d15), (a24, b1, c2, d16), (a24, b1, c2, d17), (a24, b1, c2, d18), (a24, b1, c2, d19), (a24, b1, c2, d20), (a24, b1, c2, d21), (a24, b1, c2, d22), (a24, b1, c3, d1), (a24, b1, c3, d2), (a24, b1, c3, d3), (a24, b1, c3, d4), (a24, b1, c3, d5), (a24, b1, c3, d6), (a24, b1, c3, d7), (a24, b1, c3, d8), (a24, b1, c3, d9), (a24, b1, c3, d10), (a24, b1, c3, d11), (a24, b1, c3, d12), (a24, b1, c3, d13), (a24, b1, c3, d14), (a24, b1, c3, d15), (a24, b1, c3, d16), (a24, b1, c3, d17), (a24, b1, c3, d18), (a24, b1, c3, d19), (a24, b1, c3, d20), (a24, b1, c3, d21), (a24, b1, c3, d22), (a24, b2, c1, d1), (a24, b2, c1, d2), (a24, b2, c1, d3), (a24, b2, c1, d4), (a24, b2, c1, d5), (a24, b2, c1, d6), (a24, b2, c1, d7), (a24, b2, c1, d8), (a24, b2, c1, d9), (a24, b2, c1, d10), (a24, b2, c1, d11), (a24, b2, c1, d12), (a24, b2, c1, d13), (a24, b2, c1, d14), (a24, b2, c1, d15), (a24, b2, c1, d16), (a24, b2, c1, d17), (a24, b2, c1, d18), (a24, b2, c1, d19), (a24, b2, c1, d20), (a24, b2, c1, d21), (a24, b2, c1, d22), (a24, b2, c2, d1), (a24, b2, c2, d2), (a24, b2, c2, d3), (a24, b2, c2, d4), (a24, b2, c2, d5), (a24, b2, c2, d6), (a24, b2, c2, d7), (a24, b2, c2, d8), (a24, b2, c2, d9), (a24, b2, c2, d10), (a24, b2, c2, d11), (a24, b2, c2, d12), (a24, b2, c2, d13), (a24, b2, c2, d14), (a24, b2, c2, d15), (a24, b2, c2, d16), (a24, b2, c2, d17), (a24, b2, c2, d18), (a24, b2, c2, d19), (a24, b2, c2, d20), (a24, b2, c2, d21), (a24, b2, c2, d22), (a24, b2, c3, d1), (a24, b2, c3, d2), (a24, b2, c3, d3), (a24, b2, c3, d4), (a24, b2, c3, d5), (a24, b2, c3, d6), (a24, b2, c3, d7), (a24, b2, c3, d8), (a24, b2, c3, d9), (a24, b2, c3, d10), (a24, b2, c3, d11), (a24, b2, c3, d12), (a24, b2, c3, d13), (a24, b2, c3, d14), (a24, b2, c3, d15), (a24, b2, c3, d16), (a24, b2, c3, d17), (a24, b2, c3, d18), (a24, b2, c3, d19), (a24, b2, c3, d20), (a24, b2, c3, d21), (a24, b2, c3, d22), (a24, b3, c1, d1), (a24, b3, c1, d2), (a24, b3, c1, d3), (a24, b3, c1, d4), (a24, b3, c1, d5), (a24, b3, c1, d6), (a24, b3, c1, d7), (a24, b3, c1, d8), (a24, b3, c1, d9), (a24, b3, c1, d10), (a24, b3, c1, d11), (a24, b3, c1, d12), (a24, b3, c1, d13), (a24, b3, c1, d14), (a24, b3, c1, d15), (a24, b3, c1, d16), (a24, b3, c1, d17), (a24, b3, c1, d18), (a24, b3, c1, d19), (a24, b3, c1, d20), (a24, b3, c1, d21), (a24, b3, c1, d22), (a24, b3, c2, d1), (a24, b3, c2, d2), (a24, b3, c2, d3), (a24, b3, c2, d4), (a24, b3, c2, d5), (a24, b3, c2, d6), (a24, b3, c2, d7), (a24, b3, c2, d8), (a24, b3, c2, d9), (a24, b3, c2, d10) (a24, b3, c2, d11), (a24, b3, c2, d12), (a24, b3, c2, d13), (a24, b3, c2, d14), (a24, b3, c2, d15), (a24, b3, c2, d16), (a24, b3, c2, d17), (a24, b3, c2, d18), (a24, b3, c2, d19), (a24, b3, c2, d20), (a24, b3, c2, d21), (a24, b3, c2, d22), (a24, b3, c3, d1), (a24, b3, c3, d2), (a24, b5, c3, d3), (a24, b5, c3, d4), (a24, b3, c3, c3, d5), (a24, b3, c3, d6), (a24, b3, c3, d7), (a24, b3, c3, d8), (a24, b3, c3, d9), (a24, b3, c3, d10), (a24, b3, c3, d11), (a24, b3, b3, c3, d12), (a24, b3, c3, d13), (a24, b3, c3, d14), (a24, b3, c3, d15), (a24, b3, c3, d16), (a24, b3, c3, d17), (a24, b3, c3, d18), (a24, b3, c3, d19), (a24, b3, c3, d20), (a24, b3, c3, d21), (a24, b3, c3, d22), (a24, b4, c1, d1), (a24, b4, c1, d2), (a24, b4, c1, d3), (a24, b4, c1, d4), (a24, b4, c1, d5), (a24, b4, c1, d6), (a24, b4, c1, d7), (a24, b4, c1, d8), (a24, b4, c1, d9), (a24, b4, c1, d10), (a24, b4, c1, d11), (a24, b4, c1, d12), (a24, b4, c1, d13), (a24, b4, c1, d14), (a24, b4, c1, d15), (a24, b4, c1, d16), (a24, b4, c1, d17), (a24, b4, c1, d18), (a24, b4, c1, d19), (a24, b4, c1, d20), (a24, b4, c1, d21), (a24, b4, c1, d22), (a24, b4, c2, d1), (a24, b4, c2, d2), (a24, b4, c2, d3), (a24, b4, c2, d4), (a24, b4, c2, d5), (a24, b4, c2, d6), (a24, b4, c2, d7), (a24, b4, c2, d8), (a24, b4, c2, d9), (a24, b4, c2, d10), (a24, b4, c2, d11), (a24, b4, c2, d12), (a24, b4, c2, d13), (a24, b4, c2, d14), (a24, b4, c2, d15), (a24, b4, c2, d16), (a24, b4, c2, d7), (a24, b4, c2, d18), (a24, b4, c2, d19), (a24, b4, c2, d20), (a24, b4, c2, d21), (a24, b4, c2, d22), (a24, b4, c3, d1), (a24, b4, c3, d2), (a24, b4, c3, d3), (a24, b4, c3, d4), (a24, b4, c3, d5), (a24, b4, c3, d6), (a24, b4, c3, d7), (a24, b4, c3, d8), (a24, b4, c3, d9), (a24, b4, c3, d10), (a24, b4, c3, d11), (a24, b4, c3, d12), (a24, b4, c3, d13), (a24, b4, c3, d14), (a24, b4, c3, d15), (a24, b4, c3, d16), (a24, b4, c3, d17), (a24, b4, c3, d18), (a24, b4, c3, d19), (a24, b4, c3, d20), (a24, b4, c3, d21), (a24, b4, c3, d22), (a24, b5, c1, d1), (a24, b5, c1, d2), (a24, b5, c1, d3), (a24, b5, c1, d4), (a24, b5, c1, d5), (a24, b5, c1, d6), (a24, b5, c1, d7), (a24, b5, c1, d8), (a24, b5, c1, d9), (a24, b5, c1, d10), (a24, b5, c1, d11), (a24, b5, c1, d12), (a24, b5, c1, d13), (a24, b5, c1, d14), (a24, b5, c1, d15), (a24, b5, c1, d16), a24, b5, c1, d17), (a24, b5, c1, d18), (a24, b5, c1, d19), (a24, b5, c1, d20), (a24, b5, c1, d21), (a24, b5, c1, d22), (a24, b5, c2, d1), (a24, b5, c2, d2), (a24, b5, c2, d3), (a24, b5, c2, d4), (a24, b5, c2, d5), (a24, b5, c2, d6), (a24, b5, c2, d7), (a24, b5, c2, d8), (a24, b5, c2, d9), (a24, b5, c2, d10), (a24, b, c2, d11), (a24, b5, c2, d12), (a24, b5, c2, d13), (a24, b5, c2, d14), (a24, b5, c2, d15), (a24, b5, c2, d16), (a24, b5, c2, d17), (a24, b5, c2, d18), (a24, b5, c2, d19), (a24, b5, c2, d20), (a24, b5, c2, d21), (a24, b5, c2, d22), (a24, b5, c3, d1), (a24, b5, c3, d2), (a24, b5, c3, d5), (a24, b5, c3, d4), (a24, b5, c3, d5), (a24, b5, c3, d6), (a24, b5, c3, d7), (a24, b5, c3, d8), (a24, b, c3, d9), (a24, b5, c3, d10), (a24, b5, c3, d11), (a24, b5, c3, d12), (a24, b5, c3, d13), (a24, b5, c3, d14), (a24, b5, c3, d15), (a24, b5, c3, d16, (a24, b5, c3, d17), (a24, b5, c3, d18), (a24, b5, c3, d19), (a24, b5, c3, d20), (a24, b5, c3, d21), (a24, b5, c3, d22), (a24, b6, c1, d1), (a24, b6, c1, d2), (a24, b6, c1, d3), (a24, b6, c1, d4), (a24, b6, c1, d5), (a24, b6, c1, d6), (a24, b6, c1, d7), (a24, b6, c1, d8), (a24, b6, c1, d9), (a24, b6, c1, d10), (a24, b6, c1, d11), (a24, b6, c1, d12), (a24, b6, c1, d13), (a24, b5, c1, d14), (a24, b6, c1, d15), (a24, b6, c1, d16), (a24, b6, c1, d17), (a24, b6, c1, d18), (a24, b6, c1, d19), (a24, b6, c1, d20), (a24, b6, c1, d21), (a24, b6, c1, d22), (a24, b6, c2, d1), (a24, b6, c2, d2), (a24, b6, c2, d3), (a24, b6, c2, d4), (a24, b6, c2, d5), (a24, b6, c2, d6), (a24, b6, c2, d7), (a24, b6, c2, d8), (a24, b6, c2, d9), (a24, b6, c2, d6), (a24, b6, c2, d11), (a24, b6, c2, d12), (a24, b6, c2, d13), (a24, b6, c2, d14), (a24, b6, c2, d15), (a24, b6, c2, d16), (a24, b6, c2, d17), (a24, b6, c2, d18), (a24, b6, c2, d19), (a24, b6, c2, d20), (a24, b6, c2, d21), (a24, b6, c2, d22), (a24, b6, c3, d1), (a24, b6, c3, d2), (a24, b6, c3, d3), (a24, b6, c3, d4), (a24, b6, c3, d5), (a24, b6, c3, d6), (a24, b6, c3, d7), (a24, b6, c3, d8), (a24, b6, c3, d9), (a24, b6, c3, d10), (a24, b6, c3, d11), (a24, b6, c3, d12), (a24, b6, c3, d13), (a24, b6, c3, d14), (a24, b6, c3, d15), (a24, b6, c3, d16), (a24, b6, c3, d17), (a24, b6, c3, d18), (a24, b6, c3, d19), (a24, b6, c3, d20), (a24, b6, c3, d21), (a24, b6, c3, d22), (a25, b1, c1, d1), (a25, b1, c1, d2), (a25, b1, c1, d3), (a25, b1, c1, d4), (a25, b1, c1, d5), (a25, b1, c1, d6), (a25, b1, c1, d7), (a25, b1, c1, d8), (a25, b1, c1, d9), (a25, b1, c1, d10), (a25, b1, c1, d11), (a25, b1, c1, d12), (a25, b1, c1, d13), (a25, b1, c1, d14), (a25, b1, c1, d15), (a25, b1, c1, d16), (a25, b1, c1, d17), (a25, b1, c1, d18), (a25, b1, c1, d19), (a25, b1, c1, d20), (a25, b1, c1, d21), (a25, b1, c1, d22), (a25, b1, c2, d1), (a25, b1, c2, d2), (a25, b1, c2, d3), (a25, b1, c2, d4), (a25, b1, c2, d5), (a25, b1, c2, d6), (a25, b1, c2, d7), (a25, b1, c2, d8), (a25, b1, c2, d9), (a25, b1, c2, d10), (a25, b1, c2, d11), (a25, b1, c2, d12), (a25, b1, c2, d13), (a25, b1, c2, d14), (a25, b1, c2, d15), (a25, b1, c2, d16), (a25, b1, c2, d17), (a25, b1, c2, d18), (a25, b1, c2, d19), (a25, b1, c2, d20), (a25, b1, c2, d21), (a25, b1, c2, d22), (a25, b1, c3, d1), (a25, b1, c3, d2), (a25, b1, c3, d3), (a25, b1, c3, d4), (a25, b1, c3, d5), (a25, b1, c3, d6), (a25, b1, c3, d7), (a25, b1, c3, d8), (a25, b1, c3, d9), (a25, b1, c3, d10), (a25, b1, c3, d11), (a25, b1, c3, d12), (a25, b1, c3, d13), (a25, b1, c3, d14), (a25, b1, c3, d15), (a25, b1, c3, d16), (a25, b1, c3, d17), (a25, b1, c3, d18), (a25, b1, c3, d19), (a25, b1, c3, d20), (a25, b1, c3, d21), (a25, b1, c3, d22), (a25, b2, c1, d1), (a25, b2, c1, d2), (a25, b2, c1, d3), (a25, b2, c1, d4), (a25, b2, c1, d5), (a25, b2, c1, d6), (a25, b2, c1, d7), (a25, b2, c1, d8), (a25, b2, c1, d9), (a25, b2, c1, d10), (a25, b2, c1, d11), (a25, b2, c1, d12), (a25, b2, c1, d13), (a25, b2, c1, d14), (a25, b2, c1, d15), (a25, b2, c1, d16), (a25, b2, c1, d17), (a35, b2, c1, d18), (a25, b2, c1, d19), (a25, b2, c1, d20), (a25, b2, c1, d21), (a25, b2, c1, d22), (a25, b2, c2, d1), (a25, b2, c2, d2), (a25, b2, c2, d3), (a25, b2, c2, d4), (a25, b2, c2, d5), (a25, b2, c2, d6), (a25, b2, c2, d7), (a25, b2, c2, d8), (a25, b2, c2, d9), (a25, b2, c2, d10), (a25, b2, c2, d11), (a25, b2, c2, d12), (a25, b2, c2, d13), (a25, b2, c2, d14), (a25, b2, c2, d15), (a25, b2, c2, d16), (a25, b2, c2, d17), (a25, b2, c2, d18), (a25, b2, c2, d19), (a25, b2, c2, d20), (a25, b2, c2, d21), (a25, b2, c2, d22), (a25, b2, c3, d1), (a25, b2, c3, d2), (a25, b2, c3, d3), (a25, b2, c3, d4), (a25, b2, c3, d5), (a25, b2, c3, (d6), (a25, b2, c3, d7), (a25, b2, c3, d8), (a25, b2, c3, d9), (a25, b2, c3, d10), (a25, b2, c3, d11), (a25, b2, c3, d12), (a25, b2, c3, d13), (a25, b2, c3, d14), (a25, b2, c3, d15), (a25, b2, c3, d16), (a25, b2, c3, d17), (a25, b2, c3, d18), (a25, b2, c3, d19), (a25, b2, c3, d20), (a25, b2, c3, d21), (a25, b2, c3, d22), (a25, b3, c1, d1), (a25, b3, c1, d2), (a25, b3, c1, d3), (a25, b3, c1, d4), (a25, b3, c1, d5), (a25, b3, c1, d6), (a25, b3, c1, d7), (a25, b3, c1, d8), (a25, b3, c1, d9), (a25, b3, c1, d10), (a25, b3, c1, d11), (a25, b3, c1, d12), (a25, b3, c1, d13), (a25, b3, c1, d14), (a25, b3, c1, d15), (a25, b3, c1, d16), (a25, b3, c1, d17), (a25, b3, c1, d18), (a25, b3, c1, d19), (a25, b3, c1, d20), (a25, b3, c1, d21), (a25, b3, c1, d22), (a25, b3, c2, d1), (a25, b3, c2, d2), (a25, b3, c2, d3), (a25, b3, c2, d4), (a25, b3, c2, d5), (a25, b3, c2, d6), (a25, b3, c2, d7), (a25, b3, c2, d8), (a25, b3, c2, d9), (a25, b3, c2, d10), (a25, b3, c2, d11), (a25, b3, c2, d2), (a25, b3, c2, d13), (a25, b3, c2, d14), (a25, b3, c2, d15), (a25, b3, c2, d16), (a25, b3, c2, d17), (a25, b3, c2, d18), (a25, b3, c2, d19), (a25, b3, c2, d20), (a25, b3, c2, d21), (a25, b3, c2, d22), (a25, b3, c3, d1), (a25, b3, c3, d2), (a25, b3, c3, d3), (a25, b3, c3, d4), (a25, b3, c3, d5), (a25, b3, c3, d6), (a25, b3, c3, d7), (a25, b3, c3, d3), (a25, b3, c3, d9), (a25, b3, c3, d10), (a25, b3, c3, d11), (a25, b3, c3, d12), (a25, b3, c3, d13), (a25, b3, c3, d14), (a25, b3, c3, d15), (a25, b3, c3, d16), (a25, b3, c3, d17), (a25, b3, c3, d18), (a25, b3, c3, d19), (a25, b3, c3, d20), (a25, c3, c3, d21), (a25, b3, c3, d22), (a25, b4, c1, d1), (a25, b4, c1, d2), (a25, b4, c1, d3), (a25, b4, c1, d4), (a25, b4, c1, d5), (a25, b4, c1, d6), (a25, b4, c1, d7), (a25, b4, c1, d8), (a25, b4, c1, d9), (a25, b4, c1, d10), (a25, b4, c1, d11), (a25, b4, c1, d12), (a25, b4, c1, d13), (a25, b4, c1, d14), (a25, b4, c1, d15), (a25, b4, c1, d16), (a25, b4, c1, d17), (a25, b4, c1, d18), (a25, b4, c1, d19), (a25, b4, c1, d20), (a25, b4, c1, d21), (a25, b4, c1, d22), (a25, b4, c2, d1), (a25, b4, c2, d2), (a25, b4, c2, d3), (a25, b4, c2, d4), (a25, b4, c2, d5), (a25, b4, c2, d6), (a25, b4, c2, d7), (a25, b4, c2, d8), (a25, b4, c2, d9), (a25, b4, c2, d10), (a25, b4, c2, d11), (a25, b4, c2, d12), (a25, b4, c2, d13), (a25, b4, c2, d14), (a25, b4, c2, d15), (a25, b4, c2, d16), (a25, b4, c2, d17), (a25, b4, c2, d18), (a25, b4, c2, d19), (a25, b4, c2, d20), (a25, b4, c2, d21), (a25, b4, c2, d22), (a25, b4, c3, d1), (a25, b4, c3, d2), (a25, b4, c3, d3), (a25, b4, c3, d4), (a25, b4, c3, d5), (a25, b4, c3, d6), (a25, b4, c3, d7), (a25, b4, c3, d8), (a25, b4, c3, d9), (a25, b4, c3, d10), (a25, b4, c3, d11), (a25, b4, c3, d12), (a25, b4, c3, d13), (a25, b4, c3, d14), (a25, b4, c3, d15), (a25, b4, c3, d16), (a25, b4, c3, d17), (a25, b4, c3, d18), (a25, b4, c3, d19), (a25, b4, c3, d20), (a25, b4, c3, d21), (a25, b4, c3, d22), (a25, b5, c1, d1), (a25, b5, c1, d2), (a25, b5, c1, d3), (a25, b5, c1, d4), (a25, b5, c1, d5), (a25, b5, c1, d6), (a25, b5, c1, d7), (a25, c1, d8), (a25, b5, c1, d9), (a25, b5, c1, d10), (a25, b5, c1, d11), (a25, b5, c1, d12), (a25, b5, c1, d13), (a25, b5, c1, d14), (a25, b5, c1, d15), (a25, b5, c1, d16), (a25, b5, c1, d17), (a25, b5, c1, d18), (a25, b5, c1, d19), (a25, b5, c1, d20), (a25, b5, c1, d21), (a25, b5, c1, d22), (a25, b5, c2, d1), (a25, b5, c2, d2), (a25, b5, c2, d3), (a25, b5, c2, d4), (a25, b5, c2, d5), (a25, b5, c2, d6), (a25, b5, c2, d7), (a25, b5, c2, d8), (a25, b5, c2, d9), (a25, b5, c2, d10), (a25, b5, c2, d11), (a25, b5, c2, d12), (a25, b5, c2, d13), (a25, b5, c2, d14), (a25, b5, c2, d15), (a25, b5, c2, d16), (a25, b5, c2, d17), (a25, b5, c2, d18), (a25, b5, c2, d19), (a25, b5, c2, d20), (a25, b5, c2, d21), (a25, b5, c2, d22), (a25, b5, c3, d1), (a25, b5, c3, d2), (a25, b5, c3, d3), (a25, b5, c3, d4), (a25, b5, c3, d5), (a25, b5, c3, d6), (a25, b5, c3, d7), (a25, b5, c3, d8), (a25, b5, c3, d9), (a25, b5, c3, d10), (a25, b5, c3, d11), (a25, b5, c3, d12), (a25, b5, c3, d13), (a25, b5, c3, d14), (a25, b5, c3, d15), (a25, b5, c3, d16), (a25, b5, c3, d17), (a25, b5, c3, d18), (a25, b5, c3, d19), (a25, b5, c3, d20), (a25, b5, c3, d21), (a25, b5, c3, d22), (a25, b6, c1, d1), (a25, b6, c1, d2), (a25, b6, c1, d3), (a25, b6, c1, d4), (a25, b6, c1, d5), (a25, b6, c1, d6), (a25, b6, c1, d7), (a25, b6, c1, d8), (a25, b6, c1, d9), (a25, b6, c1, d10), (a25, b6, c1, d11), (a25, b6, c1, d12), (a25, b6, c1, d13), (a25, b6, c1, d14), (a25, b6, c1, d15), (a25, b6, c1, d16), (a25, b6, c1, d17), (a25, b6, c1, d18), (a25, b6, c1, d19), (a25, b6, c1, d20), (a25, b6, c1, d21), (a25, b6, c1, d22), (a25, b6, c2, d1), (a25, b6, c2, d2), (a25, b6, c2, d3), (a25, b6, c2, d4), (a25, b6, c2, d5), (a25, b6, c2, d6), (a25, b6, c2, d7), (a25, b6, c2, d8), (a25, b6, c2, d9), (a25, b6, c2, d10), (a25, b6, c2, d11), (a25, b6, c2, d12), (a25, b6, c2, d13), (a25, b6, c2, d14), (a25, b6, c2, d15), (a25, b6, c2, d16), (a25, b6, c2, d17), (a25, b6, c2, d18), (a25, b6, c2, d19), (a25, b6, c2, d20), (a25, b6, c2, d21), (a25, b6, c2, d22), (a25, b6, c3, d1), (a25, b6, c3, d2), (a25, b6, c3, d3), (a25, b6, c3, d4), (a25, b6, c3, d5), (a25, b6, c3, d6), (a25, b6, c3, d7), (a25, b6, c3, d8), (a25, b6, c3, d9), (a25, b6, c3, d10), (a25, b6, c3, d11), (a25, b6, c3, d12), (a25, b6, c3, d13), (a25, b6, c3, d14), (a25, b6, c3, d15), (a25, b6, c3, d16), (a25, b6, c3, d17), (a25, b6, c3, d18), (a25, b6, c3, d19), (a25, b6, c3, d20), (a25, b6, c3, d21), (a25, b6, c3, d22), (a26, b1, c1, d1), (a26, b1, c1, d2), (a26, b1, c1, d3), (a26, b1, c1, d4), (a26, b1, c1, d5), (a26, b1, c1, d6), (a26, b1, c1, d7), (a26, b1, c1, d8), (a26, b1, c1, d9), (a26, b1, c1, d10), (a26, b1, c1, d11), (a26, b1, c1, d12), (a26, b1, c1, d13), (a26, b1, c1, d14), (a26, b1, c1, d15), (a26, b1, c1, d16), (a26, b1, c1, d17), (a26, b1, c1, d18), (a26, b1, c1, d19), (a26, b1, c1, d20), (a26, b1, c1, d21), (a26, b1, c1, d22), (a26, b1, c2, d1), (a26, b1, c2, d2), (a26, b1, c2, d3), (a26, b1, c2, d4), (a26, b1, c2, d5), (a25, b1, c2, d6), (a26, b1, c2, d7), (a26, b1, c2, d8), (a26, b1, c2, d9), (a26, b1, c2, d10), (a26, b1, c2, d11), (a26, b1, c2, d12), (a26, b1, c2, d13), (a26, b1, c2, d14), (a26, b1, c2, d15), (a26, b1, c2, d16), (a26, b1, c2, d17), (a26, b1, c2, d18), (a26, b1, c2, d19), (a26, b1, c2, d20), (a26, b1, c2, d21), (a26, b1, c2, d22), (a26, b1, c2, d11), (a26, b1, c3, d2), (a26, b1, c3, d3), (a26, b1, c3, d4), (a26, b1, c3, d5), (a26, b1, c3, d6), (a26, b1, c3, d7), (a26, b1, c3, d8), (a26, b1, c3, d9), (a26, b1, c3, d16), (a26, b1, c3, d11), (a26, b1, c3, d12), (a26, b1, c3, d13), (a26, b1, c3, d14), (a26, b1, c3, d15), (a26, b1, c3, d16), (a26, b1, c3, d17), (a26, b1, c3, d18), (a26, b1, c3, d19), (a26, b1, c3, d20), (a26, b1, c3, d21), (a26, b1, c3, d22), (a26, b2, c1, d1), (a26, b2, c1, d2), (a26, b2, c1, d3), (a26, b2, c1, d4), (a26, b2, c1, d5), (a26, b2, c1, d6), (a26, b2, c1, d7), (a26, b2, c1, d8), (a26, b2, c1, d9), (a26, b2, c1, d10), (a26, b2, c1, d11), (a26, b2, c1, d12), (a26, b2, c1, d13), (a26, b2, c1, d14), (a26, b2, c1, d15), (a26, b2, c1, d16), (a26, b2, c1, d17), (a26, b2, c1, d18), (a26, b2, c1, d19), (a26, b2, c1, d20), (a26, b2, c1, d21), (a26, b2, c1, d22), (a26, b2, c2, d1), (a26, b2, c2, d2), (a26, b2, c2, d3), (a26, b2, c2, d4), (a26, b2, c2, d5), (a26, b2, c2, d6), (a26, b2, c2, d7), (a26, b2, c2, d8), (a26, b2, c2, d9), (a26, b2, c2, d10), (a26, b2, c2, d11), (a26, b2, c2, d12), (a26, b2, c2, d13), (a26, b2, c2, d14), (a6, b2, c2, d15), (a26, b2, c2, d16), (a26, b2, c2, d17), (a26, b2, c2, d18), (a26, b2, c2, d19), (a26, b2, c2, d20), (a26, b2, c2, d21), (a26, b2, c2, d22), (a26, b2, c3, d1), (a26, b2, c3, d2), (a26, b2, c3, d3, (a26, b2, c3, d4), (a26, b2, c3, d5), (a26, b2, c3, d6), (a26, b2, c3, d7), (a26, b2, c3, d8), (a26, b2, c3, d9), (a26, b2, c3, d10), (a26, b2, c3, d11), (a26, b2, c3, d12), (a26, b2, c3, d13), (a26, b2, c3, d14), (a26, b2, c3, d15), (a26, b2, c3, d16), (a26, b2, c3, d17), (a26, b2, c3, d18), (a26, b2, c3, d19), (a26, b2, c3, d20), (a26, b2, c3, d21), (a26, b2, c3, d22), (a26, b3, c1, d1), (a26, b3, c1, d2), (a26, b3, c1, d3), (a26, b3, c1, d4), (a36, b3, c1, d5), (a26, b3, c1, d6), (a26, b3, c1, d7), (a26, b3, c1, d18), (a26, b3, c1, d9), (a26, b3, c1, d10), (a26, b3, c1, d11), (a26, b3, c1, d12), (a26, b5, c1, d13), (a26, b3, c1, d14), (a26, b3, c1, d15), (a26, b3, c1, d16), (a26, b3, c1, d17), (a26, b3, c1, d18), (a26, b3, c1, d19), (a26, b3, c1, d20), (a26, b3, c1, d21), (a26, b3, c1, d22), (a26, b3, c2, d1), (a26, b3, c2, d2), (a26, b3, c2, d3), (a26, b3, c2, d4), (a26, b3, c2, d5), (a26, b3, c2, d6), (a26, b3, c2, d7), (a26, b3, c2, d3), (a26, b3, c2, d9), (a26, b3, c2, d10), (a26, b3, c2, d11), (a26, b3, c2, d12), (a26, b3, c2, d13), (a26, b3, c2, d14), (a26, b3, (a26, b3, c2, d15), (a26, b3, c2, d16), (a26, b3, c2, d17), (a26, b3, c2, d18), (a26, b3, c2, d19), (a26, b3, c2, d20), (a26, b3, c2, d21), (a26, b3, c2, d22), (a26, b3, c3, d1), (a26, b3, c3, d2), (a26, b3, c3, d3), (a26, b3, c3, d14), (a26, b3, c3, d5), (a26, b3, c3, d6), (a26, b3, c3, d7), (a26, b3, c3, d8), (a26, b3, c3, d9), (a26, b3, c3, d6), (a26, b3, c3, d11), (a26, b3, c3, d12), (a26, b3, c3, d13), (a26, b3, c3, d14), (a26, b3, c3, d15), (a26, b3, c3, d16), (a26, b3, c3, d17), (a26, b3, c3, d18), (a66, b3, c3, d19), (a26, b3, c3, d20), (a26, b3, c3, d21), (a26, b3, c3, d22), (a26, b4, c1, d1), (a26, b4, c1, d2), (a26, b4, c1, d3), (a26, b4, c1, d4), (a26, b4, c1, d5), (a26, b4, c1, d6), (a26, b4, c1, d7), (a26, b4, c1, d5), (a26, b4, c1, d9), (a66, b4, c1, d10), (a26, b4, c1, d11), (a26, b4, c1, d12), (a26, b4, c1, d13), (a26, b4, c1, d14), (a26, b4, c1, d15), (a26, b4, c1, d16), (a26, b4, c1, d17), (a26, b4, c1, d18), (a26, b4, c1, d19), (a26, b4, c1, d20), (a26, b4, c1, d21), (a26, b4, c1, d22), (a26, b4, c2, d1), (a6, b4, c2, d2), (a26, b4, c2, d3), (a26, b4, c2, d4), (a76, b4, c2, d5), (a26, b4, c2, d6), (a26, b4, c2, d7), (a76, b4, c2, d8), (a6, b4, c2, d9), (a26, b4, c2, d10), (a26, b4, c2, d11), (a66, b4, c2, d12), (a26, b4, c2, d13), (a26, b4, c2, d14), (a26, b4, c2, d15), (a26, b4, c2, d16), (a26, b4, c2, d17), (a26, b4, c2, d18), (a26, b4, c2, d19), (a26, b4, c2, d20), (a26, b4, c2, d21), (a26, b4, c2, d22), (a26, b4, c3, d1), (a26, b4, c3, d2), (a26, b4, c3, d3), (a26, b4, c3, d4), (a26, b4, c3, d5), (a26, b4, c3, d6), (a26, b4, c3, d7), (a26, b4, c3, d8), (a26, b4, c3, d9), (a26, b4, c3, d10), (a26, b4, c3, d11), (a26, b4, c3, d12), (a26, b4, c3, d13), (a26, b4, c3, d14), (a26, b4, c3, d15), (a26, b4, c3, d16), (a26, b4, c3, d17), (a26, b4, c3, d18), (a26, b4, c3, d19), (a26, b4, c3, d20), (a26, b4, c3, d21), (a26, b4, c3, d22), (a26, b5, c1, d1), (a26, b5, c1, d2), (a26, b5, c1, d3), (a26, b5, c1, d4), (a26, b5, c1, d5), (a26, b5, c1, d6), (a26, b5, c1, d7), (a26, b5, c1, d8), (a26, b5, c1, d9), (a26, b5, c1, d10), (a26, b5, c1, d11), (a26, b5, c1, d12), (a26, b5, c1, d3), (a26, b5, c1, d14), (a26, b5, c1, d15), (a26, b5, c1, d16), (a26, b5, c1, d17) (a26, b5, c1, d18), (a26, b5, c1, d19), (a26, b5, c2, d20), (a26, b5, c2, d21), (a26, b5, c2, d22), (a26, b5, c2, d1), (a26, b5, c2, d2), (a26, b5, c2, d3), (a26, b5, c2, d4), (a26, b5, c2, d5), (a26, b5, c2, d6), (a26, b5, c2, d7), (a26, b5, c2, d8), (a26, b5, c2, d9), (a26, b5, c2, d10), (a26, b5, c2, d11), (a26, b5, c2, d12), (a26, b5, c2, d13), (a26, b5, c2, d14), (a26, b5, c2, d15), (a26, b5, c2, d16), (a26, b5, c2, d17), (a26, b5, c2, d18), (a26, b5, c2, d19), (a26, b5, c2, d20), (a26, b5, c2, d21), (a26, b5, c2 d22), (a26, b5, c3, d1), (a26, b5, c3, d2), (a26, b5, c3, d3), (a26, b5, c3, d4), (a26, b5, c3, d5), (a26, b5, c3, d6), (a26, b5, c3, d7), (a26, b5, c3, d8), (a26, b5, c3, d9), (a26, b5, c3, d10), (a26, b5, c3, d11), (a26, b5, c3, d12), (a26, b5, c3, d13), (a26, b5, c3, d14), (a26, b5, c3, d15), (a26, b5, c3, d16), (a26, b5, c3, d16), (a26, b5, c3, d16), (a26, b5, c3, d16), (a26, b5, c3, d16), (a26, b5, c3, d20), (a26, b5, c3, d16), (a26, b5, c3, d22), (a26, b6, c1, d1), (a26, b6, c1, d2, (a26, b6, c1, d3), (a26, b6, c1, d4), (a26, b6, c1, d5), (a26, b6, c1, d6), (a26, b6, c1, d7), (a26, b6, c1, d8), (a26, b6, c1, d9), (a26, b6, c1, d10), (a26, b6, c1, d11), (a26, b6, c1, d12), (a26, b6, c1, d13), (a26, b6, c1, d14), (a26, b6, c1, d15), (a26, b6, c1, d16), (a26, b6, c1, d17), (a26, b6, c1, d18), (a26, b6, c1, d19), (a26, b6, c1, d20), (a26, b6, c1, d21), (a26, b6, c1, d22), (a26, b6, c2, d1), (a26, b6, c2, d2), (a26, b6, c2, d3), (a26, b6, c2, d4), (a26, b6, c2, d5), (a26, b6, c2, d6), (a26, b6, c2, d7), (a26, b6, c2, d8), (a26, b6, c2, d9), (a26, b6, c2, d10), (a26, b6, c2, d11), (a26, b6, c2, d12), (a26, b6, c2, d13), (a26, b6, c2, d14), (a26, b6, c2, d15), (a26, b6, c2, d16), (a26, b6, c2, d17), (a26, b6, c2, d18), (a26, b6, c2, d19), (a26, b6, c2, d20), (a26, b6, c2, d21), (a26, b6, c2, d22), (a26, b6, c3, d1), (a26, b6, c3, d2), (a26, b6, c3, d3), (a26, b6, c3, d4), (a26, b6, c3, d5), (a26, b6, c3, d6), (a26, b6, c3, d7), (a26, b6, c3, d8), (a26, b6, c3, d9), (a26, b6, c3, d10), (a26, b6, c3, d11), (a26, b6, c3, d12), (a26, b6, c3, d13), (a26, b6, c3, d14), (a26, b6, c3, d15), (a26, b6, c3, d16), (a26, b6, c3, d17), (a26, b6, c3, d18), (a26, b6, c3, d19), (a26, b6, c3, d20), (a26, b6, c3, d21), (a26, b6, c3, d22), (a27, b1, c1, d1), (a27, b1, c1, d2), (a27, b1, c1, d3), (a27, b1, c1, d4), (a27, b1, c1, d5), (a27, b1, c1, d6), (a27, b1, c1, d7), (a27, b1, c1, d8), (a27, b1, c1, d9), (a27, b1, c1, d10), (a27, b1, c1, d11), (a27, b1, c1, d12), (a27, b1, c1, d13), (a27, b1, c1, d14), (a27, b1, c1, d15), (a27, b1, c1, d16), (a27, b1, c1, d17), (a27, b1, c1, d18), (a27, b1, c1, d19), (a27, b1, c1, d20), (a27, b1, c1, d21), (a27, b1, c1, d22), (a27, b1, c2, d1), (a27, b1, c2, d2), (a27, b1, c2, d3), (a27, b1, c2, d4), (a27, b1, c2, d5), (a27, b1, c2, d6), (a27, b1, c2, d7), (a27, b1, c2, d8), (a27, b1, c2, d9), (a27, b1, c2, d10), (a27, b1, c2, d11), (a27, b1, c2, d12), (a27, b1, c2, d13), (a27, b1, c2, d14), (a27, b1, c2, (d15), (a27, b1, c2, d16) (a27, b1, c2, d17), (a27, b1, c2, d18), (a27, b1, c2, d19), (a27, b1, c2, d20), (a27, b1, c2, d21), (a27, b1, c2, d22), (a27, b1, c3, d1), (a27, b1, c3, d2), (a27, b1, c3, d3), (a27, b1, c3, d4), (a27, b1, c3, d5), (a27, b1, c3, d6), (a27, b1, c3, d7), (a27, b1, c3, d8), (a27, b1, c3, d9), (a27, b1, c3, d10), (a27, b1, c3, d11), (a27, b1, c3, d12), (a27, b1, d13), (a27, b1, c3, d14), (a27, b1, c3, d15) (a27, b1, c3, d16), (a27, b1, c3, d17), (a27, b1, c3, d18), (a27, b1, c3, d19), (a27, b1, c3, d20), (a27, b1, c3, d21), (a27, b1, c3, d22), (a27, b2, c1, d1), (a27, b2, c1, d2), (a27, b2, c1, d3), (a21, b2, c1, d4), (a27, b2, c1, d5), (a27, b2, c1, d6), (a27, b2, c1, d7), (a27, b2, c1, d8), (a27, b2, c1, d9), (a27, b2, c1, d10), (a27, b2, c1, d11), (a27, b2, c1, d12), (a27, b2, c1, d13), (a27, b2, c1, d14), (a27, b2, c1, d15), (a27, b2, c1, d16), (a27, b2, c1, d17), (a27, b2, c1, d18), (a27, b2, c1, d19), (a27, b2, c1, d20), (a27, b2, c1, d21), (a27, b2, c1, d22), (a27, b2, c2, d1), (a27, b2, c2, d2), (a27, b2, c2, d3), (a27, b2, c2, d4), (a27, b2, c2, d5), (a27, b2, c2, d6), (a27, b2, c2, d7), (a27, b2, c2, d8), (a27, b2, c2, d9), (a27, b2, c2, d10), (a27, b2, c2, d11), (a27, b2, c2, d12), (a27, b2, c2, d13), (a27, b2, c2, d14), (a27, b2, c2, d15), (a27, b2, c2, d16), (a27, b2, c2, d17), (a27, b2, c2, d18), (a27, b2, c2, d19), (a27, b2, c2, d20), (a27, b2, c2, d21), (a27, b2, c2, d22), (a27, b2, c3, d1), (a27, b2, c3, d2), (a27, b2, c3, d3), (a27, b2, c3, d4), (a27, b2, c3, d5), (a27, b2, c3, d6), (a27, b2, c3, d7), (a27, b2, c3, d8), (a27, b2, c3, d9), (a27, b2, c3, d10), (a27, b2, c3, d11), (a27, b2, c3, d12), (a27, b2, c3, d13), (a27, b2, c3, d14), (a27, b2, c3, d15), (a27, b2, c3, did), (a27, b2, c3, d17), (a27, b2, c3, d18), (a27, b2, c3, d19), (a27, b2, c3, d20), (a27, b2, c3, d21), (a27, b2, c3, d22), (a27, b3, c1, d1), (a27, b3, c1, d2), (a27, b3, c1, d3), (a27, b3, c1, d4), (a27, b3, c1, d5), (a27, b3, c1, d6), (a27, b3, c1, d7), (a27, b3, c1, d8), (a27, b3, c1, d9), (a27, b3, c1, d10), (a27, b3, c1, d11), (a27, b3, c1, d12), (a27, b3, c1, d13), (a27, b3, c1, d14), (a27, b3, c1, d15), (a27, b3, c1, d16), (a27, b3, c1, d17), (a27, b3, c1, d18), (a27, b3, c1, d19), (a27, b3, c1, d20), (a27, b3, c1, d21), (a27, b3, c1, d22), (a27, b3, c2, d1), (a27, b3, c2, d2), (a27, b3, c2, d3), (a27, b3, c2, d4), (a27, b5, c2, d5), (a27, b3, c2, d6), (a27, b3, c2, d7), (a27, b3, c2, d8), (a27, b3, c2, d9), (a27, b3, c2, d10), (a27, b3, c2, d11), (a27, b3, c2, d12), (a27, b3, c2, d13), (a27, b3, c2, d14), (a27, b3, c2, d15), (a27, b3, c2, d16), (a27, b3, c2, d17), (a27, b3, c2, d18), (a27, b3, c2, d19), (a27, b3, c2, d20), (a27, b3, c2, d21), (a27, b3, c2, d22), (a27, b3, c3, d1), (a27, b3, c3, d2), (a27, b3, c3, d3), (a27, b3, c3, d4), (a27, b3, c3, d5), (a27, b3, c3, d6), (a27, b3, c3, d7), (a27, b3, c3, d18), (a27, b3, c3, d9), (a27, b3, c3, d10), (a7, b3, c3, d17), (a27, b3, c3, d12), (a27, b3, c3, d13), (a27, b3, c3, d14), (a27, b3, c3, d15), (a27, b3, c3, d16), (a27, b3, c3, d17), (a27, b3, c3, d18), (a27, b3, c3, d19), (a27, b3, c3, d20), (a27, b3, c3, d21), (a27, b3, c3, d22), (a27, b4, c1, d1), (a27, b4, c1, d2), (a27, b4, c1, d3), (a27, b4, c1, d4), (a27, b4, c1, d5), (a27, b4, c1, d6), (a27, b4, c1, d7), (a27, b4, c1, d8), (a27, b4, c1, d9), (a27, b4, c1, d10), (a27, b4, c1, d11), (a27, b4, c1, d12), (a27, b4, c1, d13), (a27, b4, c1, d14), (a27, b4, c1, d15), (a27, b4, c1, d16), (a27, b4, c1, d17), (a27, b4, c1, d18), (a27, b4, c1, d19), (a27, b4, c1, d20), (a27, b4, c1, d21), (a27, b4, c1, d22), (a27, b4, c2, d1), (a27, b4, c2, d2), (a27, b4, c2, d3), (a27, b4, c2, d4), (a27, b4, c2, d5), (a27, b4, c2, d6), (a27, b4, c2, d7), (a27, b4, c2, d8), (a27, b4, c2, d9), (a27, b4, c2, d10), (a27, b4, c2, d11), (a27, b4, c2, d12), (a27, b4, c2, d13), (a27, b4, c2, d14), (a27, b4, c2, d15), (a27, b4, c2, d16), (a27, b4, c2, d11), (a27, b4, c2, d18), (a27, b4, c2, d19), (a27, b4, c2, c20), (a27, b4, c2, d21), (a27, b4, c2, d22), (a27, b4, c3, d1), (a27, b4, c3, d2), (a27, b4, c3, d3), (a27, b4, c3, d4), (a27, b4, c3, d5), (a27, b4, c3, c6), (a27, b4, c3, d7), (a27, b4, c3, d3), (a27, b4, c3, d9), (a27, b4, c3, d10), (a27, b4, c3, d11), (a27, b4, c3, d12), (a27, b4, c3, d13), (a27, b4, c3, d14), (a27, b4, c3, d15), (a27, b4, c3, d16), (a27, b4, c3, d17), (a27, b4, c3, d18), (a27, b4, c3, d19), (a27, b4, c3, d20), (a27, b4, c3, d21), (a27, b4, c3, d22), (a27, b5, c1, d1), (a27, b5, c1, d2), (a27, b5, c1, d3), (a27, b5, c1, d4), (a27, b5, c1, c5), (a27, b5, c1, d6), (a27, b5, c1, d7), (a27, b5, c1, d8), (a27, b5, c1, d9), (a27, b5, c1, d10), (a27, b5, c1, (a27, b5, c1, d16), (a27, b5, c1, d17), (a27, b5, c1, d18), (a27, b5, c1, d19), (a27, b5, c1, d20), (a27, b5, c1, d21), (a27, b5, c1, d22), (a27, b5, c2, d1), (a27, b5, c2, d2), (a27, b5, c2, d3), (a27, b5, c2, d4), (a27, b5, c2, d5), (a27, b5, c2, d6), (a27, b5, c2, d7), (a21, b5, c2, d8), (a27, b5, c2, d9), (a27, b5, c2, d10), (a27, b5, c2, d11), (a27, b5, c2, d12), (a27, b5, c2, d13), (a27, b5, c2, d14), (a27, b5, c2, d15), (a27, b5, c2, d16), (a27, b5, c2, d17), (a27, b5, c2, d18), (a27, b5, c2, d19), (a27, b5, c2, d20), (a27, b5, c2, d21), (a27, b5, c2, d22), (a27, b5, c3, d1), (a27, b5, c3, d2), (a27, b5, c3, d3), (a27, b5, c3, d4), (a2, b5, c3, d5), (a27, b5, c3, d6), (a27, b5, c3, d7), (a27, b5, c3, d8), (a27, b5, c3, d9), (a27, b5, c3, d10), (a27, b5, c3, d11), (a27, b5, c3, d12), (a27, b5, c3, d13), (a27, b5, c3, d14), (a27, b5, c3, d15), (a27, b5, c3, d16), (a27, b5, c3, d17), (a27, b5, c3, d18), (a27, b5, c3, d19), (a27, b5, c3, d20), (a27, b5, c3, d21), (a27, b5, c3, d22), (a27, b6, c1, d1), (a27, b6, c1, d2), (a27, b6, c1, d3), (a27, b6, c1, d4), (a27, b6, c1, d5), (a27, b6, c1, d6), (a27, b6, c1, d7), (a27, b6, c1, d8), (a27, b6, c1, d9), (a27, b6, c1, d10), (a27, b6, c1, d11), (a27, b6, c1, d12), (a27, b6, c1, d13), (a27, b6, c1, d14), (a27, b6, c1, d15), (a27, b6, c1, d16), (a27, b6, c1, d17), (a27, b6, c1, d18), (a27, b6, c1, d19), (a27, b6, c1, d20), (a27, b6, c1, d21), (a27, b6, c1, d22), (a27, b6, c2, d1), (a27, b6, c2, d2), (a27, b6, c2, d3), (a27, b6, c2, d4), (a27, b6, c2, d5), (a27, b6, c2, d6), (a27, b6, c2, d7), (a27, b6, c2, d8), (a27, b6, c2, d9), (a27, b6, c2, d10), (a27, b6, c2, d11), (a27, b6, c2, d12), (a27, b6, c2, d13), (a27, b6, c2, d14), (a27, b6, c2, d15), (a27, b6, c2, d16), (a27, b6, c2, d17), (a27, b6, c2, d18), (a27, b6, c2, d19), (a27, b6, c2, d20), (a27, b6, c2, d21), (a27, b6, c2, d22), (a27, b6, c3, d1), (a27, b6, c3, d2), (a27, b6, c3, d3), (a27, b6, c3, d4), (a27, b6, c3, d5), (a27, b6, c3, d6), (a27, b6, c3, d7), (a27, b6, c3, d8), (a27, b6, c3, d9), (a27, b6, c3, d10), (a27, b6, c3, d15), (a27, b6, c3, d16), (a27, b6, c3, d17), (a27, b6, c3, d18), (a27, b6, c3, d19), (a27, b6, c3, d20), (a27, b6, c3, d21), (a27, b6, c3, d22), (a28, b1, c1, d1), (a28, b1, c1, d2), (a28, b1, c1, d3), (a28, b1, c1, d4), (a28, b1, c1, d5), (a28, b1, c1, d6), (a28, b1, c1, d7), (a28, b1, c1, d8), (a28, b1, c1, d9), (a28, b1, c1, d10), (a28, b1, c1, d11), (a28, b1, c1, d12), (a28, b1, c1, d13), (a28, b1, c1, d14), (a28, b1, c1, d15), (a28, b1, c1, d16), (a28, b1, c1, d17), (a28, b1, c1, d18), (a28, b1, c1, d19), (a28, b1, c1, d20), (a28, b1, c1, d21), (a28, b1, c1, d22), (a28, b1, c2, d1), (a28, b1, c2, d2), (a28, b1, c2, d3), (a28, b1, c2, d4), (a28, b1, c2, d5), (a28, b1, c2, d6), (a28, b1, c2, d7), (a28, b1, c2, d8), (a28, b1, c2, d9), (a28, b1, c2, d10), (a28, b1, c2, d11), (a28, b1, c2, d12), (a28, b1, c2, d13), (a28, b1, c2, d14), (a28, b1, c2, d15), (a28, b1, c2, d16), (a28, b1, c2, d17), (a28, b1, c2, d18), (a28, b1, c2, d19), (a28, b1, c2, d20), (a28, b1, c2, d21), (a28, b1, c2, d22), (a28, b1, c3, d1), (a28, b1, c3, d2), (a28, b1, c3, d3), (a28, b1, c3, d4), (a28, b1, c3, d5), (a28, b1, c3, d6), (a28, b1, c3, d7), (a28, b1, c3, d8), (a28, b1, c3, d9), (a28, b1, c3, d10), (a28, b1, c3, d11), (a28, b1, c3, d12), (a28, b1, c3, d13), (a28, b1, c3, d14), (a28, b1, c3, d15), (a28, b1, c3, d16), (a28, b1, c3, d17), (a28, b1, c3, d18), (a28, b1, c3, d19), (a28, b1, c3, d20), (a28, b1, c3, d21), (a28, b1, c3, d22), (a28, b2, c1, d1), (a28, b2, c1, d2), (a28, b2, c1, d3), (a28, b2, c1, d4), (a28, b2, c1, d5), (a28, b2, c1, d6), (a28, b2, c1, d7), (a28, b2, c1, d8), (a28, b2, c1, d9), (a28, b2, c1, d10), (a28, b2, c1, d11), (a28, b2, c1, d12), (a28, b2, c1, d13), (a28, b2, c1, d14), (a28, b2, c1, d15), (a28, b2, c1, d16), (a28, b2, c1, d17), (a28, b2, c1, d18), (a28, b2, c1, d19), (a28, b2, c1, d20), (a28, b2, c1, d21), (a28, b2, c1, d22), (a28, b2, c2, d1), (a28, b2, c2, d2), (a28, b2, c2, d3), (a28, b2, c2, d4), (a28, b2, c2, d5), (a28, b2, c2, d6), (a28, b2, c2, d7), (a28, b2, c2, d8), (a28, b2, c2, d9), (a28, b2, c2, d10), (a28, b2, c2, d11), (a28, b2, c2, d12), (a28, b2, c2, d13), (a28, b2, c2, d14), (a28, b2, c2, d15), (a28, b2, c2, d16), (a28, b2, c2, d17), (a28, b2, c2, d18), (a28, b2, c2, d19), (a28, b2, c2, d20), (a28, b2, c2, d21), (a28, b2, c2, d22), (a28, b2, c3, d1), (a28, b2, c3, d2), (a28, b2, c3, d3), (a28, b2, c3, d4), (a28, b2, c3, d5), (a28, b2, c3, d6), (a28, b2, c3, d7), (a28, b2, c3, d8), (a28, b2, c3, d9), (a28, b2, c3, d10), (a28, b2, c3, d11), (a28, b2, c3, d12), (a28, b2, c3, d13), (a28, b2, c3, d14), (a28, b2, c3, d15), (a28, b2, c3, d16), (a28, b2, c3, d17), (a28, b2, c3, d18), (a28, b2, c3, d19), (a28, b2, c3, d20), (a28, b2, c3, d21), (a28, b2, c3, d22), (a28, b3, c1, dl), (a28, b3, c1, d2), (a28, b3, c1, d3), (a28, b3, c1, d4), (a28, b3, c1, d5), (a28, b3, c1, d6), (a28, b3, c1, d7), (a28, b3, c1, d8), (a28, b3, c1, d9), (a28, b3, c1, d10), (a28, b3, c1, d11), (a28, b3, c1, d12), (a28, b3, c1, d13), (a28, b3, c1, d14), (a28, b3, c1, d15), (a28, b3, c1, d16), (a28, b3, c1, d17), (a28, b3, c1, d18), (a28, b3, c1, d19), (a28, b3, c1, d20), (a28, b3, c1, d21), (a28, b3, c1, d22), (a28, b3, c2, d1), (a28, b3, c2, d2), (a28, b3, c2, d3), (a28, b3, c2, d4), (a28, b3, c2, d5), (a28, b3, c2, d6), (a28, b3, c2, d7), (a28, b3, c2, d8), (a28, b3, c2, d9), (a28, b3, c2, d10), (a28, b3, c2, d11), (a28, b3, c2, d12), (a28, b3, c2, d13), (a28, b3, c2, d14), (a28, b3, c2, d15), (a28, b3, c2, d16), (a28, b3, c2, d17), (a28, b3, c2, d18), (a28, b3, c2, d19), (a28, b3, c2, d20), (a28, b3, c2, d21), (a28, b3, c2, d22), (a28, b3, c3, d1), (a28, b3, c3, d2), (a28, b3, c3, d3), (a28, b3, c3, d4), (a28, b3, c3, d5), (a28, b3, c3, d6), (a28, b3, c3, d7), (a28, b3, c3, d8), (a28, b3, c3, d9), (a28, b3, c3, d10), (a28, b3, c3, d11), (a28, b3, c3, d12), (a28, b5, c3, d13), (a28, b3, c3, d14), (a28, b3, c3, d15), (a28, b3, c3, d16), (a28, b3, c3, d17), (a28, b3, c3, d18), (a28, b3, c3, d19), (a28, b3, c3, d20), (a28, b3, c3, d21), (a28, b3, c3, d22), (a28, b4, c1, d1), (a28, b4, c1, d2), (a28, b4, c1, d3), (a28, b4, c1, d4), (a28, b4, c1, d5), (a28, b4, c1, d6), (a28, b4, c1, d7), (a28, b4, c1, d8), (a28, b4, c1, d9), (a28, b4, c1, d10), (a28, b4, c1, d11), (a28, b4, c1, d12), (a28, b4, c1, d13), (a28, b4, c1, d14), (a28, b4, c1, d15), (a28, b4, c1, d16), (a28, b4, c1, d17), (a28, b4, c1, d18), (a28, b4, c1, d19), (a28, b4, c1, d20), (a28, b4, c1, d21), (a28, b4, c1, d22), (a28, b4, c2, d1), (a28, b4, c2, d2), (a28, b4, c2, d3), (a28, b4, c2, d4), (a28, b4, c2, d5), (a28, b4, c2, d6), (a28, b4, c2, d7), (a28, b4, c2, d8), (a28, b4, c2, d9), (a28, b4, c2, d10), (a28, b4, c2, d11), (a28, b4, c2, d12), (a28, b4, c2, d13), (a28, b4, c2, d14), (a28, b4, c2, d15), (a28, b4, c2, d6), (a28, b4, c2, d7), (a28, b4, c2, d18), (a28, b4, c2, d19), (a28, b4, c2, d20), (a28, b4, c2, d21), (a28, b4, c2, d22), (a28, b4, c3, d1), (a28, b4, c3, d2), (a28, b4, c3, d3), (a28, b4, c3, d4), (a28, b4, c3, d5), (a28, b4, c3, d6), (a28, b4, c3, d7), (a28, b4, c3, d8), (a28, b4, c3, d9), (a28, b4, c3, d10), (a28, b4, c3, d11), (a28, b4, c3, d12), (a28, b4, c3, d13), (a28, b4, c3, d14), (a28, b4, c3, d15), (a28, b4, c3, d16), (a28, b4, c3, d17), (a28, b4, c3, d18), (a28, b4, c3, d19), (a28, b4, c3, d20), (a28, b4, c3, d21), (a28, b4, c3, d22), (a28, b5, c1, d1), (a28, b5, c1, d2), (a28, b5, c1, d3), (a28, b5, c1, d4), (a28, b5, c1, d5), (a28, b5, c1, d6), (a28, b5, c1, d7), (a28, b5, c1, d8), (a28, b5, c1, d9), (a28, b5, c1, d10), (a28, b5, c1, d11), (a28, b5, c1, d12), (a28, b5, c1, d13), (a28, b5, c1, d14), (a28, b5, c1, d15), (a28, b5, c1, d16), (a28, b5, c1, d17), (a28, b5, c1, d18), (a28, b5, c1, d19), (a28, b5, c1, d20), (a28, b5, c1, d21), (a28, b5, c1, d22), (a28, b5, c2, d1), (a28, b5, c2, d2), (a28, b5, c2, d1), (a28, b5, c2, d4), (a28, b5, c2, d5), (a28, b5, c2, d6), (a28, b5, c2, d7), (a28, b5, c2, d8), (a28, b5, c2, d9), (a28, b5, c2, d10), (a28, b5, c2, d11), (a28, b5, c2, d12), (a28, b5, c2, d13), (a28, b5, (c2, d14), (a28, b5, c2, d11), (a28, b5, c2, d16), (a28, b5, c2, d17), (a28, b5, c2, d18), (a28, b5, c2, d19), (a28, b5, c2, d20), (a28, b5, c2, d21), (a28, b5, c2, d22), (a28, b5, c3, d1), (a28, b5, c3, d2), (a28, b5, c3, d3), (a28, b5, c3, d4), (a28, b5, c3, d5), (a28, b5, c3, d6), (a28, b5, c3, d7), (a28, b5, c3, d8), (a28, b, c3, d9), (a28, b5, c3, d10), (a28, b5, c3, d11), (a28, b5, c3, d12), (a28, b5, c3, d13), (a28, b5, c3, d14), (a28, b5, c3, d15), (a28, b5, c3, d16), (a28, b5, c3, d17), (a28, b5, c3, d18), (a28, b5, c3, d19), (a28, b5, c3, d20), (a28, b5, c3, d21), (a28, b5, c3, d22), (a28, b6, c1, d1), (a28, b6, c1, d2), (a28, b6, c1, d3), (a28, b6, c1, d4), (a28, b6, c1, d5), (a28, b6, c1, d6), (a28, b6, c1, d7), (a28, b6, c1, d8), (a28, b6, c1, d9), (a28, b6, c1, d10), (a28, b6, c1, d11), (a28, b6, c1, d12), (a28, b6, c1, d13), (a28, b6, c1, d14), (a28, b6, c1, d15), (a28, b6, c1, d16), (a28, b6, c1, d17), (a28, b6, c1, d18), (a28, b6, c1, d19), (a28, b6, c1, d20), (a28, b6, c1, d21), (a28, b6, c1, d22), (a28, b6, c2, d1), (a28, b6, c2, d2), (a28, b6, c2, d3), (a28, b6, c2, d4), (a28, b6, c2, d5), (a28, b6, c2, d6), (a28, b6, c2, d7), (a28, b6, c2, d8), (a28, b6, c2, d9), (a28, b6, c2, d10), (a28, b6, c2, d11), (a28, b6, c2, d12), (a28, b6, c2, d13), (a28, b6, c2, d14), (a28, b6, c2, d15), (a28, b6, c2, d16), (a28, b6, c2, d17), (a28, b6, c2, d18), (a28, b6, c2, d19), (a28, b6, c2, d20), (a28, b6, c2, d21), (a28, b6, c2, d22), (a28, b6, c3, d1), (a28, b6, c3, d2), (a28, b6, c3, d3), (a28, b6, c3, d4), (a28, b6, c3, d5), (a28, b6, c3, d6), (a28, b6, c3, d7), (a28, b6, c3, d8), (a28, b6, c3, d9), (a28, b6, c3, d10), (a28, b6, c3, d11), (a28, b6, c3, d12), (a28, b6, c3, d13), (a28, b6, c3, d14), (a28, b6, c3, d15), (a28, b6, c3, d16), (a28, b6, c3, d17), (a28, b6, c3, d18), (a28, b6, c3, d19), (a28, b6, c3, d20), (a28, b6, c3, d21), (a28, b6, c3, d22), (a29, b1, c1, d1), (a29, b1, c1, d2), (a29, b1, c1, d3), (a29, b1, c1, d4), (a29, b1, c1, d5), (a29, b1, c1, d6), (a29, b1, c1, d7), (a29, b1, c1, d8), (a29, b1, c1, d9), (a29, b1, c1, d10), (a29, b1, c1, d11), (a29, b1, c1, d12), (a29, b1, c1, d13), (a29, b1, c1, d14), (a29, b1, c1, d15), (a29, b1, c1, d16), (a29, b1, c1, d17), (a29, b1, c1, d18), (a29, b1, c1, d19), (a19, b1, c1, d20), (a29, b1, c1, d21), (a29, b, c1, d22), (a29, b1, c2, d1), (a29, b1, c2, d2), (a29, b1, c2, d3), (a29, b1, c2, d4), (a29, b1, c2, d5), (a29, b1, c2, d6), (a29, b1, c2, d7), (a29, b1, c2, d8), (a29, b1, c2, d9), (a29, b1, c2, d10), (a29, b1, c2, d11), (a29, b1, c2, d12), (a29, b1, c2, d13), (a29, b1, c2, d14), (a29, b1, c2, d15), (a29, b1, c2, d16), (a29, b1, c2, d17), (a29, b1, c2, d18), (a29, b1, c2, d19), (a29, b1, c2, d20), (a29, b1, c2, d21), (a29, b1, c2, d22), (a29, b1, c3, d1), (a29, b1, c3, d2), (a29, b1, c3, d3), (a29, b1, c3, d4), (a29, b1, c3, d5), (a29, b1, c3, d6), (a29, b1, c3, d7), (a29, b1, c3, d8), (a29, b1, c3, d9), (a29, b1, c3, d10), (a29, b1, c3, d11), (a29, b1, c3, d12), (a29, b1, c3, d13), (a29, b1, c3, d14), (a29, b1, c3, d15), (a29, b1, c3, d16), (a29, b1, c3, d17), (a29, b1, c3, d18), (a29, b1, c3, d19), (a29, b1, c3, d20), (a29, b1, c3, d21), (a29, b1, c3, d22), (a29, b2, c1, d1), (a29, b2, c1, d2), (a29, b2, c1, d3), (a29, b2, c1, d4), (a29, b2, c1, d5), (a29, b2, c1, d6), (a29, b2, c1, d7), (a29, b2, c1, d8), (a29, b2, c1, d9), (a29, b2, c1, d10), (a29, b2, c1, d11), (a29, b2, c1, d12), (a29, b2, c1, d13), (a29, b2, c1, d14), (a29, b2, c1, d15), (a29, b2, c1, d16), (a29, b2, c1, d17), (a29, b2, c1, d18), (a29, b2, c1, d19), (a29, b2, c1, d20), (a29, b2, c1, d21), (a29, b2, c1, d22), (a29, b2, c2, d1), (a29, b2, c2, d2), (a29, b2, c2, d3), (a29, b2, c2, d4), (a29, b2, c2, d5), (a29, b2, c2, d6), (a29, b2, c2, d7), (a29, b2, c2, d8), (a29, b2, c2, d9), (a29, b2, c2, d10), (a29, b2, c2, d11), (a29, b2, c2, d12), (a29, b2, c2, d13), (a29, b2, c2, d14), (a29, b2, c2, d15), (a29, b2, c2, d16), (a29, b2, c2, d17), (a29, b2, c2, d18), (a29, b2, c2, d19), (a29, b2, c2, d20), (a29, b2, (c2, d21), (a29, b2, c2, d22), (a29, b2, c3, d1), (a29, b2, c3, d2), (a29, b2, c3, d3), (a29, b2, c3, d4), (a29, b2, c3, d5), (a29, b2, c3, d6), (a29, b2, c3, d7), (a29, b2, c3, d8), (a29, b2, c3, d9), (a29, b2, c3, d10), (a29, b2, c3, d11), (a29, b2, c3, d12), (a29, b2, c3, d13), (a29, b2, c3, d14), (a29, b2, c3, d15), (a29, b2, c3, d16), (a29, b2, c3, d17), (a29, b2, c3, d18), (a29, b2, c3, d19), (a29, b2, c3, d20), (a29, b2, c3, d21), (a29, b2, c3, d22), (a29, b3, c1, d1), (a29, b3, c1, d2), (a29, b3, c1, d3), (a29, b3, c1, d4), (a29, b3, c1, d5), (a29, b3, c1, d6), (a29, b3, c1, d7), (a29, b3, c1, d8), (a29, b3, c1, d9), (a29, b3, c1, d10), (a29, b3, c1, d11), (a29, b3, c1, d12), (a29, b3, c1, d13), (a29, b3, c1, d14), (a29, b3, c1, d15), (a29, b3, c1, d16), (a29, b3, c1, d17), (a29, b3, c1, d18), (a29, b3, c1, d19), (a29, b3, c1, d20), (a29, b3, c1, d21), (a29, b3, c1, d22), (a29, b3, c2, d1), (a29, b3, c2, d2), (a29, b3, c2, d3), (a29, b3, c2, d4), (a29, b3, c2, d5), (a29, b3, c2, d6), (a29, b3, c2, d7), (a29, b3, c2, d6), (a29, b3, c2, d9), (a29, b3, c2, d10), (a29, b3, c2, d11), (a29, b3, c2, d12), (a29, b3, c2, d13), (a29, b3, c2, d14), (a29, b3, c2, d15), (a29, b3, c2, d16), (a29, b3, c2, d17), (a29, b3, c2, d18), (a29, b3, c2, d19), (a29, b3, c2, d20), (a29, b3, c2, d21), (a29, b3, c2, d22), (a29, b3, c3, d1), (a29, b3, c3, d2), (a29, b3, c3, d5), (a29, b3, c3, d4), (a29, b3, c3, d5), (a29, b3, c3, d6), (a29, b3, c3, d7), (a29, b3, c3, d8), (a29, b3, c3, d9), (a29, b3, c3, d10), (a29, b3, c3, d11), (a29, b3, c3, d12), (a29, b3, c3, d13), (a29, b3, c3, d14), (a29, b3, c3, d15), (a29, b3, c3, d16), (a29, b3, c3, d17), (a29, b3, c3, d18), (a29, b3, c3, d19), (a29, b3, c3, d20), (a29, b3, c3, d21), (a29, b3, c3, d22), (a29, b4, c1, d1), (a29, b4, c1, d2), (a29, b4, c1, d3), (a29, b4, c1, d4), (a29, b4, c1, d5), (a29, b4, c1, d6), (a29, b4, c1, d7), (a29, b4, c1, d8), (a29, b4, c1, d9), (a29, b4, c1, d10), (a29, b4, c1, d11), (a29, b4, c1, d12), (a29, b4, c1, d13), (a29, b4, c1, d14), (a29, b4, c1, d15), (a29, b4, c1, d16), (a29, b4, c1, d17), (a29, b4, c1, d18), (a29, b4, c1, d19), (a29, b4, c1, d20), (a29, b4, c1, d21), (a29, b4, c1, d22), (a29, b4, c2, d1), (a29, b4, c2, d2), (a29, b4, c2, d3), (a29, b4, c2, d4), (a29, b4, c2, d5), (a29, b4, c2, d6), (a29, b4, c2, d7), (a29, b4, c2, d8), (a29, b4, c2, d9), (a29, b4, c2, d10), (a29, b4, c2, d11), (a29, b4, c2, d12), (a29, b4, c2, d13), (a29, b4, c2, d14), (a29, b4, c2, d15), (a29, b4, c2, d16), (a29, b4, c2, d17), (a29, b4, c2, d18), (a29, b4, c2, d19), (a29, b4, c2, d20), (a29, b4, c2, d21), (a29, b4, c2, d22), (a29, b4, c3, d1), (a29, b4, c3, d2), (a29, b4, c3, d3), (a29, b4, c3, d4), (a29, b4, c3, d5), (a29, b4, c3, d6), (a29, b4, c3, d7), (a29, b4, c3, d8), (a29, b4, c3, d9), (a29, b4, c3, d10), (a29, b4, c3, d11), (a29, b4, c3, d12), (a29, b4, c3, d13), (a29, b4, c3, d14), (a29, b4, c3, d15), (a29, b4, c3, d16), (a29, b4, c3, d17), (a29, b4, c3, d18), (a29, b4, c3, d19), (a29, b4, c3, d20), (a29, b4, c3, d21), (a29, b4, c3, d22), (a29, b5, c1, d1), (a29, b5, c1, d2), (a29, b5, c1, d3), (a29, b5, c1, d4), (a29, b5, c1, d5), (a29, b, c1, d6), (a29, b5, c1, d7), (a29, b5, c1, d8), (a29, b5, c1, d9), (a29, b5, c1, d10), (a29, b5, c1, d11), (a29, b5, c1, d12), (a29, b5, c1, d13), (a29, b5, c1, d14), (a29, b5, c1, d15), (a29, b5, c1, d16), (a29, b5, c1, d17), (a29, b5, c1, d18), (a29, b5, c1, d19), (a29, b5, c1, d20), (a29, b5, c1, d21), (a29, b5, c1, d22), (a29, b5, c2, d1), (a29, b5, c2, d2), (a29, b5, c2, d3), (a29, b5, c2, d4), (a29, b5, c2, d5), (a29, b5, c2, d6), (a29, b5, c2, d7), (a29, b5, c2, d8), (a29, b5, c2, d9), (a29, b5, c2, d10), (a29, b5, c2, d11), (a29, b5, c2, d12), (a29, b5, c2, d13), (a29, b5, c2, d14), (a29, b5, c2, d15), (a29, b5, c2, d16), (a29, b5, c2, d17), (a29, b5, c2, d18), (a29, b5, c2, d19), (a29, b5, c2, d20), (a29, b5, c2, d21), (a29, b5, c2, d22), (a29, b5, c3, d1), (a29, b5, c3, d2), (a29, b5, c3, d3), (a29, b5, c3, d4), (a29, b5, c3, d5), (a29, b5, c3, d6), (a29, b5, c3, d7), (a29, b5, c3, d8), (a29, b5, c3, d9), (a29, b5, c3, d10), (a29, b5, d11), (a29, b5, c3, d12), (a29, b5, c3, d13), (a29, b5, c3, d14), (a29, b5, c3, d15), (a29, b5, c3, d16), (a29, b5, c3, d17), (a29, b5, c3, d18), (a29, b5, c3, d19), (a29, b5, c3, d20), (a29, b5, c3, d21), (a29, b5, c3, d22), (a29, b6, c1, d1), (a29, b6, c1, d2), (a29, b6, c1, d3), (a29, b6, c1, d4), (a29, b6, c1, d5), (a29, b6, c1, d6, (a29, b6, c1, d7), (a29, b6, c1, d8), (a29, b6, c1, d9), (a29, b6, c1, d10), (a29, b6, c1, d11), (a29, b6, c1, d12), (a29, b6, c1, d13), (a29, b6, c1, d14), (a29, b6, c1, d15), (a29, b6, c1, d16), (a29, b6, c1, d17), (a29, b6, c1, d18), (a29, b6, c1, d19), (a29, b6, c1, d20), (a29, b6, c1, d21), (a29, b6, c1, d22), (a29, b6, c2, d1), (a29, b6, c2, d2), (a29, b6, c2, d3), (a29, b6, c2, d4), (a29, b6, c2, d5), (a29, b6, c2, d6), (a29, b6, c2, d7), (a29, b6, c2, d8), (a29, b6, c2, d9), (a29, b6, c2, d10), (a29, b6, c2, d11), (a29, b6, c2, d12), (a29, b6, c2, d13), (a29, b6, c2, d14), (a29, b6, c2, d15), (a29, b6, c2, d16), (a29, b6, c2, d17), (a29, b6, d18), (a29, b6, c2, d19), (a29, b6, c2, d20), (a29, b6, c2, d21), (a29, b6, c2, d22), (a29, b6, c3, d1), (a29, b6, c3, d2), (a29, b6, c3, d3), (a29, b6, c3, d4), (a29, b6, c3, d5), (a29, b6, c3, d6), (a29, b6, c3, d7), (a29, b6, c3, d8), (a29, b6, c3, d9), (a29, b6, c3, d10), (a29, b6, c3, d11), (a29, b6, c3, d12), (a29, b6, c3, d13), (a29, b6, c3, d14), (a29, b6, c3, d15), (a29, b6, c3, d16), (a29, b6, c3, d17), (a29, b6, c3, d18), (a29, b6, c3, d19), (a29, b6, c3, d20), (a29, b6, c3, d21), (a29, b6, c3, d22), (a30, b1, c1, d11), (a30, b1, c1, d2), (a30, b1, c1, d3), (a30, b1, c1, d14), (a30, b1, c1, d5), (a30, b1, c1, d16), (a30, b1, c1, d7), (a30, b1, c1, d8), (a30, b1, c1, d9), (a30, b1, c1, d10), (a30, b1, c1, d11), (a30, b1, c1, d12), (a30, b1, c1, d13), (a30, b1, c1, d14), (a30, b1, c1, d15), (a30, b1, c1, d16), (a30, b1, c1, d17), (a30, b1, c1, d18), (a30, b1, c1, d19), (a30, b1, c1, d20), (a30, b1, c1, d21), (a30, b1, c1, d22), (a30, b1, c2, d1), (a30, b1, c2, d2), (a30, b1, c2, d3), (a30, b1, c2, d4), (a30, b1, c2, d5), (a30, b1, c2, d6), (a30, b1, c2, d7), (a30, b1, c2, d8), (a30, b1, c2, d9), (a30, b1, c2, d10), (a30, b1, c2, d11), (a30, b1, c2, d12), (a30, b1, c2, d13), (a30, b1, c2, d14), (a30, b1, c2, d15), (a30, b1, c2, d16), (a30, b1, c2, d17), (a30, b1, c2, d18), (a30, b1, c2, d19), (a30, b1, c2, d20), (a30, b1, c2, d21), (a30, b1, c2, d22), (a30, b1, c3, d1), (a30, b1, c3, d2), (a30, b1, c3, d3), (a30, b1, c3, d4), (a30, b1, c3, d5), (a30, b1, c3, d6), (a30, b1, c3, d7), (a30, b1, c3, d8), (a30, b1, c3, d9), (a30, b1, c3, d10), (a30, b1, c3, d11), (a30, b1, c3, d12), (a30, b1, c3, d13), (a30, b1, c3, d14), (a30, b1, c3, d15), (a30, b1, c3, d16), (a30, b1, c3, d17), (a30, b1, c3, d18), (a30, b1, c3, d19), (a30, b1, c3, d20), (a30, b1, c3, d21), (a30, b1, c3, d22), (a30, b2, c1, d1), (a30, b2, c1, d2), (a30, b2, c1, d3), (a30, b2, c1, d4), (a30, b2, c1, d5), (a30, b2, c1, d6), (a30, b2, c1, d7), (a30, b2, c1, d8), (a30, b2, c1, d9), (a30, b2, c1, d10), (a30, b2, c1, d11), (a30, b2, c1, d12), (a30, b2, c1, d13), (a30, b2, c1, d14), (a30, b2, c1, d15), (a30, b2, c1, d16), (a30, b2, c1, d17), (a30, b2, c1, d18), (a30, b2, c1, d19), (a30, b2, c1, d20), (a30, b2, c1, d21), (a30, b2, c1, d22), (a30, b2, c2, d1), (a30, b2, c2, d2), (a30, b2, c2, d3), (a30, b2, c2, d4), (a30, b2, c2, d5), (a30, b2, c2, d6), (a30, b2, c2, d7), (a30, b2, c2, d8), (a30, b2, c2, d9), (a30, b2, c2, d10), (a30, b2, c2, d11), (a30, b2, c2, d12), (a30, b2, c2, d13), (a30, b2, c2, d14), (a30, b2, c2, d15), (a30, b2, c2, d16), (a30, b2, c2, d17), (a30, b2, c2, d18), (a30, b2, c2, d19), (a30, b2, c2, d20), (a30, b2, c2, d21), (a30, b2, c2, d22), (a30, b2, c3, d11), (a30, b2, c3, d2), (a30, b2, c3, d3), (a30, b2, c3, d4), (a30, b2, c3, d5), (a30, b2, c3, d16), (a30, b2, c3, d17), (a30, b2, c3, d8), (a30, b2, c3, d9), (a30, b2, c3, d10), (a30, b2, c3, d11), (a30, b2, c3, d12), (a30, b2, c3, d13), (a30, b2, c3, d14), (a30, b2, c3, d15), (a30, b2, c3, d16), (a30, b2, c3, d17), (a30, b2, c3, d18), (a30, b2, c3, d19), (a30, b2, c3, d20), (a30, b2, c3, d21), (a30, b2, c3, d22), (a30, b3, c1, d1), (a30, b3, c1, d2), (a30, b3, c1, d3), (a30, b3, c1, d4), (a30, b3, c1, d5), (a30, b3, c1, d6), (a30, b3, c1, d7), (a30, b3, c1, d8), (a30, b3, c1, d9), (a30, b3, c1, d10), (a30, b3, c1, d11), (a30, b3, c1, d12), (a30, b3, c1, d13), (a30, b3, c1, d14), (a30, b3, c1, d15), (a30, b3, c1, d16), (a30, b3, c1, d17), (a30, b3, c1, d18), (a30, b3, c1, d19), (a30, b3, c1, d20), (a30, b3, c1, d21), (a30, b3, c1, d22), (a30, b3, c2, d1), (a30, b3, c2, d2), (a30, b3, c2, d3), (a30, b3, c2, d4), (a30, b3, c2, d5), (a30, b3, c2, d6), (a30, b3, c2, d7), (a30, b3, c2, d8), (a30, b3, c2, d9), (a30, b3, c2, d10), (a30, b3, c2, d11), (a30, b3, c2, d12), (a30, b3, c2, d13), (a30, b3, c2, d14), (a60, b3, c2, d15), (a30, b3, c2, d16), (a30, b3, c2, d17), (a30, b3, c2, d18), (a30, b3, c2, d19), (a30, b3, c2, d20), (a30, b3, c2, d21), (a30, b3, c2, d22), (a30, b3, c3, d1), (a30, b3, c3, d2), (a30, b3, c3, d3), (a30, b3, c3, d4), (a30, b3, c3, d5), (a30, b3, c3, d6), (a30, b3, c3, d7), (a30, b3, c3, d8), (a30, b3, c3, d9), (a30, b3, c3, d10), (a30, b3, c3, d11), (a30, b3, c3, d12), (a30, b3, c3, d13), (a30, b6, c2, d14), (a30, b3, c3, d15), (a30, b3, c3, d16), (a30, b3, c3, d17), (a30, b3, c3, d18), (a30, b3, c3, d19), (a30, b3, c3, d20), (a30, b3, c3, d21), (a30, b3, c3, d22), (a30, b4, c1, d1), (a30, b4, c1, d2), (a30, b4, c1, d3), (a30, b4, c1, d4), (a60, b4, c1, d5), (a30, b4, c1, d6), (a30, b4, c1, d7), (a30, b4, c1, d8), (a30, b4, c1, d9), (a30, b4, c1, d10), (a30, b4, c1, d11), (a30, b4, c1, d12), (a30, b4, c1, d13), (a30, b4, c1, d14), (a30, b4, c1, d15), (a30, b4, c1, d16), (a30, b4, c1, d17), (a30, b4, c1, d18), (a30, b4, c1, d19), (a30, b4, c1, d20), (a30, b4, c1, d21), (a30, b4, c1, d22), (a30, b4, c2, d1), (a30, b4, c2, d2), (a30, b4, c2, d3), (a30, b4, c2, d4), (a30, b4, c2, d5), (a30, b4, c2, d6), (a30, b4, c2, d7), (a30, b4, c2, d8), (a30, b4, c2, d9), (a30, b4, c2, d10), (a30, b4, c2, d11), (a30, b4, c2, d12), (a30, b4, c2, d13), (a30, b4, c2, d14), (a30, b4, c2, d15), (a30, b4, c2, d16), (a30, b4, c2, d17), (a30, b4, c2, d18), (a30, b4, c2, d19), (a30, b4, c2, d20), (a30, b4, c2, d21), (a30, b4, c2, d22), (a30, b4, c2, d1), (a30, b4, c3, d2), (a30, b4, c3, d3), (a30, b4, c3, d4), (a30, b4, c3, d5), (a30, b4, c3, d6), (a30, b4, c3, d7), (a30, b4, c3, d8), (a30, b4, c3, d9), (a30, b4, c3, d10), (a30, b4, c3, d11), (a30, b4, c3, d12), (a30, b4, c3, d13), (a30, b4, c3, d14), (a30, b4, c3, d15), (a30, b4, c3, d16), (a30, b4, c3, d17), (a3, b4, c3, d18), (a30, b4, c3, d19), (a30, b4, c3, d20), (a30, b4, c3, d21), (a30, b4, c3, d22), (a30, b5, c1, d1), (a30, b5, c1, d2), (a30, b5, c1, d3), (a30, b5, c1, d4), (a30, b5, c1, d5), (a30, b5, c1, d6), (a30, b5, c1, d7), (a30, b5, c1, d8), (a30, b5, c1, d9), (a30, b5, c1, d10), (a30, b5, c1, d11), (a30, b5, c1, d12), (a30, b5, c1, d13), (a30, b5, c1, d14), (a30, b5, c1, d15), (a30, b5, c1, d16), (a30, b5, c1, d17), (a30, b5, c1, d18), (a30, b5, c1, d19), (a30, b5, c1, d20), (a30, b5, c1, d21), (a30, b5, c1, d22), (a30, b5, c2, d1), (a30, b5, c2, d2), (a30, b5, c2, d3), (a30, b5, c2, d4), (a30, b5, c2, d5), (a30, b5, c2, d6), (a30, b5, c2, d7), (a30, b5, c2, d8), (a30, b5, c2, d9), (a30, b5, c2, d10), (a30, b5, c2, d11), (a30, b5, c2, d12), (a30, b5, c2, d13), (a30, b5, c2, d14), (a30, b5, c2, d15), (a30, b5, c2, d16), (a30, b5, c2, d17), (a30, b5, c2, d18), (a30, b5, c2, d19), (a30, b5, c2, d20), (a30, b5, c2, d21), (a30, b5, c2, d22), (a30, b5, c3, d1), (a30, b5, c3, d2), (a30, b5, c3, d3), (a30, b5, c3, d4), (a30, b5, c3, d5), (a3, b5, c3, d6), (a30, b5, c3, d7), (a30, b5, c3, d8), (a30, b5, c3, d9), (a30, b5, c3, d10), (a30, b5, c3, d11), (a30, b5, c3, d12), (a30, b5, c3, d13), (a30, b5, c3, d14), (a30, b5, c3, d15), (a30, b5, c3, d16), (a30, b5, c3, d17), (a30, b5, c3, d18), (a30, b5, c3, d19), (a30, b5, c3, d20), (a30, b5, c3, d21), (a30, b5, c3, d22), (a30, b6, c1, d1), (a30, b6, c1, d2), (a30, b6, c1, d3), (a30, b6, c1, d4), (a30, b6, c1, d5), (a30, b6, c1, d6), (a30, b6, c1, d7), (a30, b6, c1, d8), (a30, b6, c1, d9), (a30, b6, c1, d10), (a30, b6, c1, d11), (a30, b6, c1, d12), (a30, b6, c1, d13), (a30, b6, c1, d14), (a30, b6, c1, d15), (a30, b6, c1, d16), (a30, b6, c1, d17), (a30, b6, c1, d18), (a30, b6, c1, d19), (a30, b6, c1, d20), (a30, b6, c1, d21), (a30, b6, c1, d22), (a30, b6, c2, d1), (a30, b6, c2, d2), (a30, b6, c2, d3), (a30, b6, c2, d4), (a30, b6, c2, d5), (a30, b6, c2, d6), (a30, b6, c2, d7), (a30, b6, c2, d8), (a30, b6, c2, d9), (a30, b6, c2, d10), (a30, b6, c2, d11), (a30, b6, c2, d12), (a30, b6, c2, d13), (a30, b6, c2, d14), (a30, b6, c2, d15), (a30, b6, c2, d16), (a30, b6, c2, d17), (a30, b6, c2, d18), (a30, b6, c2, d19), (a30, b6, c2, d20), (a30, b6, c2, d21), (a30, b6, c2, d22), (a30, b6, c3, d1), (a30, b6, c3, d2), (a30, b6, c3, d3), (a30, b6, c3, d4), (a30, b6, c3, d5), (a30, b6, c3, d6), (a30, b6, c3, d7), (a30, b6, c3, d8), (a30, b6, c3, d9), (a30, b6, c3, d10), (a30, b6, c3, d11), (a30, b6, c3, d12), (a30, b6, c3, d13), (a30, b6, c3, d14), (a30, b6, c3, d15), (a30, b6, c3, d16), (a30, b6, c3, d17), (a30, b6, c3, d18), (a30, b6, c3, d19), (a30, b6, c3, d20), (a30, b6, c3, d21), (a30, b6, c3, d22), (a31, b1, c1, d1), (a31, b1, c1, d2), (a31, b1, c1, d3), (a31, b1, c1, d4), (a31, b1, c1, d5), (a31, b1, c1, d6), (a31, b1, c1, d7), (a31, b1, c1, d8), (a31, b1, c1, d9), (a31, b1, c1, d10), (a31, b1, c1, d11), (a31, b1, c1, d12), (a31, b1, c1, d13), (a31, b1, c1, d14), (a31, b1, c1, d15), (a31, b1, c1, d16), (a31, b1, c1, d17), (a31, b1, c1, d18), (a31, b1, c1, d19), (a31, b1, c1, d20), (a31, b1, c1, d21), (a31, b1, c1, d22), (a31, b1, c2, d1), (a31, b1, c2, d2), (a31, b1, c2, d3), (a31, b1, c2, d4), (a31, b1, c2, d5), (a31, b1, c2, d6), (a31, b1, c2, d7), (a31, b1, c2, d8), (a31, b1, c2, d9), (a31, b1, c2, d10), (a31, b1, c2, d11), (a31, b1, c2, d12), (a31, b1, c2, d13), (a31, b1, c2, d14), (a31, b1, c2, d15), (a31, b1, c2, d16), (a31, b1, c2, d17), (a31, b1, c2, d18), (a31, b1, c2, d19), (a31, b1, c2, d20), (a31, b1, c2, d21), (a31, b1, c2, d22), (a31, b1, c3, d1), (a31, b1, c3, d2), (a31, b1, c3, d3), (a31, b1, c3, d4), (a31, b1, c3, d5), (a31, b1, c3, d6), (a31, b1, c3, d17), (a31, b1, c3, d8), (a31, b1, c3, d9), (a31, b1, c3, d10), (a31, b1, c3, d11), (a31, b1, c3, d12), (a31, b1, c3, d13), (a31, b1, c3, d14), (a31, b1, c3, d15), (a31, b1, c3, d16), (a31, b1, c3, d17), (a31, b1, c3, d18), (a31, b1, c3, d19), (a31, b1, c3, d20), (a31, b1, c3, d21), (a31, b1, c3, d22), (a31, b2, c1, d1), (a31, b2, c1, d2), (a31, b2, c1, d3), (a31, b2, c1, d4), (a31, b2, c1, d5), (a31, b2, c1, d6), (a31, b2, c1, d7), (a31, b2, c1, d8), (a31, b2, c1, d9), (a31, b2, c1, d10), (a31, b2, c1, d11), (a31, b2, c1, d12), (a31, b2, c1, d13), (a31, b2, c1, d14), (a31, b2, c1, d15), (a31, b2, c1, d16), (a31, b2, c1, d17), (a31, b2, c1, d18), (a31, b2, c1, d19), (a31, b2, c1, d20), (a31, b2, c1, d21), (a31, b2, c1, d22), (a31, b2, c2, d1), (a31, b2, c2, d2), (a31, b2, c2, d3), (a31, b2, c2, d4), (a31, b2, c2, d5), (a31, b2, c2, d6), (a31, b2, c2, d7), (a31, b2, c2, d8), (a31, b2, c2, d9), (a31, b2, c2, d10), (a31, b2, c2, d11), (a31, b2, c2, d12), (a31, b2, c2, d13), (a31, b2, c2, d14), (a31, b2, c2, d15), (a31, b2, c2, d16), (a31, b2, c2, d17), (a31, b2, c2, d18), (a31, b2, c2, d19), (a31, b2, c2, d20), (a31, b2, c2, d21), (a31, b2, c2, d22), (a31, b2, c3, d1), (a31, b2, c3, d2), (a31, b2, c3, d3), (a31, b2, c3, d4), (a31, b2, c3, d5), (a31, b2, c3, d6), (a31, b2, c3, d7), (a31, b2, c3, d8), (a31, b2, c3, d9), (a31, b2, c3, d10), (a31, b2, c3, d11), (a31, b2, c3, d12), (a31, b2, c3, d13), (a31, b2, c3, d14), (a31, b2, c3, d15), (a31, b2, c3, d16), (a31, b2, c3, d17), (a31, b2, c3, d18), (a31, b2, c3, d10), (a31, b2, c3, d20), (a31, b2, c3, d21), (a31, b2, c3, d22), (a31, b3, c1, d1), (a31, b3, c1, d2), (a31, b3, c1, d3), (a31, b3, c1, d4), (a31, b3, c1, d5), (a31, b3, c1, d6), (a31, b3, c1, d7), (a31, b3, c1, d8), (a31, b3, c1, d9), (a31, b3, c1, d10), (a31, b3, c1, d11), (a31, b3, c1, d12), (a31, b3, c1, d13), (a31, b3, c1, d14), (a31, b3, c1, d15), (a31, b3, c1, d16), (a31, b3, c1, d17), (a3, b3, c1, d18), (a31, b3, c1, d19), (a31, b3, c1, d20), (a31, b3, c1, d21), (a31, b3, c1, d22), (a31, b3, c2, d1), (a31, b3, c2, d2), (a31, b3, c2, d3), (a31, b3, c2, d4), (a31, b3, c2, d5), (a31, b3, c2, d6), (a31, b3, c2, d7), (a31, b3, c2, d8), (a31, b3, c2, d9), (a31, b3, c2, d10), (a31, b3, c2, d11), (a31, b3, c2, d12), (a31, b3, c2, d13), (a31, b3, c2, d14), (a2, b3, c2, d15), (a31, b3, c2, d16), (a31, b3, c2, d17), (a31, b3, c2, d18), (a31, b3, c2, d19), (a31, b3, c2, d20), (a31, b3, c2, d21), (a31, b3, c2, d22), (a31, b3, c3, d1), (a31, b3, c3, d2), (a31, b3, c3, d3), (a31, b3, c3, d4), (a31, b3, c3, d5), (a31, b3, c3, d6), (a31, b3, c3, d7), (a31, b3, c3, d8), (a31, b3, c3, d9), (a31, b3, c3, d10), (a31, b3, c3, d11), (a31, b3, c3, d12), (a31, b3, c3, d13), (a31, b3, c3, d14), (a31, b3, c3, d15), (a31, b3, c3, d16), (a31, b3, c3, d17), (a31, b3, c3, d18), (a31, b3, c3, d19), (a31, b3, c3, d20), (a31, b3, c3, d21), (a31, b3, c3, d22), (a31, b4, c1, d1), (a31, b4, c1, d2), (a31, b4, c1, d3), (a31, b4, c1, d4), (a31, b4, c1, d5), (a31, b4, c1, d6), (a31, b4, c1, d7), (a31, b4, c1, d8), (a31, b4, c1, d9), (a31, b4, c1, d10), (a31, b4, c1, d11), (a31, b4, c1, d12), (a31, b4, c1, d13), (a31, b4, c1, d14), (a31, b4, c1, d15), (a31, b4, c1, d16), (a31, b4, c1, d17), (a31, b4, c1, d18), (a31, b4, c1, d19), (a31, b4, c1, d20), (a31, b4, c1, d21), (a31, b4, c1, d22), (a31, b4, c2, d1), (a31, b4, c2, d2), (a31, b4, c2, d3), (a31, b4, c2, d4), (a31, b4, c2, d5), (a31, b4, c2, d6), (a31, b4, c2, d7), (a31, b4, c2, d8), (a31, b4, c2, d9), (a31, b4, c2, d10), (a31, b4, c2, d11), (a31, b4, c2, d12), (a31, b4, c2, d13), (a31, b4, c2, d14), (a31, b4, c2, d15), (a31, b4, c2, d16), (a31, b4, c2, d17), (a31, b4, c2, d18), (a31, b4, c2, d19), (a31, b4, c2, d20), (a31, b4, c2, d21), (a31, b4, c2, d22), (a31, b4, c3, d1), (a31, b4, c3, d2), (a31, b4, c3, d3), (a31, b4, c3, d4), (a31, b4, c3, d5), (a31, b4, c3, d6), (a31, b4, c3, d7), (a31, b4, c3, d8), (a31, b4, c3, d9), (a31, b4, c3, d10), (a31, b4, c3, d11), (a31, b4, c3, d12), (a31, b4, c3, d13), (a31, b4, c3, d14), (a31, b4, c3, d15), (a31, b4, c3, d16), (a31, b4, c3, d17), (a31, b4, c3, d18), (a31, b4, c3, d19), (a31, b4, c3, d20), (a31, b4, c3, d21), (a31, b4, c3, d22), (a31, b5, c1, d1), (a31, b5, c1, d2), (a31, b5, c1, d3), (a31, b5, c1, d4), (a31, b5, c1, d5), (a31, b5, c1, d6), (a31, b5, c1, d7), (a31, b5, c1, d8), (a31, b5, c1, d9), (a31, b5, c1, d10), (a31, b5, c1, d11), (a31, b5, c1, d12), (a31, b5, c1, d13), (a31, b5, c1, d14), (a31, b5, c1, d15), (a31, b5, c1, d16), (a31, b5, c1, d17), (a31, b5, c1, d18), (a31, b5, c1, d19), (a31, b5, c1, d20), (a31, b5, c1, d21), (a31, b5, c1, d22), (a31, b5, c2, d1), (a31, b5, c2, d2), (a31, b5, c2, d3), (a31, b5, c2, d4), (a31, b5, c2, d5), (a31, b5, c2, d6), (a31, b5, c2, d7), (a31, b5, c2, d8), (a31, b5, c2, d9), (a31, b5, c2, d10), (a31, b5, c2, d11), (a31, b5, c2, d12), (a31, b5, c2, d13), (a31, b5, c2, d14), (a31, b5, c2, d15), (a31, b5, c2, d16), (a31, b5, c2, d17), (a31, b5, c2, d18), (a31, b5, c2, d19), (a31, b5, c2, d20), (a31, b5, c2, d21), (a31, b5, c2, d22), (a31, b5, c3, d1), (a31, b5, c3, d2), (a31, b5, c3, d3), (a31, b5, c3, d4), (a31, b5, c3, d5), (a31, b5, c3, d6), (a31, b5, c3, d7), (a31, b5, c3, d8), (a31, b5, c3, d9), (a31, b5, c3, d10), (a31, b5, c3, d11), (a31, b5, c3, d12), (a31, b5, c3, d13), (a31, b5, c3, d14), (a31, b5, c3, d15), (a31, b5, c3, d16), (a31, b5, c3, d17), (a31, b5, c3, d18), (a31, b5, c3, d19), (a31, b5, c3, d20), (a31, b5, c3, d21), (a31, b5, c3, d22), (a31, b6, c1, d1), (a31, b6, c1, d2), (a31, b6, c1, d3), (a31, b6, c1, d4), (a31, b6, c3, d5), (a31, b6, c1, d6), (a31, b6, c1, d7), (a31, b6, c1, d8), (a31, b6, c1, d9), (a31, b6, c1, d10), (a31, b6, c1, d11), (a31, b6, c1, d12), (a31, b6, c1, d13), (a31, b6, c1, d14), (a31, b6, c1, d15), (a31, b6, c1, d16), (a31, b6, c1, d17), (a31, b6, c1, d18), (a31, b6, c1, d19), (a31, b6, c1, d20), (a31, b6, c1, d21), (a31, b6, c1, d22), (a31, b6, c2, d1), (a31, b6, c2, d2), (a31, b6, c2, d3), (a31, b6, c2, d4), (a31, b6, c2, d5), (a31, b6, c2, d6), (a31, b6, c2, d7), (a31, b6, c2, d18), (a31, b6, c2, d9), (a31, b6, c2, d10), (a31, b6, c2, d11), (a31, b6, c2, d12), (a31, b6, c2, d13), (a31, b6, c2, d14), (a31, b6, c2, d15), (a31, b6, c2, d16), (a31, b6, c2, d17), (a31, b6, c2, d8), (a31, b6, c2, d9), (a31, b6, c2, d20), (a31, b6, c2, d21), (a31, b6, c2, d22), (a31, b6, c3, d1), (a31, b6, c3, d2), (a31, b6, c3, d3), (a31, b6, c3, d4), (a31, b6, c3, d5), (a31, b6, c3, d6), (a31, b6, c3, d7), (a31, b6, c3, d8), (a31, b6, c3, d9), (a31, b6, c3, d10), (a31, b6, c3, d11), (a31, b6, c3, d12), (a31, b6, c3, d13), (a31, b6, c3, d14), (a31, b6, c3, d15), (a31, b6, c3, d16), (a31, b6, c3, d17), (a31, b6, c3, d18), (a31, b6, c3, d19), (a31, b6, c3, d20), (a31, b6, c3, d21), (a31, b6, c3, d22), (a32, b1, c1, d1), (a32, b1, c1, d2), (a32, b1, c1, d3), (a32, b1, c1, d4), (a32, b1, c1, d5), (a32, b1, c1, d6), (a32, b1, c1, d7), (a32, b1, c1, d8), (a32, b1, c1, d9), (a32, b1, c1, d10), (a32, b1, c1, d11), (a32, b1, c1, d12), (a32, b1, c1, d13), (a32, b1, c1, d14), (a32, b1, c1, d15), (a32, b1, c1, d16), (a32, b1, c1, d17), (a32, b1, c1, d18), (a32, b1, c1, d19), (a32, b1, c1, d20), (a32, b1, c1, d21), (a32, b1, c1, d22), (a32, b1, c2, d1), (a32, b1, c2, d2), (a32, b1, c2, d3), (a32, b1, c2, d4), (a32, b1, c2, d5), (a32, b1, c2, d6), (a32, b1, c2, d7), (a32, b1, c2, d8), (a32, b1, c2, d9), (a32, b1, c2, d10), (a32, b1, c2, d11), (a32, b1, c2, d12), (a32, b1, c2, d13), (a32, b1, c2, d14), (a32, b1, c2, d15), (a32, b1, c2, d16), (a32, b1, c2, d17), (a32, b1, c2, d18), (a32, b1, c2, d19), (a32, b1, c2, d20), (a32, b1, c2, d21), (a32, b1, c2, d22), (a32, b1, c3, d1), (a32, b1, c3, d2), (a32, b1, c3, d3), (a32, b1, c3, d4), (a32, b1, c3, d5), (a32, b1, c3, d6), (a32, b1, c3, d7), (a32, b1, c3, d8), (a32, b1, c3, d9), (a32, b1, c3, d10), (a32, b1, c3, d11), (a32, b1, c3, d12), (a32, b1, c3, d13), (a32, b1, c3, d14), (a32, b1, c3, d15), (a32, b1, c3, d16), (a32, b1, c3, d17), (a32, b1, c3, d18), (a32, b1, c3, d19), (a32, b1, c3, d20), (a32, b1, c3, d21), (a32, b1, c3, d22), (a32, b2, c1, d1), (a32, b2, c1, d2), (a32, b2, c1, d3), (a32, b2, c1, d4), (a32, b2, c1, d5), (a32, b2, c1, d6), (a32, b2, c1, d7), (a32, b2, c1, d8), (a32, b2, c1, d9), (a32, b2, c1, d10), (a32, b2, c1, d11), (a32, b2, c1, d12), (a32, b2, c1, d13), (a32, b2, c1, d14), (a32, b2, c1, d15), (a32, b2, c1, d16), (a32, b2, c1, d), (a32, b2, c1, d18), (a32, b2, c1, d19), (a32, b2, c1, d20), (a32, b2, c1, d21), (a32, b2, c1, d22), (a32, b2, c2, d1), (a82, b2, c2, d2), (a32, b2, c2, d3), (a32, b2, c2, d4), (a32, b2, c2, d5), (a32, b2, c2, d6), (a32, b2, c2, d7), (a32, b2, c2, d8), (a32, b2, c2, d9), (a32, b2, c2, d10), (a32, b2, c2, d11), (a32, b2, c2, d12), (a32, b2, c2, d13), (a32, b2, c2, d14), (a32, b2, c2, d15), (a32, b2, c2, d16), (a32, b2, c2, d17), (a32, b2, c2, d18), (a32, b2, c2, d19), (a32, b2, c2, d20), (a32, b2, c2, d21), (a32, b2, c2, d22), (a32, b2, c3, d1), (a32, b2, c3, d2), (a32, b2, c3, d3), (a32, b2, c3, d4), (a2, b2, c3, d5), (a32, b2, c3, d6), (a32, b2, c3, d7), (a32, b2, c3, d8), (a32, b2, c3, d9), (a32, b2, c3, d10), (a32, b2, c3, d11), (a32, b2, c3, d12), (a32, b2, c3, d13), (a32, b2, c3, d14), (a32, b2, c3, d15), (a32, b2, c3, d16), (a32, b2, c3, d17), (a32, b2, c3, d18), (a32, b2, c3, d19), (a32, b2, c3, d20), (a32, b2, c3, d21), (a32, b2, c3, d22), (a32, b3, c1, d1), (a32, b3, c1, d2), (a32, b3, c1, d3), (a32, b3, c1, d4), (a32, b, c1, d5), (a32, b3, c1, d6), (a32, b3, c1, d7), (a32, b, c1, d8), (a32, b3, c1, d9), (a32, b3, c1, d10), (a32, b3, c1, d11), (a32, b3, c1, d12), (a32, b3, c1, d13), (a32, b3, c1, d14), (a32, b3, c1, d15), (a32, b3, c1, d16), (a32, b3, c1, d17), (a32, b3, c1, d18), (a32, b3, c1, d19), (a32, b3, c1, d20), (a32, b3, c1, d21), (a32, b3, c1, d22), (a32, b3, c2, d1), (a32, b3, c2, d2), (a32, b3, c2, d3), (a32, b3, c2, d4), (a32, b3, c2, d5), (a32, b3, c2, d6), (a32, b3, c2, d7), (a32, b3, c2, d8), (a32, b3, c2, d9), (a32, b3, c2, d10), (a32, b3, c2, d11), (a32, b5, c2, d12), (a32, b3, c2, d13), (a32, b3, c2, d14), (a32, b3, c2, d15), (a32, b3, c2, d16), (a32, b3, c2, d17), (a32, b3, c2, d18), (a32, b, c2, d19), (a32, b3, c2, d20), (a32, b3, c2, d21), (a32, b3, c2, d22), (a32, b3, c3, d1), (a32, b3, c3, d2), (a32, b3, c3, d3), (a32, b3, c3, d4), (a32, b3, c3, d5), (a32, b3, c3, d6), (a32, b3, c3, d7), (a32, b3, c3, d8), (a32, b3, c3, d19), (a32, b3, c3, d10), (a32, b3, c3, d11), (a32, b3, c3, d12), (a32, b3, c3, d13), (a32, b3, c3, d14), (a32, b3, c3, d15), (a32, b3, c3, d16), (a32, b3, c3, d17), (a32, b3, c3, d18), (a32, b3, c3, d19), (a32, b3, c3, d20), (a32, b3, c3, d21), (a32, b3, c3, d22), (a32, b4, c1, d1), (a32, b4, c1, d2), (a32, b4, c1, d3), (a32, b4, c1, d4), (a32, b4, c1, d5), (a32, b4, c1, d6), (a32, b4, c1, d7), (a32, b4, c1, d8), (a32, b4, c1, d9), (a22, b4, c1, d10), (a32, b4, c1, d11), (a32, b4, c1, d12), (a32, b4, c1, d13), (a32, b4, c1, d14), (a32, b4, c1, d15), (a32, b4, c1, d16), (a32, b4, c1, d17), (a32, b4, c1, d18), (a32, b4, c1, d19), (a32, b4, c1, d20), (a32, b4, c1, d21), (a32, b4, c1, d22), (a32, b4, c2, d1), (a32, b4, c2, d2), (a32, b4, c2, d3), (a32, b4, c2, d4), (a32, b4, c2, d5), (a32, b4, c2, d6), (a32, b4, c2, d7), (a32, b4, c2, d8), (a32, b4, c2, d9), (a32, b4, c2, d10), (a32, b4, c2, d11), (a32, b4, c2, d12), (a32, b4, c2, d13), (a32, b4, c2, d14), (a32, b4, c2, d15), (a32, b4, c2, d16), (a32, b4, c2, d17), (a32, b4, c2, d18), (a32, b4, c2, d19), (a32, b4, c2, d20), (a32, b4, c2, d21), (a32, b4, c2, d22), (a32, b4, c3, d1), (a32, b4, c3, d2), (a32, b4, c3, d3), (a32, b4, c3, d4), (a32, b4, c3, d5), (a32, b4, c3, d6), (a32, b4, c3, d7), (a32, b4, c3, d8), (a32, b4, c3, d9), (a32, b4, c3, d10), (a32, b4, c3, d11), (a32, b4, c3, d12), (a32, b4, c3, d13), (a32, b4, c3, d14), (a32, b4, c3, d15), (a32, b4, c3, d16), (a32, b4, c3, d17), (a32, b4, c3, d18), (a32, b4, c3, d19), (a32, b4, c3, d20), (a32, b4, c3, d21), (a32, b4, c3, d22), (a32, b5, c1, d1), (a32, b5, c1, d2), (a32, b5, c1, d3), (a32, b5, c1, d4), (a32, b5, c1, d5), (a32, b5, c1, d6), (a32, b5, c1, d7), (a32, b5, c1, d8), (a32, b5, c1, d9), (a32, b5, c1, d10), (a32, b5, c1, d11), (a32, b5, c1, d12), (a32, b5, c1, d13), (a32, b5, c1, d14), (a32, b5, c1, d15), (a32, b5, c1, d16), (a32, b5, c1, d17), (a32, b5, c1, d18), (a32, b5, c1, d19), (a32, b5, c1, d20), (a32, b5, c1, d21), (a32, b5, c1, d22), (a32, b5, c2, d1), (a32, b5, c2, d2), (a32, b5, d3, (a32, b5, c2, d4), (a32, b5, c2, d5), (a32, b5, c2, d6) (a32, b5, c2, d7), (a32, b5, c2, d8), (a32, b5, c2, d9), (a32, b5, c2, d10), (a32, b5, c2, d11), (a32, b5, c2, d12), (a32, b5, c2, d13), (a32, b5, c2, d14), (a32, b5, c2, d15), (a32, b5, c2, d16), (a32, b5, c2, d17), (a32, b5, c2, d18), (a32, b5, c2, d19), (a32, b5, c2, d20), (a32, b5, c2, d21), (a32, b5, c2, d22), (a32, b5, c3, d1), (a32, b5, c3, d2), (a32, b5, c3, d3), (a32, b5, c3, d4), (a32, b5, c3, d5), (a32, b5, c3, d6), a32, b5, c3, d7), (a32, b5, c3, d8), (a32, b5, c3, d9), (a32, b5, c3, d10), (a32, b5, c3, d11), (a32, b5, c3, d12), (a32, b5, c3, d13), (a32, b5, c3, d14), (a32, b5, c3, d15), (a32, b5, c3, d16), (a32, b5, c3, d17), (a32, b5, c3, d18), (a32, b5, c3, d19), (a32, b5, c3, d20), (a32, b5, c3, d21), (a32, b5, c3, d22), (a32, b6, c1, d3), (a32, b6, c1, d2), (a32, b6, c1, d3), (a32, b6, c1, d4), (a32, b6, c1, d5), (a32, b5, c1, d6), (a32, b6, c1, d7), (a32, b6, c1, d8), (a32, b6, c1, d9), (a32, b6, c1, d10), (a32, b6, c1, d11), (a32, b6, c1, d12), (a32, b6, c1, d13) (a32, b6, c1, d14), (a32, b6, c1, d15), (a32, b6, c1, d16), (a32, b6, c1, d17), (a32, b6, c1, d18), (a32, b1, c1, d19), b6, c1, d20), (a32, b6, c1, d21), (a32, b6, c1, d22), (a32, b6, c2, d1), (a32, b6, c2, d2), (a32, b6, c2, d3), (a32, b6, c2, d4), (a32, b6, c2, d5), (a32, b6, c2, d6), (a32, b6, c2, d7), (a32, b6, c2, d8), (a32, b6, c2, d9), (a32, b6, c2, d10), (a32, b6, c2, d11), (a32, b6, c2, d12), (a32, b6, c2, d13), (a32, b6, c2, d14), (a32, b6, c2, d15), (a32, b6, c2, d16), (a32, b6, c2, d17), (a32, b6, c2, d18), (a32, b6, c2, d19), (a32, b6, c2, d20), (a32, b6, c2, d21), (a32, b6, c2, d22), (a32, b6, c3, d11), (a32, b6, c3, d2), (a32, b6, c3, d3), (a32, b6, c3, d4), (a32, b6, c3, d5), (a32, b6, c3, d6), (a32, b6, c3, d7), (a32, b6, c3, d8), (a32, b6, c3, d9), (a32, b6, c3, d10), (a32, b6, c3, d11), (a32, b6, c3, d12), (a32, b6, c3, d13), (a32, b6, c3, d14), (a32, b6, c3, d15), (a32, b6, c3, d16), (a32, b6, c3, d17), (a32, b6, c3, d18), (a32, b6, c3, d19), (a32, b6, c3, d20), (a32, b6, c3, d21), (a32, b6, c3, d22), (a33, b1, c1, d1), (a33, b1, c1, d2), (a33, b1, c1, d3), (a33, b1, c1, d4), (a33, b1, c1, d5), (a33, b1, c1, d6), (a33, b1, c1, d7), (a33, b1, c1, d8), (a33, b1, c1, d9), (a33, b1, c1, d10), (a33, b1, c1, d11), (a33, b1, c1, d12), (a33, b1, c1, d13), (a33, b1, c1, d14), (a33, b1, c1, d15), (a33, b1, c1, d16), (a33, b1, c1, d17), (a33, b1, c1, d18), (a33, b1, c1, d19), (a33, b1, c1, d20), (a33, b1, c1, d21), (a33, b1, c1, d22), (a33, b1, c2, d1), (a33, b1, c2, d2), (a33, b1, c2, d3), (a33, b1, c2, d4), (a33, b1, c2, d5), (a33, b1, c2, d6), (a33, b1, c2, d7), (a33, b1, c2, d8), (a33, b1, c2, d9), (a33, b1, c2, d10), (a33, b1, c2, d11), (a33, b1, c2, d12), (a33, b1, c2, d13), (a33, b1, c2, d14), (a33, b1, c2, d15), (a33, b1, c2, d16), (a33, b1, c2, d1), (a33, b1, c2, d18), (a33, b1, c2, d19), (a33, b1, c2, d20), (a33, b2, c2, d21), (a55, b1, c2, d22), (a33, b1, c3, d1), (a55, b1, c3, d2), (a33, b1, c3, d3), (a33, b1, c3, d4), (a33, b1, c3, d5), (a33, b1, c3, d6), (a33, b1, c3, d7), (a33, b1, c3, d8), (a33, b1, c3, d9), (a33, b1, c3, d10), (a33, b1, c3, d11), (a33, b1, c3, d12), (a33, b1, c3, d13), (a33, b1, c3, d14), (a33, b1, c3, d15), (a33, b1, c3, d16), (a33, b1, c3, d17), (a33, b1, c3, d18), (a33, b1, c3, d19), (a33, b1, c3, d20), (a33, b1, c3, d21), (a33, b1, c3, d22), (a33, b2, c1, d1), (a33, b2, c1, d2), (a33, b2, c1, d3), (a33, b2, c1, d4), (a55, b2, c1, d5), (a33, b2, c1, d6), (a33, b2, c1, d7), (a33, b2, c1, d8), (a33, b2, c1, d9), (a33, b2, c1, d10), (a33, b2, c1, d11, (a33, b2, c1, d12), (a33, b2, c1, d13), (a33, b2, c1, d14), (a33, b2, c1, d15), (a33, b2, c1, d16), (a3, b2, c1, d17), (a33, b2, c1, d18), (a33, b2, c1, d19), (a33, b2, c1, d20), (a33, b2, c1, d21), (a33, b2, c1, d22), (a33, b2, c2, d5), (a33, b2, c2, d2), (a33, b2, c2, d3), (a33, b2, c2, d4), (a33, b2, c2, d5), (a33, b2, c2, d6), (a33, b2, c2, b2, c2, d7), (a33, b2, c2, d8), (a33, b2, c2, d9), (a33, b2, c2, d10), (a33, b2, c2, d11), (a33, b2, c2, d12), (a33, b2, c2, d13), (a33, b2, c2, d14), (a33, b2, c2, d15), (a33, b2, c2, d16), (a33, b2, c2, d17), (a33, b2, c2, d18), (a33, b2, c2, d19), (a33, b2, c2, d20), (a33, b2, c2, d21), (a33, b2, c2, d22), (a33, b2, c3, d1), (a33, b2, c3, d2), (a33, b2, c3, d3), (a33, b2, c3, d4), (a33, b2, c3, d5), (a33, b2, c3, d6), (a33, b2, c3, d7), (a33, b2, c3, d8), (a33, b2, c3, d9), (a33, b2, c3, d10), (a33, b2, c3, d11), (a33, b2, c3, d12), (a33, b2, c3, d13), (a33, b2, c3, d14), (a33, b2, c3, d15), (a33, b2, c3, d16), (a33, b2, c3, d17), (a33, b2, c3, d18), (a33, b2, c3, d19), (a33, b2, c3, d20), (a33, b2, c3, d21), (a33, b2, c3, d22), (a33, b3, c1, d1), (a33, b3, c1, d2), (a33, b3, c1, d3), (a33, b3, c1, d4), (a33, b3, c1, d5), (a33, b3, c1, d6), (a33, b3, c1, d7), (a33, b3, c1, d8), (a33, b3, c1, d9), (a33, b3, c1, d10), (a33, b3, c1, d11), (a33, b3, c1, d12), (a33, b3, c1, d13), (a33, b3, c1, d14), (a33, b3, c1, d15), (a33, b3, c1, d16), (a33, b3, c1, d17), (a33, b3, c1, d18), (a33, b3, c1, d19), (a33, b3, c1, d20), (a33, b3, c1, d21), (a55, b3, c1, d22), (a33, b3, c2, d1), (a33, b3, c2, d2), (a33, b3, c2, d3), (a33, b3, c2, d4), (a33, b3, c2, d5), (a33, b3, c2, d6), (a33, b3, c2, d7), (a33, b5, c2, d8), (a33, b3, c2, d9), (a33, b3, c2, d10), (a33, b3, c2, d11), (a33, b3, c2, d12), (a33, b3, c2, d13), (a33, b3, c2, d14), (a33, b3, c2, d15), (a33, b3, c2, d16), (a33, b3, c2, d17), (a33, b3, c2, d18), (a33, b3, c2, d19), (a33, b3, c2, d20), (a33, b5, c2, d21), (a33, b3, c2, d22), (a33, b3, c3, d1), (a33, b3, c3, d2), (a33, b3, c3, d13), (a33, b3, c3, d4), (a33, b3, c3, d5), (a33, b3, c3, d6), (a33, b3, c3, d7), (a33, b3, c3, d8), (a33, b5, c3, d9), (a33, b3, c3, d10), (a33, b3, c3, d11), (a33, b3, c3, d12), (a33, b3, c3, d13), (a33, b3, c3, d14), (a33, b3, c3, d15), (a33, b3, c3, d16), (a33, b3, c3, d17), (a33, b3, c3, d18), (a33, b3, c3, d19), (a33, b3, c3, d20), (a33, b3, c3, d21), (a33, b3, c3, d22), (a33, b4, c1, d1), (a33, b4, c1, d2), (a33, b4, c1, d3), (a33, b4, c1, d4), (a33, b4, c1, d5), (a33, b4, c1, d6), (a33, b4, c1, d7), (a33, b4, c1, d8), (a33, b4, c1, d9), (a33, b4, c1, d10), (a33, b4, c1, d11), (a33, b4, c1, d12), (a33, b4, c1, d13), (a33, b4, c1, d14), (a33, b4, c1, d15), (a33, b4, c1, d16), (a33, b4, c1, d17), (a33, b4, c1, d18), (a33, b4, c1, d19), (a33, b4, c1, d20), (a33, b4, c1, d21), (a33, b4, c1, d22), (a33, b4, c2, d1), (a33, b4, c2, d2), (a33, b4, c2, d3), (a33, b4, c2, d4), (a55, b4, c2, d5), (a33, b4, c2, d6), (a55, b4, c2, d7), (a33, b4, c2, d8), (a33, b4, c2, d9), (a33, b4, c2, d10), (a33, b4, c2, d11), (a33, b4, c2, d12), (a33, b4, c2, d13), (a33, b4, c2, d14), (a33, b4, c2, d15), (a33, b4, c2, d16), (a33, b4, c2, d17), (a33, b4, c2, d18), (a33, b4, c2, d19), (a33, b4, c2, d20), (a33, b4, c2, d21), (a33, b4, c2, d22), (a33, b4, c3, d1), (a33, b4, c3, d2), (a33, b4, c3, d3), (a33, b4, c3, d4), (a33, b4, c3, d5), (a33, b4, c3, d6), (a33, b4, c3, d7), (a33, b4, c3, d8), (a33, b4, c3, d9), (a33, b4, c3, d10), (a33, b4, c3, d11), (a33, b4, c3, d12), (a33, b4, c3, d13), (a33, b4, c3, d14), (a33, b4, c3, d15), (a33, b4, c3, d16), (a33, b4, c3, d17), (a33, b4, c3, d18), (a33, b4, c3, d19), (a33, b4, c3, d20), (a33, b4, c3, d21), (a33, b4, c3, d22), (a33, b5, c1, d1), (a33, b5, c1, d2), (a33, b5, c1, d3), (a55, b5, c1, d4), (a33, b5, c1, d5), (a33, b5, c1, d6), (a33, b5, c1, d7), (a33, b5, c1, d8), (a33, b5, c1, d9), (a33, b5, c1, d10), (a33, b5, c1, d11), (a33, b5, c1, d12), (a33, b5, c1, d13), (a33, b5, c1, d14), (a33, b5, c1, d15), (a33, b5, c1, d16), (a33, b5, c1, d17), (a33, b5, c1, d18), (a33, b5, c1, d19), (a33, b5, c1, d20), (a33, b5, c1, d21), (a33, b5, c1, d22), (a33, b5, c2, d1), (a33, b5, c2, d2), (a33, b5, c2, d3), (a33, b5, c2, d4), (a33, b5, c2, d5), (a55, b5, c2, d6), (a33, b5, c2, d7), (a33, b5, c2, d8), (a33, b5, c2, d9), (a33, b5, c2, d10), (a33, b5, c2, d11), (a33, b5, c2, d12), (a33, b5, c2, d13), (a33, b5, c2, d14), (a33, b5, c2, d15), (a33, b5, c2, d16), (a33, b5, c2, d17), (a55, b5, c2, d18), (a33, b5, c2, d19), (a33, b5, c2, d20), (a33, b5, c2, d21), (a33, b5, c2, d22), (a33, b5, c3, d1), (a33, b5, c3, d2), (a33, b5, c3, d3), (a33, b5, c3, d14), (a33, b5, c3, d5), (a33, b5, c3, d6), (a33, b5, c3, d7), (a33, b5, c3, d8), (a33, b5, c3, d9), (a33, b5, c3, d10), (a33, b5, c3, d11), (a33, b5, c3, d12), (a33, b5, c3, d13), (a33, b5, c3, d14), (a33, b5, c3, d15), (a55, b5, c3, d16), (a33, b5, c3, d17), (a33, b5, c3, d18), (a33, b5, c3, d19), (a33, b5, c3, d20), (a33, b5, c3, d21), (a33, b5, c3, d22), (a55, b6, c1, d1), (a33, b6, c1, d2), (a33, b6, c1, d3), (a33, b6, c1, d4), (a33, b6, c1, d5), (a33, b6, c1, d6), (a33, b6, c1, d7), (a33, b6, c1, d8), (a33, b6, c1, d9), (a33, b6, c1, d10), (a33, b6, c1, d11), (a33, b6, c1, d12), (a33, b6, c1, d13), (a33, b6, c1, d14), (a33, b6, c1, d15), (a33, b6, c1, d16), (a33, b6, c1, d17), (a33, b1, c1, d18), (a33, b1, c1, d19), (a33, b6, c1, d20), (a33, b6, c1, d21), (a33, b6, c1, d22), (a33, b6, c2, d1), (a33, b6, c2, d2), (a33, b6, c2, d3), (a33, b6, c2, d4), (a33, b6, c2, d5), (a33, b6, c2, d6), (a33, b6, c2, d7), (a33, b6, c2, d8), (a33, b6, c2, d9), (a33, b6, c2, d10) (a33, b6, c2, d11), (a33, b6, c2, d12), (a33, d6, c2, d13), (a33, b6, c2, d14), (a33, b6, c2, d15), (a33, b6, c2, d16), (a33, b6, c2, d17), (a33, b6, c2, d18), (a33, b6, c2, d19), (a33, b6, c2, d20), (a33, b6, c2, d21), (a33, b6, c2, d22), (a33, b6, c3, d1), (a33, b6, c3, d2), (a33, b6, c3, d3), (a33, b6, c3, d4), (a33, b6, c3, d5), (a33, b6, c3, d6), (a33, b6, c3, d7), (a33, b6, c3, d8), (a33, b6, c3, d9), (a33, b6, c3, d10), (a33, b6, c3, d11), (a33, b6, c3, d12), (a33, b6, c3, d13), (a33, b6, c3, d14), (a33, b6, c3, d15), (a33, b6, c3, d16), (a33, b6, c3, d17), (a33, b6, c3, d18), (a33, b6, c3, d19), (a33, b6, c3, d20), (a33, b6, c3, d21), (a33, b6, c3, d22), (a34, b1, c1, d1), (a34, b1, c1, d2), (a34, b1, c1, d3), (a34, b1, c1, d4), (a34, b1, c1, d5), (a34, b1, c1, d6), (a34, b1, c1, d7), (a34, b1, c1, d8), (a34, b1, c1, d9), (a34, b1, c1, d10), (a34, b1, c1, d11), (a34, b1, c1, d12), (a34, b1, c1, d13), (a34, b1, c1, d14), (a34, b1, c1, d15), (a34, b1, c1, d16), (a34, b1, c1, d17), (a34, b1, c1, d18), (a34, b1, c1, d19), (a34, b1, c1, d20), (a34, b1, c1, d21), (a34, b1, c1, d22), (a34, b1, c2, d1), (a34, b1, c2, d2), (a34, b1, c2, d3), (a34, b1, c2, d4), (a34, b1, c2, d5), (a34, b1, c2, d6), (a34, b1, c2, d7), (a34, b1, c2, d8), (a34, b1, c2, d9), (a34, b1, c2, d10), (a34, b1, c2, d11), (a34, b1, c2, d12), (a34, b1, c2, d13), (a34, b1, c2, d14), (a34, b1, c2, d15), (a34, b1, c2, d16), (a34, b1, c2, d17), (a34, b1, c2, d13), (a34, b1, c2, d19), (a34, b1, c2, d20), (a34, b1, c2, d21), (a34, b1, c2, d22), (a34, b1, c3, d1), (a34, b1, c3, d2), (a34, b1, c3, d3), (a34, b1, c3, d4), (a34, b1, c3, d5), (a34, b1, c3, d6), (a34, b1, c3, d7), (a34, b1, c3, d8), (a34, b1, c3, d9), (a34, b1, c3, d10), (a34, b1, c3, d11), (a34, b1, c3, d12), (a34, b1, c3, d13), (a34, b1, c3, d14), (a34, b1, c3, d15), (a34, b1, c3, d16), (a34, b1, c3, d17), (a34, b1, c3, d18), (a34, b1, c3, d19), (a34, b1, c3, d20), (a34, b1, c3, d21), (a34, b1, c3, d22), (a34, b2, c1, d1), (a34, b2, c1, d2), (a34, b2, c1, d3), (a34, b2, c1, d4), (a34, b2, c1, d5), (a34, b2, c1, d6), (a34, b2, c1, d7), (a34, b2, c1, d8), (a34, b2, c1, d9), (a34, b2, c1, d10), (a34, b2, c1, d11), (a34, b2, c1, d12), (a34, b2, c1, d13), (a34, b2, c1, d14), (a34, b2, c1, d15), (a34, b2, c1, d16), (a34, b2, c1, d17), (a34, b2, c1, d18), (a34, b2, c1, d19), (a34, b2, c1, d20), (a34, b2, c1, d21), (a34, b2, c1, d22), (a34, b2, c2, d1), (a34, b2, c2, d2), (a34, b2, c2, d3), (a34, b2, c2, d4), (a34, b2, c2, d5), (a34, b2, c2, d6), (a34, b2, c2, d7), (a34, b2, c2, d8), (a34, b2, c2, d9), (a34, b2, c2, d10), (a34, b2, c2, d11), (a34, b2, c2, d12), (a34, b2, c2, d13), (a34, b2, c2, d14), (a34, b2, c2, d15), (a34, b2, c2, d16), (a34, b2, c2, d17), (a34, b2, c2, d18), (a34, b2, c2, d19), (a34, b2, c2, d20), (a34, b2, c2, d21), (a34, b2, c2, d22), (a34, b2, c3, d1), (a34, b2, c3, d2), (a34, b2, c3, d3), (a34, b2, c3, d4), (a34, b2, c3, d5), (a34, b2, c3, d6), (a34, b2, c3, d7), (a34, b2, c3, d8), (a34, b2, c3, d9), (a34, b2, c3, d10), (a34, b2, c3, d11), (a34, b2, c3, d12), (a34, b2, c3, d13), (a34, b2, c3, d14), (a34, b2, c3, d15), (a34, b2, c3, d16), (a34, b2, c3, d17), (a34, b2, c3, d18), (a34, b2, c3, d19), (a34, b2, c3, d20), (a34, b2, c3, d21), (a34, b2, c3, d22), (a34, b3, c1, d1), (a34, b3, c1, d2), (a34, b3, c1, d3), (a34, b3, c1, d4), (a34, b3, c1, d5), (a34, b3, c1, d6), (a34, b3, c1, d7), (a34, b3, c1, d8), (a34, b3, c1, d9), (a34, b3, c1, d10), (a34, b3, c1, d11), (a34, b3, c1, d12), (a34, b3, c1, d13), (a34, b3, c1, d14), (a34, b3, c1, d15), (a34, b3, c1, d16), (a34, b3, c1, d17), (a34, b3, c1, d18), (a34, b3, c1, d19), (a34, b3, c1, d20), (a34, b3, c1, d21), (a34, b3, c1, d22), (a34, b3, c2, d1), (a34, b3, c2, d2), (a34, b3, c2, d3), (a34, b3, c2, d4), (a34, b3, c2, d5), (a34, b3, c2, d6), (a34, b3, c2, d7), (a34, b3, c2, d8), (a34, b3, c2, d9), (a34, b3, c2, d10), (a34, b3, c2, d11), (a34, b3, c2, d12), (a34, b3, c2, d13), (a34, b3, c2, d14), (a34, b3, c2, d15), (a34, b3, c2, d16), (a34, b3, c2, d17), (a34, b3, c2, d18), (a34, b3, c2, d19), (a34, b3, c2, d20), (a34, b3, c2, d21), (a34, b3, c2, d22), (a34, b3, c3, d1), (a34, b3, c3, d2), (a34, b3, c3, d3), (a34, b3, c3, d4), (a34, b3, b3, d5), (a34, b3, c3, d6), (a34, b3, c3, d7), (a34, b3, c3, d8), (a34, b3, c3, d9), (a34, b3, c3, d10), (a34, b3, c3, d11), (a34, b3, c3, d12), (a34, b3, c3, d13), (a34, b3, c3, d14), (a34, b3, c3, d15), (a34, b3, c3, d16), (a34, b3, c3, d17), (a34, b3, c3, d18), (a34, b3, c3, d19), (a34, b3, c3, d20), (a34, b3, c3, d21), (a34, b3, c3, d22), (a34, b4, c1, d1), (a34, b4, c1, d2), (a34, b4, c1, d3), (a34, b4, c1, d4), (a34, b4, c1, d5), (a34, b4, c1, d6), (a34, b4, c1, d7), (a34, b4, c1, d8), (a34, b4, c1, d9), (a34, b4, c1, d10), (a34, b4, c1, d11), (a34, b4, c1, d12), (a34, b4, c1, d13), (a34, b4, c1, d14), (a34, b4, c1, d15), (a34, b4, c1, d16), (a3, b4, c1, d17), (a34, b4, c1, d18), (a34, b4, c1, d19), (a34, b4, c1, d20), (a34, b4, c1, d21), (a34, b4, c1, d22), (a34, b4, c2, d1), (a34, b4, c2, d2), (a34, b4, c2, d3), (a34, b4, c2, d4), (a34, b4, c2, d5), (a34, b4, c2, d6), (a34, b4, c2, d7), (a34, b4, c2, d8), (a34, b4, c2, d9), (a34, b4, c2, d10), (a34, b4, c2, d11, (a34, b4, c2, d12), (a34, b4, c2, d13), (a34, b4, c2, d14), (a34, b4, c2, d15), (a34, b4, c2, d16), (a34, b4, c2, d17), (a34, b4, c2, d18), (a34, b4, c2, d19), (a34, b4, c2, d20), (a34, b4, c2, d21), (a34, b4, c2, d22), (a34, b4, c3, d1), (a34, b4, c3, d2), (a34, b4, c3, d3), (a34, b4, c3, d4), (a34, b4, c3, d5), (a34, b4, c3, d6), (a34, b4, c3, d7), (a34, b4, c3, d8), (a34, b4, c3, d9), (a34, b4, c3, d10), (a34, b4, c3, d11), (a34, b4, c3, d12), (a34, b4, c3, d13), (a34, b4, c3, d14), (a34, b4, c3, d15), (a34, b4, c3, d16), (a34, b4, c3, d17), (a34, b4, c3, d18), (a34, b4, c3, d19), (a34, b4, c3, d20), (a34, b4, c3, d21), (a34, b4, c3, d22), (a34, b5, c1, d1), (a34, b5, c1, d2), (a34, b5, c1, d3), (a34, b5, c1, d4), (a34, b5, c1, d5), (a34, b5, c1, d6), (a34, b5, c1, d7), (a34, b5, c1, d8), (a34, b5, c1, d9), (a34, b5, c1, d10), (a34, b5, c1, d11), (a34, b5, c1, d12), (a34, b5, c1, d13), (a34, b5, c1, d14), (a34, b5, c1, d15), (a34, b5, c1, d16), (a34, b5, c1, d17), (a34, b5, c1, d18), (a34, b5, c1, d19), (a34, b5, c1, d20), (a34, b5, c1, d21), (a34, b5, c1, d22), (a34, b5, c2, d1), (a34, b5, c2, d2), (a34, b5, c2, d3), (a34, b5, c2, d4), (a34, b5, c2, d5), (a34, b5, c2, d16), (a34, b5, c2, d7), (a34, b5, c2, d8), (a34, b5, c2, d9), (a34, b5, c2, d10), (a34, b5, c2, d11), (a34, b5, c2, d12), (a34, b5, c2, d13), (a34, b5, c2, d14), (a34, b5, c2, d15), (a34, b5, c2, d16), (a34, b5, c2, d17), (a34, b5, c2, d18), (a34, b5, c2, d19), (a34, b5, c2, d20), (a34, b5, c2, d21), (a34, b5, c2, d22), (a34, b5, c3, d1), (a34, b5, c3, d2), (a34, b5, c3, d3), (a34, b5, c3, d4), (a34, b5, c3, d5), (a34, b5, c3, d6), (a34, b5, c3, d7), (a34, b5, c3, d8), (a34, b5, c3, d9), (a34, b5, c3, d10), (a34, b5, c3, d11), (a34, b5, c3, d12), (a34, b5, c3, d13), (a34, b5, c3, d14), (a34, b5, c3, d15), (a34, b5, c3, d16), (a34, b5, c3, d17), (a34, b5, c3, d18), (a34, b5, c3, d19), (a34, b5, c3, d20), (a34, b5, c3, d21), (a34, b5, c3, d22), (a34, b6, c1, d1), (a34, b6, c1, d2), (a34, b6, c1, d3), (a34, b6, c1, d4), (a34, b6, c1, d5), (a34, b6, c1, d6), (a34, b6, c1, d7), (a34, b6, c1, d8), (a34, b6, c1, d9), (a34, b6, c1, d10), (a34, b6, c1, d11), (a34, b6, c1, d12), (a34, b6, c1, d13), (a34, b6, c1, d14), (a34, b6, c1, d15), (a34, b6, c1, d16), (a34, b6, c1, d17), (a34, b6, c1, d18), (a34, b6, c1, d19), (a34, b6, c1, d20), (a34, b6, c1, d21), (a34, b6, c1, d22), (a34, b6, c2, d1), (a34, b6, c2, d2), (a34, b6, c2, d3), (a34, b6, c2, d4), (a34, b6, c2, d5), (a34, b6, c2, d6), (a34, b6, c2, d7), (a34, b6, c2, d8), (a34, b6, c2, d9), (a34, b6, c2, d10), (a34, b6, c2, d11), (a34, b6, c2, d12), (a34, b6, c2, d13), (a34, b6, c2, d14), (a34, b6, c2, d15), (a34, b6, c2, d16), (a34, b6, c2, d17), (a34, b6, c2, d18), (a34, b6, c2, d19), (a34, b6, c2, d20), (a34, b6, c2, d21), (a34, b6, c2, d22), (a34, b6, c3, d1), (a34, b6, c3, d2), (a34, b6, c3, d3), (a34, b6, c3, d4), (a34, b6, c3, d5), (a34, b6, c3, d6), (a34, b6, c3, d7), (a34, b6, c3, d8), (a34, b6, c3, d9), (a34, b6, c3, d10), (a34, b6, c3, d11), (a34, b6, c3, d12), (a34, b6, c3, d3), (a34, b6, c3, d14), (a34, b6, c3, d5), (a34, b6, c3, d16), (a34, b6, c3, d17), (a34, b6, c3, d18), (a34, b6, c3, d19), (a34, b6, c3, d20), (a34, b6, b6, d21), (a34, b6, c3, d22), (a35, b1, c1, d1), (a35, b1, c1, d2), (a35, b, c1, d3), (a35, b, c1, d4), (a35, b1, c1, d5), (a35, b, c1, d6), (a35, b1, c1, d7), (a35, b1, c1, d8), (a35, b1, c1, d9), (a35, b1, c1, d10), (a35, b1, c1, d11), (a35, b1, c1, d12), (a35, b1, c1, d13), (a35, b1, c1, d14), (a35, b1, c1, d15), (a35, b1, c1, d16), (a35, b1, c1, d17), (a35, b1, c1, d18), (a35, b1, c1, d19), (a35, b1, c1, d20), (a35, b1, c1, d21), (a35, b1, c1, d22), (a35, b1, c2, d1), (a35, b1, c2, d2), (a35, b1, c2, d3), (a35, b1, c2, d4), (a35, b1, c2, d5), (a35, b1, c2, d6), (a35, b1, c2, d7), (a35, b1, c2, d8), (a35, b1, c2, d9), (a35, b1, c2, d10), (a35, b1, c2, d11), (a35, b1, c2, d12), (a35, b1, c2, d13), (a35, b, c2, d14), (a35, b1, c2, d15), (a35, b1, c2, d16), (a35, b1, c2, d17), (a35, b1, c2, d18), (a35, b1, c2, d19), (a35, b1, c2, d20), (a35, b1, c2, d21), (a35, b1, c2, d22), (a35, b1, c3, d1), (a35, b1, c3, d2), (a35, b1, c3, d3), (a35, b1, c3, d4), (a35, b1, c3, d5), (a35, b1, c1, d6), (a35, b1, c3, d7), (a35, b1, c1, d8), (a35, b1, c3, d9), (a35, b1, c3, d10), (a35, b1, c3, d11), (a35, b1, c3, d12), (a35, b1, c3, d13), (a35, b1, c3, d14), (a35, b1, c3, d15), (a35, b1, c3, d16), (a35, b1, c3, d17), (a35, b1, c3, d18), (a35, b1, c3, d19), (a35, b1, c3, d20), (a35, b1, c3, d21), (a35, b1, c3, d22), (a35, b2, c1, d11), (a35, b2, c1, d2), (a35, b2, c1, d3), (a35, b2, c1, d4), (a35, b2, c1, d5), (a35, b2, c1, d6), (a35, b2, c1, d7), (a3, b2, c1, d8), (a35, b2, c1, d9), (a35, b2, c1, d10), (a35, b2, c1, d11), (a35, b2, c1, d12), (a35, b2, c1, d13), (a35, b2, c1, d14), (a35, (b2, c1, d15), (a35, b2, c1, d16), (a35, b2, c1, d17), (a35, b2, c1, d18), (a35, b2, c1, d19), (a35, b2, c1, d20), (a35, b2, c1, d21), (a35, b2, c1, d22), (a35, b2, c2, d1), (a35, b2, c2, d2), (a35, b2, c2, d3), (a35, b2, c2, d4), (a35, b2, c2, d5), (a35, b2, c2, d6), (a35, b2, c2, d7), (a35, b2, c2, d8), (a35, b2, c2, d9), (a35, b2, c2, d10), (a35, b2, c2, d11), (a35, b2, c2, d12), (a35, b2, c2, d13), (a35, b2, c2, d14), (a35, b2, c2, d15), (a35, b2, c2, d16), (a35, b2, c2, d17), (a35, b2, c2, d18), (a35, b2, c2, d19), (a35, b2, c2, d20), (a35, b2, c2, d21), (a35, b2, c2, d22), (a35, b2, c3, d1), (a35, b2, c3, d2), (a35, b2, c3, d3), (a35, b2, c3, d4), (a35, b2, c3, d5), (a35, b2, c3, d6), (a35, b2, c3, d7), (a35, b2, c3, d8), (a35, b2, c3, d9), (a35, b2, c3, d10), (a35, b2, c3, d11), (a35, b2, c3, d12), (a35, b2, c3, d13), (a35, b2, c3, d14), (a35, b2, c3, d15), (a35, b2, c3, d16), (a35, b2, c3, d17), (a35, b2, c3, d18), (a35, b2, c3, d19), (a35, b2, c3, d20), (a35, b2, c3, d21), (a35, b2, c3, d22), (a35, b3, c1, d1), (a35, b3, c1, d2), (a35, b3, c1, d3), (a35, b3, c1, d4), (a35, b3, c1, d5), (a35, b3, c1, d6), (a35, b3, c1, d7), (a35, b3, c1, d8), (a35, b3, c1, d9), (a35, b3, c1, d10), (a35, b3, c1, d11), (a35, b3, c1, d12), (a35, b3, c1, d13), (a35, b3, c1, d14), (a35, b3, c1, d15), (a35, b5, c1, d16), (a35, b3, c1, d17), (a35, b3, c1, d18), (a35, b3, c1, d19), (a35, b3, c1, d20), (a35, b3, c1, d21), (a35, b3, c1, d22), (a35, b3, c2, d1), (a35, b3, c2, d2), (a35, b3, c2, d3), (a35, b3, c2, d4), (a35, b3, c2, d5), (a35, b3, c2, d6), (a35, b3, c2, d7), (a35, b3, c2, d8), (a35, b3, c2, d9), (a35, b3, c2, d10), (a35, b3, c2, d11), (a35, b5, c2, d12), (a35, b5, c2, d13), (a35, b5, c2, d14), (a35, b3, c2, d15), (a35, b3, c2, d16), (a35, b3, c2, d17), (a35, b3, c2, d18), (a35, b3, c2, d19), (a35, b3, c2, d20), (a35, b3, c2, d21), (a35, b5, c2, d22), (a35, b3, c3, d1), (a35, b3, c3, d2), (a35, b3, c3, d3), (a35, b3, c3, d4), (a35, b3, c3, d5), (a35, b3, c3, d6), (a35, b3, c3, d7), (a35, b5, c3, d8), (a35, b3, c3, d9), (a35, b3, c3, d10), (a35, b3, c3, d11), (a35, b3, c3, d12), (a35, b3, c3, d13), (a35, b3, c3, d14), (a35, b3, c3, d15), (a35, b3, c3, d16), (a35, b3, c3, d17), (a35, b3, c3, d18), (a35, b3, c3, d19), (a35, b3, c3, d20), (a35, b3, c3, d21), (a35, b3, c3, d22), (a35, b4, c1, d1), (a35, b4, c1, d2), (a35, b4, c1, d3), (a35, b4, c1, d4), (a35, b4, c1, d5), (a35, b4, c1, d6), (a35, b4, c1, d7), (a5, b4, c1, d8), (a35, b4, c1, d9), (a35, b4, c1, d10), (a35, b4, c1, d11), (a35, b4, c1, d12), (a35, b4, c1, d13), (a35, b4, c1, d14), (a35, b4, c1, d15), (a35, b4, c1, d16), (a35, b4, c1, d17), (a35, b4, c1, d18), (a35, b4, c1, d19), (a35, b4, c1, d20), (a35, b4, c1, d21), (a35, b4, c1, d22), (a35, b4, c2, d1), (a35, b4, c2, d2), (a35, b4, c2, d3), (a35, b4, c2, d4), (a35, b4, c2, d5), (a35, b4, c2, d6), (a35, b4, c2, d7), (a35, b4, c2, d8), (a35, b4, c2, d9), (a35, b4, c2, d10), (a35, b4, c2, d11), (a35, b4, c2, d12), (a35, b4, c2, d13), (a35, b4, c2, d14), (a35, b4, c2, d15), (a35, b4, c2, d16), (a35, b4, c2, d17), (a35, b4, c2, d18), (a35, b4, c2, d19), (a35, b4, c2, d20), (a35, b4, c2, d21), (a35, b4, c2, d22), (a35, b4, c3, d1), (a35, b4, c3, d2), (a35, b4, c3, d3), (a35, b4, c3, d4), (a35, b4, c3, d5), (a35, b4, c3, d6), (a35, b4, c3, d7), (a35, b4, c3, d8), (a35, b4, c3, d9), (a35, b4, c3, d10), (a35, b4, c3, d11), (a35, b4, c3, d12), (a35, b4, c3, d13), (a35, b4, c8, d14), (a35, b4, c3, d15), (a35, b4, c3, d16), (a35, b4, c3, d17), (a35, b4, c3, d18), (a35, b4, c3, d19), (a35, b4, c3, d20), (a35, b4, c3, d21), (a35, b4, c3, d22), (a35, b5, c1, d1), (a35, b5, c1, d2), (a35, b5, c1, d3), (a35, b5, c1, d4), (a35, b5, c1, d5), (a35, b5, c1, d6), (a35, b5, c1, d7), (a35, b5, c1, d8), (a35, b5, c1, d9), (a35, b5, c1, d1), (a35, b5, c1, d11), (a35, b5, c1, d12), (a35, b5, c1, d13), (a35, b5, c1, d14), (a35, c1, d15), (a35, b5, c1, d16), (a35, b5, c1, d17), (a35, b5, c1, d18), (a35, b5, c1, d19), (a35, b5, c1, d20), (a35, b5, c1, d21), (a35, b5, c1, d22), (a35, b5, c2, d1), (a35, b5, c2, d2), (a35, b5, c2, d3), (a35, b5, c2, d4), (a35, b5, c2, d5), (a35, b5, c2, d6), (a35, b5, c2, d7), (a3, b5, c2, d8), (a35, b, c2, d9), (a35, b5, c2, d10), (a35, b5, c2, d11), (a35, b5, c2, d12), (a35, b5, c2, d13), (a35, b5, c2, d14), (a35, b5, c2, d15), (a35, b5, c2, d16), (a35, b5, c2, d17), (a35, b5, c2, d18), (a35, b5, c2, d19), (a35, b5, c2, d20), (a35, b5, c2, d21), (a35, b5, c2, d22), (a35, b5, c3, d1), (a35, b5, c3, d2), (a35, b5, c3, d3), (a35, b5, c3, d4), (a35, b5, c3, d5), (a35, b5, c3, d6), (a35, b5, c3, d7), (a35, b5, c3, d8), (a35, b5, c3, d9), (a35, b5, c3, d10), (a35, b5, c3, d11), (a35, b5, c3, d12), (a35, b5, c3, d13), (a35, b5, c3, d14), (a35, b5, c3, d15), (a35, b5, c3, d16), (a35, b5, c3, d17), (a35, b5, c3, d18), (a35, b5, c3, d19), (a35, b5, c3, d20), (a35, b5, c3, d21), (a35, b5, c3, d22), (a35, b6, c1, d1), (a35, b6, c1, d2), (a35, b6, c1, d3), (a35, b6, c1, d4), (a35, b6, c1, d5), (a35, b6, c1, d6), (a35, b6, c1, d7), (a35, b6, c1, d8), (a35, b6, c1, d9), (a35, b6, c1, d10), (a35, b6, c1, d11), (a35, b6, c1, d12), (a35, b6, c1, d13), (a35, b6, c1, d14), (a35, b6, c1, d15), (a35, b6, c1, d16), (a35, b6, c1, d17), (a35, b6, c1, d18), (a35, b6, c1, d19), (a35, b6, c1, d20), (a35, b6, c1, d21), (a35, b6, c1, d22), (a35, b6, c2, d1), (a35, b6, c2, d2), (a35, b6, c2, d3), (a35, b6, c2, d4), (a35, b6, c2, d5), (a35, b6, c2, d6), (a35, b6, c2, d7), (a35, b6, c2, d8), (a35, b6, c2, d9), (a35, b6, c2, d10), (a35, b6, c2, d11), (a35, b6, c2, d12), (a35, b6, c2, d13), (a35, b6, c2, d14), (a35, b6, c2, d15), (a35, b6, c2, d16), (a35, b6, c2, d17), (a35, b6, c2, d18), (a35, b6, c2, d19), (a35, b6, c2, d20), (a35, b6, c2, d21), (a35, b6, c2, d22), (a35, b6, c3, d1), (a35, b6, c3, d2), (a35, c3, d3), (a35, b6, c3, d4), (a35, b6, c3, d5), (a35, b6, c3, d6), (a35, b6, c3, d7), (a35, b6, c3, d8), (a35, b6, c3, d9), (a35, b6, c3, d10), (a35, b6, c3, d11), (a35, b6, c3, d12), (a35, b6, c3, d13), (a35, b6, c3, d14), (a35, b6, c3, d15), (a35, b6, c3, d16), (a35, b6, c3, d17), (a35, c6, c3, d18), (a35, b6, c3, d19), (a35, b6, c3, d20), (a35, b6, c3, d21), (a35, c6, c3, d22), (a36, b1, c1, d7), (a36, b1, c1, d2), (a36, b1, c1, d3), (a36, b1, c1, d4), (a36, b1, c1, d5), (a36, b1, c1, d6), (a36, b1, c1, d7), (a36, b1, c1, d8), (a36, b1, c1, d9), (a36, b1, c1, d10), (a36, b1, c1, d11), (a36, b1, c1, d12), (a36, b1, c1, d13), (a36, b1, c1, d14), (a36, b1, c1, d15), (a36, b1, c1, d16), (a36, b1, c1, d17), (a36, b1, c1, d18), (a36, b1, c1, d19), (a36, b1, c1, d20), (a36, b1, c1, d21), (a36, b1, c1, d22), (a36, b1, c2, d1), (a36, b1, c2, d2), (a36, b1, c2, d3), (a36, b1, c2, d4), (a36, b1, c2, d5), (a36, b1, c2, d6), (a36, b1, c2, d7), (a36, b1, c2, d8), (a36, b1, c2, d9), (a36, b1, c2, d10), (a36, b1, c2, d11), (a36, b1, c2, d12), (a36, b1, c2, d13), (a36, b1, c2, d14), (a36, b1, c2, d15), (a36, b1, c2, d16), (a36, b1, c2, d17), (a36, b1, c2, d18), (a36, b1, c2, d19), (a36, b1, c2, d20), (a36, b1, c2, d21), (a36, b1, c2, d22), (a36, b1, c3, d1), (a36, b1, c3, d2), (a36, b1, c3, d3), (a36, b1, c3, d4), (a36, b1, c3, d5), (a36, b1, c3, d6), (a36, b1, c3, d7), (a36, b1, c3, d8), (a36, b1, c3, d9), (a36, b1, c3, d10), (a36, b1, c3, d11), (a36, b1, c3, d12), (a36, b1, c3, d13), (a36, b1, c3, d14), (a36, b1, c3, d15), (a36, b1, c3, d16), (a36, b1, c3, d17), (a36, b1, c3, d18), (a36, b1, c3, d19), (a36, b1, c3, d20), (a36, b1, c3, d21), (a36, b1, c3, d22), (a36, b2, c1, d1), (a36, b2, c1, d2), (a36, b2, c1, d3), (a36, b2, c1, d4), (a36, b2, c1, d5), (a36, b2, c1, d6), (a36, b2, c1, d7), (a36, b2, c1, d8), (a36, b2, c1, d9), (a36, b2, c1, d10), (a36, b2, c1, d11), (a36, b2, c1, d12), (a36, b2, c1, d13), (a36, b2, c1, d14), (a36, b2, c1, d15), (a36, b2, c1, d16), (a36, b2, c1, d17), (a36, b2, c1, d18), (a36, b2, c1, d19), (a36, b2, c1, d20), (a36, b2, c1, d21), (a36, b2, c1, d22), (a36, b2, c2, d1), (a36, b2, c2, d2), (a36, b2, c2, d3), (a36, b2, c2, d4), (a36, b2, c2, d5), (a36, b2, c2, d6), (a36, b2, c2, d7), (a36, b2, c2, d8), (a36, b2, c2, d9), (a36, b2, c2, d10), (a36, b2, c2, d11), (a36, b2, c2, d12), (a36, b2, c2, d13), (a36, b2, c2, d14), (a36, b2, c2, d15), (a36, b2, c2, d16), (a36, b2, c2, d17), (a36, b2, c2, d18), (a36, b2, c2, d19), (a36, b2, c2, d20), (a36, b2, c2, d21), (a36, b2, c2, d22), (a36, b2, c3, d1), (a36, b2, c3, d2), (a36, b2, c3, d3), (a36, b2, c3, d4), (a36, b2, c3, d5), (a36, b2, c3, d6), (a36, b2, c3, d7), (a36, b2, c3, d8), (a36, b2, c3, d9), (a36, b2, c3, d10), (a36, b2, c3, d11), (a36, b2, c3, d12), (a36, b2, c3, d13), (a36, b2, c3, d14), (a36, b2, c3, d15), (a36, b2, c3, d6), (a36, b2, c3, d17), (a36, b2, c3, d18), (a36, b2, c3, d19), (a36, b2, c3, d20), (a36, b2, c3, d21), (a36, b2, c3, d22), (a36, b3, c1, d1), (a36, b3, c1, d2), (a36, b3, c1, d3), (a36, b3, c1, d4), (a36, b3, c1, d5), (a36, b3, c1, d6), (a36, b3, c1, d7), (a36, b3, c1, d8), (a36, b3, c1, d9), (a36, b3, c1, d10), (a36, b3, c1, d11), (a36, b3, c1, d12), (a36, b3, c1, d13), (a36, b3, c1, d14), (a36, b3, c1, d15), (a36, b3, c1, d16), (a36, b3, c1, d17), (a36, b3, c1, d18), (a36, b3, c1, d19), (a36, b3, c1, d20), (a36, b3, c1, d21), (a36, b3, c1, d22), (a36, b3, c2, d1), (a36, b3, c2, d2), (a36, b3, c2, d3), (a36, b3, c2, d4), (a36, b3, c2, d5), (a36, b3, c2, d6), (a36, b3, c2, d7), (a36, b3, c2, d8), (a36, b3, c2, d9), (a36, b3, c2, die), (a36, b3, c2, d11), (a36, b3, c2, d12), (a36, b3, c2, d13), (a36, b3, c2, d14), (a36, b3, c2, d15), (a36, b3, c2, d16), (a36, b3, c2, d17), (a36, b3, c2, d18), (a36, b3, c2, d19), (a36, b3, c2, d20), (a36, b3, c2, d21), (a36, b3, c2, d22), (a36, b3, c3, d1), (a36, b3, c3, d2), (a36, b3, c3, d3), (a36, b3, c3, d4), (a36, b3, c3, d5), (a36, b3, c3, d6), (a36, b3, c3, d7), (a36, b3, c3, d8), (a36, b3, c3, d9), (a36, b3, c3, d10), (a36, b3, c3, d11), (a36, b3, c3, d12), (a36, b3, c3, d13), (a36, b3, c3, d14), (a36, b3, c3, d15), (a36, b3, c3, d16), (a36, b3, c3, d17), (a36, b3, c3, d18), (a36, b3, c3, d19), (a36, b3, c3, d20), (a36, b3, c3, d21), (a36, b3, c3, d20), (a36, b4, c1, d1), (a36, b4, c1, d2), (a36, b4, c1, d3), (a36, b4, c1, d4), (a36, b4, c1, d5), (a36, b4, c1, d6), (a36, b4, c1, d7), (a36, b4, c1, d8), (a36, b4, c1, d9), (a36, b4, c1, d10), (a36, b4, c1, d11), (a36, b4, c1, d12), (a36, b4, c1, d13), (a36, b4, c1, d14), (a36, b4, c1, d15), (a36, b4, c1, d16), (a36, b4, c1, d17), (a36, b4, c1, d18), (a36, b4, c1, d19), (a36, b4, c1, d20), (a36, b4, c1, d21), (a36, b4, c1, d22), (a36, b4, c2, d1), (a36, b4, c2, d2), (a36, b4, c2, d3), (a36, b4, c2, d4), (a36, b4, c2, d5), (a36, b4, c2, d6), (a36, b4, c2, d7), (a36, b4, c2, d8), (a36, b4, c2, d9), (a36, b4, c2, d10), (a36, b4, c2, d11), (a36, b4, c2, d12), (a36, b4, c2, d13), (a36, b4, c2, d14), (a36, b4, c2, d15), (a36, b4, c2, d16), (a36, b4, c2, d17), (a36, b4, c2, d18), (a36, b4, c2, d19), (a36, b4, c2, d20), (a36, b4, c2, d21), (a36, b4, c2, d22), (a36, b4, c3, d1), (a36, b4, c3, d2), (a36, b4, c3, d3), (a36, b4, c3, d4), (a36, b4, c3, d5), (a36, b4, c3, d6), (a36, b4, c3, d7), (a36, b4, c3, d8), (a36, b4, c3, d9), (a36, b4, c3, d10), (a36, b4, c3, d11), (a36, b4, c3, d12), (a36, b4, c3, d13), (a36, b4, c3, d14), (a36, b4, c3, d15), (a36, b4, c3, d16), (a36, b4, c3, d17), (a36, b4, c3, d18), (a36, b4, c3, d19), (a36, b4, c3, d20), (a36, b4, c3, d21), (a36, b4, c3, d22), (a36, b5, c1, d1), (a36, b5, c1, d2), (a36, b5, c1, d3), (a36, b5, c1, d4), (a36, b5, c1, d5), (a36, b5, c1, d6), (a36, b5, c1, d7), (a36, b5, c1, d3), (a36, b5, c1, d9), (a36, b5, c1, d10), (a36, b5, c1, d11), (a36, b5, c1, d12), (a36, b5, c1, d13), (a36, b5, c1, d14), (a36, b5, c1, d15), (a36, b5, c1, d16), (a36, b5, c1, d17), (a36, b5, c1, d18), (a36, b5, c1, d19), (a36, b5, c1, d20), (a36, b5, c1, d21), (a36, b5, c1, d22), (a36, b5, c2, d1), (a36, b5, c2, d2), (a36, b5, c2, d3), (a36, b5, c2, d4), (a36, b5, c2, d5), (a36, b5, c2, d6), (a36, b5, c2, d7), (a36, b5, c2, d8), (a36, b5, c2, d9), (a36, b5, c2, d10), (a36, b5, c2, d11), (a36, b5, c2, d12), (a36, b5, c2, d13), (a36, b5, c2, d14), (a36, b5, c2, d15), (a36, b5, c2, d16), (a36, b5, c2, d17), (a36, b5, c2, d18), (a36, b5, c2, d19), (a36, b5, c2, d20), (a36, b5, c2, d21), (a36, b5, c2, d22), (a36, b5, c3, d1), (a16, b5, c3, d2), (a36, b5, c3, d3), (a36, b5, c3, d4), (a36, b5, c3, d5), (a36, b5, c3, d6), (a36, b5, c3, d7), (a36, b5, c3, d8), (a36, b5, c3, d9), (a36, b5, c3, d10), (a36, b5, c3, d11), (a36, b5, c3, d12), (a36, b5, c3, d13), (a36, b5, c3, d14), (a36, b5, c3, d15), (a36, b5, c3, d16), (a36, b5, c3, d17), (a36, b5, c3, d18), (a36, b5, c3, d19), (a36, b5, c3, d20), (a36, b5, c3, d21), (a36, b5, c3, d22), (a36, b6, c1, d1), (a36, b6, c1, d2), (a36, b6, c1, d3), (a36, b6, c1, d4), (a36, b6, c1, d5), (a36, b6, c1, d6), (a36, b6, c1, d7), (a36, b6, c1, d8), (a36, b6, c1, d9), (a36, b6, c1, d10), (a36, b5, c1, d11), (a36, b6, c1, d12), (a36, b6, c1, d13), (a36, b6, c1, d14), (a36, b6, c1, d15), (a36, b6, c1, d16), (a36, b6, c1, d17), (a36, b6, c1, d18), (a36, b6, c1, d19), (a36, b6, c1, d20), (a36, b6, c1, d21), (a36, b6, c1, d22), (a36, b6, c2, d1), (a36, b6, c2, d2), (a36, b6, c2, d3), (a36, b6, c2, d4), (a36, b6, c2, d5), (a36, b6, c2, d6), (a36, b6, c2, d7), (a36, b6, c2, d8), (a36, b6, c2, d9), (a36, b6, c2, d10), (a36, b6, c2, d11), (a36, b6, c2, d12), (a36, b6, c2, d13), (a36, b6, c2, d14), (a36, b6, c2, d15), (a36, b6, c2, d16), (a36, b6, c2, d17), (a36, b6, c2, d18), (a36, b6, c2, d19), (a36, b6, c2, d20), (a36, b6, c2, d21), (a36, b6, c2, d22), (a36, b6, c3, d1), (a36, b6, c3, d2), (a36, b6, c3, d3), (a36, b6, c3, d4), (a36, b6, c3, d5), (a36, b6, c3, d6), (a36, b6, c3, d7), (a36, b6, c3, d8), (a36, b6, c3, d9), (a36, b6, c3, d10), (a36, b6, c3, d11), (a36, b6, c3, d12), (a36, b6, c3, d13), (a36, b6, c3, d14), (a36, b6, c3, d15), (a36, b6, c3, d16), (a36, b6, c3, d17), (a36, b6, c3, d18), (a36, b6, c3, d19), (a36, b6, c3, d20), (a36, b6, c3, d21), (a36, b6, c3, d22), (a37, b1, c1, d1), (a37, b1, c1, d2), (a37, b1, c1, d3), (a37, b1, c1, d4), (a37, b1, c1, d5), (a37, b1, c1, d6), (a37, b1, c1, d7), (a37, b1, c1, d8), (a37, b1, c1, d9), (a37, b1, c1, d10), (a37, b1, c1, d11), (a37, b1, c1, d12), (a37, b1, c1, d13), (a37, b1, c1, d14), (a37, b1, c1, d15), (a37, b1, c1, d16), (a37, b1, c1, d17), (a37, b1, c1, d18), (a37, b1, c1, d19), (a37, b1, c1, d20), (a37, b1, c1, d21), (a37, b1, c1, d22), (a37, b1, c2, d1), (a37, b1, c2, d2), (a37, b1, c2, d3), (a37, b1, c2, d4), (a37, b1, c2, d5), (a37, b1, c2, d6), (a37, b1, c2, d7), (a37, b1, c2, d8), (a37, b1, c2, d9), (a37, b1, c2, d10), (a37, b1, c2, d11), (a37, b1, c2, d12), (a37, b1, c2, d13), (a37, b1, c2, d14), (a37, b1, c2, d15), (a37, b1, c2, d16), (a37, b1, c2, d17), (a37, b1, c2, d18), (a37, b1, c2, d19), (a37, b1, c2, d20), (a37, b1, c2, d21), (a37, b1, c2, d22), (a37, b1, c3, d1), (a37, b1, c3, d2), (a37, b1, c3, d3), (a37, b1, c3, d4), (a37, b1, c3, d5), (a37, b1, c3, d6), (a37, b1, c3, d7), (a37, b1, c3, d8), (a37, b1, c3, d9), (a37, b1, c3, d10), (a37, b1, c3, d11), (a37, b1, c3, d12), (a37, b1, c3, d13), (a37, b1, c3, d14), (a37, b1, c3, d15), (a37, b1, c3, d16), (a37, b1, c3, d17), (a37, b1, c3, d18), (a37, b1, c3, d19), (a37, b1, c3, d20), (a37, b1, c3, d21), (a37, b1, c3, d22), (a37, b2, c1, d1), (a37, b2, c1, d2), (a37, b2, c1, d3), (a37, b2, c1, d4), (a37, b2, c1, d5), (a37, b2, c1, d6), (a37, b2, c1, d7), (a37, b2, c1, d8), (a37, b2, c1, d9), (a37, b2, c1, d10), (a37, b2, c1, d11), (a37, b2, c1, d12), (a37, b2, c1, d13), (a37, b2, c1, d14), (a37, b2, c1, d15), (a37, b2, c1, d16), (a37, b2, c1, d17), (a37, b2, c1, d18), (a37, b2, c1, d19), (a37, b2, c1, d20), (a37, b2, c1, d21), (a37, b2, c1, d22), (a37, b2, c2, d1), (a37, b2, c2, d2), (a37, b2, c2, d3), (a37, b2, c2, d4), (a37, b2, c2, d5), (a37, b2, c2, d6), (a37, b2, c2, d7), (a37, b2, c2, d8), (a37, b2, c2, d9), (a37, b2, c2, d10), (a37, b2, c2, d11), (a37, b2, c2, d12), (a37, b2, c2, d13), (a37, b2, c2, d14), (a37, b2, c2, d15), (a37, b2, c2, d16), (a37, b2, c2, d17), (a37, b2, c2, d18), (a37, b2, c2, d19), (a7, b2, c2, d20), (a37, b2, c2, d21), (a37, b2, c2, d22), (a37, b2, c3, d1), (a37, b2, c3, d2), (a37, b2, c3, d3), (a37, b2, c3, d4), (a37, b2, c3, d5), (a37, b2, c3, d6), (a37, b2, c3, d7), (a37, b2, c3, d8), (a37, b2, c3, d9), (a37, b2, c3, d16), (a37, b2, c3, d11), (a37, b2, c3, d12), (a37, b2, c3, d13), (a37, b2, c3, d14), (a37, b2, c3, d15), (a37, b2, c3, d16), (a37, b2, c3, d17), (a37, b2, c3, d18), (a37, b2, c3, d19), (a37, b2, c3, d20), (a37, b2, c3, d21), (a37, b2, c3, d22), (a37, b3, c1, d1), (a37, b3, c1, d2), (a37, b3, c1, d3), (a37, b3, c1, d4), (a37, b3, c1, d5), (a37, b3, c1, d6), (a37, b3, c1, d7), (a37, b3, c1, d8), (a37, b3, c1, d9), (a37, b3, c1, d10), (a37, b3, c1, d11), (a37, b3, c1, d12), (a37, b3, c1, d13), (a37, b3, c1, d14), (a37, b3, c1, d15), (a37, b3, c1, d16), (a37, b3, c1, d17), (a37, b3, c1, d18), (a37, b3, c1, d19), (a37, b3, c1, d20), (a37, b3, c1, d21), (a37, b3, c1, d22), (a37, b3, c2, d1), (a37, b3, c2, d2), (a37, b3, c2, d3), (a37, b3, c2, d4), (a37, b3, c2, d5), (a37, b3, c2, d6), (a37, b3, c2, d7), (a37, b3, c2, d8), (a37, b3, c2, d9), (a37, b3, c2, d10), (a37, b3, c2, d11), (a37, b3, c2, d12), (a37, b3, c2, d13), (a37, b3, c2, d14), (a37, b3, c2, d15), (a37, b3, c2, d16), (a37, b3, c2, d17), (a37, b3, c2, d18), (a37, b3, c2, d19), (a37, b3, c2, d20), (a37, b3, c2, d21), (a37, b3, c2, d22), (a37, b3, c3, d1), (a37, b3, c3, d2), (a37, b3, c3, d3), (a3, b3, c3, d4), (a37, b3, c3, d5), (a37, b3, c3, d6), (a37, b3, c3, d7), (a37, b3, c3, d8), (a37, b3, c3, d9), (a37, b3, c3, d10), (a37, b3, c3, d11), (a37, b3, c3, d12), (a37, b3, c3, d13), (a37, b3, c3, d14), (a37, b3, c3, d15), (a37, b3, c3, d16), (a37, b3, c3, d17), (a37, b3, c3, d18), (a37, b3, c3, d19), (a37, b3, c3, d20), (a37, b3, c3, d21), (a37, b3, c3, d22), (a37, b4, c1, d1), (a37, b4, c1, d2), (a37, b4, c1, d3), (a37, b4, c1, d4), (a37, b4, c1, d5), (a37, b4, c1, d6), (a37, b4, c1, d7), (a37, b4, c1, d8), (a37, b4, c1, d9), (a37, b4, c1, d10), (a37, b4, c1, d11), (a37, b4, c1, d12), (a37, b4, c1, d13), (a37, b4, c1, d14), (a37, b4, c1, d15), (a37, b4, c1, d16), (a37, b4, c1, d17), (a37, b4, c1, d18), (a37, b4, c1, d19), (a37, b4, c1, d20), (a37, b4, c1, d21), (a37, b4, c1, d22), (a37, b4, c2, d1), (a37, b4, c2, d2), (a37, b4, c2, d3), (a37, b4, c2, d4), (a37, b4, c2, d5), (a37, b4, c2, d6), (a37, b4, c2, d7), (a37, b4, c2, d8), (a37, b4, c2, d9), (a37, b4, c2, d10), (a37, b4, c2, d11), (a37, b4, c2, d12), (a37, b4, c2, d13), (a37, b4, c2, d14), (a37, b4, c2, d15), (a37, b4, c2, d16), (a37, b4, c2, d17), (a37, b4, c2, d18), (a37, b4, c2, d19), (a37, b4, c2, d20), (a37, b4, c2, d21), (a37, b4, c2, d22), (a37, b4, c3, d1), (a37, b4, c3, d2), (a37, b4, c3, d3), (a37, b4, c3, d4), (a37, b4, c3, d5), (a37, b4, c3, d6), (a37, b4, c3, d7), (a37, b4, c3, d8), (a37, b4, c3, d9), (a37, b4, c3, d10), (a37, b4, c3, d11), (a37, b4, c3, d12), (a37, b4, c3, d13), (a37, b4, c3, d14), (a37, b4, c3, d15), (a37, b4, c3, d16), (a37, b4, c3, d17), (a37, b4, c3, d18), (a37, b4, c3, d19), (a37, b4, c3, d20) (a37, b4, c3, d21), (a37, b4, c3, d22), (a37, b5, c1, d1), (a37, b5, c1, d2), (a37, b5, c1, d3), (a37, b5, c1, d4), (a37, b5, c1, d5), (a37, b5, c1, d6), (a37, b5, c1, d7), (a37, b5, c1, d8), (a37, b5, c1, d9), (a37, b5, c1, d10), (a37, b5, c1, d11), (a37, b5, c1, d12), (a37, b5, c1, d13), (a37, b5, c1, d14), (a37, b5, c1, d15), (a37, b5, c1, d16), (a37, b5, c1, d17), (a37, b5, c1, d18), (a37, b5, c1, d19), (a37, b5, c1, d20), (a37, b5, c1, d21), (a37, b5, c1, d22), (a37, b5, c2, d1), (a37, b5, c2, d2), (a37, b5, c2, d3), (a37, b5, c2, d4), (a37, b5, c2, d5), (a37, b5, c2, d6), (a37, b5, c2, d7), (a37, b5, c2, d8), (a37, b5, c2, d9), (a37, b5, c2, d10), (a37, b5, c2, d11), (a37, b5, c2, d12), (a37, b5, c2, d13), (a37, b5, c2, d14), (a37, b5, c2, d15), (a37, b5, c2, d16), (a37, b5, c2, d17), (a37, b5, c2, d18), (a37, b5, c2, d19), (a37, b5, c2, d20), (a37, b5, c2, d21), (a37, b5, c2, d22), (a37, b5, c3, d1), (a37, b5, c3, d2), (a37, b5, c3, d3), (a37, b5, c3, d14), (a37, b5, c3, d5), (a37, b5, c3, d6), (a37, b5, c3, d7), (a37, b5, c3, d3), (a37, b5, c3, d9), (a37, b5, c3, d10), (a37, b5, c3, d11), (a37, b5, c3, d12), (a37, b5, c3, d13), (a37, b5, c3, d14), (a37, b5, c3, d15), (a37, b5, c3, d16), (a37, b5, c3, d17), (a37, b5, c3, d18), (a37, b5, c3, d19), (a37, b5, c3, d20), (a37, b5, c3, d21), (a37, b5, c3, d22), (a37, b6, c1, d1), (a37, b3, c1, d2), (a37, b6, c1, d3), (a37, b6, c1, d4), (a37, b6, c1, d5), (a37, b6, c1, d6), (a37, b6, c1, d7), (a37, b6, c1, d8), (a37, b6, c1, d9), (a37, b6, c1, d10), (a37, b6, c1, d11), (a37, b6, c1, d12), (a7, b6, c1, d13), (a37, b6, c1, d14), (a37, b6, c1, d15), (a37, b6, c1, d16), (a37, b6, c1, d17), (a37, b6, c1, d18), (a37, b6, c1, d19), (a37, b6, c1, d20), (a37, b6, c1, d21), (a37, b6, c1, d22), (a37, b6, c2, d1), (a37, b6, c2, d2), (a37, b6, c2, d3), (a37, b6, c2, d4), (a37, b6, c2, d5), (a37, b6, c2, d6), (a37, b6, c2, d7), (a37, b6, c2, d3), (a37, b6, c2, d9), (a37, b6, c2, d13), (a37, b6, c2, d11), (a37, b6, c2, d12), (a37, b6, c2, d13), (a37, b6, c2, d14), (a37, b6, c2, d15), (a37, b6, c2, d16), (a37, b6, c2, d17), (a37, b6, c2, d18), (a37, b6, c2, d19), (a37, b6, c2, d20), (a37, b6, c2, d21), (a7, b6, c2, d22), (a37, b6, c3, d1), (a37, b6, c3, d2), (a37, b6, c3, d3), (a37, b6, c3, d4), (a37, b6, c3, d5), (a37, b6, c3, d6), (a37, b6, c3, d7), (a37, b6, c3, d8), (a37, b6, c3, d9), (a37, b6, c3, d10), (a37, b6, c3, d11), (a37, b6, c3, d12), (a37, b6, c3, d13), (a37, b6, c3, d14), (a37, b6, c3, d15), (a37, b6, c3, d16), (a37, b6, c3, d17), (a37, b6, c3, d18), (a37, b6, c3, d19), (a37, b6, c3, d20), (a37, b6, c3, d21), (a37, b6, c3, d22), (a38, b1, c1, d1), (a38, b1, c1, d2), (a38, b1, c1, d3), (a38, b1, c1, d4), (a38, b1, c1, d5), (a38, b1, c1, d6), (a38, b1, c1, d7), (a38, b1, c1, d8), (a38, b1, c1, d9), (a38, b1, c1, d10), (a38, b1, c1, d14), (a38, b1, c1, d12), (a38, b1, c1, d13), (a38, b1, c1, d14), (a38, b1, c1, d15), (a38, b1, c1, d16), (a38, b1, c1, d17), (a38, b1, c1, d18), (a38, b1, c1, d19), (a38, b1, c1, d20), (a38, b1, c1, d21), (a38, b1, c1, d22), (a38, b1, c2, d1), (a38, b1, c2, d2), (a38, b1, c2, d3), (a38, b1, c2, d4), (a38, b1, c2, d5), (a38, b1, c2, d6), (a38, b1, c2, d7), (a38, b, c2, d8), (a38, b1, c2, d9), (a38, b1, c2, d1), (a38, b1, c2, d11), (a38, b1, c2, d12), (a38, b1, c2, d13), (a38, b1, c2, d14), (a38, b1, c2, d15), (a38, b1, c2, d16), (a38, b1, c2, d17), (a38, b1, c2, d18), (a38, b1, c2, d19), (a38, b1, c2, d20), (a38, b1, c2, d21), (a38, b1, c2, d22), (a38, b1, c3, d1), (a38, b1, c3, d2), (a38, b1, c3, d3), (a38, b1, c3, d4), (a38, b1, c3, d5), (a38, b1, c3, d6), (a38, b1, c3, d7), (a38, b1, c3, d8), (a38, b1, c3, d9), (a38, b1, c3, d10), (a38, b1, c3, d11), (a38, b1, c3, d12), (a38, b1, c3, d13), (a38, b1, c3, d14), (a38, b1, c3, d15), (a38, b1, c3, d16), (a38, b1, c3, d17), (a38, b1, c3, d18), (a38, b1, c3, d19), (a38, b1, c3, d20), (a38, b1, c3, d21), (a38, b1, c3, d22), (a38, b2, c1, d1), (a38, b2, c1, d2), (a38, b2, c1, d3), (a38, b2, c1, d4), (a38, b2, c1, d5), (a38, b2, c1, d6), (a38, b2, c1, d7), (a38, b2, c1, d8), (a38, b2, c1, d9), (a38, b2, c1, d10), (a38, b2, c1, d11), (a38, b2, c1, d12), (a38, b2, c1, d13), (a38, b2, c1, d14), (a38, b2, c1, d15), (a38, b2, c1, d16), (a38, b2, c1, d17), (a38, b2, c1, d18), (a38, b2, c1, d19), (a38, b2, c1, d20), (a38, b2, c1, d21), (a38, b2, c1, d22), (a38, b2, c2, d1), (a38, b2, c2, d2), (a38, b2, c2, d3), (a38, b2, c2, d4), (a38, b2, c2, d5), (a38, b2, c2, d6), (a38, b2, c2, d7), (a38, b2, c2, d8), (a38, b2, c2, d9), (a38, b2, c2, d10), (a38, b2, c2, d11), (a38, b2, c2, d12), (a38, b2, c2, d13), (a38, b2, c2, d14), (a38, b2, c2, d15), (a38, b2, c2, d16), (a38, b2, c2, d17), (a38, b2, c2, d18), (a38, b2, c2, d19), (a38, b2, c2, d20), (a38, b2, c2, d21), (a38, b2, c2, d22), (a38, b2, c3, d1), (a38, b2, c3, d2), (a38, b2, c3, d3), (a38, b2, c3, d4), (a38, b2, c3, d5), (a38, b2, c3, d6), (a38, b2, c3, d7), (a38, b2, c3, d8), (a38, b2, c3, d9), (a38, b2, c3, d10), (a38, b2, c3, d11), (a38, b2, c3, d12), (a38, b2, c3, d13), (a38, b2, c3, d14), (a38, b2, c3, d15), (a38, b2, c3, d16), (a38, b2, c3, d17), (a38, b2, c3, d18), (a38, b2, c3, d19), (a38, b2, c3, d20), (a38, b2, c3, d21), (a38, b2, c3, d22), (a38, b3, c1, d1), (a38, b3, c1, d2), (a38, b3, c1, d3), (a38, b3, c1, d4), (a38, b3, c1, d5), (a38, b3, c1, d6), (a38, b3, c1, d7), (a38, b3, c1, d8), (a38, b3, c1, d9), (a38, b3, c1, d10), (a38, b3, c1, d11), (a38, b3, c1, d12), (a38, b3, c1, d13), (a38, b3, c1, d14), (a38, b3, c1, d15), (a38, b3, c1, d16), (a38, b3, c1, d17), (a38, b3, c1, d18), (a38, b3, c1, d19), (a38, b3, c1, d20), (a38, b3, c1, d21), (a38, b3, c1, d22), (a38, b3, c2, d1), (a38, b3, c2, d2), (a38, b3, c2, d3), (a38, b3, c2, d4), (a38, b3, c2, d5), (a38, b3, c2, d6), (a38, b3, c2, d7), (a38, b3, c2, d8), (a38, b3, c2, d9), (a38, b3, c2, d10), (a38, b3, c2, d11), (a38, b3, c2, d12), (a38, b3, c2, d13), (a38, b3, c2, d14), (a38, b3, c2, d15), (a38, b3, c2, d16), (a38, b3, c2, d17), (a38, b3, c2, d18), (a38, b3, c2, d19), (a38, b3, c2, d20), (a38, b3, c2, d21), (a38, b3, c2, d22), (a38, b3, c3, d1), (a38, b3, c3, d2), (a38, b3, c3, d3), (a38, b3, c3, d4), (a38, b3, c3, d5), (a38, b3, c3, d6), (a38, b3, c3, d7), (a38, b3, c3, d8), (a38, b3, c3, d9), (a38, b3, c3, d10), (a38, b3, c3, d11), (a38, b3, c3, d12), (a38, b3, c3, d13), (a38, b3, c3, d14), (a38, b3, c3, d15), (a38, b3, c3, d16), (a38, b3, c3, d17), (a38, b3, c3, d18), (a38, b3, c3, d19), (a38, b3, c3, d20), (a38, b3, c3, d21), (a38, b3, c3, d22), (a38, b4, c1, d1), (a38, b4, c1, d2), (a38, b4, c1, d3), (a38, b4, c1, d4), (a38, b4, c1, d5), (a38, b4, c1, d6), (a38, b4, c1, d7), (a38, b4, c1, d8), (a38, b4, c1, d9), (a38, b4, c1, d10), (a38, b4, c1, d11), (a38, b4, c1, d12), (a38, b4, c1, d13), (a38, b4, c1, d14), (a38, b4, c1, d15), (a38, b4, c1, d16), (a38, b4, c1, d17), (a38, b4, c1, d18), (a38, b4, c1, d19), (a38, b4, c1, d20), (a38, b4, c1, d21), (a38, b4, c1, d22), (a38, b4, c2, d1), (a38, b4, c2, d2), (a38, b4, c2, d3), (a38, b4, c2, d4), (a38, b4, c2, d5), (a38, b4, c2, d6), (a38, b4, c2, d7), (a38, b4, c2, d8), (a38, b4, c2, d9), (a38, b4, c2, d10), (a38, b4, c2, d11), (a38, b4, c2, d12), (a38, b4, c2, d13), (a38, b4, c2, d14), (a38, b4, c2, d15), (a38, b4, c2, d16), (a38, b4, c2, d17), (a38, b4, c2, d18), (a38, b4, c2, d19), (a38, b4, c2, d20), (a38, b4, c2, d21), (a38, b4, c2, d22), (a38, b4, c3, d1), (a38, b4, c3, d2), (a38, b4, c3, d3), (a38, b4, c3, d4), (a38, b4, c3, d5), (a38, b4, c3, d6), (a38, b4, c3, d7), (a38, b4, c3, d8), (a38, b4, c3, d9), (a38, b4, c3, d10), (a38, b4, c3, d11), (a38, b4, c3, d12), (a38, b4, c3, d13), (a38, b4, c3, d14), (a38, b4, c3, d15), (a38, b4, c3, d16), (a38, b4, c3, d17), (a38, b4, c3, d18), (a38, b4, c3, d19), (a38, b4, c3, d20), (a38, b4, c3, d21), (a38, b4, c3, d22), (a38, b5, c1, d1), (a38, b5, c1, d2), (a38, b5, c1, d3), (a38, b5, c1, d4), (a38, b5, c1, d5), (a38, b5, c1, d6), (a38, b5, c1, d7), (a38, b5, c1, d8), (a38, b5, c1, d9), (a38, b5, c1, d10), (a38, b5, c1, d11), (a38, b5, c1, d12), (a38, b5, c1, d13), (a38, b5, c1, d14), (a38, b5, c1, d5), (a38, b5, c1, d16), (a38, b5, c1, d17), (a38, b5, c1, d18), (a38, b5, c1, d19), (a38, b5, c1, d20), (a38, b5, c1, d21), (a38, b5, c1, d22), (a38, b5, c2, d1), (a38, b5, c2, d2), (a38, b5, c2, d3), (a38, b5, c2, d4), (a38, b5, c2, d5), (a38, b5, c2, d6), (a38, b5, c2, d7), (a38, b5, c2, d8), (a38, b5, c2, d9), (a38, b5, c2, d10), (a38, b5, c2, d11), (a38, b5, c2, d12), (a38, b5, c2, d13), (a38, b5, c2, d14), (a38, b5, c2, d15), (a38, b5, c2, d16), (a38, b5, c2, d17), (a38, b5, c2, d18), (a38, b5, c2, d19), (a38, b5, c2, d20), (a38, b5, c2, d21), (a38, b5, c2, d22), (a38, b5, c3, d1), (a38, b5, c3, d2), (a38, b5, c3, d3), (a38, b5, c3, d4), (a38, b5, c3, d5), (a38, b5, c3, d6), (a38, b5, c3, d7), (a38, b5, c3, d8), (a38, b5, c3, d9), (a38, b5, c3, d1), (a38, b5, c3, d11), (a38, b5, c3, d12), (a38, b5, c3, d13), (a38, b5, c3, d14), (a38, b5, c3, d15), (a38, b5, c3, d6), (a38, b5, c3, d17), (a38, b5, c3, d18), (a38, b5, c3, d19), (a38, b5, c3, d20), (a38, b5, c3, d21), (a38, b5, c3, d22), (a38, b6, c1, d1), (a38, b6, c1, d2), (a38, b6, c1, d3), (a38, b6, c1, d4), (a38, b6, c1, d5), (a38, b6, c1, d6), (a38, b6, c1, d7), (a38, b6, c1, d8), (a38, b6, c1, d9), (a38, b6, c1, d10), (a38, b6, c1, d11), (a38, b6, c1, d12), (a38, b6, c1, d13), (a38, b6, c1, d14), (a38, b6, c1, d15), (a38, b6, c1, d16), (a38, b6, c1, d17), (a38, b6, c1, d18), (a38, b6, c1, d19), (a38, b6, c1, d20), (a38, b6, c1, d21), (a38, b6, c1, d22), (a38, b6, c2, d1), (a38, b6, c2, d2), (a38, b6, c2, d3), (a38, b6, c2, d4), (a38, b6, c2, d5), (a38, b6, c2, d6), (a38, b6, c2, d7), (a38, b6, c2, d8), (a38, b6, c2, d9), (a38, b6, c2, d10), (a38, b6, c2, d11), (a38, b6, c2, d12), (a38, b6, c2, d13), (a38, b6, c2, d14), (a38, b6, c2, d15), (a38, b6, c2, d16), (a38, b6, c2, d17), (a38, b6, c2, d18), (a38, b6, c2, d19), (a38, b6, c2, d20), (a38, b6, c2, d21), (a38, b6, c2, d22), (a38, b6, c3, d1), (a38, b6, c3, d2), (a38, b6, c3, d3), (a38, b6, c3, d4), (a38, b6, c3, d5), (a38, b6, c3, d6), (a38, b6, c3, d7), (a38, b6, c3, d8), (a38, b6, c3, d9), (a38, b6, c3, d10), (a38, b6, c3, d11), (a38, b6, c3, d12), (a38, b6, c3, d13), (a38, b6, c3, d14), (a38, b6, c3, d15), (a38, b6, c3, d16), (a38, b6, c3, d17), (a38, b6, c3, d18), (a38, b6, c3, d19), (a38, b6, c3, d20), (a38, b6, c3, d21), (a38, b6, c3, d22), (a39, b1, c1, d1), (a39, b1, c1, d2), (a39, b1, c1, d3), (a39, b1, c1, d4), (a39, b1, c1, d5), (a39, b1, c1, d6), (a39, b1, c1, d7), (a39, b1, c1, d8), (a39, b1, c1, d9), (a39, b1, c1, d10), (a39, b1, c1, d11), (a39, b1, c1, d12), (a39, b1, c1, d13), (a39, b1, c1, d14), (a39, b1, c1, d13), (a39, b1, c1, d16), (a39, b1, c1, d17), (a39, b1, c1, d18), (a39, b1, c1, d19), (a39, b1, c1, d20), (a39, b1, c1, d21), (a39, b1, c1, d22), (a39, b1, c2, d1), (a39, b1, c2, d2), (a39, b1, c2, d3), (a39, b1, c2, d4), (a39, b1, c2, d5), (a39, b1, c2, d6), (a39, b1, c2, d7), (a39, b1, c2, d8), (a39, b1, c2, d9), (a39, b1, c2, d10), (a39, b1, c2, d11), (a39, b1, c2, d12), (a39, b1, c2, d13), (a39, b1, c2, d14), (a39, b1, c2, d15), (a39, b1, c2, d10), (a39, b1, c2, d17), (a39, b1, c2, d18), (a39, b1, c2, d19), (a39, b1, c2, d20), (a39, b1, c2, d21), (a39, b1, c2, d22), (a39, b1, c3, d1), (a39, b1, c3, d2), (a39, b1, c3, d3), (a39, b1, c3, d4), (a39, b1, c3, d5), (a39, b1, c3, d6), (a39, b1, c3, d7), (a39, b1, c3, d8), (a39, b1, c3, d9), (a39, b1, c3, d10), (a39, b1, c3, d11), (a39, b1, c3, d12), (a39, b1, c3, d13), (a39, b1, c3, d14), (a39, b1, c3, d15), (a39, b1, c3, d16), (a39, b1, c3, d17), (a39, b1, c3, d18), (a39, b1, c3, d19), (a39, b1, c3, d20), (a39, b1, c3, d21), (a39, b1, c3, d22), (a39, b2, c1, d1), (a39, b2, c1, d2), (a39, b2, c1, d3), (a39, b2, c1, d4), (a39, b2, c1, d5), (a39, b2, c1, d6), (a39, b2, c1, d7), (a39, b2, c1, d8), (a39, b2, c1, d9), (a39, b2, c1, d10), (a39, b2, c1, d11), (a39, b2, c1, d12), (a39, b2, c1, d13), (a39, b2, c1, d14), (a39, b2, c1, d15), (a39, b2, c1, d6), (a39, b2, c1, d17), (a39, b2, c1, d18), (a39, b2, c1, d19), (a39, b2, c1, d20), (a39, b2, c1, d21), (a39, b2, c1, d22), (a39, b2, c2, d1), (a39, b2, c2, d2), (a39, b2, c2, d3), (a39, b2, c2, d4), (a39, b2, c2, d5), (a39, b2, c2, d6), (a39, b2, c2, d7), (a39, b2, c2, d8), (a39, b2, c2, d9), (a39, b2, c2, d10), (a39, b2, c2, d11), (a39, b2, c2, d12), (a39, b2, c2, d13), (a39, b2, c2, d14), (a39, b2, c2, d15), (a39, b2, c2, d16), (a39, b2, c2, d17), (a39, b2, c2, d18), (a39, b2, c2, d19), (a39, b2, c2, d20), (a39, b2, c2, (d21), (a39, b2, c2, d22), (a39, b2, c3, d1), (a39, b2, c3, d2), (a39, b2, c3, d3), (a39, b2, c3, d4), (a39, b2, c3, d5), (a39, b2, c3, d6), (a39, b2, c3, d7), (a39, b2, c3, d8), (a39, b2, c3, d9), (a39, b2, c3, d10), (a39, b2, c3, d11), (a39, b2, c3, d12), (a39, b2, c3, d13), (a39, b2, c3, d14), (a39, b2, c3, d15), (a39, b2, c3, d16), (a39, b2, c3, d17), (a39, b2, c3, d18), (a39, b2, c3, d19), (a39, b2, c3, d20), (a39, b2, c3, d21), (a39, b2, c3, d22), (a39, b3, c1, d1), (a39, b3, c1, d2), (a39, b3, c1, d3), (a39, b3, c1, d4), (a39, b3, c1, d5), (a39, b3, c1, d6), (a39, b3, c1, d7), (a39, b3, c1, d8), (a39, b3, c1, d9), (a39, b3, c1, d10), (a39, b3, c1, d11), (a39, b3, c1, d12), (a39, b3, c1, d13), (a39, b3, c1, d14), (a39, b3, c1, d15), (a39, b3, c1, d16), (a39, b3, c1, d17), (a39, b3, c1, d18), (a39, b3, c1, d19), (a39, b3, c1, d20), (a39, b3, c1, d21), (a39, b3, c1, d22), (a39, b3, c2, d1), (a39, b3, c2, d2), (a39, b3, c2, d3), (a39, b3, c2, d4), (a39, b3, c2, d5), (a39, b3, c2, d6), (a39, b3, c2, d7), (a39, b3, c2, d8), (a39, b3, c2, d9), (a39, b3, c2, d10), (a39, b3, c2, d11), (a39, b3, c2, d12), (a39, b3, c2, d13), (a39, b3, c2, d14), (a39, b3, c2, d15), (a39, b3, c2, d16), (a39, b3, c2, d17), (a39, b3, c2, d18), (a39, b3, c2, d19), (a39, b3, c2, d20), (a39, b3, c2, d21), (a39, b3, c2, d22), (a39, b3, c3, d1), (a39, b3, c3, d2), (a39, b3, c3, d3), (a39, b3, c3, d4), (a39, b3, c3, d5), (a39, b3, c3, d6), (a39, b3, c3, d7), (a39, b3, c3, d8), (a39, b3, c3, d9), (a39, b3, c3, d10), (a39, b3, c3, d11), (a39, b3, c3, d12), (a39, b3, c3, d13), (a39, b3, c3, d14), (a39, b3, c3, d15), (a39, b3, c3, d16), (a39, b3, c3, d17), (a39, b3, c3, d18), (a39, b3, c3, d19), (a39, b3, c3, d20), (a39, b3, c3, d21), (a39, b3, c3, d22), (a39, b4, c1, d1), (a39, b4, c1, d2), (a39, b4, c1, d3), (a39, b4, c1, d4), (a39, b4, c1, d5), (a39, b4, c1, d6), (a39, b4, c1, d7), (a39, b4, c1, d8), (a39, b4, c1, d9), (a39, b4, c1, d10), (a39, b4, c1, d11), (a39, b4, c1, d12), (a39, b4, c1, d13), (a39, b4, c1, d14), (a39, b4, c1, d15), (a39, b4, c1, d16), (a39, b4, c1, d17), (a39, b4, c1, d18), (a39, b4, c1, d19), (a39, b4, c1, d20), (a39, b4, c1, d21), (a39, b4, c1, d22), (a39, b4, c2, d1), (a39, b4, c2, d2), (a39, b4, c2, d3), (a39, b4, c2, d4), (a39, b4, c2, d5), (a39, b4, c2, d6), (a39, b4, c2, d7), (a39, b4, c2, d8), (a39, b4, c2, d9), (a39, b4, c2, d10), (a39, b4, c2, d11), (a39, b4, c2, d12), (a39, b4, c2, d13), (a39, b4, c2, d14), (a39, b4, c2, d15), (a39, b4, c2, d10), (a39, b4, c2, d17), (a39, b4, c2, d18), (a39, b4, c2, d19), (a39, b4, c2, d20), (a39, b4, c2, d21), (a39, b4, c2, d22), (a39, b4, c3, d1), (a39, b4, c3, d2), (a39, b4, c3, d3), (a39, b4, c3, d4), (a39, b4, c3, d5), (a39, b4, c3, d6), (a39, b4, c3, d7), (a39, b4, c3, d8), (a39, b4, c3, d9), (a39, b4, c3, d10), (a39, b4, c3, d11), (a39, b4, c3, d12), (a39, b4, c3, d13), (a39, b4, c3, d14), (a39, b4, c3, d15), (a39, b4, c3, d16), (a39, b4, c3, d17), (a39, b4, c3, d18), (a39, b4, c3, d19), (a39, b4, c3, d20), (a39, b4, c3, d21), (a39, b4, c3, d22), (a39, b5, c1, d1), (a39, b5, c1, d2), (a39, b5, c1, d3), (a39, b5, c1, d4), (a39, b5, c1, d5), (a39, b5, c1, d6), (a39, b5, c1, d7), (a39, b5, c1, d8), (a39, b5, c1, d9), (a39, b5, c1, d10), (a39, b5, c1, d11), (a39, b5, c1, d12), (a39, b5, c1, d13), (a39, b5, c1, d14), (a39, b5, c1, d15), (a39, b5, c1, d16), (a39, b5, c1, d17), (a39, b5, c1, d18), (a39, b5, c1, d19), (a39, b5, c1, d20), (a39, b5, c1, d21), (a39, b5, c1, d22), (a39, b5, c2, d1), (a39, b5, c2, d2), (a39, b5, c2, d3), (a39, b5, c2, d4), (a39, b5, c2, d5), (a39, b5, c2, d6), (a39, b5, c2, d7), (a39, b5, c2, d8), (a39, b5, c2, d9), (a39, b5, c2, d10), (a39, b5, c2, d11), (a39, b5, c2, d12), (a39, b5, c2, d13), (a39, b5, c2, d14), (a39, b5, c2, d15), (a39, b5, c2, d16), (a39, b5, c2, d17), (a39, b5, c2, d18), (a39, b5, c2, d19), (a39, b5, c2, d20), (a39, b5, c2, d21), (a39, b5, c2, d22), (a39, b5, c3, d1), (a39, b5, c3, d2), (a39, b5, c3, d3), (a39, b5, c3, d4), (a39, b5, c3, d5), (a39, b5, c3, d6), (a39, b5, c3, d7), (a39, b5, c3, d8), (a39, b5, c3, d9), (a39, b5, c3, d10), (a39, b5, c3, d11), (a39, b5, c3, d12), (a39, b5, c3, d13), (a39, b5, c3, d14), (a39, b5, c3, d15), (a39, b5, c3, d16), (a39, b5, c3, d17), (a39, b5, c3, d18), (a39, b5, c3, d19), (a39, b5, c3, d20), (a39, b5, c3, d21), (a39, b5, c3, d22), (a39, b6, c1, d1), (a39, b6, c1, d2), (a39, b6, c1, d3), (a39, b6, c1, d4), (a39, b6, c1, d5), (a39, b6, c1, d16), (a39, b6, c1, d7), (a39, b6, c1, d8), (a39, b6, c1, d9), (a39, b6, c1, d10), (a39, b6, c1, d11), (a39, b6, c1, d12), (a39, b6, c1, d13), (a39, b6, c1, d14), (a39, b6, c1, d15), (a39, b6, c1, d16), (a39, b6, c1, d17), (a39, b6, c1, d18), (a39, b6, c1, d19), (a39, b6, c1, d20), (a39, b6, c1, d21), (a39, b6, c1, d22), (a39, b6, c2, d1), (a39, b6, c2, d2), (a39, b6, c2, d3), (a39, b6, c2, d4), (a39, b6, c2, d5), (a39, b6, c2, d6), (a39, b6, c2, d7), (a39, b6, c2, d8), (a39, b6, c2, d9), (a39, b6, c2, d10), (a39, b6, c2, d11), (a39, b6, c2, d12), (a39, b6, c2, d13), (a39, b6, c2, d14), (a39, b6, c2, d15), (a39, b6, c2, d16), (a39, b6, c2, d17), (a39, b6, c2, d18), (a39, b6, c2, d19), (a39, b6, c2, d20), (a39, b6, c2, d21), (a39, b6, c2, d22), (a39, b6, c3, d1), (a39, b6, c3, d2), (a39, b6, c3, d3), (a39, b6, c3, d4), (a39, b6, c3, d5), (a39, b6, c3, d6), (a39, b6, c3, d7), (a39, b3, c3, c8), (a39, b6, c3, d9), (a39, b6, c3, d10), (a39, b6, c3, d11), (a39, b6, c3, d12), (a39, b6, c3, d13), (a39, b6, c3, d14), (a39, b6, c3, d15), (a39, b6, c3, d16), (a39, b6, c3, d17), (a39, b6, c3, d18), (a39, b6, c3, d19), (a39, b6, c3, d20), (a39, b6, c3, d21), (a39, b6, c3, d22), (a40, b1, c1, d1), (a40, b1, c1, d2), (a40, b1, c1, d3), (a40, b1, c1, d4), (a40, b1, c1, d5), (a40, b1, c1, d6), (a40, b1, c1, d7), (a40, b1, c1, d8), (a40, b1, c1, d9), (a40, b1, c1, d10), (a40, b1, c1, d11), (a40, b1, c1, d12), (a40, b1, c1, d13), (a40, b1, c1, d14), (a40, b1, c1, d15), (a40, b1, c1, d16), (a40, b1, c1, d17), (a40, b1, c1, d18), (a40, b1, c1, d19), (a40, b1, c1, d20), (a40, b1, c1, d21), (a40, b1, c1, d22), (a40, b1, c2, d1), (a40, b1, c2, d2), (a40, b1, c2, d3), (a40, b1, c2, d4), (a40, b1, c2, d5), (a40, b1, c2, d6), (a40, b1, c2, d7), (a40, b1, c2, d8), (a40, b1, c2, d9), (a40, b1, c2, d10), (a40, b1, c2, d11), (a40, b1, c2, d12), (a40, b1, c2, d13), (a40, b1, c2, d14), (a40, b1, c2, d15), (a40, b1, c2, d16), (a40, b1, c2, d17), (a40, b1, c2, d18), (a40, b1, c2, d19), (a40, b1, c2, d20), (a40, b1, c2, d21), (a40, b1, c2, d22), (a40, b1, c3, d1), (a40, b1, c3, d2), (a40, b1, c3, d3), (a40, b1, c3, d4), (a40, b1, c3, d5), (a40, b1, c3, d6), (a40, b1, c3, d7), (a40, b1, c3, d8), (a40, b1, c3, d9), (a40, b1, c3, d10), (a40, b1, c3, d11), (a40, b1, c3, d12), (a40, b1, c3, d13), (a40, b1, c3, d14), (a40, b1, c3, d15), (a40, b1, c3, d16), (a40, b1, c3, d17), (a40, b1, c3, d18), (a40, b1, c3, d19), (a40, b1, c3, d20), (a40, b1, c3, d21), (a40, b1, c3, d22), (a40, b2, c1, d1), (a40, b2, c1, d2), (a40, b2, c1, d3), (a40, b2, c1, d4), (a40, b2, c1, d5), (a40, b2, c1, d6), (a40, b2, c1, d7), (a40, b2, c1, d8), (a40, b2, c1, d9), (a40, b2, c1, d10), (a40, b2, c1, d11), (a40, b2, c1, d12), (a40, b2, c1, d13), (a40, b2, c1, d14), (a40, b2, c1, d15), (a40, b2, c1, d16), (a40, b2, c1, d17), (a40, b2, c1, d18), (a40, b2, c1, d19), (a40, b2, c1, d20), (a40, b2, c1, d21), (a40, b2, c1, d22), (a40, b2, c2, d1), (a40, b2, c2, d2), (a40, b2, c2, d3), (a40, b2, c2, d4), (a40, b2, c2, d5), (a40, b2, c2, d6), (a40, b2, c2, d7), (a40, b2, c2, d8), (a40, b2, c2, d9), (a40, b2, c2, d10), (a40, b2, c2, d11), (a40, b2, c2, d12), (a40, b2, c2, d13), (a40, b2, c2, d14), (a40, b2, c2, d15), (a40, b2, c2, d16), (a40, b2, c2, d17), (a40, b2, c2, d18), (a40, b2, c2, d19), (a40, b2, c2, d20), (a40, b2, c2, d21), (a40, b2, c2, d22), (a40, b2, c3, d1), (a40, b2, c3, d2), (a40, b2, c3, d3), (a40, b2, c3, d4), (a40, b2, c3, d5), (a40, b2, c3, d6), (a40, b2, c3, d7), (a40, b2, c3, d8), (a40, b2, c3, d9), (a40, b2, c3, d10), (a40, b2, c3, d11), (a40, b2, c3, d12), (a40, b2, c3, d13), (a40, b2, c3, d14), (a40, b2, c3, d15), (a40, b2, c3, d16), (a40, b2, c3, d17), (a40, b2, c3, d18), (a40, b2, c3, d19), (a40, b2, c3, d20), (a40, b2, c3, d21), (a40, b2, c3, d22), (a40, b3, c1, d1), (a40, b3, c1, d2), (a40, b3, c1, d3), (a40, b3, c1, d4), (a40, b3, c1, d5), (a40, b3, c1, d6), (a40, b3, c1, d7), (a40, b3, c1, d8), (a40, b3, c1, d9), (a40, b3, c1, d10), (a40, b3, c1, d11), (a40, b3, c1, d12), (a40, b3, c1, d13), (a40, b3, c1, d14), (a40, b3, c1, d15), (a40, b3, c1, d16), (a40, b3, c1, d17), (a40, b3, c1, d18), (a40, b3, c1, d19), (a40, b3, c1, d20), (a40, b3, c1, d21), (a40, b3, c1, d22), (a40, b3, c2, d1), (a40, b3, c2, d2), (a40, b3, c2, d3), (a40, b3, c2, d4), (a40, b3, c2, d5), (a40, b3, c2, d6), (a40, b3, c2, d7), (a40, b3, c2, d8), (a40, b3, c2, d9), (a40, b3, c2, d10), (a40, b3, c2, d11), (a40, b3, c2, d12), (a40, b3, c2, d13), (a40, b3, c2, d14), (a40, b3, c2, d15), (a40, b3, c2, d16), (a40, b3, c2, d17), (a40, b3, c2, d18), (a40, b3, c2, d19), (a40, b3, c2, d20), (a40, b3, c2, d21), (a40, b3, c2, d22), (a40, b3, c3, d1), (a40, b3, c3, d2), (a40, b3, c3, d3), (a40, b3, c3, d4), (a40, b3, c3, d5), (a40, b3, c3, d6), (a40, b3, c3, d7), (a40, b3, c3, d8), (a40, b3, c3, d9), (a4, b3, c3, d10), (a40, b3, c3, d11), (a40, b3, c3, d12), (a40, b3, c3, d13), (a40, b3, c3, d14), (a40, b3, c3, d15), (a40, b3, c3, d16), (a40, b3, c3, d17), (a40, b3, c3, d18), (a40, b3, c3, d19), (a40, b3, c3, d20), (a40, b3, c3, d21), (a40, b3, c3, d22), (a40, b4, c1, d1), (a40, b4, c1, d2), (a40, b4, c1, d3), (a40, b4, c1, d4), (a40, b4, c1, d5), (a40, b4, c1, d6), (a40, b4, c1, d7), (a40, b4, c1, d8), (a40, b4, c1, d9), (a40, b4, c1, d10), (a40, b4, c1, d11), (a40, b4, c1, d12), (a40, b4, c1, d13), (a40, b4, c1, d14), (a40, b4, c1, d15), (a40, b4, c1, d16), (a40, b4, c1, d17), (a40, b4, c1, d18), (a40, b4, c1, d19), (a40, b4, c1, d20), (a40, b4, c1, d21), (a40, b4, c1, d22), (a40, b4, c2, d1), (a40, b4, c2, d2), (a40, b4, c2, d3), (a40, b4, c2, d4), (a40, b4, c2, d5), (a40, b4, c2, d6), (a40, b4, c2, d7), (a40, b4, c2, d8), (a40, b4, c2, d9), (a40, b4, c2, d10), (a40, b4, c2, d11), (a40, b4, c2, d12), (a40, b4, c2, d13), (a40, b4, c2, d14), (a40, b4, c2, d15), (a40, b4, c2, d16), (a40, b4, c2, d17), (a40, b4, c2, d18), (a40, b4, c2, d19), (a40, b4, c2, d20), (a40, b4, c2, d21), (a40, b4, c2, d22), (a40, b4, c3, d1), (a40, b4, c3, d2), (a40, b4, c3, d3), (a40, b4, c3, d4), (a40, b4, c3, d5), (a40, b4, c3, d6), (a40, b4, c3, d7), (a40, b4, c3, d8), (a40, b4, c3, d9), (a40, b4, c3, d10), (a40, b4, c3, d11), (a40, b4, c3, d12), (a40, b4, c3, d13), (a40, b4, c3, d14), (a40, b4, c3, d15), (a40, b4, c3, d16), (a40, b4, c3, d17), (a40, b4, c3, d18), (a40, b4, c3, d19), (a40, b4, c3, d20), (a40, b4, c3, d21), (a40, b4, c3, d22), (a40, b5, c1, d1), (a40, b5, c1, d2), (a40, b5, c1, d3), (a40, b5), c1, d4), (a40, b5, c1, d5), (a40, b5, c1, (d6), (a40, b5, c1, d7), (a40, b5, c1, d8, (a40, b5, c1, d9), (a40, b5, c1, d10), (a40, b5, c1, d11), (a40, b5, c1, d12), (a40, b5, c1, d13), (a40, b5, c1, d14), (a40, b5, c1, d15), (a40, b5, c1, d16), (a40, b5, c1, d17), (a40, b5, c1, d18), (a40, b5, c1, d19), (a40, b5, c1, d20), (a40, b5, c1, d21), (a40, b5, c1, d22), (a40, b5, c2, d1), (a40, b5, c2, d2), (a40, b5, c2, d3), (a40, b5, c2, d4), (a40, b5, c2, d5), (a40, b5, c2, d6), (a40, b5, c2, d7), (a40 b5, c2, d8), (a40, b5, c2, d9), (a40, b5, c2, d10), (40, b5, c2, d11), (a40, b5, c2, d12), (a40, b5, c2, d13), (a40, b5, c2, d14), (a40, b5, c2, d15), (a40, b5, c2, d16), (a40, b5, c2, d17), (a40, b5, c2, d18), (a40, b5, c2, d19), (a40, b5, c2, d20), (a40, b5, c2, d21), (a40, b5, c2, d22), (a40, b5, c3, d1), (a40, b5, c3, d2), (a40, b5, c3, d3), (a40, b5, c3, d4), (a40, b5, c3, d5), (a40, b5, c3, d6), (a40, b5, c3, d7), (a40, b5, c3, d8), (a40, b5, c3, d9), (a40, b5, c3, d10), (a40, b5, c3, d11), (a40, b5, c3, d12), (a40, b5, c3, d13), (a40, b5, c3, d14), (a40, b5, c3, d15), (a40, b5, c3, d16), (a40, b5, c3, d17), (a40, b5, c3, d18), (a40, b5, c3, d19), (a40, b5, c3, d20), (a40, b5, c3, d21), (a40, b5, c3, d22), (a40, b6, c1, d1), (a40, b6, c1, d2), (a40, b6, c1, d3), (a40, b6, c1, d4), (a40, b6, c1, d5), (a40, b6, c1, d6), (a40, b6, c1, d7), (a40, b6, c1, d8), (a40, b6, c1, d9), (a40, b6, c1, d10), (a40, b6, c1, d11), (a40, b6, c1, d12), (a40, b6, c1, d13), (a40, b6, c1, d14), (a40, b6, c1, d15), (a40, b6, c1, d16), (a40, b6, c1, d17), (a40, b6, c1, d18), (a40, b6, c1, d19), (a40, b6, c1, d20), (a40, b6, c1, d21), (a40, b6, c1, d22), (a40, b6, c2, d1), (a40, b6, c2, d2), (a40, b6, c2, d3), (a40, b6, c2, d4), (a40, b6, c2, d5), (a40, b6, c2, d6), (a40, b6, c2, d7), (a40, b6, c2, d8), (a40, b6, c2, d9), (a40, b6, c2, d10), (a40, b6, c2, d11), (a40, b6, c2, d12), (a40, b6, c2, d13), (a40, b6, c2, d14), (a40, b6, c2, d15), (a40, b6, c2, d16), (a40, b6, c2, d17), (a40, b6, c2, d18), (a40, b6, c2, d19), (a40, b6, c2, d20), (a40, b6, c2, d21), (a40, b6, c2, d22), (a40, b6, c3, d1), (a40, b6, c3, d2), (a40, b6, c3, d3), (a40, b6, c3, d4), (a40, b6, c3, d5), (a40, b6, c3, d6), (a40, b6, c3, d7), (a40, b6, c3, d8), (a40, b6, c3, d9), (a40, b6, c3, d10), (a40, b6, c3, d11), (a40, b6, c3, d12), (a40, b6, c3, d13), (a40, b6, c3, d14), (a40, b6, c3, d15), (a40, b6, c3, d16), (a40, b6, c3, d17), (a40, b6, c3, d18), (a40, b6, c3, d19), (a40, b6, c3, d20), (a40, b6, c3, d21), (a40, b6, c3, d22), (a41, b1, c1, d1), (a41, b1, c1, d2), (a41, b1, c1, d3), (a41, b1, c1, d4), (a41, b1, c1, d5), (a41, b1, c1, d6), (a41, b1, c1, d7), (a41, b1, c1, d8), (a41, b1, c1, d9), (a41, b1, c1, d10), (a41, b1, c1 d11), (a41, b1, c1, d12), (a41, b1, c1, d13), (a41, b1, c1, d14), (a41, b1, c1, d15), (a41, b1, c1, d16), (a41, b1, c1, d17), (a41, b1, c1, d18), (a41, b1, c1, d19), (a41, b1, c1, d20), (a41, b1, c1, d21), (a41, b1, c1, d22), (a41, b1, c2, d1), (a41, b1, c2, d2), (a41, b1, c2, d3), (a41, b1, c2, d4), (a41, b1, c2, d5), (a41, b1, c2, d6), (a41, b1, c2, d7), (a41, b1, c2, d5), (a41, b1, c2, d9), (a41, b1, c2, d10), (a41, b1, c2, d11), (a41, b1, c2, d12), (a41, b1, c2, d13), (a41, b1, c2, d14), (a41, b1, c2, d15), (a41, b1, c2, d16), (a41, b1, c2, d17), (a41, b1, c2, d18), (a41, b1, c2, d19), (a41, b1, c2, d20), (a41, b1, c2, d21), (a41, b1, c2, d22), (a41, b1, c3, d1), (a41, b1, c3, d2), (a41, b1, c3, d3), (a41, b1, c3, d4), (a41, b1, c3, d5), (a41, b1, c3, d6), (a41, b1, c3, d7), (a41, b1, c3, d8), (a41, b1, c3, d9), (a41, b1, c3, d10), (a41, b1, c3, d11), (a41, b1, c3, d12), (a41, b1, c3, d13), (a41, b1, c3, d14), (a41, b1, c3, d15), (a41, b1, c3, d16), (a41, b1, c3, d17), (a41, b1, c3, d18), (a41, b1, c3, d19), (a41, b1, c3, d20), (a41, b1, c3, d21), (a41, b1, c3, d22), (a41, b2, c1, d1), (a41, b2, c1, d2), (a41, b2, c1, d3), (a41, b2, c1, d4), (a41, b2, c1, d5), (a41, b2, c1, d6), (a41, b2, c1, d7), (a41, b2, c1, d8), (a41, b2, c1, d9), (a41, b2, c1, d10), (a41, b2, c1, d11), (a41, b2, c1, d12), (a41, b2, c1, d13), (a41, b2, d14), (a41) b2, c1, d15), (a41, b2, c1, d16), (a41, b2, c1, d17), (a41, b2, c1, d18), (a41, b2, c1, d19), (a41, b2, c1, d20), (a41, b2, c1, d21), (a41, b2, c1, d22), (a41, b2, c2, d1), (a41, b2, c2, d2), (a41, b2, c2, d3), (a41, b2, c2, d4), (a41, b2, c2, d5), (a41, b2, c2, d6), (a41, b2, c2, d7), (a41, b2, c2, d8), (a41, b2, c2, d9), (a41, b2, c2, d10), (a41, b2, c2, d11), (a41, b2, c2, d12), (a41, b2, c2, d13), (a41, b2, c2, d14), (a41, b2, c2, d15), (a41, b2, c2, d16), (a41, b2, c2, d17), (a41, b2, c2, d18), (a41, b2, c2, d19), (a41, b2, c2, c2, d20), (a41, b2, c2, d21), (a41, b2, c2, d22), (a41, b2, c3, d1), (a41, b2, c3, d2), (a41, b2, c3, d3), (a41, b2, c3, d4), (a41, b2, c3, d5), (a41, b2, c3, d6), (a41, b2, c3, d7), (a41, b2, c3, d8), (a41, b2, c3, d9), (a41, b2, c3, d10), (a41, b2, c3, d11), (a41, b2, c3, d12), (a41, b2, c3, d13), (a41, b2, c3, d14), (a41, b2, c3, d15), (a41, b2, c3, d16), (a41, b2, c3, d17), (a41, b2, c3, d18), (a41, b2, c3, d19), (a41, b2, c3, d20), (a41, b2, c3, d21), (a41, b2, c3, d22), (a41, b3, c1, d1), (a41, b3, c1, d2), (a41, b3, c1, d13), (a41, b3, c1, d14), (a41, b3, c1, d5), (a41, b3, c1, d6), (a41, b3, c1, d7), (a41, b3, c1, d8), (a41, b3, c1, d9), (a41, b3, c1, d10), (a41, b3, c1, d11), (a41, b3, c1, d12), (a41, b3, c1, d13), (a41, b3, c1, d14), (a41, b3, c1, d15), (a41, b3, c1, d16), (a41, b3, c1, d17), (a41, b3, c1, d18), (a41, b3, c1, d19), (a41, b3, c1, d20), (a41, b3, c1, d21), (a41, b3, c1, d22), (a4, b3, c2, d1), (a4, b3, c2, d2), (a41, b3, c2, d3), (a41, b3, c2, d4), (a41, b3, c2, d5), (a41, b3, c2, d6), (a41, b3, d2, d7), (a4, b3, c2, d8), (a41, b3, c2, d9), (a41, b3, c2, d10), (a41, b3, c2, d11), (a41, b3, c2, d12), (a41, b3, c2, d13), (a41, b3, c2, d14), (a41, b3, c2, d15), (a41, b3, c2, d16), (a41, b3, c2, d17), (a41, b3, c2, d18), (a41, b3, c2, d19), (a41, b3, c2, 20), (a41, b3, c2, d21), (a41, b3, c2, d22), (a41, b3, c3, d1), (a41, b3, c3, d2), (a41, b3, c3, d3), (a41, b3, c3, d4), (a41, b3, c3, d5), (a41, b3, c3, d6), (a41, b3, c3, d7), (a41, b3, c3, d8), (a41, b3, c3, d9), (a41, b3, c3, d10), (a41, b3, c3, d11), (a41, b3, c3, d12), (a41, b3, c3, d13), (a41, b3, c3, d14), (a41, b3, c3, d15), (a41, b3, c3, d16), (a41, b3, c3, d17), (a41, b3, c3, d18), (a41, b3, c3, d19), (a41, b3, c3, d20), (a41, b3, c3, d21), (a41, b3, c3, d22), (a41, b4, c1, d1), (a41, b4, c1, d2), (a41, b4, c1, d3), (a41, b4, c1, d4), (a41, b4, c1, d5), (a41, b4, c1, d6), (a41, b4, c1, d7), (a41, b4, c1, d8), (a41, b4, c1, d9), (a41, b4, c1, d10), (a41, b4, c1, d11), (a41, b4, c1, d12), (a41, b4, c1, d13), (a41, b4, c1, d14), (a41, b4, c1, d15), (a41, b4, c1, d16), (a41, b4, c1, d17), (a41, b4, c1, d18), (a41, b4, c1, d19), (a41, b4, c1, d20), (a41, b4, c1, d21), (a41, b4, c1, d22), (a41, b4, c2, d1), (a41, b4, c2, d2), (a41, b4, c2, d3), (a41, b4, c2, d4), (a41, b4, c1, d5), (a41, b4, c1, d6), (a41, b4, c2, d7), (a4, b4, c1, d8), (a41, b4, c2, d9), (a41, b4, c2, d10), (a41, b4, c2, d11), (a41, b4, c2, d12), (a41, b4, c2, d13), (a41, b4, c2, d14), (a41, c2, d15), (a41, b4, c2, d16), (a41, b4, c2, d17), (a41, b4, c2, d18), (a41, b4, c2, d19), (a41, b4, c2, d20), (a41, b4, c2, d21), (a41, b4, c2, d22), (a41, b4, c3, d1), (a41, b4, c3, d2), (a41, b4, c3, d3), (a41, b4, c3, d4), (a41, b4, c3, d5), (a41, b4, c3, d6), (a41, b4, c3, d7), (a41, b4, c3, d8), (a41, b4, c3, d9), (a41, b4, c3, d10), (a41, b4, c3, d11), (a41, b4, c3, d12), (a41, b4, c3, d13), (a41, b4, c3, d14), (a41, b4, c3, d15), (a41, b4, c3, d16), (a41, b4, c3, d17), (a41, b4, c3, d18), (a41, b4, c3, d19), (a41, b4, c3, d20), (a41, b4, c3, d21), (a41, b4, c3, d22), (a41, b5, c1, d1), (a41, b5, c1, d2), (a41, b5, c1, d3), (a41, b5, c1, d4), (a41, b5, c1, d5), (a41, b5, c1, d6), (a41, b5, c1, d7), (a41, b5, c1, d8), (a41, b5, c1, d9), (a41, b5, c1, d10), (a41, b5, c1, d11), (a41, b5, c1, d12), (a41, b5, c1, d13), (a41, b5, c1, d14), (a41, b5, c1, d15), (a41, b5, c1, d16), (a41, b5, c1, d17), (a41, b5, c1, d18), (a41, b5, c1, d19), (a41, b5, c1, d20), (a41, b5, c1, d21), (a41, b5, c1, d22), (a41, b5, c2, d1), (a41, b5, c2, d2), (a41, b5, c2, d3), (a41, b5, c2, d4), (a41, b5, c2, d5), (a41, b5, c2, d6), (a41, b5, c2, d7), (a41, b5, c2, d8), (a41, b5, c2, d9), (a41, b5, c2, d10), (a41, b5, c2, d11), (a41, b5, c2, d12), (a41, b5, c2, d13), (a41, b5, c2, d14), (a41, b5, c2, d15), (a41, b5, c2, d16), (a41, b5, c2, d17), (a41, b5, c2, d18), (a41, b5, c2, d19), (a41, b5, c2, d20), (a41, b5, c2, d21), (a41, b5, c2, d22), (a41, b5, c3, d1), (a41, b5, c3, d2), (a41, b5, c3, d3), (a41, b5, c3, d4), (a41, b5, c3, d5), (a41, b5, c3, d6), (a41, b5, c3, d7), (a41, b5, c3, d8), (a41, b5, c3, d9), (a41, b5, c3, d10), (a41, b5, c3, d11), (a41, b5, c3, d12), (a41, b5, c3, d13), (a41, b5, c3, d14), (a41, b5, c3, d15), (a41, b5, c3, d16), (a41, b5, c3, d17), (a41, b5, c3, d18), (a41, b5, c3, d19), (a41, b5, c3, d20), (a41, b5, c3, d21), (a41, b5, c3, d22), (a41, b6, c1, d1), (a41, b6, c1, d2), (a41, b6, c1, d3), (a41, b6, c1, d4), (a41, b6, c1, d5), (a41, b6, c1, d6), (a41, b6, c1, d7), (a41, b6, c1, d8), (a41, b6, c1, d9), (a41, b6, c1, d10), (a41, b6, c1, d11), (a41, b6, c1, d12), (a41, b6, c1, d13), (a41, b6, c1, d14), (a41, b6, c1, d15), (a41, b6, c1, d16), (a41, b6, c1, d17), (a41, b6, c1, d18), (a41, b6, c1, d19), (a41, b6, c1, d20), (a41, b6, c1, d21), (a41, b6, c1, d22), (a41, b6, c2, d1), (a41, b6, c2, d2), (a41, b6, c2, d3), (a41, b6, c2, d4), (a41, b6, c2, d5), (a41, b6, c2, d6), (a41, b6, c2, d7), (a41, b6, c2, d8), (a41, b6, c2, d9), (a41, b6, c2, d1), (a41, b6, c2, d11), (a41, b6, c2, d12), (a41, b6, c2, d13), (a41, b6, c2, d14), (a41, b6, c2, d15), (a41, b, c2, d16), (a41, b6, c2, d17), (a41, b6, c2, d18), (a41, b6, c2, d19), (a41, b6, c2, d20), (a41, b6, c2, d21), (a41, b6, c2, d22), (a41, b6, c3, d1), (a41, b6, c3, d2), (a41, b6, c3, d3), (a41, b6, c3, d4), (a41, b6, c3, d5), (a41, b6, c3, d6), (a41, b6, c3, d7), (a41, b6, c3, d8), (a41, b6, c3, d9), (a41, b6, c3, d10), (a41, b6, c3, d11), (a41, b6, c3, d12), (a41, b, c3, d13), (a41, b6, c3, d14), (a41, b6, c3, d15), (a41, b6, c3, d16), (a41, b6, c3, d17), (a41, b6, c3, d18), (a41, b6, c3, d19), (a41, b6, c3, d20), (a41, b6, c3, d21), (a41, b6, c3, d22), (a42, b1, c1, d1), (a42, b1, c1, d2), (a42, b1, c1, d3), (a42, b1, c1, d4), (a42, b1, c1, d5), (a42, b1, c1, d6), (a42, b1, c1, d7), (a42, b1, c1, d8), (a42, b1, c1, d9), (a42, b1, c1, d10), (a42, b1, c1, d11), (a42, b1, c1, d12), (a42, b1, c1, d13), (a42, b1, c1, d14), (a42, b1, c1, d15), (a42, b1, c1, d16), (a42, b1, c1, d17), (a42, b1, c1, d18), (a42, b1, c1, d19), (a42, b1, c1, d20), (a42, b1, c1, d21), (a42, b1, c1, d22), (a42, b1, c2, d1), (a42, b1, c2, d2), (a42, b1, c2, d3), (a42, b1, c2, d4), (a42, b1, c2, d5), (a42, b1, c2, d6), (a42, b1, c2, d7), (a42, b1, c2, d8), (a42, b1, c2, d9), (a42, b1, c2, d10), (a42, b1, c2, d11), (a42, b1, c2, d12), (a42, b1, c2, d13), (a42, b1, c2, d14), (a42, b1, c2, d15), (a42, b1, c2, d16), (a42, b1, c2, d17), (a42, b1, c2, d18), (a42, b1, c2, d19), (a42, b1, c2, d20), (a42, b1, c2, d21), (a42, b1, c2, d22), (a42, b1, c3, d1), (a42, b1, c3, d2), (a42, b1, c3, d3), (a42, b1, c3, d4), (a42, b1, c3, d5), (a42, b1, c3, d6), (a42, b1, c3, d7), (a42, b1, c3, d8), (a42, b1, c3, d9), (a42, b1, c3, d10), (a42, b1, c3, d11), (a42, b1, c3, d12), (a42, b1, c3, d13), (a42, b1, c3, d14), (a42, b1, c3, d15), (a42, b1, c3, d16), (a42, b1, c3, d17), (a42, b1, c3, d18), (a42, b1, c3, d19), (a42, b1, c3, d20), (a42, b1, c3, d21), (a42, b1, c3, d22), (a42, b2, c1, d1), (a42, b2, c1, d2), (a42, b2, c1, d3), (a42, b2, c1, d4), (a42, b2, c1, d5), (a42, b2, c1, d6), (a42, b2, c1, d7), (a42, b2, c1, d8), (a42, b2, c1, d9), (a42, b2, c1, d10), (a42, b2, c1, d11), (a42, b2, c1, d12), (a42, b2, c1, d13), (a42, b2, c1, d14), (a42, b2, c1, d15), (a42, b2, c1, d16), (a42, b2, c1, d17), (a42, b2, c1, d18), (a42, b2, c1, d19), (a42, b2, c1, d20), (a42, b2, c1, d21), (a42, b2, c1, d22), (a42, b2, c2, d1), (a42, b2, c2, d2), (a42, b2, c2, d3), (a42, b2, c2, d4), (a42, b2, c2, d5), (a42, b2, c2, d6), (a42, b2, c2, d7), (a42, b2, c2, d8), (a42, b2, c2, d9), (a42, b2, c2, d10), (a42, b2, c2, d11), (a42, b2, c2, d12), (a42, b2, c2, d13), (a42, b2, c2, d14), (a42, b2, c2, d15), (a42, b2, c2, d16), (a42, b2, c2, d17), (a42, b2, c2, d18) (a42, b2, c2, d19), (a42, b2, c2, d20), (a42, b2, c2, d21), (a42, b2, c2, d22), (a42, b2, c3, d), (a42, b2, c3, d2), (a42, b2, c3, d3), (a42, b2, d4), (a42, b2, c3, d5), (a42, b2, c3, d6), (a42, b2, c3, d7), (a42, b2, c3, d8), (a42, b2, c3, d9), (a42, b2, c3, d10), (a42, b2, c3, d11), (a42, b2, c3, a12), (a42, b2, c3, d13), (a42, b2, c3, d14), (a42, b2, c3, d15), (a42, b2, c3, d16), (a42, b2, c3, d17), (a42, b2, c3, d18), (a42, b2, c3, d19), (a42, b2, c3, d20), (a42, b2, c3, d21), (a42, b2, c3, d22), (a42, b3, c1, d1), (a42, b3, c1, d2), (a42, b3, c1, d3), (a42, b3, c1, d4), (a42, b3, c1, d5), (a42, b3, c1, d6), (a42, b3, c1, d7), (a42, b3, c1, d8), (a42, b3, c1, d9), (a42, b3, c1, d10), (a42, b3, c1, d11), (a42, b3, c1, d12), (a42, b3, c1, d13), (a42, b3, c1, d14), (a42, b3, c1, d15), (a42, b3, c1, d16), (a42, b3, c1, d17), (a42, b3, c1, d8), (a42, b3, c1, d9), (a42, b3, c1, d20), (a42, b3, c1, d21), (a42, b3, c1, d22), (a42, b3, c2, d1), (a42, b3, c2, d2), (a42, b3, c2, d3), (a42, b3, c2, d4), (a42, b3, c2, d5), (a42, b3, c2, d6), (a42, b3, c2, d7), (a42, b3, c2, d8), (a42, b3, c2, d9), (a42, b3, c2, d10), (a42, b5, c2, d11), (a42, b5, c2, d2), (a42, b3, c2, d13), (a42, b3, c2, d14), (a42, b3, c2, d15), (a42, b3, c2, d16), (a42, b3, c2, d17), (a42, b3, c2, d18), (a42, b3, c2, d19), (a42, b3, c2, d20), (a42, b3, c2, d21), (a42, b3, c2, d22), (a42, b3, c3, d1), (a42, b3, c3, d2), (a42, b3, c3, d3), (a42, b3, c3, d4), (a42, b3, c3, d5), (a42, b3, c3, d6), (a42, b3, c3, d7), (a42, b3, c3, d8), (a42, b3, c3, d9), (a42, b3, c3, d10), (a42, b3, c3, d11), (a42, b3, c3, d12), (a42, b3, c3, d13), (a42, b3, c3, d14), (a42, b3, c3, d15), (a42, b3, c3, d16), (a42, b3, c3, d17), (a42, b3, c3, d18), (a42, b3, c3, d19), (a42, b3, c3, d20), (a42, b3, c3, d21), (a42, b3, c3, d22), (a42, b4, c1, d1), (a42, b4, c1, d2), (a42, b4, c1, d3), (a42, b4, c1, d4), (a42, b4, c1, d5), (a42, b4, c1, d6), (a42, b4, c1, d7), (a42, b4, c1, d3), (a42, b4, c1, d9), (a42, b4, c1, die), (a42, b4, c1, d11), (a42, b4, c1, d12), (a42, b4, c1, d13), (a42, b4, c1, d14), (a42, b4, c1, d15), (a42, b4, c1, d16), (a42, b4, c1, d17), (a42, b4, c1, d18), (a42, b4, c1, d19), (a42, b4, c1, d20), (a42, b4, c1, d21), (a42, b4, c1, d22), (a42, b4, c2, d1), (a42, b4, c2, d2), (a42, b4, c2, d3), (a42, b4, c2, d4), (a42, b4, c2, d5), (a42, b4, c2, d6), (a42, b4, c2, d7), (a42, b4, c2, d8), (a42, b4, c2, d9), (a42, b4, c2, d10), (a42, b4, c2, d11), (a42, b4, c2, d12), (a42, b4, c2, d13), (a42, b4, c2, d14), (a42, b4, c2, d15), (a42, b4, c2, d16), (a42, b4, c2, d17), (a42, b4, c2, d18), (a42, b4, c2, d19), (a42, b4, c2, d20), (a42, b4, c2, d21), (a42, b4, c2, d22), (a42, b4, c3, d1), (a42, b4, c3, d2), (a42, b4, c3, d3), (a42, b4, c3, d4), (a42, b4, c3, d5), (a42, b4, c3, d6), (a42, b4, c3, d7), (a42, b4, c3, d8), (a42, b4, c3, d9), (a42, b4, c3, d10), (a42, b4, c3, d11), (a42, b4, c3, d12), (a42, b4, c3, d13), (a42, b4, c3, d14), (a42, b4, c3, d15), (a42, b4, c3, d16), (a42, b4, c3, d17), (a42, b4, c3, d18), (a42, b4, c3, d19), (a42, b4, c3, d20), (a42, b4, c3, d21), (a42, b4, c3, d22), (a42, b5, c1, d1), (a42, b5, c1, d2), (a42, b5, c1, d3), (a42, b5, c1, d4), (a42, b5, c1, d5), (a42, b5, c1, d6), (a42, b5, c1, c7), (a42, b5, c1, d8), (a42, b5, c1, d9), (a42, b5, c1, d10), (a42, b5, c1, d11), (a42, b5, c1, d12), (a42, b5, c1, d13), (a42, b5, c1, d14), (a42, b5, c1, d15), (a42, b5, c1, d16), (a42, b5, c1, d17), (a42, b5, c1, d18), (a42, b5, c1, d19), (a42, b5, c1, d20), (a42, b5, c1, d21), (a42, b5, c1, d22), (a42, b5, c2, d1), (a42, b5, c2, d2), (a42, b5, c2, d3), (a42, b5, c2, d4), (a42, b5, c2, d5), (a42, b5, c2, d6), (a42, b5, c2, d7), (a42, b5, c2, d8), (a42, b5, c2, d9), (a42, b5, c2, d10), (a42, b5, c2, d11), (a42, b5, c2, d12), (a42, b5, c2, d13), (a42, b5, c2, d14), (a42, b5, c2, d15), (a42, b5, c2, d16), (a42, b5, c2, d17), (a42, b5, c2, d18), (a42, b5, c2, d19), (a42, b5, c2, d20), (a42, b5, c2, d21), (a42, b5, c2, d22), (a42, b5, c3, d1), (a42, b5, c3, d2), (a42, b5, c3, d3), (a42, b5, c3, d4), (a42, b5, c3, d5), (a42, b5, c3, d6), (a42, b5, c3, d7), (a42, b5, c3, d8), (a42, b5, c3, d9), (a42, b5, c3, d10), (a42, b5, c3, d11), (a42, b5, c3, d12), (a42, b5, c3, d13), (a42, b5, c3, d14), (a42, b5, c3, d15), (a42, b5, c3, d16), (a42, b5, c3, d17), (a42, b5, c3, d18), (a42, b5, c3, d19), (a42, b5, c3, d20), (a42, b5, c3, d21), (a42, b5, c3, d22), (a42, b6, c1, d1), (a42, b6, c1, d2), (a42, b6, c1, d3), (a42, b6, c1, d4), (a42, b6, c1, d5), (a42, b6, c1, d6), (a42, b6, c1, d7), (a42, b6, c1, d8), (a42, b6, c1, d9), (a42, b6, c1, d10), (a42, b6, c1, d11), (a42, b6, c1, d12), (a42, b6, c1, d13), (a42, b6, c1, d14), (a42, b6, c1, d15), (a42, (a42, b6, c1, d16), (a42, b6, c1, d17), (a42, b6, c1, d18), (a42, b6, c1, d19), (a42, b6, c1, d20), (a42, b6, c1, d21), (a42, b6, c1, d22), (a42, b6, c2, d1), (a42, b6, c2, d2), (a42, b6, c2, d3), (a42, b6, c2, d4), (a42, b6, c2, d5), (a42, b6, c2, d6), (a42, b6, c2, d7), (a42, b6, c2, d8), (a42, b6, c2, d9), (a42, b6, c2, d10), (a42, b6, c2, d11), (a42, b6, c2, d12), (a42, b6, c2, d13), (a42, b6, c2, d14), (a42, b6, c2, d15), (a42, b6, c2, d16), (a42, b6, c2, d17), (a42, b6, c2, d18), (a42, b6, c1, d19), (a42, b6, c2, d20) (a42, b6, c2, d21), (a42, b6, c2, d22), (a42, b6, c3, d1), (a42, b6, c3, d2), (a42, b6, c3, d3), (a42, b6, c3, d3), (a42, b6, c3, d4), (a42, b6, c3, d5), (a42, b6, c3, d6), (a42, b6, c3, d7), (a42, b6, c3, d8), (a42, b6, c3, d9), (a42, b6, c3, d10), (a42, b6, c3, d11), (a42, b6, c3, d12), (a42, b6, c3, d13), (a42, b6, c3, d14), (a42, b6, c3, d15), (a42, b6, c3, d16), (a42, b6, c3, d17), (a42, b6, c3, d18), (a42, b6, c3, d19), (a42, b6, c3, d20), (a42, b6, c3, d21), (a42, b6, c3, d22), (a43, b1, c1, d1), (a43, b1, c1, d2), (a43, b1, c1, d3), (a43, b1, c1, d4), (a43, b1, c1, d5), (a43, b1, c1, d6), (a43, b1, c1, d7), (a43, b1, c1, d8), (a43, b1, c1, d9), (a43, b1, c1, d10), (a43, b1, c1, d11), (a43, b1, c1, d12), (a43, b1, c1, d13), (a43, b1, c1, d14), (a43, b1, c1, d15), (a43, b1, c1, d16), (a43, b, c1, d17), (a43, b1, c1, d18), (a43, b1, c1, d19), (a43, b1, c1, d20), (a43, b1, c1, d21), (a43, b1, c1, d22), (a43, b1, c2, d1), (a43, b1, c2, d2), (a43, b1, c2, d3), (a43, b1, c2, d4), (a43, b1, c2, d5), (a43, b1, c2, d6), (a43, b1, c2, d7), (a43, b1, c2, d8), (a43, b1, c2, d9), (a43, b1, c2, d10), (a43, b1, c2, d11), (a43, b1, c2, d12), (a43, b, c2, d13), (a43, b1, c2, d14), (a43, b1, c2, d15), (a43, b1, c2, d16), (a43, b1, c2, d17), (a43, b1, c2, d18), (a43, b1, c2, d19), (a43, b1, c2, d20), (a43, b1, c2, d21), (a43, b1, c2, d22), (a43, b1, c3, d1), (a43, b1, c3, d2), (a43, b1, c3, d3), (a43, b1, c3, d4), (a43, b1, c3, d5), (a43, b1, c3, d6), (a43, b1, c3, d7), (a43, b1, c3, d8), (a43, b1, c3, d9), (a43, b1, c3, d10), (a43, b1, c3, d11), (a43, b1, c3, d12), (a43, b, c3, d13), (a43, b1, c3, d14), (a43, b1, c3, d15), (a43, b1, c3, d16), (a43, b1, c3, d17), (a43, b1, c3, d18), (a43, b1, c3, d19), (a43, b1, c3, d20), (a43, b1, c3, d21), (a43, b1, c3, d22), (a43, b2, c1, d1), (a43, b2, c1, d2), (a43, b2, c1, d3), (a43, b2, c1, d4), (a43, b2, c1, d5), (a43, b2, c1, d6), (a43, b2, c1, d7), (a43, b2, c1, d8), (a43, b2, c1, d9), (a43, b2, c1, d10), (a43, b2, c1, d11), (a43, b2, c1, d12), (a43, b2, c1, d13), (a43, b2, c1, d14), (a43, b2, c1, d15), (a43, b2, c1, d16), (a43, b2, c1, d17), (a43, b2, c1, d18), (a43, b2, c1, d19), (a43, b2, c2, d20), (a43, b2, c2, d21), (a43, b2, c1, d22), (a43, b2, c2, d1), (a43, b2, c2, d2), (a43, b2, c2, d3), (a43, b2, c2, d4), (a43, b2, c2, d5), (a43, b2, c2, d6), (a43, b2, c2, d7), (a43, b2, c2, d8), (a43, b2, c2, d9), (a43, b2, c2, d10), (a43, b2, c2, d11), (a43, b2, c2, d12), (a43, b2, c2, d13), (a43, b2, c2, d14), (a43, b2, c2, d15), (a43, b2, c2, d16), (a43, b2, c2, d17), (a43, b2, c2, a18), (a43, b2, c2, d19), (a43, b2, c2, d20), (a43, b2, c2, d21), (a43, b2, c2, d22), (a43, b2, c3, d1), (a43, b2, c3, d2), (a43, b2, c2, d3), (a43, b2, c3, d4), (a43, b2, c3, d5), (a43, b2, c3, d6), (a43, b2, c3, d7), (a43, b2, c3, d8), (a43, b2, c3, d9), (a43, b2, c3, d10), (a43, b2, c3, d11), (a43, b2, c3, d12), (a43, b2, c3, d13), (a43, b2, c3, d14), (a43, b2, c3, d15), (a43, b2, c3, d16), (a43, b2, c3, d17), (a43, b2, c3, d18), (a43, b2, c3, d19), (a43, b2, c3, d20), (a43, b2, c3, d21), (a43, b2, c3, d22), (a43, b3, c1, d1), (a43, b3, c1, d2), (a43, b3, c1, d3), (a43, b3, c1, d4), (a43, b3, c1, d5), (a43, b3, c1, d6), (a43, b3, c1, d7), (a43, b3, c1, d8), (a43, b3, c1, d9), (a43, b3, c1, d10), (a43, b3, c1, d11), (a43, b3, c1, d12), (a43, b3, c1, d13), (a43, b3, c1, d14), (a43, b3, c1, d15), (a43, b3, c1, d16), (a43, b3, c1, d17), (a43, b3, c1, d18), (a43, b3, c1, d19), (a43, b3, c1, d20), (a43, b3, c1, d21), (a43, b3, c1, d22), (a43, b3, c2, d1), (a43, b3, c2, d2), (a43, b3, c2, d3), (a43, b3, c2, d4), (a43, b3, c2, d5), (a43, b3, c2, d6), (a43, b3, c2, d7), (a43, b3, c2, d8), (a43, b3, c2, d9), (a43, b3, c2, d10), (a43, b3, c2, d11), (a43, b3, c2, d12), (a43, b3, c2, d13), (a43, b3, c2, d14), (a43, b3, c2, d15), (a43, b3, c2, d16), (a43, b3, c2, d17), (a43, b3, c2, d18), (a43, b3, c2, d19), (a43, b3, c2, d20), (a43, b3, c2, d21), (a43, b3, c2, d22), (a43, b3, c3, d1), (a43, b3, c3, d2), (a43, b3, c3, d3), (a43, b3, c3, d4), (a43, b3, c3, d5), (a43, b3, c3, d6), (a43, b3, c3, d7), (a43, b3, c3, d8), (a43, b3, c3, d9), (a43, b3, c3, d10), (a43, b3, c3, d11), (a43, b3, c3, d12), (a43, b3, c3, d13), (a43, b3, c3, d14), (a43, b3, c3, d15), (a43, b3, c3, d16), (a43, b3, c3, d17), (a43, b3, c3, d18), (a43, b3, c3, d19), (a43, b3, c3, d20), (a43, b3, c3, d21), (a43, b3, c3, d22), (a43, b4, c1, d1), (a43, b4, c1, d2), (a43, b4, c1, d3), (a43, b4, c1, d4), (a43, b4, c1, d5), (a43, b4, c1, d6), (a43, b4, c1, d7), (a43, b4, c1, d8), (a43, b4, c1, d9), (a43, b4, c1, d10), (a43, b4, c1, d11), (a43, b4, c1, d12), (a43, b4, c1, d13), (a43, b4, c1, d14), (a43, b4, c1, d15), (a43, b4, c1, d16), (a43, b4, c1, d17), (a43, b4, c1, d18), (a43, b4, c1, d19), (a43, b4, c1, d20), (a43, b4, c1, d21), (a43, b4, c1, d22), (a43, b4, c2, d1), (a43, b4, c2, d2), (a43, b4, c2, d3), (a43, b4, c2, d4), (a43, b4, c2, d5), (a43, b4, c2, d6), (a43, b4, c2, d7), (a43, b4, c2, d8), (a43, b4, c2, d9), (a43, b4, c2, d10), (a43, b4, c2, d11), (a43, b4, c2, d12), (a43, b4, c2, d13), (a43, b4, c2, d4), (a43, b4, c2, d15), (a43, b4, c2, d16), (a43, b4, c2, d17), (a43, b4, c2, d18), (a43, b4, c2, d19), (a43, b4, c2, d20), (a43, b4, c2, d21), (a43, b4, c2, d22), (a43, b4, c3, d1), (a43, b4, c3, d2), (a43, b4, c3, d3), (a43, b4, c3, d4), (a43, b4, c3, d5), (a43, b4, c3, d6), (a43, b4, c3, d7), (a43, b4, c3, d8), (a43, b4, c3, d9), (a43, b4, c3, d10), (a43, b4, c3, d11), (a43, b4, c3, d12), (a43, b4, c3, d13), (a43, b4, c3, d14), (a43, b4, c3, d15), (a43, b4, c3, d16), (a43, b4, c3, d17), (a43, b4, c3, d18), (a43, b4, c3, d19), (a43, b4, c3, d20), (a43, b4, c3, d21), (a43, b4, c3, d22), (a43, b5, c1, d1), (a43, b5, c1, d2), (a43, b5, c1, d3), (a43, b5, c1, d4), (a43, b5, c1, d5), (a43, b5, c1, d6), (a43, b5, c1, d7), (a43, b5, c1, d8), (a43, b5, c1, d9), (a43, b5, c1, d10), (a43, b5, c1, d11), (a43, b5, c1, d12), (a43, b5, c1, d13), (a43, b5, c1, d14), (a43, b5, c1, d15), (a43, b5, c1, d16), (a43, b5, c1, d17), (a43, b5, c1, d18), (a43, b5, c1, d19), (a43, b5, c1, d20), (a43, b5, c1, d21), (a43, b5, c1, d22), (a43, b5, c2, d1), (a43, b5, c2, d2), (a43, b5, c2, d3), (a43, b5, c2, d4), (a43, b5, c2, d5), (a43, b5, c2, d6), (a43, b5, c2, d7), (a43, b5, c2, d8), (a43, b5, c2, d9), (a43, b5, c2, d10), (a43, b5, c2, d11), (a43, b5, c2, d12), (a43, b5, c2, d13), (a43, b5, c2, d14), (a43, b5, c2, d15), (a43, b5, c2, d16), (a43, b5, c2, d17), (a43, b5, c2, d18), (a43, b5, c2, d19), (a43, b5, c2, d20), (a43, b5, c2, d21), (a43, b5, c2, d22), (a43, b5, c3, d1), (a43, b5, c3, d2), (a43, b5, c3, d3), (a43, b5, c3, d4), (a43, b5, c3, d5), (a43, b5, c3, d6), (a43, b5, c3, d7), (a43, b5, c3, d8), (a43, b5, c3, d9), (a43, b5, c3, d10), (a43, b5, c3, d11), (a43, b5, c3, d12), (a43, b5, c3, d13), (a43, b5, c3, d14), (a43, b5, c3, d15), (a43, b5, c3, d16), (a43, b5, c3, d17), (a43, b5, c3, d18), (a43, b5, c3, d19), (a43, b5, c3, d20), (a43, b5, c3, d21), (a43, b5, c3, d22), (a43, b6, c1, d1), (a43, b6, c1, d2), (a43, b6, c1, d3), (a43, b6, c1, d4), (a43, b6, c1, d5), (a43, c1, d6), (a43, b6, c1, d7), (a43, b6, c1, d8), (a43, b6, c1, d9), (a43, b6, c1, d10), (a43, b6, c1, d11), (a43, b6, c1, d12), (a43, b6, c1, d13), (a43, b6, c1, d14), (a43, b6, c1, d15), (a43, b6, c1, d16), (a43, b6, c1, d17), (a43, b6, c1, d18), (a43, b6, c1, d19), (a43, b6, c1, d20), (a43, b6, c1, d21), (a43, b6, c1, d22), (a43, b6, c2, d1), (a43, b6, c2, d2), (a43, b6, c2, d3), (a43, b6, c2, d4), (a43, b6, c2, d5), (a43, b6, c2, d6), (a43, b6, c2, d7), (a43, b6, c2, d8), (a43, b6, c2, d9), (a43, b6, c2, d10), (a43, b6, c2, d11), (a43, b6, c2, d12), (a43, b6, c2, d13), (a43, b6, c2, d14), (a43, b6, c2, d15), (a43, b6, c2, d16), (a43, b6, c2, d17), (a43, b6, c2, d18), (a43, b6, c2, d19), (a43, b6, c2, d20), (a43, b6, c2, d21), (a43, b6, c2, d22), (a43, b6, c3, d1), (a43, b6, c3, d2), (a43, b6, c3, d3), (a43, b6, c3, d4), (a43, b6, c3, d5), (a43, b6, c3, d6), (a43, b6, c3, d7), (a43, b6, c3, d8), (a43, b6, c3, d9), (a43, b6, c3, d10), (a43, b6, c3, d11), (a43, b6, c3, d12), (a43, b6, c3, d13), (a43, b6, c3, d14), (a43, b6, c3, d15), (a43, b6, c3, d16), (a43, b6, c3, d17), (a43, b6, c3, d18), (a43, b6, c3, d19), (a43, b6, c3, d20), (a43, b6, c3, d21), (a43, b6, c3, d22), (a44, b1, c1, d1), (a44, b1, c1, d2), (a44, b1, c1, d3), (a44, b1, c1, d4), (a44, b1, c1, d5), (a44, b1, c1, d6), (a44, b1, c1, d7), (a44, b1, c1, d8), (a44, b1, c1, d9), (a44, b1, c1, d10), (a44, b1, c1, d11), (a44, b1, c1, d12), (a44, b1, c1, d13), (a44, b1, c1, d14), (a44, b1, c1, d15), (a44, b1, c1, d16), (a44, b1, c1, d17), (a44, b1, c1, d18), (a44, b1, c1, d19), (a44, b1, c1, d20), (a44, b1, c1, d21), (a44, b1, c1, d22), (a44, b1, c2, d1), (a44, b1, c2, d2), (a44, b1, c2, d3), (a44, b1, c2, d4), (a44, b1, c2, d5), (a44, b1, c2, d6), (a44, b1, c2, d7), (a44, b1, c2, d8), (a44, b1, c2, d9), (a44, b1, c2, d10), (a44, b1, c2, d11), (a44, b1, c2, d12), (a44, b1, c2, d13), (a44, b1, c2, d14), (a44, b1, c2, d15), (a44, b1, c2, d16), (a44, b1, c2, d17), (a44, b1, c2, d18), (a44, b1, c2, d19), (a44, b1, c2, d20), (a44, b1, c2, d21), (a44, b1, c2, d22), (a44, b1, c3, d1), (a44, b1, c3, d2), (a44, b1, c3, d3), (a44, b1, c3, d4), (a44, b1, c3, d5), (a44, b1, c3, d6), (a44, b1, c3, d7), (a44, b1, c3, d8), (a44, b1, c3, d9), (a44, b1, c3, d10), (a44, b1, c3, d11), (a44, b1, c3, d12), (a44, b1, c3, d13), (a44, b1, c3, d14), (a44, b1, c3, d15), (a44, b1, c3, d16), (a44, b1, c3, d17), (a44, b1, c3, d18), (a44, b1, c3, d19), (a44, b1, c3, d20), (a44, b1, c3, d21), (a44, b1, c3, d22), (a44, b2, c1, d1), (a44, b2, c1, d2), (a44, b2, c1, d3), (a44, b2, c1, d4), (a44, b2, c1, d5), (a44, b2, c1, d6), (a44, b2, c1, d7), (a44, b2, c1, d5), (a44, b2, c1, d9), (a44, b2, c1, d10), (a44, b2, c1, d11), (a44, b2, c1, d12), (a44, b2, c1, d13), (a44, b2, c1, d14), (a44, b2, c1, d15), (a44, b2, c1, d16), (a44, b2, c1, d17), (a44, b2, c1, d18), (a44, b2, c1, d19), (a44, b2, c1, d20), (a44, b2, c1, d21), (a44, b2, c1, d22), (a44, b2, c2, d1), (a44, b2, c2, d2), (a44, b2, c2, d3), (a44, b2, c2, d4), (a44, b2, c2, d5), (a44, b2, c2, d6), (a44, b2, c2, d7), (a44, b2, c2, d8), (a44, b2, c2, d9), (a44, b2, c2, d10), (a44, b2, c2, d11), (a44, b2, c2, d12), (a44, b2, c2, d13), (a44, b2, c2, d14), (a44, b2, c2, d15), (a44, b2, c2, d16), (a44, b2, c2, d17), (a44, b2, c2, d18), (a44, b2, c2, d19), (a44, b2, c2, d20), (a44, b2, c2, d21), (a44, b2, c2, d22), (a44, b2, c3, d1), (a44, b2, c3, d2), (a44, b2, c3, d3), (a44, b2, c3, d4), (a44, b2, c3, d5), (a44, b2, c3, d6), (a44, b2, c3, d7), (a44, b2, c3, d8), (a44, b2, c3, d9), (a44, b2, c3, d10), (a44, b2, c3, d11), (a44, b2, c3, d12), (a44, b2, c3, d13), (a44, b2, c3, d14), (a44, b2, c3, d15), (a44, b2, c3, d16), (a44, b2, c3, d17), (a44, b2, c3, d8), (a44, b2, c3, d19), (a44, b2, c3, d20), (a44, b2, c3, d21), (a44, b2, c3, d22), (a44, b3, c1, d1), (a44, b3, c1, d2), (a44, b3, c1, d3), (a44, b3, c1, d4), (a44, b3, c1, d5), (a44, b3, c1, d6), (a44, b3, c1, d7), (a44, b3, c1, d8), (a44, b3, c1, d9), (a44, b3, c1, d10), (a44, b3, c1, d11), (a44, b3, c1, d12), (a44, b3, c1, d13), (a44, b3, c1, d14), (a44, b3, c1, d15), (a44, b3, c1, d16), (a44, b3, c1, d17), (a44, b3, c1, d18), (a44, b3, c1, d19), (a44, b3, c1, d20), (a44, b3, c1, d21), (a44, b3, c1, d22), (a44, b3, c2, d1), (a44, b3, c2, d2), (a44, b3, c2, d3), (a44, b3, c2, d4), (a44, b3, c2, d5), (a44, b3, c2, d6), (a44, b3, c2, d7), (a44, b3, c2, d8), (a44, b3, c2, d9), (a44, b3, c2, d10), (a44, b3, c2, d11), (a44, b3, c2, d12), (a44, b3, c2, d13), (a44, b3, c2, d14), (a44, b3, c2, d15), (a44, b3, c2, d16), (a44, b3, c2, d17), (a44, b3, c2, d18), (a44, b3, c2, d19), (a44, b3, c2, d20), (a44, b5, c2, d21), (a44, b3, c2, d22), (a44, b3, c3, d1), (a44, b3, c3, d2), (a44, b3, c3, d3), (a44, b3, c3, d4), (a44, b3, c3, d5), (a44, b3, c3, d6), (a44, b3, c3, d7), (a44, b3, c3, d8), (a44, b3, c3, d9), (a44, b3, c3, d10), (a44, b3, c3, d11), (a44, b3, c3, d12), (a44, b3, c3, d13), (a44, b3, c3, d14), (a44, b3, c3, d15), (a44, b3, c3, d16), (a44, b3, c3, d17), (a44, b3, c3, d18), (a44, b3, c3, d19), (a44, b3, c3, d20), (a44, b3, c3, d21), (a44, b3, c3, d22), (a44, b4, c1, d1), (a44, b4, c1, d2), (a44, b4, c1, d3), (a44, b4, c1, d4), (a44, b4, c1, d5), (a44, b4, c1, d6), (a44, b4, c1, d7), (a44, b4, c1, d8), (a44, b4, c1, d9), (a44, b4, c1, d10), (a44, b4, c1, d11), (a44, b4, c1, d12), (a44, b4, c1, d13), (a44, b4, c1, d14), (a44, b4, c1, d15), (a44, b4, c1, d16), (a44, b4, c1, d17), (a44, b4, c1, d18), (a44, b4, c1, d9), (a44, b4, c1, d20), (a44, b4, c1, d21), (a44, b4, c1, d22), (a44, b4, c2, d1), (a44, b4, c2, d2), (a44, b4, c2, d3), (a44, b4, c2, d4), (a44, b4, c2, d5), (a44, b4, c2, d6), (a44, b4, c2, d7), (a44, b4, c2, d8), (a44, b4, c2, d9), (a44, b4, c2, d10), (a44, b4, c2, d11), (a44, b4, c2, d12), (a44, b4, c2, d13), (a44, b4, c2, d14), (a44, b4, c2, d15), (a44, b4, c2, d16), (a44, b4, c2, d17), (a44, b4, c2, d18), (a44, b4, c2, d19), (a44, b4, c2, d20), (a44, b4, c2, d21), (a44, b4, c2, d22), (a44, b4, c3, d1), (a44, b4, c3, d2), (a44, b4, c3, d3), (a44, b4, c3, d4), (a44, b4, c3, d5), (a44, b4, c3, d6), (a44, b4, c3, d7), (a44, b4, c3, d8), (a44, b4, c3, d9), (a44, b4, c3, d10), (a44, b4, c3, d11), (a44, b4, c3, d12), (a44, b4, c3, d13), (a44, b4, c3, d14), (a44, b4, c3, d15), (a44, b4, c3, d16), (a44, b4, c3, d17), (a44, b4, c3, d18), (a44, b4, c3, d19), (a44, b4, c3, d20), (a44, b4, c3, d21), (a44, b4, c3, d22), (a44, b5, c1, d1), (a44, b5, c1, d2), (a44, b5, c1, d3), (a44, b5, c1, d4), (a44, b5, c1, d5), (a44, b5, c1, d6), (a44, b5, c1, d7), (a44, b5, c1, d3), (a44, b5, c1, d9), (a44, b5, c1, d10), (a44, b5, c1, d11), (a44, b5, c1, d12), (a44, b5, c1, d13), (a44, b5, c1, d14), (a44, b5, c1, d15), (a44, b5, c1, d16), (a44, b5, c1, d17), (a44, b5, c1, d18), (a44, b5, c1, d19), (a44, b5, c1, d20), (a44, b5, c1, d21), (a44, b5, c1, d22), (a44, b5, c2, d1), (a44, b5, c2, d2), (a44, b5, c2, d3), (a44, b5, c2, d4), (a44, b5, c2, d5), (a44, b5, c2, d6), (a44, b5, c2, d7), (a44, b6, c2, d8), (a44, b5, c2, d9), (a44, b5, c2, d10), (a44, b5, c2, d11), (a44, b5, c2, d12), (a44, b5, c2, d13), (a44, b5, c2, d14), (a44, b5, c2, d15), (a44, b5, c2, d16), (a44, b5, c2, d17), (a44, b5, c2, d18), (a44, b5, c2, d19), (a44, b5, c2, d20), (a44, b5, c2, d21), (a44, b5, c2, d22), (a44, b5, c3, d1), (a44, b5, c3, d2), (a44, b5, c3, d3), (a44, b5, c3, d4), (a44, b5, c3, d5), (a44, b5, c3, d6), (a44, b5, c3, d7), (a44, b5, c3, d8), (a44, b5, c3, d9), (a44, b5, c3, d10), (a44, b5, c3, d11), (a44, b5, c3, d12), (a44, b5, c3, d13), (a44, b5, c3, d14), (a44, b5, c3, d15), (a44, b5, c3, d16), (a44, b5, c3, d17), (a44, b5, c3, d18), (a44, b5, c3, d19), (a44, b5, c3, d20), (a44, b5, c3, d21), (a44, b5, c3, d22), (a44, b6, c1, d1), (a44, b6, c1, d2), (a44, b6, c1, d3), (a44, b6, c1, d4), (a44, b6, c1, d5), (a44, b6, c1, d6), (a44, b6, c1, d1), (a44, b6, c1, d8), (a44, b6, c1, d9), (a44, b6, c1, d10), (a44, b6, c1, d11), (a44, b6, c1, d12), (a44, b6, c1, d13), (a44, b6, c1, d14), (a44, b6, c1, d15), (a44, b6, c1, d16), (a44, b6, c1, d17), (a44, b6, c1, d13), (a44, b6, c1, d19), (a44, b6, c1, d20), (a44, b6, c1, d21), (a44, b6, c1, d22), (a44, b6, c2, d1), (a44, b6, c2, d2), (a44, b6, c2, d3), (a44, b6, c2, d4), (a44, b6, c2, d5), (a44, b6, c2, d6), (a44, b6, c2, d7), (a44, b6, c2, d8), (a44, b6, c2, d9), (a44, b6, c2, d10), (a44, b6, c2, d11), (a44, b6, c2, d12), (a44, b6, c2, d13), (a44, b6, c2, d14), (a44, b6, c2, d15), (a44, b6, c2, d16), (a44, b6, c2, d17), (a44, b6, c2, d18), (a44, b6, c2, d19), (a44, b6, c2, d20), (a44, b6, c2, d21), (a44, b6, c2, d22), (a44, b6, c3, d1), (a44, b6, c3, d2), (a44, b6, c3, d3), (a44, b6, c3, d4), (a44, b6, c3, d5), (a44, b6, c3, d6), (a44, b6, c3, d7), (a44, b6, c3, d8), (a44, b6, c3, d9), (a44, b6, c3, d10), (a44, b6, c3, d11), (a44, b6, c3, d12), (a44, b6, c3, d13), (a44, b6, c3, d14), (a44, b6, c3, d15), (a44, b6, c3, d16), (a44, b6, c3, d17), (a44, b6, c3, d18), (a44, b6, c3, d19), (a44, b6, c3, d20), (a44, b6, c3, d21), (a44, b6, c3, d22), (a45, b1, c1, d1), (a45, b1, c1, d2), (a45, b1, c1, d3), (a45, b1, c1, d4), (a45, b1, c1, d5), (a45, b1, c1, d6), (a45, b1, c1, d7), (a45, b1, c1, d8), (a45, b1, c1, d9), (a45, b1, c1, d10), (a45, b1, c1, d11), (a45, b1, c1, d12), (a45, b1, c1, d13), (a45, b1, c1, d14), (a45, b1, c1, d15), (a45, b1, c1, d16), (a45, b1, c1, d17), (a45, b1, c1, d18), (a45, b1, c1, d19), (a45, b1, c1, d20), (a45, b1, c1, d21), (a45, b1, c1, d22), (a45, b1, c2, d1), (a45, b1, c2, d2), (a45, b1, c2, d3), (a45, b1, c2, d4), (a45, b1, c2, d5), (a45, b1, c2, d6), (a45, b1, c2, d7), (a45, b1, c2, d8), (a45, b1, c2, d9), (a45, b1, c2, d10), (a45, b1, c2, d11), (a45, b1, c2, d12), (a45, b1, c2, d13), (a45, b1, c2, d14), (a45, b1, c2, d15), (a45, b1, c2, d16), (a45, b1, c2, d17), (a45, b1, c2, d18), (a45, b1, c2, d19), (a45, b1, c2, d20), (a45, b1, c2, d21), (a45, b1, c2, d22), (a45, b1, c3, d1), (a45, b1, c3, d2), (a45, b1, c3, d3), (a45, b1, c3, d4), (a45, b1, c3, d5), (a45, b1, c3, d6), (a45, b1, c3, d7), (a45, b1, c3, d8), (a45, b1, c3, d9), (a45, b1, c3, d10), (a45, b1, c3, d11), (a45, b1, c3, d12), (a45, b1, c3, d13), (a45, b1, c3, d14), (a45, b1, c3, d15), (a45, b1, c3, d16), (a45, b1, c3, d17), (a45, b1, c3, d18), (a45, b1, c3, d19), (a45, b1, c3, d20), (a45, b1, c3, d21), (a45, b1, c3, d22), (a45, b2, c1, d1), (a45, b2, c1, d2), (a45, b2, c1, d3), (a45, b2, c1, d4), (a45, b2, c1, d5), (a45, b2, c1, d6), (a45, b2, c1, d7), (a45, b2, c1, d8), (a45, b2, c1, d9), (a45, b2, c1, d10), (a45, b2, c1, d11), (a45, b2, c1, d12), (a45, b2, c1, d13), (a45, b2, c1, d14), (a45, b2, c1, d15), (a45, b2, c1, d16), (a45, b2, c1, d17), (a45, b2, c1, d18), (a45, b2, c1, d19), (a45, b2, c1, d20), (a45, b2, c1, d21), (a45, b2, c1, d22), (a45, b2, c2, d1), (a45, b2, c2, d2), (a45, b2, c2, d3), (a45, b2, c2, d4), (a45, b2, c2, d5), (a45, b2, c2, d6), (a45, b2, c2, d7), (a45, b2, c2, d8), (a45, b2, c2, d9), (a45, b2, c2, d10), (a45, b2, c2, d11), (a45, b2, c2, d12), (a45, b2, c2, d13), (a45, b2, c2, d14), (a45, b2, c2, d15), (a45, b2, c2, d16), (a45, b2, c2, d17), (a45, b2, c2, d18), (a45, b2, c2, d19), (a45, b2, c2, d20), (a45, b2, c2, d21), (a45, b2, c2, d22), (a45, b2, c3, d1), (a45, b2, c3, d2), (a45, b2, c3, d3), (a45, b2, c3, d4), (a45, b2, c3, d5), (a45, b2, c3, d6), (a45, b2, c3, d7), (a45, b2, c3, d3), (a45, b2, c3, d9), (a45, b2, c3, d10), (a45, b2, c3, d11), (a45, b2, c3, d12), (a45, b2, c3, d13), (a45, b2, c3, d14), (a45, b2, c3, d15), (a45, b2, c3, d16), (a45, b2, c3, d17), (a45, b2, c3, d18), (a45, b2, c3, d19), (a45, b2, c3, d20), (a45, b2, c3, d21), (a45, b2, c3, d22), (a45, b5, c1, d1), (a45, b3, c1, d2), (a45, b5, c1, d3), (a45, b3, c1, d4), (a45, b3, c1, d5), (a45, b3, c1, d6), (a45, b3, c1, d7), (a45, b3, c1, d8), (a45, b3, c1, d9), (a45, b3, c1, d10), (a45, b3, c1, d11), (a45, b3, c1, d12), (a45, b3, c1, d13), (a45, b3, c1, d14), (a45, b3, c1, d15), (a45, b3, c1, d16), (a45, b3, c1, d17), (a45, b3, c1, d18), (a45, b3, c1, d19), (a45, b3, c1, d20), (a45, b3, c1, d21), (a45, b3, c1, d22), (a45, b3, c2, d1), (a45, b5, c2, d2), (a45, b3, c2, d3), (a45, b3, c2, d4), (a45, b3, c2, d5), (a45, b3, c2, d6), (a45, b3, c2, d7), (a45, b3, c2, d3), (a45, b3, c2, d9), (a45, b3, c2, d10), (a45, b3, c2, d11), (a45, b3, c2, d12), (a45, b3, c2, d13), (a45, b3, c2, d14), (a45, b3, c2, d15), (a45, b3, c2, d16), (a45, b3, c2, d17), (a45, b3, c2, d18), (a45, b3, c2, d19), (a45, b3, c2, d20), (a45, b3, c2, d21), (a45, b3, c2, d22), (a45, b3, c3, d1), (a45, b3, c3, d2), (a45, b3, c3, d3), (a45, b3, c3, d4), (a45, b3, c3, d5), (a45, b3, c3, d6), (a45, b3, c3, d7), (a45, b3, c3, d8), (a45, b3, c3, d9), (a45, b3, c3, d10), (a45, b3, c3, d11), (a45, b3, c3, d12), (a45, b3, c3, d13), (a45, b3, c3, d14), (a45, b5, c3, d15), (a45, b3, c3, d16), (a45, b3, c3, d17), (a45, b3, c3, d13), (a45, b3, c3, d19), (a45, b3, c3, d20), (a45, b3, c3, d21), (a45, b3, c3, d22), (a45, b4, c1, d1), (a45, b4, c1, d2), (a45, b4, c1, d3), (a45, b4, c1, d4), (a45, b4, c1, d5), (a45, b4, c1, d6), (a45, b4, c1, d7), (a45, b4, c1, d8), (a45, b4, c1, d9), (a45, b4, c1, d10), (a45, b4, c1, d11), (a45, b4, c1, d12), (a45, b4, c1, d13), (a45, b4, c1, d14), (a45, b4, c1, d15), (a45, b4, c1, d16), (a45, b4, c1, d17), (a45, b4, c1, d18), (a45, b4, c1, d19), (a45, b4, c1, d20), (a45, b4, c1, d21), (a45, b4, c1, d22), (a45, b4, c2, d1), (a45, b4, c2, d2), (a45, b4, c2, d3), (a45, b4, c2, d4), (a45, b4, c2, d5), (a45, b4, c2, d6), (a45, b4, c2, d7), (a45, b4, c2, d8), (a45, b4, c2, d9), (a45, b4, c2, d10), (a45, b4, c2, d11), (a45, b4, c2, d12), (a45, b4, c2, d13), (a45, b4, c2, d14), (a45, b4, c2, d15), (a45, b4, c2, d16), (a45, b4, c2, d17), (a45, b4, c2, d18), (a45, b4, c2, d19), (a45, b4, c2, d20), (a45, b4, c2, d21), (a45, b4, c2, d22), (a45, b4, c3, d1), (a45, b4, c3, d2), (a45, b4, c3, d3), (a45, b4, c3, d4), (a45, b4, c3, d5), (a45, b4, c3, d6), (a45, b4, c3, d7), (a45, b4, c3, d8), (a45, b4, c3, d9), (a45, b4, c3, d10), (a45, b4, c3, d11), (a45, b4, c3, d12), (a45, b4, c3, d13), (a45, b4, c3, d14), (a45, b4, c3, d15), (a45, b4, c3, d16), (a45, b4, c3, d17), (a45, b4, c3, d18), (a45, b4, c3, d19), (a45, b4, c3, d20), (a45, b4, c3, d21), (a45, b4, c3, d22), (a45, b5, c1, d1), (a45, b5, c1, d2), (a45, b5, c1, d3), (a45, b5, c1, d4), (a45, b5, c1, d5), (a45, b5, c1, d6), (a45, b5, c1, d7), (a45, b5, c1, d8), (a45, b1, c1, d9), (a45, b5, c1, d10), (a45, b5, c1, d11), (a45, b5, c1, d12), (a45, b5, c1, d13), (a45, b5, c1, d14), (a45, b5, c1, d15), (a45, b5, c1, d16), (a45, b5, c1, d17), (a45, b5, c1, d18), (a45, b5, c1, d19), (a45, b5, c1, d20), (a45, b5, c1, d21), (a45, b5, c1, d22), (a45, b5, c2, d1), (a45, b5, c2, d2), (a45, b5, c2, d3), (a45, b5, c2, d4), (a45, b5, c2, d5), (a45, b5, c2, d6), (a45, b5, c2, d7), (a45, b5, c2, d3), (a45, b5, c2, d9), (a45, b5, c2, d10), (a45, b5, c2, d11), (a45, b5, c2, d12), (a45, b5, c2, d13), (a45, b5, c2, d14), (a45, b5, c2, d15), (a45, b5, c2, d16), (a45, b5, c2, d17), (a45, b5, c2, d18), (a45, b5, c2, d19), (a45, b5, c2, d20), (a45, b5, c2, d21), (a45, b5, c2, d22), (a45, b5, c3, d1), (a45, b5, c3, d2), (a45, b5, c3, d3), (a45, b5, c3, d4), (a45, b5, c3, d5), (a45, b5, c3, d6), (a45, b5, c3, d7), (a45, b5, c3, d8), (a45, b5, c3, d9), (a45, b5, c3, d10), (a45, b5, c3, d11), (a45, b5, c3, d12), (a45, b5, c3, d13), (a45, b5, c3, d14), (a45, b5, c3, d15), (a45, b5, c3, d16), (a45, b5, c3, d17), (a45, b5, c3, d18), (a45, b5, c3, d19), (a45, b5, c3, d20), (a45, b5, c3, d21), (a45, b5, c3, d22), (a45, b6, c1, d1), (a45, b6, c1, d2), (a45, b6, c1, d3), (a45, b6, c1, d4), (a45, b6, c1, d5), (a45, b6, c1, d6), (a45, b6, c1, d7), (a45, b6, c1, d8), (a45, b6, c1, d9), (a45, b6, c1, d10), (a45, b6, c1, d11), (a45, b6, c1, d12), (a45, b6, c1, d13), (a45, b6, c1, d14), (a45, b6, c1, d15), (a45, b6, c1, d16), (a45, b6, c1, d17), (a45, b6, c1, d18), (a45, b6, c1, d19), (a45, b6, c1, d20), (a45, b6, c1, d21), (a45, b6, c1, d22), (a45, b6, c2, d1), (a45, b6, c2, d2), (a45, b6, c2, d3), (a45, b6, c2, d4), (a45, b6, c2, d5), (a45, b6, c2, d6), (a45, b6, c2, d7), (a45, b6, c2, d8), (a45, b6, c2, d9), (a45, b6, c2, d10), (a45, b6, c2, d11), (a45, b6, c2, d12), (a45, b2, c2, d13), (a45, b6, c2, d14), (a45, b6, c2, d15), (a45, b6, c2, d16), (a45, b6, c2, d17), (a45, b6, c2, d18), (a45, b6, c2, d19), (a45, b6, c2, d20), (a45, b6, c2, d21), (a45, b6, c2, d22), (a45, b6, c3, d1), (a45, b6, c3, d2), (a45, b6, c3, d3), (a45, b6, c3, d4), (a45, b6, c3, d5), (a45, b6, c3, d10), (a45, b6, c3, d7), (a45, b6, c3, d8), (a45, b6, c3, d9), (a45, b6, c3, d10), (a45, b6, c3, d11), (a45, b6, c3, d12), (a45, b6, c3, d13), (a45, b6, c3, d14), (a45, b6, c3, d15), (a45, b6, c3, d16), (a45, b6, c3, d17), (a45, b6, c3, d18), (a45, b6, c3, d19), (a45, b6, c3, d20), (a45, b6, c3, d21), (a45, b6, c3, d22), (a46, b1, c1, d1), (a46, b1, c1, d2), (a46, b1, c1, d3), (a46, b1, c1, d4), (a46, b1, c1, d5), (a46, b1, c1, d6), (a46, b1, c1, d7), (a46, b1, c1, d8), (a46, b1, c1, d9), (a46, b1, c1, d10), (a46, b1, c1, d11), (a46, b1, c1, d12), (a46, b1, c1, d13), (a46, b1, c1, d14), (a46, b1, c1, d15), (a46, b1, c1, d16), (a46, b1, c1, d17), (a46, b1, c1, d18), (a46, b1, c1, d19), (a46, b1, c1, d20), (a46, b1, c1, d21), (a46, b1, c1, d22), (a46, b1, c2, d1), (a46, b1, c2, d2), (a46, b1, c2, d3), (a46, b1, c2, d4), (a46, b1, c2, d5), (a46, b1, c2, d6), (a46, b1, c2, d7), (a46, b1, c2, d8), (a46, b1, c2, d9), (a46, b1, c2, d10), (a46, b1, c2, d11), (a46, b1, c2, d12), (a46, b1, c2, d13), (a46, b, c2, d14), (a46, b1, c2, d15), (a46, b1, c2, d16), (a46, b1, c2, d17), (a46, b1, c2, d18), (a46, b1, c2, d19) (a46, b1, c2, d20), (a46, b1, c2, d21), (a46, b1, c2, d22), (a46, b1, c3, d1), (a46, b1, c3, d2), (a46, b1, c3, d3), (a46, b1, c3, d4), (a46, b1, c3, d5), (a46, b1, c3, d6), (a46, b1, c3, d7), (a46, b1, c3, d8), (a46, b1, c3, d9), (a46, b1, c3, d10), (a46, b1, c3, d11), (a46, b1, c3, d12), (a46, b1, c3, d13), (a46, b1, c3, d14), (a46, b1, c3, d15), (a46, b1, c3, d16), (a46, b1, c3, d17), (a46, b1, c3, d18), (a46, b1, c3, d19), (a46, b1, c3, d20), (a46, b1, c3, d21), (a46, b1, c3, d22), (a46, b2, c1, d1), (a46, b2, c1, d2), (a46, b2, c1, d3), (a46, b2, c1, d4), (a46, b2, c1, d5), (a46, b2, c1, d6), (a46, b2, c1, d7), (a46, b2, c1, d8), (a46, b2, c1, d9), (a46, b2, c1, d10), (a46, b2, c1, d11), (a46, b2, c1, d12), (a46, b2, c1, d13), (a46, b2, c1, d14), (a46, b2, c1, d15), (a46, b2, c1, d16), (a46, b2, c1, d17), (a46, b2, c1, d18), (a46, b2, c1, d19), (a46, b2, c1, d20), (a46, b2, c1, d21), (a46, b2, c1, d22), (a46, b2, c2, d1), (a46, b2, c2, d2), (a46, b2, c2, d3), (a46, b2, c2, d4), (a46, b2, c2, d5), (a46, b2, c2, d6), (a46, b2, c2, d7), (a46, b2, c2, d8), (a46, b2, c2, d9), (a46, b2, c2, d10), (a46, b2, c2, d11), (a46, b2, c2, d12), (a46, b2, c2, d13), (a46, b2, c2, d14), (a46, b2, c2, d15), (a46, b2, c2, d16), (a46, b2, c2, d17), (a46, b2, c2, d18), (a46, b2, c2, d19), (a46, b2, c2, d20), (a46, b2, c2, d21), (a46, b2, c2, d22), (a46, b2, c3, d1), (a46, b2, c3, d2), (a46, b2, c3, d3), (a46, b2, c3, d4), (a46, b2, c3, d5), (a46, b2, c3, d6), (a46, b2, c3, d7), (a46, b2, c3, d8), (a46, b2, c3, d9), (a46, b2, c3, d10), (a46, b2, c3, d11), (a46, b2, c3, d12), (a46, b2, c3, d13), (a46, b2, c3, d14), (a46, b2, c3, d15), (a46, b2, c3, d16), (a46, b2, c3, d17), (a46, b2, c3, d18), (a46, b2, c3, d19), (a46, b2, c3, d20), (a46, b2, c3, d21), (a46, b2, c3, d22), (a46, b3, c1, d1), (a46, b3, c1, d2), (a46, b3, c1, d3), (a46, b3, c1, d4), (a46, b3, c1, d5), (a46, b3, c1, d6), (a46, b3, c1, d7), (a46, b3, c1, d8), (a46, b3, c1, d9), (a46, b3, c1, d10), (a46, b3, c1, d11), (a46, b3, c1, d12), (a46, b3, c1, d13), (a46, b3, c1, d14), (a46, b3, c1, d15), (a46, b3, c1, d16), (a46, b3, c1, d17), (a46, b3, c1, d18), (a46, b3, c1, d19), (a46, b3, c1, d20), (a46, b3, c1, d21), (a46, b3, c1, d22), (a46, b3, c2, d1), (a46, b3, c2, d2), (a46, b3, c2, d3), (a46, b3, c2, d4), (a46, b3, c2, d5), (a46, b3, c2, d6), (a46, b3, c2, d7), (a46, b3, c2, d8), (a46, b3, c2, d9), (a46, b3, c2, d10), (a46, b3, c2, d11), (a46, b3, c2, d12), (a46, b3, c2, d13), (a46, b3, c2, d14), (a46, b3, c2, d15), (a46, b3, c2, d16), (a46, b3, c2, d17), (a46, b3, c2, d18), (a46, b3, c2, d19), (a46, b3, c2, d20), (a46, b3, c2, d21), (a46, b3, c2, d22), (a46, b3, c3, d1), (a46, b3, c3, d2), (a46, b3, b3, d), (a46, b3, c3, d4), (a46, b3, c3, d5), (a46, b3, c3, d6), (a46, b3, c3, d7), (a46, b3, c3, d8), (a46, b3, c3, d9), (a46, b3, c3, d10), (a46, b3, c3, d11), (a46, b5, c3, d12), (a46, b3, c3, d13), (a46, b3, c3, d14), (a46, b3, c3, d6), (a46, b3, c3, d16), (a46, b3, c3, d17), (a6, b3, c3, d18), (a46, b3, c3, d19), (a46, b3, c3, d20), (a46, b3, c3, d21), (a46, b3, c3, d22), (a46, b4, c1, d1), (a46, b4, c1, d2), (a46, b4, c1, d3), (a46, b4, c1, d4), (a46, b4, c1, d5), (a46, b4, c1, d6), (a46, b4, c1, d7), (a46, b4, c1, d8), (a46, b4, c1, d9), (a46, b4, c1, d10), (a46, b4, c1, d11), (a46, b4, c1, d12), (a46, b4, c1, d13), (a46, b4, c1, d14), (a46, b4, c1, d15), (a46, b4, c1, d16), (a46, b4, c1, d17), (a46, b4, c1, d18), (a46, b4, c1, d19), (a46, b4, c1, d20), (a46, b4, c1, d21), (a46, b4, c1, d22), (a46, b4, c2, d1), (a46, b4, c2, d2), (a46, b4, c2, d3), (a46, b4, c2, d4), (a46, b4, c2, d5), (a46, b4, c2, d6), (a46, b4, c2, d7), (a46, b4, c2, d8), (a46, b4, c2, d9), (a46, b4, c2, d10), (a46, b4, c2, d11), (a46, b4, c2, d12), (a46, b4, c2, d3), (a4, b4, c2, d14), (a46, b4, c2, d15), (a46, b4, c2, d16), (a46, b4, c2, d17), (a46, b4, c2, d18), (a46, b4, c2, d19), (a46, b4, c2, d20), (a46, b4, c2, d21), (a46, b4, c2, d22), (a46, b4, c3, d1), (a46, b4, c3, d2), (a46, b4, c3, d3), (a46, b4, c3, d4), (a46, b4, c3, d5), (a46, b4, c3, d6), (a46, b4, c3, d7), (a46, b4, c3, d8), (a46, b4, c3, d9), (a46, b4, c3, d10), (a46, b4, c3, d11), (a46, b4, c3, d12), (a46, b4, c3, d13), (a46, b4, c3, d14), (a46, b4, c3, d15), (a46, b4, c3, d6), (a46, b4, c3, d17), (a46, b4, c3, d18), (a46, b4, c3, d19), (a46, b4, c3, d20), (a46, b4, c3, d21), (a46, b4, c3, d22), (a46, b5, c1, d1), (a46, b5, c1, d2), (a46, b5, c1, d3), (a46, b5, c1, d4), (a4, b5, c1, d5), (a46, b5, c1, d6), (a46, b5, c1, d7), (a46, b5, c1, d8), (a46, b5, c1, d9), (a46, b5, c1, d10), (a46, b5, c1, d11), (a46, b5, c1, d12), (a46, b5, c1, d13), (a46, b5, c1, d14), (a46, b5, c1, d15), (a46, b5, c1, d16), (a46, b5, c1, d17), (a46, b5, c1, d18), (a46, b5, c1, d19), (a46, b5, c1, d20), (a46, b5, c1, d21), (a46, b5, c1, d22), (a46, b5, c2, d1), (a46, b5, c2, d2), (a46, b5, c2, d3), (a46, b5, c2, d4), (a46, b5, c2, d5), (a46, b5, c2, d5), (a46, b5, c2, d7), (a46, b, c2, d8), (a46, b5, c2, d9), (a46, b5, c2, d10), (a46, b5, c2, d11), (a46, b5, c2, d12), (a46, b5, c2, d13), (a46, b5, c2, d14), (a46, b5, c2, d15), (a46, b5, c2, d16), (a46, b5, c2, d17), (a46, b5, c2, d18), (a46, b5, c2, d19), (a46, b5, c2, d20), (a46, b5, c2, d21), (a46, b5, c2, d22), (a46, b5, c3, d1), (a46, b5, c3, d2), (a46, b, c3, d3), (a46, b5, c3, d4), (a46, b5, c3, d5), (a46, b5, c3, d6), (a46, b5, c3, d7), (a46, b5, c3, d8), (a46, b5, c3, d9), (a46, b5, c3, d10), (a46, b5, c3, d11), (a46, b5, c3, d12), (a46, b5, c3, d3), (a46, b5, c3, d4), (a46, b5, c3, d15), (a46, b5, c3, d16), (a46, b5, c3, d17), (a46, b5, c3, d18), (a46, b5, c3, d19), (a46, b5, c3, d20), (a46, b5, c3, d21), (a46, b5, c3, d22), (a46, b6, c6, d1), (a46, b5, c1, d2), (a46, b6, c1, d3), (a46, b6, c1, d4), (a46, b6, c1, d5), (a46, b6, c1, d16), (a46, b6, c1, d7), (a46, b6, c1, d8), (a46, b6, c1, d9), (a46, b6, c1, d10), (a46, b6, c1, d21), (a46, b6, c1, d12), (a46, b6, c1, d13), (a46, b6, c1, d14), (a46, b6, c1, d15), (a46, b6, c1, d16), (a46, b6, c1, d17), (a46, b6, c1, d18), (a46, (b6, c1, d19), (a46, b6, c1, d20), (a46, b6, c1, d21), (a46, c1, d22), (a46, b6, c2, d1), (a46, b6, c2, d2), (a46, b6, c2, d3), (a46, b6, c2, d4), (a46, b6, c2, d5), (a46, b6, c2, d6), (a46, b6, c2, d7), (a46, b6, c2, d8), (a46, b6, c2, d9), (a46, b6, c2, d10), (a46, b6, c2, d11), (a46, b6, c2, d12), (a46, b6, c2, d13), (a46, b6, c2, d14), (a46, b6, c2, d15), (a46, b6, c2, d16), (a46, b6, c2, d17), (a46, b6, c2, d18), (a46, b6, c2, d19), (a46, b6, c2, d20), (a46, b6, c2, d21), (a46, b6, c2, d22), (a46, b6, c3, d1), (a46, b6, c3, d2), (a46, b6, c3, d3), (a46, b6, c3, d4), (a46, b6, c3, d5), (a46, b6, c3, d6), (a46, b6, c3, d7), (a46, b6, c3, d8), (a46, b6, c3, c9), (a46, b6, c3, d10), (a46, b6, c3, d11), (a46, b6, c3, d12), (a46, b6, c3, d13), (a46, b6, c3, d14), (a46, b6, c3, d15), (a46, b6, c3, d16), (a46, b6, c3, d17), (a46, b6, c3, d18), (a46, b6, c3, d19), (a46, b6, c3, d20), (a46, b6, c3, d21), (a46, b6, c3, d22), (a47, b1, c1, d1), (a47, b1, c1, d2), (a47, b1, c1, d3), (a47, b1, c1, d4), (a47, b1, c1, d5), (a47, b1, c1, d6), (a47, b1, c1, d7), (a47, b1, c1, d8), (a47, b1, c1, d9), (a47, b1, c1, d10), (a47, b1, c1, d11), (a47, b1, c1, d12), (a47, b1, c1, d13), (a47, b1, c1, d14), (a47, b1, c1, d15), (a47, b1, c1, d16), (a47, b1, c1, d17), (a47, b1, c1, d18), (a47, b1, c1, d19), (a47, b1, c1, d20), (a47, b1, c1, d21), (a47, b1, c1, d22), (a47, b1, c2, d1), (a47, b1, c2, d2), (a47, b1, c2, d3), (a47, b1, c2, d4), (a47, b1, c2, d5), (a47, b1, c2, d6), (a47, b1, c2, d7), (a47, b1, c2, d8), (a47, b1, c2, d9), (a47, b1, c2, d10), (a47, b1, c2, d11), (a47, b1, c2, d12), (a47, b1, c2, d13), (a47, b1, c2, d14), (a47, b1, c2, d15), (a47, b1, c2, d16), (a47, b1, c2, d17), (a47, b1, c2, d18), (a47, b1, c2, d19), (a47, b1, c2, d20), (a47, b1, c2, d21), (a47, b1, c2, d22), (a47, b1, c3, d1), (a47, b1, c3, d2), (a47, b1, c3, d3), (a47, b1, c3, d4), (a47, b1, c3, d5), (a47, b1, c3, d6), (a47, b1, c3, d7), (a47, c3, d8), (a47, b1, c3, d9), (a47, b1, c3, d10), (a47, b1, c3, d11), (a47, b1, c3, d12), (a47, b1, c3, d13), (a47, b1, c3, d14), (a47, b1, c3, d15), (a47, b1, c3, d16), (a47, b1, c3, d17), (a47, b1, c3, d18), (a47, b1, c3, d19), (a47, b1, c3, d20), (a47, b1, c3, d21), (a47, b1, c3, d22), (a47, b2, c1, d1), (a47, b2, c1, d2), (a47, b2, c1, d3), (a47, b2, c1, d4), (a47, b2, c1, d5), (a47, b2, c1, d6), (a47, b2, c1, d7), (a47, b2, c1, d3), (a47, b2, c1, d9), (a47, b2, c1, d10), (a47, b2, c1, d11), (a47, b2, c1, d12), (a47, b2, c1, d13), (a47, b2, c1, d14), (a47, b2, c1, d15), (a47, b2, c1, d16), (a47, b2, c1, d17), (a47, b2, c1, d18), (a47, b2, c1, d19), (a47, b2, c1, d20), (a47, b2, c1, d21), (a47, b2, c1, d22), (a47, b2, c2, d1), (a47, b2, c2, d2), (a47, b2, c2, d3), (a47, b2, c2, d4), (a47, b2, c2, d5), (a47, b2, c2, d6), (a47, b2, c2, d7), (a47, b2, c2, d8), (a47, b2, c2, d9), (a47, b2, c2, d10), (a47, b2, c2, d11), (a47, b2, c2, d12), (a47, b2, c2, d13), (a47, b2, c2, d14), (a47, b2, c2, d15), (a47, b2, c2, d16), (a47, b2, c2, d17), (a47, b2, c2, d18), (a47, b2, c2, d19), (a47, b2, c2, d20), (a47, b2, c2, d21), (a47, b2, c2, d22), (a47, b2, c3, d1), (a47, b2, c3, d2), (a47, b2, c3, d3), (a47, b2, c3, d4), (a47, b2, c3, d5), (a47, b2, c3, d6), (a47, b2, c3, d7), (a47, b2, c3, d3), (a47, b2, c3, d9), (a47, b2, c3, d10), (a47, b2, c3, d11), (a47, b2, c3, d12), (a47, b2, c3, d13), (a47, b2, c3, d14), (a47, b2, c3, d15), (a47, b2, c3, d16), (a47, b2, c3, d17), (a47, b2, c3, d18), (a47, b2, c3, d19), (a47, b2, c3, d20), (a47, b2, c3, d21), (a47, b2, c3, d22), (a47, b3, c1, d1), (a47, b3, c1, d2), (a47, b3, c1, d3), (a47, b3, c1, d4), (a47, b3, c1, d5), (a47, b3, c1, d6), (a47, b3, c1, d7), (a47, b3, c1, d8), (a47, b3, c1, d9), (a47, b3, c1, d10), (a47, b3, c1, d11), (a47, b3, c1, d12), (a47, b3, c1, d13), (a47, b3, c1, d14), (a47, b3, c1, d15), (a47, b3, c1, d16), (a47, b3, c1, d17), (a47, b3, c1, d18), (a47, b3, c1, d19), (a47, b3, c1, d20), (a47, b3, c1, d21), (a47, b3, c1, d22), (a47, b3, c2, d1), (a47, b3, c2, d2), (a47, b3, c2, d3), (a47, b3, c2, d4), (a47, b3, c2, d5), (a47, b3, c2, d6), (a47, b3, c2, d7), (a47, b3, c2, d8), (a47, b3, c2, d9), (a47, b3, c2, d10), (a47, b3, c2, d11), (a47, b3, c2, d12), (a47, b3, c2, d13), (a47, b3, c2, d14), (a47, b3, c2, d15), (a47, b3, c2, d16), (a47, b3, c2, d17), (a47, b3, c2, d18), (a47, b3, c2, d19), (a47, b3, c2, d20), (a47, b3, c2, d21), (a47, b5, c2, d22), (a47, b3, c3, d1), (a47, b3, c3, d2), (a47, b3, c3, d3), (a47, b3, c3, d4), (a47, b3, c3, d5), (a47, b3, c3, d6), (a47, b3, c3, d7), (a47, b3, c3, d8), (a47, b3, c3, d9), (a47, b3, c3, d10), (a47, b3, c3, d11), (a47, b3, c3, d12), (a47, b3, c3, d13), (a47, b3, c3, d14), (a47, b3, c3, d15), (a47, b3, c3, d16), (a47, b3, c3, d17), (a47, b3, c3, d18), (a47, b3, c3, d19), (a47, b3, c3, d20), (a47, b3, c3, d21), (a47, b3, c3, d22), (a47, b4, c1, d1), (a47, b4, c1, d2), (a47, b4, c1, d3), (a47, b4, c1, d4), (a47, b4, c1, d5), (a47, b4, c1, d6), (a47, b4, c1, d7), (a47, b4, c1, d8), (a47, b4, c1, d9), (a47, b4, c1, d10), (a47, b4, c1, d11), (a47, b4, c1, d12), (a47, b4, c1, d13), (a47, b4, c1, d14), (a47, b4, c1, d15), (a47, b4, c1, d16), (a47, b4, c1, d17), (a47, b4, c1, d18), (a47, b4, c1, d19), (a47, b4, c1, d20), (a47, b4, c1, d21), (a47, b4, c1, d22), (a47, b4, c2, d1), (a47, b4, c2, d2), (a47, b4, c2, d3), (a47, b4, c2, d4), (a47, b4, c2, d5), (a47, b4, c2, d6), (a47, b4, c2, d7), (a47, b4, c2, d8), (a47, b4, c2, d9), (a47, b4, c2, d10), (a47, b4, c2, d11), (a47, b4, c2, d12), (a47, b4, c2, d13), (a47, b4, c2, d14), (a47, b4, c2, d15), (a47, b4, c2, d16), (a47, b4, c2, d17), (a47, b4, c2, d18), (a47, b4, c2, d19), (a47, b4, c2, d20), (a47, b4, c2, d21), (a47, b4, c2, d22), (a47, b4, c3, d1), (a47, b4, c3, d2), (a47, b4, c3, d3), (a47, b4, c3, d4), (a47, b4, c3, d5), (a47, b4, c3, d3), (a47, b4, c3, d7), (a47, b4, c3, d8), (a47, b4, c3, d9), (a47, b4, c3, d10), (a47, b4, c3, d11), (a47, b4, c3, d12), (a47, b4, c3, d13), (a47, b4, c3, d14), (a47, b4, c3, d15), (a47, b4, c3, d16), (a47, b4, c3, d17), (a47, b4, c3, d18), (a47, b4, c3, d19), (a47, b4, c3, d20), (a47, b4, c3, d21), (a47, b4, c3, d22), (a47, b5, c1, d1), (a47, b5, c1, d2), (a47, b5, c1, d3), (a47, b5, c1, d4), (a47, b5, c1, d5), (a47, b5, c1, d6), (a47, b5, c1, d7), (a47, b5, c1, d8), (a47, b5, c1, d9), (a47, b5, c1, d10), (a47, b5, c1, d11), (a47, b5, c1, d12), (a47, b5, c1, d13), (a47, b5, c1, d14), (a47, b5, c1, d15), (a47, b5, c1, d16), (a47, b5, c1, d17), (a47, b5, c1, d18), (a47, b5, c1, d19), (a47, b5, c1, d20), (a47, b5, c1, d21), (a47, b5, c1, d22), (a47, b5, c2, d1), (a47, b5, c2, d2), (a47, b5, c2, d3), (a47, b5, c2, d4), (a47, b5, c2, d5), (a47, b5, c2, d6), (a47, b5, c2, d7), (a47, b5, c2, d8), (a47, b5, c2, d9), (a47, b5, c2, d10), (a47, b5, c2, d11), (a47, b5, c2, d12), (a47, b5, c2, d1), (a47, b5, c2, d14), (a47, b5, c2, d15), (a47, b5, c2, d16), (a47, b5, c2, d17), (a47, b5, c2, d18), (a47, b5, c2, d19), (a47, b5, c2, d20), (a47, b5, c2, d21), (a47, b5, c2, d22), (a47, b5, c3, d1), (a47, b5, c3, d2), (a47, b5, c3, d3), (a47, b5, c3, d4), (a47, b5, c3, d5), (a47, b5, c3, d6), (a47, b5, c3, d7), (a47, b5, c3, d8), (a47, b5, c3, d9), (a47, b5, c3, d10), (a47, b5, c3, d11), (a47, b5, c3, d12), (a47, b5, c3, d13), (a47, b5, c8, d14), (a47, b5, c3, d15), (a47, b5, c3, d16), (a47, b5, c3, d17), (a47, b5, c3, d18), (a47, b5, c3, d19), (a47, b5, c3, d20), (a47, b5, c3, d21), (a47, b5, c3, d22), (a47, b6, c1, d1), (a47, b6, c1, d2), (a47, b6, c1, d3), (a47, b6, c1, d4), (a47, b6, c1, d5), (a47, b6, c1, d6), (a47, b6, c1, d7), (a47, b6, c1, d8), (a47, b6, c1, d9), (a47, b6, c1, d10), (a47, b6, c1, d11), (a47, b6, c1, d12), (a47, b6, c1, d13), (a47, b6, c1, d14), (a47, b6, c1, d15), (a47, b6, c1, d16), (a47, b6, c1, d17), (a47, b6, c1, d18), (a47, b6, c1, d19), (a47, b6, c1, d20), (a47, b6, c1, d21), (a47, b6, c1, d22), (a47, b6, c2, d1), (a47, b6, c2, d2), (a47, b6, c2, d3), (a47, b6, c2, d4), (a47, b6, c2, d5), (a47, b6, c2, d6), (a47, b6, c2, d7), (a47, b6, c2, d8), (a47, b6, c2, d9), (a47, b6, c2, d10), (a47, b6, c2, d11), (a47, b6, c2, d12), (a47, b6, c2, d13), (a47, b6, c2, d14), (a47, b6, c2, d15), (a47, b6, c2, d16), (a47, b6, c2, d17), (a47, b6, c2, d18), (a47, b6, c2, d19), (a47, b6, c2, (d20), (a47, b6, c2, d21), (a47, b6, c2, d22), (a47, b6, c3, d1), (a47, b6, c3, d2), (a47, b6, c3, d3), (a47, b6, c3, d4), (a47, b6, c3, d5), (a47, b6, c3, d6), (a47, b6, c3, d7), (a47, b6, c3, d8), (a47, b6, c3, d9), (a47, b6, c3, d10), (a47, b6, c3, d11), (a47, b6, c3, d12), (a47, b6, c3, d13), (a47, b6, c3, d14), (a47, b6, c3, d15), (a47, b6, c3, d16), (a47, b6, c3, d17), (a47, b6, c3, d18), (a47, b6, c3, d19), (a47, b6, c3, d20), (a47, b6, c3, d21), (a47, b6, c3, d22), (a48, b1, c1, d1), (a48, b1, c1, d2), (a48, b1, c1, d3), (a48, b1, c1, d4), (a48, b1, c1, d5), (a48, b1, c1, d6), (a48, b1, c1, d7), (a48, b1, c1, d8), (a48, b1, c1, d9), (a48, b1, c1, d10), (a48, b1, c1, d11), (a48, b1, c1, d12), (a48, b1, c1, d13), (a48, b1, c1, d14), (a48, b1, c1, d15), (a48, b1, c1, d16), (a48, b1, c1, d17), (a48, b1, c1, d18), (a48, b1, c1, d19), (a48, b1, c1, d20), (a48, b1, c1, d21), (a48, b1, c1, d22), (a48, b1, c2, d1), (a48, b1, c2, d2), (a48, b1, c2, d3), (a48, b1, c2, d4), (a48, b1, c2, d5), (a48, b1, c2, d6), (a48, b1, c2, d7), (a48, b1, c2, d8), (a48, b1, c2, d9), (a48, b1, c2, d10), (a48, b1, c2, d11), (a48, b1, c2, d12), (a48, b1, c2, d13), (a48, b1, c2, d14), (a48, b1, c2, d15), (a48, b1, c2, d16), (a48, b1, c2, d17), (a48, b1, c2, d18), (a48, b1, c2, d19), (a48, b1, c2, d20), (a48, b1, c2, d21), (a48, b1, c2, d22), (a48, b1, c3, d1), (a48, b1, c3, d2), (a48, b1, c3, d3), (a48, b1, c3, d4), (a48, b1, c3, d5), (a48, b1, c3, d6), (a48, b1, c3, d7), (a48, b1, c3, d8), (a48, b1, c3, d9), (a48, b1, c3, d10), (a48, b1, c3, d11), (a48, b1, c3, d12), (a48, b1, c3, d13), (a48, b1, c3, d14), (a48, b1, c3, d15), (a48, b1, c3, d16), (a48, b1, c3, d17), (a48, b1, c3, d18), (a48, b1, c3, d19), (a48, b1, c3, d20), (a48, b1, c3, d21), (a48, b1, c3, d22), (a48, b2, c3, d1), (a48, b2, c1, d2), (a48, b2, c1, d3), (a48, b2, c1, d4), (a48, b2, c1, d5), (a48, b2, c1, d6), (a48, b2, c1, d7), (a48, b2, c1, d8), (a48, b2, c1, d9), (a48, b2, c1, d10), (a48, b2, c1, d11), (a48, b2, c1, d12), (a48, b2, c1, d13), (a48, b2, c1, d14), (a48, b2, c1, d15), (a48, b2, c1, d16), (a48, b2, c1, d17), (a48, b2, c1, d18), (a48, b2, c1, d19), (a48, b2, c1, d20), (a48, b2, c1, d21), (a48, b2, c1, d22), (a48, b2, c2, d1), (a48, b2, c2, d2), (a48, b2, c2, d3), (a48, b2, c2, d4), (a48, b2, c2, d5), (a48, b2, c2, d6), (a48, b2, c2, d7), (a48, b2, c2, d8), (a48, b2, c2, d9), (a48, b2, c2, d10), (a48, b2, c2, d11), (a48, b2, c2, d12), (a48, b2, c2, d13), (a48, b2, c2, d14), (a48, b2, c2, d15), (a48, b2, c2, d16), (a48, b2, c2, d17), (a48, b2, c2, d18), (a48, b2, c2, d19), (a48, b2, c2, d20), (a48, b2, c2, d21), (a48, b2, c2, d22), (a48, b2, c3, d), (a48, b2, c3, d2), (a48, b2, c3, d3), (a48, b2, c3, d4), (a48, b2, c3, d5), (a48, b2, c3, d6), (a48, b2, c3, d7), (a48, b2, c3, d8), (a48, b2, c3, d9), (a48, b2, c3, d10), (a48, b2, c3, d11), (a48, b2, c3, d12), (a48, b2, c3, d13), (a48, b2, c3, d14), (a48, b2, c3, d15), (a48, b2, c3, d16), (a48, b2, c3, d17), (a48, b2, c3, d18), (a48, b2, c3, d19), (a48, b2, c3, d20), (a48, b2, c3, d21), (a48, b2, c3, d22), (a48, b3, c1, d1), (a48, b3, c1, d2), (a48, b3, c1, d3), (a48, b3, c1, d4), (a48, b3, c1, d5), (a48, b3, c1, d6), (a48, b3, c1, d7), (a48, b3, c1, d8), (a48, b3, c1, d9), (a48, b3, c1, d10), (a48, b3, (, d11), (a48, b3, c1, d12), (a48, b3, c1, d13), (a48, b3, c1, d14), (a48, b3, c1, d15), (a48, b3, c1, d16), (a48, b3, c1, d17), (a48, b3, c1, d18), (a48, b3, c1, d19), (a48, b3, c1, d20), (a48, b3, c1, d21), (a48, b3, c1, d22), (a48, b3, c2, d1), (a48, b3, c2, d2), (a48, b3, c2, d3), (a48, b3, c2, d4), (a48, b3, c2, d5), (a48, b3, c2, d6), (a48, b3, c2, d7), (a48, b3, c2, d8), (a48, b3, c2, d9), (a48, b3, c2, d10), (a48, b3, c2, d11), (a48, b3, c2, d12), (a48, b3, c2, d13), (a48, b3, c2, d14), (a48, b3, c2, d15), (a48, b3, c2, d16), (a48, b3, c2, d17), (a48, b3, c2, d18), (a48, b3, c2, d69), (a48, b3, c2, d20), (a48, b3, c2, d21), (a48, b3, c2, d22), (a48, b3, c3, d1), (a48, b3, c3, d2), (a48, b3, c3, d3), (a48, b3, c3, d4), (a48, b3, c3, d5), (a48, b3, c3, d6), (a48, b3, c3, d7), (a48, b3, c3, d8), (a48, b3, c3, d9), (a48, b3, c3, d10), (a48, b3, c3, d11), (a48, b3, c3, d12), (a48, b3, c3, d13), (a48, b3, c3, d14), (a48, b3, c3, d15), (a48, b5, c3, d16), (a48, b5, c3, d17), (a48, b5, c3, d18), (a48, b3, c3, d19), (a48, b3, c3, d20), (a48, b3, c3, d21), (a48, b3, c3, d22), (a48, b4, c1, d1), (a48, b4, c1, d2), (a48, b4, c1, d3), (a48, b4, c1, d4), (a48, b4, c1, d5), (a48, b4, c1, d6), (a48, b4, c1, d7), (a48, b4, c1, d8), (a48, b4, c1, d9), (a48, b4, c1, d10), (a48, b4, c1, d11), (a48, b4, c1, d12), (a48, b4, c1, d13), (a48, b4, c1, d14), (a48, b4, c1, d15), (a48, b4, c1, d16), (a48, b4, c1, d17), (a48, b4, c1, d18), (a48, b4, c1, d19), (a48, b4, c1, d20), (a48, b4, c1, d21), (a48, b4, c1, d22), (a48, b4, c2, d1), (a48, b4, c2, d2), (a48, b4, c2, d3), (a48, b4, c2, d4), (a48, b4, c2, d15), (a48, b4, c2, d16), (a48, b4, c2, d7), (a48, b4, c2, d8), (a48, b4, c2, d9), (a48, b4, c2, d10), (a48, b4, c2, d11), (a48, b4, c2, d12), (a48, b4, c2, d13), (a48, b4, c2, d14), (a48, b4, c2, d15), (a48, b4, c2, d16), (a48, b4, c2, d17), (a48, b4, c2, d18), (a48, b4, c2, d19), (a48, b4, c2, d20), (a48, b4, c2, d21), (a48, b4, c2, d22), (a48, b4, c3, d1), (a48, b4, c3, d2), (a48, b4, c3, d3), (a48, b4, c3, d4), (a48, b4, c3, d5), (a48, b4, c3, d6), (a48, b4, c3, d7), (a48, b4, c3, d8), (a48, b4, c3, d9), (a48, b4, c3, d10), (a48, b4, c3, d11), (a48, b4, c3, d12), (a48, b4, c3, d13), (a48, b4, c3, d14), (a48, b4, c3, d15), (a48, b4, c3, d16), (a48, b4, c3, d17), (a48, b4, c3, d18), (a48, b4, c3, d19), (a48, b4, c3, d20), (a48, b4, c3, d21), (a48, b4, c3, d22), (a48, b5, c1, d1), (a48, b5, c1, d2), (a48, b5, c1, d3), (a48, b5, c1, d4), (a48, b5, c1, d5), (a48, b5, c1, d6), (a48, b5, c1, d7), (a48, b5, c1, d8), (a48, b5, c1, d9), (a48, b5, c1, d10), (a48, b5, c1, d11), (a48, b5, c1, d12), (a48, b5, c1, d13), (a48, b5, c1, d14), (a48, b5, c1, d15), (a48, b5, c1, d16), (a48, b5, c1, d17), (a48, b5, c1, d18), (a48, b5, c1, d19), (a48, b5, c1, d20), (a48, b5, c1, d21), (a48, b5, c1, d22), (a48, b5, c2, d1), (a48, b5, c2, d2), (a48, b5, c2, d3), (a48, b5, c2, d4), (a48, b5, c2, d5), (a48, b5, c2, d6), (a48, b5, c2, d7), (a48, b5, c2, d8), (a48, b5, c2, d9), (a48, b5, c2, d10), (a48, b5, c2, d11), (a48, b5, c2, d12), (a48, b5, c2, d13), (a48, b5, c2, d14), (a48, b5, c2, d15), (a48, b5, c2, d16), (a48, b5, c2, d17), (a48, b5, c2, d18), (a48, b5, c2, d19), (a48, b5, c2, d20), (a48, b5, c2, d21), (a48, b5, c2, d22), (a48, b5, c3, d1), (a48, b5, c3, d2), (a48, b5, c3, d3), (a48, b5, c3, d4), (a48, b5, c3, d5), (a48, b5, c3, d6), (a48, b5, c3, d7), (a48, b5, c3, d8), (a48, b5, c3, d9), (a48, b5, c3, d10), (a48, b5, c3, d11), (a48, b5, c3, d12), (a48, b5, c3, d13), (a48, b5, c3, d14), (a48, b5, c3, d15), (a48, b5, c3, d16), (a48, b5, c3, d17), (a48, b5, c3, d18), (a48, b5, c3, d19), (a48, b5, c3, d20), (a48, b5, c3, d21), (a48, b5, c3, d22), (a48, b6, c1, d1), (a48, b6, c1, d2), (a48, b6, c1, d3), (a48, b6, c1, d4), (a48, b6, c1, d5), (a48, b6, c1, d6), (a48, b6, c1, d7), (a48, b6, c1, d8), (a48, b6, c1, d9), (a48, b6, c1, d10), (a48, b6, c1, d11), (a48, b6, c1, d12), (a48, b6, c1, d13), (a48, b6, c1, d14), (a48, b6, c1, d15), (a48, b6, c1, d16), (a48, b6, c1, d17), (a48, b6, c1, d18), (a48, b6, c1, d19), (a48, b6, c1, d20), (a48, b6, c1, d21), (a48, b6, c1, d22), (a48, b6, c2, d1), (a48, b6, c2, d2), (a48, b6, c2, d3), (a48, b6, c2, d4), (a48, b6, c2, d5), (a48, b6, c2, d6), (a48, b6, c2, d7), (a48, b6, c2, d8), (a48, b6, c2, d9), (a48, b6, c2, d10), (a48, b6, c2, d11), (a48, b6, c2, d12), (a48, b6, c2, d13), (a48, b6, c2, d14), (a48, b6, c2, d15), (a48, b6, c2, d16), (a48, b6, c2, d17), (a48, b6, c2, d18), (a48, b6, c2, d19), (a48, b6, c2, d20), (a48, b6, c2, d21), (a48, b6, c2, d22), (a48, b6, c3, d1), (a48, b6, c3, d2), (a48, b6, c3, d3), (a48, b6, c3, d4), (a48, b6, c3, d5), (a48, b6, c3, d6), (a48, b6, c3, d7), (a48, b6, c3, d8), (a48, b6, c3, d9), (a48, b6, c3, d10), (a48, b6, c3, d11), (a48, b6, c3, d12), (a48, b6, c3, d13), (a48, b6, c3, d14), (a48, b6, c3, d15), (a48, b6, c3, d16), (a48, b6, c3, d17), (a48, b6, c3, d18), (a48, b6, c3, d19), (a48, b6, c3, d20), (a48, b6, c3, d21), (a48, b6, c3, d22), (a49, b1, c1, d1), (a49, b1, c1, d2), (a49, b1, c1, d3), (a49, b1, c1, d4), (a49, b1, c1, d5), (a49, b1, c1, d6), (a49, b1, c1, d7), (a49, b1, c1, d5), (a49, b1, c1, d9), (a49, b1, c1, d10), (a49, b1, c1, d11), (a49, b1, c1, d12), (a49, b1, c1, d13), (a49, b1, c1, d14), (a49, b1, c1, d15), (a49, b1, c1, d16), (a49, b1, c1, d17), (a49, b1, c1, d18), (a49, b1, c1, d19), (a49, b1, c1, d20), (a49, b1, c1, d21), (a49, b1, c1, d22), (a49, b1, c2, d1), (a49, b1, c2, d2), (a49, b1, c2, d3), (a49, b1, c2, d4), (a49, b1, c2, d5), (a49, b1, c2, d6), (a49, b1, c2, d7), (a49, b1, c2, d8), (a49, b1, c2, d9), (a49, b1, c2, d10), (a49, b1, c2, d11), (a49, b1, c2, d12), (a49, b1, c2, d13), (a49, b1, c2, d14), (a49, b1, c2, d15), (a49, b1, c2, d16), (a49, b1, c2, d17), (a49, b1, c2, d18), (a49, b1, c2, d19), (a49, b1, c2, d20), (a49, b1, c2, d21), (a49, b1, c2, d22), (a49, b1, c3, d1), (a49, b1, c3, d2), (a49, b1, c3, d3), (a49, b1, c3, d4), (a49, b1, c3, d5), (a49, b1, c3, d6), (a49, b1, c3, d7), (a49, b1, c3, d8), (a49, b1, c3, d9), (a49, b1, c3, d10), (a49, b1, c3, d11), (a49, b1, c3, d12), (a49, b1, c3, d13), (a49, b1, c3, d14), (a49, b1, c3, d15), (a49, b1, c3, d16), (a49, b1, c3, d17), (a49, b1, c3, d18), (a49, b1, c3, d19), (a49, b1, c3, d20), (a49, b1, c3, d21), (a49, b, c3, d2), (a49, b1, c3, d22), (a49, b2, c1, d1), (a49, b2, c1, d2), (a49, b2, c1, d3), (a49, b2, c1, d4), (a49, b2, c1, d5), (a49, b2, c1, d6), (a49, b2, c1, d7), (a49, b2, c1, d8), (a49, b2, c1, d9), (a49, b2, c1, d10), (a49, b2, c1, d11), (a49, b2, c1, d12), (a49, b2, c1, d13), (a49, b2, c1, d14), (a49, b2, c1, d15), (a49, b2, c1, d16), (a49, b2, c1, d17), (a49, b2, c1, d18), (a49, b2, c1, d19), (a49, b2, c1, d20), (a49, b2, c1, d21), (a49, b2, c1, d22), (a49, b2, c2, d1), (a49, b2, c2, d2), (a49, b2, c2, d3), (a49, b2, c2, d4), (a49, b2, c2, d5), (a49, b2, c2, d6), (a49, b2, c2, d7), (a49, b2, c2, d8), (a49, b2, c2, d9), (a49, b2, c2, d10), (a49, b2, c2, d11), (a49, b2, c2, d12), (a49, b2, c2, d13), (a49, b2, c2, d14), (a49, b2, c2, d15), (a49, b2, c2, d16), (a49, b2, c2, d17), (a49, b2, c2, d18), (a49, b2, c2, d19), (a49, b2, c2, d20), (a49, b2, c2, d21), (a49, b2, c2, d22), (a49, b2, c3, d1), (a49, b2, c3, d2), (a49, b2, c3, d3), (a49, b2, c3, d4), (a49, b2, c3, d5), (a49, b2, d6), (a49, b2, c3, d7), (a49, b2, c3, d8), (a49, b2, c3, d9), (a49, b2, c3, d10), (a49, b2, c3, d11), (a49, b2, c3, d12), (a49, b2, c3, d13), (a49, b2, c3, d14), (a49, b2, c3, d15), (a49, b2, c3, d16), (a49, b2, c3, d17), (a49, b2, c3, d18), (a49, b2, c3, d19), (a49, b2, c3, d20), (a49, b2, c3, d21), (a49, b2, c3, d22), (a49, b3, c1, d1), (a49, b3, c1, d2), (a49, b3, c1, d3), (a49, b3, c1, d4), (a49, b3, c1, d5), (a49, b3, c1, d6), (a49, b3, c1, d7), (a49, b3, c1, d8), (a49, b3, c1, d9), (a49, b3, c1, d10), (a49, b3, c1, d11), (a49, b3, c1, d12), (a49, b3, c1, d13), (a49, b3, c1, d14), (a49, b3, c1, d15), (a49, b3, c1, d16), (a49, b3, c1, d17), (a49, b3, c1, d18), (a49, b3, c1, d19), (a49, b3, c1, d20), (a49, b3, c1, d21), (a49, b3, c1, d22), (a49, b3, c2, d1), (a49, b3, c2, d2), (a49, b3, c2, d3), (a49, b3, c2, d4), (a49, b3, c2, d5), (a49, b3, c2, d6), (a49, b3, c2, d7), (a49, b3, c2, d8), (a49, b3, c2, d9), (a49, b3, c2, d10), (a49, b3, c2, d11), (a49, b3, c2, d12), (a49, b5, c2, d13), (a49, b3, c2, d14), (a49, b3, c2, d15), (a49, b3, c2, d16), (a49, b3, c2, d17), (a49, b3, c2, d18), (a49, b3, c2, d19), (a49, b3, c2, d20), (a49, b3, c2, d21), (a49, b3, c2, d22), (a49, b5, c3, d1), (a49, b3, c3, d2), (a49, b3, c3, d3), (a49, b3, c3, d4), (a49, b3, c3, d5), (a49, b3, c3, d6), (a49, b3, c3, d7), (a49, b3, c3, d8), (a49, b3, c3, d9), (a49, b3, c3, d10), (a49, b3, c3, d11), (a49, b3, c3, d12), (a49, b3, c3, d13), (a49, b3, c3, d14), (a49, b3, c3, d15), (a49, b3, c3, d16), (a49, b3, c3, d17), (a49, b3, c3, d18), (a49, b3, c3, d19), (a49, b3, c1, d20), (a49, b3, c1, d21), (a49, b3, c3, d22), (a49, b4, c1, d1), (a49, b4, c1, d2), (a49, b4, c1, d3), (a49, b4, c1, d4), (a49, b4, c1, d5), (a49, b4, c1, d6), (a49, b4, c1, d7), (a49, b4, c1, d8), (a49, b4, c1, d9), (a49, b4, c1, d10), (a49, b4, c1, d11), (a49, b4, c1, d12), (a49, b4, c1, d13), (a49, b4, c1, d14), (a49, b4, c1, d15), (a49, b4, c1, d16), (a49, b4, c1, d17), (a49, b4, c1, d18), (a49, b4, c1, d19), (a49, b4, c1, d20), (a49, b4, c1, d21), (a49, b4, c1, d22), (a49, b4, c2, d1), (a49, b4, c2, d2), (a49, b4, c2, d3), (a49, b4, c2, d4), (a49, b4, c2, d5), (a49, b4, c2, d6), (a49, b4, c2, d7), (a49, b4, c2, d8), (a49, b4, c2, d9), (a49, b4, c2, d10), (a49, b4, c2, d11), (a49, b4, c2, d12), (a49, b4, c2, d13), (a49, b4, c2, d14), (a49, b4, c2, d15), (a49, b4, c2, d16), (a49, b4, c2, d17), (a49, b4, c2, d18), (a49, b4, c2, d19), (a49, b4, c2, d20), (a49, b4, c2, d21), (a49, b4, c2, d22), (a49, b4, c3, d1), (a49, b4, c3, d2), (a49, b4, c3, d3), (a49, b4, c3, d4), (a49, b4, c3, d5), (a49, b4, c3, d6), (a49, b4, c3, d7), (a49, b4, c3, d8), (a49, b4, c3, d9), (a49, b4, c3, d10), (a49, b4, c3, d11), (a49, b4, c3, d12), (a49, b4, c3, d13), (a49, b4, c3, d14), (a49, b4, c3, d15), (a49, b4, c3, d16), (a49, b4, c3, d17), (a49, b4, c3, d18), (a49, b4, c3, d19), (a49, b4, c3, d20), (a49, b4, c3, d21), (a49, b4, c3, d22), (a49, b5, c1, d1), (a49, b5, c1, d2), (a49, b5, c1, d3), (a49, b5, c1, d4), (a49, b5, c1, d5), (a49, b5, c1, d6), (a49, b5, c1, d7), (a49, b5, c1, d8), (a49, b5, c1, d9), (a49, b5, c1, d10), (a49, b5, c1, d11), (a49, b5, c1, d12), (a49, b5, c1, d13), (a49, b5, c1, d14), (a49, b5, c1, d15), (a49, b5, c1, d16), (a49, b5, c1, d17), (a49, b5, c1, d18), (a49, b5, c1, d19), (a49, b5, c1, d20), (a49, b5, c1, d21), (a49, b5, c1, d22), (a49, b5, c2, d1), (a49, b5, c2, d2), (a49, b5, c2, d3), (a49, b5, c2, d4), (a49, b5, c2, d5), (a49, b5, c2, d6), (a49, b5, c2, d7), (a49, b5, c2, d8), (a49, b5, c2, d9), (a49, b5, c2, d10), (a49, b5, c2, d11), (a49, b5, c2, d12), (a49, b5, c2, d13), (a49, b5, c2, d14), (a49, b5, c2, d15), (a49, b5, c2, d16), (a49, b5, c2, d17), (a49, b5, c2, d18), (a49, b5, c2, d19), (a49, b5, c2, d20), (a49, b5, c2, d21), (a49, b5, c2, d22), (a49, b5, c3, d1), (a49, b5, c3, d2), (a49, b5, c3, d3), (a49, b5, c3, d4), (a49, b5, c3, d5), (a49, b5, c3, d6), (a49, b5, c3, d7), (a49, b5, c3, d8), (a49, b5, c3, d9), (a49, b5, c3, d10), (a49, b5, c3, d11), (a49, b5, c3, d12), (a49, b5, c3, d13), (a49, b5, c3, d14), (a49, b5, c3, d15), (a49, b5, c3, d16), (a49, b5, c3, d17), (a49, b5, c3, d18), (a49, b5, c3, d19), (a49, b5, c3, d20), (a49, b5, c3, d21), (a49, b5, c3, d22), (a49, b6, c1, d1), (a49, b6, c1, d2), (a49, b6, c1, d3), (a49, b6, c1, d4), (a49, b6, c1, d5), (a49, b6, c1, d6), (a49, b6, c1, d7), (a49, b6, c1, d8), (a49, b6, c1, d9), (a49, b6, c1, d10), (a49, b6, c1, d11), (a49, b6, c1, d12), (a49, b6, c1, d13), (a49, b6, c1, d14), (a49, b6, c1, d15), (a49, b6, c1, d16), (a49, b6, c1, d17), (a49, b6, c1, d18), (a49, b6, c1, d19), (a49, b6, c1, d20), (a49, b6, c1, d21), (a49, b6, c1, d22), (a49, b6, c2, d1), (a49, b6, c2, d2), (a49, b6, c2, d3), (a49, b6, c2, d4), (a49, b6, c2, d5), (a49, b6, c2, d6), (a49, b6, c2, d7), (a49, b6, c2, d8), (a49, b6, c2, d9), (a49, b6, c2, d10), (a49, b6, c2, d11), (a49, b6, c2, d12), (a49, b6, c2, d13), (a49, b6, c2, d14), (a49, b6, c2, d15), (a49, b6, c2, d16), (a49, b6, c2, d17), (a49, b6, c2, d18), (a49, b6, c2, d19), (a49, b6, c2, d20), (a49, b6, c2, d21), (a49, b6, c2, d22), (a49, b6, c3, d1), (a49, b6, c3, d2), (a49, b6, c3, d3), (a49, b6, c3, d4), (a49, b6, c3, d5), (a49, b6, c3, d6), (a49, b6, c3, d7), (a49, b6, c3, d8), (a49, b6, c3, d9), (a49, b6, c3, d10), (a49, b6, c3, d11), (a49, b6, c3, d12), (a49, b6, c3, d13), (a49, b6, c3, d14), (a49, b6, c3, d15), (a49, b6, c3, d16), (a49, b6, c3, d17), (a49, b6, c3, d18), (a49, b6, c3, d19), (a49, b6, c3, d20), (a49, b6, c3, d21), (a49, b6, c3, d22), (a50, b1, c1, d1), (a50, b1, c1, d2) (a50, b1, c1, d3), (a50, b1, c1, d4), (a50, b1, c1, d15), (a50, b1, c1, d6), (a50, b1, c1, d7), (a50, b1, c1, d8), (a50, b1, c1, d9), (a50, b1, c1, d10), (a50, b1, c1, d11), (a50, b1, c1, d12), (a50, b1, c1, d13), (a50, b1, c1, d14), (a50, b1, c1, d15), (a50, b1, c1, d16), (a50, b1, c1, d17), (a50, b1, c1, d18), (a50, b1, c1, d19), (a50, b1, c1, d20), (a50, b1, c1, d21), (a50, b1, c1, d22), (a50, b1, c2, d1), (a50, b1, c2, d2), (a50, b1, c2, d3), (a50, b1, c2, d4), (a50, b1, c2, d5), (a50, b1, c2, d6), (a50, b1, c2, d7), (a50, b1, c2, d8), (a50, b1, c2, d9), (a50, b1, c2, d10), (a50, b1, c2, d11), (a50, b1, c2, d12), (a50, b1, c2, d13), (a50, b1, c2, d14), (a50, b1, c2, d15), (a50, b1, c2, d16), (a50, b1, c2, d17), (a50, b1, c2, d18), (a50, b1, c2, d19), (a50, b1, c2, d20), (a50, b1, c2, d21), (a50, b1, c2, d22), (a50, b1, c3, d1), (a50, b1, c3, d2), (a50, b1, c3, d3), (a50, b1, c3, d4), (a50, b1, c3, d5), (a50, b1, c3, d6), (a50, b1, c3, d7), (a50, b1, c3, d8), (a50, b1, c3, d9), (a50, b1, c3, d10), (a50, b1, c3, d11), (a50, b1, c3, d12), (a50, b1, c3, d13), (a50, b1, c3, d14), (a50, b1, c3, d15), (a50, b1, c3, d16), (a50, b1, c3, d17), (a50, b1, c3, d18), (a50, b1, c3, d19), (a50, b1, c3, d20), (a50, b1, c3, d21), (a50, b1, c3, d22), (a50, b2, c1, d1), (a50, b2, c1, d2), (a50, b2, c1, d3), (a50, b2, c1, d4), (a50, b2, c1, d5), (a50, b2, c1, d6), (a50, b2, c1, d7), (a50, b2, c1, d8), (a50, b2, c1, d9), (a50, b2, c1, d10), (a50, b2, c1, d11), (a50, b2, c1, d12), (a50, b2, c1, d13), (a50, b2, c1, d14), (a50, b2, c1, d15), (a50, b2, c1, d16), (a50, b2, c1, d17), (a50, b2, c1, d18), (a50, b2, c1, d19), (a50, b2, c1, d20), (a50, b2, c1, d21), (a50, b2, c1, d22), (a50, b2, c2, d1), (a50, b2, c2, d2), (a50, b2, c2, d3), (a50, b2, c2, d4), (a50, b2, c2, d5), (a50, b2, c2, d6), (a50, b2, c2, d7), (a50, b2, c2, d8), (a50, b2, c2, d9), (a50, b2, c2, d10), (a50, b2, c2, d11), (a50, b2, c2, d12), (a50, b2, c2, d13), (a50, b2, c2, d14), (a50, b2, c2, d15), (a50, b2, c2, d16), (a50, b2, c2, d17), (a50, b2, c2, d18), (a50, b2, c2, d19), (a50, b2, c2, d20), (a50, b2, c2, d21), (a50, b2, c2, d22), (a50, b2, c3, d1), (a50, b2, c3, d2), (a50, b2, c3, d3), (a50, b2, c3, d4), (a50, b2, c3, d5), (a50, b2, c3, d6), (a50, b2, c3, d7), (a50, b2, c3, d8), (a50, b2, c3, d9), (a50, b2, c3, d10), (a50, b2, c3, d11), (a50, b2, c3, d12), (a50, b2, c3, d13), (a50, b2, c3, d14), (a50, b2, c3, d15), (a50, b2, c3, d16), (a50, b2, c3, d17), (a50, b2, c3, d18), (a50, b2, c3, d19), (a50, b2, c3, d20), (a50, b2, c3, d21), (a50, b2, c3, d22), (a50, b3, c1, d1), (a50, b3, c1, d2), (a50, b3, c1, d3), (a50, b3, c1, d4), (a50, b3, c1, d5), (a50, b3, c1, d6), (a50, b3, c1, d7), (a50, b3, c1, d8), (a50, b3, c1, d9), (a50, b3, c1, d10), (a50, b3, c1, d11), (a50, b3, c1, d12), (a50, b3, c1, d13), (a50, b3, c1, d14), (a50, b3, c1, d15), (a50, b3, c1, d16), (a50, b3, c1, d17), (a50, b3, c1, d18), (a50, b3, c1, d19), (a50, b3, c1, d20), (a50, b3, c1, d21), (a50, b3, c1, d22), (a50, b3, c2, d1), (a50, b3, c2, d2), (a50, b3, c2, d3), (a50, b3, c2, d4), (a50, b3, c2, d5), (a50, b3, c2, d6), (a50, b3, c2, d7), (a50, b3, c2, d8), (a50, b3, c2, d9), (a50, b3, c2, d11), (a50, b3, c2, d11), (a50, b3, c2, d12), (a50, b3, c2, d13), (a50, b3, c2, d14), (a50, b3, c2, d15), (a50, b3, c2, d16), (a50, b3, c2, d17), (a50, b3, c2, d18), (a50, b3, c2, d19), (a50, b3, c2, d20), (a50, b3, c2, d21), (a50, b3, c2, d22), (a50, b3, c3, d1), (a50, b3, c3, d2), (a50, b3, c3, d3), (a50, b3, c3, d4), (a50, b3, c3, d5), (a50, b3, c3, d6), (a50, b3, c3, d7), (a50, b3, c3, d8), (a50, b3, c3, d9), (a50, b3, c3, d10), (a50, b3, c3, d11), (a50, b3, c2, d12), (a50, b3, c3, d13), (a50, b3, c3, d14), (a50, b3, c3, d15), (a50, b3, c3, d16), (a50, b3, c3, d17), (a50, b3, c3, d18), (a50, b3, c3, d19), (a50, b3, c3, d20), (a50, b3, c3, d21), (a50, b3, c3, d22), (a50, b4, c1, d1), (a50, b4, c1, d2), (a50, b4, c1, d3), (a50, b4, c1, d4), (a50, b4, c1, d5), (a50, b4, c1, d6), (a50, b4, c1, d7), (a50, b4, c1, d8), (a50, b4, c1, d9), (a50, b4, c1, d10), (a50, b4, c1, d11), (a50, b4, c1, d12), (a50, b4, c1, d13), (a50, b4, c1, d14), (a50, b4, c1, d15), (a50, b4, c1, d16), (a50, b4, c1, d17), (a50, b4, c1, d18), (a50, b4, c1, d19), (a50, b4, c1, d20), (a50, b4, c1, d21), (a50, b4, c1, d22), (a50, b4, c2, d1), (a50, b4, c2, d2), (a50, b4, c2, d3), (a50, b4, c2, d4), (a50, b4, c2, d5), (a50, b4, c2, d6), (a50, b4, c2, d7), (a50, b4, c2, d8), (a50, b4, c2, d9), (a50, b4, c2, d10), (a50, b4, c2, d11), (a50, b4, c2, d12), (a50, b4, c2, d13), (a50, b4, c2, d14), (a50, b4, c2, d15), (a50, b4, c2, d16), (a50, b4, c2, d17), (a50, b4, c2, d18), (a50, b4, c2, d19), (a50, b4, c2, d20), (a50, b4, c2, d21), (a50, b4, c2, d22), (a50, b4, c3, d1), (a50, b4, c3, d2), (a50, b4, c3, d3), (a50, b4, c3, d4), (a50, b4, c3, d5), (a50, b4, c3, d6), (a50, b4, c3, d7), (a50, b4, c3, d8), (a50, b4, c3, d9), (a50, b4, c3, d10), (a50, b4, c3, d11), (a50, b4, c3, d12), (a50, b4, c3, d13), (a50, b4, c3, d14), (a50, b4, c3, d15), (a50, b4, c3, d16), (a50, b4, c3, d17), (a50, b4, c3, d18), (a50, b4, c3, d19), (a50, b4, c3, d20), (a50, b4, c3, d21), (a50, b4, c3, d22), (a50, b5, c1, d1), (a50, b5, c1, d2), (a50, b5, c1, d3), (a50, b5, c1, d4), (a50, b5, c1, d5), (a50, b5, c1, d6), (a50, b5, c1, d7), (a50, b5, c1, d8), (a50, b5, c1, d9), (a50, b5, c1, d10), (a50, b5, c1, d11), (a50, b5, c1, d12), (a50, b5, c1, d13), (a50, b5, c1, d14), (a50, b5, c1, d15), (a50, b5, c1, d16), (a50, b5, c1, d17), (a50, b5, c1, d18), (a50, b5, c1, d19), (a50, b5, c1, d20), (a50, b5, c1, d21), (a50, b5, c1, d22), (a50, b5, c2, d1), (a50, b5, c2, d2), (a50, b5, c2, d3), (a50, b5, c2, d4), (a50, b5, c2, d5), (a50, b5, c2, d6), (a50, b5, c2, d7), (a50, b5, c2, d8), (a50, b5, c2, d9), (a50, b5, c2, d10), (a50, b5, c2, d11), (a50, b5, c2, d12), (a50, b5, c2, d13), (a50, b5, c2, d14), (a50, b5, c2, d15), (a50, b5, c2, d16), (a50, b5, c2, d17), (a50, b5, c2, d18), (a50, b5, c2, d19), (a50, b5, c2, d20), (a50, b5, c2, d21), (a50, b5, c2, d22), (a50, b5, c3, d1), (a50, b5, c3, d2), (a50, b5, c3, d3), (a50, b5, c3, d4), (a50, b5, c3, d5), (a50, b5, c3, d6), (a50, b5, c3, d7), (a50, b5, c3, d8), (a50, b5, c3, d9), (a50, b5, c3, d10), (a50, b5, c3, d11), (a50, b5, c3, d12), (a50, b5, c3, d13), (a50, b5, c3, d14), (a50, b5, c3, d15), (a50, b5, c3, d16), (a50, b5, c3, d17), (a50, b5, c3, d18), (a50, b5, c3, d19), (a50, b5, c3, d20), (a50, b5, c3, d21), (a50, b5, c3, d22), (a50, b6, c1, d1), (a50, b6, c1, d2), (a50, b6, c1, d3), (a50, b6, c1, d4), (a50, b6, c1, d5), (a50, b, c1, d6), (a50, b6, c1, d7), (a50, b6, c1, d8), (a50, b6, c1, d9), (a50, b6, c1, d10), (a50, b6, c1, d11), (a50, b6, b6, c1, d12), (a50, b6, c1, d13), (a50, b6, c1, d14), (a50, b6, c1, d15), (a50, b6, c1, d16), (a50, b6, c1, d17), (a50, b6, c1, d18), (a50, b6, c1, d19), (a50, b6, c1, d20), (a50, b6, c1, d21), (a50, b6, c1, d22), (a50, b6, c2, d1), (a50, b6, c2, d2), (a50, b6, c2, d3), (a50, b6, c2, d4), (a50, b6, c2, d5), (a50, b6, c2, d6), (a50, b6, c2, d7), (a50, b6, c2, d8), (a50, b6, c2, d9), (a50, b6, c2, d10), (a50, b6, c2, d11), (a50, b6, c2, d12), (a50, b6, c2, d13), (a50, b6, c2, d14), (a50, b, c2, d15), (a50, b6, c2, d16), (a50, b6, c2, d17), (a50, b6, c2, d18), (a50, b6, c2, d19), (a50, b6, c2, d20), (a50, b6, c2, d21), (a50, b6, c2, d22), (a50, b6, c3, d1), (a50, b6, c3, d2), (a50, b6, c3, d3), (a50, b6, c3, d4), (a50, b6, c3, d5), (a50, b6, c3, d6), (a50, b6, c3, d7), (a50, b6, c3, d5), (a50, b6, c3, d9), (a50, b6, c3, d10), (a50, b6, c3, d11), (a50, b6, c3, d12), (a50, b6, c3, d13), (a50, b6, c3, d14), (a50, b6, c3, d15), (a50, b6, c3, d16), (a50, b6, c3, d17), (a50, b6, c3, d8), (a50, b6, c3, d19), (a50, b6, c3, d20), (a50, b6, c3, d21), (a50, b6, c3, d22), (a51, b1, c1, d1), (a51, b1, c1, d2), (a51, b1, c1, d3), (a51, b1, c1, d4), (a51, b1, c1, d5), (a51, b1, c1, d6), (a51, b1, c1, d7), (a51, b1, c1, d8), (a51, b1, c1, d9), (a51, b1, c1, d10), (a51, b1, c1, d11), (a51, b1, c1, d12), (a51, b1, c1, d13), (a51, b1, c1, d14), (a51, b1, c1, d15), (a51, b1, c1, d16), (a51, b1, c1, d17), (a51, b1, c1, d18), (a51, b1, c1, d19), (a51, b1, c1, d20), (a51, b1, c1, d21), (a51, b1, c1, d22), (a51, b1, c2, d1), (a51, b1, c2, d2), (a51, b1, c2, d3), (a51, b1, c2, d4), (a51, b1, c2, d5), (a51, b1, c2, d6), (a51, b1, c2, d7), (a51, b1, c2, d8), (a51, b1, c2, d9), (a51, b1, c2, d10), (a51, b1, c2, d11), (a51, b1, c2, d12), (a51, c2, d13), (a51, b1, c2, d14), (a51, b1, c2, d15), (a51, b1, c2, d16), (a51, b1, c2, d17), (a51, b1, c2, d18), (a51, b1, c2, d19), (a51, b1, c2, d20), (a51, b1, c2, d21), (a51, b1, c2, d22), (a51, b1, c3, d1), (a51, b1, c3, d2), (a51, b1, c3, d3), (a51, b1, c3, d4), (a51, b1, c3, d5), (a51, b1, c3, d6), (a51, b1, c3, d7), (a51, b1, c3, d8), (a51, b1, c3, d9), (a51, b1, c3, d10), (a51, b1, c3, d11), (a51, b1, c3, d12), (a51, b1, c3, d13), (a51, b1, c3, d14), (a51, b1, c3, d15), (a51, b1, c3, d16), (a51, b1, c3, d17), (a51, b1, c3, d18), (a51, b1, c3, d19), (a51, b1, c3, d20), (a51, b1, c3, d21), (a51, b1, c3, d22), (a51, b2, c1, d1), (a51, b2, c1, d2), (a51, b2, c1, d3), (a51, b2, c1, d4), (a51, b2, c1, d5), (a51, b2, c1, d6), (a51, b2, c1, d7), (a51, b2, c1, d8), (a51, b2, c1, d9), (a51, b2, c1, d10), (a51, b2, c1, d11), (a51, b2, c1, d12), (a51, b2, c1, d13), (a51, b2, c1, d14), (a51, b2, c1, d15), (a51, b2, c1, d16), (a51, b2, c1, d17), (a51, b2, c1, d18), (a51, b2, c1, d19), (a51, b2, c1, d20), (a51, b2, c1, d21), (a51, b2, c1, d22), (a51, b2, c2, d1), (a51, b2, c2, d2), (a51, b2, c2, d3), (a51, b2, c2, d4), (a51, b2, c2, d5), (a51, b2, c2, d6), (a51, b2, c2, d7), (a51, b2, c2, d8), (a51, b2, c2, d9), (a51, b2, c2, d10), (a51, b2, c2, d11), (a51, b2, c2, d12), (a51, b2, c2, d13), (a51, b2, c2, d14), (a51, b2, c2, d15), (a51, b2, c2, d16), (a51, b2, c2, d17), (a51, b2, c2, d18), (a51, b2, c2, d19), (a51, b2, c2, d20), (a51, b2, c2, d21), (a51, b2, c2, d22), (a51, b2, c3, d1), (a51, b2, c3, d2), (a51, b2, c3, d3), (a51, b2, c3, d4), (a51, b2, c3, d5), (a51, b2, c3, d6), (a51, b2, c3, d7), (a51, b2, c3, d8), (a51, b2, c3, d9), (a51, b2, c3, d10), (a51, b2, c3, d11), (a51, b2, c3, d12), (a51, b2, c3, d13), (a51, b2, c3, d14), (a51, b2, c3, d15), (a51, b2, c3, d16), (a51, b2, c3, d17), (a51, b2, c3, d18), (a51, b2, c3, d19), (a51, b2, c3, d20), (a51, b2, c3, d21), (a51, b2, c3, d22), (a51, b3, c1, d1), (a51, b3, c1, d2), (a51, b3, c1, d3), (a51, b3, c1, d4), (a51, b3, c1, d5), (a51, b3, c1, d6), (a51, b3, c1, d7), (a51, b3, c1, d8), (a15, b3, c1, d9), (a51, b3, c1, d1), (a51, b3, c1, d11), (a51, b3, c1, d12), (a51, b3, c1, d13), (a51, b3, c1, d14), (a51, b3, c1, d15), (a51, b3, c1, d16), (a51, b3, c1, d17), (a51, b3, c1, d18), (a51, b3, c1, d19), (a51, b3, c1, d20), (a51, b3, c1, d21), (a51, b3, c1, d22), (a51, b3, c2, d1), (a51, b3, c2, d2), (a51, b3, c2, d3), (a51, b3, c2, d4), (a51, b3, c2, d5), (a51, b3, c2, d6), (a51, b3, c2, d7), (a51, b3, c2, d8), (a51, b3, c2, d9), (a51, b3, c2, d10), (a51, b3, c2, d11), (a51, b3, c2, d12), (a51, b3, c2, d13), (a51, b3, c2, d14), (a51, b3, c2, d15), (a51, b3, c2, d16), (a51, b3, c2, d17), (a51, b3, c2, d18), (a51, b3, c2, d19), (a51, b3, c2, d20), (a51, b3, c2, d21), (a51, b3, c2, d22), (a51, b3, c3, d1), (a51, b3, c3, d2), (a51, b3, c3, d3), (a51, b3, c3, d4), (a51, b3, c3, d5), (a51, b3, c3, d6), (a51, b3, c3, d7), (a51, b3, c3, d5), (a51, b3, c3, d9), (a51, b3, c3, d10), (a51, b3, c3, d11), (a51, b3, c3, d12), (a51, b3, c3, d13), (a51, b3, c3, d14), (a51, b3, c3, d15), (a51, b3, c3, d16), (a51, b, c3, d17), (a51, b3, c3, d18), (a51, b3, c3, d19), (a51, b3, c3, d20), (a51, b3, c3, d21), (a51, b3, c3, d22), (a51, b4, c1, d1), (a51, b4, c1, d2), (a51, b4, c1, d3), (a51, b4, c1, d4), (a51, b4, c1, d5), (a51, b4, c1, d6), (a51, b4, c1, d7), (a51, b4, c1, d8), (a51, b4, c1, d9), (a51, b4, c1, d10), (a51, b4, c1, d11), (a51, b4, c1, d12), (a51, b4, c1, d13), (a51, b4, c1, d14), (a51, b4, c1, d15), (a51, b4, c1, d16), (a51, b4, c1, d17), (a51, b4, c1, d18), (a51, b4, c1, d19), (a51, b4, c1, d20), (a51, b4, c1, d21), (a51, b4, c1, d22), (a51, b4, c2, d1), (a51, b4, c2, d2), (a51, b4, c2, d3), (a51, b4, c2, d4), (a51, b4, c2, d5), (a51, b4, c2, d6), (a51, b4, c2, d7), (a51, b4, c2, d8), (a51, b4, c2, d9), (a51, b4, c2, d10), (a51, b4, c2, d11), (a51, b4, c2, d12), (a51, b4, c2, d13), (a51, b4, c2, d14), (a51, b4, c2, d15), (a51, b4, c2, d16), (a51, b4, c2, d17), (a51, b4, c2, d18), (a51, b4, c2, d19), (a51, b4, c2, d20), (a51, b4, c2, d21), (a51, b4, c2, d22), (a51, b4, c3, d1), (a51, b4, c3, d2), (a51, b4, c3, d3), (a51, b4, c3, d4), (a51, b4, c3, d5), (a1, b4, c3, d6), (a51, b4, c3, d7), (a51, b4, c3, d8), (a51, b4, c3, d9), (a51, b4, c3, d10), (a51, b4, c3, d11), (a51, b4, c3, d12), (a51, b4, c3, d13), (a51, b4, c3, d14), (a51, b4, c3, d15), (a51, b4, c3, d16), (a51, b4, c3, d17), (a51, b4, c3, d18), (a51, b4, c3, d19), (a51, b4, c3, d20), (a51, b4, c3, d21), (a51, b4, c3, d22), (a51, b5, c1, d1), (a51, b5, c1, d2), (a51, b5, c1, d3), (a51, b5, c1, d4), (a51, b5, c1, d5), (a51, b5, c1, d6), (a51, b5, c1, d7), (a51, b5, c1, d8), (a51, b5, c1, d9), (a51, b5, c1, d10), (a51, b5, c1, d11), (a51, b5, c1, d12), (a51, b5, c1, d13), (a51, b5, c1, d14), (a51, b5, c1, d15), (a51, b5, c1, d16), (a51, b5, c1, d17), (a51, b5, c1, d18), (a51, b5, c5, d19), (a51, b5, c1, d20), (a51, b5, c1, d21), (a51, b5, d22), (a51, b5, c2, d1), (a51, b5, c2, d2), (a51, b5, c2, d3), (a51, b5, c2, d4), (a51, b5, c2, d5), (a51, b5, c2, d6), (a51, b5, c2, d7), (a51, b5, c2, d8), (a51, b5, c2, d9), (a51, b5, c2, d10), (a51, b5, c2, d11), (a51, b5, c2, d12), (a51, b5, c2, d13), (a51, b5, c2, d14), (a51, b5, c2, d15), (a51, b5, c2, d16), (a51, b5, c2, d17), (a51, b5, c2, d18), (a51, b5, c2, d19), (a51, b5, c2, d20), (a51, b5, c2, d21), (a51, b5, c2, d22), (a51, b5, c3, d1), (a51, b5, c3, d2), (a51, b5, c3, d3), (a51, b5, c3, d4), (a51, b5, c3, d5), (a51, b5, c3, d6), (a51, b5, c3, d7), (a51, b5, c3, d5), (a51, b5, c3, d9), (a51, b5, c3, d10), (a51, b5, c3, d11), (a51, b5, c3, d12), (a51, b5, c3, d13), (a51, b5, c3, d14), (a51, b5, c3, d15), (a51, b5, c3, d16), (a51, b5, c3, d17), (a51, b5, c3, d18), (a51, b5, c3, d19), (a51, b5, c3, d20), (a51, b5, c3, d21), (a51, b5, c3, d22), (a51, b6, c1, d1), (a51, b6, c1, d2), (a51, b6, cl d3), (a51, b6, c1, d4), (a51, b6, c1, d5), (a51, b6, c1, d6), (a51, b6, c1, d7), (a51, b6, c1, d8), (a51, b6, c1, d9), (a51, b6, c1, d10), (a51, b6, c1, d11), (a51, b6, c1, d12), (a51, b6, c1, d13), (a51, b6, c1, d14), (a51, b6, c1, d15), (a51, b6, c1, d16), (a51, b6, c1, d17), (a51, b6, c1, d18), (a51, b6, c1, d19), (a51, b6, c1, d20), (a51, b6, c1, d21), (a51, b6, c1, d22), (a51, b6, c2, d1), (a51, b6, c2, d2), (a51, b6, c2, d3), (a51, b6, c2, d4), (a51, b6, c2, d5), (a51, b6, c2, d6), (a51, b6, c2, d7), (a51, b6, c2, d8), (a51, b6, c2, d9), (a51, b6, c2, d10), (a51, b6, c2, d11), (a51, b6, c2, d12), (a51, b6, c2, d13), (a51, b6, c2, d14), (a51, b6, c2, d15), (a51, b6, c2, d16), (a51, b6, c2, d17), (a51, b6, c2, d18), (a51, b6, c2, d19), (a51, b6, c2, d20), (a51, b6, c2, d21), (a51, b6, c2, d22), (a51, b6, c3, d1), (a51, b6, c3, d2), (a51, b6, c3, d3), (a51, b6, c3, d4), (a51, b6, c3, d5), (a51, b6, c3, d6), (a51, b6, c3, d7), (a51, b6, c3, d8), (a51, b6, c3, d9), (a51, b6, c3, d10), (a51, b6, c3, d11), (a51, b6, c3, d12), (a51, b6, c3, d13), (a51, b6, c3, d14), (a51, b6, c3, d15), (a51, b6, c3, d16), (a51, b6, c3, d17), (a51, b6, c3, d18), (a51, b6, c3, d19), (a51, b6, c3, d20), (a51, b6, c3, d21), (a51, b6, c3, d22), (a52, b1, c1, d1), (a52, b1, c1, d2), (a52, b1, c1, d3), (a52, b1, c1, d4), (a52, b1, c1, d5), (a52, b1, c1, d6), (a52, b1, c1, d7), (a52, b1, c1, d3), (a52, b1, c1, d9), (a52, b1, c1, d10), (a52, b1, c1, d11), (a52, b1, c1, d12), (a52, b1, c1, d13), (a52, b1, c1, d14), (a52, b1, c1, d15), (a52, b1, c1, d16), (a52, b1, c1, d17), (a52, b1, c1, d18), (a52, b1, c1, d19), (a52, b1, c1, d20), (a52, b1, c1, d21), (a52, b1, c1, d22), (a52, b1, c2, d1), (a52, b1, c2, d2), (a52, b1, c2, d3), (a52, b1, c2, d4), (a52, b1, c2, d5), (a52, b1, c2, d6), (a52, b1, c2, d7), (a52, b1, c2, d3), (a52, b1, c2, d9), (a52, b1, c2, d10), (a52, b1, c2, d11), (a52, b1, c2, d12), (a52, b1, c2, d13), (a52, b1, c2, d14), (a52, b1, c2, d15), (a52, b1, c2, d16), (a52, b1, c2, d17), (a52, b1, c2, d18), (a52, b1, c2, d19), (a52, b1, c2, d20), (a52, b1, c2, d21), (a52, b1, c2, d22), (a52, b1, c3, d1), (a52, b1, c3, d2), (a52, b1, c3, d3), (a52, b1, c3, d4), (a52, b1, c3, d5), (a52, b1, c3, d6), (a52, b1, c3, d7), (a52, b1, c3, d8), (a52, b1, c3, d9), (a52, b1, c3, d10), (a2, b1, c3, d11), (a52, b1, c3, d12), (a52, b1, c3, d13), (a52, b1, c3, d14), (a52, b1, c3, d15), (a52, b1, c3, d16), (a52, b1, c3, d17), (a52, b1, c3, d18), (a52, b1, c3, d19), (a52, b1, c3, d20), (a52, b1, c3, d21), (a52, b1, c3, 22), (a52, b2, c1, d1), (a52, b2, c1, d2), (a52, b2, c1, d3), (a52, b2, c1, d4), (a52, b2, c1, d5), (a52, b2, c1, d6), (a52, b2, c1, d7), (a52, b2, c1, d8), (a52, b2, c1, d9), (a52, b2, c1, d10), (a52, b2, c1, d11), (a52, b2, c1, d12), (a52, b2, c1, d13), (a52, b2, c1, d14), (a52, b2, c1, d15), (a52, b2, c1, d16), (a52, b2, c1, d17), (a52, b2, c1, d18), (a52, b2, c1, d19), (a52, b2, c1, d20), (a52, b2, c1, d21), (a52, b2, c1, d22), (a52, b2, c2, d1), (a52, b2, c2, d2), (a52, b2, c2, d3), (a52, b2, c2, d4), (a52, b2, c2, d5), (a52, b2, c2, d6), (a52, b2, c2, d7), (a52, b2, c2, d8), (a52, b2, c2, d9), (a52, b2, c2, d10), (a52, b2, c2, d11), (a52, b2, c2, d12), (a52, b2, c2, d13), (a52, b2, c2, d14), (a52, b2, c2, d15), (a52, b2, c2, d16), (a52, b2, c2, d17), (a52, b2, c2, d18), (a52, b2, c2, d19), (a52, b2, c2, d20), (a52, b2, c2, d21), (a52, b2, c2, d22), (a52, b2, c3, d1), (a52, b2, c3, d2), (a52, b2, c3, d3), (a52, b2, c3, d4), (a52, b2, c3, d5), (a52, b2, c3, d6), (a52, b2, c3, d7), (a52, b2, c3, d8), (a52, b2, c3, d9), (a52, b2, c3, d10), (a52, b2, c3, d11), (a52, b2, c3, d12), (a52, b2, c3, d13), (a52, b2, c3, d14), (a52, b2, c3, d15), (a52, b2, c3, d16), (a52, b2, c3, d17), (a52, b2, c3, d18), (a52, b2, c3, d19), (a52, b2, c3, d20), (a52, b2, c3, d21), (a52, b2, c3, d22), (a52, b3, c1, d1), (a52, b3, c1, d2), (a52, b3, c1, d3, (a52, b3, c1, d4), (a52, b3, c1, d5), (a52, b3, c1, d6), (a52, b3, c1, d7), (a52, b3, c1, d8), (a52, b3, c1, d9), (a52, b3, c1, d10), (a52, b3, c1, d11), (a52, b3, c1, d12), (a52, b3, c1, d13), (a52, b3, c1, d14), (a52, b3, c1, d15), (a52, b3, c1, d16), (a52, b3, c1, d17), (a52, b3, c1, d18), (a52, b3, c1, d19), (a52, b3, c1, d20), (a52, b3, c1, d21), (a52, b3, c1, d22), (a52, b3, c2, d1), (a52, b3, c2, d2), (a52, b3, c2, d3), (a52, b3, c2, d4), (a52, b3, c2, d5), (a52, b3, c2, d6), (a52, b3, c2, d7), (a52, b3, c2, d8), (a52, b5, c2, d9), (a52, b3, c2, d10), (a52, b3, c2, d11), (a52, b3, c2, d12), (a52, b3, c2, d13), (a52, b3, c2, d14), (a52, b3, c2, d15), (a52, b3, c2, d16), (a52, b3, c2, d17), (a52, b3, c2, d18), (a52, b3, c2, d19), (a52, b3, c2, d20), (a52, b3, c2, d21), (a52, b3, c2, d22), (a52, b3, c3, d1), (a52, b3, c3, d2), (a52, b3, c3, d3), (a52, b3, c3, d4), (a52, b5, c3, d5), (a52, b3, c3, d6, (a52, b3, c3, d7), (a52, b3, c3, d8), (a52, b3, c3, d9), (a52, b3, c3, d10), (a52, b3, c3, d11), (a52, b3, c3, d12), (a52, b3, c3, d13), (a52, b5, c3, d14), (a52, b5, c3, d15), (a52, b3, c3, d16), (a52, b3, c3, d17), (a52, b3, c3, d18), (a52, b3, c3, d19), (a52, b3, c3, d20), (a52, b5, c3, d21), (a52, b3, c3, d22), (a52, b4, c1, d1), (a52, b4, c1, d2), (a52, b4, c1, d3), (a52, b4, c1, d4), (a52, b4, c1, d5), (a52, b4, c1, d6), (a52, b4, c1, d7), (a52, b4, c1, d8), (a52, b4, c1, d9), (a52, b4, c1, d10), (a52, b4, c1, d11), (a52, b4, c1, d12), (a52, b4, c1, d13), (a52, b4, c1, d14), (a52, b4, c1, d15), (a52, b4, c1, d16), (a52, b4, c1, d17), (a52, b4, c1, d18), (a52, b4, c1, d19), (a52, b4, c1, d20), (a52, b4, c1, d21), (a52, b4, c1, d22), (a52, b4, c2, d1), (a52, b4, c2, d2), (a52, b4, c2, d3), (a52, b4, c2, d4), (a52, b4, c2, d5), (a52, b4, c2, d6), (a52, b4, c2, d7), (a52, b4, c2, d8), (a52, b4, c2, d9), (a52, b4, c2, d10), (a52, b4, c2, d11), (a52, b4, c2, d12), (a52, b4, c2, d13), (a52, b4, c2, d14), (a52, b4, c2, d15), (a52, b4, c2, d16), (a52, b4, c2, d17), (a52, b4, c2, d18), (a52, b4, c2, d19), (a52, b4, c2, d20), (a52, b4, c2, d21), (a52, b4, c2, d22), (a52, b4, c3, d1), (a52, b4, c3, d2), (a52, b4, c3, d3), (a52, b4, c3, d4), (a52, b4, c3, d5), (a52, b4, c3, d6), (a52, b4, c3, d7), (a52, b4, c3, d8), (a52, b4, c3, d9), (a52, b4, c3, d10), (a52, b4, c3, d11), (a52, b4, c3, d12), (a52, b4, c3, d13), (a52, b4, c3, d14), (a52, b4, c3, d15), (a52, b4, c3, d16), (a52, b4, c3, d17), (a52, b4, c3, d18), (a52, b4, c3, d19), (a52, b4, c3, d20), (a52, b4, c3, d21), (a52, b4, c3, d22), (a2, b5, c1, d1), (a52, b5, c1, d2), (a52, b5, c1, d3), (a52, b5, c1, d4), (a52, b5, c1, d5), (a52, b5, c1, d6), (a52, b5, c1, d7), (a52, b5, c1, d8), (a52, b5, c1, d9), (a52, b5, c1, d10), (a52, b5, c1, d11), (a52, b5, c1, d12), (a52, b5, c1, d13), (a52, b5, c1, d14), (a52, b5, c1, d15), (a52, b5, c1, d16), (a52, b5, c1, d17), (a52, b5, c1, d18), (a52, b5, c1, d19), (a52, b5, c1, d20), (a52, b5, c1, d21), (a52, b5, c1, d22), (a52, b5, c2, d1), (a52, b5, c2, d2), (a52, b5, c2, d3), (a52, b5, c2, d4), (a52, b5, c2, d5), (a52, b5, c2, d6), (a52, b5, c2, d17), (a52, b5, c2, d18), (a52, b5, c2, d9), (a52, b5, c2, d10), (a52, b5, c2, d11), (a52, b5, c2, d12), (a52, b5, c2, d13), (a52, b5, c2, d14), (a52, b5, c2, d15), (a52, b5, c2, d16), (a52, b5, c2, d17), (a52, b5, c2, d18), (a52, b5, c2, d19), (a52, b5, c2, d20), (a52, b5, c2, d21), (a52, b5, c2, d22), (a52, b5, c3, d1), (a52, b5, c3, d2), (a52, b5, c3, d3), (a52, b5, c3, d4), (a52, b5, c3, d5), (a52, b5, c3, d6), (a52, b5, c3, d7), (a52, b5, c3, d8), (a52, b5, c3, d9), (a52, b5, c3, d10), (a52, b5, c3, d11), (a52, b5, c3, d12), (a52, b5, c3, d13), (a52, b5, c3, d14), (a2, b5, c3, d15), (a52, b5, c3, d16), (a52, b5, c3, d17), (a52, b5, c3, d18), (a52, b5, c3, d19), (a52, b5, c3, d20), (a52, b5, c3, d21), (a52, b5, c3, d22), (a52, b6, c1, d1), (a52, b6, c1, d2), (a52, b6, c1, d3), (a52, b6, c1, d4), (a52, b6, c1, d5), (a52, b6, c1, d6), (a52, b6, c1, d7), (a52, b6, c1, d8), (a52, b6, c1, d9), (a52, b6, c1, d10), (a52, b6, c1, d11), (a52, b6, c1, d12), (a52, b6, c1, d13), (a52, b6, c1, d14), (a52, b6, c1, d15), (a52, b6, c1, d16), (a52, b6, c1, d17), (a52, b6, c1, d18), (a52, b6, c1, d19), (a52, b6, c1, d20), (a52, b6, c1, d21), (a52, b6, c1, d22), (a52, b6, c2, d1), (a52, b6, c2, d2), (a52, b6, c2, d3), (a52, b6, c2, d4), (a52, b6, c2, d5), (a52, b6, c2, d6), (a52, b6, c2, d7), (a52, b6, c2, d8), (a52, b6, c2, d9), (a52, b6, c2, d10), (a52, b6, c2, d11), (a52, b6, c2, d12), (a52, b6, c2, d13), (a52, b6, c2, d14), (a52, b6, c2, d15), (a52, b6, c2, d16), (a52, b6, c2, d17), (a52, b6, c2, d18), (a52, b6, c2, d19), (a52, b6, c2, d20), (a52, b6, c2, d21), (a52, b6, c2, d22), (a52, b6, c3, d1), (a52, b6, c3, d2), (a52, b6, c3, d3), (a52, b6, c3, d4), (a52, b6, c3, d5), (a52, b6, c3, d6), (a52, b6, c3, d7), (a52, b6, c3, d8), (a52, b6, c3, d9), (a52, b6, c3, d10), (a52, b6, c3, d11), (a52, b6, c3, d12), (a52, b6, c3, d13), (a52, b6, c3, d14), (a52, b6, c3, d15), (a52, b6, c3, d16), (a52, b6, c3, d17), (a52, b6, c3, d18), (a52, b6, c3, d19), (a52, b6, c3, d20), (a52, b6, c3, d21), (a52, b6, c3, d22), (a53, b1, c1, d1), (a53, b1, c1, d2), (a53, b1, c1, d3), (a53, b1, c1, d4), (a53, b1, c1, d5), (a53, b1, c1, d6), (a53, b1, c1, d7), (a53, b1, c1, d8), (a53, b1, c1, d9), (a53, b1, c1, d10), (a53, b1, c1, d11), (a53, b1, c1, d12), (a53, b1, c1, d13), (a53, b1, c1, d14), (a53, b1, c1, d15), (a53, b1, c1, d16), (a53, b1, c1, d17), (a53, b1, c1, d18), (a53, b1, c1, d19), (a53, b1, c1, d20), (a53, b1, c1, d21), (a53, b1, c1, d22), (a53, b1, c2, d1), (a53, b1, c2, d2), (a53, b1, c2, d3), (a53, b1, c2, d4), (a53, b1, c2, d5), (a53, b1, c2, d6), (a53, b1, c2, d7), (a53, b1, c2, d8), (a53, b1, c2, d9), (a53, b1, c2, d10), (a53, b1, c2, d11), (a53, b1, c2, d12), (a53, b1, c2, d13), (a53, b1, c2, d14), (a53, b1, c2, d15), (a53, b1, c2, d16), (a53, b1, c2, d17), (a53, b1, c2, d18), (a53, b1, c2, d19), (a53, b1, c2, d20), (a53, b1, c2, d21), (a53, b1, c2, d22), (a53, b1, c3, d1), (a53, b1, c3, d2), (a5, b1, c3, d3), (a53, b1, c3, d4), (a53, b1, c3, d5), (a53, b1, c3, d6), (a53, b1, c3, d7), (a53, b1, c3, d8), (a53, b1, c3, d9), (a53, b1, c3, d10), (a53, b1, c3, d11), (a53, b1, c3, d12), (a53, b1, c3, d13), (a53, b, c3, d14), (a53, b1, c3, d15), (a53, b1, c3, d16), (a53, b1, c3, d17), (a53, b1, c3, d18), (a53, b1, c3, d19), (a53, b1, c3, d20), (a53, b1, c3, d21), (a53, b1, c3, d22), (a53, b2, c1, d1), (a53, b2, c1, d2), (a53, b2, c1, d3), (a53, b2, c1, d4), (a53, b2, c1, d5), (a53, b2, c1, d6), (a53, b2, c1, d7), (a53, b2, c1, d8), (a53, b2, c1, d9), (a53, b2, c1, d10), (a53, b2, c1, d11), (a53, b2, c1, d12), (a53, b2, c1, d13), (a53, b2, c1, d14), (a53, b2, c1, d15), (a53, b2, c1, d16), (a53, b2, c1, d17), (a53, b2, c1, d18), (a53, b2, c1, d19), (a53, b2, c1, d20), (a53, b2, c1, d21), (a53, b2, c1, d22), (a53, b2, c2, d1), (a53, b2, c2, d2), (a53, b2, c2, d3), (a53, b2, c2, d4), (a53, b2, c2, d5), (a53, b2, c2, d6), (a53, b2, c2, d7), (a53, b2, c2, d8), (a53, b2, c2, d9), (a53, b2, c2, d10), (a53, b2, c2, d11), (a53, b2, c2, d12), (a53, b2, c2, d13), (a53, b2, c2, d14), (a53, b2, c2, d15), (a53, b2, c2, d16), (a53, b2, c2, d17), (a53, b2, c2, d18), (a53, b2, c2, d19), (a53, b2, c2, d20), (a53, b2, c2, d21), (a53, b2, c2, d22), (a53, b2, c3, d1), (a53, b2, c3, d2), (a53, b2, c3, d3), (a53, b2, c3, d4), (a53, b2, c3, d5), (a53, b2, c3, d6), (a53, b2, c3, d7), (a53, b2, c3, d8), (a53, b2, c3, d9), (a53, b2, c3, d10), (a53, b2, c3, d11), (a53, b2, c3, d12), (a53, b2, c3, d13), (a53, b2, c3, d14), (a53, b2, c3, d15), (a53, b2, c3, d16), (a53, b2, c3, d17), (a53, b2, c3, d18), (a53, b2, c3, d19), (a53, b2, c3, d20), (a53, b2, c3, d21), (a53, b2, c3, d22), (a53, b3, c1, d1), (a53, b3, c1, d2), (a53, b3, c1, d3), (a53, b3, c1, d4), (a53, b3, c1, d5), (a53, b3, c1, d6), (a53, b3, c1, d7), (a53, b3, c1, d8), (a53, b3, c1, d9), (a53, b3, c1, d10), (a53, b3, c1, d11), (a53, b3, c1, d12), (a53, b5, c1, d13), (a53, b5, c1, d14), (a53, b5, c1, d15), (a53, b3, c1, d16), (a53, b3, c1, d17), (a53, b3, c1, d18), (a53, b3, c1, d19), (a53, b3, c1, d20), (a53, b3, c1, d21), (a53, b3, c1, d22), (a53, b3, c2, d1), (a53, b3, c2, d2), (a53, b3, c2, d3), (a53, b3, c2, d4), (a53, b3, c2, d5), (a53, b3, c2, d6), (a53, b3, c2, d7), (a53, b3, c2, d8), (a53, b3, c2, d9), (a53, b3, c2, d10), (a53, b3, c2, d11), (a53, b3, c2, d12), (a53, b3, c2, d13), (a53, b3, c2, d14), (a53, b5, c2, d15), (a53, b5, c2, d16), (a53, b5, c2, d17), (a53, b3, c2, d18), (a53, b3, c2, d19), (a53, b3, c2, d20), (a53, b3, c2, d21), (a53, b3, c2, d22), (a53, b3, c3, d1), (a53, b3, c3, d2), (a53, b3, c3, d3), (a53, b3, c3, d4), (a53, b3, c3, d5), (a53, b3, c3, d6), (a53, b3, c3, d7), (a53, b3, c3, d8), (a53, b3, c3, d9), (a53, b3, c3, d10), (a53, b3, c3, d11), (a53, b3, c3, d12), (a53, b3, c3, d14), (a53, b3, c3, d15), (a53, b3, c3, d16), (a53, b3, c3, d17), (a53, b3, c3, d18), (a53, b3, c3, d19), (a53, b3, c3, d20), (a53, b3, c3, d21), (a53, b3, c3, d22), (a53, b4, c1, d1), (a53, b4, c1, d2), (a53, b4, c1, d3), (a53, b4, c1, d4), (a53, b4, c1, d5), (a53, b4, c1, d6), (a53, b4, c1, d7), (a53, b4, c1, d8), (a53, b4, c1, d9), (a53, b4, c1, d10), (a53, b4, c1, d11), (a53, b4, c1, d12), (a53, b4, c1, d13), (a53, b4, c1, d14), (a53, b4, c1, d15), (a53, b4, c1, d16), (a53, b4, c1, d17), (a53, b4, c1, d18), (a53, b4, c1, d19), (a53, b4, c1, d20), (a53, b4, c1, d21), (a53, b4, c1, d22), (a53, b4, c2, d1), (a53, b4, c2, d2), (a53, b4, c2, d3), (a53, b4, c2, d4), (a53, b4, c2, d5), (a53, b4, c2, d6), (a53, b4, c2, d7), (a53, b4, c2, d8), (a53, b4, c2, d9), (a53, b4, c2, d10), (a53, b4, c2, d11), (a53, b4, c2, d12), (a53, b4, c2, d13), (a53, b4, c2, d14), (a53, b4, c2, d15), (a53, b4, c2, d16), (a53, b4, c2, d17), (a53, b4, c2, d18), (a53, b4, c2, d19), (a53, b4, c2, d20), (a53, b4, c2, d21), (a53, b4, c2, d22), (a53, b4, c3, d1), (a53, b4, c3, d2), (a53, b4, c3, d3), (a53, b4, c3, d4), (a53, b4, c3, d5), (a53, b4, c3, d6), (a53, b4, c3, d7), (a53, b4, c3, d8), (a53, b4, c3, d9), (a53, b4, c3, d10), (a53, b4, c3, d11), (a53, b4, c3, d12), (a53, b4, c3, d13), (a53, b4, c3, d14), (a3, b4, c3, d15), (a53, b4, c3, d16), (a53, b4, c3, d17), (a53, b4, c3, d18), (a53, b4, c3, d19), (a53, b4, c3, d20), (a53, b4, c3, d21), (a53, b4, c3, d22), (a53, b5, c1, d1), (a53, b5, c1, d2), (a53, b5, c1, d3), (a53, b5, c1, d4), (a53, b5, c1, d5), (a53, b, c1, d6), (a53, b5, c1, d7), (a53, b5, c1, d8), (a53, b5, c1, d9), (a53, b5, c1, d10), (a53, b5, c1, d11), (a53, b5, c1, d12), (a53, b5, c1, d13), (a53, b5, c1, d14), (a53, b5, c1, d15), (a53, b5, c1, d16), (a53, b5, c1, d17), (a53, b5, c1, d18), (a53, b5, c1, dig), (a53, b5, c1, d20), (a53, b5, c1, d21), (a53, b5, c1, d22), (a53, b5, c2, d1), (a53, b5, c2, d2), (a53, b5, c2, d3), (a53, b5, c2, d4), (a53, b5, c2, d5), (a53, b5, c2, d6), (a53, b5, c2, d7), (a53, b5, c2, d8), (a53, b5, c2, d9), (a53, b5, c2, d10), (a53, b5, c2, d11), (a53, b5, c2, d12), (a53, b5, c2, d13), (a53, b5, c2, d14), (a53, b5, c2, d15), (a53, b5, c2, d16), (a53, b5, c2, d17), (a53, b5, c2, d18), (a53, b5, c2, d19), (a53, b5, c2, d20), (a53, b5, c2, d21), (a53, b5, c2, d22), (a53, b5, c3, d1), (a53, b5, c3, d2), (a53, b5, c3, d3), (a53, b5, c3, d4), (a53, b5, c3, d5), (a53, b5, c3, d6), (a53, b5, c3, d7), (a53, b5, c3, d8), (a53, b5, c3, d9), (a53, b5, c3, d10), (a53, b5, c3, d11), (a53, b5, c3, d12), (a53, b5, c3, d13), (a53, b5, c3, d14), (a53, b5, c3, d15), (a53, b5, c3, d16), (a53, b5, c3, d17), (a53, b5, c3, d18), (a53, b5, c3, d19), (a53, b5, c3, d20), (a53, b5, c3, d21), (a53, b5, c3, d22), (a53, b6, c1, d1), (a53, b6, c1, d2), (a53, b6, c1, d3), (a53, b6, c1, d4), (a53, b6, c1, d5), (a53, b6, c1, d6), (a53, b6, c1, d7), (a53, b6, c1, d8), (a53, b6, c1, d9), (a53, b6, c1, d10), (a53, b6, c1, d11), (a53, b6, c1, d12), (a53, b6, c1, d13), (a53, b6, c1, d14), (a53, b6, c1, d15), (a53, b6, c1, d16), (a53, b6, c1, d17), (a53, b6, c1, d18), (a53, b6, c1, d19), (a53, b6, c1, d20), (a53, b6, c1, d21), (a53, b6, c1, d22), (a53, b6, c2, d1), (a53, b6, c2, d2), (a53, b6, c2, d3), (a53, b6, c2, d4), (a53, b6, c2, d5), (a53, b6, c2, d6), (a53, b6, c2, d7), (a53, b6, c2, d8), (a53, b6, c2, d9), (a53, b6, c2, d10), (a53, b6, c2, d11), (a53, b6, c2, d12), (a53, b6, c2, d13), (a53, b6, c2, d14), (a53, b6, c2, d15), (a53, b6, c2, d16), (a53, b6, c2, d17), (a53, b6, c2, d18), (a53, b6, c2, d19), (a53, b6, c2, d20), (a53, b6, c2, d21), (a53, b6, c2, d22), (a53, b6, c3, d1), (a53, b6, c3, d2), (a53, b6, c3, d3), (a53, b6, c3, d4), (a53, b6, c3, d5), (a53, b6, c3, d6), (a53, b6, c3, d7), (a53, b6, c3, d8), (a53, b6, c3, d9), (a53, b6, c3, d10), (a53, b6, c3, d11), (a53, b6, c3, d12), (a53, b6, c3, d13), (a53, b6, c3, d14), (a53, b6, c3, d15), (a53, b6, c3, d16), (a53, b6, c3, d17), (a53, b6, c3, d18), (a53, b6, c3, d19), (a53, b6, c3, d20), (a53, b6, c3, d21), (a53, b6, c3, d22), (a54, b1, c1, d1), (a54, b1, c1, d2), (a54, b1, c1, d3), (a54, b1, c1, d4), (a54, b1, c1, d5), (a54, b1, c1, d6), (a54, b1, c1, d7), (a54, b1, c1, d8), (a54, b1, c1, d9), (a54, b1, c1, d10), (a54, b1, c1, d11), (a54, b1, c1, d12), (a54, b1, c1, d13), (a54, b1, c1, d14), (a54, b1, c1, d15), (a54, b1, c1, d16), (a54, b1, c1, d17), (a54, b1, c1, d18), (a54, b1, c1, d19), (a54, b1, c1, d20), (a54, b1, c1, d21), (a54, b1, c1, d22), (a54, b1, c2, d1), (a54, b1, c2, d2), (a54, b1, c2, d3), (a54, b1, c2, d4), (a54, b1, c2, d5), (a54, b1, c2, d6), (a54, b1, c2, d7), (a54, b1, c2, d8), (a54, b1, c2, d9), (a54, b1, c2, d10), (a54, b1, c2, d11), (a54, b1, c2, d12), (a54, b1, c2, d13), (a54, b1, c2, d14), (a54, b1, c2, d15), (a54, b1, c2, d16), (a54, b1, c2, d17), (a54, b1, c2, d18), (a54, b1, c2, d19), (a54, b1, c2, d20), (a54, b1, c2, d21), (a54, b1, c2, d22), (a54, b1, c3, d1), (a54, b1, c3, d2), (a54, b1, c3, d3), (a54, b1, c3, d4), (a54, b1, c3, d5), (a54, b1, c3, d6), (a54, b1, c3, d7), (a54, b1, c3, d8), (a54, b1, c3, d9), (a54, b1, c3, d10), (a54, b1, c3, d11), (a54, b1, c3, d12), (a54, b1, c3, d13), (a54, b1, c3, d14), (a54, b1, c3, d15), (a54, b1, c3, d16), (a54, b1, c3, d17), (a54, b1, c3, d18), (a54, b1, c3, d19), (a54, b1, c3, d20), (a54, b1, c3, d21), (a54, b1, c3, d22), (a54, b2, c1, d1), (a54, b2, c1, d2), (a54, b2, c1, d3), (a54, b2, c1, d4), (a54, b2, c1, d5), (a54, b2, c1, d6), (a54, b2, c1, d7), (a54, b2, c1, d8), (a54, b2, c1, d9), (a54), b2, c1, d10), (a54, b2, c1, d11), (a54, b2, c1, d12), (a54, b2, c1, d13), (a54, b2, c1, d14), (a54, b2, c1, d15), (a54, b2, c1, d16), (a54, b2, c1, d17), (a54, b2, c1, d18), (a54, b2, c1, d19), (a54, b2, c1, d20), (a54, b2, c1, d21), (a54, b2, c1, d22), (a54, b2, c2, d1), (a54, b2, c2, d2), (a54, b2, c2, d3), (a54, b2, c2, d4), (a54, b2, c2, d5), (a54, b2, c2, d6), (a54, b2, c2, d7), (a54, b2, c2, d8), (a54, b2, c2, d9), (a54, b2, c2, d10), (a54, b2, c2, d11), (a54, b2, c2, d12), (a54, b2, c2, d13), (a54, b2, c2, d14), (a54, b2, c2, d15), (a54, b2, c2, d16), (a54, b2, c2, d17), (a54, b2, c2, d18), (a54, b2, c2, d19), (a54, b2, c2, d20), (a54, b2, c2, d21), (a54, b2, c2, d22), (a54, b2, c3, d1), (a54, b2, c3, d2), (a54, b2, c3, d3), (a54, b2, c3, d4), (a54, b2, c3, d5), (a54, b2, c3, d6), (a54, b2, c3, d7), (a54, b2, c3, d8), (a54, b2, c3, d9), (a54, b2, c3, d10), (a54, b2, c3, d11), (a54, b2, c3, d12), (a54, b2, c3, d13), (a54, b2, c3, d14), (a54, b2, c3, d15), (a54, b2, c3, d16), (a54, b2, c3, d17), (a54, b2, c3, d18), (a54, b2, c3, d19), (a54, b2, c3, d20), (a54, b2, c3, d21), (a54, b2, c3, d22), (a54, b3, c1, d1), (a54, b3, c1, d2), (a54, b3, c1, d3), (a54, b3, c1, d4), (a54, b3, c1, d5), (a54, b3, c1, d6), (a54, b3, c1, d7), (a54, b3, c1, d8), (a54, b3, c1, d9), (a54, b3, c1, d10), (a54, b3, c1, d11), (a54, b3, c1, d12), (a54, b3, c1, d13), (a54, b3, c1, d14), (a54, b3, c1, d15), (a54, b3, c1, d16), (a54, b3, c1, d17), (a54, b3, c1, d13), (a54, b3, c1, d19), (a54, b3, c1, d20), (a54, b3, c1, d21), (a54, b3, c1, d22), (a54, b3, c2, d1), (a54, b3, c2, d2), (a54, b3, c2, d3), (a54, b3, c2, d4), (a54, b3, c2, d5), (a54, b3, c2, d6), (a54, b3, c2, d7), (a54, b3, c2, d8), (a54, b3, c2, d9), (a54, b3, c2, d10), (a54, b3, c2, d11), (a54, b3, c2, d2), (a54, b3, c2, d3), (a54, b3, c2, d14), (a54, b3, c2, d15), (a54, b3, c2, d16), (a54, b3, c2, d17), (a54, b3, c2, d18), (a54, b3, c2, d19), (a54, b3, c2, d20), (a54, b3, c2, d21), (a54, b3, c2, d22), (a54, b3, c3, d1), (a54, b3, c3, d2), (a54, b3, c3, d3), (a54, b3, c3, d4), (a54, b3, c3, d5), (a54, b3, c3, d6), (a54, b3, c3, d7), (a54, b3, c3, d8), (a54, b3, c3, d9), (a54, b3, c3, d10), (a54, b3, c3, d11), (a54, b3, c3, d12), (a54, b5, c3, d13), (a54, b3, c3, d14), (a54, b3, c3, d15), (a54, b3, c3, d16), (a54, b3, c3, d17), (a54, b3, c3, d18), (a54, b3, c3, d19), (a54, b3, c3, d20), (a54, b3, c3, d21), (a54, b3, c3, d22), (a54, b4, c1, d1), (a54, b4, c1, d2), (a54, b4, c1, d3), (a54, b4, c1, d4), (a54, b4, c1, d5), (a54, b4, c1, d6), (a54, b4, c1, d7), (a54, b4, c1, d8), (a54, b4, c1, d9), (a54, b4, c1, d10), (a54, b4, c1, dl), (a54, b4, c1, d12), (a54, b4, c1, d13), (a54, b4, c1, d14), (a54, b4, c1, d15), (a54, b4, c1, d16), (a54, b4, c1, d17), (a54, b4, c1, d18), (a54, b4, c1, d19), (a54, b4, c1, d20), (a54, b4, c1, d21), (a54, b4, c1, d22), (a54, b4, c2, d1), (a54, b4, c2, d2), (a54, b4, c2, d3), (a54, b4, c2, d4), (a54, b4, c2, d5), (a54, b4, c2, d6), (a54, b4, c2, d7), (a54, b4, c2, d8), (a54, b4, c2, d9), (a54, b4, c2, d10), (a54, b4, c2, d1), (a54, b4, c2, d12), (a54, b4, c2, d13), (a54, b4, c2, d14), (a54, b4, c2, d15), (a54, b4, c2, d16), (a54, b4, c2, d17), (a54, b4, c2, d18), (a54, b4, c2, d19), (a54, b4, c2, d20), (a54, b4, c2, d21), (a54, b4, c2, d22), (a54, b4, c3, d1), (a54, b4, c3, d2), (a54, b4, c3, d3), (a54, b4, c3, d4), (a54, b4, c3, d5), (a54, b4, c3, d6), (a54, b4, c3, d7), (a54, b4, c3, d8), (a54, b4, c3, d9), (a54, b4, c3, d10), (a54, b4, c3, d11), (a54, b4, c3, d2), (a54, b4, c3, d3), (a54, b4, c3, d14), (a54, b4, c3, d15), (a54, b4, c3, d16), (a54, b4, c3, d17), (a54, b4, c3, d18), (a54, b4, c3, d19), (a54, b4, c3, d20), (a54, b4, c3, d21), (a54, b4, c3, d22), (a54, b5, c1, d1), (a54, b5, c1, d2), (a54, b5, c1, d3), (a54, b5, c1, d4), (a54, b5, c1, d5), (a54, b5, c1, d6), (a54, b5, c1, d7), (a54, b5, c1, d8), (a54, b5, c1, d9), (a54, b5, c1, d10), (a54, b5, c1, d11), (a54, b5, c1, d12), (a54, b5, c1, d13), (a54, b5, c1, d14), (a54, b5, c1, d15), (a54, b5, c1, d16), (a54, b5, c1, d17), (a54, b5, c1, d18), (a54, b5, c1, d19), (a54, b5, c1, d20), (a54, b5, c1, d21), (a54, b5, c1, d22), (a54, b5, c2, d1), (a54, b5, c2, d2), (a54, b5, c2, d3), (a54, b5, c2, d4), (a54, b5, c2, d5), (a54, b5, c2, d6), (a54, b5, c2, d7), (a54, b5, c2, d8), (a54, b5, c2, d9), (a54, b5, c2, d10), (a54, b5, c2, d11), (a54, b5, c2, d12), (a54, b5, c2, d13), (a54, b5, c2, d14), (a54, b5, c2, d15), (a54, b5, c2, d16), (a54, b5, c2, d17), (a54, b5, c2, d18), (a54, b5, c2, d19), (a54, b5, c2, d20), (a54, b5, c2, d21), (a54, b5, c2, d22), (a54, b5, c3, d1), (a54, b5, c3, d2), (a54, b5, c3, d3), (a54, b5, c3, d4), (a54, b5, c3, d5), (a54, b5, c3, d6), (a54, b5, c3, d7), (a54, b5, c3, d8), (a54, b5, c3, d9), (a54, b5, c3, d10), (a54, b5, c3, d11), (a54, b5, c3, d12), (a54, b5, c3, d13), (a54, b5, c3, d14), (a54, b5, c3, d15), (a54, b5, c3, d6), (a54, b5, c3, d17), (a54, b5, c3, d6), (a54, b5, c3, d19), (a54, b5, c3, d20), (a54, b5, c3, d21), (a54, b5, c3, d22), (a54, b6, c1, d1), (a54, b6, c1, d2), (a54, b6, c1, d3), (a54, b6, c1, d4), (a54, b6, c1, d5), (a54, b6, c1, d6), (a54, b6, c1, d7), (a54, b6, c1, d8), (a54, b6, c1, d9), (a54, b6, c1, d10), (a54, b6, c1, d11), (a54, b6, c1, d12), (a54, b6, c1, d13), (a54, b6, c1, d14), (a54, b6, c1, d15), (a54, b6, c1, d16), (a54, b6, c1, d17), (a54, b6, c1, d18), (a54, b6, c1, d19), (a54, b6, c1, d20), (a54, b6, c1, d21), (a54, b6, c1, d22), (a54, b6, c2, d1), (a54, b6, c2, d2), (a54, b6, c2, d3), (a54, b6, c2, d4), (a54, b6, c2, d5), (a54, b6, c2, d6), (a54, b6, c2, d7), (a54, b6, c2, d8), (a54, b6, c2, d9), (a54, b6, c2, d10), (a54, b6, c2, d11), (a54, b6, c2, d12), (a54, b6, c2, d13), (a54, b6, c2, d14), (a54, b6, c2, d15), (a54, b6, c2, d16), (a54, b6, c2, d17), (a54, b6, c2, d18), (a54, b6, c2, d19), (a54, b6, c2, d20), (a54, b6, c2, d21), (a54, b6, c2, d22), (a54, b6, c3, d1), (a54, b6, c3, d2), (a54, b6, c3, d3), (a54, b6, c3, d4), (a54, b6, c3, d5), (a54, b6, c3, d6), (a54, b6, c3, d7), (a54, b6, c3, d8), (a54, b6, c3, d9), (a54, b6, c3, d10), (a54, b6, c3, d11), (a54, b6, c3, d12), (a54, b6, c3, d13), (a54, b6, c3, d14), (a54, b6, c3, d15), (a54, b6, c3, d16), (a54, b6, c3, d17), (a54, b6, c3, d18), (a54, b6, c3, d19), (a54, b6, c3, d20) (a54, b6, c3, d21), (a54, b6, c3, d22), (a55, b1, c1, d1), (a55, b1, c1, d2), (a55, b1, c1, d3), (a55, b1, c1, d4), (a55, b1, c1, d5), (a55, b1, c1, d6), (a55, b1, c1, d7), (a55, b1, c1, d3), (a55, b1, c1, d9), (a55, b1, c1, d10), (a55, b1, c1, d11), (a55, b1, c1, d12), (a55, b1, c1, d13), (a55, b1, c1, d14), (a55, b1, c1, d15), (a55, b1, c1, d16), (a55, b1, c1, d17), (a55, b1, c1, d13), (a55, b1, c1, d19), (a55, b1, c1, d20), (a55, b1, c1, d21), (a55, b1, c1, d22), (a55, b1, c2, d1), (a55, b1, c2, d2), (a55, b1, c2, d3), (a55, b1, c2, d4), (a55, b1, c2, d5), (a55, b1, c2, d6), (a55, b1, c2, d7), (a55, b1, c2, d8), (a55, b1, c2, d9), (a55, b1, c2, d10), (a55, b1, c2, d11), (a55, b1, c2, d12), (a55, b1, c2, d13), (a55, b1, c2, d14), (a55, b1, c2, d15), (a55, b1, c2, d16), (a55, b1, c2, d17), (a55, b1, c2, d18), (a55, b1, c2, d19), (a55, b1, c2, d20), (a55, b1, c2, d21), (a55, b1, c2, d22), (a55, b1, c3, d1), (a35, b1, c3, d2), (a55, b1, c3, d3), (a55, b1, c3, d4), (a55, b1, c3, d5), (a55, b1, c3, d6), (a55, b1, c3, d7), (a55, b1, c3, d8), (a55, b1, c3, d9), (a55, b1, c3, d10), (a55, b1, c3, d11), (a55, b1, c3, d12), (a55, b1, c3, d13), (a55, b1, c3, d14), (a55, b1, c3, d15), (a55, b1, c3, d16), (a55, b1, c3, d17), (a55, b1, c3, d18), (a55, b1, c3, d19), (a55, b1, c3, d20), (a55, b1, c3, d21), (a55, b1, c3, d22), (a55, b2, c1, d1), (a55, b2, c1, d2), (a55, b2, c1, d3), (a55, b2, c1, d4), (a55, b2, c1, d5), (a55, b2, c1, d6), (a55, b2, c1, d7), (a55, b2, c1, d8), (a55, b2, c1, d9), (a55, b2, c1, d10), (a55, b2, c1, d11), (a55, b2, c1, d12), (a55, b2, c1, d13), (a55, b2, c1, d14), (a55, b2, c1, d15), (a55, b2, c1, d16), (a55, b2, c1, d17), (a55, b2, c1, d18), (a55, b2, c1, d19), (a55, b2, c1, d20), (a55, b2, c1, d21), (a55, b2, c1, d22), (a55, b2, c2, d1), (a55, b2, c2, d2), (a55, b2, c2, d3), (a55, b2, c2, d4), (a55, b2, c2, d5), (a55, b2, c2, d6), (a55, b2, c2, d7), (a55, b2, c2, d8), (a55, b2, c2, d9), (a55, b2, c2, d10), (a55, b2, c2, d11), (a55, b2, c2, d12), (a55, b2, c2, d13), (a55, b2, c2, d14), (a55, b2, c2, d15), (a55, b2, c2, d16), (a55, b2, c2, d17), (a55, b2, c2, d18), (a55, b2, c2, d19), (a55, b2, c2, d20), (a55, b2, c2, d21), (a55, b2, c2, d22), (a55, b2, c3, d1), (a55, b2, c3, d2), (a55, b2, c3, d3), (a55, b2, c3, d4), (a55, b2, c3, d5), (a55, b2, c3, d6), (a55, b2, c3, d7), (a55, b2, c3, d8), (a55, b2, c3, d9), (a55, b2, c3, d10), (a55, b2, c3, d11), (a55, b2, c3, d12), (a55, b2, c3, d13), (a55, b2, c3, d14), (a55, b2, c3, d15), (a55, b2, c3, d16), (a55, b2, c3, d17), (a55, b2, c3, d18), (a55, b2, c3, d19), (a55, b2, c3, d20), (a55, b2, c3, d21), (a55, b2, c3, d22), (a55, b3, c1, d1), (a55, b3, c1, d2), (a55, b3, c1, d3), (a55, b3, c1, d4), (a55, b3, c1, d5), (a55, b3, c1, d6), (a55, b3, c1, d7), (a55, b3, c1, d8), (a55, b3, c1, d9), (a55, b3, c1, d10), (a55, b3, c1, d11), (a55, b3, c1, d12), (a55, b3, c1, d13), (a55, b3, c1, d14), (a55, b3, c1, d15), (a55, b3, c1, d16), (a55, b3, c1, d17), (a55, b3, c1, d18), (a55, b3, c1, d19), (a55, b3, c1, d20), (a55, b3, c1, d21), (a55, b3, c1, d22), (a55, b3, c2, d1), (a55, b3, c2, d2), (a55, b3, c2, d3), (a55, b3, c2, d4), (a55, b3, c2, d5), (a55, b3, c2, d6), (a55, b3, c2, d7), (a55, b3, c2, d8), (a55, b3, c2, d9), (a55, b3, c2, d10), (a55, b3, c2, d1), (a55, b3, c2, d2), (a55, b3, c2, d13), (a55, b3, c2, d14), (a5, b3, c2, d15), (a55, b3, c2, d16), (a55, b3, c2, d17), (a55, b3, c2, d18), (a55, b3, c2, d19), (a55, b3, c2, d20), (a55, b3, c2, d21), (a55, b3, c2, d22), (a55, b3, c3, d1), (a55, b3, c3, d2), (a55, b3, c3, d3), (a55, b3, c3, d4), (a55, b3, c3, d5), (a55, b3, c3, d6), (a55, b3, c3, d7), (a55, b3, c3, d8), (a55, b3, c3, d9), (a55, b3, c3, d10), (a55, b3, c3, d11), (a55, b3, c3, d12), (a55, b3, c3, d13), (a55, b3, c3, d14), (a55, b3, c3, d15), (a55, b3, c3, d6), (a55, b3, c3, d17), (a55, b3, c3, d18), (a55, b3, c3, d19), (a55, b3, c3, d20), (a55, b3, c3, d21), (a55, b3, c3, d22), (a55, b4, c1, d1), (a55, b4, c1, d2), (a55, b4, c1, d3), (a55, b4, c1, d4), (a55, b4, c1, d5), (a55, b4, c1, d6), (a55, b4, c1, d7), (a55, b4, c1, d8), (a55, b4, c1, d9), (a55, b4, c1, d10), (a55, b4, c1, d11), (a55, b4, c1, d12), (a55, b4, c1, d13), (a55, b4, c1, d14), (a55, b4, c1, d15), (a55, b4, c1, d16), (a55, b4, c1, d17), (a55, b4, c1, d18), (a55, b4, c1, d19), (a55, b4, c1, d20), (a55, b4, c1, d21), (a55, b4, c1, d22), (a55, b4, c2, d1), (a55, b4, c2, d2), (a55, b4, c2, d3), (a55, b4, c2, d4), (a55, b4, c2, d5), (a55, b4, c2, d6), (a55, b4, c2, d7), (a55, b4, c2, d8), (a55, b4, c2, d9), (a55, b4, c2, d10), (a55, b4, c2, d11), (a55, b4, c2, d12), (a55, b4, c2, d13), (a55, b4, c2, d14), (a55, b4, c2, d15), (a55, b4, c2, d16), (a55, b4, c2, d17), (a55, b4, c2, d18), (a55, b4, c2, d19), (a55, b4, c2, d20), (a55, b4, c2, d21), (a55, b4, c2, d22), (a55, b4, c3, d1), (a55, b4, c3, d2), (a55, b4, c3, d3), (a55, b4, c3, d4), (a55, b4, c3, d5), (a55, b4, c3, d6), (a55, b4, c3, d7), (a55, b4, c3, d8), (a55, b4, c3, d9), (a55, b4, c3, d10), (a55, b4, c3, d11), (a55, b4, c3, d12), (a55, b4, c3, d13), (a55, b4, c3, d14), (a55, b4, c3, d15), (a55, b4, c3, d16), (a55, b4, c3, d17), (a55, b4, c3, d18), (a55, b4, c3, d19), (a55, b4, c3, d20), (a55, b4, c3, d21), (a55, b4, c3, d22), (a55, b5, c1, d1), (a55, b5, c1, d2), (a55, b5, c1, d3), (a55, b5, c1, d4), (a35, b5, c1, d5), (a55, b5, c1, d6), (a55, b5, c1, d7), (a55, b5, c1, d8), (a55, b5, c1, d9), (a5, b5, c1, d10), (a55, b5, c1, d11), (a55, b5, c1, d12), (a55, b5, c1, d13), (a55, b5, c1, d14) (a55, b5, c1, d15), (a55, b5, c1, d16), (a55, b5, c1, d17), (a55, b5, c1, d18), (a55, b5, c1, d19) (a55, b5, c1, d20), (a55, b5, c1, d21), (a55, b5, c1, d22), (a55, b5, c2, d1), (a55, b5, c2, d2), (a55, b5, c2, d3), (a55, b5, c2, d4), (a55, b5, c2, d5), (a55, b5, c2, d6), (a55, b5, c2, d7), (a55, b5, c2, d8), (a35, b5, c2, d9), (a55, b5, c2, d10), (a55, b5, c2, d11), (a55, b5, c2, d12), (a55, b5, c2, d13), (a55, b5, c2, d14), (a55, b5, c2, d15), (a55, b5, c2, d16), (a55, b5, c2, d17), (a55, b5, c2, d18), (a55, b5, c2, d19), (a55, b5, c2, d20), (a55, b5, c2, d21), (a55, b5, c2, d22), (a55, b5, c3, d1), (a55, b5, c3, d2), (a55, b5, c3, d3), (a55, b5, c3, d4), (a55, b5, c3, d5), (a55, b5, c3, d6), (a55, b5, c3, d7), (a55, b5, c3, d8), (a55, b5, c3, d9), (a55, b5, c3, d10), (a55, b5, c3, d11), (a55, b5, c3, d12), (a55, b5, c3, d13), (a55, b5, c3, d14), (a55, b5, c3, d15), (a55, b5, c3, d16), (a55, b5, c3, d17), (a55, b5, c3, d18), (a55, b5, c3, d19), (a55, b5, c3, d20), (a55, b5, c3, d21), (a55, b5, c3, d22), (a55, b6, c1, d1), (a55, b6, c1, d2), (a55, b6, c1, d3), (a55, b6, c1, d4), (a55, b6, c1, d5), (a55, b6, c1, d6), (a55, b6, c1, d7), (a55, b6, c1, d8), (a55, b6, c1, d9), (a55, b6, c1, d10), (a55, b6, c1, d11), (a55, b6, c1, d12), (a55, b6, c1, d13), (a55, b6, c1, d14), (a55, b6, c1, d15), (a55, b6, c1, d16), (a55, b6, c1, d17), (a55, b6, c1, d18), (a55, b6, c1, d19), (a55, b6, c1, d20), (a55, b6, c1, d21), (a55, b6, c1, d22), (a55, b6, c2, d1), (a55, b6, c2, d2), (a55, b6, c2, d3), (a55, b6, c2, d4), (a55, b6, c2, d5), (a55, b6, c2, d6), (a55, b6, c2, d7), (a55, b6, c2, d8), (a55, b6, c2, d9), (a55, b6, c2, d10), (a55, b6, c2, d11), (a55, b6, c2, d12), (a55, b6, c2, d13), (a55, b6, c2, d14), (a55, b6, c2, d15), (a55, b6, c2, d16), (a55, b6, c2, d17), (a55, b6, c2, d18), (a55, b6, c2, d19), (a55, b6, c2, d20), (a55, b6, c2, d21), (a55, b6, c2, d22), (a55, b6, c3, d1), (a55, b6, c3, d2), (a55, b6, c3, d3), (a55, b6, c3, d4), (a55, b6, c3, d5), (a55, b6, c3, d6), (a55, b6, c3, d7), (a55, b6, c3, d8), (a55, b6, c3, d9), (a55, b6, c3, d10), (a55, b6, c3, d11), (a55, b6, c3, d12), (a55, b6, c3, d13), (a55, b6, c3, d14), (a55, b6, c3, d15), (a55, b6, c3, d16), (a55, b6, c3, d17), (a55, b6, c3, d18), (a55, b6, c3, d19), (a55, b6, c3, d20), (a55, b6, c3, d21), (a55, b6, c3, d22), (a56, b1, c1, d1), (a56, b1, c1, d2), (a56, b1, c1, d3), (a56, b1, c1, d4), (a56, b1, c1, d5), (a56, b1, c1, d6), (a56, b1, c1, d7), (a56, b1, c1, d8), (a56, b1, c1, d9), (a56, b1, c1, d10), (a56, b1, c1, d11), (a56, b1, c1, d12), (a56, b1, c1, d13), (a56, b1, c1, d14), (a56, b1, c1, d15), (a56, b1, c1, d16), (a56, b1, c1, d17), (a56, b1, c1, d18), (a56, b1, c1, d19), (a56, b1, c1, d20), (a56, b1, c1, d21), (a56, b1, c1, d22), (a56, b1, c2, d1), (a56, b1, c2, d2), (a56, b1, c2, d3), (a56, b1, c2, d4), (a56, b1, c2, d5), (a56, b1, c2, d6), (a56, b1, c2, d7), (a56, b1, c2, d8), (a56, b1, c2, d9), (a56, b1, c2, d10), (a56, b1, c2, d11), (a56, b1, c2, d12), (a5, b1, c2, d13), (a56, b1, c2, d14), (a56, b1, c2, d15), (a56, b1, c2, d16), (a56, b1, c2, d17), (a56, b1, c2, d18), (a56, b1, c2, d19), (a56, b1, c2, d20), (a56, b1, c2, d21), (a56, b1, c2, d22), (a56, b1, c3, d1), (a56, b1, c3, d2), (a56, b1, c3, d3), (a56, b1, c3, d4), (a56, b1, c1, d5), (a56, b2, c1, d6, (a56, b1, c3, d7), (a56, b1, c3, d8), (a56, b1, c3, d9), (a56, b1, c1, d10), (a56, b2, c1, d11), (a56, b2, c1, d12), (a56, b2, c1, d13), (a56, b2, c1, d14), (a56, b2, c1, d19), (a56, b2, c1, d20), (a56, b2, c1, d21), (a56, b2, c1, d22), (a56, b2, c2, d1), (a56, b2, c2, d2), (a56, b2, c2, d3), (a56, b2, c2, d4), (a56, b2, c2, d5), (a56, b2, c2, d6), (a56, b2, c2, d7), (a55, b2, c2, d8), (a56, b2, c2, d9), (a56, b2, c2, d10), (a56, b2, c2, d11), (a56, b2, c2, d12), (a56, b2, c2, d13), (a56, b2, c2, d13), (a56, b2, c2, d14, (a56, b2, c2, d15), (a56, b2, c2, d16), (a56, b2, c2, d17), (a56, b2, c2, d18), (a56, b2, c2, d19), (a56, b2, c2, d20), (a56, b2, c2, d21), (a56, b2, c2, d22), (a56, b2, c3, d1), (a56, b2, c3, d2), (a56, b2, c3, d3) (a56, b2, c3, d4), (a56, b2, c3, d5), (a56, b2, c1, d6), (a56, b2, c3, d7), (a56, b2, c3, d8), (a56, b2, c3, d9), (a56, b2, c3, d10), (a56, b2, c3, d11), (a56, b2, c3, d12), (a56, b2, c3, d13), (a56, b2, c3, d14), (a56, b2, c3, d15), (a56, b2, c3, d16), (a56, b2, c3, d17), (a56, b2, c3, d18), (a56, b2, c3, d19), (a56, b2, c3, d20), (a56, b2, c3, d21), (a56, b2, c3, d22), (a56, b3, c1, d1), (a56, b3, c1, d2), (a56, b3, c1, d3), (a56, b3, c1, d4), (a56, b3, c1, d5), (a56, b3, c1, d6), (a56, b3, c1, d7), (a56, b3, c1, d8), (a56, b5, c1, d9), (a56, b3, c1, d10), (a56, b3, c1, d11), (a56, b3, c1, d12), (a56, b3, c1, d13), (a56, b3, c1, d14), (a56, b3, c1, d15), (a56, b3, c1, d16), (a56, b3, c1, d17), (a56, b3, c1, d18), (a56, b3, c1, d19), (a56, b3, c1, d20), (a56, b3, c1, d21), (a56, b3, c1, d22), (a56, b3, c2, d1), (a56, b3, c2, d2), (a56, b3, c2, d3), (a56, b3, c2, d4), (a56, b3, c2, d5), (a56, b3, c2, d6), (a56, b3, c2, d7), (a56, b3, c2, d8), (a56, b3, c2, d9), (a56, b3, c2, d10), (a56, b3, c2, d11), (a56, b3, c2, d12), (a56, b3, c2, d13), (a56, b3, c2, d14), (a56, b3, c2, d15), (a56, b3, c2, d16), (a56, b3, c2, d17), (a56, b3, c2, d18), (a56, b3, c2, d19), (a56, b3, c2, d20), (a56, b3, c2, d21), (a56, b3, c2, d22), (a56, b3, c3, d1), (a56, b3, c3, d2), (a56, b3, c3, d3), (a56, b3, c3, d4), (a56, b3, c3, d5), (a56, b3, c3, d6), (a56, b3, c3, d7), (a56, b3, c3, d8), (a56, b3, c3, d9), (a50, b3, c3, d10), (a56, b3, c3, d11), (a56, b3, c3, d12), (a56, b3, c3, d13), (a56, b3, c3, d14), (a56, b3, c3, d15), (a56, b3, c3, d16), (a56, b3, c3, d17), (a56, b3, c3, d18), (a56, b3, c3, d19), (a56, b3, c3, d20), (a56, b3, c3, d21), (a56, b3, c3, d22), (a56, b4, c1, d1), (a56, b4, c1, d2), (a53, b4, c1, d3), (a56, b4, c1, d4), (a56, b4, c1, d5), (a56, b4, c1, d6), (a56, b4, c1, d7), (a56, b4, c1, d8), (a56, b4, c1, d9), (a56, b4, c1, d10), (a56, b4, c1, d11), (a56, b4, c1, d12), (a56, b4, c1, d13), (a56, b4, c1, d14), (a56, b4, c1, d15), (a56, b4, c1, d16), (a56, b4, c1, d17), (a56, b4, c1, d18), (a56, b4, c1, d19), (a56, b4, c1, d20), (a56, b4, c1, d21), (a56, b4, c1, d22), (a56, b4, c2, d1), (a56, b4, c2, d2), (a56, b4, c2, d3), (a56, b4, c2, d4), (a56, b4, c2, d5), (a56, b4, c2, d6), (a56, b4, c2, d7), (a56, b4, c2, d8), (a56, b4, c2, d9), (a56, b4, c2, d10), (a56, b4, c2, d11), (a56, b4, c2, d12), (a56, b4, c2, d13), (a56, b4, c2, d14), (a56, b4, c2, d15), (a56, b4, c2, d16), (a56, b4, c2, d17), (a56, b4, c2, d18), (a56, b4, c2, d19), (a56, b4, c2, d20), (a56, b4, c2, d21), (a56, b4, c2, d22), (a56, b4, c3, d1), (a56, b4, c3, d2), (a56, b4, c3, d3), (a53, b4, c3, d4), (a56, b4, c3, d5), (a56, b4, c3, d6), (a56, b4, c3, d7), (a56, b4, c3, d8), (a56, b4, c3, d9), (a56, b4, c3, d10), (a56, b4, c3, d11), (a56, b4, c3, d12), (a56, b4, c3, d13), (a56, b4, c3, d14), (a56, b4, c3, d15), (a56, b4, c3, d16), (a56, b4, c3, d17), (a56, b4, c3, d18), (a56, b4, c3, d19), (a56, b4, c3, d20), (a56, b4, c3, d21), (a56, b4, c3, d22), (a56, b5, c1, d1), (a56, b5, c1, d2), (a56, b5, c1, d3), (a56, b5, c1, d4), (a56, b5, c1, d5), (a56, b5, c1, d6), (a56, b5, c1, d7), (a56, b5, c1, d8), (a56, b5, c1, d9), (a56, b5, c1, d10), (a56, b5, c1, d11), (a56, b5, c1, d12), (a56, b5, c1, d13), (a56, b5, c1, d14), (a56, b5, c1, d15), (a56, b5, c1, d16), (a56, b5, c1, d17), (a56, b5, c1, d18), (a56, b5, c1, d19), (a56, b5, c1, d20), (a56, b5, c1, d21), (a56, b5, c1, d22), (a56, b5, c2, d1), (a56, b5, c2, d2), (a56, b5, c2, d3), (a56, b5, c2, d4), (a56, b5, c2, d5), (a56, b5, c2, d6), (a56, b5, c2, d7), (a56, b5, c2, d8), (a56, b5, c2, d9), (a56, b5, c2, d10), (a56, b5, c2, d11), (a56, b5, c2, d12), (a56, b5, c2, d13), (a56, b5, c2, d14), (a56, b5, c2, d15), (a56, b5, c2, d16), (a56, b5, c2, d17), (a56, b5, c2, d18), (a56, b5, c2, d19), (a56, b5, c2, d20), (a56, b5, c2, d21), (a56, b5, c2, d22), (a56, b5, c3, d1), (a56, b5, c3, d2), (a56, b5, c3, d3), (a56, b5, c3, d4), (a56, b5, c3, d5), (a56, b5, c3, d6), (a56, b5, c3, d7), (a56, b5, c3, d8), (a56, b5, c3, d9), (a56, b5, c3, d10), (a56, b5, c3, d11), (a56, b5, c3, d12), (a56, b5, c3, d13), (a56, b5, c3, d14), (a56, b5, c3, d15), (a56, b5, c3, d16), (a56, b5, c3, d17), (a56, b5, c3, d18), (a56, b5, c3, d19), (a56, b5, c3, d20), (a56, b5, c3, d21), (a56, b5, c3, d22), (a56, b6, c1, d1), (a56, b6, c1, d2), (a56, b6, c1, d3), (a56, b6, c1, d4), (a56, b6, c1, d5), (a56, b6, c1, d6), (a56, b6, c1, d7), (a56, b6, c1, d8), (a56, b6, c1, d9), (a56, b6, c1, d10), (a56, b6, c1, d11), (a56, b6, c1, d12), (a56, b6, c1, d13), (a56, b6, c1, d14), (a56, b6, c1, d15), (a56, b6, c1, d16), (a56, b6, c1, d17), (a56, b6, c1, d18), (a56, b6, c1, d19), (a56, b6, c1, d20), (a56, b6, c1, d21), (a56, b6, c1, d22), (a56, b6, c2, d1), (a56, b6, c2, d2), (a56, b6, c2, d3), (a56, b6, c2, d4), (a56, b6, c2, d5), (a56, b6, c2, d6), (a56, b6, c2, d7), (a56, b6, c2, d8), (a56, b6, c2, d19), (a56, b6, c2, d10), (a56, b6, c2, d11), (a56, b6, c2, d12), (a56, b6, c2, d13), (a56, b6, c2, d14), (a56, b6, c2, d15), (a56, b6, c2, d16), (a56, b6, c2, d17), (a56, b6, c2, d18), (a56, b6, c2, d19), (a56, b6, c2, d20), (a56, b6, c2, d21), (a56, b6, c2, d22), (a56, b6, c3, d1), (a56, b6, c3, d2), (a56, b6, c3, d3), (a56, b6, c3, d4), (a56, b6, c3, d5), (a56, b6, c3, d6), (a56, b6, c3, d7), (a56, b6, c3, d8), (a56, b6, c3, d9), (a56, b6, c3, d10), (a56, b6, c3, d11), (a56, b6, c3, d12), (a56, b6, c3, d13), (a56, b6, c3, d14), (a56, b6, c3, d15), (a56, b6, c3, d16), (a56, b6, c3, d17), (a56, b6, c3, d18), (a56, b6, c3, d19), (a56, b6, c3, d20), (a56, b6, c3, d21), (a56, b6, c3, d22), (a57, b1, c1, d1), (a57, b1, c1, d2), (a57, b1, c1, d3), (a57, b1, c1, d4), (a57, b1, c1, d5), (a57, b1, c1, d6), (a37, b1, c1, d7), (a57, b1, c1, d8), (a57, b1, c1, d9), (a57, b1, c1, d10), (a57, b1, c1, d11), (a57, b1, c1, d12), (a57, b1, c1, d13), (a57, b1, c1, d14), (a57, b1, c1, d15), (a57, b1, c1, d16), (a51, b1, c1, d17), (a57, b1, c1, d18), (a57, b1, c1, d19), (a7, b1, c1, d20), (a57, b1, c1, d21), (a57, b1, c1, d22), (a57, b1, c2, d1), (a57, b1, c2, d2), (a57, b1, c2, d3), (a57, b1, c2, d4), (a37, b1, c2, d5), (a57, b1, c2, d6), (a57, b1, c2, d7), (a57, b1, c2, d8), (a57, b1, c2, d9), (a57, b1, c2, d10), (a57, b1, c2, d11), (a57, b1, c2, d12), (a57, b1, c2, d13), (a57, b1, c2, d14), (a57, b1, c2, d15), (a57, b1, c2, d16), (a57, b1, c2, d17), (a57, b1, c2, d18), (a57, b1, c2, d19), (a57, b1, c2, d20), (a57, b1, c2, d21), (a57, b1, c2, d22), (a57, b1, c3, d1), (a57, b1, c3, d2), (a57, b1, c3, d3), (a57, b1, c3, d4), (a57, b1, c3, d5), (a57, b1, c3, d6), (a57, b1, c3, d7), (a57, b1, c3, d8), (a57, b1, c3, d9), (a57, b1, c3, d10), (a57, b1, c3, d11), (a57, b1, c3, d12), (a57, b1, c3, d13), (a57, b1, c3, d14), (a57, b1, c3, d15), (a57, b1, c3, d16), (a57, b1, c3, d17), (a57, b1, c3, d18), (a57, b1, c3, d19), (a57, b1, c3, d20), (a57, b1, c3, d21), (a57, b1, c3, d22), (a57, b2, c1, d1), (a57, b2, c1, d2), (a57, b2, c1, d3), (a57, b2, c1, d4), (a57, b2, c1, d5), (a57, b2, c1, d6), (a57, b2, c1, d7), (a57, b2, c1, d8), (a57, b2, c1, d9), (a57, b2, c1, d10), (a57, b2, c1, d11), (a57, b2, c1, d12), (a57, b2, c1, d13), (a57, b2, c1, d14), (a57, b2, c1, d15), (a57, b2, c1, d16), (a57, b2, c1, d17), (a57, b2, c1, d18), (a57, b2, c1, d19), (a57, b2, c1, d20), (a57, b2, c1, d21), (a57, b2, c1, d22), (a57, b2, c2, d1), (a57, b2, c2, d2), (a57, b2, c2, d3), (a57, b2, c2, d4), (a57, b2, c2, d5), (a57, b2, c2, d6), (a57, b2, c2, d7), (a57, b2, c2, d8), (a57, b2, c2, d9), (a57, b2, c2, d10), (a57, b2, c2, d11), (a57, b2, c2, d12), (a57, b2, c2, d13), (a57, b2, c2, d14), (a57, b2, c2, d15), (a57, b2, c2, d16), (a57, b2, c2, d17), (a57, b2, c2, d18), (a57, b2, c2, d19), (a57, b2, c2, d20), (a57, b2, c2, d21), (a57, b2, c2, d22), (a57, b2, c3, d1), (a57, b2, c3, d2), (a57, b2, c3, d3), (a57, b2, c3, d4), (a57, b2, c3, d5), (a5, b2, c3, d6), (a57, b2, c3, d7), (a57, b2, c3, d8), (a57, b2, c3, d9), (a57, b2, c3, d10), (a57, b2, c3, d11), (a57, b2, c3, d12), (a57, b2, c3, d13), (a57, b2, c3, d14), (a57, b2, c3, d15), (a57, b2, c3, d16), (a57, b2, c3, d17), (a57, b2, c3, d18), (a57, b2, c3, d19), (a57, b2, c3, d20), (a57, b2, c3, d21), (a57, b2, c3, d22), (a57, b3, c1, d1), (a57, b3, c1, d2), (a57, b3, c1, d3), (a57, b3, c1, d4), (a57, b3, c1, d5), (a57, b3, c1, d6), (a57, b3, c1, d7), (a57, b3, c1, d8), (a57, b3, c1, d9), (a57, b3, c1, d10), (a57, b3, c1, d11), (a57, b3, c1, d12), (a57, b3, c1, d13), (a57, b3, c1, d14), (a57, b3, c1, d15), (a57, b3, c1, d16), (a57, b3, c1, d17), (a57, b3, c1, d18), (a57, b3, c1, d19), (a57, b3, c1, d20), (a57, b3, c1, d21), (a57, b3, c1, d22), (a57, b3, c2, d1), (a57, b3, c2, d2), (a57, b3, c2, d3), (a57, b3, c2, d4), (a57, b3, c2, d5), (a57, b3, c2, d6), (a57, b3, c2, d7), (a57, b3, c2, d8), (a57, b3, c2, d9), (a57, b3, c2, d10), (a57, b3, c2, d11), (a57, b3, c2, d12), (a57, b3, c2, d13), (a57, b3, c2, d14), (a57, b3, c2, d15), (a57, b3, c2, d16), (a57, b3, c2, d17), (a57, b3, c2, d18), (a57, b3, c2, d19), (a57, b3, c2, d20), (a57, b3, c2, d21), (a57, b3, c2, d22), (a57, b3, c3, d1), (a57, b3, c3, d2), (a57, b3, c3, d3), (a57, b3, c3, d4), (a57, b3, c3, d5), (a57, b3, c3, d6), (a57, b3, c3, d7), (a57, b3, c3, d8), (a57, b3, c3, d9), (a57, b3, c3, d10), (a57, b3, c3, d11), (a57, b3, c3, d12), (a57, b3, c3, d13), (a57, b3, c3, d14), (a57, b3, c3, d15), (a57, b3, c3, d16), (a57, b3, c3, d17), (a57, b3, c3, d18), (a57, b3, c3, d19), (a57, b3, c3, d20), (a57, b3, c3, d21), (a57, b3, c3, d22), (a57, b4, c1, d1), (a57, b4, c1, d2), (a57, b4, c1, d3), (a57, b4, c1, d4), (a57, b4, c1, d5), (a57, b4, c1, d6), (a57, b4, c1, d7), (a57, b4, c1, d8), (a57, b4, c1, d9), (a57, b4, c1, d10), (a57, b4, c1, d11), (a57, b4, c1, d12), (a57, b4, c1, d13), (a57, b4, c1, d14), (a57, b4, c1, d15), (a57, b4, c1, d16), (a57, b4, c1, d17), (a57, b4, c1, d18), (a57, b4, c1, d19), (a57, b4, c1, d20), (a57, b4, c1, d21), (a57, b4, c1, d22), (a57, b4, c2, d1), (a57, b4, c2, d2), (a57, b4, c2, d3), (a57, b4, c2, d4), (a57, b4, c2, d5), (a57, b4, c2, d6), (a57, b4, c2, d7), (a57, b4, c2, d5), (a57, b4, c2, d9), (a57, b4, c2, d10), (a57, b4, c2, d11), (a57, b4, c2, d12), (a57, b4, c2, d13), (a57, b4, c2, d14), (a57, b4, c2, d15), (a57, b4, c2, d16), (a57, b4, c2, d17), (a57, b4, c2, d18), (a57, b4, c2, d19), (a57, b4, c2, d20), (a57, b4, c2, d21), (a57, b4, c2, d22), (a57, b4, c3, d), (a57, b4, c3, d2), (a57, b4, c3, d3), (a57, b4, c3, d4), (a57, b4, c3, d5), (a57, b4, c3, d6), (a57, b4, c3, d7), (a57, b4, c3, d8), (a57, b4, c3, d9), (a57, b4, c3, d10), (a57, b4, c3, d11), (a57, b4, c3, d12), (a57, b4, c3, d13), (a57, b4, c3, d14), (a57, b4, c3, d15), (a57, b4, c3, d16), (a57, b4, c3, d17), (a57, b4, c3, d18), (a57, b4, c3, d19), (a57, b4, c3, d20), (a57, b4, c3, d21), (a57, b4, c3, d22), (a57, b5, c1, d1), (a57, b5, c7, d2), (a57, b5, c1, d3), (a57, b5, c1, d4), (a57, b5, c1, d5), (a57, b5, c1, d6), (a57, b5, c1, d7), (a57, b5, c1, d8), (a57, b5, c1, d9), (a57, b5, c1, d10), (a57, b5, c1, d11), (a57, b5, c1, d12), (a57, b5, c1, d13), (a57, b5, c1, d14), (a57, b5, c1, d15), (a57, b5, c1, d16), (a57, b5, c1, d17), (a57, b5, c1, d18), (a57, b5, c1, d19), (a57, b5, c1, d20), (a57, b5, c1, d21), (a57, b5, c1, d22), (a57, b5, c2, d1), (a57, b5, c2, d2), (a57, b5, c2, d3), (a57, b5, c2, d4), (a57, b5, c2, d5), (a57, b5, c2, d6), (a57, b5, c2, d7), (a57, b5, c2, d8), (a57, b5, c2, d9), (a57, b5, c2, d10), (a57, b5, c2, d11), (a57, b5, c2, d12), (a57, b5, c2, d13), (a57, b5, c2, d14), (a57, b5, c2, d15), (a57, b5, c2, d16), (a57, b5, c2, d17), (a57, b5, c2, d18), (a57, b5, c2, d19), (a57, b5, c2, d20), (a57, b5, c2, d21), (a57, b5, c2, d22), (a57, b5, c3, d1), (a57, b5, c3, d2), (a57, b5, c3, d3), (a57, b5, c3, d4), (a57, b5, c3, d5), (a57, b5, c3, d6), (a57, b5, c3, d7), (a57, b5, c3, d8), (a57, b5, c3, d9), (a57, b5, c3, d10), (a57, b5, c3, d11), (a57, b5, c3, d12), (a57, b5, c3, d13), (a57, b5, c3, d14), (a57, b5, c3, d15), (a57, b5, c3, d16), (a57, b5, c3, d17), (a57, b5, c3, d18), (a57, b5, c3, d19), (a57, b5, c3, d20), (a57, b5, c3, d21), (a57, b5, c3, d22), (a57, b6, c1, d1), (a57, b6, c1, d2), (a57, b6, c1, d3), (a57, b6, c1, d4), (a57, b6, c1, d5), (a57, b6, c1, d6), (a57, b6, c1, d7), (a57, b6, c1, d8), (a57, b6, c1, d9), (a57, b6, c1, d10), (a57, b6, c1, d11), (a57, b6, c1, d12), (a57, b6, c1, d13), (a57, b6, c1, d14), (a57, b6, c1, d15), (a57, b6, c1, d16), (a57, b6, c1, d17), (a57, b6, c1, d18), (a57, b6, c1, d19), (a57, b6, c1, d20), (a57, b6, c1, d21), (a57, b6, c1, d22), (a57, b6, c2, d1), (a57, b6, c2, d2), (a57, b6, c2, d3), (a57, b6, c2, d4), (a57, b6, c2, d5), (a57, b6, c2, d6), (a57, b6, c2, d7), (a57, b6, c2, d8), (a57, b6, c2, d9), (a57, b6, c2, d10), (a57, b6, c2, d11), (a57, b6, c2, d12), (a57, b6, c2, d13), (a57, b6, c2, d14), (a57, b6, c2, d15), (a57, b6, c2, d16), (a57, b6, c2, d17), (a57, b6, c2, d18), (a57, b6, c2, d19), (a57, b6, c2, d20), (a57, b6, c2, d21), (a57, b6, c2, d22), (a57, b6, c3, d1), (a57, b6, c3, d2), (a57, b6, c3, d3), (a57, b6, c3, d4), (a57, b6, c3, d5), (a57, b6, c3, d6), (a57, b6, c3, d7), (a57, b6, c3, d8), (a57, b6, c3, d9), (a57, b6, c3, d10), (a57, b6, c3, d11), (a57, b6, c3, d12), (a57, b6, c3, d13), (a57, b6, c3, d14), (a57, b6, c3, d15), (a57, b6, c3, d16), (a57, b6, c3, d17), (a57, b6, c3, d18), (a57, b6, c3, d19), (a57, b6, c3, d20), (a57, b6, c3, d21), (a57, b6, c3, d22), (a58, b1, c1, d1), (a58, b1, c1, d2), (a58, b1, c1, d3), (a58, b1, c1, d4), (a58, b1, c1, d5), (a58, b1, c1, d6), (a58, b1, c1, d7), (a58, b1, c1, d8), (a58, b1, c1, d9), (a58, b1, c1, d10), (a58, b1, c1, d11), (a58, b1, c1, d12), (a58, b1, c1, d13), (a58, b1, c1, d14), (a58, b1, c1, d15), (a58, b1, c1, d16), (a58, b1, c1, d17), (a55, b1, c1, d18), (a58, b1, c1, d19), (a58, b1, c1, d20), (a58, b1, c1, d21), (a58, b1, c1, d22), (a58, b1, c2, d1), (a58, b1, c2, d2), (a58, b1, c2, d3), (a58, b1, c2, d4), (a58, b1, c2, d5), (a58, b1, c2, d6), (a58, b1, c2, d7), (a58, b1, c2, d8), (a58, b1, c2, d9), (a58, b1, c2, d10), (a58, b1, c2, d11), (a58, b1, c2, d12), (a58, b1, c2, d13), (a58, b1, c2, d14) (a58, b1, c2, d15), (a58, b1, c2, d16), (a58, b1, c2, d17), (a58, b1, c2, d18), (a58, b1, c2, d19), (a58, b1, c2, d20), (a58, b1, c2, d21), (a58, b1, c2, d22), (a58, b1, c3, d1), (a58, b1, c3, d2), (a58, b1, c3, d3), (a58, b1, c3, d4), (a58, b1, c3, d5), (a58, b1, c3, d6), (a58, b1, c3, d7), (a58, b1, c3, d8), (a58, b1, c3, d9), (a58, b1, c3, d10), (a58, b1, c3, d11), (a58, b, c3, d12), (a58, b1, c3, d13), (a58, b1, c3, d14), (a58, b1, c3, d15), (a58, b1, c3, d16), (a58, b1, c3, d17), (a58, b1, c3, d18), (a58, b1, c3, d19), (a58, b1, c3, d20), (a58, b1, c3, d21), (a58, b1, c3, d22), (a58, b2, c1, d1), (a58, b2, c1, d2), (a58, b2, c1, d3), (a58, b2, c1, d4), (a58, b2, c1, d5), (a58, b2, c1, d6), (a58, b2, c1, d7), (a58, b2, c1, d8), (a58, b2, c1, d9), (a58, b2, c1, d10), (a58, b2, c1, d11), (a58, b2, c1, d12), (a58, b2, c1, d13), (a58, b2, c1, d14), (a58, b2, c1, d15), (a58, b2, c1, d16), (a58, b2, c1, d17), (a58, b2, c1, d18), (a58, b2, c1, d19), (a58, b2, c1, d20), (a58, b2, c1, d21), (a58, b2, c1, d22), (a55, b2, c2, d1), (a58, b2, c2, d2), (a58, b2, c2, d3), (a58, b2, c2, d4), (a58, b2, c2, d5), (a58, b2, c2, d6), (a58, b2, c2, d7), (a58, b2, c2, d8), (a58, b2, c2, d9), (a58, b2, c2, d10), (a58, b2, c2, d11), (a58, b2, c2, d12), (a58, b2, c2, d13), (a58, b2, c2, d14), (a58, b2, c2, d15), (a58, b2, c2, d16), (a58, b2, c2, d17), (a58, b2, c2, d18), (a58, b2, c2, d19), (a58, b2, c2, d20), (a58, b2, c2, d21), (a58, b2, c2, d22), (a58, b2, c3, d1), (a58, b2, c3, d2), (a58, b2, c3, d3), (a58, b2, c3, d4), (a58, b2, c3, d5), (a58, b2, c3, d6), (a58, b2, c3, d7), (a58, b2, c3, d8), (a58, b2, c3, d9), (a58, b2, c3, d10), (a58, b2, c3, d11), (a58, b2, c3, d12), (a58, b2, c3, d13), (a58, b2, c3, d14), (a58, b2, c3, d15), (a58, b2, c3, d6), (a58, b2, c3, d17), (a58, b2, c3, d18), (a58, b2, c3, d19), (a58, b2, c3, d20), (a58, b2, c3, d21), (a58, b2, c3, d22), (a58, b3, c1, d1), (a58, b3, c1, d2), (a58, b3, c1, d3), (a58, b3, c1, d4), (a58, b3, c1, d5), (a58, b3, c1, d6), (a58, b3, c1, d7), (a58, b3, c1, d8), (a58, b3, c1, d9), (a58, b3, c1, d10), (a58, b3, c1, d11), (a58, b3, c1, d12), (a58, b3, c1, d13), (a58, b3, c1, d14), (a58, b3, c1, d15), (a58, b3, c1, d16), (a58, b3, c1, d7), (a58, b3, c1, d18), (a58, b3, c1, d19), (a58, b3, c1, d20), (a58, b3, c1, d21), (a58, b3, c1, d22), (a58, b3, c2, d1), (a58, b3, c2, d2), (a58, b3, c2, d3), (a58, b3, c2, d4), (a58, b3, c2, d5), (a58, b3, c2, d6), (a58, b3, c2, d7), (a58, b3, c2, d8), (a58, b3, c2, d9), (a58, b3, c2, d10), (a58, b3, c2, d11), (a58, b3, c2, d12), (a58, b3, c2, d13), (a58, b3, c2, d14), (a58, b3, c2, d15), (a58, b3, c2, d16), (a58, b3, c2, d17), (a58, b3, c2, d18), (a58, b3, c2, d19), (a58, b3, c2, d20), (a58, b3, c2, d21), (a58, b3, c2, d22), (a58, b3, c3, d1), (a58, b3, c3, d2), (a58, b3, c3, d3), (a58, b3, c3, d4), (a58, b3, c3, d5), (a58, b3, c3, d6), (a58, b3, c3, d7), (a58, b3, c3, d8), (a58, b3, c3, d9), (a58, b3, c3, d10), (a58, b3, c3, d11), (a58, b3, c3, d12), (a58, b3, c3, d13), (a58, b3, c3, d14), (a58, b3, c3, d15), (a58, b3, c3, d16), (a58, b3, c3, d17), (a58, b3, c3, d18), (a58, b3, c3, d19), (a58, b3, c3, d20), (a58, b3, c3, d21), (a58, b3, c3, d22), (a58, b4, c1, d1), (a58, b4, c1, d2), (a58, b4, c1, d3), (a58, b4, c1, d4), (a58, b4, c1, d5), (a58, b4, c1, d6), (a58, b4, c1, d7), (a58, b4, c1, d8), (a58, b4, c1, d9), (a58, b4, c1, d10), (a58, b4, c1, d11), (a58, b4, c1, d12), (a58, b4, c1, d13), (a58, b4, c1, d14), (a58, b4, c1, d15), (a58, b4, c1, d16), (a58, b4, c1, d17), (a58, b4, c1, d18), (a58, b4, c1, d19), (a58, b4, c1, d20), (a58, b4, c1, d21), (a58, b4, c1, d22), (a58, b4, c2, d1), (a58, b4, c2, d2), (a58, b4, c2, d3), (a58, b4, c2, d4), (a58, b4, c2, d5), (a58, b4, c2, d6), (a58, b4, c2, d7), (a58, b4, c2, d8), (a58, b4, c2, d9), (a58, b4, c2, d10), (a58, b4, c2, d11), (a58, b4, c2, d12), (a58, b4, c2, d13), (a58, b4, c2, d14), (a58, b4, c2, d15), (a58, b4, c2, d16), (a58, b4, c2, d17), (a58, b4, c2, d18), (a58, b4, c2, d19), (a58, b4, c2, d20), (a58, b4, c2, d21), (a58, b4, c2, d22), (a58, b4, c3, d1), (a58, b4, c3, d2), (a58, b4, c3, d3), (a58, b4, c3, d4), (a58, b4, c3, d5), (a58, b4, c3, d6), (a58, b4, c3, d7), (a58, b4, c3, d8), (a58, b4, c3, d9), (a58, b4, c3, d10), (a58, b4, c3, d11), (a58, b4, c3, d12), (a58, b4, c3, d13), (a58, b4, c3, d14), (a58, b4, c3, d15), (a58, b4, c3, d16), (a58, b4, c3, d17), (a58, b4, c3, d18), (a58, b4, c3, d19), (a58, b4, c3, d20), (a58, b4, c3, d21), (a58, b4, c3, d22), (a58, b5, c1, d1), (a58, b5, c1, d2), (a58, b5, c1, d3), (a58, b5, c1, d4), (a58, b5, c1, d5), (a58, b5, c1, d6), (a58, b5, c1, d7), (a58, b5, c1, d8), (a58, b5, c1, d9), (a58, b5, c1, d10), (a58, b5, c1, d11), (a58, b5, c1, d12), (a58, b5, c1, d13), (a58, b5, c1, d14), (a58, b5, c1, d15), (a58, b5, c1, d16), (a58, b5, c1, d17), (a58, b5, c1, d18), (a58, b5, c1, d19), (a58, b5, c1, d20), (a58, b5, c1, d21), (a58, b5, c1, d22), (a58, b5, c2, d1), (a58, b5, c2, d2), (a58, b5, c2, d3), (a58, b5, c2, d4), (a58, b5, c2, d5), (a58, b5, c2, d6), (a58, b5, c2, d7), (a58, b5, c2, d8), (a58, b5, c2, d9), (a58, b5, c2, d10), (a58, b5, c2, d11), (a58, b5, c2, d12), (a58, b5, c2, d13), (a58, b5, c2, d14), (a58, b5, c2, d15), (a58, b5, c2, d16), (a58, b5, c2, d17), (a58, b5, c2, d18), (a58, b5, c2, d19), (a58, b5, c2, d20), (a58, b5, c2, d21), (a58, b5, c2, d22), (a58, b5, c3, d1), (a58, b5, c3, d2), (a58, b5, c3, d3), (a58, b5, c3, d4), (a58, b5, c3, d5), (a58, b5, c3, d6), (a58, b5, c3, d7), (a58, b5, c3, d8), (a58, b5, c3, d9), (a58, b5, c3, d10), (a58, b5, c3, d11), (a58, b5, c3, d12), (a58, b5, c3, d13), (a58, b5, c3, d14), (a58, b5, c3, d15), (a58, b5, c3, d16), (a58, b5, c3, d17), (a58, b5, c3, d18), (a58, b5, c3, d19), (a58, b5, c3, d20), (a58, b5, c3, d21), (a58, b5, c3, d22), (a58, b6, c1, d1), (a58, b6, c1, d2), (a58, b6, c1, d3), (a58, b6, c1, d4), (a58, b6, c1, d5), (a58, b6, c1, d6), (a58, b6, c1, d7), (a58, b6, c1, d8), (a58, b6, c1, d9), (a58, b6, c1, d10), (a58, b6, c1, d11), (a58, b6, c1, d12), (a58, b6, c1, d13), (a58, b6, c1, d14), (a58, b6, c1, d15), (a58, b6, c1, d16), (a58, b6, c1, d17), (a58, b6, c1, d18), (a58, b6, c1, d19), (a58, b6, c1, d20), (a58, b6, c1, d21), (a58, b6, c1, d22), (a58, b6, c2, d1), (a58, b6, C2, d2), (a58, b6, c2, d3), (a58, b6, c2, d4), (a58, b6, c2, d5), (a58, b6, c2, d6), (a58, b6, c2, d7), (a58, b6, c2, d8), (a58, b6, c2, d9), (a58, b6, c2, d10), (a58, b6, c2, d11), (a58, b6, c2, d12), (a58, b6, c2, d13), (a58, b6, c2, d14), (a58, b6, c2, d15), (a58, b6, c2, d16), (a58, b6, c2, d17), (a58, b6, c2, d18), (a58, b6, c2, d19), (a58, b6, c2, d20), (a58, b6, c2, d21), (a58, b6, c2, d22), (a58, b6, c3, d1), (a58, b6, c3, d2), (a58, be, c3, d3), (a58, b6, c3, d4), (a58, b6, c3, d5), (a58, b6, c3, d6), (a58, b6, c3, d7), (a58, b6, c3, d8), (a58, b6, c3, d9), (a58, b6, c3, d10), (a58, be, c3, d11), (a58, b6, c3, d12), (a58, b6, c3, d13), (a58, b6, c3, d14), (a58, b6, c3, d15), (a58, b6, c3, d16), (a58, b6, c3, d17), (a58, b6, c3, (d18), (a58, b6, c3, d19), (a58, b6, c3, d20), (a58, b6, c3, d21), (a58, b6, c3, d22), (a59, b1, c1, d1), (a59, b1, c1, d2), (a59, b1, c1, d3), (a59, b1, c1, d4), (a59, b1, c1, d5), (a59, b1, c1, d6), (a59, b1, c1, d7), (a59, b1, c1, d8), (a59, b1, c1, d9), (a59, b1, c1, d10), (a59, b1, c1, d11), (a59, b1, c1, d12), (a59, b1, c1, d13), (a59, b1, c1, d14), (a59, b1, c1, d15), (a59, b1, c1, d16), (a59, b1, c1, d17), (a59, b1, c1, d18), (a59, b1, c1, d19), (a59, b1, c1, d20), (a59, b1, c1, d21), (a59, b1, c1, d22), (a59, b1, c2, d1), (a59, b1, c2, d2), (a59, b1, c2, d3), (a59, b1, c2, d4), (a59, b1, c2, d5), (a59, b1, c2, d6), (a59, b1, c2, d7), (a59, b1, c2, d8), (a59, b1, c2, d9), (a59, b1, c2, d10), (a59, b1, c2, d11), (a59, b1, c2, d12), (a59, b1, c2, d13), (a59, b1, c2, d14), (a59, b1, c2, d15), (a59, b1, c2, die), (a59, b1, c2, d17), (a59, b1, c2, d18), (a59, b1, c2, d19), (a59, b1, c2, d20), (a59, b1, c2, d21), (a59, b1, c2, d22), (a59, b1, c3, d1), (a59, b1, c3, d2), (a59, b1, c3, d3), (a59, b1, c3, d4), (a59, b1, c3, d5), (a59, b1, c3, d6), (a59, b1, c3, d7), (a59, b1, c3, d8), (a59, b1, c3, d9), (a59, b1, c3, d10), (a59, b1, c3, d11), (a59, b1, c3, d12), (a59, b1, c3, d13), (a59, b1, c3, d14), (a59, b1, c3, d15), (a59, b1, c3, d16), (a59, b1, c3, d17), (a59, b1, c3, d18), (a59, b1, c3, d19), (a59, b1, c3, d20), (a59, b1, c3, d21), (a59, b1, c3, d22), (a59, b2, c1, d1), (a59, b2, c1, d2), (a59, b2, c1, d3), (a59, b2, c1, d4), (a59, b2, c1, d5), (a59, b2, c1, d6), (a59, b2, c1, d7), (a59, b2, c1, d8), (a59, b2, c1, d9), (a59, b2, c1, d10), (a59, b2, c1, d11), (a59, b2, c1, d12), (a59, b2, c1, d13), (a59, b2, c1, d14), (a59, b2, c1, d15), (a59, b2, c1, d16), (a59, b2, c1, d17), (a59, b2, c1, d18), (a59, b2, c1, d19), (a59, b2, c1, d20), (a59, b2, c1, d21), (a59, b2, c1, d22), (a59, b2, c2, d1), (a59, b2, c2, d2), (a59, b2, c2, d3), (a59, b2, c2, d4), (a59, b2, c2, d5), (a59, b2, c2, d6), (a59, b2, c2, d7), (a59, b2, c2, d8), (a59, b2, c2, d9), (a59, b2, c2, d10), (a59, b2, c2, d11), (a59, b2, c2, d12), (a59, b2, c2, d13), (a59, b2, c2, d14), (a59, b2, c2, d15), (a59, b2, c2, d16), (a59, b2, c2, d17), (a55, b2, c2, d18), (a59, b2, c2, d19), (a59, b2, c2, d20), (a59, b2, c2, d21), (a59, b2, c2, d22), (a59, b2, c3, d1), (a59, b2, c3, d2), (a59, b2, c3, d3), (a59, b2, c3, d4), (a59, b2, c3, d5), (a59, b2, c3, d6), (a59, b2, c3, d7), (a59, b2, c3, d8), (a59, b2, c3, d9), (a59, b2, c3, d10), (a59, b2, c3, d11), (a59, b2, c3, d12), (a59, b2, c3, d13), (a59, b2, c3, d14), (a59, b2, c3, d15), (a59, c2, c3, d16), (a59, b2, c3, d17), (a59, b2, c3, d18), (a59, b2, c3, d19), (a59, b2, c3, d20), (a59, b2, c3, d21), (a59, b2, c3, d22), (a59, b3, c1, d1), (a59, b3, c1, d2), (a59, b3, c1, d3), (a59, b3, c1, d4), (a59, b3, c1, d5), (a59, b3, c1, d6), (a59, b3, c1, d7), (a59, b3, c1, d8), (a59, b3, c1, d9), (a59, b3, c1, d10), (a59, b3, c1, d11), (a59, b3, c1, d12), (a59, b3, c1, d13), (a59, b3, c1, d14), (a59, b3, c1, d15), (a59, b3, c1, d16), (a59, b3, c1, d17), (a59, b3, c1, d18), (a59, b3, c1, d19), (a59, b3, c1, d20), (a59, b3, c1, d21), (a59, b3, c1, d22), (a59, b3, c2, d1), (a59, b3, c2, d2), (a59, b3, c2, d3), (a59, b3, c2, d4), (a59, b3, c2, d5), (a59, b3, c2, d6), (a59, b3, c2, d7), (a59, b3, c2, d8), (a59, b3, c2, d9), (a59, b3, c2, d10), (a59, b3, c2, d11), (a59, b3, c2, d12), (a59, b3, c2, d13), (a59, b3, c2, d14), (a59, b3, c2, d15), (a59, b3, c2, d16), (a59, b3, c2, d17), (a59, b3, c2, d18), (a59, b3, c2, d19), (a59, b3, c2, d20), (a59, b3, c2, d21), (a59, b3, c2, d22), (a59, b3, c3, d1), (a59, b3, c3, d2), (a59, b3, c3, d3), (a59, b3, c3, d4), (a59, b3, c3, d5), (a59, b3, c3, d6), (a59, b3, c3, d7), (a59, b3, c3, d8), (a59, b3, c3, d9), (a59, b3, c3, d10), (a59, b3, c3, d11), (a59, b3, c3, d12), (a59, b3, c3, d13), (a59, b3, c3, d14), (a59, b3, c3, d15), (a59, b3, c3, d16), (a59, b3, c3, d17), (a59, b3, c3, d18), (a59, b3, c3, d19), (a59, b3, c3, d20), (a59, b3, c3, d21), (a59, b3, c3, d22), (a59, b4, c1, d1), (a59, b4, c1, d2), (a59, b4, c1, d3), (a59, b4, c1, d4), (a59, b4, c1, d5), (a59, b4, c1, d6), (a59, b4, c1, d7), (a59, b4, c1, d8), (a59, b4, c1, d9), (a59, b4, c1, d10), (a59, b4, c1, d11), (a59, b4, c1, d12), (a59, b4, c1, d13), (a59, b4, c1, d14), (a59, b4, c1, d15), (a59, b4, c1, d16), (a59, b4, c1, d17), (a59, b4, c1, d18), (a59, b4, c1, d19), (a59, b4, c1, d20), (a59, b4, c1, d21), (a59, b4, c1, d22), (a59, b4, c2, d1), (a59, b4, c2, d2), (a59, b4, c2, d3), (a59, b4, c2, d4), (a59, b4, c2, d5), (a59, b4, c2, d6), (a59, b4, c2, d7), (a59, b4, c2, d8), (a59, b4, c2, d9), (a59, b4, c2, d10), (a59, b4, c2, d11), (a59, b4, c2, d12), (a59, b4, c2, d13), (a59, b4, c2, d14), (a59, b4, c2, d15), (a59, b4, c2, d16), (a59, b4, c2, d17), (a59, b4, c2, d18), (a59, b4, c2, d19), (a59, b4, c2, d20), (a59, b4, c2, d21), (a59, b4, c2, d22), (a59, b4, c3, d1), (a59, b4, c3, d2), (a59, b4, c3, d3), (a59, b4, c3, d4), (a59, b4, c3, d5), (a59, b4, c3, d6), (a59, b4, c3, d7), (a59, b4, c3, d8), (a59, b4, c3, d9), (a59, b4, c3, d10), (a59, b4, c3, d11), (a59, b4, c3, d12), (a59, b4, c3, d13), (a59, b4, c3, d14), (a59, b4, c3, d15), (a59, b4, c3, d16), (a59, b4, c3, d17), (a59, b4, c3, d18), (a59, b4, c3, d19), (a59, b4, c3, d20), (a59, b4, c3, d21), (a59, b4, c3, d22), (a59, b5, c1, d1), (a59, b5, c1, d2), (a59, b5, c1, d3), (a59, b5, c1, d4), (a59, b5, c1, d5), (a59, b5, c1, d6), (a59, b5, c1, d7), (a59, b5, c1, d8), (a59, b5, c1, d9), (a59, b5, c1, d10), (a59, b5, c1, d11), (a59, b5, c1, d12), (a59, b5, c1, d13), (a59, b5, c1, d14), (a59, b5, c1, d15), (a59, b5, c1, d16), (a59, b5, c1, d17), (a59, b5, c1, d18), (a59, b5, c1, d19), (a59, b5, c1, d20), (a59, b5, c1, d21), (a59, b5, c1, d22), (a59, b5, c2, d1), (a59, b5, c2, d2), (a59, b5, c2, d3), (a59, b5, c2, d4), (a59, b5, c2, d5), (a59, b5, c2, d16), (a59, b5, c2, d7), (a59, b5, c2, d18), (a59, b5, c2, d9), (a59, b5, c2, d10), (a59, b5, c2, d11), (a59, b5, c2, d12), (a59, b5, c2, d13), (a59, b5, c2, d14), (a59, b5, c2, d15), (a59, b5, c2, d16), (a59, b5, c2, d17), (a59, b5, c2, d18), (a59, b5, c2, d19), (a59, b5, c2, d20), (a59, b5, c2, d21), (a59, b5, c2, d22), (a59, b5, c3, d1), (a59, b5, c3, d2), (a59, b5, c3, d3), (a59, b5, c3, d4), (a59, b5, c3, d5), (a59, b5, c3, d6), (a59, b5, c3, d7), (a59, b5, c3, d8), (a59, b5, c3, d9), (a59, b5, c3, d10), (a59, b5, c3, d11), (a59, b5, c3, d12), (a59, b5, c3, d13), (a59, b5, c3, d14), (a59, b5, c3, d15), (a59, b5, c3, d16), (a59, b5, c3, d17), (a59, b5, c3, d18), (a59, b5, c3, d19), (a59, b5, c3, d20), (a59, b5, c3, d21), (a59, b5, c3, d22), (a59, b6, c1, d11), (a59, b6, c1, d2), (a59, b6, c1, d3), (a59, b6, c1, d4), (a59, b6, c1, d5), (a59, b6, c1, d6), (a59, b6, c1, d7), (a59, b6, c1, d8), (a59, b6, c1, d9), (a59, b6, c1, d10), (a59, b6, c1, d11), (a59, b6, c1, d12), (a59, b6, c1, d13), (a59, b6, c1, d14), (a59, b6, c1, d15), (a59, b6, c1, d16), (a59, b6, c1, d17), (a59, b6, c1, d18), (a59, b6, c1, d19), (a59, b6, c1, d20), (a59, b6, c1, d21), (a59, b6, c1, d22), (a59, b6, c2, d1), (a59, b6, c2, d2), (a59, b6, c2, d3), (a59, b6, c2, d4), (a59, b6, c2, d5), (a59, b6, c2, d6), (a59, b6, c2, d7), (a59, b6, c2, d8), (a59, b6, c2, d9), (a59, b6, c2, d10), (a59, b6, c2, d11), (a59, b6, c2, d12), (a59, b6, c2, d13), (a59, b6, c2, d14), (a59, b6, c2, d15), (a59, b6, c2, d16), (a59, b6, c2, d17), (a59, b6, c2, d18), (a55, b6, c2, d19), (a59, b6, c2, d20), (a59, b6, c2, d21), (a59, b6, c2, d22), (a59, b6, c3, d1), (a59, b6, c3, d2), (a59, b6, c3, d3), (a59, b6, c3, d4), (a59, b6, c3, d5), (a59, b6, c3, d6), (a59, b6, c3, d7), (a59, b6, c3, d6), (a59, b6, c3, d9), (a59, b6, c3, d10), (a59, b6, c3, d11), (a59, b6, c3, d12), (a59, b6, c3, d13), (a59, b6, c3, d14), (a59, b6, c3, d15), (a59, b6, c3, d16), (a59, b6, c3, d17), (a59, b6, c3, d18), (a59, b6, c3, d19), (a59, b6, c3, d20), (a59, b6, c3, d21), (a59, b6, c3, d22), (a60, b1, c1, d1), (a60, b1, c1, d2), (a60, b1, c1, d3), (a60, b1, c1, d4), (a60, b1, c1, d5), (a60, b1, c1, d6), (a60, b1, c1, d7), (a60, b1, c1, d8), (a60, b1, c1, d9), (a60, b1, c1, d10), (a60, b1, c1, d11), (a60, b1, c1, d12), (a60, b1, c1, d13), (a60, b1, c1, d14), (a60, b1, c1, d15), (a60, b1, c1, d16), (a60, b1, c1, d17), (a60, b1, c1, d18), (a60, b1, c1, d19), (a60, b1, c1, d20), (a60, b1, c1, d21), (a60, b1, c1, d22), (a60, b1, c2, d1), (a60, b1, c2, d2), (a60, b1, c2, d3), (a60, b1, c2, d4), (a60, b1, c2, d5), (a60, b1, c2, d6), (a60, b1, c2, d7), (a60, b1, c2, d8), (a60, b1, c2, d9), (a60, b1, c2, d10), (a60, b1, c2, d11), (a60, b1, c2, d12), (a60, b1, c2, d13), (a60, b1, c2, d14), (a60, b1, c2, d15), (a60, b1, c2, d16), (a60, b1, c2, d17), (a60, b1, c2, d18), (a60, b1, c2, d19), (a60, b1, c2, d20), (a60, b1, c2, d21), (a60, b1, c2, d22), (a60, b1, c3, d1), (a60, b1, c3, d2), (a60, b1, c3, d3), (a60, b1, c3, d4), (a60, b1, c3, d5), (a60, b1, c3, d6), (a60, b1, c3, d7), (a60, b1, c3, d8), (a60, b1, c3, d9), (a60, b1, c3, d10), (a60, b1, c3, d11), (a60, b1, c3, d12), (a60, b1, c3, d13), (a60, b1, c3, d14), (a60, b1, c3, d15), (a60, b1, c3, d16), (a60, b1, c3, d17), (a60, b1, c3, d18), (a60, b1, c3, d19), (a60, b1, c3, d20), (a60, b1, c3, d21), (a60, b1, c3, d22), (a60, b2, c1, d1), (a60, b2, c1, d2), (a60, b2, c1, d3), (a60, b2, c1, d4), (a60, b2, c1, d5), (a60, b2, c1, d6), (a60, b2, c1, d7), (a60, b2, c1, d8), (a60, b2, c1, d9), (a60, b2, c1, d10), (a60, b2, c1, d11), (a60, b2, c1, d12), (a60, b2, c1, d13), (a60, b2, c1, d14), (a60, b2, c1, d15), (a60, b2, c1, d16), (a60, b2, c1, d17), (a60, b2, c1, a18), (a60, b2, c1, d19), (a60, b2, c1, d20), (a60, b2, c1, d21), (a60, b2, c1, d22), (a60, b2, c2, d1), (a60, b2, c2, d2), (a60, b2, c2, d3), (a60, b2, c2, d4), (a60, b2, c2, d5), (a60, b2, c2, d6), (a60, b2, c2, d7), (a60, b2, c2, d5), (a60, b2, c2, d9), (a60, b2, c2, d10), (a60, b2, c2, d11), (a60, b2, c2, d12), (a60, b2, c2, d13), (a60, b2, c2, d14), (a60, b2, c2, d15), (a60, b2, c2, d16), (a60, b2, c2, d17), (a60, b2, c2, d18), (a60, b2, c2, d19), (a60, b2, c2, d20), (a60, b2, c2, d21), (a60, b2, c2, d22), (a60, b2, c3, d1), (a60, b2, c3, d2), (a60, b2, c3, d3), (a60, b2, c3, d4), (a60, b2, c3, d5), (a60, b2, c3, d6), (a60, b2, c3, d7), (a60, b2, c3, d8), (a60, b2, c3, d9), (a60, b2, c3, d10), (a60, b2, c3, d11), (a60, b2, c3, d12), (a60, b2, c3, d13), (a60, b2, c3, d14), (a60, b2, c3, d15), (a60, b2, c3, d16), (a60, b2, c3, d17), (a60, b2, c3, d18), (a60, b2, c3, d19), (a60, b2, c3, d20), (a60, b2, c3, d21), (a60, b2, c3, d22), (a60, b3, c1, d1), (a60, b3, c1, d2), (a60, b3, c1, d3), (a60, b5, c1, d4), (a60, b5, c1, d5), (a60, b3, c1, d6), (a60, b3, c1, d7), (a60, b3, c1, d8), (a60, b3, c1, d9), (a60, b3, c1, d10), (a60, b3, c1, d11), (a60, b3, c1, d12), (a60, b3, c1, d13), (a60, b3, c1, d14), (a60, b3, c1, d15), (a60, b3, c1, d16), (a60, b3, c1, d17), (a60, b5, c1, d18), (a60, b3, c1, d19), (a60, b3, c1, d20), (a60, b3, c1, d21), (a60, b3, c1, d22), (a60, b3, c2, d1), (a60, b3, c2, d2), (a60, b3, c2, d3), (a60, b3, c2, d4), (a60, b3, c2, d5), (a60, b3, c2, d6), (a60, b3, c2, d7), (a60, b3, c2, d8), (a60, b3, c2, d9), (a60, b3, c2, d10), (a60, b3, c2, d11), (a60, b3, c2, d12), (a60, b3, c2, d13), (a60, b3, c2, d14), (a60, b3, c2, d15), (a60, b5, c2, d16), (a60, b3, c2, d17), (a60, b3, c2, d18), (a60, b3, c2, d19), (a60, b3, c2, d20), (a60, b3, c2, d21), (a60, b3, c2, d22), (a60, b3, c3, d1), (a60, b3, c3, d2), (a60, b3, c3, d3) (a60, b3, c3, d4), (a60, b3, c3, d5), (a60, b3, c3, d6), (a60, b3, c3, d7), (a60, b3, c3, d8), (a60, b3, c3, d9), (a60, b3, c3, d10), (a60, b3, c3, d11), (a60, b3, c3, d12), (a60, b3, c3, d13), (a60, b3, c3, d14), (a60, b3, c3, d15), (a60, b3, c3, d16), (a60, b3, c3, d17), (a60, b3, c3, d18), (a60, b3, c3, d19), (a60, b3, c3, d20), (a60, b3, c3, d21), (a60, b3, c3, d22), (a60, b4, c1, d1), (a60, b4, c1, d2), (a60, b4, c1, d3), (a60, b4, c1, d4), (a60, b4, c1, d5), (a60, b4, c1, d6), (a60, b4, c1, d7), (a60, b4, c1, d5), (a60, b4, c1, d9), (a60, b4, c1, d10), (a60, b4, c1, d11), (a60, b4, c1, d12), (a60, b4, c1, d13), (a60, b4, c1, d14), (a60, b4, c1, d15), (a60, b4, c1, d16), (a60, b4, c1, d17), (a60, b4, c1, d18), (a60, b4, c1, d19), (a60, b4, c1, d20), (a60, b4, c1, d21), (a60, b4, c2, d22), (a60, b4, c2, d1), (a60, b4, c2, d2), (a60, b4, c2, d3), (a60, b4, c2, d4), (a60, b4, c2, d5), (a60, b4, c2, d6), (a60, b4, c2, d7), (a60, b4, c2, d8), (a60, b4, c2, d9), (a60, b4, c2, d10), (a60, b4, c2, d11), (a60, b4, c2, d12), (a60, b4, c2, d13), (a60, b4, c2, d14), (a60, b4, c2, d15), (a60, b4, c2, d16), (a60, b4, c2, d17), (a60, b4, c2, d18), (a60, b4, c2, d19), (a60, b4, c2, d20), (a60, b4, c2, d21), (a60, b4, c2, d22), (a60, b4, c3, d1), (a60, b4, c3, d2), (a60, b4, c3, d3), (a60, b4, c3, d4), (a60, b4, c3, d5), (a60, b4, c3, d6), (a60, b4, c3, d7), (a60, b4, c3, d8), (a60, b4, c3, d9), (a60, b4, c3, d10), (a60, b4, c3, d11), (a60, b4, c3, d12), (a60, b4, c3, d13), (a60, b4, c3, d14), (a60, b4, c3, d15), (a60, b4, c3, d16), (a60, b4, c3, d17), (a60, b4, c3, d18), (a60, b4, c3, d19), (a60, b4, c3, d20), (a60, b4, c3, d21), (a60, b4, c3, d22), (a60, b5, c1, d1), (a60, b5, c1, d2), (a60, b5, c1, d3), (a60, b5, c1, d4), (a60, b5, c1, d5), (a60, b5, c1, d6), (a60, b5, c1, d7), (a60, b5, c1, d8), (a60, b5, c1, d9), (a60, b5, c1, d10), (a60, b5, c1, d11), (a60, b5, c1, d12), (a60, b5, c1, d13), (a60, b5, c1, d14), (a60, b5, c1, d15), (a60, b5, c1, d16), (a60, b5, c1, d17), (a60, b5, c1, d18), (a60, b5, c1, d19), (a60, b5, c1, d20), (a60, b5, c1, d21), (a60, b5, c1, d22), (a60, b5, c2, d1), (a60, b5, c2, d2), (a60, b5, c2, d3), (a60, b5, c2, d4), (a60, b5, c2, d5), (a60, b5, c2, d6), (a60, b5, c2, d7), (a60, b5, c2, d8), (a60, b5, c2, d9), (a60, b5, c2, d10), (a60, b5, c2, d11), (a60, b5, c2, d12), (a60, b5, c2, d13), (a60, b5, c2, d14), (a60, b5, c2, d15), (a60, b5, c2, d16), (a60, b5, c2, d17), (a60, b5, c2, d18), (a60, b5, c2, d19), (a60, b5, c2, d20), (a60, b5, c2, d21), (a60, b5, c2, d22), (a60, b5, c3, d1), (a60, b5, c3, d2), (a60, b5, c3, d3), (a60, b5, c3, d4), (a60, b5, c3, d5), (a60, b5, c3, d6), (a60, b5, c3, d7), (a60, b5, c3, d8), (a60, b5, c3, d9), (a60, b5, c3, d10), (a60, b5, c3, d11), (a60, b5, c3, d12), (a60, b5, c3, d13), (a60, b5, c3, d14), (a60, b5, c3, d15), (a60, b5, c3, d16), (a60, b5, c3, d17), (a60, b5, c3, d18), (a60, b5, c3, d19), (a60, b5, c3, d20), (a60, b5, c3, d21), (a60, b5, c3, d22), (a60, b6, c1, d1), (a60, b6, c1, d2), (a60, b6, c1, d3), (a60, b6, c1, d4), (a60, b6, c1, d5), (a60, b6, c1, d6), (a60, b6, c1, d7), (a60, b6, c1, d8), (a60, b6, c1, d9), (a60, b6, c1, d10), (a60, b6, c1, d11), (a60, b6, c1, d12), (a60, b6, c1, d13), (a60, b6, c1, d14), (a60, b6, c1, d15), (a60, b6, c1, d16), (a60, b6, c1, d17), (a60, b6, c1, d18), (a60, b6, c1, d19), (a60, b6, c1, d20), (a60, b6, (c1, d21), (a60, b6, c1, d22), (a60, b6, c2, d1), (a60, b6, c2, d2), (a60, b6, c2, d13), (a60, b6, c2, d4), (a60, b6, c2, d5), (a60, b6, c2, d6), (a60, b6, c2, d7), (a60, b6, c2, d8), (a60, b6, c2, d9), (a60, b6, c2, d10), (a60, b6, c2, d11), (a60, b6, c2, d12), (a60, b6, c2, d13), (a60, b6, c2, d14), (a60, b6, c2, d15), (a60, b6, c2, d16), (a60, b6, c2, d17), (a60, b6, c2, d18), (a60, b6, c2, d19), (a60, b6, c2, d20), (a60, b6, c2, d21), (a60, b6, c2, d22), (a60, b6, c3, d1), (a60, b6, c3, d2), (a60, b6, c3, d3), (a60, b6, c3, d4), (a60, b6, c3, d5), (a60, b6, c3, d6), (a60, b6, c3, d7), (a60, b6, c3, d3), (a60, b6, c3, d9), (a60, b6, c3, d10), (a60, b6, c3, d11), (a60, b6, c3, d12), (a60, b6, c3, d13), (a60, b6, c3, d14), (a60, b6, c3, d15), (a60, b6, c3, d16), (a60, b6, c3, d17), (a60, b6, c3, d18), (a60, b6, c3, d19), (a60, b6, c3, d20), (a60, b6, c3, d21), (a60, b6, c3, d22), (a61, b1, c1, d1), (a61, b1, c1, d2), (a61, b1, c1, d3), (a61, b1, c1, d4), (a61, b1, c1, d5), (a61, b1, c1, d6), (a61, b1, c1, d7), (a61, b1, c1, d8), (a61, b1, c1, d9), (a61, b1, c1, d10), (a61, b1, c1, d11), (a61, b1, c1, d12), (a61, b1, c1, d13), (a61, b1, c1, d14), (a61, b1, c1, d15), (a61, b1, c1, d16), (a61, b1, c1, d17), (a61, b1, c1, d18), (a61, b1, c1, d19), (a61, b1, c1, d20), (a61, b1, c1, d21), (a61, b1, c1, d22), (a61, b1, c2, d1), (a61, b1, c2, d2), (a61, b1, c2, d3), (a61, b1, c2, d4), (a61, b1, c2, d5), (a61, b1, c2, d6), (a61, b1, c2, d7), (a61, b1, c2, d8), (a61, b1, c2, d9), (a61, b1, c2, d10), (a61, b1, c2, d11), (a61, b1, c2, d12), (a61, b1, c2, d13), (a61, b1, c2, d14), (a61, b1, c2, d15), (a61, b1, c2, d16), (a61, b1, c2, d17), (a61, b1, c2, d18), (a61, b1, c2, d19), (a61, b1, c2, d20), (a61, b1, c2, d21), (a61, b1, c2, d22), (a61, b1, c3, d1), (a61, b1, c3, d2), (a61, b1, c3, d3), (a61, b1, c3, d4), (a61, b1, c3, d5), (a61, b1, c3, d6), (a61, b1, c3, d7), (a61, b1, c3, d8), (a61, b1, c3, d9), (a61, b1, c3, d10), (a61, b1, c3, d11), (a61, b1, c3, d12), (a61, b1, c3, d13), (a61, b1, c3, d14), (a61, b1, c3, d15), (a61, b1, c3, d16), (a61, b3, c3, d17), (a61, b1, c3, d18), (a61, b1, c3, d19), (a61, b1, c3, d20), (a61, b1, c3, d21), (a61, b1, c3, d22), (a61, b2, c1, d1), (a61, b2, c1, d2), (a61, b2, c1, d3), (a61, b2, c1, d4), (a61, b2, c1, d5), (a61, b2, c1, d6), (a61, b2, c1, d7), (a61, b2, c1, d8), (a61, b2, c1, d9), (a61, b2, c1, d10), (a61, b2, c1, d11), (a61, b2, c1, d12), (a61, b2, c1, d13), (a61, b2, c1, d14), (a61, b2, c1, d15), (a61, b2, c1, d16), (a61, b2, c1, d17), (a61, b2, c1, d18), (a61, b2, c1, d19), (a61, b2, c1, d20), (a61, b2, c1, d21), (a61, b2, c1, d22), (a61, b2, c2, d1), (a61, b2, c2, d2), (a61, b2, c2, d3), (a61, b2, c2, d4), (a61, b2, c2, d5), (a61, b2, c2, d6), (a61, b2, c2, d7), (a61, b2, c2, d8), (a61, b2, c2, d9), (a61, b2, c2, d10), (a61, b2, c2, d11), (a61, b2, c2, d12), (a61, b2, c2, d13), (a61, b2, c2, d14), (a61, b2, c2, d15), (a61, b2, c2, d16), (a61, b2, c2, d17), (a61, b2, c2, d18), (a61, b2, c2, d19), (a61, b2, c2, d20), (a61, b2, c2, d21), (a61, b2, c2, d22), (a61, b2, c3, d1), (a61, b2, c3, d2), (a61, b2, c3, d3), (a61, b2, c3, d4), (a61, b2, c3, d5), (a61, b2, c3, d6), (a61, b2, c3, d7), (a61, b2, c3, d8), (a61, b2, c3, d9), (a61, b2, c3, d10), (a61, b2, c3, d11), (a61, b2, c3, d12), (a6, b2, c3, d13), (a61, b2, c3, d14), (a61, b2, c3, d15), (a61, b2, c3, d16), (a61, b2, c3, d17), (a61, b2, c3, d18), (a61, b2, c3, d19), (a61, b2, c3, d20), (a61, b2, c3, d21), (a61, b2, c3, d22), (a61, b3, c1, d1), (a61, b3, c1, d2), (a61, b3, c1, d3), (a61, b3, c1, d4), (a61, b3, c1, d5), (a61, b3, c1, d6), (a61, b3, c1, d7), (a61, b3, c1, d8), (a61, b3, c1, d9), (a61, b3, c1, d10), (a61, b3, c1, d11), (a61, b3, c1, d12), (a61, b3, c1, d13), (a61, b3, c1, d14), (a61, b3, c1, d15), (a61, b3, c1, d16), (a61, b3, c1, d17), (a61, b3, c1, d18), (a61, b3, c1, d19), (a61, b3, c1, d20), (a61, b3, c1, d21), (a61, b3, c1, d22), (a61, b3, c2, d1), (a61, b3, c2, d2), (a61, b3, c2, d3), (a61, b3, c2, d4), (a61, b3, c2, d5), (a61, b3, c2, d6), (a61, b3, c2, d7), (a61, b3, c2, d8), (a61, b3, c2, d9), (a61, b3, c2, d10), (a61, b3, c2, d11), (a61, b3, c2, d12), (a61, b3, c2, d13), (a61, b3, c2, d14), (a61, b3, c2, d15), (a61, b3, c2, d16), (a61, b3, c2, d17), (a61, b3, c2, d18), (a61, b3, c2, d19), (a61, b3, c2, d20), (a61, b3, c2, d21), (a61, b3, c2, d22), (a61, b3, c3, d1), (a61, b3, c3, d2), (a61, b3, c3, d3), (a61, b3, c3, d4), (a61, b3, c3, d5), (a61, b3, c3, d6), (a61, b3, c3, d7), (a61, b3, c3, d8), (a61, b3, c3, d9), (a61, b3, c3, d10), (a61, b3, c3, d11), (a61, b3, c3, d12), (a61, b3, c3, d13), (a61, b3, c3, d14), (a61, b3, c3, d15), (a61, b3, c3, d16), (a61, b3, c3, d17), (a61, b3, c3, d18), (a61, b3, c3, d19), (a61, b3, c3, d20), (a61, b3, c3, d21), (a61, b3, c1, d22), (a61, b4, c1, d1), (a61, b4, c1, d2), (a6, b4, c1, d3), (a36, b4, c1, d4), (a61, b4, c1, d5), (a61, b4, c1, d6), (a61, b4, c1, d7), (a61, b4, c1, d8), (a61, b4, c1, d9), (a61, b4, c1, d10), (a61, b4, c1, d11), (a61, b4, c1, d12), (a61, b4, c1, d13), (a61, b4, c1, d14), (a14, b4, c1, d15), (a61, b4, c1, d16), (a6, b4, c1, d17), (a6, b4, c1, d18), (a61, b4, c1, d19), (a61, b4, c1, d20), (a61, b4, c1, d21), (a61, b4, c1, d22), (a61, b4, c2, d1), (a61, b4, c2, d2), (a61, b4, c2, d3), (a61, b4, c2, d4), (a61, b4, c2, d5), (a1, b4, c2, d6), (a61, b4, c2, d7), (a61, b4, c2, d8), (a61, b4, c2, d9), (a61, b4, c2, d10), (a61, b4, c2, d11), (a61, b4, c2, d12), (a11, b4, c2, d13), (a61, b4, c2, d14), (a61, b4, c2, d15), (a61, b4, c2, d16), (a61, b4, c2, d17), (a1, b4, c2, d18), (a61, b4, c2, d19), (a61, b4, c2, d20), (a61, b4, c2, d21), (a61, b4, c2, d22), (a61, b4, c3, d1), (a61, b4, c3, d2), (a61, b4, c3, d3), (a61, b4, c3, d4), (a61, b4, c3, d5), (a61, b4, c3, d6), (a61, b4, c3, d7), (a61, b4, c3, d8), (a61, b4, c3, d9), (a61, b4, c3, d10), (a61, b4, c3, d11), (a61, b4, c3, d12), (a61, b4, c3, d13), (a61, b4, c3, d14), (a61, b4, c3, d15), (a61, b4, c3, d16), (a61, b4, c3, d17), (a61, b4, c3, d18), (a61, b4, c3, d19), (a61, b4, c3, d20), (a61, b4, c3, d21), (a61, b4, c3, d22), (a61, b5, c1, d1), (a61, b5, c1, d2), (a61, b5, c1, d3), (a61, b5, c1, d4), (a61, b5, c1, d5), (a61, b5, c1, d6), (a61, b5, c1, d7), (a61, b5, c1, d8), (a61, b5, c1, d9), (a61, b5, c1, d10), (a61, b5, c1, d11), (a61, b5, c1, d12), (a61, b5, c1, d13), (a61, b5, c1, d14), (a61, b5, c1, d15), (a61, b5, c1, d16), (a61, b5, c1, d17), (a61, b5, c1, d18), (a61, b5, c1, d19), (a61, b5, c1, d20), (a61, b5, c1, d21), (a61, b5, c1, d22), (a61, b5, c2, d1), (a61, b5, c2, d2), (a61, b5, c2, d3), (a61, b5, c2, d4), (a61, b5, c2, d5), (a61, b5, c2, d6), (a61, b5, c2, d7), (a61, b5, c2, d8), (a61, b5, c2, d9), (a61, b5, c2, d10), (a61, b5, c2, d11), (a61, b5, c2, d12), (a61, b5, c2, d13), (a61, b5, c2, d14), (a61, b5, c2, d15), (a61, b5, c2, d16), (a61, b5, c2, d17), (a61, b5, c2, d18), (a61, b5, c2, d19), (a61, b5, c2, d20), (a61, b, c2, d21), (a61, b5, c2, d22), (a61, b5, c3, d1), (a61, b5, c3, d2), (a61, b5, c3, d3), (a61, b5, c3, d4), (a61, b5, c3, d5), (a61, b5, c3, d6), (a61, b5, c3, d7), (a61, b5, c3, d8), (a61, b5, c3, d9), (a61, b5, c3, d10), (a61, b5, c3, d11), (a61, b5, c3, d12), (a61, b5, c3, d13), (a61, b5, c3, d14), (a61, b5, c3, d15), (a61, b5, c3, d16), (a61, b5, c3, d17), (a61, b5, c3, d18), (a61, b5, c3, d19), (a61, b5, c3, d20), (a61, b5, c3, d21), (a61, b5, c3, d22), (a61, b6, c1, d1), (a61, b6, c1, d2), (a61, b6, c1, d3), (a61, b6, c1, d4), (a61, b6, c1, d5), (a61, b6, c1, d6), (a61, b6, c1, d7), (a61, b6, c1, d8), (a61, b6, c1, d9), (a61, b6, c1, d10), (a61, b6, c1, d11), (a61, b6, c1, d12), (a61, b6, c1, d13), (a61, b6, c1, d14), (a61, b6, c1, d15), (a61, b6, c1, d16), (a61, b6, c1, d17), (a61, b6, c1, d18), (a61, b6, c1, d19), (a61, b6, c1, d20), (a61, b6, c1, d21), (a61, b6, c1, d22), (a61, b6, c2, d1), (a61, b6, c2, d2), (a61, b6, c2, d3), (a61, b6, c2, d4), (a61, b6, c2, d5), (a61, b6, c2, d6), (a61, b6, c2, d7), (a61, b6, c2, d8), (a61, b6, c2, d9), (a61, b6, c2, d10), (a61, b6, c2, d11), (a61, b6, c2, d12), (a61, b6, c2, d13), (a61, b6, c2, d14), (a61, b6, b2, d15), (a61, b6, c2, d16), (a61, b6, c2, d17), (a61, b6, c2, d18), (a61, b6, c2, d19), (a61, b6, c2, d20), (a61, b6, c2, d21), (a61, b6, c2, d22), (a61, b6, c3, d1), (a61, b6, c3, d2), (a61, b6, c3, d3), (a61, b6, c3, d4), (a61, b6, c3, d5), (a61, b6, c3, d6), (a61, b6, c3, d7), (a61, c3, d8), (a61, b6, c3, d9), (a61, b6, c3, d10), (a61, b6, c3, d11), (a61, b6, c3, d12), (a61, b6, c3, d13), (a61, b6, c3, d14), (a61, b6, c3, d15), (a61, b6, c3, d16), (a61, b6, c3, d17), (a61, b6, c3, d18), (a61, b6, c3, d19), (a61, b6, c3, d20), (a61, b6, c3, d21), (a61, b6, c3, d22), (a62, b1, c1, d1), (a62, b1, c1, d2), (a62, b1, c1, d3), (a62, b1, c1, d4), (a62, b1, c1, d5), (a62, b1, c1, d6), (a62, b1, c1, d7), (a62, b1, c1, d8), (a62, b1, c1, d9), (a62, b1, c1, d10), (a62, b1, c1, d11), (a62, b1, c1, d12), (a62, b1, c1, d13), (a62, b1, c1, d14), (a62, b1, c1, d15), (a62, b1, c1, d16), (a62, b1, c1, d17), (a62, b1, c1, d18), (a62, b1, c1, d19), (a62, b1, c1, d20), (a62, b1, c1, d21), (a62, b1, c1, d22), (a62, b1, c2, d1), (a62, b1, c2, d2), (a62, b1, c2, d3), (a62, b1, c2, d4), (a62, b1, c2, d5), (a62, b1, c2, d6), (a62, b1, c2, d7), (a62, b1, c2, d8), (a62, b1, c2, d9), (a62, b1, c2, d10), (a62, b1, c2, d11), (a62, b1, c2, d12), (a62, b1, c2, d13), (a62, b1, c2, d14), (a62, b1, c2, d15), (a62, b1, c2, d16), (a62, b1, c2, d17), (a62, b1, c2, d18), (a62, b1, c2, d19), (a62, b1, c2, d20), (a62, b1, c2, d21), (a62, b1, c2, d22), (a62, b1, c3, d1), (a62, b1, c3, d2), (a62, b1, c3, d3), (a62, b1, c3, d4), (a62, b1, c3, d5), (a62, b1, c3, d6), (a62, b1, c3, d7), (a62, b1, c3, d8), (a62, b1, c3, d9), (a62, b1, c3, d10), (a62, b1, c3, d11), (a62, b1, c3, d12), (a62, b1, c3, d13), (a62, b1, c3, d14), (a62, b1, c3, d15), (a62, b1, c3, d16), (a62, b1, c3, d17), (a62, b1, c3, d13), (a62, b1, c3, d19), (a62, b1, c3, d20), (a62, b1, c3, d21), (a62, b1, c3, d22), (a62, b2, c1, d1), (a62, b2, c1, d2), (a62, b2, c1, d3), (a62, b2, c1, d6), (a62, b2, c1, d5), (a62, b2, c1, d6), (a62, b2, c1, d7), (a62, b2, c1, d8), (a62, b2, c1, d9), (a62, b2, c1, d10), (a62, b2, c1, d11), (a62, b2, c1, d12), (a62, b2, c1, d13), (a62, b2, c1, d14), (a62, b2, c1, d15), (a62, b2, c1, d16), (a62, b2, c1, d17), (a62, b2, c1, d18), (a62, b2, c1, d19), (a62, b2, c1, d20), (a62, b2, c1, d21), (a62, b2, c1, d22), (a62, b2, c2, d1), (a62, b2, c2, d2), (a62, b2, c2, d3), (a62, b2, c2, d4), (a62, b2, c2, d5), (a62, b2, c2, d6), (a62, b2, c2, d7), (a62, b2, c2, d8), (a62, b2, c2, d9), (a62, b2, c2, d10), (a62, b2, c2, d11), (a62, b2, c2, d12), (a62, b2, c2, d13), (a62, b2, c2, d14), (a62, b2, c2, d15), (a62, b2, c2, d16), (a62, b2, c2, d17), (a62, b2, c2, d18), (a62, b2, c2, d19), (a62, b2, c2, d20), (a62, b2, c2, d21), (a62, b2, c2, d22), (a62, b2, c3, d1), (a62, b2, c3, d2), (a62, b2, c3, d3), (a62, b2, c3, d4), (a62, b2, c3, d5), (a62, b2, c3, d6), (a62, b2, c3, d7), (a62, b2, c3, d8), (a62, b2, c3, d9), (a62, b2, c3, d10), (a62, b2, c3, d11), (a62, b2, c3, d12), (a62, b2, c3, d13), (a62, b2, c3, d14), (a62, b2, c3, d15), (a62, b2, c3, d16), (a62, b2, c3, d17), (a62, b2, c3, d18), (a62, b2, c3, d19), (a62, b2, c3, d20), (a62, b2, c3, d21), (a62, b2, c3, d22), (a62, b3, c1, d1), (a62, b3, c1, d2), (a62, b3, c1, d3), (a62, b3, c1, d4), (a62, b3, c1, d5), (a62, b3, c1, d6), (a62, b3, c1, d7), (a62, b3, c1, d8), (a62, b3, c1, d9), (a62, b3, c1, d10), (a62, b3, c1, d11), (a62, b3, c1, d12), (a62, b3, c1, d13), (a62, b3, c1, d14), (a62, b3, c1, d15), (a62, b3, c1, d16), (a62, b3, c1, d17), (a62, b3, c1, d18), (a62, b3, c1, d19), (a62, b3, c1, d20), (a62, b3, c1, d21), (a62, b3, c1, d22), (a62, b3, c2, d1), (a62, b3, c2, d2), (a62, b3, c2, d3), (a62, b3, c2, d4), (a62, b3, c2, d5), (a62, b3, c2, d6), (a62, b3, c2, d7), (a62, b3, c2, d8), (a62, b3, c2, d9), (a62, b3, c2, d19), (a62, b3, c2, d11), (a62, b3, c2, d12), (a62, b3, c2, d13), (a62, b5, c2, d14), (a62, b3, c2, d15), (a62, b3, c2, d16), (a62, b3, c2, d17), (a62, b3, c2, d18), (a62, b3, c2, d19), (a62, b3, c2, d20), (a62, b3, c2, d21), (a62, b3, c2, d22), (a62, b3, c3, d1), (a62, b3, c3, d2), (a62, b3, c3, d3), (a62, b3, c3, d4), (a62, b3, c3, d5), (a62, b3, c3, d6), (a62, b3, c3, d7), (a62, b3, c3, d6), (a62, b3, c3, d9), (a62, b3, c3, d10), (a62, b3, c3, d11), (a62, b3, c3, d12), (a62, b3, c3, d13), (a62, b3, c3, d14), (a62, b3, c3, d15), (a62, b3, c3, d16), (a62, b3, c3, d17), (a62, b3, c3, d18), (a62, b3, c3, d19), (a62, b3, c3, d20), (a62, b3, c3, d21), (a62, b3, c3, d22), (a62, b4, c1, d1), (a62, b4, c1, d2), (a62, b4, c1, d3), (a62, b4, c1, d4), (a62, b4, c1, d5), (a62, b4, c1, d6), (a62, b4, c1, d7), (a62, b4, c1, d8), (a62, b4, c1, d9), (a62, b4, c1, d10), (a62, b4, c1, d11), (a62, b4, c1, d12), (a62, b4, c1, d13), (a62, b4, c1, d14), (a62, b4, c1, d15), (a62, b4, c1, d16), (a62, b4, c1, d17), (a62, b4, c1, d18), (a62, b4, c1, d19), (a62, b4, c1, d20), (a62, b4, c1, d21), (a62, b4, c1, d22), (a62, b4, c2, d1), (a62, b4, c2, d2), (a62, b4, c2, d13), (a62, b4, c2, d4), (a62, b4, c2, d5), (a62, b4, c2, d6), (a62, b4, c2, d7), (a62, b4, c2, d8), (a62, b4, c2, d9), (a62, b4, c2, d10), (a62, b4, c2, d11), (a62, b4, c2, d12), (a62, b4, c2, d13), (a62, b4, c2, d14), (a62, b4, c2, d15), (a62, b4, c2, d16), (a62, b4, c2, d17), (a62, b4, c2, d18), (a62, b4, c2, d19), (a62, b4, c2, d20), (a62, b4, c2, d21), (a62, b4, c2, d22), (a62, b4, c3, d1), (a62, b4, c3, d2), (a62, b4, c3, d3), (a62, b4, c3, d4), (a62, b4, c3, d5), (a62, b4, c3, d6), (a62, b4, c3, d7), (a62, b4, c3, d8), (a62, b4, c3, d9), (a62, b4, c3, d10), (a62, b4, c3, d11), (a62, b4, c3, d12), (a62, b4, c3, d13), (a62, b4, c3, d14), (a62, b4, c3, d15), (a62, b4, c3, d16), (a62, b4, c3, d17), (a62, b4, c3, d18), (a62, b4, c3, d19), (a62, b4, c3, d20), (a62, b4, c3, d21), (a62, b4, c3, d22), (a62, b5, c1, d1), (a62, b5, c1, d2), (a62, b5, c1, d3), (a62, b5, c1, d4), (a62, b5, c1, d5), (a62, b5, c1, d6), (a62, b5, c1, d7), (a62, b5, c1, d8), (a62, b5, c1, d9), (a62, b5, c1, d10), (a62, b5, c1, d11), (a62, b5, c1, d12), (a62, b5, c1, d13), (a62, b5, c1, d14), (a62, b5, c1, d15), (a62, b5, c1, d16), (a62, b5, c1, d17), (a62, b5, c1, d18), (a62, b5, c1, d19), (a62, b5, c1, d20), (a62, b5, c1, d21), (a62, b5, c1, d22), (a62, b5, c2, d1), (a62, b5, c2, d2), (a62, b5, c2, d3), (a62, b5, c2, d4), (a62, b5, c2, d5), (a62, b5, c2, d6), (a62, b5, c2, d7), (a62, b5, c2, d8), (a62, b5, c2, d9), (a62, b5, c2, d10), (a62, b5, c2, d11), (a62, b5, c2, d12), (a62, b5, c2, d13), (a62, b5, c2, d14), (a62, b5, c2, d15), (a62, b5, c2, d16), (a62, b5, c2, d17), (a62, b5, c2, d18), (a62, b5, c2, d19), (a62, b5, c2, d20), (a62, b5, c2, d21), (a62, b5, c2, d22), (a62, b5, c3, d1), (a62, b5, c3, d2), (a62, b5, c3, d13), (a62, b5, c3, d4), (a62, b5, c3, d5), (a62, b5, c3, d6), (a62, b5, c3, d7), (a62, b5, c3, d8), (a62, b5, c3, d9), (a62, b5, c3, d10), (a62, b5, c3, d11), (a62, b5, c3, d12), (a62, b5, c3, d13), (a62, b5, c3, d14), (a62, b5, c3, d15), (a62, b5, c3, d16), (a62, b5, c3, d17), (a62, b5, c3, d18), (a62, b5, c3, d19), (a62, b5, c3, d20), (a62, b5, c3, d21), (a62, b5, c3, d22), (a62, b3, c1, d1), (a62, b6, c1, d2), (a62, b6, c1, d3), (a62, b6, c1, d4), (a62, b6, c1, d5), (a62, b6, c1, d6), (a62, b6, c1, d7), (a62, b6, c1, d8), (a62, b6, c1, d9), (a62, b6, c1, d19), (a62, b6, c1, d11), (a62, b6, c1, d12), (a62, b6, c1, d13), (a62, b6, c1, d14), (a62, b6, c1, d15), (a62, b6, c1, d16), (a62, bb, c1, d17), (a62, b6, c1, d18), (a62, b6, c1, d19), (a62, b6, c1, d20), (a62, b6, c1, d21), (a62, b6, c1, d22), (a62, b6, c2, d1), (a62, b6, c2, d2), (a62, b3, c2, d3), (a62, bb, c2, d4), (a62, b6, c2, d5), (a62, b6, c2, d6), (a62, b6, c2, d7), (a62, b6, c2, d8), (a62, b6, c2, d9), (a62, b6, c2, d10), (a62, b6, c2, d11), (a62, b6, c2, d12), (a62, b6, c2, d13), (a62, b6, c2, d14), (a62, b6, c2, d15), (a62, b6, c2, d16), (a62, b6, c2, d17), (a62, b6, c2, d18), (a62, b6, c2, d19), (a62, b6, c2, d20), (a62, b6, c2, d21), (a62, b6, c2, d22), (a62, b6, c3, d1), (a62, b6, c3, d2), (a62, b6, c3, d3), (a62, b6, c3, d4), (a62, b6, c3, d5), (a62, b6, c3, d6), (a62, b6, c3, d7), (a62, b6, c3, d3), (a62, b6, c3, d9), (a62, b6, c3, d10), (a62, b6, c3, d11), (a62, b6, c3, d12), (a62, b6, c3, d13), (a62, b6, c3, d14), (a62, b6, c3, d15), (a62, b6, c3, d16), (a62, b6, c3, d17), (a62, b6, c3, d18), (a62, b6, c3, d19), (a62, b6, c3, d20), (a62, bb, c3, d21), (a62, b6, c3, d22), (a63, b1, c1, d1), (a63, b1, c1, d2), (a63, b1, c1, d3), (a63, b1, c1, d4), (a63, b1, c1, d5), (a63, b1, c1, d6), (a63, b1, c1, d7), (a63, b1, c1, d8), (a63, b1, c1, d9), (a63), b1, c1, d10), (a63, b1, c1, d11), (a63, b1, c1, d12), (a63, b1, c1, d13), (a63, b1, c1, d14), (a63, b1, c1, d15), (a63, b1, c1, d16), (a63, b1, c1, d17), (a63, b1, c1, d18), (a63, b1, c1, d19), (a63, b1, c1, d20), (a63, b1, c1, d21), (a63, b1, c1, d22), (a63, b1, c2, d1), (a63, b1, c2, d2), (a63, b1, c2, d3), (a63, b1, c2, d4), (a63, b1, c2, d5), (a63, b1, c2, d6), (a63, b1, c2, d7), (a63, b1, c2, d8), (a63, b1, c2, d9), (a63, b1, c2, d9), (a63, b1, c2, d11), (a63, b1, c2, d12), (a63, b1, c2, d13), (a63, b1, c2, d14), (a63, b1, c2, d15), (a63, b1, c2, d16), (a63, b1, c2, d17), (a63, b1, c2, d18), (a63, b1, c2, d19), (a63, b1, c2, d20), (a63, b1, c2, d21), (a63, b1, c2, d22), (a63, b1, c3, d1), (a63, b1, c3, d2), (a63, b1, c3, d3), (a63, b1, c3, d4), (a63, b1, c3, d5), (a63, b1, c3, d6), (a63, b1, c3, d7), (a63, b1, c3, d8), (a63, b1, c3, d9), (a63, b1, c3, d16), (a63, b1, c3, d11), (a63, b1, c3, d12), (a63, b1, c3, d13), (a63, b1, c3, d14), (a63, b1, c3, d15), (a63, b1, c3, d16), (a63, b1, c3, d17), (a63, b1, c3, d18), (a63, b1, c3, d19), (a63, b1, c3, d20), (a63, b1, c3, d21), (a63, b1, c3, d22), (a63, b2, c1, d1), (a63, b2, c1, d2), (a63, b2, c1, d3), (a63, b2, c1, d4), (a63, b2, c1, d5), (a63, b2, c1, d6), (a63, b2, c1, d7), (a63, b2, c1, d8), (a63, b2, c1, d9), (a63, b2, c1, d10), (a63, b2, c1, d11), (a63, b2, c1, d12), (a63, b2, c1, d13), (a63, b2, c1, d14), (a63, b2, c1, d15), (a63, b2, c1, d16), (a63, b2, c1, d17), (a63, b2, c1, d18), (a63, b2, c1, d19), (a63, b2, c1, d20), (a63, b2, c1, d21), (a63, b2, c1, d22), (a63, b2, c2, d1), (a63, b2, c2, d2), (a63, b2, c2, d3), (a63, b2, c2, d4), (a63, b2, c2, d5), (a63 b2, c2, d6), (a63, b2, c2, d7), (a63, b2, c2, d8), (a63, b2, c2, d9), (a63, b2, c2, d10), (a63, b2, c2, d11), (a63, b2, c2, d12), (a63, b2, c2, d13), (a63, b2, c2, d14), (a63, b2, c2, d15), (a63, b2, c2, d16), (a63, b2, c2, d17), (a63, b2, c2, d18), (a63, b2, c2, d19), (a63, b2, c2, d20), (a63, b2, c2, d21), (a63, b2, c2, d22), (a63, b2, c3, d1), (a63, b2, c3, d2), (a63, b2, c3, d3), (a63, b2, c3, d4), (a63, b2, c3, d5), (a63, b2, c3, d6), (a63, b2, c3, d7), (a63, b2, c3, d8), (a63, b2, c3, d9), (a63, b2, c3, d10), (a63, b2, c3, d11), (a63, b2, c3, d12), (a63, b2, c3, d13), (a63, b2, c3, d14), (a63, b2, c3, d15), (a63, b2, c3, d16), (a63, b2, c3, d17), (a63, b2, c3, d18), (a63, b2, c3, d19), (a63, b2, c3, d20), (a63, b2, c3, d21), (a63, b2, c3, d22), (a63, b3, c1, d1), (a63, b3, c1, d2), (a63, b3, c1, d3), (a63, b3, c1, d4), (a63, b3, c1, d5), (a63, b3, c1, d6), (a63, b3, c1, d7), (a63, b3, c1, d8), (a63, b3, c1, d9), (a63, b3, c1, d10), (a63, b3, c1, d11), (a63, b3, c1, d2), (a63, b3, c1, d13), (a63, b3, c1, d14), (a63, b3, c1, d15), (a63, b3, c1, d16), (a63, b3, c1, d17), (a63, b3, c1, d18), (a63, b3, c1, d19), (a63, b3, c1, d20), (a63, b3, c1, d21), (a63, b3, c1, d22), (a63, b3, c2, d1), (a63, b3, c2, d2), (a63, b3, c2, d3), (a63, b3, c2, d4), (a63, b3, c2, d5), (a63, b3, c2, d6), (a63, b3, c2, d7), (a63, b3, c2, d8), (a63, b3, c2, d9), (a3, b3, c2, d10), (a63, b3, c2, b11), (a63, b3, c2, d12), (a63, b3, c2, d19), (a63, b5, c2, d14), (a63, b3, c2, d5), (a63, b3, c2, d16), (a63, b3, c2, d17), (a63, b3, c2, d18), (a63, b3, c2, d19), (a63, b3, c2, d20), (a63, b3, c2, d21), (a63, b3, c2, d22), (a63, b3, c3, d1), (a63, b3, c3, d2), (a63, b3, c3, d3), (a63, b5, c3, d4), (a63, b3, c3, d5), (a63, b3, c3, d6), (a63, b3, c3, d7), (a63, b3, c3, d8), (a63, b3, c3, d9), (a63, b3, c3, d10), (a63, b3, c3, d11), (a63, b3, c3, d12), (a63, b3, c3, d13), (a63, b3, c3, d14), (a63, b3, c3, d15), (a63, b3, c3, d16), (a63, b3, c3, d17), (a63, b3, c3, d8), (a63, b3, c3, d19), (a63, b3, c3, d20), (a63, b3, c3, d21), (a63, b3, c3, d22), (a63, b4, c1, d1), (a63, b4, c1, d2), (a63, b4, c1, d3), (a63, b4, c1, d4), (a63, b4, c1, d5), (a63, b4, c1, d6), (a63, b4, c1, d7), (a63, b4, c1, d8), (a63, b4, c1, d9), (a63, b4, c1, d10), (a63, b4, c1, d11), (a63, b4, c1, d12), (a63, b4, c1, d13), (a63, b4, c1, d14), (a63, b4, c1, d15), (a63, b4, c1, d16), (a63, b4, c1, d17), (a63, b4, c1, d18), (a63, b4, c1, d9), (a63, b4, c1, d20), (a63, b4, c1, d21), (a63, b4, c1, d22), (a63, b4, c2, d1), (a63, b4, c2, d2), (a63, b4, c2, d3), (a63, b4, c2, d4), (a63, b4, c2, d5), (a63, b4, c2, d6), (a63, b4, c2, d7), (a63, b4, c2, d8), (a63, b4, c2, d9), (a63, b4, c2, d10), (a63, b4, c2, d11), (a63, b4, c2, d12), (a63, b4, c2, d13), (a63, b4, c2, d14), (a63, b4, c2, d15), (a63, b4, c2, d16), (a63, b4, c2, d17), (a63, b4, c2, d18, (a63, b4, c2, d19), (a63, b4, c2, d20), (a63, b4, c2, d21), (a63, b4, c2, d22), (a63, b4, c3, d1), (a63, b4, c3, d2), (a63, b4, c3, d3), (a63, b4, c3, d4), (a63, b4, c3, d5), (a63, b4, c3, d6), (a63, b4, c3, d7), (a63, b4, c3, d8), (a63, b4, c3, d9), (a63, b4, c3, d10), (a63, b4, c3, d11), (a63, b4, c3, d12), (a63, b4, c3, d13), (a63, b4, c3, d14), (a63, b4, c3, d15), (a63, b4, c3, d16), (a63, b4, c3, d17), (a63, b4, c3, d18), (a63, b4, c3, d19), (a63, b4, c3, d20), (a63, b4, c3, d21), (a63, b4, c3, d22), (a63, b5, c1, d1), (a63, b5, c1, d2), (a63, b5, c1, d3), (a63, b5, c1, d4), (a63, b5, c1, d5), (a63, b5, c1, d6), (a63, b5, c1, d7), (a63, b5, c1, d8), (a63, b5, c1, d9), (a63, b5, c1, d10), (a63, b5, c1, (a63, b5, c1, d16), (a63, b5, c1, d17), (a63, b5, c1, d18), (a63, b5, c1, d19), (a63, b5, c1, d20), (a63, b5, c1, d21), (a63, b5, c1, d22), (a63, b5, c2, d1), (a63, b5, c2, d2), (a63, b5, c2, d3), (a63, b5, c2, d4), (a63, b5, c2, d5), (a63, b5, c2, d6), (a63, b5, c2, d7), (a63, b5, c2, d8), (a63, b5, c2, d9), (a63, b5, c2, d10), (a63, b5, c2, d11), (a63, b5, c2, d12), (a63, b5, c2, d13), (a63, b5, c2, d14), (a63, b5, c2, d15), (a63, b5, c2, d16), (a63, b5, c2, d17), (a63, b5, c2, d18), (a63, b5, c2, d19), (a63, b5, c2, d20), (a63, b5, c2, d21), (a63, b5, c2, d22), (a63, b5, c3, d1), (a63, b5, c3, d2), (a63, b5, c3, d3), (a63, b5, c3, d4), (a63, b5, c3, d5), (a63, b5, c3, d6), (a63, b5, c3, d7), (a63, b5, c3, d8), (a63, b5, c3, d9), (a63, b5, c3, d10), (a63, b5, c3, d11), (a63, b5, c3, d12), (a63, b5, c3, d13), (a63, b5, c3, d14), (a63, b5, c3, d15), (a63, b5, c3, d16), (a63, b5, c3, d17), (a63, b5, c3, d18), (a63, b5, c3, d19), (a63, b5, c3, d20), (a63, b5, c3, d21), (a63, b5, c3, d22), (a63, b6, c1, d1), (a63, b6, c1, d2), (a63, b6, c1, d3), (a63, b6, c1, d4), (a63, b6, c1, d5), (a63, b6, c1, d6), (a63, b6, c1, d7), (a63, b6, c1, d8), (a63, b6, c1, d19), (a63, b6, c1, d6), (a63, b6, c1, d11), (a63, b6, c1, d12), (a63, b6, c1, d13), (a63, b6, c1, d14), (a63, b6, c1, d15), (a63, b6, c1, d16), (a63, b6, c1, d17), (a63, b6, c1, d18), (a63, b6, c1, d19), (a63, b6, c1, d20), (a63, b6, c1, d21), (a63, b6, c1, d22), (a63, b6, c2, d1), (a63, b6, c2, d2), (a63, b6, c2, d3), (a63, b6, c2, d4), (a63, b6, c2, d5), (a63, b6, c2, d6), (a63, b6, c2, d7), (a63, b6, c2, d8), (a63, b6, c2, d9), (a63, b6, c2, d10), (a63, b6, c2, d11), (a63, b6, c2, d12), (a63, b6, c2, d13), (a63, b6, c2, d14), (a63, b6, c2, d15), (a63, b6, c2, d16), (a63, b6, c2, d17), (a63, b6, c2, d18), (a63, b6, c2, d19), (a63, b6, c2, d20), (a63, b6, c2, d21), (a63, b6, c2, d22), (a63, b6, c3, d1), (a63, b6, c3, d2), (a63, b6, c3, d3), (a63, b6, c3, d4), (a63, b6, c3, d5), (a63, b6, c3, d6), (a63, b6, c3, d7), (a63, b6, c3, d8), (a63, b6, c3, d9), (a63, b6, c3, d10), (a63, b6, c3, d11), (a63, b6, c3, d12), (a63, b6, c3, d13), (a63, b6, c3, d14), (a63, b6, c3, d15), (a63, b6, c3, d16), (a63, b6, c3, d17), (a63, b6, c3, d18), (a63, b6, c3, d19), (a63, b6, c3, d20), (a63, b6, c3, d21), (a63, b6, c3, d22), (a64, b1, c1, d1), (a64, b1, c1, d2), (a64, b1, c1, d3), (a64, b1, c1, d4), (a64, b1, c1, d5), (a64, b1, c1, d6), (a64, b1, c1, d7), (a64, b1, c1, d8), (a64, b1, c1, d9), (a64, b1, c1, d10), (a64, b1, c1, d11), (a64, b1, c1, d12), (a64, b1, c1, d13), (a64, b1, c1, d14), (a64, b1, c1, d15), (a64, b1, c1, d16), (a64, b1, c1, d17), (a64, b1, c1, d18), (a64, b1, c1, d19), (a64, b1, c1, d20), (a64, b1, c1, d21), (a64, b1, c1, d22), (a64, b1, c2, d1), (a64, b1, c2, d2), (a64, b1, c2, d3), (a64, b1, c2, d4), (a64, b1, c2, d5), (a64, b1, c2, d6), (a64, b1, c2, d7), (a64, b1, c2, d8), (a64, b1, c2, d9), (a64, b1, c2, d10), (a64, b1, c2, d11), (a64, b1, c2, d12), (a64, b1, c2, d13), (a64, b1, c2, d14), (a64, b1, c2, d15), (a64, b1, c2, d16), (a64, b1, c2, d17), (a64, b1, c2, d18), (a64, b1, c2, d19), (a64, b1, c2, d20), (a64, b1, c2, d21), (a64, b1, c2, d22), (a64, b1, c3, d1), (a64, b1, c3, d2), (a64, b1, c3, d3), (a64, b1, c3, d4), (a64, b1, c3, d5), (a64, b1, c3, d6), (a64, b1, c3, d7), (a64, b1, c3, d8), (a64, b1, c3, d9), (a64, b1, c3, d10), (a64, b1, c3, d11), (a64, b1, c3, d12), (a64, b1, c3, d13), (a64, b1, c3, d14), (a64, b1, c3, d15), (a64, b1, c3, d16), (a64, b, c3, d17), (a64, b1, c3, d18), (a64, b1, c3, d19), (a64, b1, c3, d20), (a64, b1, c3, d21), (a64, b1, c3, d22), (a64, b2, c1, d1), (a64, b2, c1, d2), (a64, b2, c1, d3), (a64, b2, c1, d4), (a64, b2, c1, d5), (a64, b2, c1, d6), (a64, b2, c1, d7), (a64, b2, c1, d8), (a64, b2, c1, d9), (a64, b2, c1, d10), (a64, b2, c1, d11), (a64, b2, c1, d12), (a64, b2, c1, d13), (a64, b2, c1, d14), (a64, b2, c1, d16), (a64, b2, c1, d16), (a64, b2, c1, d17), (a64, b2, c1, d18), (a64, b2, c1, d19), (a64, b2, c1, d20), (a64, b2, c1, d21), (a64, b2, c1, d22), (a64, b2, c2, d1), (a64, b2, c2, d2), (a64, b2, c2, d3), (a64, b2, c2, d4), (a64, b2, c2, d5), (a64, b2, c2, d6), (a64, b2, c2, d7), (a64, b2, c2, d8), (a64, b2, c2, d9), (a64, b2, c2, d10), (a64, b2, c2, d11), (a64, b2, c2, d12), (a64, b2, c2, d13), (a64, b2, c2, d4), (a64, b2, c2, d15) (a64, b2, c2, d16), (a64, b2, c2, d17), (a64, b2, c2, d18) (a64, b2, c2, d19), (a64, b2, c2, d20), (a64, b2, c2, d21), (a64, b2, c2, d22), (a64, b2, c3, d1), (a64, b2, c3, d2), (a64, b2, c3, d3), (a64, b2, c3, d4), (a64, b2, c3, d5), (a64, b2, c3, d6), (a64, b2, c3, d7), (a64, b2, c3, d8), (a64, b2, c3, d9), (a64, b2, c3, d10), (a64, b2, c3, d11), (a64, b2, c3, d12), (a64, b2, c3, d13), (a64, b2, c3, d14), (a64, b2, c3, d15), (a64, b2, c3, d16), (a64, b2, c3, d17), (a64, b2, c3, d18), (a64, b2, c3, d19), (a64, b2, c3, d20), (a64, b2, c3, d21), (a64, b2, c3, d22), (a64, b3, c1, d1), (a64, b3, c1, d2), (a64, b3, c1, d3), (a64, b3, c1, d4), (a64, b3, c1, d5), (a64, b3, c1, d6), (a64, b3, c1, d7), (a64, b3, c1, d8), (a64, b3, c1, d9), (a64, b3, c1, d10), (a64, b3, c1, d11), (a64, b3, c1, d12), (a64, b3, c1, d13), (a64, b3, c1, d14), (a64, b3, c1, d15), (a64, b3, c1, d16), (a64, b3, c1, d17), (a64, b3, c1, d18), (a64, b3, c1, d19), (a64, b3, c1, d20), (a64, b3, c1, d21), (a64, b3, c1, d22), (a64, b3, c2, d1), (a64, b3, c2, d2), (a64, b3, c2, d3), (a64, b3, c2, d4), (a64, b3, c2, d5), (a64, b3, c2, d6), (a64, b3, c2, d7), (a64, b3, c2, d8), (a64, b3, c2, d9), (a64, b3, c2, d10), (a64, b3, c2, d11), (a64, b5, c2, d12), (a64, b3, c2, d13), (a64, b3, c2, d14), (a64, b3, c2, d15), (a64, b3, c2, d16), (a64, b3, c2, d17), (a64, b3, c2, d18), (a64, b3, c2, d19), (a64, b3, c2, d20), (a64, b3, c2, d21), (a64, b3, c2, d22), (a64, b3, c3, d1), (a64, b3, c3, d2), (a64, b3, c3, d3), (a64, b3, c3, d4), (a64, b3, c3, d5), (a64, b3, c3, d6), (a64, b3, c3, d7), (a64, b3, c3, d8), (a64, b3, c3, d9), (a64, b3, c3, d10), (a64, b3, c3, d11), (a64, b3, c3, d12), (a64, b3, c3, d13), (a64, b3, c3, d14), (a64, b3, c3, d15), (a64, b3, c3, d16), (a64, b3, c3, d17), (a64, b3, c3, d18), (a64, b3, c3, d19), (a64, b3, c3, d20), (a64, b3, c3, d21), (a64, b3, c3, d22), (a64, b4, c1, d1), (a64, b4, c1, d2), (a64, b4, c1, d3), (a64, b4, c1, d4), (a64, b4, c1, d5), (a64, b4, c1, d6), (a64, b4, c1, d7), (a64, b4, c1, d8), (a64, b4, c1, d9), (a64, b4, c1, d10), (a64, b4, c1, d11), (a64, b4, c1, d12), (a64, b4, c1, d13), (a64, b4, c1, d14), (a64, b4, c1, d15), (a64, b4, c1, d6), (a64, b4, c1, d17), (a64, b4, c1, d18), (a64, b4, c1, d19), (a64, b4, c1, d20), (a64, b4, c1, d21), (a64, b4, c1, d22), (a64, b4, c2, d1), (a64, b4, c2, d2), (a64, b4, c2, d3), (a64, b4, c2, d4), (a64, b4, c2, d5), (a64, b4, c2, d6), (a64, b4, c2, d7), (a64, b4, c2, d8), (a64, b4, c2, d9), (a64, b4, c2, d10), (a64, b4, c2, d11), (a64, b4, c2, d12), (a64, b4, c2, d13), (a64, b4, c2, d14), (a64, b4, c2, d15), (a64, b4, c2, d16), (a64, b4, c2, d17), (a64, b4, c2, d8), (a64, b4, c2, d19), (a64, b4, c2, d20), (a64, b4, c2, d21), (a64, b4, c2, d22), (a64, b4, c3, d1), (a64, b4, c3, d2), (a64, b4, c3, d3), (a64, b4, c3, d4), (a64, b4, c3, d5), (a6, b4, c3, d6), (a64, b4, c3, d7), (a64, b4, c3, d8), (a64, b4, c3, d9), (a64, b4, c3, d10), (a64, b4, c3, d11), (a6, b4, c3, d12), (a64, b4, c3, d13), (a64, b4, c3, d14), (a64, b4, c3, d15), (a64, b4, c3, d16), (a64, b4, c3, d17), (a64, b4, b4, c3, d18), (a64, b4, c3, d19), (a64, b4, c3, d20), (a64, b4, c3, d21), (a64, b4, c3, d22), (a64, b5, c1, d1), (a64, b5, c1, d2), (a64, b5, c1, d3), (a64, b5, c1, d4), (a64, b5, c1, d5), (a64, b5, c1, d6), (a64, b5, c1, d7), (a64, b5, c1, d3), (a64, b5, c1, d9), (a64, b5, c1, d10), (a64, b5, c1, d11), (a64, b5, c1, d12), (a64, b5, c1, d13), (a64, b5, c1, d14), (a64, b5, c1, d15), (a64, b5, c1, d16), (a64, b5, c1, d17), (a64, b5, c1, d18), (a64, b5, c1, d19), (a64, b5, c1, d20), (a64, b5, c1, d21), (a64, b5, c1, d22), (a64, b5, c2, d1), (a64, b5, c2, d2), (a64, b5, c2, d3), (a64, b5, c2, d4), (a64, b5, c2, d5), (a64, b5, c2, d6), (a64, b5, c2, d7), (a64, b5, c2, d8), (a64, b5, c2, d9), (a64, b5, c2, d10), (a64, b5, c2, d11), (a64, b5, c2, d12), (a64, b5, c2, d13), (a64, b5, c2, d14), (a64, b5, c2, d15), (a64, b5, c2, d16), (a64, b5, c2, d17), (a64, b5, c2, d18), (a64, b5, c2, d19), (a64, b5, c2, d20), (a64, b5, c2, d21), (a64, b5, c2, d22), (a64, b5, c3, d1), (a64, b5, c3, d2), (a64, b5, c3, d3), (a64, b5, c3, d4), (a64, b5, c3, d5), (a64, b5, c3, d6), (a64, b5, c3, d7), (a64, b5, c3, d8), (a64, b5, c3, d9), (a64, b5, c3, d10), (a64, b5, c3, d11), (a64, b5, c3, d12), (a64, b5, c3, d13), (a64, b5, c3, d14), (a64, b5, c3, d15), (a64, b5, c3, d16), (a64, b5, c3, d17), (a64, b5, c3, d18), (a64, b5, c3, d19), (a64, b5, c3, d20), (a64, b5, c3, d21), (a64, b5, c3, d22), (a64, b6, c1, d1), (a64, b6, c1, d2), (a64, b6, c1, d3), (a64, b6, c1, d4), (a64, b6, c1, d5), (a64, b6, c1, d6), (a64, b5, c1, d7), (a64, b6, c1, d8), (a64, b6, c1, d9), (a64, b6, c1, d10), (a64, b6, c1, d11), (a64, b6, c1, d12), (a64, b6, c1, d13), (a64, b6, c1, d14), (a64, b6, c1, d15), (a64, b6, c1, d16), (a64, b6, c1, d17), (a64, b6, c1, d18), (a64, b6, c1, d19), (a64, b6, c1, d20), (a64, b6, c1, d21), (a64, b6, c1, d22), (a64, b6, c2, d1), (a64, b6, c2, d2), (a64, b6, c2, d3), (a64, b6, c2, d4), (a64, b6, c2, d5), (a64, b6, c2, d6), (a64, b6, c2, d7), (a64, b6, c2, d8), (a64, b6, c2, d9), (a64, b6, c2, d10), (a64, b6, c2, d11), (a64, b6, c2, d12), (a64, b6, c2, d13), (a64, b6, c2, d14), (a64, b6, c2, d15), (a64, b6, c2, d16), (a64, b6, c2, d17), (a64, b6, c2, d18), (a64, b6, c2, d19), (a64, b6, c2, d20), (a64, b6, c2, d21), (a64, b6, c2, d22), (a64, b6, c3, d1), (a64, b6, c3, d2), (a64, b6, c3, d3), (a64, b6, c3, d4), (a64, b6, c3, d5), (a64, b6, c3, d6), (a64, b6, c3, d7), (a64, b6, c3, d8), (a64, b6, c3, d9), (a64, b6, c3, d10), (a64, b6, c3, d11), (a64, b6, c3, d12), (a64, b6, c3, d13), (a64, b6, c3, d14), (a64, b6, c3, d15), (a64, b6, c3, d16), (a64, b6, c3, d17), (a64, b6, c3, d18), (a64, b6, c3, d19), (a64, b6, c3, d20), (a64, b6, c3, d21), (a64, b6, c3, d22), (a65, b1, c1, d1), (a65, b1, c1, d2), (a65, b1, c1, d3), (a65, b1, c1, d4), (a6, b1, c1, d5), (a65, b1, c1, d6), (a65, b1, c1, d7), (a65, b1, c1, d8), (a65, b1, c1, d9), (a65, b1, c1, d10), (a65, b1, c1, d11), (a65, b1, c1, d12), (a65, b1, c1, d13), (a65, b1, c1, d14), (a65, b1, c1, d15), (a65, b1, c1, d16), (a65, b1, c1, d17), (a65, b1, c1, d18), (a65, b1, c1, d19), (a65, b1, c1, d20), (a65, b1, c1, d21), (a65, b1, c1, d22), (a65, b1, c2, d1), (a65, b1, c2, d2), (a65, b1, c2, d3), (a65, b1, c2, d4), (a65, b1, c2, d5), (a65, b1, c2, d6), (a65, b1, c2, d7), (a65, b1, c2, d8), (a65, b1, c2, d9), (a65, b1, c2, d10), (a65, b1, c2, d11), (a65, b1, c2, d12), (a65, b1, c2, d13), (a65, b1, c2, d14), (a65, b1, c2, d15), (a65, b1, c2, d10), (a65, b1, c2, d17), (a65, b1, c2, d18), (a65, b1, c2, d19), (a65, b1, c2, d20), (a65, b1, c2, d21), (a65, b1, c2, d22), (a65, b1, c3, d1), (a65, b1, c3, d2), (a65, b1, c3, d3), (a65, b1, c3, d4), (a65, b1, c3, d5), (a65, b1, c3, d6), (a65, b1, c3, d7), (a65, b1, c3, d8), (a65, b1, c3, d9), (a65, b1, c3, d10), (a65, b1, c3, d11), (a65, b1, c3, d12), (a65, b1, c3, d13), (a65, b1, c3, d14), (a65, b1, c3, d15), (a65, b1, c3, d16), (a65, b1, c3, d17), (a65, b1, c3, d18), (a65, b1, c3, d19), (a65, b1, c3, d20), (a65, b1, c3, d21), (a65, b1, c3, d22), (a65, b2, c1, d1), (a65, b2, c1, d2), (a65, b2, c1, d3), (a65, b2, c1, d4), (a65, b2, c1, d5), (a65, b2, c1, d6), (a65, b2, c1, d7), (a65, b2, c1, d8), (a65, b2, c1, d9), (a65, b2, c1, d10), (a65, b2, c1, d11), (a65, b2, c1, d12), (a65, b2, c1, d13), (a65, b2, c1, d14), (a65, b2, c1, d15), (a65, b2, c1, d16), (a65, b2, c1, d17), (a65, b2, c1, d18), (a65, b2, c1, d19), (a65, b2, c1, d20), (a65, b2, c1, d21), (a65, b2, c1, d22), (a65, b2, c2, d1), (a65, b2, c2, d2), (a65, b2, c2, d3), (a65, b2, c2, d4), (a65, b2, c2, d5), (a65, b2, c2, d6), (a65, b2, c2, d7), (a65, b2, c2, d8), (a65, b2, c2, d9), (a65, b2, c2, d10), (a65, b2, c2, dl), (a65, b2, c2, d12), (a65, b2, c2, d13), (a65, b2, c2, d14), (a65, b2, c2, d15), (a65, b2, c2, d16), (a65, b2, c2, d17), (a65, b2, c2, d18), (a65, b2, c2, d19), (a65, b2, c2, d20), (a65, b2, c2, d21), (a65, b2, c2, d22), (a65, b2, c3, d1), (a65, b2, c3, d2), (a65, b2, c3, d3), (a65, b2, c3, d4), (a65, b2, c3, d5), (a65, b2, c3, d6), (a65, b2, c3, d7), (a65, b2, c3, d8), (a65, b2, c3, d9), (a65, b2, c3, d10), (a65, b2, c3, d11), (a65, b2, c3, d12), (a65, b2, c3, d13), (a65, b2, c3, d14), (a65, b2, c3, d15), (a65, b2, c3, d16), (a65, b2, c3, d17), (a65, b2, c3, d18), (a65, b2, c3, d19), (a65, b2, c3, d20), (a65, b2, c3, d21), (a65, b2, c3, d22), (a65, b3, c1, d1), (a65, b3, c1, d2), (a65, b3, c1, d3), (a65, b3, c1, d4), (a65, b3, c1, d5), (a65, b3, c1, d6), (a65, b3, c1, d7), (a65, b3, c1, d8), (a65, b3, c1, d9), (a65, b3, c1, d10), (a65, b3, c1, d11), (a65, b3, c1, d12), (a65, b3, c1, d13), (a65, b3, c1, d14), (a65, b3, c1, d15), (a65, b3, c1, d16), (a65, b3, c1, d17), (a65, b3, c1, d18), (a65, b3, c1, d19), (a65, b3, c1, d20), (a65, b3, c1, d21), (a65, b3, c1, d22), (a65, b3, c2, d1), (a65, b3, c2, d2), (a65, b3, c2, d3), (a65, b3, c2, d4), (a65, b3, c2, d5), (a65, b3, c2, d6), (a65, b3, c2, d7), (a65, b3, c2, d8), (a65, b3, c2, d9), (a65, b3, c2, d10), (a65, b3, c2, d11), (a65, b3, c2, d12), (a65, b3, c2, d13), (a65, b3, c2, d14), (a65, b3, c2, d15), (a65, b3, c2, d16), (a65, b3, c2, d17), (a65, b3, c2, d18), (a65, b3, c2, d19), (a65, b3, c2, d20), (a65, b3, c2, d21), (a65, b3, c2, d22), (a65, b3, c3, d1), (a65, b3, c3, d2), (a65, b3, c3, d3), (a65, b3, c3, d4), (a65, b3, c3, d5), (a65, b3, c3, d6), (a65, b3, c3, d7), (a65, b3, c3, d8), (a65, b3, c3, d9), (a65, b3, c3, d10), (a65, b3, c3, d11), (a65, b3, c3, d12), (a65, b3, c3, d13), (a65, b3, c3, d14), (a65, b3, c3, d15), (a65, b3, c3, d16), (a65, b3, c3, d17), (a65, b3, c3, d18), (a65, b3, c3, d19), (a65, b3, c3, d20), (a65, b3, c3, d21), (a65, b3, c3, d22), (a65, b4, c1, d1), (a65, b4, c1, d2), (a65, b4, c1, d3), (a65, b4, c1, d4), (a65, b4, c1, d5), (a65, b4, c1, d6), (a65, b4, c1, d7), (a65, b4, c1, d8), (a65, b4, c1, d9), (a65, b4, c1, d10), (a65, b4, c1, d11), (a65, b4, c1, d12), (a65, b4, c1, d13), (a65, b4, c1, d14), (a65, b4, c1, d15), (a65, b4, c1, d16), (a65, b4, c1, d17), (a65, b4, c1, d18), (a65, b4, c1, d19), (a65, b4, c1, d20), (a65, b4, c1, d21), (a65, b4, c1, d22), (a65, b4, c2, d1), (a65, b4, c2, d2), (a65, b4, c2, d3), (a65, b4, c2, d4), (a65, b4, c2, d5), (a65, b4, c2, d6), (a65, b4, c2, d7), (a65, b4, c2, d8), (a65, b4, c2, d9), (a65, b4, c2, d10), (a65, b4, c2, d11), (a65, b4, c2, d12), (a65, b4, c2, d13), (a65, b4, c2, d14), (a65, b4, c2, d15), (a65, b4, c2, d16), (a65, b4, c2, d17), (a65, b4, c2, d18), (a65, b4, c2, d19), (a65, b4, c2, d20), (a65, b4, c2, d21), (a65, b4, c2, d22), (a65, b4, c3, d1), (a65, b4, c3, d2), (a65, b4, c3, d3), (a65, b4, c3, d4), (a65, b4, c3, d5), (a65, b4, c3, d6), (a65, b4, c3, d7), (a65, b4, c3, d8), (a65, b4, c3, d9), (a65, b4, c3, d10), (a65, b4, c3, d11), (a65, b4, c3, d12), (a65, b4, c3, d13), (a65, b4, c3, d14), (a65, b4, c3, d15), (a65, b4, c3, d16), (a65, b4, c3, d17), (a65, b4, c3, d18), (a65, b4, c3, d19), (a65, b4, c3, d20), (a65, b4, c3, d21), (a65, b4, c3, d22), (a65, b5, c1, d1), (a65, b5, c1, d2), (a65, b5, c1, d3), (a65, b5, c1, d4), (a65, b5, c1, d5), (a65, b5, c1, d6), (a65, b5, c1, d7), (a65, b5, c1, d8), (a65, b5, c1, d6), (a65, b5, c1, d10), (a65, b5, c1, d11), (a65, b5, c1, d12), (a65, b5, c1, d13), (a65, b5, c1, d14), (a65, b5, c1, d15), (a65, b5, c1, d16), (a65, b5, c1, d17), (a65, b5, c1, d18), (a65, b5, c1, d19), (a65, b5, c1, d20), (a65, b5, c1, d21), (a65, b5, c1, d22), (a65, b5, c2, d1), (a65, b5, c2, d2), (a65, b5, c2, d3), (a65, b5, c2, d4), (a65, b5, c2, d5), (a65, b5, c2, d16), (a65, b5, c2, d17), (a65, b5, c2, d18), (a65, b5, c2, d9), (a65, b5, c2, d10), (a65, b5, c2, d11), (a65, b5, c2, d12), (a65, b5, c2, d13), (a65, b5, c2, d14), (a65, b5, c2, d15), (a65, b5, c2, d16), (a65, b5, c2, d17), (a65, b5, c2, d18), (a65, b5, c2, d19), (a65, b5, c2, d20), (a65, b5, c2, d21), (a65, b5, c2, d22), (a65, b5, c3, d1), (a65, b5, c3, d2), (a65, b5, c3, d3), (a65, b5, c3, d4), (a65, b5, c3, d5), (a65, b5, c3, d6), (a65, b5, c3, d7), (a65, b5, c3, d8), (a65, b5, c3, d9), (a65, b5, c3, d10), (a65, b5, c3, d11), (a65, b5, c3, d12), (a65, b5, c3, d13), (a65, b5, c3, d14), (a65, b5, c3, d15), (a65, b5, c3, d16), (a65, b5, c3, d17), (a65, b5, c3, d18), (a65, b5, c3, d19), (a65, b5, c3, d20), (a65, b5, c3, d21), (a65, b5, c3, d22), (a65, b6, c1, d1), (a65, b6, c1, d2), (a65, b6, c1, d3), (a65, b6, c1, d4), (a65, b6, c1, d5), (a65, b6, c1, d6), (a65, b6, c1, d7), (a65, b6, c1, d8), (a65, b6, c1, d9), (a65, b6, c1, d10), (a65, b6, c1, d11), (a65, b6, c1, d12), (a65, b6, c1, d13), (a65, b6, c1, d14), (a65, b6, c1, d15), (a65, b6, c1, d16), (a65, b6, c1, d17), (a65, b6, c1, d18) (a65, b6, c1, d19), (a65, b6, c1, d20), (a65, b6, c1, d21), (a65, b6, c1, d22), (a65, b6, c2, d1), (a65, b6, c2, d2), (a65, b6, c2, d3), (a65, b6, c2, d4), (a65, b6, c2, d5), (a65, b6, c2, d6), (a65, b6, c2, d7), (a65, b6, c2, d8), (a65, b6, c2, d9), (a65, b6, c2, d10), (a65, b6, c2, d11), (a65, b6, c2, d12), (a65, b6, c2, d13), (a65, b6, c2, d14), (a65, b6, c2, d15), (a65, b6, c2, d16), (a65, b6, c2, d17), (a65, b6, c2, d18), (a65, b6, c2, d19), (a65, b6, c2, d20), (a65, b6, c2, d21), (a65, b6, c2, d22), (a65, b6, C3, d1), (a65, b6, c3, d2), (a65, b6, c3, d13), (a65, b6, c3, d4), (a65, b6, c3, d5), (a65, b6, c3, d6), (a65, b6, c3, d7), (a65, b6, c3, d8), (a65, b6, c3, d9), (a65, b6, c3, d10), (a65, b6, c3, d11), (a65, b6, c3, d12), (a65, b6, c3, d13), (a65, b6, c3, d14), (a65, b6, c3, d15), (a65, b6, c3, d16), (a65, b6, c3, d17), (a65, b6, c3, d18), (a65, b6, c3, d19), (a65, b6, c3, d20), (a65, b6, c3, d21), (a65, b6, c3, d22), (a66, b1, c1, d1), (a66, b1, c1, d2), (a66, b1, c1, d3), (a66, b1, c1, d4), (a66, b1, c1, d5), (a50, b1, c1, d6), (a66, b1, c1, d7), (a66, b1, c1, d8), (a66, b1, c1, d9), (a66, b1, c1, d10), (a66, b1, c1, d11), (a66, b1, c1, d12), (a66, b1, c1, d13), (a60, b1, c1, d14), (a6, b1, c1, d15), (a66, b1, c1, d16), (a66, b1, c1, d17), (a66, b1, c1, d18), (a66, b1, c1, d19), (a66, b1, c1, d20), (a66, b1, c1, d21), (a66, b1, c1, d22), (a66, b1, c2, d1), (a66, b1, c2, d2), (a66, b1, c2, d3), (a66, b1, c2, d4), (a66, b1, c2, d5), (a66, b1, c2, d6), (a66, b1, c2, d7), (a66, b1, c2, d8), (a66, b1, c2, d9), (a66, b1, c2, d10), (a66, b1, c2, d11), (a66, b1, c2, d12), (a66, b1, c2, d13), (a66, b1, c2, d14), (a66, b1, c2, d5), (a66, b1, c2, d16), (a66, b1, c2, d17), (a66, b1, c2, d18), (a66, b1, c2, d19), (a66, b1, c2, d20), (a66, b1, c2, d21), (a66, b1, c2, d22), (a66, b1, c3, d1), (a66, b1, c3, d2), (a66, b1, c3, d3), (a66, b1, c3, d4), (a66, b1, c3, d5), (a66, b1, c3, d6), (a66, b1, c3, d7), (a66, b1, c3, d8), (a66, b1, c3, d9), (a66, b1, c3, d10), (a66, b1, c3, d11), (a66, b1, c3, d12), (a66, b1, c3, d13), (a66, b1, c3, d14), (a66, b1, c3, d15), (a66, b1, c3, d16), (a66, b1, c3, d17), (a66, b1, c3, d18), (a66, b1, c3, d19), (a66, b1, c3, d20), (a66, b1, c3, d21), (a66, b1, c3, d22), (a66, b2, c1, d1), (a66, b2, c1, d2), (a66, b2, c1, d3), (a66, b2, c1, d4), (a66, b2, c1, d5), (a66, b2, c1, d6), (a66, b2, c1, d7), (a66, b2, c1, d8), (a66, b2, c1, d9), (a66, b2, c1, d10), (a66, b2, c1, d11), (a66, b2, c1, d12), (a66, b2, c1, d13), (a66, b2, c1, d14), (a66, b2, c1, d15), (a66, b2, c1, d16), (a66, b2, c1, d17), (a66, b2, c1, d18), (a66, b2, c1, d19), (a66, b2, c1, d20), (a66, b2, c1, d21), (a66, b2, c1, d22), (a66, b2, c2, d1), (a66, b2, c2, d2), (a66, b2, c2, d3), (a66, b2, c2, d4), (a66, b2, c2, d5), (a66, b2, c2, d6), (a66, b2, c2, d7), (a66, b2, c2, d8), (a66, b2, c2, d9), (a66, b2, c2, d10), (a66, b2, c2, d11), (a66, b2, c2, d12), (a66, b2, c2, d13), (a66, b2, c2, d14), (a66, b2, c2, d15), (a66, b2, c2, d16), (a66, b2, c2, d17), (a66, b2, c2, d18), (a66, b2, c2, d19), (a66, b2, c2, d20), (a66, b2, c2, d21), (a66, b2, c2, d22), (a66, b2, c3, d1), (a66, b2, c3, d2), (a66, b2, c3, d3), (a66, b2, c3, d4), (a66, b2, c3, d5), (a66, b2, c3, d6), (a66, b2, c3, d7), (a66, b2, c3, d8), (a66, b2, c3, d9), (a66, b2, c3, d10), (a66, b2, c3, d11), (a66, b2, c3, d12), (a66, b2, c3, d13), (a66, b2, c3, d14), (a66, b2, c3, d15), (a66, b2, c3, d11), (a66, b2, c3, d17), (a66, b2, c3, d18), (a66, b2, c3, d19), (a66, b2, c3, d20), (a66, b2, c3, d21), (a66, b2, c3, d22), (a66, b3, c1, d1), (a66, b3, c1, d2), (a66, b3, c1, d3), (a66, b3, c1, d4), (a66, b3, c1, d5), (a66, b3, c1, d6), (a66, b3, c1, d7), (a66, b3, c1, d8), (a66, b3, c1, d9), (a66, b3, c1, d10), (a66, b3, c1, (a66, (a6, b3, c1, d12), (a6, b3, c1, d13), (a66, b3, c1, d14), (a6, b1, c1, d15), (a66, b3, c1, d16), (a66, b3, c1, d17), (a66, b3, c1, d18), (a66, b3, c1, d19) (a66, b3, c1, d20), (a6, b3, c1, d21), (a66, b3, c1, d22), (a66, b3, c2, d1), (a66, b3, c2, d2), (a66, b3, c2, d3), (a66, b3, c2, d4), (a66, b3, c2, d5), (a66, b3, c2, d6), (a66, b3, c2, d7), (a66, b3, c2, d8), (a66, b3, c2, d9), (a66, b3, c2, d10), (a66, b3, c2, d11), (a66, b3, c2, d12), (a66, b3, c2, d13), (a66, b3, c2, d14), (a66, b3, c2, d15), (a66, b3, c2, d16), (a66, b3, c2, d17), (a6, b3, c2, d18), (a66, b3, c2, d19), (a66, b3, c2, d20), (a66, b3, c2, d21), (a66, b3, c2, d22), (a66, b3, c3, d1), (a66, b3, c3, d2), (a66, b3, c3, d3), (a66, b3, c3, d4), (a66, b3, c3, d5), (a66, b3, c3, d6), (a66, b3, c3, d7), (a66, b3, c3, d8), (a66, b3, c3, d9), (a66, b3, c3, d10), (a66, b3, c3, d11), (a66, b3, c3, d12), (a66, b3, c3, d13), (a66, b3, c3, d14), (a66, b3, c3, d15), (a66, b3, c3, d16), (a66, b3, c3, d17), (a66, b3, c3, d18), (a66, b5, c3, d19), (a66, b3, c3, d20), (a66, b3, c3, d21), (a66, b3, c3, d22), (a66, b4, c1, d1), (a66, b4, c1, d2), (a66, b4, c1, d3), (a66, b4, c1, d4), (a66, b4, c1, d5), (a66, b4, c1, d6), (a66, b4, c1, d7), (a66, b4, c1, d8), (a66, b4, c1, d9), (a66, b4, c1, d10), (a66, b4, c1, d11), (a66, b4, c1, d12), (a66, b4, c1, d13), (a66, b4, c1, d14), (a66, b4, c1, d15), (a66, b4, c1, d16), (a66, b4, c1, d17), (a66, b4, c1, d18), (a66, b4, c1, d19), (a66, b4, c1, d20), (a66, b4, c1, d21), (a66, b4, c1, d22), (a66, b4, c2, d1), (a66, b4, c2, d2), (a66, b4, c2, d3), (a66, b4, c2, d4), (a6, b4, c2, d5), (a66, b4, c2, d6), (a66, b4, c2, d7), (a66, b4, c2, d8), (a66, b4, c2, d9), (a66, b4, c2, d10), (a66, b4, c2, d11), (a66, b4, c2, d12), (a66, b4, c2, d13), (a66, b4, c2, d14), (a66, b4, c2, d15), (a66, b4, c2, d16), (a66, b4, c2, d17), (a66, b4, c2, d18), (a66, b4, c2, d19), (a66, b4, c2, d20), (a66, b4, c2, d21), (a66, b4, c2, d22), (a66, b4, c3, d1), (a66, b4, c3, d2), (a66, b4, c3, d3), (a66, b4, c3, d4), (a66, b4, c3, d5), (a66, b4, c3, d6), (a66, b4, c3, d7), (a66, b4, c3, d8), (a66, b4, c3, d9), (a66, b4, c3, d10), (a66, b4, c3, d11), (a66, b4, c3, d12), (a66, b4, c3, d13), (a66, b4, c3, d14), (a66, b4, c3, d15), (a66, b4, c3, d16), (a66, b4, c3, d17), (a66, b4, c3, d18), (a66, b4, c3, d19), (a66, b4, c3, d20), (a66, b4, c3, d21), (a66, b4, c3, d22), (a66, b5, c1, d1), (a66, b5, c1, d2), (a66, b5, c1, d3), (a66, b5, c1, d4), (a66, b5, c1, d5), (a66, b5, c1, d6), (a66, b5, c1, d7), (a66, b5, c1, d8), (a66, b5, c1, d9), (a66, b5, c1, d10), (a66, b5, c1, d11), (a66, b5, c1, d12), (a66, b5, c1, d13), (a66, b5, c1, d14), (a66, b5, c1, d15), (a66, b5, c1, d16), (a66, b5, c1, d17), (a66, b5, c1, d18), (a66, b5, c1, d19), (a66, b5, c1, d20), (a66, b5, c1, d21), (a66, b5, c1, d22), (a66, b5, c2, d1), (a66, b5, c2, d2), (a66, b5, c2, d3), (a66, b5, c2, d4), (a66, b5, c2, d5), (a66, b5, c2, d6), (a66, b5, c2, d7), (a66, b5, c2, d8), (a66, b5, c2, d9), (a66, b5, c2, d10), (a66, b5, c2, d11), (a66, b5, c2, d12), (a66, b5, c2, d13), (a66, b5, c2, d14), (a66, b5, c2, d15), (a66, b5, c2, d16), (a66, b5, c2, d17), (a66, b5, c2, d18), (a66, b5, c2, d19), (a66, b5, c2, d20), (a66, b5, c2, d21), (a66, b5, c2, d22), (a66, b5, c3, d1), (a66, b5, c3, d2), (a66, b5, c3, d3), (a66, b5, c3, d4), (a66, b5, c3, d5), (a66, b5, c3, d6), (a66, b5, c3, d7), (a66, b5, c3, d8), (a66, b5, c3, d9), (a66, b5, c3, d10), (a66, b5, c3, d11), (a66, b5, c3, d12), (a66, b5, c3, d13), (a66, b5, c3, d14), (a66, b5, c3, d15), (a66, b5, c3, d16), (a66, b5, c3, d17), (a66, b5, c3, d18), (a66, b5, c3, d19), (a66, b5, c3, d20), (a66, b5, c3, d21), (a66, b5, c3, d22), (a66, b6, c1, d1), (a66, c6, c1, d2), (a66, b6, c1, d3), (a66, b6, c1, d4), (a66, b6, c1, d5), (a66, b6, c1, d6), (a66, b6, c1, d7), (a66, b6, c1, d8), (a66, b6, c1, d9), (a66, b6, c1, d10), (a66, b6, c1, d11), (a66, b6, c1, d12), (a66, b6, c1, d13), (a66, b6, c1, d14), (a66, b6, c1, d15), (a66, b6, c1, d16), (a66, b6, c1, d17), (a66, b6, c1, d18), (a66, b6, c1, d19), (a66, b6, c1, d20), (a66, b6, c1, d21), (a66, b6, c1, d22), (a66, b6, c2, d1), (a66, b6, c2, d2), (a66, b6, c2, d3), (a66, b6, c2, d4), (a66, b6, c2, d5), (a66, b6, c2, d6), (a66, b6, c2, d7), (a66, b6, c2, d8), (a66, b6, c2, d9), (a66, b6, c2, d10), (a66, b6, c2, d11), (a66, b6, c2, d12), (a66, b6, c2, d12), (a66, b6, c2, d14), (a66, b6, c2, d15), (a66, b6, c2, d16), (a66, b6, c2, d17), (a66, b6, c2, d18), (a66, b6, c2, d19), (a66, b6, c2, d20), (a66, b6, c2, d21), (a66, b6, c2, d22), (a66, b6, c3, d1), (a66, b6, c3, d2), (a66, b6, c3, d3), (a66, b6, c3, d4), (a66, b6, c3, d5), (a66, b6, c3, d6), (a66, b6, c3, d7), (a66, b6, c3, d8), (a66, b6, c3, d9), (a66, b6, c3, d10), (a66, b6, c3, d11), (a66, b6, c3, d12), (a66, b6, c3, d13), (a66, b6, c3, d14), (a66, b6, c3, d15), (a66, b6, c3, d16), (a66, b6, c3, d17), (a66, b6, c3, d18), (a66, b6, c3, d19), (a66, b6, c3, d20), (a66, b6, c3, d21), (a66, b6, c3, d22), (a67, b1, c1, d1), (a67, b1, c1, d2), (a67, b1, c1, d3), (a67, b1, c1, d4), (a67, b1, c1, d5), (a67, b1, c1, d6), (a67, b1, c1, d7), (a67, b1, c1, d8), (a67, b1, c1, d9), (a67, b1, c1, d10), (a67, b1, c1, d11), (a6, b1, c1, d12), (a67, b1, c1, d13), (a67, b1, c1, d14), (a67, b1, c1, d15), (a67, b1, c1, d16), (a67, b1, c1, d17), (a67, b1, c1, d18), (a67, b1, c1, d19), (a67, b1, c1, d20), (a67, b1, c1, d21), (a67, b1, c1, d22), (a67, b1, c2, d1), (a67, b1, c2, d2), (a67, b1, c2, d3), (a67, b1, c2, d4), (a67, b1, c2, d5), (a67, b1, c2, d6), (a67, b1, c2, d7), (a67, b1, c2, d8), (a67, b1, c2, d9), (a67, b1, c2, d10), (a67, b1, c2, d11), (a67, b1, c2, d12), (a67, b1, c2, d13), (a67, b1, c2, d14), (a67, b1, c2, d15), (a67, b1, c2, d16), (a67, b1, c2, d17), (a67, b1, c2, d18), (a67, b1, c2, d19), (a67, b1, c2, d20), (a67, b1, c2, d21), (a67, b1, c3, d22), (a67, b1, c3, d1), (a67, b1, c3, d2), (a67, b1, c3, d3), (a67, b1, c3, d4), (a67, c3, d5), (a67, b1, c3, d6), (a67, b1, c3, d7), (a67, b1, c3, d8), (a67, b1, c3, d9), (a67, b1, c3, d10), (a67, b1, c3, d11), (a67, b1, c3, d12), (a67, b1, c3, d13), (a61, b1, c3, d14), (a67, b1, c3, d15), (a67, b1, c3, d16), (a67, b1, c3, d17), (a67, b1, c3, d18), (a67, b1, c3, d19), (a67, b1, c3, d20), (a67, b1, c3, d21), (a67, b1, c3, d22), (a67, b2, c1, d1), (a37, b2, c1, d2), (a67, b2, c1, d3), (a61, b2, c1, d4), (a67, b2, c1, d5), (a67, b2, c1, d6), (a67, b2, c1, d7), (a67, b2, c1, d8), (a67, b2, c1, d9), (a67, b2, c1, d10), (a67, b2, c1, d11), (a67, b2, c1, d12), (a67, b2, c1, d13), (a67, b2, c1, d14), (a67, b2, c1, d15), (a67, b2, c1, d16), (a67, b2, c1, d17), (a67, b2, c1, d18), (a7, b2, c1, d19), (a67, b2, c1, d20), (a67, b2, c1, d21), (a67, b2, c1, d22), (a67, b2, c2, d1), (a67, b2, c2, d2), (a67, b2, c2, d3), (a67, b2, c2, d4), (a67, b2, c2, d5), (a67, b2, c2, d6), (a67, b2, c2, d7), (a67, b2, c2, d8), (a67, b2, c2, d9), (a67, b2, c2, d10), (a67, b2, c2, d11), (a67, b2, c2, d12), (a67, b2, c2, d13), (a67, b2, c2, d14), (a67, b2, c2, d15), (a67, b2, c2, d16), (a67, b2, c2, d17), (a67, b2, c2, d18), (a67, b2, c2, d91), (a67, b2, c2, d20), (a67, b2, c2 d21), (a67, b2, c2, d22), (a67, b2, c3, d1), (a67, b2, c3, d2), (a67, b2, c3, d3), (a67, b2, c1, d4), (a67, b2, c3, d5), (a67, b2, c3, d6), (a67, b2, c3, d7), (a67, b2, c3, d8), (a67, b2, c3, d9), (a6, b2, 3, d10), (a7, b2, c3, d11), (a67, b2, c3, d12), (a67, b2, c3, d13), (a67, b2, c3, d14), (a67, b2, c3, d15), (a67, b2, c3, d16), (a67, b2, c3, d17), (a67, b2, c3, d18), (a67, b2, c3, d19), (a67, b2, c3, d20), (a67, b2, c3, d21), (a67, b2, c3, d22), (a67, b3, c1, d1), (a67, b3, c1, d2), (a67, b3, c1, d3), (a67, b3, c1, d4), (a67, b3, c1, d5), (a67, b3, c1, d6), (a67, b3, c1, d7), (a67, b3, c1, d8), (a67, b3, c1, d9), (a67, b3, c1, d10), (a67, b3, c1, d11), (a67, b3, c1, d12), (a67, b3, c1, d13), (a67, b3, c1, d14), (a67, b3, c1, d15), (a67, b3, c1, d16), (a67, b3, c1, d16), (a67, b3, c1, d17), (a67, b3, c1, d18), (a67, b3, c1, d19), (a67, b3, c1, d20), (a67, b3, c1, d21), (a67, b3, c1, d22), (a67, b3, c2, d1), (a67, b3, c2, d2), (a67, b3, c2, d3), (a67, b3, c2, d4), (a67, b3, c2, d5), (a67, b3, c2, d6), (a67, b3, c2, d7), (a67, b3, c2, d8), (a67, b3, c2, d9), (a67, b3, c2, d10), (a67, b3, c2, d11), (a67, b3, c2, d12), (a67, b3, c2, d13), (a67, b3, c2, d14), (a67, b3, c2, d15), (a67, b3, c2, d16), (a67, b3, c2, d17), (a67, b3, c2, d18), (a67, b3, c2, d19), (a67, b3, c2, d20), (a67, b3, c2, d21), (a67, b3, c2, d22), (a67, b3, c3, d11), (a67, b3, c3, d2), (a67, b3, c3, d3), (a67, b3, c3, d4), (a67, b3, c3, d5), (a67, b3, c3, d6), (a67, b3, c3, d7), (a67, b3, c3, d8), (a67, b3, c3, d9), (a67, b3, c3, d10), (a67, b3, c3, d11), (a67, b3, c3, d12), (a67, b3, c3, d13), (a67, b3, c3, d14), (a67, b3, c3, d15), (a67, b3, c3, d16), (a67, b3, c3, d17), (a67, b3, c3, d18), (a67, b3, c3, d19), (a67, b3, c3, d20), (a67, b3, c3, d21), (a67, b3, c3, d22), (a67, b4, c1, d1), (a67, b4, c1, d2), (a67, b4, c1, d3), (a67, b4, c1, d4), (a67, b4, c1, d5), (a67, b4, c1, d6), (a67, b4, c1, d7), (a67, b4, c1, d8), (a67, b4, c1, d9), (a67, b4, c1, d10), (a67, b4, c1, d11), (a67, b4, c1, d12), (a67, b4, c1, d13), (a67, b4, c1, d14), (a67, b4, c1, d15), (a67, b4, c1, d16), (a67, b4, c1, d17), (a67, b4, c1, d18), (a67, b4, c1, d19), (a67, b4, c1, d20), (a67, b4, c1, d21), (a67, b4, c1, d22), (a67, b4, c2, d1), (a67, b4, c2, d2), (a67, b4, c2, d3), (a67, b4, c2, d4), (a67, b4, c2, d5), (a67, b4, c2, d6), (a67, b4, c2, d7), (a67, b4, c2, d8), (a67, b4, c2, d9), (a67, b4, c2, d10), (a67, b4, c2, d11), (a67, b4, c2, d12), (a67, b4, c2, d13), (a67, b4, c2, d14), (a67, b4, c2, d15), (a67, b4, c2, d16), (a67, b4, c2, d17), (a67, b4, c2, d18), (a67, b4, c2, d19), (a67, b4, c2, d20), (a67, b4, c2, d21), (a67, b4, c2, d22), (a67, b4, c3, d1), (a67, b4, c3, d2), (a67, b4, c3, d3), (a67, b4, c3, d4), (a67, b4, c3, d5), (a67, b4, c3, d6), (a67, b4, c3, d7), (a67, b4, c3, d8), (a67, b4, c3, d9), (a67, b4, c3, d10), (a67, b4, c3, d11), (a67, b4, c3, d12), (a67, b4, c3, d13), (a67, b4, c3, d4), (a67, b4, c3, d15), (a67, b4, c3, d16), (a67, b4, c3, d17), (a67, b4, c3, d18), (a67, b4, c3, d19), (a67, b4, c3, d20), (a67, b4, c3, d21), (a67, b4, c3, d22), (a67, b5, c1, d1), (a67, b5, c1, d2), (a67, b5, c1, d3), (a67, b5, c1, d4), (a67, b5, c1, d5), (a67, b5, c1, d6), (a67, b5, c1, d7), (a67, b5, c1, d8), (a67, b5, c1, d9), (a67, b5, c1, d10), (a67, b5, c1, d11), (a67, b5, c1, d12), (a67, b5, c1, d13), (a67, b5, c1, d14), (a67, b5, c1, d15), (a67, b5, c1, d16), (a67, b5, c1, d17), (a67, b5, c1, d18), (a67, b5, c1, d19), (a67, b5, c1, d20), (a67, b5, c1, d21), (a67, b5, c1, d22), (a67, b5, c2, d1), (a67, b5, c2, d2), (a67, b5, c2, d3), (a67, b5, c2, d4), (a67, b5, c2, d5), (a67, b5, c2, d6), (a67, b5, c2, d7), (a67, b5, c2, d8), (a67, b5, c2, d9), (a67, b5, c2, d10), (a67, b5, c2, d11), (a67, b5, c2, d12), (a67, b5, c2, d13), (a67, b5, c2, d14), (a67, b5, c2, d15), (a67, b5, c2, d16), (a67, b5, c2, d17), (a67, b5, c2, d18), (a67, b5, c2, d19), (a67, b5, c2, d20), (a67, b5, c2, d21), (a67, b5, c2, d22), (a67, b5, c3, d1), (a67, b5, c3, d2), (a67, b5, c3, d3), (a67, b5, c3, d4), (a67, b5, c3, d5), (a67, b5, c3, d6), (a67, b5, c3, d7), (a67, b5, c3, d8), (a67, b5, c3, d9), (a67, b5, c3, d6), (a67, b5, c3, d11), (a67, b5, c3, d12), (a67, b5, c3, d13), (a67, b5, c3, d14), (a67, b5, c3, d15), (a67, b5, c3, d16), (a67, b5, c3, d17), (a67, b5, c3, d18), (a67, b5, c3, d19), (a67, b5, c3, d20), (a67, b5, c3, d21), (a67, b5, c3, d22), (a67, b6, c1, d1), (a67, b6, c1, d2), (a67, b6, c1, d3), (a67, b6, c1, d4), (a67, b6, c1, d5), (a67, b6, c1, d6), (a67, b6, c1, d7), (a67, b6, c1, d8), (a67, b6, c1, d9), (a67, b6, c1, d10), (a67, b6, c1, d11), (a67, b6, c1, d12), (a67, b6, c1, d13), (a67, b6, c1, d14), (a67, b6, c1, d15), (a67, b6, c1, d16), (a67, b6, c1, d17), (a67, b6, c1, d18), (a67, b6, c1, d19), (a67, b6, c1, d20), (a61, b6, c1, d21), (a67, b6, c1, d22), (a67, b6, c2, d1), (a67, b6, c2, d2), (a67, b6, c2, d3), (a67, b6, c2, d4), (a67, b6, c2, d5), (a67, b6, c2, d6), (a67, b6, c2, d7), (a67, b6, c2, d8), (a67, b6, c2, d9), (a67, b6, c2, d10), (a67, b6, c2, d11), (a67, b6, c2, d12), (a67, b6, c2, d13), (a67, b6, c2, d14), (a67, b6, c2, d15), (a67, b6, c2, d16), (a67, b6, c2, d17), (a67, b6, c2, d18), (a67, b6, c2, d19), (a67, b6, c2, d20), (a67, b6, c2, d21), (a67, b6, c2, d22), (a67, b6, c3, d1), (a67, b6, c3, d2), (a67, b6, c3, d3), (a67, b6, c3, d4), (a67, b6, c3, d5), (a67, b6, c3, d6), (a67, b6, c3, d7), (a67, b6, c3, d8), (a67, b6, c3, d9), (a67, b6, c3, d10), (a67, b6, c3, d11), (a67, b6, c3, d12), (a67, b6, c3, d13), (a67, b6, c3, d14), (a67, b6, c3, d15), (a67, b6, c3, d16), (a67, b6, c3, d17), (a67, b6, c3, d18), (a67, b6, c3, d19), (a67, b6, c3, d20), (a67, b6, c3, d21), (a67, b6, c3, d22), (a68, b1, c1, d1), (a68, b1, c1, d2), (a68, b1, c1, d3), (a68, b1, c1, d4), (a68, b1, c1, d5), (a68, b1, c1, d6), (a68, b1, c1, d7), (a68, b1, c1, d8), (a68, b1, c1, d9), (a68, b1, c1, d10), (a68, b1, c1, d11), (a68, b1, c1, d12), (a68, b1, c1, d13), (a68, b1, c1, d14), (a68, b1, c1, d15), (a68, b1, c1, d16), (a68, b1, c1, d17), (a68, b1, c1, d18), (a68, b1, c1, d19), (a68, b1, c1, d20), (a68, b1, c1, d21), (a68, b1, c1, d22), (a68, b1, c2, d1), (a68, b1, c2, d2), (a68, b1, c2, d3), (a68, b1, c2, d4), (a68, b1, c2, d5), (a68, b1, c2, d6), (a68, b1, c2, d7), (a68, b1, c2, d8), (a68, b1, c2, d9), (a68, b1, c2, d10), (a68, b1, c2, d11), (a68, b1, c2, d12), (a68, b1, c2, d13), (a68, b1, c2, d14), (a68, b1, c2, d15), (a68, b1, c2, d16), (a68, b1, c2, d17), (a68, b1, c2, d18), (a68, b1, c2, d19), (a68, b1, c2, d20), (a68, b1, c2, d21), (a68, b1, c2, d22), (a68, b1, c3, d1), (a68, b1, c3, d2), (a68, b1, c3, d3), (a68, b1, c3, d4), (a68, b1, c3, d5), (a68, b1, c3, d6), (a68, b1, c3, d7), (a68, b1, c3, d8), (a68, b1, c3, d9), (a68, b1, c3, d10), (a68, b1, c3, d11), (a68, b1, c3, d12), (a68, b1, c3, d13), (a68, b1, c3, d14), (a68, b1, c3, d15), (a68, b1, c3, d16), (a68, b1, c3, d17), (a68, b1, c3, d18), (a68, b1, c3, d19), (a68, b1, c3, d20), (a68, b, c3, d21), (a68, b1, c3, d22), (a68, b2, c1, d1), (a68, b2, c1, d2), (a68, b2, c1, d3), (a68, b2, c1, d4), (a68, b2, c1, d5), (a68, b2, c1, d6), (a68, b2, c1, d7), (a68, b2, c1, d8), (a68, b2, c1, d9), (a68, b2, c1, d10), (a68, b2, c1, d11), (a68, b2, c1, d12), (a68, b2, c1, d13), (a68, b2, c1, d14), (a68, b2, c1, d15), (a68, b2, c1, d16), (a68, b2, c1, d17), (a68, b2, c1, d18), (a68, b2, c1, d19), (a68, b2, c1, d20), (a68, b2, c1, d21), (a68, b2, c1, d22), (a68, b2, c2, d1), (a68, b2, c2, d2), (a68, b2, c2, d3), (a68, b2, c2, d4), (a68, b2, c2, d5), (a68, b2, c2, d6), (a68, b2, c2, d7), (a68, b2, c2, d8), (a68, b2, c2, d9), (a68, b2, c2, d10), (a68, b2, c2, d11), (a68, b2, c2, d12), (a68, b2, c2, d13), (a68, b2, c2, d14), (a68, b2, c2, d15), (a68, b2, c2, d16), (a68, b2, c2, d17), (a68, b2, c2, d18), (a68, b2, c2, d19), (a68, b2, c2, d20), (a68, b2, c2, d21), (a68, b2, c2, d22), (a68, b2, c3, d1), (a68, b2, c3, d2), (a68, b2, c3, d3), (a68, b2, c3, d4), (a68, b2, c3, d5), (a68, b2, c3, d6), (a68, b2, c3, d7), (a68, b2, c3, d8), (a68, b2, c3, d9), (a68, b2, c3, d10), (a68, b2, c3, d11), (a68, b2, c3, d12), (a68, b2, c3, d13), (a68, b2, c3, d14), (a68, b2, c3, d15), (a68, b2, c3, d16), (a68, b2, c3, d17), (a68, b2, c3, d18), (a68, b2, c3, d19), (a68, b2, c3, d20), (a68, b2, c3, d21), (a68, b2, c3, d22), (a68, b3, c1, d1), (a68, b3, c1, d2), (a68, b3, c1, d3), (a68, b3, c1, d4), (a68, b3, c1, d5), (a68, b3, c1, d6), (a68, b3, c1, d7), (a68, b3, c1, d8), (a68, b3, c1, d9), (a68, b3, c1, d10), (a68, b3, c1, d11), (a68, b3, c1, d12), (a68, b3, c1, d13), (a68, b3, c1, d14), (a68, b3, c1, d15), (a68, b3, c1, d16), (a68, b3, c1, d17), (a68, b3, c1, d18), (a68, b3, c1, d19), (a68, b3, c1, d20), (a68, b3, c1, d21), (a68, b3, c1, d22), (a68, b3, c2, d1), (a68, b3, c2, d2), (a68, b3, c2, d3), (a68, b3, c2, d4), (a68, b3, c2, d5), (a68, b3, c2, d6), (a68, b3, c2, d7), (a68, b3, c2, d8), (a68, b3, c2, d9), (a68, b3, c2, d10), (a68, b3, c2, d11), (a68, b3, c2, d12), (a68, b3, c2, d13), (a68, b3, c2, d14), (a68, b3, c2, d15), (a68, b3, c2, d16), (a68, b3, c2, d17), (a68, b3, c2, d18), (a68, b3, c2, d19), (a68, b3, c2, d20), (a68, b3, c2, d21), (a68, b3, c2, d22), (a68, b3, c3, d1), (a68, b3, c3, d2), (a68, b3, c3, d3), (a68, b3, c3, d4), (a68, b3, c3, d5), (a68, b3, c3, d6), (a68, b3, c3, d7), (a68, b3, c3, d8), (a68, b3, c3, d9), (a68, b3, c3, d10), (a68, b3, c3, d11), (a68, b3, c3, d12), (a68, b3, c3, d13), (a68, b3, c3, d14), (a68, b3, c3, d15), (a68, b3, c3, d16), (a68, b3, c3, d17), (a68, b3, c3, d18), (a68, b3, c3, d19), (a68, b3, c3, d20), (a68, b3, c3, d21), (a68, b3, c3, d22), (a68, b4, c1, d1), (a68, b4, c1, d2), (a68, b4, c1, d3), (a68, b4, c1, d4), (a68, b4, c1, d5), (a68, b4, c1, d6), (a68, b4, c1, d7), (a68, b4, c1, d8), (a68, b4, c1, d9), (a68, b4, c1, d10), (a68, b4, c1, d11), (a68, b4, c1, d12), (a68, b4, c1, d13), (a68, b4, c1, d14), (a68, b4, c1, d15), (a68, b4, c1, d16), (a68, b4, c1, d17), (a68, b4, c1, d18), (a68, b4, c1, d19), (a68, b4, c2, d1), (a68, b4, c2, d2), (a68, b4, c2, d3), (a68, b4, c2, d4), (a68, b4, c2, d5), (a68, b4, c2, d6), (a68, b4, c2, d7), (a68, b4, c2, d8), (a68, b4, c2, d9), (a68, b4, c2, d10), (a68, b4, c2, d11), (a68, b4, c2, d12), (a68, b4, c2, d13), (a68, b4, c2, d14), (a68, b4, c2, d15), (a68, b4, c2, d16), (a68, b4, c2, d17), (a68, b4, c2, d18), (a68, b4, c2, d19), (a68, b4, c2, d20), (a68, b4, c2, d21), (a68, b4, c2, d22), (a68, b4, c3, d1), (a68, b4, c3, d2), (a68, b4, c3, d3), (a68, b4, c3, d14), (a68, b4, c3, d5), (a68, b4, c3, d6), (a68, b4, c3, d7), (a68, b4, c3, d8), (a68, b4, c3, d9), (a68, b4, c3, d10), (a68, b4, c3, d11), (a68, b4, c3, d12), (a68, b4, c3, d13), (a68, b4, c3, d14), (a68, b4, c3, d15), (a68, b4, c3, d16), (a68, b4, c3, d17), (a68, b4, c3, d18), (a68, b4, c3, d19), (a68, b4, c3, d20), (a68, b4, c3, d21), (a68, b4, c3, d22), (a68, b5, c1, d1), (a68, b5, c1, d2), (a68, b5, c1, d3), (a68, b5, c1, d4), (a68, b5, c1, d5), (a68, b5, c1, d6), (a68, b5, c1, d7), (a68, b5, c1, d8), (a68, b5, c1, d9), (a68, b5, c1, d10), (a68, b5, c1, d11), (a68, b5, c1, d12), (a68, b5, c1, d13), (a68, b5, c1, d14), (a68, b5, c1, d15), (a68, b5, c1, d16), (a68, b5, c1, d17), (a68, b5, c1, d18), (a68, b5, c1, d19), (a68, b5, c1, d20), (a68, b5, c1, d21), (a68, b5, c1, d22), (a68, b5, c2, d1), (a68, b5, c2, d2), (a68, b5, c2, d3), (a68, b5, c2, d4), (a68, b5, c2, d5), (a68, b5, c2, d6), (a68, b5, c2, d7), (a68, b5, c2, d8), (a68, b5, c2, d9), (a68, b5, c2, d10), (a68, b5, c2, d11), (a68, b5, c2, d12), (a68, b5, c2, d13), (a68, b5, c2, d14), (a68, b5, c2, d15), (a68, b5, c2, d16), (a68, b5, c2, d17), (a68, b5, c2, d18), (a68, b5, c2, d19), (a68, b5, c2, d20), (a68, b5, c2, d21), (a68, b5, c2, d22), (a68, b5, c3, d1), (a68, b5, c3, d2), (a38, b5, c3, d3), (a68, b5, c3, d4), (a38, b5, c3, d5), (a68, b5, c3, d5), (a55, b5, c3, d7), (a68, b5, c3, d8), (a68, b5, c3, d9), (a68, b5, c3, d10), (a68, b5, c3, d11), (a68, b5, c3, d12), (a55, b5, c3, d13), (a68, b5, c3, d14), (a55, b5, c3, d15), (a68, b5, c3, d16), (a68, b5, c3, d17), (a68, b5, c3, d18), (a68, b5, c3, d19), (a68, b5, c3, d20), (a55, b5, c3, d21), (a68, b5, c3, d22), (a68, b5, c1, d1), (a68, b5, c1, d2), (a55, b5, c1, d3), (a68, b5, c1, d4), (a68, b6, c1, d5), (a68, b5, c1, d6), (a68, b6, c1, d7), (a68, b6, c1, d8), (a68, b6, c1, d9), (a68, b6, c1, d10), (a68, b6, c1, d11), (a68, b6, c1, d12), (a68, b6, c1, d13), (a68, b6, c1, d14), (a68, b6, c1, d15), (a68, b6, c1, d16), (a68, b6, c1, d17), (a68, b6, c1, d18), (a68, b6, c1, d19), (a68, b6, c1, d20), (a68, b6, c1, d21), (a68, b6, c1, d22), (a68, b6, c2, d1), (a68, b6, c2, d2), (a68, b6, c2, d3), (a68, b6, c2, d4), (a68, b6, c2, d5), (a68, b6, c2, d6), (a68, b6, c2, d7), (a68, b6, c2, d8), (a68, b6, c2, d9), (a68, b6, c2, d10), (a68, b6, c2, d11), (a68, b6, c2, d12), (a68, b6, c2, d13), (a68, b6, c2, d14), (a68, b6, c2, d15), (a68, b6, c2, d16), (a68, b6, c2, d17), (a68, b6, c2, d18), (a68, b6, c2, d19), (a68, b6, c2, d20), (a68, b6, c2, d21), (a68, b6, c2, d22), (a68, b6, c3, d1), (a68, b6, c3, d2), (a68, b6, c3, d3), (a68, b6, c3, d4), (a68, b6, c3, d5), (a68, b6, c3, d6), (a68, b6, c3, d7), (a68, b6, c3, d8), (a68, b6, c3, d9), (a68, b6, c3, d10), (a68, b6, c3, d11), (a68, b6, c3, d12), (a68, b6, c3, d13), (a68, b6, c3, d14), (a68, b6, c3, d15), (a68, b6, c3, d16), (a68, b6, c3, d17), (a68, b6, c3, d18), (a68, b6, c3, d19), (a68, b6, c3, d20), (a68, b6, c3, d21), (a68, b6, c3, d22), (a69, b1, c1, d1), (a69, b1, c1, d2), (a69, b1, c1, d3), (a69, b1, c1, d4), (a69, b1, c1, d5), (a69, b1, c1, d6), (a69, b1, c1, d7), (a69, b1, c1, d8), (a69, b1, c1, d9), (a69, b1, c1, d10), (a69, b1, c1, d11), (a69, b1, c1, d12), (a69, b1, c1, d13), (a69, b1, c1, d14), (a69, b1, c1, d15), (a69, b1, c1, d10), (a69, b1, c1, d17), (a69, b1, c1, d18), (a69, b1, c1, d19), (a69, b1, c1, d20), (a69, b1, c1, d21), (a69, b1, c1, d22), (a69, b1, c2, d1), (a69, b1, c2, d2), (a69, b1, c2, d3), (a69, b1, c2, d4), (a69, b1, c2, d5), (a69, b1, c2, d6), (a69, b1, c2, d7), (a66, b1, c2, d8), (a69, b1, c2, d9), (a69, b1, c2, d10), (a69, b1, c2, d11), (a69, b1, c2, d12), (a69, b1, c2, d13), (a69, b1, c2, d14), (a69, b1, c2, d15), (a66, b1, c2, d16), (a69, b1, c2, d17), (a69, b1, c2, d18), (a69, b1, c2, d19), (a59, b1, c2, d20), (a69, b1, c2, d21), (a69, b1, c2, d22), (a69, b1, c3, d1), (a69, b1, c3, d2), (a69, b1, c3, d3), (a69, b1, c3, d4), (a69, b1, c3, d5), (a69, b1, c3, d6), (a69, b1, c3, d7), (a69, b1, c3, d8), (a69, b1, c3, d9), (a69, b1, c3, d10), (a69, b1, c3, d11), (a69, b1, c3, d12), (a69, b1, c3, d13), (a69, b1, c3, d14), (a69, b1, c3, d15), (a69, b1, c3, d16), (a69, b1, c3, d17), (a69, b1, c3, d18), (a69, b1, c3, d19), (a69, b1, c3, d20), (a69, b1, c3, d21), (a69, b1, c3, d22), (a69, b2, c1, d1), (a69, b2, c1, d2), (a69, b2, c1, d3), (a69, b2, c1, d4), (a69, b2, c1, d5), (a69, b2, c1, d6), (a69, b2, c1, d7), (a69, b2, c1, d8), (a69, b2, c1, d19), (a69, b2, c1, d10), (a69, b2, c1, d11), (a69, b2, c1, d12), (a69, b2, c1, d13), (a69, b2, c1, d14), (a69, b2, c1, d15), (a69, b2, c1, d16), (a69, b2, c1, d17), (a69, b2, c1, d18), (a9, b2, c1, d19), (a69, b2, c1, d20), (a69, b2, c1, d21), (a69, b2, c1, d22), (a69, b2, c2, d1), (a69, b2, c2, d2), (a69, b2, c2, d3), (a69, b2, c2, d4), (a69, b2, c2, d5), (a69, b2, c2, d6), (a69, b2, c2, d7), (a69, b2, c2, d8), (a69, b2, c2, d9), (a69, b2, c2, d10), (a69, b2, c2, d11), (a69, b2, c2, d12), (a69, b2, c2, d13), (a69, b2, c2, d14), (a69, b2, c2, d15), (a69, b2, c2, d16), (a69, b2, c2, d17), (a69, b2, c2, d18), (a69, b2, c2, d10), (a69, b2, c2, d20), (a69, b2, c2, d21), (a66, b2, c2, d22), (a69, b2, c3, d1), (a69, b2, c3, d2), (a69, b2, c3, d3), (a69, b2, c3, d4), (a66, b2, c3, d5), (a69, b2, c3, d6), (a69, b2, c3, d7), (a69, b2, c3, d8), (a69, b2, c3, d9), (a69, b2, c3, d10), (a69, b2, c3, d11), (a69, b2, c3, d12), (a69, b2, c3, d13), (a69, b2, c3, d14), (a69, b2, c3, d15), (a69, b2, c3, d16), (a69, b2, c3, d17), (a69, b2, c3, d18), (a66, b2, c3, d19), (a69, b2, c3, d20), (a69, b2, c3, d21), (a69, b2, c3, d22), (a69, b2, c3, d1), (a69, b2, c3, d2), (a69, b3, c1, d3), (a69, b3, c1, d4), (a69, b3, c1, d5), (a69, b3, c1, d6), (a69, b3, c1, d7), (a69, b3, c1, d8), (a69, b3, c1, d9), (a69, b3, c1, d10), (a69, b3, c1, d11), (a69, b3, c1, d12), (a69, b3, c1, d13), (a69, b3, c1, d14), (a69, b3, c1, d15), (a69, b3, c1, d16), (a69, b3, c1, d17), (a69, b3, c1, d18), (a66, b3, c1, d19), (a69, b3, c1, d20), (a69, b3, c1, d21), (a69, b3, c1, d22), (a69, b3, c2, d1), (a66, b3, c2, d2), (a69, b3, c2, d3), (a69, b3, c2, d4), (a69, b3, c2, d5), (a66, b3, c2, d6), (a69, b3, c2, d7), (a69, b3, c2, d8), (a69, b3, c2, d9), (a69, b3, c2, d10), (a69, b3, c2, d11), (a69, b3, c2, d12), (a69, b3, c2, d13), (a69, b3, c2, d14), (a69, b3, c2, d15), (a69, b3, c2, d16), (a69, b3, c2, d17), (a69, b3, c2, d18), (a69, b3, c2, d19), (a69, b3, c2, d20), (a69, b3, c2, d21), (a69, b3, c2, d22), (a69, b3, c3, d1), (a69, b3, c3, d2), (a69, b3, c3, d3), (a69, b3, c3, d4), (a69, b3, c3, d5), (a69, b3, c3, d6), (a69, b3, c3, d7), (a69, b3, c3, d3), (a69, b3, c3, d9), (a69, b3, c3, d10), (a69, b3, c3, d11), (a69, b3, c3, d12), (a69, b3, c3, d13), (a69, b3, c3, d14), (a69, b3, c3, d15), (a69, b3, c3, d16), (a69, b3, c3, d17), (a69, b3, c3, d18), (a69, b5, c3, d19), (a69, b3, c3, d20), (a69, b3, c3, d21), (a69, b3, c3, d22), (a69, b4, c1, d1), (a69, b4, c1, d2), (a69, b4, c1, d3), (a69, b4, c1, d4), (a69, b4, c1, d5), (a69, b4, c1, d6), (a69, b4, c1, d7), (a69, b4, c1, d8), (a69, b4, c1, d9), (a69, b4, c1, d10), (a69, b4, c1, d11), (a69, b4, c1, d12), (a69, b4, c1, d13), (a69, b4, c1, d14), (a69, b4, c1, d15), (a69, b4, c1, d16), (a69, b4, c1, d17), (a69, b4, c1, d18), (a69, b4, c1, d19), (a69, b4, c1, d20), (a69, b4, c1, d21), (a69, b4, c1, d22), (a69, b4, c2, d1), (a69, b4, c2, d2), (a69, b4, c2, d3), (a69, b4, c2, d4), (a69, b4, c2, d5), (a69, b4, c2, d6), (a66, b4, c2, d7), (a69, b4, c2, d3), (a69, b4, c2, d9), (a69, b4, c2, d10), (a69, b4, c2, d11), (a69, b4, c2, d12), (a69, b4, c2, d13), (a69, b4, c2, d14), (a69, b4, c2, d15), (a69, b4, c2, d16), (a69, b4, c2, d17), (a69, b4, c2, d13), (a69, b4, c2, d14), (a69, b4, c2, d20), (a66, b4, c2, d21), (a69, b4, c2, d22), (a69, b4, c3, d1), (a69, b4, c3, d2), (a69, b4, c3, d3), (a69, b4, c3, d4), (a66, b4, c3, d5), (a69, b4, c3, d6), (a69, b4, c3, d7), (a69, b4, c3, d8), (a69, b4, c3, d9), (a69, b4, c3, d10), (a69, b4, c3, d11), (a69, b4, c3, d12), (a69, b4, c3, d13), (a69, b4, c3, d14), (a69, b4, c3, d15), (a69, b4, c3, d16), (a69, b4, c3, d17), (a69, b4, c3, d18), (a69, b4, c3, d19), (a66, b4, c3, d20), (a69, b4, c3, d21), (a69, b4, c3, d22), (a69, b5, c1, d1), (a69, b5, c1, d2), (a69, b5, c1, d3), (a69, b5, c1, d4), (a69, b5, c1, d5), (a39, b5, c1, d6), (a69, b5, c1, d7), (a69, b5, c1, d8), (a69, b5, c1, d9), (a69, b5, c1, d10), (a69, b5, c1, d11), (a69, b5, c1, d12), (a69, b5, c1, d13), (a69, b5, c1, d14), (a69, b5, c1, d15), (a69, b5, c1, d16), (a69, b5, c1, d17), (a69, b5, c1, d18), (a69, b5, c1, d19), (a69, b5, c1, d20), (a69, b5, c1, d21), (a69, b5, c1, d22), (a69, b5, c2, d1), (a69, b5, c2, d2), (a69, b5, c2, d3), (a69, b5, c2, d4), (a69, b5, c2, d5), (a69, b5, c2, d6), (a69, b5, c2, d7), (a69, b5, c2, d8), (a69, b5, c2, d9), (a69, b5, c2, d10), (a69, b5, c2, d11), (a69, b5, c2, d12), (a69, b5, c2, d13), (a69, b5, c2, d14), (a69, b5, c2, d15), (a69, b5, c2, d16), (a69, b5, c2, d17), (a69, b5, c2, d18), (a69, b5, c2, d19), (a69, b5, c2, d20), (a69, b5, c2, d21), (a69, b5, c2, d22), (a69, b5, c3, d1), (a69, b5, c3, d2), (a69, b5, c3, d3), (a69, b5, c3, d4), (a69, b5, c3, d5), (a69, b5, c3, d6), (a69, b5, c3, d7), (a69, b5, c3, d8), (a69, b5, c3, d9), (a69, b5, c3, d10), (a69, b5, c3, d11), (a69, b5, c3, d12), (a69, b5, c3, d13), (a69, b5, c3, d14), (a69, b5, c3, d15), (a69, b5, c3, d16), (a69, b5, c3, d17), (a69, b5, c3, d18), (a69, b5, c3, d19), (a69, b5, c3, d20), (a69, b5, c3, d21), (a69, b5, c3, d22), (a69, b6, c1, d1), (a69, b6, c1, d2), (a69, b6, c1, d3), (a69, b6, c1, d4), (a69, b6, c1, d5), (a69, b6, c1, d6), (a69, b6, c1, d7), (a69, b6, c1, d8), (a69, b6, c1, d9), (a69, b6, c1, d10), (a69, b6, c1, d11), (a69, b6, c1, d12), (a69, b6, c1, d13), (a69, b6, c1, d14), (a69, b6, c1, d15), (a69, b6, c1, d16), (a69, b6, c1, d17), (a69, b6, c1, d18), (a69, b6, c1, d19), (a69, b6, c1, d20), (a69, b6, c1, d21), (a69, b6, c1, d22), (a69, b6, c2, d1), (a69, b6, c2, d2), (a69, b6, c2, d3), (a69, b6, c2, d4), (a69, b6, c2, d5), (a69, b6, c2, d6), (a69, b6, c2, d7), (a69, b6, c2, d8), (a69, b6, c2, d9), (a69, b6, c2, d10), (a69, b6, c2, d11), (a69, b6, c2, d12), (a69, b6, c2, d13), (a69, b6, c2, d14), (a69, b6, c2, d15), (a69, b6, c2, d16), (a69, b6, c2, d17), (a69, b6, c2, d18), (a69, b6, c2, d19), (a69, b6, c2, d20), (a69, b6, c2, d21), (a69, b6, c2, d22), (a69, b6, c3, d1), (a69, b6, c3, d2), (a69, b6, c3, d3), (a69, b6, c3, d4), (a69, b6, c3, d5), (a69, b6, c3, d6), (a69, b6, c3, d7), (a69, b6, c3, d8), (a69, b6, c3, d9), (a69, b6, c3, d10), (a69, b6, c3, d11), (a69, b6, c3, d12), (a69, b6, c3, d13), (a69, b6, c3, d14), (a69, b6, c3, d15), (a69, b6, c3, d16), (a69, b6, c3, d17), (a69, b6, c3, d18), (a69, b6, c3, d19), (a69, b6, c3, d20), (a69, b6, c3, d21), (a69, b6, c3, d22), (a70, b1, c1, d1), (a70, b1, c1, d2), (a70, b1, c1, d3), (a70, b1, c1, d4), (a70, b1, c1, d5), (a70, b1, c1, d6), (a70, b1, c1, d7), (a70, b1, c1, d8), (a70, b1, c1, d9), (a70, b1, c1, d10), (a70, b1, c1, d11), (a70, b1, c1, d12), (a70, b1, c1, d13), (a70, b1, c1, d14), (a70, b1, c1, d15), (a70, b1, c1, d16), (a70, b1, c1, d17), (a70, b1, c1, d18), (a70, b1, c1, d19), (a70, b1, c1, d20), (a70, b1, c1, d21), (a70, b1, c1, d22), (a70, b1, c2, d1), (a70, b1, c2, d2), (a70, b1, c2, d3), (a70, b1, c2, d4), (a70, b1, c2, d5), (a70, b1, c2, d6), (a70, b1, c2, d7), (a70, b1, c2, d8), (a70, b1, c2, d9), (a70, b1, c2, d10), (a70, b1, c2, d11), (a70, b1, c2, d12), (a70, b1, c2, d13), (a70, b1, c2, d14), (a70, b1, c2, d15), (a70, b1, c2, d16), (a70, b1, c2, d17), (a70, b1, c2, d18), (a70, b1, c2, d19), (a70, b1, c2, d20), (a70, b1, c2, d21), (a70, b1, c2, d22), (a70, b1, c3, d1), (a70, b1, c3, d2), (a70, b1, c3, d3), (a70, b1, c3, d4), (a70, b1, c3, d5), (a70, b1, c3, d6), (a70, b1, c3, d7), (a70, b1, c3, d8), (a70, b1, c3, d9), (a70, b1, c3, d10), (a70, b1, c3, d11), (a70, b1, c3, d12), (a70, b1, c3, d13), (a70, b1, c3, d14), (a70, b1, c3, d15), (a70, b1, c3, d16), (a70, b1, c3, d17), (a70, b1, c3, d18), (a70, b1, c3, d19), (a70, b1, c3, d20), (a70, b1, c3, d21), (a70, b1, c3, d22), (a70, b2, c1, d1), (a70, b2, c1, d2), (a70, b2, c1, d3), (a70, b2, c1, d4), (a70, b2, c1, d5), (a70, b2, c1, d6), (a70, b2, c1, d7), (a70, b2, c1, d8), (a70, b2, c1, d9), (a70, b2, c1, d10), (a70, b2, c1, d11), (a70, b2, c1, d12), (a70, b2, c1, d13), (a70, b2, c1, d14), (a70, b2, c1, d15), (a70, b2, c1, d16), (a70, b2, c1, d17), (a70, b2, c1, d18), (a70, b2, c1, d19), (a70, b2, c1, d20), (a70, b2, c1, d21), (a70, b2, c1, d22), (a70, b2, c2, d1), (a70, b2, c2, d2), (a70, b2, c2, d3), (a70, b2, c2, d4), (a70, b2, c2, d5), (a70, b2, c2, d6), (a70, b2, c2, d7), (a70, b2, c2, d8), (a70, b2, c2, d9), (a70, b2, c2, d10), (a70, b2, c2, d11), (a70, b2, c2, d12), (a70, b2, c2, d13), (a70, b2, c2, d14), (a70, b2, c2, d15), (a70, b2, c2, d16), (a70, b2, c2, d17), (a70, b2, c2, d18), (a70, b2, c2, d19), (a70, b2, c2, d20), (a70, b2, c2, d21), (a70, b2, c2, d22), (a70, b2, c3, d1), (a70, b2, c3, d2), (a70, b2, c3, d3), (a70, b2, c3, d4), (a70, b2, c3, d5), (a70, b2, c3, d6), (a70, b2, c3, d7), (a70, b2, c3, d8), (a70, b2, c3, d9), (a70, b2, c3, d10), (a70, b2, c3, d11), (a70, b2, c3, d12), (a70, b2, c3, d13), (a70, b2, c3, d14), (a70, b2, c3, d15), (a70, b2, c3, d16), (a70, b2, c3, d17), (a70, b2, c3, d18), (a70, b2, c3, d19), (a70, b2, c3, d20), (a70, b2, c3, d21), (a70, b2, c3, d22), (a70, b3, c1, d1), (a70, b3, c1, d2), (a70, b3, c1, d3), (a70, b3, c1, d4), (a70, b3, c1, d5), (a70, b3, c1, d6), (a70, b3, c1, d7), (a70, b3, c1, d8), (a70, b3, c1, d9), (a70, b3, c1, d10), (a70, b3, c1, d11), (a70, b3, c1, d12), (a70, b3, c1, d13), (a70, b3, c1, d14), (a70, b3, c1, d15), (a70, b3, c1, d16), (a70, b3, c1, d17), (a70, b3, c1, d18), (a70, b3, c1, d19), (a70, b3, c1, d20), (a70, b3, c1, d21), (a70, b3, c1, d22), (a70, b3, c2, d1), (a70, b3, c2, d2), (a70, b3, c2, d3), (a70, b3, c2, d4), (a70, b3, c2, d5), (a70, b3, c2, d6), (a70, b3, c2, d7), (a70, b3, c2, d8), (a70, b3, c2, d9), (a70, b3, c2, d10), (a70, b3, c2, d11), (a70, b3, c2, d12), (a70, b3, c2, d13), (a70, b3, c2, d14), (a70, b3, c2, d15), (a70, b3, c2, d16), (a70, b3, c2, d17), (a70, b3, c2, d18), (a70, b3, c2, d19), (a70, b3, c2, d20), (a70, b3, c2, d21), (a70, b3, c2, d22), (a70, b3, c3, d1), (a70, b3, c3, d2), (a70, b3, c3, d3), (a70, b3, c3, d4), (a70, b3, c3, d5), (a70, b3, c3, d6), (a70, b3, c3, d7), (a70, b3, c3, d8), (a70, b3, c3, d9), (a70, b3, c3, d10), (a70, b3, c3, d11), (a70, b3, c3, d12), (a70, b3, c3, d13), (a70, b3, c3, d14), (a70, b3, c3, d15), (a70, b3, c3, d16), (a70, b3, c3, d17), (a70, b3, c3, d18), (a70, b3, c3, d19), (a70, b3, c3, d20), (a70, b3, c3, d21), (a70, b3, c3, d22), (a70, b4, c1, d1), (a70, b4, c1, d2), (a70, b4, c1, d3), (a70, b4, c1, d4), (a70, b4, c1, d5), (a70, b4, c1, d6), (a70, b4, c1, d7), (a70, b4, c1, d8), (a70, b4, c1, d9), (a70, b4, c1, d10), (a70, b4, c1, d11), (a70, b4, c1, d12), (a70, b4, c1, d13), (a70, b4, c1, d14), (a70, b4, c1, d15), (a70, b4, c1, d16), (a70, b4, c1, d17), (a70, b4, c1, d18), (a70, b4, c1, d19), (a70, b4, c1, d20), (a70, b4, c1, d21), (a70, b4, c1, d22), (a70, b4, c2, d1), (a70, b4, c2, d2), (a70, b4, c2, d3), (a70, b4, c2, d4), (a70, b4, c2, d5), (a70, b4, c2, d3), (a70, b4, c2, d7), (a70, b4, c2, d8), (a70, b4, c2, d9), (a70, b4, c2, d10), (a70, b4, c2, d11), (a70, b4, c2, d12), (a70, b4, c2, d13), (a70, b4, c2, d14), (a70, b4, c2, d15), (a70, b4, c2, d16), (a70, b4, c2, d17), (a70, b4, c2, d18), (a70, b4, c2, d19), (a70, b4, c2, d20), (a70, b4, c2, d21), (a70, b4, c2, d22), (a70, b4, c3, d1), (a70, b4, c3, d2), (a70, b4, c3, d3), (a70, b4, c3, d4), (a70, b4, c3, d5), (a70, b4, c3, d6), (a70, b4, c3, d7), (a70, b4, c3, d8), (a70, b4, c3, d9), (a70, b4, c3, d10), (a70, b4, c3, d11), (a70, b4, c3, d1), (a70, b4, c3, d13), (a70, b4, c3, d14), (a70, b4, c3, d15), (a70, b4, c3, d16), (a70, b4, c3, d17), (a70, b4, c3, d18), (a70, b4, c3, d19), (a70, b4, c3, d20), (a70, b4, c3, d21), (a70, b4, c3, d22), (a70, b5, c1, d1), (a70, b5, c1, d2), (a70, b5, c1, d3), (a70, b5, c1, d4), (a70, b5, c1, d5), (a70, b5, c1, d6), (a70, b5, c1, d7), (a70, b5, c1, d8), (a70, b5, c1, d9), (a70, b5, c1, d10), (a70, b5, c1, d11), (a70, b5, c1, d12), (a70, b5, c1, d13), (a70, b5, c1, d14), (a70, b5, c1, d15), (a70, b5, c1, d16), (a70, b5, c1, d17), (a70, b5, c1, d18), (a70, b5, c1, d19), (a70, b5, c1, d20), (a70, b5, c1, d21), (a70, b5, c1, d22), (a70, b5, c2, d1), (a70, b5, c2, d2), (a70, b5, c2, d3), (a70, b5, c2, d4), (a70, b5, c2, d5), (a70, b5, c2, d6), (a70, b5, c2, d7), (a70, b5, c2, d8), (a70, b5, c2, d9), (a70, b5, c2, d10), (a70, b5, c2, d11), (a70, b5, c2, d12), (a70, b5, c2, d13), (a70, b5, c2, d14), (a70, b5, c2, d15), (a70, b5, c2, d16), (a70, b5, c2, d17), (a70, b5, c2, d18), (a70, b5, c2, d19), (a70, b5, c2, d20), (a70, b5, c2, d21), (a70, b5, c2, d22), (a70, b5, c3, d1), (a70, b5, c3, d2), (a70, b5, c3, d3), (a70, b5, c3, d4), (a70, b5, c3, d5), (a70, b5, c3, d6), (a70, b5, c3, d7), (a70, b5, c3, d8), (a70, b5, c3, d9), (a70, b5, c3, d10), (a70, b5, c3, d11), (a70, b5, c3, d12), (a70, b5, c3, d13), (a70, b5, c3, d14), (a70, b5, c3, d15), (a70, b5, c3, d16), (a70, b5, c3, d17), (a10, b5, c3, d18), (a70, b5, c3, d19), (a70, b5, c3, d20), (a70, b5, c3, d21), (a70, b5, c3, d22), (a70, b5, c1, d1), (a70, b6, c1, d2), (a70, b6, c1, d3), (a70, b6, c1, d4), (a70, b6, c1, d5), (a70, b6, c1, d6), (a70, b6, c1, d7), (a70, b6, c1, d8), (a70, b6, c1, d9), (a70, b6, c1, d10), (a70, b6, c1, d11), (a70, b6, c1, d12), (a70, b6, c1, d13), (a70, b6, c1, d14), (a70, b6, c1, d15), (a70, b6, c1, d16), (a70, b6, c1, d17), (a70, b6, c1, d18), (a7, b2, c1, d19), (a70, b6, c1, d20), (a70, b6, c1, d21), (a70, b6, c1, d22), (a70, b6, c2, d1), (a70, b6, c2, d2), (a70, b6, c2, d3), (a70, b6, c2, d4), (a70, b6, c2, d5), (a70, b6, c2, d6), (a70, b6, c2, d7, (a70, b6, c2, d8), (a70, b6, c2, d9), (a70, b6, c2, d10), (a70, b6, c2, d11), (a70, b6, c2, d12), (a70, b6, c2, d13), (a70, b6, c2, d14), (a70, b6, c2, d15), (a70, b6, c2, d16), (a70, b6, c2, d17), (a70, b6, c2, d18), (a70, b6, c2, d19), (a70, b6, c2, d20), (a70, b6, c2, d21), (a70, b6, c2, d22), (a70, b6, c3, d1), (a70, b6, c3, d2), (a70, b6, c3, d3), (a70, b6, c3, d4), (a70, b6, c3, d5), (a70, b6, c3, d6), (a70, b6, c3, d7), (a70, b6, c3, d8), (a70, b6, c3, d9), (a70, b6, c3, d10), (a70, b6, c3, d11), (a70, b6, c3, d12), (a70, b6, c3, d13), (a70, c3, d14), (a70, b6, c3, d15), (a70, b6, c3, d16), (a70, b6, c3, d17), (a70, b6, c3, d18), (a70, b6, c3, d19), (a70, b6, c3, d20), (a70, b6, c3, d21), (a70, b6, c3, d22), (a71, b1, c1, d1), (a71, b1, c1, d2), (a71, b1, c1, d3), (a71, b1, c1, d4), (a71, b1, c1, d5), (a71, b1, c1, d6), (a71, b1, c1, d7), (a71, b1, c1, d8), (a71, b1, c1, d9), (a71, b1, c1, d10), (a71, b1, c1, d11), (a71, b1, c1, d12), (a71, b1, c1, d13), (a71, b1, c1, d14), (a71, b1, c1, d15), (a17, b1, c1, d16), (a71, b1, c1, d17), (a7, b1, c1, d18), (a71, b1, c1, d19), (a1, b1, c1, d20), (a1, b1, c1, d21), (a71, b1, c1, d22), (a71, b1, c2, d1), (a71, b1, c2, d2), (a71, b1, c2, d3), (a71, b1, c2, d4), (a1, b1, c2, d5), (a71, b1, c2, d6), (a71, b1, c2, d7), (a71, b1, c2, d8), (a71, b1, c2, d9), (a71, b1, c2, d10), (a71, b1, c2, d11), (a71, b1, c2, d12), (a71, b1, c2, d13), (a71, b1, c2, d14), (a71, b1, c2, d15), (a71, b1, c2, d16), (a71, b1, c2, d17), (a71, b1, c2, d18), (a71, b1, c2, d19), (a71, b1, c2, d20), (a71, b1, c2, d21), (a71, b1, c2, d22), (a71, b1, c3, d1), (a71, b1, c3, d2), (a71, b1, c3, d3), (a71, b1, c3, d4), (a71, b1, c3, d5), (a71, b1, c3, d6), (a71, b1, c3, d7), (a71, b1, c3, d8), (a71, b1, c3, d9), (a71, b1, c3, d10), (a71, b1, c3, d11), (a71, b1, c3, d12), (a71, b1, c3, d13), (a71, b1, c3, d14), (a71, b1, c3, d15), (a71, b1, c3, d16), (a71, b1, c3, d17), (a71, b1, c3, d18), (a71, b1, c3, d19), (a71, b1, c3, d20), (a71, b1, c3, d21), (a71, b1, c3, d22), (a71, b2, c1, d1), (a71, b2, c1, d2), (a71, b2, c1, d3), (a71, b2, c1, d4), (a71, b2, c1, d5), (a71, b2, c1, d6), (a71, b2, c1, d7), (a71, b2, c1, d8), (a71, b2, c1, d9), (a71, b2, c1, d10), (a71, b2, c1, d11), (a71, b2, c1, d12), (a71, b2, c1, d13), (a71, b2, c1, d14), (a71, b2, c1, d15) (a71, b2, c1, d16), (a71, b2, c1, d17), (a71, b2, c1, d18), (a71, b2, c1, d19), (a71, b2, c1, d20), (a71, b2, c1, d21), (a71, b2, c1, d22), (a71, b2, c2, d1), (a71, b2, c2, d2), (a71, b2, c2, d3), (a71, b2, c2, d4), (a71, b2, c2, d5), (a71, b2, c2, d6), (a71, b2, c2, d7), (a71, b2, c2, d8), (a71, b2, c2, d9), (a71, b2, c2, d10), (a71, b2, c2, d11), (a71, b2, c2, d12), (a71, b2, c2, d13), (a71, b2, c2, d14), (a71, b2, c2, d15), (a71, b2, c2, d16), (a71, b2, c2, d17), (a71, b2, c2, d18), (a71, b2, c2, d19), (a71, b2, c2, d20), (a71, b2, c2, d21), (a71, b2, c2, d22), (a71, b2, c3, d1), (a71, b2, c3, d2), (a71, b2, c3, d3), (a71, b2, c3, d4), (a71, b2, c3, d5), (a71, b2, c3, d6), (a71, b2, c3, d7), (a71, b2, c3, d8), (a71, b2, c3, d9), (a71, b2, c3, d10), (a71, b2, c3, d11), (a71, b2, c3, d2), (a71, b2, c3, d13), (a71, b2, c3, d14), (a71, b2, c3, d15), (a71, b2, c3, d16), (a71, b2, c3, d17), (a71, b2, c3, d18), (a71, b2, c3, d19), (a71, b2, c3, d20), (a7, b2, c3, d21), (a71, b2, c3, d22), (a71, b3, c1, d1), (a71, b3, c1, d2), (a71, b3, c1, d3), (a71, b3, c1, d4), (a71, b3, c1, d5), (a71, b3, c1, d6), (a71, b3, c1, d7), (a71, b3, c1, d8), (a71, b3, c1, d9), (a71, b3, c1, d10), (a71, b3, c1, d11), (a71, b3, c1, d12), (a71, b3, c1, d13), (a71, b3, c1, d14), (a71, b3, c1, d15), (a71, b3, c1, d16), (a71, b3, c1, d17), (a71, b3, c1, d18), (a71, b3, c1, d19), (a71, b3, c1, d20), (a71, b3, c1, d21), (a71, b3, c1, d22), (a71, b3, c2, d1), (a71, b3, c2, d2), (a71, b3, c2, d3), (a71, b3, c2, d4), (a71, b3, c2, d5), (a71, b3, c2, d6), (a71, b3, c2, d7), (a71, b3, c2, d8), (a71, b3, c2, d19), (a71, b3, c2, d10), (a71, b3, c2, d11), (a71, b3, c2, d12), (a71, b3, c2, d13), (a71, b3, c2, d14), (a71, b3, c2, d15), (a71, b3, c2, d16), (a71, b3, c2, d17), (a71, b3, c2, d18), (a71, b3, c2, d19), (a71, b3, c2, d20), (a71, b3, c2, d21), (a71, b3, c2, d22), (a71, b3, c3, d1), (a71, b3, c3, d2), (a71, b3, c3, d3), (a71, b3, c3, d4), (a71, b3, d5), (a71, b3, c3, d6), (a71, b3, c3, d7), (a71, b3, c3, d8), (a71, b3, c3, d9), (a71, b3, c3, d10), (a71, b3, c3, d11), (a71, b3, c3, d12), (a71, b3, c3, d13), (a71, b3, c3, d14), (a71, b3, c3, d15), (a71, b3, c3, d16), (a71, b3, c3, d17), (a71, b3, c3, d18), (a71, b3, c3, d19), (a71, b3, c3, d20), (a71, b3, c3, d21), (a71, b3, c3, d22), (a71, b4, c1, d1), (a71, b4, c1, d2), (a71, b4, c1, d3), (a71, b4, c1, d4), (a71, b4, c1, d5), (a71, b4, c1, d6), (a71, b4, c1, d7), (a71, b4, c1, d8), (a71, b4, c1, d9), (a71, b4, c1, d10), (a71, b4, c1, d11), (a71, b4, c1, d12), (a71, b4, c1, d13), (a71, b4, c1, d14), (a71, b4, c1, d15), (a71, b4, c1, d16), (a71, b4, c1, d17), (a71, b4, c1, d18), (a71, b4, c1, d19), (a71, b4, c1, d20), (a71, b4, c1, d21), (a71, b4, c1, d22), (a71, b4, c2, d1), (a71, b4, c2, d2), (a71, b4, c2, d3), (a71, b4, c2, d4), (a71, b4, c2, d5), (a71, b4, c2, d6), (a71, b4, c2, d7), (a71, b4, c2, d8), (a71, b4, c2, d9), (a71, b4, c2, d10), (a71, b4, c2, d11), (a71, b4, c2, d12), (a71, b4, c2, d13), (a71, b4, c2, d14), (a71, b4, c2, d15), (a71, b4, c2, d16), (a71, b4, c2, d17), (a71, b4, c2, d18), (a71, b4, c2, d19), (a71, b4, c2, d20), (a71, b4, c2, d21), (a71, b4, c2, d22), (a71, b4, c3, d1), (a71, b4, c3, d2), (a71, b4, c3, d3), (a71, b4, c3, d4), (a71, b4, c3, d5), (a71, b4, c3, d6), (a71, b4, c3, d7), (a71, b4, c3, d8), (a71, b4, c3, d9), (a71, b4, c3, d10), (a71, b4, c3, d11), (a71, b4, c3, d12), (a71, b4, d13), (a71, b4, c3, d14), (a71, b4, c3, d15), (a71, b4, c3, d16), (a71, b4, c3, d17), (a71, b4, c3, d18), (a71, b4, c3, d19), (a71, b4, c3, d20), (a71, b4, c3, d21), (a71, b4, c3, d22), (a71, b5, c1, d1), (a71, b5, c1, d2), (a71, b5, c1, d3), (a71, b5, c1, d4), (a71, b5, c1, d5), (a71, b5, c1, d6), (a71, b5, c1, d7), (a71, b5, c1, d8), (a71, b5, c1, d9), (a71, b5, c1, d10), (a71, b5, c1, d11), (a71, b5, c1, d12), (a71, b5, c1, d13), (a71, b5, c1, d14), (a71, b5, c1, d15), (a71, b5, c1, d16), (a71, b5, c1, d17), (a71, b5, c1, d18), (a71, b5, c1, d19), (a71, b5, c1, d20), (a71, b5, c1, d21), (a71, b5, c1, d22), (a71, b5, c2, d1), (a71, b5, c2, d2), (a71, b5, c2, d3), (a71, b5, c2, d4), (a71, b5, c2, d5), (a71, b5, c2, d6), (a71, b5, c2, d7), (a71, b5, c2, d8), (a71, b5, c2, d9), (a71, b5, c2, d10), (a71, b5, c2, d11), (a71, b5, c2, d12), (a71, b5, c2, d13), (a71, b5, c2, d14), (a71, b5, c2, d15), (a71, b5, c2, d16), (a71, b5, c2, d17), (a71, b5, c2, d18), (a71, b5, c2, d19), (a71, b5, c2, d20), (a71, b5, c2, d21), (a71, b5, c2, d22), (a71, b5, c3, d1), (a71, b5, c3, d2), (a71, b5, c3, d3), (a71, b5, c3, d4), (a71, b5, c3, d5), (a71, b5, c3, d6), (a71, b5, c3, d7), (a71, b5, c3, d8), (a71, b5, c3, d9), (a71, b5, c3, d10), (a71, b5, c3, d11), (a71, b5, c3, d12), (a71, b5, c3, d13), (a71, b5, c3, d14), (a71, b5, c3, d15), (a71, b5, c3, d16), (a71, b5, c3, d17), (a71, b5, c3, d18), (a71, b5, c3, d19), (a71, b5, c3, d20), (a71, b5, c3, d21), (a71, b5, c3, d22), (a71, b6, c1, d1), (a71, b6, c1, d2), (a71, b6, c1, d3), (a71, b6, c1, d4), (a71, b6, c1, d5), (a71, b6, c1, d6), (a71, b6, c1, d7), (a71, b6, c1, d8), (a71, b6, c1, d9), (a71, b6, c1, d10), (a71, b6, c1, d11), (a71, b6, c1, d12), (a71, b6, c1, d13), (a71, b6, c1, d14), (a71, b6, c1, d15), (a71, b6, c1, d16), (a71, b6, c1, d17), (a71, b6, c1, d18), (a71, b6, c1, d19), (a71, b6, c1, d20), (a71, b6, c1, d21), (a71, b6, c1, d22), (a71, b6, c2, d1), (a71, b6, c2, d2), (a71, b6, c2, d13), (a71, b6, c2, d4), (a71, b6, c2, d5), (a71, b6, c2, d16), (a71, b6, c2, d7), (a71, b6, c2, d8), (a71, b6, c2, d9), (a71, b6, c2, d10), (a71, b6, c2, d11), (a71, b6, c2, d12), (a71, b6, c2, d13), (a71, b6, c2, d14), (a71, b6, c2, d15), (a71, b6, c2, d16), (a71, b6, c2, d17), (a71, b6, c2, d18), (a71, b6, c2, d19), (a71, b6, c2, d20), (a71, b6, c2, d21), (a71, b6, c2, d22), (a71, b6, c3, d1), (a71, b6, c3, d2), (a71, b6, c3, d3), (a71, b6, c3, d4), (a71, b6, c3, d5), (a71, b6, c3, d6), (a71, b6, c3, d7), (a71, b6, c3, d8), (a71, b6, c3, d9), (a71, b6, c3, d10), (a71, b6, c3, d11), (a71, b6, c3, d12), (a71, b6, c3, d13), (a71, b6, c3, d14), (a71, b6, c3, d15), (a71, b6, c3, d16), (a71, b6, c3, d17), (a71, b6, c3, d18), (a71, b6, c3, d19), (a71, b6, c3, d20), (a71, b6, c3, d21), (a71, b6, c3, d22), (a72, b1, c1, d1), (a72, b1, c1, d2), (a72, b1, c1, d3), (a72, b1, c1, d4), (a72, b, c1, d5), (a72, b1, c1, d6), (a72, b1, c1, d7), (a72, b1, c1, d8), (a72, b1, c1, d9), (a72, b1, c1, d10), (a72, b1, c1, d11), (a72, b1, c1, d12), (a72, b1, c1, d13), (a72, b1, c1, d14), (a72, b1, c1, d15), (a72, b1, c1, d16), (a72, b1, c1, d17), (a72, b1, c1, d18), (a72, b, c1, d19), (a72, b1, c1, d20), (a72, b1, c1, d21), (a72, b1, c1, d22), (a72, b1, c2, d1), (a72, b1, c2, d2), (a72, b1, c2, d3), (a72, b1, c2, d4), (a72, b1, c2, d5), (a72, b1, c2, d6), (a72, b1, c2, d7), (a72, b1, c2, d8), (a72, b1, c2, d9), (a72, b1, c2, d10), (a72, b1, c2, d11), (a72, b1, c2, d12), (a72, b1, c2, d13), (a72, b, c2, d14), (a72, b1, c2, d15), (a72, b1, c2, d16), (a72, b1, c2, d1), (a72, b1, c2, d18), (a72, b1, c2, d19), (a72, b1, c2, d20), (a72, b1, c2, d21), (a72, b1, c2, d22), (a72, b1, c3, d1), (a72, b1, c3, d2), (a72, b1, c3, d3), (a72, b1, c3, d4), (a72, b1, c3, d5), (a72, b1, c3, d6), (a72, b1, c3, d7), (a72, b1, c3, d8), (a72, b1, c3, d9), (a72, b1, c3, d10), (a72, b1, c3, d11), (a72, b1, c3, d12), (a72, b1, c3, d13), (a72, b1, c3, d14), (a72, b1, c3, d15), (a72, b1, c3, d16), (a72, b1, c3, d17), (a72, b1, c3, d18), (a72, b1, c3, d19), (a72, b1, c3, d20), (a72, b1, c3, d21), (a72, b1, c3, d22), (a72, b2, c1, d1), (a72, b2, c1, d2), (a72, b2, c1, d3), (a72, b2, c1, d4), (a72, b2, c1, d5), (a72, b2, c1, d6), (a72, b2, c1, d7), (a72, b2, c1, d8), (a72, b2, c1, d9), (a72, b2, c1, d10), (a72, b2, c1, d11), (a72, b2, c1, d12), (a72, b2, c1, d13), (a72, b2, c1, d14), (a72, b2, c1, d15), (a72, b2, c1, d16), (a72, b2, c1, d17), (a72, b2, c1, d18), (a72, b2, c1, d19), (a72, b2, c1, d20), (a72, b2, c1, d21), (a72, b2, c1, d22), (a72, b2, c2, d1), (a72, b2, c2, d2), (a72, b2, c2, d3), (a72, b2, c2, d4), (a72, b2, c2, d5), (a72, b2, c2, d6), (a72, b2, c2, d7), (a72, b2, c2, d8), (a72, b2, c2, d9), (a72, b2, c2, d10), (a72, b2, c2, d11), (a72, b2, c2, d12), (a72, b2, c2, d13), (a72, b2, c2, d14), (a72, b2, c2, d15), (a72, b2, c2, d16), (a72, b2, c2, d17), (a72, b2, c2, d18), (a72, b2, c2, d19), (a72, b2, c2, d20), (a72, b2, c2, d21), (a72, b2, c2, d22), (a72, b2, c3, d1), (a72, b2, c3, d2), (a72, b2, c3, d3), (a72, b2, c3, d4), (a72, b2, c3, d5), (a72, b2, c3, d6), (a72, b2, c3, d7), (a72, b2, c3, d18), (a72, b2, c3, d9), (a72, b2, c3, d10), (a72, b2, c3, d11), (a72, b2, c3, d12), (a72, b2, c3, d13), (a72, b2, c3, d14), (a72, b2, c3, d15), (a72, b2, c3, d16), (a72, b2, c3, d17), (a72, b2, c3, d18), (a72, b2, c3, d19), (a72, b2, c3, d20), (a72, b2, c3, d21), (a72, b2, c3, d22), (a72, b3, c1, d1), (a72, b3, c1, d2), (a72, b3, c1, d3), (a72, b3, c1, d4), (a72, b3, c1, d5), (a72, b3, c1, d6), (a72, b3, c1, d7), (a72, b3, c1, d8), (a72, b3, c1, d9), (a72, b3, c1, d10), (a72, b3, c1, d11), (a72, b3, c1, d12), (a72, b3, c1, d13), (a72, b3, c1, d14), (a72, b3, c1, d15), (a72, b3, c1, d16), (a72, b3, c1, d17), (a72, b3, c1, d18), (a72, b3, c1, d19), (a72, b3, c1, d20), (a72, b3, c1, d21), (a72, b3, c1, d22), (a72, b3, c2, d1), (a72, b3, c2, d2), (a72, b3, c2, d3), (a72, b3, c2, d4), (a72, b3, c2, d5), (a72, b3, c2, d6), (a72, b3, c2, d7), (a72, b3, c2, d8), (a72, b3, c2, d9), (a72, b3, c2, d10), (a72, b3, c2, d11), (a72, b3, c2, d12), (a72, b3, c2, d13), (a72, b3, c2, d14), (a72, b3, c2, d15), (a72, b3, c2, d16), (a72, b3, c2, d17), (a72, b3, c2, d18), (a72, b3, c2, d19), (a72, b3, c2, d20), (a72, b3, c2, d21), (a72, b3, c2, d22), (a72, b3, c3, d1), (a72, b3, c3, d2), (a72, b3, c3, d3), (a72, b3, c3, d4), (a72, b3, c3, d5), (a72, b3, c3, d6), (a72, b3, c3, d7), (a72, b3, c3, d8), (a72, b3, c3, d9), (a72, b3, c3, d10), (a72, b3, c3, d11), (a72, b3, c3, d12), (a72, b3, c3, d13), (a72, b3, c3, d14), (a72, b3, c3, d15), (a72, b3, c3, d16), (a72, b3, c3, d17), (a72, b3, c3, d18), (a72, b3, c3, d19), (a72, b3, c3, d20), (a72, b3, c3, d21), (a72, b3, c3, d22), (a72, b4, c1, d1), (a72, b4, c1, d2), (a72, b4, c1, d3), (a72, b4, c1, d4), (a72, b4, c1, d5), (a72, b4, c1, d6), (a72, b4, c1, d7), (a72, b4, c1, d8), (a72, b4, c1, d9), (a72, b4, c1, d10), (a72, b4, c1, d11), (a72, b4, c1, d12), (a72, b4, c1, d13), (a72, b4, c1, d14), (a72, b4, c1, d15), (a72, b4, c1, d13), (a72, b4, c1, d17), (a72, b4, c1, d18), (a72, b4, c1, d19), (a72, b4, c1, d20), (a72, b4, c1, d21), (a72, b4, c1, d22), (a72, b4, c2, d1), (a72, b4, c2, d2), (a72, b4, c2, d3), (a72, b4, c2, d4), (a72, b4, c2, d5), (a72, b4, c2, d6), (a72, b4, c2, d7), (a72, b4, c2, d8), (a72, b4, c2, d9), (a72, b4, c2, d10), (a72, b4, c2, d11), (a72, b4, c2, d12), (a72, b4, c2, d13), (a72, b4, c2, d14), (a72, b4, c2, d15), (a72, b4, c2, d16), (a72, b4, c2, d17), (a72, b4, c2, d18), (a72, b4, c2, d19), (a72, b4, c2, d20), (a72, b4, c2, d21), (a72, b4, c2, d22), (a72, b4, c3, d11), (a72, b4, c3, d2), (a72, b4, c3, d3), (a72, b4, c3, d4), (a72, b4, c3, d5), (a72, b4, c3, d6), (a72, b4, c3, d7), (a72, b4, c3, d8), (a72, b4, c3, d9), (a72, b4, c3, d10), (a72, b4, c3, d11), (a72, b4, c3, d12), (a72, b4, c3, d13), (a72, b4, c3, d14), (a72, b4, c3, d15), (a72, b4, c3, d16), (a72, b4, c3, d17), (a72, b4, c3, d18), (a72, b4, c3, d19), (a72, b4, c3, d20), (a72, b4, c3, d21), (a72, b4, c3, d22), (a72, b5, c1, d1), (a72, b5, c1, d2), (a72, b5, c1, d3), (a72, b5, c1, d4), (a72, b5, c1, d5), (a72, b5, c1, d6), (a72, b5, c1, d7), (a72, b5, c1, d8), (a72, b5, c1, d9), (a72, b5, c1, d10), (a72, b5, c1, d11), (a72, b5, c1, d12), (a72, b5, c1, d13), (a72, b5, c1, d14), (a72, b5, c1, d15), (a72, b5, c1, d16), (a72, b5, c1, d17), (a72, b5, c1, d18), (a72, b5, c1, d19), (a72, b5, c1, d20), (a72, b5, c1, d21), (a72, b5, c1, d22), (a72, b5, c2, d1), (a72, b5, c2, d2), (a72, b5, c2, d3), (a72, b5, c2, d4), (a72, b5, c2, d5), (a72, b5, c2, d6), (a72, b5, c2, c4, d7), (a72, b5, c2, d8), (a72, b5, c2, d9), (a72, b5, c2, d10), (a72, b5, c2, d11), (a72, b5, c2, d12), (a72, b5, c2, d13), (a72, b5, c2, d14), (a72, b5, c2, d15), (a72, b5, c2, d16), (a72, b5, c2, d17), (a72, b5, c2, d18), (a72, b5, c2, d19), (a72, b5, c2, d20), (a72, b5, c2, d21), (a72, b5, c2, d22), (a72, b5, c3, d1), (a72, b5, c3, d2), (a72, b5, c3, d3), (a72, b5, c3, d4), (a72, b5, c3, d5), (a72, b5, c3, d6), (a72, b5, c3, d7), (a72, b5, c3, d8), (a72, b5, c3, d9), (a72, b5, c3, d10), (a72, b5, c3, d11), (a72, b5, c3, d12), (a72, b5, c3, d13), (a72, b5, c3, d14), (a72, b5, c3, d15), (a72, b5, c3, d16), (a72, b5, c3, d17), (a72, b5, c3, d18), (a72, b5, c3, d19), (a72, b5, c3, d20), (a72, b5, c3, d21), (a72, b5, c3, d22), (a72, b6, c1, d1), (a72, b6, c1, d2), (a72, b6, c1, d3), (a72, b6, c1, d4), (a72, b6, c1, d5), (a72, b6, c1, d6), (a72, b6, c1, d7), (a72, b6, d8), (a72, b6, c1, d9), (a72, b6, c1, d10), (a72, b6, c1, d11), (a72, b6, c1, d12), (a72, b6, c1, d13), (a72, b6, c1, d14), (a72, b6, c1, d15), (a72, b6, c1, d16), (a72, b6, c1, d17), (a72, b6, c1, d18), (a72, b6, c1, d19), (a72, b6, c1, d20), (a72, b6, c1, d21), (a72, b6, c1, d22), (a72, b6, c2, d1), (a72, b6, c2, d2), (a72, b6, c2, d3), (a72, b6, c2, d4), (a72, b6, c2, d5), (a72, b6, c2, d6), (a72, b6, c2, d7), (a72, b6, c2, d8), (a72, b6, c2, d9), (a72, b6, c), d10), (a72, bb, c2, d11), (a72, b6, c2, d12), (a72, b6, c2, d13), (a72, b6, c2, d14), (a72, b6, c2, d15), (a72, b6, c2, d16), (a72, b6, c2, d17), (a72, b6, c2, d18), (a72, b6, c2, d19), (a72, b6, c2, d20), (a72, b6, c2, d21), (a72, b6, c2, d22), (a72, b6, c3, d1), (a72, b6, c3, d2), (a72, b6, c3, d3), (a72, b6, c3, d4), (a72, b6, c3, d5), (a72, b6, c3, d6), (a72, b6, c3, d7), (a72, b6, c3, d8), (a72, b6, c3, d9), (a72, b6, c3, d10), (a72, b6, c3, d11), (a72, b6, c3, d12), (a72, b6, c3, d13), (a72, b6, c3, d14), (a72, b6, c3, d15), (a72, b6, c3, d16), (a72, b6, c3, d17), (a72, b6, c3, d18), (a72, b6, c3, d19), (a72, b6, c3, d20), (a72, b6, c3, d21), (a72, b6, c3, d22), (a73, b1, c1, d1), (a73, b1, c1, d2), (a73, b1, c1, d3), (a73, b1, c1, d4), (a73, b1, c1, d5), (a73, b1, c1, d6), (a73, b1, c1, d7), (a73, b1, c1, d8), (a73, b1, c1, d9), (a73, b1, c1, d10), (a73, b1, c1, d11), (a73, b1, c1, d12), (a73, b1, c1, d13), (a73, b1, c1, d14), (a73, b1, c1, d15), (a73, b1, c1, d16), (a73, b1, c1, d17), (a73, b1, c1, d18), (a73, b1, c1, d19), (a73, b1, c1, d20), (a73, b1, c1, d21), (a73, b1, c1, d22), (a73, b1, c2, d1), (a73, b1, c2, d2), (a73, b1, c2, d3), (a73, b1, c2, d14), (a73, b1, c2, d5), (a73, b1, c2, d6), (a73, b1, c2, d7), (a73, b1, c2, d8), (a73, b1, c2, d9), (a73, b1, c2, d10), (a73, b1, c2, d11), (a73, b1, c2, d12), (a73, b1, c2, d13), (a73, b1, c2, d14), (a73, b1, c2, d15), (a73, b1, c2, d16), (a73, b1, c2, d17), (a73, b1, c2, d16), (a73, b1, c2, d19), (a73, b1, c2, d20), (a73, b1, c2, d21), (a73, b1, c2, d22), (a73, b1, c3, d1), (a73, b1, c3, d2), (a73, b1, c3, d3), (a73, b1, c3, d4), (a73, b1, c3, d5), (a73, b1, c3, d6), (a73, b1, c3, d7), (a73, b1, c3, d8), (a73, b1, c3, d9), (a73, b1, c3, d10), (a73, b1, c3, a11), (a73, b1, c3, d12), (a73, b1, c3, d13), (a73, b1, c3, d14), (a73, b1, c3, d15), (a73, b1, c3, d16), (a73, b1, c3, d17), (a73, b1, c3, d18), (a73, b1, c3, d19), (a73, b1, c3, d20), (a73, b1, c3, d21), (a73, b1, c3, d22), (a73, b2, c1, d1), (a73, b2, c1, d2), (a73, b2, c1, d3), (a73, b2, c1, d4), (a73, b2, c1, d5), (a73, b2, c1, d6), (a73, b2, c1, d7), (a73, b2, c1, d8), (a73, b2, c1, d9), (a73, b2, c1, d10), (a73, b2, c1, d11), (a73, b2, c1, d12), (a73, b2, c1, d13), (a73, b2, c1, d14), (a73, b2, c1, d15), (a73, b2, c1, d16), (a73, b2, c1, d17), (a73, b2, c1, d18), (a73, b2, c1, d19), (a73, b2, c1, d20), (a73, b2, c1, d21), (a73, b2, c1, d22), (a73, b2, c2, d1), (a73, b2, c2, d2), (a73, b2, c2, d3), (a73, b2, c2, d4), (a73, b2, c2, d5), (a73, b2, c2, d6), (a73, b2, c2, d7), (a73, b2, c2, d8), (a73, b2, c2, d9), (a73, b2, c2, d10), (a73, b2, c2, d11), (a73, b2, c2, d12), (a73, b2, c2, d13), (a73, b2, c2, d14), (a73, b2, c2, d15), (a73, b2, c2, d16), (a73, b2, c2, d17), (a73, b2, c2, d18), (a73, b2, c2, d19), (a73, b2, c2, d20), (a73, b2, c2, d21), (a73, b2, c2, d22), (a73, b2, c3, d1), (a73, b2, c3, d2), (a73, b2, c3, d3), (a73, b2, c3, d4), (a73, b2, c3, d5), (a73, b2, c3, d6), (a73, b2, c3, d7), (a73, b2, c3, d8), (a73, b2, c3, d9), (a73, b2, c3, d10), (a73, b2, c3, d11), (a73, b2, c3, d12), (a73, b2, c3, d13), (a73, b2, c3, d14), (a73, b2, c3, d15), (a73, b2, c3, d16), (a73, b2, c3, d17), (a73, b2, c3, d18), (a73, b2, c3, d19), (a73, b2, c3, d20), (a73, b2, c3, d21), (a73, b2, c3, d22), (a73, b3, c1, d1), (a73, b3, c1, d2), (a73, b3, c1, d3), (a73, b3, c1, d4), (a73, b3, c1, d5), (a73, b3, c1, d6), (a73, b3, c1, d7), (a73, b3, c1, d8), (a73, b3, c1, d9), (a73, b3, c1, d10), (a73, b3, c1, d11), (a73, b3, c1, d12), (a73, b3, c1, d13), (a73, b3, c1, d14), (a73, b3, c1, d15), (a73, b3, c1, d16), (a3, b3, c1, d17), (a73, b3, c1, d18), (a73, b3, c1, d19), (a73, b3, c1, d20), (a73, b3, c1, d21), (a73, b3, c1, d22), (a73, b3, c2, d1), (a73, b3, c2, d2, (a73, b3, c2, d3), (a73, b3, c2, d4), (a73, b3, c2, d5), (a73, b3, c2, d6), (a73, b3, c2, d7), (a73, b3, c2, d8), (a73, b3, c2, d9), (a73, b3, c2, d10), (a73, b3, c2, d11), (a73, b3, c2, d12), (a73, b3, c2, d13), (a73, b3, c2, d14), (a73, b3, c2, d15), (a73, b3, c2, d20), (a73, b3, c2, d21), (a73, b3, c2, d22), (a73, b3, c3, d1), (a73, b3, c3, d2), (a73, b3, c3, d3), (a73, b3, c3, d4), (a73, b3, c3, d5), (a73, b3, c3, d16), (a73, b3, c3, d7), (a73, b3, c3, d8), (a73, b3, c3, d9), (a73, b3, c3, d10), (a73, b3, c3, d11), (a73, b3, c3, d12), (a73, b3, c3, d13), (a73, b3, c3, d14), (a73, b3, c3, d15), (a73, b3, c3, d16), (a73, b3, c3, d17), (a73, b3, c3, d18), (a73, b3, c3, d19), (a73, b3, c3, d20), (a73, b3, c3, d21), (a73, b3, c3, d22), (a73, b4, c1, d1), (a73, b4, c1, d2), (a73, b4, c1, d3), (a73, b4, c1, d4), (a73, b4, c1, d5), (a73, b4, c1, d6), (a73, b4, c1, d7), (a73, b4, c1, d8), (a73, b4, c1, d9), (a73, b4, c1, d10), (a73, b4, c1, d11), (a73, b4, c1, d12), (a73, b4, c1, d13), (a73, b4, c1, d14), (a73, b4, c1, d15), (a73, b4, c1, d16), (a72, b4, c1, d17), (a73, b4, c1, d18), (a73, b4, c1, d20), (a73, b4, c1, d20), (a73, b4, c1, d21), (a73, b4, c1, d22), (a73, b4, c2, d1), (a73, b4, c2, d2), (a73, b4, c2, d3), (a73, b4, c2, d4), (a73, b4, c2, d5), (a73, b4, c2, d6), (a73, b4, c2, d7), (a73, b4, c2, d8), (a73, b4, c2, d9), (a73, b4, c2, d10), (a73, b4, c2, d11), (a73, b4, c2, d12), (a73, b4, c2, a1a), (a73, b4, c2, d14), (a73, b4, c2, d15), (a73, b4, c2, d16), (a73, b4, c2, d17), (a73, b4, c2, d18), (a73, b4, c2, d19), (a73, b4, c2, d20), (a73, b4, c2, d21), (a73, b4, c2, d22), (a73, b4, c3, d1), (a73, b4, c3, d2), (a73, b4, c3, d3), (a73, b4, c3, d4), (a73, b4, c3, d5), (a73, b4, c3, d6), (a73, b4, c3, d7), (a73, b4, c3, d8), (a73, b4, c3, d9), (a73, b4, c3, d10), (a73, b4, c3, d11), (a73, b4, c3, d12), (a73, b4, c3, d13), (a73, b4, c3, d14), (a73, b4, c3, d15), (a73, b4, c3, d16), (a73, b4, c3, d17), (a73, b4, c3, d18), (a73, b4, c3, d19), (a73, b4, c3, d20), (a73, b4, c3, d21), (a73, b4, c3, d22), (a73, b5, c1, c1), (a73, b5, c1, d2), (a73, b5, c1, d3), (a73, b5, c1, d4), (a73, b5, c1, d5), (a73, b5, c1, d6), (a73, b5, c1, d7), (a7, b5, c1, d8), (a73, b5, c1, d9), (a73, b5, c1, d10), (a73, b5, c1, d11), (a73, b5, c1, d12), (a73, b5, c1, d13), (a73, b5, c1, d14), (a73, b5, c1, d15), (a73, b5, c1, d16), (a73, b5, c1, d17), (a73, b5, c1, d3), (a73, b5, c1, d19), (a73, b5, c1, d20), (a73, b5, c1, d21), (a73, b5, c1, d22), (a73, b5, c2, d1), (a73, b5, c2, d2), (a73, b5, c2, d3), (a73, b5, c2, d4), (a73, b5, c2, d5), (a73, b5, c2, d6), (a73, b5, c2, d7), (a73, b5, c2, d8), (a73, b5, c2, d9), (a73, b5, c2, d10), (a, b5, c2, d11), (a73, b5, c2, d12), (a73, b5, c2, d13), (a, b5, c2, d14), (a73, b5, c2, d15), (a73, b5, c2, d16), (a73, b5, c2, d17), (a73, b5, c2, d18), (a73, b5, c2, d19), (a73, b5, c2, d20), (a73, b5, c2, d21), (a73, b5, c2, d22), (a73, b5, c3, d1), (a73, b5, c3, d2), (a73, b5, c3, d3), (a73, b5, c3, d4), (a73, b5, c3, d5), (a73, b5, c3, d6), (a73, b5, c3, d7), (a73, b5, c3, d8), (a73, b5, c3, d9), (a73, b5, c3, d10), (a73, b5, c3, d11), (a73, b5, c3, d12), (a73, b5, c3, d13), (a73, b5, c3, d14), (a73, b5, c3, d15), (a73, b5, c3, d16), (a73, b5, c3, d17), (a73, b5, c3, d18), (a73, b5, c3, d19), (a73, b5, c3, d20), (a73, b5, c3, d21), (a73, b5, c3, d22), (a73, b6, c1, d11), (a73, b6, c1, d2), (a3, b6, c1, d3), (a73, b6, c1, d4), (a73, b6, c1, d5), (a73, b6, c1, d6), (a73, b6, c1, d7), (a73, b6, c1, d8), (a13, b6, c1, d9), (a73, b6, c1, d10), (a73, b6, c1, d11), (a73, b6, c1, d12), (a73, b6, c1, d13), (a73, b6, c1, d14), (a73, b6, c1, d15), (a73, b6, c1, d16), (a73, b6, c1, d17), (a73, b6, c1, d18), (a73, b6, c1, d19), (a73, b6, c1, d20), (a73, b6, c1, d21), (a73, b6, c1, d22), (a73, b6, c2, d11), (a73, b6, c2, d2), (a73, b6, c2, d3), (a73, b6, c2, d4), (a73, b6, c2, d5), (a73, b6, c2, d6), (a73, b6, c2, d7), (a73, b6, c2, d8), (a73, b6, c2, d9), (a73, b6, c2, d10), (a73, b6, c2, d11), (a73, b6, c2, d12), (a73, b6, c2, d13), (a73, b6, c2, d14), (a73, b6, c2, d15), (a73, b6, c2, d16), (a73, b6, c2, d17), (a73, b6, c2, d18), (a73, b6, c2, d19), (a73, b6, c2, d20), (a73, b6, c2, d21), (a73, b6, c2, d22), (a73, b3, c3, d1), (a73, b6, c3, d2), (a73, b6, c3, d3), (a73, b6, c3, d4), (a73, b6, (a73, d5), (a73, b6, c3, d6), (a73, b6, c3, d7), (a73, b6, c3, d8), (a73, b6, c3, d9), (a73, b6, c3, d10), (a73, b6, c3, a11), (a73, b6, c3, d12), (a73, b6, c3, d13), (a73, b6, c3, d14), (a73, b6, c3, d15), (a73, b6, c3, d16), (a73, b6, c3, d17), (a73, b6, d3, d18), (a73, b6, c3, d19), (a73, b6, c3, d20), (a73, b6, c3, d21), (a73, b6, c3, d22), (a74, b1, c1, d1), (a74, b1, c1, d2), (a74, b1, c1, d3), (a74, b1, c1, d4), (a74, b1, c1, d5), (a74, b1, c1, d6), (a74, b1, c1, d7), (a74, b1, c1, d8), (a74, b1, c1, d9), (a74, b1, c1, d10), (a74, b1, c1, d11), (a74, b1, c1, d12), (a74, b1, c1, d13), (a74, b1, c1, d14), (a74, b1, c1, d15), (a74, b1, c1, d16), (a74, b1, c1, d17), (a74, b1, c1, d18), (a74, b1, c1, d19), (a74, b1, c1, d20), (a74, b1, c1, d21), (a74, b1, c1, d22), (a74, b1, c2, d1), (a74, b1, c2, d2), (a74, b1, c2, d3), (a74, b1, c2, d4), (a74, b1, c2, d5), (a74, b1, c2, d5), (a74, b1, c2, d7), (a74, b1, c2, d8), (a74, b1, c2, d9), (a74, b1, c2, d10), (a74, b1, c2, d11), (a74, b1, c2, d12), (a74, b1, c2, d13), (a74, b1, c2, d14), (a74, b1, c2, d15), (a74, b1, c2, d16), (a74, b1, c2, d17), (a74, b1, c2, d18), (a74, b1, c2, d19), (a74, b1, c2, d20), (a74, b1, c2, d21), (a74, b1, c2, d22), (a74, b1, c3, d1), (a74, b1, c3, d2), (a74, b1, c3, d3), (a74, b1, c3, d4), (a74, b1, c3, d5), (a74, b1, c3, d6), (a74, b1, c3, d7), (a74, b1, c3, d8), (a74, b1, c3, d9), (a74, b1, c3, d10), (a74, b1, c3, d11), (a74, b1, c3, d12), (a74, b1, c3, d13), (a74, b1, c3, d14), (a74, b1, c3, d15), (a74, b1, c3, d16), (a74, b1, c3, d17), (a74, b1, c3, d18), (a74, b1, c3, d20), (a74, b1, c3, d20), (a74, b1, c3, d21), (a74, b1, c3, d22), (a74, b2, c1, d1), (a74, b2, c1, d2), (a74, b2, c1, d3), (a74, b2, c1, d4), (a74, b2, c1, d5), (a74, b2, c1, d6), (a74, b2, c1, d7), (a74, b2, c1, d8), (a74, b2, (a74, d9), (a74, b2, c1, d10), (a74, b2, c1, d11), (a74, b2, c1, d12), (a74, b2, c1, d13), (a74, b2, c1, d14), (a74, b2, c1, d15), (a74, b2, c1, d16), (a74, b2, c1, d17), (a74, b2, c1, d18), (a74, b2, c1, d19), (a74, b2, c1, d20), (a74, b2, c1, d21), (a74, b2, c1, d22), (a74, b2, c2, d1), (a74, b2, c2, d2), (a74, b2, c2, d3), (a74, b2, c2, d4), (a74, b2, c2, d5), (a74, b2, c2, d6), (a74, b2, c2, d7), (a14, b2, c2, d8), (a74, b2, c2, d9), (a74, b2, c2, d10), (a74, b2, c2, d11), (a74, b2, c2, d12), (a74, b2, c2, d13), (a74, b2, c2, d14), (a74, b2, c2, d15), (a74, b2, c2, d16), (a74, b2, c2, d17), (a74 b2, c2, d18), (a74, b2, c2, d19), (a74, b2, c2, d20), (a74, b2, c2, d21), (a74, b2, c2, d22), (a74, b2, c3, d1), (a74, b2, c3, d2), (a74, b2, c3, d3), (a74, b2, c3, d4), (a74, b2, c3, d5), (a74, b2, c3, d6), (a74, b2, c3, d7), (a74, b2, c3, d8), (a74, b2, c3, d9), (a74, b2, c3, d10), (a74, b2, c3, d11), (a74, b2, c3, d12), (a74, b2, c3, d13), (a74, b2, c3, d14), (a74, b2, c3, d15), (a74, b2, c3, d16), (a74, b2, c3, d17), (a74, b2, c3, d18), (a74, b2, c3, d19), (a74, b2, c3, d20), (a74, b2, c3, d21), (a74, b2, c3, d22), (a74, b3, c1, d1), (a74, b3, c1, d2), (a74, b3, c1, d3), (a74, b3, c1, d4), (a74, b3, c1, d5), (a74, b3, c1, d6), (a74, b3, c1, d7), (a74, b3, c1, d8), (a74, b3, c1, d9), (a74, b3, c1, d10), (a74, b3, c1, d11), (a74, b3, c1, d12), (a74, b3, c1, d13), (a74, b3, c1, d14), (a74, b3, c1, d13), (a74, b3, c1, d15), (a74, b3, c1, d16), (a74, b3, c1, d17), (a74, b3, c1, d18), (a74, b3, c1, d19), (a74, b3, c1, d20), (a74, b3, c1, d21), (a74, b3, c1, d22), (a74, b3, c2, d1), (a74, b3, c2, d2) (a74, b3, c2, d3), (a74, b3, c2, d4), (a74, b3, c2, d5), (a74, b3, c2, d6), (a74, b3, c2, d7), (a74, b3, c2, d8), (a74, b3, c2, d9), (a74, b3, c2, d10), (a74, b3, c2, d11), (a74, b3, c2, d12), (a74, b3, c2, d13), (a74, b3, c2, d14), (a74, b3, c2, d15), (a74, b3, c2, d16), (a74, b3, c2, d17), (a74, b3, c2, d18), (a74, b, c2, d19), (a74, b3, c2, d20), (a74, b3, c2, d21), (a74, b3, c2, d22), (a74, b3, c3, d1), (a74, b3, c3, d2), (a74, b3, c3, d3), (a74, b3, c3, d4), (a74, b3, c3, d5), (a74, b3, c3, d6), (a74, b3, c3, d7), (a74, b3, c3, d8), (a74, b3, c3, d9), (a74, b3, c3, d10), (a74, b3, c3, d11), (a74, b3, c3, d12), (a74, b3, c3, d13), (a74, b3, c3, d14), (a74, b3, c3, d15), (a74, b3, c3, d16), (a74, b3, c3, d17), (a74, b3, c3, d18), (a74, b3, c3, d19), (a74, b3, c3, d20), (a74, b3, c3, d21), (a74, b3, c3, d22), (a74, b4, c1, d1), (a74, b4, c1, d2), (a74, b4, c1, d3), (a74, b4, c1, d4), (a74, b4, c1, d5), (a74, b4, c1, d6), (a74, b4, c1, d7), (a74, b4, c1, d8), (a74, b4, c1, d9), (a74, b4, c1, d10), (a74, b4, c1, d11), (a74, b4, c1, d12), (a74, b4, c1, d13), (a74, b4, c1, d14), (a74, b4, c1, d15), (a74, b4, c1, d16), (a74, b4, c1, d17), (a74, b4, c1, d18), (a74, b4, c1, d19), (a74, b4, c1, d20), (a74, b4, c1, d21), (a74, b4, c1, d22), (a74, b4, c2, d1), (a74, b4, c2, d2), (a74, b4, c2, d13), (a74, b4, c2, d4), (a74, b4, c2, d5), (a74, b4, c2, d6), (a74, b4, c2, d7), (a74, b4, c2, d3), (a74, b4, c2, d9), (a74, b4, c2, d10), (a74, b4, c2, d11), (a74, b4, c2, d12), (a74, b4, c2, d13), (a74, b4, c2, d14), (a74, b4, c2, d15), (a74, b4, c2, d16), (a74, b4, c2, d17), (a74, b4, c2, d18), (a74, b4, c2, d19), (a74, b4, c2, d20), (a74, b4, c2, d21), (a74, b4, c2, d22), (a74, b4, c2, d1), (a74, b4, c3, d2), (a74, b4, c3, d3), (a74, b4, c3, d4), (a74, b4, c3, d5), (a74, b4, c3, d6), (a74, b4, c3, d7), (a74, b4, c3, d8), (a74, b4, c3, d9), (a74, b4, c3, d10), (a74, b4, c3, d11), (a74, b4, c3, d12), (a74, b4, c3, d13), (a74, b4, c3, d14), (a74, b4, c3, d15), (a74, b4, c3, d16), (a74, b4, c3, d17), (a74, b4, c3, d18), (a74, b4, c3, d19), (a74, b4, c3, d20), (a74, b4, c3, d21), (a74, b4, c3, d22), (a74, b5, c1, d1), (a74, b5, c1, d2), (a74, b5, c1, d3), (a74, b5, c1, d4), (a74, b5, c1, d5), (a74, b5, c1, d6), (a74, b5, c1, d7), (a74, b5, c1, d3), (a74, b5, c1, d9), (a74, b5, c1, d10), (a74, b5, c1, d11), (a74, b5, c1, d12), (a74, b5, c1, d13), (a74, b5, c1, d14), (a74, b5, c1, d15), (a74, b5, c1, d16), (a74, b5, c1, d17), (a74, b5, c1, d18), (a74, b5, c1, d19), (a74, b5, c1, d20), (a74, b5, c1, d21), (a74, b5, c1, d22), (a74, b5, c2, d1), (a74, b5, c2, d2), (a74, b5, c2, d3), (a74, b5, c2, d4), (a74, b5, c2, d5), (a74, b5, c2, d6), (a74, b5, c2, d7), (a74, b5, c2, d8), (a74, b5, c2, d19), (a74, b5, c2, d10), (a74, b5, c2, d11), (a74, b5, c2, d12), (a74, b5, c2, d13), (a74, b5, c2, d14), (a74, b5, c2, d15), (a74, b5, c2, d16), (a74, b5, c2, d17), (a74, b5, c2, d18), (a74, b5, c2, d19), (a74, b5, c2, d20), (a74, b5, c2, d21), (a74, b5, c2, d22), (a74, b5, c3, d1), (a74, b5, c3, d2), (a74, b5, c3, d3), (a74, b5, c3, d4), (a74, b5, c3, d5), (a74, b5, c3, d6), (a74, b5, c3, d7), (a74, b5, c3, d8), (a74, b5, c3, d1), (a74, b5, c3, d10), (a74, b5, c3, d11), (a74, b5, c3, d12), (a74, b5, c3, d13), (a74, b5, c3, d14), (a74, b5, c3, d15), (a74, b5, c3, d16), (a74, b5, c3, d17), (a74, b5, c3, d18), (a74, b5, c3, d19), (a74, b5, c3, d20), (a74, b5, c3, d21), (a74, b5, c3, d22), (a74, b6, c1, d1), (a74, b6, c1, d2), (a74, b6, c1, d3), (a74, b6, c1, d4), (a74, b6, c1, d5), (a74, b6, c1, d6), (a74, b6, c1, d7), (a74, b6, c1, d8), (a74, b6, c1, d9), (a74, b6, c1, d6), (a74, b6, c1, d11), (a74, b6, c1, d12), (a74, b6, c1, d13), (a74, b6, c1, d14), (a74, b6, c1, d15), (a74, b6, c1, d16), (a74, b6, c1, d17), (a74, b6, c1, d18), (a74, b6, c1, d19), (a74, b6, c1, d20), (a74, b6, c1, d21), (a74, b6, c1, d22), (a74, b6, c2, d1), (a74, b6, c2, d2), (a74, b6, c2, d3), (a74, b6, c2, d4), (a74, b6, c2, d5), (a74, b6, c2, d6), (a74, b6, c2, d7), (a74, b6, c2, d8), (a74, b6, c2, d9), (a74, b6, c2, d10), (a74, b6, c2, d11), (a74, b6, c2, d12), (a74, b6, c2, d13), (a74, b6, c2, d14), (a74, b6, c2, d15), (a74, b6, c2, d16), (a74, b6, c2, d17), (a74, b6, c2, d18), (a74, b6, c2, d19), (a74, b6, c2, d20), (a74, b6, c2, d21), (a74, b6, c2, d22), (a74, b6, c3, d1), (a74, b6, c3, d2), (a74, b6, c3, d3), (a74, b6, c3, d4), (a74, b6, c3, d5), (a74, b6, c3, d6), (a74, b6, c3, d7), (a74, b6, c3, d8), (a74, b6, c3, d9), (a74, b6, c3, d10), (a74, b6, c3, d11), (a74, b6, c3, d12), (a74, b6, c3, d13), (a74, b6, c3, d14), (a74, b6, c3, d15), (a74, b6, c3, d16), (a74, b6, c3, d17), (a74, b6, c3, d18), (a74, b6, c3, d19), (a74, b6, c3, d20), (a74, b6, c3, d21), (a74, b6, c3, d22), (a75, b1, c1, d1), (a75, b1, c1, d2), (a75, b1, c1, d3), (a75, b1, c1, d4), (a75, b1, c1, d5), (a75, b1, c1, d6), (a75, b1, c1, d7), (a75, b1, c1, d8), (a75, b1, c1, d9), (a75, b1, c1, d10), (a75, b1, c1, d11), (a75, b1, c1, d12), (a75, b1, c1, d13), (a75, b1, c1, d14), (a75, b1, c1, d15), (a75, b1, c1, d16), (a75, b1, c1, d17), (a75, b1, c1, d18), (a75, b1, c1, d19), (a75, b1, c1, d20), (a75, b1, c1, d21), (a75, b1, c1, d22), (a75, b1, c2, d1), (a75, b1, c2, d2), (a75, b1, c2, d3), (a75, b1, c2, d4), (a75, b1, c2, d5), (a75, b1, c2, d6), (a75, b1, c2, d7), (a75, b1, c2, d8), (a75, b1, c2, d9), (a75, b1, c2, d10), (a75, b1, c2, d11), (a75, b1, c2, d12), (a75, b1, c2, d13), (a75, b1, c2, d14), (a75, b1, c2, d15), (a75, b1, c2, d16), (a75, b1, c2, d17), (a75, b1, c2, d18), (a75, b1, c2, d19), (a75, b1, c2, d20), (a75, b1, c2, d21), (a75, b1, c2, d22), (a75, b1, c3, d1), (a75, b1, c3, d2), (a75, b1, c3, d3), (a75, b1, c3, d4), (a75, b1, c3, d5), (a75, b1, c3, d6), (a75, b1, c3, d7), (a75, b1, c3, d8), (a75, b1, c3, d9), (a75, b1, c3, d10), (a75, b1, c3, d11), (a75, b1, c3, d12), (a75, b1, c3, d13), (a75, b1, c3, d14), (a75, b1, c3, d15), (a75, b1, c3, d16), (a75, b1, c3, d17), (a75, b1, c3, d18), (a75, b1, c3, d19), (a75, b1, c3, d20), (a75, b1, c3, d21), (a75, b1, c3, d22), (a75, b2, c1, d1), (a75, b2, c1, d2), (a75, b2, c1, d3), (a75, b2, c1, d4), (a75, b2, c1, d5), (a75, b2, c1, d6), (a75, b2, c1, d7), (a75, b2, c1, d8), (a75, b2, c1, d9), (a75, b2, c1, d10), (a75, b2, c1, d11), (a75, b2, c1, d12), (a75, b2, c1, d13), (a75, b2, c1, d14), (a75, b2, c1, d15), (a75, b2, c1, d16), (a75, b2, c1, d17), (a75, b2, c1, d18), (a75, b2, c1, d19), (a75, b2, c1, d20), (a75, b2, c1, d21), (a75, b2, c1, d22), (a75, b2, c2, d1), (a75, b2, c2, d2), (a75, b2, c2, d3), (a75, b2, c2, d4), (a75, b2, c2, d5), (a75, b2, c2, d6), (a75, b2, c2, d7), (a75, b2, c2, d8), (a75, b2, c2, d9), (a75, b2, c2, d10), (a75, b2, c2, d11), (a75, b2, c2, d12), (a75, b2, c2, d13), (a75, b2, c2, d14), (a75, b2, c2, d15), (a75, b2, c2, d16), (a75, b2, c2, d17), (a75, b2, c2, d18), (a75, b2, c2, d19), (a75, b2, c2, d20), (a75, b2, c2, d21), (a75, b2, c2, d22), (a75, b2, c3, d1), (a75, b2, c3, d2), (a75, b2, c3, d3), (a75, b2, c3, d4), (a75, b2, c3, d5), (a75, b2, c3, d16), (a75, b2, c3, d7), (a75, b2, c3, d8), (a75, b2, c3, d9), (a75, b2, c3, d10), (a75, b2, c3, d11), (a75, b2, c3, d12), (a75, b2, c3, d13), (a75, b2, c3, d14), (a75, b2, c3, d15), (a75, b2, c3, d16), (a75, b2, c3, d17), (a75, b2, c3, d18), (a75, b2, c3, d19), (a75, b2, c3, d20), (a75, b2, c3, d21), (a75, b2, c3, d22), (a75, b3, c1, d1), (a75, b3, c1, d2), (a75, b3, c1, d3), (a75, b3, c1, d4), (a75, b3, c1, d5), (a75, b3, c1, d6), (a75, b3, c1, d7), (a75, b3, c1, d8), (a75, b3, c1, d9), (a75, b3, c1, d10), (a75, b3, c1, d11), (a75, b3, c1, d12), (a75, b3, c1, d13), (a75, b3, c1, d14), (a75, b3, c1, d15), (a75, b3, c1, d16), (a75, b3, c1, d17), (a75, b3, c1, d18), (a75, b3, c1, d19), (a75, b3, c1, d20), (a75, b3, c1, d21), (a75, b3, c1, d22), (a75, b3, c2, d1), (a75, b3, c2, d2), (a75, b3, c2, d3), (a75, b3, c2, d4), (a75, b3, c2, d5), (a75, b3, c2, d6), (a75, b3, c2, d7), (a75, b3, c2, d8), (a75, b3, c2, d9), (a75, b3, c2, d10), (a75, b3, c2, d11), (a75, b3, c2, d12), (a75, b3, c2, d13), (a75, b3, c2, d14), (a75, b3, c2, d15), (a75, b3, c2, d16), (a75, b3, c2, d17), (a75, b3, c2, d18), (a75, b3, c2, d19), (a75, b3, c2, d20), (a75, b3, c2, d21), (a75, b3, c2, d22), (a75, b3, c3, d1), (a75, b3, c3, d2), (a75, b3, c3, d3), (a75, b3, c3, d4), (a75, b3, c3, d5), (a75, b3, c3, d6), (a75, b3, c3, d7), (a75, b3, c3, d8), (a75, b3, c3, d9), (a75, b3, c3, d10), (a75, b3, c3, d11), (a75, b3, c3, d12), (a75, b3, c3, d13), (a75, b3, c3, d14), (a75, b3, c3, d15), (a75, b5, c3, d16), (a75, b5, c3, d17), (a75, b3, c3, d18), (a75, b3, c3, d19), (a75, b3, c3, d20), (a75, b3, c3, d21), (a75, b3, c3, d22), (a75, b4, c1, d1), (a75, b4, c1, d2), (a75, b4, c1, d3), (a75, b4, c1, d4), (a75, b4, c1, d5), (a75, b4, c1, d6), (a75, b4, c1, d7), (a75, b4, c1, d8), (a75, b4, c1, d9), (a75, b4, c1, d10), (a75, b4, c1, (a75, b4, c1, d16), (a75, b4, c1, d17), (a75, b4, c1, d18), (a75, b4, c1, d19), (a75, b4, c1, d20), (a75, b4, c1, d21), (a75, b4, c1, d22), (a75, b4, c2, d1), (a75, b4, c2, d2), (a75, b4, c2, d3), (a75, b4, c2, d4), (a75, b4, c2, d5), (a75, b4, c2, d6), (a75, b4, c2, d7), (a75, b4, c2, d8), (a75, b4, c2, d9), (a75, b4, c2, d10), (a75, b4, c2, d11), (a75, b4, c2, d12), (a75, b4, c2, d13), (a75, b4, c2, d14), (a75, b4, c2, d15), (a75, b4, c2, d16), (a75, b4, c2, d17), (a75, b4, c2, d18), (a75, b4, c2, d19), (a75, b4, c2, d20), (a75, b4, c2, d21), (a75, b4, c2, d22), (a75, b4, c3, d1), (a75, b4, c3, d2), (a75, b4, c3, d3), (a75, b4, c3, d4), (a75, b4, c3, d5), (a75, b4, c3, d6), (a75, b4, c3, d7), (a75, b4, c3, d8), (a75, b4, c3, d9), (a75, b4, c3, d10), (a75, b4, c3, d11), (a75, b4, c3, d12), (a75, b4, c3, d13), (a75, b4, c3, d14), (a75, b4, c3, d15), (a75, b4, c3, d16), (a75, b4, c3, d17), (a75, b4, c3, d18), (a75, b4, c3, d19), (a75, b4, c3, d20), (a75, b4, c3, d21), (a75, b4, c3, d22), (a75, b5, c1, d1), (a75, b5, c1, d2), (a75, b5, c1, d3), (a75, b5, c1, d4), (a75, b5, c1, d5), (a75, b5, c1, d6), (a75, b5, c1, d7), (a75, b5, c1, d8), (a75, b5, c1, d9), (a75, b5, c1, d10), (a75, b5, c1, d11), (a75, b5, c1, d12), (a75, b5, c1, d13), (a75, b5, c1, d14), (a75, b5, c1, d15), (a75, b5, c1, d16), (a75, b5, c1, d17), (a75, b5, c1, d18), (a75, b5, c1, d19), (a75, b5, c1, d20), (a15, b5, c1, d21), (a75, b5, c1, d22), (a75, b5, c2, d1), (a75, b5, c2, d2), (a75, b5, c2, d3), (a75, b5, c2, d4), (a75, b5, c2, d5), (a75, b5, c2, d6), (a75, b5, c2, d7), (a75, b5, c2, d8), (a75, b5, c2, d9), (a75, b5, c2, d10), (a75, b5, c2, d11), (a75, b5, c2, d12), (a75, b5, c2, d13), (a75, b5, c2, d14), (a75, b5, c2, d15), (a75, b5, c2, d16), (a75, b5, c2, d17), (a75, b5, c2, d18), (a15, b5, c2, d19), (a75, b5, c2, d20), (a75, b5, c2, d21), (a75, b5, c2, d22), (a75, b5, c3, d1), (a75, b5, c3, d2), (a75, b5, c3, d3), (a75, b5, c3, d4), (a75, b5, c3, d5), (a75, b5, c3, d6), (a75, b5, c3, d7), (a75, b5, c3, d8), (a75, b5, c3, d9), (a75, b5, c3, d10), (a75, b5, c3, d11), (a75, b5, c3, d12), (a75, b5, c3, d13), (a75, b5, c3, d14), (a75, b5, c3, d15), (a75, b5, c3, d16), (a75, b5, c3, d17), (a75, b5, c3, d18), (a75, b5, c3, d19), (a75, b5, c3, d20), (a75, b5, c3, d21), (a75, b5, c3, d22), (a75, b6, c1, d1), (a75, b6, c1, d2), (a75, b6, c1, d3), (a75, b6, c1, d4), (a75, b6, c1, d5), (a75, b6, c1, d6), (a75, b6, c1, d7), (a75, b6, c1, d8), (a75, b6, c1, d9), (a75, b6, c1, d10), (a75, b6, c1, d11), (a75, b6, c1, d12), (a75, b6, c1, d13), (a75, b6, c1, d14), (a75, b6, c1, d15), (a75, b6, c1, d16), (a75, b6, c1, d17), (a75, b6, c1, d18), (a75, b6, c1, d19), (a75, b6, c1, d20), (a75, b6, c1, d21), (a75, b6, c1, d22), (a75, b6, c2, d1), (a75, b6, c2, d2), (a15, b6, c2, d3), (a75, b6, c2, d4), (a75, b6, c2, d5), (a75, b6, c2, d6), (a75, b6, c2, d7), (a75, b6, c2, d8), (a75, b6, c2, d9), (a75, b6, c2, d10), (a75, b6, c2, d11), (a75, b6, c2, d12), (a75, b6, c2, d13), (a75, b6, c2, d14), (a75, b6, c2, d15), (a75, b6, c2, d16), (a75, b6, c2, d17), (a75, b6, c2, d18), (a75, b6, c2, d19), (a75, b6, c2, d20), (a75, b6, c2, d21), (a75, b6, c2, d22), (a75, b6, c3, d1), (a75, b6, c3, d2), (a75, b6, c3, d3), (a75, b6, c3, d4), (a75, b6, c3, d5), (a75, b6, c3, d6), (a7, b6, c3, d7), (a75, b6, c3, d8), (a75, b6, c3, d9), (a75, b6, c3, d10), (a75, b6, c3, d11), (a75, b6, c3, d12), (a75, b6, c3, d13), (a75, b6, c3, d14), (a75, b6, c3, d15), (a75, b6, c3, d16), (a75, b6, c3, d17), (a75, b6, c3, d18), (a75, b6, c3, d19), (a75, b6, c3, d20), (a75, b6, c3, d21), (a75, b6, c3, d22), (a76, b1, c1, d1), (a76, b1, c1, d2), (a76, b1, c1, d3), (a76, b1, c1, d4), (a76, b1, c1, d5), (a76, b1, c1, d6), (a76, b1, c1, d7), (a76, b1, c1, d8), (a76, b1, c1, d9), (a76, b1, c1, d10), (a76, b1, c1, d11), (a76, b1, c1, d12), (a76, b1, c1, d13), (a76, b1, c1, d14), (a76, b1, c1, d15), (a76, b1, c1, d16), (a76, b1, c1, d17), (a76, b1, c1, d18), (a76, b1, c1, d19), (a76, b1, c1, d20), (a76, b1, c1, d21), (a76, b1, c1, d22), (a76, b1, c2, d1), (a76, b1, c2, d2), (a76, b1, c2, d3), (a76, b1, c2, d4), (a76, b1, c2, d5), (a76, b1, c2, d6), (a76, b1, c2, d17), (a76, b1, c2, d18), (a76, b1, c2, d9), (a76, b1, c2, d10), (a76, b1, c2, d11), (a76, b1, c2, d12), (a76, b1, c2, d13), (a76, b1, c2, d14), (a76, b1, c2, d15), (a76, b1, c2, d16), (a76, b1, c2, d17), (a76, b1, c2, d18), (a76, b1, c2, d19), (a76, b1, c2, d20), (a76, b1, c2, d21), (a76, b1, c2, d22), (a76, b1, c3, d1), (a76, b1, c3, d2), (a76, b1, c3, d3), (a76, b1, c3, d4), (a76, b1, c3, d5), (a76, b1, c3, d6), (a76, b1, c3, d7), (a76, b1, c3, d8), (a76, b1, c3, d9), (a76, b1, c3, d10), (a76, b1, c3, d11), (a76, b1, c3, d12), (a76, b1, c3, d13), (a76, b1, c3, d14), (a76, b1, c3, d15), (a76, b1, c3, d16), (a76, b1, c3, d17), (a76, b1, c3, d18), (a76, b1, c3, d19), (a76, b1, c3, d20), (a76, b1, c3, d21), (a76, b1, c3, d22), (a76, b2, c1, d1), (a76, b2, c1, d2), (a76, b2, c1, d3), (a76, b2, c1, d4), (a76, b2, c1, d5), (a76, b2, c1, d6), (a76, b2, c1, d7), (a76, b2, c1, d8), (a76, b2, c1, d9), (a76, b2, c1, d10), (a76, b2, c1, d11), (a76, b2, c1, d12), (a76, b2, c1, d13), (a76, b2, c1, d14), (a70, b2, c1, d15), (a76, b2, c1, d16), (a76, b2, c1, d17), (a76, b2, c1, d18), (a76, b2, c1, d19), (a76, b2, c1, d20), (a76, b2, c1, d21), (a76, b2, c1, d22), (a76, b2, c2, d1), (a76, b2, c2, d2), (a76, b2, c2, d3), (a76, b2, c2, d4), (a76, b2, c2, d5), (a76, b2, c2, d6), (a76, b2, c2, d7), (a76, b2, c2, d8), (a76, b2, c2, d9), (a76, b2, c2, d10), (a76, b2, c2, d11), (a76, b2, c2, d12), (a76, b2, c2, d13), (a76, b2, c2, d14), (a76, b2, c2, d15), (a76, b2, c2, d16), (a76, b2, c2, d17), (a76, b2, c2, d18), (a76, b2, c2, d19), (a76, b2, c2, d20), (a76, b2, c2, d21), (a76, b2, c2, d22), (a76, b2, c3, di), (a76, b2, c3, d2), (a76, b2, c3, d3), (a76, b2, c3, d4), (a76, b2, c3, d5), (a76, b2, c3, d6), (a76, b2, c3, d7), (a76, b2, c3, d8), (a76, b2, c3, d9), (a76, b2, c3, d10), (a76, b2, c3, d11), (a76, b2, c3, d12), (a76, b2, c3, d13), (a76, b2, c3, d14), (a76, b2, c3, d15), (a76, b2, c3, d16), (a76, b2, c3, d17), (a76, b2, c3, d18), (a76, b2, c3, d19), (a76, b2, c3, d20), (a76, b2, c3, d21), (a76, b2, c3, d22), (a76, b3, c1, d1), (a76, b3, c1, d2), (a76, b3, c1, d3), (a76, b3, c1, d4), (a76, b3, c1, d5), (a76, b3, c1, d6), (a76, b3, c1, d7), (a76, b3, c1, d8), (a76, b3, c1, d9), (a76, b3, c1, d10), (a76, b3, c1, d11), (a76, b3, c1, d2), (a76, b3, c1, d13), (a76, b3, c1, d14), (a76, b3, c1, d15), (a76, b3, c1, d16), (a76, b3, c1, d17), (a76, b3, c1, d18), (a76, b3, c1, d19), (a76, b3, c1, d20), (a76, b3, c1, d21), (a76, b3, c1, d22), (a76, b3, c2, d1), (a76, b3, c2, d2), (a76, b3, c2, d3), (a76, b3, c2, d4), (a76, b3, c2, d5), (a76, b3, c2, d6), (a76, b3, c2, d7), (a76, b3, c2, d8), (a76, b3, c2, d9), (a76, b3, c2, d10), (a76, b3, c2, d11), (a76, b3, c2, d12), (a76, b3, c2, d13), (a76, b3, c2, d14), (a76, b3, c2, d15), (a76, b3, c2, d16), (a76, b3, c2, d17), (a76, b3, c2, d18), (a76, b3, c2, d19), (a76, b3, c2, d20), (a76, b3, c2, d21), (a76, b3, c2, d22), (a76, b3, c3, d1), (a76, b3, c3, d2), (a76, b3, c3, d3), (a76, b3, c3, d4), (a76, b3, c3, d5), (a76, b3, c3, d6), (a76, b3, c3, d7), (a76, b3, c3, d8), (a76, b3, c3, d9), (a76, b3, c3, d10), (a76, b3, c3, d11), (a76, b3, c3, d12), (a76, b3, c3, d13), (a76, b3, c3, d14), (a76, b3, c3, d15), (a76, b3, c3, d16), (a76, b3, c3, d17), (a76, b3, c3, d18), (a76, b3, c3, d19), (a76, b3, c3, d20), (a76, b3, c3, d21), (a76, b3, c3, d22), (a76, b4, c1, d1), (a76, b4, c1, d2), (a76, b4, c1, d3), (a6, b4, c1, d4), (a76, b4, c1, d5), (a76, b4, c1, d6), (a76, b4, c1, d7), (a76, b4, c1, d8), (a76, b4, c1, d9), (a76, b4, c1, d10), (a76, b4, c1, d11), (a76, b4, c1, d12), (a76, b4, c1, d13), (a76, b4, c1, d14), (a76, b4, c1, d15), (a76, b4, c1, d16), (a76, b4, c1, d17), (a76, b4, c1, d18), (a76, b4, c1, d19), (a76, b4, c1, d20), (a76, b4, c1, d21), (a76, b4, c1, d22), (a76, b4, c2, d1), (a76, b4, c2, d2), (a76, b4, c2, d3), (a76, b4, c2, d4), (a76, b4, c2, d5), (a76, b4, c2, d6), (a76, b4, c2, d7), (a76, b4, c2, d8), (a76, b4, c2, d9), (a76, b4, c2, d10), (a76, b4, c2, d11), (a76, b4, c2, d12), (a76, b4, c2, d13), (a76, b4, c2, d14), (a76, b4, c2, d15), (a76, b4, c2, d16), (a76, b4, c2, d17), (a76, b4, c2, d18), (a76, b4, c2, d19), (a76, b4, c2, d20), (a76, b4, c2, d21), (a76, b4, c2, d22), (a76, b4, c3, d1), (a76, b4, c3, d2), (a76, b4, c3, d3), (a76, b4, c3, d4), (a76, b4, c3, d5), (a76, b4, c3, d6), (a76, b4, c3, d7), (a76, b4, c3, d8), (a76, b4, c3, d9), (a76, b4, c3, d10), (a76, b4, c3, d11), (a76, b4, c3, d12), (a76, b4, c3, d13), (a76, b4, c3, d14), (a76, b4, c3, d15), (a76, b4, c3, d16), (a76, b4, c3, d17), (a76, b4, c3, d18), (a76, b4, c3, d19), (a76, b4, c3, d20), (a76, b4, c3, d21), (a76, b4, c3, d22), (a76, b5, c1, d1), (a76, b5, c1, d2), (a76, b5, c1, d3), (a76, b5, c1, d4), (a76, b5, c1, d5), (a76, b5, c1, d6), (a76, b5, c1, d7), (a76, b5, c1, d8), (a76, b5, c1, d9), (a76, b5, c1, d10), (a76, b5, c1, d11), (a76, b5, c1, d12), (a76, b5, c1, d13), (a76, b5, c1, d14), (a76, b5, c1, d15), (a76, b5, c1, d16), (a76, b5, c1, d17), (a76, b5, c1, d18), (a76, b5, c1, d19), (a76, b5, c1, d20), (a76, b5, c1, d21), (a76, b5, c1, d22), (a76, b5, c2, d1), (a76, b5, c2, d2), (a76, b5, c2, d3), (a76, b5, c2, d4), (a76, b5, c2, d5), (a76, b5, c2, d6), (a76, b5, c2, d7), (a76, b5, c2, d3), (a76, b5, c2, d9), (a76, b5, c2, d10), (a76, b5, c2, d11), (a76, b5, c2, d12), (a76, b5, c2, d13), (a76, b5, c2, d14), (a76, b5, c2, d15), (a76, b5, c2, d16), (a76, b5, c2, d17), (a76, b5, c2, d18), (a76, b5, c2, d19), (a76, b5, c2, d20), (a76, b5, c2, d21), (a76, b5, c2, d22), (a76, b5, c3, d1), (a76, b5, c3, d2), (a76, b5, c3, d3), (a76, b5, c3, d4), (a76, b5, c3, d5), (a76, b5, c3, d6), (a76, b5, c3, d7), (a76, b5, c3, d8), (a76, b5, c3, d9), (a76, b5, c3, d10), (a76, b5, c3, d11), (a76, b5, c3, d12), (a76, b5, c3, d13), (a76, b5, c3, d14), (a76, b5, c3, d15), (a76, b5, c3, d16), (a76, b5, c3, d17), (a76, b5, c3, d18), (a76, b5, c3, d19), (a76, b5, c3, d20), (a76, b5, c3, d21), (a76, b5, c3, d22), (a76, b6, c1, d1), (a76, b6, c1, d2), (a76, b6, c1, d3), (a76, b6, c1, d4), (a76, b6, c1, d5), (a76, b6, c1, d6), (a76, b6, c1, d7), (a76, b6, c1, d8), (a76, b6, c1, d9), (a76, b6, c1, d10), (a76, b6, c1, d11), (a76, b6, c1, d12), (a76, b6, c1, d13), (a76, b6, c1, d14), (a76, b6, c1, d15), (a76, b6, c1, d16), (a76, b6, c1, d17), (a76, b6, c1, d18), (a76, b6, c1, d19), (a76, b6, c1, d20), (a76, b6, c1, d21), (a76, b6, c1, d22), (a76, b6, c2, d1), (a76, b6, c2, d2), (a76, b6, c2, d3), (a76, b6, c2, d4), (a76, b6, c2, d5), (a76, b6, c2, d6), (a76, b6, c2, d7), (a76, b6, c2, d8), (a76, b6, c2, d9), (a76, b6, c2, d10), (a76, b6, c2, d11), (a76, b6, c2, d12), (a76, b6, c2, d13), (a76, b6, c2, d14), (a76, b6, c2, d15), (a76, b6, c2, d16), (a76, b6, c2, d17), (a76, b6, c2, d18), (a76, b6, c2, d19), (a76, b6, c2, d20), (a76, b6, c2, d21), (a76, b6, c2, d22), (a76, b6, c3, d1), (a76, b6, c3, d2), (a76, b6, c3, d3), (a76, b6, c3, d4), (a76, b6, c3, d5), (a76, b6, c3, d6), (a76, b6, c3, d7), (a76, b6, c3, d8), (a76, b6, c3, d9), (a76, b6, c3, d10), (a76, b6, c3, d11), (a76, b6, c3, d12), (a76, b6, c3, d13), (a76, b6, c3, d14), (a76, b6, c3, d15), (a76, b6, c3, d16), (a76, b6, c3, d17), (a76, b6, c3, d18), (a76, b6, c3, d19), (a76, b6, c3, d20), (a76, b6, c3, d21), (a76, b6, c3, d22), (a77, b1, c1, d1), (a77, b1, c1, d2), (a77, b1, c1, d3), (a77, b1, c1, d4), (a77, b1, c1, d5), (a77, b1, c1, d6), (a77, b1, c1, d7), (a77, b1, c1, d3), (a77, b1, c1, d9), (a77, b1, c1, d10), (a77, b1, c1, d11), (a77, b1, c1, d12), (a77, b1, c1, d13), (a77, b1, c1, d14), (a77, b1, c1, d15), (a77, b1, c1, d16), (a77, b1, c1, d17), (a77, b1, c1, d18), (a77, b1, c1, d19), (a77, b1, c1, d20), (a77, b1, c1, d21), (a77, b1, c1, d22), (a77, b1, c2, d1), (a77, b1, c2, d2), (a77, b1, c2, d3), (a77, b1, c2, d4), (a77, b1, c2, d5), (a77, b1, c2, d6), (a77, b1, c2, d7), (a77, b1, c2, d8), (a77, b1, c2, d9), (a77, b1, c2, d10), (a77, b1, c2, d11), (a77, b1, c2, d12), (a77, b1, c2, d13), (a77, b1, c2, d14), (a77, b1, c2, d15), (a77, b1, c2, d16), (a77, b1, c2, d17), (a77, b1, c2, d18), (a77, b1, c2, d19), (a77, b1, c2, d20), (a77, b1, c2, d21), (a77, b1, c2, d22), (a77, b1, c3, d1), (a77, b1, c3, d2), (a77, b1, c3, d3), (a77, b1, c3, d4), (a77, b1, c3, d5), (a77, b1, c3, d6), (a77, b1, c3, d7), (a77, b1, c3, d8), (a77, b1, c3, d9), (a77, b1, c3, d10), (a77, b1, c3, d11), (a77, b1, c3, d12), (a77, b1, c3, d13), (a77, b1, c3, d14), (a77, b1, c3, d15), (a77, b1, c3, d16), (a77, b1, c3, d17), (a77, b1, c3, d18), (a77, b1, c3, d19), (a77, b1, c3, d20), (a77, b1, c3, d21), (a77, b1, c3, d22), (a77, b2, c1, d1), (a77, b2, c1, d2), (a77, b2, c1, d3), (a77, b2, c1, d4), (a77, b2, c1, d5), (a77, b2, c1, d6), (a77, b2, c1, d7), (a77, b2, c1, d8), (a77, b2, c1, d9), (a77, b2, c1, d10), (a77, b2, c1, d11), (a77, b2, c1, d12), (a77, b2, c1, d13), (a77, b2, c1, d14), (a77, b2, c1, d15), (a77, b2, c1, d16), (a77, b2, c1, d17), (a77, b2, c1, d18), (a77, b2, c1, d19), (a77, b2, c1, d20), (a77, b2, c1, d21), (a77, b2, c1, d22), (a77, b2, c2, d1), (a77, b2, c2, d2), (a77, b2, c2, d3), (a77, b2, c2, d4), (a77, b2, c2, d5), (a77, b2, c2, d6), (a77, b2, c2, d7), (a77, b2, c2, d8), (a77, b2, c2, d9), (a77, b2, c2, d10), (a77, b2, c2, d11), (a77, b2, c2, d12), (a77, b2, c2, d13), (a77, b2, c2, d14), (a77, b2, c2, d15), (a77, b2, c2, d16), (a77, b2, c2, d17), (a77, b2, c2, d18), (a77, b2, c2, d19), (a77, b2, c2, d20), (a77, b2, c2, d21), (a77, b2, c2, d22), (a77, b2, c3, d1), (a77, b2, c3, d2), (a77, b2, c3, d3), (a77, b2, c3, d4), (a77, b2, c3, d5), (a77, b2, c3, d6), (a77, b2, c3, d7), (a77, b2, c3, d8), (a77, b2, c3, d9), (a77, b2, c3, d10), (a77, b2, c3, d11), (a77, b2, c3, d12), (a77, b2, c3, d13), (a77, b2, c3, d14), (a77, b2, c3, d15), (a77, b2, c3, d16), (a77, b2, c3, d17), (a77, b2, c3, d18), (a77, b2, c3, d19), (a77, b2, c3, d20), (a7, b2, c3, d21), (a77, b2, c3, d22), (a77, b3, c1, d1), (a77, b3, c1, d2), (a77, b3, c1, d3), (a77, b3, c1, d4), (a77, b3, c1, d5), (a77, b3, c1, d6), (a77, b3, c1, d7), (a77, b3, c1, d8), (a77, b3, c1, d9), (a77, b3, c1, d10), (a77, b3, c1, d11), (a77, b3, c1, d12), (a77, b3, c1, d13), (a77, b3, c1, d14), (a77, b3, c1, d15), (a77, b3, c1, d16), (a77, b3, c1, d17), (a77, b3, c1, d18), (a77, b3, c1, d19), (a77, b3, c1, d20), (a77, b3, c1, d21), (a77, b3, c1, d22), (a77, b3, c2, d1), (a77, b3, c2, d2), (a77, b3, c2, d3), (a77, b3, c2, d4), (a77, b3, c2, d5), (a77, b3, c2, d6), (a77, b3, c2, d7), (a77, b3, c2, d8), (a77, b3, c2, d9), (a77, b3, c2, d10), (a77, b3, c2, d11), (a77, b3, c2, d12), (a77, b3, c2, d13), (a77, b3, c2, d14), (a77, b3, c2, d15), (a77, b3, c2, d16), (a77, b3, c2, d17), (a77, b3, c2, d18), (a77, b3, c2, d19), (a77, b3, c2, d20), (a77, b3, c2, d21), (a77, b3, c2, d22), (a77, b3, c3, dl), (a77, b3, c3, d2), (a77, b3, c3, d3), (a77, b3, c3, d4), (a77, b3, c3, d5), (a77, b3, c3, d6), (a77, b3, c3, d7), (a77, b3, c3, d8), (a77, b3, c3, d9), (a77, b3, c3, d10), (a77, b3, c3, d11), (a77, b3, c3, d12), (a77, b3, c3, d13), (a77, b3, c3, d14), (a77, b3, c3, d15), (a77, b3, c3, d16), (a77, b3, c3, d17), (a77, b3, c3, d18), (a77, b3, c3, d19), (a77, b3, c3, d20), (a77, b3, c3, d21), (a77, b3, c3, d22), (a77, b4, c1, d1), (a77, b4, c1, d2), (a77, b4, c1, d3), (a77, b4, c1, d4), (a77, b4, c1, d5), (a77, b4, c1, d6), (a77, b4, c1, d7), (a77, b4, c1, d8), (a77, b4, c1, d9), (a77, b4, c1, d10), (a77, b4, c1, d11), (a77, b4, c1, d12), (a77, b4, c1, d13), (a77, b4, c1, d14), (a77, b4, c1, d15), (a77, b4, c1, d16), (a77, b4, c1, d17), (a77, b4, c1, d18), (a77, b4, c1, d19), (a77, b4, c1, d20), (a77, b4, c1, d21), (a77, b4, c1, d22), (a77, b4, c2, d1), (a77, b4, c2, d2), (a77, b4, c2, d3), (a77, b4, c2, d4), (a77, b4, c2, d5), (a77, b4, c2, d6), (a77, b4, c2, d7), (a77, b4, c2, d8), (a77, b4, c2, d9), (a77, b4, c2, d10), (a77, b4, c2, d11), (a77, b4, c2, d12), (a77, b4, c2, d13), (a77, b4, c2, d14), (a77, b4, c2, d15), (a77, b4, c2, d16), (a77, b4, c2, d17), (a77, b4, c2, d18), (a77, b4, c2, d19), (a77, b4, c2, d20), (a77, b4, c2, d21), (a77, b4, c2, d22), (a77, b4, c3, d1), (a77, b4, c3, d2), (a77, b4, c3, d3), (a77, b4, c3, d4), (a77, b4, c3, d5), (a77, b4, c3, d6), (a7, b4, c3, d7), (a77, b4, c3, d8), (a77, b4, c3, d9), (a77, b4, c3, d10), (a77, b4, c3, d11), (a77, b4, c3, d12), (a77, b4, c3, d13), (a77, b4, c3, d14), (a77, b4, c3, d15), (a77, b4, c3, d16), (a77, b4, c3, d17), (a77, b4, c3, d18), (a77, b4, c3, d19), (a77, b4, c3, d20), (a77, b4, c3, d21), (a77, b4, c3, d22), (a77, b5, c1, d1), (a77, b5, c1, d2), (a77, b6, c1, d3), (a77, b5, c1, d4), (a77, b5, c1, d5), (a77, b5, c1, d6), (a77, b5, c1, d7), (a77, b5, c1, d8), (a77, b5, c1, d9), (a77, b5, c1, d10), (a77, b5, c1, d11), (a77, b5, c1, d12), (a77, b5, c1, d13), (a77, b5, c1, d14), (a17, b5, c1, d15), (a77, b5, c1, d16), (a77, b5, c1, d17), (a77, b5, d18), (a77, b5, c1, d19), (a77, b5, c1, d20), (a77, b5, c1, d21), (a77, b5, c1, d22), (a77, b5, c2, d1), (a77, b5, c2, d2), (a77, b5, c2, d3), (a77, b5, c2, d4), (a77, b5, c2, d5), (a77, b5, c2, d6), (a77, b5, c2, d7), (a77, b5, c2, d8), (a77, b5, c2, d9), (a77, b5, c2, d10), (a77, b5, c2, d11), (a77, b5, c2, d12), (a77, b5, c2, d13), (a77, US, c2, d14), (a77, b5, c2, d15), (a77, b5, c2, d16), (a77, b5, c2, d17), (a77, b5, c2, d18), (a77, b5, c2, d19), (a77, b5, c2, d20), (a77, b5, c2, d21), (a77, b5, c2, d22), (a77, b5, c3, d1), (a77, b5, c3, d2), (a77, b5, c3, d3), (a77, b5, c3, d4), (a77, b5, c3, d5), (a77, b5, c3, d6), (a77, b5, c3, d7), (a77, b5, c3, d8), (a77, b5, c3, d9), (a77, b5, c3, d10), (a77, b5, c3, d11), (a77, b5, c3, d12), (a77, b5, c3, d13), (a77, b5, c3, d14), (a77, b5, c3, d15), (a77, b5, c3, d16), (a77, b5, c3, d17), (a77, b5, c3, d18), (a77, b5, c3, d19), (a77, b5, c3, d20), (a77, b5, c3, d21), (a77, b5, c3, d22), (a77, b6, c1, d1), (a77, b6, c1, d2), (a77, b6, c1, d3), (a77, b6, c1, d4), (a77, b6, c1, d5), (a77, b6, c1, d6), (a77, b6, c1, d7), (a77, b6, c1, d8), (a77, b6, c1, d9), (a77, c1, d10), (a77, b6, c1, d11), (a77, b6, c1, d12), (a77, b6, c1, d13), (a77, b6, c1, d14), (a77, b6, c1, d15), (a77, b6, c1, d16), (a77, b6, c1, d17), (a77, b6, c1, d18), (a77, b6, c1, d19), (a77, b6, c1, d20), (a77, b6, c1, d21), (a77, b6, c1, d22), (a77, b6, c2, d1), (a77, b6, c2 d2), (a77, b6, c2, d3), (a77, b6, c2, d4), (a77, b6, c2, d5), (a77, b6, c2, d6), (a77, b6, c2, d7), (a77, b6, c2, d8), (a77, b6, c2, d9), (a77, b6, c2, d10), (a77, b6, c2, d11), (a77, b6, c2, d12), (a77, b6, c2, d13), (a77, b6, c2, d14), (a77, b6, c2, d15), (a77, b6, c2, d10), (a77, b6, c2, d17), (a77, b6, c2, d18), (a77, b6, c2, d19), (a77, b6, c2, d20), (a77, b6, c2, d21), (a77, b6, c2, d22), (a77, b6, c3, d1), (a77, b6, c3, d2), (a77, b6, c3, d3), (a77, b6, c3, d4), (a77, b6, c3, d5), (a77, b6, c3, d6), (a77, b6, c3, d7), (a77, b6, c3, d8), (a77, b6, c3, d9), (a77, b6, c3, d10), (a77, b6, c3, d11), (a77, b6, c3, d12), (a77, b6, c3, d13), (a77, b6, c3, d14), (a77, b6, c3, d15), (a77, b6, c3, d16), (a77, b6, c3, d17), (a77, b6, c3, d18), (a77, b6, c3, d19), (a77, b6, c3, d20), (a77, b6, c3, d21), (a77, b6, c3, d22), (a78, b1, c1, d11), (a78, b1, c1, d2), (a78, b1, c1, d3), (a78, b1, c1, d4), (a78, b1, c1, d5), (a78, b1, c1, d6), (a78, b1, c1, d7), (a78, b1, c1, d8), (a78, b1, c1, d9), (a78, b1, c1, d10), (a78, b1, c1, d11), (a78, b1, c1, d12), (a78, b1, c1, d13), (a78, b1, c1, d14), (a78, b1, c1, d15), (a78, b1, c1, d16), (a78, b1, c1, d17), (a78, b1, c1, d18), (a78, b1, c1, d19), (a78, b1, c1, d20), (a78, b1, c1, d21), (a78, b1, c1, d22), (a78, b1, c2, d1), (a78, b1, c2, d2), (a78, b1, c2, d3), (a78, b1, c2, d4), (a78, b1, c2, d5), (a78, b1, c2, d6), (a78, b1, c2, d7), (a78, b1, c2, d8), (a78, b1, c2, d9), (a78, b1, c2, d10), (a78, b1, c2, (a78, b1, c2, d16), (a78, b1, c1, d17), (a78, b1, c2, d18), (a78, b1, c2, d19), (a78, b1, c2, d20), (a78, b1, c2, d21), (a78, b1, c2, d22), (a78, b1, c3, d1), (a78, b1, c3, d2), (a78, b1, c3, d13), (a78, b1, c3, d4), (a78, b1, c3, d5), (a78, b1, c3, d6), (a78, b1, c3, d7), (a78, b1, c3, d8), (a78, b1, c3, d9), (a78, b1, c3, d10), (a78, b1, c3, d11), (a78, b1, c3, d12), (a78, b1, c3, d13), (a78, b1, c3, d14), (a78, b1, c3, d15), (a78, b1, c3, d16), (a78, b1, c3, d17), (a78, b1, c3, d18), (a78, b1, c3, d19), (a78, b1, c3, d20), (a78, b1, c3, d21), (a78, b1, c3, d22), (a78, b2, c1, d1), (a78, b2, c1, d2), (a78, b2, c1, d3), (a78, b2, c1, d4), (a78, b2, c1, d5), (a78, b2, c1, d6), (a78, b2, c1, d7), (a78, b2, c1, d8), (a78, b2, c1, d9), (a78, b2, c1, d10), (a78, b2, c1, d11), (a78, b2, c1, d12), (a78, b2, c1, d13), (a78, b2, c1, d14), (a78, b2, c1, d15), (a78, b2, c1, d16), (a78, b2, c1, d17), (a78, b2, c1, d18), (a78, b2, c1, d19), (a78, b2, c1, d20), (a78, b2, c1, d21), (a78, b2, c1, d22), (a78, b2, c2, d1), (a78, b2, c2, d2), (a78, b2, c2, d3), (a78, b2, c2, d4), (a78, b2, c2, d5), (a78, b2, c2, d6), (a78, b2, c2, d7), (a78, b2, c2, d8), (a78, b2, c2, d9), (a78, b2, c2, d10), (a78, b2, c2, d11), (a78, b2, c2, d12), (a78, b2, c2, d13), (a78, b2, c2, d14), (a78, b2, c2, d15), (a78, b2, c2, d16), (a78, b2, c2, d17), (a78, b2, c2, d18), (a78, b2, c2, d19), (a78, b2, c2, d20), (a78, b2, c2, d21), (a78, b2, c2, d22), (a78, b2, c3, d1), (a78, b2, c3, d2), (a78, b2, c3, d3), (a78, b2, c3, d4), (a78, b2, c3, d5), (a78, b2, c3, d6), (a78, b2, c3, d7), (a78, b2, c3, d8), (a78, b2, c3, d9), (a78, b2, c3, d10), (a78, b2, c3, d11), (a78, b2, c3, d12), (a78, b2, c3, d13), (a78, b2, c3, d14), (a78, b2, c3, d15), (a78, b2, c3, d16), (a78, b2, c3, d17), (a78, b2, c3, d18), (a78, b2, c3, d19), (a78, b2, c3, d20), (a78, b2, c3, d21), (a78, b2, c3, d22), (a78, b3, c1, d1), (a78, b3, c1, d2), (a78, b3, c1, d3), (a78, b3, c1, d4), (a78, b3, c1, d5), (a78, b3, c1, d6), (a78, b3, c1, d7), (a78, b3, c1, d8), (a78, b3, c1, d9), (a78, b3, c1, d10), (a78, b3, c1, d11), (a78, b3, c1, d12), (a78, b3, c1, d13), (a78, b3, c1, d14), (a78, b3, c1, d15), (a78, b3, c1, d16), (a78, b3, c1, d17), (a78, b3, c1, d18), (a78, b3, c1, d19), (a78, b3, c1, d20), (a78, b3, c1, d21), (a78, b3, c1, d22), (a78, b3, c2, d1), (a78, b3, c2, d2), (a78, b3, c2, d3), (a78, b3, c2, d4), (a78, b3, c2, d5), (a78, b3, c2, d6), (a78, b3, c2, d7), (a78, b3, c2, d8), (a78, b3, c2, d9), (a78, b3, c2, d10), (a78, b3, c2, d11), (a78, b3, c2, d12), (a78, b3, c2, d13), (a78, b3, c2, d14), (a78, b3, c2, d15), (a78, b3, c2, d16), (a78, b3, c2, d17), (a78, b3, c2, d18), (a78, b3, c2, d19), (a78, b3, c2, d20), (a78, b3, c2, d21), (a78, b3, c2, d22), (a78, b3, c3, d1), (a78, b3, c3, d2), (a78, b3, c3, d3), (a78, b3, c3, d4), (a78, b3, c3, d5), (a78, b3, c3, d6), (a78, b3, c3, d7), (a78, b3, c3, d8), (a78, b3, c3, d9), (a78, b3, c3, d10), (a78, b3, c3, d11), (a78, b3, c3, d12), (a78, b3, c3, d13), (a78, b3, c3, d14), (a78, b3, c3, d15), (a78, b3, c3, d16), (a78, b3, c3, d17), (a78, b3, c3, d18), (a78, b3, c3, d19), (a78, b3, c3, d20), (a78, b3, c3, d21), (a78, b3, c3, d22), (a78, b4, c1, d1), (a78, b4, c1, d2), (a78, b4, c1, d3), (a78, b4, c1, d4), (a78, b4, c1, d5), (a78, b4, c1, d6), (a78, b4, c1, d7), (a78, b4, c1, d8), (a78, b4, c1, d9), (a78, b4, c1, d10), (a78, b4, c1, d11), (a78, b4, c1, d12), (a78, b4, c1, d13), (a78, b4, c1, d14), (a78, b4, c1, d15), (a78, b4, c1, d16), (a78, b4, c1, d17), (a78, b4, c1, d18), (a78, b4, c1, d19), (a78, b4, c1, d20), (78, b4, c1, d21), (a78, b4, c1, d22), (a78, b4, c2, d1), (a78, b4, c2, d2), (a78, b4, c2, d3), (a78, b4, c2, d4), (a78, b4, c2, d5), (a78, b4, c2, d6), (a78, b4, c2, d7), (a78, b4, c2, d8), (a78, b4, c2, d9), (a78, b4, c2, d10), (a78, b4, c2, d11), (a78, b4, c2, d12), (a78, b4, c2, d13), (a78, b4, c2, d14), (a78, b4, c2, d15), (a78, b4, c2, d16), (a78, b4, c2, d17), (a78, b4, c2, d18), (a78, b4, c2, d19), (a78, b4, c2, d20), (a78, b4, c2, d21), (a78, b4, c2, d22), (a78, b4, c3, d1), (a78, b4, c3, d2), (a78, b4, c3, d3), (a78, b4, c3, d4), (a78, b4, c3, d5), (a78, b4, c3, d6), (a78, b4, c3, d7), (a78, b4, c3, d8), (a78, b4, c3, d9), (a78, b4, c3, d10), (a78, b4, c3, d11), (a78, b4, c3, d12), (a78, b4, c3, d13), (a78, b4, c3, d14), (a78, b4, c3, d15), (a78, b4, c3, d16), (a78, b4, c3, d17), (a78, b4, c3, d18), (a78, b4, c3, d19), (a78, b4, c3, d20), (a78, b4, c3, d21), (a78, b4, c3, d22), (a78, b5, c1, d1), (a78, b5, c1, d2), (a78, b5, c1, d3), (a78, b5, c1, d4), (a78, b5, c1, d5), (a78, b5, c1, d6), (a78, b5, c1, d7), (a78, b5, c1, d8), (a78, b5, c1, d9), (a78, b5, c1, d10), (a78, b5, c1, d11), (a78, b5, c1, d12), (a78, b5, c1, d13), (a78, b5, c1, d14), (a78, b5, c1, d15), (a78, b5, c1, d16), (a78, b5, c1, d17), (a78, b5, c1, d18), (a78, b5, c1, d19), (a78, b5, c1, d20), (a78, b5, c1, d21), (a78, b5, c1, d22), (a78, b5, c2, d1), (a78, b5, c2, d2), (a78, b5, c2, d3), (a78, b5, c2, d4), (a78, b5, c2, d5), (a78, b5, c2, d6), (a78, b5, c2, d7), (a78, b5, c2, d8), (a78, b5, c2, d9), (a78, b5, c2, d10), (a78, b5, c2, d11), (a78, b5, c2, d12), (a78, b5, c2, d13), (a78, b5, c2, d14), (a78, b5, c2, d15), (a78, b5, c2, d16), (a78, b5, c2, d17), (a78, b5, c2, d18), (a78, b5, c2, d19), (a78, b5, c2, d20), (a78, b5, c2, d21), (a78, b5, c2, d22), (a78, b5, c3, d1), (a78, b5, c3, d2), (a78, b5, c3, d3), (a78, b5, c3, d4), (a78, b5, c3, d5), (a78, b5, c3, d6), (a78, b5, c3, d7), (a78, b5, c3, d8), (a78, b5, c3, d9), (a78, b5, c3, d10), (a78, b5, c3, d11), (a78, b5, c3, d12), (a78, b5, c3, d13), (a78, b5, c3, d14), (a78, b5, c3, d15), (a78, b5, c3, d16), (a78, b5, c3, d17), (a78, b5, c3, d18), (a78, b5, c3, d19), (a78, b5, c3, d20), (a78, b5, c3, d21), (a78, b5, c3, d22), (a78, b6, c1, d1), (a78, b6, c1, d2), (a78, b6, c1, d3), (a78, b6, c1, d4), (a78, b6, c1, d5), (a78, b6, c1, d6), (a78, b6, c1, d7), (a78, b6, c1, d8), (a78, b6, c1, d9), (a78, b6, c1, d10), (a78, b6, c1, d11), (a78, b6, c1, d12), (a78, b6, c1, d13), (a78, b6, c1, d14), (a78, b6, c1, d15), (a78, b6, c1, d16), (a78, b6, c1, d17), (a78, b6, c1, d18), (a78, b6, c1, d19), (a78, b6, c1, d20), (a78, b6, c1, d21), (a78, b6, c1, d22), (a78, b6, c2, d1), (a78, b6, c2, d2), (a78, b6, c2, d3), (a78, b6, c2, d4), (a78, b6, c2, d5), (a78, b6, c2, d6), (a78, b6, c2, d7), (a78, b6, c2, d8), (a78, b6, c2, d9), (a78, b6, c2, d16), (a78, b6, c2, d17), (a78, b6, c2, d12), (a78, b6, c2, d13), (a78, b6, c2, d14), (a78, b6, c2, d15), (a78, b6, c2, d16), (a78, b6, c2, d17), (a78, b6, c2, d18), (a78, b6, c2, d19), (a78, b6, c2, d20), (a78, b6, c2, d21), (a78, b6, c2, d22), (a78, b6, c3, d1), (a78, b6, c3, d2), (a78, b6, c3, d3), (a78, b6, c3, d4), (a78, b6, c3, d15), (a78, b6, c3, d16), (a78, b6, c3, d7), (a78, b6, c3, d8), (a78, b6, c3, d9), (a78, b6, c3, d10), (a78, b6, c3, d11), (a78, b6, c3, d12), (a78, b6, c3, d13), (a78, b6, c3, d14), (a78, b6, c3, d15), (a78, b6, c3, d16), (a78, b6, c3, d17), (a78, b6, c3, d18), (a78, b6, c3, d19), (a78, b6, c3, d20), (a78, b6, c3, d21), (a78, b6, c3, d22), (a79, b1, c1, d1), (a79, b1, c1, d2), (a79, b1, c1, d3), (a79, b1, c1, d4), (a79, b1, c1, d5), (a79, b1, c1, d6), (a79, b1, c1, d7), (a79, b1, c1, d8), (a79, b1, c1, d9), (a79, b1, c1, d10), (a79, b1, c1, d11), (a79, b1, c1, d12), (a79, b1, c1, d13), (a79, b1, c1, d14), (a79, b1, c1, d15), (a79, b1, c1, d16), (a79, b1, c1, d17), (a79, b1, c1, d18), (a79, b1, c1, d19), (a79, b1, c1, d20), (a79, b1, c1, d21), (a79, b1, c1, d22), (a79, b1, c2, d1), (a79, b1, c2, d2), (a79, b1, c2, d3), (a79, b1, c2, d4), (a79, b1, c2, d5), (a79, b1, c2, d6), (a79, b1, c2, d7), (a79, b1, c2, d8), (a79, b1, c2, d9), (a79, b1, c2, d10), (a79, b1, c2, d11), (a79, b1, c2, d12), (a79, b1, c2, d13), (a79, b1, c2, d14), (a79, b1, c2, d15), (a79, b1, c2, d16), (a79, b1, c2, d17), (a79, b1, c2, d18), (a79, b1, c2, d9), (a79, b1, c2, d20), (a79, b1, c2, d21), (a79, b1, c2, d22), (a79, b1, c3, d7), (a79, b1, c3, b1, c3, d7), (a79, b1, c3, d8), (a79, b1, c3, d9), (a79, b1, c3, d10), (a79, b1, c3, d11), (a79, b1, c3, d12), (a79, b1, c3, d13), (a79, b1, c3, d14), (a79, b1, c3, d15), (a79, b1, c3, d16), (a79, b1, c3, d17), (a79, b1, c3, d18), (a79, b1, c3, d19), (a79, b1, c3, d20), (a79, b1, c3, d21), (a79, b1, c3, d22), (a79, b2, c1, d1), (a79, b2, c1, d2), (a79, b2, c1, d3), (a79, b2, c1, d4), (a79, b2, c1, d5), (a79, b2, c1, d6), (a79, b2, c1, d7), (a79, b2, c1, d8), (a79, b2, c1, d9), (a79, b2, c1, d10), (a79, b2, c1, d11), (a79, b2, c1, d12), (a79, b2, c1, d13), (a79, b2, c1, d14), (a79, b2, c1, d15), (a79, b2, c1, d16), (a79, b2, c1, d17), (a79, b2, c1, d18), (a79, b2, c1, d19), (a79, b2, c1, d20), (a79, b2, c1, d21), (a79, b2, c1, d22), (a79, b2, c2, d1), (a79, b2, c2, d2), (a79, b2, c2, d3), (a79, b2, c2, d4), (a79, b2, c2, d5), (a79, b2, c2, d6), (a79, b2, c2, d7), (a79, b2, c2, d8), (a79, b2, c2, d9), (a79, b2, c2, d10), (a79, b2, c2, d11), (a79, b2, c2, d12), (a79, b2, c2, d13), (a79, b2, c2, d14), (a79, b2, c2, d15), (a79, b2, c2, d16), (a79, b2, c2, d17), (a79, b2, c2, d18), (a79, b2, c2, d19), (a79, b2, c2, d20), (a79, b2, c2, d21), (a79, b2, c2, d22), (a79, b2, c3, d1), (a79, b2, c3, d2), (a79, b2, c3, d3), (a79, b2, c3, d4), (a79, b2, c3, d5), (a79, b2, c3, d6), (a79, b2, c3, d7), (a79, b2, c3, d8), (a79, b2, c3, d9), (a79, b2, c3, d10), (a79, b2, c3, d11), (a79, b2, c3, d12), (a79, b2, c3, d13), (a79, b2, c3, d14), (a79, b2, c3, d15), (a79, b2, c3, d16), (a79, b2, c3, d17), (a79, b2, c3, d18), (a79, b2, c3, d19), (a79, b2, c3, d20), (a79, b2, c3, d21), (a79, b2, c3, d22), (a79, b3, c1, d1), (a79, b3, c1, d2), (a79, b3, c1, d3), (a79, b3, c1, d4), (a79, b3, c1, d5), (a79, b3, c1, d6), (a79, b3, c1, d7), (a79, b3, c1, d8), (a79, b3, c1, d9), (a79, b3, c1, d10), (a79, b3, c1, d11), (a79, b3, c1, d12), (a79, b3, c1, d13), (a79, b3, c1, d14), (a79, b3, c1, d15), (a79, b3, c1, d16), (a79, b3, c1, d17), (a79, b3, c1, d18), (a79, b3, c1, d19), (a79, b3, c1, d20), (a79, b3, c1, d21), (a79, b3, c1, d22), (a79, b3, c2, d1), (a79, b3, c2, d2), (a79, b3, c2, d3), (a79, b3, c2, d4), (a79, b3, c2, d5), (a79, b3, c2, d6), (a79, b3, c2, d7), (a79, b3, c2, d8), (a79, b3, c2, d9), (a79, b3, c2, d10), (a79, b3, c2, d11), (a79, b3, c2, d12), (a79, b3, c2, d13), (a79, b3, c2, d14), (a79, b3, c2, d15), (a79, b3, c2, d16), (a79, b3, c2, d17), (a79, b3, c2, d18), (a79, b3, c2, d19), (a79, b3, c2, d20), (a79, b3, c2, d21), (a79, b3, c2, d22), (a79, b3, c3, d1), (a79, b3, c3, d2), (a79, b3, c3, d3), (a79, b3, c3, d4), (a79, b3, c3, d5), (a79, b3, c3, d6), (a79, b3, c3, d7), (a79, b3, c3, d8), (a79, b3, c3, d9), (a79, b3, c3, d10), (a79, b3, c3, d11), (a79, b3, c3, d12), (a79, b3, c3, d13), (a79, b3, c3, d14), (a79, b3, c3, d15), (a79, b3, c3, d16), (a79, b3, c3, d17), (a79, b3, c3, d18), (a79, b3, c3, d19), (a79, b3, c3, d20), (a79, b3, c3, d21), (a79, b3, c3, d22), (a79, b4, c1, d1), (a79, b4, c1, d2), (a79, b4, c1, d3), (a79, b4, c1, d4), (a79, b4, c1, d5), (a79, b4, c1, d6), (a79, b4, c1, d7), (a79, b4, c1, d8), (a79, b4, c1, d9), (a79, b4, c1, d10), (a79, b4, c1, d11), (a79, b4, c1, d12), (a79, b4, c1, d13), (a79, b4, c1, d14), (a79, b4, c1, d15), (a79, b4, c1, d16), (a79, b4, c1, d17), (a79, b4, c1, d18), (a79, b4, c1, d19), (a79, b4, c1, d20), (a79, b4, c1, d21), (a79, b4, c1, d22), (a79, b4, c2, d1), (a79, b4, c2, d2), (a79, b4, c2, d3), (a79, b4, c2, d4), (a79, b4, c2, d5), (a79, b4, c2, d6), (a79, b4, c2, d7), (a79, b4, c2, d8), (a79, b4, c2, d9), (a79, b4, c2, d10), (a79, b4, c2, d11), (a79, b4, c2, d12), (a79, b4, c2, d13), (a79, b4, c2, d14), (a79, b4, c2, d15), (a79, b4, c2, d16), (a79, b4, c2, d17), (a79, b4, c2, d18), (a79, b4, c2, d19), (a79, b4, c2, d20), (a79, b4, c2, d21), (a79, b4, c2, d22), (a79, b4, c3, d1), (a79, b4, c3, d2), (a79, b4, c3, d3), (a79, b4, c3, d4), (a79, b4, c3, d5), (a79, b4, c3, d6), (a79, b4, c3, d7), (a79, b4, c3, d8), (a79, b4, c3, d9), (a79, b4, c3, d10), (a79, b4, c3, d11), (a79, b4, c3, d12), (a79, b4, c3, d13), (a79, b4, c3, d14), (a79, b4, c3, d15), (a79, b4, c3, d16), (a79, b4, c3, d17), (a79, b4, c3, d18), (a79, b4, c3, d19), (a79, b4, c3, d20), (a79, b4, c3, d21), (a79, b4, c3, d22), (a79, b5, c1, d1), (a79, b5, c1, d2), (a79, b5, c1, d3), (a79, b5, c1, d4), (a79, b5, c1, d5), (a79, b5, c1, d6), (a79, b5, c1, d7), (a79, b5, c1, d8), (a79, b5, c1, d9), (a79, b5, c1, d10), (a79, b5, c1, d11), (a79, b5, c1, d12), (a79, b5, c1, d13), (a7, b5, c1, d14), (a79, b5, c1, d15), (a79, b5, c1, d16), (a79, b5, c1, d17), (a79, b5, c1, d18), (a79, b5, c1, d19), (a79, b5, c1, d20), (a79, b5, c1, d21), (a79, b5, c1, d22), (a79, b5, c2, d1), (a79, b5, c2, d2), (a79, b5, c2, d3), (a79, b5, c2, d4), (a79, b5, c2, d5), (a79, b5, c2, d6), (a79, b5, c2, d7), (a79, b5, c2, d8), (a79, b5, c2, d9), (a79, b5, c2, d10), (a79, b5, c2, d11), (a79, b5, c2, d12), (a79, b5, c2, d13), (a79, b5, c2, d14), (a79, b5, c2, d15), (a79, b5, c2, d16), (a79, b5, c2, d17), (a79, b5, c2, d18), (a79, b5, c2, d19), (a79, b5, c2, d20), (a79, b5, c2, d21), (a79, b5, c2, d22), (a79, b5, c3, d1), (a79, b5, c3, d2), (a79, b5, c3, d3), (a79, b5, c3, d4), (a79, b5, c3, d5), (a79, b5, c3, d6), (a79, b5, c3, d7), (a79, b5, c3, d8), (a79, b5, c3, d9), (a79, b5, c3, d10), (a79, b5, c3, d11), (a79, b5, c3, d12), (a79, b5, c3, d13), (a79, b5, c3, d14), (a79, b5, c3, d15), (a79, b5, c3, d16), (a79, b5, c3, d17), (a79, b5, c3, d18), (a79, b5, c3, d19), (a79, b5, c3, d20), (a79, b5, c3, d21), (a79, b5, c3, d22), (a79, b6, c1, d1), (a79, b6, c1, d2), (a79, b6, c1, d3), (a79, b6, c1, d4), (a79, b6, c1, d5), (a79, b6, c1, d6), (a79, b6, c1, d7), (a79, b6, c1, d8), (a79, b6, c1, d9), (a79, b6, c1, d10), (a79, b6, c1, d11), (a79, b6, c1, d12), (a79, b6, c1, d13), (a79, b6, c1, d14), (a79, b6, c1, d15), (a79, b6, c1, d16), (a79, b6, c1, d17), (a79, b6, c1, d18), (a79, b6, c1, d19), (a79, b6, c1, d20), (a79, b6, c1, d21), (a79, b6, c1, d22), (a79, b6, c2, d1), (a79, b6, c2, d2), (a79, b6, c2, d3), (a79, b6, c2, d4), (a79, b6, c2, d5), (a79, b6, c2, d6), (a79, b6, c2, d7), (a79, b6, c2, d8), (a79, b6, c2, d9), (a79, b6, c2, d10), (a79, b6, c2, d11), (a79, b6, c2, d12), (a79, b6, c2, d13), (a79, b6, c2, d14), (a79, b6, c2, d15), (a79, b6, c2, d16), (a79, b6, c2, d17), (a79, b6, c2, d18), (a79, b6, c2, d19), (a79, b6, c2, d20), (a79, b6, c2, d21), (a79, b6, c2, d22), (a79, b6, c3, d1), (a79, b6, c3, d2), (a79, b6, c3, d3), (a79, b6, c3, d4), (a79, b6, c3, d5), (a79, b6, c3, d6), (a79, b6, c3, d7), (a79, b6, c3, d8), (a79, b6, c3, d9), (a79, b6, c3, d10), (a79, b6, c3, d11), (a79, b6, c3, d12), (a79, b6, c3, d13), (a79, b6, c3, d14), (a79, b6, c3, d15), (a79, b6, c3, d16), (a79, b6, c3, d17), (a79, b6, c3, d18), (a79, b6, c3, d19), (a79, b6, c3, d20), (a79, b6, c3, d21), (a79, b6, c3, d22), (a80, b1, c1, d1), (a80, b1, c1, d2), (a80, b1, c1, d3), (a80, b1, c1, d4), (a80, b1, c1, d5), (a80, b1, c1, d6), (a80, b1, c1, d7), (a80, b1, c1, d8), (a80, b1, c3, d9), (a80, b1, c1, d10), (a80, b1, c1, d11), (a80, b1, c1, d12), (a80, b1, c1, d13), (a80, b1, c1, d14), (a80, b1, c1, d15), (a80, b1, c1, d16), (a80, b1, c1, d17), (a80, b1, c1, d18), (a80, b1, c1, d19), (a80, b1, c1, d20), (a80, b1, c1, d21), (a80, b1, c1, d22), (a80, b1, c2, d1), (a80, b1, c2, d2), (a80, b1, c2, d3), (a80, b1, c2, d4), (a80, b1, c2, d5), (a80, b1, c2, d6), (a80, b1, c2, d7), (a80, b1, c2, d8), (a80, b1, c2, d9), (a80, b1, c2, d10), (a80, b1, c2, d11), (a80, b1, c2, d12), (a80, b1, c2, d13), (a80, b1, c2, d14), (a80, b1, c2, d15), (a80, b1, c2, d16), (a80, b1, c2, d17), (a80, b1, c2, d18), (a80, b1, c2, d19), (a80, b1, c2, d20), (a80, b1, c2, d21), (a80, b1, c2, d22), (a80, b1, c3, d1), (a80, b1, c3, d2), (a80, b1, c3, d3), (a80, b1, c3, d4), (a80, b1, c3, d5), (a80, b1, c3, d6), (a80, b1, c3, d7), (a80, b1, c3, d8), (a80, b1, c3, d9), (a80, b1, c3, d10), (a80, b1, c3, d11), (a80, b1, c3, d12), (a80, b1, c3, d13), (a80, b1, c3, d14), (a80, b1, c3, d15), (a80, b1, c3, d16), (a80, b1, c3, d17), (a80, b1, c3, d18), (a80, b1, c3, d19), (a80, b1, c3, d20), (a80, b1, c3, d21), (a80, b1, c3, d22), (a80, b2, c1, d1), (a80, b2, c1, d2), (a80, b2, c1, d3), (a80, b2, c1, d4), (a80, b2, c1, d5), (a80, b2, c1, d6), (a80, b2, c1, d7), (a80, b2, c1, d8), (a80, b2, c1, d9), (a80, b2, c1, d10), (a80, b2, c1, d11), (a80, b2, c1, d12), (a80, b2, c1, d13), (a80, b2, c1, d14), (a80, b2, c1, d15), (a80, b2, c1, d16), (a80, b2, c1, d17), (a80, b2, c1, d18), (a80, b2, c1, d19), (a80, b2, c1, d20), (a80, b2, c1, d21), (a80, b2, c1, d22), (a80, b2, c2, d1), (a80, b2, c2, d2), (a80, b2, c2, d3), (a80, b2, c2, d4), (a80, b2, c2, d5), (a80, b2, c2, d6), (a80, b2, c2, d7), (a80, b2, c2, d8), (a80, b2, c2, d9), (a80, b2, c2, d10), (a80, b2, c2, d11), (a80, b2, c2, d12), (a80, b2, c2, d13), (a80, b2, c2, d14), (a80, b2, c2, d15), (a80, b2, c2, d16), (a80, b2, c2, d17), (a80, b2, c2, d18), (a80, b2, c2, d19), (a80, b2, c2, d20), (a80, b2, c2, d21), (a80, b2, c2, d22), (a80, b2, c3, d1), (a80, b2, c3, d2), (a80, b2, c3, d3), (a80, b2, c3, d4), (a80, b2, c3, d5), (a80, b2, c3, d6), (a80, b2, c3, d7), (a80, b2, c3, d8), (a80, b2, c3, d9), (a80, b2, c3, d10), (a80, b2, c3, d11), (a80, b2, c3, d12), (a80, b2, c3, d13), (a80, b2, c3, d14), (a50, b2, c3, d15), (a80, b2, c3, d16), (a80, b2, c3, d17), (a80, b2, c3, d18), (a80, b2, c3, d19), (a80, b2, c3, d20), (a80, b2, c3, d21), (a80, b2, c3, d22), (a80, b3, c1, d1), (a80, b3, c1, d2), (a80, b3, c1, d3), (a80, b3, c1, d4), (a80, b3, c1, d5), (a80, b3, c1, d6), (a80, b3, c1, d7), (a80, b3, c1, d8), (a50, b3, c1, d9), (a80, b3, c1, d10), (a80, b3, c1, d11), (a80, b3, c1, d12), (a80, b3, c1, d13), (a80, b3, c1, d14), (a80, b3, c1, d15), (a80, b3, c1, die), (a80, b3, c1, d17), (a80, b3, c1, d18), (a80, b3, c1, d19), (a80, b3, c1, d20), (a80, b3, c1, d21), (a80, b3, c1, d22), (a50, b3, c2, d1), (a80, b3, c2, d2), (a80, b3, c2, d3), (a80, b3, c2, d4), (a80, b3, c2, d5), (a80, b3, c2, d6), (a80, b3, c2, d7), (a80, b3, c2, d8), (a80, b3, c2, d9), (a80, b3, c2, d10), (a80, b3, c2, d11), (a80, b3, c2, d12), (a80, b3, c2, d13), (a80, b3, c2, d14), (a80, b3, c2, d15), (a80, b3, c2, d16), (a80, b3, c2, d17), (a80, b3, c2, d18), (a80, b3, c2, d19), (a80, b3, c2, d20), (a80, b3, c2, d21), (a80, b3, c2, d22), (a80, b3, c3, d1), (a80, b3, c3, d2), (a80, b3, c3, d3), (a80, b3, c3, d4), (a80, b3, c3, d5), (a50, b3, c3, d6), (a80, b3, c3, d7), (a50, b3, c3, d8), (a80, b3, c3, d9), (a80, b3, c3, d10), (a80, b3, c3, d11), (a80, b3, c3, d12), (a80, b3, c3, d13), (a80, b3, c3, d14), (a80, b3, c3, d15), (a80, b3, c3, d16), (a80, b3, c3, d17), (a80, b3, c3, d18), (a80, b3, c3, d19), (a80, b3, c3, d20), (a80, b3, c3, d21), (a80, b3, c3, d22), (a80, b4, c1, d1), (a80, b4, c1, d2), (a80, b4, c1, d3), (a50, b4, c1, d4), (a80, b4, c1, d5), (a80, b4, c1, d6), (a80, b4, c1, d7), (a80, b4, c1, d8), (a80, b4, c1, d9), (a50, b4, c1, d10), (a80, b4, c1, d11), (a80, b4, c1, d12), (a80, b4, c1, d13), (a80, b4, c1, d14), (a80, b4, c1, d15), (a80, b4, c1, d16), (a80, b4, c1, d17), (a80, b4, c1, d18), (a50, b4, c1, d19), (a80, b4, c1, d20), (a80, b4, c1, d21), (a80, b4, c1, d22), (a80, b4, c2, d1), (a80, b4, c2, d2), (a80, b4, c2, d3), (a80, b4, c2, d4), (a80, b4, c2, d5), (a80, b4, c2, d6), (a80, b4, c2, d7), (a80, b4, c2, d8), (a80, b4, c2, d9), (a80, b4, c2, d10), (a80, b4, c2, d11), (a80, b4, c2, d12), (a80, b4, c2, d13), (a80, b4, c2, d14), (a80, b4, c2, d15), (a80, b4, c2, d16), (a80, b4, c2, d17), (a80, b4, c2, d18), (a80, b4, c2, d19), (a80, b4, c2, d20), (a50, b4, c2, d21), (a80, b4, c2, d22), (a80, b4, c3, d1), (a80, b4, c3, d2), (a80, b4, c3, d3), (a80, b4, c3, d4), (a80, b4, c3, d5), (a80, b4, c3, d6), (a80, b4, c3, d7), (a80, b4, c3, d8), (a80, b4, c3, d9), (a80, b4, c3, d10), (a80, b4, c3, d11), (a80, b4, c3, d12), (a80, b4, c3, d13), (a80, b4, c3, d14), (a80, b4, c3, d15), (a80, b4, c3, d16), (a80, b4, c3, d17), (a80, b4, c3, d18), (a80, b4, c3, d19), (a80, b4, c3, d20), (a80, b4, c3, d21), (a80, b4, c3, d22), (a80, b5, c1, d1), (a80, b5, c1, d2), (a80, b5, c1, d3), (a80, b5, c1, d4), (a80, b5, c1, d5), (a80, b5, c1, d6), (a80, b5, c1, d7), (a80, b5, c1, d8), (a80, b5, c1, d9), (a80, b5, c1, d10), (a80, b5, c1, d11), (a80, b5, c1, d12), (a80, b5, c1, d13), (a80, b5, c1, d14), (a80, b5, c1, d15), (a80, b5, c1, d16), (a80, b5, c1, d17), (a80, b5, c1, d18), (a80, b5, c1, d19), (a80, b5, c1, d20), (a80, b5, c1, d21), (a80, b5, c1, d22), (a80, b5, c2, d1), (a80, b5, c2, d2), (a80, b5, c2, d3), (a80, b5, c2, d4), (a80, b5, c2, d5), (a80, b5, c2, d6), (a80, b5, c2, d7), (a80, b5, c2, d8), (a80, b5, c2, d9), (a80, b5, c2, d10), (a80, b5, c2, d11), (a80, b5, c2, d12), (a80, b5, c2, d13), (a80, b5, c2, d14), (a80, b5, c2, d15), (a80, b5, c2, d16), (a80, b5, c2, d17), (a80, b5, c2, d18), (a80, b5, c2, d19), (a80, b5, c2, d20), (a80, b5, c2, d21), (a80, b5, c2, d22), (a80, b5, c3, d11), (a80, b5, c3, d2), (a80, b5, c3, d3), (a80, b5, c3, d4), (a80, b5, c3, d5), (a80, b5, c3, d6), (a80, b5, c3, d7), (a80, b5, c3, d8), (a80, b5, c3, d9), (a80, b5, c3, d10), (a80, b5, c3, d11), (a80, b5, c3, d12), (a80, b5, c3, d13), (a80, b5, c3, d14), (a80, b5, c3, d15), (a80, b5, c3, d16), (a80, b5, c3, d17), (a80, b5, c3, d18), (a80, b5, c3, d19), (a80, b5, c3, d20), (a80, b5, c3, d21), (a80, b5, c3, d22), (a80, b6, c1, d1), (a80, b6, c1, d2), (a80, b6, c1, d3), (a50, b6, c1, d4), (a80, b6, c1, d5), (a80, b6, c1, d6), (a80, b6, c1, d7), (a80, b6, c1, d8), (a80, b6, c1, d9), (a80, b6, c1, d10), (a80, b6, c1, d11), (a80, b6, c1, d12), (a80, b6, c1, d13), (a80, b6, c1, d14), (a80, b6, c1, d15), (a80, b6, c1, d16), (a80, b6, c1, d17), (a80, b6, c1, d18), (a80, b6, c1, d19), (a80, b6, c1, d20), (a80, b6, c1, d21), (a80, b6, c1, d22), (a80, b6, c2, d1), (a50, b6, c2, d2), (a80, b6, c2, d3), (a80, b6, c2, d4), (a80, b6, c2, d5), (a80, b6, c2, d6), (a80, b6, c2, d7), (a80, b6, c2, d8), (a80, b6, c2, d9), (a80, b6, c2, d10), (a80, b6, c2, d11), (a80, b6, c2, d12), (a80, b6, c2, d13), (a80, b6, c2, d14), (a80, b6, c2, d15), (a80, b6, c2, d16), (a80, b6, c2, d7), (a80, b6, c2, d18), (a80, b6, c2, d19), (a80, b6, c2, d20), (a80, b6, c2, d21), (a80, b6, c2, d22), (a80, b6, c3, d1), (a80, b6, c3, d2), (a80, b6, c3, d3), (a80, b6, c3, d4), (a80, b6, c3, d5), (a80, b6, c3, d6), (a80, b6, c3, d7), (a80, b6, c3, d8), (a80, b6, c3, d9), (a80, b6, c3, d10), (a80, b6, c3, d11), (a80, b6, c3, d12), (a80, b6, c3, d13), (a80, b6, c3, d14), (a80, b6, c3, d15), (a80, b6, c3, d16), (a80, b6, c3, d17), (a80, b6, c3, d18), (a80, b6, c3, d19), (a80, b6, c3, d20), (a80, b6, c3, d21), (a80, b6, c3, d22), (a81, b1, c1, d1), (a81, b1, c1, d2), (a81, b1, c1, d3), (a81, d4), (a81, b1, c1, d5), (a81, b1, c1, d6), (a81, b1, c1, d7), (a81, b1, c1, d8), (a81, b1, c1, d9), (a81, b1, c1, d10), (a81, b1, c1, d11), (a81, b1, c1, d2), (a81, b1, c1, d13), (a81, b1, c1, d14), (a81, b1, c1, d5), (a81, b1, c1, d16), (a81, b1, c1, d17), (a81, b1, c1, d18), (a81, b1, c1, d19), (a81, b1, c1, d20), (a81, b1, c1, d21), (a81, b1, c1, d22), (a81, b1, c2, d1), (a81, b1, c2, d2), (a81, b1, c2, d3), (a81, b1, c2, d4), (a81, b1, c2, d5), (a81, b1, c2, d6), (a81, b1, c2, d7), (a81, b1, c2, d8), (a81, b1, c2, d9), (a81, b1, c2, d10), (a81, b1, c2, d11), (a81, b1, c2, d12), (a81, b1, c2, d3), (a81, b, c2, d14), (a81, b1, c2, d15), (a81, b1, c2, d16), (a81, b1, c2, d17), (a81, b1, c2, d18), (a81, b1, c2, d19), (a81, b1, c2, d20), (a81, b1, c2, d21), (a81, b, c2, d22), (a81, b1, c3, d1), (a81, b1, c3, d2), (a81, b1, c3, d3), (a81, b1, c3, d4), (a81, b1, c3, d5), (a81, b1, c3, d6), (a81, b1, c3, d7), (a81, b1, c3, d8), (a8, b1, c3, d9), (a81, b1, c3, d10), (a81, b1, c3, d11), (a81, b1, c3, d12), (a81, b1, c3, d13), (a81, b1, c3, d14), (a81, b1, c3, d15), (a81, b1, c3, d16), (a81, b1, c3, d17), (a81, b1, c3, d18), (a81, b1, c3, d19), (a81, b1, c3, d20), (a81, b1, c3, d21), (a81, b1, c3, d22), (a81, b2, c1, d1), (a81, b2, c1, d2), (a81, b2, c1, d3), (a81, b2, c1, d4), (a81, b2, c1, d5), (a81, b2, c1, d6), (a81, b2, c1, d7), (a81, b2, c1, d8), (a81, b2, c1, d9), (a81, b2, c1, d10), (a81, b2, c1, d11), (a81, b2, c1, d12), (a81, b2, c1, d13), (a81, b2, c1, d14), (a81, b2, c1, d15), (a81, b2, c1, d16), (a81, b2, c1, d17), (a81, b2, c1, d18), (a81, b2, c1, d19) (a81, b2, c1, d20), (a81, b2, c1, d21), (a81, b2, c1, d22), (a81, b2, c2, d1), (a81, b2, c2, d2), (a81, b2, c2, d3), (a81, b2, c2, d4), (a81, b2, c2, d5), (a81, b2, c2, d6), (a81, b2, c2, d7), (a81, b2, c2, d8), (a81, b2, c2, d9), (a81, b2, c2, d10), (a81, b2, c2, d11), (a81, b2, c2, d12), (a81, b2, c2, d13), (a81, b2, c2, d14), (a81, b2, c2, d15), (a81, b2, c2, d16), (a81, b2, c2, d17), (a81, b2, c2, d18), (a81, b2, c2, d19), (a81, b2, c2, d20), (a81, b2, c2, d21), (a81, b2, c2, d22), (a81, b2, c3, d1), (a81, b2, c3, d2), (a81, b2, c3, d3), (a81, b2, c3, d4), (a81, b2, c3, d5), (a81, b2, c3, d6), (a81, b2, c3, d7), (a81, b2, c3, d8), (a81, b2, c3, d9), (a81, b2, c3, d10), (a81, b2, c3, d11), (a81, b2, c3, d12), (a81, b2, c3, d13), (a81, b2, c3, d14), (a81, b2, c3, d15), (a81, b2, c3, d16), (a81, b2, c3, d17), (a81, b2, c3, d18), (a81, b2, c3, d19), (a81, b2, c3, d20), (a81, b2, c3, d21), (a81, b2, c3, d22), (a81, b3, c1, d1), (a81, b3, c1, d2), (a81, b3, c1, d3), (a81, b3, c1, d4), (a81, b3, c1, d5), (a81, b5, c1, d6), (a81, b3, c1, d7), (a81, b3, c1, d8), (a81, b, c1, d9), (a81, b3, c1, d10), (a81, b3, c1, d11), (a81, b3, c1, d12), (a81, b3, c1, d13), (a81, b3, c1, d14), (a81, b3, c1, d15), (a81, b3, c1, d16), (a81, b3, c1, d17), (a81, b5, c1, d8), (a81, b5, c1, d19), (a81, b3, c1, d20), (a8, b3, c1, d21), (a81, b3, c1, d22), (a81, b3, c2, d1), (a81, b3, c2, d2), (a81, b3, c2, d3), (a81, b3, c2, d4), (a81, b3, c2, d5), (a81, b3, c2, d6), (a81, b3, c2, d7), (a81, b3, c2, d8), (a81, b3, c2, d9), (a81, b3, c2, d1), (a81, b3, c2, d11), (a81, b3, c2, d12), (a81, b3, c2, d13), (a81, b3, c2, d14), (a81, b3, c2, d15), (a81, b3, c2, d16), (a81, b3, c2, d17), (a81, b3, c2, d18), (a81, b3, c2, d19), (a81, b3, c2, d20), (a81, b3, c2, d21), (a81, b3, c2, d22), (a81, b3, c3, d1), (a81, b3, c3, d2), (a81, b3, c3, d3), (a81, b3, c3, d4), (a81, b3, c3, d5), (a81, b3, c3, d6), (a81, b3, c3, d7), (a81, b3, c3, d8), (a81, b3, c3, d9), (a81, b3, c3, d10), (a81, b3, c3, d11), (a81, b3, c3, d12), (a81, b3, c3, d13), (a81, b3, c3, d14), (a81, b3, c3, d15), (a81, b3, c3, d16), (a81, b3, c3, d17), (a81, b3, c3, d18), (a81, b3, c3, d19), (a81, b3, c3, d20), (a81, b3, c3, d21), (a81, b3, c3, d22), (a81, b4, c1, d1), (a81, b4, c1, d2), (a81, b4, c1, d3), (a81, b4, c1, d4), (a81, b4, c1, d5), (a81, b4, c1, d6), (a81, b4, c1, d7), (a81, b4, c1, d8), (a81, b4, c1, d9), (a81, b4, c1, d10), (a81, b4, c1, d11), (a81, b4, c1, d12), (a81, b4, c1, d13), (a81, b4, c1, d14), (a81, b4, c1, d15), (a81, b4, c1, d16), (a81, b4, c1, d17), (a81, b4, c1, d18), (a81, b4, c1, d19), (a81, b4, c1, d20), (a81, b4, c1, d21), (a8, b4, c1, d22), (a81, b4, c2, d1), (a8, b4, c2, d2), (a81, b4, c2, d3), (a81, b4, c2, d4), (a81, b4, c2, d5), (a81, b4, c2, d6), (a81, b4, c2, d7), (a81, b4, c2, d8), (a81, b4, c2, d9), (a81, b4, c2, d10), (a81, b4, c2, d11), (a81, b4, c2, d12), (a81, b4, c2, d13), (a81, b4, c2, d14), (a81, b4, c2, d15), (a81, b4, c2, d16), (a81, b4, c2, d17), (a81, b4, c2, d18), (a81, b4, c2, d19), (a81, b4, c2, d20), (a81, b4, c2, d21), (a81, b4, c2, d22), (a81, b4, c3, d1), (a81, b4, c3, d2), (a81, b4, c3, d3), (a81, b4, c3, d4), (a81, b4, c3, d5), (a8, b4, c3, d6), (a81, b4, c3, d7), (a81, b4, c3, d18), (a81, b4, c3, d9), (a81, b4, c3, d10), (a81, b4, c3, d11), (a81, b4, c3, d12), (a81, b4, c3, d13), (a81, b4, c3, d14), (a81, b4, c3, d15), (a81, b4, c3, d16), (a81, b4, c3, d17), (a81, b4, c3, d18), (a81, b4, c3, d19), (a81, b4, c3, d20), (a81, b4, c3, d21), (a81, b4, c3, d22), (a81, b5, c1, d1), (a81, b5, c1, d2), (a81, b5, c1, d3), (a81, b5, c1, d4), (a81, b5, c1, d5), (a81, b5, c1, d16), (a81, b5, c1, d7), (a81, b5, c1, d8), (a81, b5, c1, d9), (a81, b5, c1, d10), (a81, b5, c1, d11), (a81, b5, c1, d12), (a81, b6, c1, d13), (a81, b5, c1, d14), (a81, b5, (c1, d15), (a81, b5, c1, d16), (a81, b5, c1, d17), (a81, b5, c1, d18), (a81, b5, c1, d19), (a81, b5, c1, d20), (a81, b5, c1, d21), (a81, b5, c1, d22), (a81, b5, c2, d1), (a81, b5, c2, d2), (a81, b5, c2, d3), (a81, b5, c2, d4), (a81, b5, c2, d5), (a81, b5, c2, d16), (a81, b5, c2, d7), (a81, b5, c2, d8), (a81, b5, c2, d9), (a81, b5, c2, d10), (a81, b5, c2, d11), (a81, b5, c2, d12), (a81, b5, c2, d13), (a81, b5, c2, d14), (a81, b5, c2, d15), (a81, b5, c2, d16), (a81, b5, c2, d17), (a81, b5, c2, d18), (a81, b5, c2, d19), (a81, b5, c2, d20), (a81, b5, c2, d21), (a81, b5, c2, d22), (a81, b5, c3, d11), (a81, b5, c3, d12), (a81, b5, c3, d13), (a81, b5, c3, d14), (a81, b5, c3, d15), (a81, b5, c3, d6), (a81, b5, c3, d7), (a81, b5, c3, d8), (a81, b5, c3, d9), (a81, b5, c3, d10), (a81, b5, c3, d11), (a81, b5, c3, d12), (a81, b5, c3, d13), (a81, b5, c3, d14), (a81, b5, c3, d15), (a81, b5, c3, d16), (a81, b5, c3, d17), (a81, b5, c3, d18), (a81, b5, c3, d19), (a81, b5, c3, d20), (a81, b5, c3, d21), (a81, b5, c3, d22), (a81, b6, c1, d1), (a81, b6, c1, d2), (a81, b1, c1, d3), (a81, b6, c1, d4), (a81, b6, c1, d5), (a81, b6, c1, d6), (a81, b6, c1, d7), (a81, b6, c1, d8), (a81, b6, c1, d9), (a81, b6, c1, d10), (a81, b6, c1, d11), (a81, b6, c1, d11), (a81, b6, b 1, d113), (a81, b6, c1, d14), (a81, b6, c1, d85), (a81, b6, c1, d116), (a81, b3, c1, d117), (a81, b6, c1, d18), (a81, b6, c1, d19), (a81, b6, c1, d20), (a81, b6, c1, d21), (a81, b6, c1, d22), (a81, b6, c2, d1), (a81, b6, c2, d12), (a81, b6, c2, d13), (a81, b6, c2, d14), (a81, b6, c2, d15), (a81, b6, c2, d6), (a81, b6, c2, d7), (a81, b6, c2, d18), (a81, b6, c2, d5), (a81, b6, c2, d10), (a81, b6, c2, d11), (a81, b6, c2, d12), (a81, b6, c2, d13), (a81, b 6, c2, d14), (a81, b6, c2, d15), (a81, b6, c2, d16), (a81, b6, c2, d17), (a81, b3, c2, d18), (a81, b6, c2, d19), (a81, b6, c2, d20), (a81, b6, c2, d21), (a81, b6, c2, d22), (a81, b6, c3, d1), (a81, b6, c3, d2), (a81, b6, c3, d3), (a81, b6, c3, d4), (a81, b6, c3, d5), (a81, b6, c3, d6), (a81, b6, c3, d7), (a81, b6, c3, d8), (a81, b6, c3, d9), (a81, b6, c3, d10), (a81, b6, c3, d11), (a81, b6, c3, d12), (a81, b6, c3, d13), (a81, b3, c3, d14), (a81, b6, c3, d15), (a81, b6, c3, d16), (a81, b6, c3, d17), (a81, b6, c3, d18), (a81, b6, c3, d19), (a81, b6, c3, d20), (a81, b6, c3, d21), (a81, b6, c3, d22), (a82, b1, c1, d1), (a82, b1, c1, d2), (a82, b1, c1, d3), (a82, b1, c1, d4), (a82, b1, c1, d5), (a82, b1, c1, d6), (a82, b1, c1, d7), (a82, b1, c1, d8), (a82, b1, c1, d9), (a82, b1, c1, d10), (a82, b1, c1, d11), (a82, b1, c1, d12), (a82, b1, c1, d13), (a82, b1, c1, d14), (a82, b1, c1, d15), (a82, b1, c1, d16), (a82, b1, c1, d17), (a82, b1, c1, d18), (a82, b1, c1, d19), (a82, b1, c1, d20), (a82, b1, c1, d21), (a82, b1, c1, d22), (a82, b1, c2, d1), (a82, b1, c2, d2), (a82, b1, c2, d3), (a82, b1, c2, d4), (a82, b1, c2, d5), (a82, b1, c2, d6), (a82, b1, c2, d7), (a82, b1, c2, d8), (a82, b1, c2, d9), (a82, b1, c2, d10), (a82, b1, c2, d11), (a82, b1, c2, d12), (a82, b1, c2, d13), (a82, b1, c2, d14), (a82, b1, c2, d15), (a82, b1, c2, d16), (a82, b1, c2, d17), (a82, b1, c2, d18), (a82, b1, c2, d19), (a82, b1, c2, d20), (a82, b1, c2, d21), (a82, b1, c2, d22), (a82, b1, c3, d1), (a82, b1, c3, d2), (a82, b1, c3, d3), (a82, b1, c3, d4), (a82, b1, c3, d5), (a82, b1, c3, d6), (a82, b1, c3, d7), (a82, b1, c3, d8), (a82, b1, c3, d9), (a82, b1, c3, d10), (a82, b1, c3, (a82, b1, c3, d16), (a82, b1, c3, d17), (a82, b1, c3, d18), (a82, b1, c3, d19), (a82, b1, c3, d20), (a82, b1, c3, d21), (a82, b1, c3, d22), (a82, b2, c1, d1), (a82, b2, c1, d2), (a82, b2, c1, d3), (a82, b2, c1, d4), (a82, b2, c1, d5), (a82, b2, c1, d6), (a82, b2, c1, d7), (a82, b2, c1, d8), (a82, b2, c1, d9), (a82, b2, c1, d10), (a82, b2, c1, d11), (a82, b2, c1, d12), (a82, b2, c1, d13), (a82, b2, c1, d14), (a82, b2, c1, d15), (a82, b2, c1, d16), (a82, b2, c1, d17), (a82, b2, c1, d18), (a82, b2, c1, d19), (a82, b2, c1, d20), (a82, b2, c1, d21), (a82, b2, c1, d22), (a82, b2, c2, d1), (a82, b2, c2, d2), (a82, b2, c2, d3), (a82, b2, c2, d4), (a82, b2, c2, d5), (a82, b2, c2, d6), (a82, b2, c2, d7), (a82, b2, c2, d8), (a82, b2, c2, d9), (a82, b2, c2, d10), (a82, b2, c2, d11), (a82, b2, c2, d12), (a82, b2, c2, d13), (a82, b2, c2, d14), (a82, b2, c2, d15), (a82, b2, c2, d16), (a82, b2, c2, d17), (a82, b2, c2, d18), (a82, b2, c2, d19), (a82, b2, c2, d20), (a82, b2, c2, d21), (a82, b2, c2, d22), (a82, b2, c3, d1), (a82, b2, c3, d12), (a82, b2, c3, d3), (a82, b2, c3, d4), (a82, b2, c3, d5), (a82, b2, c3, d6), (a82, b2, c3, d7), (a82, b2, c3, d8), (a82, b2, c3, d9), (a82, b2, c3, d10), (a82, b2, c3, d11), (a82, b2, c3, d12), (a82, b2, c3, d13), (a82, b2, c3, d14), (a82, b2, c3, d15), (a82, b2, c3, d16), (a82, b2, c3, d17), (a82, b2, c3, d18), (a82, b2, c3, d19), (a82, b2, c3, d20), (a82, b2, c3, d21), (a82, b2, c3, d22), (a82, b3, c1, d1), (a82, b3, c1, d2), (a82, b3, c1, d3), (a82, b3, c1, d4), (a82 b3, c1, d5), (a82, b3, c1, d6), (a82, b3, c1, d7), (a82, b3, c1, d8), (a82, b3, c1, d9), (a82, b3, c1, d10), (a82, b3, c1, d11), (a82, b3, c1, d12), (a82, b3, c1, d13), (a82, b3, c1, d14), (a82, b3, c1, d15), (a82, b3, c1, d16), (a82, b3, c1, d17), (a82, b3, c1, d18), (a82, b3, c1, d19), (a82, b3, c1, d20), (a82, b3, c1, d21), (a82, b3, c1, d22), (a82, b3, c2, d1), (a82, b3, c2, d2), (a82, b3, c2, d3), (a82, b3, c2, d4), (a82, b3, c2, d5), (a82, b3, c2, d6), (a82, b3, c2, d7), (a82, b3, c2, d8), (a82, b3, c2, d9), (a82, b3, c2, d10), (a82, b3, c2, d11), (a82, b3, c2, d12), (a82, b3, c2, d13), (a82, b3, c2, d14), (a82, b3, c2, d15), (a82, b3, c2, d16), (a82, b3, c2, d17), (a82, b3, c2, d18), (a82, b3, c2, d19), (a82, b3, c2, d20), (a82, b3, c2, d21), (a82, b3, c2, d22), (a82, b3, c3, d1), (a82, b3, c3, d2), (a82, b3, c3, d3), (a82, b3, c3, d4), (a82, b3, c3, d5), (a82, b3, c3, d6), (a82, b3, c3, d7), (a82, b3, c3, d8), (a82, b3, c3, d9), (a82, b3, c3, d10), (a82, b3, c3, d11), (a82, b3, c3, d12), (a82, b3, c3, d13), (a82, b3, c3, d14), (a82, b3, c3, d15), (a82, b3, c3, d16), (a82, b3, c3, d17), (a82, b3, c3, d18), (a82, b3, c3, d19), (a82, b3, c3, d20), (a82, b5, c3, d21), (a82, b3, c3, d22), (a82, b4, c1, d1), (a82, b4, c1, d2), (a82, b4, c1, d3), (a82, b4, c1, d4), (a82, b4, c1, d5), (a82, b4, c1, d6), (a82, b4, c1, d7), (a82, b4, c1, d8), (a82, b4, c1, d9), (a82, b4, c1, d10), (a82, b4, c1, d11), (a82, b4, c1, d12), (a82, b4, c1, d13), (a82, b4, c1, d14), (a82, b4, c1, d15), (a82, b4, c1, d16), (a82, b4, c1, d17), (a82, b4, c1, d18), (a82, b4, c1, d19), (a82, b4, c1, d20), (a82, b4, c1, d21), (a82, b4, c1, d22), (a82, b4, c2, d1), (a82, b4, c2, d2), (a82, b4, c2, d3), (a82, b4, c2, d4), (a82, b4, c2, d5), (a82, b4, c2, d6), (a82, b4, c2, d7), (a82, b4, c2, d8), (a82, b4, c2, d9), (a82, b4, c2, d1), (a82, b4, c2, d11), (a82, b4, c2, d12), (a82, b4, c2, d13), (a82, b4, c2, d14), (a82, b4, c2, d15), (a82, b4, c2, d16), (a82, b4, c2, d17), (a82, b4, c2, d18), (a82, b4, c2, d19), (a82, b4, c2, d20), (a82, b4, c2, d21), (a82, b4, c2, d22), (a82, b4, c3, d1), (a82, b4, c3, d2), (a82, b4, c3, d3), (a82, b4, c3, d4), (a82, b4, c3, d5), (a82, b4, c3, d6), (a82, b4, c3, d7), (a82, b4, c3, d8), (a82, b4, c3, d9), (a82, b4, c3, d10), (a82, b4, c3, d11), (a82, b4, c3, d12), (a82, b4, c3, d13), (a82, b4, c3, d14), (a82, b4, c3, d15), (a82, b4, c3, d16), (a82, b4, c3, d17), (a82, b4, c3, d18), (a82, b4, c3, d19), (a82, b4, c3, d20), (a82, b4, c3, d21), (a82, b4, c3, d22), (a82, b5, c1, d1), (a82, b5, c1, d2), (a82, b5, c1, d3), (a82, b5, c1, d4), (a82, b5, c1, d5), (a82, b5, c1, d6), (a82, b5, c1, d7), (a82, b5, c1, d8), (a82, b5, c1, d9), (a82, b5, c1, d10), (a82, b5, c1, d1), (a82, b5, c1, d12), (a82, b5, c1, d13), (a82, b5, c1, d14), (a82, b5, c1, d15), (a82, b5, c1, d16), (a82, b5, c1, d17), (a82, b5, c1, d18), (a82, b5, c1, d19), (a82, b5, c1, d20), (a82, b5, c1, d21), (a82, b5, c1, d22), (a82, b5, c2, d1), (a82, b5, c2, d2), (a82, b5, c2, d3), (a82, b5, c2, d4), (a82, b5, c2, d5), (a82, b5, c2, d6), (a82, b5, c2, d7), (a82, b5, c2, d8), (a82, b5, c2, d9), (a82, b5, c2, d10), (a82, b5, c2, d11), (a82, b5, c2, d12), (a82, b5, c2, d13), (a82, b5, c2, d14), (a82, b5, c2, d15), (a82, b5, c2, d16), (a82, b5, c2, d17), (a82, b5, c2, d18), (a82, b5, c2, d19), (a82, b5, c2, d20), (a82, b5, c2, d21), (a82, b5, c2, d22), (a82, b5, c3, d1), (a82, b5, c3, d2), (a82, b5, c3, d3), (a82, b5, c3, d4), (a82, b5, c3, d5), (a82, b5, c3, d6), (a82, b5, c3, d7), (a82, b5, c3, d8), (a82, b5, c3, d9), (a82, b5, c3, d10), (a82, b5, c3, d11), (a82, b5, c3, d12), (a82, b5, c3, d13), (a82, b5, c3, d14), (a82, b5, c3, d15), (a82, b5, c3, d16), (a82, b5, c3, d17), (a82, b5, c3, d18), (a82, b5, c3, d19), (a82, b5, c3, d20), (a82, b5, c3, d21), (a82, b5, c3, d22), (a82, b6, c1, d1), (a82, b6, c1, d2), (a82, b6, c1, d3), (a82, b6, c1, d4), (a82, b6, c1, d5), (a82, b6, c1, d6), (a82, b6, c1, d7), (a82, b6, c1, d8), (a82, bb, c1, d9), (a82, b6, c1, d10), (a82, b6, c1, d11), (a82, b6, c1, d12), (a82, b6, c1, d13), (a82, b6, c1, d14), (a82, b6, c1, d15), (a82, b6, c1, d16), (a82, b6, c1, d17), (a82, b6, c1, d18), (a82, b6, c1, d19), (a82, b6, c1, d20), (a82, b6, c1, d21), (a82, b6, c1, d22), (a82, b6, c2, d1), (a82, b6, c2, (d2), (a82, b6, c2, d3), (a82, bb, c2, d4), (a82, b6, c2, d5), (a82, b6, c2, d6), (a82, b6, c2, d7), (a82, b6, c2, d8), (a82, b6, c2, d9), (a82, b6, c2, d10), (a82, b6, c2, d11), (a82, bb, c2, d12), (a82, b6, c2, d13), (a82, b6, c2, d14), (a82, b6, c2, d15), (a82, b6, c2, d16), (a82, b6, c2, div), (a82, bb, c2, d18), (a82, b6, c2, d19), (a82, b6, c2, d20), (a82, b6, c2, d21), (a82, b6, c2, d22), (a82, b6, c3, d1), (a82, b6, c3, d2), (a82, b6, c3, d3), (a82, b6, c3, d4), (a82, b6, c3, d5), (a82, b6, c3, d6), (a82, b6, c3, d7), (a82, b6, c3, d8), (a82, b6, c3, d9), (a82, b6, c3, d10), (a82, b6, c3, d11), (a82, b6, c3, d12), (a82, b6, c3, d13), (a82, b6, c3, d14), (a82, b6, c3, d15), (a82, b6, c3, d16), (a82, b6, c3, d17), (a82, b6, c3, d18), (a82, b6, c3, d19), (a82, b6, c3, d20), (a82, b6, c3, d21), (a82, b6, c3, d22), (a83, b1, c1, d1), (a83, b1, c1, d2), (a83, b1, c1, d3), (a83, b1, c1, d4), (a83, b1, c1, d5), (a83, b1, c1, d6), (a83, b1, c1, d7), (a83, b1, c1, d8), (a83, b1, c1, d9), (a83, b1, c1, d10), (a83, b1, c1, d11), (a83, b1, c1, d12), (a83, b1, c1, d13), (a83, b1, c1, d14), (a83, b1, c1, d15), (a83, b1, c1, d16), (a83, b1, c1, d17), (a83, b1, c1, d18), (a83, b1, c1, d19), (a83, b1, c1, d20), (a83, b1, c1, d21), (a83, b1, c1, d22), (a83, b1, c2, d1), (a83, b1, c2, d2), (a83, b1, c2, d3), (a83, b1, c2, d4), (a83, b1, c2, d5), (a83, b1, c2, d6), (a83, b1, c2, d7), (a83, b1, c2, d8), (a83, b1, c2, d9), (a83, b1, c2, d10), (a83, b1, c2, d11), (a83, b1, c2, d12), (a83, b1, c2, d13), (a83, b1, c2, d14), (a83, b1, c2, d15), (a83, b1, c2, d16), (a83, b1, c2, d17), (a83, b1, c2, d18), (a83, b1, c2, d19), (a83, b1, c2, d20), (a83, b1, c2, d21), (a83, b1, c2, d22), (a83, b1, c3, d1), (a83, b1, c3, d2), (a83, b1, c3, d3), (a83, b1, c3, d4), (a83, b1, c3, d5), (a83, b1, c3, d6), (a83, b1, c3, d7), (a83, b1, c3, d8), (a83, b1, c3, d9), (a83, b1, c3, d10), (a83, b1, c3, d11), (a83, b1, c3, d12), (a83, b1, c3, d13), (a83, b1, c3, d14), (a83, b1, c3, d15), (a83, b1, c3, d16), (a83, b1, c3, d17), (a83, b1, c3, d18), (a83, b1, c3, d19), (a83, b1, c3, d20), (a83, b1, c3, d21), (a83, b1, c3, d22), (a83, b2, c1, d1), (a83, b2, c1, d2), (a83, b2, c1, d3), (a83, b2, c1, d4), (a83, b2, c1, d5), (a83, b2, c1, d6), (a83, b2, c1, d7), (a83, b2, c1, d8), (a83, b2, c1, d9), (a83, b2, c1, d10), (a83, b2, c1, d11), (a83, b2, c1, d12), (a83, b2, c1, d13), (a83, b2, c1, d14), (a83, b2, c1, d15), (a83, b2, c1, d16), (a83, b2, c1, d17), (a83, b2, c1, d18), (a83, b2, c1, d19), (a83, b2, c1, d20), (a83, b2, c1, d21), (a83, b2, c1, d22), (a83, b2, c2, d1), (a83, b2, c2, d2), (a83, b2, c2, d3), (a83, b2, c2, d4), (a83, b2, c2, d5), (a83, b2, c2, d6), (a83, b2, c2, d7), (a83, b2, c2, d8), (a83, b2, c2, d9), (a83, b2, c2, d10), (a83, b2, c2, d11), (a83, b2, c2, d12), (a83, b2, c2, d13), (a83, b2, c2, d14), (a83, b2, c2, d15), (a83, b2, c2, d16), (a83, b2, c2, d17), (a83, b2, c2, d18), (a83, b2, c2, d19), (a83, b2, c2, d20), (a83, b2, c2, d21), (a8, b2, c2, d22), (a83, b2, c3, d1), (a83, b2, c3, d2), (a83, b2, c3, d3), (a83, b2, c3, d4), (a83, b2, c3, d5), (a83, b2, c3, d6), (a83, b2, c3, d7), (a83, b2, c3, d8), (a83, b2, c3, d9), (a83, b2, c3, d10), (a83, b2, c3, d11), (a83, b2, c3, d12), (a83, b2, c3, d13), (a83, b2, c3, d14), (a83, b2, c3, d15), (a83, b2, c3, d16), (a83, b2, c3, d17), (a83, b2, c3, d18), (a83, b2, c3, d19), (a83, b2, c3, d20), (a83, b2, c3, d21), (a83, b2, c3, d22), (a83, b2, c1, d1), (a83, b3, c1, d2), (a83, b5, c1, d5), (a83, b5, c1, d4), (a83, b5, c1, d5), (a83, b5, c1, d6), (a83, b5, c1, d7), (a83, b3, c1, d8), (a83, b3, c1, d9), (a83, b5, c1, d10), (a83, b3, c1, d11), (a83, b3, c1, d12), (a83, b3, c1, d13), (a83, b5, c1, d14), (a83, b3, c1, d15), (a83, b3, c1, d16), (a83, b5, c1, d17), (a83, b5, c1, d18), (a83, b3, c1, d19), (a83, b3, c1, d20), (a83, b3, c1, d21), (a83, b3, c1, d22), (a83, b3, c2, d1), (a83, b3, c2, d2), (a83, b3, c2, d3), (a83, b5, c2, d4), (a83, b3, c2, d5), (a83, b3, c2, d6), (a83, b3, c2, d7), (a83, b3, c2, d8), (a83, b3, c2, d9), (a83, b3, c2, d10), (a83, b3, c2, d11), (a83, b3, c2, d12), (a83, b3, c2, d13), (a83, b3, c2, d14), (a83, b3, c2, d15), (a83, b3, c2, d16), (a83, b3, c2, d17), (a83, b5, c2, d18), (a83, b3, c2, d19), (a83, b3, c2, d20), (a83, b3, c2, d21), (a83, b3, c2, d22), (a83, b3, c3, d1), (a83, b5, c3, d2), (a83, b3, c3, d3), (a83, b3, c3, d4), (a83, b3, c3, d5), (a83, b5, c3, d6), (a83, b3, c3, d7), (a83, b3, c3, d8), (a83, b5, c3, d9), (a83, b3, c3, d10), (a83, b3, c3, d11), (a83, b3, c3, d12), (a83, b3, c3, d13), (a83, b3, c3, d14), (a83, b3, c3, d15), (a83, b3, c3, d16), (a83, b3, c3, d17), (a83, b3, c3, d18), (a83, b3, c3, d19), (a83, b3, c3, d20), (a83, b3, c3, d21), (a83, b3, c3, d22), (a83, b4, c1, d1), (a83, b4, c1, d2), (a83, b4, c1, d3), (a83, b4, c1, d4), (a83, b4, c1, d5), (a83, b4, c1, d6), (a83, b4, c1, d7), (a83, b4, c1, d8), (a83, b4, c1, d9), (a83, b4, c1, d10), (a83, b4, c1, d11), (a83, b4, c1, d12), (a83, b4, c1, d13), (a83, b4, c1, d14), (a83, b4, c1, d15), (a83, b4, c1, d16), (a83, b4, c1, d17), (a83, b4, c1, d18), (a83, b4, c1, d19), (a83, b4, c1, d20), (a83, b4, c1, d21), (a83, b4, c1, d22), (a83, b4, c2, d1), (a83, b4, c2, d2), (a83, b4, c2, d3), (a83, b4, c2, d4), (a83, b4, c2, d5), (a83, b4, c2, d6), (a83, b4, c2, d7), (a83, b4, c2, d8), (a83, b4, c2, d19), (a83, b4, c2, d10), (a83, b4, c2, d11), (a83, b4, c2, d12), (a83, b4, c2, d13), (a83, b4, c2, d14), (a83, b4, c2, d15), (a83, b4, c2, d16), (a83, b4, c2, d17), (a83, b4, c2, d18), (a83, b4, c2, d19), (a83, b4, c2, d20), (a83, b4, c2, d21), (a83, b4, c2, d22), (a83, b4, c3, d1), (a83, b4, c3, d2), (a83, b4, c3, d3), (a83, b4, c3, d4), (a83, b4, c3, d5), (a83, b4, c3, d6), (a83, b4, c3, d7), (a83, b4, c3, d8), (a83, b4, c3, d9), (a83, b4, c3, d10), (a83, b4, c3, d11), (a83, b4, c3, d12), (a83, b4, c3, d13), (a83, b4, c3, d14), (a83, b4, c3, d15), (a83, b4, c3, d16), (a83, b4, c3, d17), (a83, b4, c3, d18), (a83, b4, c3, d19), (a83, b4, c3, d20), (a83, b4, c3, d21), (a83, b4, c3, d22), (a83, b5, c1, d11), (a83, b5, c1, d2), (a83, b5, c1, d3), (a83, b5, c1, d4), (a83, b5, c1, d5), (a83, b5, c1, d6), (a83, b5, c1, d7), (a83, b5, c1, d8), (a83, b5, c1, d9), (a83, b5, c1, d10), (a53, b5, c1, d11), (a83, b5, c1, d12), (a33, b5, c1, d13), (a83, b5, c1, d14), (a83, b5, c1, d15), (a83, b5, c1, d16), (a83, b5, c1, d17), (a83, b5, c1, d18), (a83, b5, c1, d19), (a83, b5, c1, d20), (a83, b5, c1, d21), (a83, b5, c1, d22), (a83, b5, c2, d1), (a83, b5, c2, d2), (a83, b5, c2, d3), (a83, b5, c2, d4), (a83, b5, c2, d5), (a83, b5, c2, d6), (a83, b5, c2, d7), (a83, b5, c2, d8), (a83, b5, c2, d9), (a83, b5, c2, d10), (a83, b5, c2, d11), (a83, b5, c2, d12), (a83, b5, c2, d13), (a83, b5, c2, d14), (a83, b5, c2, d15), (a83, b5, c2, d16), (a83, b5, c2, d17), (a83, b5, c2, d18), (a53, b5, c2, d19), (a83, b5, c2, d20), (a83, b5, c2, d21), (a83, b5, c2, d22), (a83, b5, c3, d1), (a83, b5, c3, d2), (a83, b5, c3, d3), (a83, b5, c3, d4), (a83, b5, c3, d5), (a83, b5, c3, d6), (a83, b5, c3, d7), (a83, b5, c3, d8), (a53, b5, c3, d9), (a83, b5, c3, d10), (a53, b5, c3, d11), (a83, b5, c3, d12), (a83, b5, c3, d13), (a83, b5, c3, d14), (a83, b5, c3, d15), (a83, b5, c3, d16), (a83, b5, c3, d17), (a83, b5, c3, d18), (a83, b5, c3, d19), (a83, b5, c3, d20), (a83, b5, c3, d21), (a83, b5, c3, d22), (a83, b6, c1, d1), (a83, b6, c1, d2), (a83, b6, c1, d3), (a83, b6, c1, d4), (a83, b6, c1, d5), (a83, b6, c1, d6), (a83, b6, c1, d7), (a83, b6, c1, d8), (a83, b6, c1, d9), (a53, b6, c1, d10), (a83, b6, c1, d11), (a83, b6, c1, d12), (a83, b6, c1, d13), (a83, b6, c1, d14), (a83, b6, c1, d15), (a83, b6, c1, d16), (a83, b6, c1, d17), (a83, b6, c1, d18), (a83, b6, c1, d19), (a83, b6, c1, d20), (a83, b6, c1, d21), (a83, b6, c1, d22), (a83, b6, c2, d1), (a83, b6, c2, d2), (a83, b6, c2, d3), (a83, b6, c2, d4), (a83, b6, c2, d5), (a83, b6, c2, d6), (a83, b6, c2, d7), (a83, b6, c2, d8), (a83, b6, c2, d9), (a53, b6, c2, d10), (a83, b6, c2, d11), (a83, b6, c2, d12), (a53, b6, c2, d13), (a83, b6, c2, d14), (a83, b6, c2, d15), (a83, b6, c2, d16), (a83, b6, c2, d17), (a83, b6, c2, d18), (a83, b6, c2, d19), (a83, b6, c2, d20), (a83, b6, c2, d21), (a83, b6, c2, d22), (a83, b6, c3, d1), (a83, b6, c3, d2), (a83, b6, c3, d3), (a83, b6, c3, d4), (a83, b6, c3, d5), (a83, b6, c3, (d6), (a83, b6, c3, d7), (a83, b6, c3, d8), (a83, b6, c3, d9), (a83, b6, c3, d10), (a83, b6, c3, d11), (a83, b6, c3, d12), (a83, b6, c3, d13), (a83, b6, c3, d14), (a83, b6, c3, d15), (a83, b6, c3, d16), (a83, b6, c3, d17), (a53, b6, c3, d18), (a83, b6, c3, d19), (a83, b6, c3, d20), (a83, b6, c3, d21), (a83, b6, c3, d22), (a84, b1, c1, d1), (a84, b1, c1, d2), (a84, b1, c1, d3), (a84, b1, c1, d4), (a84, b1, c1, d5), (a84, b1, c1, d6), (a84, b1, c1, d7), (a84, b1, c1, d8), (a84, b1, c1, d9), (a84, b1, c1, d10), (a84, b1, c1, d11), (a84, b1, c1, d12), (a84, b1, c1, d13), (a84, b1, c1, d14), (a84, b1, c1, d15), (a84, b1, c1, d10), (a84, b1, c1, d17), (a84, b1, c1, d18), (a84, b1, c1, d19), (a84, b1, c1, d20), (a84, b1, c1, d21), (a84, b1, c1, d22), (a84, b1, c2, d1), (a84, b1, c2, d2), (a84, b1, c2, d3), (a84, b1, c2, d4), (a84, b1, c2, d5), (a84, b1, c2, d6), (a84, b1, c2, d7), (a84, b1, c2, d8), (a84, b1, c2, d9), (a84, b1, c2, d10), (a84, b1, c2, d11), (a84, b1, c2, d12), (a84, b1, c2, d13), (a84, b1, c2, d14), (a84, b1, c2, d15), (a84, b1, c2, d16), (a84, b1, c2, d17), (a84, b1, c2, d18), (a84, b1, c2, d19), (a84, b1, c2, d20), (a84, b1, c2, d21), (a84, b1, c2, d22), (a84, b1, c3, d1), (a84, b1, c3, d2), (a84, b1, c3, d3), (a84, b1, c3, d4), (a84, b1, c3, d5), (a84, b1, c3, d6), (a84, b1, c3, d7), (a84, b1, c3, d8), (a84, b1, c1, d9), (a84, b1, c3, d10), (a84, b1, c3, d11), (a84, b1, c3, d12), (a84, b1, c3, d13), (a84, b1, c3, d14), (a84, b1, c3, d15), (a84, b1, c3, d16), (a84, b1, c3, d17), (a84, b1, c3, d18), (a84, b1, c3, d19), (a84, b1, c3, d20), (a84, b1, c3, d21), (a84, b1, c3, d22), (a84, b2, c1, d1), (a84, b2, c1, d2), (a84, b2, c1, d3), (a84, b2, c1, d4), (a84, b2, c1, d5), (a84, b2, c1, d6), (a84, b2, c1, d7), (a84, b2, c1, d8), (a84, b2, c1, d9), (a84, b2, c1, d10), (a84, b2, c1, d11), (a84, b2, c1, d12), (a84, b2, c1, d13), (a84, b2, c1, d14), (a84, b2, c1, d15), (a84, b2, c1, d16), (a84, b2, c1, d17), (a84, b2, c1, d18), (a84, b2, c1, d19), (a84, b2, c1, d20), (a84, b2, c1, d21), (a84, b2, c1, d22), (a84, b2, c2, d1), (a84, b2, c2, d2), (a84, b2, c2, d3), (a84, b2, c2, d4), (a84, b2, c2, d5), (a84, b2, c2, d6), (a84, b2, c2, d7), (a84, b2, c2, d8), (a84, b2, c2, d9), (a84, b2, c2, d10), (a84, b2, c2, d11), (a84, b2, c2, d12), (a84, b2, c2, d13), (a84, b2, c2, d14), (a84, b2, c2, d15), (a84, b2, c2, d16), (a84, b2, c2, d17), (a84, b2, c2, d18), (a84, b2, c2, d19), (a84, b2, c2, d20), (a84, b2, c2, d21), (a84, b2, c2, d22), (a84, b2, c3, d1), (a84, b2, c3, d2), (a84, b2, c3, d3), (a84, b2, c3, d4), (a84, b2, c3, d5), (a84, b2, c3, d6), (a84, b2, c3, d7), (a84, b2, c3, d8), (a84, b2, c3, d9), (a84, b2, c3, d10), (a84, b2, c3, d11), (a84, b2, c3, d12), (a84, b2, c3, d13), (a84, b2, c3, d14), (a84, b2, c3, d15), (a84, b2, c3, d16), (a84, b2, c3, d17), (a84, b2, c3, d18), (a84, b2, c3, d19), (a84, b2, c3, d20), (a84, b2, c3, d21), (a84, b2, c3, d22), (a84, b3, c1, d1), (a84, b3, c1, d2), (a84, b3, c1, d3), (a84, b5, c1, d4), (a84, b3, c1, d5), (a84, b3, c1, d6), (a84, b3, c1, d7), (a84, b3, c1, d8), (a84, b3, c1, d9), (a84, b3, c1, d10), (a84, b3, c1, d11), (a84, b3, c1, d12), (a84, b3, c1, d13), (a84, b3, c1, d14), (a84, b3, c1, d15), (a84, b3, c1, d16), (a84, b3, c1, d17), (a84, b3, c1, d18), (a84, b3, c1, d19), (a84, b3, c1, d20), (a84, b3, c1, d21), (a84, b3, c1, d22), (a84, b3, c2, d1), (a84, b3, c2, d2), (a84, b3, c2, d3), (a84, b3, c2, d4), (a84, b3, c2, d5), (a84, b3, c2, d6), (a84, b3, c2, d7), (a84, b3, c2, d8), (a84, b3, c2, d9), (a84, b3, c2, d10), (a84, b3, c2, d11), (a84, b3, c2, d12), (a84, b3, c2, d13), (a84, b3, c2, d14), (a84, b5, c2, d15), (a84, b3, c2, d16), (a84, b3, c2, d17), (a84, b3, c2, d18), (a84, b3, c2, d19), (a84, b3, c2, d20), (a84, b3, c2, d21), (a84, b3, c2, d22), (a84, b3, c3, d1), (a84, b3, c3, d2), (a84, b3, c3, d3), (a84, b3, c3, d4), (a84, b3, c3, d5), (a84, b3, c3, d6), (a84, b3, c3, d7), (a84, b3, c3, d8), (a84, b3, c3, d9), (a84, b3, c3, d10), (a84, b3, c3, d11), (a84, b3, c3, d12), (a84, b3, c3, d13), (a84, b3, c3, d14), (a84, b3, c3, d15), (a84, b3, c3, d16), (a84, b3, c3, d17), (a84, b3, c3, d18), (a84, b3, c3, d19), (a84, b3, c3, d20), (a84, b3, c3, d21), (a84, b3, c3, d22), (a84, b4, c1, d1), (a84, b4, c1, d2), (a84, b4, c1, d3), (a84, b4, c1, d4), (a84, b4, c1, d5), (a84, b4, c1, d6), (a84, b4, c1, d7), (a84, b4, c1, d8), (a84, b4, c1, d9), (a84, b4, c1, d10), (a84, b4, c1, d11), (a84, b4, c1, d12), (a84, b4, c1, d13), (a84, b4, c1, d14), (a84, b4, c1, d15), (a84, b4, c1, d16), (a84, b4, b4, d17), (a84, b4, c1, d18), (a84, b4, c1, d19), (a84, b4, c1, d20), (a84, b4, c1, d21), (a84, b4, c1, d22), (a84, b4, c2, d1), (a84, b4, c2, d2), (a84, b4, c2, d3), (a84, b4, c2, d4), (a84, b4, c2, d5), (a84, b4, c2, d6), (a84, b4, c2, d7), (a84, b4, c2, d8), (a84, b4, c2, d9), (a84, b4, c2, d10), (a84, b4, c2, d11), (a84, b4, c2, d12), (a84, b4, c2, d13), (a84, b4, c2, d14), (a84, b4, c2, d15), (a84, b4, c2, d16), (a84, b4, c2, d17), (a84, b4, c2, d18), (a84, b4, c2, d19), (a84, b4, c2, d20), (a84, b4, c2, d21), (a84, b4, c2, d22), (a84, b4, c3, d1), (a84, b4, c3, d2), (a84, b4, c3, d3), (a84, b4, c3, d4), (a84, b4, c3, d5), (a84, b4, c3, d6), (a84, b4, c3, d7), (a84, b4, c3, d8), (a84, b4, c3, d9), (a84, b4, c3, d10), (a84, b4, c3, d11), (a84, b4, c3, d12), (a84, b4, c3, d13), (a84, b4, c3, d14), (a84, b4, c3, d15), (a84, b4, c3, d16), (a84, b4, c3, d17), (a84, b4, c3, d18), (a84, b4, c3, d19), (a84, b4, c3, d20), (a84, b4, c3, d21), (a84, b4, c3, d22), (a84, b5, c1, d1), (a84, b5, c1, d2), (a84, b5, c1, d3), (a84, b5, c1, d4), (a84, b5, c1, d5), (a84, b5, c1, d6), (a84, b5, c1, d7), (a84, b5, c1, d8), (a84, b5, c1, d9), (a84, b5, c1, d10), (a84, b5, c1, d11), (a84, b5, c1, d12), (a84, b5, c1, d13), (a84, b5, c1, d14), (a84, b5, c1, d15), (a84, b5, c1, d16), (a84, b5, c1, d17), (a84, b5, c1, d18), (a84, b5, c1, d19), (a84, b5, c1, d20), (a84, b5, c1, d21), (a84, b5, c1, d22), (a84, b5, c2, d1), (a84, b5, c2, d2), (a84, b5, c2, d3), (a84, b5, c2, d4), (a84, b5, c2, d5), (a84, b5, c2, d6), (a84, b5, c2, d7), (a84, b5, c2, d8), (a84, b5, c2, d9), (a84, b5, c2, d10), (a84, b5, c2, d11), (a84, b5, c2, d12), (a84, b5, c2, d13), (a84, b5, c2, d14), (a84, b5, c2, d15), (a84, b5, c2, d16), (a84, b5, c2, d17) (a84, b5, c2, d18), (a84, b5, c2, d19), (a84, b5, c1, d20), (a84, b5, c1, d21), (a84, b5, c1, d22), (a84, b5, c3, d1), (a84, b5, c3, d2), (a84, b5, c3, d3), (a84, b5, c3, d4), (a84, b5, c3, d5), (a84, b5, c3, d6), (a84, b5, c3, d7), (a84, b5, c3, d8), (a84, b5, c3, d9), (a84, b5, c3, d10), (a84, b5, c3, d11), (a84, b5, c3, d12), (a84, b5, c3, d13), (a84, b5, c3, d14), (a84, b5, c3, d15), (a84, b5, c3, d16), (a84, b5, c3, d17), (a84, b5, c3, d18), (a84, b5, c3, d19), (a84, b5, c3, d20), (a84, b5, c3, d21), (a84, b5, c3, d22), (a84, b6, c1, d1), (a84, b6, c1, d2), (a84, b6, c1, d3), (a84, b6, c1, d4), (a84, b6, c1, d5), (a84, b6, c1, d6), (a84, b6, c1, d7), (a84, b6, c1, d8), (a84, b6, c1, d9), (a84, b6, c1, d10), (a84, b6, c1, d11), (a84, b6, c1, d12), (a84, b6, c1, d13), (a84, b6, c1, d14), (a84, b6, c1, d15), (a84, b6, c1, d16), (a84, b6, c1, d17), (a84, b6, c1, d18), (a84, b6, c1, d19), (a84, b6, c1, d20), (a84, b6, c1, d21), (a84, b6, c1, d22), (a84, b6, c2, d1), (a84, b6, c2, d2), (a84, b6, c2, d3), (a84, b6, c2, d4), (a84, b6, c2, d5), (a84, b6, c2, d6), (a84, b6, c2, d7), (a84, b6, c2, d8), (a84, b1, c2, d9), (a84, b6, c2, d10), (a84, b6, c2, d11), (a84, b6, c2, d12), (a84, b6, c2, d13), (a84, b6, c2, d14), (a84, b6, c2, d15), (a84, b6, c2, d16), (a84, b6, c2, d17), (a84, b6, c2, d18), (a84, b6, c2, d19), (a84, b6, c2, d20), (a84, b6, c2, d21), (a84, b6, c2, d22), (a84, b6, c3, d1), (a84, b6, c3, d2), (a84, b6, c3, d3), (a84, b6, c3, d4), (a84, bb, c3, d5), (a84, bb, c3, d6), (a84, b6, c3, d7), (a84, b6, c3, d8), (a84, b6, c3, d9), (a84, b6, c3, d10), (a84, b6, c3, d11), (a84, b6, c3, d12), (a84, b6, c3, d13), (a84, b6, c3, d14), (a84, b6, c3, d15), (a84, b6, c3, d16), (a84, b6, c3, d17), (a84, b6, c3, d18), (a84, b6, c3, d19), (a84, b6, c3, d20), (a84, b6, c3, d21), (a84, b6, c3, d22), (a85, b1, c1, d1), (a85, b1, c1, d2), (a85, b1, c1, d3), (a85, b1, c1, d4), (a85, b1, c1, d5), (a85, b1, c1, d6), (a85, b1, c1, d7), (a85, b1, c1, d8), (a85, b1, c1, d9), (a85, b1, c1, d10), (a85, b1, c1, d11), (a85, b1, c1, d12), (a85, b1, c1, d13), (a85, b1, c1, d14), (a85, b1, c1, d15), (a85, b1, c1, d16), (a85, b1, c1, d17), (a85, b1, c1, d18), (a85, b1, c1, d19), (a85, b1, c1, d20), (a85, b1, b1, d21), (a85, b1, c1, d22), (a85, b1, c2, d1), (a85, b1, c2, d2), (a85, b1, c2, d3), (a85, b1, c2, d4), (a85, b1, c2, d5), (a85, b1, c2, d6), (a85, b1, c2, d7), (a85, b1, c2, d8), (a85, b1, c2, d9), (a85, b1, c2, d10), (a85, b1, c2, d11), (a85, b1, c2, d12), (a85, b1, c2, d13), (a85, b1, c2, d14), (a85, b1, c2, d15), (a85, b1, c2, d16), (a85, b1, c2, d17), (a85, b1, c2, d18), (a85, b1, c2, d19), (a85, b1, c2, d20), (a85, b1, c2, d21), (a85, b1, c2, d22), (a85, b1, c3, d1), (a85, b1, c3, d2), (a85, b1, c3, d3), (a85, b1, c3, d4), (a85, b1, c3, d5), (a85, b1, c3, d6), (a85, b1, c3, d7), (a85, b1, c3, d8), (a85, b1, c3, d9), (a85, b1, c3, d10), (a85, b1, c3, d11), (a85, b1, c3, d12), (a85, b1, c3, d13), (a85, b1, c3, d14), (a85, b1, c3, d15), (a85, b1, c3, d16), (a85, b1, c3, d17), (a85, b1, c3, d18), (a85, b1, c3, d19), (a85, b1, c3, d20), (a85, b1, c3, d21), (a85, b1, c3, d22), (a85, b2, c1, d1), (a85, b2, c1, d2), (a85, b2, c1, d3), (a85, b2, c1, d4), (a85, b2, c1, d5), (a85, b2, c1, d6), (a85, b2, c1, d7), (a85, b2, c1, d8), (a85, b2, c1, d9), (a85, b2, c1, d10), (a35, b2, c1, d11), (a85, b2, c1, d12), (a85, b2, c1, d13), (a85, b2, c1, d14), (a85, b2, c1, d15), (a85, b2, c1, d16), (a85, b2, c1, d17), (a85, b2, c1, d18), (a85, b2, c1, d19), (a85, b2, c1, d20), (a85, b2, c1, d21), (a85, b2, c1, d22), (a85, b2, c2, d1), (a85, b2, c2, d2), (a85, b2, c2, d3), (a85, b2, c2, d4), (a85, b2, c2, d4), (a85, b2, c2, d7), (a85, b2, c2, d8), (a85, b2, c2, d9), (a85, b2, c2, d10), (a85, b2, c2, d11), (a85, b2, c2, d12), (a85, b2, c2, d13), (a85, b2, c2, d14), (a85, b2, c2, d16), (a85, b2, c2, d16), (a85, b2, c2, d17), (a85, b2, c2, d18), (a85, b2, c2, d19), (a85, b2, c2, d20), (a85, b2, c2, d21), (a85, b2, c2, d22), (a85, b2, c3, d1), (a85, b2, c3, d2), (a85, b2, c3, d3), (a85, b2, c3, d14), (a85, b2, c3, d5), (a85, b2, c3, d6), (a85, b2, c3, d7), (a85, b2, c3, d8), (a85, b2, c3, d9), (a83, b2, c3, d10), (a85, b2, c3, d11), (a85, b2, c3, d12), (a85, b2, c3, d13), (a85, b2, c3, d14), (a85, b2, c3, d15), (a85, b2, c3, d16), (a85, b2, c3, d17), (a85, b2, c3, d18), (a85, b2, c3, d19), (a85, b2, c3, d20), (a85, b2, c3, d21), (a85, b2, c3, d22), (a85, b3, c1, d1), (a85, b3, c1, d2), (a85, b3, c1, d3), (a85, b2, c1, d4), (a85, b3, c1, d5), (a85, b3, c1, d6), (a85, b3, c1, d7), (a85, b3, c1, d5), (a85, b3, c1, d9), (a85, b3, c1, d10), (a85, b3, c1, d11), (a85, b3, c1, d12), (a35, b3, c1, d13), (a85, b3, c1, d14), (a85, b3, c1, d15), (a85, b3, c1, d16), (a85, b3, c1, d17), (a85, b3, c1, d18), (a85, b3, c1, d19), (a83, b3, c1, d20), (a85, b3, c1, d21), (a35, b3, c1, d22), (a85, b3, c2, d1), (a85, b3, c2, d2), (a85, b3, c2, d3), (a85, b5, c2, d4), (a85, b3, c2, d5), (a85, b3, c2, d6), (a85, b3, c2, d7), (a85, b3, c2, d8), (a85, b3, c2, d9), (a85, b3, c2, d10), (a85, b3, c2, d11), (a85, b3, c2, d12), (a85, b3, c2, d13), (a85, b3, c2, d14), (a85, b3, c2, d15), (a85, b3, c2, d16), (a85, b3, c2, d17), (a85, b3, c2, d18), (a85, b3, c2, d19), (a85, b3, c2, d20), (a85, b3, c2, d21), (a85, b3, c2, d22), (a85, b3, c3, d1), (a85, b3, c3, d2), (a85, b3, c3, d3), (a85, b3, c3, d4), (a85, b3, c3, d5), (a85, b3, c3, d6), (a85, b3, c3, d7), (a83, b3, c3, d8), (a85, b3, c3, d9), (a85, b3, c3, d10), (a85, b3, c3, d11), (a85, b3, c3, d12), (a85, b3, c3, d13), (a85, b3, c3, d14), (a85, b3, c3, d15), (a85, b3, c3, d16), (a85, b3, c3, d17), (a85, b3, c3, d18), (a85, b3, c3, d18), (a85, b3, c3, d20), (a85, b3, c3, d21), (a85, b3, c3, d22), (a85, b4, c1, d1), (a85, b4, c1, d2), (a85, b4, c1, d3), (a85, b4, c1, d4), (a85, b4, c1, d5), (a85, b4, c1, d6), (a85, b4, c1, d7), (a85, b4, c1, d8), (a85, b4, c1, d9), (a85, b4, c1, d10), (a85, b4, c1, d11), (a85, b4, c1, d12), (a85, b4, c1, d13), (a85, b4, c1, d14), (a85, b4, c1, d15), (a85, b4, c1, d16), (a85, b4, c1, d17), (a85, b4, c1, d18), (a85, b4, c1, d19), (a85, b4, c1, d20), (a85, b4, c1, d21), (a85, b4, c1, d22), (a85, b4, c2, d1), (a85, b4, c2, d2), (a85, b4, c2, d3), (a85, b4, c2, d4), (a85, b4, c2, d5), (a85, b4, c2, d6), (a85, b4, c2, d7), (a85, b4, c2, d8), (a85, b4, c2, d9), (a85, b4, c2, d10), (a85, b4, c2, d11), (a85, b4, c2, d12), (a85, b4, c2, d13), (a85, b4, c2, d14), (a85, b4, c2, d15), (a85, b4, c2, d16), (a85, b4, c2, d17), (a85, b4, c2, d18), (a85, b4, c2, d19), (a85, b4, c2, d20), (a85, b4, c2, d21), (a85, b4, c2, d22), (a85, b4, c3, d1), (a85, b4, c3, d2), (a85, b4, c3, d3), (a85, b4, c3, d4), (a85, b4, c3, d5), (a85, b4, c3, d6), (a85, b4, c3, d7), (a85, b4, c3, d8), (a85, b4, c3, d9), (a85, b4, c3, d10), (a85, b4, c3, d11), (a85, b4, c3, d12), (a85, b4, c3, d13), (a85, b4, c3, d14), (a85, b4, c3, d15), (a85, b4, c3, d16), (a85, b4, c3, d17), (a85, b4, c3, d18), (a85, b4, c3, d19), (a85, b4, c3, d20), (a85, b4, c3, d21), (a85, b4, c3, d22), (a85, b5, c1, d), (a85, b5, c1, d2), (a85, b5, c1, d3), (a85, b5, c1, d4), (a85, b5, c1, d5), (a85, b5, c1, d6), (a85, b5, c1, d7), (a85, b5, c1, d8), (a85, b5, c1, d9), (a85, b5, c1, d10), (a85, b5, c1, d11), (a85, b5, c1, d12), (a83, b5, c1, d13), (a85, b5, c1, d14), (a85, b5, c1, d15), (a85, b5, c1, d16), (a85, b5, c1, d17), (a85, b5, c1, d18), (a85, b5, c1, d9), (a85, b5, c1, d20), (a85, b5, c1, d21), (a85, b5, c1, d22), (a85, b5, c2, d1), (a85, b5, c2, d2), (a85, b5, c2, d3), (a85, b5, c2, d4), (a85, b5, c2, d5), (a85), (a85, c2, d6), (a85, b5, c2, d7), (a85, b5, c2, d8), (a85, b5, c2, d9), (a85, b5, c2, d10), (a85, b5, c2, d11), (a85, b5, c2, d12), (a85, b5, c2, d13), (a85, b5, c2, d14), (a85, b5, c2, d15), (a85, b5, c2, d16), (a85, b5, c2, d17), (a85, b5, c2, d18), (a85, b5, c2, d19), (a85, b5, c2, d20), (a85, b5, c2, d21), (a85, b5, c2, d22), (a85, b5, c3, d1), (a85, b5, c3, d2), (a85, b5, c3, d3), (a85, b5, c3, d4), (a85, b5, c3, d5), (a85, b5, c3, d6), (a85, b5, c3, d7), (a85, b5, c3, d8), (a85, b5, c3, d9), (a85, b5, c3, d10), (a85, b5, c3, d11), (a85, b5, c3, d12), (a85, b5, c3, d13), (a85, b5, c3, d14), (a85, b5, c3, d15), (a85, b5, c3, d16), (a85, b5, c3, d17), (a85, b5, c3, d18), (a85, b5, c3, d19), (a85, b5, c3, d20), (a85, b5, c3, d21), (a85, b5, c3, d22), (a85, b6, c1, d1), (a85, b6, c1, d2), (a85, b6, c1, d3), (a85, b6, c1, d4), (a85, b6, c1, d5), (a85, b6, c1, d6), (a85, b6, c1, d7), (a85, b6, c1, d8), (a85, b6, c1, d9), (a85, b6, c1, d10), (a85, b6, c1, d11), (a85, b6, c1, d12), (a85, b6, c1, d13), (a85, b6, c1, d14), (a85, b6, c1, d15), (a85, b6, c1, d16), (a85, b6, c1, d17), (a85, b6, c1, d18), (a85, b6, c1, d19), (a85, b6, c1, d20), (a85, b6, c1, d21), (a5, b6, c1, d22), (a85, b6, c2, d1), (a85, b6, c2, d2), (a85, b6, c2, d3), (a85, b6, c2, d4), (a85, b6, c2, d5), (a85, b6, c2, d6), (a85, b6, c2, d7), (a85, b6, c2, d8), (a85, b6, c2, d9), (a85, b6, c2, d10), (a85, b6, c2, d11), (a85, b6, c2, d12), (a85, b6, c2, d13), (a85, b6, c2, d14), (a85, b6, c2, d15), (a85, b6, c2, d16), (a85, b6, c2, d17), (a85, b6, c2, d18), (a85, b6, c2, d19), (a85, b6, c2, d20), (a85, b6, c2, d21), (a85, b6, c2, d22), (a85, b6, c3, d1), (a85, b6, c3, d2), (a85, b6, c3, d3), (a85, b6, c3, d4), (a85, b6, c3, d5), (a85, b6, c3, d6), (a85, b6, c3, d7), (a85, b6, c3, d8), (a85, b6, c3, d9), (a85, b6, c3, d10), (a85, b6, c3, d11), (a85, b6, c3, d12), (a85, b6, c3, d13), (a85, b6, c3, d14), (a85, b6, c3, d15), (a85, b6, c3, d16), (a85, b6, c3, d17), (a85, b6, c3, d18), (a85, b6, c3, d19), (a85, b6, c3, d20), (a85, b6, c3, d21), (a85, b6, c3, d22), (a86, b1, c1, d1), (a86, b1, c1, d2), (a86, b1, c1, d3), (a86, b1, c1, d4), (a86, b1, c1, d5), (a86, b1, c1, d6), (a86, b1, c1, d7), (a86, b1, c1, d8), (a86, b1, c1, d9), (a86, b1, c1, d10), (a86, b1, c1, d11), (a86, b1, c1, d12), (a86, b1, c1, d13), (a86, b1, c1, d14), (a86, b1, c1, d15), (a86, b1, c1, d16), (a86, b1, c1, d17), (a86, b1, c1, d18), (a86, b1, c1, d19), (a86, b1, c1, d20), (a86, b1, c1, d21), (a86, b1, c1, d22), (a86, b1, c2, d1), (a86, b1, c2, d2), (a86, b1, c2, d3), (a86, b1, c2, d4), (a86, b1, c2, d5), (a86, b1, c2, d6), (a86, b1, c2, d7), (a86, b1, c2, d8), (a86, b1, c2, d9), (a86, b1, c2, d10), (a86, b1, c2, d11), (a86, b1, c2, d12), (a86, b1, c2, d13), (a86, b1, c2, d14), (a86, b1, c2, d15), (a86, b1, c2, d16), (a86, b1, c2, d17), (a86, b1, c2, d18), (a86, b1, c2, d19), (a86, b1, c2, d20), (a86, b1, c2, d21), (a86, b1, c2, d22), (a86, b1, c3, d1), (a86, b1, c3, d2), (a86, b1, c3, d3), (a86, b1, c3, d4), (a86, b1, c1, d5), (a86, b1, c3, d6), (a86, b1, c3, d7), (a86, b1, c3, d8), (a86, b1, c3, d9), (a86, b1, c3, d10), (a86, b1, c3, d11), (a86, b1, c3, d12), (a86, b1, c3, d13), (a86, b1, c3, d14), (a86, b1, c3, d15), (a86, b1, c3, d16), (a86, b1, c3, d17), (a86, b1, c3, d18), (a86, b1, c3, d19), (a86, b1, c3, d20), (a86, b1, c3, d21), (a86, b1, c3, d22), (a86, b2, c1, d1), (a86, b2, c1, d2), (a86, b2, c1, d3), (a86, b2, c1, d4), (a86, b2, c1, d5), (a86, b2, c1, d6), (a86, b2, c1, d7), (a86, b2, c1, d8), (a86, b2, c1, d9), (a86, b2, c1, d10), (a86, b2, c1, d11), (a86, b2, c1, d12), (a86, b2, c1, d13), (a86, b2, c1, d14), (a86, b2, c1, d15), (a86, b2, c1, d16), (a86, b2, c1, d17), (a86, b2, c1, d18), (a86, b2, c1, d19), (a86, b2, c1, d20), (a86, b2, c1, d21), (a86, b2, c1, d22) (a86, b2, c2, d1), (a86, b2, c2, d2), (a86, b2, c2, d3), (a86, b2, c2, d4), (a86, b2, c2, d5), (a86, b2, c2, d6), (a86, b2, c2, d7), (a86, b2, c2, d8), (a86, b2, c2, d9), (a86, b2, c2, d10), (a86, b2, c2, d11), (a86, b2, c2, d12), (a86, b2, c2, d13), (a86, b2, c2, d14), (a86, b2, c2, d15), (a86, b2, c2, d16), (a86, b2, c2, d17), (a86, b2, c2, d18), (a86, b2, c2, d19), (a86, b2, c2, d20), (a86, b2, c2, d21), (a86, b2, c2, d22), (a86, b2, c3, d11), (a86, b2, c3, d2), (a86, b2, c3, d3), (a86, b2, c3, d4), (a86, b2, c3, d5), (a86, b2, c3, d6), (a86, b2, c3, d7), (a86, b2, c3, d8), (a86, b2, c3, d9), (a86, b2, c3, d10), (a86, b2, c3, d11), (a86, b2, c3, d12), (a86, b2, c3, d13), (a86, b2, c3, d14), (a86, b2, c3, d15), (a86, b2, c3, d16), (a86, b2, c3, d17), (a86, b2, c3, d18), (a86, b2, c3, d19), (a86, b2, c3, d20), (a86, b2, c3, d21), (a86, b2, c3, d22), (a83, b3, c1, d1), (a83, b3, c1, d2), (a86, b3, c1, d3), (a86, b3, c1, d4), (a86, b3, c1, d5), (a86, b3, c1, d6), (a86, b3, c1, d7), (a86, b3, c1, d8), (a86, b3, c1, d9), (a86, b3, c1, d10), (a86, b3, c1, d11), (a86, b3, c1, d12), (a86, b3, c1, d13), (a86, b3, c1, d14), (a86, b3, c1, d15), (a86, b3, c1, d16), (a86, b3, c1, d17), (a86, b3, c1, d18), (a86, b3, c1, d19), (a86, b3, c1, d20), (a86, b3, c1, d21), (a86, b3, c1, d22), (a86, b3, c2, d1), (a86, b3, c2, d2), (a86, b3, c2, d3), (a86, b3, c2, d4), (a86, b3, c2, d5), (a86, b3, c2, d6), (a86, b3, c2, d7), (a86, b3, c2, d8), (a86, b3, c2, d9), (a86, b3, c2, d10), (a86, b3, c2, d11), (a86, b3, c2, d12), (a86, b3, c2, d13), (a86, b3, c2, d14), (a86, b3, c2, d15), (a86, b3, c2, d16), (a86, b3, c2, d17), (a86, b3, c2, d18), (a86, b3, c2, d19), (a86, b3, c2, d20), (a86, b3, c2, d21), (a86, b3, c2, d22), (a86, b3, c3, d1), (a86, b3, c3, d2), (a86, b3, c3, d3), (a86, b3, c3, d4), (a86, b3, c3, d5), (a86, b3, c3, d6), (a86, b3, c3, d7), (a86, b3, c3, d8), (a86, b3, c3, d9), (a86, b3, c3, d10), (a86, b3, c3, d11), (a86, b3, c3, d12), (a86, b3, c3, d13), (a86, b3, c3, d14), (a86, b3, c3, d15), (a86, b3, c3, d16), (a86, b3, c3, d17), (a86, b3, c3, d18), (a86, b3, c3, d19), (a86, b3, c3, d20), (a86, b3, c3, d21), (a86, b3, c3, d22), (a86, b4, c1, d1), (a86, b4, c1, d2), (a86, b4, c1, d3), (a86, b4, c1, d4), (a86, b4, c1, d5), (a86, b4, c1, d6), (a86, b4, c1, d7), (a86, b4, c1, d8), (a86, b4, c1, d9), (a86, b4, c1, d10), (a86, b4, c1, d11), (a86, b4, c1, d12), (a86, b4, c1, d13), (a86, b4, c1, d14), (a86, b4, c1, d15), (a86, b4, c1, d16), (a86, b4, c1, d17), (a86, b4, c1, d18), (a86, b4, c1, d19), (a86, b4, c1, d20), (a86, b4, c1, d21), (a86, b4, c1, d22), (a86, b4, c2, d1), (a86, b4, c2, d2), (a86, b4, c2, d3), (a86, b4, c2, d4), (a86, b4, c2, d5), (a86, b4, c2, d6), (a86, b4, c2, d7), (a86, b4, c2, d8), (a86, b4, c2, d9), (a86, b4, c2, d6), (a86, b4, c2, d11), (a86, b4, c2, d12), (a86, b4, c2, d13), (a86, b4, c2, d14), (a86, b4, c2, d15), (a86, b4, c2, d16), (a86, b4, c2, d17), (a86, b4, c2, d18), (a86, b4, c2, d19), (a86, b4, c2, d20), (a86, b4, c2, d21), (a86, b4, c2, d22), (a86, b4, c3, d1), (a86, b4, c3, d2), (a86, b4, c3, d13), (a86, b4, c3, d4), (a86, b4, c3, d5), (a86, b4, c3, d6), (a86, b4, c3, d7), (a86, b4, c3, d8), (a86, b4, c3, d9), (a86, b4, c3, d10), (a86, b4, c3, d11), (a86, b4, c3, d12), (a86, b4, c3, d13), (a86, b4, c3, d14), (a86, b4, c3, d15), (a86, b4, c3, d16), (a86, b4, c3, d17), (a86, b4, c3, d18), (a86, b4, c3, d19), (a86, b4, c3, d20), (a86, b4, c3, d21), (a86, b4, c3, d22), (a86, b5, c1, d1), (a86, b5, c1, d2), (a86, b5, c1, d3), (a86, b5, c1, d4), (a6, b5, c1, d5), (a86, b5, c1, d6), (a86, b5, c1, d7), (a86, b5, c1, d8), (a86, b5, c1, d9), (a86, b5, c1, d10), (a86, b5, c1, d11), (a86, b5, c1, d12), (a86, b5, c1, d13), (a86, b5, c1, d14), (a86, b5, c1, d15), (a86, b5, c1, d16), (a86, b5, c1, d17), (a86, b5, c1, d18), (a86, b5, c1, d19), (a86, b5, c1, d20), (a86, b5, c1, d21), (a86, b5, c1, d22), (a86, b5, c2, d1), (a86, b5, c2, d2), (a86, b5, c2, d3), (a86, b5, c2, d4), (a86, b5, c2, d5), (a86, b5, c2, d6), (a86, b5, c2, d7), (a86, b5, c2, d8), (a86, b5, c2, d9), (a86, b5, c2, d10), (a36, b5, c2, d11), (a86, b5, c2, d12), (a86, b5, c2, d13), (a86, b5, c2, d14), (a86, b5, c2, d15), (a86, b5, c2, d16), (a86, b5, c2, d17), (a86, b5, c2, d18), (a86, b5, c2, d19), (a36, b5, c2, d20), (a86, b5, c2, d21), (a86, b5, c2, d22), (a86, b5, c3, d1), (a86, b5, c3, d2), (a86, b5, c3, d3), (a86, b5, c3, d4), (a86, b5, c3, d5), (a86, b5, c3, d6), (a86, b5, c3, d7), (a86, b5, c3, d8), (a86, b5, c3, d9), (a86, b5, c3, d10), (a86, b5, c3, d11), (a86, b5, c3, d12), (a86, b5, c3, d13), (a86, b5, c3, d14), (a86, b5, c3, d15), (a86, b5, c3, d16), (a86, b5, c3, d17), (a86, b5, c3, d18), (a86, b5, c3, d19), (a86, b5, c3, d20), (a86, b5, c3, d21), (a86, b5, c3, d22), (a86, b6, c1, d1), (a86, b6, c1, d2), (a86, b6, c1, d3), (a86, b6, c1, d4), (a86, b6, c1, d5), (a86, b6, c1, d6), (a86, b6, c1, d7), (a86, b6, c1, d8), (a86, b6, c1, d9), (a86, b6, c1, d10), (a86, b6, c1, d11), (a86, b6, c1, d12), (a86, b6, c1, d13), (a86, b6, c1, d14), (a86, b6, c1, d15), (a86, b6, c1, d16), (a86, b6, c1, d17), (a86, b6, c1, d18), (a86, b6, c1, d19), (a86, b6, c1, d20), (a86, b6, c1, d21), (a86, b6, c1, d22), (a86, b6, c2, d1), (a86, b6, c2, d2), (a86, b6, c2, d3), (a86, b6, c2, d4), (a86, b6, c2, d5), (a86, b6, c2, d6), (a86, b63, c2, d7), (a86, b6, c2, d8), (a86, b6, c2, d9), (a86, b6, c2, d10), (a86, b6, c2, d11), (a8, b6, c2, d12), (a86, b6, c2, d13), (a86, b6, c2, d14), (a86, b6, c2, d15), (a86, b6, c2, d16), (a86, b6, c2, d17), (a86, b6, c2, d18), (a86, b6, c2, d19), (a86, b6, c2, d20), (a86, b6, c2, d21), (a86, b6, c2, d22), (a86, b6, c3, d1), (a86, b6, c3, d2), (a86, b6, c3, d3), (a86, b6, c3, d4), (a86, b6, c3, d5), (a86, b6, c3, d6), (a86, b6, c3, d6), (a86, b6, c3, d8), (a86, b6, c3, d9), (a86, b6, c3, d10), (a86, b6, c3, d11), (a86, b6, c3, d12), (a86, b6, c3, d13), (a86, b6, c3, d14), (a86, b6, c3, d15), (a86, b6, c3, d16), (a86, b6, c3, d17), (a86, b6, c3, d18), (a86, b6, c3, d19), (a86, b6, c3, d20), (a86, b6, c3, d21), (a86, b6, c3, d22), (a87, b1, c1, d1), (a87, b1, c1, d2), (a87, b1, c1, d3) (a57, b1, c1, d4), (a87, b1, c1, d5), (a87, b1, c1, d6), (a87, b1, c1, d7), (a87, b1, c1, d8), (a87, b1, c1, d9), (a87, b1, c1, d10), (a87, b1, c1, d11), (a87, b1, c1, d12), (a87, b1, c1, d13), (a87, b1, c1, d14), (a87, b1, c1, d15), (a87, b1, c1, d16), (a87, b1, c1, d17), (a87, b1, c1, d18), (a87, b1, c1, d19), (a87, b1, c1, d20), (a87, b1, c1, d21), (a87, b1, c1, d22), (a87, b1, c2, d1), (a87, b1, c2, d2), (a87, b1, c2, d3), (a87, b1, c2, d4), (a87, b1, c2, d5), (a87, b1, c2, d6), (a87, b1, c2, d7), (a87, b1, c2, d8), (a87, b1, c2, d9), (a87, b1, c2, d10), (a87, b1, c2, d11), (a87, b1, c2, d12), (a87, b1, c2, d13), (a87, b1, c2, d14), (a87, b1, c2, d15), (a87, b1, c2, d16), (a87, b1, c2, d17), (a87, b1, c2, d18), (a87, b1, c2, d19), (a87, b1, c1, d20), (a87, b1, c2, d21), (a87, b1, c2, d22), (a87, b1, c3, d1), (a87, b1, c3, d2), (a87, b1, c3, d3), (a87, b1, c3, d4), (a87, b1, c3, d5), (a87, b1, c3, d6), (a87, b1, c3, d7), (a87, b1, c3, d8), (a87, b1, c3, d9), (a87, b1, c3, d10), (a87, b1, c3, d11), (a87, b1, c3, d12), (a87, b1, c3, d13), (a87, b1, c3, d14), (a87, b1, c3, d15), (a87, b1, c3, d16), (a87, b1, c3, d17), (a87, b1, c3, d18), (a87, b1, c3, d19), (a87, b1, c3, d20), (a87, b1, c3, d21), (a87, b1, c3, d22), (a87, b2, c1, d1), (a87, b2, c1, d2), (a87, b2, c1, d3), (a87, b2, c1, d4), (a87, b2, c1, d5), (a87, b2, c1, d6), (a87, b2, c1, d7), (a87, b2, c1, d8), (a87, b2, c1, d9), (a87, b2, c1, d10), (a87, b2, c1, d11), (a87, b2, c1, d12), (a87, b2, c1, d13), (a87, b2, c1, d14), (a87, b2, c1, d15), (a87, b2, c1, d16), (a87, b2, c1, d17), (a87, b2, c1, d18), (a87, b2, c1, d19), (a87, b2, c1, d20), (a87, b2, c1, d21), (a87, b2, c1, d22), (a87, b2, c2, d1), (a87, b2, c2, d2), (a87, b2, c2, d3), (a87, b2, c2, d4), (a87, b2, c2, d5), (a87, b2, c2, d6), (a87, b2, c2, d7), (a87, b2, c2, d8), (a87, b2, c2, d9), (a87, b2, c2, d10), (a87, b2, c2, d11), (a87, b2, c2, d12), (a87, b2, c2, d13), (a87, b2, c2, d14), (a87, b2, c2, d15), (a87, b2, c2, d16), (a87, b2, c2, d17), (a87, b2, c2, d18), (a87, b2, c2, d19), (a87, b2, c2, d20), (a87, b2, c2, d21), (a87, b2, c2, d22), (a87, b2, c3, d1), (a87, b2, c3, d2), (a87, b2, c3, d3), (a87, b2, c3, d4), (a87, b2, c3, d5), (a87, b2, c3, d6), (a87, b2, c3, d7), (a87, b2, c3, d8), (a87, b2, c3, d9), (a87, b2, c3, d10), (a87, b2, c3, d11), (a87, b2, c3, d12), (a87, b2, c3, d13), (a87, b2, c3, d14), (a87, b2, c3, d15), (a37, b2, c3, d16), (a87, b2, c3, d17), (a87, b2, c3, d18), (a87, b2, c3, d19), (a87, b2, c3, d20), (a87, b2, c3, d21), (a87, b2, c3, d22), (a87, b3, c1, d1), (a87, b3, c1, d2), (a87, b3, c1, d3), (a87, b3, c1, d4), (a87, b3, c1, d5), (a87, b3, c1, d6), (a87, b3, c1, d7), (a87, b3, c1, d8), (a87, b3, c1, d9), (a87, b3, c1, d10), (a87, b3, c1, d11), (a87, b3, c1, d12), (a87, b3, c1, d13), (a87, b3, c1, d14), (a87, b3, c1, d15), (a87, b3, c1, d16), (a87, b3, c1, d17), (a87, b3, c1, d18), (a87, b3, c1, d19), (a87, b3, c1, d20), (a87, b3, c1, d21), (a87, b3, c1, d22), (a87, b3, c2, d1), (a87, b3, c2, d2), (a87, b3, c2, d3), (a87, b3, c2, d4), (a87, b3, c2, d5), (a87, b3, c2, d6), (a87, b3, c2, d7), (a87, b3, c2, d8), (a87, b3, c2, d9), (a87, b3, c2, d10), (a87, b3, c2, d11), (a87, b3, c2, d12), (a87, b3, c2, d13), (a87, b3, c2, d14), (a87, b3, c2, d15), (a87, b3, c2, d16), (a87, b3, c2, d17), (a87, b5, c2, d18), (a87, b3, c2, d19), (a87, b3, c2, d20), (a87, b3, c2, d21), (a87, b3, c2, d22), (a87, b3, c3, d1), (a87, b3, c3, d2), (a87, b3, c3, d3), (a87, b3, c3, d4), (a87, b3, c3, d5), (a87, b3, c3, d6), (a87, b3, c3, d7), (a87, b3, c3, d8), (a87, b3, c3, d9), (a87, b3, c3, d10), (a87, b3, c3, d11), (a87, b3, c3, d12), (a87, b3, c3, d13), (a37, b3, c3, d14), (a37, b3, c3, d15), (a87, b3, c3, d16), (a87, b3, c3, d17), (a87, b3, c3, d18), (a87, b3, c3, d19), (a87, b3, c3, d20), (a87, b3, c3, d21), (a87, b3, c3, d22), (a87, b4, c1, d1), (a7, b4, c1, d12), (a87, b4, c1, d3), (a87, b4, c1, d4), (a87, b4, c1, d5), (a87, b4, c1, d6), (a87, b4, c1, d7), (a87, b4, c1, d8), (a87, b4, c1, d9), (a87, b4, c1, d10), (a87, b4, c1, d11), (a87, b4, c1, d12), (a87, b4, c1, d13), (a87, b4, c1, d14), (a87, b4, c1, d15), (a87, b4, c1, d16), (a87, b4, c1, d17), (a87, b4, c1, d18), (a87, b4, c1, d19), (a87, b4, c1, d20), (a87, b4, c1, d21), (a87, b4, c1, d22), (a87, b4, c2, d1), (a87, b4, c2, d2), (a87, b4, c2, d3), (a87, b4, c2, d4), (a87, b4, c2, d5), (a37, b4, c2, d6), (a87, b4, c2, d7), (a87, b4, c2, d8), (a87, b4, c2, d9), (a87, b4, c2, d10), (a87, b4, c2, d11), (a87, b4, c2, d12), (a87, b4, c2, d13), (a87, b4, c2, d14), (a87, b4, c2, d15), (a87, b4, c2, d16), (a87, b4, c2, d17), (a87, b4, c2, d18), (a87, b4, c2, d19), (a87, b4, c2, d20), (a87, b4, c2, d21), (a87, b4, c2, d22), (a87, b4, c3, d1), (a87, b4, c3, d2), (a87, b4, c3, d3), (a87, b4, c3, d14), (a87, b4, c3, d5), (a87 b4, c3, d6), (a87 b4, c3, d7), (a87, b4, c3, d8), (a87, b4, c3, d9), (a87, b4, c3, d10), (a87, b4, c3, d11), (a87, b4, c3, d12), (a87, b4, c3, d13), (a87, b4, c3, d14), (a87, b4, c3, d15), (a87, b4, c3, d16), (a87, b4, c3, d17), (a87, b4, c3, d18), (a87, b4, c3, d19), (a87, b4, c3, d20), (a87, b4, c3, d21), (a87, b4, c3, d22), (a87, b5, c1, d1), (a87, b5, c1, d2), (a87, b5, c1, d3), (a87, b5, c1, d4), (a87, b5, c1, d5), (a37, b5, c1, d6), (a87, b5, c1, d7), (a87, b5, c1, d8), (a37, b5, c1, d9), (a87, b5, c1, d10), (a87, b5, c1, d11), (a87, b5, c1, d12), (a37, b5, c1, d13), (a87, b5, c1, d14), (a87, b5, c1, d15), (a87, b5, c1, d16), (a87, b5, c1, d17), (a37, b5, c1, d18), (a87, b5, c1, d19), (a87, b5, c1, d20), (a87, b5, c1, d21), (a87, b5, c1, d22), (a87, b5, c2, d1), (a87, b5, c2, d2), (a87, b5, c2, d3), (a87, b5, c2, d4), (a87, b5, c2, d5), (a87, b5, c2, d6), (a87, b5, c2, d7), (a87, b5, c2, d8), (a87, b5, c2, d9), (a87, b5, c2, d10), (a87, b5, c2, d11), (a87, b5, c2, d12), (a87, b5, c2, d13), (a87, b5, c2, d14), (a87, b5, c2, d15), (a87, b5, c2, d16), (a87, b5, c2, d17), (a87, b5, c2, d18), (a87, b5, c2, d19), (a87, b5, c2, d20), (a87, b5, c2, d21), (a87, b5, c2, d22), (a87, b5, c3, d1), (a87, b5, c3, d2), (a87, b5, c3, d3), (a87, b5, c3, d4), (a87, b5, c3, d5), (a87, b5, c3, d6), (a37, b5, c3, d7), (a87, b5, c3, d8), (a87, b5, c3, d9), (a87, b5, c3, d10), (a87, b5, c3, d11), (a87, b5, c3, d12, (a87, b5, c3, d13), (a87, b5, c3, d14), (a87, b5, c3, d15), (a87, b5, c3, d16), (a87, b5, c3, d17), (a87, b5, c3, d18), (a87, b5, c3, d19), (a87, b5, c3, d20), (a87, b5, c3, d21), (a87, b5, c3, d22), (a87, b6, c1, d1), (a87, b6, c1, d2), (a87, b6, c1, d3), (a87, b6, c1, d4), (a87, b6, c1, d5), (a87, b6, c1, d6), (a87, b6, c1, d7), (a87, b6, c1, d8), (a87, b6, c1, d9), (a87, b6, c1, d10), (a87, b6, c1, d11), (a87, b6, c1, d12), (a87, b6, c1, d13), (a87, b6, c1, d14), (a87, b6, c1, d15), (a87, b6, c1, d16), (a87, b6, c1, d17), (a87, b6, c1, d18), (a87, b6, c1, d19), (a87, b6, c1, d20), (a87, b6, c1, d21), (a87, b6, c1, d22), (a87, b6, c2, d1), (a87, b6, c2, d2), (a87, b6, c2, d3), (a87, b6, c2, d4), (a87, b6, c2, d5), (a87, b6, c2, d6), (a87, b6, c2, d7), (a87, b6, c2, d8), (a87, b6, c2, d9), (a87, b6, c2, d10), (a87, b6, c2, d11), (a87, b6, c2, d12), (a87, b6, c2, d13), (a87, b6, c2, d14), (a87, b6, c2, d15), (a87, b6, c2, d16), (a87, b6, c2, d17), (a87, b6, c2, d18), (a87, b6, c2, d19), (a37, b6, c2, d20), (a87, b6, c2, d21), (a87, b6, c2, d22), (a87, b6, c3, d1), (a87, b6, c3, d2), (a87, b6, c3, d3), (a87, b6, c3, d4), (a87, b6, c3, d5), (a87, b6, c3, d6), (a87, b6, c3, d7), (a87, b6, c3, d8), (a87, b6, c3, d9), (a87, b6, c3, d10), (a87, b6, c3, d11), (a87, b6, c3, d12), (a87, b6, c3, d13), (a87, b6, c3, d14), (a87, b6, c3, d15), (a87, b6, c3, d16), (a87, b6, c3, d17), (a87, b6, c3, d18), (a87, b6, c3, d19), (a87, b6, c3, d20), (a87, b6, c3, d21), (a87, b6, c3, d22), (a88, b1, c1, d1), (a88, b1, c1, d2), (a88, b1, c1, d3), (a88, b1, c1, d4), (a88, b1, c1, d5), (a38, b1, c1, d6), (a88, b1, c1, d7), (a88, b1, c1, d8), (a88, b1, c1, d9), (a88, b, c1, d10), (a88, b1, c1, d11), (a88, b1, c1, d12), (a88, b1, c1, d13), (a88, b1, c1, d14), (a88, b1, c1, d15), (a88, b1, c1, d16), (a88, b1, c1, d17), (a88, b1, c1, d18), (a88, b1, c1, d19), (a88, b1, c1, d20), (a88, b1, c1, d21), (a88, b, c1, d22), (a88, b1, c2, d1), (a88, b1, c2, d2), (a88, b1, c2, d3), (a88, b1, c2, d4), (a88, b1, c2, d5), (a88, b1, c2, d6), (a88, b1, c2, d7), (a88, b1, c2, d8), (a88, b1, c2, d9), (a88, b1, c2, d10), (a88, b1, c2, d11), (a88, b1, c2, d12), (a88, b1, c2, d13), (a88, b1, c2, d14), (a88, b1, c2, d15), (a88, b1, c2, d16), (a88, b1, c2, d17), (a88, b1, c2, d18), (a88, b1, c2, d19), (a88, b1, c2, d20), (a88, b1, c2, d21), (a88, b1, c2, d22), (a88, b1, c3, d1), (a88, b1, c3, d2), (a88, b1, c3, d3), (a88, b1, c3, d4), (a88, b1, c3, d5), (a88, b1, c3, d6), (a88, b1, c3, d7), (a88, b1, c3, d8), (a88, b1, c3, d9), (a88, b1, c3, d10), (a88, b1, c3, d11), (a88, b1, c3, d12), (a8, b1, c3, d13), (a88, b1, c3, d14), (a88, b1, c3, d15), (a88, b1, c3, d16), (a88, b1, c3, d17), (a88, b1, c3, d18), (a88, b1, c3, d19), (a88, b1, c3, d20), (a88, b1, c3, d21), (a88, b1, c3, d22), (a88, b2, c1, d1), (a88, b2, c1, d2), (a88, b2, c1, d3), (a88, b2, c1, d4), (a88, b2, c1, d5), (a88, b2, c1, d6), (a88, b2, c1, d7), (a88, b2, c1, d8), (a88, b2, c1, d9), (a88, b2, c1, d10), (a88, b2, c1, d11), (a88, b2, c1, d12), (a88, b2, c1, d13), (a88, b2, c1, d14), (a88, b2, c1, d15), (a88, b2, c1, d16), (a88, b2, c3, d17), (a88, b2, c1, d18), (a88, b2, c1, d19), (a88, b2, c1, d20), (a88, b2, c1, d21), (a88, b2, c1, d22), (a88, b2, c2, d1), (a88, b2, c2, d2), (a88, b2, c2, d3), (a88, b2, c2, d4), (a88, b2, c2, d5), (a88, b2, c2, d6), (a88, b2, c2, d7), (a88, b2, c2, d8), (a88, b2, c2, d9), (a88, b2, c2, d10), (a88, b2, c2, d11), (a88, b2, c2, d12), (a88, b2, c2, d13), (a88, b2, c2, d14), (a88, b2, c2, d15), (a88, b2, c2, d16), (a88, b2, c2, d17), (a88, b2, c2, d18), (a88, b2, c2, d19), (a88, b2, c2, d20), (a88, b2, c2, d21), (a88, b2, c2, d22), (a88, b2, c3, d1), (a88, b2, c3, d2), (a88, b2, c3, d3), (a88, b2, c3, d4), (a88, b2, c3, d5), (a88, b2, c3, d6), (a88, b2, c1, d7), (a88, b2, c3, d8), (a88, b2, c3, d9), (a88, b2, c3, d10), (a88, b2, c3, d11), (a88, b2, c3, d12), (a88, b2, c3, d13), (a88, b2, c3, d14), (a88, b2, c3, d15), (a88, b2, c3, d16), (a88, b2, c3, d17), (a88, b2, c3, d18), (a88, b2, c3, d19), (a88, b2, c3, d20), (a88, b2, c3, d21), (a88, b2, c3, d22), (a88, b3, c1, d1), (a88, b3, c1, d2), (a88, b3, c1, d3), (a88, b3, c1, d4), (a88, b3, c1, d5), (a38, b3, c1, d6), (a88, b3, c1, d7), (a88, b3, c1, d8), (a88, b3, c1, d9), (a88, b3, c1, d10), (a88, b3, c1, d11), (a88, b3, c1, d12), (a88, b3, c1, d13), (a88, b3, c1, d14), (a88, b3, c1, d15), (a88, b3, c1, d16), (a88, b3, c1, d17), (a88, b3, c1, d18), (a88, b3, c1, d19), (a88, b3, c1, d20), (a88, b3, c1, d21), (a88, b3, c1, d22), (a88, b3, c2, d1), (a88, b3, c2, d2), (a88, b3, c2, d3), (a88, b3, c2, d4), (a88, b3, c2, d5), (a88, b3, c2, d6), (a88, b3, c2, d7), (a88, b3, c2, d8), (a88, b3, c2, d9), (a88, b3, c2, d10), (a88, b3, c2, d11), (a88, b3, c2, d12), (a38, b3, c2, d13), (a88, b3, c2, d14), (a88, b3, c2, d15), (a88, b3, c2, d16), (a88, b3, c2, d17), (a88, b3, c2, d18), (a88, b3, c2, d19), (a88, b3, c2, d20), (a88, b3, c2, d21), (a88, b3, c2, d22), (a88, b3, c3, d1), (a88, b3, c3, d2), (a88, b3, c3, d3), (a88, b3, c3, d4), (a88, b3, c3, d5), (a88, b3, c3, d6), (a88, b3, c3, d7), (a88, b3, c3, d8), (a88, b3, c3, d9), (a88, b3, c3, d10), (a88, b3, c3, d11), (a88, b3, c3, d12), (a88, b3, c3, d13), (a88, b3, c3, d14), (a88, b3, c3, d15), (a88, b3, c3, d16), (a88, b3, c3, d17), (a88, b3, c3, d18), (a88, b3, c3, d19), (a88, b3, c3, d20), (a88, b3, c3, d21), (a88, b3, c3, d22), (a88, b4, c1, d1), (a88, b4, c1, d2), (a88, b4, c1, d3), (a88, b4, c1, d4), (a88, b4, c1, d5), (a88, b4, c1, d6), (a88, b4, c1, d7), (a88, b4, c1, d8), (a88, b4, c1, d9), (a38, b4, c1, d10), (a88, b4, c1, d11), (a88, b4, c1, d12), (a88, b4, c1, d13), (a88, b4, c1, d14), (a88, b4, c1, d15), (a88, b4, c1, d16), (a88, b4, c1, d17), (a88, b4, c1, d18), (a88, b4, c1, d19), (a88, b4, c1, d20), (a88, b4, c1, d21), (a88, b4, c1, d22), (a88, b4, c2, d1) (a88, b4, c2, d2), (a88, b4, c2, d5), (a88, b4, c2, d4), (a88, b4, c2, d5), (a88, b4, c2, d6), (a88, b4, c2, d7), (a88, b4, c2, d8), (a88, b4, c2, d9), (a88, b4, c2, d10), (a88, b4, c2, d11), (a88, b4, c2, d12), (a88, b4, c2, d13), (a88, b4, c2, d14), (a88, b4, c2, d15), (a88, b4, c2, d16), (a88, b4, c2, d17), (a88, b4, c2, d18), (a88, b4, c2, d19), (a88, b4, c2, d20), (a88, b4, c2, d21), (a88, b4, c2, d22), (a88, b4, c3, d1), (a88, b4, c3, d2), (a88, b4, c3, d3), (a88, b4, c3, d4), (a88, b4, c3, d5), (a88, b4, c3, d6), (a88, b4, c3, d7), (a88, b4, c3, d8), (a88, b4, c3, d9), (a88, b4, c3, d10), (a88, b4, c3, d11), (a88, b4, c3, d12), (a88, b4, c3, d13), (a88, b4, c3, d14), (a88, b4, c3, d15), (a88, b4, c3, d16), (a88, b4, c3, d17), (a88, b4, c3, d18), (a88, b4, c3, d19), (a88, b4, c3, d20), (a88, b4, c3, d21), (a88, b4, c3, d22), (a88, b5, c1, d1), (a88, b5, c1, d2), (a88, b5, c1, d3), (a88, b5, c1, d4), (a88, b5, c1, d5), (a88, b5, c1, d6), (a88, b5, c1, d7), (a88, b5, c1, d8), (a88, b5, c1, d9), (a88, b5, c1, d10), (a88, b5, c1, d11), (a88, b5, c1, d12), (a88, b5, c1, d13), (a88, b5, c1, d14), (a88, b5, c1, d15), (a88, b5, c1, d16), (a88, b5, c1, d17), (a88, b5, c1, d18), (a88, b5, c1, d19), (a88, b5, c1, d20), (a88, b5, c1, d21), (a88, b5, c1, d22), (a88, b5, c2, d1), (a88, b5, c2, d2), (a88, b5, c2, d3), (a88, b5, c2, d4), (a88, b5, c2, d5), (a88, b5, c2, d6), (a88, b5, c2, d7), (a88, b5, c2, d8), (a88, b5, c2, d9), (a88, b5, c2, d10), (a88, b5, c2, d11), (a88, b5, c2, d12), (a88, b5, c2, d13), (a88, b5, c2, d14), (a88, b5, c2, d15), (a88, b5, c2, d16), (a88, b5, c2, d17), (a88, b5, c2, d18), (a88, b5, c2, d19), (a88, b5, c2, d20), (a88, b5, c2, d21), (a88, b5, c2, d22), (a88, b5, c3, d1), (a88, b5, c3, d2), (a88, b5, c3, d3), (a88, b5, c3, d4), (a88, b5, c3, d5), (a88, b5, c3, d6), (a88, b5, c3, d7), (a88, b5, c3, d8), (a88, b5, c3, d9), (a88, b5, c3, d10), (a88, b5, c3, d11), (a88, b5, c3, d12), (a88, b5, c3, d13), (a88, b5, c3, d14), (a88, b5, c3, d15), (a88, b5, c3, d16), (a88, b5, c3, d17), (a88, b5, c3, d18), (a88, b5, c3, d19), (a88, b5, c3, d20), (a88, b5, c3, d21), (a88, b5, c3, d22), (a88, b6, c1, d1), (a88, b6, c1, d2), (a88, b6, c1, d3), (a88, b6, c1, d4), (a88, b6, c1, d5), (a88, b6, c1, d6), (a88, b6, c1, d7), (a88, b6, c1, d8), (a88, b6, c1, d9), (a88, b6, c1, d10), (a88, b6, c1, d11), (a88, b6, c1, d12), (a88, b6, c1, d13), (a38, b6, c1, d14), (a88, b6, c1, d15), (a88, b6, c1, d16), (a88, b6, c1, d17), (a88, b6, c1, d18), (a88, b6, c1, d19), (a88, b6, c1, d20), (a88, b6, c1, d21), (a88, b6, c1, d22), (a88, b6, c2, d1), (a88, b6, c2, d2), (a88, b6, c2, d3), (a88, b6, c2, d4), (a88, b6, c2, d5), (a88, b6, c2, d6), (a88, b6, c2, d7), (a88, b6, c2, d8), (a88, b6, c2, d9), (a88, b6, c2, d10), (a88, b6, c2, d11), (a88, b6, c2, d12), (a88, b6, c2, d13), (a88, b6, c2, d14), (a88, b6, c2, d15), (a88, b6, c2, d16), (a88, b6, c2, d17), (a88, b6, c2, d18), (a88, b6, c2, d19), (a88, b6, c2, d20), (a88, b6, c2, d21), (a88, b6, c2, d22), (a88, b6, c3, d1), (a88, b6, c3, d2), (a88, b6, c3, d3), (a88, b6, c3, d4), (a88, b6, c3, d5), (a88, b6, c3, d6), (a88, b6, c3, d7), (a88, b6, c3, d8), (a88, b6, c3, d9), (a88, b6, c3, d10), (a88, b6, c3, d11), (a88, b6, c3, d12), (a88, b6, c3, d13), (a88, b6, c3, d14), (a88, b6, c3, d15), (a88, b6, c3, d16), (a88, b6, c3, d17), (a88, b6, c3, d18), (a88, b6, c3, d19), (a88, b6, c3, d20), (a88, b6, c3, d21), (a88, b6, c3, d22), (a89, b1, c1, d1), (a89, b1, c1, d2), (a89, b1, c1, d3), (a89, b1, c1, d4), (a89, b1, c1, d5), (a89, b1, c1, d6), (a89, b1, c1, d7), (a89, b1, c1, d8), (a89, b1, c1, d9), (a89, b1, c1, d10), (a89, b1, c1, d11), (a89, b1, c1, d12), (a89, b1, c1, d13), (a89, b1, c1, d14), (a89, b1, c1, d15), (a89, b1, c1, d16), (a89, b1, c1, d17), (a89, b1, c1, d18), (a89, b1, c1, d19), (a89, b1, c1, d20), (a89, b1, c1, d21), (a89, b1, c1, d22), (a89, b1, c2, d1), (a89, b1, c2, d2), (a89, b1, c2, d3), (a89, b1, c2, d4), (a89, b1, c2, d5), (a89, b1, c2, d6), (a89, b1, c2, d7), (a89, b1, c2, d8), (a89, b1, c2, d9), (a89, b1, c2, d10), (a89, b1, c2, d11), (a89, b1, c2, d12), (a89, b1, c2, d13), (a89, b1, c2, d14), (a89, b1, c2, d15), (a89, b1, c2, d16), (a89, b1, c2, d17), (a89, b1, c2, d18), (a89, b1, c2, d19), (a89, b1, c2, d20), (a89, b1, c2, d21), (a89, b1, c2, d22), (a89, b1, c3, d1), (a89, b1, c3, d2), (a89, b1, c3, d3), (a89, b1, c3, d4), (a89, b1, c3, d5), (a88, b1, c3, d6), (a89, b1, c3, d7), (a89, b1, c3, d8), (a89, b1, c3, d9), (a89, b1, c3, d10), (a89, b1, c3, d11), (a89, b1, c3, d12), (a89, b1, c3, d13), (a89, b1, c3, d14), (a89, b1, c3, d15), (a89, b1, c3, d16), (a89, b1, c3, d17), (a89, b1, c3, d18), (a89, b1, c3, d19), (a89, b1, c3, d20), (a89, b1, c3, d21), (a89, b1, c3, d22), (a89, b2, c1, d1), (a89, b2, c1, d2), (a89, b2, c1, d5), (a89, b2, c1, d4), (a89, b2, c1, d5), (a89, b2, c1, d6), (a89, b2, c1, d7), (a89, b2, c1, d8), (a89, b2, c1, d9), (a89, b2, c1, d10), (a89, b2, c1, d11), (a89, b2, c1, d12), (a89, b2, c1, d13), (a89, b2, c1, d14), (a89, b2, c1, d15), (a89, b2, c1, d16), (a89, b2, c1, d17), (a89, b2, c1, d18), (a89, b2, c1, d19), (a89, b2, c1, d20), (a89, b2, c1, d21), (a89, b2, c1, d22), (a89, b2, c2, d1), (a89, b2, c2, d2), (a89, b2, c2, d3), (a89, b2, c2, d4), (a89, b2, c2, d5), (a89, b2, c2, d6), (a89, b2, c2, d7), (a89, b2, c2, d8), (a89, b2, c2, d9), (a89, b2, c2, d10), (a89, b2, c2, d11), (a89, b2, c2, d12), (a89, b2, c2, d13), (a89, b2, c2, d14), (a89, b2, c2, d15), (a89, b2, c2, $d_{16}$), (a89, b2, c2, d17), (a89, b2, c2, d18), (a89, b2, c2, d19), (a89, b2, c2, d20), (a89, b2, c2, d21), (a89, b2, c2, d22), (a89, b2, c3, d1), (a89, b2, c3, d2), (a89, b2, c3, d3), (a89, b2, c3, d4), (a89, b2, c3, d5), (a89, b2, c3, d6), (a89, b2, c3, d7), (a89, b2, c3, d8), (a89, b2, c3, d9), (a89, b2, c3, d10), (a89, b2, c3, d11), (a89, b2, c3, d12), (a89, b2, c3, d13), (a89, b2, c3, d14), (a89, b2, c3, d15), (a89, b2, c3, d16), (a89, b2, c3, d17), (a89, b2, c3, d18), (a89, b2, c3, d19), (a89, b2, c3, d20), (a89, b2, c3, d21), (a89, b2, c3, d22), (a89, b3, c1, d1), (a89, b3, c1, d2), (a89, b3, c1, d3), (a89, b3, c1, d4), (a89, b3, c1, d5), (a89, b3, c1, d6), (a89, b3, c1, d7), (a89, b3, c1, d8), (a89, b3, c1, d9), (a89, b3, c1, d10), (a89, b3, c1, d11), (a89, b3, c1, d12), (a89, b3, c1, d13), (a89, b3, c1, d14), (a89, b3, c1, d15), (a89, b3, c1, d6), (a89, b3, c1, d17), (a89, b3, c1, d18), (a89, b3, c1, d19), (a89, b3, c1, d20), (a89, b3, c1, d21), (a89, b3, c1, d22), (a89, b3, c2, d1), (a89, b3, c2, d2), (a89, b3, c2, d3), (a89, b3, c2, d4), (a89, b3, c2, d5), (a89, b3, c2, d6), (a89, b3, c2, d7), (a89, b3, c2, d8), (a89, b3, c2, d9), (a89, b3, c2, d10), (a89, b3, c2, d11), (a89, b3, c2, d12), (a89, b3, c2, d13), (a89, b3, c2, d14), (a89, b3, c2, d15), (a89, b3, c2, d16), (a89, b3, c2, d17), (a89, b3, c2, d18), (a89, b3, c2, d19), (a89, b3, c2, d20), (a89, b3, c2, d21), (a89, b3, c2, d22), (a89, b3, c3, d11), (a89, b3, c3, d2), (a89, b3, c3, d3), (a89, b3, c3, d4), (a89, b3, c3, d5), (a89, b3, c3, d6), (a39, b3, c3, d7), (a39, b3, c3, d8), (a89, b3, c3, d9), (a89, b3, c3, d10), (a89, b3, c3, d11), (a89, b3, c3, d12), (a89, b3, c3, d13), (a39, b3, c3, d14), (a89, b3, c3, d15), (a89, b3, c3, d16), (a89, b3, c3, d17), (a89, b3, c3, d18), (a89, b3, c3, d19), (a89, b3, c3, d20), (a89, b3, c3, d21), (a89, b3, c3, d22), (a89, b4, c1, d1), (a89, b4, c1, d2), (a89, b4, c1, d3), (a89, b4, c1, d4), (a88, b4, c1, d5), (a89, b4, c1, d6), (a89, b4, c1, d7), (a89, b4, c1, d8), (a89, b4, c1, d9), (a89, b4, c1, d10), (a89, b4, c1, d11), (a89, b4, c1, d12), (a89, b4, c1, d13), (a89, b4, c1, d14), (a88, b4, c1, d15), (a89, b4, c1, d16), (a89, b4, c1, d17), (a89, b4, c1, d18), (a89, b4, c1, d19), (a89, b4, c1, d20), (a89, b4, c1, d21), (a89, b4, c1, d22), (a89, b4, c2, d1), (a89, b4, c2, d2), (a89, b4, c2, d3), (a89, b4, c2, d4), (a89, b4, c2, d5), (a89, b4, c2, d6), (a89, b4, c2, d7), (a89, b4, c2, d8), (a88, b4, c2, d9), (a39, b4, c2, d10), (a89, b4, c2, d11), (a89, b4, c2, d12), (a89, b4, c2, d13), (a89, b4, c2, d14), (a89, b4, c2, d15), (a89, b4, c2, d16), (a89, b4, c2, d17), (a89, b4, c2, d18), (a39, b4, c2, d19), (a89, b4, c2, d20), (a89, b4, c2, d21), (a89, b4, c2, d22), (a89, b4, c3, d1), (a89, b4, c3, d2), (a89, b4, c3, d3), (a89, b4, c3, d4), (a89, b4, c3, d5), (a89, b4, c3, d6), (a89, b4, c3, d7), (a89, b4, c3, d8), (a89, b4, c3, d9), (a89, b4, c3, d10), (a88, b4, c3, d11), (a89, b4, c3, d12), (a89, b4, c3, d13), (a89, b4, c3, d14), (a89, b4, c3, d15), (a89, b4, c3, d16), (a89, b4, c3, d17), (a89, b4, c3, d18), (a89, b4, c3, d19), (a88, b4, c3, d20), (a39, b4, c3, d21), (a89, b4, c3, d22), (a89, b5, c1, d1), (a89, b5, c1, d2), (a89, b5, c1, d3), (a89, b5, c1, d4), (a89, b5, c1, d5), (a89, b5, c1, d6), (a89, b5, c1, d7), (a89, b5, c1, d8), (a89, b5, c1, d9), (a89, b5, c1, d10), (a89, b5, c1, d11), (a89, b5, c1, d12), (a89, b5, c1, d13), (a89, b5, c1, d14), (a89, b5, c1, d15), (a89, b5, c1, d16), (a89, b5, c1, d17), (a89, b5, c1, d18), (a89, b5, c1, d19), (a89, b5, c1, d20), (a89, b5, c1, d21), (a89, b5, c1, d22), (a89, b5, c2, d1), (a89, b5, c2, d2), (a89, b5, c2, d3), (a89, b5, c2, d4), (a89, b5, c2, d5), (a89, b5, c2, d6), (a89, b5, c2, d7), (a89, b5, c2, d8), (a89, b5, c2, d9), (a89, b5, c2, d10), (a89, b5, c2, d11), (a89, b5, c2, d12), (a89, b5, c2, d13), (a89, b5, (c2, d15), (a89, b5, c2, d16), (a89, b5, c2, d17), (a89, b5, c2, d18), (a89, b5, c2, d19), (a89, b5, c2, d20), (a89, b5, c2, d21), (a89, b5, c2, d22), (a89, b5, c3, d1), (a89, b5, c3, d2), (a89, b5, c3, d3), (a89, b5, c3, d4), (a89, b5, c3, d5), (a89, b5, c3, d6), (a89, b5, c3, d7), (a89, b5, c3, d5), (a89, b5, c3, d9), (a89, b5, c3, d10), (a39, b5, c3, d11), (a89, b5, c3, d12), (a88, b5, c3, d13), (a89, b5, c3, d14), (a39, b5, c3, d15), (a89, b5, c3, d16), (a39, b5, c3, d17), (a89, b5, c3, d18), (a89, b5, c3, d19), (a89, b5, c3, d20), (a89, b5, c3, d21), (a89, b5, c3, d22), (a89, b6, c1, d1), (a89, b6, c1, d2), (a89, b6, c1, d3), (a89, b6, c1, d4), (a89, b6, c1, d5), (a89, b6, c1, d6), (a89, b6, c1, d7), (a89, b6, c1, d8), (a89, b6, c1, d9), (a89, b6, c1, d10), (a89, b6, c1, d11), (a89, b6, c1, d12, (a89, b6, c1, d13), (a89, b6, c1, d14), (a89, b6, c1, d15), (a89, b1, c1, d16), (a89, b1, c1, d17), (a89, b1, c1, d18), (a89, b1, c1, d19), (a89, b1, c1, d20), (a89, b6, c1, d21), (a89, b6, c1, d22), (a89, b6, c2, d1), (a89, b6, c2, d2), (a89, b6, c2, d3), (a89, b6, c2, d4, (a89, b6, c2, d5), (a89, b6, c2, d6), (a89, b6, c2, d7), (a89, b6, c2, d8), (a89, b6, c2, d9), (a89, b6, c2, d10), (a89, b6, c2, d11), (a89, b6, c2, d12), (a89, b6, c2, d13), (a89, b6, c2, d14), (a89, b6, c2, d15), (a89, b6, c2, d16), (a89, b6, c2, d17), (a89, b6, c2, d18), (a89, b6, c2, d19), (a89, b6, c2, d20), (a89, b6, c2, d21), (a89, b6, c2, d22), (a89, b6, c3, d1), (a89, b6, c3, d2), (a89, b6, c3, d3), (a89, b6, c3, d4), (a89, b6, c3, d5), (a89, b6, c3, d6), (a89, b6, c3, d7), (a89, b6, c3, d8), (a89, b6, c3, d9), (a89, b6, c3, d10), (a89, b6, c3, d11), (a89, b6, c3, d12), (a89, b6, c3, d13), (a89, b6, c3, d14), (a89, b6, c3, d15), (a89, b6, c3, d16), (a89, b6, c3, d17), (a89, b6, c3, d18), (a89, b6, c3, d19), (a89, b6, c3, d20), (a89, b6, c3, d21), (a89, b6, c3, d22), (a90, b1, c1, d1), (a90, b1, c1, d2), (a90, b1, c1, d3), (a90, b1, c1, d4), (a90, b1, c1, d5), (a90, b1, c1, d6), (a90, b1, c1, d7), (a90, b1, c1, d8), (a90, b1, c1, d9), (a90, b1, c1, d10), (a90, b1, c1, d11), (a90, b1, c1, d12), (a90, b1, c1, d13), (a90, b1, c1, d14), (a90, b1, c1, d15), (a90, b1, c1, d16), (a90, b1, c1, d17), (a90, b1, c1, d18), (a90, b1, c1, d19), (a90, b1, c1, d20), (a90, b1, c1, d21), (a90, b1, c1, d22), (a90, b1, c2, d1), (a90, b1, c2, d2), (a90, b1, c2, d3), (a90, b1, c2, d4), (a90, b1, c2, d5), (a90, b1, c2, d6), (a90, b1, c2, d7), (a90, b1, c2, d8), (a90, b1, c2, d9), (a90, b1, c2, d10), (a90, b1, c2, d11), (a90, b1, c2, d12), (a90, b1, c2, d13), (a90, b1, c2, d14), (a90, b1, c2, d15), (a90, b1, c2, d16), (a90, b, c2, d17), (a90, b1, c2, d18), (a90, b1, c2, d19), (a90, b1, c2, d20), (a90, b1, c2, d21), (a90, b1, c2, d22), (a90, b1, c3, d1), (a90, b1, c3, d2), (a90, b1, c3, d3), (a90, b1, c3, d4), (a90, b1, c3, d5), (a90, b1, c3, d6), (a90, b1, c3, d7), (a90, b1, c3, d8), (a90, b1, c3, d9), (a90, b1, c3, d10), (a90, b1, c3, d11), (a90, b1, c3, d12), (a90, b1, c3, d13), (a90, b1, c3, d14), (a90, b1, c3, d15), (a90, b1, c3, d16), (a90, b, c3, d17), (a90, b1, c3, d18), (a90, b1, c3, d19), (a90, b1, c3, d20), (a90, b1, c3, d21), (a90, b1, c3, d22), (a90, b2, c1, d1), (a90, b2, c1, d2), (a90, b2, c1, d3), (a90, b2, c1, d4), (a90, b2, c1, d5), (a90, b2, c1, d6), (a90, b2, c1, d7), (a90, b2, c1, d8), (a90, b2, c1, d9), (a90, b2, c1, d10), (a90, b2, c1, d11), (a90, b2, c1, d12), (a90, b2, c1, d13), (a90, b2, c1, d14), (a90, b2, c1, d15), (a90, b2, c1, d16), (a90, b2, c1, d17), (a90, b2, c., d18), (a90, b2, c1, d19), (a90, b2, c1, d20), (a90, b2, c1, d21), (a90, b2, c1, d22), (a90, b2, c2, d1), (a90, b2, c2, d2), (a90, b2, c2, d3), (a90, b2, c2, d4), (a90, b2, c2, d5), (a90, b2, c2, d6), (a90, b2, c2, d7), (a90, b2, c2, d8), (a90, b2, c2, d9), (a90, b2, c2, d10), (a90, b2, c2, d11), (a90, b2, c2, d12), (a90, b2, c2, d13), (a90, b2, c2, d14), (a90, b2, c2, d15), (a90, b2, c2, d16), (a90, b2, c2, d17), (a90, b2, c2, d18), (a90, b2, c2, d19), (a90, b2, c2, d20), (a90, b2, c2, d21), (a90, b2, c2, d22), (a90, b2, c3, d1), (a90, b2, c3, d2), (a90, b2, c3, d3), (a90, b2, c3, d4), (a90, b2, c3, d5), (a90, b2, c3, d16), (a90, b2, c3, d7), (a90, b2, c3, d8), (a90, b2, c3, d9), (a90, b2, c3, d10), (a90, b2, c3, d11), (a90, b2, c3, d12), (a90, b2, c3, d13), (a90, b2, c3, d14), (a90, b2, c3, d15), (a90, b2, c3, d16), (a90, b2, c3, d17), (a90, b2, c3, d18), (a90, b2, c3, d19), (a90, b2, c3, d20), (a90, b2, c3, d21), (a90, b2, c3, d22), (a90, b3, c1, d1), (a90, b3, c1, d2), (a90, b3, c1, d3), (a90, b3, c1, d4), (a90, b3, c1, d5), (a90, b3, c1, d16), (a90, b3, c1, d7), (a90, b3, c1, d8), (a90, b3, c1, d9), (a90, b3, c1, d10), (a90, b3, c1, d11), (a90, b3, c1, d12), (a90, b3, c1, d13), (a90, b3, c1, d14), (a90, b3, c1, d15), (a90, b3, c1, d16), (a90, b3, c1, d17), (a90, b3, c1, d18), (a90, b3, c1, d19), (a90, b3, c1, d20), (a90, b3, c1, d21), (a90, b3, c1, d22), (a90, b3, c2, d1), (a90, b3, c2, d2), (a90, b3, c2, d13), (a90, b3, c2, d4), (a90, b3, c2, d5), (a90, b3, c2, d6), (a90, b3, c2, d7), (a90, b3, c2, d3), (a90, b3, c2, d9), (a90, b3, c2, d10), (a90, b3, c2, d11), (a90, b3, c2, d12), (a90, b3, c2, d13), (a90, b3, c2, d14), (a90, b3, c2, d15), (a90, b3, c2, d16), (a90, b3, c2, d17), (a90, b3, c2, d18), (a90, b3, c2, d19), (a90, b3, c2, d20), (a90, b3, c2, d21), (a90, b3, c2, d22), (a90, b3, c3, d1), (a90, b3, c3, d2), (a90, b3, c3, d3), (a90, b3, c3, d4), (a90, b3, c3, d5), (a90, b3, c3, d6), (a90, b3, c3, d7), (a90, b3, c3, d8), (a90, b3, c3, d9), (a90, b3, c3, d10), (a90, b3, c3, d11), (a90, b3, c3, d12), (a90, b3, c3, d13), (a90, b3, c3, d14), (a90, b3, c3, d15), (a90, b3, c3, d16), (a90, b3, c3, d17), (a90, b3, c3, d18), (a90, b3, c3, d19), (a90, b3, c3, d20), (a90, b3, c3, d21), (a90, b3, c3, d22), (a90, b4, c1, d1), (a90, b4, c1, d2), (a90, b4, c1, d3), (a90, b4, c1, d4), (a90, b4, c1, d5), (a90, b4, c1, d6), (a90, b4, c1, d7), (a90, b4, c1, d8), (a90, b4, c1, d9), (a90, b4, c1, d10), (a90, b4, c1, d11), (a90, b4, c1, d12), (a90, b4, c1, d13), (a90, b4, c1, d14), (a90, b4, c1, d15), (a90, b4, c1, d16), (a90, b4, c1, d17), (a90, b4, c1, d18), (a90, b4, c1, d19), (a90, b4, c1, d20), (a90, b4, c1, d21), (a90, b4, c1, d22), (a90, b4, c2, d1), (a90, b4, c2, d2), (a90, b4, c2, d3), (a90, b4, c2, d4), (a90, b4, c2, d5), (a90, b4, c2, d6), (a90, b4, c2, d7), (a90, b4, c2, d8), (a90, b4, c2, d9), (a90, b4, c2, d10), (a90, b4, c2, d11), (a90, b4, c2, d12), (a90, b4, c2, d13), (a90, b4, c2, d14), (a90, b4, c2, d15), (a90, b4, c2, d16), (a90, b4, c2, d17), (a90, b4, c2, d18), (a90, b4, c2, d19), (a90, b4, c2, d20), (a90, b4, c2, d21), (a90, b4, c2, d22), (a90, b4, c3, d1), (a90, b4, c3, d2), (a90, b4, c3, d3), (a90, b4, c3, d4), (a90, b4, c3, d5), (a90, b4, c3, d6), (a90, b4, c3, d7), (a90, b4, c3, d8), (a90, b4, c3, d9), (a90, b4, c3, d10), (a90, b4, c3, d11), (a90, b4, c3, d12), (a90, b4, c3, d13), (a90, b4, c3, d14), (a90, b4, c3, d15), (a90, b4, c3, d16), (a90, b4, c3, d17), (a90, b4, c3, d18), (a90, b4, c3, d19), (a90, b4, c3, d20), (a90, b4, c3, d21), (a90, b4, c3, d22), (a90, b5, c1, d1), (a90, b5, c1, d2), (a90, b5, c1, d3), (a90, b5, c1, d4), (a90, b5, c1, d5), (a90, b5, c1, d6), (a90, b5, c1, d7), (a90, b5, c1, d8), (a90, b5, c1, d9), (a90, b5, c1, d10), (a90, b5, c1, d11), (a90, b5, c1, d12), (a90, b5, c1, d3), (a90, b5, c1, d14), (a90, b5, c1, d15), (a90, b5, c1, d16), (a90, b5, c1, d17), (a90, b5, c1, d18), (a90, b5, c1, d19), (a90, b5, c1, d20), (a90, b5, c1, d21), (a90, b5, c1, d22), (a90, b5, c2, d1), (a90, b5, c2, d2), (a90, b5, c2, d3), (a90, b5, c2, d4), (a90, b5, c2, d5), (a90, b5, c2, d6), (a90, b5, c2, d7), (a90, b5, c2, d8), (a90, b5, c2, d9), (a90, b5, c2, d10), (a90, b5, c2, d11), (a90, b5, c2, d12), (a90, b5, c2, d13), (a90, b5, c2, d14), (a90, b5, c2, d15), (a90, b5, c2, d16), (a90, b5, c2, d17), (a90, b5, c2, d18), (a90, b5, c2, d19), (a90, b5, c2, d20), (a90, b5, c2, d21), (a90, b5, c2, d22), (a90, b, c3, d1), (a90, b5, c3, d2), (a90, b5, c3, d3), (a90, b5, c3, d4), (a90, b5, c3, d5), (a90, b5, c3, d6), (a90, b5, c3, d7), (a90, b5, c3, d8), (a90, b5, c3, d9), (a90, b5, c3, d10), (a90, b5, c3, d11), (a90, b5, c3, d12), (a90, b5, c3, d13), (a90, b5, c3, d14), (a90, b5, c3, d15), (a90, b5, c3, d16), (a90, b5, c3, d17), (a90, b5, c3, d18), (a90, b5, c3, d19), (a90, b5, c3, d20), (a90, b5, c3, d21), (a90, b5, c3, d22), (a90, b6, c2, d1), (a90, b6, c2, d2), (a90, b6, c1, d3), (a90, b6, c1, d4), (a90, b6, c1, d5), (a90, b6, c1, d6), (a90, b6, c1, d7), (a90, b6, c1, d8), (a90, b6, c1, d9), (a90, b6, c1, d10), (a90, b6, c1, d11), (a90, b6, c1, d12), (a90, b6, c1, d13), (a90, b6, c1, d14), (a90, b6, c1, d15), (a90, b6, c1, d16), (a90, b6, c1, d17), (a90, b6, c1, d18), (a90, b6, c1, d19), (a90, b6, c1, d20), (a90, b6, c1, d21), (a90, b6, c1, d22), (a90, b6, c2, d1), (a90, b6, c2, d2), (a90, b6, c2, d3), (a90, b6, c2, d4), (a90, b6, c2, d5), (a90, b6, c2, d6), (a90, b6, c2, d7), (a90, b6, c2, d8), (a90, b6, c2, d9), (a90, b6, c2, d10), (a90, b6, c2, d11), (a90, b6, c2, d12), (a90, b6, c2, d13), (a90, b6, c2, d14), (a90, b6, c2, d15), (a90, b6, c2, d16), (a90, b6, c2, d17), (a90, b6, c2, d18), (a90, b6, c2, d19), (a90, b6, c2, d20), (a90, b6, c2, d21), (a90, b6, c2, d22), (a90, b6, c3, d1), (a90, b6, c3, d2), (a90, b6, c3, d3), (a90, b6, c3, d4), (a90, b6, c3, d5), (a90, b6, c3, d6), (a90, b6, c3, d7), (a90, b6, c3, d8), (a90, b6, c3, d9), (a90, b6, c3, d10), (a90, b6, c3, d11), (a90, b6, c3, d12), (a90, b6, c3, d3), (a90, b6, c3, d14), (a90, b6, c3, d15), (a90, b6, c3, d16), (a90, b6, c3, d17), (a90, b6, c3, d18), (a90, b6, c3, d19), (a90, b6, c3, d20), (a90, b6, c3, d21), (a90, b6, c3, d22)

The compound represented by the general formula (A) includes an optical isomer thereof and a racemate thereof.

Test Example 1

Enzyme Inhibitory Activity of Test Compound on EGFR and HER2

EGFR and HER2 purified from an insect cell expression system, and a biotinylated substrate (synthetic peptide of glutamic acid:tyrosine=4:1) were added to a 384-well plate with ATP added thereto, and an enzyme reaction was performed at room temperature. After completion of the enzyme reaction, an anti-phosphorylated tyrosine antibody labeled with europium and streptavidin labeled with alphycocyanine were added, and a phosphorylated tyrosine residue was quantified by a time resolution fluorescence method.

(Preparation of Test Compound)

A test compound was adjusted to 10 mM using DMSO.

Further, using 10% DMSO solution, a 1 mM solution was prepared, and this was regarded as a maximum concentration point.

As a dilution series, a 4-fold dilution series was prepared to a 10 stage.

(Reagent Preparation)

Preparation of Buffer:

As a buffer, TBS containing 10 mM $MgCl_2$, 5 mM $MnCl_2$, 0.2 mM $Na_3VO_4$, and 0.1% BSA was used.

Enzyme:

As EGFR and HER2 enzymes, those purified from an insect cell expression system were purchased from Carna Biosciences, Inc.

An EGFR enzyme solution was adjusted to 250 ng/ml using a buffer. HER2 kinase was adjusted to 1000 ng/ml using a buffer.

Substrate Solution:

As a substrate, biotinylated poly-Glu-Tyr (4:1, manufactured by CISbio) was used. A concentration was adjusted to 3.125 µg/ml using the above buffer.

ATP Solution:

An ATP concentration on study of the EGFR enzyme was adjusted to 125 µM using the buffer.

An ATP concentration on study of the HER2 enzyme was adjusted to 290 µM.

Detection Reagent:

For preparing a detection reagent, TBS containing 30 mM EDTA, 0.8M KF and 0.1% BSA was used.

An anti-phosphorylated tyrosine antibody labeled with europium, PT-66K (CISbio) was adjusted to 195 ng/ml, and streptavidin labeled with alphycocyanine, SA-XL(CISbio) was adjusted to 5 µg/ml.

(Assay Method)

As an assay plate, a 384-well plate was used. Per one well, 1.1 µl of a test compound, 4 µl of a substrate solution, and 4 µl of an enzyme solution were added, and 2 µl of an ATP solution was added to initiate an enzyme reaction. The enzyme reaction was performed at room temperature for 60 minutes, and 10 µl of a detection reagent was added to complete the reaction. One hour after completion of the reaction, time resolution fluorescent measurement was performed.

(Assessment Method)

Using 10% DMSO in place of a test compound, and letting a signal at addition of ATP to be 0% inhibition (enzyme activity 100%), and letting a signal in the absence of ATP to be 100% inhibition (enzyme activity 0%), the inhibitory activity at addition of a test compound was calculated.

The inhibitory activity ($IC_{50}$ value, nM) of compounds described in Examples on EGFR and HER2 is shown below.

TABLE 50

| Compound No. | EGFR (nM) | HER2 (nM) |
|---|---|---|
| V-6 | 6.5 | 3.6 |
| V-7 | 36 | 76 |
| V-43 | 186 | 151 |
| VIII-7 | 103 | 348 |

TABLE 50-continued

| Compound No. | EGFR (nM) | HER2 (nM) |
|---|---|---|
| VIII-10 | 409 | 484 |
| VIII-11 | 43 | 45 |
| VIII-12 | 209 | 227 |
| VIII-13 | 300 | 888 |
| VIII-19 | 89 | 115 |
| VIII-20 | 29 | 31 |
| VIII-27 | 33 | 43 |
| VIII-28 | 162 | 167 |
| VIII-29 | 102 | 513 |
| VIII-32 | 50 | 46 |
| VIII-35 | 11 | 25 |
| VIII-40 | 9.3 | 19.2 |
| VIII-41 | 12 | 15 |
| VIII-42 | 10 | 11 |
| VIII-44 | 26 | 6.3 |
| VIII-45 | 58 | 152 |
| VIII-46 | 82 | 104 |
| VIII-47 | 12 | 23 |
| VIII-48 | 44 | 15 |
| VIII-49 | 28 | 31 |
| VIII-50 | 19 | 15 |
| VIII-51 | 45 | 64 |
| VIII-52 | 19 | 28 |
| VIII-53 | 79 | 80 |
| VIII-55 | 19 | 68 |
| VIII-56 | 7.9 | 13.8 |
| VIII-57 | 301 | 803 |
| VIII-58 | 207 | 236 |
| VIII-59 | 115 | 278 |
| VIII-60 | 54 | 30 |
| VIII-61 | 30 | 24 |
| VIII-62 | 22 | 22 |
| VIII-63 | 9.6 | 9.2 |
| VIII-64 | 52 | 88 |
| VIII-65 | 97 | 98 |
| VIII-66 | 27 | 43 |
| VIII-67 | 16 | 14 |
| VIII-68 | 19 | 25 |
| VIII-69 | 43 | 28 |
| VIII-70 | 63 | 31 |
| VIII-71 | 130 | 199 |
| VIII-72 | 6.3 | 11 |
| VIII-73 | 275 | 199 |
| VIII-74 | 164 | 150 |
| VIII-75 | 50 | 34 |
| VIII-76 | 162 | 216 |
| VIII-77 | 217 | 246 |
| VIII-78 | 111 | 410 |
| VIII-80 | 23 | 29 |
| VIII-81 | 9.8 | 17.7 |
| VIII-82 | 7.6 | 7.5 |
| VIII-83 | 164 | 121 |
| VIII-84 | 44 | 47 |
| VIII-85 | 32 | 33 |
| VIII-86 | 244 | 304 |
| VIII-87 | 642 | 476 |
| VIII-88 | 47 | 56 |
| VIII-89 | 27 | 24 |
| VIII-90 | 93 | 97 |
| VIII-91 | 74 | 83 |
| VIII-92 | 32 | 36 |
| VIII-93 | 453 | 321 |
| VIII-94 | 213 | 150 |
| VIII-95 | 209 | 176 |
| VIII-96 | 20 | 20 |
| VIII-97 | 19 | 22 |
| VIII-98 | 21 | 21 |
| VIII-99 | 84 | 84 |
| VIII-100 | 208 | 203 |
| VIII-101 | 56 | 129 |
| VIII-102 | 72 | 121 |
| VIII-103 | 3.9 | 5.6 |
| VIII-104 | 238 | 202 |
| VIII-105 | 14 | 14 |
| VIII-106 | 160 | 148 |
| VIII-107 | 150 | 135 |
| VIII-108 | 53 | 56 |
| VIII-109 | 23 | 18 |
| VIII-110 | 29 | 35 |
| VIII-111 | 37 | 55 |
| VIII-112 | 11 | 13 |
| VIII-113 | 9.7 | 12 |
| VIII-114 | 57 | 69 |
| VIII-116 | 37 | 25 |
| VIII-117 | 47 | 63 |
| VIII-118 | 197 | 223 |
| VIII-119 | 81 | 77 |
| VIII-120 | 83 | 29 |
| VIII-121 | 17 | 18 |
| VIII-122 | 29 | 24 |

TABLE 51

| Compound No. | EGFR (nM) | HER2 (nM) |
|---|---|---|
| VIII-123 | 24 | 38 |
| VIII-124 | 40 | 38 |
| VIII-125 | 118 | 103 |
| VIII-126 | 101 | 123 |
| VIII-127 | 37 | 35 |
| VIII-128 | 15 | 17 |
| VIII-129 | 7.1 | 6.8 |
| VIII-130 | 8.1 | 5.2 |
| VIII-131 | 5.8 | 4.4 |
| VIII-132 | 14 | 14 |
| VIII-133 | 8.4 | 7.1 |
| VIII-134 | 7.1 | 7.4 |
| VIII-135 | 7.6 | 8.1 |
| VIII-136 | 21 | 21 |
| VIII-137 | 13 | 14 |
| VIII-139 | 5 | 3.8 |
| VIII-140 | 5.5 | 4.3 |
| VIII-141 | 10 | 7.9 |
| VIII-142 | 5.5 | 4.4 |
| VIII-143 | 3.5 | 3.6 |
| VIII-145 | 9.4 | 8.9 |
| VIII-146 | 12 | 10 |
| VIII-147 | 13 | 13 |
| VIII-148 | 6.1 | 5.8 |
| VIII-149 | 13 | 14 |
| VIII-150 | 12 | 11 |
| VIII-151 | 20 | 10 |
| VIII-152 | 2.4 | 4.3 |
| VIII-153 | 10 | 11 |
| VIII-154 | 9.5 | 9 |
| VIII-155 | 10 | 8 |
| VIII-156 | 7 | 6.4 |
| VIII-157 | 4.1 | 4 |
| VIII-158 | 3.8 | 3.8 |
| VIII-159 | 16 | 19 |
| VIII-160 | 17 | 18 |
| VIII-161 | 14 | 15 |
| VIII-162 | 51 | 62 |
| VIII-163 | 23 | 27 |
| VIII-164 | 7.3 | 7.6 |
| VIII-165 | 11 | 11 |
| VIII-167 | 4.8 | 4.2 |
| VIII-168 | 8 | 9 |
| VIII-169 | 13 | 15 |
| VIII-170 | 5 | 5.6 |
| VIII-171 | 9.9 | 11.7 |
| VIII-172 | 14 | 16 |
| VIII-173 | 4.8 | 3.9 |
| VIII-174 | 25 | 28 |
| VIII-176 | 23 | 26 |
| VIII-177 | 7.3 | 5.8 |
| VIII-178 | 8.1 | 8.2 |
| VIII-179 | 4.6 | 5 |
| VIII-180 | 7.8 | 6 |
| VIII-181 | 6.2 | 5.9 |
| VIII-182 | 4.7 | 7.3 |
| VIII-183 | 7.1 | 8.3 |
| VIII-184 | 10 | 7 |

TABLE 51-continued

| Compound No. | EGFR (nM) | HER2 (nM) |
|---|---|---|
| VIII-185 | 6.8 | 12.5 |
| VIII-186 | 19 | 26 |
| VIII-187 | 10 | 9 |
| VIII-188 | 20 | 30 |
| VIII-189 | 17 | 27 |
| VIII-190 | 8.9 | 11.1 |
| VIII-191 | 17 | 42 |
| VIII-192 | 6.2 | 14.2 |
| VIII-193 | 14 | 15 |
| VIII-194 | 8.6 | 13 |
| VIII-195 | 45 | 43 |
| VIII-196 | 11 | 20 |
| VIII-197 | 9 | 21 |
| VIII-198 | 3.6 | 4.6 |
| VIII-199 | 6.3 | 5.2 |
| VIII-200 | 9.7 | 9.6 |
| VIII-205 | 17 | 13 |
| VIII-207 | 21 | 17 |
| VIII-208 | 28 | 23 |
| VIII-209 | 38 | 30 |
| VIII-210 | 42 | 14 |
| VIII-211 | 23 | 18 |
| VIII-213 | 18 | 25 |
| VIII-214 | 4.5 | 3.3 |
| VIII-216 | 22 | 7 |
| VIII-218 | 76 | 22 |
| VIII-219 | 26 | 20 |
| VIII-220 | 263 | 449 |
| VIII-221 | 143 | 168 |
| VIII-223 | 253 | 217 |
| VIII-224 | 122 | 118 |
| VIII-225 | 47 | 70 |
| VIII-226 | 20 | 10 |
| IX-1 | 138 | 203 |
| IX-4 | 193 | 334 |
| IX-6 | 344 | 326 |
| IX-8 | 426 | 549 |

Test Example 2

Test of In Vitro Cell Proliferation Inhibition of Test Compound

As a human-derived cancer cell strain, BT-474 was used. Cells were all cultured in a 37° C., 5% $CO_2$ incubator in a medium in which 1.0% bovine fetal serum (ICN) and 50 units ml penicillin/50 µg/ml streptomycin solution (GIBCO) were added to Dulbecco's Modified Essential Medium (DMEM, Nacalai Tesque, Inc). Each 3000/well of cells were seeded on a 96-well plate (Sumitomo Bakelite Co., Ltd.) and, on the next day, a drug was added to a maximum concentration of $3 \times 10^{-10}$ to $10^{-5}$ M. After cultured for 3 days, WST (water-soluble tetrazolium salt) assay was performed, and an $IC_{50}$ value was calculated.

The proliferation inhibitory activity ($IC_{50}$ value, nM) of compounds described in Examples on BT-474 is shown below.

TABLE 52

| Compound No. | BT-474 (nM) |
|---|---|
| V-6 | 110 |
| V-7 | 134 |
| V-43 | 71 |
| VIII-7 | 63 |
| VIII-10 | 27 |
| VIII-11 | 26 |
| VIII-12 | 69 |
| VIII-13 | 64 |

TABLE 52-continued

| Compound No. | BT-474 (nM) |
|---|---|
| VIII-20 | 37 |
| VIII-27 | 13 |
| VIII-28 | 72 |
| VIII-29 | 77 |
| VIII-32 | 32 |
| VIII-35 | 24 |
| VIII-40 | 9 |
| VIII-41 | 14 |
| VIII-42 | 24 |
| VIII-44 | 28 |
| VIII-45 | 13 |
| VIII-46 | 12 |
| VIII-47 | 4 |
| VIII-48 | 28 |
| VIII-49 | 28 |
| VIII-50 | 27 |
| VIII-51 | 9 |
| VIII-52 | 9 |
| VIII-53 | 12 |
| VIII-55 | 25 |
| VIII-56 | 14 |
| VIII-57 | 15 |
| VIII-58 | 37 |
| VIII-59 | 11 |
| VIII-60 | 14 |
| VIII-61 | 11 |
| VIII-62 | 12 |
| VIII-63 | 13 |
| VIII-64 | 22 |
| VIII-65 | 30 |
| VIII-66 | 8 |
| VIII-67 | 32 |
| VIII-68 | 41 |
| VIII-69 | 16 |
| VIII-70 | 7 |
| VIII-71 | 17 |
| VIII-72 | 21 |
| VIII-73 | 12 |
| VIII-74 | 28 |
| VIII-75 | 22 |
| VIII-76 | 12 |
| VIII-77 | 11 |
| VIII-78 | 35 |
| VIII-80 | 35 |
| VIII-81 | 8 |
| VIII-82 | 16 |
| VIII-83 | 13 |
| VIII-84 | 28 |
| VIII-85 | 11 |
| VIII-86 | 13 |
| VIII-87 | 6 |
| VIII-88 | 12 |
| VIII-89 | 25 |
| VIII-90 | 9 |
| VIII-91 | 24 |
| VIII-92 | 29 |
| VIII-93 | 38 |
| VIII-94 | 26 |
| VIII-95 | 25 |
| VIII-96 | 30 |
| VIII-97 | 11 |
| VIII-98 | 65 |
| VIII-99 | 24 |
| VIII-100 | 16 |
| VIII-101 | 12 |
| VIII-102 | 7 |
| VIII-103 | 11 |
| VIII-104 | 60 |
| VIII-105 | 10 |
| VIII-106 | 16 |
| VIII-107 | 23 |
| VIII-108 | 31 |
| VIII-109 | 40 |
| VIII-110 | 21 |
| VIII-111 | 15 |
| VIII-112 | 8 |
| VIII-113 | 13 |

TABLE 52-continued

| Compound No. | BT-474 (nM) |
|---|---|
| VIII-114 | 37 |
| VIII-116 | 50 |
| VIII-117 | 20 |
| VIII-118 | 22 |
| VIII-119 | 31 |
| VIII-120 | 32 |
| VIII-121 | 10 |
| VIII-122 | 14 |
| VIII-123 | 31 |
| VIII-124 | 14 |
| VIII-125 | 10 |
| VIII-126 | 9 |
| VIII-127 | 61 |
| VIII-128 | 37 |
| VIII-129 | 12 |
| VIII-130 | 50 |
| VIII-131 | 14 |
| VIII-132 | 18 |
| VIII-133 | 43 |
| VIII-134 | 14 |
| VIII-135 | 28 |
| VIII-136 | 53 |
| VIII-137 | 78 |
| VIII-139 | 32 |
| VIII-140 | 30 |
| VIII-141 | 46 |
| VIII-142 | 31 |
| VIII-143 | 24 |
| VIII-145 | 21 |
| VIII-146 | 45 |
| VIII-147 | 25 |
| VIII-148 | 26 |
| VIII-149 | 28 |
| VIII-150 | 30 |
| VIII-151 | 47 |
| VIII-152 | 22 |
| VIII-153 | 21 |
| VIII-154 | 31 |
| VIII-155 | 28 |
| VIII-156 | 24 |
| VIII-157 | 25 |
| VIII-158 | 27 |
| VIII-159 | 15 |
| VIII-160 | 47 |
| VIII-161 | 49 |
| VIII-162 | 42 |
| VIII-163 | 38 |
| VIII-164 | 31 |
| VIII-165 | 23 |
| VIII-167 | 21 |
| VIII-168 | 44 |
| VIII-169 | 35 |
| VIII-170 | 19 |
| VIII-171 | 52 |
| VIII-172 | 70 |
| VIII-173 | 40 |

TABLE 53

| Compound No. | BT-474 (nM) |
|---|---|
| VIII-174 | 14 |
| VIII-176 | 26 |
| VIII-177 | 79 |
| VIII-178 | 36 |
| VIII-179 | 48 |
| VIII-180 | 5 |
| VIII-181 | 13 |
| VIII-182 | 20 |
| VIII-183 | 10 |
| VIII-184 | 9 |
| VIII-185 | 12 |
| VIII-186 | 29 |

TABLE 53-continued

| Compound No. | BT-474 (nM) |
|---|---|
| VIII-187 | 24 |
| VIII-188 | 40 |
| VIII-189 | 25 |
| VIII-190 | 14 |
| VIII-191 | 33 |
| VIII-192 | 24 |
| VIII-193 | 25 |
| VIII-194 | 25 |
| VIII-195 | 29 |
| VIII-196 | 28 |
| VIII-197 | 14 |
| VIII-198 | 10 |
| VIII-199 | 33 |
| VIII-200 | 8 |
| VIII-205 | 31 |
| VIII-207 | 68 |
| VIII-208 | 27 |
| VIII-209 | 19 |
| VIII-210 | 31 |
| VIII-211 | 16 |
| VIII-213 | 33 |
| VIII-214 | 25 |
| VIII-216 | 32 |
| VIII-218 | 41 |
| VIII-219 | 45 |
| VIII-220 | 23 |
| VIII-221 | 15 |
| VIII-223 | 6 |
| VIII-224 | 1.2 |
| VIII-225 | 7 |
| VIII-226 | 5 |

Test Example 3

Assessment Test of In Vivo Anti-tumor of Test Compound

NCI-N87 cells (human stomach cancer cell strain) were transplanted into a mammary fat pad of a female nude mouse (BALB/cA Jcl-nu/nu, CLEA Japan, Inc) at $5 \times 10^6$ cells/mouse (day 0). On day 5, a long diameter and a short diameter of a tumor were measured with a caliper, and mice were divided into groups (N=6) so that a tumor size between groups became equal. A test compound (20, 80 mg/kg) suspended in a 0.5% methylcellulose (MC) solution was orally administered from day 5 on for 1.5 consecutive days, and the anti-tumor effect was expressed by a ratio (T/C %) of an average value of a tumor size between a compound-administered group (T) and a control (C, 0.5% MC) group on day 20.

Results of in vivo anti-tumor assessment of a compound VIII-11 are shown in Table 54, and results of in vivo anti-tumor assessment of a compound VIII-66 are shown in Table 55.

TABLE 54

| Mean of tumor size (mm³) | Control group | 20 mg/kg administrated group | 80 mg/kg administrated group |
|---|---|---|---|
| day 5 | 192 | 197 | 197 |
| day 20 | 655 | 356 | 193 |
| T/C % | 100% | 54% | 29% |

TABLE 55

| Mean of tumor size (mm³) | Control group | 20 mg/kg administrated group | 80 mg/kg administrated group |
|---|---|---|---|
| day 5 | 150 | 134 | 150 |
| day 20 | 483 | 154 | 17 |
| T/C % | 100% | 32% | 4% |

Preparation Examples

Preparation Example 1

A granule containing the following ingredient is prepared.

| Ingredient | Compound represented by the formula (I) | 10 mg |
|---|---|---|
| | Lactose | 700 mg |
| | Corn starch | 274 mg |
| | HPC-L | 16 mg |
| | | 1000 mg |

The compound represented by the formula (I) and lactose are passed through a 60 mesh sieve. Corn starch is passed through a 1.20 mesh sieve. These are mixed with a V-type mixing machine. An aqueous solution of HPC-L (low viscosity hydroxypropylcellulose) is added to a mixture powder, and this is kneaded, granulated (extrusion granulation, pore diameter 0.5 to 1 mm), and dried. The resulting dry granule is sieved with a vibration sieve (12/60 mesh) to obtain a granule.

Preparation Example 2

A powder for filling into a capsule containing the following ingredients is prepared.

| Ingredient | Compound represented by the formula (I) | 10 mg |
|---|---|---|
| | Lactose | 79 mg |
| | Corn starch | 10 mg |
| | Magnesium stearate | 1 mg |
| | | 100 mg |

The compound represented by the formula (I), and lactose are passed through a 60 mesh sieve. Corn starch is passed through a 120 mesh sieve. These and magnesium stearate are mixed with a V-type mixing machine. 10 trituration 100 mg is filled into a No. 5 hard gelatin capsule.

Preparation Example 3

A granule for filling into a capsule containing the following ingredients is prepared.

| Ingredient | Compound represented by the formula (I) | 15 mg |
|---|---|---|
| | Lactose | 90 mg |
| | Corn starch | 42 mg |
| | HPC-L | 3 mg |
| | | 150 mg |

The compound represented by the formula (I), and lactose are passed through a 60 mesh sieve. Corn starch is passed through a 120 mesh sieve. These are mixed, a HPL-L solution is added to a mixture powder, and this is kneaded, granulated, and dried. The resulting dry granule is adjusted in a size, 150 mg of which is filled into a No. 4 hard gelatin capsule.

Preparation Example 4

A tablet containing the following ingredients is prepared.

| Ingredient | Compound represented by the formula (I) | 10 mg |
|---|---|---|
| | Lactose | 90 mg |
| | Microcrystaline cellulose | 30 mg |
| | CMC-Na | 15 mg |
| | Magnesium stearate | 5 mg |
| | | 150 mg |

The compound represented by the formula (I), lactose, microcrystalline cellulose. CMC-Na (carboxymethylcellulose sodium salt) are passed through a 60 mesh sieve, and mixed. Magnesium stearate is mixed into a mixture powder to obtain a mixture powder for tabletting. The present mixed powder is directly compressed to obtain a 150 mg tablet.

Preparation Example 5

An intravenous preparation is prepared as follows:

| Compound represented by the formula I | 100 mg |
|---|---|
| Saturated fatty acid glyceride | 1000 ml |

A solution of the above ingredients is intravenously administered to patient at a rate of 1 ml per minute.

INDUSTRIAL APPLICABILITY

Since the present compound has the excellent action of inhibiting an EGF receptor and HER2, and is highly safe, it is useful as a medicament, inter alia, a therapeutic for a cancer.

The invention claimed is:
1. A compound represented by the general formula (I):

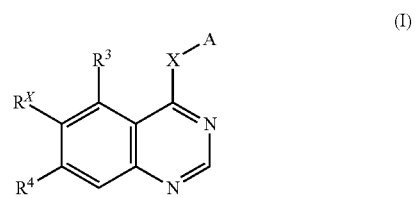

(I)

wherein Rx is a group represented by the formula:

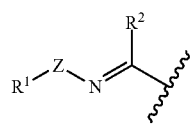

wherein $R^1$ is a hydrogen atom, optionally substituted alkyl, optionally substituted alkenyl, optionally substituted aryl, or an optionally substituted non-aromatic nitrogen-containing heterocyclic group;

Z is —O—;

R² is a hydrogen atom, optionally substituted alkyl, optionally substituted alkenyl, optionally substituted alkynyl, optionally substituted cycloalkyl, optionally substituted aryl, or optionally substituted heteroaryl;

R³ and R⁴ are independently a hydrogen atom, optionally substituted alkyl, optionally substituted alkenyl, optionally substituted alkynyl, optionally substituted alkyloxy, optionally substituted alkenyloxy, halogen, hydroxy, mercapto, or optionally substituted amino;

X is —O—, —S—, —N(R¹²)—, or alkylene which may be intervened with —O—, —S—, or —N(R¹³)—;

R¹² and R¹³ are independently a hydrogen atom, alkyl, acyl, alkyloxycarbonyl, alkenyloxycarbonyl, or aralkyloxycarbonyl; and A is a group represented by the formula:

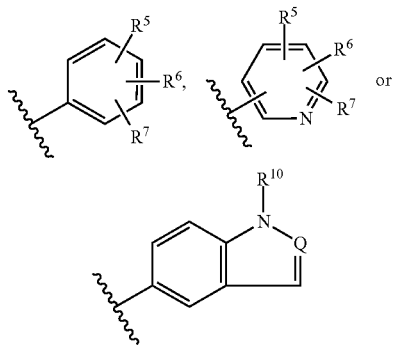

wherein R⁵ is a hydrogen atom, halogen, optionally substituted alkyloxy, optionally substituted alkenyloxy, optionally substituted alkynyloxy, or a group represented by the formula: —Y—R⁸ wherein Y is —O—, —S—, —SO₂—, or alkylene which may be intervened with —O—, —S—, or —N(R⁹)—; R⁸ is optionally substituted aryl or optionally substituted heteroaryl;

R⁹ is a hydrogen atom, alkyl, acyl, alkyloxycarbonyl, alkenyloxycarbonyl, or aralkyloxycarbonyl;

R⁶ and R⁷ are independently a hydrogen atom, optionally substituted alkyl, optionally substituted alkenyl, optionally substituted alkynyl, optionally substituted alkyloxy, optionally substituted alkenyloxy, optionally substituted alkynyloxy, halogen, hydroxy, mercapto, cyano, or optionally substituted amino;

R²⁰ is optionally substituted alkyl, optionally substituted alkenyl, optionally substituted alkynyl, or a group represented by the formula:

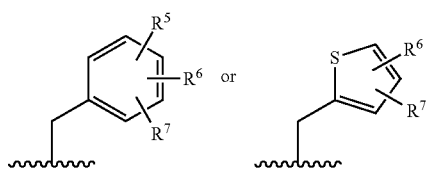

wherein R⁵, R⁶ and R⁷ are as defined above;

Q is N or CH, wherein the aryl is selected from the group consisting of phenyl, 1-naphthyl, 2-naphthyl and anthryl, wherein the heteroaryl is selected from the group consisting of pyrrolyl, furyl, thienyl, imidazolyl, pyrazolyl, isothiazolyl, isooxazolyl, oxazolyl, thiazolyl, pyridyl, pyrazinyl, pyrimidinyl, pyridazinyl, triazolyl, tetrazolyl, oxadiazolyl, thiadiazolyl, indolydinyl, isoindolyl, indolyl, indazolyl, purinyl, quinolizinyl, isoquinolyl, quinolyl, phthalazinyl, naphthyridinyl, quinolanyl, quinazolinyl, cinnolinyl, pteridinyl, carbazolyl, phenanthridinyl, acridinyl, dibenzofuranyl, benzoimidazolyl, benzoisooxazolyl, benzooxazolyl, benzooxadiazolyl, benzoisothiazolyl, benzothiazolyl, benzofuryl, benzothienyl, 4,5-dihydronaphtho[1,2-d]thiazolyl, 4H-chromeno[4,3-d]thiazolyl, 4H-thiochromeno[4,3-d]thiazolyl, 4,5-dihydrothiazolo[5,4-c]quinolyl, 8H-indeno[1,2-d]thiazolyl, and 5,6-dihydro-4H-3-thia-1-azabenzo[e]azulenyl, wherein the non-aromatic heterocyclic group is selected from the group consisting of pyrrolidinyl, pyrrolinyl, imidazolidinyl, imidazolinyl, pyrazolidinyl, pyrazolinyl, piperidyl, piperazinyl, indolinyl, isoindolinyl, morpholinyl, tetrahydrofuranyl, dihydropyranyl, tetrahydropyranyl, dioxolanyl, tetrahydrothienyl, dihydrothiopyranyl, tetrahydrothiofuranyl, decahydroisoquinolinyl, azepinyl, oxepinyl, dihydrooxepinyl, tetrahydrooxepinyl, oxepanyl, 4,5,6,7-tetrahydrothieno[3,2]pyridyl, 2-oxa-5-aza-bicyclo[2.2.1]hepta-5-yl, and hexahydropyrazyl[2.1-b][1,3]ozadin8-yl, wherein the non-aromatic nitrogen-containing heterocyclic group is selected from the group consisting of azetidinyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, 1,4-thiazinyl, thiomorpholinyl, decahydroisoquinolyl, azepinyl, diazepinyl, 4,5,6,7-tetrahydrothieno[3,2]pyridyl, 2-oxa-5-aza-bicyclo[2.2.1]hept-5-yl, and hexahydropyrazyl[2.1b][1,3]oxazin-8-yl, wherein a substituent of the optionally substituted aryl, the optionally substituted heteroaryl and the optionally substituted non-aromatic heterocylic group is selected from the group consisting of optionally substituted alkyl (as a substituent, halogen, hydroxy, nitro, cyano, carboxy, alkyloxy, alkyloxycarbonyl or acyl), cycloalkyl, alkenyl, alkynyl, hydroxy, alkyloxy, aralkyloxy, mercapto, alkylthio, halogen, nitro, cyano, carboxy, alkyloxycarbonyl, aryloxycarbonyl, haloalkyl, haloalkyloxy, optionally substituted amino, optionally substituted aminocarbonyl, acyl, acyloxy, optionally substituted aryl (as a substituent, halogen, hydroxy, nitro, cyano, carboxy, alkyloxy, alkyloxycarbonyl or acyl), optionally substituted heteroaryl (as a substituent, halogen, hydroxy, nitro, cyano, carboxy, alkyloxy, alkyloxycarbonyl or acyl), an optionally substituted non-aromatic heterocyclic group (as a substituent, halogen, hydroxy, nitro, cyano, carboxy, alkyloxy, alkyloxycarbonyl or acyl), optionally substituted aralkyl (as a substituent, halogen, hydroxy, nitro, cyano, carboxy, alkyloxy, alkyloxycarbonyl or acyl), alkylsulfonyl, guanidino, an azo group, —N═N (optionally substituted phenyl), and optionally substituted ureido, and wherein a substituent of the optionally substituted non-aromatic nitrogen-containing heterocyclic group is selected from the group consisting of alkyloxycarbonyl, aminocarbonyl, optionally substituted with a substituent selected from substituent group G consisting of alkyl, alkenyl, and aralkyl, cyano, alkyl optionally substituted with a substituent selected from substituent group M consisting of cyano, hydroxy, carboxy, aminocarbonyl, alkyloxycarbonyl, and alkyloxy, alkylsulfonyl, alkylsulfonylalkylcarbonyl, cycloalkyl, hydroxy, alkyloxy, mercapto, alkylthio, halogen, nitro, carboxy, haloalkyl, halo alkyloxy, acyl, acyloxy, aryl, aryloxy, aralkyl, aralkyloxy, a non-aromatic nitrogen-containing heterocyclic group, alkylcarbonylamino, aminocarbonyloxy, optionally substituted amino, oxo, guanidino, an azo group, and optionally substituted ureido, or its pharmaceutically acceptable salt.

2. The compound according to claim 1, wherein $R^1$ is alkyl optionally substituted with a substituent selected from substituent group A consisting of hydroxy, heteroaryl, carboxy, optionally substituted amino, an optionally substituted non-aromatic nitrogen-containing heterocyclic group, optionally substituted aminocarbonyl, and optionally substituted non-aromatic nitrogen-containing heterocyclic carbonyl, or a non-aromatic nitrogen-containing heterocyclic group optionally substituted with a substituent selected from a substituent group B consisting of alkyloxycarbonyl, optionally substituted aminocarbonyl, oxo, amino, carboxy, cyano, cyanoalkyl, hydroxyalkyl, alkylcarbonylamino, alkylsulfonylamino, and aminocarbonylalkyl;

or its pharmaceutically acceptable salt.

3. The compound according to claim 1, wherein $R^1$ is alkyl substituted with amino optionally substituted with a substituent selected from a substituent group C consisting of alkyl, alkenyl, alkynyl, optionally substituted aryl, araklyl, alkyloxy, hydroxyalkyl, hydroxyalkyloxyalkyl, haloalkyl, aminoalkyl optionally substituted with 1 or 2 alkyl(s), alkylsulfonyl, alklysulfonylalkyl, alkylcarbonyl optionally substituted with halogen or alkyloxy, alkyloxycarbonyl, optionally substituted cycloalkyl, carboxyalkyl, optionally substituted aminocarbonylalkyl, optionally substituted aminocarbonyloxyalkyl, alkyloxyalkyl, alkylthioalkyl, alkylcarbonylaminoalkyl, alkylsulfonylaminoalkyl, alkylsulfonyl(alkyl)aminoalkyl, alkyloxycarbonylalkyl, alkylthio(hydroxy)alkyl, cycloalkylalkyl, cyanoalkyl, optionally substituted aminoalkylcarbonyl, optionally substituted heteroaryl, heteroarylalkyl, hydroxyalkyloxyalkyl, an optionally substituted non-aromatic heterocyclic group, or optionally substituted non-aromatic heterocyclic alkyl, alkyl substituted with a non-aromatic nitrogen-containing heterocyclic group optionally substituted with a substituent selected from substituent group D consisting of halogen; aryl; hydroxy; oxo; optionally substituted aminocarbonyl; alkyloxycarbonyl; alkyl optionally substituted with a substituent selected from a substituent group H consisting of optionally substituted aminocarbonyl, cyano, alkyloxy, alkylsulfonylamino, amino, carboxy, alkyloxycarbonyl, and hydroxy; alkylaminocarbonyl; carboxy; cyano; alkylsulfonyl; alkylcarbonyl; alkenylcarbonyl; alkylsulfonylalkylcarbonyl; alkyloxyalkylcarbonyl; alkylcarbonylamino; aminocarbonyloxy; a non-aromatic nitrogen-containing heterocyclic group; and non-aromatic heterocyclic carbonyl, or a non-aromatic nitrogen-containing heterocyclic group optionally substituted with a substituent selected from a substituent group B consisting of alkyloxycarbonyl, optionally substituted aminocarbonyl, oxo, amino, carboxy, cyano, cyanoalkyl, hydroxyalkyl, alkylcarbonylamino, alkylsulfonylamino, and aminocarbonylalkyl;

or its pharmaceutically acceptable salt.

4. The compound according to claim 1, wherein $R^{19}$ is alkyl optionally substituted with a substituent selected from substituent group A consisting of hydroxy, heteroaryl, carboxy, optionally substituted amino, an optionally substituted non-aromatic nitrogen-containing heterocyclic group, optionally substituted aminocarbonyl, and optionally substituted non-aromatic nitrogen-containing heterocyclic carbonyl, aryl optionally substituted with a substituent selected from substituent group I consisting of alkyloxycarbonyl, optionally substituted aminocarbonyl, cyano, cyanoalkyl, hydroxyalkyl, and aminocarbonylalkyl, or heteroaryl optionally substituted with a substituent selected from substituent group I, or its pharmaceutically acceptable salt.

5. The compound according to claim 1, wherein $R^{19}$ is alkyl substituted with amino optionally substituted with a substituent selected from substituent group C consisting of alkyl, alkenyl, alkynyl, optionally substituted aryl, araklyl, alkyloxy, hydroxyalkyl, hydroxyalkyloxyalkyl, haloalkyl, aminoalkyl optionally substituted with 1 or 2 alkyl(s), alkylsulfonyl, alklysulfonylalkyl, alkylcarbonyl optionally substituted with halogen or alkyloxy, alkyloxycarbonyl, optionally substituted cycloalkyl, carboxyalkyl, optionally substituted aminocarbonylalkyl, optionally substituted aminocarbonyloxyalkyl, alkyloxyalkyl, alkylthioalkyl, alkylcarbonylaminoalkyl, alkylsulfonylaminoalkyl, alkylsulfonyl(alkyl)aminoalkyl, alkyloxycarbonylalkyl, alkylthio(hydroxy)alkyl, cycloalkylalkyl, cyanoalkyl, optionally substituted aminoalkylcarbonyl, optionally substituted heteroaryl, heteroarylalkyl, hydroxyalkyloxyalkyl, an optionally substituted non-aromatic heterocyclic group, and optionally substituted non-aromatic heterocyclic alkyl, or alkyl substituted with a non-aromatic nitrogen-containing heterocyclic group optionally substituted with a substituent selected from substituent group D consisting of halogen; aryl; hydroxy; oxo; optionally substituted aminocarbonyl; alkyloxycarbonyl; alkyl optionally substituted with a substituent selected from a substituent group H consisting of optionally substituted aminocarbonyl, cyano, alkyloxy, alkylsulfonylamino, amino, carboxy, alkyloxycarbonyl, and hydroxy; alkylaminocarbonyl; carboxy; cyano; alkylsulfonyl; alkylcarbonyl; alkenylcarbonyl; alkylsulfonylalkylcarbonyl; alkyloxyalkylcarbonyl; alkylcarbonylamino; aminocarbonyloxy; a non-aromatic nitrogen-containing heterocyclic group; and non-aromatic heterocyclic carbonyl;

or its pharmaceutically acceptable salt.

6. The compound according to claim 1, wherein $W^1$ is a group represented by a non-aromatic nitrogen-containing heterocyclic group optionally substituted with a substituent selected from substituent group J consisting of alkyl, cyanoalkyl, hydroxyalkyl, aminocarbonylalkyl, alkyloxy, alkyloxycarbonyl, optionally substituted aminocarbonyl, and cyano, or a group represented by heteroaryl optionally substituted with a substituent selected from substituent group J, or its pharmaceutically acceptable salt.

7. The compound according to claim 1, wherein $R^2$ is a hydrogen atom, C1-C6 alkyl optionally substituted with halogen, C2-C6 alkenyl, C2-C6 alkynyl, halogen, or phenyl, or its pharmaceutically acceptable salt.

8. The compound according to claim 1, wherein one of $R^3$ and $R^4$ is a hydrogen atom, and the other is a hydrogen atom, optionally substituted alkyloxy or optionally substituted alkenyloxy, its pharmaceutically acceptable salt.

9. The compound according to claim 1, wherein X is —NH—, or its pharmaceutically acceptable salt.

10. The compound according to claim 1, wherein A is a group represented by the formula:

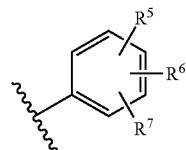

wherein $R^5$ is a hydrogen atom or halogen; $R^6$ is halogen or alkynyl; and $R^7$ is a hydrogen atom,
or its pharmaceutically acceptable salt.

11. The compound according to claim 1, wherein A is a group represented by the formula:

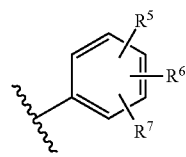

wherein $R^5$ is alkyloxy optionally substituted with a substituent selected from substituent group E consisting of carboxy, alkoxyoxycarbonyl, cycloalkyl, and optionally substituted aminocarbonyl;
alkenyloxy optionally substituted with a substituent selected from substituent group E, or alkynyloxy optionally substituted with a substituent selected from substituent group E;
$R^6$ is optionally substituted alkynyl, optionally substituted alkyloxy, or halogen; and
$R^7$ is a hydrogen atom;
or its pharmaceutically acceptable salt.

12. The compound according to claim 1, wherein A is a group represented by the formula:

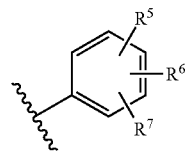

wherein $R^5$ is a group represented by the formula: —Y—$R^8$ wherein Y is alkylene which may be intervened with —O—;
$R^8$ is phenyl optionally substituted with a substituent selected from substituent group F consisting of halogen, carboxy, alkyl, haloalkyl, hydroxyalkyl, alkyloxy, alkyloxycarbonyl, and optionally substituted amino;
pyridyl optionally substituted with a substituent selected from substituent group F;
furyl optionally substituted with a substituent selected from substituent group F;
thienyl optionally substituted with a substituent selected from substituent group F;
thiazolyl optionally substituted with a substituent selected from substituent group F; or
oxazolyl optionally substituted with a substituent selected from substituent group F;
$R^6$ is optionally substituted alkynyl, optionally substituted alkyloxy, or halogen; and
$R^7$ is a hydrogen atom;
or its pharmaceutically acceptable salt.

13. The compound according to claim 1, which is represented by the formula (I-Q):

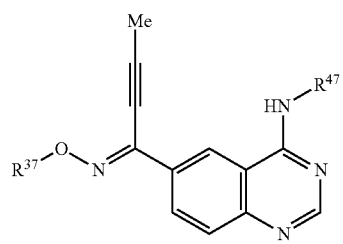

(I-Q)

wherein $R^{47}$ is a group represented by the formula:

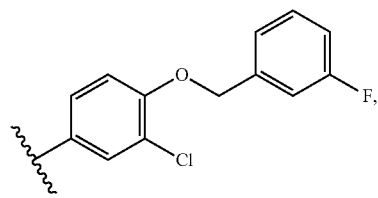

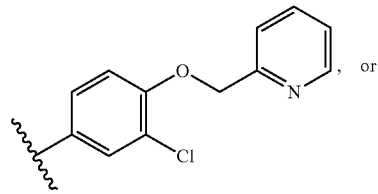

, or

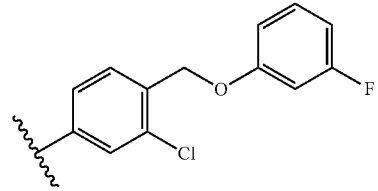

and
$R^{37}$ is alkyl substituted with amino optionally substituted with alkyl, hydroxyalkyl, alkylcarbonylaminoalkyl or a non-aromatic heterocyclic group;
alkyl substituted with a non-aromatic nitrogen-containing heterocyclic group optionally substituted with alkyl, hydroxyalkyl, or alkylcarbonylamino; or
a non-aromatic nitrogen-containing heterocyclic group substituted with hydroxyalkyl;
or its pharmaceutically acceptable salt.

14. A pharmaceutical composition containing the compound as defined in claim 1 as an active ingredient.

* * * * *